(12) United States Patent
Colley et al.

(10) Patent No.: US 11,705,226 B2
(45) Date of Patent: *Jul. 18, 2023

(54) DATA BASED CANCER RESEARCH AND TREATMENT SYSTEMS AND METHODS

(71) Applicant: Tempus Labs, Chicago, IL (US)

(72) Inventors: Shane Colley, Chicago, IL (US); Isaiah Simpson, Chicago, IL (US); Brian Reuter, Chicago, IL (US); Robert Tell, Chicago, IL (US); Hailey Lefkofsky, Chicago, IL (US); Hunter Lane, Chicago, IL (US); Kevin White, Chicago, IL (US); Nike Beaubier, Chicago, IL (US); Stephen Bush, Chicago, IL (US); Aly Khan, Chicago, IL (US); Denise Lau, Chicago, IL (US); Kaanan Shah, Chicago, IL (US); Eric Lefkofsky, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 525 days.

This patent is subject to a terminal disclaimer.

(21) Appl. No.: 16/657,804

(22) Filed: Oct. 18, 2019

(65) Prior Publication Data

US 2021/0090694 A1    Mar. 25, 2021

Related U.S. Application Data

(60) Provisional application No. 62/902,950, filed on Sep. 19, 2019.

(51) Int. Cl.
*G16H 10/60* (2018.01)
*G16H 15/00* (2018.01)
(Continued)

(52) U.S. Cl.
CPC ............ *G16H 10/60* (2018.01); *G16H 15/00* (2018.01); *G16H 20/40* (2018.01); *G16H 50/20* (2018.01);
(Continued)

(58) Field of Classification Search
CPC ........ G16H 10/60; G16H 15/00; G16H 20/40; G16H 50/70; G16H 50/30; G16H 50/50;
(Continued)

(56) References Cited

U.S. PATENT DOCUMENTS

2010/0029498 A1*  2/2010  Gnirke ................. C12Q 1/6869
                                                                506/9
2014/0365242 A1* 12/2014  Neff ....................... G16H 10/60
                                                                705/3

(Continued)

OTHER PUBLICATIONS

Austin, P. The use of propensity score methods with survival or time-to-event outcomes: reporting measures of effect similar to those used in randomized experiments, Stat Med. Mar. 30, 2014; 33(7): 1242-1258.

(Continued)

*Primary Examiner* — John P Go
*Assistant Examiner* — Chad A Newton
(74) *Attorney, Agent, or Firm* — Quarles & Brady LLP

(57) ABSTRACT

A method and system for storing user application programs and micro-service programs, for each of multiple patients that have cancerous cells and receive treatment, includes obtaining clinical records data in original forms, storing it in a semi-structured first database, generating sequencing data for the patient's cancerous and normal cells using a next generation genomic sequencer, storing the sequencing data in the first database, shaping at least some of the first database data to generate system structured data optimized for searching and including clinical record data, storing the structured data in a second database, for each user applica- (Continued)

tion program, selecting an application-specific subset of data from the second database and storing it in a structure optimized for application program interfacing in a third database, wherein an orchestration manager operatively connected to one or more micro-service programs receives status messages and initiates a respective micro-service program when program prerequisites are satisfied.

86 Claims, 508 Drawing Sheets
(265 of 508 Drawing Sheet(s) Filed in Color)
Specification includes a Sequence Listing.

(51) Int. Cl.
*G16H 20/40* (2018.01)
*G16H 50/70* (2018.01)
*G16H 50/30* (2018.01)
*G16H 50/50* (2018.01)
*G16H 50/20* (2018.01)

(52) U.S. Cl.
CPC ............. *G16H 50/30* (2018.01); *G16H 50/50* (2018.01); *G16H 50/70* (2018.01)

(58) Field of Classification Search
CPC ........ G16H 50/20; G16H 30/40; G16H 10/40; G16B 25/00; G16B 20/00; G16B 40/00
See application file for complete search history.

(56) References Cited

U.S. PATENT DOCUMENTS

2015/0324527 A1* 11/2015 Siegel .................... G16B 50/30 705/3
2016/0085910 A1  3/2016 Bruand
2020/0004751 A1* 1/2020 Stennett ................. G06N 20/00

OTHER PUBLICATIONS

Ayers, M, et al. "IFN-?-related mRNA profile predicts clinical response to PD-1 blockade." The Journal of clinical investigation 127.8 (2017): 2930-2940.
Bray, F., et al. "Global cancer statistics 2018: GLOBOCAN estimates of incidence and mortality worldwide for 36 cancers in 185 countries." CA: a cancer journal for clinicians 68.6 (2018): 394-424.
Bray, N. L., et al. "Near-optimal probabilistic RNA-seq quantification." Nature biotechnology 34.5 (2016): 525.
Clinical Trial NCT03051035, First-in-Human Study of KO-947 in Non-Hematological Malignancies, posted Feb. 13, 2017.
Cseh B, et al. "RAF" neighborhood: protein-protein interaction in the Raf/Mek/Erk pathway. FEBS Lett. 2014;588:2398-2406.
Dienstmann, R., et al. "Database of genomic biomarkers for cancer drugs and clinical targetability in solid tumors." Cancer discovery 5.2 (2015): 118-123.
Dobin, A., et al. "STAR: ultrafast universal RNA-seq aligner." Bioinformatics 29.1 (2013): 15-21.
Faust, G. G., et al. "SAMBLASTER: fast duplicate marking and structural variant read extraction." Bioinformatics 30.17 (2014): 2503-2505.
Kitano, A., et al. "Tumour-infiltrating lymphocytes are correlated with higher expression levels of PD-1 and PD-L1 in early breast cancer." ESMO open 2.2 (2017): e000150.
Knight T, et al. Ras/Raf/MEK/ERK pathway activation in childhood acute lymphoblastic leukemia and its therapeutic targeting. Front Oncol. 2014;4:160.
Layer, R. M., et al. "LUMPY: a probabilistic framework for structural variant discovery." Genome biology 15.6 (2014): R84.
Li, H., et al. "Fast and accurate long-read alignment with Burrows—Wheeler transform." Bioinformatics 26.5 (2010): 589-595.
Liao, Y., et al. "featurecounts: an efficient general purpose program for assigning sequence reads to genomic features." Bioinformatics 30.7 (2013): 923-930.
McLaughlin, J., et al. "Quantitative assessment of the heterogeneity of PD-L1 expression in non-small-cell lung cancer." JAMA oncology 2.1 (2016): 46-54.
Newman, A. M. et al. Robust enumeration of cell subsets from tissue expression profiles. Nat. Methods 12, 453-7 (2015).
Richards, S. et al. Standards and guidelines for the interpretation of sequence variants: a joint consensus recommendation of the American College of Medical Genetics and Genomics and the Association for Molecular Pathology. Genet. Med. 17, 405-24 (2015).
Robinson, D. R. et al. Integrative clinical genomics of metastatic cancer. Nature 548, 297-303. 2017.
Rooney, M. S., et al. Molecular and Genetic Properties of Tumors Associated with Local Immune Cytolytic Activity. Cell 160, 48-61 (2015).
Rosenbaum, P. R., et al. "The central role of the propensity score in observational studies for causal effects." Biometrika 70.1 (1983): 41-55.
Rubinsteyn, A., et al. "Predicting peptide-MHC binding affinities with imputed training data." BioRxiv (2016): 054775.
Stuart, E. Matching methods for causal inference: a review and a look forward, Statistical Science (2010) 25(1):1-21.
Szolek, A, et al. "OptiType: precision HLA typing from next-generation sequencing data." Bioinformatics 30.23 (2014): 3310-3316.
Teng, MWL, et al. "Classifying cancers based on T-cell infiltration and PD-L1." Cancer research 75.11 (2015): 2139-2145.
Vassilakopoulou, M., et al. "Evaluation of PD-L1 expression and associated tumor-infiltrating lymphocytes in aryngeal squamous cell carcinoma." Clinical Cancer Research 22.3 (2016): 704-713.
Velcheti, V., et al. "Programmed death ligand-1 expression in non-small cell lung cancer." Laboratory investigation 94.1 (2014): 107.
Wei, S.C., et al. "Fundamental mechanisms of immune checkpoint blockade therapy." Cancer discovery 8.9 (2018): 1069-1086.
Wimberly, H. et al. "PD-L1 expression correlates with tumor-infiltrating lymphocytes and response to neoadjuvant chemotherapy in breast cancer." Cancer immunology research 3.4 (2015): 326-332.

* cited by examiner

| Exemplary Oncology Panel - 1711 Genes |||||||||| 
|---|---|---|---|---|---|---|---|---|---|
| No. | Symbol | No. | Symbol | No. | Symbol | No. | Symbol | No. | Symbol |
| 1 | AATK | 39 | ALK | 77 | ATAD2 | 115 | BCLAF1 | 153 | BTK |
| 2 | ABCA1 | 40 | ALKBH6 | 78 | ATAD2B | 116 | BCOR | 154 | BTRC |
| 3 | ABCB1 | 41 | ALOX12B | 79 | ATF1 | 117 | BCORL1 | 155 | BUB1 |
| 4 | ABCB11 | 42 | ALOX5 | 80 | ATM | 118 | BCR | 156 | BUB1B |
| 5 | ABCB4 | 43 | AMER1 | 81 | ATR | 119 | BDNF | 157 | BUB3 |
| 6 | ABCC1 | 44 | APC | 82 | ATRX | 120 | BID | 158 | CACNA1C |
| 7 | ABCC2 | 45 | APEX1 | 83 | AURKA | 121 | BIRC2 | 159 | CACNA1S |
| 8 | ABCG1 | 46 | APH1A | 84 | AURKB | 122 | BIRC3 | 160 | CACNB2 |
| 9 | ABCG2 | 47 | APOA1 | 85 | AURKC | 123 | BIRC5 | 161 | CADM2 |
| 10 | ABI1 | 48 | APOB | 86 | AXIN1 | 124 | BIRC8 | 162 | CALR |
| 11 | ABL1 | 49 | AR | 87 | AXIN2 | 125 | BLK | 163 | CAMTA1 |
| 12 | ABL2 | 50 | ARAF | 88 | AXL | 126 | BLM | 164 | CAPRIN2 |
| 13 | ACE | 51 | AREG | 89 | B2M | 127 | BLNK | 165 | CARD10 |
| 14 | ACSL6 | 52 | ARFRP1 | 90 | BABAM1 | 128 | BMI1 | 166 | CARD11 |
| 15 | ACTA2 | 53 | ARHGAP10 | 91 | BACH1 | 129 | BMPR1A | 167 | CARD6 |
| 16 | ACTC1 | 54 | ARHGAP26 | 92 | BACH2 | 130 | BMPR1B | 168 | CARD8 |
| 17 | ACVR1 | 55 | ARHGAP35 | 93 | BAG4 | 131 | BMX | 169 | CARM1 |
| 18 | ACVR1B | 56 | ARID1A | 94 | BAP1 | 132 | BPTF | 170 | CASC11 |
| 19 | ACVR2A | 57 | ARID1B | 95 | BARD1 | 133 | BRAF | 171 | CASP8 |
| 20 | ACVR2B | 58 | ARID2 | 96 | BAX | 134 | BRCA1 | 172 | CBFA2T2 |
| 21 | ADAM17 | 59 | ARID5B | 97 | BAZ1A | 135 | BRCA2 | 173 | CBFA2T3 |
| 22 | ADAMTS20 | 60 | ARNT | 98 | BAZ1B | 136 | BRD1 | 174 | CBFB |
| 23 | ADGRA2 | 61 | ARNT2 | 99 | BAZ2A | 137 | BRD2 | 175 | CBL |
| 24 | ADGRB3 | 62 | ARPC1A | 100 | BAZ2B | 138 | BRD3 | 176 | CBLB |
| 25 | ADGRL2 | 63 | ARPC1B | 101 | BBC3 | 139 | BRD4 | 177 | CBLC |
| 26 | ADGRL3 | 64 | ARTN | 102 | BCAR3 | 140 | BRD7 | 178 | CBX1 |
| 27 | ADRB1 | 65 | ARX | 103 | BCL10 | 141 | BRD8 | 179 | CBX2 |
| 28 | ADRB2 | 66 | ASCL1 | 104 | BCL11A | 142 | BRD9 | 180 | CBX3 |
| 29 | AFF1 | 67 | ASCL2 | 105 | BCL11B | 143 | BRDT | 181 | CBX4 |
| 30 | AFF2 | 68 | ASCL3 | 106 | BCL2 | 144 | BRIP1 | 182 | CBX5 |
| 31 | AFF3 | 69 | ASCL4 | 107 | BCL2A1 | 145 | BRPF1 | 183 | CBX6 |
| 32 | AHR | 70 | ASCL5 | 108 | BCL2L1 | 146 | BRPF3 | 184 | CBX7 |
| 33 | AIP | 71 | ASH1L | 109 | BCL2L11 | 147 | BRWD1 | 185 | CBX8 |
| 34 | AJUBA | 72 | ASH2L | 110 | BCL2L2 | 148 | BRWD3 | 186 | CCDC6 |
| 35 | AKAP9 | 73 | ASPSCR1 | 111 | BCL3 | 149 | BTC | 187 | CCNB3 |
| 36 | AKT1 | 74 | ASXL1 | 112 | BCL6 | 150 | BTG1 | 188 | CCND1 |
| 37 | AKT2 | 75 | ASXL2 | 113 | BCL7A | 151 | BTG2 | 189 | CCND2 |
| 38 | AKT3 | 76 | ASXL3 | 114 | BCL9 | 152 | BTG3 | 190 | CCND3 |

Fig. 22a

| \multicolumn{10}{|c|}{Exemplary Oncology Panel - 1711 Genes} |
|---|---|---|---|---|---|---|---|---|---|
| No. | Symbol | No. | Symbol | No. | Symbol | No. | Symbol | No. | Symbol |
| 38 | AKT3 | 76 | ASXL3 | 114 | BCL9 | 152 | BTG3 | 190 | CCND3 |
| 191 | CCNE1 | 229 | CDK14 | 267 | CHD4 | 305 | CSF2RA | 343 | DAXX |
| 192 | CCNE2 | 230 | CDK15 | 268 | CHD5 | 306 | CSF2RB | 344 | DBH |
| 193 | CCNL1 | 231 | CDK16 | 269 | CHD6 | 307 | CSF3R | 345 | DCC |
| 194 | CD1D | 232 | CDK17 | 270 | CHD7 | 308 | CSK | 346 | DCUN1D1 |
| 195 | CD22 | 233 | CDK18 | 271 | CHD9 | 309 | CSNK1D | 347 | DCUN1D2 |
| 196 | CD274 | 234 | CDK19 | 272 | CHEK1 | 310 | CSNK1E | 348 | DDB2 |
| 197 | CD276 | 235 | CDK2 | 273 | CHEK2 | 311 | CTCF | 349 | DDIT3 |
| 198 | CD28 | 236 | CDK20 | 274 | CHIC1 | 312 | CTCFL | 350 | DDR1 |
| 199 | CD40 | 237 | CDK3 | 275 | CHIC2 | 313 | CTLA4 | 351 | DDR2 |
| 200 | CD40LG | 238 | CDK4 | 276 | CHUK | 314 | CTNNA1 | 352 | DDX3X |
| 201 | CD44 | 239 | CDK5 | 277 | CIC | 315 | CTNNA2 | 353 | DDX5 |
| 202 | CD70 | 240 | CDK6 | 278 | CIITA | 316 | CTNNA3 | 354 | DDX6 |
| 203 | CD79A | 241 | CDK7 | 279 | CKS1B | 317 | CTNNB1 | 355 | DEK |
| 204 | CD79B | 242 | CDK8 | 280 | CKS2 | 318 | CTNND1 | 356 | DHFR |
| 205 | CD80 | 243 | CDK9 | 281 | CLIP1 | 319 | CTSD | 357 | DHH |
| 206 | CD86 | 244 | CDKN1A | 282 | CMPK1 | 320 | CTSL | 358 | DIAPH1 |
| 207 | CDC14A | 245 | CDKN1B | 283 | CNKSR1 | 321 | CTSS | 359 | DIAPH2 |
| 208 | CDC20 | 246 | CDKN1C | 284 | CNOT3 | 322 | CUL3 | 360 | DIAPH3 |
| 209 | CDC25A | 247 | CDKN2A | 285 | CNTFR | 323 | CUL4A | 361 | DICER1 |
| 210 | CDC25B | 248 | CDKN2B | 286 | COL3A1 | 324 | CUL4B | 362 | DIRAS3 |
| 211 | CDC25C | 249 | CDKN2C | 287 | COMT | 325 | CUX1 | 363 | DIS3 |
| 212 | CDC42 | 250 | CDKN3 | 288 | COPS3 | 326 | CYLD | 364 | DKC1 |
| 213 | CDC6 | 251 | CDX1 | 289 | CRBN | 327 | CYP17A1 | 365 | DMXL1 |
| 214 | CDC73 | 252 | CDX2 | 290 | CREB1 | 328 | CYP1A2 | 366 | DNM2 |
| 215 | CDH1 | 253 | CEBPA | 291 | CREB3L1 | 329 | CYP21A2 | 367 | DNMT1 |
| 216 | CDH10 | 254 | CEBPB | 292 | CREB3L2 | 330 | CYP2A6 | 368 | DNMT3A |
| 217 | CDH11 | 255 | CEBPD | 293 | CREB3L4 | 331 | CYP2B6 | 369 | DNMT3B |
| 218 | CDH2 | 256 | CEBPE | 294 | CREBBP | 332 | CYP2C19 | 370 | DNMT3L |
| 219 | CDH20 | 257 | CEBPG | 295 | CREM | 333 | CYP2C8 | 371 | DOCK2 |
| 220 | CDH3 | 258 | CEBPZ | 296 | CRHR1 | 334 | CYP2C9 | 372 | DOT1L |
| 221 | CDH5 | 259 | CECR2 | 297 | CRK | 335 | CYP2D6 | 373 | DPYD |
| 222 | CDH7 | 260 | CENPE | 298 | CRKL | 336 | CYP2J2 | 374 | DRD1 |
| 223 | CDK1 | 261 | CES1 | 299 | CRLF2 | 337 | CYP2R1 | 375 | DRD2 |
| 224 | CDK10 | 262 | CES2 | 300 | CRTC1 | 338 | CYP3A4 | 376 | DSC2 |
| 225 | CDK11A | 263 | CHD1 | 301 | CRTC2 | 339 | CYP3A5 | 377 | DSG2 |
| 226 | CDK11B | 264 | CHD1L | 302 | CRTC3 | 340 | CYP4F2 | 378 | DSP |
| 227 | CDK12 | 265 | CHD2 | 303 | CSF1 | 341 | DACH1 | 379 | DUSP22 |
| 228 | CDK13 | 266 | CHD3 | 304 | CSF1R | 342 | DACH2 | 380 | DVL1 |

Fig. 22b

| Exemplary Oncology Panel - 1711 Genes ||||||||||
|---|---|---|---|---|---|---|---|---|---|
| No. | Symbol | No. | Symbol | No. | Symbol | No. | Symbol | No. | Symbol |
| 191 | CCNE1 | 229 | CDK14 | 267 | CHD4 | 305 | CSF2RA | 343 | DAXX |
| 192 | CCNE2 | 230 | CDK15 | 268 | CHD5 | 306 | CSF2RB | 344 | DBH |
| 193 | CCNL1 | 231 | CDK16 | 269 | CHD6 | 307 | CSF3R | 345 | DCC |
| 194 | CD1D | 232 | CDK17 | 270 | CHD7 | 308 | CSK | 346 | DCUN1D1 |
| 195 | CD22 | 233 | CDK18 | 271 | CHD9 | 309 | CSNK1D | 347 | DCUN1D2 |
| 196 | CD274 | 234 | CDK19 | 272 | CHEK1 | 310 | CSNK1E | 348 | DDB2 |
| 197 | CD276 | 235 | CDK2 | 273 | CHEK2 | 311 | CTCF | 349 | DDIT3 |
| 198 | CD28 | 236 | CDK20 | 274 | CHIC1 | 312 | CTCFL | 350 | DDR1 |
| 199 | CD40 | 237 | CDK3 | 275 | CHIC2 | 313 | CTLA4 | 351 | DDR2 |
| 200 | CD40LG | 238 | CDK4 | 276 | CHUK | 314 | CTNNA1 | 352 | DDX3X |
| 201 | CD44 | 239 | CDK5 | 277 | CIC | 315 | CTNNA2 | 353 | DDX5 |
| 202 | CD70 | 240 | CDK6 | 278 | CIITA | 316 | CTNNA3 | 354 | DDX6 |
| 203 | CD79A | 241 | CDK7 | 279 | CKS1B | 317 | CTNNB1 | 355 | DEK |
| 204 | CD79B | 242 | CDK8 | 280 | CKS2 | 318 | CTNND1 | 356 | DHFR |
| 205 | CD80 | 243 | CDK9 | 281 | CLIP1 | 319 | CTSD | 357 | DHH |
| 206 | CD86 | 244 | CDKN1A | 282 | CMPK1 | 320 | CTSL | 358 | DIAPH1 |
| 207 | CDC14A | 245 | CDKN1B | 283 | CNKSR1 | 321 | CTSS | 359 | DIAPH2 |
| 208 | CDC20 | 246 | CDKN1C | 284 | CNOT3 | 322 | CUL3 | 360 | DIAPH3 |
| 209 | CDC25A | 247 | CDKN2A | 285 | CNTFR | 323 | CUL4A | 361 | DICER1 |
| 210 | CDC25B | 248 | CDKN2B | 286 | COL3A1 | 324 | CUL4B | 362 | DIRAS3 |
| 211 | CDC25C | 249 | CDKN2C | 287 | COMT | 325 | CUX1 | 363 | DIS3 |
| 212 | CDC42 | 250 | CDKN3 | 288 | COPS3 | 326 | CYLD | 364 | DKC1 |
| 213 | CDC6 | 251 | CDX1 | 289 | CRBN | 327 | CYP17A1 | 365 | DMXL1 |
| 214 | CDC73 | 252 | CDX2 | 290 | CREB1 | 328 | CYP1A2 | 366 | DNM2 |
| 215 | CDH1 | 253 | CEBPA | 291 | CREB3L1 | 329 | CYP21A2 | 367 | DNMT1 |
| 216 | CDH10 | 254 | CEBPB | 292 | CREB3L2 | 330 | CYP2A6 | 368 | DNMT3A |
| 217 | CDH11 | 255 | CEBPD | 293 | CREB3L4 | 331 | CYP2B6 | 369 | DNMT3B |
| 218 | CDH2 | 256 | CEBPE | 294 | CREBBP | 332 | CYP2C19 | 370 | DNMT3L |
| 219 | CDH20 | 257 | CEBPG | 295 | CREM | 333 | CYP2C8 | 371 | DOCK2 |
| 220 | CDH3 | 258 | CEBPZ | 296 | CRHR1 | 334 | CYP2C9 | 372 | DOT1L |
| 221 | CDH5 | 259 | CECR2 | 297 | CRK | 335 | CYP2D6 | 373 | DPYD |
| 222 | CDH7 | 260 | CENPE | 298 | CRKL | 336 | CYP2J2 | 374 | DRD1 |
| 223 | CDK1 | 261 | CES1 | 299 | CRLF2 | 337 | CYP2R1 | 375 | DRD2 |
| 224 | CDK10 | 262 | CES2 | 300 | CRTC1 | 338 | CYP3A4 | 376 | DSC2 |
| 225 | CDK11A | 263 | CHD1 | 301 | CRTC2 | 339 | CYP3A5 | 377 | DSG2 |
| 226 | CDK11B | 264 | CHD1L | 302 | CRTC3 | 340 | CYP4F2 | 378 | DSP |
| 227 | CDK12 | 265 | CHD2 | 303 | CSF1 | 341 | DACH1 | 379 | DUSP22 |
| 228 | CDK13 | 266 | CHD3 | 304 | CSF1R | 342 | DACH2 | 380 | DVL1 |

Fig. 22c

| Exemplary Oncology Panel - 1711 Genes | | | | | | | | | |
|---|---|---|---|---|---|---|---|---|---|
| No. | Symbol | No. | Symbol | No. | Symbol | No. | Symbol | No. | Symbol |
| 381 | DVL2 | 419 | EPHA5 | 457 | EXT1 | 495 | FGF14 | 533 | FOSL2 |
| 382 | DVL3 | 420 | EPHA6 | 458 | EXT2 | 496 | FGF16 | 534 | FOXA1 |
| 383 | DYRK2 | 421 | EPHA7 | 459 | EXTL1 | 497 | FGF17 | 535 | FOXA2 |
| 384 | E2F1 | 422 | EPHA8 | 460 | EZH1 | 498 | FGF18 | 536 | FOXA3 |
| 385 | E2F3 | 423 | EPHB1 | 461 | EZH2 | 499 | FGF19 | 537 | FOXG1 |
| 386 | E2F5 | 424 | EPHB2 | 462 | FADD | 500 | FGF2 | 538 | FOXL1 |
| 387 | E2F6 | 425 | EPHB3 | 463 | FAM175A | 501 | FGF20 | 539 | FOXL2 |
| 388 | E2F7 | 426 | EPHB4 | 464 | FAM46C | 502 | FGF21 | 540 | FOXM1 |
| 389 | EBF1 | 427 | EPHB6 | 465 | FANCA | 503 | FGF22 | 541 | FOXN3 |
| 390 | ECT2L | 428 | EPOR | 466 | FANCB | 504 | FGF23 | 542 | FOXO1 |
| 391 | EED | 429 | ERBB2 | 467 | FANCC | 505 | FGF3 | 543 | FOXO3 |
| 392 | EGF | 430 | ERBB3 | 468 | FANCD2 | 506 | FGF4 | 544 | FOXO4 |
| 393 | EGFR | 431 | ERBB4 | 469 | FANCE | 507 | FGF5 | 545 | FOXP1 |
| 394 | EGR1 | 432 | ERCC1 | 470 | FANCF | 508 | FGF6 | 546 | FOXP2 |
| 395 | EGR2 | 433 | ERCC2 | 471 | FANCG | 509 | FGF7 | 547 | FOXP3 |
| 396 | EHF | 434 | ERCC3 | 472 | FANCI | 510 | FGF8 | 548 | FOXP4 |
| 397 | EHMT1 | 435 | ERCC4 | 473 | FANCL | 511 | FGF9 | 549 | FOXQ1 |
| 398 | EHMT2 | 436 | ERCC5 | 474 | FANCM | 512 | FGFR1 | 550 | FRK |
| 399 | EIF1AX | 437 | EREG | 475 | FAS | 513 | FGFR2 | 551 | FRS2 |
| 400 | ELANE | 438 | ERF | 476 | FASLG | 514 | FGFR3 | 552 | FRS3 |
| 401 | ELF1 | 439 | ERG | 477 | FAT1 | 515 | FGFR4 | 553 | FSHR |
| 402 | ELF2 | 440 | ESCO1 | 478 | FAT2 | 516 | FGR | 554 | FUBP1 |
| 403 | ELF3 | 441 | ESCO2 | 479 | FAT3 | 517 | FH | 555 | FUS |
| 404 | ELF4 | 442 | ESPL1 | 480 | FAT4 | 518 | FHIT | 556 | FYN |
| 405 | ELF5 | 443 | ESR1 | 481 | FBN1 | 519 | FIGF | 557 | FZR1 |
| 406 | ELK1 | 444 | ESR2 | 482 | FBXO11 | 520 | FKBP10 | 558 | G6PC3 |
| 407 | ELK3 | 445 | ESRRA | 483 | FBXO8 | 521 | FKBP5 | 559 | G6PD |
| 408 | ELK4 | 446 | ETS1 | 484 | FBXW11 | 522 | FKBP9 | 560 | GAB1 |
| 409 | ELP3 | 447 | ETS2 | 485 | FBXW7 | 523 | FLCN | 561 | GAB2 |
| 410 | EML4 | 448 | ETV1 | 486 | FEN1 | 524 | FLI1 | 562 | GABPA |
| 411 | EMSY | 449 | ETV2 | 487 | FER | 525 | FLT1 | 563 | GALNT12 |
| 412 | EP300 | 450 | ETV3 | 488 | FES | 526 | FLT3 | 564 | GATA1 |
| 413 | EPCAM | 451 | ETV3L | 489 | FEV | 527 | FLT3LG | 565 | GATA2 |
| 414 | EPGN | 452 | ETV4 | 490 | FGF1 | 528 | FLT4 | 566 | GATA3 |
| 415 | EPHA1 | 453 | ETV5 | 491 | FGF10 | 529 | FOLH1 | 567 | GATA5 |
| 416 | EPHA2 | 454 | ETV6 | 492 | FGF11 | 530 | FOS | 568 | GATA6 |
| 417 | EPHA3 | 455 | ETV7 | 493 | FGF12 | 531 | FOSB | 569 | GDNF |
| 418 | EPHA4 | 456 | EWSR1 | 494 | FGF13 | 532 | FOSL1 | 570 | GFI1 |

Fig. 22d

Exemplary Oncology Panel - 1711 Genes

| No. | Symbol | No. | Symbol | No. | Symbol | No. | Symbol | No. | Symbol |
|---|---|---|---|---|---|---|---|---|---|
| 571 | GFI1B | 609 | HBEGF | 647 | HOXA13 | 685 | IKBKAP | 723 | ING1 |
| 572 | GFRA4 | 610 | HCK | 648 | HOXA3 | 686 | IKBKB | 724 | ING4 |
| 573 | GGCX | 611 | HDAC1 | 649 | HOXA9 | 687 | IKBKE | 725 | INHBA |
| 574 | GHR | 612 | HDAC10 | 650 | HOXB13 | 688 | IKZF1 | 726 | INPP4B |
| 575 | GID4 | 613 | HDAC11 | 651 | HOXB3 | 689 | IKZF2 | 727 | INSR |
| 576 | GLA | 614 | HDAC2 | 652 | HOXC10 | 690 | IKZF3 | 728 | INSRR |
| 577 | GLCCI1 | 615 | HDAC3 | 653 | HOXC11 | 691 | IL10RA | 729 | INTS12 |
| 578 | GLI1 | 616 | HDAC4 | 654 | HOXC13 | 692 | IL10RB | 730 | IQGAP1 |
| 579 | GLI2 | 617 | HDAC5 | 655 | HOXD10 | 693 | IL11RA | 731 | IQGAP2 |
| 580 | GLI3 | 618 | HDAC6 | 656 | HOXD11 | 694 | IL12RB1 | 732 | IQGAP3 |
| 581 | GLIS1 | 619 | HDAC7 | 657 | HOXD13 | 695 | IL12RB2 | 733 | IRAK1 |
| 582 | GLIS2 | 620 | HDAC8 | 658 | HOXD3 | 696 | IL13RA1 | 734 | IRF4 |
| 583 | GLIS3 | 621 | HDAC9 | 659 | HOXD4 | 697 | IL15RA | 735 | IRF5 |
| 584 | GNA11 | 622 | HDGF | 660 | HR | 698 | IL17RA | 736 | IRF6 |
| 585 | GNA13 | 623 | HELLS | 661 | HRAS | 699 | IL17RB | 737 | IRS1 |
| 586 | GNAQ | 624 | HES1 | 662 | HSD11B2 | 700 | IL17RC | 738 | IRS2 |
| 587 | GNAS | 625 | HES2 | 663 | HSD3B1 | 701 | IL18R1 | 739 | IRS4 |
| 588 | GNRHR | 626 | HES4 | 664 | HSP90AA1 | 702 | IL18RAP | 740 | ITK |
| 589 | GOT1 | 627 | HEY1 | 665 | HSP90AB1 | 703 | IL1R1 | 741 | ITPKB |
| 590 | GPC3 | 628 | HEY2 | 666 | HSPBAP1 | 704 | IL1R2 | 742 | JADE1 |
| 591 | GPC5 | 629 | HGF | 667 | HTR1A | 705 | IL1RAP | 743 | JAK1 |
| 592 | GPS2 | 630 | HIF1A | 668 | HTR2A | 706 | IL20RA | 744 | JAK2 |
| 593 | GRB10 | 631 | HIF1AN | 669 | ICK | 707 | IL20RB | 745 | JAK3 |
| 594 | GRB2 | 632 | HIST1H1E | 670 | ICOS | 708 | IL21R | 746 | JARID2 |
| 595 | GRB7 | 633 | HIST1H3B | 671 | ICOSLG | 709 | IL22RA1 | 747 | JAZF1 |
| 596 | GREM1 | 634 | HIST1H4E | 672 | ID1 | 710 | IL22RA2 | 748 | JMJD1C |
| 597 | GRIN2A | 635 | HLA-A | 673 | ID2 | 711 | IL23R | 749 | JMJD4 |
| 598 | GRK4 | 636 | HLA-B | 674 | ID3 | 712 | IL2RA | 750 | JMJD6 |
| 599 | GRK5 | 637 | HLF | 675 | ID4 | 713 | IL2RB | 751 | JMJD7 |
| 600 | GRM3 | 638 | HLTF | 676 | IDH1 | 714 | IL2RG | 752 | JMJD8 |
| 601 | GRM8 | 639 | HMGA1 | 677 | IDH2 | 715 | IL3 | 753 | JUN |
| 602 | GSK3A | 640 | HMGA2 | 678 | IFNLR1 | 716 | IL3RA | 754 | JUNB |
| 603 | GSK3B | 641 | HMGCR | 679 | IGF1 | 717 | IL4R | 755 | JUND |
| 604 | GSTT1 | 642 | HNF1A | 680 | IGF1R | 718 | IL5RA | 756 | JUP |
| 605 | GTPBP4 | 643 | HNF1B | 681 | IGF2 | 719 | IL6R | 757 | KAT2A |
| 606 | GUCY1A2 | 644 | HNRNPA3 | 682 | IGF2R | 720 | IL6ST | 758 | KAT2B |
| 607 | H3F3A | 645 | HOXA10 | 683 | IHH | 721 | IL7R | 759 | KAT5 |
| 608 | HAX1 | 646 | HOXA11 | 684 | IKBIP | 722 | IL9R | 760 | KAT6A |

Fig. 22e

| Exemplary Oncology Panel - 1711 Genes ||||||||||
|---|---|---|---|---|---|---|---|---|---|
| No. | Symbol | No. | Symbol | No. | Symbol | No. | Symbol | No. | Symbol |
| 761 | KAT6B | 799 | KMT2B | 837 | MAGED1 | 875 | MAPK1 | 913 | MIPOL1 |
| 762 | KAT7 | 800 | KMT2C | 838 | MAGI2 | 876 | MAPK10 | 914 | MITF |
| 763 | KAT8 | 801 | KMT2D | 839 | MAK | 877 | MAPK11 | 915 | MKL1 |
| 764 | KCNH2 | 802 | KMT2E | 840 | MALT1 | 878 | MAPK12 | 916 | MKL2 |
| 765 | KCNJ5 | 803 | KRAS | 841 | MAML1 | 879 | MAPK13 | 917 | MLF1 |
| 766 | KCNQ1 | 804 | LATS1 | 842 | MAML2 | 880 | MAPK14 | 918 | MLH1 |
| 767 | KDM1A | 805 | LATS2 | 843 | MAML3 | 881 | MAPK15 | 919 | MLH3 |
| 768 | KDM1B | 806 | LCK | 844 | MAMLD1 | 882 | MAPK3 | 920 | MLLT1 |
| 769 | KDM2A | 807 | LDB1 | 845 | MAOA | 883 | MAPK4 | 921 | MLLT10 |
| 770 | KDM2B | 808 | LDLR | 846 | MAP2K1 | 884 | MAPK6 | 922 | MLLT11 |
| 771 | KDM3A | 809 | LEF1 | 847 | MAP2K2 | 885 | MAPK7 | 923 | MLLT3 |
| 772 | KDM3B | 810 | LEPR | 848 | MAP2K3 | 886 | MAPK8 | 924 | MLLT6 |
| 773 | KDM4A | 811 | LGR4 | 849 | MAP2K4 | 887 | MAPK9 | 925 | MLST8 |
| 774 | KDM4B | 812 | LGR5 | 850 | MAP2K5 | 888 | MAST1 | 926 | MN1 |
| 775 | KDM4C | 813 | LGR6 | 851 | MAP2K6 | 889 | MAST2 | 927 | MNX1 |
| 776 | KDM4D | 814 | LHCGR | 852 | MAP2K7 | 890 | MATK | 928 | MOB1A |
| 777 | KDM5A | 815 | LIFR | 853 | MAP3K1 | 891 | MAU2 | 929 | MOB1B |
| 778 | KDM5B | 816 | LMNA | 854 | MAP3K10 | 892 | MAX | 930 | MOS |
| 779 | KDM5C | 817 | LMO1 | 855 | MAP3K11 | 893 | MBD1 | 931 | MPG |
| 780 | KDM5D | 818 | LMO2 | 856 | MAP3K12 | 894 | MBD3 | 932 | MPL |
| 781 | KDM6A | 819 | LMO7 | 857 | MAP3K13 | 895 | MC1R | 933 | MRE11A |
| 782 | KDM6B | 820 | LMTK2 | 858 | MAP3K14 | 896 | MCL1 | 934 | MSH2 |
| 783 | KDM7A | 821 | LMTK3 | 859 | MAP3K15 | 897 | MCPH1 | 935 | MSH3 |
| 784 | KDM8 | 822 | LPP | 860 | MAP3K19 | 898 | MDM2 | 936 | MSH4 |
| 785 | KDR | 823 | LRP1B | 861 | MAP3K2 | 899 | MDM4 | 937 | MSH6 |
| 786 | KDSR | 824 | LRP5 | 862 | MAP3K3 | 900 | MDS2 | 938 | MSI2 |
| 787 | KEAP1 | 825 | LRP6 | 863 | MAP3K4 | 901 | MECOM | 939 | MST1 |
| 788 | KEL | 826 | LRRK2 | 864 | MAP3K5 | 902 | MED12 | 940 | MST1R |
| 789 | KHSRP | 827 | LSM1 | 865 | MAP3K6 | 903 | MED12L | 941 | MTAP |
| 790 | KIF1B | 828 | LTK | 866 | MAP3K7 | 904 | MED29 | 942 | MTCP1 |
| 791 | KIT | 829 | LYL1 | 867 | MAP3K8 | 905 | MEF2B | 943 | MTDH |
| 792 | KITLG | 830 | LYN | 868 | MAP3K9 | 906 | MEN1 | 944 | MTOR |
| 793 | KLF12 | 831 | LZTR1 | 869 | MAP4 | 907 | MERTK | 945 | MUSK |
| 794 | KLF4 | 832 | MAD1L1 | 870 | MAP4K1 | 908 | MET | 946 | MUTYH |
| 795 | KLF5 | 833 | MAD2L1 | 871 | MAP4K2 | 909 | MGA | 947 | MXD1 |
| 796 | KLF6 | 834 | MAD2L2 | 872 | MAP4K3 | 910 | MGMT | 948 | MYB |
| 797 | KLF8 | 835 | MAF | 873 | MAP4K4 | 911 | MID1 | 949 | MYBL1 |
| 798 | KMT2A | 836 | MAFB | 874 | MAP4K5 | 912 | MINK1 | 950 | MYBL2 |

Fig. 22f

| Exemplary Oncology Panel - 1711 Genes | | | | | | | | | |
|---|---|---|---|---|---|---|---|---|---|
| No. | Symbol | No. | Symbol | No. | Symbol | No. | Symbol | No. | Symbol |
| 951 | MYBPC3 | 989 | NF2 | 1027 | NPM1 | 1065 | PAK2 | 1103 | PDPK1 |
| 952 | MYC | 990 | NFATC1 | 1028 | NPPB | 1066 | PAK3 | 1104 | PDS5A |
| 953 | MYCL | 991 | NFATC2 | 1029 | NPR1 | 1067 | PAK4 | 1105 | PDS5B |
| 954 | MYCN | 992 | NFATC3 | 1030 | NQO1 | 1068 | PAK6 | 1106 | PEAR1 |
| 955 | MYD88 | 993 | NFATC4 | 1031 | NR0B1 | 1069 | PAK7 | 1107 | PEG3 |
| 956 | MYH11 | 994 | NFE2L2 | 1032 | NR3C1 | 1070 | PALB2 | 1108 | PERP |
| 957 | MYH7 | 995 | NFIA | 1033 | NR3C2 | 1071 | PALLD | 1109 | PGF |
| 958 | MYL2 | 996 | NFIB | 1034 | NR4A1 | 1072 | PARK2 | 1110 | PGR |
| 959 | MYL3 | 997 | NFIC | 1035 | NR4A2 | 1073 | PARP1 | 1111 | PHB |
| 960 | MYLK | 998 | NFIX | 1036 | NR4A3 | 1074 | PARP2 | 1112 | PHF1 |
| 961 | MYOD1 | 999 | NFKB1 | 1037 | NRAS | 1075 | PARP4 | 1113 | PHF2 |
| 962 | NA | 1000 | NFKB2 | 1038 | NRG1 | 1076 | PATZ1 | 1114 | PHF6 |
| 963 | NAB1 | 1001 | NFKBIA | 1039 | NRG2 | 1077 | PAX1 | 1115 | PHF8 |
| 964 | NAB2 | 1002 | NFKBIB | 1040 | NRG3 | 1078 | PAX2 | 1116 | PHIP |
| 965 | NAT2 | 1003 | NFKBID | 1041 | NRG4 | 1079 | PAX3 | 1117 | PHLPP1 |
| 966 | NBN | 1004 | NFKBIE | 1042 | NRIP1 | 1080 | PAX4 | 1118 | PHLPP2 |
| 967 | NCK1 | 1005 | NFKBIZ | 1043 | NRTN | 1081 | PAX5 | 1119 | PHOX2A |
| 968 | NCK2 | 1006 | NGF | 1044 | NSD1 | 1082 | PAX6 | 1120 | PHOX2B |
| 969 | NCOA1 | 1007 | NHP2 | 1045 | NT5C2 | 1083 | PAX7 | 1121 | PICALM |
| 970 | NCOA2 | 1008 | NIPBL | 1046 | NTF3 | 1084 | PAX8 | 1122 | PIK3C2A |
| 971 | NCOA3 | 1009 | NKX2-1 | 1047 | NTF4 | 1085 | PAX9 | 1123 | PIK3C2B |
| 972 | NCOA4 | 1010 | NKX2-2 | 1048 | NTRK1 | 1086 | PAXIP1 | 1124 | PIK3C2G |
| 973 | NCOR1 | 1011 | NKX2-3 | 1049 | NTRK2 | 1087 | PBRM1 | 1125 | PIK3C3 |
| 974 | NCOR2 | 1012 | NKX2-4 | 1050 | NTRK3 | 1088 | PBX1 | 1126 | PIK3CA |
| 975 | NCSTN | 1013 | NKX2-5 | 1051 | NUMB | 1089 | PBX2 | 1127 | PIK3CB |
| 976 | NDRG1 | 1014 | NKX2-6 | 1052 | NUMBL | 1090 | PBX3 | 1128 | PIK3CD |
| 977 | NEK1 | 1015 | NKX2-8 | 1053 | NUP214 | 1091 | PBX4 | 1129 | PIK3CG |
| 978 | NEK10 | 1016 | NKX3-1 | 1054 | NUP93 | 1092 | PCBP1 | 1130 | PIK3R1 |
| 979 | NEK11 | 1017 | NKX3-2 | 1055 | NUP98 | 1093 | PCSK9 | 1131 | PIK3R2 |
| 980 | NEK2 | 1018 | NLRP1 | 1056 | NUTM1 | 1094 | PDCD1 | 1132 | PIK3R3 |
| 981 | NEK3 | 1019 | NOD2 | 1057 | NUTM2A | 1095 | PDCD1LG2 | 1133 | PIK3R4 |
| 982 | NEK4 | 1020 | NONO | 1058 | NUTM2B | 1096 | PDGFA | 1134 | PIM1 |
| 983 | NEK5 | 1021 | NOP10 | 1059 | NUTM2F | 1097 | PDGFB | 1135 | PIM2 |
| 984 | NEK6 | 1022 | NOTCH1 | 1060 | NUTM2G | 1098 | PDGFC | 1136 | PIM3 |
| 985 | NEK7 | 1023 | NOTCH2 | 1061 | ODC1 | 1099 | PDGFD | 1137 | PKHD1 |
| 986 | NEK8 | 1024 | NOTCH2NL | 1062 | OLIG2 | 1100 | PDGFRA | 1138 | PKP2 |
| 987 | NEK9 | 1025 | NOTCH3 | 1063 | OSMR | 1101 | PDGFRB | 1139 | PLA2G2A |
| 988 | NF1 | 1026 | NOTCH4 | 1064 | PAK1 | 1102 | PDK1 | 1140 | PLAG1 |

Fig. 22g

| Exemplary Oncology Panel - 1711 Genes ||||||||||
|---|---|---|---|---|---|---|---|---|---|
| No. | Symbol | No. | Symbol | No. | Symbol | No. | Symbol | No. | Symbol |
| 1141 | PLAGL1 | 1179 | PRDM12 | 1217 | PSEN2 | 1255 | RAD51 | 1293 | RIT1 |
| 1142 | PLAGL2 | 1180 | PRDM13 | 1218 | PSENEN | 1256 | RAD51AP1 | 1294 | RNF213 |
| 1143 | PLCG1 | 1181 | PRDM14 | 1219 | PSIP1 | 1257 | RAD51B | 1295 | RNF40 |
| 1144 | PLCG2 | 1182 | PRDM15 | 1220 | PSPN | 1258 | RAD51C | 1296 | RNF43 |
| 1145 | PLK1 | 1183 | PRDM16 | 1221 | PTCH1 | 1259 | RAD51D | 1297 | ROBO2 |
| 1146 | PLK2 | 1184 | PRDM2 | 1222 | PTCH2 | 1260 | RAD52 | 1298 | ROCK1 |
| 1147 | PLK3 | 1185 | PRDM4 | 1223 | PTEN | 1261 | RAD54B | 1299 | ROCK2 |
| 1148 | PLK4 | 1186 | PRDM5 | 1224 | PTGIS | 1262 | RAD54L | 1300 | ROR1 |
| 1149 | PMAIP1 | 1187 | PRDM6 | 1225 | PTGS1 | 1263 | RAF1 | 1301 | ROR2 |
| 1150 | PML | 1188 | PRDM7 | 1226 | PTGS2 | 1264 | RAP1GDS1 | 1302 | ROS1 |
| 1151 | PMS1 | 1189 | PRDM8 | 1227 | PTK2 | 1265 | RARA | 1303 | RPA1 |
| 1152 | PMS2 | 1190 | PRDM9 | 1228 | PTK2B | 1266 | RARB | 1304 | RPL5 |
| 1153 | PNRC1 | 1191 | PREX2 | 1229 | PTK6 | 1267 | RARG | 1305 | RPN1 |
| 1154 | POLD1 | 1192 | PRF1 | 1230 | PTK7 | 1268 | RASA1 | 1306 | RPS6KB1 |
| 1155 | POLE | 1193 | PRKACA | 1231 | PTPN11 | 1269 | RB1 | 1307 | RPS6KB2 |
| 1156 | POR | 1194 | PRKACB | 1232 | PTPN2 | 1270 | RBM10 | 1308 | RPTOR |
| 1157 | POT1 | 1195 | PRKAG2 | 1233 | PTPN21 | 1271 | RBM14 | 1309 | RRM1 |
| 1158 | POU2AF1 | 1196 | PRKAR1A | 1234 | PTPN6 | 1272 | RBM15 | 1310 | RSPO2 |
| 1159 | POU2F2 | 1197 | PRKAR1B | 1235 | PTPRB | 1273 | RBMX | 1311 | RSPO3 |
| 1160 | POU5F1 | 1198 | PRKCI | 1236 | PTPRC | 1274 | RBMXL1 | 1312 | RUNX1 |
| 1161 | POU5F1B | 1199 | PRKD1 | 1237 | PTPRD | 1275 | RBMXL2 | 1313 | RUNX1T1 |
| 1162 | POU5F2 | 1200 | PRKDC | 1238 | PTPRF | 1276 | RBPJ | 1314 | RUNX2 |
| 1163 | POU6F1 | 1201 | PRLR | 1239 | PTPRG | 1277 | REC8 | 1315 | RUNX3 |
| 1164 | POU6F2 | 1202 | PRMT1 | 1240 | PTPRJ | 1278 | RECQL4 | 1316 | RUVBL1 |
| 1165 | PPARA | 1203 | PRMT2 | 1241 | PTPRK | 1279 | REL | 1317 | RXRA |
| 1166 | PPARD | 1204 | PRMT3 | 1242 | PTPRM | 1280 | RELA | 1318 | RYK |
| 1167 | PPARG | 1205 | PRMT5 | 1243 | PTPRQ | 1281 | RELB | 1319 | RYR1 |
| 1168 | PPFIA1 | 1206 | PRMT6 | 1244 | PTPRR | 1282 | RET | 1320 | RYR2 |
| 1169 | PPM1D | 1207 | PRMT7 | 1245 | PTPRT | 1283 | RHEB | 1321 | SAMD9 |
| 1170 | PPP1R1C | 1208 | PRMT8 | 1246 | PTTG1 | 1284 | RHOA | 1322 | SAV1 |
| 1171 | PPP2R1A | 1209 | PRPF40B | 1247 | PVT1 | 1285 | RHOB | 1323 | SBDS |
| 1172 | PPP2R1B | 1210 | PRPF6 | 1248 | RAB23 | 1286 | RHOH | 1324 | SCN5A |
| 1173 | PPP2R2B | 1211 | PRRX1 | 1249 | RAB25 | 1287 | RHOT1 | 1325 | SDHA |
| 1174 | PPP6C | 1212 | PRRX2 | 1250 | RABEP1 | 1288 | RICTOR | 1326 | SDHAF2 |
| 1175 | PRCC | 1213 | PRSS1 | 1251 | RAC1 | 1289 | RIPK1 | 1327 | SDHB |
| 1176 | PRDM1 | 1214 | PRSS3 | 1252 | RAC2 | 1290 | RIPK2 | 1328 | SDHC |
| 1177 | PRDM10 | 1215 | PRSS8 | 1253 | RAD21 | 1291 | RIPK3 | 1329 | SDHD |
| 1178 | PRDM11 | 1216 | PSEN1 | 1254 | RAD50 | 1292 | RIPK4 | 1330 | SET |

Fig. 22h

| Exemplary Oncology Panel - 1711 Genes | | | | | | | | | |
|---|---|---|---|---|---|---|---|---|---|
| No. | Symbol | No. | Symbol | No. | Symbol | No. | Symbol | No. | Symbol |
| 1331 | SETBP1 | 1369 | SLC19A1 | 1407 | SMC4 | 1445 | SPRY2 | 1483 | SUV420H2 |
| 1332 | SETD1A | 1370 | SLC22A1 | 1408 | SMC5 | 1446 | SPRY3 | 1484 | SUZ12 |
| 1333 | SETD1B | 1371 | SLC22A2 | 1409 | SMC6 | 1447 | SRC | 1485 | SYK |
| 1334 | SETD2 | 1372 | SLC22A3 | 1410 | SMCHD1 | 1448 | SRGAP3 | 1486 | SYNE1 |
| 1335 | SETD3 | 1373 | SLC22A6 | 1411 | SMO | 1449 | SRMS | 1487 | TAF1 |
| 1336 | SETD4 | 1374 | SLC26A3 | 1412 | SMURF1 | 1450 | SRSF2 | 1488 | TAF15 |
| 1337 | SETD5 | 1375 | SLC47A1 | 1413 | SMURF2 | 1451 | SS18 | 1489 | TAF1L |
| 1338 | SETD6 | 1376 | SLC47A2 | 1414 | SMYD1 | 1452 | SS18L1 | 1490 | TAL1 |
| 1339 | SETD7 | 1377 | SLC6A3 | 1415 | SMYD2 | 1453 | SSTR1 | 1491 | TAL2 |
| 1340 | SETD8 | 1378 | SLC6A4 | 1416 | SMYD3 | 1454 | SSTR2 | 1492 | TAOK1 |
| 1341 | SETD9 | 1379 | SLCO1A2 | 1417 | SMYD4 | 1455 | SSTR3 | 1493 | TAOK2 |
| 1342 | SETDB1 | 1380 | SLCO1B1 | 1418 | SMYD5 | 1456 | SSTR4 | 1494 | TAOK3 |
| 1343 | SETDB2 | 1381 | SLCO1B3 | 1419 | SOCS1 | 1457 | SSTR5 | 1495 | TBC1D12 |
| 1344 | SETMAR | 1382 | SLCO2B1 | 1420 | SOS1 | 1458 | SSX1 | 1496 | TBL1X |
| 1345 | SF1 | 1383 | SLIT2 | 1421 | SOS2 | 1459 | SSX2 | 1497 | TBL1XR1 |
| 1346 | SF3A1 | 1384 | SLX4 | 1422 | SOX1 | 1460 | SSX3 | 1498 | TBP |
| 1347 | SF3B1 | 1385 | SMAD1 | 1423 | SOX10 | 1461 | SSX4 | 1499 | TBX18 |
| 1348 | SFPQ | 1386 | SMAD2 | 1424 | SOX17 | 1462 | STAG1 | 1500 | TBX2 |
| 1349 | SFRP1 | 1387 | SMAD3 | 1425 | SOX2 | 1463 | STAG2 | 1501 | TBX22 |
| 1350 | SGK1 | 1388 | SMAD4 | 1426 | SOX21 | 1464 | STARD3 | 1502 | TBX3 |
| 1351 | SGOL1 | 1389 | SMAD5 | 1427 | SOX3 | 1465 | STAT1 | 1503 | TBXAS1 |
| 1352 | SGOL2 | 1390 | SMAD6 | 1428 | SOX8 | 1466 | STAT2 | 1504 | TCEB1 |
| 1353 | SH2B3 | 1391 | SMAD7 | 1429 | SOX9 | 1467 | STAT3 | 1505 | TCF12 |
| 1354 | SH2D1A | 1392 | SMAD9 | 1430 | SP100 | 1468 | STAT4 | 1506 | TCF3 |
| 1355 | SH3GL1 | 1393 | SMARCA1 | 1431 | SP110 | 1469 | STAT5A | 1507 | TCF4 |
| 1356 | SHB | 1394 | SMARCA2 | 1432 | SP140 | 1470 | STAT5B | 1508 | TCF7 |
| 1357 | SHC1 | 1395 | SMARCA4 | 1433 | SP140L | 1471 | STAT6 | 1509 | TCF7L1 |
| 1358 | SHC2 | 1396 | SMARCA5 | 1434 | SP3 | 1472 | STK11 | 1510 | TCF7L2 |
| 1359 | SHC3 | 1397 | SMARCB1 | 1435 | SPDEF | 1473 | STK19 | 1511 | TCL1A |
| 1360 | SHC4 | 1398 | SMARCC1 | 1436 | SPEN | 1474 | STK3 | 1512 | TCL1B |
| 1361 | SHFM1 | 1399 | SMARCD1 | 1437 | SPI1 | 1475 | STK36 | 1513 | TEAD1 |
| 1362 | SHH | 1400 | SMARCD2 | 1438 | SPIB | 1476 | STK4 | 1514 | TEAD2 |
| 1363 | SHOC2 | 1401 | SMARCD3 | 1439 | SPIC | 1477 | STYK1 | 1515 | TEAD3 |
| 1364 | SKI | 1402 | SMARCE1 | 1440 | SPOP | 1478 | SUFU | 1516 | TEAD4 |
| 1365 | SKIL | 1403 | SMC1A | 1441 | SPOPL | 1479 | SULT1A1 | 1517 | TEC |
| 1366 | SKOR1 | 1404 | SMC1B | 1442 | SPRED1 | 1480 | SUV39H1 | 1518 | TEF |
| 1367 | SKP2 | 1405 | SMC2 | 1443 | SPRED2 | 1481 | SUV39H2 | 1519 | TEK |
| 1368 | SLC15A2 | 1406 | SMC3 | 1444 | SPRED3 | 1482 | SUV420H1 | 1520 | TENM2 |

Fig. 22i

| \multicolumn{10}{c}{Exemplary Oncology Panel - 1711 Genes} |
| No. | Symbol | No. | Symbol | No. | Symbol | No. | Symbol | No. | Symbol |
| --- | --- | --- | --- | --- | --- | --- | --- | --- | --- |
| 1521 | TERC | 1559 | TNFRSF14 | 1597 | TSHZ3 | 1635 | WAS | 1673 | XRCC2 |
| 1522 | TERF1 | 1560 | TNFRSF17 | 1598 | TWIST1 | 1636 | WASL | 1674 | YAP1 |
| 1523 | TERT | 1561 | TNK1 | 1599 | TWIST2 | 1637 | WHSC1 | 1675 | YEATS4 |
| 1524 | TET1 | 1562 | TNK2 | 1600 | TXK | 1638 | WHSC1L1 | 1676 | YES1 |
| 1525 | TET2 | 1563 | TNKS | 1601 | TYK2 | 1639 | WIF1 | 1677 | YWHAB |
| 1526 | TET3 | 1564 | TNKS2 | 1602 | TYRO3 | 1640 | WISP1 | 1678 | YWHAE |
| 1527 | TFE3 | 1565 | TNNI3 | 1603 | U2AF1 | 1641 | WNK1 | 1679 | YWHAH |
| 1528 | TFEB | 1566 | TNNT2 | 1604 | U2AF2 | 1642 | WNK2 | 1680 | YWHAQ |
| 1529 | TFEC | 1567 | TOP1 | 1605 | UBE2D1 | 1643 | WNK3 | 1681 | YWHAZ |
| 1530 | TFG | 1568 | TOP2A | 1606 | UBE2D2 | 1644 | WNK4 | 1682 | YY1 |
| 1531 | TGFA | 1569 | TOP2B | 1607 | UBE2D3 | 1645 | WNT1 | 1683 | ZAP70 |
| 1532 | TGFB1 | 1570 | TP53 | 1608 | UBE2D4 | 1646 | WNT10A | 1684 | ZBTB16 |
| 1533 | TGFB2 | 1571 | TP53BP1 | 1609 | UBE4A | 1647 | WNT10B | 1685 | ZBTB20 |
| 1534 | TGFBR1 | 1572 | TP63 | 1610 | UBR5 | 1648 | WNT11 | 1686 | ZBTB33 |
| 1535 | TGFBR2 | 1573 | TPM1 | 1611 | UGT1A1 | 1649 | WNT16 | 1687 | ZBTB5 |
| 1536 | THPO | 1574 | TPMT | 1612 | UGT1A4 | 1650 | WNT2 | 1688 | ZBTB7B |
| 1537 | TIE1 | 1575 | TPTE | 1613 | UHRF1 | 1651 | WNT2B | 1689 | ZC3H12A |
| 1538 | TINF2 | 1576 | TPTE2 | 1614 | UHRF2 | 1652 | WNT3 | 1690 | ZC3H12D |
| 1539 | TLK1 | 1577 | TRAF1 | 1615 | USB1 | 1653 | WNT3A | 1691 | ZC3H7B |
| 1540 | TLK2 | 1578 | TRAF2 | 1616 | USP9X | 1654 | WNT4 | 1692 | ZCCHC7 |
| 1541 | TLR1 | 1579 | TRAF3 | 1617 | USP9Y | 1655 | WNT5A | 1693 | ZEB2 |
| 1542 | TLR10 | 1580 | TRAF3IP1 | 1618 | UTY | 1656 | WNT5B | 1694 | ZFHX3 |
| 1543 | TLR2 | 1581 | TRAF3IP2 | 1619 | VAV1 | 1657 | WNT6 | 1695 | ZMYM3 |
| 1544 | TLR4 | 1582 | TRAF3IP3 | 1620 | VAV2 | 1658 | WNT7A | 1696 | ZMYND11 |
| 1545 | TLR5 | 1583 | TRAF6 | 1621 | VAV3 | 1659 | WNT7B | 1697 | ZMYND8 |
| 1546 | TLR6 | 1584 | TRAF7 | 1622 | VDR | 1660 | WNT8A | 1698 | ZNF217 |
| 1547 | TLR7 | 1585 | TRIB1 | 1623 | VEGFA | 1661 | WNT8B | 1699 | ZNF384 |
| 1548 | TLR8 | 1586 | TRIB2 | 1624 | VEGFB | 1662 | WNT9A | 1700 | ZNF423 |
| 1549 | TLR9 | 1587 | TRIB3 | 1625 | VEGFC | 1663 | WNT9B | 1701 | ZNF444 |
| 1550 | TLX1 | 1588 | TRIM24 | 1626 | VGLL1 | 1664 | WRN | 1702 | ZNF471 |
| 1551 | TLX2 | 1589 | TRIM28 | 1627 | VGLL2 | 1665 | WT1 | 1703 | ZNF521 |
| 1552 | TLX3 | 1590 | TRIM33 | 1628 | VGLL3 | 1666 | WWTR1 | 1704 | ZNF607 |
| 1553 | TMC6 | 1591 | TRIM66 | 1629 | VGLL4 | 1667 | XBP1 | 1705 | ZNF639 |
| 1554 | TMC8 | 1592 | TRIO | 1630 | VHL | 1668 | XIAP | 1706 | ZNF668 |
| 1555 | TMEM127 | 1593 | TRRAP | 1631 | VHLL | 1669 | XIRP2 | 1707 | ZNF703 |
| 1556 | TMEM43 | 1594 | TSC1 | 1632 | VKORC1 | 1670 | XPA | 1708 | ZNF704 |
| 1557 | TMPRSS2 | 1595 | TSC2 | 1633 | VTCN1 | 1671 | XPC | 1709 | ZNF750 |
| 1558 | TNFAIP3 | 1596 | TSHR | 1634 | WAPL | 1672 | XPO1 | 1710 | ZNRF3 |
|  |  |  |  |  |  |  |  | 1711 | ZRSR2 |

Fig. 22j

| \multicolumn{8}{|c|}{Exemplary Clinically Actionable Tier 1 - 130 Genes} |
|---|---|---|---|---|---|---|---|

| No. | Symbol | No. | Symbol | No. | Symbol | No. | Symbol |
|---|---|---|---|---|---|---|---|
| 1 | ABCB1 | 39 | ERBB3 | 77 | MDM2 | 114 | ROS1 |
| 2 | ABL1 | 40 | ERBB4 | 78 | MET | 115 | RUNX1 |
| 3 | AKT1 | 41 | ERCC1 | 79 | MGMT | 116 | SGK1 |
| 4 | AKT2 | 42 | ERCC2 | 80 | MITF | 117 | SMAD4 |
| 5 | ALK | 43 | EREG | 81 | MLH1 | 118 | SMARCA4 |
| 6 | AR | 44 | ESR1 | 82 | MTOR | 119 | SMARCB1 |
| 7 | ARAF | 45 | ETS2 | 83 | MYD88 | 120 | SMO |
| 8 | AREG | 46 | FANCA | 84 | NF1 | 121 | STK11 |
| 9 | ATM | 47 | FANCC | 85 | NF2 | 122 | TOP1 |
| 10 | ATRX | 48 | FBXW7 | 86 | NOTCH1 | 123 | TOP2A |
| 11 | AURKA | 49 | FGF3 | 87 | NPM1 | 124 | TP53 |
| 12 | B2M | 50 | FGFR1 | 88 | NRAS | 125 | TSC1 |
| 13 | BCL2L11 | 51 | FGFR2 | 89 | NRG1 | 126 | TSC2 |
| 14 | BIRC5 | 52 | FGFR3 | 90 | NTRK1 | 127 | UGT1A1 |
| 15 | BRAF | 53 | FLCN | 91 | NTRK3 | 128 | VEGFA |
| 16 | BRCA1 | 54 | FLT3 | 92 | PAL82 | 129 | VHL |
| 17 | BRCA2 | 55 | FOXP3 | 93 | PDGFRA | 130 | WT1 |
| 18 | BRD4 | 56 | GNA11 | 94 | PDGFRB | | |
| 19 | BTK | 57 | GNAQ | 95 | PGR | | |
| 20 | CCND1 | 58 | HDAC2 | 96 | PIK3CA | | |
| 21 | CD274 | 59 | HGF | 97 | PIK3CB | | |
| 22 | CDK4 | 60 | HIF1A | 98 | PIK3R1 | | |
| 23 | CDK6 | 61 | HRAS | 99 | PLCG2 | | |
| 24 | CDKN1A | 62 | IDH1 | 100 | PML | | |
| 25 | CDKN1B | 63 | IDH2 | 101 | PMS2 | | |
| 26 | CDKN2A | 64 | IGF1R | 102 | POLE | | |
| 27 | CEBPA | 65 | IGF2 | 103 | PTCH1 | | |
| 28 | CHEK2 | 66 | JAK1 | 104 | PTEN | | |
| 29 | CSF3R | 67 | JAK2 | 105 | PTGS2 | | |
| 30 | CTLA4 | 68 | JUN | 106 | RAC1 | | |
| 31 | CTNNB1 | 69 | KDR | 107 | RAD50 | | |
| 32 | DDR2 | 70 | KIT | 108 | RAD51C | | |
| 33 | DNMT1 | 71 | KMT2A | 109 | RAF1 | | |
| 34 | DNMT3A | 72 | KRAS | 110 | RB1 | | |
| 35 | DPYD | 73 | LRP1B | 111 | RET | | |
| 36 | EGFR | 74 | MAP2K1 | 112 | RICTOR | | |
| 37 | EPHB4 | 75 | MAP2K2 | 113 | RNF43 | | |

Fig. 23

| \multicolumn{4}{l}{41 Clinically Actionable RNA Based Gene Rearrangements} | | | |
|---|---|---|---|
| No. | Symbol | No. | Symbol |
| 1 | ABL1 | 22 | NRG1 |
| 2 | ALK | 23 | NTRK1 |
| 3 | BCL11A | 24 | NTRK2 |
| 4 | BCL2 | 25 | NTRK3 |
| 5 | BCR | 26 | PDGFRA |
| 6 | BRAF | 27 | PDGFRB |
| 7 | BRD4 | 28 | PML |
| 8 | CBFB | 29 | RET |
| 9 | CCDC6 | 30 | ROS1 |
| 10 | CCND1 | 31 | TFE3 |
| 11 | CTLA4 | 32 | JAK2 |
| 12 | EGFR | 33 | CRLF2 |
| 13 | ESR1 | 34 | RAF1 |
| 14 | ETV6 | 35 | NOTCH2 |
| 15 | FGFR1 | 36 | AKT3 |
| 16 | FGFR2 | 37 | ERBB4 |
| 17 | FGFR3 | 38 | NOTCH1 |
| 18 | FLT3 | 39 | PTC1 |
| 19 | KMT2A | 40 | TMPRSS2 |
| 20 | MET | 41 | RARA |
| 21 | NR4A3 | | |

Fig. 24

Exemplary Variant Data

| id | 1 | chr_pos_ref_alt | chrom | pos | ref | alt | sample_type | variant_caller | variant_type | coverage | base_fraction | mutation_effect | gene | mutation_name | filtered | filters_applied |
|---|---|---|---|---|---|---|---|---|---|---|---|---|---|---|---|---|
| 2049 | | 1_1275563_G_C | 1 | 1275563 | G | C | somatic | freebayes | SNP | 325 | 9.23 | splice_region_variant&intron_variant | DVL1 | c.770-6C>G | 0 | |
| 2050 | | 1_1650797_ATTT_GTT | 1 | 1650797 | ATTT | GTT TC | somatic | freebayes | MNP | 431 | 19.03 | missense_variant | CDK11B | p.EKC107EKR | 0 | |
| 2051 | | 1_10435441_TTTG_T | 1 | 10435441 | TTTG | T | somatic | freebayes | INDEL | 273 | 6.2 | intron_variant | KIF1B | c.5276+26_527 6+30del GTT | 0 | |
| 2052 | | 1_14105094_AGAG_A | 1 | 14105094 | AGAG | A | somatic | freebayes | INDEL | 371 | 3.23 | disruptive_inframe_deletion | PRDM2 | p.E273del | 1 | val_reads, val_reads, val_support |
| 2053 | | 1_23107918_G_A | 1 | 23107918 | G | A | somatic | freebayes | SNP | 501 | 2 | synonymous_variant | EPHB2 | p.T22T | 1 | val_reads, val_reads, val_support |
| 2054 | | 1_25234555_A_G | 1 | 25234555 | A | G | somatic | freebayes | SNP | 686 | 10.35 | intron_variant | RUNX3 | c.587-64T>C | 0 | |
| 2055 | | 1_25234574_C_T | 1 | 25234574 | C | T | somatic | freebayes | SNP | 735 | 8.16 | intron_variant | RUNX3 | c.587-66G>A | 0 | |
| 2056 | | 1_27022833_T_G | 1 | 27022833 | T | G | somatic | freebayes | SNP | 126 | 9.73 | 5_prime_UTR_variant | ARID1A | c.62T>G | 0 | |
| 2057 | | 1_44072576_C_T | 1 | 44072576 | C | T | somatic | freebayes | SNP | 632 | 1.42 | missense_variant | PTPRF | p.T1266M | 1 | val_reads, val_reads, val_support |
| 2058 | | 1_46494558_CT_C | 1 | 46494558 | CT | C | somatic | freebayes | INDEL | 421 | 2.38 | frameshift_variant | MAST2 | p.F726fs | 1 | val_reads, val_reads, val_support |

Fig. 25

| ID | Exemplary CNV Data | | | | | | | |
|---|---|---|---|---|---|---|---|---|
| | Chromosome | Start | End | Gene | MeanT | MeanN | Amp | Copy_Number |
| 1 | 1 | 63183 | 63353 | | 17.68 | 119.37 | Loss | 1 |
| 2 | 1 | 63431 | 63601 | | 17.68 | 230.63 | Loss | 1 |
| 3 | 1 | 63612 | 63782 | | 18.42 | 243.16 | Loss | 1 |
| 4 | 1 | 69426 | 69596 | | 1.47 | 0 | Loss | 1 |
| 5 | 1 | 91451 | 91621 | | 0 | 0.74 | Loss | 1 |
| 6 | 1 | 931276 | 931446 | | 284.42 | 1234.21 | Loss | 1 |
| 7 | 1 | 932001 | 932171 | | 37.58 | 92.84 | Loss | 1 |
| 8 | 1 | 934428 | 934822 | HES4 | 85.49 | 268.59 | Loss | 1 |
| 9 | 1 | 934889 | 935010 | HES4 | 242.7 | 979.08 | Loss | 1 |
| 10 | 1 | 935061 | 935382 | HES4 | 153.78 | 543.52 | Loss | 1 |

Fig. 26

| Heme Related - xT Gene Panel | | | |
|---|---|---|---|
| No. | Symbol | No. | Symbol |
| 1 | ARHGAP26 | 35 | MAP3K7 |
| 2 | BCL10 | 36 | MAPK1 |
| 3 | BCL11B | 37 | MIB1 |
| 4 | BCL7A | 38 | MKI67 |
| 5 | BCR | 39 | NCOR2 |
| 6 | BIRC3 | 40 | NT5C2 |
| 7 | CBLB | 41 | NUP98 |
| 8 | CBLC | 42 | P2RY8 |
| 9 | CD22 | 43 | PCBP1 |
| 10 | CD70 | 44 | PHF6 |
| 11 | CIITA | 45 | PIM1 |
| 12 | CKS1B | 46 | POT1 |
| 13 | CSF3R | 47 | RAD21 |
| 14 | CUX1 | 48 | RHOA |
| 15 | CXCR4 | 49 | SETBP1 |
| 16 | DDX3X | 50 | SGK1 |
| 17 | DNM2 | 51 | SMARCA1 |
| 18 | EBF1 | 52 | SMC1A |
| 19 | ECT2L | 53 | SMC3 |
| 20 | EPOR | 54 | SRSF2 |
| 21 | ETV6 | 55 | STAT5A |
| 22 | FBXO11 | 56 | STAT5B |
| 23 | FHIT | 57 | STAT6 |
| 24 | FOXO1 | 58 | SUZ12 |
| 25 | FOXO3 | 59 | TBL1XR1 |
| 26 | HDAC1 | 60 | TCF3 |
| 27 | HDAC4 | 61 | TCL1A |
| 28 | HIST1H1E | 62 | TNFRSF17 |
| 29 | HIST1H3B | 63 | TP63 |
| 30 | KMT2B | 64 | TRAF3 |
| 31 | LEF1 | 65 | TUSC3 |
| 32 | MAF | 66 | WHSC1 |
| 33 | MAFB | 67 | ZRSR2 |
| 34 | MALT1 | | |

Fig. 27a

| Heme and Solid Tumor Related - xT Gene Panel |||||||||||
|---|---|---|---|---|---|---|---|---|---|---|
| No. | Symbol | No. | Symbol | No. | Symbol | No. | Symbol | No. | Symbol | No. | Symbol |
| 1 | ABCB1 | 39 | CBL | 77 | ERBB2 | 115 | GATA1 | 153 | MAP2K2 | 191 | PDCD1 |
| 2 | ABCC3 | 40 | CCND1 | 78 | ERBB3 | 116 | GATA2 | 154 | MAP2K4 | 192 | PDCD1LG2 |
| 3 | ABL1 | 41 | CCND2 | 79 | ERBB4 | 117 | GATA3 | 155 | MAP3K1 | 193 | PDGFRA |
| 4 | AKT1 | 42 | CCND3 | 80 | ERG | 118 | GNA11 | 156 | MCL1 | 194 | PDGFRB |
| 5 | AKT2 | 43 | CCNE1 | 81 | ESR1 | 119 | GNA13 | 157 | MDM2 | 195 | PDK1 |
| 6 | AKT3 | 44 | CD274 | 82 | ETS1 | 120 | GNAQ | 158 | MDM4 | 196 | PIK3CA |
| 7 | ALK | 45 | CD79A | 83 | ETV1 | 121 | GNAS | 159 | MED12 | 197 | PIK3CG |
| 8 | AMER1 | 46 | CD79B | 84 | ETV4 | 122 | GRIN2A | 160 | MEF2B | 198 | PIK3R1 |
| 9 | APC | 47 | CDC73 | 85 | ETV5 | 123 | HGF | 161 | MEN1 | 199 | PIK3R2 |
| 10 | AR | 48 | CDH1 | 86 | EWSR1 | 124 | HNF1A | 162 | MET | 200 | PLCG2 |
| 11 | ARAF | 49 | CDK12 | 87 | EZH2 | 125 | HRAS | 163 | MITF | 201 | PPP2R1A |
| 12 | ARID1A | 50 | CDK4 | 88 | FAM46C | 126 | HSP90AA1 | 164 | MLH1 | 202 | PRDM1 |
| 13 | ARID2 | 51 | CDK6 | 89 | FANCA | 127 | IDH1 | 165 | MPL | 203 | PRKAR1A |
| 14 | ASXL1 | 52 | CDK8 | 90 | FANCC | 128 | IDH2 | 166 | MRE11A | 204 | PTCH1 |
| 15 | ATM | 53 | CDKN1B | 91 | FANCD2 | 129 | IKBKE | 167 | MSH2 | 205 | PTEN |
| 16 | ATR | 54 | CDKN2A | 92 | FANCE | 130 | IKZF1 | 168 | MSH3 | 206 | PTPN11 |
| 17 | ATRX | 55 | CDKN2B | 93 | FANCF | 131 | IL7R | 169 | MSH6 | 207 | RAD50 |
| 18 | AURKA | 56 | CDKN2C | 94 | FANCG | 132 | INPP4B | 170 | MTOR | 208 | RAD51 |
| 19 | AURKB | 57 | CEBPA | 95 | FANCL | 133 | IRF1 | 171 | MUTYH | 209 | RAF1 |
| 20 | AXIN1 | 58 | CHD2 | 96 | FAS | 134 | IRF4 | 172 | MYC | 210 | RARA |
| 21 | AXL | 59 | CHEK1 | 97 | FBXW7 | 135 | IRS2 | 173 | MYCL | 211 | RB1 |
| 22 | B2M | 60 | CHEK2 | 98 | FGF10 | 136 | JAK1 | 174 | MYCN | 212 | RET |
| 23 | BAP1 | 61 | CIC | 99 | FGF14 | 137 | JAK2 | 175 | MYD88 | 213 | RICTOR |
| 24 | BARD1 | 62 | CREBBP | 100 | FGF23 | 138 | JAK3 | 176 | NF1 | 214 | RNF43 |
| 25 | BCL2 | 63 | CRKL | 101 | FGF3 | 139 | JUN | 177 | NF2 | 215 | ROS1 |
| 26 | BCL6 | 64 | CRLF2 | 102 | FGF4 | 140 | KAT6A | 178 | NFE2L2 | 216 | RPTOR |
| 27 | BCOR | 65 | CSF1R | 103 | FGF6 | 141 | KDM5A | 179 | NFKBIA | 217 | RUNX1 |
| 28 | BCORL1 | 66 | CTCF | 104 | FGFR1 | 142 | KDM5C | 180 | NKX2-1 | 218 | SDHA |
| 29 | BLM | 67 | CTNNA1 | 105 | FGFR2 | 143 | KDM6A | 181 | NOTCH1 | 219 | SDHB |
| 30 | BRAF | 68 | CTNNB1 | 106 | FGFR3 | 144 | KDR | 182 | NOTCH2 | 220 | SDHC |
| 31 | BRCA1 | 69 | DAXX | 107 | FGFR4 | 145 | KEAP1 | 183 | NPM1 | 221 | SDHD |
| 32 | BRCA2 | 70 | DDR2 | 108 | FLCN | 146 | KIT | 184 | NRAS | 222 | SETD2 |
| 33 | BRD4 | 71 | DNMT3A | 109 | FLT1 | 147 | KLHL6 | 185 | NTRK1 | 223 | SF3B1 |
| 34 | BRIP1 | 72 | DOT1L | 110 | FLT3 | 148 | KMT2A | 186 | NTRK2 | 224 | SMAD2 |
| 35 | BTK | 73 | EGFR | 111 | FLT4 | 149 | KMT2C | 187 | NTRK3 | 225 | SMAD4 |
| 36 | CALR | 74 | EP300 | 112 | FOXL2 | 150 | KRAS | 188 | PALB2 | 226 | SMARCA4 |
| 37 | CARD11 | 75 | EPHA7 | 113 | FOXP1 | 151 | LRP1B | 189 | PAX5 | 227 | SMARCB1 |
| 38 | CBFB | 76 | EPHB1 | 114 | FRS2 | 152 | MAP2K1 | 190 | PBRM1 | 228 | SMO |

Fig. 27b1

| Heme and Solid Tumor Related - xT Gene Panel ||
|---|---|
| No. | Symbol |
| 229 | SOCS1 |
| 230 | SOX10 |
| 231 | SOX2 |
| 232 | SPEN |
| 233 | SPOP |
| 234 | SRC |
| 235 | STAG2 |
| 236 | STAT3 |
| 237 | STAT4 |
| 238 | STK11 |
| 239 | SUFU |
| 240 | TAF1 |
| 241 | TET2 |
| 242 | TGFBR2 |
| 243 | TMPRSS2 |
| 244 | TNFAIP3 |
| 245 | TNFRSF14 |
| 246 | TOP1 |
| 247 | TP53 |
| 248 | TSC1 |
| 249 | TSC2 |
| 250 | TSHR |
| 252 | U2AF1 |
| 253 | VHL |
| 254 | WT1 |
| 255 | XPO1 |

Fig. 27b2

| Solid Tumor Related - xT Gene Panel ||||||||||
|---|---|---|---|---|---|---|---|---|---|
| No. | Symbol | No. | Symbol | No. | Symbol | No. | Symbol | No. | Symbol |
| 1 | ABL2 | 39 | CYP1B1 | 77 | FGF8 | 115 | HLA-DQB1 | 153 | MAD2L2 |
| 2 | ACTA2 | 40 | CYP2D6 | 78 | FGF9 | 116 | HLA-DQB2 | 154 | MAX |
| 3 | ACVR1B | 41 | CYP3A5 | 79 | FH | 117 | HLA-DRA | 155 | MC1R |
| 4 | AJUBA | 42 | DDB2 | 80 | FLG | 118 | HLA-DRB1 | 156 | MGMT |
| 5 | APOB | 43 | DICER1 | 81 | FNTB | 119 | HLA-DRB5 | 157 | MLH3 |
| 6 | ARHGAP35 | 44 | DIRC2 | 82 | FOXA1 | 120 | HLA-DRB6 | 158 | MLLT3 |
| 7 | ARID1B | 45 | DIS3 | 83 | FOXQ1 | 121 | HLA-E | 159 | MS4A1 |
| 8 | ARID5B | 46 | DIS3L2 | 84 | FUBP1 | 122 | HLA-F | 160 | MTAP |
| 9 | ASNS | 47 | DKC1 | 85 | G6PD | 123 | HLA-G | 161 | MTHFR |
| 10 | ATIC | 48 | DPYD | 86 | GALNT12 | 124 | HNF1B | 162 | MTRR |
| 11 | ATP7B | 49 | DYNC2H1 | 87 | GATA4 | 125 | HOXB13 | 163 | MYB |
| 12 | AXIN2 | 50 | EGF | 88 | GATA6 | 126 | HSPH1 | 164 | MYH11 |
| 13 | BCL2L1 | 51 | EGLN1 | 89 | GEN1 | 127 | IDO1 | 165 | NBN |
| 14 | BCL2L11 | 52 | ELF3 | 90 | GLI1 | 128 | IFIT1 | 166 | NCOR1 |
| 15 | BCLAF1 | 53 | ENG | 91 | GPC3 | 129 | IFIT2 | 167 | NHP2 |
| 16 | BMPR1A | 54 | EPCAM | 92 | GPS2 | 130 | IFIT3 | 168 | NOP10 |
| 17 | BTG1 | 55 | EPHA2 | 93 | GREM1 | 131 | IFNAR1 | 169 | NOTCH3 |
| 18 | BUB1B | 56 | EPHB2 | 94 | GRM3 | 132 | IFNAR2 | 170 | NQO1 |
| 19 | C10orf54 | 57 | ERCC1 | 95 | GSTP1 | 133 | IFNGR1 | 171 | NRG1 |
| 20 | C11orf30 | 58 | ERCC2 | 96 | H19 | 134 | IFNGR2 | 172 | NSD1 |
| 21 | C11orf65 | 59 | ERCC3 | 97 | H3F3A | 135 | IFNL3 | 173 | NTHL1 |
| 22 | C3orf70 | 60 | ERCC4 | 98 | HAS3 | 136 | IL10RA | 174 | NUDT15 |
| 23 | C8orf34 | 61 | ERCC5 | 99 | HAVCR2 | 137 | IL15 | 175 | PAK1 |
| 24 | CASP8 | 62 | ERCC6 | 100 | HDAC2 | 138 | IL2RA | 176 | PALLD |
| 25 | CASR | 63 | ERRFI1 | 101 | HIF1A | 139 | IL6R | 177 | PARK2 |
| 26 | CBR3 | 64 | ETS2 | 102 | HIST1H4E | 140 | ING1 | 178 | PAX3 |
| 27 | CCDC6 | 65 | FAM175A | 103 | HLA-A | 141 | IRF2 | 179 | PAX7 |
| 28 | CD19 | 66 | FANCB | 104 | HLA-B | 142 | ITPKB | 180 | PAX8 |
| 29 | CD40 | 67 | FANCI | 105 | HLA-C | 143 | KEL | 181 | PDPK1 |
| 30 | CDKN1A | 68 | FANCM | 106 | HLA-DMA | 144 | KIF1B | 182 | PHOX2B |
| 31 | CDKN1C | 69 | FAT1 | 107 | HLA-DMB | 145 | KLLN | 183 | PIAS4 |
| 32 | CEP57 | 70 | FCGR2A | 108 | HLA-DOA | 146 | KMT2D | 184 | PIK3C2B |
| 33 | CFTR | 71 | FCGR3A | 109 | HLA-DOB | 147 | LAG3 | 185 | PIK3CB |
| 34 | CHD4 | 72 | FDPS | 110 | HLA-DPA1 | 148 | LDLR | 186 | PIK3CD |
| 35 | CTC1 | 73 | FGF1 | 111 | HLA-DPB1 | 149 | LMNA | 187 | PML |
| 36 | CTLA4 | 74 | FGF2 | 112 | HLA-DPB2 | 150 | LMO1 | 188 | PMS1 |
| 37 | CTRC | 75 | FGF5 | 113 | HLA-DQA1 | 151 | LYN | 189 | PMS2 |
| 38 | CYLD | 76 | FGF7 | 114 | HLA-DQA2 | 152 | LZTR1 | 190 | POLD1 |

Fig. 27c1

| Solid Tumor Related - xT Gene Panel | | | | | | | | | |
|---|---|---|---|---|---|---|---|---|---|
| No. | Symbol | No. | Symbol | No. | Symbol | No. | Symbol | No. | Symbol |
| 191 | POLE | 209 | RAD51D | 227 | SEMA3C | 245 | TCF7L2 | 262 | XPC |
| 192 | POLH | 210 | RAD54L | 228 | SH2B3 | 246 | TIGIT | 263 | XRCC1 |
| 193 | POU2F2 | 211 | RANBP2 | 229 | SLC26A3 | 247 | TMEM127 | 264 | XRCC2 |
| 194 | PPP1R15A | 212 | RASA1 | 230 | SLC47A2 | 248 | TMEM173 | 265 | XRCC3 |
| 195 | PPP2R2A | 213 | RBM10 | 231 | SLIT2 | 249 | TNF | 266 | YEATS4 |
| 196 | PPP6C | 214 | RECQL4 | 232 | SLX4 | 250 | TNFRSF9 | 267 | ZFHX3 |
| 197 | PRCC | 215 | RINT1 | 233 | SMAD3 | 251 | TOP2A | 268 | ZNF217 |
| 198 | PREX2 | 216 | RIT1 | 234 | SMARCE1 | 252 | TPM1 | 269 | ZNF471 |
| 199 | PRSS1 | 217 | RNF139 | 235 | SOD2 | 253 | TPMT | 270 | ZNF620 |
| 200 | PRSS2 | 218 | RPL5 | 236 | SOX9 | 254 | TYMS | 271 | ZNF750 |
| 201 | PTCH2 | 219 | RPS15 | 237 | SPINK1 | 255 | UBE2T | 272 | ZNRF3 |
| 202 | PTPN13 | 220 | RPS6KB1 | 238 | SPRED1 | 256 | UGT1A1 | | |
| 203 | PTPN22 | 221 | RSF1 | 239 | SYK | 257 | UGT1A9 | | |
| 204 | PTPRD | 222 | RUNX1T1 | 240 | TANC1 | 258 | UMPS | | |
| 205 | QKI | 223 | RXRA | 241 | TAP1 | 259 | VEGFA | | |
| 206 | RAC1 | 224 | SCG5 | 242 | TAP2 | 260 | WEE1 | | |
| 207 | RAD51B | 225 | SDHAF2 | 243 | TBC1D12 | 261 | WRN | | |
| 208 | RAD51C | 226 | SEC23B | 244 | TBX3 | 262 | XPA | | |

Fig. 27c2

| Gene Rearrangement By DNA Sequencing - xT Gene Panel | | | |
|---|---|---|---|
| No. | Symbol | No. | Symbol |
| 1 | ABL1 | 12 | NRG1 |
| 2 | ALK | 13 | NTRK1 |
| 3 | BCR | 14 | NTRK3 |
| 4 | BRAF | 15 | PAX8 |
| 5 | EGFR | 16 | PDGFRA |
| 6 | ETV6 | 17 | PML |
| 7 | EWSR1 | 18 | RARA |
| 8 | FGFR2 | 19 | RET |
| 9 | FGFR3 | 20 | ROS1 |
| 10 | MYB | 21 | TMPRSS2 |
| 11 | MYC | | |

Fig. 27d

| \multicolumn{10}{|c|}{Additional Exemplary Gene Panel} |
|---|---|---|---|---|---|---|---|---|---|
| No. | Symbol | No. | Symbol | No. | Symbol | No. | Symbol | No. | Symbol |
| 1 | ABL1 | 39 | (EMSY) | 77 | CUL3 | 115 | FGF6 | 153 | ID3 |
| 2 | ACVR1B | 40 | CALR | 78 | CUL4A | 116 | FGFR1 | 154 | IDH1 |
| 3 | AKT1 | 41 | CARD11 | 79 | CXCR4 | 117 | FGFR2 | 155 | IDH2 |
| 4 | AKT2 | 42 | CASP8 | 80 | CYP17A1 | 118 | FGFR3 | 156 | IGF1R |
| 5 | AKT3 | 43 | CBFB | 81 | DAXX | 119 | FGFR4 | 157 | IKBKE |
| 6 | ALK | 44 | CBL | 82 | DDR1 | 120 | FH | 158 | IKZF1 |
| 7 | ALOX12B | 45 | CCND1 | 83 | DDR2 | 121 | FLCN | 159 | INPP4B |
| 8 | AMER1 | 46 | CCND2 | 84 | DIS3 | 122 | FLT1 | 160 | IRF2 |
| 9 | APC | 47 | CCND3 | 85 | DNMT3A | 123 | FLT3 | 161 | IRF4 |
| 10 | AR | 48 | CCNE1 | 86 | DOT1L | 124 | FOXL2 | 162 | IRS2 |
| 11 | ARAF | 49 | CD22 | 87 | EED | 125 | FUBP1 | 163 | JAK1 |
| 12 | ARFRP1 | 50 | CD274 | 88 | EGFR | 126 | GABRA6 | 164 | JAK2 |
| 13 | ARID1A | 51 | (PD-L1) | 89 | EP300 | 127 | GATA3 | 165 | JAK3 |
| 14 | ASXL1 | 52 | CD70 | 90 | EPHA3 | 128 | GATA4 | 166 | JUN |
| 15 | ATM | 53 | CD79A | 91 | EPHB1 | 129 | GATA6 | 167 | KDM5A |
| 16 | ATR | 54 | CD79B | 92 | EPHB4 | 130 | GID4 | 168 | KDM5C |
| 17 | ATRX | 55 | CDC73 | 93 | ERBB2 | 131 | GNA11 | 169 | KDM6A |
| 18 | AURKA | 56 | CDH1 | 94 | ERBB3 | 132 | GNA13 | 170 | KDR |
| 19 | AURKB | 57 | CDK12 | 95 | ERBB4 | 133 | GNAQ | 171 | KEAP1 |
| 20 | AXIN1 | 58 | CDK4 | 96 | ERCC4 | 134 | GNAS | 172 | KEL |
| 21 | AXL | 59 | CDK6 | 97 | ERG | 135 | GRM3 | 173 | KIT |
| 22 | BAP1 | 60 | CDK8 | 98 | ERRFI1 | 136 | GSK3B | 174 | KLHL6 |
| 23 | BARD1 | 61 | CDKN1A | 99 | ESR1 | 137 | H3F3A | 175 | KMT2A |
| 24 | BCL2 | 62 | CDKN1B | 100 | EZH2 | 138 | HDAC1 | 176 | KMT2D |
| 25 | BCL2L1 | 63 | CDKN2A | 101 | FAM46C | 139 | HGF | 177 | KRAS |
| 26 | BCL2L2 | 64 | CDKN2B | 102 | FANCA | 140 | HNF1A | 178 | LTK |
| 27 | BCL6 | 65 | CDKN2C | 103 | FANCC | 141 | HRAS | 179 | LYN |
| 28 | BCOR | 66 | CEBPA | 104 | FANCG | 142 | HSD3B1 | 180 | MAF |
| 29 | BCORL1 | 67 | CHEK1 | 105 | FANCL | 143 | FGF6 | 181 | MAP2K1 |
| 30 | BRAF | 68 | CHEK2 | 106 | FAS | 144 | FGFR1 | 182 | MAP2K2 |
| 31 | BRCA1 | 69 | CIC | 107 | FBXW7 | 145 | FGFR2 | 183 | MAP2K4 |
| 32 | BRCA2 | 70 | CREBBP | 108 | FGF10 | 146 | FGFR3 | 184 | MAP3K1 |
| 33 | BRD4 | 71 | CRKL | 109 | FGF12 | 147 | FGFR4 | 185 | MAP3K13 |
| 34 | BRIP1 | 72 | CSF1R | 110 | FGF14 | 148 | FH | 186 | MAPK1 |
| 35 | BTG1 | 73 | CSF3R | 111 | FGF19 | 149 | FLCN | 187 | MCL1 |
| 36 | BTG2 | 74 | CTCF | 112 | FGF23 | 150 | FLT1 | 188 | MDM2 |
| 37 | BTK | 75 | CTNNA1 | 113 | FGF3 | 151 | FLT3 | 189 | MDM4 |
| 38 | C11orf30 | 76 | CTNNB1 | 114 | FGF4 | 152 | FOXL2 | 190 | MED12 |

Fig. 28a

| Additional Exemplary Gene Panel ||||||||||
|---|---|---|---|---|---|---|---|---|---|
| No. | Symbol | No. | Symbol | No. | Symbol | No. | Symbol | No. | Symbol |
| 191 | MSH3 | 216 | P2RY8 | 241 | PRDM1 | 266 | RPTOR | 291 | TBX3 |
| 192 | MSH6 | 217 | PALB2 | 242 | PRKAR1A | 267 | SDHA | 292 | TEK |
| 193 | MST1R | 218 | PARK2 | 243 | PRKCI | 268 | SDHB | 293 | TET2 |
| 194 | MTAP | 219 | PARP1 | 244 | PTCH1 | 269 | SDHC | 294 | TGFBR2 |
| 195 | MTOR | 220 | PARP2 | 245 | PTEN | 270 | SDHD | 295 | TIPARP |
| 196 | MUTYH | 221 | PARP3 | 246 | PTPN11 | 271 | SETD2 | 296 | TNFAIP3 |
| 197 | MYC | 222 | PAX5 | 247 | PTPRO | 272 | SF3B1 | 297 | TNFRSF14 |
| 198 | MYCL | 223 | PBRM1 | 248 | QKI | 273 | SGK1 | 298 | TP53 |
| 199 | MYCN | 224 | PDCD1 | 249 | RAC1 | 274 | SMAD2 | 299 | TSC1 |
| 200 | MYD88 | 225 | PDCD1LG2 | 250 | RAD21 | 275 | SMAD4 | 300 | TSC2 |
| 201 | NBN | 226 | PDGFRA | 251 | RAD51 | 276 | SMARCA4 | 301 | TYRO3 |
| 202 | NF1 | 227 | PDGFRB | 252 | RAD51B | 277 | SMARCB1 | 302 | U2AF1 |
| 203 | NF2 | 228 | PDK1 | 253 | RAD51C | 278 | SMO | 303 | VEGFA |
| 204 | NFE2L2 | 229 | PIK3C2B | 254 | RAD51D | 279 | SNCAIP | 304 | VHL |
| 205 | NFKBIA | 230 | PIK3C2G | 255 | RAD52 | 280 | SOCS1 | 305 | WHSC1 |
| 206 | NKX2-1 | 231 | PIK3CA | 256 | RAD54L | 281 | SOX2 | 306 | WHSC1L1 |
| 207 | NOTCH1 | 232 | PIK3CB | 257 | RAF1 | 282 | SOX9 | 307 | WT1 |
| 208 | NOTCH2 | 233 | PIK3R1 | 258 | RARA | 283 | SPEN | 308 | XPO1 |
| 209 | NOTCH3 | 234 | PIM1 | 259 | RB1 | 284 | SPOP | 309 | XRCC2 |
| 210 | NPM1 | 235 | PMS2 | 260 | RBM10 | 285 | SRC | 310 | ZNF217 |
| 211 | NRAS | 236 | POLD1 | 261 | REL | 286 | STAG2 | 311 | ZNF703 |
| 212 | NT5C2 | 237 | POLE | 262 | RET | 287 | STAT3 | | |
| 213 | NTRK1 | 238 | PPARG | 263 | RICTOR | 288 | STK11 | | |
| 214 | NTRK2 | 239 | PPP2R1A | 264 | RNF43 | 289 | SUFU | | |
| 215 | NTRK3 | 240 | PPP2R2A | 265 | ROS1 | 290 | SYK | | |

Fig. 28b

Audit Record (Each record memorializes an order event)

| AID (UUID of Audit Log Entry) | OID (UUID of Order) | IID (UUID of Item) | Created Timestamp | Event Type<br>Order Created<br>Oder Item Delete<br>Order Item Added<br>Item In Progress<br>Item QC fail<br>Item Cancelled<br>Item Modified<br>Item Pause<br>Item Stop | JSON Representation Of New Order | Comment |
|---|---|---|---|---|---|---|
| 2852 | 2854 | 2856 | 2858 | 2860 | 2862 | 2864 |

| PATIENTS PROJECTS TEMPLATES VALUESETS MAGNET QA MANAGER VALIDATIONS MANAGER | | | | | |
|---|---|---|---|---|---|
| | | | | | Create New |
| NAME | DESCRIPTION | CREATED AT | CREATED BY | LEVEL | EDIT▾ |
| Lytic count must be a number if operator is. | Value must be a num | 12/18/18 05:56:50 | 35894307-7c21-4025-abff-89aecb6bb3b3 | ERROR | Edit |
| Menopause status | Patient is not female | 03/21/19 09:05:05 | ea31e4ba-f842-45ba-965c-87584a496cda | WARNING | Edit |
| Diagnosis cannot be duplicate | Duplicate tissue of origin | 12/18/18 05:56:50 | 35894307-7c21-4025-abff-89aecb6bb3b3 | WARNING | Edit |
| Lab tests test result is name | Must be a number | 12/18/18 05:56:50 | 35894307-7c21-4025-abff-89aecb6bb3b3 | ERROR | Edit |
| Date Validations | Invalid date | 12/18/18 05:56:50 | 35894307-7c21-4025-abff-89aecb6bb3b3 | ERROR | Edit |
| Gene raw result | Must be number | 02/28/19 04:55:39 | 7b9efc70-df76-463e-bb80-4939b4bcfa607 | ERROR | Edit |
| Tumor characterizations tumor size | Tumor image size and units are required | 12/18/18 05:56:50 | 35894307-7c21-4025-abff-89aecb6bb3b3 | ERROR | Edit |
| Tumor characterization before earliest date of diagnosis | Data must be after diagnosis or earliest identification | 12/18/18 05:56:50 | 35894307-7c21-4025-abff-89aecb6bb3b3 | ERROR | Edit |
| Lab test lower limit is less than upper limit | Lower limits must be less than upper limit | 12/18/18 05:56:50 | 35894307-7c21-4025-abff-89aecb6bb3b3 | ERROR | Edit |
| Immunophenotyping result text is a number | Should be a Number | 12/18/18 05:56:50 | 35894307-7c21-4025-abff-89aecb6bb3b3 | ERROR | Edit |
| Lab tests test result and test text can't exits together | Excess field | 12/18/18 05:56:50 | 35894307-7c21-4025-abff-89aecb6bb3b3 | ERROR | Edit |

Fig. 87

Edit validation

Name
Tumor characterizations tumor size

Description
Tumor image size and units are required

Level
ERROR ▼

Effective As Of
03/23/2019

For [ all ▼ ] in [Type. to get suggestions...]
                                    3432

Add Block

ADVANCED EDITION

Save Validation

Save Validation

PATIENTS PROJECTS TEMPLATES VALUESETS MAGNET QA MANAGER VALIDATIONS MANAGER

Edit validation

Name
Tumor characterizations tumor size

Effective As Of
03/23/2019

Level          Description
ERROR ▼    Tumor image size and units are required

For  all ▼  in demographics: Demographics
diagnosis: Diagnosis
treatmentsAndOutcomes: Treatments and outcomes
geneticTestingAndLabs: Genetic Testing and Labs

3442

Add Block

Save Validation

ADVANCED EDITION

Save Validation

Screen 3510 — PATIENTS | PROJECTS | TEMPLATES | VALUESETS | MAGNET | QA MANAGER | VALIDATIONS MANAGER

QA | MANAGE COHORTS | MANAGE QUERIES 3512

SEARCH
+Summary Search  +Patient Blob Search  +Validation Search  +Activities Search 3512
[Search]   3512

Go To Jobs

| ☐ PATIENT ID | PROJECT | ABSTRACTORS | QA | IRR | IRR REVIEWER SCORE | COHORTS | ACTIVITY | VALIDATION | 0 PATIENTS |
|---|---|---|---|---|---|---|---|---|---|
| NAME | | | | | | | | | |

| condition_occurrence_id | person_id | condition_concept_id | condition_start | condition_end | condition_type_concept_id | visit_occurrence_id | condition_source_value | condition_source_concept_id |
|---|---|---|---|---|---|---|---|---|
| 12345567893 | ABC12308945456 | 352051182 | 7/25/17 | 7/25/17 | 447886827 | 455348672 | C32.9 | 7993289 |

Fig. 140

| drug_concept_id | person_id | drug_exposure_start | drug_exposure_end | drug_source_value | drug_source_concept_id | route_source_value | dose_source_value | dose_unit_source_value |
|---|---|---|---|---|---|---|---|---|
| 45329866 | ABC123D0EF456 | 7/28/17 | 7/28/17 | PACLITAXEL 6 MG/mL CONCENTRATE, IV | 72370 | intravenous | | ml |

Fig. 141

| Field | Value |
|---|---|
| Text | "The patient was given Tylenol 50mg at 10:35am." |
| Medication | Tylenol |
| Active Ingredient | acetaminophen |
| Dosage | 50mg |
| Date Administered | 01/01/2001 10:35:01 am CST |
| Document | Progress Note 01_01_01.pdf |
| Page | 3 |
| UMLS CUI | C1234567 |
| UMLS_AUI | RXNORM#12345 |

Fig. 163

Receive Target/Objective pairs and prior and/or forward feature set for a cohort of patients Identify metastatic sites to predict Receive prediction values for each patient of the cohort for each metastatic site Graph predictions of metastasis to sites on body for a selected patient of the cohort

6930 — Control

| | |
|---|---|
| Censorship rate | 0.54 |
| Distinct meds (Pre) | 8.88 |
| Distinct meds (Post) | 7.43 |

| Drugs Taken (Pre) | % |
|---|---|
| dexamethasone | 2.9 |
| docusate | 2.3 |
| heparin | 2.2 |
| ondansetron | 2.1 |
| acetaminophen / hydrocodone | 2 |
| cisplatin | 2 |
| sodium chloride | 1.7 |
| morphine | 1.7 |
| palonosetron | 1.6 |
| magnesium sulfate | 1.4 |

| Drugs Taken (Post) | % |
|---|---|
| dexamethasone | 19.8 |
| ondansetron | 11.8 |
| cisplatin | 11.8 |
| palonosetron | 10.6 |
| lorazepam | 8.2 |
| etoposide | 8 |
| fosaprepitant | 7.7 |
| prochlorperazine | 6.8 |
| pemetrexed | 5.8 |
| magnesium sulfate | 5.1 |

6932 — Treatment

| | |
|---|---|
| Censorship rate | 0.26 |
| Distinct meds (Pre) | 5.56 |
| Distinct meds (post) | 12.25 |

| Drugs Taken (Pre) | % |
|---|---|
| dexamethasone | 26.3 |
| docusate | 2 |
| heparin | 1.7 |
| ondansetron | 17.7 |
| acetaminophen / hydrocodone | 2.3 |
| cisplatin | 12.8 |
| sodium chloride | 3.9 |
| morphine | 2.9 |
| palonosetron | 12.5 |
| magnesium sulfate | 3.8 |

| Drugs Taken (Post) | % |
|---|---|
| dexamethasone | 33.9 |
| ondansetron | 21.7 |
| cisplatin | 4 |
| palonosetron | 25.6 |
| lorazepam | 13.9 |
| etoposide | 9.6 |
| fosaprepitant | 7.9 |
| prochlorperazine | 15.6 |
| pemetrexed | 20.4 |
| magnesium sulfate | 4.5 |

Fig. 221D

Impact of propensity score matching (range = high)

| Control | | Treatment | |
|---|---|---|---|
| Censorship rate | 0.32 | Censorship rate | 0.18 |
| Distinct meds (Pre) | 2 | Distinct meds (Pre) | 2.7 |
| Distinct meds (Post) | 6.34 | Distinct meds (Post) | 29.17 |
| Drugs Taken (Pre) | % | Drugs Taken (Pre) | % |
| oxycodone | 1.3 | oxycodone | <1 |
| acetaminophen | 1.3 | acetaminophen | 2.2 |

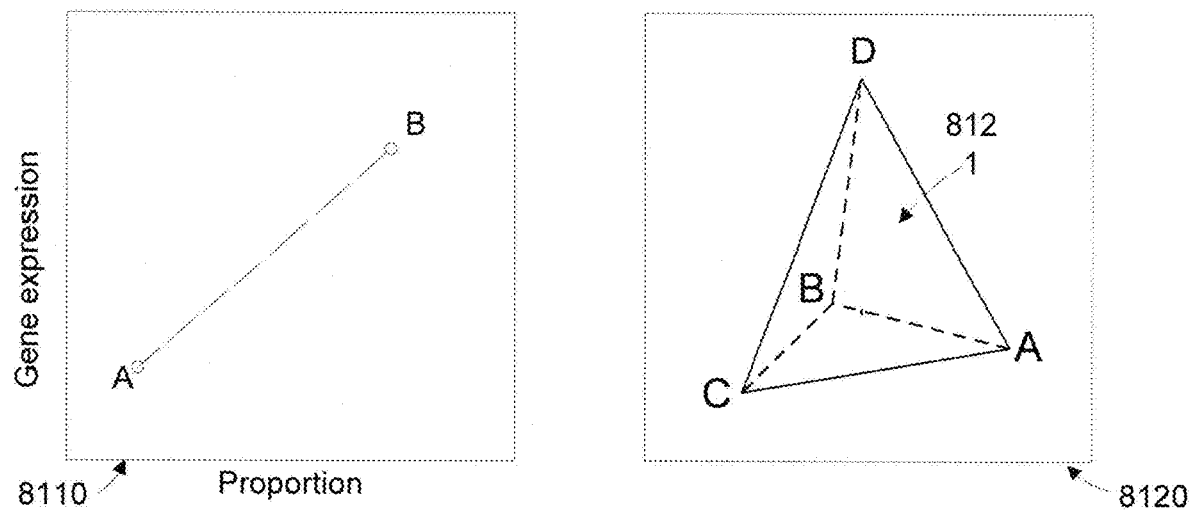
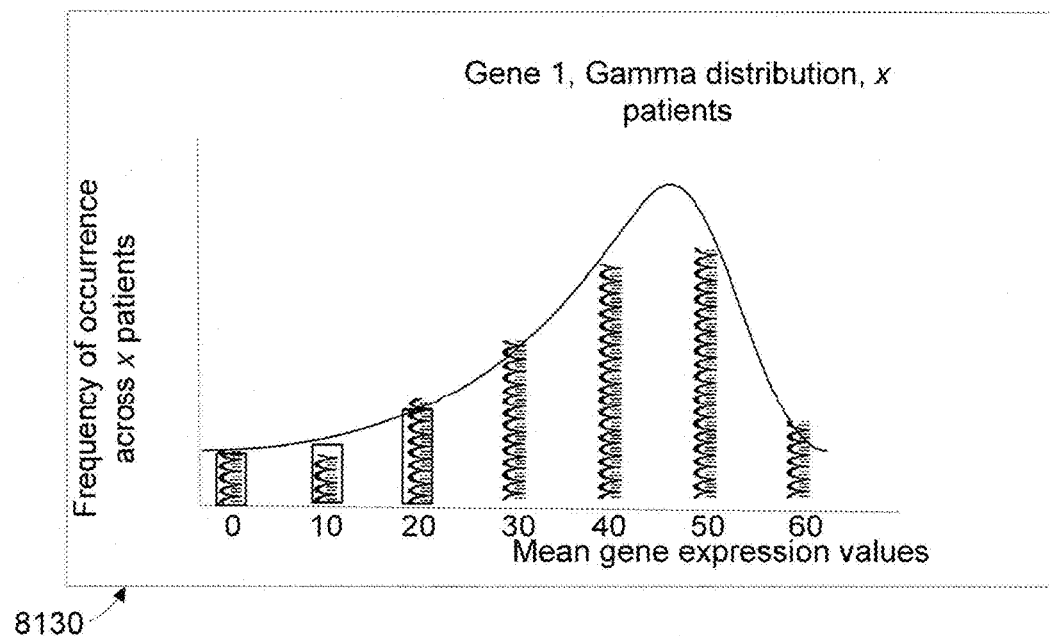
Fig. 242

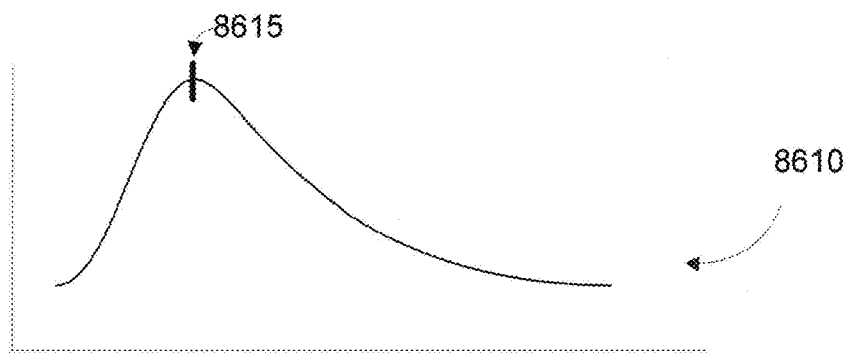
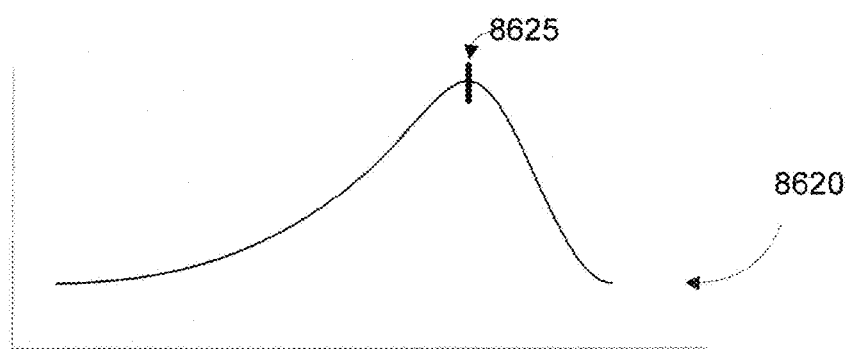
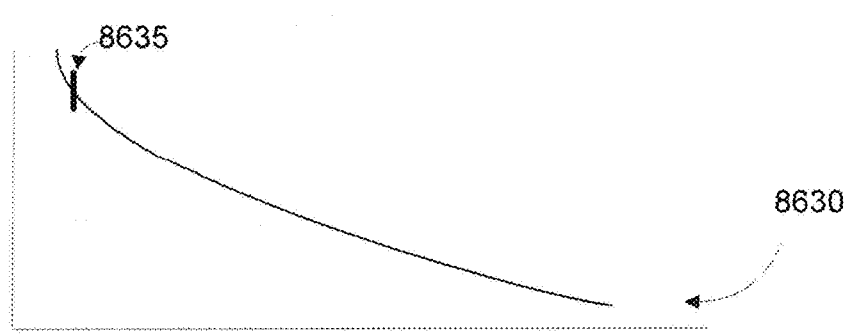
Fig. 247

| ABCB1 | ABCC3 | ABL1 | ABL2 | ACTA2 | ACVR1B | AJUBA | AKT1 | AKT2 | AKT3 | ALK |
|---|---|---|---|---|---|---|---|---|---|---|
| AMER1 | APC | APOB | AR | ARAF | ARHGAP26 | ARHGAP35 | ARID1A | ARID1B | ARID2 | ARID5B |
| ASNS | ASXL1 | ATIC | ATM | ATP7B | ATR | ATRX | AURKA | AURKB | AXIN1 | AXIN2 |
| AXL | B2M | BAP1 | BARD1 | BCL2 | BCL2L1 | BCL2L11 | BCL6 | BCL7A | BCL10 | BCL11B |
| BCLAF1 | BCOR | BCORL1 | BCR | BIRC3 | BLM | BMPR1A | BRAF | BRCA1 | BRCA2 | BRD4 |
| BRIP1 | BTG1 | BTK | BU81B | C3orf70 | C8orf34 | C10orf54 | C11orf30 | C11orf65 | CALR | CARD11 |
| CASP8 | CASR | CBFB | CBL | CBLB | CBLC | CBR3 | CCDC6 | CCND1 | CCND2 | CCND3 |
| CCNE1 | CD19 | CD22 | CD40 | CD70 | CD79A | CD79B | CD274 | CDC73 | CDH1 | CDK4 |
| CDK6 | CDK8 | CDK12 | CDKN1A | CDKN1B | CDKN1C | CDKN2A | CDKN2B | CDKN2C | CEBPA | CEP57 |
| CFTR | CHD2 | CHD4 | CHEK1 | CHEK2 | CIC | CIITA | CKS1B | CREBBP | CRKL | CRLF2 |
| CSF1R | CSF3R | CTC1 | CTCF | CTLA4 | CTNNA1 | CTNNB1 | CTRC | CUX1 | CXCR4 | CYLD |
| CYP1B1 | CYP2D6 | CYP3A5 | DAXX | DDB2 | DDR2 | DDX3X | DICER1 | DIRC2 | DIS3 | DIS3L2 |
| DKC1 | DNM2 | DNMT3A | DOT1L | DPYD | DYNC2H1 | EBF1 | ECT2L | EGF | EGFR | EGLN1 |
| ELF3 | ENG | EP300 | EPCAM | EPHA2 | EPHA7 | EPHB1 | EPHB2 | EPOR | ERBB2 | ERBB3 |
| ERBB4 | ERCC1 | ERCC2 | ERCC3 | ERCC4 | ERCC5 | ERCC6 | ERG | ERRFI1 | ESR1 | ETS1 |
| ETS2 | ETV1 | ETV4 | ETV5 | ETV6 | EWSR1 | EZH2 | FAM46C | FAM175A | FANCA | FANCB |
| FANCC | FANCD2 | FANCE | FANCF | FANCG | FANCI | FANCL | FANCM | FAS | FAT1 | FBXO11 |
| FBXW7 | FCGR2A | FCGR3A | FDPS | FGF1 | FGF2 | FGF3 | FGF4 | FGF5 | FGF6 | FGF7 |
| FGF8 | FGF9 | FGF10 | FGF14 | FGF23 | FGFR1 | FGFR2 | FGFR3 | FGFR4 | FH | FHIT |
| FLCN | FLG | FLT1 | FLT3 | FLT4 | FNTB | FOXA1 | FOXL2 | FOXO1 | FOXO3 | FOXP1 |
| FOXQ1 | FRS2 | FUBP1 | G6PD | GALNT12 | GATA1 | GATA2 | GATA3 | GATA4 | GATA6 | GEN1 |
| GLI1 | GNA11 | GNA13 | GNAO | GNAS | GPC3 | GPS2 | GREM1 | GRIN2A | GRM3 | GSTP1 |
| H3F3A | H19 | HAS3 | HAVCR2 | HDAC1 | HDAC2 | HDAC4 | HGF | HIF1A | HIST1H1E | HIST1H3B |
| HIST1H4E | HLA-A | HLA-B | HLA-C | HLA-DMA | HLA-DMB | HLA-DOA | HLA-DOB | HLA-DPA1 | HLA-DPB1 | HLA-DPB2 |
| HLA-DQA1 | HLA-DQA2 | HLA-DQB1 | HLA-DQB2 | HLA-DRA | HLA-DRB1 | HLA-DRB5 | HLA-DRB6 | HLA-E | HLA-F | HLA-G |
| HNF1A | HNF1B | HOXB13 | HRAS | HSP90AA1 | HSPH1 | IDH1 | IDH2 | IDO1 | IFIT1 | IFIT2 |
| IFIT3 | IFNAR1 | IFNAR2 | IFNGR1 | IFNGR2 | IFNL3 | IKBKE | IKZF1 | IL2RA | IL6R | IL7R |
| IL10RA | IL15 | ING1 | INPP4B | IRF1 | IRF2 | IRF4 | IRS2 | ITPKB | JAK1 | JAK2 |
| JAK3 | JUN | KAT6A | KDM5A | KDM5C | KDM6A | KDR | KEAP1 | KEL | KIF1B | KIT |
| KLHL6 | KLLN | KMT2A | KMT2B | KMT2C | KMT2D | KRAS | LAG3 | LDLR | LEF1 | LMNA |
| LMO1 | LRP1B | LYN | LZTR1 | MAD2L2 | MAF | MAFB | MALT1 | MAP2K1 | MAP2K2 | MAP2K4 |
| MAP3K1 | MAP3K7 | MAPK1 | MAX | MC1R | MCL1 | MDM2 | MDM4 | MED12 | MEF2B | MEN1 |
| MET | MGMT | MIB1 | MITF | MKI67 | MLH1 | MLH3 | MLLT3 | MPL | MRE11A | MS4A1 |
| MSH2 | MSH3 | MSH6 | MTAP | MTHFR | MTOR | MTRR | MUTYH | MYB | MYC | MYCL |
| MYCN | MYD88 | MYH11 | NBN | NCOR1 | NCOR2 | NF1 | NF2 | NFE2L2 | NFKBIA | NHP2 |
| NKX2-1 | NOP10 | NOTCH1 | NOTCH2 | NOTCH3 | NPM1 | NQO1 | NRAS | NRG1 | NSD1 | NT5C2 |
| NTHL1 | NTRK1 | NTRK2 | NTRK3 | NUDT15 | NUP98 | P2RY8 | PAK1 | PALB2 | PALLD | PARK2 |
| PAX3 | PAX5 | PAX7 | PAX8 | PBRM1 | PCBP1 | PDCD1 | PDCD1LG2 | PDGFRA | PDGFRB | PDK1 |
| PDPK1 | PHF6 | PHOX2B | PIAS4 | PIK3C2B | PIK3CA | PIK3CB | PIK3CD | PIK3CG | PIK3R1 | PIK3R2 |
| PIM1 | PLCG2 | PML | PMS1 | PMS2 | POLD1 | POLE | POLH | POT1 | POU2F2 | PPP1R15A |

Fig. 251A

| PPP2R1A | PPP2R2A | PPP6C | PRCC | PRDM1 | PREX2 | PRKAR1A | PRSS1 | PRSS2 | PTCH1 | PTCH2 |
|---|---|---|---|---|---|---|---|---|---|---|
| PTEN | PTPN11 | PTPN13 | PTPN22 | PTPRD | QKI | RAC1 | RAD21 | RAD50 | RAD51 | RAD51B |
| RAD51C | RAD51D | RAD54L | RAF1 | RANBP2 | RARA | RASA1 | RB1 | RBM10 | RECQL4 | RET |
| RHOA | RICTOR | RINT1 | RIT1 | RNF43 | RNF139 | ROS1 | RPL5 | RPS6KB1 | RPS15 | RPTOR |
| RSF1 | RUNX1 | RUNX1T1 | RXRA | SCG5 | SDHA | SDHAF2 | SDHB | SDHC | SDHD | SEC23B |
| SEMA3C | SETBP1 | SETD2 | SF3B1 | SGK1 | SH2B3 | SLC26A3 | SLC47A2 | SLIT2 | SLX4 | SMAD2 |
| SMAD3 | SMAD4 | SMARCA1 | SMARCA4 | SMARCB1 | SMARCE1 | SMC1A | SMC3 | SMO | SOCS1 | SOD2 |
| SOX2 | SOX9 | SOX10 | SPEN | SPINK1 | SPOP | SPRED1 | SRC | SRSF2 | STAG2 | STAT3 |
| STAT4 | STAT5A | STAT5B | STAT6 | STK11 | SUFU | SUZ12 | SYK | TAF1 | TANC1 | TAP1 |
| TAP2 | TBC1D12 | TBL1XR1 | TBX3 | TCF3 | TCF7L2 | TCL1A | TERT | TET2 | TGFBR2 | TIGIT |
| TMEM127 | TMEM173 | TMPRSS2 | TNF | TNFAIP3 | TNFRSF9 | TNFRSF14 | TNFRSF17 | TOP1 | TOP2A | TP63 |
| TP63 | TPM1 | TPMT | TRAF3 | TSC1 | TSC2 | TSHR | TUSC3 | TYMS | U2AF1 | UBE2T |
| UGT1A1 | UGT1A9 | UMPS | VEGFA | VHL | WEE1 | WHSC1 | WRN | WT1 | XPA | XPC |
| XPO1 | XRCC1 | XRCC2 | XRCC3 | YEATS4 | ZFHX3 | ZNF217 | ZNF471 | ZNF620 | ZNF750 | ZNRF3 |
| ZRSR2 | | | | | | | | | | |

Fig. 251B

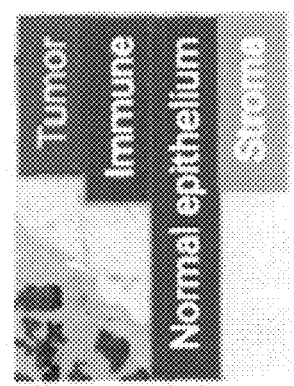
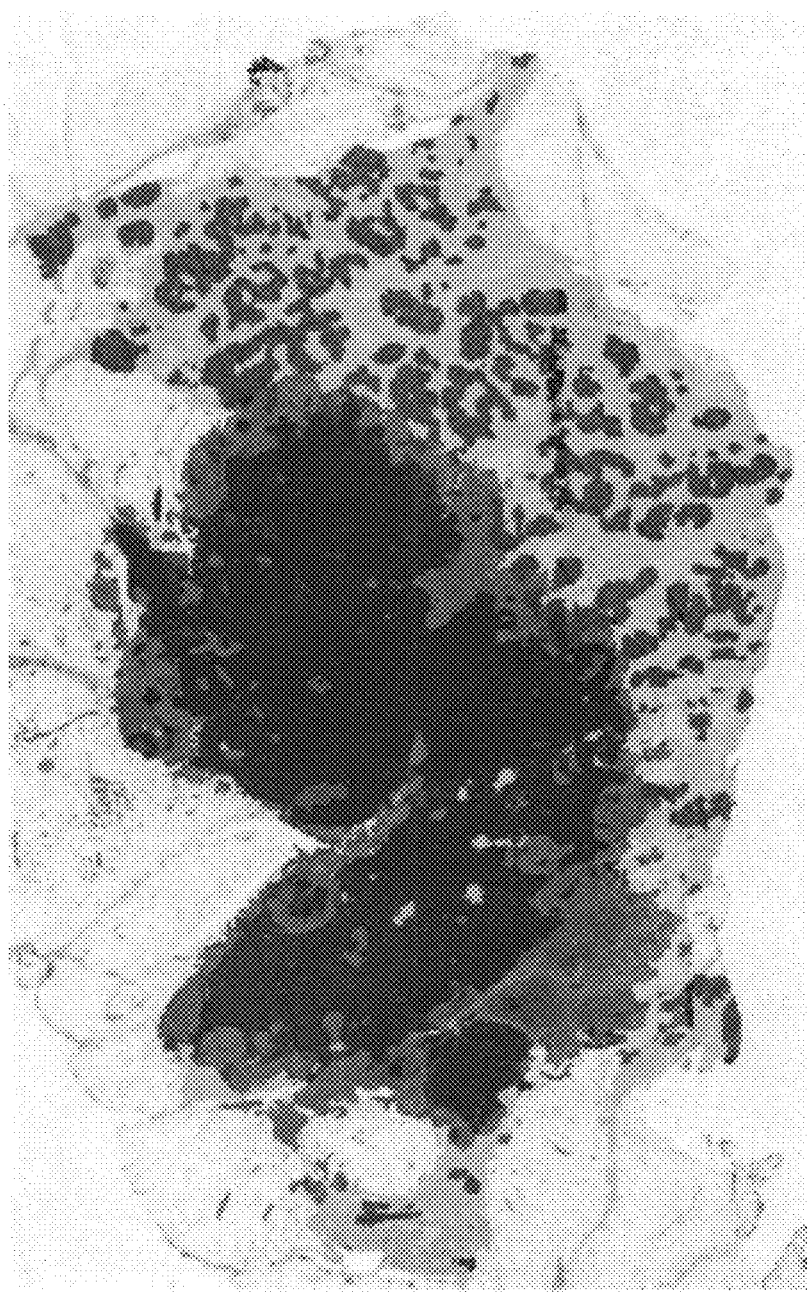
Fig. 254A

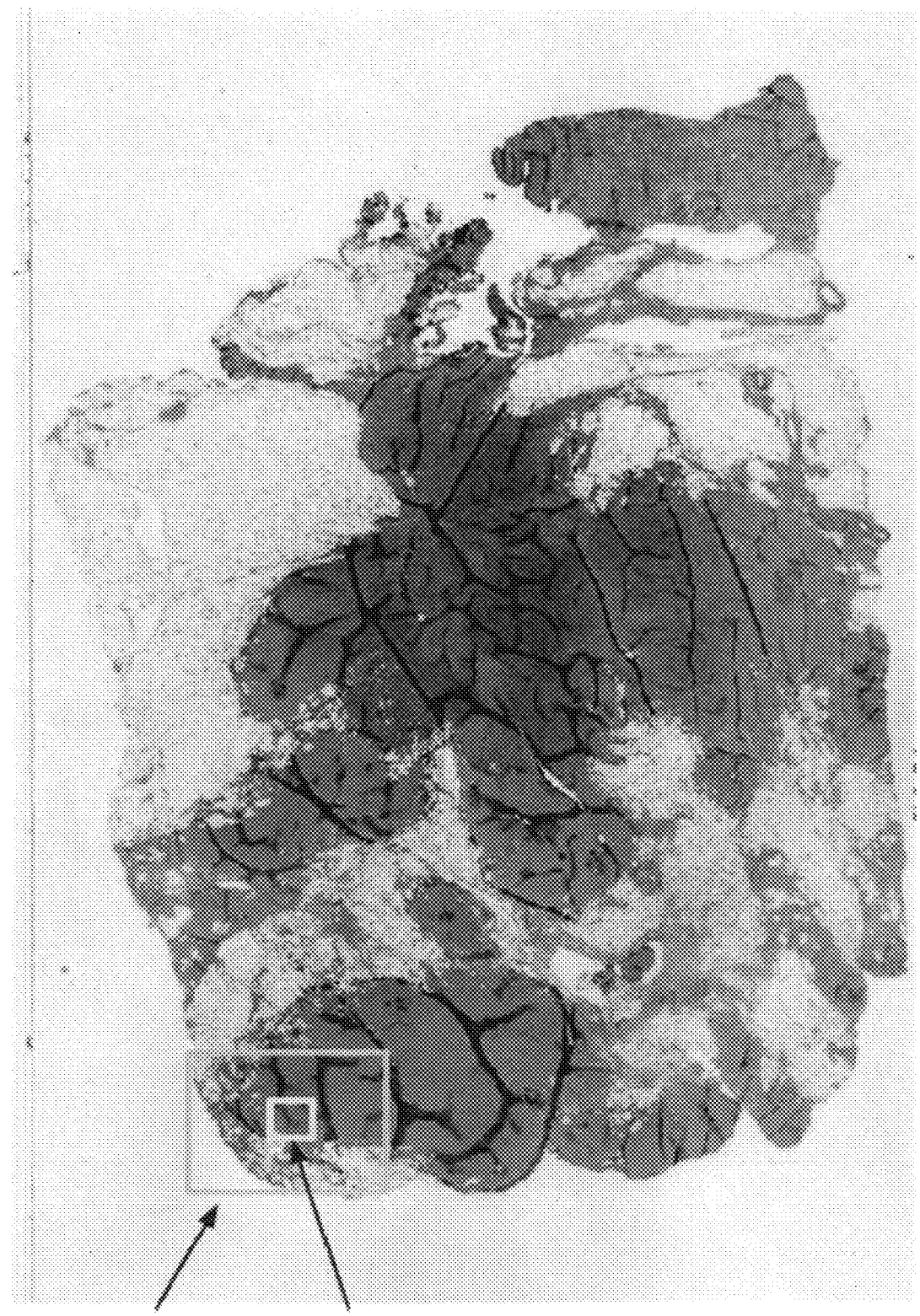

Fig. 257B

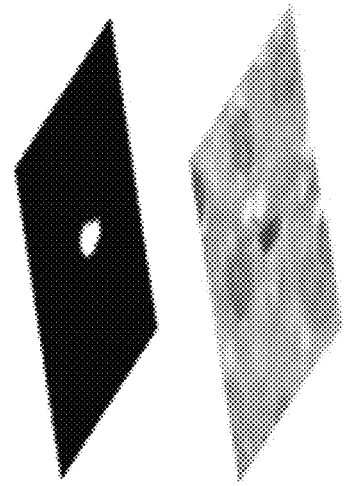
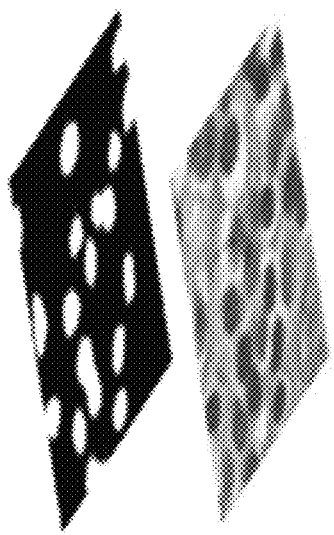
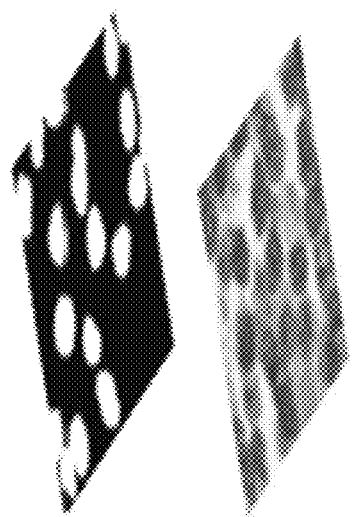
Fig. 259

|  | Test cohort | | | Training cohort | | |
| --- | --- | --- | --- | --- | --- | --- |
|  | PD-L1+ (N = 41) | PD-L1- (N = 41) | Overall (N=82) | PD-L1+ (N = 28) | PD-L1- (N = 20) | Overall (N=48) |
| Age (yr) | | | | | | |
| Average | 70 | 73 | 72 | 70 | 68 | 69 |
| Range | 38 - 93 | 57 - 86 | 38 - 93 | 50 - 87 | 36 - 84 | 36 - 87 |
| Sex | | | | | | |
| Male | 26 (63%) | 17 (41%) | 43 (52%) | 12 (43%) | 13 (65%) | 25 (52%) |
| Female | 15 (37%) | 24 (59%) | 39 (48%) | 16 (57%) | 7 (35%) | 23 (48%) |
| Smoking History | | | | | | |
| Current/Former smoker | 31 (76%) | 30 (73%) | 61 (74%) | 21 (75%) | 13 (65%) | 34 (71%) |
| Never smoker | 4 (10%) | 7 (17%) | 11 (13%) | 3 (11%) | 3 (15%) | 6 (13%) |
| N/A | 6 (15%) | 4 (10%) | 10 (12%) | 4 (14%) | 4 (20%) | 8 (17%) |
| Overall Stages | | | | | | |
| IA/IB | 11 (27%) | 16 (39%) | 27 (33%) | 7 (25%) | 8 (40%) | 15 (31%) |
| IIA/IIB | 6 (15%) | 11 (27%) | 17 (21%) | 5 (18%) | 2 (10%) | 7 (15%) |
| IIIA/IIIB | 10 (24%) | 7 (17%) | 17 (21%) | 3 (11%) | 2 (10%) | 5 (10%) |
| IV | 8 (20%) | 6 (15%) | 14 (17%) | 11 (39%) | 8 (40%) | 19 (40%) |
| N/A | 6 (15%) | 1 (2%) | 7 (8%) | 2 (7%) | 0 (0%) | 2 (4%) |
| Histology Subtypes | | | | | | |
| Adenocarcinoma | 30 (73%) | 31 (76%) | 61 (74%) | 20 (71%) | 17 (85%) | 37 (77%) |
| Squamous cell carcinoma | 7 (17%) | 10 (24%) | 17 (21%) | 7 (25%) | 3 (15%) | 10 (21%) |
| Adenosquamous | 4 (10%) | 0 (0%) | 4 (5%) | 1 (4%) | 0 (0%) | 1 (2%) |
| Tissue Acquisition | | | | | | |
| Needle Biopsy | 15 (37%) | 5 (12%) | 20 (24%) | 12 (43%) | 4 (20%) | 16 (33%) |
| Surgical resection | 26 (63%) | 36 (88%) | 62 (76%) | 16 (57%) | 16 (80%) | 32 (67%) |

Fig. 260D

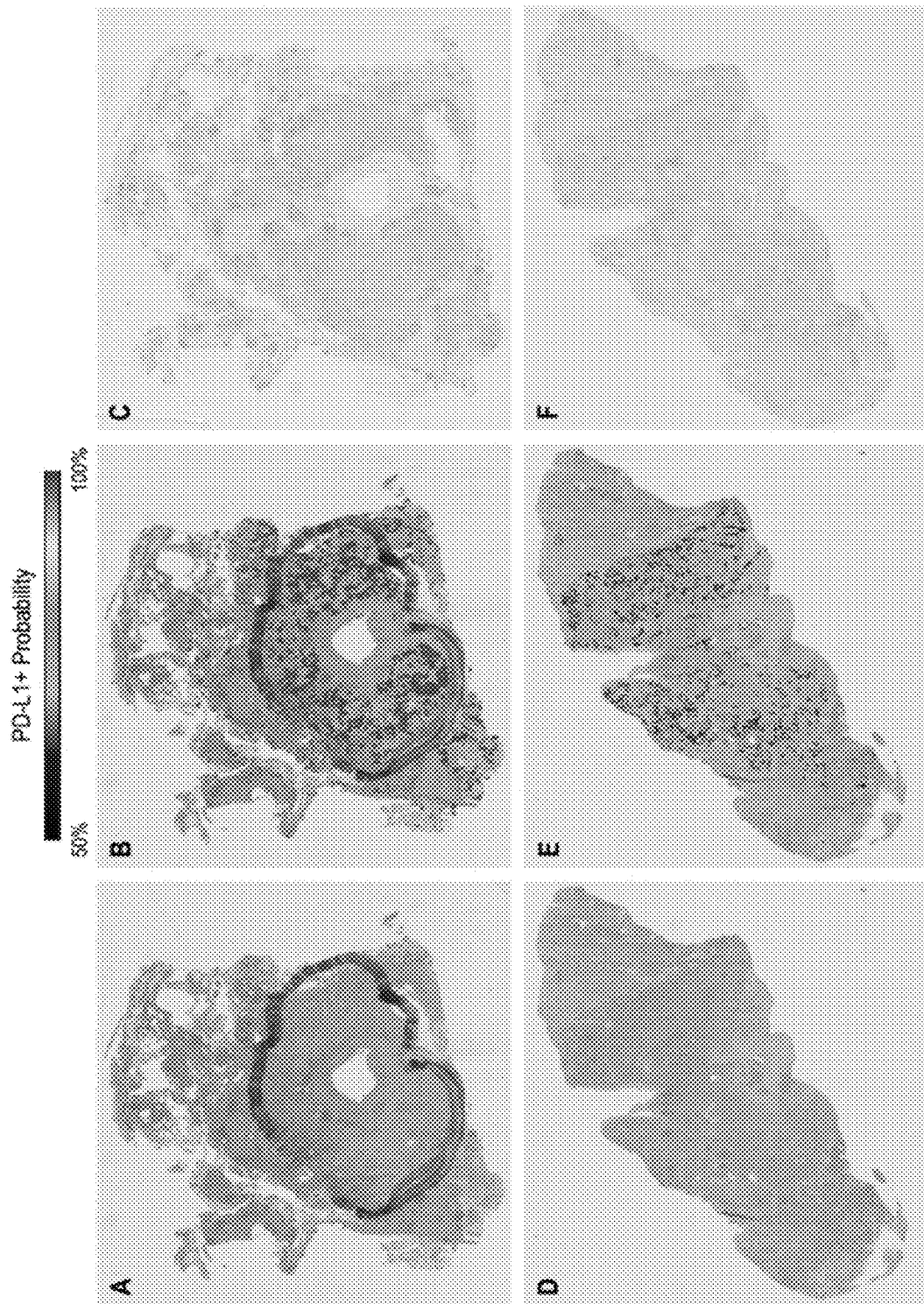
Fig. 261A-F

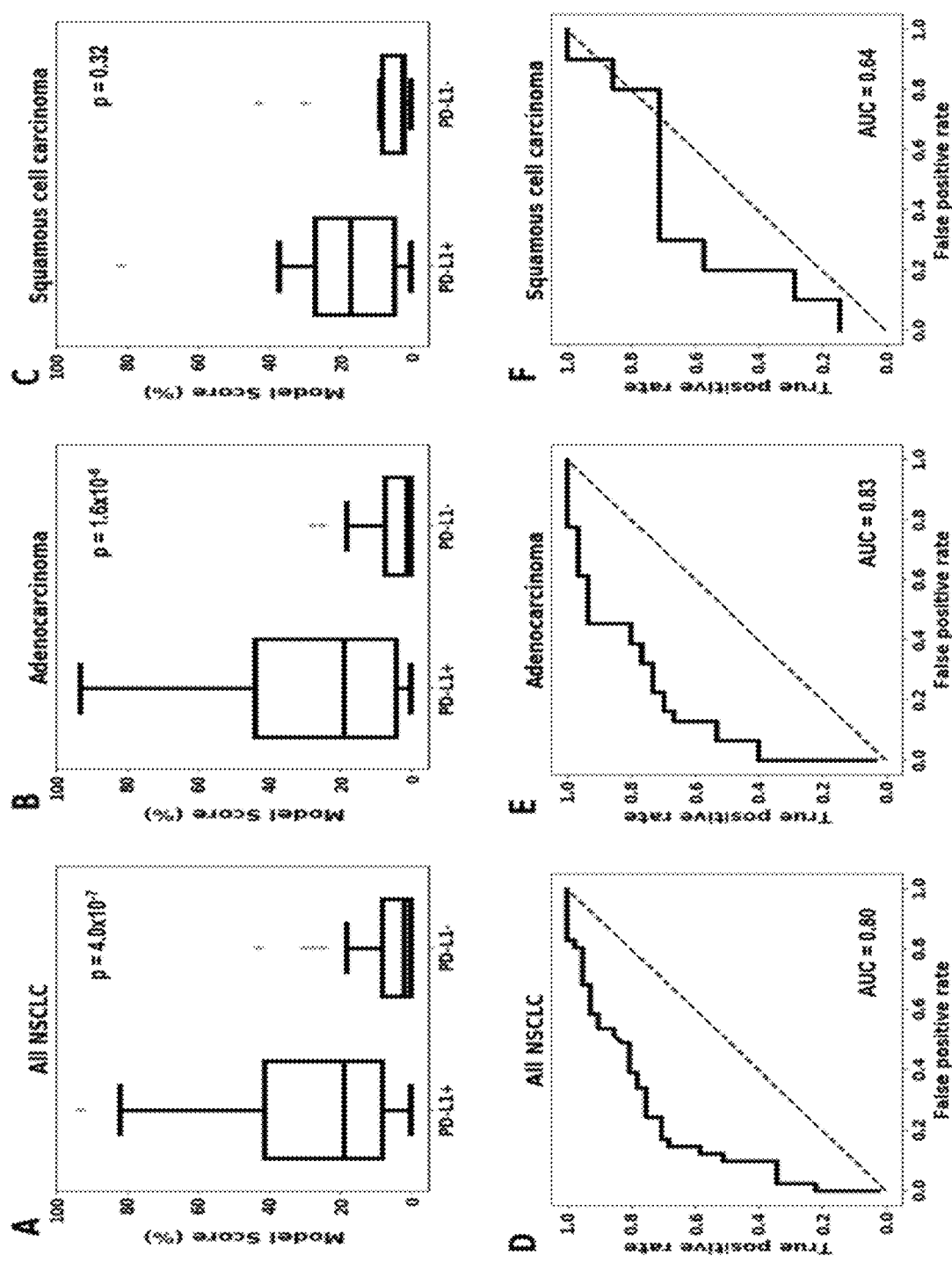
Fig. 262A-F

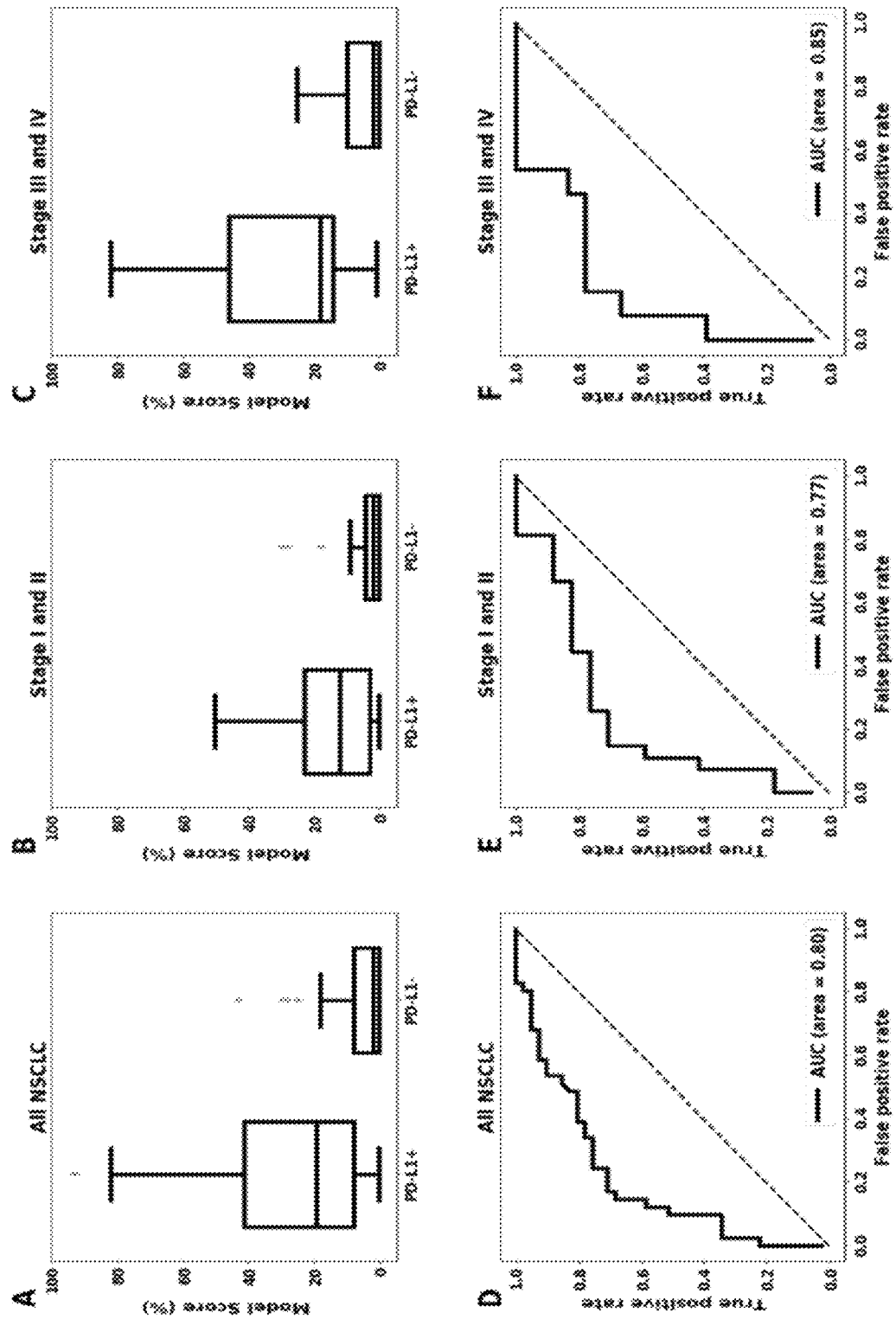
Fig. 264A-F

SITE RESEARCH EXPERIENCE

In general, what is your site's current/recent experience with oncology clinical trials?

How many oncology studies has your site participated in over the past 5 years? 

What percentage of those studies are/were interventional? 

What percentage of those studies are/were:

Phase 1 

Phase 2 

Phase 3 

Phase 4 

How many active oncology clinical trials do you currently have in the following categories:

Industry sponsored 

Investigator initiated 

Cooperative group/governmental 

Other (please specify): 

How many patients have been enrolled on oncology clinical trials in the last 5 years? 

How many of those patients received IP in the last year? 

Does your site have experience with the following types of therapies or trials:

| | | |
|---|---|---|
| Biological Agents (BSL 1-2) | ☐ Yes | ☐ No |
| CAR-T | ☐ Yes | ☐ No |
| Intra-tumoral injection (ultrasound, operating room, or interventional radiology) | ☐ Yes | ☐ No |
| Radiopharmaceutical agents | ☐ Yes | ☐ No |

Does your site have a local Institutional Review Board (IRB)? ☐ Yes ☐ No

Can your site work with a central Institutional Review Board (IRB)? ☐ Yes ☐ No

Has your site worked with Advarra or Quorum as the IRB of record in the past? ☐ Yes ☐ No What is the process for your site to establish a central IRB as the IRB of record?

Does your Facility have other review boards that need to approve the study prior to IRB/ERB/Ethics Committee submission? ☐ Yes ☐ No If yes, please describe:

Has your site had an FDA audit in the last 5 years? ☐ Yes ☐ No

If yes, did you receive an FDA form 483? ☐ Yes ☐ No

If yes, please attach the findings of the FDA form 483.

How many sponsor audits has your site had in the last 5 years?

Have you had any major findings? ☐ Yes ☐ No

If yes, please describe:

INVESTIGATIONAL PRODUCT (IP)

Can your facility receive, store, prepare, dispense, and return/destroy controlled substances and IP as required by local law?  ◯ Yes  ◯ No If no, please explain limitations (such as a central off-site pharmacy):

Would your site ever need to send IP to or receive IP from any affiliate site(s)?  ◯ Yes  ◯ No If yes, please explain:

What types of IP administration can your site support? Please check all that apply:
◯ Injection  ◯ IV  ◯ Suspension  ◯ Intrathecal  ◯ Other (please specify):

Pharmacy Information

Pharmacy Name

Contact First Name                         Last Name

Address

Floor/Room/Suite

Additional Address Info

Country

State/Province/Region

City                                        Zip/Postal Code

Phone Number                                Fax Number

Email Address

RECORDS AND DOCUMENTATION

For trials, what type of source documents will be used?
☐ Paper ☐ Electronic ☐ Both Does your site have secure storage for patient study records?
☐ Yes ☐ No What is your site's plan for long term storage of patient records?

What type of Electronic Health Records (EHR) / Electronic Medical Records (EMR) system do you use?

What Electronic Data Capture (EDC) systems has your staff used for clinical trials? Please check all that apply:
☐ None ☐ Inform ☐ Rave ☐ Oracle Remote Data Capture (RDC)
☐ Other (please specify):

SITE CAPABILITIES　　　　　　　　　　　　　　　　　　　　　11700

Can your site support patient visits and all study activities on weekends ☐ Yes ☐ No
or after hours?

If no, please explain any limitations:
[_____]

Can your site support in-patient admissions for research studies? ☐ Yes ☐ No

What languages do you need for consents or other patient-facing documents?
[_____]

Does your site have access to translators and/or translation support ☐ Yes ☐ No
for study activities (such as consent or other study instructions)?

Lab:
Does your facility contain and use a local lab? ☐ Yes ☐ No

| Field | |
|---|---|
| Lab Name | |
| Contact First Name | Last Name |
| Address | |
| Floor/Room/Suite | |
| Additional Address Info | |
| Country | |
| State/Province/Region | |
| City | Zip/Postal Code |
| Phone Number | Fax Number |
| Email Address | |

Local Lab Accreditation (Select all the apply)
☐ None   ☐ GLP   ☐ CLIA   ☐ CAP   ☐ ISO   ☐ Other (please specify):
[_____]

SITE CAPABILITIES ← 11700

Can your site support patient visits and all study activities on weekends or after hours?   ☐ Yes   ☐ No If no, please explain any limitations:

[          ]

Can your site support in-patient admissions for research studies?   ☐ Yes   ☐ No What languages do you need for consents or other patient-facing documents?

[          ]

Does your site have access to translators and/or translation support for study activities (such as consent or other study instructions)?   ☐ Yes   ☐ No Lab:
Does your facility contain and use a local lab?   ☐ Yes   ☐ No Lab Name [          ]

Contact First Name [          ]   Last Name [          ]

Address [          ]

Floor/Room/Suite [          ]

Additional Address Info [          ]

Country [          ]

State/Province/Region [          ]

City [          ]   Zip/Postal Code [          ]

Phone Number [          ]   Fax Number [          ]

Email Address [          ]

Local Lab Accreditation (Select all the apply)
☐ None   ☐ GLP   ☐ CLIA   ☐ CAP   ☐ ISO   ☐ Other (please specify):
[          ]

DIAGNOSTIC

| | | |
|---|---|---|
| Bronchoscopy | Yes | No |
| Colonoscopy | Yes | No |
| ECG/EKG Electrocardiogram | Yes | No |
| Echocardiogram (ECHO)/Stress ECHO | Yes | No |
| Electroencephalogram (EEG) | Yes | No |
| Endoscopy | Yes | No |
| Fluoroscopy | Yes | No |
| Holter Monitor | Yes | No |
| Mammography | Yes | No |
| Multigated Acquisition (MUGA) | Yes | No |
| Nuclear medicine (e.g. Bone scan, thyroid scan, thallium cardiac stress test) | Yes | No |

GENERAL

| | | |
|---|---|---|
| Centrifuge | Yes | No |
| Refrigerated Centrifuge | Yes | No |
| Refrigerator (2 to 8 Degrees C) | Yes | No |
| Freezer (-20 to -30 Degrees C) | Yes | No |
| Freezer (-70 to -80 Degrees C) | Yes | No |
| Freezer (Liquid Nitrogen -135 Degrees C) | Yes | No |
| For all temperature monitored equipment, does the equipment include min/max monitoring with backup power, temperature alarm, and a temperature log? | Yes | No |

If no, please explain any limitations:

SOPs

Please confirm that your site has appropriate standard operating procedures (SOPs) for each of the below categories:

| | Yes | No |
|---|---|---|
| Clinic policies and procedures | Yes | No |
| Equipment maintenance and calibration | Yes | No |
| FDA audit readiness and response | Yes | No |
| Informed consent, including minors and vulnerable populations | Yes | No |
| IP records, dispensing, storage, and destruction | Yes | No |
| IRB/Regulatory | Yes | No |
| Monitor visits | Yes | No |
| PI responsibilities and delegation of authority | Yes | No |
| Privacy and records management | Yes | No |
| Protocol implementation | Yes | No |
| Staff training and retraining | Yes | No |
| Subject recruitment | Yes | No |
| Toxicity management and safety reporting | Yes | No |

If no, please explain:

SITE CONTACT LIST

Cancer Center Leader
Name
Email

Expected PI(s)
Name
Email

Coordinator(s)
Name
Email

Regulatory Contact
Name
Email

Budget/Contract
Name
Email

Other
Name
Email

Clinical Trials/Research Leader
Name
Email

Other Clinical Trial Administrator(s)
Name
Email

Lead Research Nurse
Name
Email

Primary Legal Contact
Name
Email

IT Contact
Name
Email

Fig. 300

|  | Gene A | Gene B | Gene C | Gene D | Gene E | Gene F | ... |
|---|---|---|---|---|---|---|---|
| Patient 1 | 1 | 0 | 0 | 1 | 1 | 1 |  |
| Patient 2 | 1 | 0 | 0 | 1 | 1 | 0 |  |
| Patient 3 | 1 | 0 | 1 | 0 | 0 | 0 |  |
| Patient 4 | 0 | 1 | 0 | 0 | 0 | 0 |  |
| Patient 5 | 1 | 1 | 0 | 0 | 0 | 0 |  |
| ... |  |  |  |  |  |  |  |

Fig. 307A

|  | Patient 1 | Patient 2 | Patient 3 | Patient 4 | Patient 5 |
|---|---|---|---|---|---|
| Patient 1 | 1 | 0.87 | 0.7 | 0.17 | 0.71 |
| Patient 2 | 0.87 | 1 | 0.79 | 0.21 | 0.8 |
| Patient 3 | 0.7 | 0.79 | 1 | 0.23 | 0.9 |
| Patient 4 | 0.17 | 0.21 | 0.23 | 1 | 0.5 |
| Patient 5 | 0.71 | 0.8 | 0.9 | 0.5 | 1 |

Fig. 307D

Normal — A.10
    AAAGTCTGACATCCTGAAA    (SEQ ID NO:3)

Insertion
    Bi-nucleotide — A.20
        AAAGTGTGTCTGACATCCTGAAA    (SEQ ID NO:4)
    Tri-nucleotide — A.30
        AAAGTCGTCGTCTGACATCCTGAAA    (SEQ ID NO:5)
    Gene — A.40
        AAAGTCTGACATCCTGGTCTGACATCCTGAAA    (SEQ ID NO:6)

Deletion
    Sequence — A.50
        AAAGTC_ATCCTGAAA    (SEQ ID NO:7)
    Gene — A.60
        AAA_TGAAA Inversion
    Sequence — A.70
        AAAGCAGTCTATCCTGAAA    (SEQ ID NO:8)
    Gene — A.80
        AAAGTCCTACAGTCTGAAA    (SEQ ID NO:9)

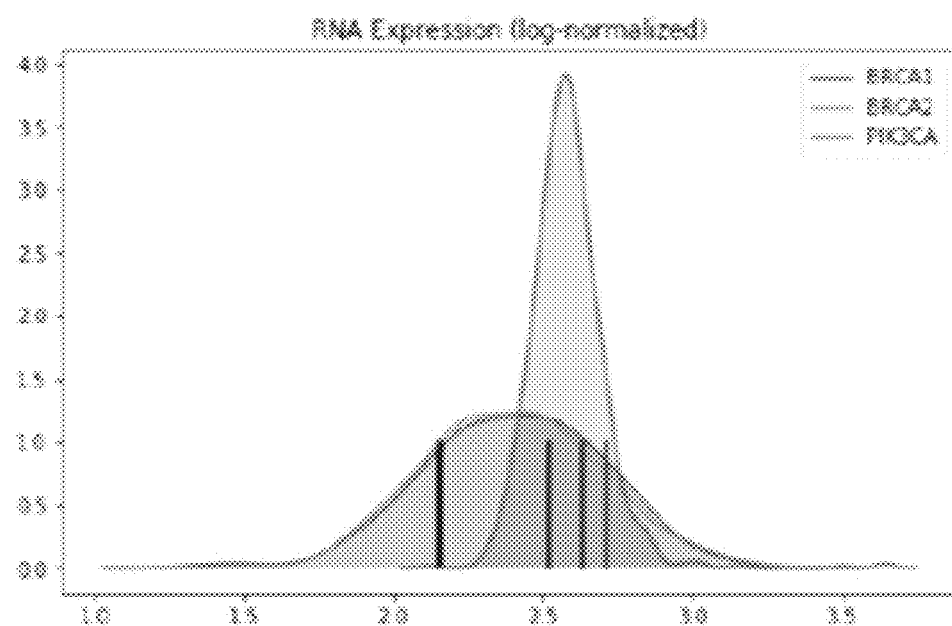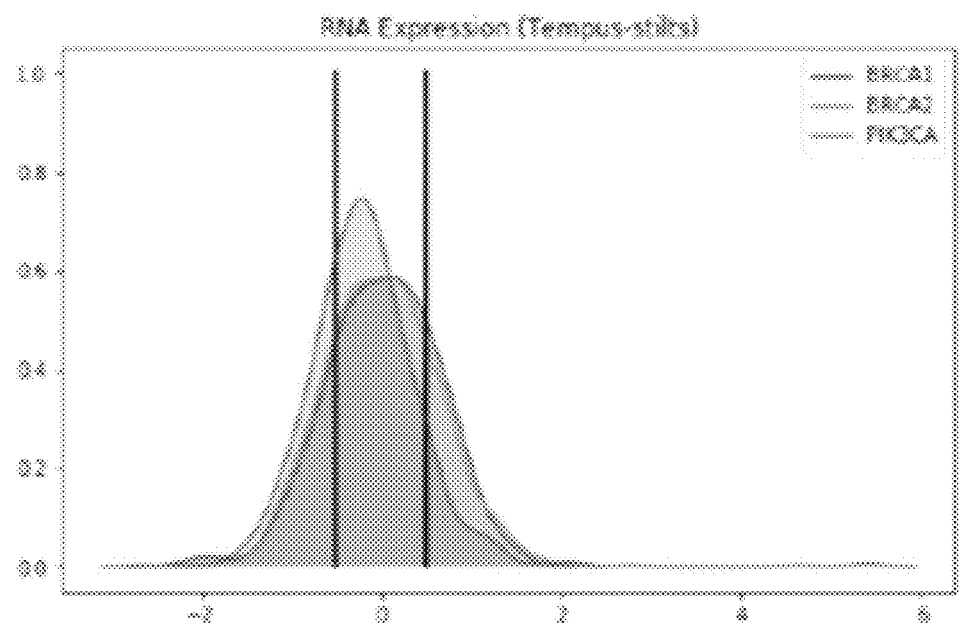
Fig. 337A-B

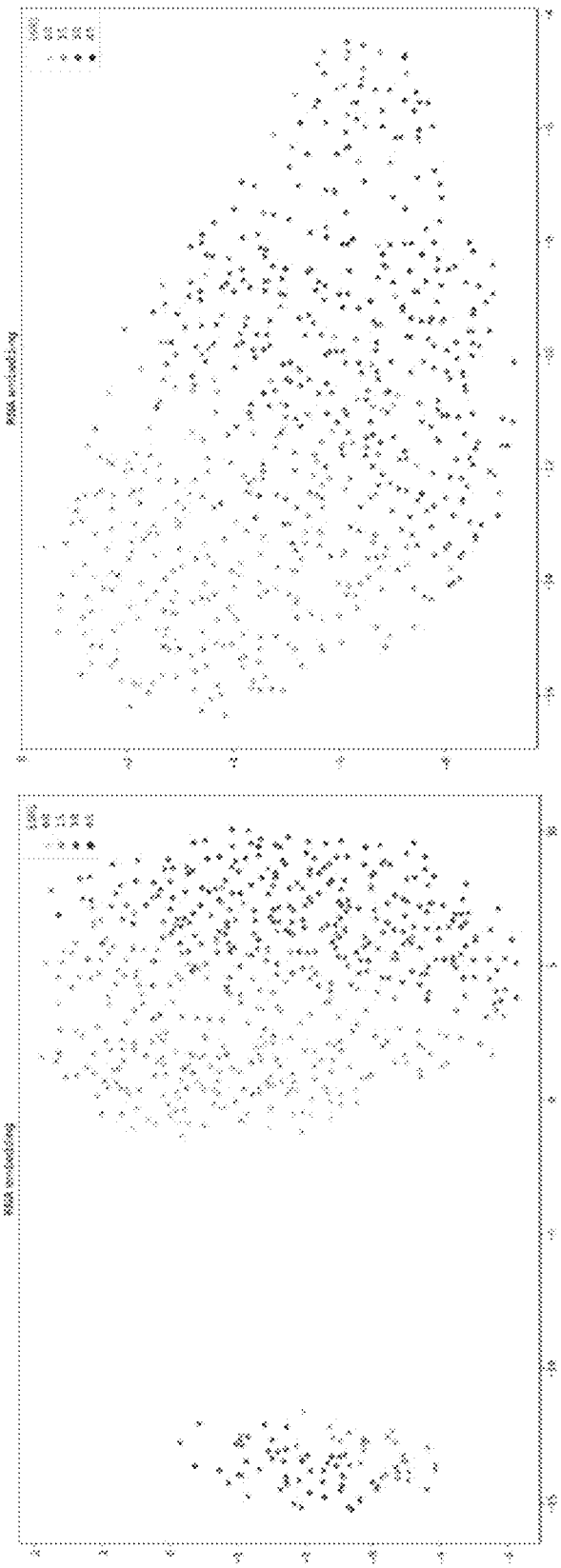
Fig. 338A-B

| Cancer Type | Primary versus Metastatic Recurrence | Sex | Self-Reported Race or Ethnicity |
|---|---|---|---|
| Brain, n=50 | Primary, n=50<br>Recurrent, n=0 | Female, n=20<br>Male, n=30 | African American/Black, n=2<br>Asian, n=0<br>Hispanic, n=0<br>Mixed-race, n=1<br>White, n=17<br>Unknown, n=30 |
| Breast, n=50 | Primary, n=44<br>Recurrent, n=6 | Female, n=50<br>Male, n=0 | African American/Black, n=4<br>Asian, n=0<br>Hispanic, n=5<br>Mixed-race, n=1<br>White, n=31<br>Unknown, n=9 |
| Colorectal, n=50 | Primary, n=44<br>Recurrent, n=6 | Female, n=22<br>Male, n=28 | African American/Black, n=4<br>Asian, n=0<br>Hispanic, n=4<br>Mixed-race, n=1<br>White, n=21<br>Unknown, n=20 |
| Endometrial, n=50 | Primary, n=45<br>Recurrent, n=5 | Female, n=50<br>Male, n=0 | African American/Black, n=8<br>Asian, n=1<br>Hispanic, n=2<br>Mixed-race, n=0<br>White, n=26<br>Unknown, n=13 |
| Lung, n=50 | Primary, n=45<br>Recurrent, n=5 | Female, n=28<br>Male, n=22 | African American/Black, n=1<br>Asian, n=0<br>Hispanic, n=1<br>Mixed-race, n=0<br>White, n=22<br>Unknown, n=26 |
| Ovarian, n=50 | Primary, n=46<br>Recurrent, n=4 | Female, n=50<br>Male, n=0 | African American/Black, n=4<br>Asian, n=1<br>Hispanic, n=2<br>Mixed-race, n=0<br>White, n=28<br>Unknown, n=15 |
| Pancreatic, n=50 | Primary, n=44<br>Recurrent, n=6 | Female, n=24<br>Male, n=26 | African American/Black, n=3<br>Asian, n=0<br>Hispanic, n=1<br>Mixed-race, n=0<br>White, n=19<br>Unknown, n=27 |
| Prostate, n=50 | Primary, n=47<br>Recurrent, n=3 | Female, n=0<br>Male, n=50 | African American/Black, n=1<br>Asian, n=0<br>Hispanic, n=2<br>Mixed-race, n=1<br>White, n=31<br>Unknown, n=15 |
| Rare, n=50 | Primary, n=47<br>Recurrent, n=3 | Female, n=19<br>Male, n=31 | African American/Black, n=3<br>Asian, n=0<br>Hispanic, n=2<br>Mixed-race, n=0<br>White, n=21<br>Unknown, n=24 |
| Unknown, n=50 | Primary, n=49<br>Recurrent, n=1 | Female, n=25<br>Male, n=25 | African American/Black, n=5<br>Asian, n=0<br>Hispanic, n=4<br>Mixed-race, n=0<br>White, n=24<br>Unknown, n=17 |

Fig. 345

| Evidence Tier | Number of patients | Percentage of patients |
|---|---|---|
| IA | 77 | 15.4 |
| IB | 72 | 14.4 |
| IIC | 154 | 30.8 |
| IID | 155 | 31 |

Fig. 367

| Gene | Evidence level | PubMed reference number (PMID) |
|---|---|---|
| AKT2 | preclinical | 22842582 |
| AR | preclinical | 24356815 |
| CCND1 | preclinical | 19874578 |
| CCNE1 | preclinical | 26204491 |
| CDKN2A | clinical research | 23746666 |
| EGFR | clinical research | 24039832, 22056021 |
| ERBB2 | clinical research | 27108243, 20728210, 21172893, 12525520, 20003286 |
| ERBB2 | preclinical | 23816254, 23204226 |
| ERBB2 | case study | 21380780, 25601188, 27044931 |
| ERBB3 | clinical research | 25520391 |
| ERBB3 | preclinical | 25216528, 25916654 |
| FGFR1 | preclinical | 24771645, 26015511, 26637881 |
| FGFR1 | case study | 27535980 |
| MET | clinical research | 25434379, 28696366, 25584489, 26439803, 24101053 |
| MET | preclinical | 21864475, 24140933 |
| MET | case study | 22389872, 8077049 |
| MGMT | clinical research | 17442989 |
| MYC | preclinical | 25505253, 23461061 |
| MYC | case study | 28089283 |
| MYCL | preclinical | 27276402 |
| NRG1 | clinical research | 26137564 |
| NRG1 | preclinical | 25542901, 21840482, 20227043, 26204491 |
| NRG1 | case study | 28573357 |
| PAX8 | consensus | 24800185 |
| RET | preclinical | 26686064 |
| RET | case study | 20696054 |

GERMLINE VARIANT DETAILS

CLINICAL HISTORY

- Release from: Family Center ICU

- Biopsy: Lung
  MRI: Abdomen

- Admitted to: Family Center ICU

- Started Palbociclib
  Ended Gemcitabine

- CT: Chest

- Started Gemcitabine

- Diagnosis: Pancreatic ductal adenocarcinoma T2 N0 M0
  CT: Chest
  Pancreaticoduodenectomy
  Family Center ICU
  Comorbidity: Diabetes

| Gene | Does Tempus sequence {Gene}? | Is {Gene} included on the Tempus xT panel? | Is {Gene} included on the Tempus xE panel? |
|---|---|---|---|
| ABCB1 | TRUE | TRUE | FALSE |
| ABCB4 | FALSE | FALSE | FALSE |
| ABCC3 | TRUE | TRUE | FALSE |
| ABL1 | TRUE | TRUE | FALSE |
| ABL2 | TRUE | TRUE | FALSE |
| ACTA2 | TRUE | TRUE | FALSE |
| ACVR1B | TRUE | TRUE | FALSE |
| AJUBA | TRUE | TRUE | FALSE |
| AKT1 | TRUE | TRUE | TRUE |
| AKT2 | TRUE | TRUE | TRUE |
| AKT3 | TRUE | TRUE | FALSE |
| ALK | TRUE | TRUE | TRUE |
| ALK4 | FALSE | FALSE | FALSE |
| AMER1 | TRUE | TRUE | FALSE |
| APC | TRUE | TRUE | TRUE |
| APLNR | TRUE | TRUE | FALSE |
| APOB | TRUE | TRUE | FALSE |
| AR | TRUE | TRUE | TRUE |
| ARAF | TRUE | TRUE | TRUE |
| ARHGAP26 | TRUE | TRUE | FALSE |
| ARHGAP35 | TRUE | TRUE | FALSE |
| ARID1A | TRUE | TRUE | TRUE |
| ARID1B | TRUE | TRUE | FALSE |
| ARID2 | TRUE | TRUE | FALSE |
| ARID5B | TRUE | TRUE | FALSE |
| ASNS | TRUE | TRUE | FALSE |
| ASXL1 | TRUE | TRUE | FALSE |

Fig. 432C

| Gene | Somatic | Mutation Type | Variant | Drug | My patient has a Somatic Gene fusion Mutation Type mutation. Can I give them |
|---|---|---|---|---|---|
| BRCA2 | | | | Mitomycin C | An in vivo study in 2005 found that BRCA2 mutations of CAPAN1 treated with |
| CDKN2A | | | | Palbociclib | The TAPUR study found that pancreatic cancer patients with a CDKN2A mutation do |
| EGFR | | | | Erlotinib | A study in 2011 followed a metastatic pancreatic cancer patient with an EGFR |
| EGFR | | | | Afatinib | A 2016 study on pancreatic cancer and Afatinib found that the drug showed |
| FANCC | | | | Mitomycin C | An in vivo study in 2005 found that BRCA2 mutations of CAPAN1 treated with |
| FANCG | | | | Mitomycin C | An in vivo study in 2005 found that BRCA2 mutations of CAPAN1 treated with |
| HER2 | | missense | | Pertuzumab | A 2014 in vivo and in vitro study on pancreatic cancer found that HER3 expression is |
| HER2 | | | | Larotrectinib | |
| HER3 | | overexpression | | Pertuzumab | A 2014 in vivo and in vitro study on pancreatic cancer found that HER3 expression is |
| HER3 | | | | Cetuximab | |
| HER3 | | | | Iopofosine | |
| KRAS | | | | Gemcitabine | Verpafenib with a Pan-RAF inhibitor has been found to be effective in preclinical trials |
| KRAS | | | codon 12 | Larotrectinib | A study in 2013 found that advanced pancreatic cancer patients with KRAS codon 12 |
| MTFK | | gene fusion positive | | Larotrectinib | Larotrectinib can be used as a second-line treatment or treatment for a recurrence in |
| NTRK1 | | missense | | Larotrectinib | |
| NTRK1 and ERBB3 | | missense | | | |
| STK11 | | | | Docetaxel | In 2008, a patient with P53 was diagnosed with acinar cell carcinoma of the pancreas |

Fig. 432D

SEQUENCE LISTING

```
<160> NUMBER OF SEQ ID NOS: 10

<210> SEQ ID NO 1
<211> LENGTH: 13
<212> TYPE: DNA
<213> ORGANISM: Artificial Sequence
<220> FEATURE:
<223> OTHER INFORMATION: Hypothetical- Model gene

<400> SEQUENCE: 1
gtctgacatc ctg                                                        13

<210> SEQ ID NO 2
<211> LENGTH: 13
<212> TYPE: DNA
<213> ORGANISM: Artificial Sequence
<220> FEATURE:
<223> OTHER INFORMATION: Hypothetical- Example of end-to-end gene
      reversal

<400> SEQUENCE: 2
gtcctacagt ctg                                                        13

<210> SEQ ID NO 3
<211> LENGTH: 19
<212> TYPE: DNA
<213> ORGANISM: Artificial Sequence
<220> FEATURE:
<223> OTHER INFORMATION: Hypothetical- Model gene

<400> SEQUENCE: 3
aaagtctgac atcctgaaa                                                  19
```

```
<210> SEQ ID NO 4
<211> LENGTH: 23
<212> TYPE: DNA
<213> ORGANISM: Artificial Sequence
<220> FEATURE:
<223> OTHER INFORMATION: Hypothetical- Example of bi-nucleotide
      insertion

<400> SEQUENCE: 4
aaagtgtgtc tgacatcctg aaa                                              23

<210> SEQ ID NO 5
<211> LENGTH: 25
<212> TYPE: DNA
<213> ORGANISM: Artificial Sequence
<220> FEATURE:
<223> OTHER INFORMATION: Hypothetical- Example of tri-nucleotide
      insertion

<400> SEQUENCE: 5
aaagtcgtcg tctgacatcc tgaaa                                            25

<210> SEQ ID NO 6
<211> LENGTH: 32
<212> TYPE: DNA
<213> ORGANISM: Artificial Sequence
<220> FEATURE:
<223> OTHER INFORMATION: Hypothetical- Model gene with insertion

<400> SEQUENCE: 6
aaagtctgac atcctggtct gacatcctga aa                                    32

<210> SEQ ID NO 7
<211> LENGTH: 15
<212> TYPE: DNA
<213> ORGANISM: Artificial Sequence
<220> FEATURE:
<223> OTHER INFORMATION: Hypothetical- Example of deletion
<220> FEATURE:
<221> NAME/KEY: misc_feature
<222> LOCATION: (6)..(7)
<223> OTHER INFORMATION: Deletion site

<400> SEQUENCE: 7
aaagtcatcc tgaaa                                                       15

<210> SEQ ID NO 8
<211> LENGTH: 19
<212> TYPE: DNA
<213> ORGANISM: Artificial Sequence
<220> FEATURE:
<223> OTHER INFORMATION: Hypothetical- Example of inversion

<400> SEQUENCE: 8
aaagcagtct atcctgaaa                                                   19

<210> SEQ ID NO 9
<211> LENGTH: 19
<212> TYPE: DNA
<213> ORGANISM: Artificial Sequence
<220> FEATURE:
<223> OTHER INFORMATION: Hypothetical- Model gene with inversion

<400> SEQUENCE: 9
aaagtcctac agtctgaaa                                                   19
```

```
<210> SEQ ID NO 10
<211> LENGTH: 148
<212> TYPE: DNA
<213> ORGANISM: Artificial Sequence
<220> FEATURE:
<223> OTHER INFORMATION: Hypothetical- Model gene target region

<400> SEQUENCE: 10
aaagtctgac atcctgaaaa aagtctgaca tcctgaaaaa agtctgacat cctgaaaaaa      60
gtctgacatc ctgaaaaaag tctgacatcc tgaaaaaagt ctgacatcct gaaaaaagtc    120
tgacatcctg aaaaagtct gacatcct                                         148
```

DATA BASED CANCER RESEARCH AND TREATMENT SYSTEMS AND METHODS

PRIOR APPLICATIONS INCORPORATED BY REFERENCE

Each of the following patent applications is incorporated herein in its entirety by reference for any and all permissible purposes. U.S. Provisional Patent Application No. 62/735,349, filed Sep. 24, 2018. U.S. Provisional Patent Application No. 62/745,946, titled "Microsatellite Instability Determination System and Related Methods", filed Oct. 15, 2018. U.S. Provisional Patent Application No. 62/746,997, titled "Data Based Cancer Research and Treatment Systems and Methods", filed Oct. 17, 2018. U.S. Provisional Patent Application No. 62/753,504, titled "User Interface, System, and Method for Cohort Analysis", filed Dec. 31, 2018. U.S. Provisional Patent Application No. 62/774,854, titled "System and Method Including Machine Learning for Clinical Concept Identification, Extraction, and Prediction", filed Dec. 3, 2018. U.S. Provisional Patent Application No. 62/786,739, titled "A Method and Process for Predicting and Analyzing Patient Cohort Response, Progression, and Survival", filed Oct. 31, 2018. U.S. Provisional Patent Application No. 62/786,756, titled "Transcriptome Deconvolution of Metastatic Tissue Samples", filed Dec. 31, 2018. U.S. Provisional Patent Application No. 62/787,047, titled "Artificial Intelligence Segmentation of Tissue Images", filed Dec. 31, 2018. U.S. Provisional Patent Application No. 62/787,249, titled "Automated Quality Assurance Testing of Structured Clinical Data", filed Dec. 31, 2018. U.S. Provisional Patent Application No. 62/824,039, titled "PD-L1 Prediction Using H&E Slide Images", filed Apr. 17, 2019. U.S. Provisional Patent Application No. 62/835,336, titled "Collaborative Intelligence Method and System", filed Mar. 26, 2019. U.S. Provisional Patent Application No. 62/835,339, titled "Collaborative Artificial Intelligence Method and Apparatus", filed Apr. 17, 2019. U.S. Provisional Patent Application No. 62/835,489, titled "Systems and Methods for Interrogating Raw Clinical Documents for Characteristic Data", filed Apr. 17, 2019. U.S. Provisional Patent Application No. 62/854,400, titled "A Pan-Cancer Model to Predict the Pd-L1 Status of a Cancer Cell Sample Using Rna Expression Data and Other Patient Data", filed May 30, 2019. U.S. Provisional Patent Application No. 62/855,646, titled "Collaborative Artificial Intelligence Method and Apparatus", filed Jun. 24, 2019. U.S. Provisional Patent Application No. 62/855,913, titled "Systems and Methods of Clinical Trial Evaluation", filed May 31, 2019. U.S. Provisional Patent Application No. 62/873,693, titled "Adaptive Order Fulfillment and Tracking Methods and Systems", filed Jul. 12, 2019. U.S. Provisional Patent Application No. 62/882,466, titled "Data-based Mental Disorder Research and Treatment Systems and Methods", filed Aug. 2, 2019. U.S. Provisional Patent Application No. 62/888,163, titled "Cellular Pathway Report", filed Aug. 16, 2019. U.S. Provisional Patent Application No. 62/902,950, titled "System and Method for Expanding Clinical Options for Cancer Patients using Integrated Genomic Profiling", filed Sep. 19, 2019. U.S. patent application Ser. No. 16/289,027, titled "Mobile Supplementation, Extraction, and Analysis of Health Records", filed Feb. 28, 2019. U.S. patent application Ser. No. 16/412,362, titled "A Generalizable and Interpretable Deep Learning Framework for Predicting MSI From Histopathology Slide Images", filed May 14, 2019. U.S. patent application Ser. No. 16/581,706, titled "Methods of Normalizing and Correcting RNA Expression Data", filed Sep. 24, 2019. U.S. provisional application No. 62/890,178, titled "Unsupervised Learning and Prediction of Line of Therapy From High-Dimensional Longitudinal Medications Data", filed on Aug. 22, 2019.

STATEMENT REGARDING FEDERALLY SPONSORED RESEARCH OR DEVELOPMENT

Not applicable.

SEQUENCE LISTING

A Sequence Listing accompanies this application and is submitted as an ASCII text file of the sequence listing named "166619_00035_ST25.txt" which is 2.74 KB in size and was created on Apr. 28, 2020. The sequence listing is electronically submitted via EFS-Web and is incorporated herein by reference in its entirety.

INCORPORATION-BY-REFERENCE OF MATERIAL SUBMITTED AS A TEXT FILE VIA THE OFFICE ELECTRONIC FILING SYSTEM (EFS-WEB)

The instant application contains a table that has been submitted in ASCII format via EFS-web and is hereby incorporated by reference in its entirety. Said ASCII copy, created Oct. 17, 2019, is named TABLE-1-List-of-genes.txt and is 147,138 bytes in size.

LENGTHY TABLES

The patent contains a lengthy table section. A copy of the table is available in electronic form from the USPTO web site (https://seqdata.uspto.gov/?pageRequest=docDetail&DocID=US11705226B2). An electronic copy of the table will also be available from the USPTO upon request and payment of the fee set forth in 37 CFR 1.19(b)(3).

BACKGROUND OF THE DISCLOSURE

Data Based Cancer Research and Treatment Systems and Methods

The present invention relates to systems and methods for obtaining and employing data related to physical and genomic patient characteristics as well as diagnosis, treatments and treatment efficacy to provide a suite of tools to healthcare providers, researchers and other interested parties enabling those entities to develop new cancer state-treatment-results insights and/or improve overall patient healthcare and treatment plans for specific patients.

The present disclosure is described in the context of a system related to cancer research, diagnosis, treatment and results analysis. Nevertheless, it should be appreciated that the present disclosure is intended to teach concepts, features and aspects that will be useful in many different health related contexts and therefore the specification should not be considered limited to a cancer related systems unless specifically indicated for some system aspect. Thus, the concepts disclosed herein should be considered disease agnostic unless indicated otherwise and therefore may be implemented to support physicians dealing with other disease states including but not limited to depression, diabetes, Parkinson's, Alzheimer's, etc. For example, a depression related system is described in part in U.S. provisional patent application No. 62/882,466 which was filed on Aug. 2, 2019 which is titled "Data-Based Mental Disorder Research and Treatment Systems and Methods" which is incorporated herein in its entirety by reference.

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, data abstractors, physicians, pathologists, radiologists, data scientists, and many other persons with specialized skill sets.

The term "physician" will be used to refer generally to any health care provider including but not limited to a primary care physician, a medical specialist, a physician, a nurse, a medical assistant, etc., The term "researcher" will be used to refer generally to any person that performs research including but not limited to a pathologist, a radiologist, a physician, a data scientist, or some other health care provider. One person may operate both a physician and a researcher while others may simply operate in one of those capacities.

The phrase "system specialist" will be used generally to refer to any provider employee that operates within the disclosed systems to collect, develop, analyze or otherwise process system data, tissue samples or other information types (e.g., medical images) to generate any intermediate system work product or final work product where intermediate work product includes any data set, conclusions, tissue or other samples, grown tissues or samples, or other information for consumption by one or more other system specialists and where final work product includes data, conclusions or other information that is placed in a final or conclusory report for a system client or that operates within the system to perform research, to adapt the system to changing needs, data types or client requirements. For instance, the phrase "abstractor specialist" will be used to refer to a person that consumes data available in clinical records provided by a physician to generate normalized and structured data for use by other system specialists, the phrase "programming specialist" will be used to refer to a person that generates or modifies application program code to accommodate new data types and or clinical insights, etc.

The phrase "system user" will be used generally to refer to any person that uses the disclosed system to access or manipulate system data for any purpose and therefore will generally include physicians and researchers that work for the provider or that partner with the provider to perform services for patients or for other partner research institutions as well as system specialists that work for the provider.

The phrase "cancer state" will be used to refer to a cancer patient's overall condition including diagnosed cancer, location of cancer, cancer stage, other cancer characteristics (e.g., tumor characteristics), other user conditions (e.g., age, gender, weight, race, habits (e.g., smoking, drinking, diet)), other pertinent medical conditions (e.g., high blood pressure, dry skin, other diseases, etc.), medications, allergies, other pertinent medical history, current side effects of cancer treatments and other medications, etc.

The term "consume" will be used to refer to any type of consideration, use, modification, or other activity related to any type of system data, tissue samples, etc., whether or not that consumption is exhaustive (e.g., used only once, as in the case of a tissue sample that cannot be reproduced) or inexhaustible so that the data, sample, etc., persists for consumption by multiple entities (e.g., used multiple times as in the case of a simple data value).

The term "consumer" will be used to refer to any system entity that consumes any system data, samples, or other information in any way including each of specialists, physicians, researchers, clients that consume any system work product, and software application programs or operational code that automatically consume data, samples, information or other system work product independent of any initiating human activity.

The phrase "treatment planning process" will be used to refer to an overall process that includes one or more sub-processes that process clinical and other patient data and samples (e.g., tumor tissue) to generate intermediate data deliverables and eventually final work product in the form of one or more final reports provided to system clients. These processes typically include varying levels of exploration of treatment options for a patient's specific cancer state but are typically related to treatment of a specific patient as opposed to more general exploration for the purpose of more general research activities. Thus, treatment planning may include data generation and processes used to generate that data, consideration of different treatment options and effects of those options on patient illness, etc., resulting in ultimate prescriptive plans for addressing specific patient ailments.

Medical treatment prescriptions or plans are typically based on an understanding of how treatments affect illness (e.g., treatment results) including how well specific treatments eradicate illness, duration of specific treatments, duration of healing processes associated with specific treatments and typical treatment specific side effects. Ideally treatments result in complete elimination of an illness in a short period with minimal or no adverse side effects. In some cases cost is also a consideration when selecting specific medical treatments for specific ailments.

Knowledge about treatment results is often based on analysis of empirical data developed over decades or even longer time periods during which physicians and/or researchers have recorded treatment results for many different patients and reviewed those results to identify generally successful ailment specific treatments. Researchers and physicians give medicine to patients or treat an ailment in some other fashion, observe results and, if the results are good, the researchers and physicians use the treatments again to treat similar ailments. If treatment results are bad, a researcher foregoes prescribing the associated treatment for a next encountered similar ailment and instead tries some other treatment, hopefully based on prior treatment efficacy data. Treatment results are sometimes published in medical journals and/or periodicals so that many physicians can benefit from a treating physician's insights and treatment results.

In many cases treatment results for specific illnesses vary for different patients. In particular, in the case of cancer treatments and results, different patients often respond differently to identical or similar treatments. Recognizing that different patients experience different results given effectively the same treatments in some cases, researchers and physicians often develop additional guidelines around how to optimize ailment treatments based on specific patient cancer state. For instance, while a first treatment may be best for a young relatively healthy woman suffering colon cancer, a second treatment associated with fewer adverse side effects may be optimal for an older relatively frail man with a similar colon same cancer diagnosis. In many cases patient conditions related to cancer state may be gleaned from clinical medical records, via a medical examination and/or via a patient interview, and may be used to develop a personalized treatment plan for a patient's specific cancer state. The idea here is to collect data on as many factors as possible that have any cause-effect relationship with treatment results and use those factors to design optimal personalized treatment plans.

In treatment of at least some cancer states, treatment and results data is simply inconclusive. To this end, in treatment of some cancer states, seemingly indistinguishable patients with similar conditions often react differently to similar treatment plans so that there is no cause and effect between patient conditions and disparate treatment results. For instance, two women may be the same age, indistinguishably physically fit and diagnosed with the same exact cancer state (e.g., cancer type, stage, tumor characteristics, etc.). Here, the first woman may respond to a cancer treatment plan well and may recover from her disease completely in 8 months with minimal side effects while the second woman, administered the same treatment plan, may suffer several severe adverse side effects and may never fully recover from her diagnosed cancer. Disparate treatment results for seemingly similar cancer states exacerbate efforts to develop treatment and results data sets and prescriptive activities. In these cases, unfortunately, there are cancer state factors that have cause and effect relationships to specific treatment results that are simply currently unknown and therefore those factors cannot be used to optimize specific patient treatments at this time.

Genomic sequencing has been explored to some extent as another cancer state factor (e.g., another patient condition) that can affect cancer treatment efficacy. To this end, at least some studies have shown that genetic features (e.g., DNA related patient factors (e.g., DNA and DNA alterations) and/or DNA related cancerous material factors (e.g., DNA of a tumor)) as well as RNA and other genetic sequencing data can have cause and effect relationships with at least some cancer treatment results for at least some patients. For instance, in one chemotherapy study using SULT1A1, a gene known to have many polymorphisms that contribute to a reduction of enzyme activity in the metabolic pathways that process drugs to fight breast cancer, patients with a SULT1A1 mutation did not respond optimally to tamoxifen, a widely used treatment for breast cancer. In some cases these patients were simply resistant to the drug and in others a wrong dosage was likely lethal. Side effects ranged in severity depending on varying abilities to metabolize tamoxifen. Raftogianis R, Zalatoris J. Walther S. *The role of pharmacogenetics in cancer therapy, prevention and risk.* Medical Science Division. 1999: 243-247. Other cases where genetic features of a patient and/or a tumor affect treatment efficacy are well known.

While corollaries between genomic features and treatment efficacy have been shown in a small number of cases, it is believed that there are likely many more genomic features and treatment results cause and effect relationships that have yet to be discovered. Despite this belief, genetic testing in cancer cases is the rare exception, not the norm, for several reasons. One problem with genetic testing is that testing is expensive and has been cost prohibitive in many cases.

Another problem with genetic testing for treatment planning is that, as indicated above, cause and effect relationships have only been shown in a small number of cases and therefore, in most cancer cases, if genetic testing is performed, there is no linkage between resulting genetic factors and treatment efficacy. In other words, in most cases how genetic test results can be used to prescribe better treatment plans for patients is unknown so the extra expense associated with genetic testing in specific cases cannot be justified. Thus, while promising, genetic testing as part of first-line cancer treatment planning has been minimal or sporadic at best.

While the lack of genetic and treatment efficacy data makes it difficult to justify genetic testing for most cancer patients, perhaps the greater problem is that the dearth of genomic data in most cancer cases impedes processes required to develop cause and effect insights between genetics and treatment efficacy in the first place. Thus, without massive amounts of genetic data, there is no way to correlate genetic factors with treatment efficacy to develop justification for the expense associated with genetic testing in future cancer cases.

Yet one other problem posed by lack of genomic data is that if a researcher develops a genomic based treatment efficacy hypothesis based on a small genomic data set in a lab, the data needed to evaluate and clinically assess the hypothesis simply does not exist and it often takes months or even years to generate the data needed to properly evaluate the hypothesis. Here, if the hypothesis is wrong, the researcher may develop a different hypothesis which, again, may not be properly evaluated without developing a whole new set of genomic data for multiple patients over another several year period.

For some cancer states treatments and associated results are fully developed and understood and are generally consistent and acceptable (e.g., high cure rate, no long term effects, minimal or at least understood side effects, etc.). In other cases, however, treatment results cause and effect data associated with other cancer states is underdeveloped and/or inaccessible for several reasons. First, there are more than 250 known cancer types and each type may be in one of first through four stages where, in each stage, the cancer may have many different characteristics so that the number of possible "cancer varieties" is relatively large which makes the sheer volume of knowledge required to fully comprehend all treatment results unwieldy and effectively inaccessible.

Second, there are many factors that affect treatment efficacy including many different types of patient conditions where different conditions render some treatments more efficacious for one patient than other treatments or for one patient as opposed to other patients. Clearly capturing specific patient conditions or cancer state factors that do or may have a cause and effect relationship to treatment results is not easy and some causal conditions may not be appreciated and memorialized at all.

Third, for most cancer states, there are several different treatment options where each general option can be customized for a specific cancer state and patient condition set. The plethora of treatment and customization options in many cases makes it difficult to accurately capture treatment and results data in a normalized fashion as there are no clear standardized guidelines for how to capture that type of information.

Fourth, in most cases patient treatments and results are not published for general consumption and therefore are simply not accessible to be combined with other treatment and results data to provide a more fulsome overall data set. In this regard, many physicians see treatment results that are within an expected range of efficacy and conclude that those results cannot add to the overall cancer treatment knowledge base and therefore those results are never published. The problem here is that the expected range of efficacy can be large (e.g., 20% of patients fully heal and recover, 40% live for an extended duration, 40% live for an intermediate duration and 20% do not appreciably respond to a treatment plan) so that all treatment results are within an "expected" efficacy range and treatment result nuances are simply lost.

Fifth, currently there is no easy way to build on and supplement many existing illness-treatment-results databases so that as more data is generated, the new data and associated results cannot be added to existing databases as evidence of treatment efficacy or to challenge efficacy. Thus, for example, if a researcher publishes a study in a medical journal, there is no easy way for other physicians or researchers to supplement the data captured in the study. Without data supplementation over time, treatment and results corollaries cannot be tested and confirmed or challenged.

Sixth, the knowledge base around cancer treatments is always growing with different clinical trials in different stages around the world so that if a physician's knowledge is current today, her knowledge will be dated within months if not weeks. Thousands of oncological articles are published each year and many are verbose and/or intellectually arduous to consume (e.g., the articles are difficult to read and internalize), especially by extremely busy physicians that have limited time to absorb new materials and information. Distilling publications down to those that are pertinent to a specific physician's practice takes time and is an inexact endeavor in many cases.

Seventh, in most cases there is no clear incentive for physicians to memorialize a complete set of treatment and results data and, in fact, the time required to memorialize such data can operate as an impediment to collecting that data in a useful and complete form. To this end, prescribing and treating physicians are busy diagnosing and treating patients based on what they currently understand and painstakingly capturing a complete set of cancer state, treatment and results data without instantaneously reaping some benefit for patients being treated in return (e.g. a new insight, a better prescriptive treatment tool, etc.) is often perceived as a "waste" of time. In addition, because time is often of the essence in cancer treatment planning and plan implementation (e.g., starting treatment as soon as possible can increase efficacy in many cases), most physicians opt to take more time attending to their patients instead of generating perfect and fulsome treatments and results data sets.

Eighth, the field of next generation sequencing ("NGS") for cancer genomics is new and NGS faces significant challenges in managing related sequencing, bioinformatics, variant calling, analysis, and reporting data. Next generation sequencing involves using specialized equipment such as a next generation gene sequencer, which is an automated instrument that determines the order of nucleotides in DNA and RNA. The instrument reports the sequences as a string of letters, called a read, which the analyst compares to one or more reference genomes of the same genes, which is like a library of normal and variant gene sequences associated with certain conditions. With no settled NGS standards, different NGS providers have different approaches for sequencing cancer patient genomics and, based on their sequencing approaches, generate different types and quantities of genomics data to share with physicians, researchers, and patients. Different genomic datasets exacerbate the task of discerning and, in some cases, render it impossible to discern, meaningful genetics-treatment efficacy insights as required data is not in a normalized form, was never captured or simply was never generated.

In addition to problems associated with collecting and memorializing treatment and results data sets, there are problems with digesting or consuming recorded data to generate useful conclusions. For instance, recorded cancer state, treatment and results data is often incomplete. In most cases physicians are not researchers and they do not follow clearly defined research techniques that enforce tracking of all aspects of cancer states, treatments and results and therefore data that is recorded is often missing key information such as, for instance, specific patient conditions that may be of current or future interest, reasons why a specific treatment was selected and other treatments were rejected, specific results, etc. In many cases where cause and effect relationships exist between cancer state factors and treatment results, if a physician fails to identify and record a causal factor, the results cannot be tied to existing cause and effect data sets and therefore simply cannot be consumed and added the overall cancer knowledge data set in a meaningful way.

Another impediment to digesting collected data is that physicians often capture cancer state, treatment and results data in forms that make it difficult if not impossible to process the collected information so that the data can be normalized and used with other data from similar patient treatments to identify more nuanced insights and to draw more robust conclusions. For instance, many physicians prefer to use pen and paper to track patient care and/or use personal shorthand or abbreviations for different cancer state descriptions, patient conditions, treatments, results and even conclusions. Using software to glean accurate information from hand written notes is difficult at best and the task is exacerbated when hand written records include personal abbreviations and shorthand representations of information that software simply cannot identify with the physician's intended meaning.

One positive development in the area of cancer treatment planning has been establishment of cancer committees or boards at cancer treating institutions where committee members routinely consider treatment planning for specific patient cancer states as a committee. To this end, it has been recognized that the task of prescribing optimized treatment plans for diagnosed cancer states is exacerbated by the fact that many physicians do not specialize in more than one or a small handful of cancer treatment options (e.g., radiation therapy, chemotherapy, surgery, etc.). For this reason, many physicians are not aware of many treatment options for specific ailment-patient condition combinations, related treatment efficacy and/or how to implement those treatment options. In the case of cancer boards, the idea is that different board members bring different treatment experiences, expertise and perspectives to bear so that each patient can benefit from the combined knowledge of all board members and so that each board member's awareness of treatment options continually expands.

While treatment boards are useful and facilitate at least some sharing of experiences among physicians and other healthcare providers, unfortunately treatment committees only consider small snapshots of treatment options and associated results based on personal knowledge of board members. In many cases boards are forced to extrapolate from "most similar" cancer states they are aware of to craft patient treatment plans instead of relying on a more fulsome collection of cancer state-treatment-results data, insights and conclusions. In many cases the combined knowledge of board members may not include one or several important perspectives or represent important experience bases so that a final treatment plan simply cannot be optimized.

To be useful cancer state, treatment and efficacy data and conclusions based thereon have to be rendered accessible to physicians, researchers and other interested parties. In the case of cancer treatments where cancer states, treatments, results and conclusions are extremely complicated and nuanced, physician and researcher interfaces have to present massive amounts of information and show many data corollaries and relationships. When massive amounts of information are presented via an interface, interfaces often become extremely complex and intimidating which can result in misunderstanding and underutilization. What is needed are well designed interfaces that make complex data sets simple to understand and digest. For instance, in the case of cancer states, treatments and results, it would be useful to provide interfaces that enable physicians to consider de-identified patient data for many patients where the data is specifically arranged to trigger important treatment and results insights. It would also be useful if interfaces had interactive aspects so that the physicians could use filters to access different treatment and results data sets, again, to trigger different insights, to explore anomalies in data sets, and to better think out treatment plans for their own specific patients.

In some cases specific cancers are extremely uncommon so that when they do occur, there is little if any data related to treatments previously administered and associated results. With no proven best or even somewhat efficacious treatment option to choose from, in many of these cases physicians turn to clinical trials.

Cancer research is progressing all the time at many hospitals and research institutions where clinical trials are always being performed to test new medications and treatment plans, each trial associated with one or a small subset of specific cancer states (e.g., cancer type, state, tumor location and tumor characteristics). A cancer patient without other effective treatment options can opt to participate in a clinical trial if the patient's cancer state meets trial requirements and if the trial is not yet fully subscribed (e.g., there is often a limit to the number of patients that can participate in a trial).

At any time there are several thousand clinical trials progressing around the world and identifying trial options for specific patients can be a daunting endeavor. Matching patient cancer state to a subset of ongoing trials is complicated and time consuming. Pairing down matching trials to a best match given location, patient and physician requirements and other factors exacerbates the task of considering trial participation. In addition, considering whether or not to recommend a clinical trial to a specific patient given the possibility of trial treatment efficacy where the treatments are by their very nature experimental, especially in light of specific patient conditions, is a daunting activity that most physicians do not take lightly. It would be advantageous to have a tool that could help physicians identify clinical trial options for specific patients with specific cancer states and to access information associated with trial options.

As described above, optimized cancer treatment deliberation and planning involves consideration of many different cancer state factors, treatment options and treatment results as well as activities performed by many different types of service providers including, for instance, physicians, radiologists, pathologists, lab technicians, etc. One cancer treatment consideration most physicians agree affects treatment efficacy is treatment timing where earlier treatment is almost always better. For this reason, there is always a tension between treatment planning speed and thoroughness where one or the other of speed and thoroughness suffers.

One other problem with current cancer treatment planning processes is that it is difficult to integrate new pertinent treatment factors, treatment efficacy data and insights into existing planning databases. In this regard, known treatment planning databases and application programs have been developed based on a predefined set of factors and insights and changing those databases and applications often requires a substantial effort on the part of a software engineer to accommodate and integrate the new factors or insights in a meaningful way where those factors and insights are properly considered along with other known factors and insights. In some cases the substantial effort required to integrate new factors and insights simply means that the new factors or insights will not be captured in the database or used to affect planning. In other cases the effort means that the new factors or insights are only added to the system at some delayed time after a software engineer has applied the required and substantial reprogramming effort. In still other cases, the required effort means that physicians that want to apply new insights and factors may attempt to do so based on their own experiences and understandings instead of in a more scripted and rules based manner. Unfortunately, rendering a new insight actionable in the case of cancer treatment is a literal matter of life and death and therefore any delay or inaccurate application can have the worst effect on current patient prognosis.

One other problem with existing cancer treatment efficacy databases and systems is that they are simply incapable of optimally supporting different types of system users. To this end, data access, views and interfaces needed for optimal use are often dependent upon what a system user is using the system for. For instance, physicians often want treatment options, results and efficacy data distilled down to simple correlations while a cancer researcher often requires much more detailed data access required to develop new hypothesis related to cancer state, treatment and efficacy relationships. In known systems, data access, views and interfaces are often developed with one consuming client in mind such as, for instance, physicians, pathologists, radiologists, a cancer treatment researcher, etc., and are therefore optimized for that specific system user type which means that the system is not optimized for other user types and cannot be easily changed to accommodate needs of those other user types.

With the advent of NGS it has become possible to accurately detect genetic alterations in relevant cancer genes in a single comprehensive assay with high sensitivity and specificity. However, the routine use of NGS testing in a clinical context faces several challenges. First, many tissue samples include minimal high quality DNA and RNA required for meaningful testing. In this regard, nearly all clinical specimens comprise formalin fixed paraffin embedded tissue (FFPET), which, in many cases, has been shown to include degraded DNA and RNA. Exacerbating matters, many samples available for testing contain limited amounts of tissue, which in turn limits the amount of nucleic acid attainable from the tissue. For this reason, accurate profiling in clinical specimens requires an extremely sensitive assay capable of detecting gene alterations in specimens with a low tumor percentage. Second, millions of bases within the tumor genome are assayed. For this reason, rigorous statistical and analytical approaches for validation are required in order to demonstrate the accuracy of NGS technology for use in clinical settings and in developing cause and effect efficacy insights.

Most of the features of next generation sequencing (NGS) are compartmentalized into individual laboratories. To this end, there are labs which focus on DNA, labs which focus on RNA, labs focusing on IHC, labs focused on specific components of an overall patient view in NGS but their reports are curated on a completely sectionalized component of a patient's overall health. There lacks a central component which combines all of the elements that make NGS powerful as a predictor of patient responses and best treatments. As described above, expecting a physician to act as a central component to the system is placing a substantial burden on an individual who has substantial difficulty sharing the benefits of their expertise with all of the other thousands of physicians when there are an overwhelming number of sources of information that need to be consumed to make full use of all the NGS components individually.

Thus, what is needed is a system that is capable of efficiently capturing all treatment relevant data including cancer state factors, treatment decisions, treatment efficacy and exploratory factors (e.g., factors that may have a causal relationship to treatment efficacy) and structuring that data to optimally drive different system activities including memorialization of data and treatment decisions, database analytics and user applications and interfaces. In addition, the system should be highly and rapidly adaptable so that it can be modified to absorb new data types and new treatment and research insights as well as to enable development of new user applications and interfaces optimized to specific user activities.

Adaptive Order Fulfillment and Tracking Methods and Systems

The field of the disclosure is complex medical testing order processing and management methods and systems and more specifically adaptive order processing systems for generating customized complex orders including items to be facilitated by many different system resources, managing those resources to complete order items and ultimately generate order reports and to enable visualization of real time and historical order status.

Hereafter, unless indicated otherwise, the following terms and phrases will be used as described. The term "physician" will be used to refer generally to any health care provider including but not limited to a primary care physician, a medical specialist, an oncologist, a psychiatrist, a nurse, a medical assistant, etc.

The phrase "cancer state" will be used to refer to a cancer patient's overall condition including diagnosed cancer, location of cancer, cancer stage, other cancer characteristics, other user conditions (e.g., age, gender, weight, race, genetics, habits (e.g., smoking, drinking, diet)), other pertinent medical conditions (e.g., high blood pressure, other diseases, etc.), medications, other pertinent medical history, current side effects of cancer treatments and other medications, etc.

The term "consume" will be used to refer to any type of consideration, use, or other activity related to any type of system data, tissue samples, etc., whether or not that consumption is exhaustive (e.g., used only once, as in the case of a tissue sample that cannot be reproduced) or persists for use by multiple entities (e.g., used multiple times as in the case of a simple data value).

The term "specialist" will be used to refer to any person other than the physician that operates within the disclosed systems to collect, develop, analyze or otherwise process system data, tissue samples or other information types (e.g., medical images) to generate any intermediate system work product or final work product where intermediate work product includes any data set, conclusions, tissue or other samples, grown tissues or samples, or other information for consumption by one or more other system specialists and where final work product includes data, conclusions or other information that is placed in a final or conclusory report for a system client. For instance, the phrase "abstractor specialist" will be used to refer to a person that consumes data available in clinical records provided by a physician to generate normalized data for use by other system specialists, the phrase "sequencing specialist" will be used to refer to a person that consumes a tissue sample to generate DNA and/or RNA genomic data for use by other system specialists, the phrase "pathology specialist" will be used to refer to a scientist or physician specializing in pathology, etc.

The phrase "system entity" will be used to refer to any department, specialist, software application, etc., that performs any activity related to system data, tissue samples, or other system information. For instance, a genome sequencing lab and a radiology department are two examples of system entities. As another instance, an application program that receives radiology images and uses that data to generate a three dimensional representation of a tumor and surrounding tissue as well as the tumor's location and juxtaposition within the surrounding tissue is another system entity.

The phrase "deliverable consumer" will be used to refer to any system entity that consumes any system data, samples, or other information in any way including both specialists and software application programs that automatically consume data, samples, information or other deliverables independent of any initiating human activity.

The phrase "treatment planning" will be used to refer to an overall process that includes one or more sub-processes that process clinical and other data and samples (e.g., tumor tissue) to generate intermediate data deliverables and eventually final work product in the form of one or more final reports provided to clients. Thus, treatment planning may include data generation and processes used to generate that data as well as ultimate prescriptive plans for addressing a patient's ailments.

Medical treatment prescriptions and treatment plans are typically based on an understanding of how treatments affect illness (e.g., treatment results) including how well specific treatments eradicate illness, duration of specific treatments, duration of healing processes associated with specific treatments and typical treatment specific side effects. Ideally treatments result in complete elimination of an illness in a short period with minimal or no adverse side effects. In some cases cost is also a consideration when selecting specific medical treatments for specific ailments.

Knowledge about treatment results is often based on analysis of empirical data developed over decades or even longer time periods during which physicians and/or researchers have recorded treatment results for many different patients and reviewed those results to identify generally successful ailment specific treatments. Researchers and physicians give medicine to patients or treat an ailment in some other fashion, observe results and, if the results are good, the researchers and physicians use the treatments again for similar ailments. If treatment results are bad, a researcher foregoes prescribing the associated treatment for a next encountered similar ailment and instead tries some other treatment. Treatment results are sometimes published in medical journals and/or periodicals so that many physicians can benefit from a treating physician's insights and treatment results.

Optimized cancer treatment planning, or precision medicine, for specific patients and cancer states is challenging for several reasons. First, more than most illnesses, time is of the essence when it comes to most cancer treatments where delay by just a few weeks or even days can have life and death consequences for an afflicted patient. Unfortunately, thorough and optimized cancer treatment planning is extremely complex requiring a series of activities by many specialists with different technical disciplines, all of which take time.

Second, there are more than 250 known cancer types and each type may be in one of first through fourth stages where, in each stage, the cancer may have many different characteristics so that the number of possible "cancer varieties" is relatively large which makes the sheer volume of knowledge required to fully comprehend all possible treatment results unwieldy and effectively inaccessible.

Third, for most cancer states, there are several different treatment options where each general option can be customized for a specific cancer state and patient condition. In many cases there are combinations of different treatment options which complicate the planning process even further. Understanding all treatment options and combinations for a specific case is a daunting task which is exacerbated over time as more treatment options and combinations of options are identified and developed.

Fourth, for some cancer states there are no accepted best treatment plan practices and, in these cases, physicians often have to turn to clinical studies to find treatment options for associated patients. Even in some cases where best treatment practices have been developed, one or more clinical trials may present better options for some cancer states given treatment results or other factors. Unfortunately there are hundreds and at times even thousands of clinical cancer studies being performed all the time where there are cancer state related qualifications as well as timing requirements for most of the studies. Diligently tracking all studies, timing and state qualifications is essentially impossible for any physician.

Fifth, physicians often manage cancer treatment planning processes and therefore are charged with ordering third party services to generate work product for assessing next steps in the process. Here, physicians apply judgement and rely on past experiences applied to new or changing patient conditions to assess next steps and, in many cases, there are no clear dependencies within the overall system so that the physician's decision making points end up slowing down the overall treatment planning process.

Sixth, it is known that cancer state factors (e.g., diagnosed cancer, location of cancer, cancer stage, other cancer characteristics, other user conditions (e.g., age, gender, weight, race, genetics, habits (e.g., smoking, drinking, diet)), other pertinent medical conditions (e.g., high blood pressure, other diseases, etc.), medications, other pertinent medical history, current side effects of cancer treatments and other medications, etc.) and combinations of those factors render some treatments more efficacious for one patient than other treatments or for one patient as opposed to other patients. Awareness of those factors and their effects is extremely important and difficult to master and apply, especially under the pressure of time constraints when delay can appreciably affect treatment efficacy and even treatment options and when there are new insights into treatment efficacy all the time.

Seventh, in many cases complex and time consuming processes are required to identify factors needed to select optimized cancer treatments and initiation of some of those processes is dependent on the results of prior processes. For instance, a tumor sample has to be collected from a patient prior to developing a genetic panel for the tumor, the panel has to be completed prior to analyzing panel results to identify relevant factors and the factors have to be analyzed prior to selecting treatments and/or clinical studies to select for a specific patient.

The complexity of treatment selection processes and advantages associated with expedited selection and treatments have made it impossible for a physician to independently understand, develop and consider all relevant factors in a vacuum and more and more physicians are relying on expert third party service providers to perform diagnostic and data development tests and analysis and identify cancer state treatment options and trial options. To this end, an exemplary service provider may accept orders from physicians to perform genetic tests on patient and tumorous tissues, obtain clinical cancer state data for specific patients, analyze test results along with other cancer state factors, identify optimized treatment and trial options and generate reports usable by the physicians to make optimized decisions. The tasks associated with provider services are diverse, each requiring substantial expertise and/or experience to perform. In many cases tasks required to fulfill a service request include a plethora of both manual and automated tasks performed by different provider entities where many tasks cannot be initiated until one more other tasks are completed (e.g., one task may rely on data and information generated by five other tasks to be initiated). For these reasons, providers typically employ many differently skilled experts and automated systems to perform tasks, one expert or system handing off results to the next to facilitate a sequence of processes.

In many cases these service providers are used by many physicians and the number is growing precipitously as testing and results analysis become more complex and the results more informative and valuable to cancer state diagnosis and treatment prescriptions. The sheer volume of service orders that has resulted has led to cases where providers are having difficulty meeting service request demands in a timely fashion. The press of time has led to development of best service practices whereby a provider follows very specific sequential processes in an attempt to efficiently complete tasks required to intake orders and ultimately generate timely reports. An exemplary order process for developing genetic patient and tumor data, considering that data in conjunction with other cancer state factors, selecting treatment recommendations and/or clinical trial recommendations and reporting to a physician may take 2 or more weeks and may include the following sequenced sub-processes.

First, a physician prepares and faxes a requisition form to a service provider which is manually entered into a spreadsheet pursuant to an order entry process. Here, periodically, excerpts of the spreadsheet are provided to a wet lab process and a report generation process indicating samples which are expected and the processing instructions for those samples. At some later date (e.g., a few days later), the wet lab process receives patient and tumor samples from the physician which are accessioned into a spreadsheet and notifications of the sample accessions are pushed to an order process, a variant science process, and the report generation process.

A pathology specialist reviews the samples and enters details into the spreadsheet and that data is pushed to the report generation process. Pursuant to the wet lab process, the samples are prepared for sequencing and are put into the sequencer and analysis instructions are pushed to the variant call process. A bioinformatics process waits for sequencer output and analyzes patient data test data and then pushes results and instructions to a variant categorization process. The variant categorization process performs analysis on patient data and pushes data to a clinical therapies process and a clinical trials process as well as to the report generation process. The clinical therapies process curates treatment recommendations which are pushed to the report generation process. In parallel, the clinical trials process curates treatment recommendations which are also pushed to the report generation process. The report generation process, having captured all of the data, produces a final report which is reviewed by a specialist and then pushed out to the order process for delivery to the requesting physician.

While scripted push type sequenced processes like the one described above have some advantages, they also have several shortcomings. First, in general, data push type systems are a problem because each data producer process typically needs to conform to the requirements of at least one and in many cases several consumer processes. This leads to a double-bottom-line struggle for the producer, which, in addition to being concerned with the production of specific data itself, also needs to adapt to constraints of the consumer processes (e.g., is affected by time requirements of the consumer process, has to provide data in a format suitable for the consumer process, etc.). This problem is amplified when a producer process must push data to multiple consumer processes, adapting to the constraints of each.

Second, in a push type system, if data or a push notification is lost, in many cases it is difficult to detect that event (e.g., if a stochastic notification is not received or properly recorded, how can the lack of notification be detected?).

Third, the above exemplary push type order process only describes a perfectly operating sequence where each of the processes produces correct data on a first attempt and where process handoffs between provider entities are seamless. In reality problems routinely occur in complex order processes and sequences. In a push type system, at least some producer processes need to push additional signals to other affected business processes, generally upstream processes which have already executed. This results in a circular dependency where a process A depends on a process B, and process B also depends on process A. Circular dependencies tend to result in excessive coupling between processes. Adding handling of exception flows to a push-centric model tends to result in an overabundance of dependencies, where most processes know about most other processes. This overabundance of dependencies is a burden to allowing any process iteration which is required in many cases and under many sets of circumstances.

Fourth, in known systems, many data pushes consist of manual tasks (e.g., manual handoff steps), such as hand entering data into a spreadsheet, taking excerpts of a spreadsheet and emailing them to a colleague in another business unit, passing printouts between teams, etc. Manual handoff of data occurs generally because the pattern of pushing data between processes requires a large number of complex notifications. In cases where a process iterates, necessary iterations often occurs faster than systems can be built to adapt to the messages, especially when considering exception flows.

Fifth, the exemplary push type system allows for the complete instruction set for a downstream consumer to materialize within a producer process which obscures any understanding of how an order will be or has been processed.

Sixth, in a push type system where processes are built based on decentralized instructions, mismatches between producer processes and consumer processes have been known to inadvertently occur, especially in cases where processes are extremely complex.

Seventh, in push type systems, producers routinely push data forward to consumer processes. Here, in order to handle processing loads efficiently, each process tends to place incoming data onto a queue and, as a result, each process creates and maintains its own data and task queueing mechanism so that the system maintains many redundant queues.

Eighth, processes in a push type system are generally self-contained other than accepting pushes and sending pushes to other external processes. These self-contained processes are generally responsible for tracking their own inputs and outputs, and for capturing and indexing data products appropriately. Ideally, all these push type processes would preserve the most important data including data useable to link through the processes from an originating order to ultimate data products in oncological reports resulting in perfect bookkeeping. In practice, this has not been the case and, in many cases, it has proven difficult to unambiguously join a process's data products with an originating order and final report.

Ninth, the sheer volume of cancer related studies, trials, and new relevant technologies routinely leads to new insights, procedures and processes. Each new insight, procedure or process may need to be worked into an existing process sequence. In a push system reworking a sequence is complex as different consumers have different requirements that need to be supported and therefore, in many cases, new insight, process and procedure support is delayed and patients cannot quickly benefit from those types of developments.

Tenth, while a third party service provider can define and support "optimized reports" for physicians, in many cases there will be a range of acceptable process sequences and report types given circumstances and therefore different physicians or specific institutions may have process and report preferences. In a scripted push type system it is difficult to support many different client process and report preferences.

Systems and Methods for Interrogating Clinical Documents for Characteristic Data The present invention relates to systems and methods for obtaining and employing data related to patient characteristics, such as physical, clinical, or genomic characteristics, as well as diagnosis, treatments, and treatment efficacy to provide a suite of tools to healthcare providers, researchers, and other interested parties enabling those entities to develop new insights utilizing disease states, treatments, results, genomic information and other clinical information to improve overall patient healthcare.

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, clinical trial designers, data abstractors, oncologists, neurologists, psychiatrists, data scientists, and many other persons with specialized skill sets.

The term "physician" will be used to refer generally to any health care provider including but not limited to a primary care physician, a medical specialist, an oncologist, a neurologist, a nurse, and a medical assistant, among others.

The term "researcher" will be used to refer generally to any person that performs research including but not limited to a radiologist, a data scientist, or other health care provider. One person may be both a physician and a researcher while others may simply operate in one of those capacities.

The phrase "system specialist" will be used generally to refer to any provider employee that operates within the disclosed systems to collect, develop, analyze or otherwise process system data, tissue samples or other information types (such as medical images) to generate any intermediate system work product or final work product where intermediate work product includes any data set, conclusions, tissue or other samples, or other information for consumption by one or more other system specialists and where final work product includes data, conclusions or other information that is placed in a final or conclusory report for a system client or that operates within the system to perform research, to adapt the system to changing needs, data types or client requirements. For instance, the phrase "abstractor specialist" will be used to refer to a person that consumes data available in clinical records provided by a physician (such as primary care physician or psychiatrist) to generate normalized and structured data for use by other system specialists. The phrase "programming specialist" will be used to refer to a person that generates or modifies application program code to accommodate new data types and or clinical insights, etc.

The phrase "system user" will be used generally to refer to any person that uses the disclosed system to access or manipulate system data for any purpose, and therefore will generally include physicians and researchers that work for the provider or that partner with the provider to perform services for patients or for other partner research institutions as well as system specialists that work for the provider.

The term "consume" will be used to refer to any type of consideration, use, modification, or other activity related to any type of system data, saliva samples, etc., whether or not that consumption is exhaustive (such as used only once, as in the case of a saliva sample that cannot be reproduced) or inexhaustible so that the data, sample, etc., persists for consumption by multiple entities (such as used multiple times as in the case of a simple data value). The term "consumer" will be used to refer to any system entity that consumes any system data, samples, or other information in any way including each of specialists, physicians, researchers, clients that consume any system work product, and software application programs or operational code that automatically consume data, samples, information or other system work product independent of any initiating human activity.

Medical treatment prescriptions or plans are typically based on an understanding of how treatments affect illness (such as treatment results) including how well specific treatments eradicate illness, duration of specific treatments, duration of healing processes associated with specific treatments and typical treatment-specific side effects. Ideally, treatments result in complete elimination of an illness in a short period with minimal or no adverse side effects. In some cases, cost is also a consideration when selecting specific medical treatments for specific ailments.

Knowledge about treatment results is often based on analysis of empirical data developed over decades or even longer time periods, during which physicians and/or researchers have recorded treatment results for many different patients and reviewed those results to identify generally successful ailment specific treatments. Researchers and physicians give medicine to patients or treat an ailment in some other fashion, observe results and, if the results are good, use the treatments again for similar ailments. If treatment results are bad, a physician forgoes prescribing the associated treatment for a next encountered similar ailment and instead tries some other treatment. Treatment results are sometimes published in medical journals and/or periodicals so that many physicians can benefit from a treating physician's insights and treatment results.

In many cases treatment results for specific diseases vary for different patients. In particular, different patients often respond differently to identical or similar treatments. Recognizing that different patients experience different results given effectively the same treatments in some cases, researchers and physicians often develop additional guidelines around how to optimize ailment treatments based on specific patient disease state. For instance, while a first treatment may be best for a younger, relatively healthy woman, a second treatment associated with fewer adverse side effects may be optimal for an older, relatively frail man with the same diagnosis. In many cases, patient conditions related to the disease state may be gleaned from clinical medical records, via a medical examination and/or via a patient interview, and may be used to develop a personalized treatment plan for a specific ailment. The idea here is to collect data on as many factors as possible that have any cause-effect relationship with treatment results and use those factors to design optimal personalized treatment plans.

Genetic testing has been explored as another disease state factor (such as another patient condition) that can affect treatment efficacy. It is believed that there are likely many DNA and treatment result cause-and-effect relationships that have yet to be discovered. One problem with genetic testing is that the testing is expensive and can be cost prohibitive in many cases—oftentimes, insurance companies refuse to cover the cost.

Another problem with genetic testing for treatment planning is that, if genetic testing is performed, often there is no clear linkage between resulting genetic factors and treatment efficacy. In other words, in most cases, how genetic test results can be used to prescribe better treatment plans for patients is not fully known, so the extra expense associated with genetic testing in specific cases cannot be justified. Thus, while promising, genetic testing as part of treatment planning has been minimal or sporadic at best.

In most cases, patient treatments and results are not published for general consumption and therefore are simply not accessible to be combined with other treatment and results data to provide a more fulsome overall data set. In this regard, many physicians see treatment results that are within an expected range of efficacy and may conclude that those results cannot add to the overall treatment knowledge base; those results often are not published. The problem here is that the expected range of efficacy can be large (such as 20% of patients experience a significant reduction in symptoms, 40% of patients experience a moderate reduction in symptoms, 20% experience a mild reduction in symptoms, and 20% do not respond to a treatment plan) so that all treatment results are within an expected efficacy range and treatment result nuances are simply lost.

Additionally, there is no easy way to build on and supplement many existing illness-treatment-results databases. As such, as more data is generated, the new data and associated results cannot be added to existing databases as evidence of treatment efficacy or to challenge efficacy. Thus, for example, if a researcher publishes a study in a medical journal, there is no easy way for other physicians or researchers to supplement the data captured in the study. Without data supplementation over time, treatment and results corollaries cannot be tested and confirmed or challenged.

The knowledge base around treatments is always growing with different clinical trials in different stages around the world so that if a physician's knowledge is current today, his knowledge will be dated within months. Thousands of articles relevant to diseases are published each year and many are verbose and/or intellectually thick so that the articles are difficult to read and internalize, especially by extremely busy physicians that have limited time to absorb new materials and information. Distilling publications down to those that are pertinent to a specific physician's practice takes time and is an inexact endeavor in many cases.

In most cases there is no clear incentive for physicians to memorialize a complete set of treatment and results data and, in fact, the time required to memorialize such data can operate as an impediment to collecting that data in a useful and complete form. To this end, prescribing and treating physicians know what they know and painstakingly capturing a complete set of disease state, treatment and results data without getting something in return (such as a new insight, a better prescriptive treatment tool, etc.) may be perceived as burdensome to the physician.

In addition to problems associated with collecting and memorializing treatment and results data sets, there are problems with digesting or consuming recorded data to generate useful conclusions. For instance, recorded disease state, treatment and results data is often incomplete. In most cases physicians are not researchers and they do not follow clearly defined research techniques that enforce tracking of all aspects of disease states, treatments and results. As a result, data that is recorded is often missing key information such as, for instance, specific patient conditions that may be of current or future interest, reasons why a specific treatment was selected and other treatments were rejected, specific results, etc. In many cases where cause and effect relationships exist between disease state factors and treatment results, if a physician fails to identify and record a causal factor, the results cannot be tied to existing cause and effect data sets and therefore simply cannot be consumed and added to the overall disease knowledge data set in a meaningful way.

Another impediment to digesting collected data is that physicians often capture disease state, treatment and results data in forms that make it difficult if not impossible to process the collected information so that the data can be normalized and used with other data from similar patient treatments to identify more nuanced insights and to draw more robust conclusions. For instance, many physicians prefer to use pen and paper to track patient care and/or use personal shorthand or abbreviations for different disease state descriptions, patient conditions, treatments, results and even conclusions. Using software to glean accurate information from hand written notes is difficult at best and the task is exacerbated when hand written records include personal abbreviations and shorthand representations of information that software simply cannot identify with the physician's intended meaning.

To be useful, disease state, treatment and results data and conclusions based thereon have to be rendered accessible to physicians, researchers and other interested parties. In the case of disease treatments where disease states, treatments, results and conclusions are extremely complicated and nuanced, physician and researcher interfaces have to present massive amounts of information and show many data corollaries and relationships. When massive amounts of information are presented via an interface, interfaces often become extremely complex and intimidating, which can result in misunderstanding and underutilization. What is needed are well designed interfaces that make complex data sets simple to understand and digest. For instance, in the case of disease states, treatments and results, it would be useful to provide interfaces that enable physicians to consider de-identified patient data for many patients where the data is specifically arranged to trigger important treatment and results insights. It would also be useful if interfaces had interactive aspects so that the physicians could use filters to access different treatment and results data sets, again, to trigger different insights, to explore anomalies in data sets, and to better think out treatment plans for their own specific patients.

Disease research is progressing all the time at many hospitals and research institutions where clinical trials are always being performed to test new medications and treatment plans. A patient without other effective treatment options can opt to participate in a clinical trial if the patient's disease state meets trial requirements and if the trial is not yet fully enrolled (such as there is often a limit to the number of patients that can participate in a trial).

At any time there are several thousand clinical trials progressing around the world, and identifying trial options for specific patients can be a daunting endeavor. Matching a patient disease state to a subset of ongoing trials is complicated and time consuming. Paring down matching trials to a best match given location, patient and physician requirements and other factors exacerbates the task of considering trial participation. In addition, considering whether or not to recommend a clinical trial to a specific patient given the possibility of trial treatment efficacy where the treatments are by their very nature experimental, especially in light of specific patient conditions, is a daunting activity that most physicians do not take lightly. It would be advantageous to have a tool that could help physicians identify clinical trial options for specific patients with specific disease states and to access information associated with trial options.

One other problem with current disease treatment planning processes is that it is difficult to integrate new pertinent treatment factors, treatment efficacy data and insights into existing planning databases. In this regard, known treatment planning databases have been developed with a predefined set of factors and insights and changing those databases often requires a substantial effort on the part of a software engineer to accommodate and integrate the new factors or insights in a meaningful way where those factors and insights are correctly correlated with other known factors and insights. In some cases the required substantial effort simply means that the new factor or insight will not be captured in the database or used to affect planning while in other cases the effort means that the new factor or insight is only added to the system at some delayed time required to apply the effort.

One other problem with existing disease treatment efficacy databases and systems is that they are simply incapable of optimally supporting different types of system users. To this end, data access, views and interfaces needed for optimal use are often dependent upon what a system user is using the system for. For instance, physicians often want treatment options, results and efficacy data distilled down to simple recommendations while a researcher often requires much more detailed data access to develop new hypothesis related to disease state, treatment and efficacy relationships. In known systems, data access, views and interfaces are often developed with one consuming client in mind such as, for instance, general practitioners, radiologists, a treatment researcher, etc., and are therefore optimized for that specific system user type which means that the system is not optimized for other user types.

Pharmacogenomics is the study of the role of the human genome in drug response. Aptly named by combining pharmacology and genomics, pharmacogenomics analyzes how the genetic makeup of an individual affects their response to drugs. It deals with the influence of genetic variation on drug response in patients by correlating gene expression pharmacokinetics (drug absorption, distribution, metabolism, and elimination) and pharmacodynamics (effects mediated through a drug's biological targets). Although both terms relate to drug response based on genetic influences, pharmacogenetics focuses on single drug-gene interactions, while pharmacogenomics encompasses a more genome-wide association approach, incorporating genomics and epigenetics while dealing with the effects of multiple genes on drug response. One aim of pharmacogenomics is to develop rational means to optimize drug therapy, with respect to the patients' genotype, to ensure maximum efficiency with minimal adverse effects. Pharmacogenomics and pharmacogenetics may be used interchangeably throughout the disclosure.

The human genome consists of twenty-three pairs of chromosomes, each containing between 46 million and 250 million base pairs (for a total of approximately 3 billion base pairs), each base pair having complementary nucleotides (the pairing that is commonly described with a double helix). For each chromosome, the location of a base pair may be referred to by its locus, or index number for the base pair in that chromosome. Typically, each person receives one copy of a chromosome from their mother and the other copy from their father.

Conventional approaches to bring pharmacogenomics into precision medicine for the treatment, diagnosis, and analysis of diseases include the use of single nucleotide polymorphism (SNP) genotyping and detection methods (such as through the use of a SNP chip). SNPs are one of the most common types of genetic variation. A SNP is a genetic variant that only spans a single base pair at a specific locus. When individuals do not have the same nucleotide at a particular locus, a SNP may be defined for that locus. SNPs are the most common type of genetic variation among people. Each SNP represents a difference of a single DNA building block. For example, a SNP may describe the replacement of the nucleotide cytosine (C) with the nucleotide thymine (T) at a locus.

Furthermore, different nucleotides may exist at the same locus within an individual. A person may have one nucleotide in a first copy of a particular chromosome and a distinct nucleotide in the second copy of that chromosome, at the same locus. For instance, loci in a person's first copy of a chromosome may have this nucleotide sequence-AAGCCTA, and the second copy may have this nucleotide sequence at the same loci-AAGCTTA. In other words, either C or T may be present at the 5th nucleotide position in that sequence. A person's genotype at that locus can be described as a list of the nucleotides present at each copy of the chromosome, at that locus. SNPs with two nucleotide options typically have three possible genotypes (a pair of matching nucleotides of the first type, one of each type of nucleotide, and a pair of matching nucleotides of the second type—AA, AB, and BB). In the example above, the three genotypes would be CC, CT, and TT. In a further example, at locus 68,737,131 the rs16260 variant is defined for gene CDH1 (in chromosome 16) where (C;C) is the normal genotype where C is expected at that locus, and (A;A) and (A;C) are variations of the normal genotype.

While SNPs occur normally throughout a person's DNA, they occur almost once in every 1,000 nucleotides on average, which means there are roughly 4 to 5 million SNPs in a person's genome. There have been more than 100 million SNPs detected in populations around the world. Most commonly, these variations are found in the DNA between genes (regions of DNA known as "introns"), where they can act as biological markers, helping scientists locate genes that are associated with disease.

SNPs are not the only genetic variant possible in the human genome. Any deviation in a person's genome sequences when compared to normal, reference genome sequences may be referred to as a variant. In some cases, a person's physical health can be affected by a single variant, but in other cases it is only affected by a combination of certain variants located on the same chromosome. When variants in a gene are located on the same chromosome that means the variants are in the same allele of the gene. An allele may be defined as a continuous sequence of a region of a DNA molecule that has been observed in an individual organism, especially when the sequence of that region has been shown to have variations among individuals. When certain genetic tests, like NGS, detect more than one variant in a gene, it is possible to know whether those variants are in the same allele. Some genetic tests do not have this capability.

Certain groups of variants that exist together in the same chromosome may form a specific allele that is known to alter a person's health. Occasionally, a single allele may not affect a person's health, unless that person also has a specific combination of alleles. Sometimes an allele or allele combination is reported or published in a database or other record with its health implications (for instance, that having the allele or allele combination causes a person to be an ultrafast metabolizer; intermediate metabolizer; or poor metabolizer; etc.). Exemplary records include those from the American College of Medical Genetics and Genomics (ACMG), the Association for Molecular Pathology (AMP), or the Clinical Pharmacogenetics Implementation Consortium (CPIC). These published alleles may each have a designated identifier, and one category of identifiers is the * (star) allele system. For example, for each gene, each star allele may be numbered *1, *2, *3, etc., where *1 is generally the reference or normal allele. As an example, the CYP2D6 gene has over 100 reported variant alleles.

Developed before NGS, microarray assays have been a common genetic test for detecting variants. Microarray assays use biochips with DNA probes bound to the biochip surface (usually in a grid pattern). Some of these biochips are called SNP chips. A solution with DNA molecules from one or more biological samples is introduced to the biochip surface. Each DNA molecule from a sample has a fluorescent dye or another type of dye attached. Often the color of the dye is specific to the sample, and this allows the assay to distinguish between two samples if multiple samples are introduced to the biochip surface at the same time.

If the solution contains a DNA sequence that is complementary to one of the probes affixed to the biochip, the DNA sequence will bind to the probe. After all unbound DNA molecules are washed away, any sample DNA bound to the probe will fluoresce or create another visually detectable signal. The location and sequence of each probe is known, so the location of the visually detectable signal indicates what bound, complementary DNA sequence was present in the samples and the color of the dye indicates from which sample the DNA sequence originated. The probe sequences on the biochip each only contain one sequence, and the probes bind specifically to one complementary sequence in the DNA, meaning that most probes can only detect one type of mutation or genetic variant. This also means that a microarray will not detect a sequence that is not targeted by the probes on the biochip. It cannot be used to find new variants. This is one reason that next generation sequencing is more useful than microarrays.

The fact that a probe only detects one specific DNA sequence means that the microarray cannot determine whether two detected variants are in the same allele unless the loci of the variants are close enough that a single probe can span both loci. In other words, the number of nucleotides between the two variants plus the number of nucleotides within each variant must be smaller than the number of nucleotides in the probe otherwise the microarray cannot detect whether two variants are in the same DNA strand, which means they are in the same allele.

Also, each probe will bind to its complementary sequence within a unique temperature range and range of concentrations of components in the DNA solution introduced to each biochip. Because it is difficult to simultaneously achieve optimal binding conditions for all probes on a microarray (such as the microarrays used in SNP Chips), any DNA from a sample has the potential to hybridize to probes that are not perfectly complementary to the sample DNA sequence and cause inaccurate test results.

Furthermore, disadvantages of microarrays include the limited number of probes present to target biomarkers due to the surface area of the biochip, the misclassification of variants that do not bind to probes as a normal genotype, and the overall misclassification of the genotype of the patient. Due to the limited processing efficiency of SNP chips, conventional microarray approaches are inefficient in detecting biomarkers and their many included variations.

Taqman assays have limitations similar to those of microarrays. If a taqman assay probe is an exact match for a complementary sequence in a DNA molecule from a sample, the DNA molecule gets extended, similar to NGS. However, instead of reporting what the sequence of each nucleotide type is in the DNA extension, the assay only reports whether extension occurred or not. This leads to the same limitations as SNP chips. Other genetic tests, such as dot blots and southern blots, have similar limitations.

Thus, what is needed is a system that is capable of efficiently capturing all treatment relevant data including disease state factors, treatment decisions, treatment efficacy and exploratory factors (such as factors that may have a causal relationship to treatment efficacy) and structuring that data to optimally drive different system activities including memorialization of data and treatment decisions, database analytics and user applications and interfaces. In addition, the system should be highly and rapidly adaptable so that it can be modified to absorb new data types and new treatment and research insights as well as to enable development of new user applications and interfaces optimized to specific user activities.

Automated Quality Assurance Testing of Structured Clinical Data

This application is directed to systems and methods for ensuring accurate data entry in one or more computer systems.

In precision medicine, physicians and other clinicians provide medical care designed to optimize efficiency or therapeutic benefit for patients on the basis of their particular characteristics. Each patient is different, and their different needs and conditions can present a challenge to health systems that must grapple with providing the right resources to their clinicians, at the right time, for the right patients. Health systems have a significant need for systems and methods that allow for precision-level analysis of patient health needs, in order to provide the right resources, at the right time, to the right patients.

Rich and meaningful data can be found in source clinical documents and records, such as diagnosis, progress notes, pathology reports, radiology reports, lab test results, follow-up notes, images, and flow sheets. These types of records are referred to as "raw clinical data". However, many electronic health records do not include robust structured data fields that permit storage of clinical data in a structured format. Where electronic medical record systems capture clinical data in a structured format, they do so with a primary focus on data fields required for billing operations or compliance with regulatory requirements. The remainder of a patient's record remains isolated, unstructured and inaccessible within text-based or other raw documents, which may even be stored in adjacent systems outside of the formal electronic health record. Additionally, physicians and other clinicians would be overburdened by having to manually record hundreds of data elements across hundreds of discrete data fields.

As a result, most raw clinical data is not structured in the medical record. Hospital systems, therefore, are unable to mine and/or uncover many different types of clinical data in an automated, efficient process. This gap in data accessibility can limit a hospital system's ability to plan for precision medicine care, which in turn limits a clinician's ability to provide such care.

Several software applications have been developed to provide automated structuring, e.g., through natural language processing or other efforts to identify concepts or other medical ontological terms within the data. Like manual structuring, however, many of such efforts remain limited by errors or incomplete information.

Efforts to structure clinical data also may be limited by conflicting information within a single patient's record or among multiple records within an institution. For example, where health systems have structured their data, they may have done so in different formats. Different health systems may have one data structure for oncology data, a different data structure for genomic sequencing data, and yet another different data structure for radiology data. Additionally, different health systems may have different data structures for the same type of clinical data. For instance, one health system may use one EMR for its oncology data, while a second health system uses a different EMR for its oncology data. The data schema in each EMR will usually be different. Sometimes, a health system may even store the same type of data in different formats throughout its organization. Determination of data quality across various data sources is both a common occurrence and challenge within the healthcare industry.

What is needed is a system that addresses one or more of these challenges.

Mobile Supplementation, Extraction, and Analysis of Health Records

A system and method implemented in a mobile platform are described herein that facilitate the capture of documentation, along with the extraction and analysis of data embedded within the data.

In the medical field, physicians often have a wealth of knowledge and experience to draw from when making decisions. At the same time, physicians may be limited by the information they have in front of them, and there is a vast amount of knowledge about which the physician may not be aware or which is not immediately recallable by the physician. For example, many treatments may exist for a particular condition, and some of those treatments may be experimental and not readily known by the physician. In the case of cancer treatments, in particular, even knowing about a certain treatment may not provide the physician with "complete" knowledge, as a single treatment may be effective for some patients and not for others, even if they have the same type of cancer. Currently, little data or knowledge is available to distinguish between treatments or to explain why some patients respond better to certain treatments than do other patients.

One of the tools from which physicians can draw besides their general knowledge in order to get a better understanding of a patient's condition is the patient's electronic health record ("EHR") or electronic medical record ("EMR"). Those records, however, may only indicate a patient's historical status with respect to a disease, such as when the patient first presented with symptoms, how it has progressed over time, etc. Current medical records may not provide other information about the patient, such as their genetic sequence, gene mutations, variations, expressions, and other genomic information. Conversely, for those patients that have undergone genetic sequencing or other genetic testing, the results of those tests often consist of data but little to no analysis regarding the significance of that data. Without the ability to understand the significance of that report data and how it relates to their patients' diagnoses, the physicians' abilities to make informed decisions on potential treatment protocols may be hindered.

Services exist that can provide context or that can permit detailed analysis given a patient's genetic information. As discussed, however, those services may be of little use if the physician does not have ready access to them. Similarly, even if the physician has access to more detailed patient information, such as in the form of a lab report from a lab provider, and also has access to another company that provides analytics, the value of that data is diminished if the physician does not have a readily available way to connect the two.

Further complicating the process of ensuring that a physician has ready access to useful information, with regard to the capture of patient genetic information through genetic testing, the field of next generation sequencing ("NGS") for genomics is new. NGS involves using specialized equipment such as a next generation gene sequencer, which is an automated instrument that determines the order of nucleotides in DNA and/or RNA. The instrument reports the sequences as a string of letters, called a read. An analyst then compares the read to one or more reference genomes of the same genes, which is like a library of normal and variant gene sequences associated with certain conditions. With no settled NGS standards, different NGS providers have different approaches for sequencing patient genomics and, based on their sequencing approaches, generate different types and quantities of genomics data to share with physicians, researchers, and patients. Different genomic datasets exacerbate the task of discerning meaningful genetics-treatment efficacy insights, as required data may not be in a normalized form, was never captured, or simply was never generated.

Another issue that clinicians also experience when attempting to obtain and interpret aspects of EMRs and EHRs is that conventional EHR and EMR systems lack the ability to capture and store critical components of a patient's history, demographics, diagnosis, treatments, outcomes, genetic markers, etc., because many such systems tend to focus on billing operations and compliance with regulatory requirements that mandate collection of a certain subset of attributes. This problem may be exacerbated by the fact that parts of a patient's record which may include rich and meaningful data (such as diagnoses and treatments captured in progress or follow-up notes, flow sheets, pathology reports, radiology reports, etc.) remain isolated, unstructured, and inaccessible within the patient's record as uncatalogued, unstructured documents stored in accompanying systems. Conventional methods for identifying and structuring this data are reliant on human analysts reviewing documents and entering the data into a record system manually. Many conventional systems in use lack the ability to mine and/or uncover this information, leading to gaps in data accessibility and inhibiting a physician's ability to provide optimal care and/or precision medicine.

What is needed are an apparatus, system, and/or method that address one or more of these challenges.

A Generalizable and Interpretable Deep Learning Framework for Predicting MSI from Histopathology Slide Images The present disclosure relates to examining microsatellite instability of a sample and, more particularly, to predicting microsatellite instability from histopathology slide images.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cancer immunotherapies, such as checkpoint blockade therapy and cancer vaccines, have shown striking clinical success in a wide range of malignancies, particularly those with melanoma, lung, bladder, and colorectal cancers. Recently, the Food & Drug Administration (FDA) announced approval of checkpoint blockade to treat cancers with a specific genomic indication known as microsatellite instability (MSI). For the first time, the FDA has recognized the use of a genomic profile, rather than an anatomical tumor type (e.g., endometrial or gastric tumor types), as a criterion in the drug approval process. There are currently only a handful of FDA approved checkpoint blockade antibodies. Based on results from ongoing clinical trials, checkpoint blockade antibodies appear poised to make a major impact in tumors with microsatellite instability. However, challenges in the assessment and use of MSI are considerable.

Despite the promise of MSI as a genomic indication for driving treatment, several challenges remain. In particular, conventional techniques for diagnostic testing of MSI require specialized pathology labs having sophisticated equipment (e.g., clinical next-generation sequencing) and extensive optimization of protocols for specific assays (e.g., defective mismatch pair (dMMR) immunohistochemistry (IHC) or microsatellite instability (MSI) PCR). Such techniques limit widespread MSI testing.

There is a need for new easily accessible techniques of diagnostic testing for MSI and for assessing MSI in an efficient manner, across population groups, for producing better optimized drug treatment recommendations and protocols.

Microsatellite Instability Determination System and Related Methods

The present disclosure relates to the use of next generation sequencing to determine microsatellite instability (MSI) status.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Microsatellite instability (MSI) is a clinically actionable genomic indication for cancer immunotherapies. MSI is a type of genomic instability that occurs in repetitive DNA regions and results from defects in DNA mismatch repair. MSI occurs in a variety of cancers. This mismatch repair defect results in a hyper-mutated phenotype where alterations accumulate in the repetitive microsatellite regions of DNA. In Microsatellite Instability-High (MSI-H) tumors, the number of short tandem repeats present in microsatellite regions differ significantly from the number of repeats that are in the DNA of a benign cell.

In clinical MSI PCR testing, tumors with length differences in 2 or more of the 5 microsatellite markers on the Bethesda panel are unstable and considered Microsatellite Instability-High (MSI-H). Microsatellite Stable (MSS) tumors are tumors that have no functional defects in DNA mismatch repair and have no significant differences between tumor and normal in any of the 5 microsatellite regions. Microsatellite Instability-Low (MSI-L) is a tumor with an intermediate phenotype that has 1 unstable marker. Overall, MSI-H is observed in 15% of sporadic colorectal tumors worldwide and has been reported in other cancer types including uterine and gastric cancers.

Predicting <OBJECTIVE> from Patient Records

The present disclosure relates to predicting patient objectives from a narrowly selected feature set, and, more particularly, to predict <objective> from a narrowly selected feature set.

Extracting meaningful medical features from an ever expanding quantity of health information tabulated for a similarly expanding cohort of patients having a multitude of sparsely populated features is a difficult endeavor. Identifying which medical features from the tens of thousands of features available in health information are most probative to training and utilizing a prediction engine only compounds the difficulty. Features which may be relevant to predictions may only be available in a small subset of patients and features which are not relevant may be available in many patients. What is needed is a system which may ingest these impossibly comprehensive scope of available data across entire populations of patients to identify features which apply to the largest number of patients and establish a model for prediction of an objective. When there are multiple objectives to choose from, what is needed is a system which may curate the medical features extracted from patient health information to a specific model associated with the prediction of the desired objective.

Evaluating Effect of Event on Condition Using Propensity Scoring

The present disclosure relates generally to a computer-implemented tool that uses a propensity model to identify comparable test and control groups among a base subject population and that allows evaluating impact of treatment on a subject's condition.

In pharmaceutical and medical fields, the common goal is to evaluate the effect of a drug or a therapy on patient's characteristics including those related to patient's survival. Proper evaluation of treatment effectiveness would allow prescribing treatments with precision, thereby avoiding or decreasing medical mistakes and increasing patient survival. This is a challenging task, given a multitude of characteristics patients have and differences between patients.

Selection and evaluation of a treatment or medication typically includes comparing patients' populations. The standard way of performing clinical trials is randomized clinical trials. Observational, nonrandomized data analysis is another frequently used approach. The observational data analysis differs from randomized trials in that there is no reason to believe that populations being studied are free of correlation with an observed outcome. For example, comparison of breast cancer patients who had surgery to those breast cancer patients who did not have a surgery can be akin to comparing apples and oranges, because the patients that had surgery had a reason for their surgery (meaning that they were not selected at random) and they are thus fundamentally different from those patients who did not have surgery.

In observational studies, confounding variables may compromise a proper assessment of a result of a clinical research trial. Confounding occurs when a difference in the outcome (or lack thereof) between treated and untreated subjects can be explained entirely or partly by imbalance of other causes of the outcome in the compared groups. Potential confounders may thus effect a validity of observational studies.

Accordingly, there is a need in improved implementations of observational approaches for evaluating effectiveness of a treatment for a patient.

Transcriptome Deconvolution of Metastatic Tissue Samples

The present disclosure relates to the transcriptome analysis of mixed cell type populations and, more particularly, to techniques for the deconvolution of RNA transcript sequences quantified in metastatic tumor tissues.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Solid tumors are heterogeneous mixtures of cell populations composed of tumor cells, nearby stromal and normal epithelial cells, immune and vascular cells. Transcriptome profiling of tumor samples by standard RNA (ribonucleic acid) sequencing methods measures the average gene expression of the cell types present in the sample at the time of sampling, the samples generally including both tumor (target) and non-tumor (non-target) cells. The expression profile is largely shaped by the sample's tumor architecture. Tumor purity, i.e., the proportion of cancerous cells in the sample, can directly influence the sequencing results, genomic interpretation, and any consequent proposed associations with clinical outcomes. Put another way, as clinical tumor samples comprise a mixed population of cells, many of which are non-tumor cells, a resulting gene expression profile may not concisely reveal clinically relevant associations. The dependence on tumor purity and the challenge it poses to genomic interpretation is most pronounced in metastatic cancers, where the tumor and the non-cancerous background tissue can have different gene expression profiles, due to the tumor originating in a tissue that is distinct from the background tissue where the tumor has metastasized. In other words, RNA expression from normal adjacent cells to the tumor could increase or wash out the relevant expression signal for a given gene and result in the erroneous interpretation of over or under expression and subsequent treatment recommendations.

Motivated to understand tumor heterogeneity and to model transcription profiles in cancer, a few computational approaches have been developed to estimate cell type specific expression profiles in tumor cells. These methods have mainly focused on the disassociation of immune cells from tumor samples and require known expression references from well characterized cell-type specific genes, or transcriptomes from purified cell populations. In spite of existing methods, the deconvolution of tumor gene expression from the surveyed mixture of cell populations containing unwanted normal cells in the collected tissue remains a challenging task. There is a need for improved transcriptome deconvolution techniques.

Calculating Cell-Type RNA Profiles for Diagnosis and Treatment

The present disclosure relates to generating and applying RNA profiles to identify cell types and their proportions in patient samples, to improve precision of treatment selection and monitoring.

Acquisition and analysis of subjects' genetic information through genetic testing in the field of next-generation sequencing ("NGS") for genomics is a rapidly evolving field. NGS involves using specialized equipment, such as a next-generation gene sequencer, which is an automated instrument that determines the order of nucleotides in DNA and/or RNA. The instrument reports the sequences as a string of letters, called a read. These reads allow the identification of genes, variants, or sequences of nucleotides in the human genome. An analyst compares these reads from genes to one or more reference genomes of the same genes, variants, or sequences of nucleotides. Identification of certain genetic mutations or particular variants plays an important role in selecting the most beneficial line of therapy for a patient.

Pharmacogenomics is the study of the role of the human genome in drug response. Aptly named by combining pharmacology and genomics, pharmacogenomics analyzes how the genetic makeup of an individual affects their response to drugs. It deals with the influence of genetic variation on drug response in patients by correlating gene expression pharmacokinetics (drug absorption, distribution, metabolism, and elimination) and pharmacodynamics (effects mediated through a drug's biological targets). The term pharmacogenomics is often used interchangeably with pharmacogenetics. Although both terms relate to drug response based on genetic influences, pharmacogenetics focuses on single drug-gene interactions, while pharmacogenomics encompasses a more genome-wide association approach, incorporating genomics and epigenetics while dealing with the effects of multiple genes on drug response. This information may assist medical professionals in choosing which treatment to prescribe to a patient.

The challenge of interpreting RNA sequencing information and isolating biomarkers for disease susceptibility and/or pharmacogenomic effects is rooted in a lack of structured information between the human genome and patient/clinical information such as disease progression and treatment information. While many projects are ongoing worldwide to identify affordable, scalable single-cell sequencing techniques, a viable solution has yet to be implemented in commercial practice.

Accordingly, there is a need in improved tools for analysis and interpretation of genetic and clinical patient data, including bulk-cell sequencing data, to make inferences about disease susceptibility and pharmacogenomics and thereby make appropriate treatment decisions, which can improve overall patient healthcare.

PD-L1 Prediction Using H&E Slide Images

The present disclosure relates to techniques for the analysis of medical images and, more particularly, to techniques for analysis of histological slides other images of cancerous tissue.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

To guide a medical professional in diagnosis, prognosis and treatment assessment of a patient's cancer, it is common to extract and inspect tumor samples from the patient. Visual inspection can reveal growth patterns of the cancer cells in the tumor in relation to the healthy cells near them and the presence of immune cells within the tumor. Pathologists, members of a pathology team, other trained medical professionals, or other human analysts visually analyze thin slices of tumor tissue mounted on glass microscope slides to classify each region of the tissue as one of many tissue classes that are present in a tumor sample. This information aids the pathologist in determining characteristics of the cancer tumor in the patient, which can inform treatment decisions. A pathologist will often assign one or more numerical scores to a slide, based on a visual approximation. Numerical scores assigned during microscope slide analysis include tumor purity, which reflects the percentage of the tissue that is formed by tumor cells.

Characteristics of the tumor may include tumor grade, tumor purity, degree of invasiveness of the tumor, degree of immune infiltration into the tumor, cancer stage, and anatomic origin site of the tumor, which can be important for diagnosing and treating a metastatic tumor. These details about the cancer can help a physician monitor the progression of cancer within a patient and can help hypothesize which anti-cancer treatments are likely to be successful in eliminating cancer cells from the patient's body.

Another tumor characteristic is the presence of specific biomarkers or other molecules of interest in or near the tumor, including the molecule known as programmed death ligand 1 (PD-L1). This disclosure is intended for use with any cancer type, but one example of a cancer type that needs to be diagnosed and assessed is non-small cell lung cancer. Non-small cell lung cancer (NSCLC) is the most common type of lung cancer, affecting over 1.5 million people worldwide (Bray et al., CA: A Cancer Journal for Clinicians (2018); doi: 10.3322/caac.21492).

The disease often responds poorly to standard of care chemoradiotherapy and has a high incidence of recurrence, resulting in low 5-year survival rates (2-4). Advances in immunology show that NSCLC frequently elevates the expression of programmed death-ligand 1 (PD-L1) to bind to programmed death-1 (PD-1) expressed on the surface of T-cells (5,6). PD-1 and PD-L1 binding deactivates T-cell antitumor responses, enabling NSCLC to evade targeting by the immune system (7). The discovery of the interplay between tumor progression and immune response has led to the development and regulatory approval of PD-1/PD-L1 checkpoint blockade immunotherapies like nivolumab and pembrolizumab (8-10). Anti-PD-1 and anti-PO-L1 antibodies restore antitumor immune response by disrupting the interaction between PD-1 and PD-L1 (11). Notably, PD-L1-positive NSCLC patients treated with these checkpoint inhibitors achieve durable tumor regression and improved survival (12-16).

As the role of immunotherapy in oncology expands, it is useful to accurately assess tumor PD-L1 status to identify patients who may benefit from PD-1/PD-L1 checkpoint blockade immunotherapy. Immunohistochemistry (IHC) staining of tumor tissues acquired from biopsy or surgical specimens is commonly employed to assess PD-L1 status (17-19). However, IHC staining can be limited by insufficient tissue samples and, in some settings, a lack of resources (20,21).

Hematoxylin and eosin (H&E) staining is a longstanding method of analyzing tissue morphological features for malignancy diagnosis, including NSCLC (22,23). Furthermore, H&E slides may capture tissue visual characteristics that are associated with PD-L1 status. For example, Velcheti et al (2014) and McLaughlin et al (2016) both observed that PD-L1 positive NSCLC tended to have higher levels of tumor infiltrating lymphocytes (TILs) (Velcheti et al., Laboratory Investigation (2014); doi: 10.1038/labinvest.2013.130 and McLaughlin et al., JAMA Oncology American Medical Association (2016); doi: 10.1001/jamaoncol.2015.3638). However, quantification of TI Ls using H&E slides is laborious and affected by interobserver variability (25,26). Moreover, TIIs may be inadequate to fully describe the complexity of the tumor microenvironment and its relationship with PD-L1 status. For example, an increased density of TILs has been associated with PD-L1+ status in multiple malignancies (McLaughlin et al., JAMA Oncology American Medical Association (2016); doi: 10.1001/jamaoncol.2015.3638, Wimberly et al., Cancer Immunology Research (2015); doi: 10.1158/2326-6066.CIR-14-0133, Kitano et al., ESMO Open (2017); doi: 10.1136/esmoopen-2016-000150, and Vassilakopoulou et al., Clinical Cancer Research (2016); doi: 10.1158/1078-0432.CCR-15-1543). However, manual quantification of TI Ls on WSIs is subjective and time-consuming. Furthermore, the microenvironment driven by the interaction between a tumor and the immune system is highly complex, and therefore high levels of TIIs and PD-L1 expression may not always co-occur (Teng et al., Cancer Research (2015); doi: 10.1158/0008-5472. CAN-15-0255).

Furthermore, manually analyzing microscope slides with H&E and/or IHC staining is time consuming and requires a trained medical professional. As mentioned, because numerical scores are assigned by approximation, their values are often subjective.

Technological advances have enabled the digitization of histopathology H&E and IHC slides into high resolution whole slide images (WSIs), providing opportunities to develop computer vision tools for a wide range of clinical applications (27-29). High-resolution, digital images of microscope slides make it possible to use artificial intelligence to analyze the slides and classify the tissue components by tissue class. Recently, deep learning applications to pathology images have shown tremendous promise in predicting treatment outcomes (30), disease subtypes (31,32), lymph node status (27,28), and genetic characteristics (30, 33,34) in various malignancies. Deep learning is a subset of machine learning wherein models are built with a number of discrete neural node layers, imitating the structure of the human brain (35).

These models learn to recognize complex visual features from WSIs by iteratively updating the weighting of each neural node based on the training examples (29).

A Convolutional Neural Network ("CNN") is a deep learning algorithm that analyzes digital images by assigning one class label to each input image. Slides, however, include more than one type of tissue, including the borders between neighboring tissue classes. There is a need to classify different regions as different tissue classes, in part to study the borders between neighboring tissue classes and the presence of immune cells among tumor cells. For a traditional CNN to assign multiple tissue classes to one slide image, the CNN would need to separately process each section of the image that needs a tissue class label assignment. Neighboring sections of the image overlap, so processing each section separately creates a high number of redundant calculations and is time consuming.

A Fully Convolutional Network (FCN) can analyze an image and assign classification labels to each pixel within the image, so a FCN is more useful for analyzing images that depict objects with more than one classification. A FCN generates an overlay map to show the location of each classified object in the original image. However, FCN deep learning algorithms that analyze digital slides would require training data sets of images with each pixel labeled as a tissue class, which requires too much annotation time and processing time to be practical. In digital images of slides, each edge of the image may contain more than 10,000-100, 000 pixels. The full image may have at least 1O,OQQA2-1 OO,OQQA2 pixels, which forces long algorithm run times due to the intense computation required. The high number of pixels makes it infeasible to use traditional FCNs to segment digital images of slides.

Cellular Pathway Report

The present invention relates to systems and methods for obtaining and employing data related to physical and genomic patient characteristics as well as diagnosis, treatments and treatment efficacy to provide a suite of tools to healthcare providers, researchers and other interested parties enabling those entities to develop new cancer state-treatment-results insights and/or improve overall patient healthcare and treatment plans for specific patients.

The phrase "treatment planning process" will be used to refer to an overall process that includes one or more sub-processes that process clinical and other patient data and samples (e.g., tumor tissue) to generate intermediate data deliverables and eventually final work product in the form of one or more final reports provided to system clients. These processes typically include varying levels of exploration of treatment options for a patient's specific cancer state but are typically related to treatment of a specific patient as opposed to more general exploration for the purpose of more general research activities. Thus, treatment planning may include data generation and processes used to generate that data, consideration of different treatment options and effects of those options on patient illness, etc., resulting in ultimate prescriptive plans for addressing specific patient ailments.

The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, data abstractors, physicians, pathologists, radiologists, data scientists, and many other persons with specialized skill sets.

The term "physician" will be used to refer generally to any health care provider including but not limited to a primary care physician, a medical specialist, a physician, a nurse, a medical assistant, etc., The phrase "cancer state" will be used to refer to a cancer patient's overall condition including diagnosed cancer, location of cancer, cancer stage, other cancer characteristics (e.g., tumor characteristics), other user conditions (e.g., age, gender, weight, race, habits (e.g., smoking, drinking, diet)), other pertinent medical conditions (e.g., high blood pressure, dry skin, other diseases, etc.), medications, allergies, other pertinent medical history, current side effects of cancer treatments and other medications, etc.

The term "partner" will be used to refer to an entity or person that interacts with the provider to accomplish the treatment planning process. Typical partners include treating physicians and oncology laboratories, one or each of which may provide data to the provider in order for the provider to perform analysis and provide treatment planning services. For example, a partner physician may provide clinical data such about a particular patient such as, without limitation, the patient's cancer state, while a laboratory may provide accompanying information about the patient and/or may provide tissue samples (i.e., tumor biopsies) of the patient's cancerous cells.

Medical treatment prescriptions or plans are typically based on an understanding of how treatments affect illness (e.g., treatment results) including how well specific treatments eradicate illness, duration of specific treatments, duration of healing processes associated with specific treatments and typical treatment specific side effects. Ideally treatments result in complete elimination of an illness in a short period with minimal or no adverse side effects. In some cases cost is also a consideration when selecting specific medical treatments for specific ailments.

In many cases treatment results for specific illnesses vary for different patients. In particular, in the case of cancer treatments and results, different patients often respond differently to identical or similar treatments. Recognizing that different patients experience different results given effectively the same treatments in some cases, researchers and physicians often develop additional guidelines around how to optimize ailment treatments based on specific patient cancer state. For instance, while a first treatment may be best for a young, relatively healthy woman suffering colon cancer, a second treatment associated with fewer adverse side effects may be optimal for an older, relatively frail man with a similar or same colon cancer diagnosis. In many cases, patient conditions related to cancer state may be gleaned from clinical medical records, via a medical examination and/or via a patient interview, and may be used to develop a personalized treatment plan for a patient's specific cancer state. The idea here is to collect data on as many factors as possible that have any cause-effect relationship with treatment results and use those factors to design optimal, personalized treatment plans.

In treatment of at least some cancer states, treatment and results data is simply inconclusive. To this end, in treatment of some cancer states, seemingly indistinguishable patients with similar conditions often react differently to similar treatment plans so that there is no apparent cause and effect relationship between patient conditions and disparate treatment results. For instance, two women may be the same age, indistinguishably physically fit, and diagnosed with the same exact cancer state (e.g., cancer type, stage, tumor characteristics, etc.). Here, the first woman may respond to a cancer treatment plan well and may recover from her disease completely in 8 months with minimal side effects while the second woman, administered the same treatment plan, may suffer several severe adverse side effects and may never fully recover from her diagnosed cancer. Disparate treatment results for seemingly similar cancer states exacerbate efforts to develop treatment and results data sets and prescriptive activities. In these cases, unfortunately, there are cancer state factors that have cause and effect relationships to specific treatment results that are simply unknown currently and, therefore, those factors cannot be used to optimize specific patient treatments at this time.

Genomic sequencing has been explored to some extent as another cancer state factor (e.g., another patient condition) that can affect cancer treatment efficacy. To this end, at least some studies have shown that genetic features (e.g., DNA related patient factors (e.g., DNA and DNA alterations) and/or DNA related cancerous material factors (e.g., DNA of a tumor)) as well as RNA and other genetic sequencing data can have cause and effect relationships with at least some cancer treatment results for at least some patients. For instance, in one chemotherapy study using SULT1A1, a gene known to have many polymorphisms that contribute to a reduction of enzyme activity in the metabolic pathways that process drugs to fight breast cancer, patients with a SULT1A1 mutation did not respond optimally to tamoxifen, a widely used treatment for breast cancer. In some cases these patients were simply resistant to the drug and in others a wrong dosage was likely lethal. Side effects ranged in severity depending on varying abilities to metabolize tamoxifen. Raftogianis R, Zalatoris J. Walther S. The role of pharmacogenetics in cancer therapy, prevention and risk. Medical Science Division. 1999: 243-247. Other cases in which genetic features of a patient and/or a tumor affect treatment efficacy are well known.

The knowledge base around cancer treatments is always growing with different clinical trials in different stages around the world, such that if a physician's knowledge is current today, her knowledge will be dated within months if not weeks. Thousands of oncological articles are published each year and many are verbose and/or intellectually arduous to consume (e.g., the articles are difficult to read and internalize), especially by extremely busy physicians who have limited time to absorb new materials and information. Distilling publications down to those that are pertinent to a specific physician's practice takes time and is an inexact endeavor in many cases.

One positive development in the area of cancer treatment planning has been establishment of cancer committees or boards at cancer treating institutions where committee members routinely consider treatment planning for specific patient cancer states as a committee. To this end, it has been recognized that the task of prescribing optimized treatment plans for diagnosed cancer states is exacerbated by the fact that many physicians do not specialize in more than one or a small handful of cancer treatment options (e.g., radiation therapy, chemotherapy, surgery, etc.). For this reason, many physicians are not aware of many treatment options for specific ailment-patient condition combinations, related treatment efficacy, and/or how to implement those treatment options. In the case of cancer boards, the idea is that different board members bring different treatment experiences, expertise, and perspectives to bear so that each patient can benefit from the combined knowledge of all board members and so that each board member's awareness of treatment options continually expands.

While treatment boards are useful and facilitate at least some sharing of experiences among physicians and other healthcare providers, unfortunately treatment committees only consider small snapshots of treatment options and associated results based on personal knowledge of board members. In many cases boards are forced to extrapolate from "most similar" cancer states they are aware of to craft patient treatment plans instead of relying on a more fulsome collection of cancer state-treatment-results data, insights, and conclusions. In many cases the combined knowledge of board members may not include one or several important perspectives or represent important experience bases so that a final treatment plan simply cannot be optimized.

To be useful, cancer state, treatment, and efficacy data, and conclusions based thereon have to be rendered accessible to physicians, researchers, and other interested parties. In the case of cancer treatments where cancer states, treatments, results, and conclusions are extremely complicated and nuanced, physician and researcher interfaces have to present massive amounts of information and show many data corollaries and relationships. When massive amounts of information are presented via an interface, interfaces often become extremely complex and intimidating which can result in misunderstanding and underutilization. What is needed are well designed interfaces that make complex data sets simple to understand and digest. For instance, in the case of cancer states, treatments, and results, it would be useful to provide interfaces that enable physicians to consider de-identified patient data for many patients where the data is specifically arranged to trigger important treatment and results insights. It would also be useful if interfaces had interactive aspects so that the physicians could use filters to access different treatment and results data sets, again, to trigger different insights, to explore anomalies in data sets, and to better think out treatment plans for their own specific patients.

In some cases, specific cancers are extremely uncommon so that when they do occur, there is little if any data related to treatments previously administered and associated results. With no proven best or even somewhat efficacious treatment option to choose from, in many of these cases physicians turn to clinical trials.

Cancer research is progressing all the time at many hospitals and research institutions where clinical trials are always being performed to test new medications and treatment plans, each trial associated with one or a small subset of specific cancer states (e.g., cancer type, state, tumor location and tumor characteristics). A cancer patient without other effective treatment options can opt to participate in a clinical trial if the patient's cancer state meets trial requirements and if the trial is not yet fully subscribed (e.g., there is often a limit to the number of patients that can participate in a trial).

At any time there are several thousand clinical trials progressing around the world and identifying trial options for specific patients can be a daunting endeavor. Matching patient cancer state to a subset of ongoing trials is complicated and time consuming. Pairing down matching trials to a best match given location, patient and physician requirements, and other factors exacerbates the task of considering trial participation. In addition, considering whether or not to recommend a clinical trial to a specific patient given the possibility of trial treatment efficacy where the treatments are by their very nature experimental, especially in light of specific patient conditions, is a daunting activity that most physicians do not take lightly. It would be advantageous to have a tool that could help physicians identify clinical trial options for specific patients with specific cancer states and to access information associated with trial options.

As described above, optimized cancer treatment deliberation and planning involves consideration of many different cancer state factors, treatment options and treatment results as well as activities performed by many different types of service providers including, for instance, physicians, radiologists, pathologists, lab technicians, etc. One cancer treatment consideration most physicians agree affects treatment efficacy is treatment timing where earlier treatment is almost always better. For this reason, there is always a tension between treatment planning speed and thoroughness, where one or the other of speed and thoroughness suffers.

One other problem with current cancer treatment planning processes is that it is difficult to integrate new pertinent treatment factors, treatment efficacy data and insights into existing planning databases. In this regard, known treatment planning databases and application programs have been developed based on a predefined set of factors and insights and changing those databases and applications often requires a substantial effort on the part of a software engineer to accommodate and integrate the new factors or insights in a meaningful way where those factors and insights are properly considered along with other known factors and insights. In some cases, the substantial effort required to integrate new factors and insights simply means that the new factors or insights will not be captured in the database or used to affect planning. In other cases, the effort means that the new factors or insights are only added to the system at some delayed time after a software engineer has applied the required and substantial reprogramming effort. In still other cases, the required effort means that physicians that want to apply new insights and factors may attempt to do so based on their own experiences and understandings instead of in a more scripted and rules based manner. Unfortunately, rendering a new insight actionable in the case of cancer treatment is a literal matter of life and death and, therefore, any delay or inaccurate application can have the worst effect on current patient prognosis.

One other problem with existing cancer treatment efficacy databases and systems is that they are simply incapable of optimally supporting different types of system users. To this end, data access, views, and interfaces needed for optimal use are often dependent upon what a system user is using the system for. For instance, physicians often want treatment options, results and efficacy data distilled down to simple correlations while a cancer researcher often requires much more detailed data access required to develop new hypothesis related to cancer state, treatment and efficacy relationships. In known systems, data access, views, and interfaces are often developed with one consuming client in mind such as, for instance, physicians, pathologists, radiologists, a cancer treatment researcher, etc., and are therefore optimized for that specific system user type which means that the system is not optimized for other user types and cannot be easily changed to accommodate needs of those other user types.

With the advent of NGS it has become possible to accurately detect genetic alterations in relevant cancer genes in a single comprehensive assay with high sensitivity and specificity. However, the routine use of NGS testing in a clinical context faces several challenges. First, many tissue samples include minimal high quality DNA and RNA required for meaningful testing. In this regard, nearly all clinical specimens comprise formalin fixed paraffin embedded tissue (FFPET), which, in many cases, has been shown to include degraded DNA and RNA. Exacerbating matters, many samples available for testing contain limited amounts of tissue, which in turn limits the amount of nucleic acid attainable from the tissue. For this reason, accurate profiling in clinical specimens requires an extremely sensitive assay capable of detecting gene alterations in specimens with a low tumor percentage. Second, millions of bases within the tumor genome are assayed. For this reason, rigorous statistical and analytical approaches for validation are required in order to demonstrate the accuracy of NGS technology for use in clinical settings and in developing cause and effect efficacy insights.

Systems and Methods of Clinical Trial Evaluation

The present disclosure relates to systems and methods for facilitating the extraction and analysis of data embedded within clinical trial information and patient records. More particularly, the present disclosure relates to systems and methods for matching patients with clinical trials and validating clinical trial site capabilities.

The present disclosure is described in the context of a system that utilizes an established database of clinical trials (e.g., clinicaltrials.gov, as provided by the U.S. National Library of Medicine). Nevertheless, it should be appreciated that the present disclosure is intended to teach concepts, features, and aspects that can be useful with any information source relating to clinical trials, including, for example, independently documented clinical trials, internally/privately developed clinical trials, a plurality of clinical trial databases, and the like.

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, data abstractors, site specialists, data scientists, and many other persons with specialized skill sets.

The term "physician" will be used to refer generally to any health care provider including but not limited to a primary care physician, a medical specialist, a neurologist, a radiologist, a geneticist, and a medical assistant, among others.

The term "data abstractor" will be used to refer to a person that consumes data available in clinical records provided by a physician (such as primary care physician or specialist) to generate normalized and structured data for use by other system specialists, and/or within the system.

The term "clinical trial" will be used to refer to a research study in which human volunteers are assigned to interventions (e.g., a medical product, behavior, or procedure) based on a protocol and are then evaluated for effects on biomedical or health outcomes.

Existing clinical trial databases and systems can be web-based resources that provide patients, providers, physicians, researchers, and the general public with access to information on publicly and privately supported clinical studies. Often, there are a large number of clinical trials being conducted at any given time, and typically the clinical trials relate to a wide range of diseases and conditions. In some instances, clinical trials are performed at or using the resources of multiple sites, such as hospitals, laboratories, and universities. Each site that participates in a given clinical trial must have the proper equipment, protocols, and staff expertise, among other things.

Clinical trial databases and systems receive information on each clinical trial via the submission of data by the principal investigator (PI) or sponsor (or related staff). As an example, the public website clinicaltrials.gov is maintained by the National Library of Medicine (NLM) at the National Institutes of Health (NIH). Most of the records on clinicaltrials.gov describe clinical trials.

The information on clinicaltrials.gov is typically provided and updated by the sponsor (or PI) of the particular clinical trial. Studies and clinical trials are generally submitted (that is, registered) to relevant websites and databases when they begin, and the information may be updated as-needed throughout the study or trial. Studies and clinical trials listed in the database span the United States, as well as over two hundred additional countries. Notably, clinicaltrials.gov and/or other clinical trial databases may not contain information about all the clinical trials conducted in the United States (or globally), because not all studies are currently required by law to be registered. Additionally, trial databases are often not maintained to include the most up-to-date information about the conduct of any particular study.

In general, each clinical trial record (such as on clinicaltrials.gov), presents summary information about a study protocol which can include the disease or condition, the proposed intervention (e.g., the medical product, behavior, or procedure being studied), title, description, and design of the trial, requirements for participation (eligibility criteria), locations where the trial is being conducted (sites), and/or contact information for the sites.

Notably, clinical trial databases and websites often express the clinical trial information using free text (i.e., unstructured data). For example, one trial on clinicaltrials.gov is a Phase I/II clinical trial using the drugs sapacitabine and olaparib. According to the study description, "the FDA (the U.S. Food and Drug Administration) has approved Olaparib as a treatment for metastatic HER2 negative breast cancer with a BRCA mutation. Olaparib is an inhibitor of PARP (poly [adenosine diphosphate-ribose] polymerase), which means that it stops PARP from working. PARP is an enzyme (a type of protein) found in the cells of the body. In normal cells when DNA is damaged, PARP helps to repair the damage. The FDA has not approved Sapacitabine for use in patients including people with this type of cancer. Sapacitabine and drugs of its class have been shown to have antitumor properties in many types of cancer, e.g., leukemia, lung, breast, ovarian, pancreatic and bladder cancer. Sapacitabine may help to stop the growth of some types of cancers. In this research study, the investigators are evaluating the safety and effectiveness of Olaparib in combination with Sapacitabine in BRCA mutant breast cancer." The trial has fourteen inclusion criteria and twenty exclusion criteria, each described using free text. One inclusion criteria for the clinical trial is "Documented germline mutation in BRCA1 or BRCA2 that is predicted to be deleterious or suspected deleterious (known or predicted to be detrimental/lead to loss of function). Testing may be completed by any CLIA-certified laboratory." Another inclusion criteria for the clinical trial states that the patient must have "Adequate organ and bone marrow function as defined below:
 Hemoglobin >=10 g/dL
 Absolute neutrophil count (ANC) >=1.5×109/L
 Platelet count >=100×109/L
 Total bilirubin <=1.5× institutional upper limit of normal (ULN)

AST(SGOT)/ALT (SGPT)<=2.5× institutional ULN, OR
AST(SGOT)/ALT (SGPT)<=5× institutional ULN if liver
   metastases are present
Creatinine Clearance estimated (using the Cockcroft-
   Gault equation) of >=51 mL/min."

When described with free text, inclusion criteria requires a physician or other person to review the inclusion criteria compared to a patient's medical record to determine whether the patient is eligible for the study. Some patient health information is in the form of structured data, where health information resides within a fixed field within a record or file, such as a database or a spreadsheet. The free text nature of the inclusion criteria presented by websites such as clinicaltrials.gov does not lend itself to simple matching with structured data, and inclusion criteria that are described on the website require analysis of multiple structured data fields. For example, the inclusion criteria "Documented germline mutation in BRCA1 or BRCA2 that is predicted to be deleterious or suspected deleterious (known or predicted to be detrimental/lead to loss of function). Testing may be completed by any CLIA-certified laboratory" requires analysis of 1) the particular mutation, 2) whether it is germline, 3) whether it is deleterious, predicted to be detrimental, or leads to a loss of function, 4) whether it was tested in a CLIA-certified laboratory. With respect to unstructured clinical trial data, efficiently determining factors such as eligibility criteria for a potential patient participant often becomes unmanageable.

Thus, what is needed is a system that is capable of efficiently capturing all relevant clinical trial and patient data, including disease/condition data, trial eligibility criteria, trial site features and constraints, and/or clinical trial status (recruiting, active, closed, etc.). Further, what is needed is a system capable of structuring that data to optimally drive different system activities including one or more of efficiently matching patients to clinical trials, activating new sites for an existing clinical trial, and updating site information, among other things. In addition, the system should be highly and rapidly adaptable so that it can be modified to absorb new data types and new clinical trial information, as well as to enable development of new user applications and interfaces optimized to specific user activities.

User Interface, System, and Method for Cohort Analysis

This disclosure relates to spatially projecting relationships in multidimensional data and, in particular, techniques for analyzing multidimensional datasets requiring the minimization of non-convex optimization functions.

Many fields of technology (e.g., bioinformatics, financial services, forensics, and academia) are scaling their information visualization services to meet consumer demands for identifying relationships between members of large sets of data that require substantial computational resources to perform with conventional techniques. As the scale of these datasets extend beyond tens of thousands of members, there is a need for an efficient and parallelizable technique to process, quantify, and display similarities (or dissimilarities) between members in an intuitive and understandable way. Existing techniques utilize clustering algorithms or multi-dimensional scaling algorithms which require minimization of an optimization function; which, for convex functions over large data sets, is relatively quick. However, when minimizing a non-convex function over a large data set, the requirement for computational resources, such as computation time, increases exponentially because optimization techniques cannot assume that any local minima detected is the global minima of the optimization function and must continue iteratively processing until all domain values of the function have been processed before concluding the global minima has been found. These techniques may consume significant resources and bog down processing and memory availability of the computing system that generates an ultimate user interface.

Such processing problems may be exacerbated when the user interface permits selection of a reference member from among the plurality of available members and/or customization of the criteria by which the members will be compared, and those abilities mean that the comparative determinations may need to be done "on-the-fly," as it would be impractical or consume too many system resources to precompile those calculations. For example, when comparing members in a multi-factor data set, convex optimization techniques (e.g. gradient descent) may be used to determine and visually quantify similarity among those members. Such conventional convex optimization techniques converge to a final value quickly, but they often result in an incorrect final value when the convergence is located at a local minima incorrectly presumed to be the global minima.

What is needed is a user interface and/or an underlying system and method that address one or more of these drawbacks.

Identifying Copy Number Variation Location, Length, and Quantity from Genetic Sequence Data The present invention relates to the field of identifying the location, length, and quantity of copy number variations (CNV) in a patient's genome for analysis to improve the patient's subsequent treatment selections and standards of care and, in particular, to the treatment selections and standards of care for oncological diagnosis.

The human genome was completely mapped in April 2003 by the Human Genome Project and opened the door for progress in numerous fields of study focused on the sequence of nucleotide base pairs that make up human deoxyribonucleic acid (DNA). Nucleotides are generally referenced according to one of four nucleobases (cytosine [C], guanine [G], adenine [A] or thymine [T]) and are joined to one another according to base pairing rules (A with T and C with G) to form base pairs that, when chained together, make up double-stranded DNA. The human genome has over six billion of these nucleotides packaged into two sets of twenty-three chromosomes, one set inherited from each parent, encoding over thirty-thousand genes. The order in which the nucleotide types are arranged is known as the molecular sequence, genetic sequence, or genome. While it was initially believed that each of these over thirty-thousand genes were represented as two copies in a genome, recent discoveries have revealed that portions of these genes or other segments of DNA, ranging in size from tens to millions of base pairs, can vary in copy number.

The capture of patient genetic information through genetic testing in the field of next generation sequencing ("NGS") for genomics is a new and rapidly evolving field. NGS involves using specialized equipment such as a next generation gene sequencer, which is an automated instrument that determines the order of nucleotides in DNA and/or ribonucleic acid (RNA). The instrument reports the sequences as a string of letters, called a read. These reads allow the identification of genes, variants, or sequences of nucleotides in the human genome. An analyst compares these reads from genes to one or more reference genomes of the same genes, variants, or sequences of nucleotides. Each version of a gene that is found in a population is known as an allele. If two alleles of a single gene in a cell are not identical, the cell is described as heterozygous with respect to that specific gene. This concept is referred to as the zygosity of the gene.

One of the fields that appreciated the full human genome mapping, CNV, focuses on analyzing these genes, variants, alleles, or sequences of nucleotides to identify deviations from the normal genome and any subsequent implications. CNV are the phenomenon in which structural variations may occur in sections of nucleotides, or base pairs, that include repetitions, deletions, or inversions. FIG. 311 is an illustration of the various types of CNV .A.00 that occur in the human genome. An example normal sequence .A.10 of DNA may contain a representative gene, GTCTGA-CATCCTG (SEQ ID NO:1). For repeated sections, the number of repeats in the genome varies between individuals and may include short or long repeats. Short repeats including bi-nucleotide repetitions .A.20 (GT-GT) or tri-nucleotide repetitions .A.30 (GTC-GTC) and long repeats including repeats of entire genes themselves .A.40 (GTCTGA-CATCCTG; SEQ ID NO:1). Deletions include missing sections of the DNA, such as a sequence of nucleotides .A.50 (TGAC). In some circumstances, a entire gene itself .A.60 is deleted from one or both sets of chromosomes, creating a special type of genetic event known as loss of heterozygosity (LOH). LOH is a subtype of CNV specifically dealing with the deletions of alleles from the DNA. LOH is a common genetic event in cancer whereby one allele is lost, leading to part of the genome appearing homozygous in the tumor and heterozygous in matching normal DNA. Inversions include end-to-end sequence reversals .A.70 (CAGTCT) and end-to-end gene reversals .A.80 (GTCCTACAGTCTG; SEQ ID N0:2). While the study of these structural variations was initially limited to individual changes that could be seen through light microscopes, the advent of NGS has allowed identification of submicroscopic structural variations on a genome-wide scale. With the explosion of CNV being detected due to new technology, the extent to which these new CNV contributes to human disease is not yet fully understood. While it is recognized that susceptibility to diseases (including some cancers) are associated with elevated copy numbers of particular genes and that when certain genes are duplicated they may create dosage imbalances in medications, identifying which CNV are responsible for which diseases or pharmacogenomic effects on the whole genome requires further study.

Pharmacogenomics is the study of the role of the human genome in drug response. Aptly named by combining pharmacology and genomics, pharmacogenomics analyzes how the genetic makeup of an individual affects their response to drugs. It deals with the influence of genetic variation on drug response in patients by correlating gene expression pharmacokinetics (drug absorption, distribution, metabolism, and elimination) and pharmacodynamics (effects mediated through a drug's biological targets). The term pharmacogenomics is often used interchangeably with pharmacogenetics. Although both terms relate to drug response based on genetic influences, pharmacogenetics focuses on single drug-gene interactions, while pharmacogenomics encompasses a more genome-wide association approach, incorporating genomics and epigenetics while dealing with the effects of multiple genes on drug response. Pharmacogenomics and pharmacogenetics may be used interchangeably throughout the disclosure. This information may assist medical professionals in choosing which treatment to prescribe to their patient.

The challenge of identifying CNV and isolating their manifestations with disease susceptibility and/or pharmacogenomic effects is rooted in a lack of structured information between the human genome and patient/clinical information such as disease progression and treatment information. In attempts to make progress in identifying CNV as biomarkers, the Hospital for Sick Children has established the 'Database of Genomic Variants' to list CNV found in the general population and the Wellcome Trust Sanger Institute has developed a database of CNVs (called DECIPHER) associated with clinical conditions.

What is needed is a platform for identifying the number of both new and known CNV in a patient's DNA/RNA and referencing CNV occurrence with patient/clinical information through the proper analysis tools to make inferences about disease susceptibility and pharmacogenomics that can be used to make treatment decisions which improve overall patient healthcare.

Methods of Normalizing and Correcting RNA Expression Data

The present disclosure relates to normalizing and correcting gene expression data and, more particularly, to normalizing and correcting gene expression data across varied gene expression databases.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Experiments examining gene expression are valuable in assessing patient response and projected responses to various treatments. There are relatively large databases of gene expression data, such as The Cancer Genome Atlas (TCGA) project database, the Genotype-Tissue Expression (GTEx) project database, and others. Unfortunately, gene expression data, in particular from RNA sequencing experiments, can be highly sensitive to biases in sample type, sample preparation, and sequencing protocol. The result is gene expression data across databases and data sets that cannot be readily compared, and certainly not if a relatively high level of specificity and sensitivity is required for data analysis. As such, there is a desire for techniques to combine data across gene expression datasets to provide functionally useful and comparable gene expression data.

For gene expression data in the form of RNA sequencing data (referred to herein as "RNA seq" or "RNAseq" data), for example, main sources of bias are varied. Biases arise from tissue type (e.g., fresh frozen (FF) or formalin fixed, paraffin embedded (FFPE)), and RNA selection method (e.g., exon capture or poly-A RNA selection). For datasets sequenced using exome capture, for example, subtle differences between the different exome capture kits arise upon careful inspection.

Examining these biases across multiple RNA seq datasets, it becomes clear that synchronizing RNA seq data is exceedingly challenging.

A Pan-Cancer Model to Predict the PD-L1 Status of a Cancer Cell Sample Using RNA Expression Data and Other Patient Data Physicians treating cancer patients may run tests on their patients' biospecimens to predict what treatment is most likely to treat the patient's cancer. One type of test that physicians may order determines whether their patient's cancer cells create or contain certain biomarkers or another treatment-related molecule of interest. In some instances, the biomarker is programmed death ligand 1 (PD-L1), also known as CD274.

The percentage of cancer cells that express PD-L1 protein in a patient can predict whether immunotherapy treatments, especially immune checkpoint blockade treatments, are likely to successfully eliminate or reduce the number of the patient's cancer cells. Examples of checkpoint blockade treatments are antibodies that target PD-L1 or programmed death ligand 1 (PD-1), the receptor for PD-L1, in order to activate the immune system to eliminate cancer cells Currently, immunohistochemistry (IHC) staining, fluorescence in situ hybridization (FISH), or reverse phase protein array (RPPA) may be used to detect any treatment-related molecule of interest in tumor tissue or another cancer cell sample.

For IHC staining, a thin slice of tumor tissue (approximately 5 microns thick) or a blood smear of cancer cells is affixed to glass microscope slides to create a histology slide, also known as a pathology slide. The slide is submerged in a liquid solution containing antibodies. Each antibody is designed to bind to one copy of the target biomarker molecule on the slide and is coupled with an enzyme that then converts a substrate into a visible dye. This stain allows a trained pathologist or other trained analyst to visually inspect the location of target molecules on the slide.

A portion of the cells on the slide may be normal cells, and another portion of cells are cancer cells. If a cancer cell on the slide displays IHC staining, it is considered positive for expressing the IHC target, such as PD-L1. Generally, an analyst views the slide to estimate the percentage of the total cancer cells that are positive and compares it to a threshold value. If the percentage exceeds that threshold, the cancer cell sample on the slide is designated as positive for that biomarker.

Similarly FISH and RPPA can be used to visually detect and quantify copies of the PD-L1 protein and/or CD274 RNA in a cancer cell sample. If the results of these assays exceed a selected threshold value, the cancer cell sample can be labeled as PD-L1 positive.

There are several disadvantages of using IHC, FISH, or RPPA to determine the biomarker status of a cancer cell sample.

The process of conducting IHC staining, FISH, and RPPA requires time, trained technicians, equipment and antibodies or other reagents, all of which can be expensive.

Often, an IHC slide analyst does not have enough time to count all of the cancer cells on an IHC-stained slide and inaccurately estimates the percentage of stained cancer cells by eye. Because the estimate is subjective, any two analysts may disagree when determining whether a slide exceeds a PD-L1 threshold. There are similar challenges for FISH and RPPA.

IHC staining, FISH, and RPPA assays may require up to ten slices of tumor tissue from a biopsy or a sample of blood taken from the patient. Collecting cancer cells through biopsies or blood draws subjects the patient to discomfort and inconvenience, so the amount of cancer cells available for testing is limited. Often, the tissue is needed for other tests, including genetic sequence analysis.

Therefore, there is a need for systems and methods that predict the PD-L1 status of cancer cells beyond those which currently are used in the art.

A Method and Process for Predicting and Analyzing Patient Cohort Response, Progression, and Survival A system and method are described herein that facilitate the discovery of insights of therapeutic significance, through the automated analysis of patterns occurring in patient clinical, molecular, phenotypic, and response data, and enabling further exploration via a fully integrated, reactive user interface.

DESCRIPTION OF THE RELATED ART

In the medical field, generally, and in the area of cancer research and treatment, in particular, voluminous amounts of data are generated and collected for each patient. This data may include demographic information, such as the patient's age, gender, height, weight, smoking history, geographic location, etc. The data also may include clinical components, such as tumor type, location, size, and stage, as well as treatment data including medications, dosages, treatment therapies, mortality rates, etc. Moreover, more advanced analysis also may include genetic information about the patient and/or tumor, including genetic markers, mutations, etc.

Despite this wealth of data, there is a dearth of meaningful ways to compile and analyze the data quickly, efficiently, and comprehensively.

What are needed are a user interface, system, and method that overcome one or more of these challenges.

Collaborative Artificial Intelligence Method and System

The field of this disclosure is systems for accessing and manipulating large complex data sets in ways that enable system users to develop new insights and conclusions with minimal user-interface friction hindering access and manipulation.

While the present disclosure describes various innovations that will be useful in many different industries (e.g., healthcare, scientific and medical research, law, oil exploration, travel, etc.), unless indicated otherwise, in the interest of simplifying this explanation, the innovations will be described in the context of an exemplary healthcare worker that collaborates with patients to diagnose ailment states, prescribe treatments and administer those treatments to improve overall patient health. In addition, while many different types of healthcare workers (e.g., doctors, psychologists, physical therapists, nurses, administrators, researchers, insurance experts, pharmacists, etc.) in many different medical disciplines (e.g., cancer, Alzheimer's disease, Parkinson's disease, mental illnesses) will benefit from the disclosed innovations, unless indicated otherwise, the innovations will be described in the context of an exemplary oncologist/researcher (hereinafter "oncologist") that collaborates with patients to diagnose cancer states (e.g., all physiological, habit, history, genetic and treatment efficacy factors), understand and evaluate existing data and guidelines for patients similar to their patient, prescribe treatments and administer those treatments to improve overall patient health and that performs cancer research.

Many professions require complex thought where people need to consider many factors when selecting solutions to encountered situations, hypothesize new factors and solutions and test new factors and solutions to make sure that they are effective. For instance, oncologists considering specific patient cancer states, optimally should consider many different factors when assessing the patient's cancer state as well as many factors when crafting and administering an optimized treatment plan. For example, these factors include the patient's family history, past medical conditions, current diagnosis, genomic/molecular profile of the patient's hereditary DNA and of the patient's tumor's DNA, current nationally recognized guidelines for standards of care within that cancer subtype, recently published research relating to that patient's condition, available clinical trials pertaining to that patient, available medications and other therapeutic interventions that may be a good option for the patient and data from similar patients. In addition, cancer and cancer treatment research are evolving rapidly so that researchers need to continually utilize data, new research and new treatment guidelines to think critically about new factors and treatments when diagnosing cancer states and optimized treatment plans.

In particular, it is no longer possible for an oncologist to be familiar with all new research in the field of cancer care. Similarly, it is extremely challenging for an oncologist to be able to manually analyze the medical records and outcomes of thousands or millions of cancer patients each time an oncologist wants to make a specific treatment recommendation regarding a particular patient being treated by that oncologist. As an initial matter, oncologists do not even have access to health information from institutions other than their own. In the United States, the federal law known as the Health Insurance Portability and Accountability Act of 1996 ("HIPAA") places significant restrictions on the ability of one health care provider to access health records of another health care provider. In addition, health care systems face administrative, technical, and financial challenges in making their data available to a third party for aggregation with similar data from other health care systems. To the extent health care information from multiple patients seen at multiple providers has been aggregated into a single repository, there is a need for a system and method that structures that information using a common data dictionary or library of data dictionaries. Where multiple institutions are responsible for the development of a single, aggregated repository, there can be significant disagreement over the structure of the data dictionary or data dictionaries, the methods of accessing the data, the individuals or other providers permitted to access the data, the quantity of data available for access, and so forth. Moreover, the scope of the data that is available to be searched is overwhelming for any oncologist wishing to conduct a manual review. Every patient has health information that includes hundreds or thousands of data elements. When including sequencing information in the health information to be accessed and analyzed, such as from next-generation sequencing, the volume of health information that could be analyzed grows intensely. A single FASTQ or BAM file that is produced in the course of whole-exome sequencing, for instance, takes up gigabytes of storage, even though it includes sequencing for only the patient's exome, which is thought to be about 1-2% of the whole human genome.

In this regard, an oncologist may have a simple question—"what is the best medication for this particular patient?"—the answer to which requires an immense amount of health information, analytical software modules for analyzing that information, and a hardware framework that permits those modules to be executed in order to provide an answer. Almost all queries/ideas/concepts are works in progress that evolve over time as critical thinking is applied and additional related factors and factor relationships are recognized and/or better understood. All queries start as a hypothesis rooted in consideration of a set of interrelated raw material (e.g., data). The hypothesis is usually tested by asking questions related to the hypothesis and determining if the hypothesis is consistent and persists when considered in light of the raw material and answers to the questions. Consistent/persistent hypothesis become relied upon ideas (i.e., facts) and additional raw material for generating next iterations of the initial ideas as well as completely new ideas.

When considering a specific cancer state, an oncologist considers known factors (e.g., patient conditions, prior treatments, treatment efficacy, etc.), forms a hypothesis regarding optimized treatment, considers that hypothesis in light of prior data and prior research relating similar cancer states to treatment efficacies and, where the prior data indicates high efficacy regarding the treatment hypothesis, may prescribe the hypothesized treatment for a patient. Where data indicates poor treatment efficacy the oncologist reconsiders and generates a different hypothesis and continues the iterative testing and conclusion cycle until an efficacious treatment plan is identified. Cancer researchers perform similar iterative hypothesis, data testing and conclusion processes to derive new cancer research insights.

Tools have been and continue to be developed to help oncologists diagnose cancer states, select and administer optimized treatments and explore and consider new cancer state factors, new cancer states (e.g., diagnosis), new treatment factors, new treatments and new efficacy factors. For instance, massive cancer databases have been developed and are maintained for access and manipulation by oncologists to explore diagnosis and treatment options as well as new insights and treatment hypothesis. Computers enable access to and manipulation of cancer data and derivatives thereof.

Cancer data tends to be voluminous and multifaceted so that many useful representations include substantial quantities of detail and specific arrangements of data or data derivatives that are optimally visually represented. For this reason, oncological and research computer workstations typically include conventional interface devices like one or more large flat panel display screens for presenting data representations and a keyboard, mouse, or other mechanical input device for entering information, manipulating interface tools and presenting many different data representations. In many cases a workstation computer/processor runs electronic medical records (EMR) or medical research application programs (hereinafter "research applications") that present different data representations along with on screen cursor selectable control icons for selecting different data access and manipulation options.

While conventional computers and workstations operate well as data access and manipulation interfaces, they have several shortcomings. First, using a computer interface often requires an oncologist to click many times, on different interfaces, to find a specific piece of information. This is a cumbersome and time consuming process which often does not result in the oncologist achieving the desired result and receiving the answer to the question they are trying to ask.

Second, in many cases it is hard to capture hypothetical queries when they occur and the ideas are lost forever. Queries are not restricted to any specific time schedule and therefore often occur at inconvenient times when an oncologist is not logged into a workstation and using a research application usable to capture and test the idea. For instance, an oncologist may be at home when she becomes curious about some aspect of a patient's cancer state or some statistic related to one of her patients or when she first formulates a treatment hypothesis for a specific patient's cancer state. In this case, where the oncologist's workstation is at a remote medical facility, the oncologist cannot easily query a database or capture or test the hypothesis.

Also, in this case, even if the oncologist can use a laptop or other home computer to access a research application from home, the friction involved with engaging the application often has an impeding effect. In this regard, application access may require the oncologist to retrieve a laptop or physically travel to a stationary computer in her home, boot up the computer operating system, log onto the computer (e.g., enter user name and password), select and start a research application, navigate through several application screenshots to a desired database access tool suite and then enter a query or hypothesis defining information in order to initiate hypothesis testing. This application access friction is sufficient in many cases to dissuade immediate queries or hypothesis capture and testing, especially in cases where an oncologist simply assumes she will remember the query or hypothesis the next time she access her computer interface. As anyone who has a lot of ideas knows, ideas are fleeting and therefore ideas not immediately captured are often lost. More importantly, oncologists typically have limited amounts of time to spend on each patient case and need to have their questions and queries resolved immediately while they are evaluating information specific to that patient.

Third, in many cases a new query or hypothesis will occur to an oncologist while engaged in some other activity unrelated to oncological activities. Here, as with many people, immediate consideration and testing via a conventional research application is simply not considered. Again, no immediate capture can lead to lost ideas.

Fourth, in many cases oncological and research data activities will include a sequence of consecutive questions or requests (hereinafter "requests") that hone in on increasingly detailed data responses where the oncologist/researcher has to repeatedly enter additional input to define next level requests as intermediate results are not particularly interesting. In addition, while visual representations of data responses to oncological and research requests are optimal in many cases, in other cases visual representations tend to hamper user friendliness and can even be overwhelming. In these cases, while the visual representations are usable, the representations can require appreciable time and effort to consume presented information (e.g., reading results, mentally summarizing results, etc.). In short, conventional oncological interfaces are often clunky to use.

Moreover, today, oncologists and other professionals have no simple mechanism for making queries of large, complex databases and receiving answers in real time, without needing to interact with electronic health record systems or other cumbersome software solutions. In particular, there is a need for systems and methods that allow a provider to query a device using his or her voice, with questions relating to the optimal care of his or her patient, where the answers to those questions are generated from unique data sets that provide context and new information relative to the patient, including vast amounts of real world historical clinical information combined with other forms of medical data such as molecular data from omics sequencing and imaging data, as well as data derived from such data using analytics to determine which path is most optimal for that singular patient Thus, what is needed is an intuitive interface for complex databases that enables oncologists, researchers, and other professionals and database users to access and manipulate data in various ways to generate queries and test hypothesis or new ideas thereby thinking through those ideas in the context of different data sets with minimal access and manipulation friction. It would be advantageous if the interface were present at all times or at least portable so that it is available essentially all the time. It would also be advantageous if a system associated with the interface would memorialize user-interface interactions thereby enabling an oncologist or researcher to reconsider the interactions at a subsequent time to re-engage for the purpose of continuing a line of questions or hypothesis testing without losing prior thoughts.

It would also be advantageous to have a system that captures an oncologist's thoughts for several purposes such as developing better healthcare aid systems, generating automated records and documents and offering up services like appointment, test and procedure scheduling, prescription preparation, etc.

Unsupervised Learning and Prediction of Lines of Therapy from High-Dimensional Longitudinal Medications Data Line of Therapy (LoT) is standard nomenclature for discussing treatment with antineoplastic medications. Both the National Comprehensive Cancer Network and Association for Clinical Oncology (ASCO), groups which issue Standard of Care (SoC) treatment guidelines present their findings in the LoT framework. Oncologists consider these guidelines closely as they plan courses of treatment for their patients. Additionally, the LoT construct is considered by regulatory agencies, payers (both private and institutional), and provider groups as they plan for, approve, and pay for new anti-cancer medications. As such, pharmaceutical companies also approach their planning and trial design considering LoT and the potential impact/benefit for patients realized by their new medications. Doctors frequently recap patient history to another doctor by highlighting the LoT prescribed to the patient, any negative effects, progressions, or intervening events, and any subsequent changes to the LoT to compensate or adapt treatment to improve the patient's outcome. Unfortunately, this type of informal recap is never entered into a patient's electronic medical/health record (EMR/EHR). When physicians agree to provide a patient's EMR, it is desirable to parse through the records provided and pull out the LoTs, as well as significant, intervening events (including progression, regression, metastasis, length of time) and provide them to the physician for their convenience and to improve physician understanding of the LoT history for each patient.

This is a difficult task to accomplish because the information recoverable from EHR and/or progress notes alone is never complete. There are a number of inaccuracies, inconsistencies, missing records, and other incomplete entries that may (or may not) appear in the record that need to be considered. For example, an oncologist may consider two LoTs: one with a combination of medications/treatments/therapies A and B, or C as a monotherapy. The patient's insurance provider may deny the employment of C due to cost reasons, so the patient receives A and B. After a series of administrations, the patient may find this combination too detrimental to overall health, so the patient transitions to a maintenance therapy of B alone. In the EMR, all of these medications may appear recorded for several months, even when the patient never even received C, and only had A for a portion of the time. Afterwards, the oncologist may order a CT scan to observe growth of the tumor. When the patient returns to the doctor six months later because their symptoms worsened, the doctor may note the symptoms worsening in the progress note as a progression event and list medications A and D, or the doctor may only list medication D, leaving the record ambiguous as to the medications A, B, and C. From an abstraction perspective, the EMR merely records that medications A, B, and C were prescribed and six months later D. The EMR may record a CT scan as well as the symptoms worsening around the six month time frame. The difficulty in developing LoTs from these records is many-fold:

1) If the patient never took, or discontinued, medications, then a LoT indicating that they were taken is not reliable from a data science perspective.

2) From an industry perspective, a change to a LoT that merely adjusts medications to avoid negative side effects to a medication is not a new LoT, but the same LoT. So medications changes are not always indicative of a new LoT. Identifying whether a change in medications coincides with a progression event, worsening symptoms, or any other significant intervening event may be tricky; for example, if the patient did not take medication C because of insurance issues or medication B because of negative side effects, this may be difficult to rectify against worsening symptoms as a LoT change or merely avoiding negative side effects for the original LoT.

3) From a data science perspective, It may be difficult to impute whether medications A, B, and/or C were continued for the entire year in part or whole, even after medication D was prescribed. (This leads to the question is a first Lot A, B, C and a second LoT D, D and A, D and B, D and C, or D, A, and B ... etc).

4) From a clinician perspective, certain drugs, while having a change in name, may be considered essentially the same drug.

5) Patients receive many medications as part of therapy, called 'supportive care' medications, that are irrelevant for LoT assignment. Further, differentiating these is not necessarily straightforward, as medications that are considered 'supportive care' versus 'primary care' differ by cancer type.

6) Data source heterogeneity. EHR and curation from progress notes differ from source to source and requires harmonization to a common standard prior to LoT determination.

7) Overcoming the burdens and complications of patchy data. Few patients have their cancer treatment records completely covered by both EHR and curated progress notes. Oftentimes, only one or the other is available, and when both are present, they describe discordant portions of the patient timeline. This complicates matters, especially when records commonly note the start of a set of medications, but rarely when they were stopped.

Currently, there does not exist any algorithm for predicting, digesting, or imputing LoTs from EMR. This generally requires a skilled practitioner manually reviewing the file to make these determinations on a case by case basis for every patient which is costly and time consuming. Machine learning may be applied to consider all medications across all patients based on their frequency, common occurrences of medications changes for certain diagnosis with intervening events that typically reflect a LoT may be predicted from incomplete data. To address this, a machine learning approach that synthesizes heuristics (hard rules) with clinical insights (soft rules) and an Expectation-Maximization (EM) algorithm to make effective predictions using machine learning algorithms (MLA) may be considered.

SUMMARY OF THE DISCLOSURE

Data Based Cancer Research and Treatment Systems and Methods

It has been recognized that an architecture where system processes are compartmentalized into loosely coupled and distinct micro-services that consume defined subsets of system data to generate new data products for consumption by other micro-services as well as other system resources enables maximum system adaptability so that new data types as well as treatment and research insights can be rapidly accommodated. To this end, because micro-services operate independently of other system resources to perform defined processes where the only development constraints are related to system data consumed and data products generated, small autonomous teams of scientists and software engineers can develop new micro-services with minimal system constraints thereby enabling expedited service development.

The system enables rapid changes to existing micro-services as well as development of new micro-services to meet any data handling and analytical needs. For instance, in a case where a new record type is to be ingested into an existing system, a new record ingestion micro-service can be rapidly developed for new record intake purposes resulting in addition of the new record in a raw data form to a system database as well as a system alert notifying other system resources that the new record is available for consumption. Here, the intra-micro-service process is independent of all other system processes and therefore can be developed as efficiently and rapidly as possible to achieve the service specific goal. As an alternative, an existing record ingestion micro-service may be modified independent of other system processes to accommodate some aspect of the new record type. The micro-service architecture enables many service development teams to work independently to simultaneously develop many different micro-services so that many aspects of the overall system can be rapidly adapted and improved at the same time.

According to another aspect of the present disclosure, in at least some disclosed embodiments system data may be represented in several differently structured databases that are optimally designed for different purposes. To this end, it has been recognized that system data is used for many different purposes such as memorialization of original records or documents, for data progression memorialization and auditing, for internal system resource consumption to generate interim data products, for driving research and analytics, and for supporting user application programs and related interfaces, among others. It has also been recognized that a data structure that is optimal for one purpose often is sub-optimal for other purposes. For instance, data structured to optimize for database searching by a data scientist may have a completely different structure than data optimized to drive a physician's application program and associated user interface. As another instance, data optimized for database searching by a data scientist usually has a different structure than raw data represented in an original clinical medical record that is stored to memorialize the original record.

By storing system data in purpose specific data structures, a diverse array of system functionality is optimally enabled. Advantages include simpler and more rapid application and micro-service development, faster analytics and other system processes and more rapid user application program operations.

Particularly useful systems disclosed herein include three separate databases including a "data lake" database, a "data vault" database and a "data marts" database. The data lake database includes, among other data, original raw data as well as interim micro-service data products and is used primarily to memorialize original raw data and data progression for auditing purposes and to enable data recreation that is tied to prior points in time. The data vault database includes data structured optimally to support database access and manipulation and typically includes routinely accessed original data as well as derived data. The data marts database includes data structured to support specific user application programs and user interfaces including original as well as derived data.

In at least some embodiments, at least some inventive systems combine compartmentalized NGS data together and deliver powerful insights that utilize artificial intelligence integrated data mining. AI based predictive algorithms, combination of NGS data from all applicable sources, and having an evolution over time of patient histories provides insights that are combine with an extensive, up-to-date knowledge database and resulting benefits and insights are passed on to physicians via intuitive and simplified interfaces in ways that are easily digested by treating physicians to provide the best in personalized, precision medicine to patients.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

Adaptive Order Fulfillment and Tracking Methods and Systems

A disclosed adaptive order system includes an order management system that receives basic initial service request information from a physician and uses that information to generate complex and fully defined system orders suitable to drive an entire process associated with patient record intake, genetic sequencing and other tests, variant calling and characterization, treatment and clinical trial selection and reporting. Among other things, an exemplary order includes a set of business processes referred to hereinafter as "items" that must be performed in order to generate data products that are required to either instantiate a completed instance of an oncological report as an end work product or that are needed as intervening data required to drive other order item completion.

In at least some embodiments, the order management system includes order templates which specify specific items for specific order types as well as dependencies (e.g., which items depend on completion of other items to be initiated). For instance, for an exemplary order, the order management system automatically selects either one or several template types required to fulfill an order. For example, an order may require two different DNA tests and each test may correspond to a different template that maps out a sequence of items to be completed. In this case, both test templates would be used to generate an order map that combines items from each template. Where several templates are selected, the management system is programmed to identify duplicate items and where possible, remove duplicate items from an eventual system order.

In particularly advantageous embodiments the adaptive order system also includes an "order hub" that receives and stores orders from the order management system and thereafter manages the entire adaptive order system per order items, dependencies, and other information. The adaptive system has been developed for use with a distributed order processing system including a plurality of microservices or micro-service programs where each microservice performs one or more items to yield one or more data products. As several examples, an exemplary accession sample item tracks receipt of a physical specimen from a patient and physician, a variant call item tracks completion of a pipeline that is managed by a bioinformatics team, and a variant characterization item tracks completion of a variant characterization analysis, etc.

The order hub tracks item completion and determines when all dependencies for each item have been successfully completed. Once dependencies have been completed for a specific item, the order hub broadcasts a notification that the specific item can be initiated by one of the microservices that is responsible for completing items of the specific type. A broadcast may be sent directly to a microservice via a direct notification system or generally to all microservices via an indirect notification system. The microservice that performs the specific service either immediately performs the item or adds the item to a queue to be performed once microservice resources required to perform the item are available. One of the microservices initiates the item and, upon initiation, transmits an "in progress" notification to the order hub that the service has been initiated. Where data products from other completed items are required, the microservice accesses those data products.

Upon completion of an item, a microservice transmits an item "item complete" notification to the order hub indicating that the item has been completed. In addition, the microservice stores the data product in one or more system database(s) for subsequent access by other items or other system services generally.

In particularly advantageous systems the order hub only performs a limited set of tasks including storing and monitoring orders and order item statuses and generating notifications to system microservices in order to initiate item processing when dependencies are met. Thus, in some systems the order hub never receives data products and microservices simply store generated data products in a network access storage (NAS) system (e.g., Amazon Web Services (AWS) cloud based Simple Storage Service (S3)).

In some cases the notification that an item is complete and its data product(s) is stored in a database takes the form of a fulfillment address that indicates the virtual network location of the data product. Here, the order hub uses the fulfillment address as an item status indication and, in at least some embodiments, when a microservice executing another item requires the data product, the microservice polls the order hub for the fulfillment ID (e.g., the address at which the data product has been stored), receives the fulfillment ID, and then uses that ID to access the required data product. In other cases where microservices and the order hub use identical database address formats for data storage and retrieval, when a microservice requires a data product generated by another item, the microservice will have enough information from the order hub notification and other sources to resolve the database address or location at which the data product is stored without requiring additional information from the order hub.

In at least some embodiments the order hub maintains an audit log that tracks orders and item activities. For instance, each time a new order is created or an existing order is modified (e.g., items are added to or deleted from the order), a distinct and time stamped audit record may be generated memorializing the order change. Similarly, any order item status change event such as when an order is initiated (e.g., in progress), completed, cancelled, paused, or deemed low quality (e.g., a quality control (QC) fail) for any reason, a distinct and time stamped audit record may be generated and stored to memorialize the order status event change.

In at least some cases order hub may use the audit log to generate a visual representation of a current status of an order and/or a time based historical visual representation of order status. For instance, in some cases a directed acyclic graph (DAG) representation may be generated that includes a set of item icons or DAG vertices representing order items where the vertices are linked together by process flow lines or edges to indicate when one item is dependent on others. In some cases item vertices will be distinguished with short item labels and may be color coded or otherwise visually distinguished based on item status at a time associated with a specific view of the order status. For instance, if a system user selects a view of a first order on Mar. 13, 2019 which corresponds to a time when the first order was partially completed, the DAG representation may use different colors to highlight item icons indicating not initiated, in progress, complete, QC fail and pause statuses. Other visual representations are contemplated.

Systems and Methods for Interrogating Clinical Documents for Characteristic Data The present disclosure includes systems and methods for interrogating raw clinical documents for characteristic data.

Some embodiments of the present disclosure provide a method for validating abstracted patient data. The method can include receiving original patient data. The method can further include displaying, via a user interface, the original patient data and a data entry form. Additionally, the method can include receiving a first data entry in a first data entry field corresponding to the data entry form, the first data entry based on the original patient data. The method can include identifying, based on the first data entry, an expected second data entry corresponding to a second data entry field. The method can further include displaying, via the user interface, a warning indicator corresponding to the expected second data entry.

Some embodiments of the present disclosure provide a method for generating abstracted patient data. The method can include receiving original patient data corresponding to a patient. The method can further include identifying an assigned project for the patient, and identifying a data template corresponding to the assigned project. Additionally, the method can include generating a data entry form based on the data template, the data entry form having a plurality of data entry fields. The method can include displaying, via a user interface, the original patient data and the data entry form. The method can further include populating the plurality of data entry fields based on the original patient data.

Automated Quality Assurance Testing of Structured Clinical Data

In one aspect, a system and method that provides automated quality assurance testing of structured clinical data derived from raw data or other, differently-structured data is disclosed. The system may analyze the clinical data on its own merits using one or more data validation checks or automated test suites in order to determine whether the structured version of the data satisfies a threshold for accuracy. The test suites may rely on an iterative or recursive methodology, in which previous analyses and their respective successes or failures may be used to support or modify the test suites.

Additionally or alternatively, the system may employ inter-rater reliability techniques, in which a plurality of users may evaluate identical portions of a data set to determine an accurate structured result for that data and/or to determine the accuracy of one or more of the user's attempts to structure the data.

Mobile Supplementation, Extraction, and Analysis of Health Records

In one aspect, a method includes the steps of: capturing, with a mobile device, a next generation sequencing (NGS) report comprising a NGS medical information about a sequenced patient; extracting at least a plurality of the NGS medical information using an entity linking engine; and providing the extracted plurality of the NGS medical information into a structured data repository.

In another aspect, a method includes the steps of: receiving an electronic representation of a medical document; matching the document to a template model; extracting features from the template model using one or more masks to generate a plurality of expected information types; for each extracted feature, processing the document as a sequence of one or more masked regions by applying the one or more masks; and identifying health information from the one or more masked regions, and verifying the identified health information applies to the expected information types.

In yet another aspect, a method includes the steps of capturing an image of a document using the camera on a mobile device, transmitting the captured image to a server, receiving health information abstracted from the document from the server, and validating an accuracy of the abstracted health information.

In still another, a system provides mechanisms for automatically processing clinical documents in bulk, identifying and extracting key characteristics, and generating machine learning models that are refined and optimized through the use of continuous training data.

A Generalizable and Interpretable Deep Learning Framework for Predicting MSI from Histopathology Slide Images The present application presents a deep learning framework to directly learn from histopathology slides and predict MSI status. We describe frameworks that combine adversarial-based mechanism for deep learning on histopathology images. These frameworks improve model generalizability to tumor types including those not observed in training. Furthermore, these frameworks can also perform guided backpropagation on histopathology slides to facilitate visual interpretation of our classification model. We systematically evaluate our framework across different cancer types and demonstrate that our framework offers a novel solution to developing generalizable and interpretable deep learning models for digital pathology.

In accordance with an example, a computing device configured to generate an image-based microsatellite instability (MSI) prediction model, the computing device comprising one or more processors configured to: obtain a set of stained histopathology images from one or more image sources, the set of stained histopathology images having a first cancer type-specific bias; store in a database, using the one or more computing devices, an association between the histopathology slide images and the plurality of MSI classification labels; apply a statistical model to analyze the set of stained histopathology images and predict an initial baseline MSI status, the initial baseline MSI prediction status exhibiting cancer type-specific bias; apply an adversarial training to the baselines MSI prediction status; and generate an adversarial trained MSI prediction model configured to predict MSI status for subsequent stained histopathology images, the adversarial trained MSI prediction model characterized by a reduction in cancer type-specific bias in comparison to the initial baseline MSI prediction status model.

In accordance with another example, a computer-implemented method to generate an image-based microsatellite instability (MSI) prediction model, the method comprising: obtaining a set of stained histopathology images from one or more image sources, the set of stained histopathology images having a first cancer type-specific bias; storing in a database, using the one or more computing devices, an association between the histopathology slide images and the plurality of MSI classification labels; applying a statistical model to analyze the set of stained histopathology images and predicting an initial baseline MSI status, the initial baseline MSI prediction status exhibiting cancer type-specific bias; applying an adversarial training to the baselines MSI prediction status; and generating an adversarial trained MSI prediction model configured to predict MSI status for subsequent stained histopathology images, the adversarial trained MSI prediction model characterized by a reduction in cancer type-specific bias in comparison to the initial baseline MSI prediction status model.

In some examples, the statistical model is a Neural Network, Support Vector Machine (SVM), or other machine learning process. In some examples, the statistical model is a deep learning classifier.

In some examples, one or more processors are configured to: obtain at least one of the subsequent stained histopathology images; apply the adversarial trained MSI prediction model to the at least one subsequent stained histopathology image and predict MSI status; examine the at least one subsequent stained histopathology image and identify patches of associated with the MSI status; and generate a guided backpropagation histopathology image from the at least one subsequent stained histopathology image, the guided backpropagation histopathology image depicting the patches associated with the MSI status.

In some examples, patches comprise pixels or groups of pixels. In some examples, those patches correspond to topology and/or morphology of pixels or groups of pixels.

In some examples, subsequent stained histopathology images are examined and patches associated with the MSI status are identified using a gradient-weighted class activation map.

In accordance with another example, a computing device configured to generate an image-based microsatellite instability (MSI) prediction model, the computing device comprising one or more processors configured to: obtain a set of stained histopathology images from one or more image sources, the set of stained histopathology images having a first cancer type-specific bias; store in a database, using the one or more computing devices, an association between the histopathology slide images and the plurality of MSI classification labels; and apply a statistical model to analyze the set of stained histopathology images and generate a trained MSI prediction model configured to predict MSI status for subsequent stained histopathology images.

Microsatellite Instability Determination System and Related Methods

The present application presents techniques for determining microsatellite instability (MSI) directly from microsatellite region mappings for specific loci in the genome. The techniques include an MSI assay that may employ a support vector machine (SVM) classifier to assess MSI. The assay may be a tumor-normal MSI assay in some examples. In other examples, the assay may be a tumor-only MSI assay. The techniques provide an automated process for MSI testing and MSI status prediction via a supervised machine learning process.

In accordance with an example, a computer-implemented method of indicating a likelihood of microsatellite instability comprises: for each locus in a plurality of microsatellite instability (MSI) loci: mapping a first plurality of genomic sequencing reads from a tumor specimen to the locus; mapping a second plurality of genomic sequencing reads from a matched-normal specimen to the locus; comparing the mapping of the first plurality to the mapping of the second plurality and determining the likelihood of microsatellite instability based on the comparison; and generating a report indicating the determined likelihood of microsatellite instability.

In accordance with an example, the plurality of MSI loci includes at least one locus listed in Table 1 below.

In accordance with an example, the plurality of MSI loci includes all of the loci listed in Table 1 below.

In accordance with an example, the plurality of MSI loci includes at least one locus on a chromosome listed in Table 1 below.

In accordance with an example, each locus in the plurality of MSI loci is positioned on a chromosome listed in Table 1 below.

In accordance with an example, mapping the first plurality comprises mapping reads containing 3-6 base pairs, and mapping the second plurality comprises mapping reads containing 3-6 base pairs In accordance with an example, mapping the first plurality of genomic sequencing reads comprises mapping at least 30-40 genomic sequencing reads from the tumor sample; and mapping the second plurality of genomic sequencing reads comprises mapping at least 30-40 genomic sequencing reads from the normal sample.

In accordance with an example, the computer-implemented method includes when mapping the first plurality of genomic sequencing reads, determining if at least 20-30 microsatellites meet a coverage minimum; and when mapping the second plurality of genomic sequencing reads, determining if at least 20-30 microsatellites meet a coverage minimum.

In accordance with an example, the computer-implemented method includes if at least 20-30 microsatellites do not meet the coverage minimum when mapping the second plurality of genomic sequencing reads, then replacing the mapping of the second plurality of genomic sequencing reads with mean and variance data from a trained sequencing data before performing the comparison.

In accordance with an example, the computer-implemented method includes comparing the mapping of the first plurality to the mapping of the second plurality and determining the likelihood of microsatellite instability based on the comparison by measuring changes in the number of repeat units in the first plurality of genomic sequencing reads from the tumor specimen to the number of repeat units in the second plurality of genomic sequencing reads from the matched-normal specimen.

In accordance with an example, the computer-implemented method includes comparing the mapping of the first plurality to the mapping of the second plurality and determining the likelihood of microsatellite instability based on the comparison using a Kolmogorov-Smirov test.

In accordance with an example, the computer-implemented method includes determining the likelihood of microsatellite instability based on a p value.

In accordance with an example, the computer-implemented method includes determining the likelihood of microsatellite instability as microsatellite instability high (MSI-H), microsatellite stable (MSI-S), or microsatellite equivocal (MSI-E).

In accordance with an example, MSI-H is >about 70% probability, MSI-E is between about 50% and about 70% probability, and MSI-S is <about 50%, where "about" is defined as between 0% to 10%+/−difference.

In accordance with an example, the computer-implemented method includes determining a therapeutic for a subject based on the determined likelihood of microsatellite instability.

In accordance with an example, the therapeutic is selected from the group consisting of fluoropyrimidine, oxaliplatin, irinotecan, Ipilimumab, nivolumab, Pembrolizumab, an anti-PD-L1 antibody (e.g., durvalumab), an anti-CTLA antibody (e.g., tremelimumab), and checkpoint inhibitor (e.g., PD-1 inhibitor, PD-L1 inhibitor, PD-L2 inhibitor, CTLA-4 inhibitor).

In accordance with an example, a computing device is provided to perform the computer-implemented methods herein.

In accordance with an example, a computing device configured to indicate a likelihood of microsatellite instability, the computing device comprising one or more processors configured to: for each locus in a plurality of microsatellite instability (MSI) loci: map a first plurality of genomic sequencing reads from a tumor specimen to the locus; map a second plurality of genomic sequencing reads from a matched-normal specimen to the locus; compare the mapping of the first plurality to the mapping of the second plurality and determine the likelihood of microsatellite instability based on the comparison; and generate a report indicating the determined likelihood of microsatellite instability.

Evaluating Effect of Event on Condition Using Propensity Scoring

Advantageously, the present disclosure provides solutions to the above-identified and other shortcomings in the art. Thus, in some embodiments, the systems and methods described herein allow predicting and evaluating an effect of an event (e.g., medication, treatment, etc., sometimes collectively referred to as a "treatment" herein) on a patient and/or a patient's condition. This is performed by identifying "matching" treatment and control groups or cohorts that include subjects that are similar in terms of clinical and other characteristics that influence a decision to prescribe a certain treatment. The degree to which the treatment and control groups are similar to one another, a size of the groups, and other characteristics, can be adjusted such that the treatment and control groups can be selected based on desired goals of a clinical trial.

Also, the described systems and methods allow evaluating a patient's survival based on the treatment and the time when the treatment was administered. For example, the effect of an anti-cancer treatment on a patient having cancer can be evaluated by comparing treatment and control groups selected for this evaluation.

In some embodiments, an interactive tool (or dashboard) is provided that allows direct comparison of the treatment and control groups based on adjusting a propensity value threshold, including identifying differences in survival among the treatment and control groups. The propensity value threshold is used to tune the propensity scoring model such that subjects assigned propensity scores that satisfy the propensity value threshold are selected.

As mentioned above, in observational studies, it may be challenging to compare the control and treatment groups because of confounding variables. The present invention allows identifying a control group or cohort with an improved precision and more meaningful similarity to a treatment group or cohort, such that more robust comparison between the treatment and control groups is feasible. The selected control group may be referred to as a "synthetic" control group that is selected for a certain study of an effect of a medication, treatment, or another event, and given the properties of a corresponding contrasted treatment group. The described tool provides a user interface that allows selecting the treatment and control groups "on-the fly," as described in more detail below. Also, the tool allows assessing patients' demographic, clinical and other characteristics that are associated with the effect of an event on a patient and/or patient's condition.

In some embodiments, a method of evaluating an effect of an event on a condition using a base population of subjects that each have the condition is provided. The evaluation of the effect of the event on the condition may include building and training a propensity scoring model that can determine a likelihood of the subject's being prescribed a treatment for the condition, at one or more points of a time period (e.g., at one or more points of the subject's clinical interaction timeline). The likelihood is determined in the form of a propensity score that is similar for the identified treatment and control groups. In some embodiments, the method includes determining a propensity prediction for a first plurality of subjects of the base population who have not incurred the event, and identifying a second plurality of subjects in the base population who have incurred the event. The propensity prediction may include a prediction, for each respective subject in the first plurality of subjects, for one or more time points in a respective time period (e.g., a subject's medical record), of a probability of each of the time points being a so-called anchor point, which is the time of the event for the respective subject. In other words, the anchor point is an instance of time when the subject in the first plurality of subjects was likely to have incurred the event. In some embodiments, an anchor point, selected among the anchor points predicted for each of the one or more time points in the respective time period, is the time point assigned the greatest probability across the anchor point predictions. Thus, the anchor point is a point in time at which the event "would have most likely occurred" for the subject who in fact did not incur the event. At the anchor point, a subject in the control group is presumed to be most similar (in terms of clinical features or other characteristics) to one or more subjects in the treatment group.

In some embodiments, the anchor point is predicted as a time period from the occurrence of the first condition until the time when the subject was most likely to have incurred the event. The anchor point is a treatment likelihood reference point that defines when the treatment would have begun for the subject. Thus, for survival analysis, the anchor point of a subject in the control group is a starting point for a survival curve.

In embodiments of the present disclosure, the second plurality of subjects are subjects who incurred the event (e.g., those who received a medication or treatment), whereas the first plurality of subjects are subjects who are likely to have incurred the event but have not incurred it. These two cohorts do not overlap. Each of the second plurality of subjects is associated with an event start date—a date at which the event first incurred (e.g., a treatment began), and each of the first plurality of subjects is associated with a single independent corresponding anchor point. The first plurality of subjects can be, for example, subjects that have clinical features similar to those of the second plurality of subjects and that, while being likely to have been prescribed a certain treatment (to incur the event which can be that treatment), were not prescribed the treatment and did not receive it at any time.

Once the anchor point is determined for each subject in the first plurality of subjects, the described methods compares the first plurality of subjects to the second plurality of subjects, thereby evaluating the effect of the event on the first condition. The comparison can involve comparison of a survival objective of the first plurality of subjects to a survival objective of the second plurality of subjects. This can be done using, at least in part, the event start date for each respective subject in the second plurality of subjects (i.e., a time point when that subject incurred the event) and the single independent corresponding anchor point for each respective subject in the second plurality of subjects. For example, first survival curves can be generated for the first plurality of subjects (with the data aligned to the event start dates), and second survival curves can be generated for the second plurality of subjects (with the data aligned to the determined anchor points), and the first and second survival curves are displayed in a format suitable for assessment of the effect of the event on the first condition and on survival.

In some embodiments, the propensity predictions are generated using a propensity scoring model, also referred to herein as a propensity model. The propensity model is a machine-leaning model that is trained on the base population of subjects, based at least in part on a plurality of features, which can be temporal or static. Various demographic, genomic, and clinical features can be selected for building a model, which can be done automatically and/or manually. In some embodiments, the propensity model is applied to the base population of subjects to identify a patient profile for patients who are likely to incur the event (e.g., to receive a treatment).

In some embodiments, a computer-implemented method of evaluating an effect of an event on a first condition using a base population of subjects that each have the first condition is provided. The method comprises (A) obtaining a propensity value threshold; (B) identifying a first plurality of subjects in the base population and a start date of an event for each respective subject in the first plurality of subjects at which the respective subject incurs the event; and (C) using a propensity scoring model to select a second plurality of subjects from the base population, wherein the second plurality of subjects are other than the first plurality of subjects. The using (D) is done by performing a first procedure that comprises, for a respective subject in the base population: (i) applying a corresponding plurality of features for the respective subject in the base population to the propensity model tuned to the propensity value threshold, wherein a first subset of the corresponding plurality of features for which data was acquired for the respective subject is associated with a respective time period and a second subset of the corresponding plurality of features for which data was acquired for the respective subject are static, the applying (i) thereby obtaining one or more anchor point predictions for the respective subject, wherein each anchor point prediction is associated with a corresponding instance of time in the respective time period and includes a probability that a corresponding instance of time is a start date for the event for the respective subject, and (ii) assigning an anchor point for the respective subject to be the corresponding instance of time that is associated with the anchor point prediction that has the greatest probability across the anchor point predictions.

The method also includes determining a survival objective of the first plurality of subjects and a survival objective of the second plurality of subjects using the event start date for each respective subject in the first plurality of subjects and the anchor point for each respective subject in the second plurality of subjects to evaluate the effect of the event on the first condition.

Other embodiments are directed to systems, portable consumer devices, and computer readable media associated with the methods described herein. Any embodiment disclosed herein, when applicable, can be applied to any aspect of the methods described herein.

Transcriptome Deconvolution of Metastatic Tissue Samples

The present application presents novel techniques for transcriptome deconvolution and in particular techniques for using transcriptome deconvolution to assess metastatic cancer samples. In an example, the present techniques are used to examine metastatic tumors from multiple cancer types.

In one example, the present techniques include quantifying the proportion of a sample that is normal cells, compared to the proportion that is tumor or cancer cells. In one example, the samples are 4,754 cancer and liver normal samples. The present techniques may include the quantification of transcriptome signatures to estimate the proportion of non-tumor cells in mixture samples. Certain techniques include adjusting gene expression profiles in a regression-based approach against reference samples, based on the proportion of the sample that is estimated to be healthy tissue. This adjustment of gene expression profiles in the tumor may be utilized to accurately model tumor features in a sample such as, for instance, the prediction of cancer type, detection of over and under expression of gene and pathway activity, characterization of cancer molecular subtypes/networks, biomarker discovery, and clinical associations, among others, to inform better response or resistance to treatment.

In some examples, the present techniques may quantify metastatic samples. In an example, the proportion of liver in each sample in a set of 4,754 cancer and liver normal samples is quantified and then used to train a non-negative least squares model to estimate liver proportion in mixture samples. The liver normal samples may be non-tumorous liver tissue. The information derived from the samples may be RNA expression data, such as measured RNA levels. The mixture samples may be metastatic tissue samples, including tumor and background non-tumor cancer site cells, such as normal tissue adjacent to the metastasized tumor, which may be included as part of a biopsy or surgical removal. Estimated liver proportions across mixture samples may then be utilized to adjust gene expression profiles in a regression-based approach. The techniques, while described as used for liver samples and liver cancer, can be extended to other types of tissue samples or cancers, whether those samples are metastatic or not.

The cancer in some aspects is one selected from the group consisting of acute lymphocytic cancer, acute myeloid leukemia, alveolar rhabdomyosarcoma, bone cancer, brain cancer, breast cancer (e.g., triple negative breast cancer), cancer of the anus, anal canal, or anorectum, cancer of the eye, cancer of the intrahepatic bile duct, cancer of the joints, cancer of the head or neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal cancer (e.g., gastrointestinal carcinoid tumor), glioblastoma, Hodgkin lymphoma, hypopharynx cancer, hematological malignancy, kidney cancer, larynx cancer, liver cancer, lung cancer (e.g., non-small cell lung cancer (NSCLC), small cell lung cancer (SCLC), bronchioloalveolar carcinoma), malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. The listing of cancers herein is not intended to be exhaustive in scope, other cancers may be considered as well.

In an example, a computer-implemented method comprises: performing clustering on RNA expression data corresponding to a plurality of samples, where each sample is assigned to at least one of a plurality of clusters; generating a deconvoluted RNA expression data model comprising at least one cluster identified as corresponding to biological indication of one or more pathologies; receiving additional RNA expression data of a sample of tumor tissue; deconvoluting the additional RNA expression data based in part on the deconvoluted RNA expression data model; and classifying the sample of tumor tissue as the biological indication of one or more pathologies.

In some examples, clustering on the RNA expression data is performed using a grade of membership clustering operation. In some examples, the grade of membership clustering operation is performed iteratively until the at least one cluster corresponding to the biological indication is identified.

In some examples, the generated deconvoluted RNA expression data model comprises a first dimension reflecting a number of samples and a second dimension reflecting a number of genes in the RNA expression data.

In accordance with another example, a computer-implemented method comprises: receiving RNA expression data for a tissue sample of interest; comparing the received RNA expression data to a deconvoluted RNA expression model comprising at least one cluster identified as corresponding to biological indication of one or more pathologies; and determining a pathology type for the tissue sample of interest based on the comparison.

In some examples, comparing the received RNA expression data to the deconvoluted RNA expression model includes deconvoluting the received RNA expression data.

In accordance with another example, a computer-implemented method comprises: receiving RNA expression data for a tissue sample of interest; comparing the received RNA expression data to a deconvoluted RNA expression model comprising at least one cluster identified as corresponding to biological indication of one or more cell types; and determining one or more cell types present in the tissue sample of interest based on the comparison.

In some examples, the one or more cell types comprises cell populations, collections of cells, populations of cells, stem cells, and/or organoids.

In accordance with another example, a method, comprises: receiving RNA expression information of a sample of tumor tissue; generating a deconvolution of the RNA expression information; and determining a biological indication of the tumor tissue based in part on the deconvolution.

In some examples, the biological indication is a cancer type. In some examples, the biological indication of the tumor tissue is a metastatic cancer.

In some examples, determining the biological indication of the tumor tissue includes: generating enriched gene expressions; and classifying the enriched gene expressions in a biological indication data model. In some examples, generating enriched gene expressions includes: receiving membership associations to each cluster of the plurality of clusters; and scaling the RNA expression information for one or more genes based in part on the corresponding membership associations to each cluster.

In some examples, deconvolution is performed with a supervised machine learning model, a semi-supervised machine learning model, or an unsupervised machine learning model.

In some examples, the RNA expression data is raw. In some examples, the RNA expression data is normalized RNA expression data.

Calculating Cell-Type RNA Profiles for Diagnosis and Treatment

In some embodiments, methods are provided for analyzing RNA sequencing and imaging data from multiple biological samples to generate cell-type RNA profiles for cell types, and to apply the cell-type RNA profiles to a new (test) biological sample obtained from a patient to determine a cell type composition of the patient. The ability to determine a cell type composition (e.g., a cancer composition) may be used in various clinical applications. The present disclosure provides a more precise analysis of a sample composition that existing approaches.

In embodiments of the present disclosure, the methods can identify known cell types, as well as unknown cell types, for cell types in various tissues and at different stages of cell maturations. Each cell type may be represented by a respective cell-type RNA profile that defines gene expression (abundance) levels for each gene in a plurality of genes for that cell-type RNA profile. In some embodiments, the gene expression levels for each gene in a cell-type RNA profile are modeled as a distribution, such as a gamma, normal, or another distribution.

In embodiments, each sample, such as, e.g., a pathology slide or any other form having a boundary, is modeled as a sum of parts with their percentage summing up to 100% (or 1, if proportions are used). This constraint allows applying machine-learning algorithms to generate and train models until convergence to an optimal solution in a time-efficient manner, such that a number of cell types, their respective profiles, and their proportions that best describe a sample composition are identified.

In some aspects, a method for determining a cancer composition of a subject is provided which in some embodiments includes, at a computer system having one or more processors and memory storing one or more programs for execution by the one or more processors, generating, in electronic form, for each respective genetic target in a first plurality of genetic targets, a corresponding shape parameter, the first plurality of genetic targets obtained based on RNA sequencing of one or more respective biological samples obtained from a respective tumor specimen of each respective subject across a plurality of subjects. The method further includes, obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target; and refining a first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types.

The method further comprises using the respective calculated cell type RNA expression profile for each calculated cell type in the plurality of calculated cell types to determine a cancer composition of a subject.

Systems and Methods of Clinical Trial Evaluation

One implementation of the present disclosure is a method for matching a patient to a clinical trial. The method includes receiving text-based criteria for the clinical trial, including a molecular marker. Additionally, the method includes associating at least a portion of the text-based criteria to one or more pre-defined data fields containing molecular marker information. The method further includes comparing a molecular marker of the patient to the one or more pre-defined data fields, and generating a report for a provider. The report is based on the comparison and includes a match indication of the patient to the clinical trial.

Another implementation of the present disclosure is a method of matching a patient to a clinical trial. The method includes receiving health information from an electronic medical record corresponding to the patient. Additionally, the method includes determining data elements within the health information using at least one of an optical character recognition (OCR) method and a natural language processing (NLP) method. The method further includes comparing the data elements to pre-determined trial criteria, including trial inclusion criteria and trial exclusion criteria. Additionally, the method includes determining at least one matching clinical trial, based on the comparing of the data elements to the predetermined trial criteria, and notifying a practitioner associated with the patient of the at least one matching clinical trial.

To the accomplishment of the foregoing and related ends, the disclosure, then, includes the features hereinafter fully described. The following description and the annexed drawings set forth in detail certain illustrative aspects of the disclosure. However, these aspects are indicative of but a few of the various ways in which the principles of the disclosure can be employed. Other aspects, advantages and novel features of the disclosure will become apparent from the following detailed description of the invention when considered in conjunction with the drawings.

Methods of Normalizing and Correcting RNA Expression Data

The present application presents techniques for normalizing and correcting gene expression data across varied gene expression databases.

In exemplary embodiments, techniques are provided for normalizing RNA sequence data and for correcting RNA sequence data to establish a uniform gene expression database. The techniques further provide for on-boarding new gene expression data into the uniform gene expression database enriching the new gene expression data for better utilization with existing gene expression data.

Such techniques provide numerous advantages, including unifying actual gene expression data and parsing that data into different tumor profiles to allow for more accurate analysis of gene expression data, including, for example, greatly reducing database access speeds and data processing times. The present techniques can combine data across gene expression datasets to provide functionally useful and comparable gene expression data that have heretofore been unavailable.

In accordance with an example, a computer-implemented method includes: generating, from a comparison of a normalized RNA sequence dataset against a standard RNA sequence dataset, at least one conversion factor for applying to a next RNA sequence dataset; and correcting RNA sequence data of the next RNA sequence dataset using the at least one conversion factor.

In some examples, the computer-implemented method further includes: including the RNA sequence data of the next gene expression dataset into the standard gene expression dataset.

In some examples, the computer-implemented method includes: obtaining a gene expression dataset comprising the RNA sequence data for one or more genes, normalizing the RNA sequence data using gene length data, guanine-cytosine (GC) content data, and depth of sequencing data; and performing a correction on the RNA sequence data against the standard gene expression dataset by comparing the sequence data for at least one gene in the gene expression dataset to sequence data in the standard gene expression dataset.

In some examples, such normalization is performed by normalizing the gene length data for at least one gene to reduce systematic bias, normalizing the GC content data for the at least one gene to reduce systematic bias, and normalizing the depth of sequencing data for each sample.

In some examples, generating the at least one conversion factor includes: for a sample gene, obtaining sample data from the normalized dataset and obtaining sample data from the standard gene expression dataset; determining a statistical mapping between the sample data of the normalized dataset and the sample data of the standard gene expression dataset; and determining the at least one conversion factor using the statistical mapping.

In some examples, determining the statistical mapping includes determining a linear mapping model between the sample data of the normalized dataset and the sample data of the standard gene expression dataset.

In some examples, the computer-implemented method includes: determining an intercept and a beta value for the linear mapping model; and determining the at least one conversion factor using the statistical mapping from the intercept and the beta value.

In accordance with another example, a computing device comprising one or more memories and one or more processors is configured to: generate, from a normalization of an RNA sequence data against a standard RNA sequence dataset, at least one conversion factor for applying to a next RNA sequence dataset; and correct RNA sequence data of the next RNA sequence dataset using the at least one conversion factor.

In some examples, the computing device is configured to include the corrected RNA sequence data of the next RNA sequence dataset into the standard RNA sequence dataset.

In some examples, the computing device is configured to: obtain a gene expression dataset comprising the RNA sequence data for one or more genes, the RNA sequence data including gene length data, guanine-cytosine (GC) content data, and/or depth of sequencing data; and normalize the RNA sequence data to remove systematic known biases.

In some examples, the computing device is configured to: normalize the gene length data for the one or more genes to reduce systematic bias; normalize the GC content data for the one or more genes to reduce systematic bias; and normalize the depth of sequencing data for the RNA sequence data.

In some examples, the computing device is configured to: for a sample gene, obtain sample data from a normalized RNA sequence dataset and obtaining sample data from the standard RNA sequence dataset; determine a statistical mapping between the sample data of the normalized RNA sequence dataset and the sample data of the standard RNA sequence dataset; and determine the at least one conversion factor using the statistical mapping.

In some examples, the computing device is configured to: determine an intercept and a beta value for the linear mapping model; and determine the at least one conversion factor using the statistical mapping from the intercept and the beta value.

In accordance with another example, a computer-implemented method includes: generating, from a normalization of gene expression data against another gene expression dataset, at least one conversion factor for applying to a next gene expression dataset; and correcting gene sequence data of the next gene expression dataset using the at least one conversion factor.

In accordance with an example, a computer-implemented method comprises: receiving, at one or more processors, a gene expression dataset; identifying within the gene expression dataset, using a regression technique implemented by the one or more processors, gene expression data having multiple modal expression peaks; for the gene expression data, normalizing, using the one or more processors, a spacing between each of the multiple model expression peaks to form a normalized gene expression data; and storing the normalized gene expression data in a normalized gene expression dataset.

In accordance with another example, a computer-implemented method comprises: receiving, at one or more processors, a RNA sequence dataset; identifying within the gene expression dataset, using a regression technique implemented by the one or more processors, a plurality of RNA expression data each having a bimodal distribution comprising two expression peaks; for each of the plurality of RNA expression data, normalizing, using the one or more processors, a spacing between the two expression peaks such that each of the plurality of RNA expression data has the same spacing between the two expression peaks; and storing the normalized RNA expression data in a normalized RNA sequence dataset.

A Pan-Cancer Model to Predict the PD-L1 Status of a Cancer Cell Sample Using RNA Expression Data and Other Patient Data The present disclosure provides computer-implemented methods of identifying programmed-death ligand 1 (PD-L1) expression status of a subject's sample comprising a cancer cell. In exemplary embodiments, the method comprises (a) receiving an unlabeled expression data set for the subject's sample and (b) aligning the unlabeled expression data set to labeled expression data according to a trained PD-L1 predictive model, wherein the trained PD-L1 predictive model has been trained with a plurality of labeled expression data sets, each labeled expression data set comprising expression data for a sample of a labeled cancer type and a labeled PD-L1 expression status, wherein aligning the unlabeled gene expression data set to labeled expression data according to the trained PD-L1 predictive model identifies PD-L1 expression status for the subject's sample.

The present disclosure also provides a method of preparing a clinical decision support information (CDSI) report. In exemplary embodiments, the method comprises (a) receiving a subject's sample, (b) identifying PD-L1 expression status of the subject's sample as determined by an alignment of an unlabeled gene expression data set of the subject's sample to labeled expression data according to a trained PD-L1 predictive model, (c) preparing a CDSI report for the subject based on the PD-L1 expression status identified in step (b), wherein the CDSI report comprises the subject's identity, the PD-L1 expression status identified in step (b), and, optionally, one or more of the date on which the sample was obtained from the subject, the sample type, a list of candidate drugs correlating with the PD-L1 expression status, data from images of the subject's tumor or cancer, image features, clinical data of the subject, epigenetic data of the subject, data from the subject's medical history and/or family history, subject's pharmacogenetic data, subject's metabolomics data, tumor mutational burden (TMB), microsatellite instability (MSI) status, estimates of immune infiltration, immunotherapy resistance mutations, estimates of the inflammatory status of the tumor microenvironment, and human leukocyte antigen (HLA) type.

A clinical decision support information (CDSI) report prepared by the presently disclosed method are further provided by the present disclosure.

Methods of determining treatment for a subject with cancer are further provided herein. In exemplary aspects, the method comprises consulting a clinical decision support information (CDSI) report of the present disclosure. In exemplary aspects, the treatment is an immune checkpoint blockade therapy comprising treatment with one or more of ipilimumab, nivolumab, pembrolizumab, atezolizumab, avelumab, durvalumab.

Computing devices configured to identify programmed-death ligand 1 (PD-L1) expression status of a subject's sample comprising a cancer cell, are further provided herein. In exemplary aspects, the computing device comprises one or more processors configured to: receive an unlabeled expression data set for the subject's sample; align the unlabeled expression data set to labeled expression data according to a trained PD-L1 predictive model, wherein the trained predictive model is trained with a plurality of labeled expression data sets, each labeled expression data set comprising expression data for a sample of a labeled cancer type and a labeled PD-L1 expression status; and predict PD-L1 expression status for the subject's sample from the alignment of the unlabeled gene expression data set to labeled expression data according to the trained PD-L1 predictive model.

A Method and Process for Predicting and Analyzing Patient Cohort Response, Progression, and Survival In one aspect, a system and user interface are provided to predict an expected response of a particular patient population or cohort when provided with a certain treatment. In order to accomplish those predictions, the system uses a pre-existing dataset to define a sample patient population, or "cohort," and identifies one or more key inflection points in the distribution of patients exhibiting each attribute of interest in the cohort, relative to a general patient population distribution, thereby targeting the prediction of expected survival and/or response for a particular patient population.

The system described herein facilitates the discovery of insights of therapeutic significance, through the automated analysis of patterns occurring in patient clinical, molecular, phenotypic, and response data, and enabling further exploration via a fully integrated, reactive user interface.

Collaborative Artificial Intelligence Method and System

It has been recognized that a relatively small and portable voice activated and audio responding interface device (hereinafter "collaboration device") can be provided enabling oncologists to conduct at least initial database access and manipulation activities. In at least some embodiments, a collaboration device includes a processor linked to each of a microphone, a speaker and a wireless transceiver (e.g., transmitter and receiver). The processor runs software for capturing voice signals generated by an oncologist. An automated speech recognition (ASR) system converts the voice signals to a text file which is then processed by a natural language processor (NLP) or other artificial intelligence module to generate a data operation (e.g., commands to perform some data access or manipulation process such as a query, a filter, a memorialization, a clearing of prior queries and filter results, note etc.).

In at least some embodiments the collaboration device is used within a collaboration system that includes a server that maintains and manipulates an industry specific data repository. The data operation is received by the collaboration server and used to access and/or manipulate data the database data thereby generating a data response. In at least some cases, the data response is returned to the collaboration device as an audio file which is broadcast to the oncologist as a result associated with the original query.

In some cases the voice signal to text file transcription is performed by the collaboration device processor while in other cases the voice signal is transmitted from the collaboration device to the collaboration server and the collaboration server does the transcription to a text file. In some cases the text file is converted to a data operation by the collaboration device processor and in other cases that conversion is performed by the collaboration server. In some cases the collaboration server maintains or has access to the industry specific database so that the server operates as an intermediary between the collaboration device and the industry specific database.

In at least some embodiments the collaboration device is a dedicated collaboration device that is provided solely as an interface to the collaboration server and industry specific database. In these cases, the collaboration interface device may be on all the time and may only run a single dedicated application program so that the device does not require any boot up time and can be activated essentially immediately via a single activation activity performed by an oncologist.

For instance, in some cases the collaboration device may have motion sensors (e.g., an accelerometer, a gyroscope, etc.) linked to the processor so that the simple act of picking up the device causes the processor to activate a research application. In other cases the collaboration device processor may be programmed to "listen" for the phrase "Hey query" and once received, activate to capture a next voice signal utterance that operates as seed data for generating the text file. In other cases the processor may be programmed to listen for a different activation phrase, such as a brand name of the system or a combination of a brand name plus a command indication. For instance, if the brand name of the system is "One" then the activation phrase may be "One" or "Go One" or the like. In still other cases the collaboration device may simply listen for voice signal utterances that it can recognize as oncological queries and may then automatically use any recognized query as seed data for text generation.

In addition to providing audio responses to data operations, in at least some cases the system automatically records and stores data operations (e.g., data defining the operations) and responses as a collaboration record for subsequent access. The collaboration record may include one or the other or both of the original voice signal and broadcast response or the text file and a text response corresponding to the data response. Here, the stored collaboration record provides details regarding the oncologist's search and data operation activities that help automatically memorialize the hypothesis or idea the oncologist was considering. In a case where an oncologist asks a series of queries, those queries and data responses may be stored as a single line of questioning so that they together provide more detail for characterizing the oncologist's initial hypothesis or idea. At a subsequent time, the system may enable the oncologist to access the memorialized queries and data responses so that she can re-enter a flow state associated therewith and continue hypothesis testing and data manipulation using a workstation type interface or other computer device that includes a display screen and perhaps audio devices like speakers, a microphone, etc., more suitable for presenting more complex data sets and data representations.

In addition to simple data search queries, other voice signal data operation types are contemplated. For instance, the system may support filter operations where an oncologist voice signal message defines a sub-set of the industry specific database set. For example, the oncologist may voice the message "Access all medical records for male patients over 45 years of age that have had pancreatic cancer since 1990", causing the system to generate an associated subset of data that meet the specified criteria.

Importantly, some data responses to oncological queries will be "audio suitable" meaning that the response can be well understood and comprehended when broadcast as an audio message. In other cases a data response simply may not be well suited to be presented as an audio output. For instance, where a query includes the phrase "Who is the patient that I saw during my last office visit last Thursday?", an audio suitable response may be "Mary Brown." On the other hand, if a query is "List all the medications that have been prescribed for males over 45 years of age that have had pancreatic cancer since 1978" and the response includes a list of 225 medications, the list would not be audio suitable as it would take a long time to broadcast each list entry and comprehension of all list entries would be dubious at best.

In cases where a data response is optimally visually presented, the system may take alternate or additional steps to provide the response in an intelligible format to the user. The system may simply indicate as part of an audio response that response data would be more suitably presented in visual format and then present the audio response. If there is a proximate large display screen, the system may pair with that display and present visual data with or without audio data. The system may simply indicate that no suitable audio response is available.

Thus, at least some inventive embodiments enable intuitive and rapid access to complex data sets essentially anywhere within a wireless communication zone so that an oncologist can initiate thought processes in real time when they occur. By answering questions when they occur, the system enables oncologists to dig deeper in the moment into data and continue the thought process through a progression of queries. Some embodiments memorialize an oncologist's queries and responses so that at subsequent times the oncologist can reaccess that information and continue queries related thereto. In cases where visual and audio responses are available, the system may adapt to provide visual responses when visual capabilities are present or may simply store the visual responses as part of a collaboration record for subsequent access when an oncologist has access to a workstation or the like.

In at least some embodiments the disclosure includes a method for interacting with a database to access data therein, the method for use with a collaboration device including a speaker, a microphone and a processor, the method comprising the steps of associating separate sets of state-specific intents and supporting information with different clinical report types, the supporting information including at least one intent-specific data operation for each state-specific intent, receiving a voice query via the microphone seeking information, identifying a specific patient associated with the query, identifying a state-specific clinical report associated with the identified patient, attempting to select one of the state-specific intents associated with the identified state-specific clinical report as a match for the query, upon selection of one of the state-specific intents, performing the at least one data operation associated with the selected state-specific intent to generate a result, using the result to form a query response and broadcasting the query response via the speaker.

In some cases the method is for use with at least a first database that includes information in addition the clinical reports, the method further including, in response to the query, obtaining at least a subset of the information in addition to the clinical reports, the step of using the result to form a query response including using the result and the additional obtained information to form the query response.

In some cases the at least one data operation includes at least one data operation for accessing additional information from the database, the step of obtaining at least a subset includes obtaining data per the at least one data operation for accessing additional information from the database.

Some embodiments include a method for interacting with a database to access data therein, the method for use with a collaboration device including a speaker, a microphone and a processor, the method comprising the steps of associating separate sets of state-specific intents and supporting information with different clinical report types, the supporting information including at least one intent-specific primary data operation for each state-specific intent, receiving a voice query via the microphone seeking information, identifying a specific patient associated with the query, identifying a state-specific clinical report associated with the identified patient, attempting to select one of the state-specific intents associated with the identified state-specific clinical report as a match for the query, upon selection of one of the state-specific intents, performing the primary data operation associated with the selected state-specific intent to generate a result, performing a supplemental data operation on data from a database that includes data in addition to the clinical report data to generate additional information, using the result and the additional information to form a query response and broadcasting the query response via the speaker.

Some embodiments include a method of audibly broadcasting responses to a user based on user queries about a specific patient molecular report, the method comprising receiving an audible query from the user to a microphone coupled to a collaboration device, identifying at least one intent associated with the audible query, identifying at least one data operation associated with the at least one intent, associating each of the at least one data operations with a first set of data presented on the molecular report, executing each of the at least one data operations on a second set of data to generate response data, generating an audible response file associated with the response data and providing the audible response file for broadcasting via a speaker coupled to the collaboration device.

In at least some cases the audible query includes a question about a nucleotide profile associated with the patient. In at least some cases the nucleotide profile associated with the patient is a profile of the patient's cancer. In at least some cases the nucleotide profile associated with the patient is a profile of the patient's germline. In at least some cases the nucleotide profile is a DNA profile. In at least some cases the nucleotide profile is an RNA expression profile. In at least some cases the nucleotide profile is a mutation biomarker.

In at least some cases the mutation biomarker is a BRCA biomarker. In at least some cases the audible query includes a question about a therapy. In at least some cases the audible query includes a question about a gene. In at least some cases the audible query includes a question about a clinical data. In at least some cases the audible query includes a question about a next-generation sequencing panel. In at least some cases the audible query includes a question about a biomarker.

In at least some cases the audible query includes a question about an immune biomarker. In at least some cases the audible query includes a question about an antibody-based test. In at least some cases the audible query includes a question about a clinical trial. In at least some cases the audible query includes a question about an organoid assay. In at least some cases the audible query includes a question about a pathology image. In at least some cases the audible query includes a question about a disease type. In at least some cases the at least one intent is an intent related to a biomarker. In at least some cases the biomarker is a BRCA biomarker. In at least some cases the at least one intent is an intent related to a clinical condition. In at least some cases the at least one intent is an intent related to a clinical trial.

In at least some cases the at least one intent is related to a drug. In at least some cases the drug intent is related to a drug is chemotherapy. In at least some cases the drug intent is an intent related to a PARP inhibitor intent. In at least some cases the at least one intent is related to a gene. In at least some cases the at least one intent is related to immunology. In at least some cases the at least one intent is related to a knowledge database. In at least some cases the at least one intent is related to testing methods. In at least some cases the at least one intent is related to a gene panel. In at least some cases the at least one intent is related to a report. In at least some cases the at least one intent is related to an organoid process. In at least some cases the at least one intent is related to imaging.

In at least some cases the at least one intent is related to a pathogen. In at least some cases the at least one intent is related to a vaccine. In at least some cases the at least one data operation includes an operation to identify at least one treatment option. In at least some cases the at least one data operation includes an operation to identify knowledge about a therapy. In at least some cases the at least one data operation includes an operation to identify knowledge related to at least one drug. <<e.g. "What drugs are associated with high CD40 expression?">> In at least some cases the at least one data operation includes an operation to identify knowledge related to mutation testing. <<e.g. "was Dwayne Holder's sample tested for a KMT2D mutation">> In at least some cases the at least one data operation includes an operation to identify knowledge related to mutation presence. <<e.g. "Does Dwayne Holder have a KMT2C mutation?>> In at least some cases the at least one data operation includes an operation to identify knowledge related to tumor characterization. <<e.g. "Could Dwayne Holder's tumor be a BRCA2 driven tumor?">> In at least some cases the at least one data operation includes an operation to identify knowledge related to testing requirements. <<<e.g. "What tumor percentage does Tempus require for TMB results?">> In at least some cases the at least one data operation includes an operation to query for definition information. <<e.g. "What is PDL1 expression?">> In at least some cases the at least one data operation includes an operation to query for expert information. <<e.g. "What is the clinical relevance of PDL1 expression?"; "What are the common risks associated with the Whipple procedure?">> In at least some cases the at least one data operation includes an operation to identify information related to recommended therapy. <<e.g. "Dwayne Holder is in the 88th percentile of PDL1 expression, is he a candidate for immunotherapy?">> In at least some cases the at least one data operation includes an operation to query for information relating to a patient. <e.g. Dwayne Holder>> In at least some cases the at least one data operation includes an operation to query for information relating to patients with one or more clinical characteristics similar to the patient. <<e.g. "What are the most common adverse events for patients similar to Dwayne Holder?">>

In at least some cases the at least one data operation includes an operation to query for information relating to patient cohorts. <<e.g. "What are the most common adverse events for pancreatic cancer patients?">> In at least some cases the at least one data operation includes an operation to query for information relating to clinical trials. <<e.g. Which clinical trials is Dwayne the best match for?">>

In at least some cases the at least one data operation includes an operation to query about a characteristic relating to a genomic mutation. In at least some cases the characteristic is loss of heterozygosity. In at least some cases the characteristic reflects the source of the mutation. In at least some cases the source is germline. In at least some cases the source is somatic. In at least some cases the characteristic includes whether the mutation is a tumor driver. In at least some cases the first set of data comprises a patient name.

In at least some cases the first set of data comprises a patient age. In at least some cases the first set of data comprises a next-generation sequencing panel. In at least some cases the first set of data comprises a genomic variant. In at least some cases the first set of data comprises a somatic genomic variant. In at least some cases the first set of data comprises a germline genomic variant. In at least some cases the first set of data comprises a clinically actionable genomic variant. In at least some cases the first set of data comprises a loss of function variant. In at least some cases the first set of data comprises a gain of function variant.

In at least some cases the first set of data comprises an immunology marker. In at least some cases the first set of data comprises a tumor mutational burden. In at least some cases the first set of data comprises a microsatellite instability status. In at least some cases the first set of data comprises a diagnosis. In at least some cases the first set of data comprises a therapy. In at least some cases the first set of data comprises a therapy approved by the U.S. Food and Drug Administration. In at least some cases the first set of data comprises a drug therapy. In at least some cases the first set of data comprises a radiation therapy. In at least some cases the first set of data comprises a chemotherapy. In at least some cases the first set of data comprises a cancer vaccine therapy. In at least some cases the first set of data comprises an oncolytic virus therapy.

In at least some cases the first set of data comprises an immunotherapy. In at least some cases the first set of data comprises a pembrolizumab therapy. In at least some cases the first set of data comprises a CAR-T therapy. In at least some cases the first set of data comprises a proton therapy. In at least some cases the first set of data comprises an ultrasound therapy. In at least some cases the first set of data comprises a surgery. In at least some cases the first set of data comprises a hormone therapy. In at least some cases the first set of data comprises an off-label therapy.

In at least some cases the first set of data comprises an on-label therapy. In at least some cases the first set of data comprises a bone marrow transplant event. In at least some cases the first set of data comprises a cryoablation event. In at least some cases the first set of data comprises a radiofrequency ablation. In at least some cases the first set of data comprises a monoclonal antibody therapy. In at least some cases the first set of data comprises an angiogenesis inhibitor. In at least some cases the first set of data comprises a PARP inhibitor.

In at least some cases the first set of data comprises a targeted therapy. In at least some cases the first set of data comprises an indication of use. In at least some cases the first set of data comprises a clinical trial. In at least some cases the first set of data comprises a distance to a location conducting a clinical trial. In at least some cases the first set of data comprises a variant of unknown significance. In at least some cases the first set of data comprises a mutation effect.

In at least some cases the first set of data comprises a variant allele fraction. In at least some cases the first set of data comprises a low coverage region. In at least some cases the first set of data comprises a clinical history. In at least some cases the first set of data comprises a biopsy result. In at least some cases the first set of data comprises an imaging result. In at least some cases the first set of data comprises an MRI result.

In at least some cases the of data comprises a CT result. In at least some cases the first set of data comprises a therapy prescription. In at least some cases the first set of data comprises a therapy administration. In at least some cases the first set of data comprises a cancer subtype diagnosis. In at least some cases the first set of data comprises an cancer subtype diagnosis by RNA class. In at least some cases the first set of data comprises a result of a therapy applied to an organoid grown from the patient's cells. In at least some cases the first set of data comprises a tumor quality measure. In at least some cases the first set of data comprises a tumor quality measure selected from at least one of the set of PD-L1, MMR, tumor infiltrating lymphocyte count, and tumor ploidy. In at least some cases the first set of data comprises a tumor quality measure derived from an image analysis of a pathology slide of the patient's tumor. In at least some cases the first set of data comprises a signaling pathway associated with a tumor of the patient.

In at least some cases the signaling pathway is a HER pathway. In at least some cases the signaling pathway is a MAPK pathway. In at least some cases the signaling pathway is a MDM2-TP53 pathway. In at least some cases the signaling pathway is a PI3K pathway. In at least some cases the signaling pathway is a mTOR pathway.

In at least some cases the at least one data operations includes an operation to query for a treatment option, the first set of data comprises a genomic variant, and the associating step comprises adjusting the operation to query for the treatment option based on the genomic variant. In at least some cases the at least one data operations includes an operation to query for a clinical history data, the first set of data comprises a therapy, and the associating step comprises adjusting the operation to query for the clinical history data element based on the therapy. In at least some cases the clinical history data is medication prescriptions, the therapy is pembrolizumab, and the associating step comprises adjusting the operation to query for the prescription of pembrolizumab.

In at least some cases the second set of data comprises clinical health information. In at least some cases the second set of data comprises genomic variant information. In at least some cases the second set of data comprises DNA sequencing information. In at least some cases the second set of data comprises RNA information. In at least some cases the second set of data comprises DNA sequencing information from short-read sequencing. In at least some cases the second set of data comprises DNA sequencing information from long-read sequencing. In at least some cases the second set of data comprises RNA transcriptome information. In at least some cases the second set of data comprises RNA full-transcriptome information. In at least some cases the second set of data is stored in a single data repository. In at least some cases the second set of data is stored in a plurality of data repositories.

In at least some cases the second set of data comprises clinical health information and genomic variant information. In at least some cases the second set of data comprises immunology marker information. In at least some cases the second set of data comprises microsatellite instability immunology marker information. In at least some cases the second set of data comprises tumor mutational burden immunology marker information. In at least some cases the second set of data comprises clinical health information comprising one or more of demographic information, diagnostic information, assessment results, laboratory results, prescribed or administered therapies, and outcomes information.

In at least some cases the second set of data comprises demographic information comprising one or more of patient age, patient date of birth, gender, race, ethnicity, institution of care, comorbidities, and smoking history. In at least some cases the second set of data comprises diagnosis information comprising one or more of tissue of origin, date of initial diagnosis, histology, histology grade, metastatic diagnosis, date of metastatic diagnosis, site or sites of metastasis, and staging information. In at least some cases the second set of data comprises staging information comprising one or more of TNM, ISS, DSS, FAB, RAI, and Binet. In at least some cases the second set of data comprises assessment information comprising one or more of performance status (including ECOG or Karnofsky status), performance status score, and date of performance status.

In at least some cases the second set of data comprises laboratory information comprising one or more of type of lab (e.g. CBS, CMP, PSA, CEA), lab results, lab units, date of lab service, date of molecular pathology test, assay type, assay result (e.g. positive, negative, equivocal, mutated, wild type), molecular pathology method (e.g. IHC, FISH, NGS), and molecular pathology provider. In at least some cases the second set of data comprises treatment information comprising one or more of drug name, drug start date, drug end date, drug dosage, drug units, drug number of cycles, surgical procedure type, date of surgical procedure, radiation site, radiation modality, radiation start date, radiation end date, radiation total dose delivered, and radiation total fractions delivered.

In at least some cases the second set of data comprises outcomes information comprising one or more of Response to Therapy (e.g. CR, PR, SD, PD), RECIST score, Date of Outcome, date of observation, date of progression, date of recurrence, adverse event to therapy, adverse event date of presentation, adverse event grade, date of death, date of last follow-up, and disease status at last follow up. In at least some cases the second set of data comprises information that has been de-identified in accordance with a de-identification method permitted by HIPAA.

In at least some cases the second set of data comprises information that has been de-identified in accordance with a safe harbor de-identification method permitted by HIPAA. In at least some cases the second set of data comprises information that has been de-identified in accordance with a statistical de-identification method permitted by HIPAA. In at least some cases the second set of data comprises clinical health information of patients diagnosed with a cancer condition.

In at least some cases the second set of data comprises clinical health information of patients diagnosed with a cardiovascular condition. In at least some cases the second set of data comprises clinical health information of patients diagnosed with a diabetes condition. In at least some cases the second set of data comprises clinical health information of patients diagnosed with an autoimmune condition. In at least some cases the second set of data comprises clinical health information of patients diagnosed with a lupus condition.

In at least some cases the second set of data comprises clinical health information of patients diagnosed with a psoriasis condition. In at least some cases the second set of data comprises clinical health information of patients diagnosed with a depression condition. In at least some cases the second set of data comprises clinical health information of patients diagnosed with a rare disease.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE SEVERAL VIEWS OF THE DRAWINGS

The patent or application contains at least one drawing in color. Copies of this patent or patent application publication with color drawings will be provided by the Office upon request and payment of the necessary fee.

FIGS. 22a through 22j include an exemplary 1711 gene panel listing that may be interrogated during genomic sequencing in at least some embodiments of the present disclosure;

FIG. 23 includes a clinically actionable 130 gene panel listing that may be interrogated during genomic sequencing in at least some embodiments of the present disclosure;

FIG. 24 includes a clinically actionable 41 RNA based gene rearrangements listing that may be interrogated during genomic sequencing in at least some embodiments of the present disclosure;

FIG. 25 includes a table that lists exemplary variant data that is consistent with at least some aspects of the present disclosure;

FIG. 26 includes exemplary CVA data that is consistent with at least some implementations and aspects of the present disclosure;

FIGS. 27a through 27d includes additional gene panel tables that may be interrogated in at least some embodiments of the present disclosure;

FIGS. 28a and 28b include yet one other gene panel table that may be interrogated;

FIG. 73 is a schematic illustrating an audit record format specification that is consistent with at least some aspects of the present disclosure;

FIG. 81 is another image of an example graphical user interface (GUI), according to aspects of the present disclosure;

FIG. 82 is another image of an example graphical user interface (GUI), according to aspects of the present disclosure;

FIG. 83 is another image of an example graphical user interface (GUI), according to aspects of the present disclosure;

FIG. 84 is another image of an example graphical user interface (GUI), according to aspects of the present disclosure;

FIG. 85 is another image of an example graphical user interface (GUI), according to aspects of the present disclosure;

FIG. 86 is another image of an example graphical user interface (GUI), according to aspects of the present disclosure;

FIG. 87 is another image of an example graphical user interface (GUI), according to aspects of the present disclosure;

FIG. 92 is another image of an example graphical user interface (GUI), according to aspects of the present disclosure;

FIG. 93 is another image of an example graphical user interface (GUI), according to aspects of the present disclosure;

FIG. 95 is another image of an example graphical user interface (GUI), according to aspects of the present disclosure;

FIG. 97 is another image of an example graphical user interface (GUI), according to aspects of the present disclosure;

FIG. 99 is another image of an example graphical user interface (GUI), according to aspects of the present disclosure;

FIG. 100 is another image of an example graphical user interface (GUI), according to aspects of the present disclosure;

Figure 101:
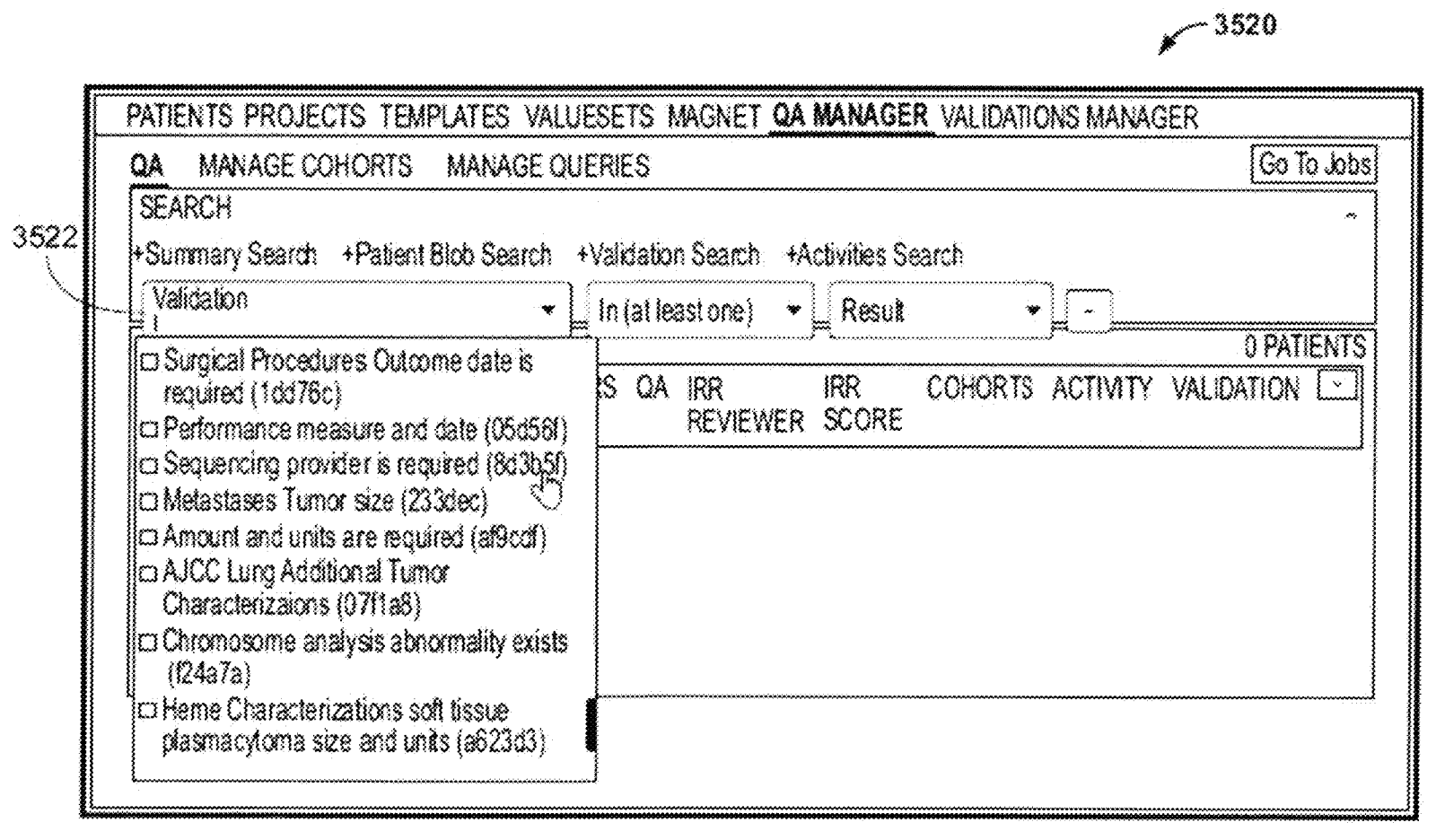

FIG. 101 is another image of an example graphical user interface (GUI), according to aspects of the present disclosure;

FIG. 102 is another image of an example graphical user interface (GUI), according to aspects of the present disclosure;

FIG. 103 is another image of an example graphical user interface (GUI), according to aspects of the present disclosure;

FIG. 105 is another image of an example graphical user interface (GUI), according to aspects of the present disclosure;

FIG. 107 is another image of an example graphical user interface (GUI), according to aspects of the present disclosure;

FIG. 108 is another image of an example graphical user interface (GUI), according to aspects of the present disclosure;

FIG. 109 is another image of an example graphical user interface (GUI), according to aspects of the present disclosure;

Figure 110:
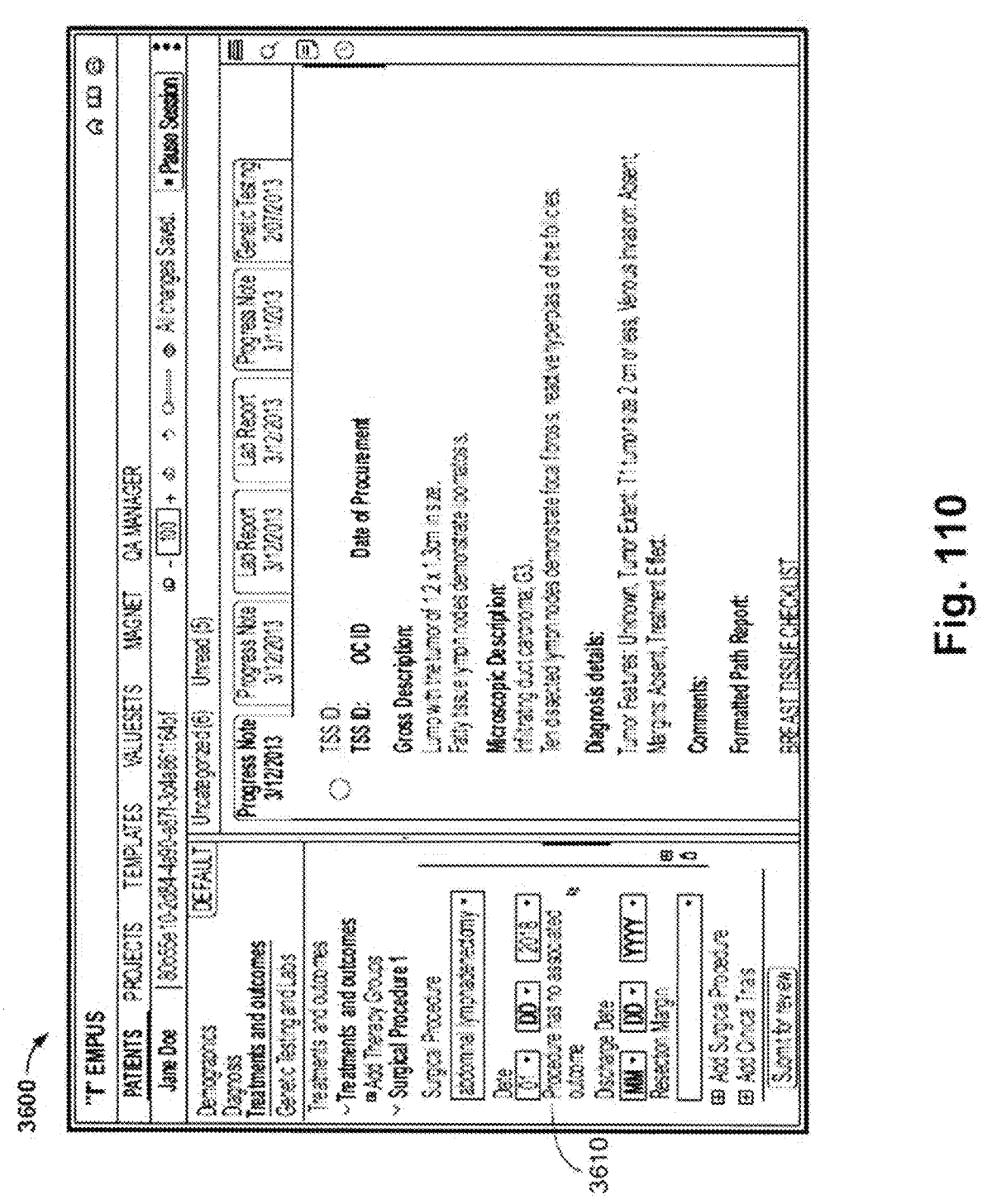

FIG. 110 is another image of an example graphical user interface (GUI), according to aspects of the present disclosure;

Figure 111:
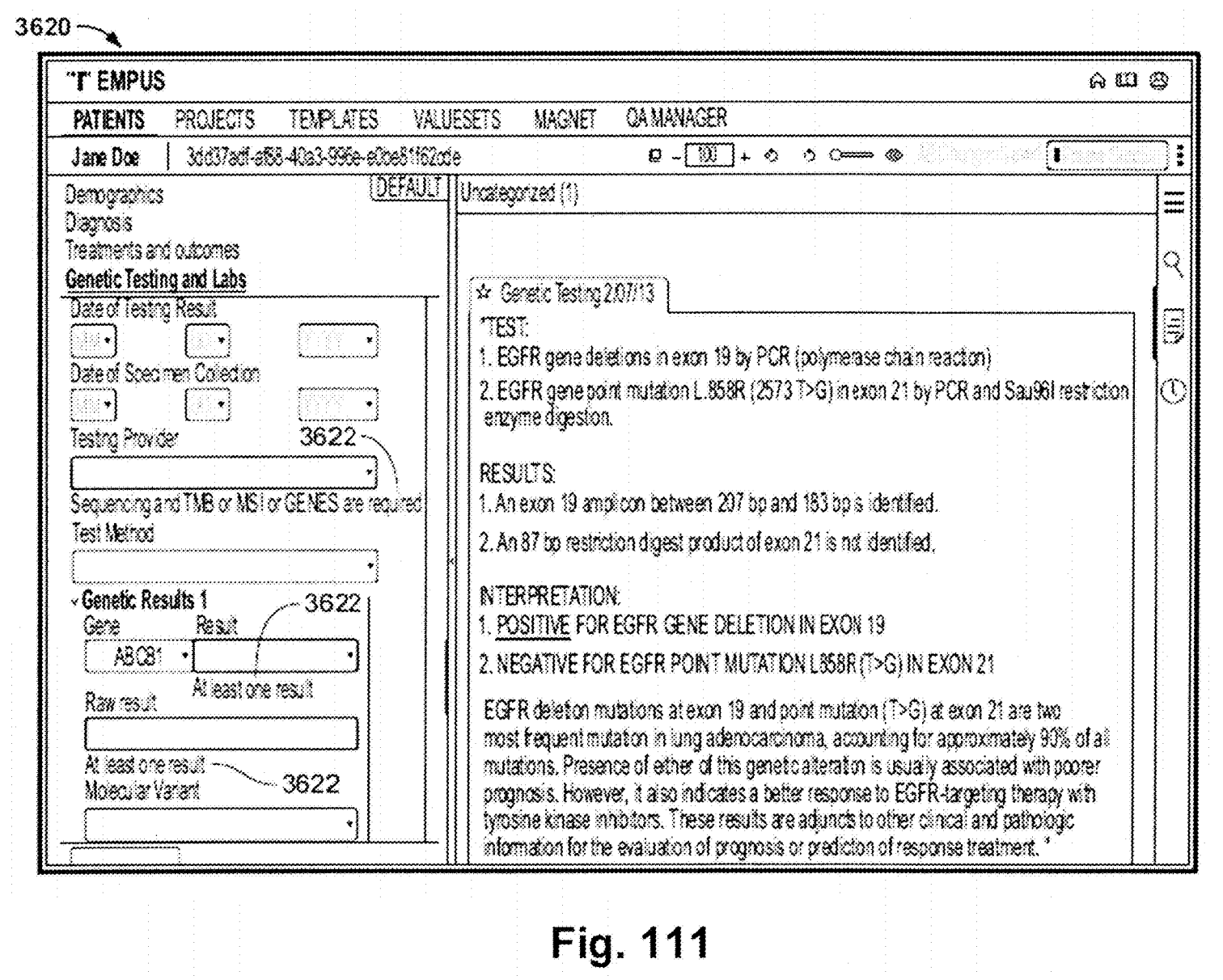

FIG. 111 is another image of an example graphical user interface (GUI), according to aspects of the present disclosure;

FIG. 112 is another image of an example graphical user interface (GUI), according to aspects of the present disclosure;

FIG. 113 is another image of an example graphical user interface (GUI), according to aspects of the present disclosure;

FIG. 114 is another image of an example graphical user interface (GUI), according to aspects of the present disclosure;

FIG. 115 is another image of an example graphical user interface (GUI), according to aspects of the present disclosure;

FIG. 116 is another image of an example graphical user interface (GUI), according to aspects of the present disclosure;

FIG. 117 is another image of an example graphical user interface (GUI), according to aspects of the present disclosure;

FIG. 118 is another image of an example graphical user interface (GUI), according to aspects of the present disclosure;

FIG. 119 is another image of an example graphical user interface (GUI), according to aspects of the present disclosure;

FIG. 120 is another image of an example graphical user interface (GUI), according to aspects of the present disclosure;

FIG. 121 is another image of an example graphical user interface (GUI), according to aspects of the present disclosure;

FIG. 122 is another image of an example graphical user interface (GUI), according to aspects of the present disclosure;

FIG. 123 is another image of an example graphical user interface (GUI), according to aspects of the present disclosure;

FIG. 124 is another image of an example graphical user interface (GUI), according to aspects of the present disclosure;

Figure 125:
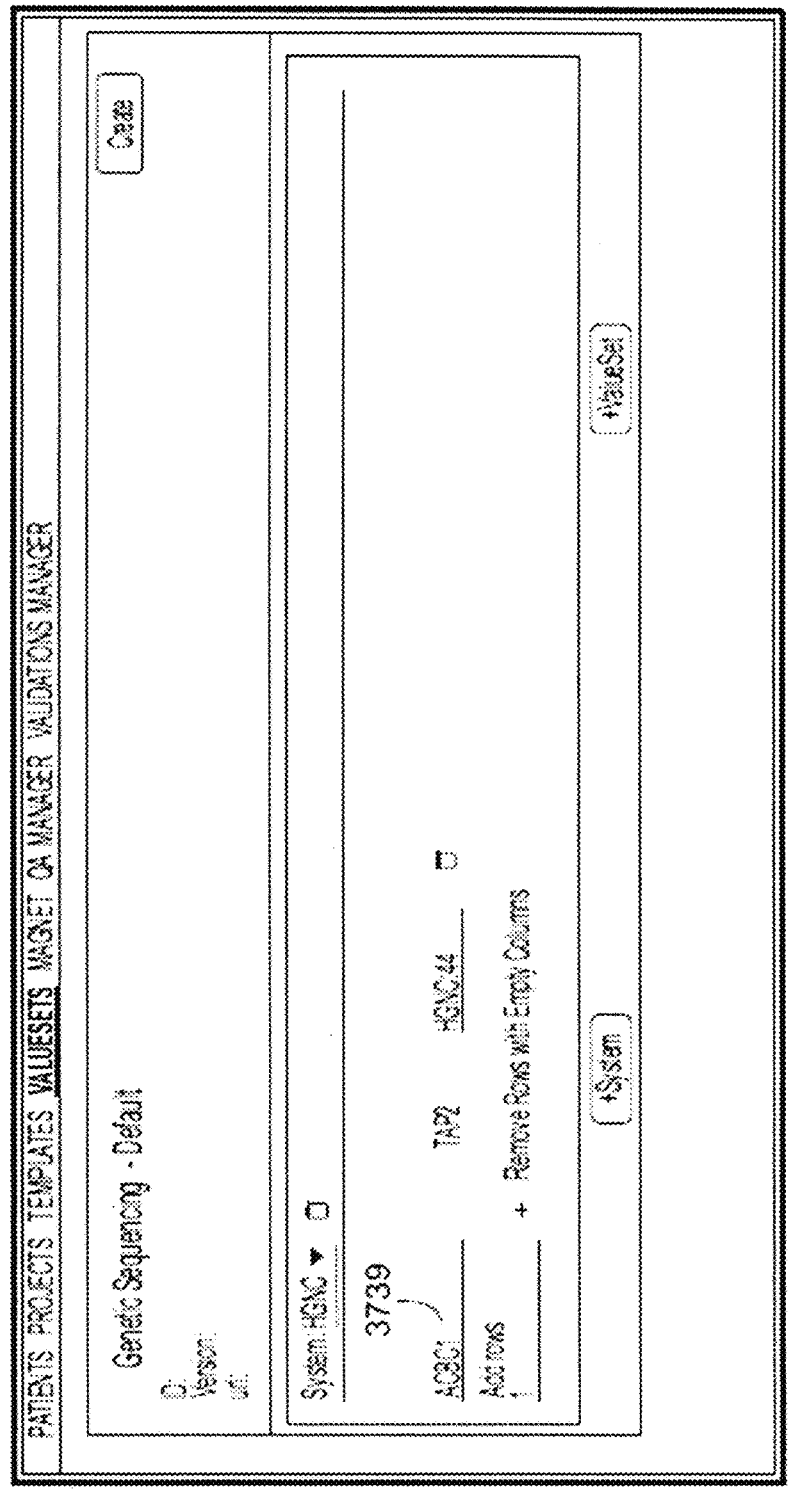
Figure 126:
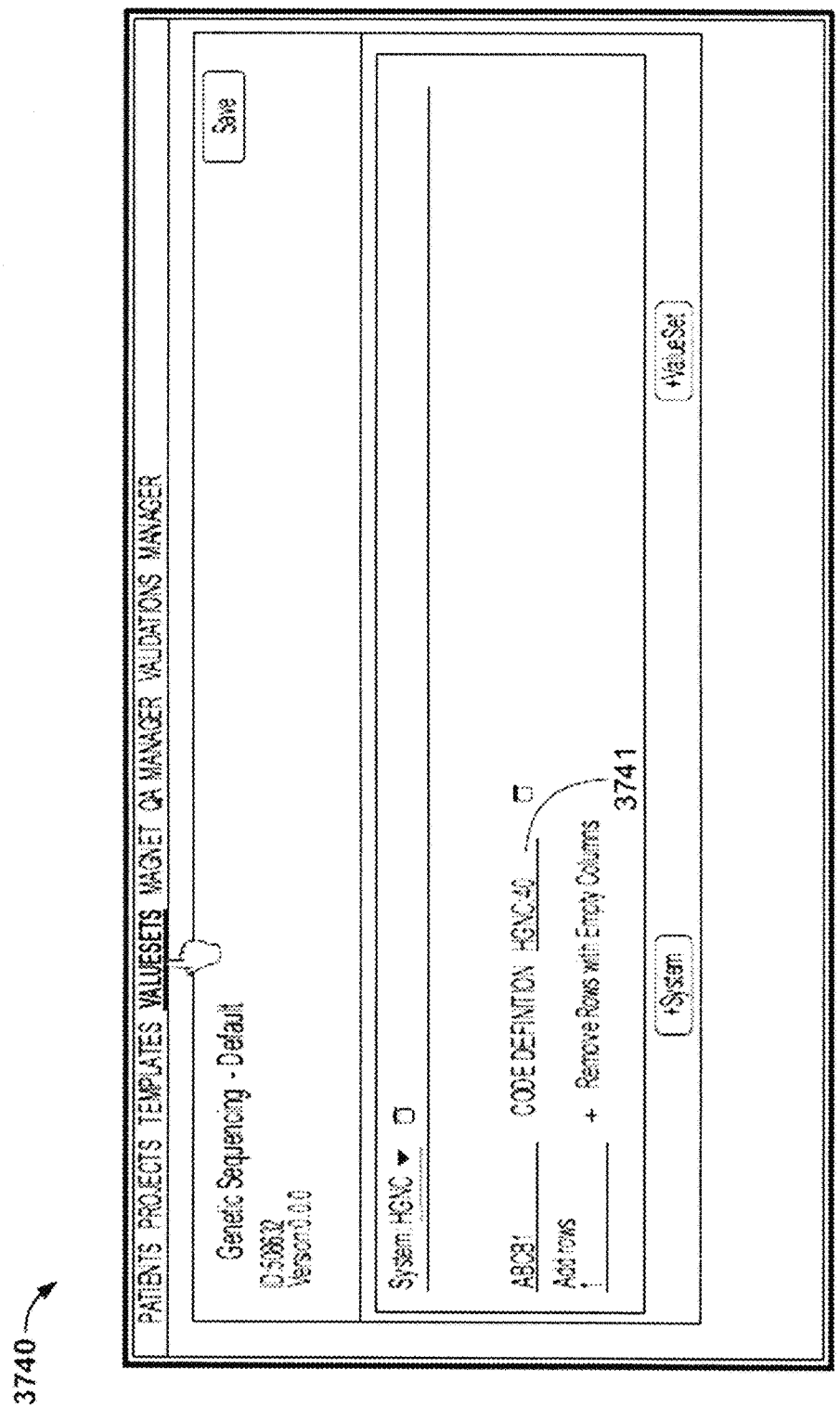
Figure 127:
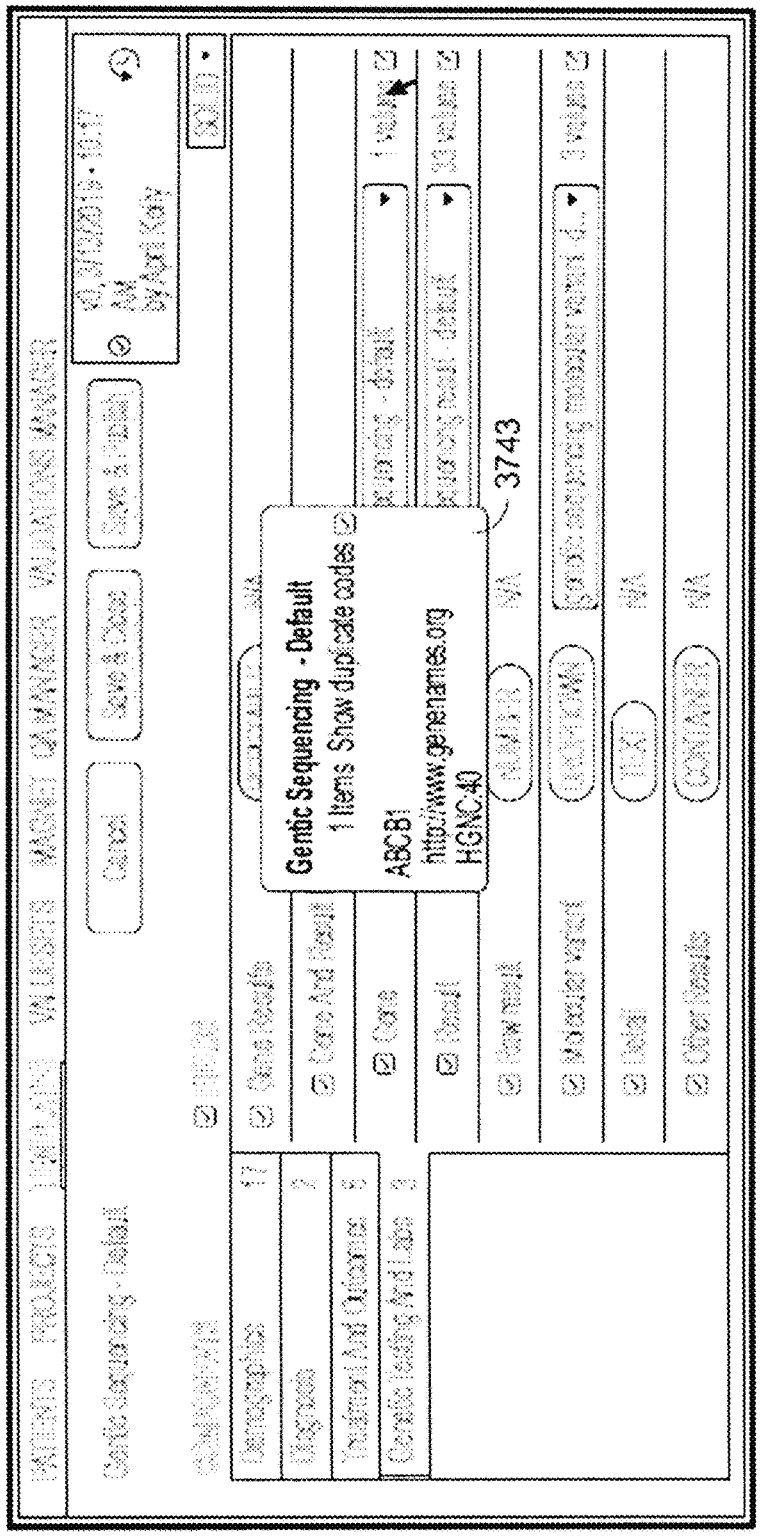
Figure 128:
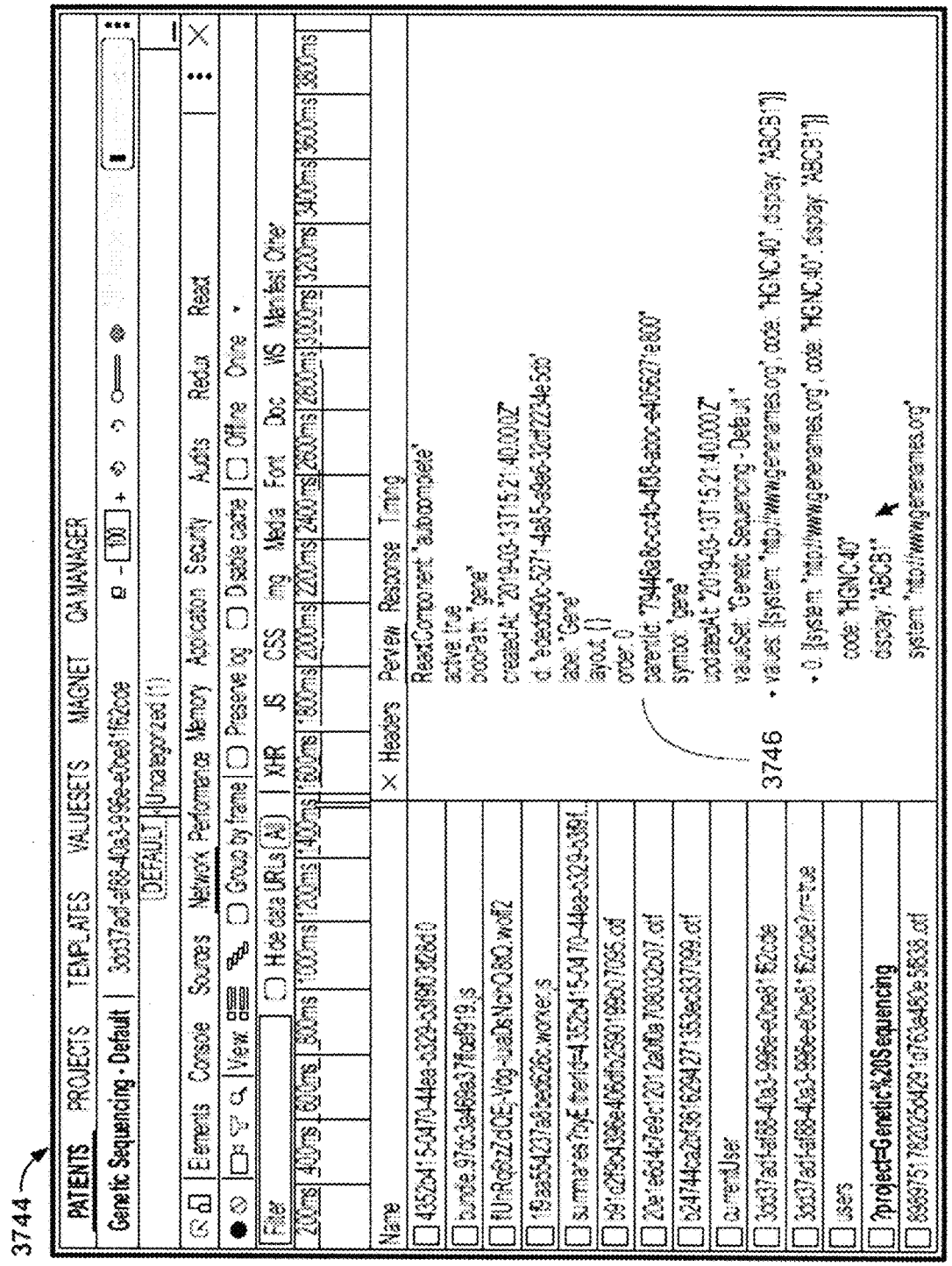
Figure 129:
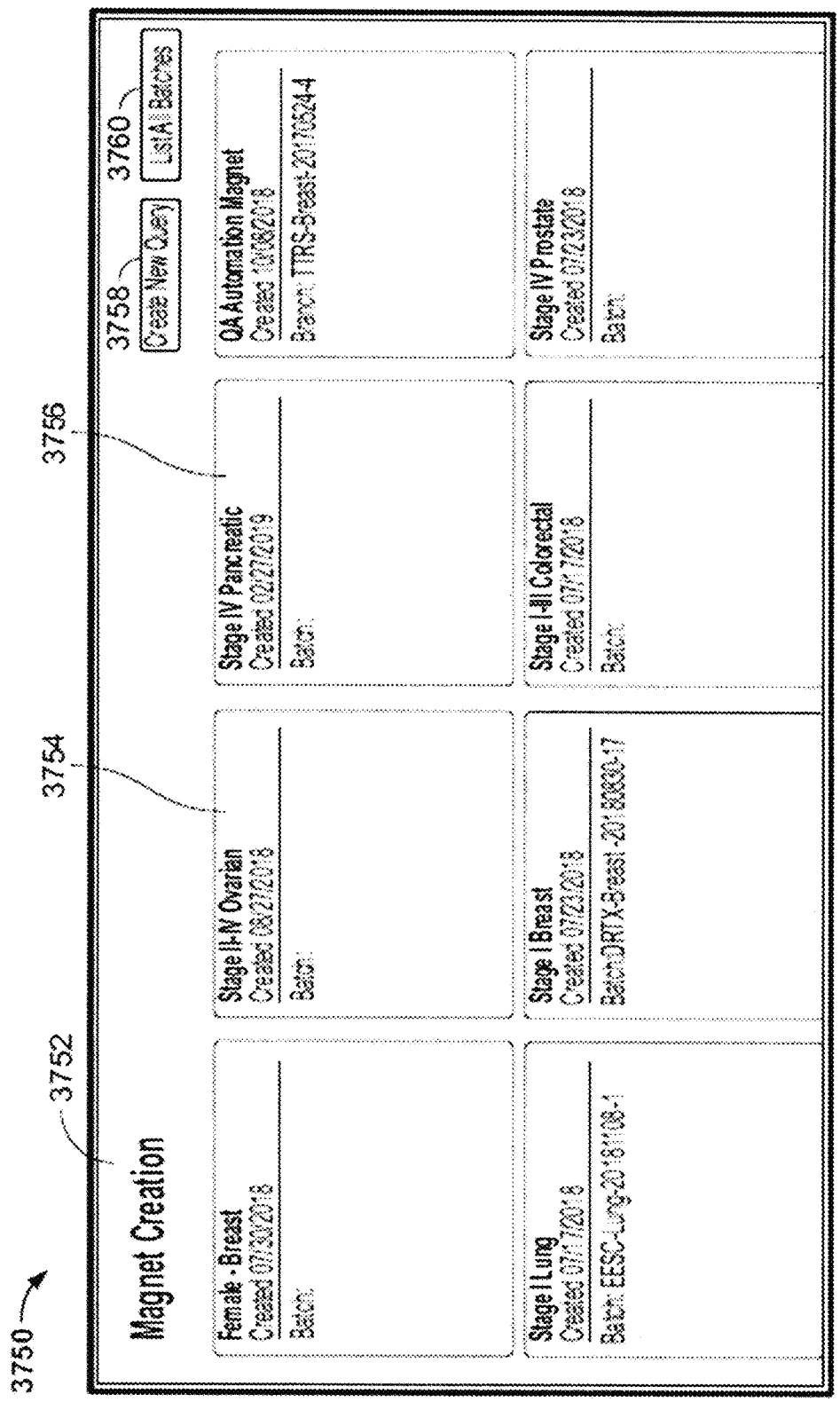
Figure 130:
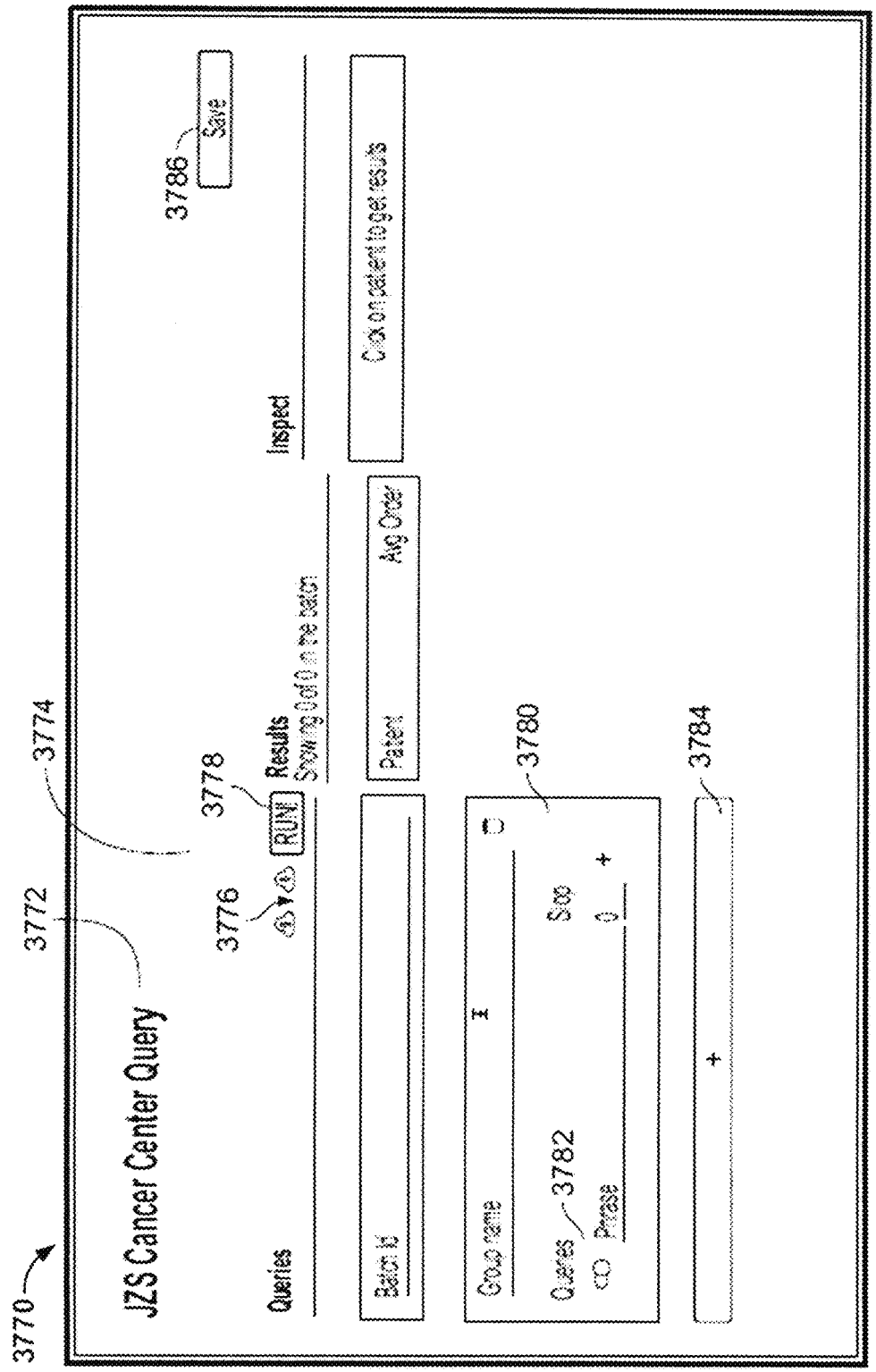
Figure 134:
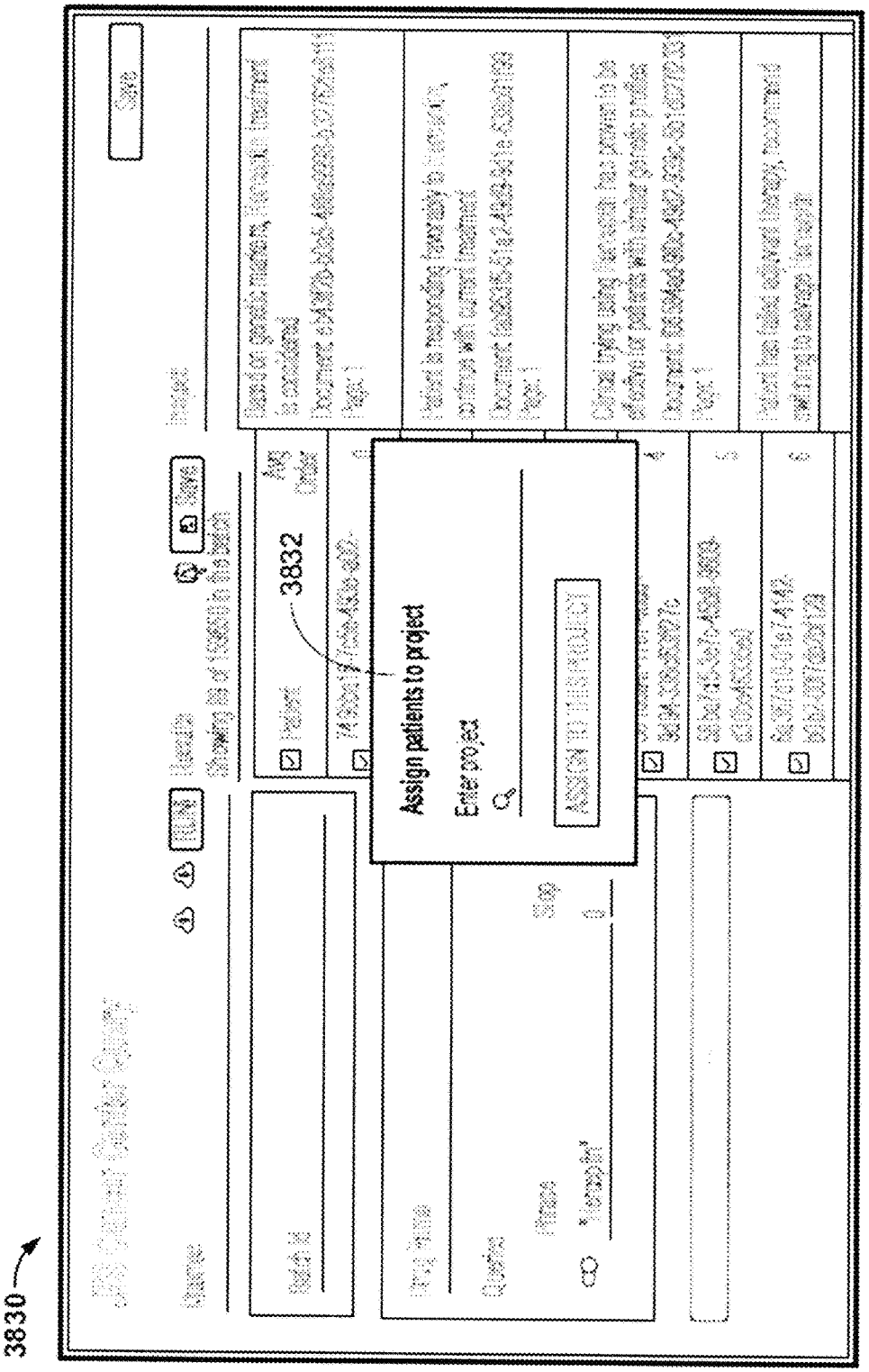
Figure 135:
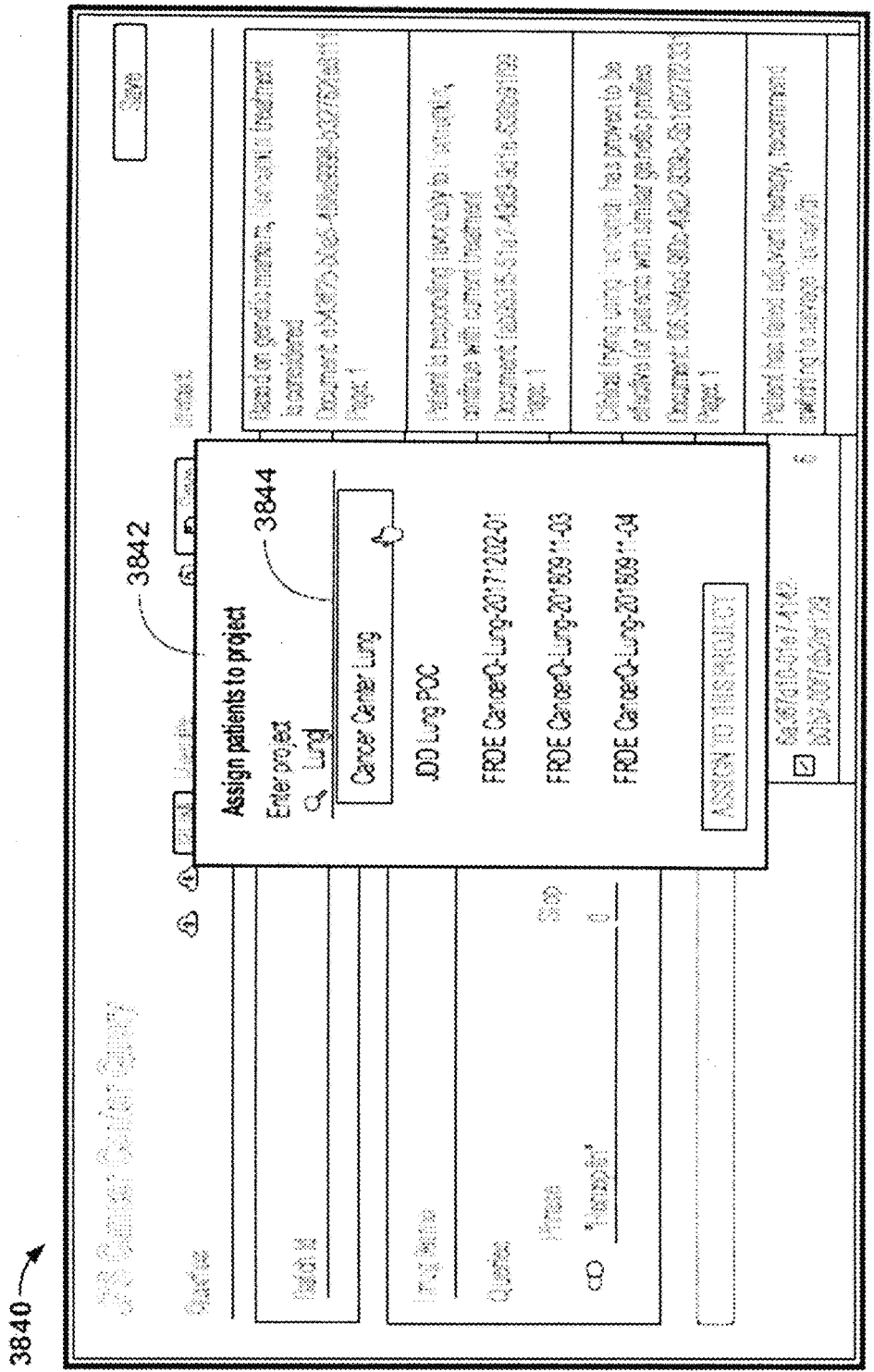
Figure 137:
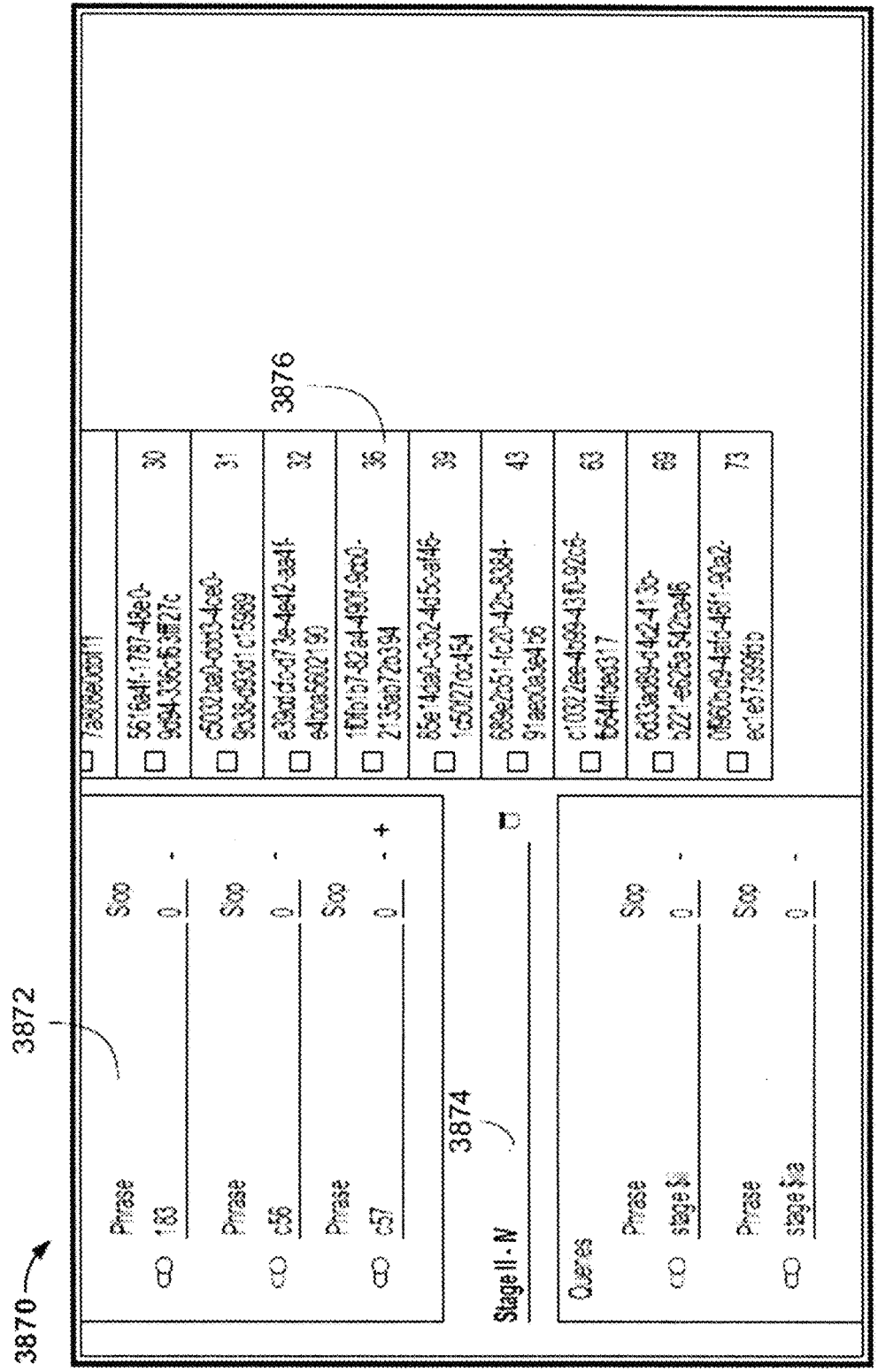
Figure 139:
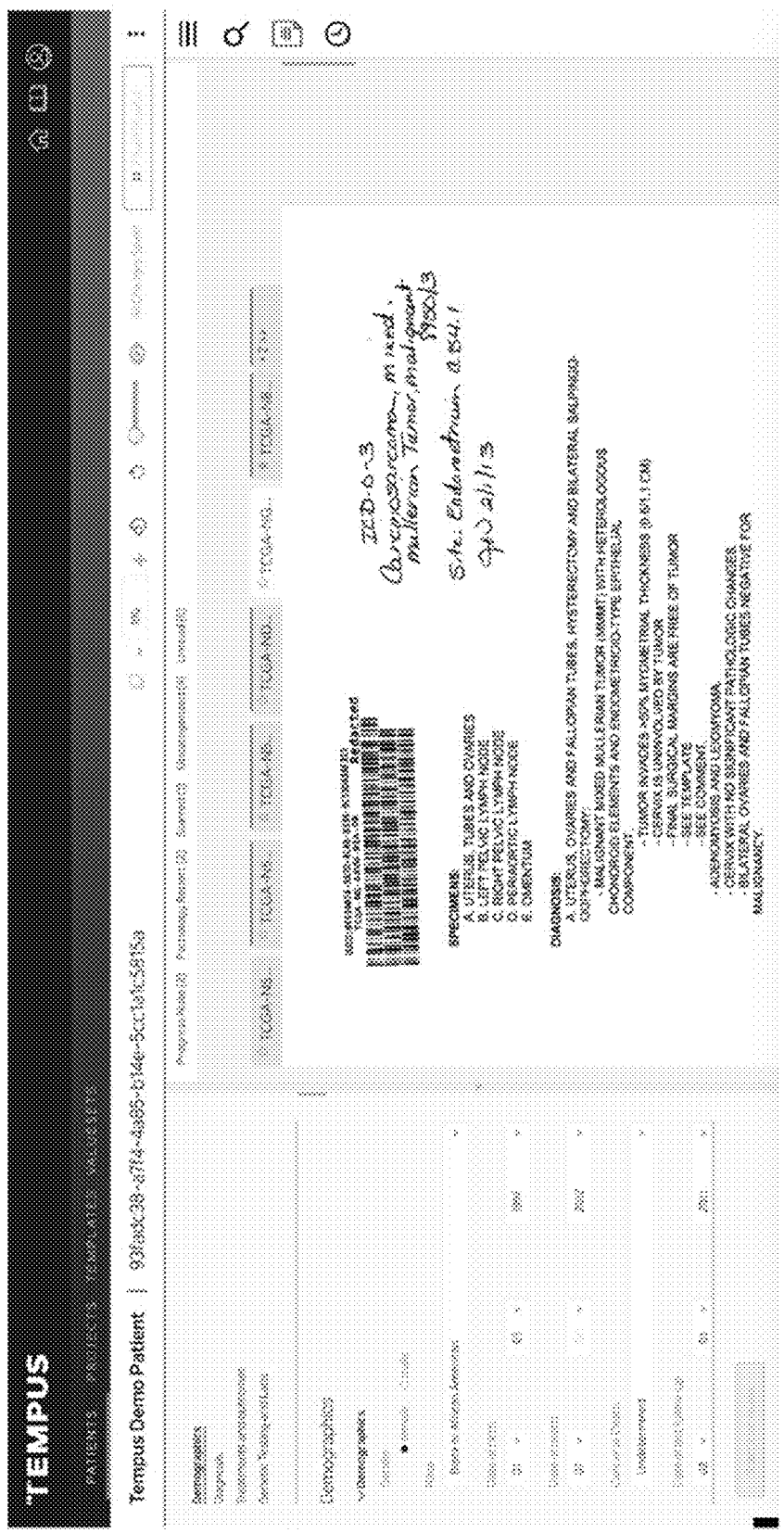
Figure 142:
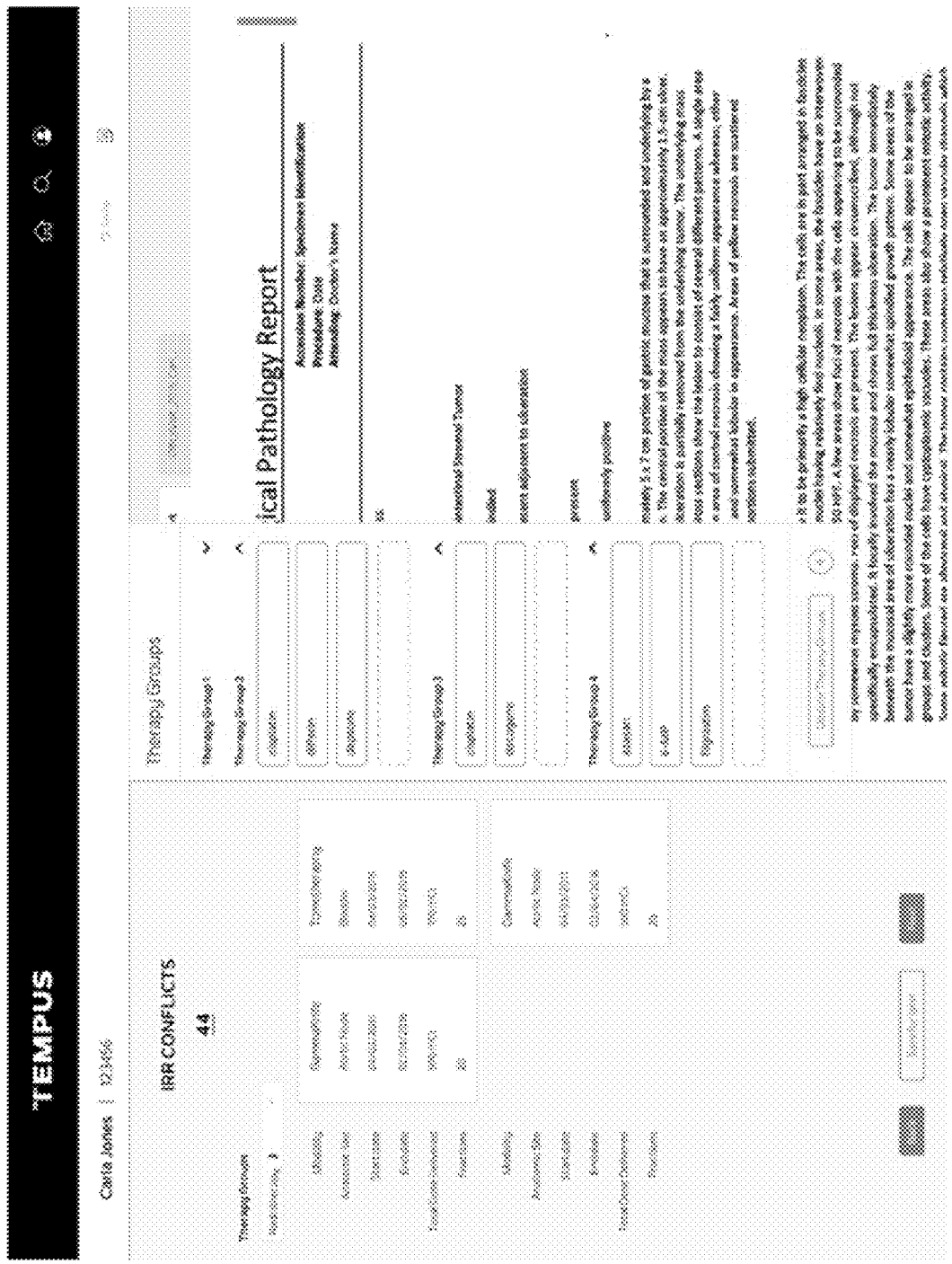
Figure 143:
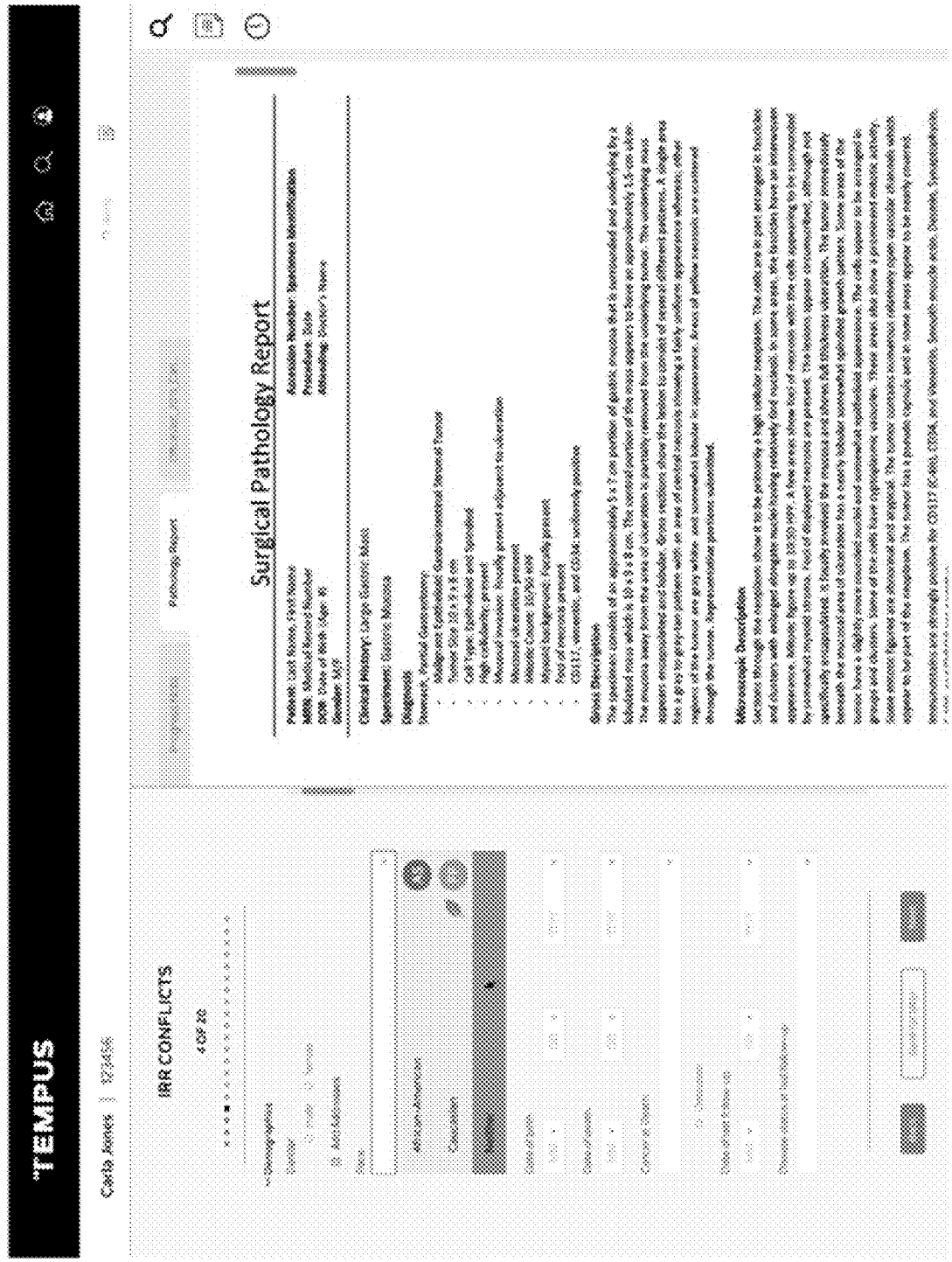
Figure 144:
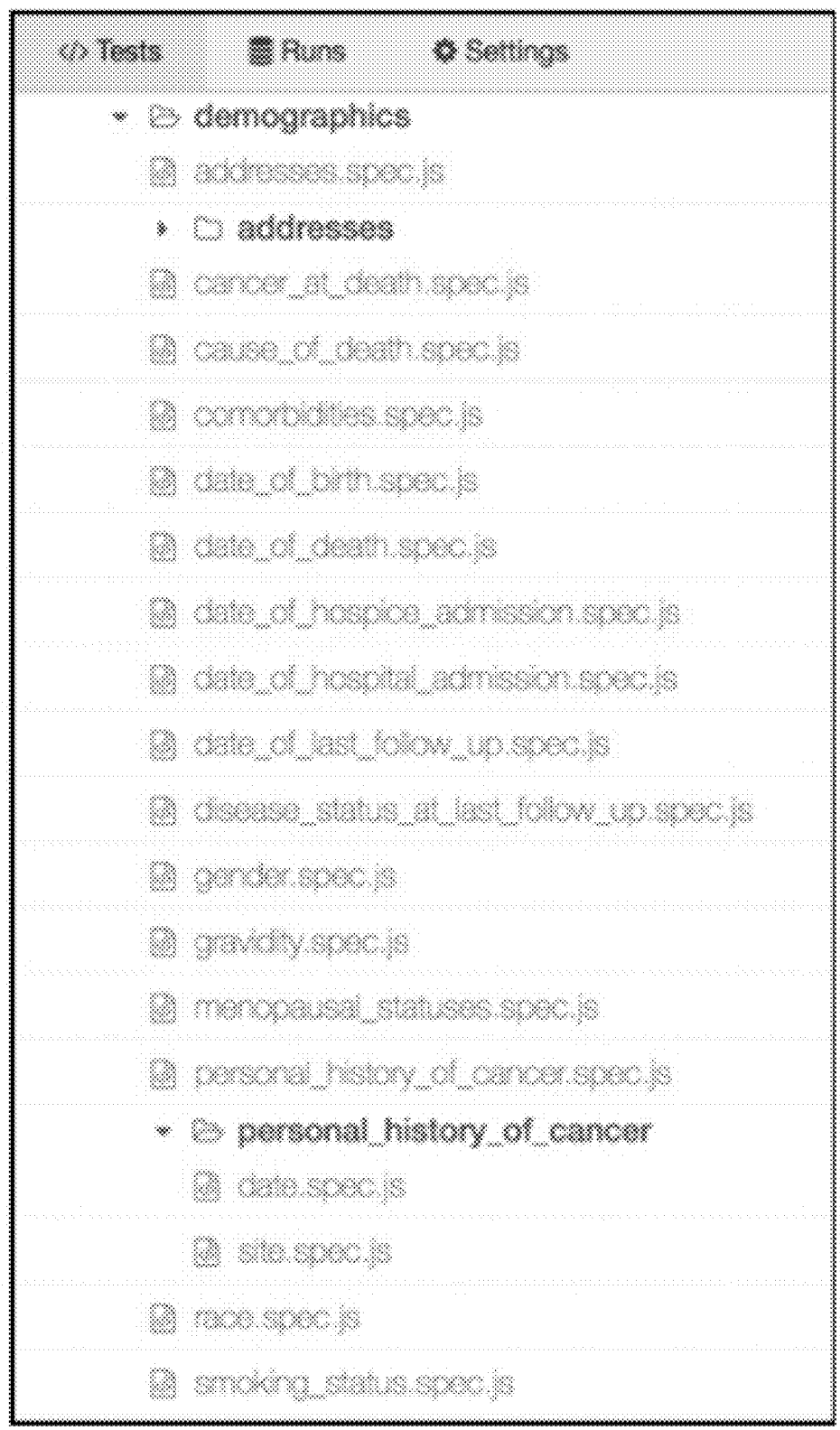
Figure 145:
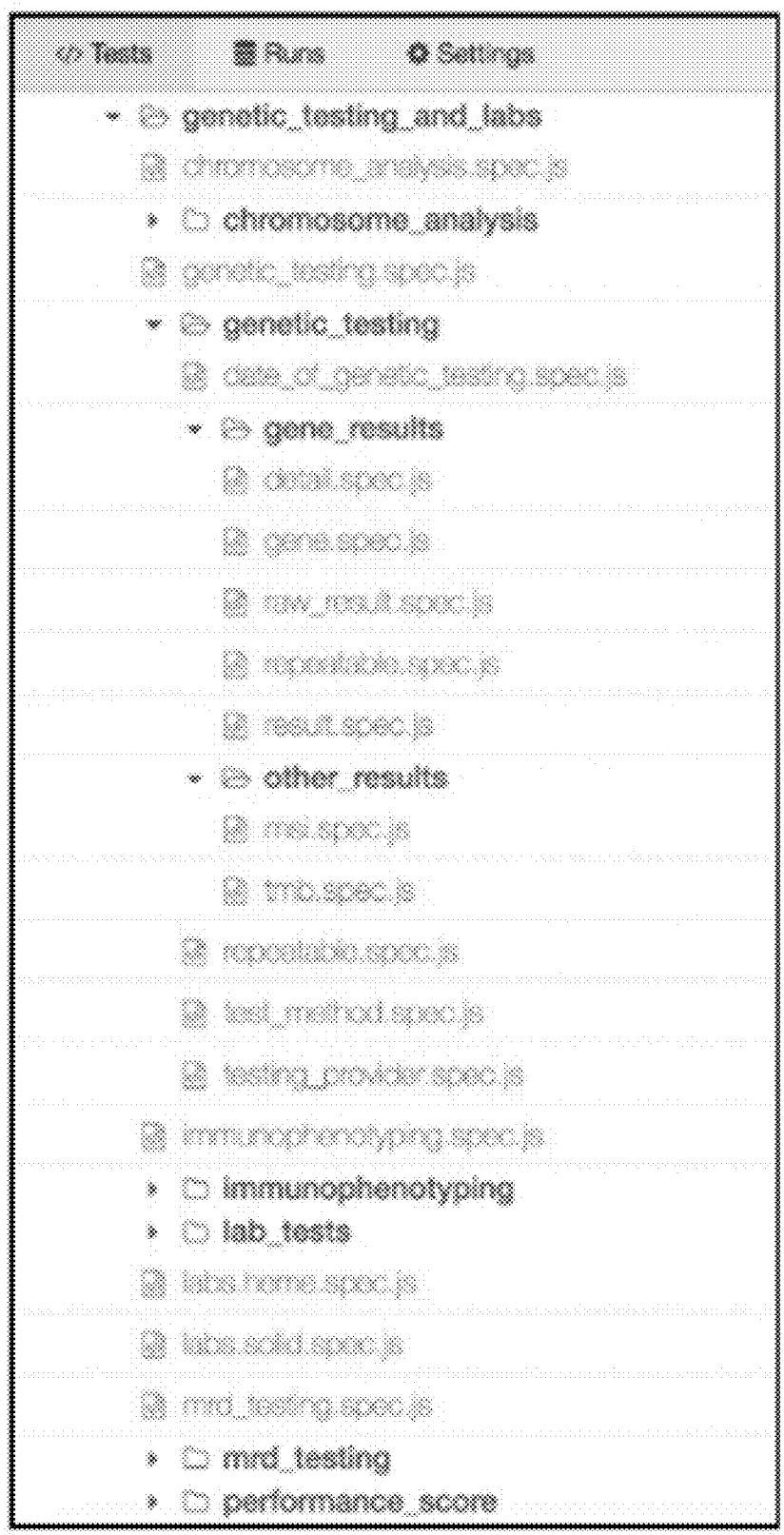
Figure 146:
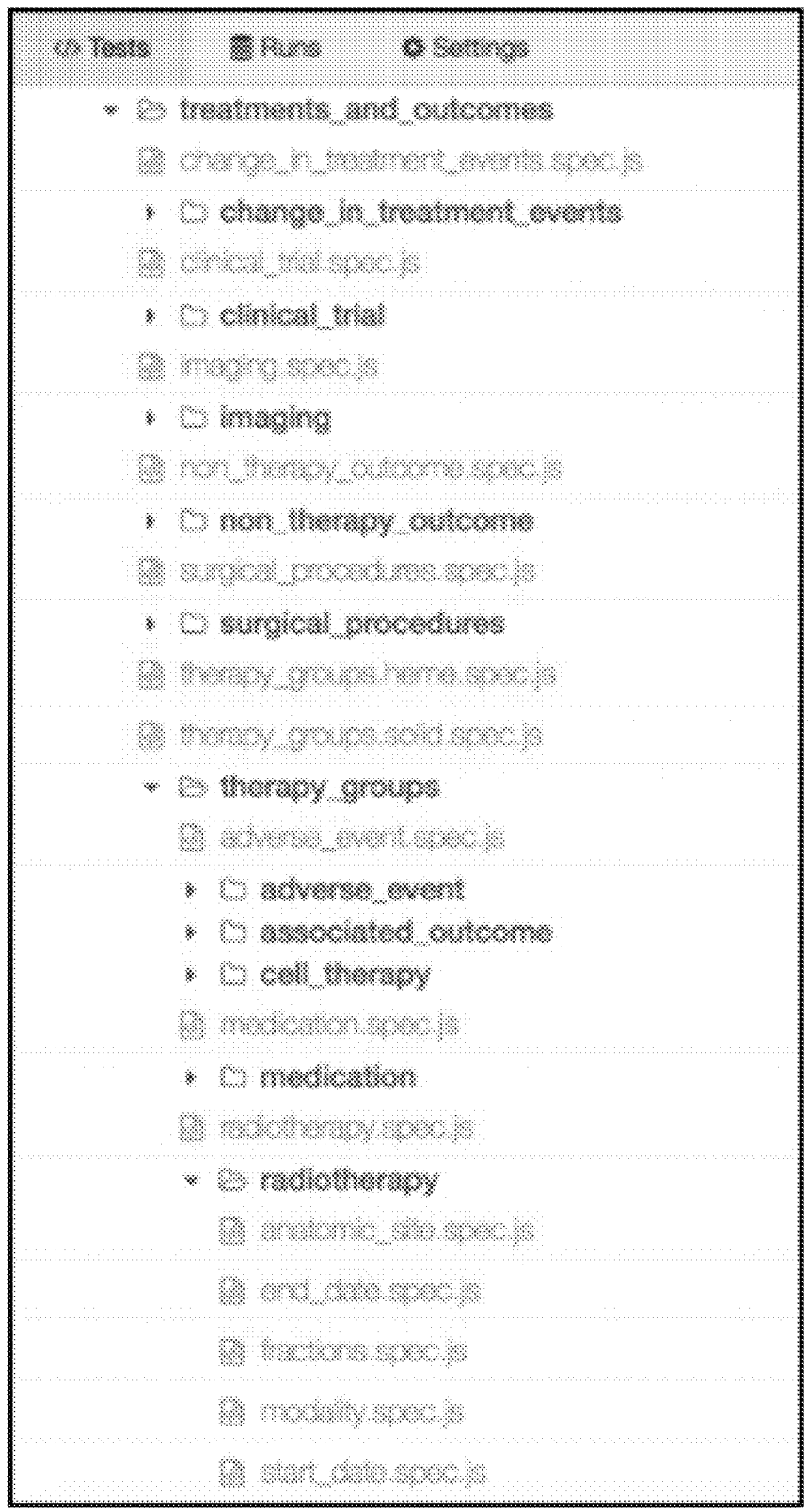
Figure 147:
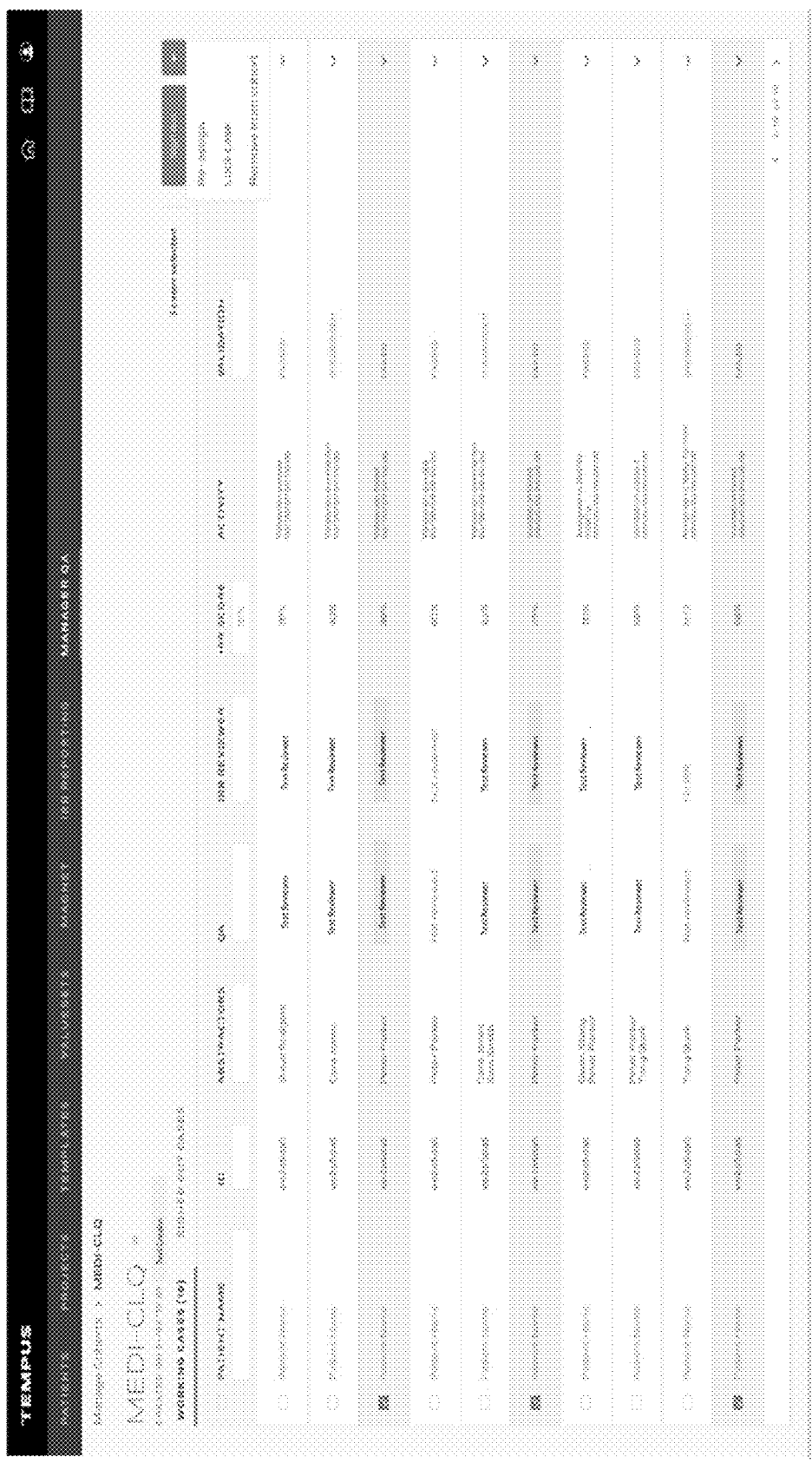
Figure 148:
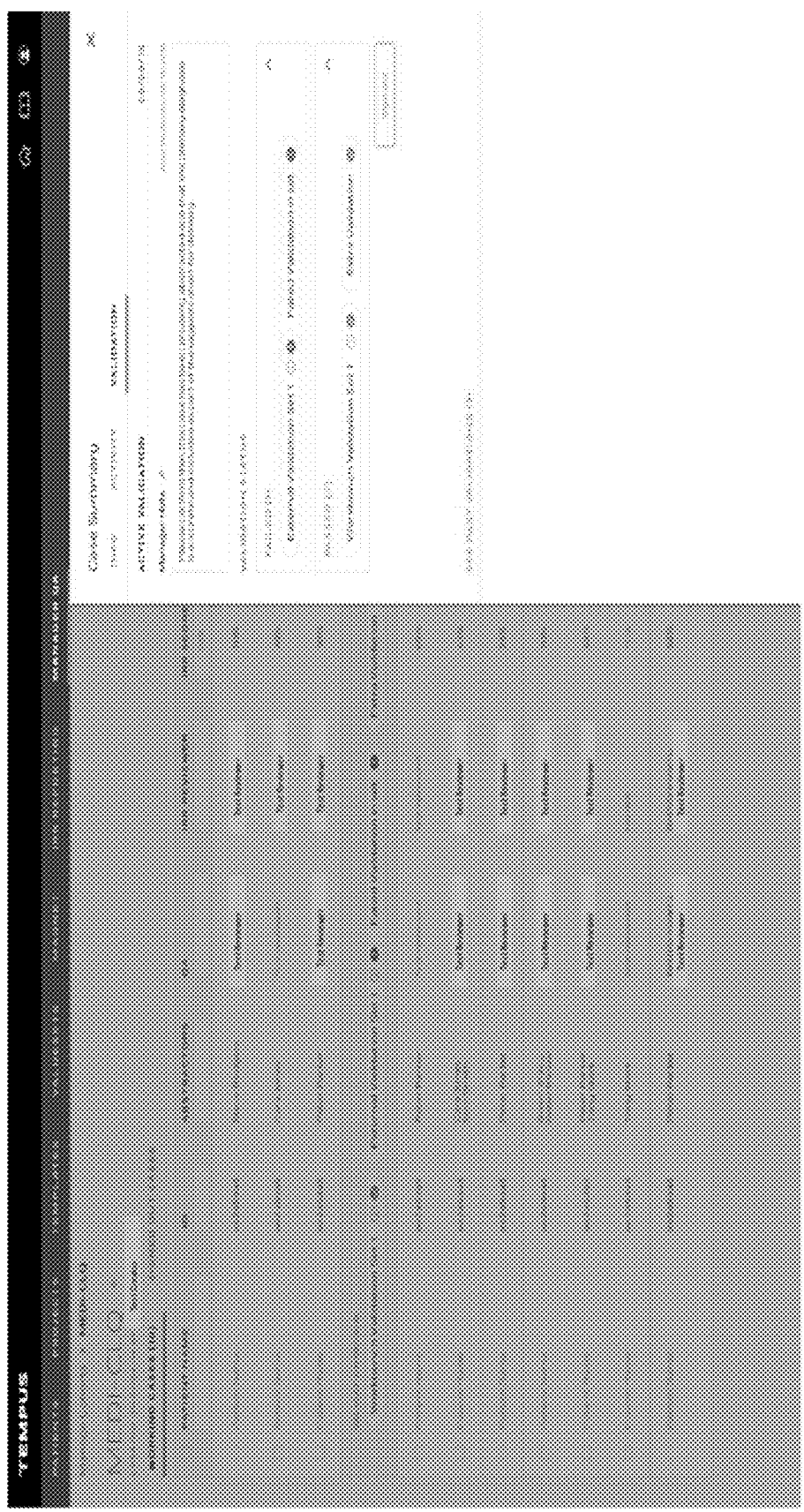
Figure 149:
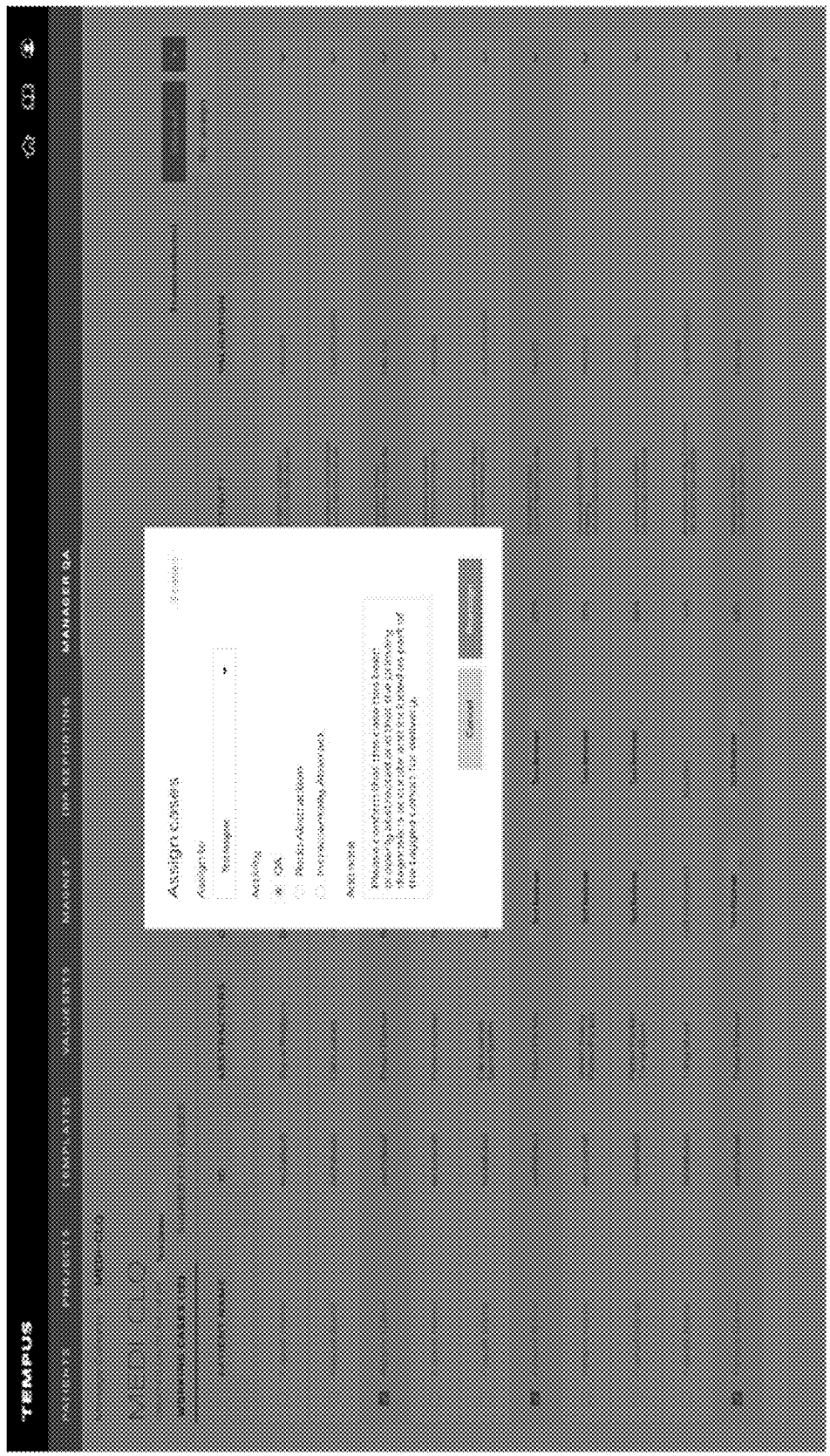
Figure 150:
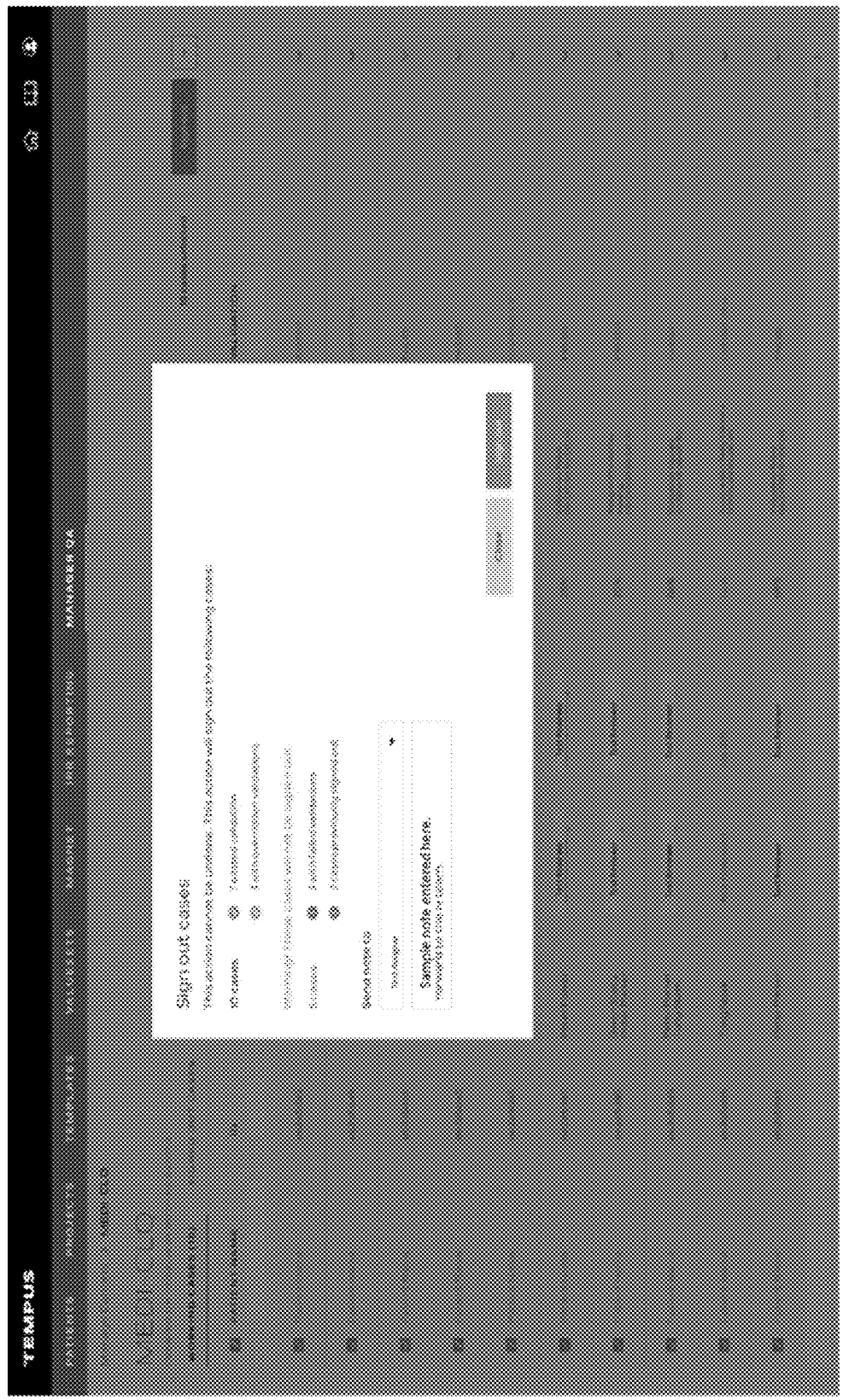
Figure 151:
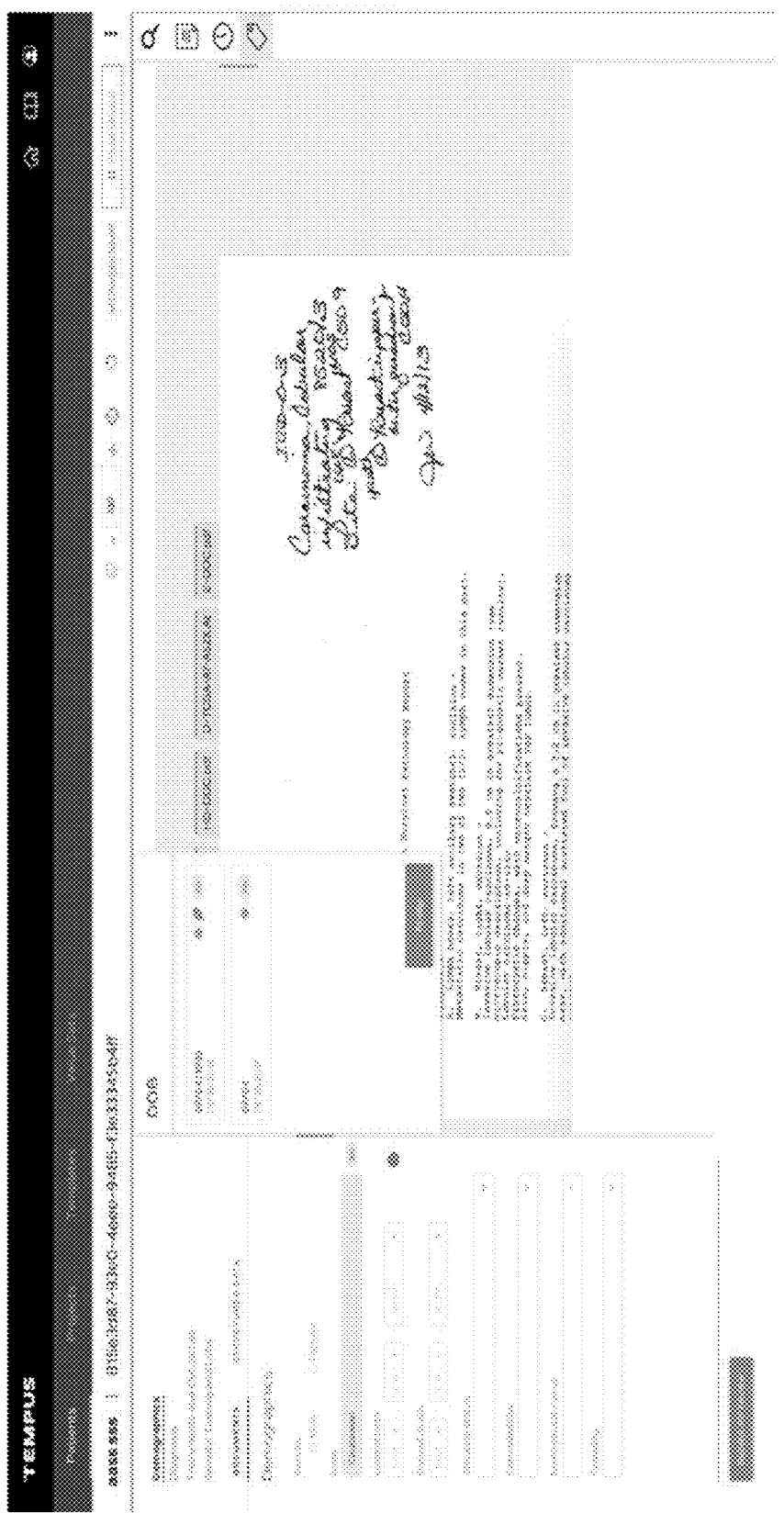
Figure 152:
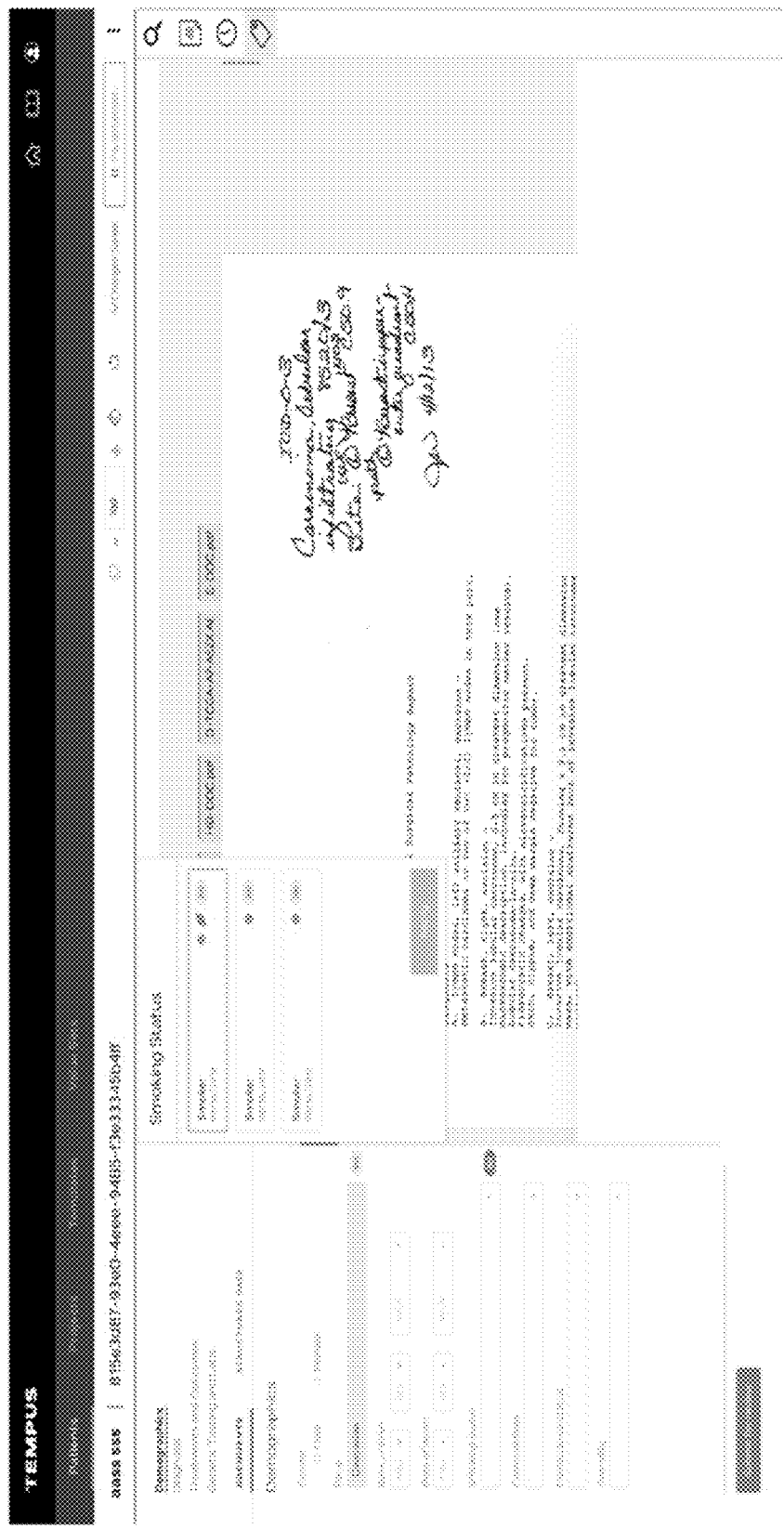
Figure 153:
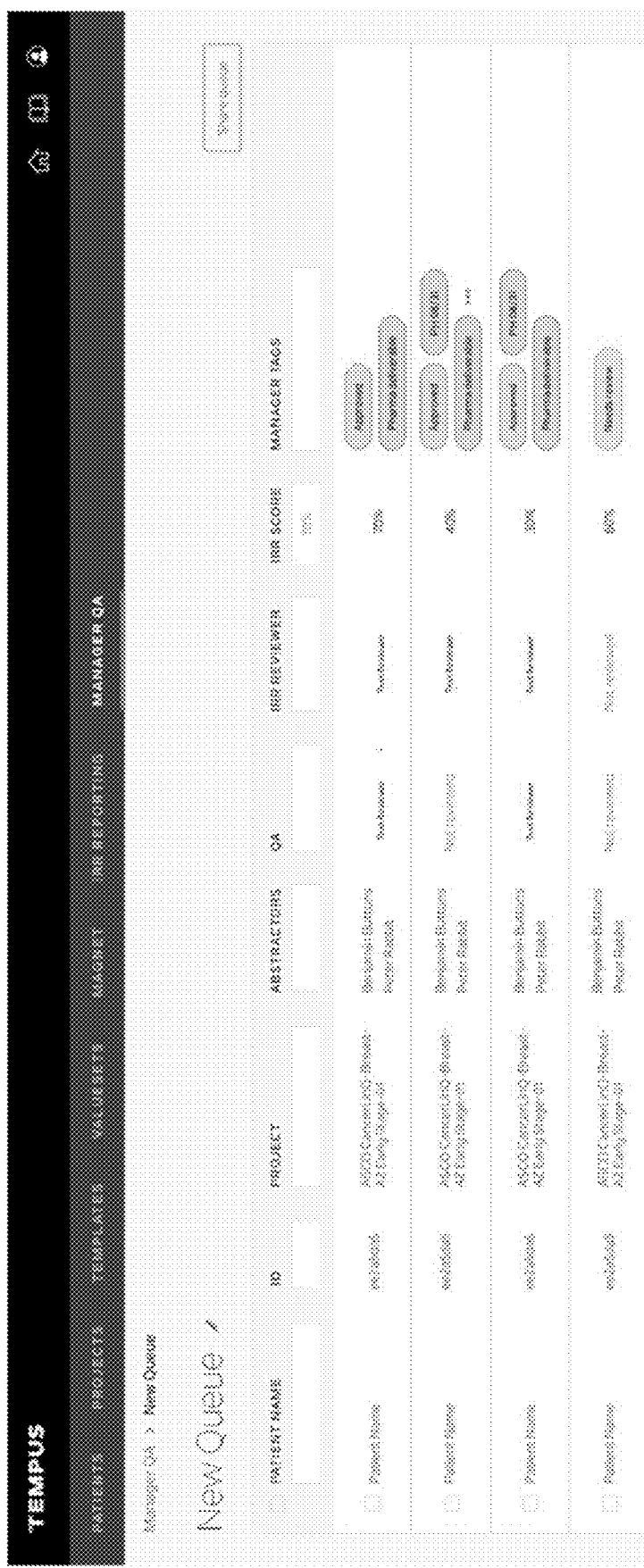
Figure 154:
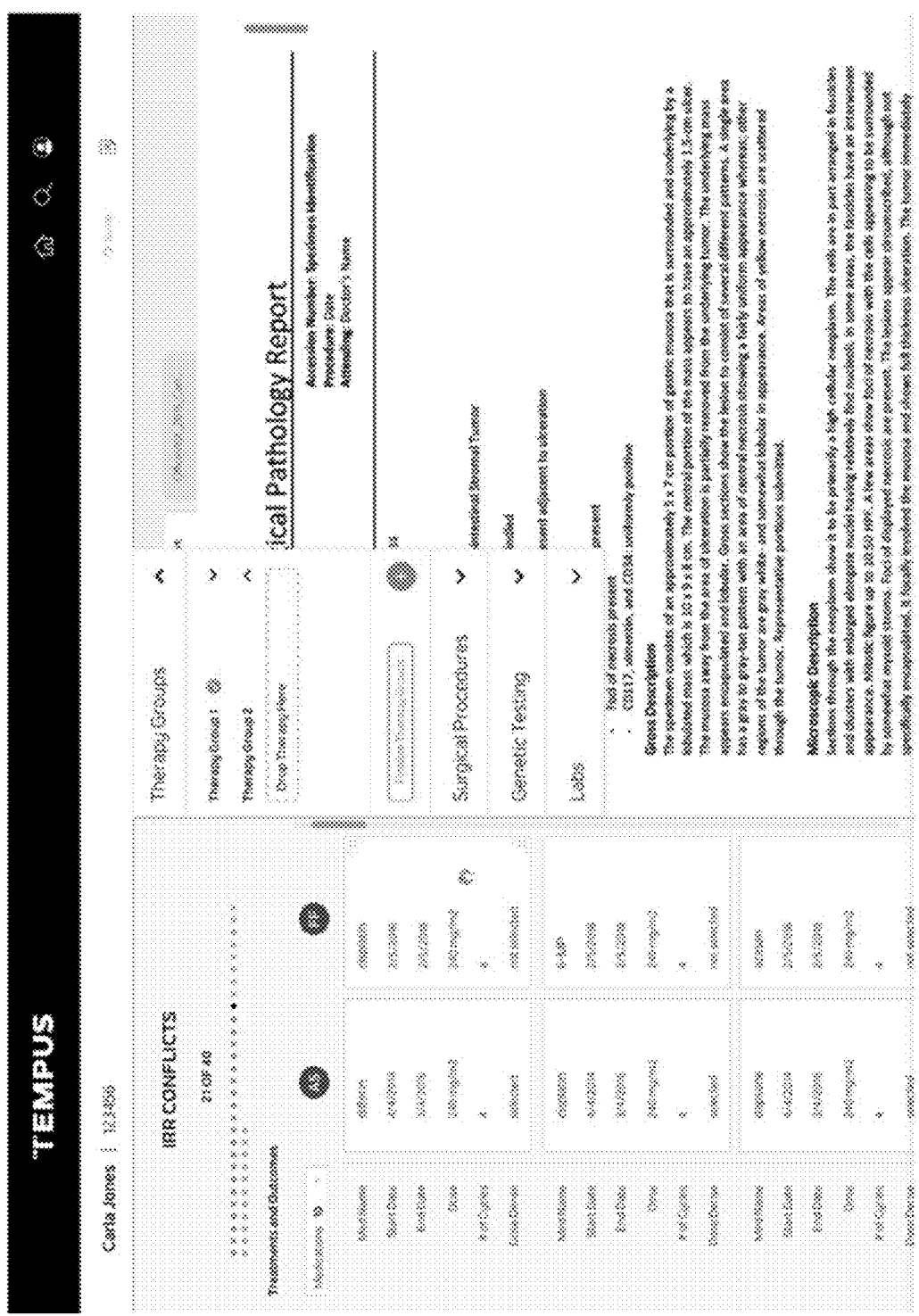
Figure 155:
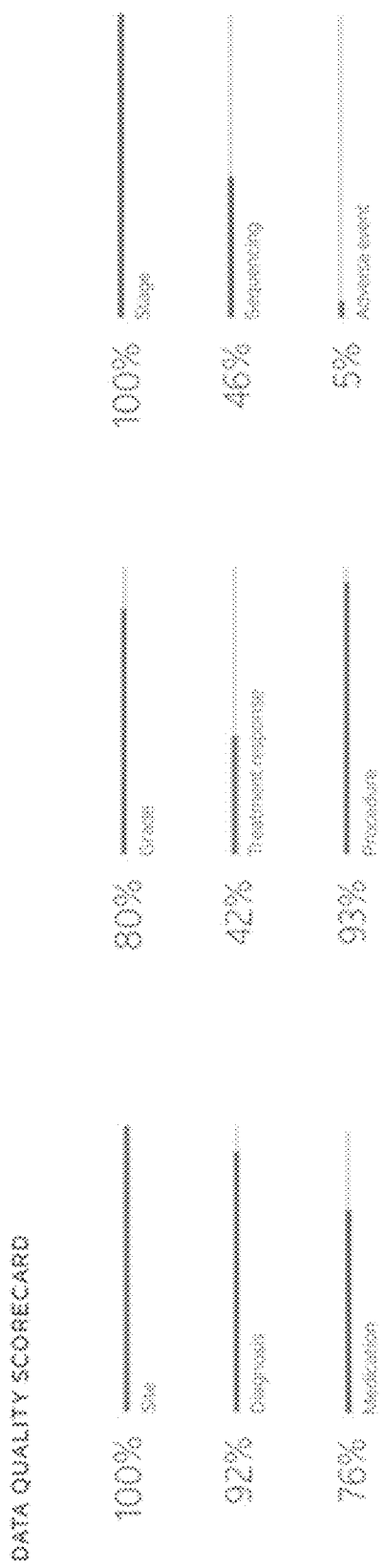
Figure 156:
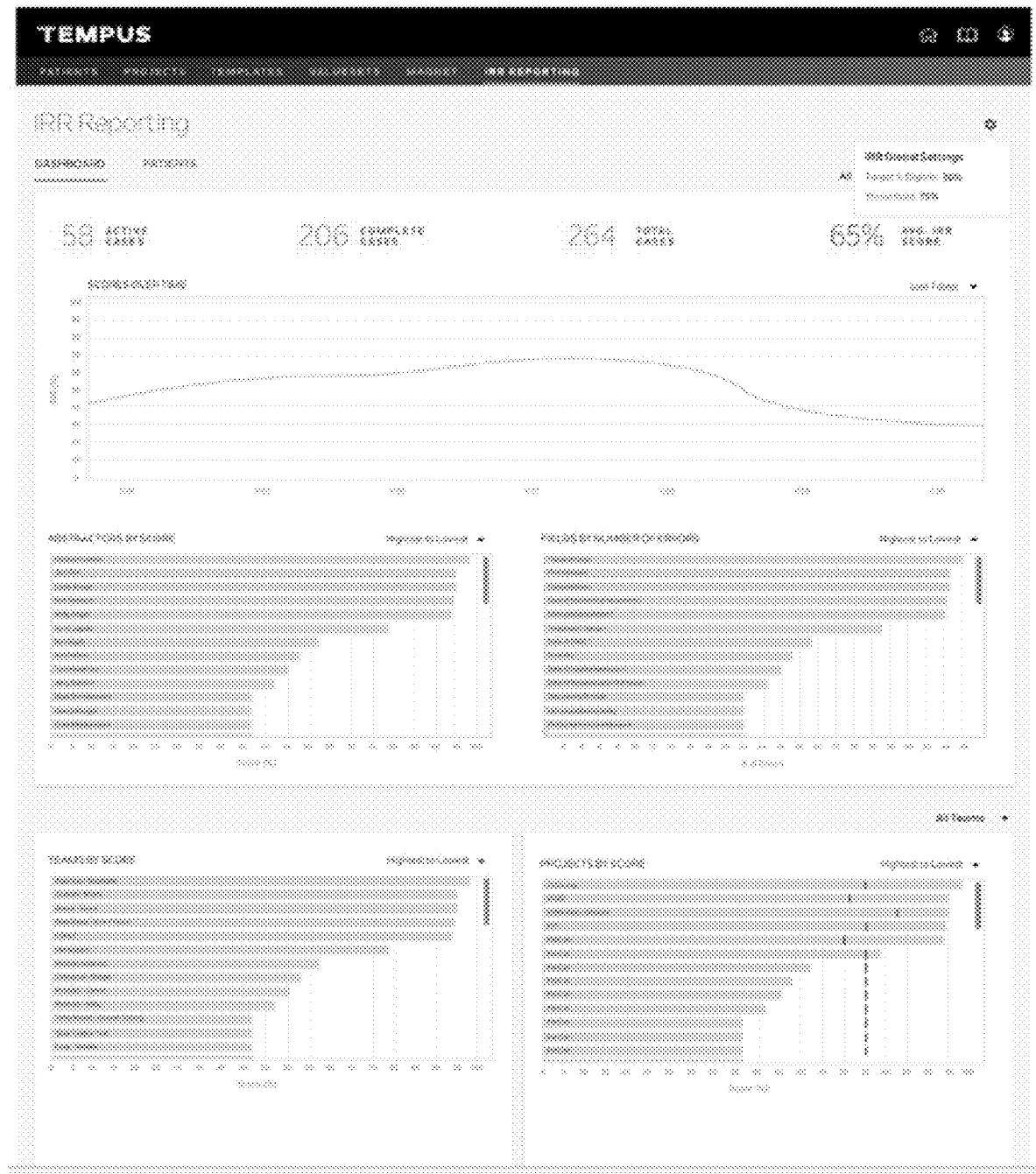
Figure 157:
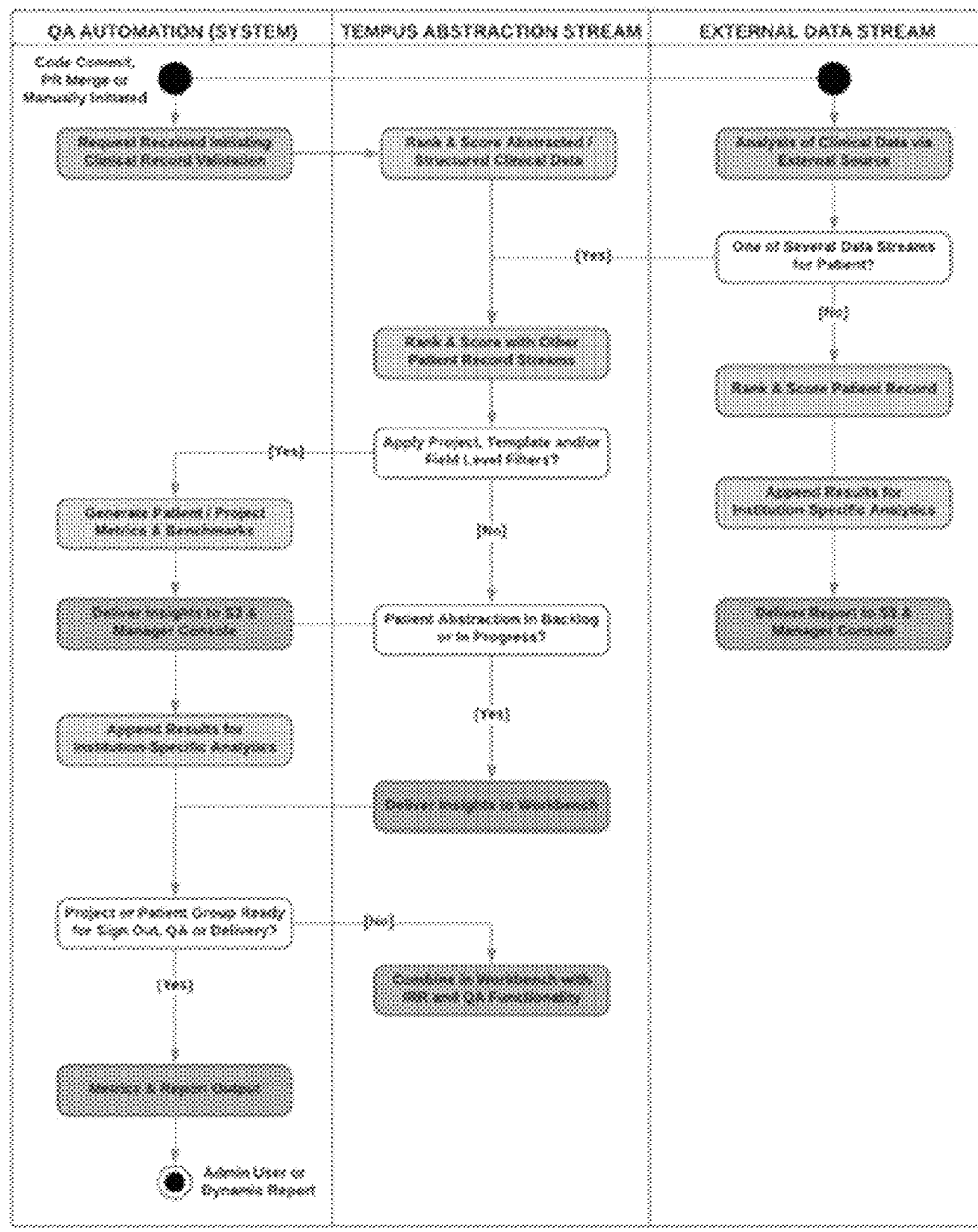
Figure 158:
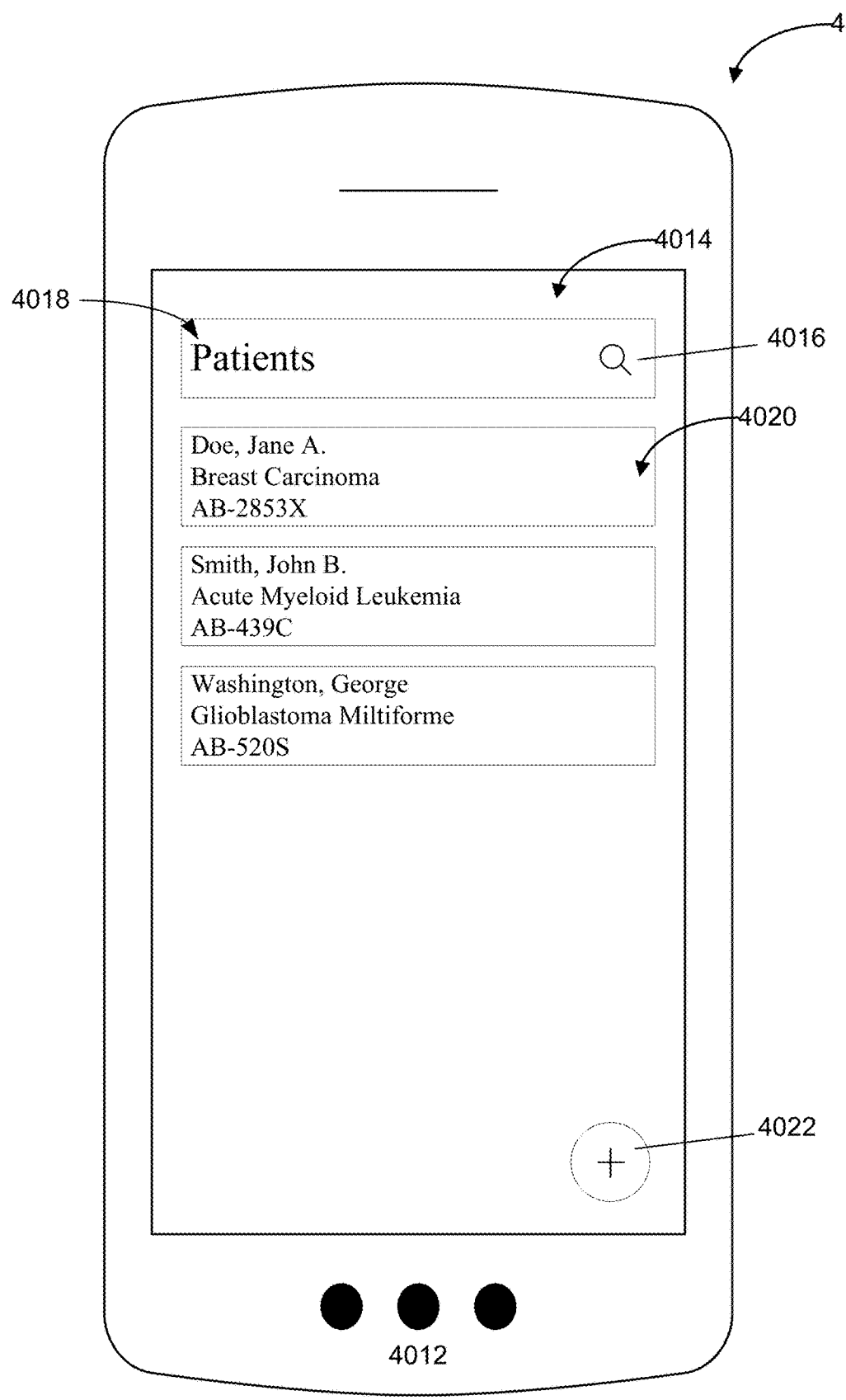
Figure 159:
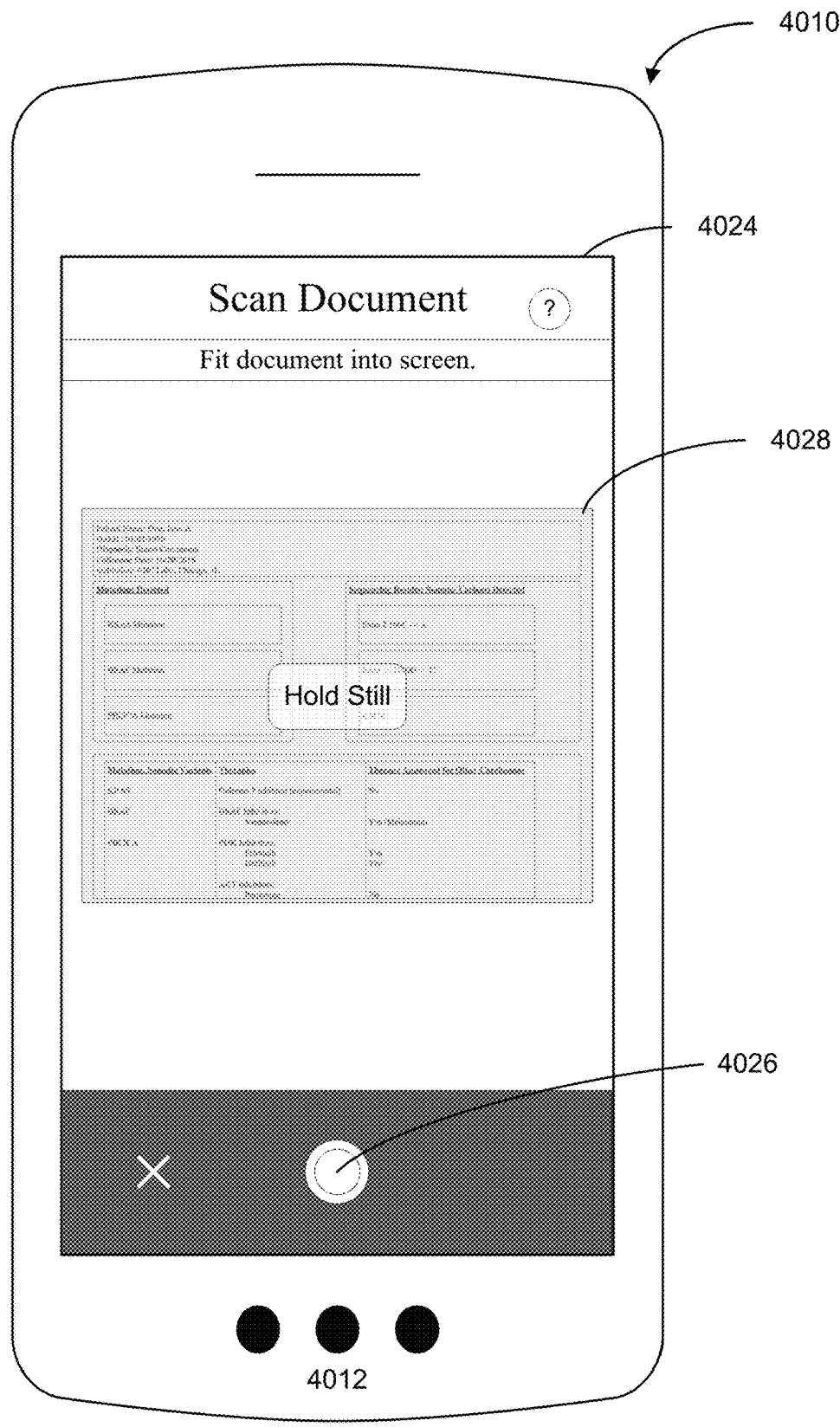
Figure 160:
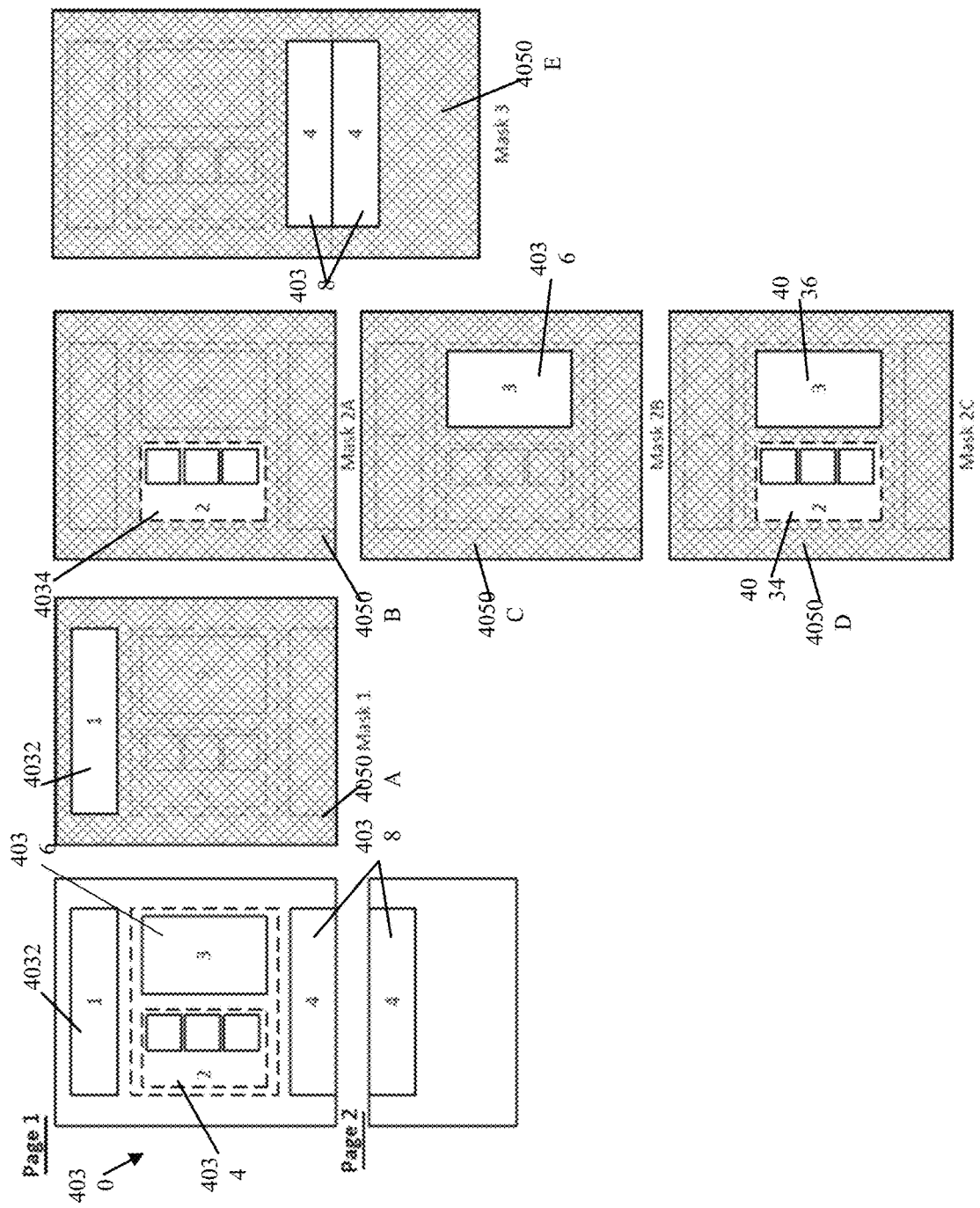
Figure 161A:
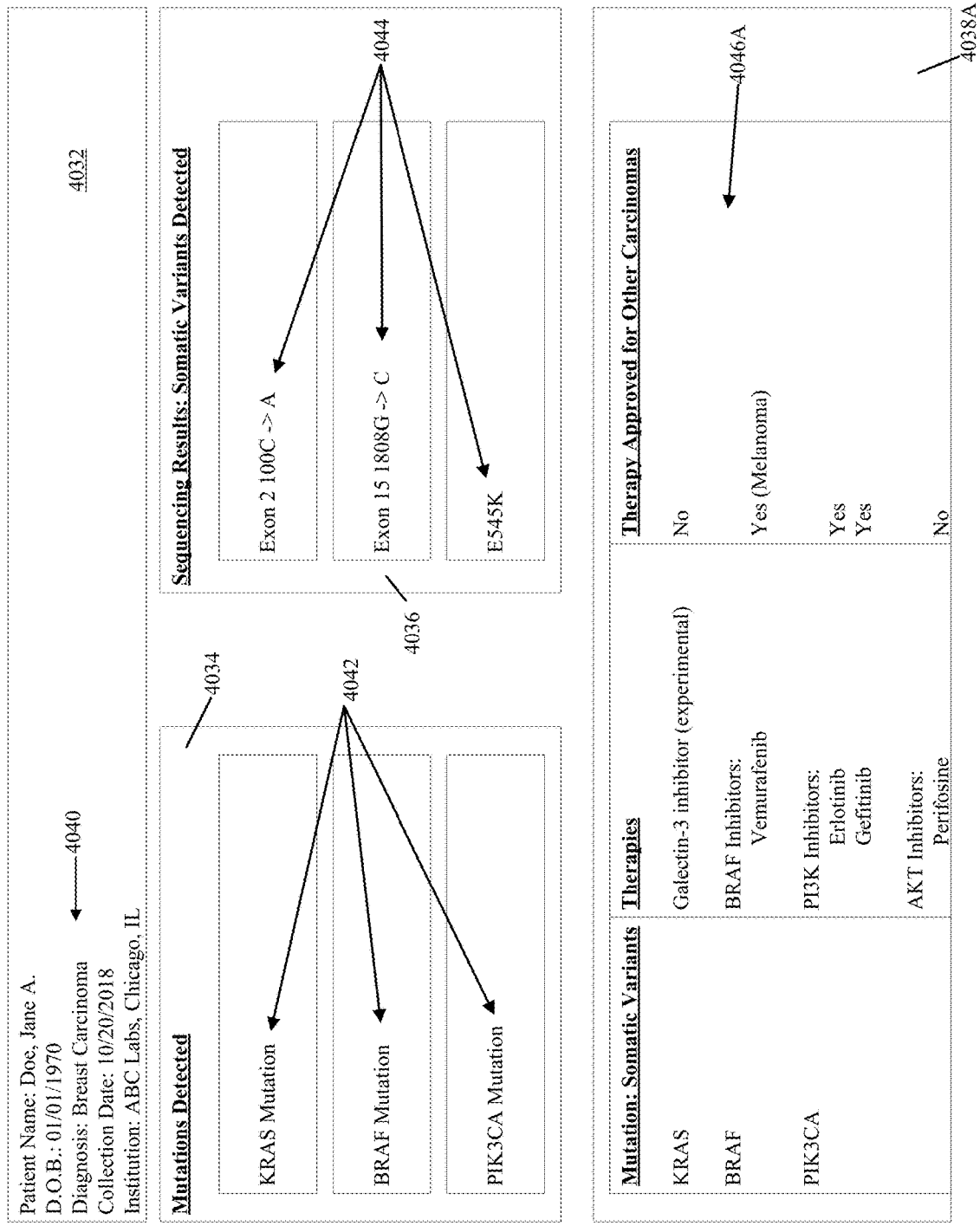
Figure 161B:
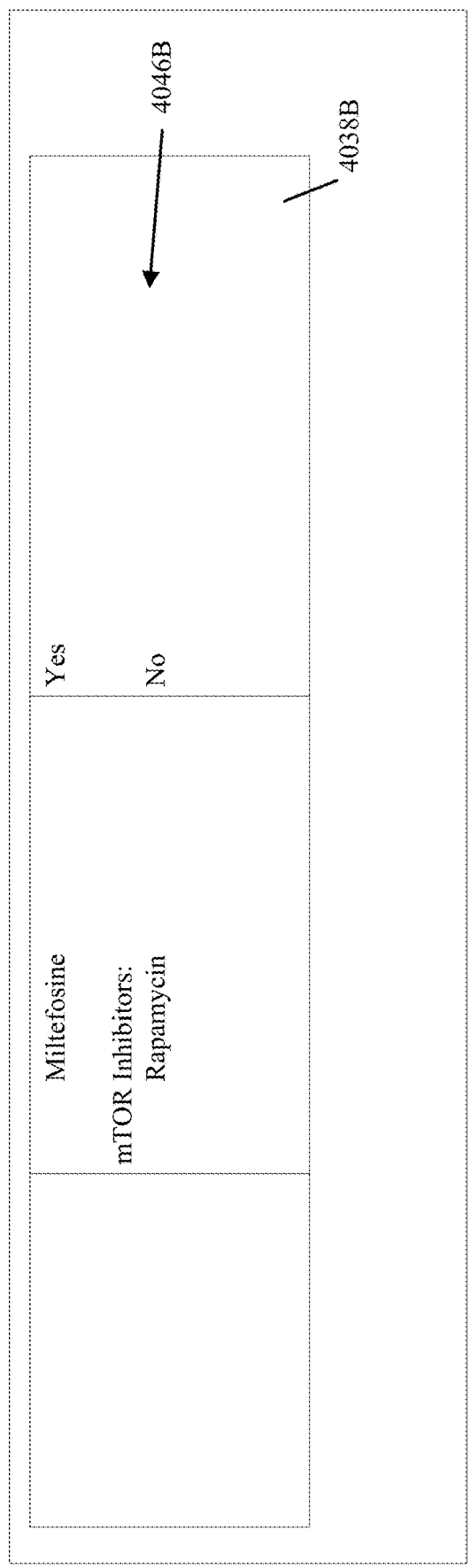
Figure 162:
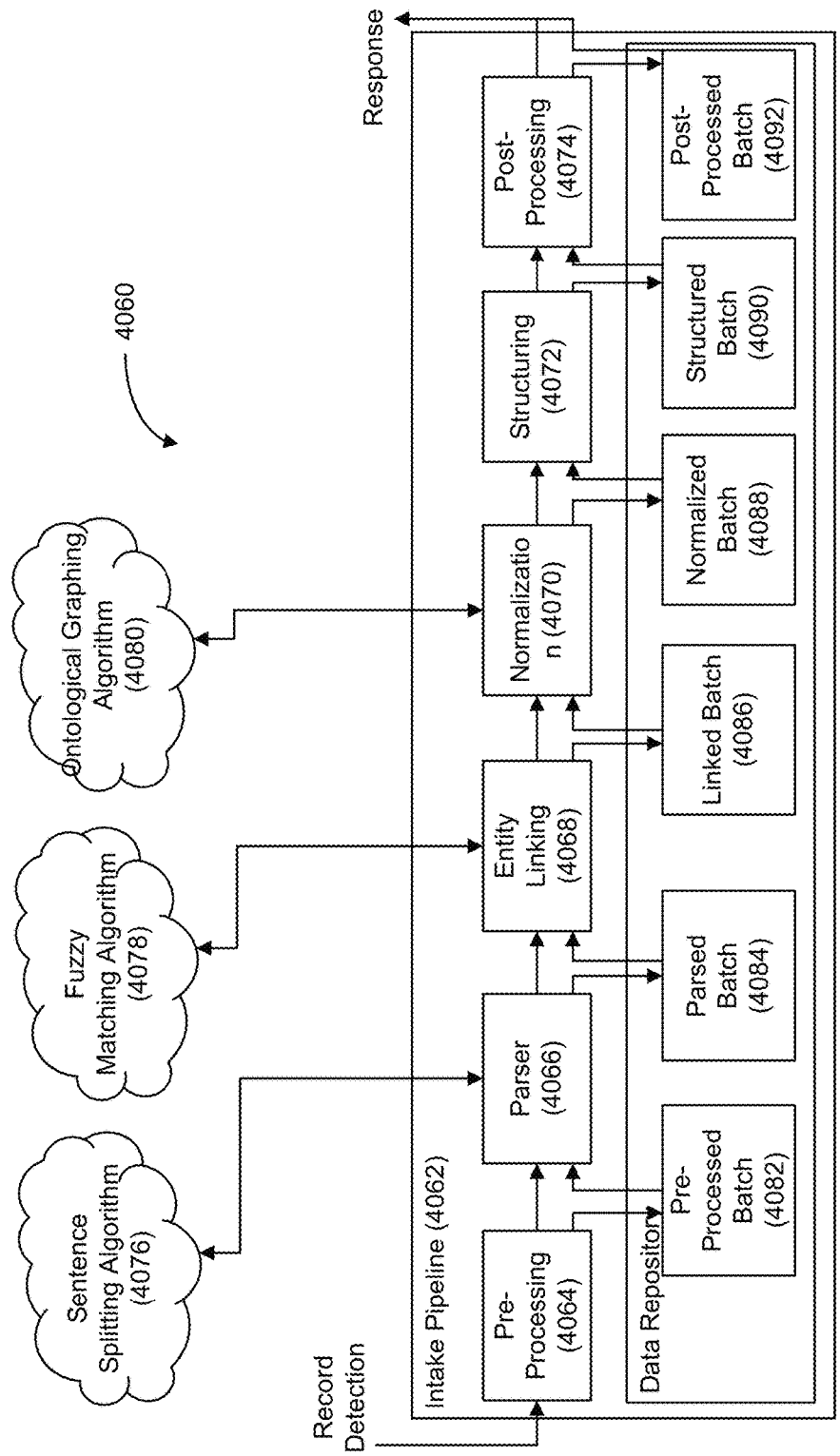
Figure 164:
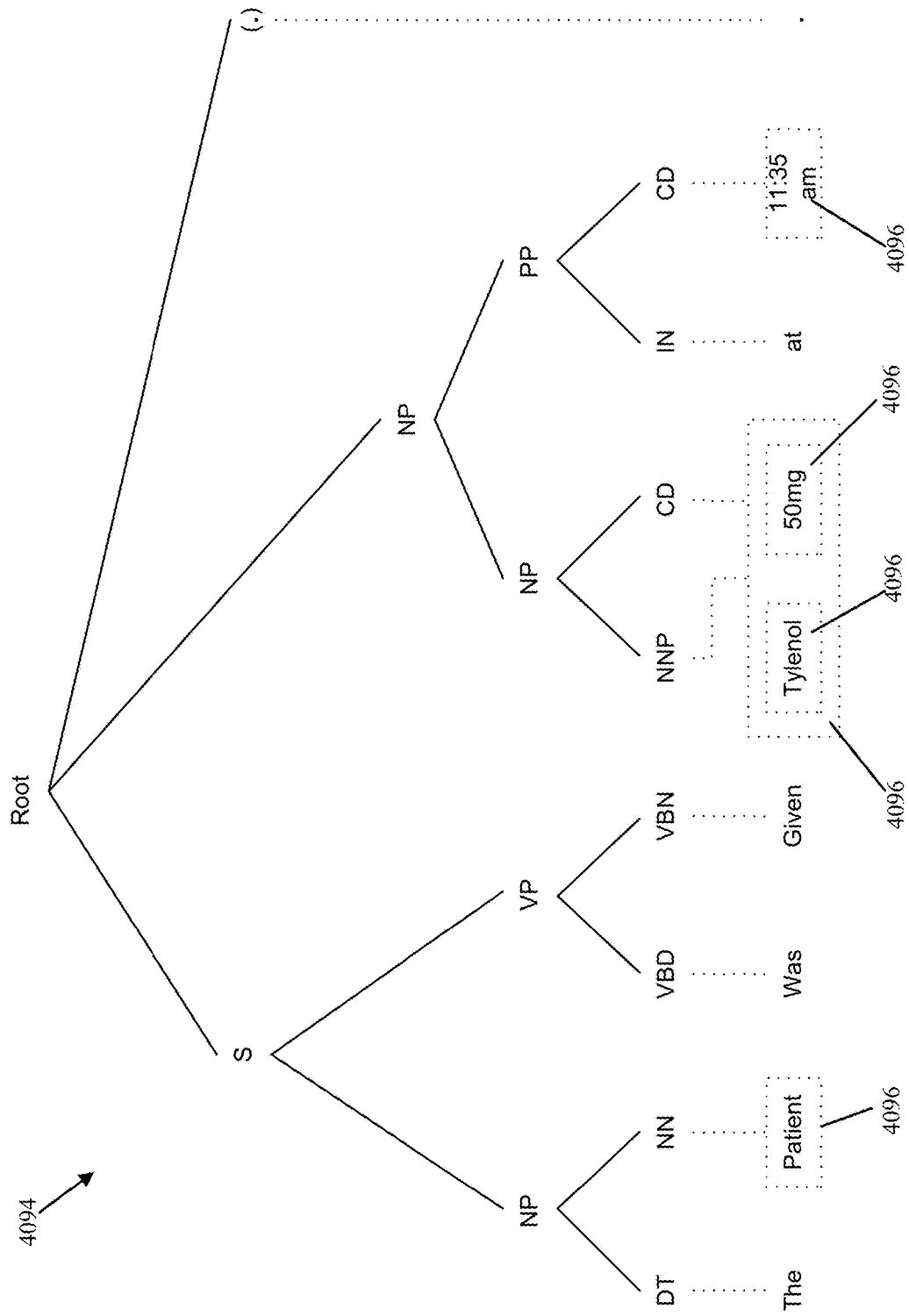
Figure 165:
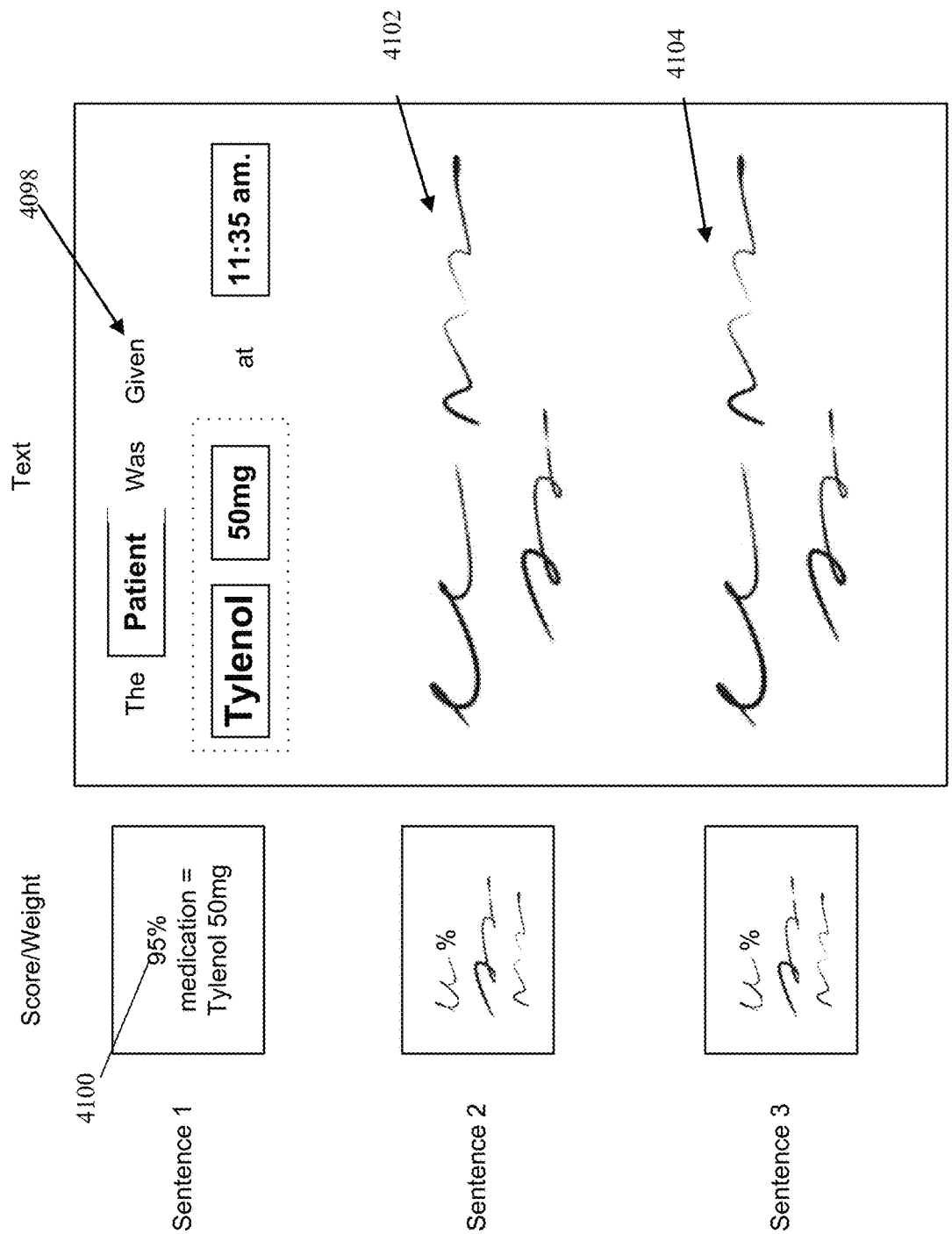
Figure 166:
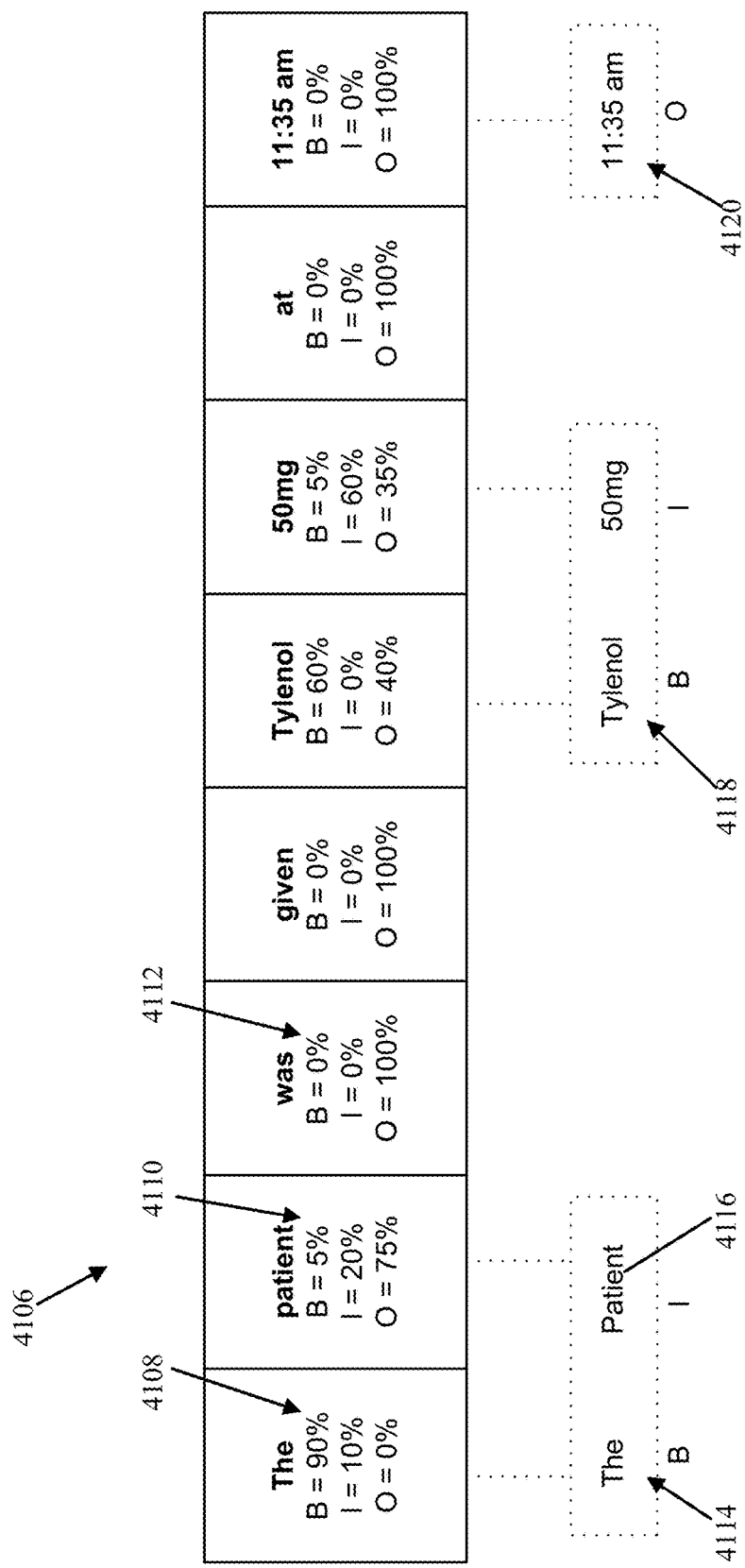
Figure 167:
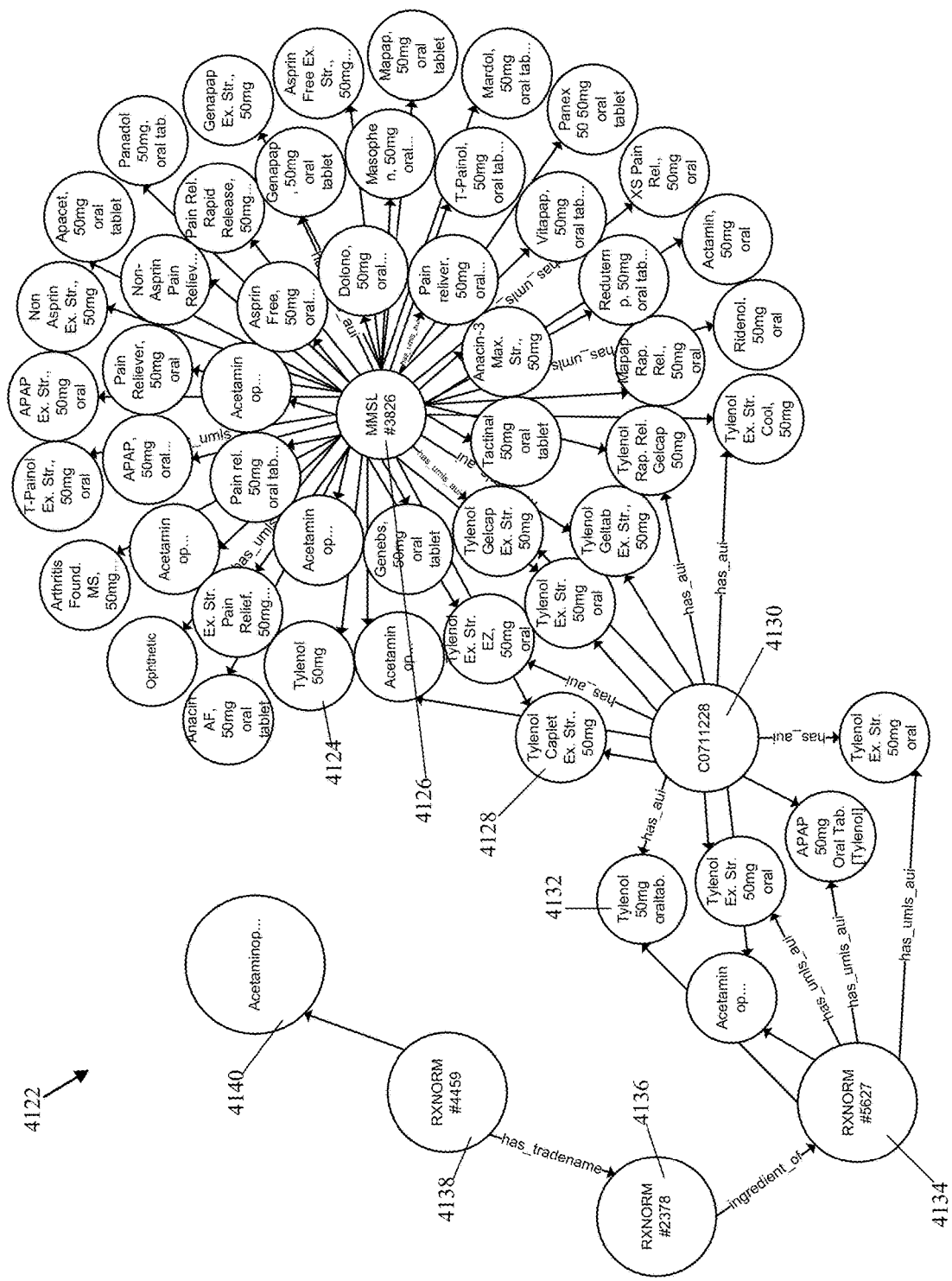
Figure 168:
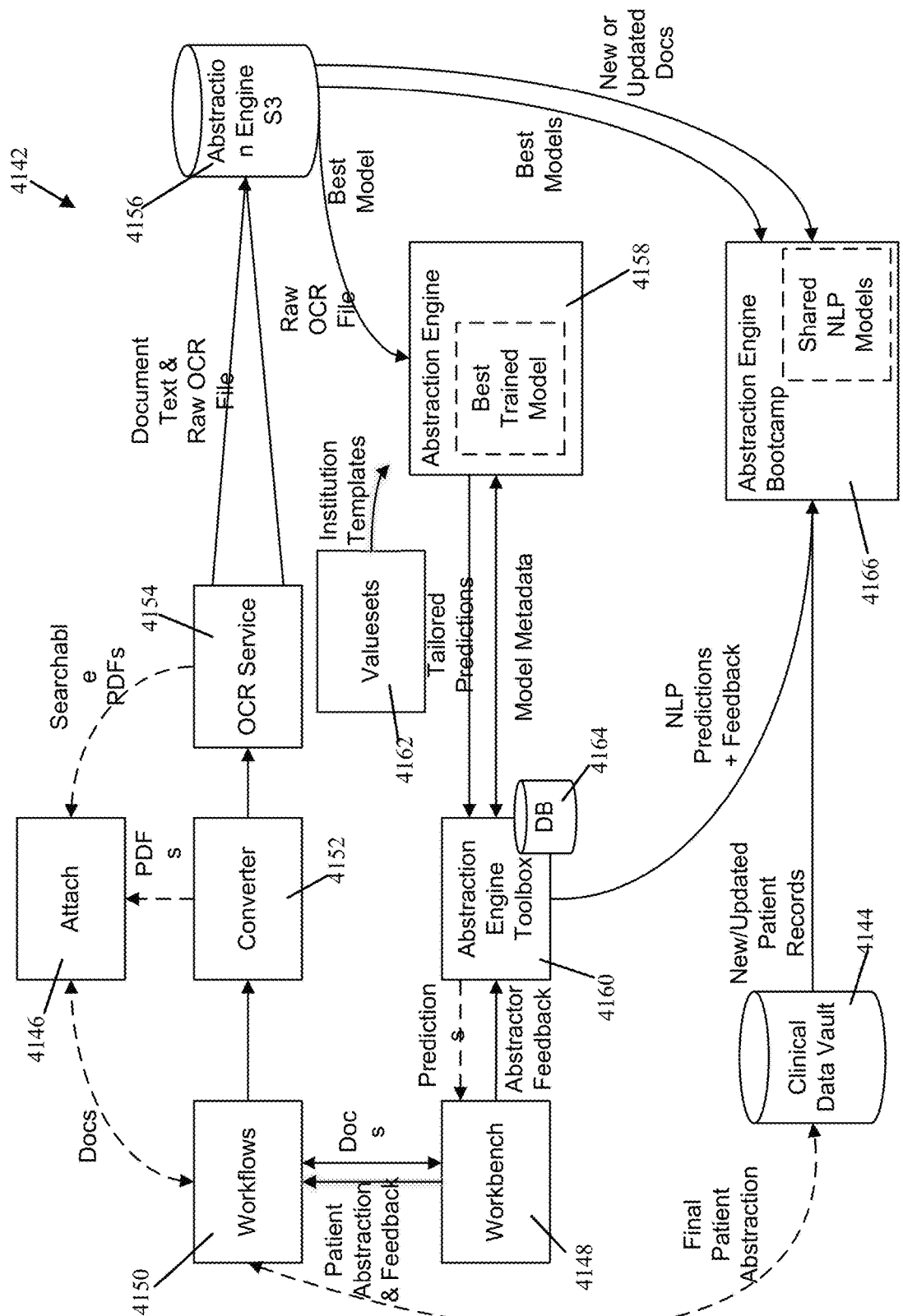
Figure 169:
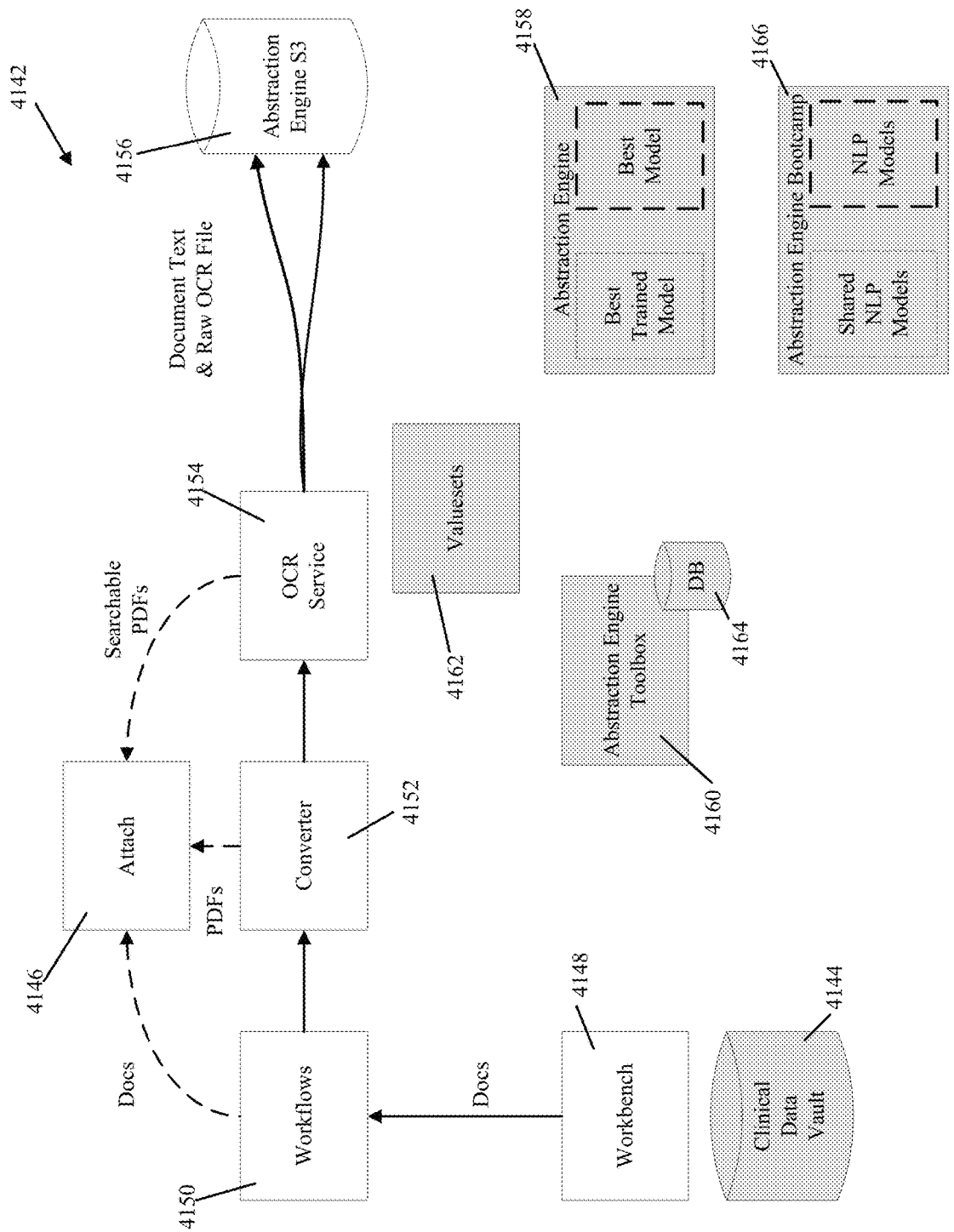
Figure 170:
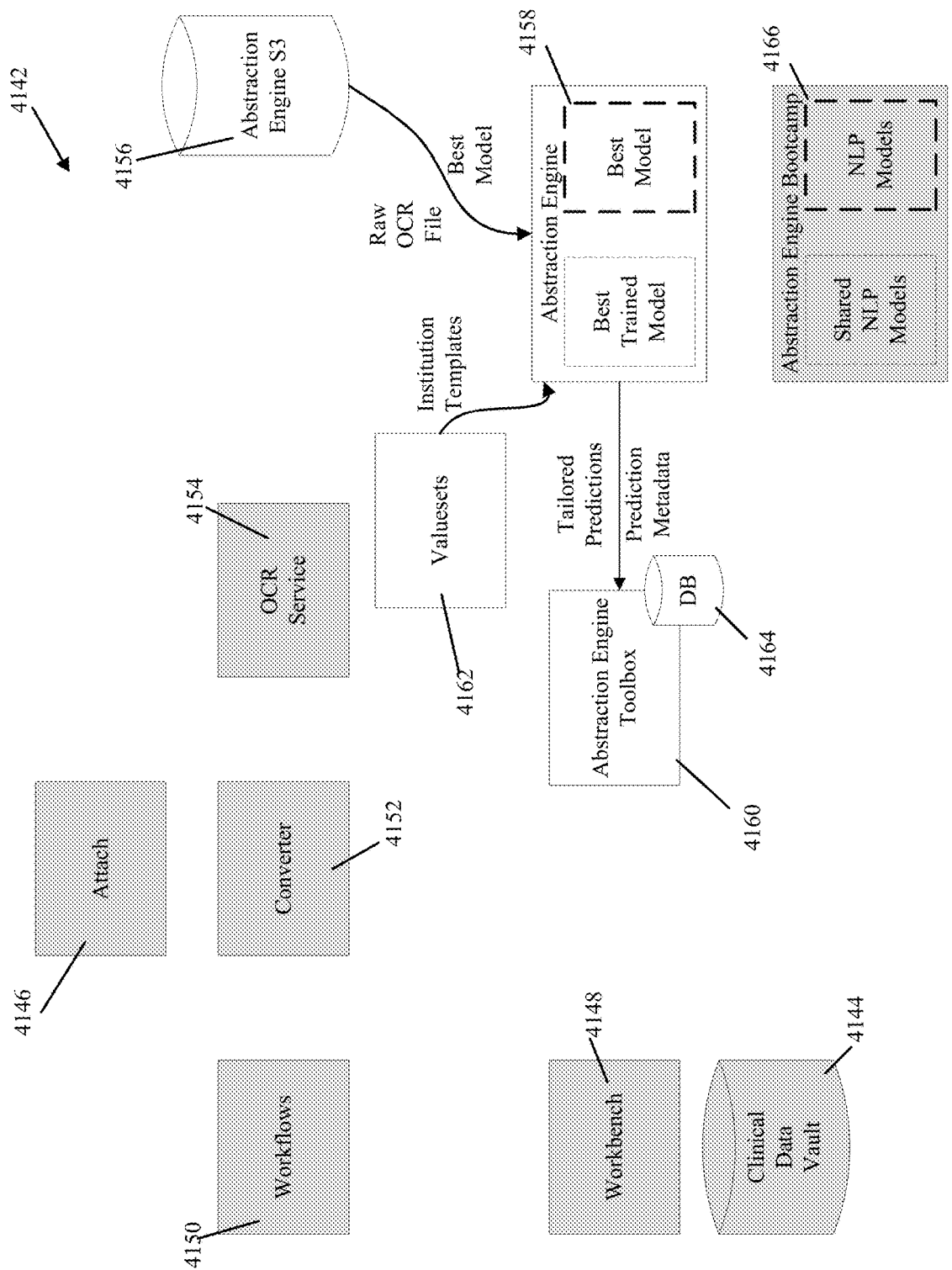
Figure 171:
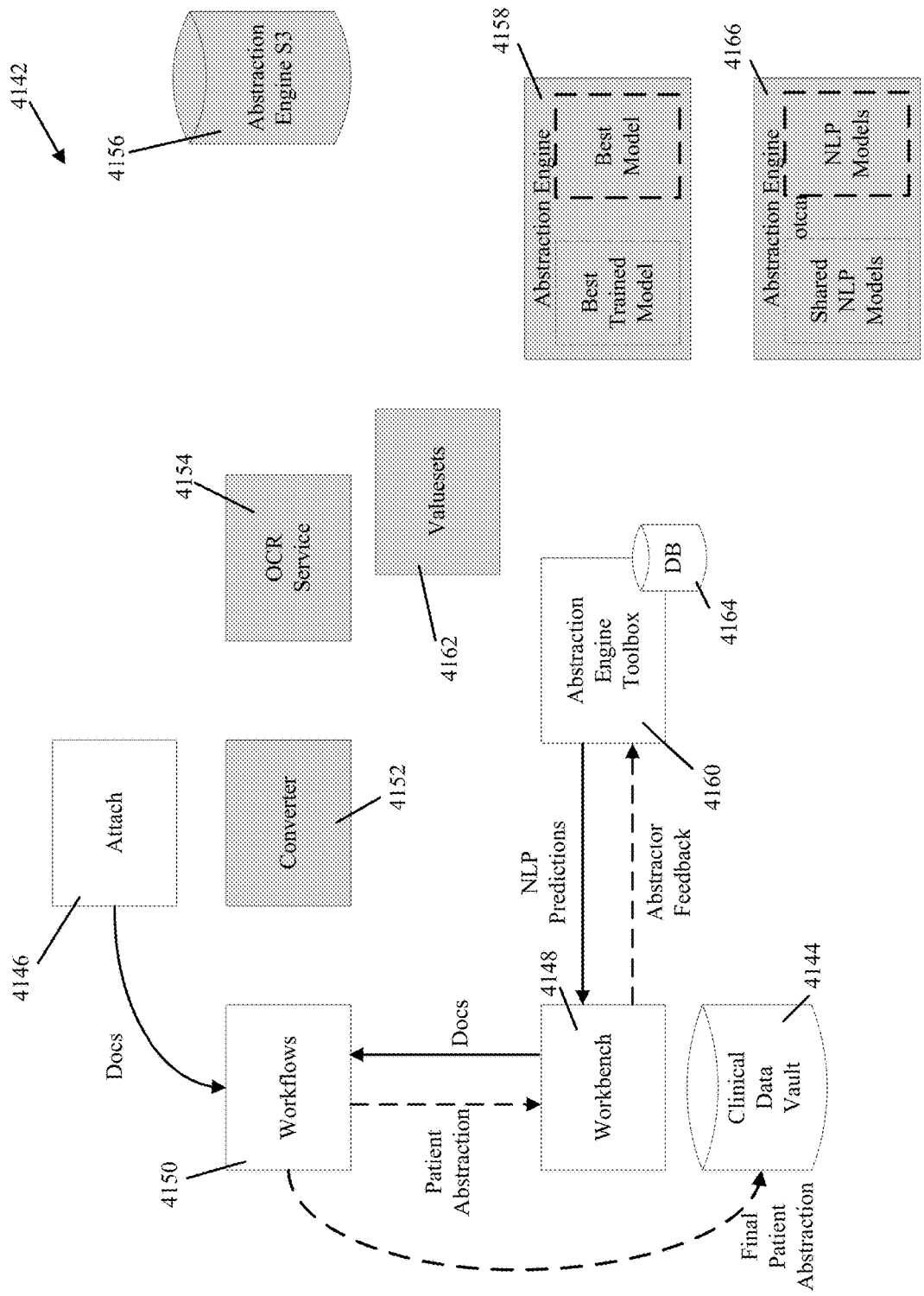
Figure 172:
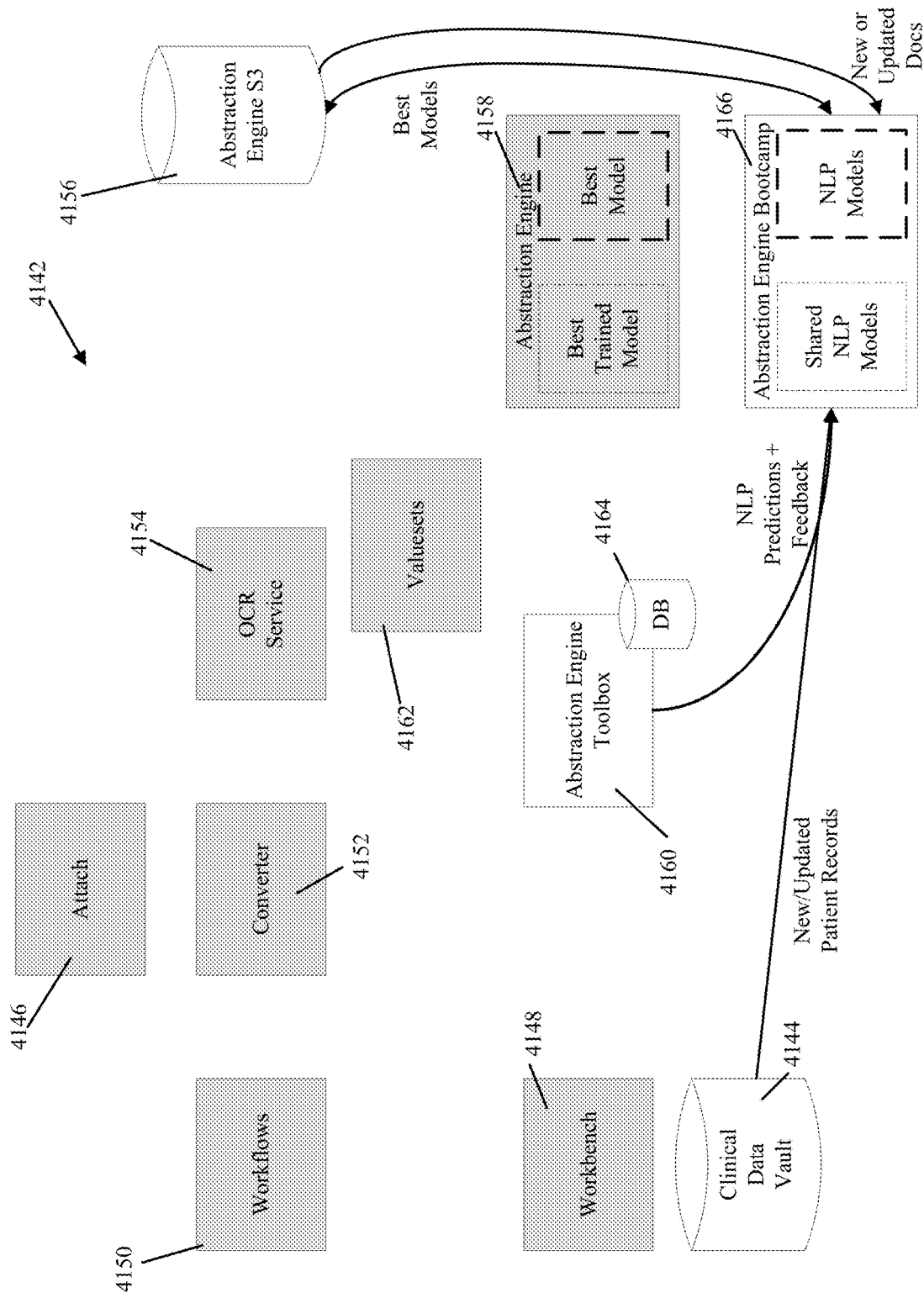
Figure 173:
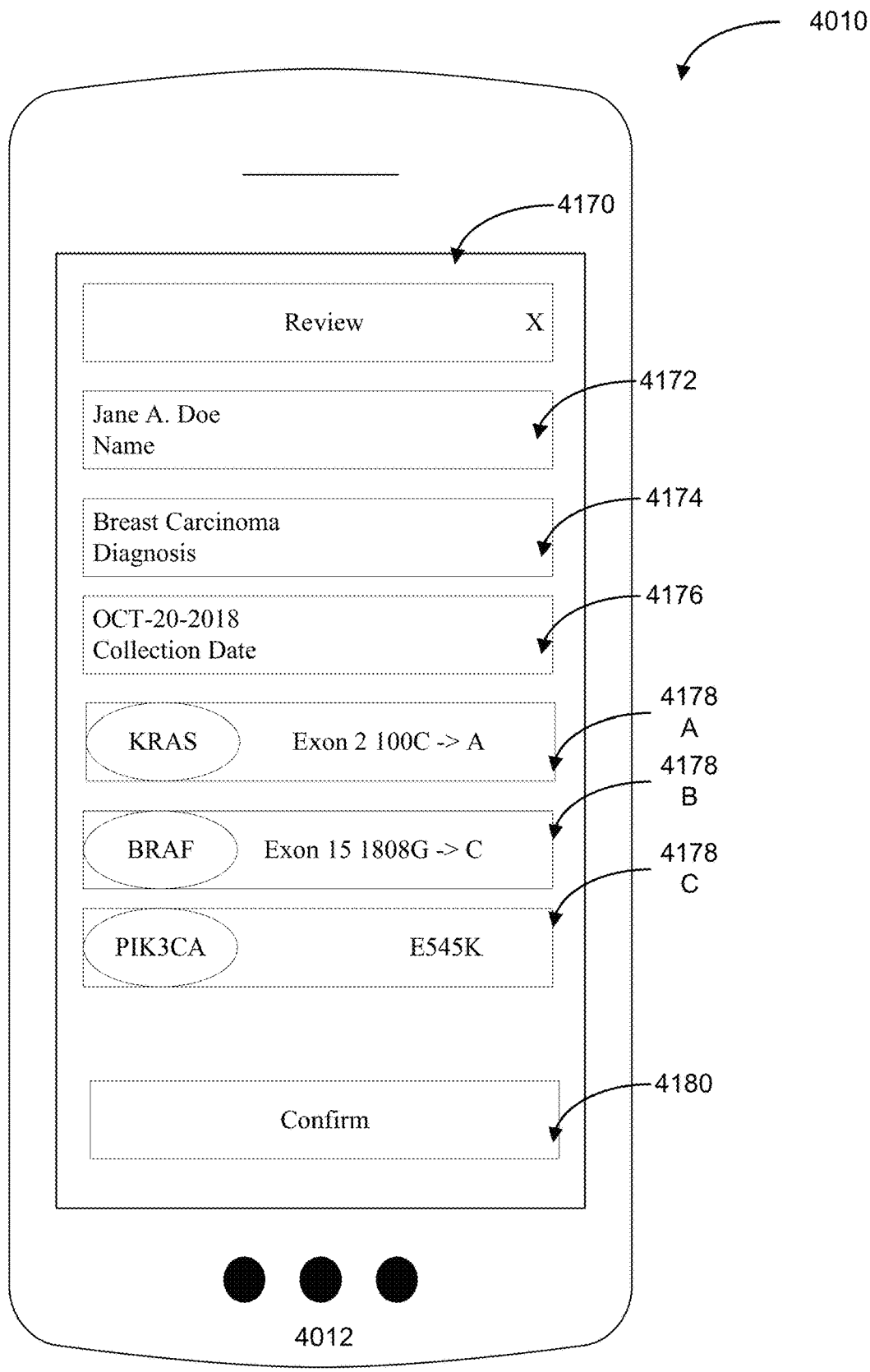
Figure 174:
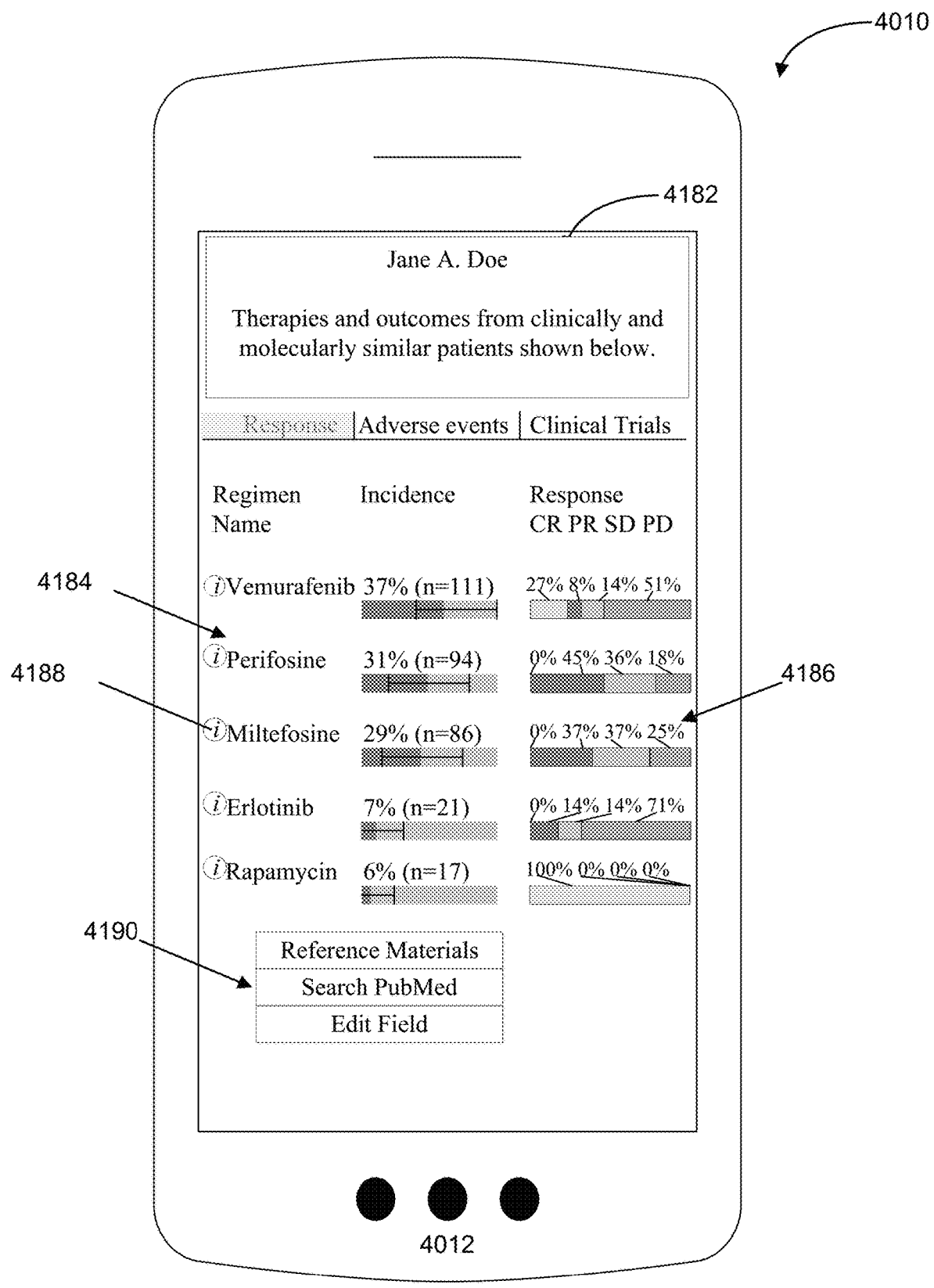
Figure 175:
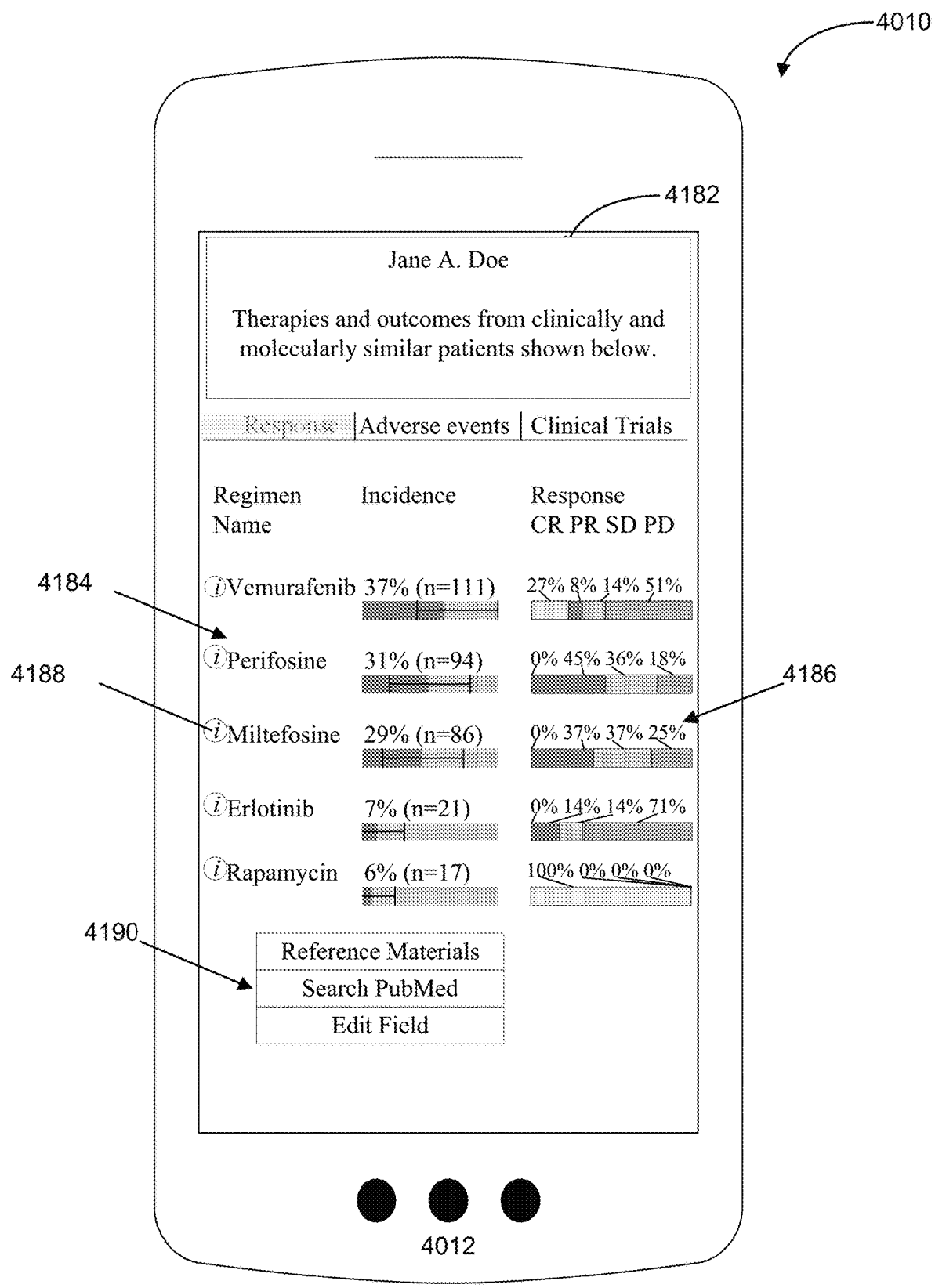
Figure 176:
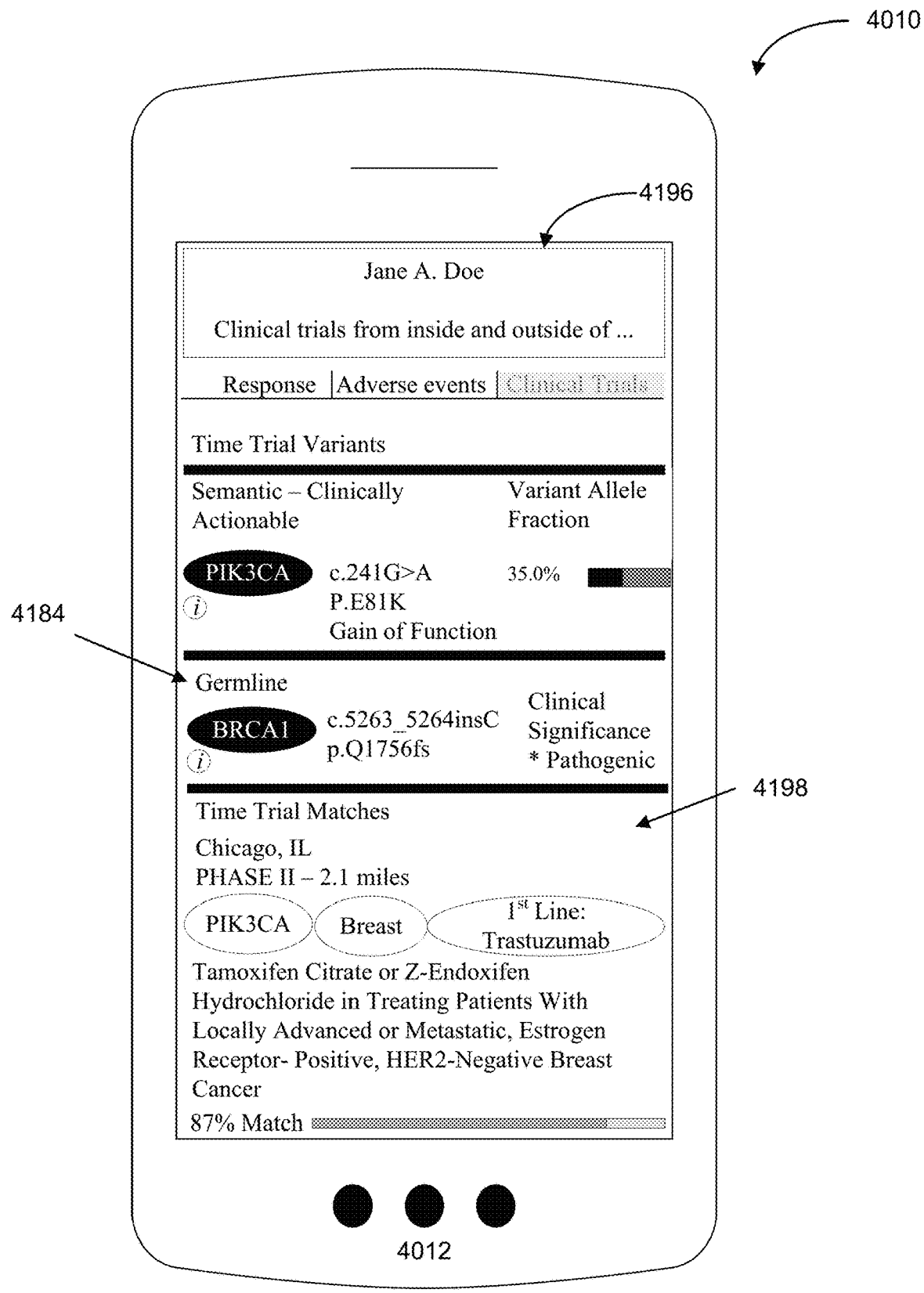
Figure 177:
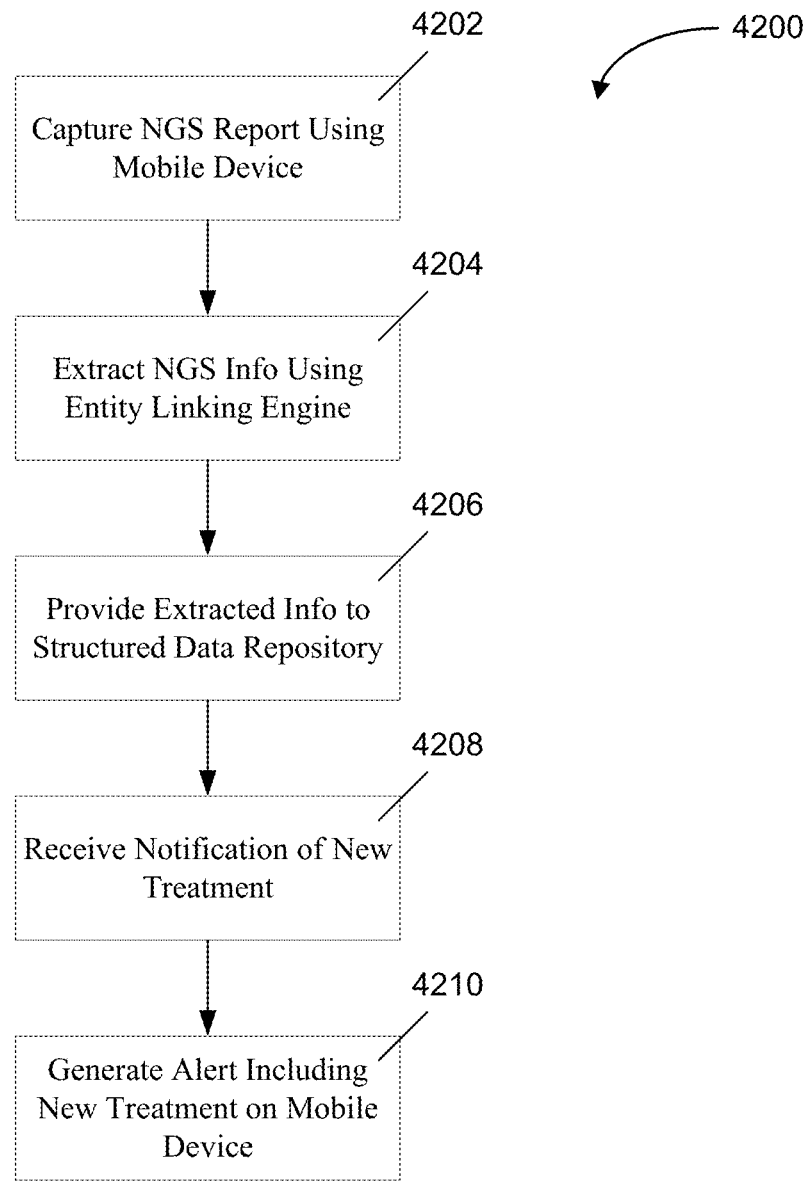
Figure 178:
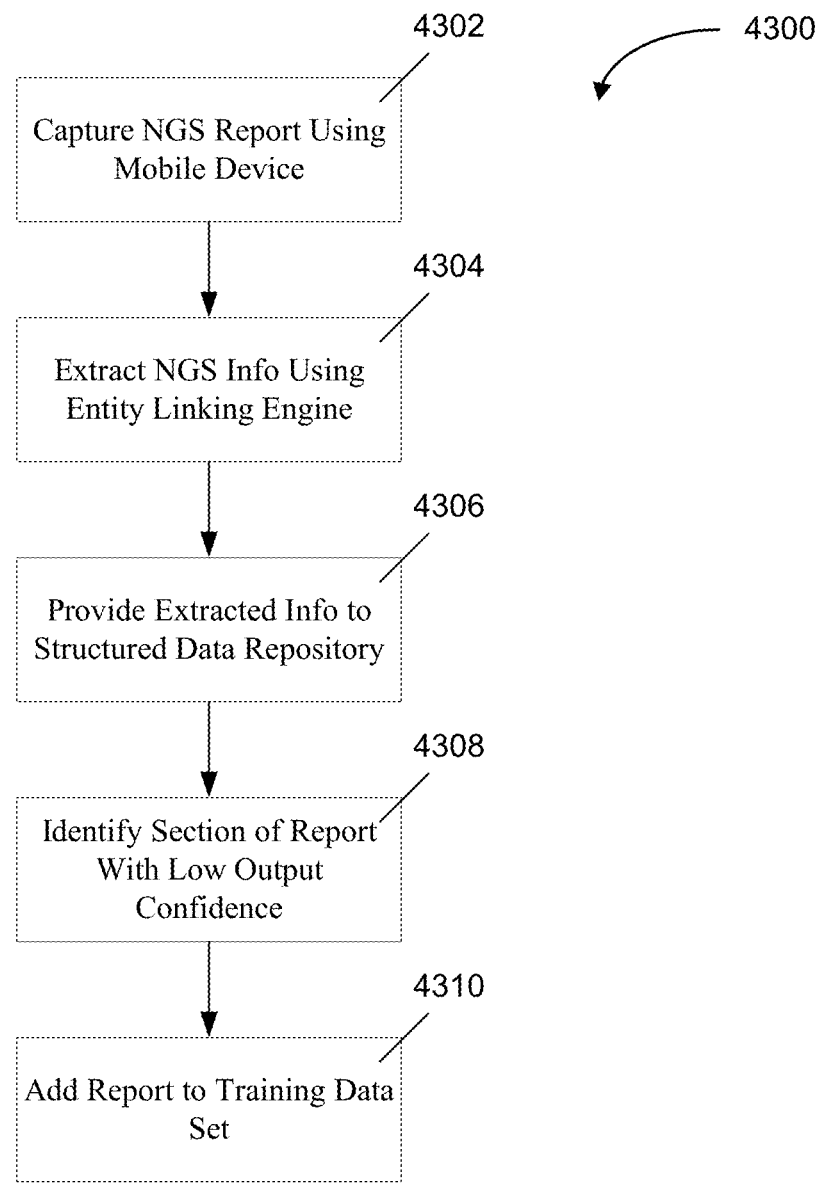
Figure 179:
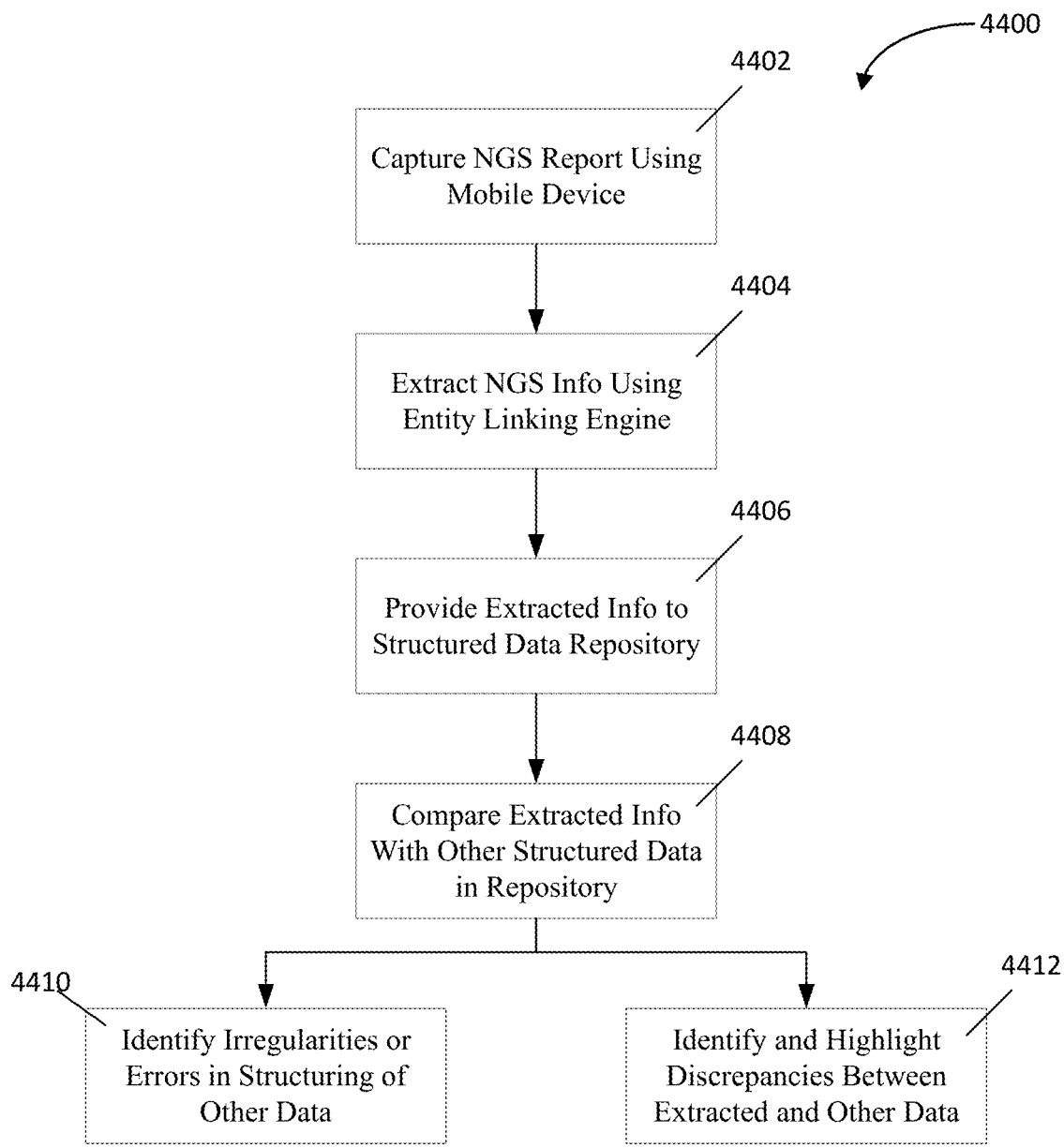
Figure 180:
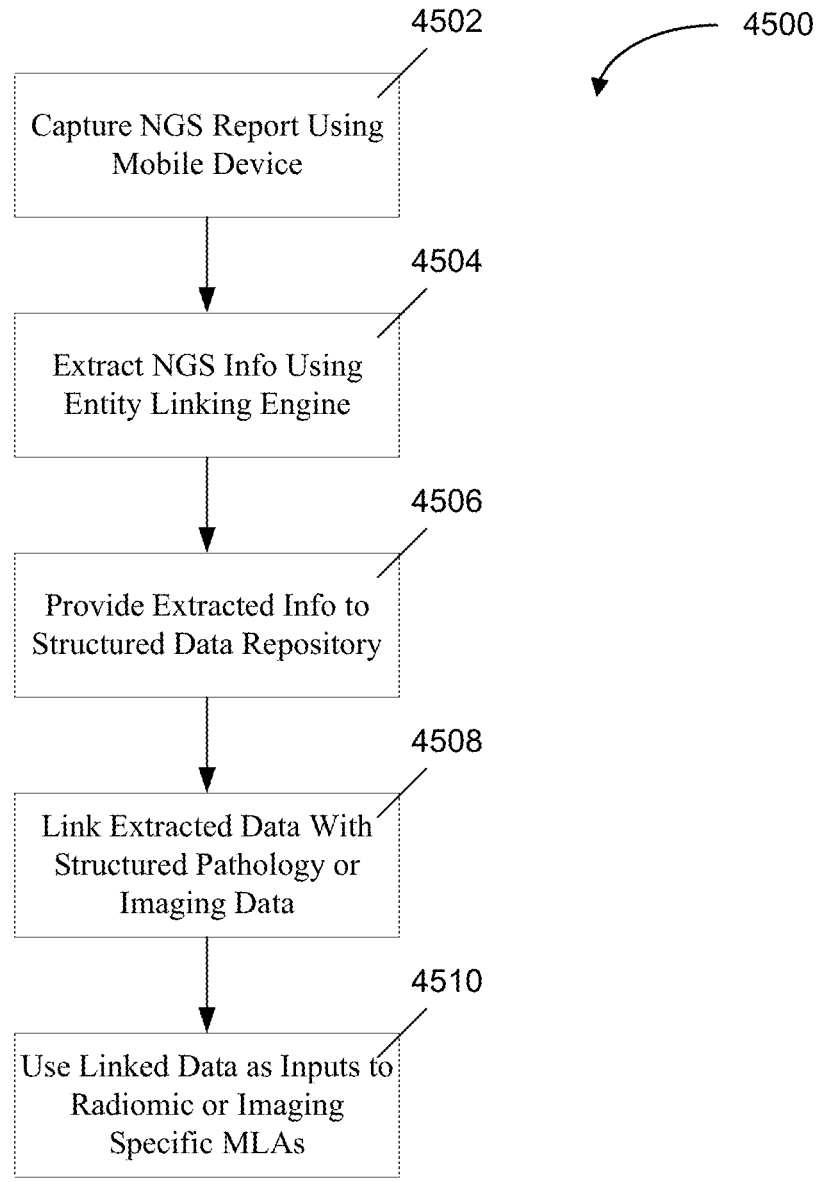
Figure 181:
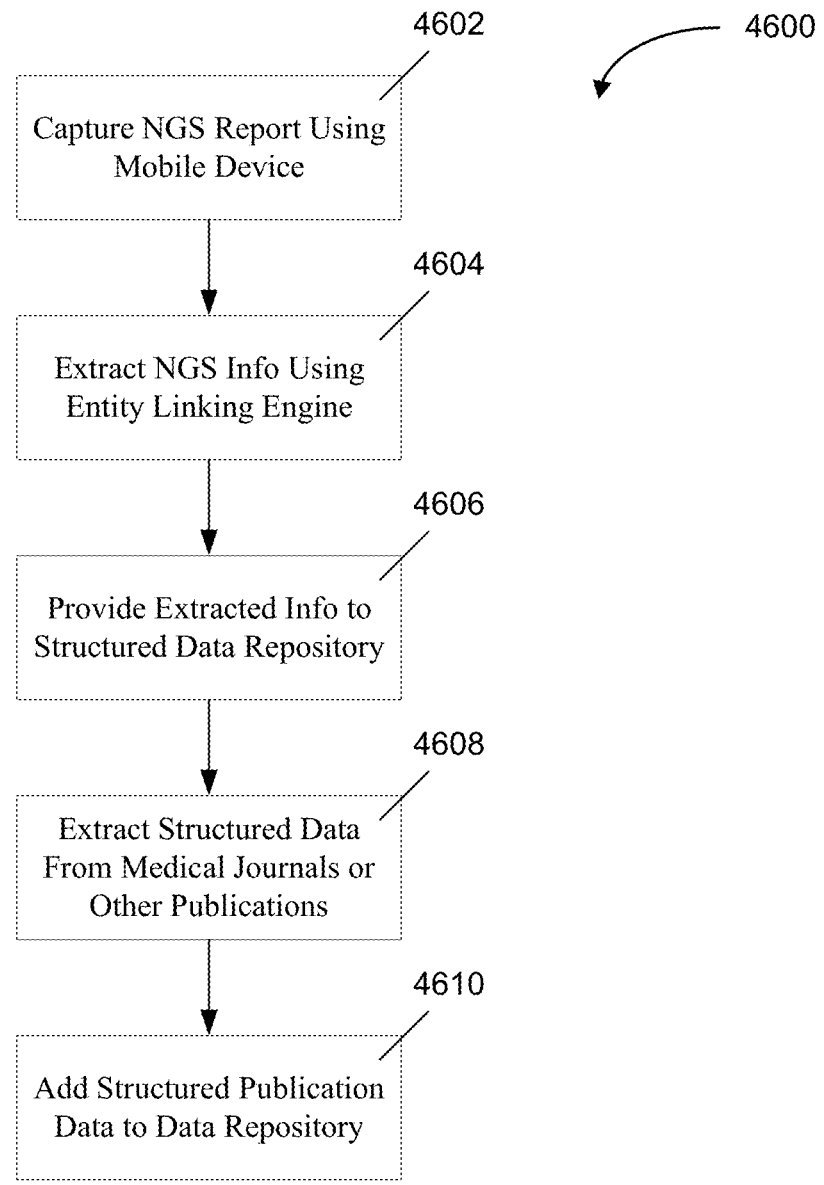
Figure 182:
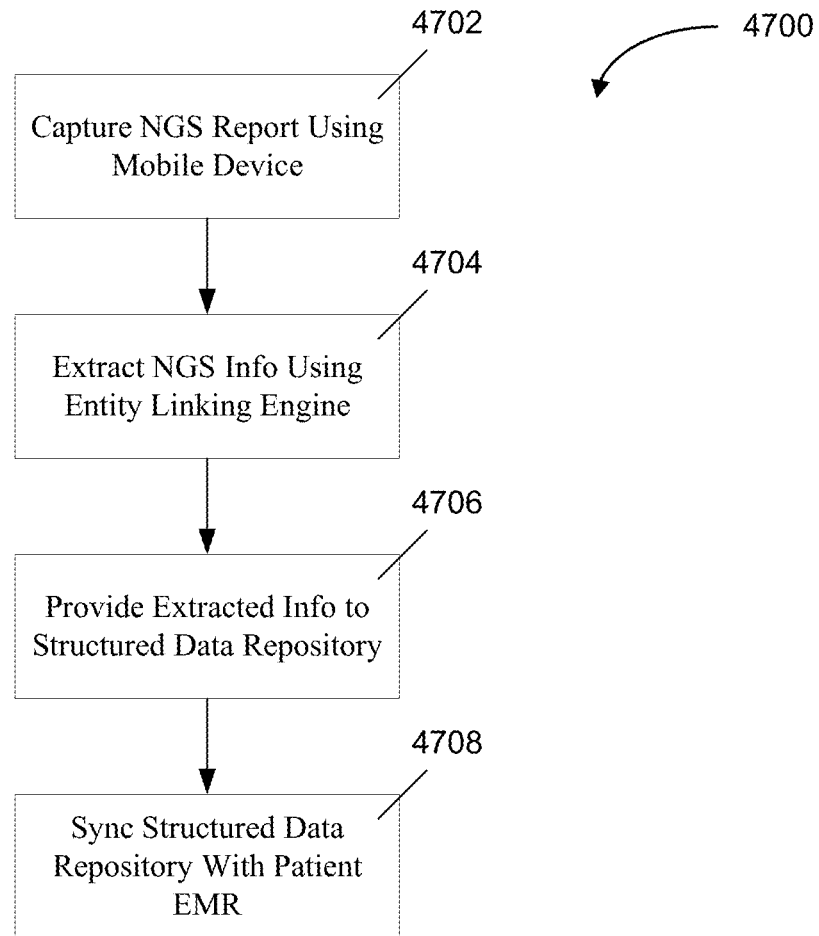
Figure 183:
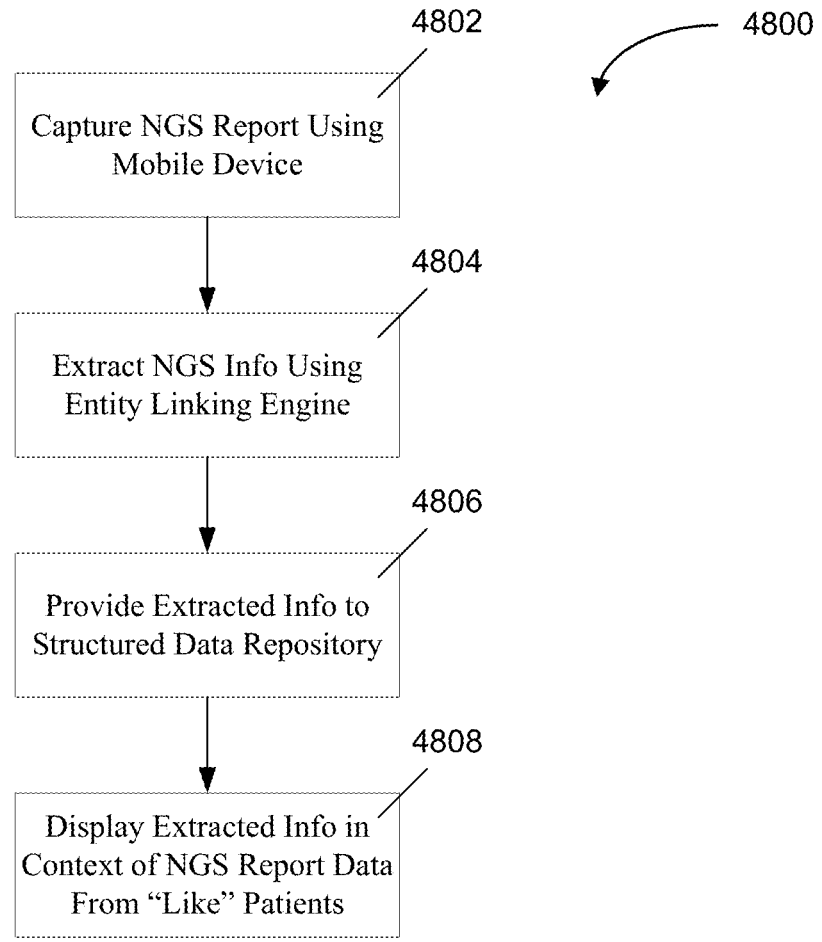
Figure 184:
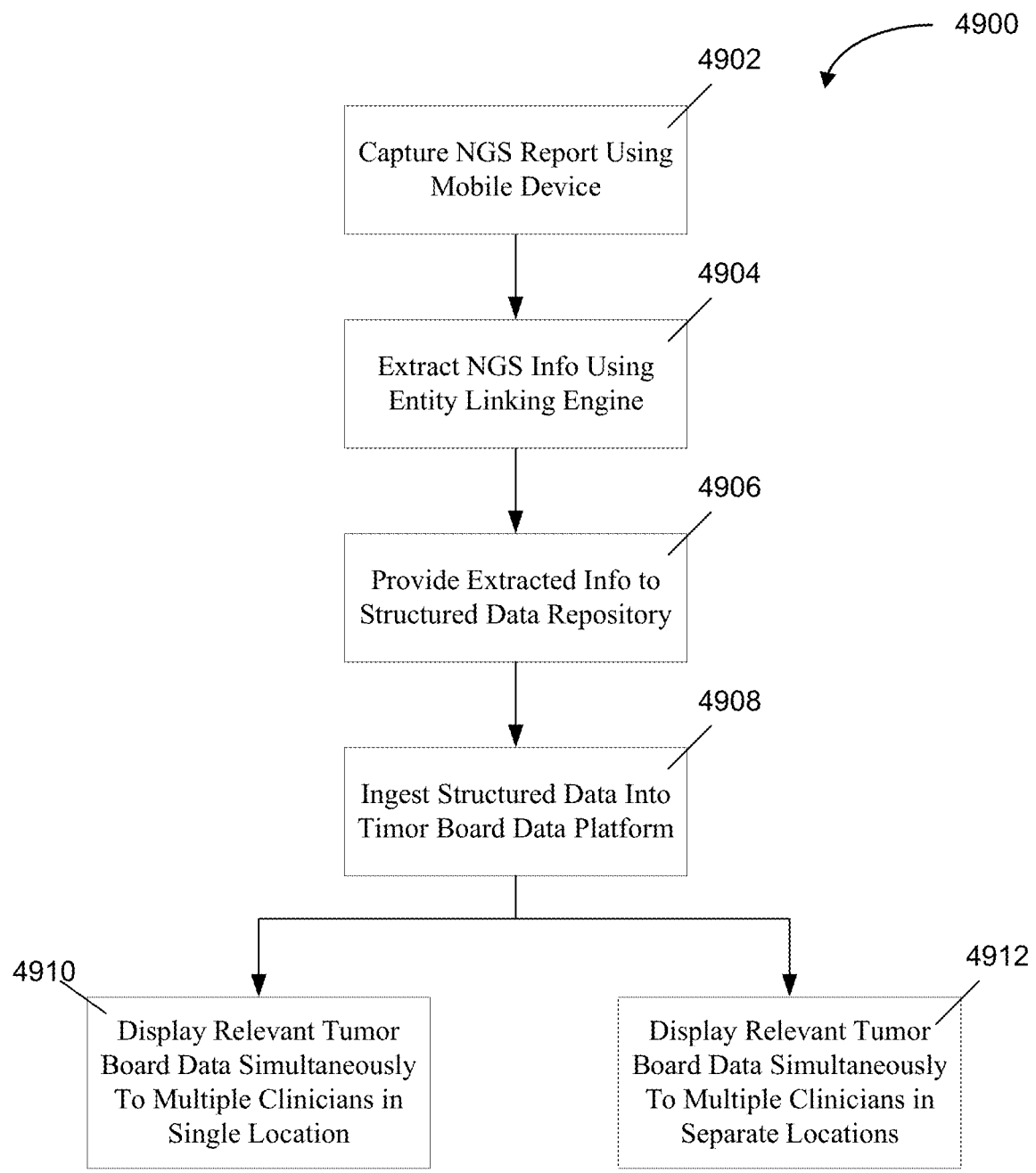
Figure 185:
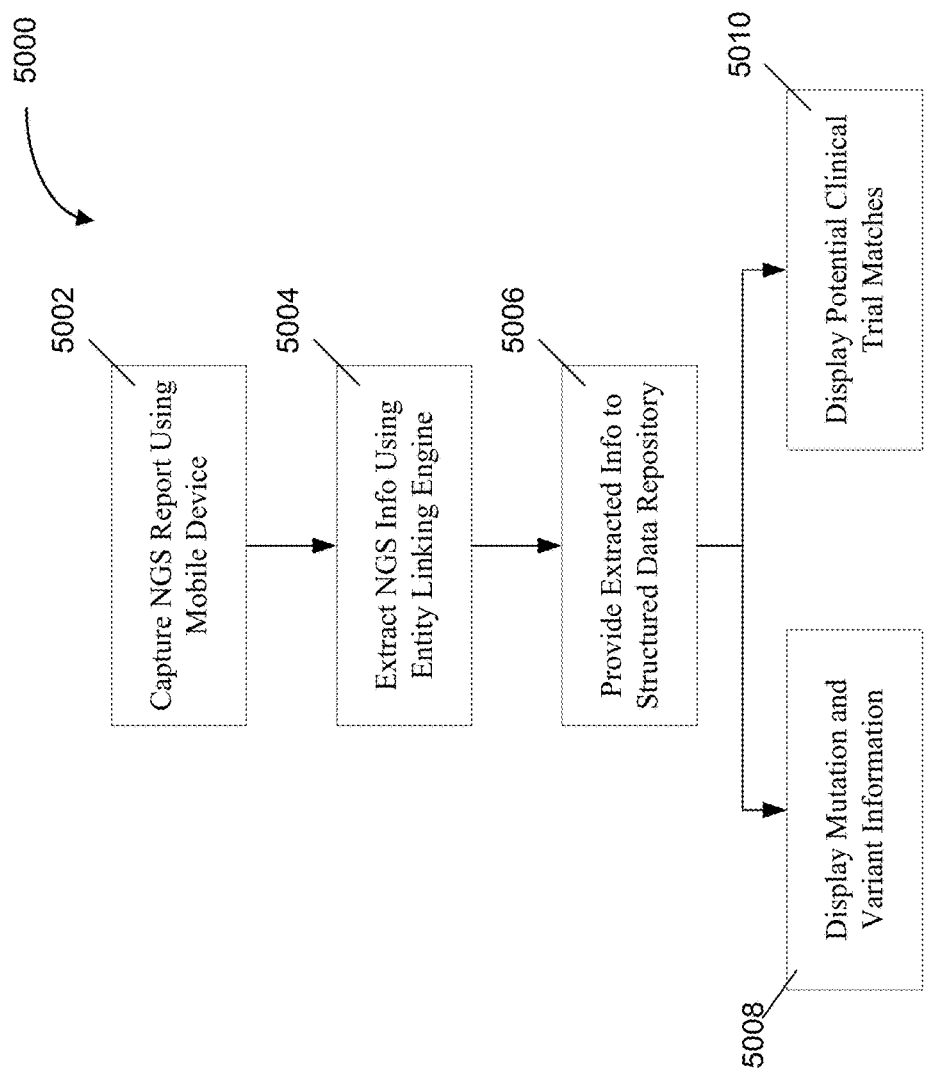
Figure 186:
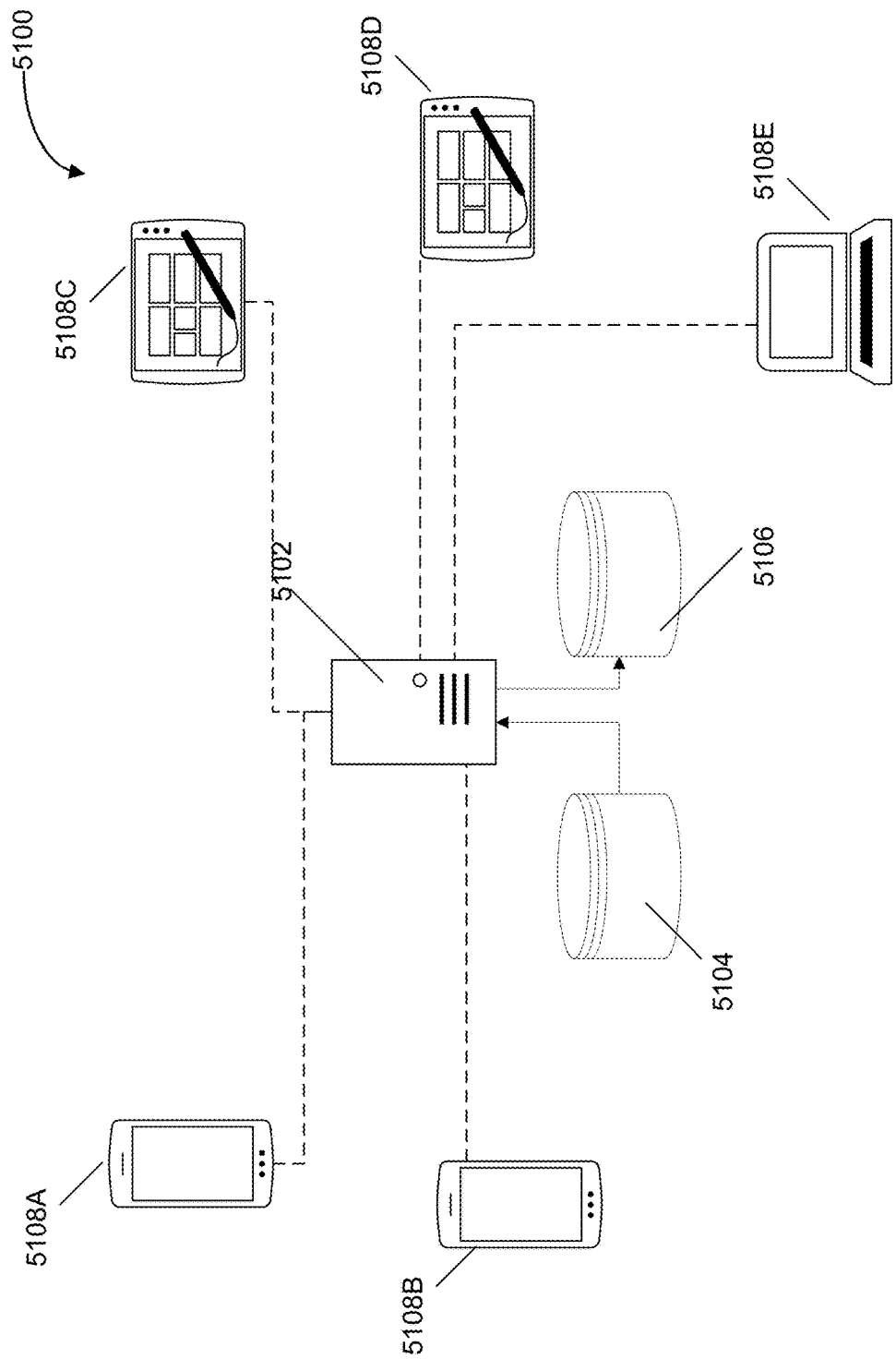
Figure 187A:
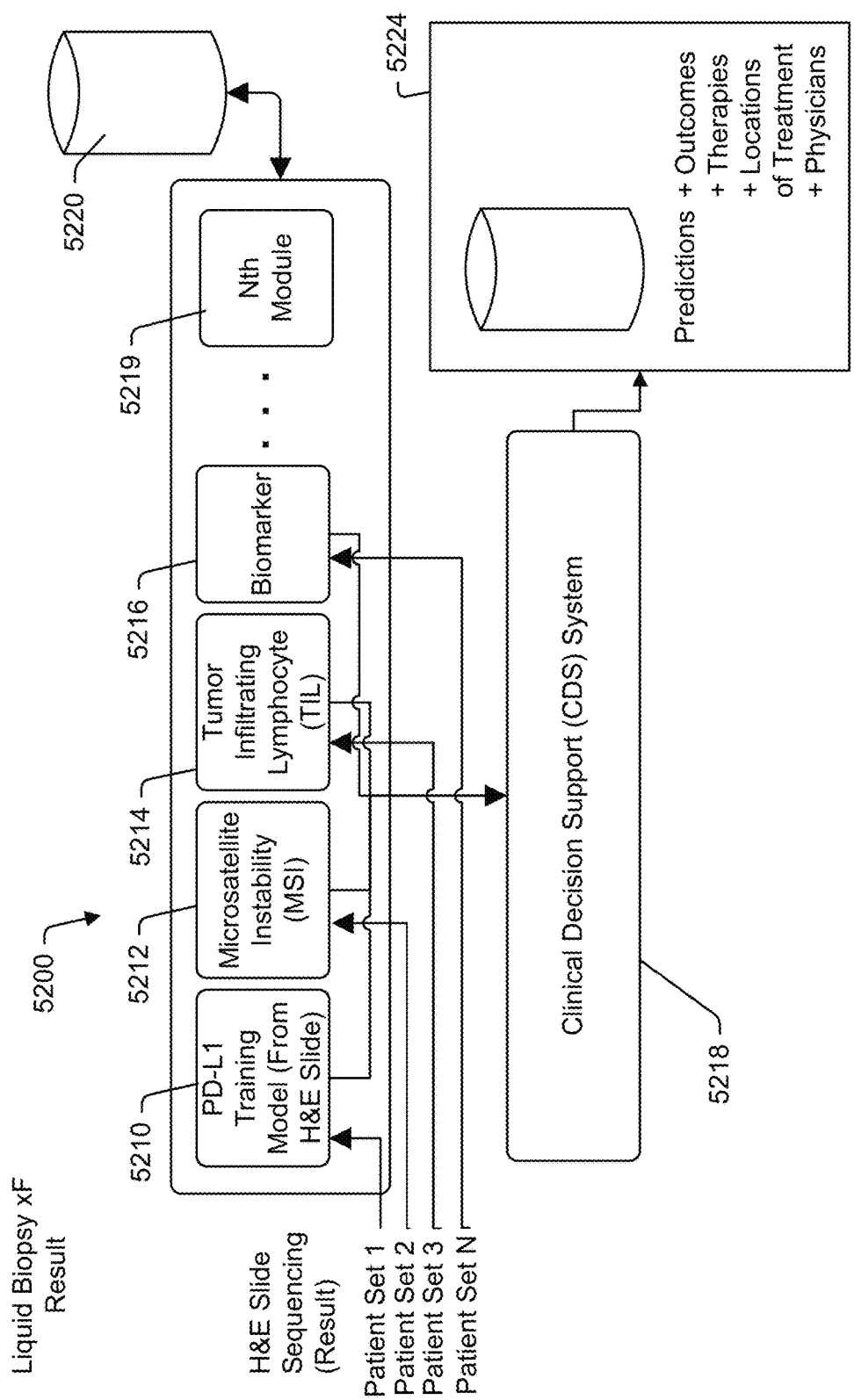
Figure 187B:
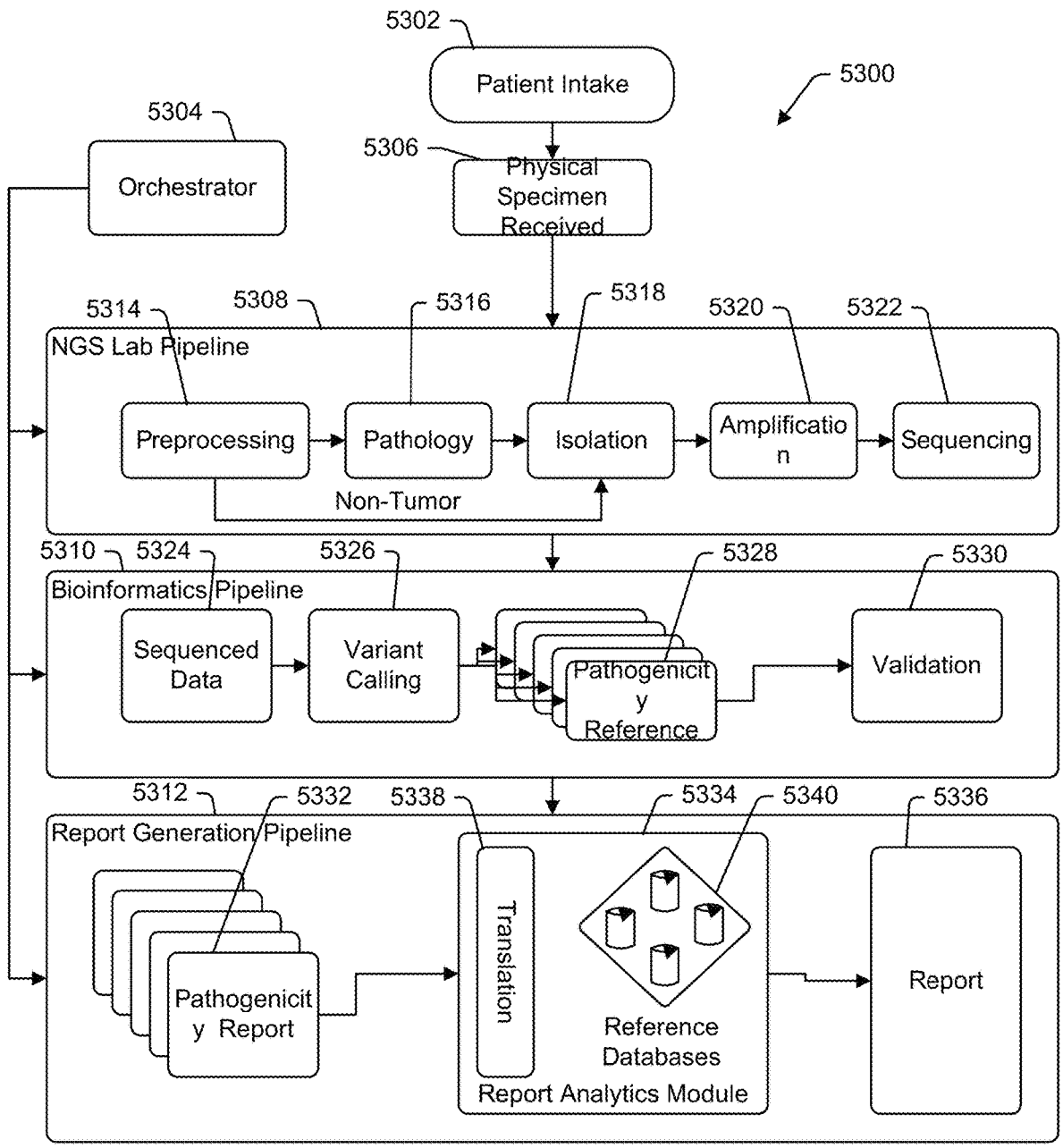
Figure 187C:
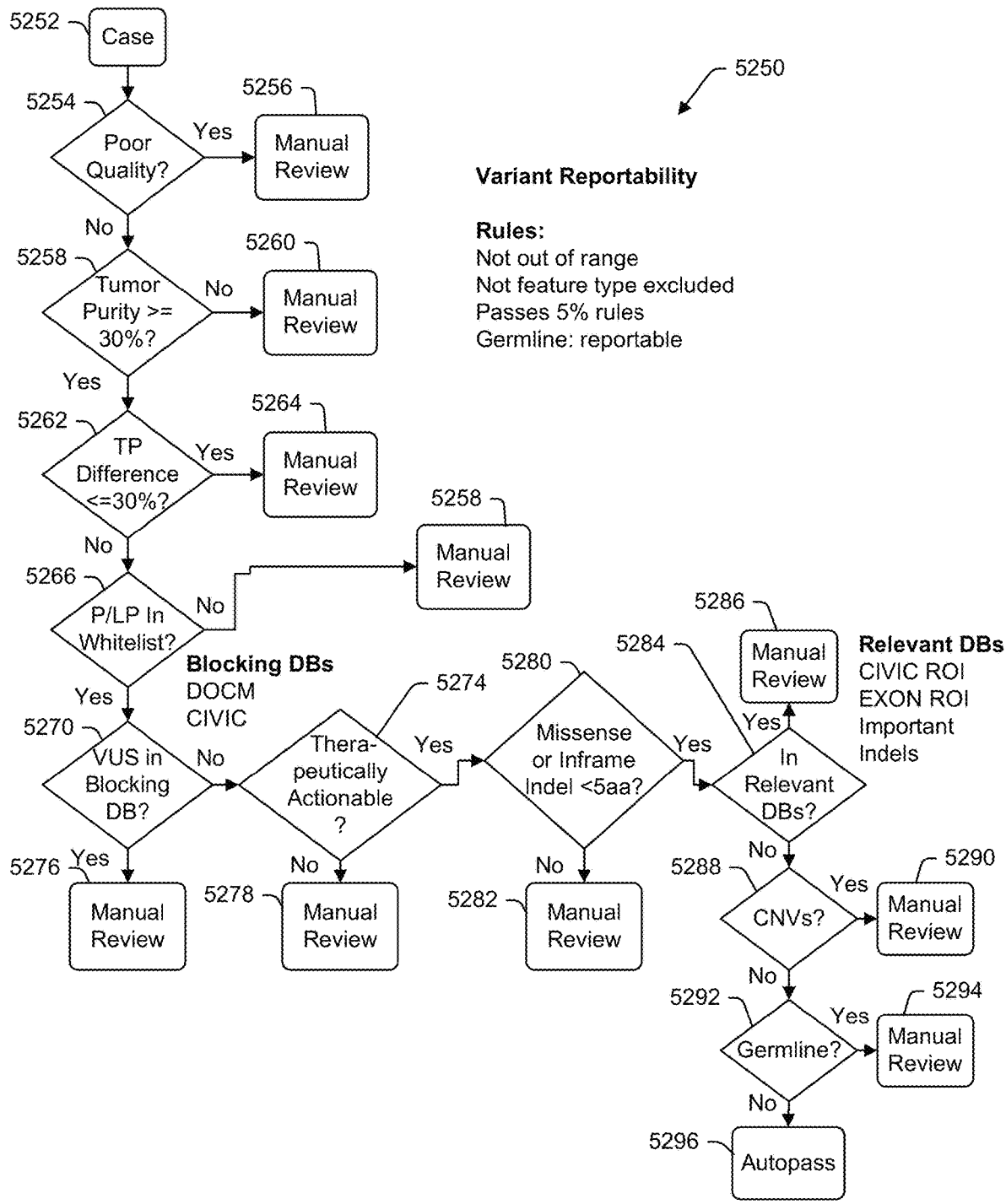
Figure 188:
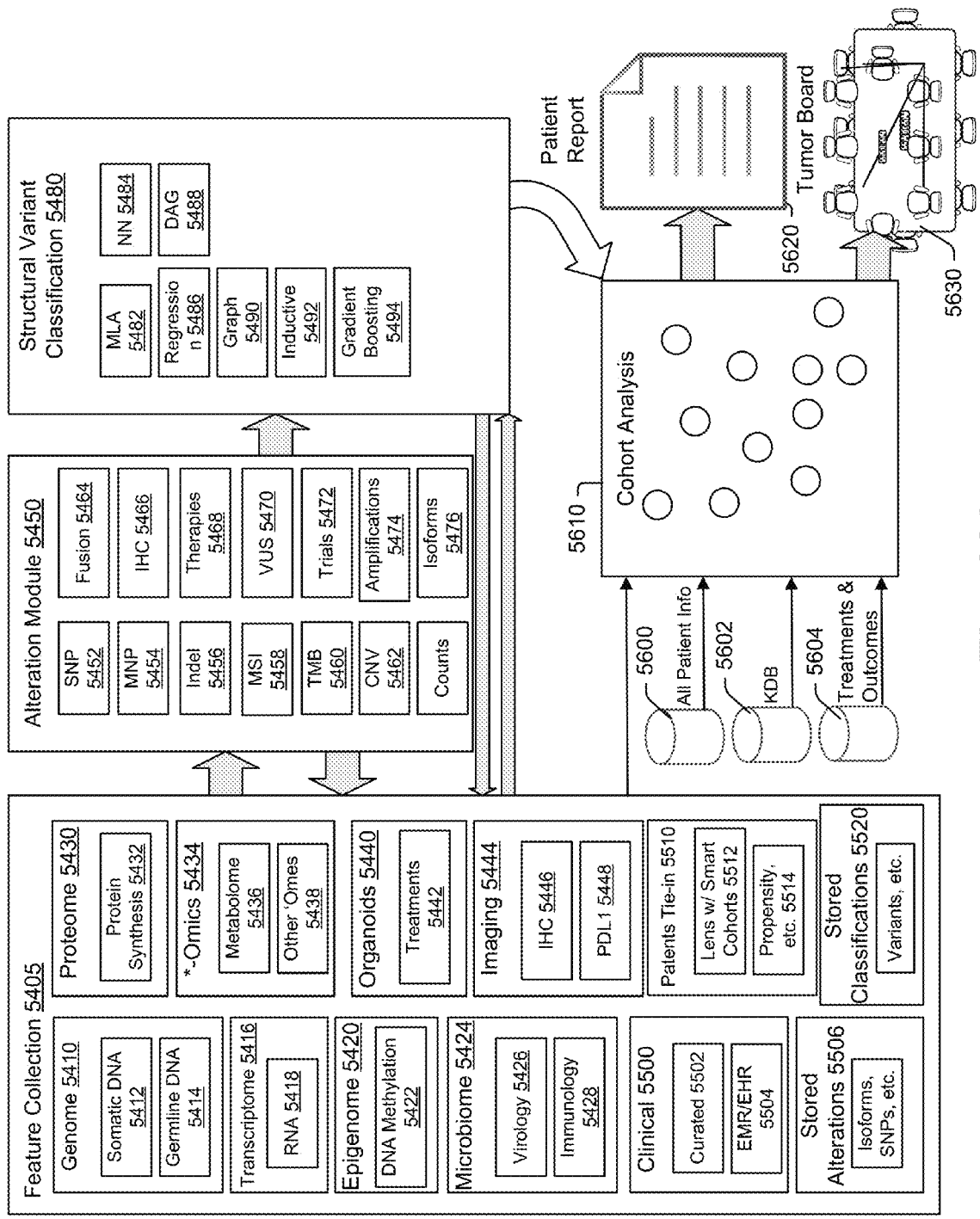
Figure 189:
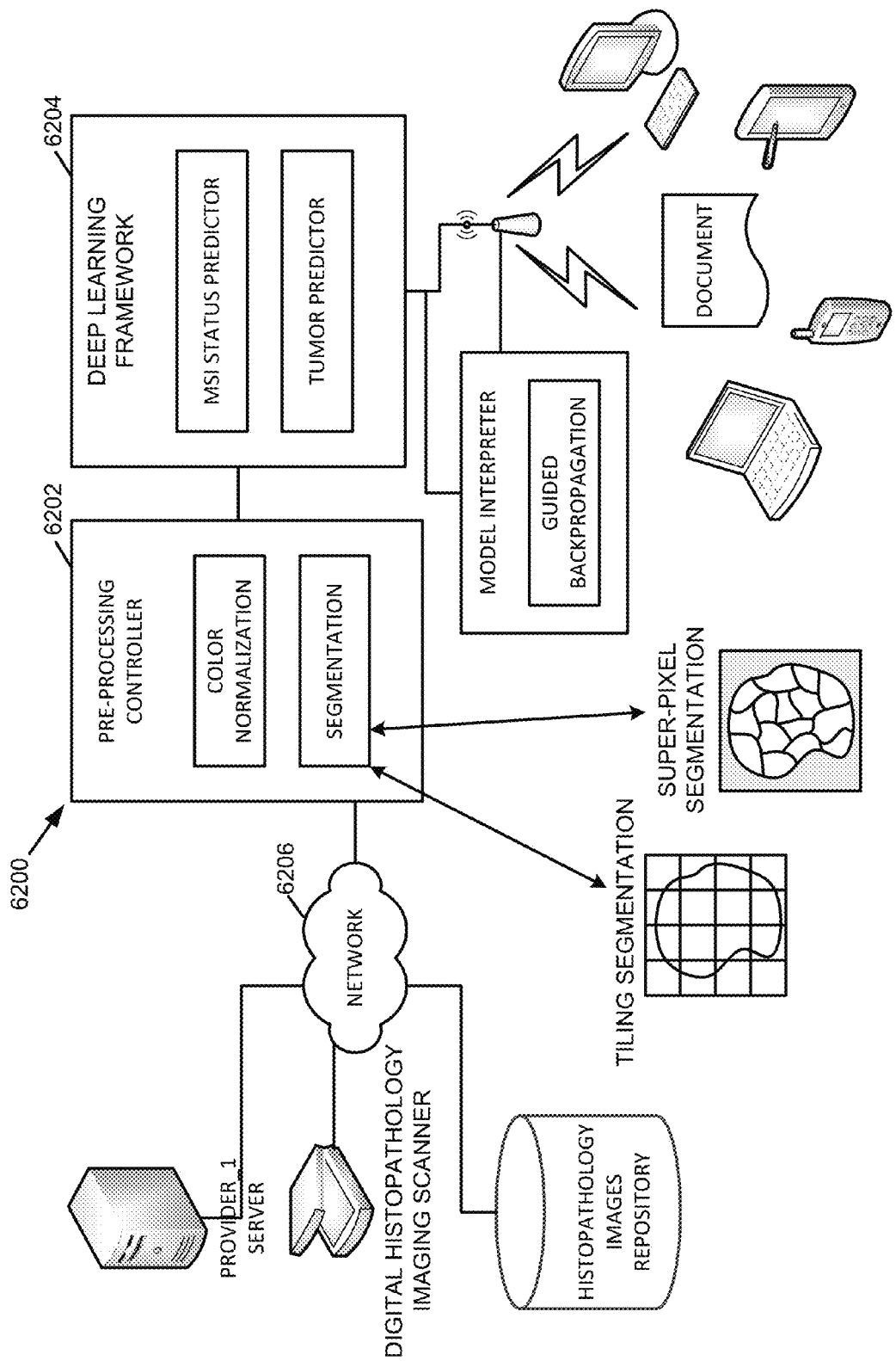
Figure 190:
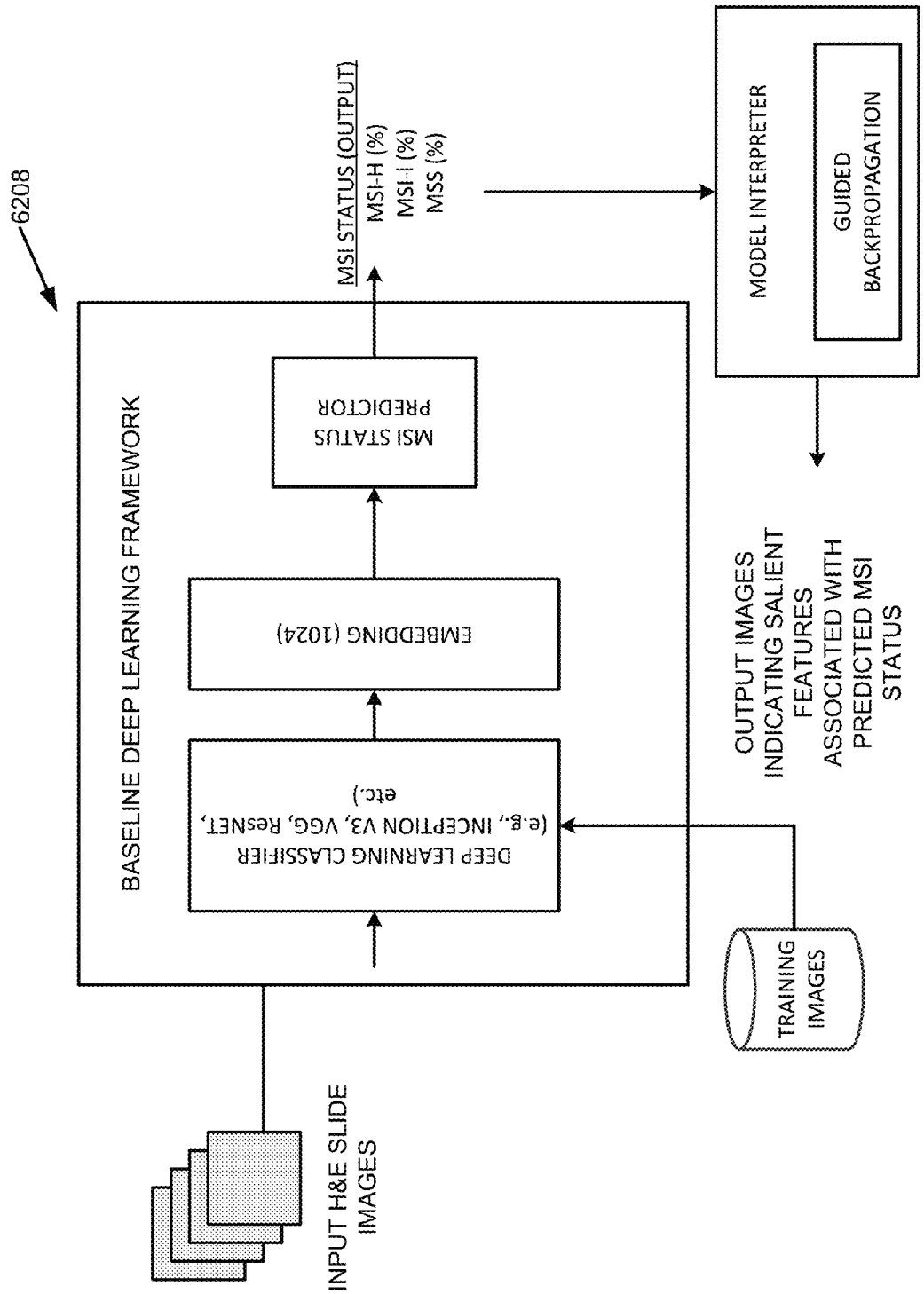
Figure 191:
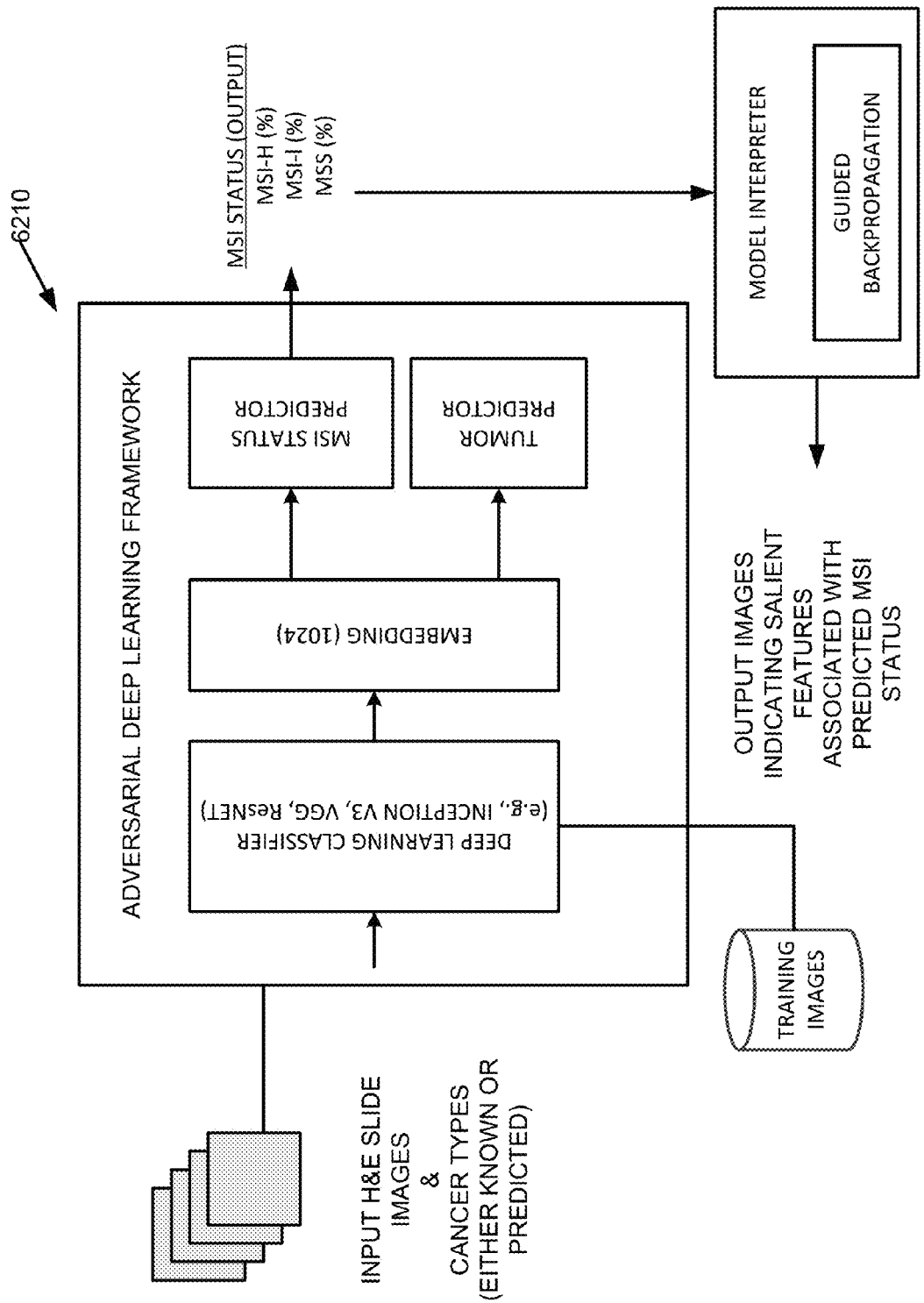
Figure 192:
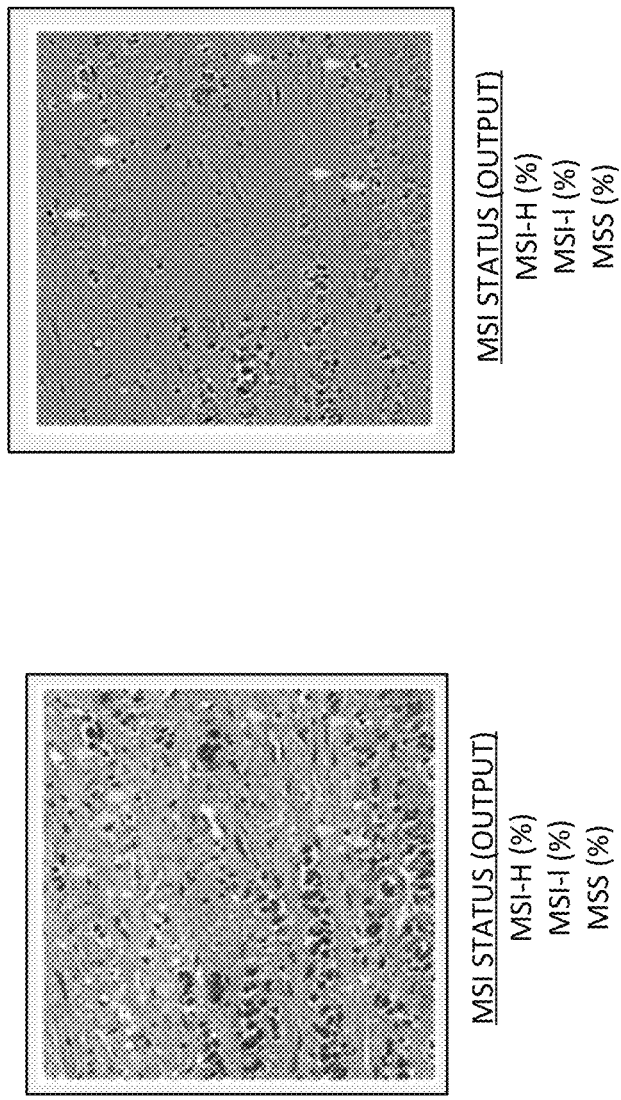
Figure 193:
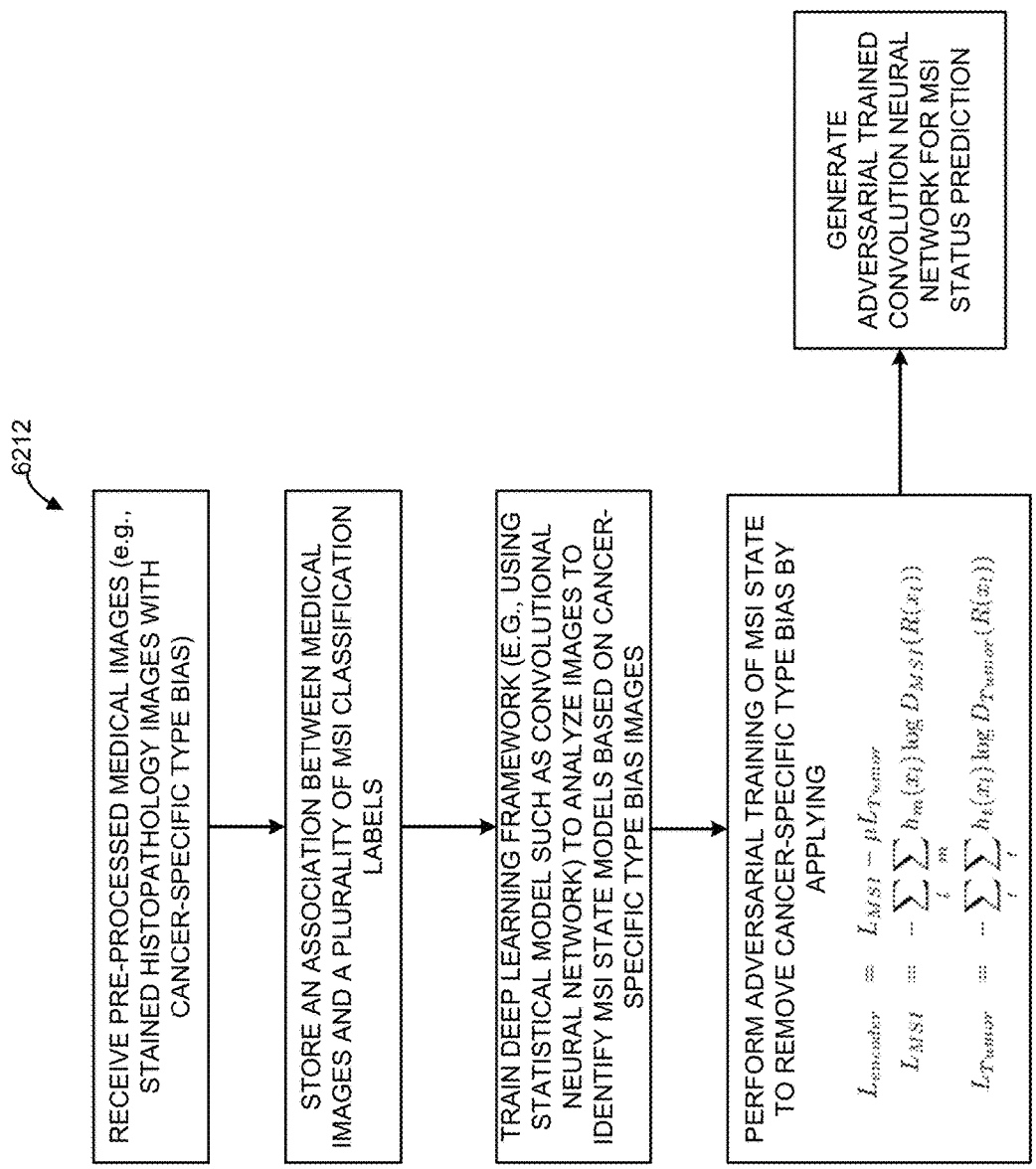
Figure 194:
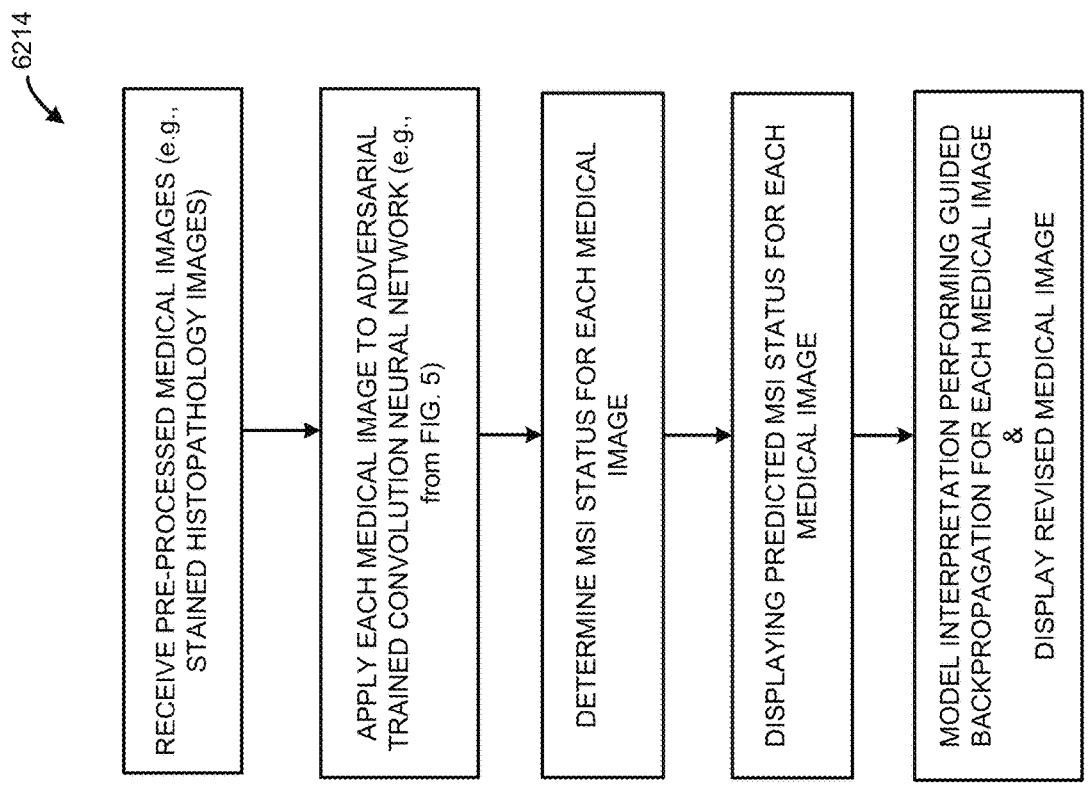
Figures 195A, 195B:
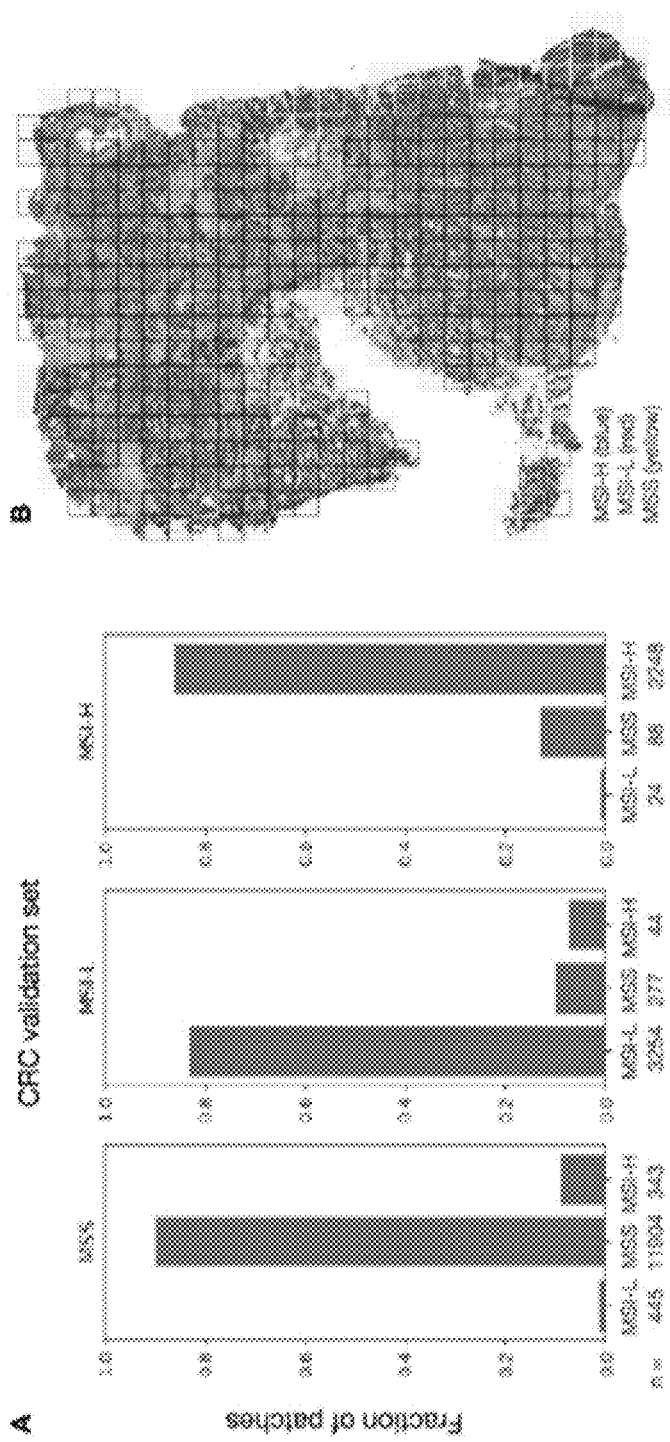

FIG. 125 is another image of an example graphical user interface (GUI), according to aspects of the present disclosure;

FIG. 126 is another image of an example graphical user interface (GUI), according to aspects of the present disclosure;

FIG. 127 is another image of an example graphical user interface (GUI), according to aspects of the present disclosure;

FIG. 128 is another image of an example graphical user interface (GUI), according to aspects of the present disclosure;

FIG. 129 is another image of an example graphical user interface (GUI), according to aspects of the present disclosure;

FIG. 130 is another image of an example graphical user interface (GUI), according to aspects of the present disclosure;

Figure 131:
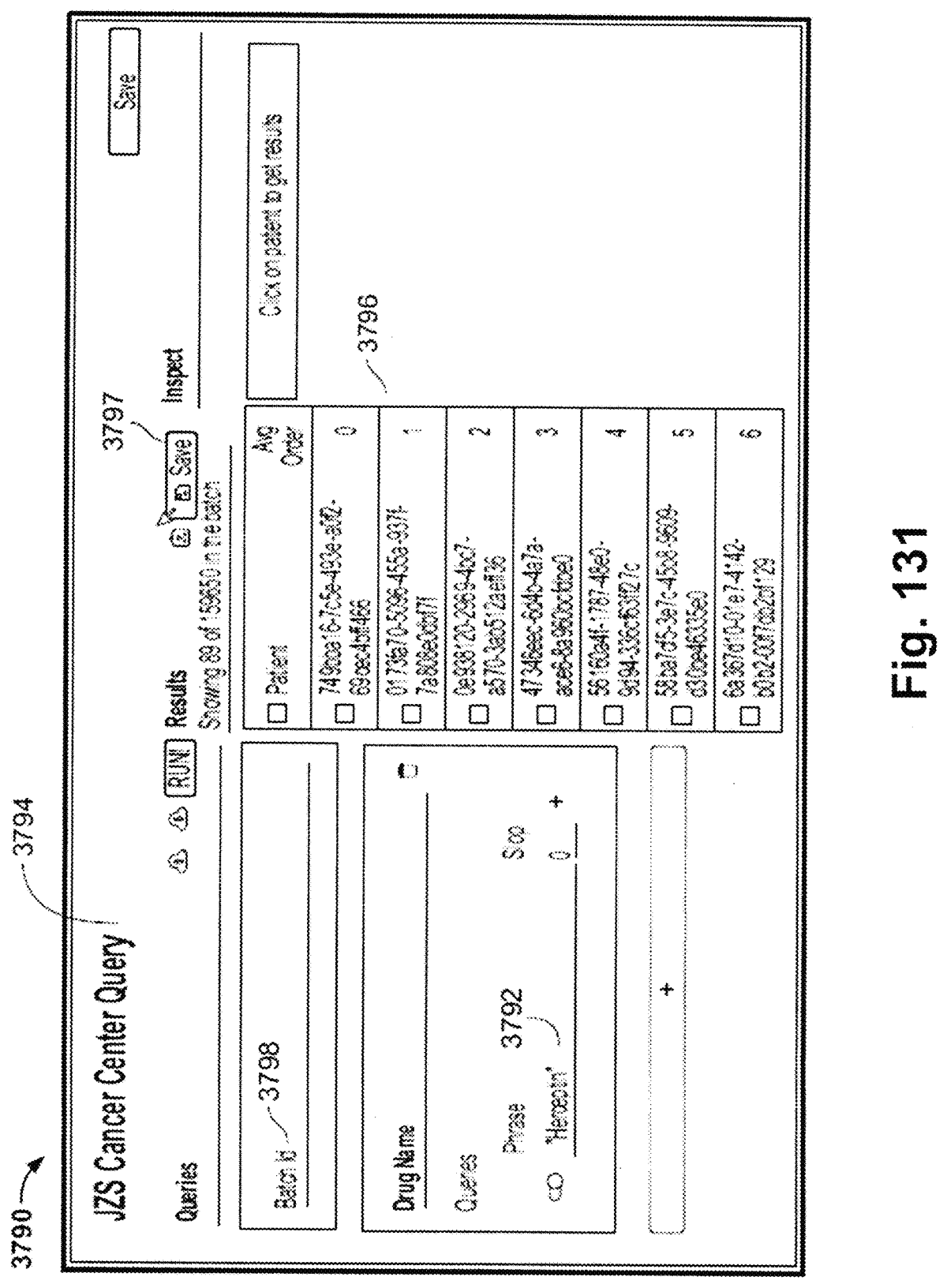

FIG. 131 is another image of an example graphical user interface (GUI), according to aspects of the present disclosure;

Figure 132:
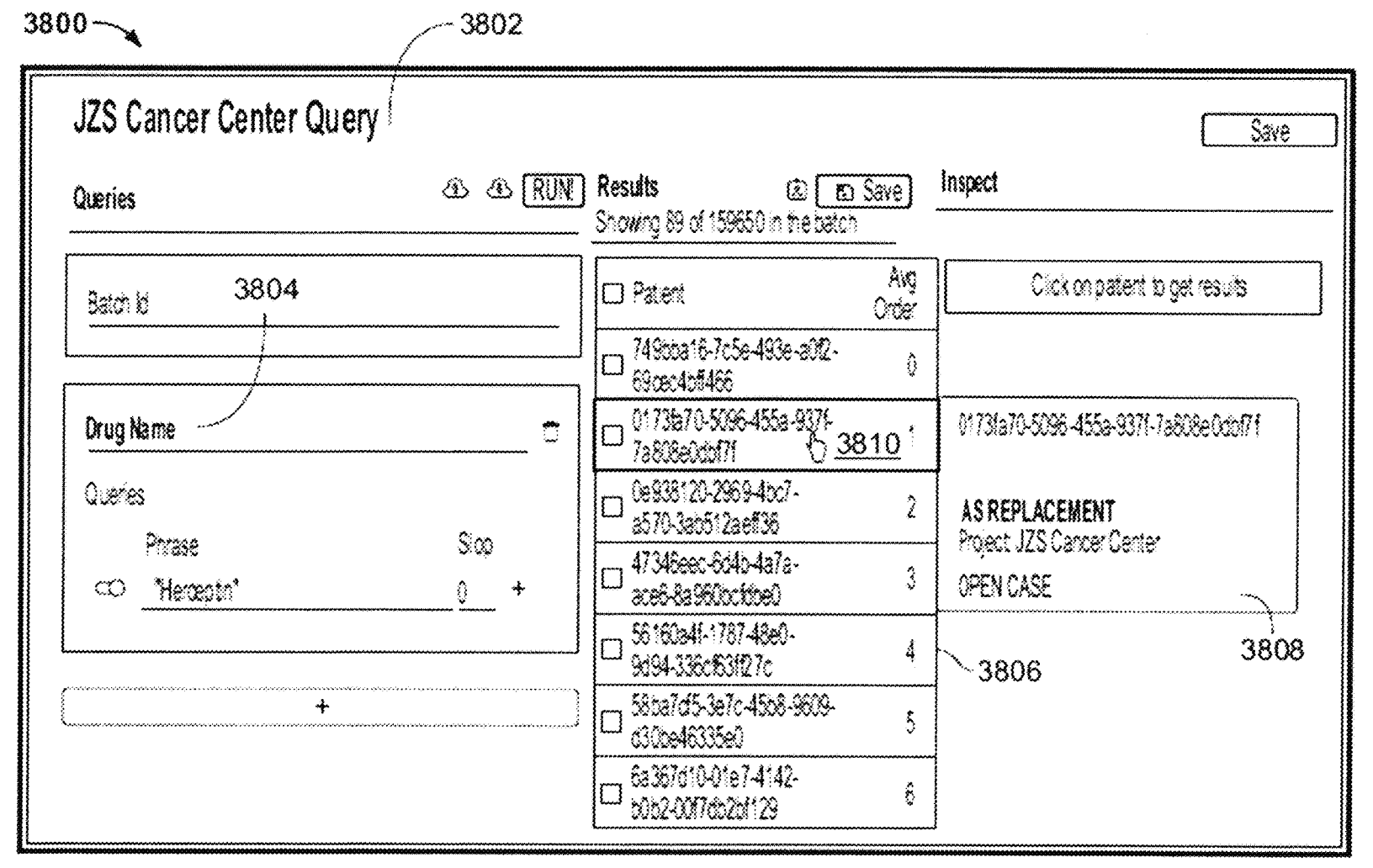

FIG. 132 is another image of an example graphical user interface (GUI), according to aspects of the present disclosure;

Figure 133:
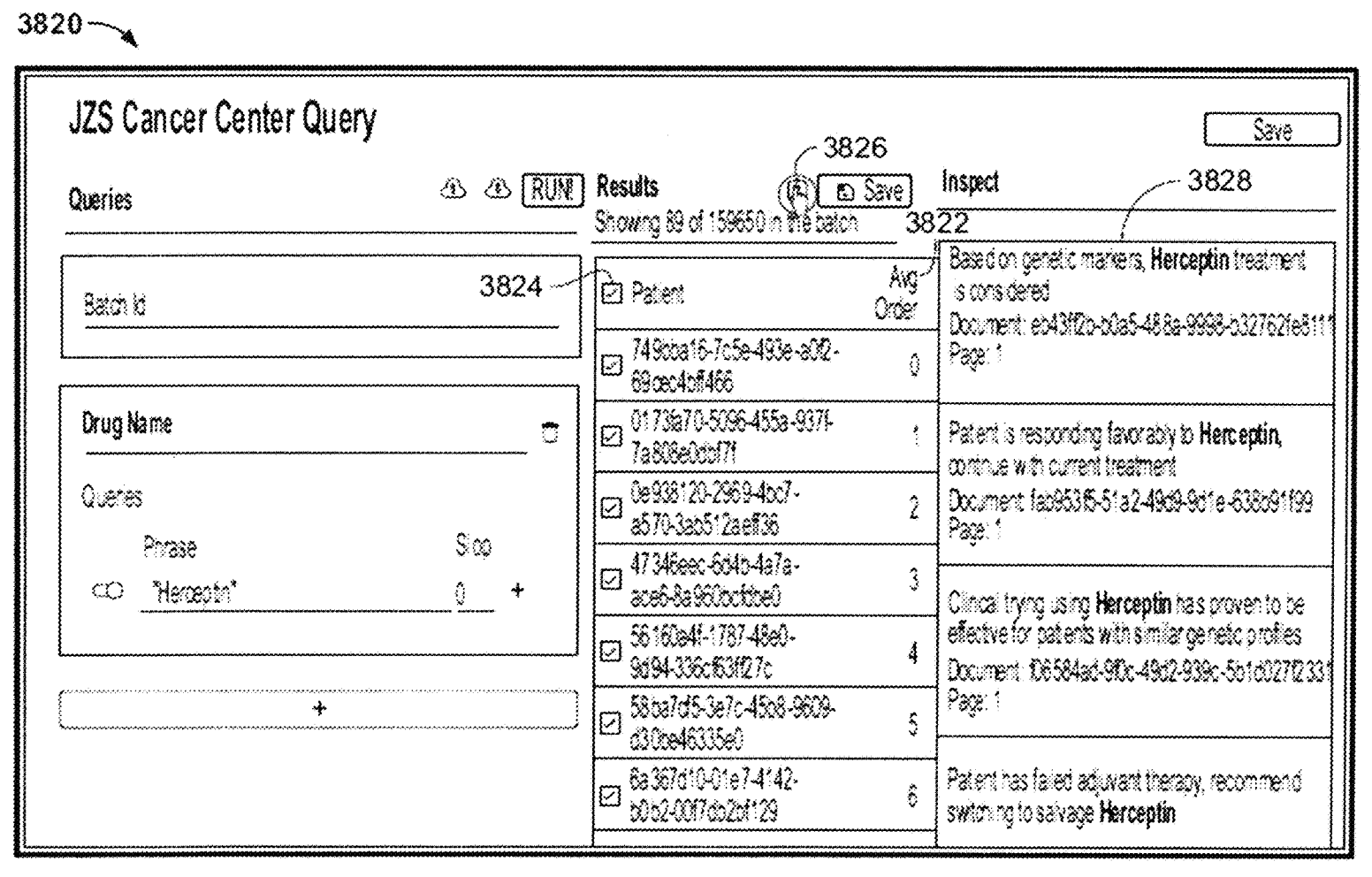

FIG. 133 is another image of an example graphical user interface (GUI), according to aspects of the present disclosure;

FIG. 134 is another image of an example graphical user interface (GUI), according to aspects of the present disclosure;

FIG. 135 is another image of an example graphical user interface (GUI), according to aspects of the present disclosure;

Figure 136:
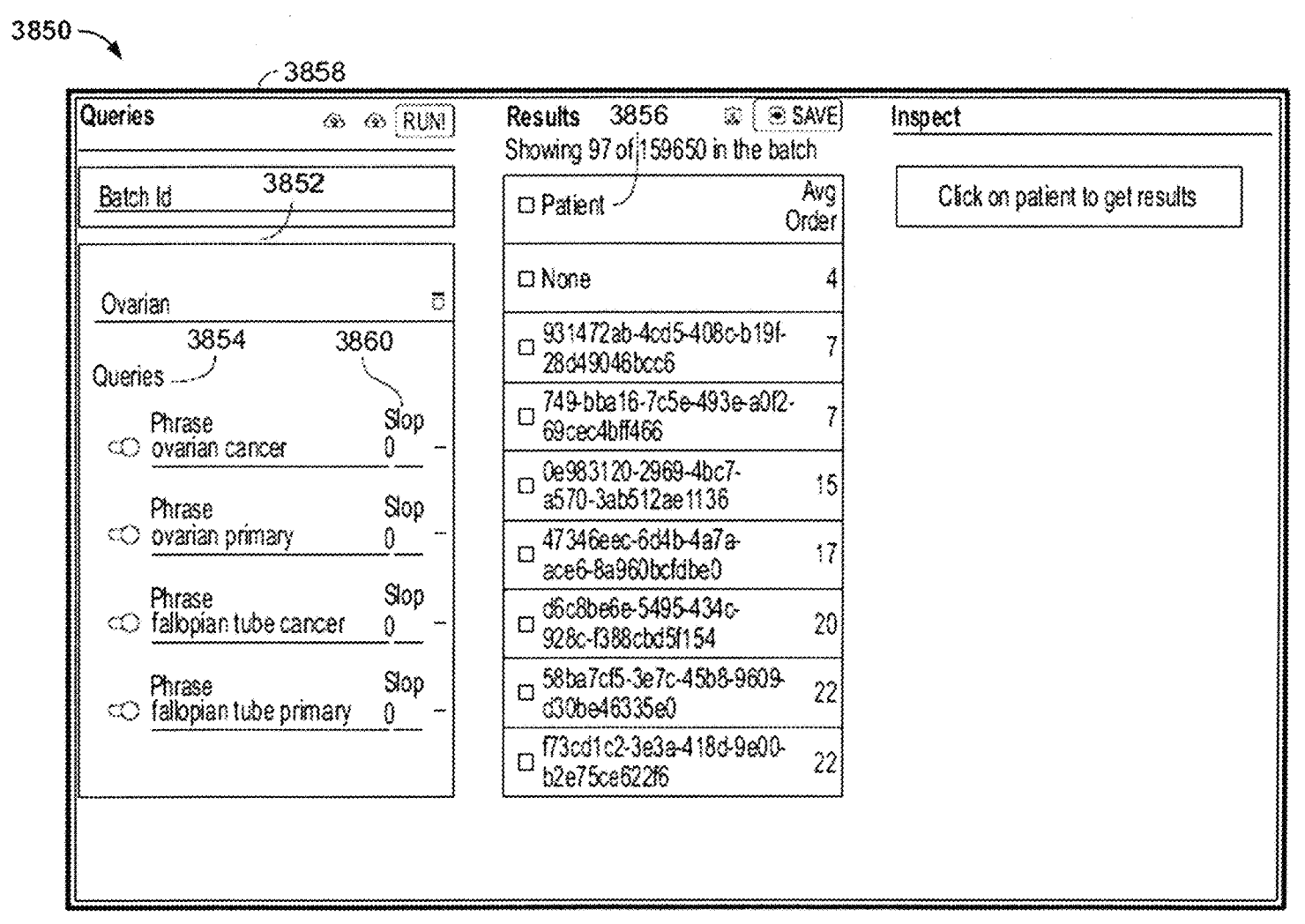

FIG. 136 is another image of an example graphical user interface (GUI), according to aspects of the present disclosure;

FIG. 137 is another image of an example graphical user interface (GUI), according to aspects of the present disclosure;

Figure 138:
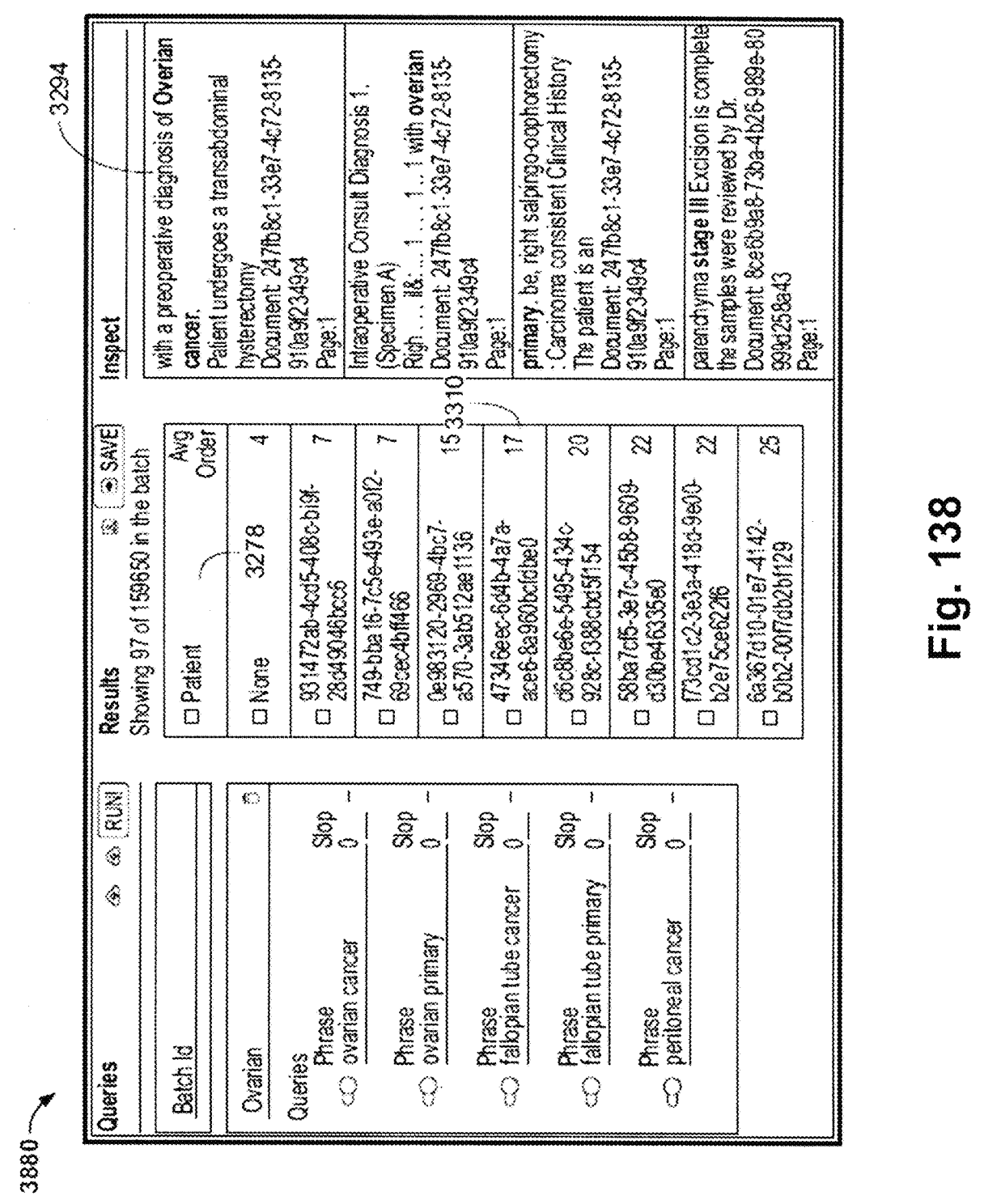

FIG. 138 is another image of an example graphical user interface (GUI), according to aspects of the present disclosure;

FIG. 139 shows an exemplary user interface that a clinical data analyst may utilize to structure clinical data from raw clinical data;

FIG. 140 depicts one example of EMR-extracted structured data that includes a payload of diagnosis-related data;

FIG. 141 depicts one example of EMR-extracted structured data that includes a payload of medication-related data;

FIG. 142 depicts a user interface that may be used by a conflict resolution user when a complex disagreement is identified for a patient record;

FIG. 143 depicts a user interface that may be used by a conflict resolution user when a more straightforward disagreement is identified for a patient record;

FIG. 144 depicts a list of test suites within a "demographics" root level category;

FIG. 145 depicts an exemplary test suite for determining sufficiency of a structured and/or abstracted instance of genetic testing;

FIG. 146 depicts a second exemplary test suite for determining sufficiency of a structured and/or abstracted instance of genetic testing;

FIG. 147 depicts one example of a user interface through which a manager-level user can view and maintain validations, quickly determine which patient cases have passed or failed, obtain the specific detail about any failed validation, and quickly re-assign cases for further manual QA and issue resolution prior to clinical sign-out and approval;

FIG. 148 depicts an exemplary user interface for performing quality assurance testing based on generic abstractions from raw documents;

FIG. 149 depicts an exemplary user interface that is used to provide abstraction across multiple streams of raw clinical data and documents;

FIG. 150 depicts an exemplary user interface for performing an inter-rater reliability analysis;

FIG. 151 depicts another exemplary user interface;

FIG. 152 depicts another visualization of the exemplary user interface of FIG. 151;

FIG. 153 depicts one example of various metrics or reports generated by the present system;

FIG. 154 depicts a second example of various metrics or reports generated by the present system;

FIG. 155 depicts a third example of various metrics or reports generated by the present system;

FIG. 156 depicts a fourth example of various metrics or reports generated by the present system;

FIG. 157 reflects a generalized process flow diagram for carrying out the method disclosed herein, from raw data importation, through data structuring, and then through automated quality assurance testing;

FIG. 158 is a depiction of a home screen of a mobile clinician assistant application;

FIG. 159 is a depiction of a document capture screen of the application;

FIG. 160 depicts an exemplary tabular extraction approach involving a plurality of different masks;

FIG. 161A is a depiction of a standard report to which the masks of FIG. 160 may be applied in order to extract and analyze the data contained therein;

FIG. 161B is a continuation of the report of FIG. 161A;

FIG. 162 is an exemplary pipeline for processing electronic records into structured results;

FIG. 163 is an exemplary table representing a structured result;

FIG. 164 is an exemplary constituency-based parse tree representation according to an embodiment;

FIG. 165 is an exemplary word weighing representation according to an embodiment;

FIG. 166 is an exemplary sequence labeling classification representation according to an embodiment;

FIG. 167 is an exemplary ontological graph database for viewing links between different dictionaries;

FIG. 168 is an exemplary architecture for implementing an embodiment of the pipeline of FIG. 162;

FIG. 169 is an exemplary representation of the patient upload portion of the architecture;

FIG. 170 is an exemplary representation of the prediction generation portion of the architecture;

FIG. 171 is an exemplary representation of the abstraction portion of the architecture;

FIG. 172 is an exemplary representation of the feedback and training portion of the architecture;

FIG. 173 is a depiction of a data verification screen of the application for verifying and/or editing data imported into the application and/or patient record as a result of data capture from one or more documents;

FIG. 174 is a depiction of a first cohort reporting screen of the application that includes one or more treatment regimens administered to patients in the cohort, along with relevant response data for each regimen;

FIG. 175 is a depiction of a second cohort reporting screen that includes the treatment regimen(s) of FIG. 174, along with relevant adverse event data for each regimen;

FIG. 176 is a depiction of a third cohort reporting screen that includes potential clinical trial matches;

FIG. 177 is a flowchart depicting one implementation of the present disclosure;

FIG. 178 is a flowchart depicting a second implementation of the present disclosure;

FIG. 179 is a flowchart depicting a third implementation of the present disclosure;

FIG. 180 is a flowchart depicting a fourth implementation of the present disclosure;

FIG. 181 is a flowchart depicting a fifth implementation of the present disclosure;

FIG. 182 is a flowchart depicting a sixth implementation of the present disclosure;

FIG. 183 is a flowchart depicting a seventh implementation of the present disclosure;

FIG. 184 is a flowchart depicting an eighth implementation of the present disclosure;

FIG. 185 is a flowchart depicting a ninth implementation of the present disclosure;

FIG. 186 is an exemplary system diagram for carrying out the methods described herein;

FIG. 187A is a schematic illustrating a system that includes trainable AI modules that are consistent with at least some aspects of the present description;

FIG. 187B is a schematic illustrating a pipeline system that is consistent with at least some aspects of the present disclosure;

FIG. 187C is an auto-pass process that is consistent with at least some aspects of the present disclosure;

FIG. 188 is a schematic illustrating yet another system that is consistent with at least some aspects of the present disclosure;

FIG. 189 is a schematic illustration of an example deep learning microsatellite instability (MSI) predictor system for predicting MSI directly from medical images, such as histopathology images;

FIG. 190 is a schematic Illustration of a deep learning framework for MSI predictor status, as may be implemented in the system of FIG. 189, in accordance with an example. The framework is a naïve deep learning model without adversarial training;

FIG. 191 is a schematic illustration of a deep learning framework for MSI predictor status, as may be implemented in the system of FIG. 190, in accordance with another example. The framework includes an MSI predictor (classifier) model and an adversarial trained tumor type (classifier) model;

FIG. 192 illustrates example output from the schematic of FIG. 191, including predicted MSI states and visual representation of MSI status, in accordance with an example;

FIG. 193 is a block diagram of an example method for performing adversarial training of a deep learning framework to develop an MSI predictor model and a tumor predictor model;

FIG. 194 is a block diagram of an example method for performing MSI prediction on received testing medical images using the adversarial trained deep learning framework of FIG. 191, in accordance with an example;

FIG. 195A are plots of the distribution of patch-level classifications within samples grouped by clinically determined MSI status. CRC validation data is shown.

Figure 8:
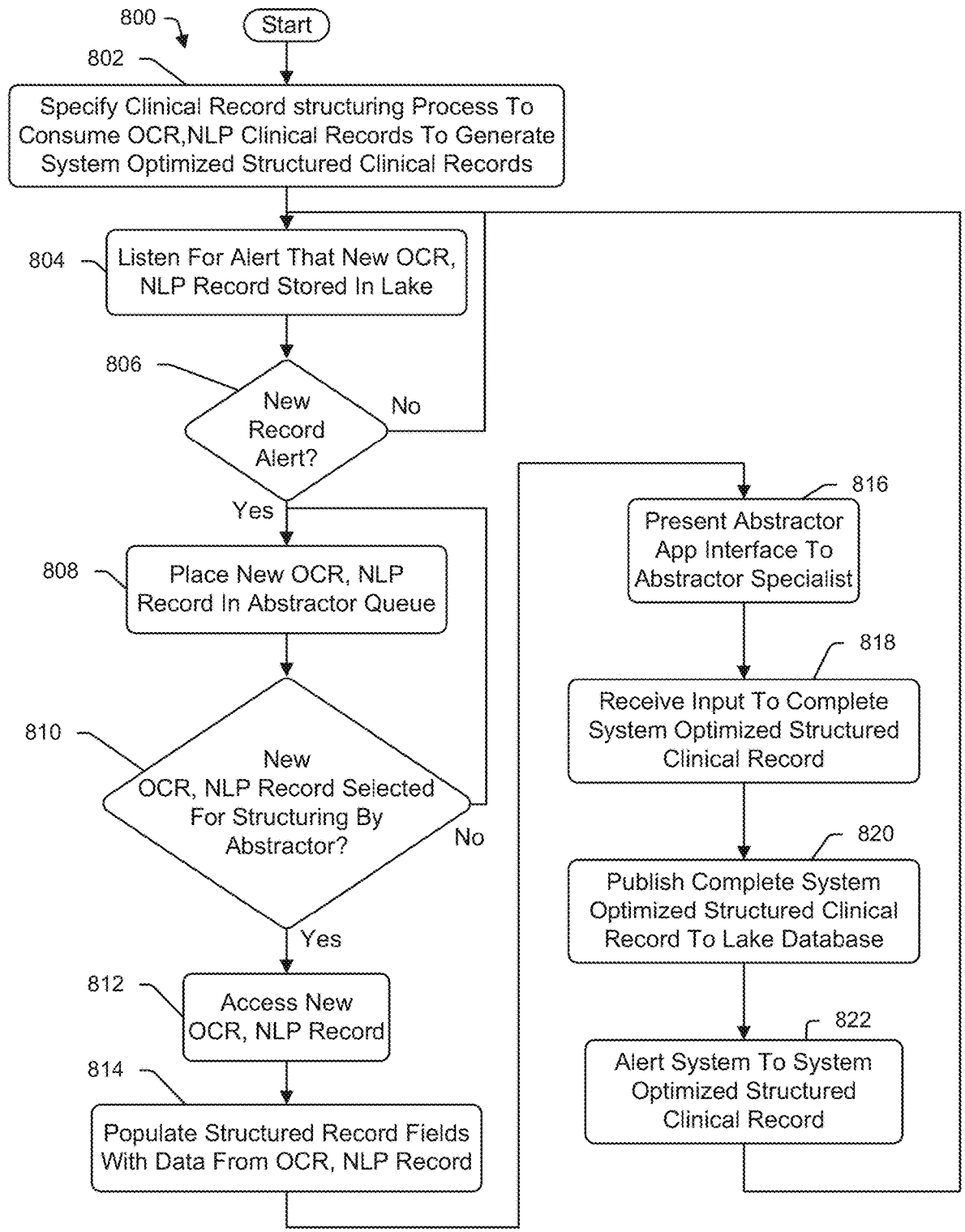
FIG. 8 is a is a flow chart illustrating a process similar to the FIG. 6 process, albeit where the micro-service is a data structuring service.
Figures 196A, 196B:
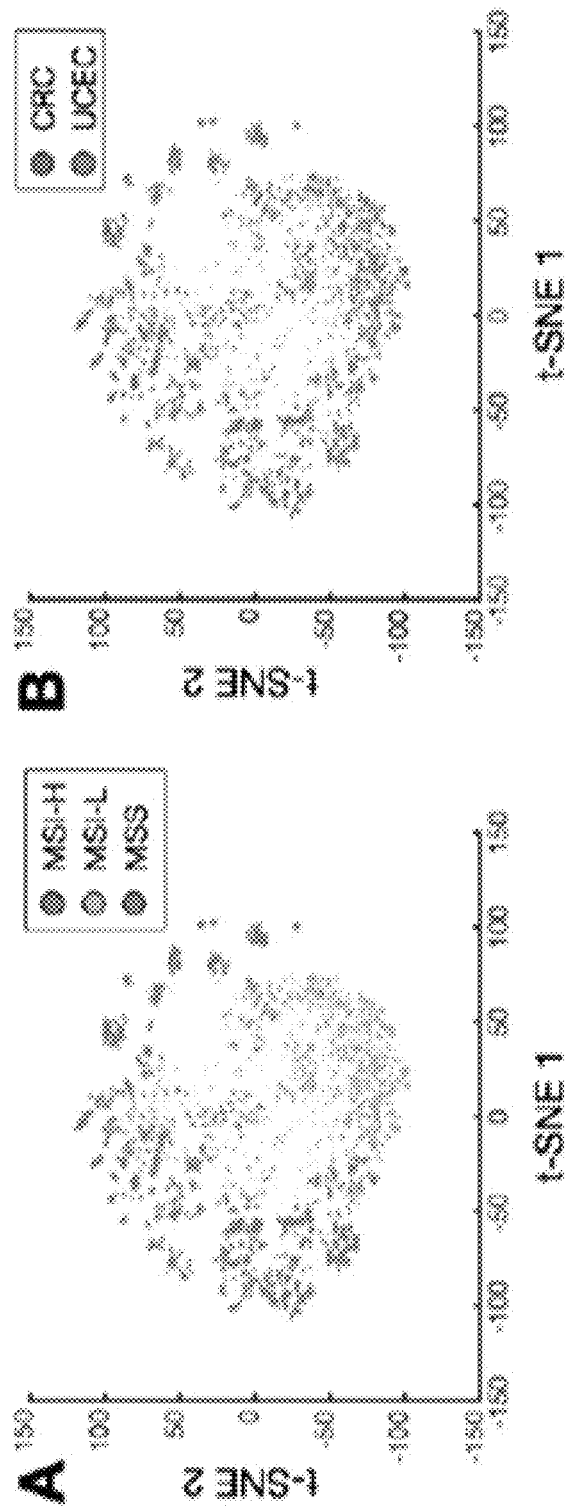
Figure 197:
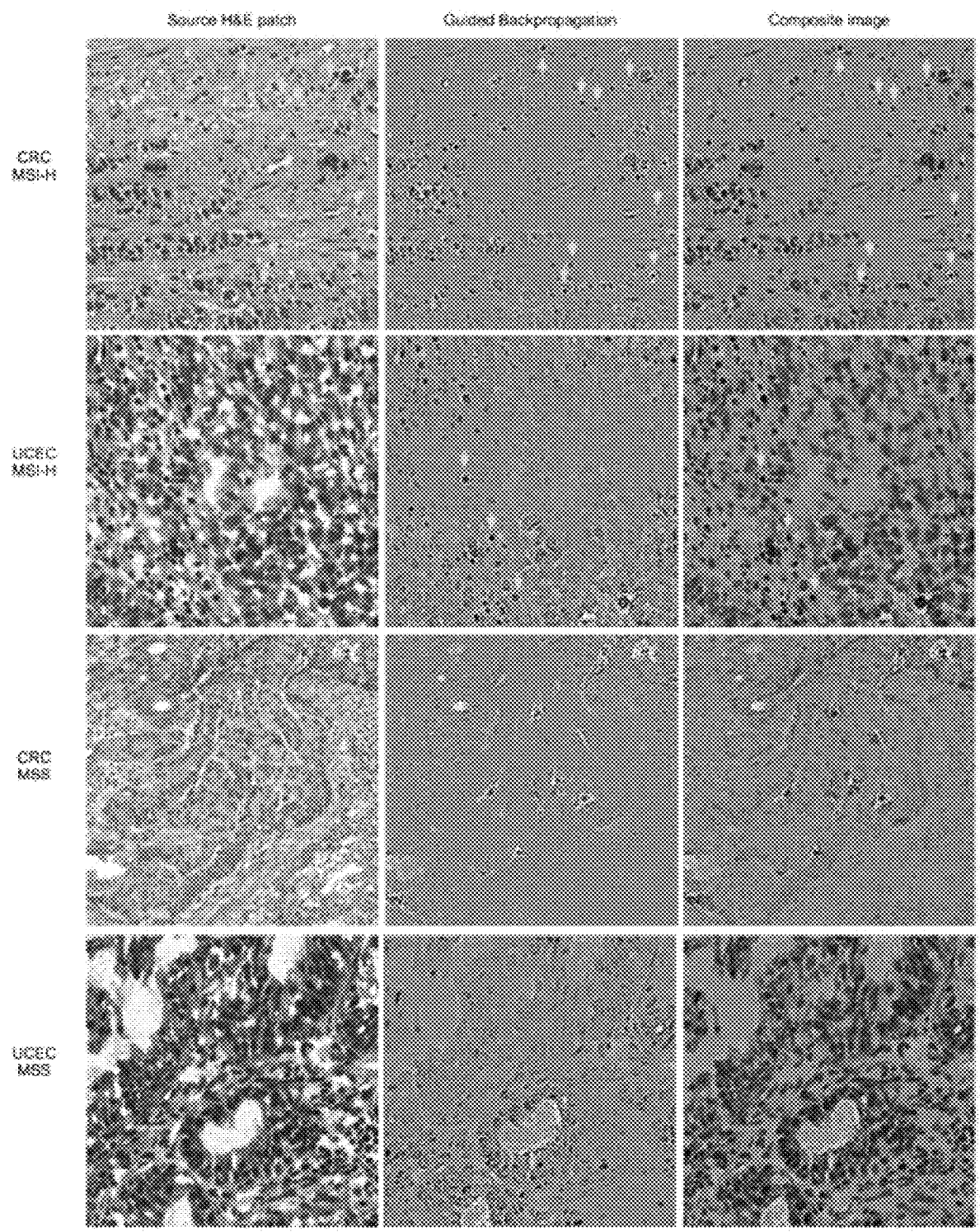
Figure 198:
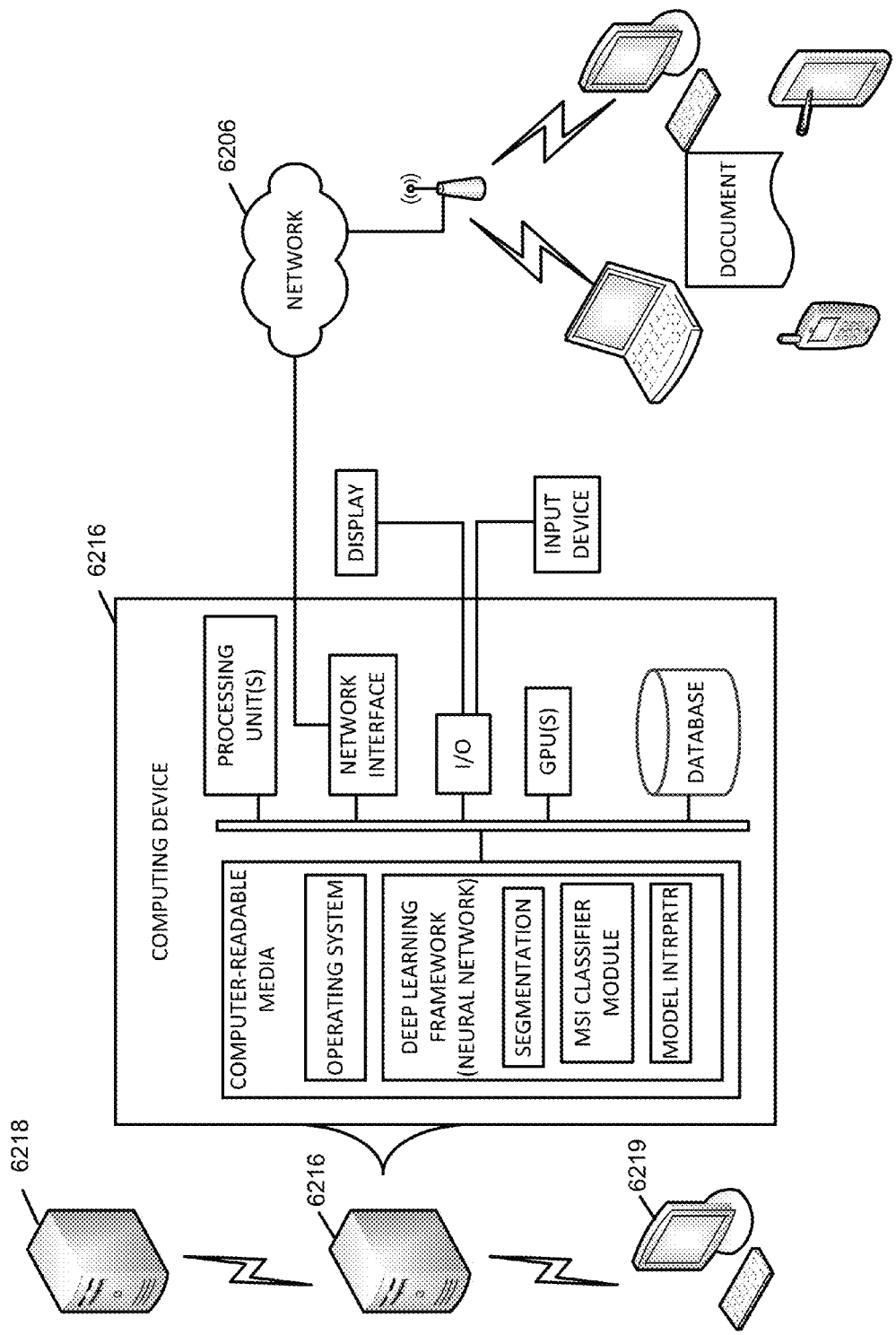
Figure 199:
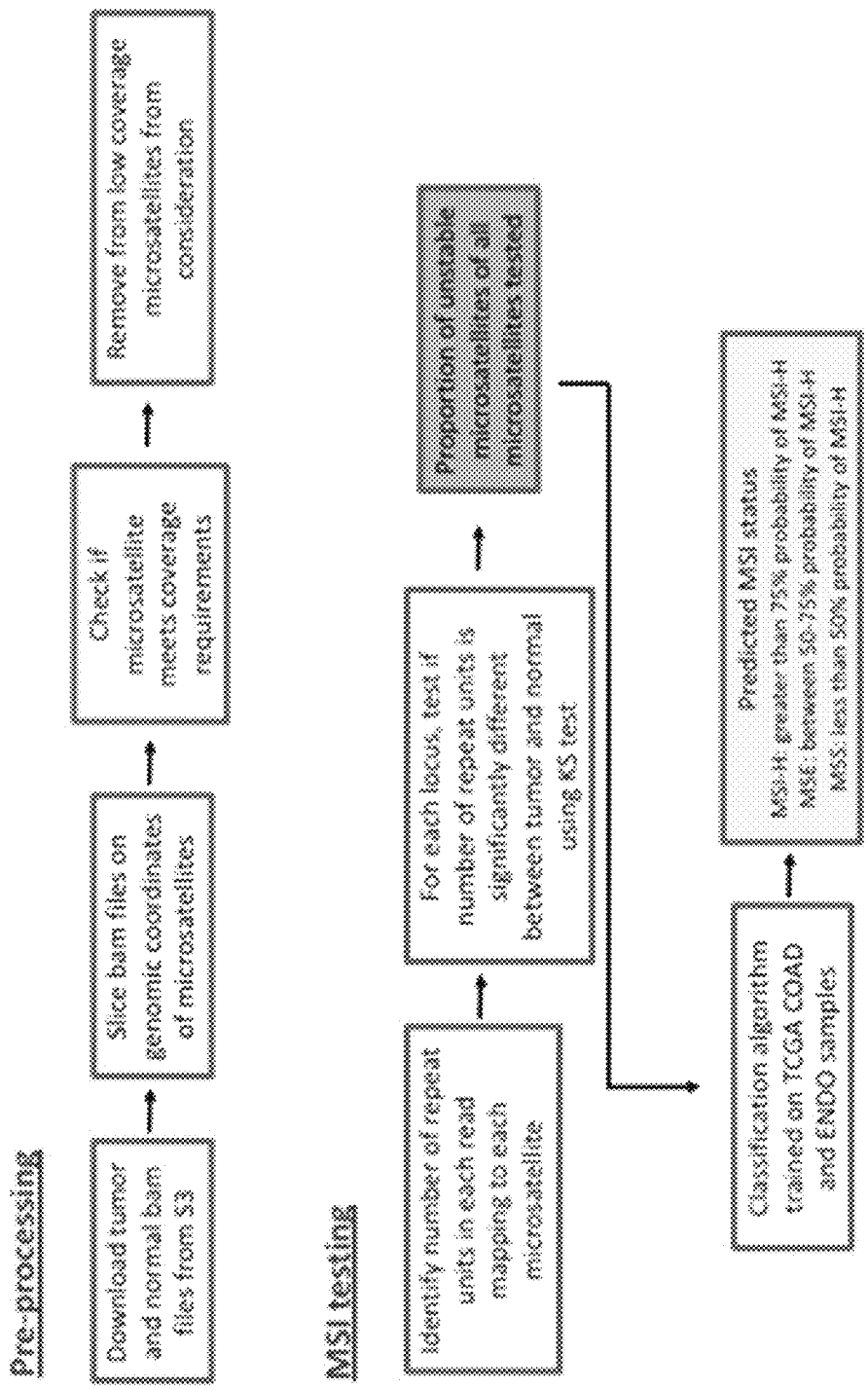
Figure 200:
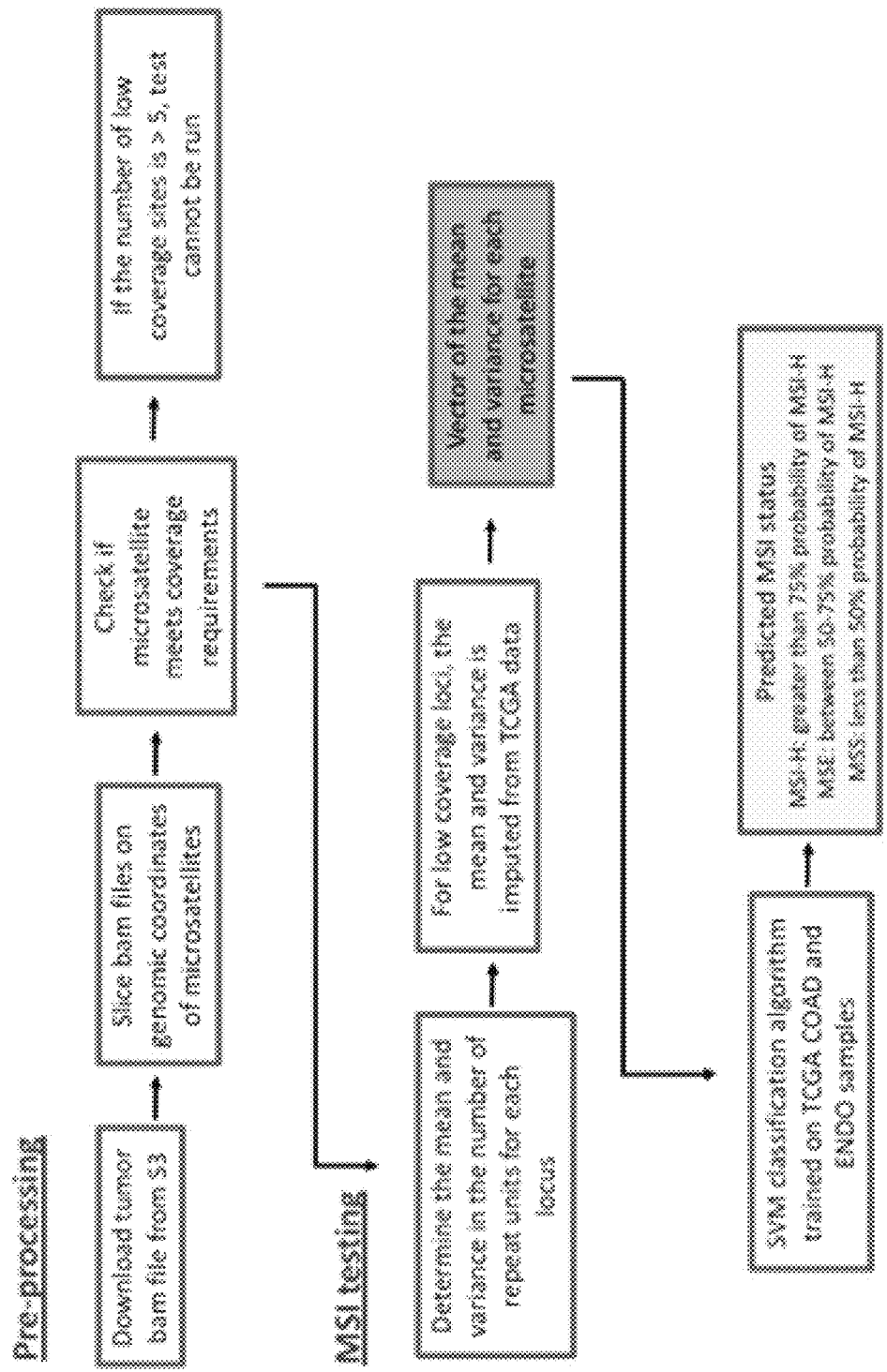
Figure 201:
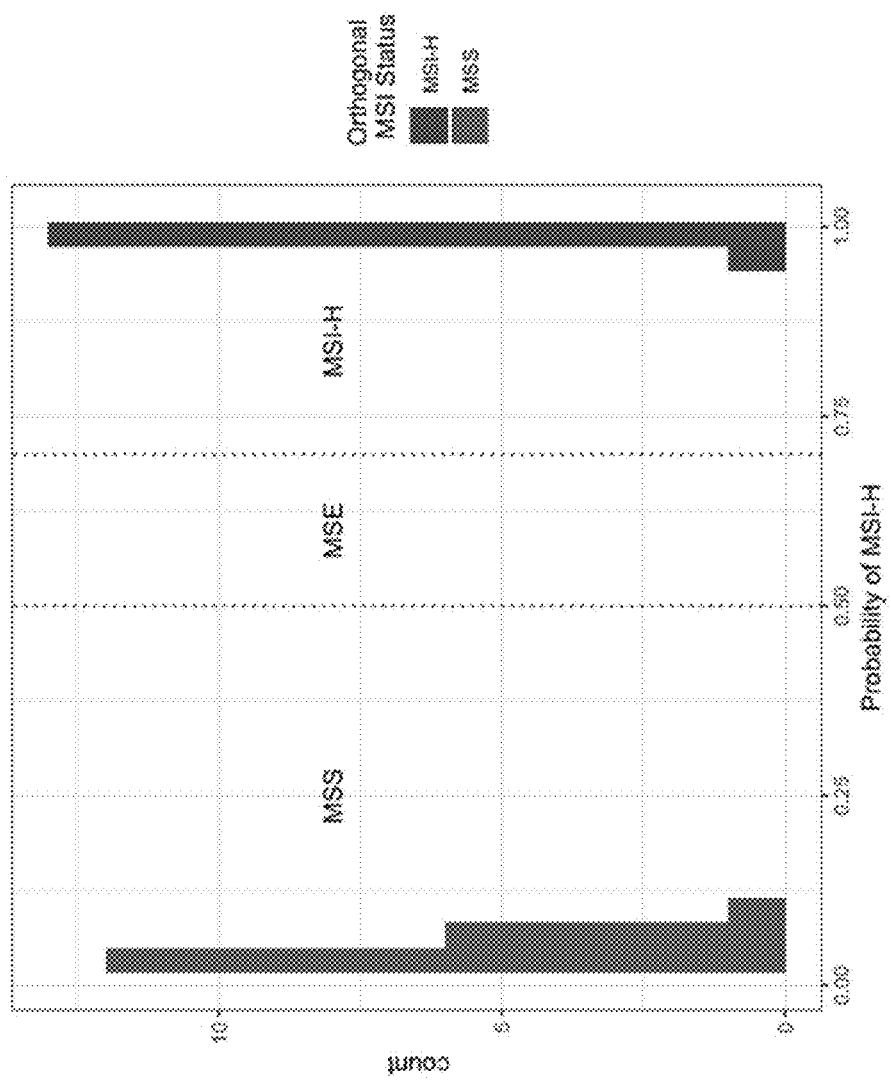
Figure 202:
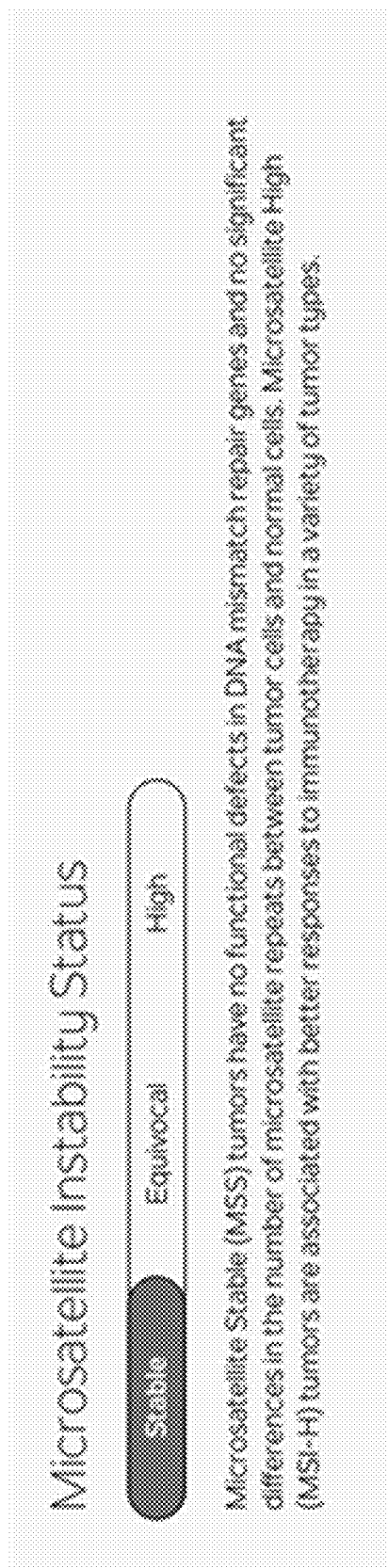
Figure 203:
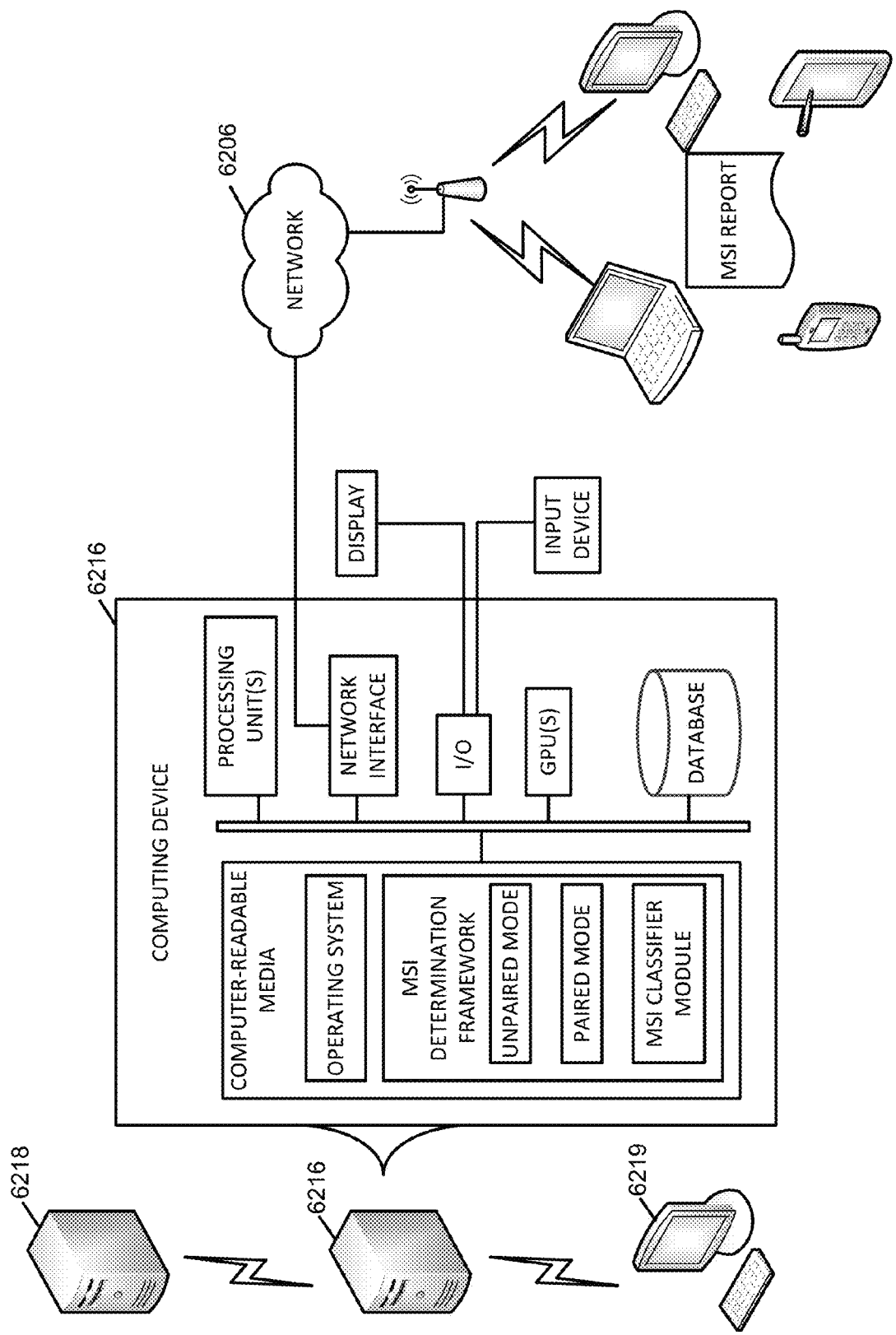
Figure 204:
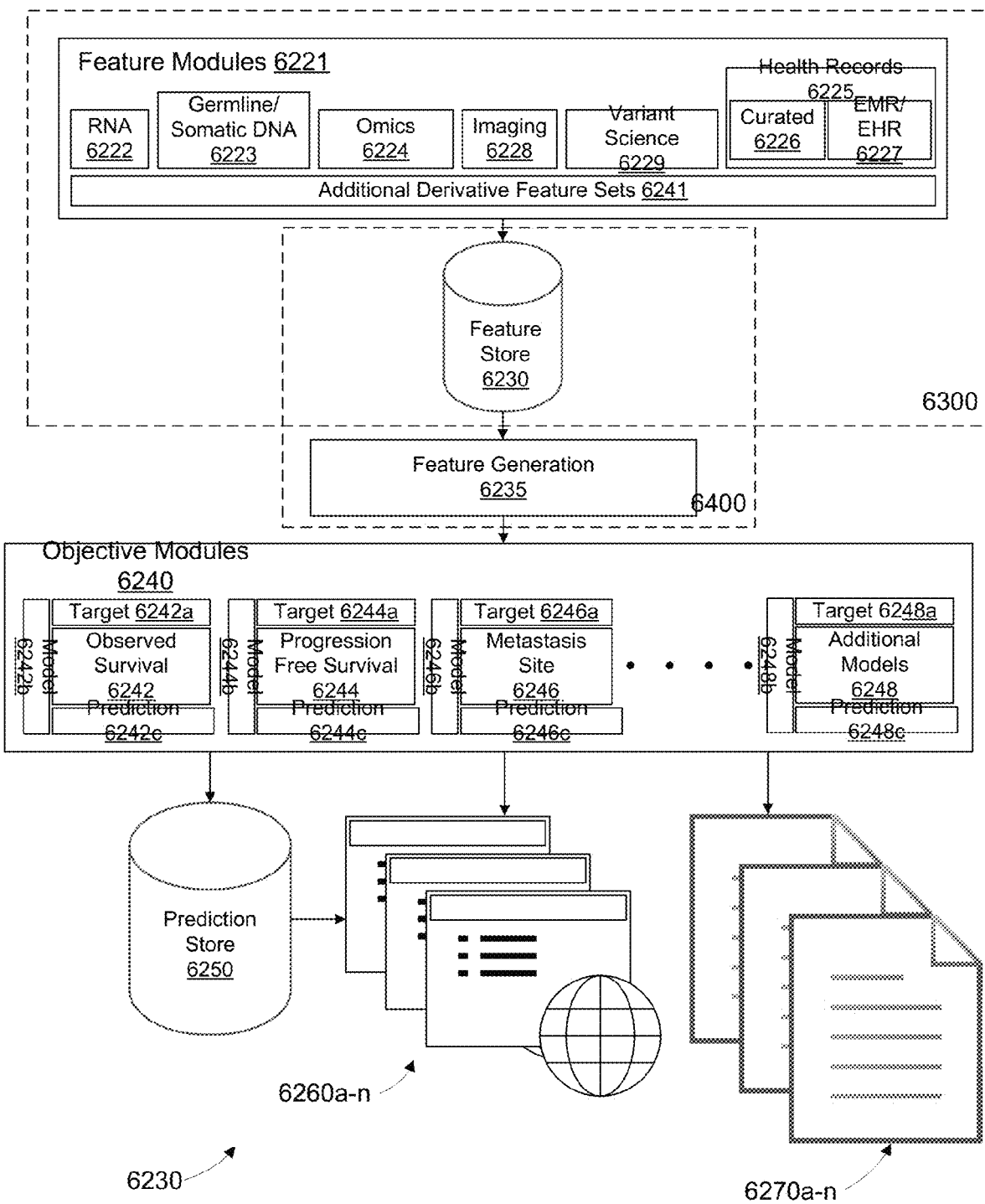
Figure 205:
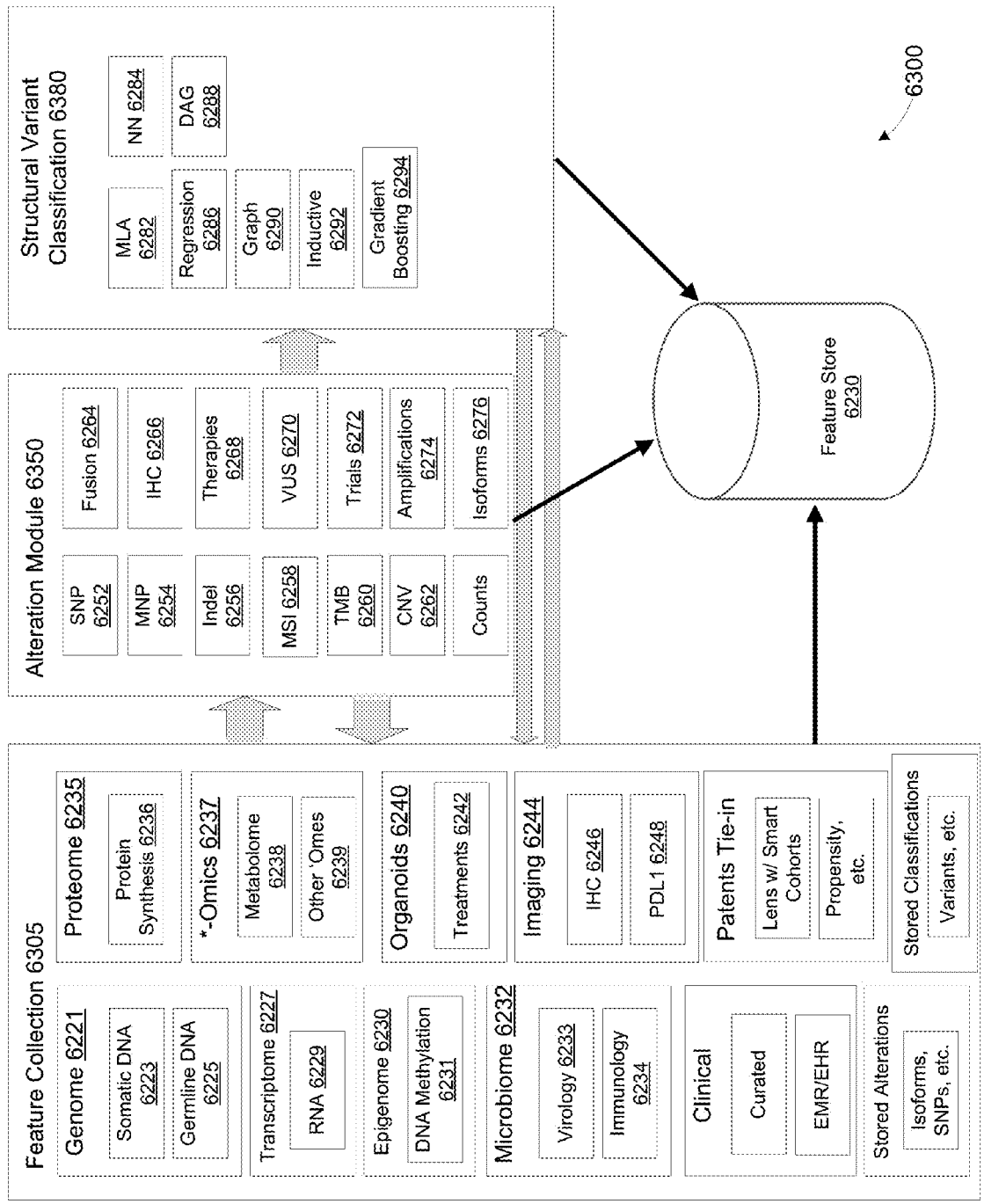
Figure 206:
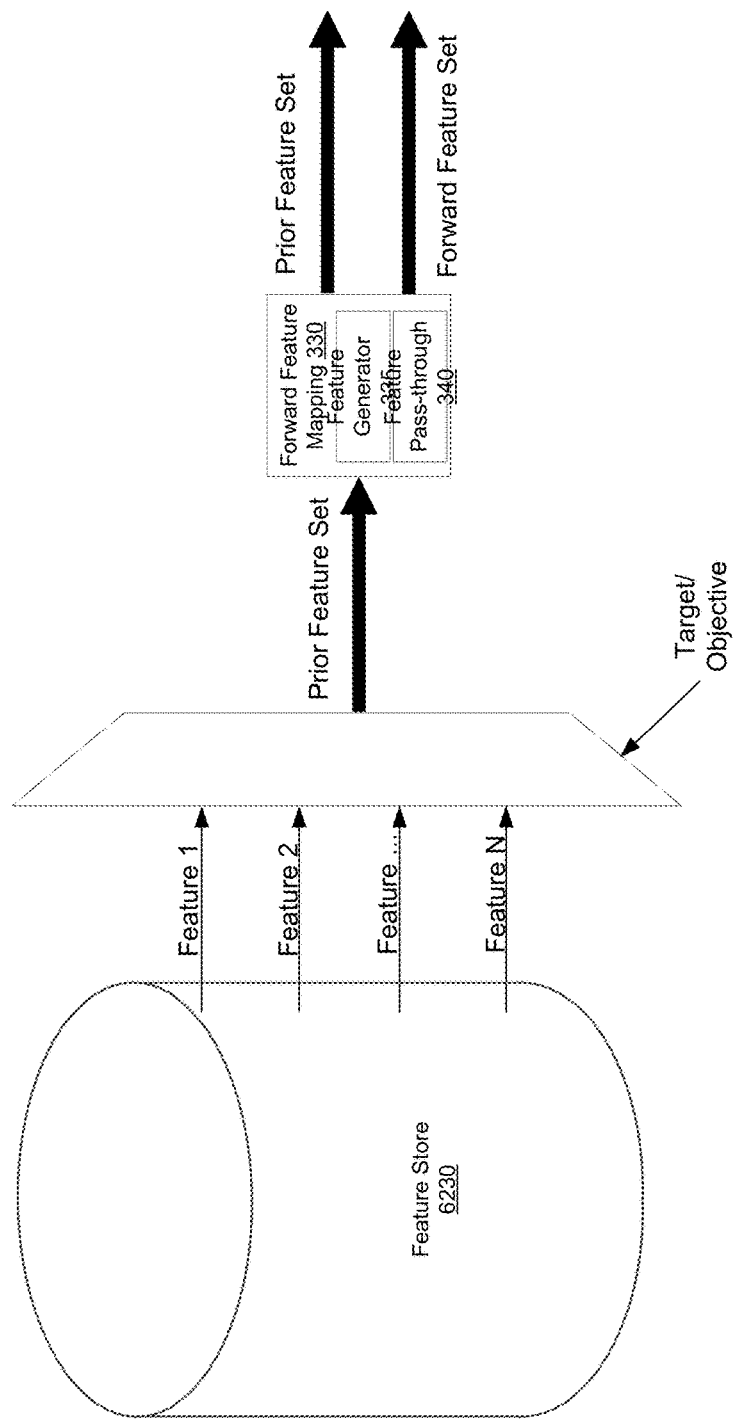
Figure 207:
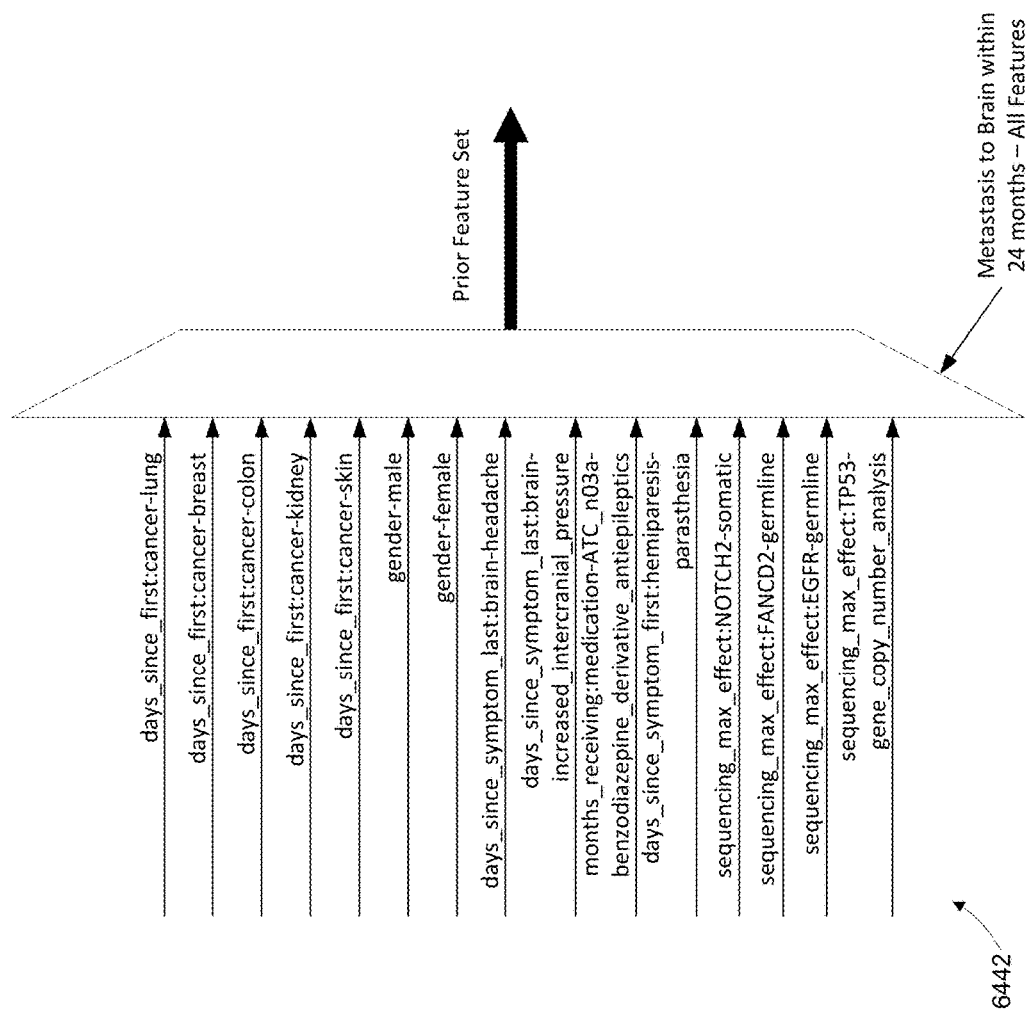
Figure 208:
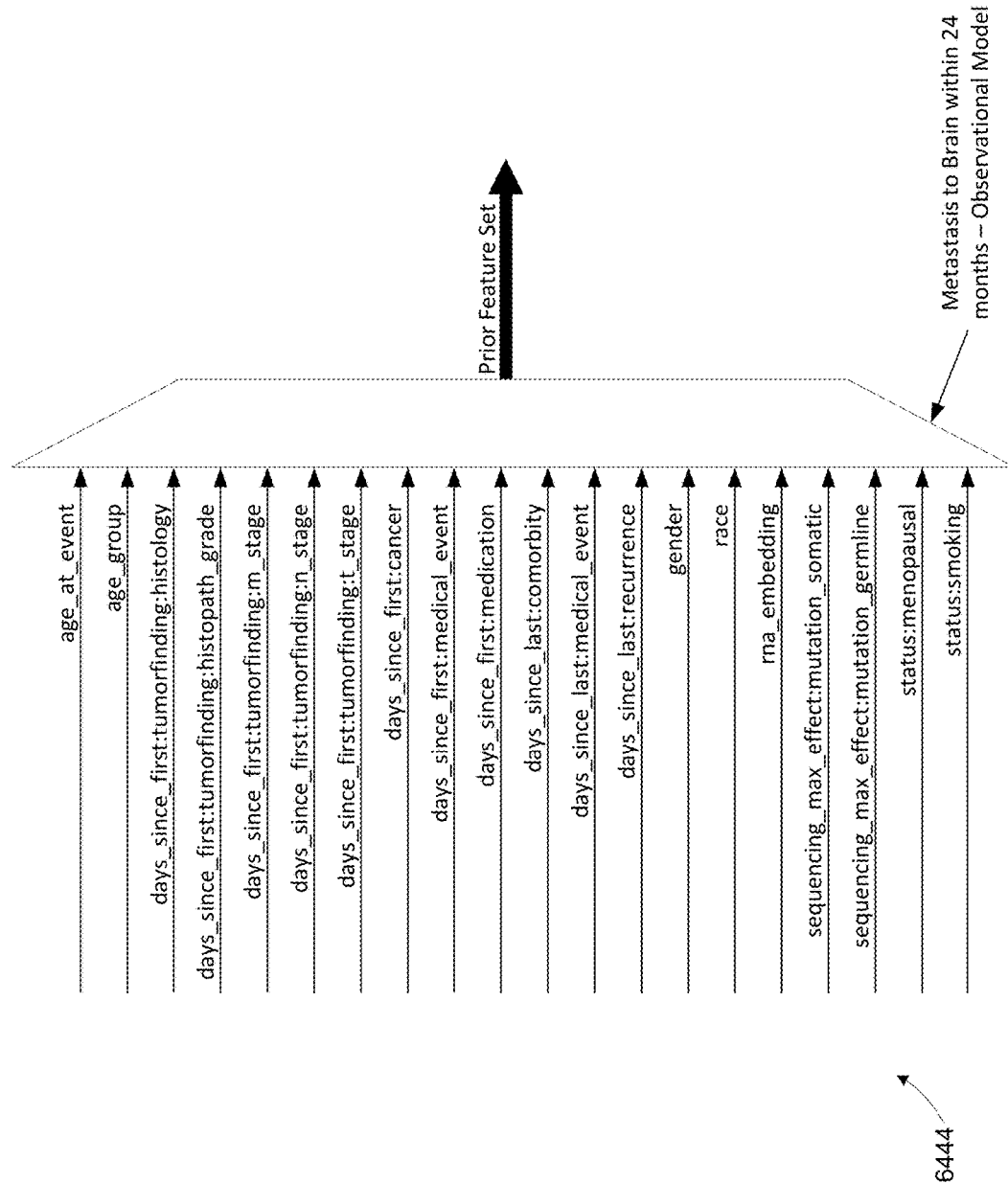
Figure 209:
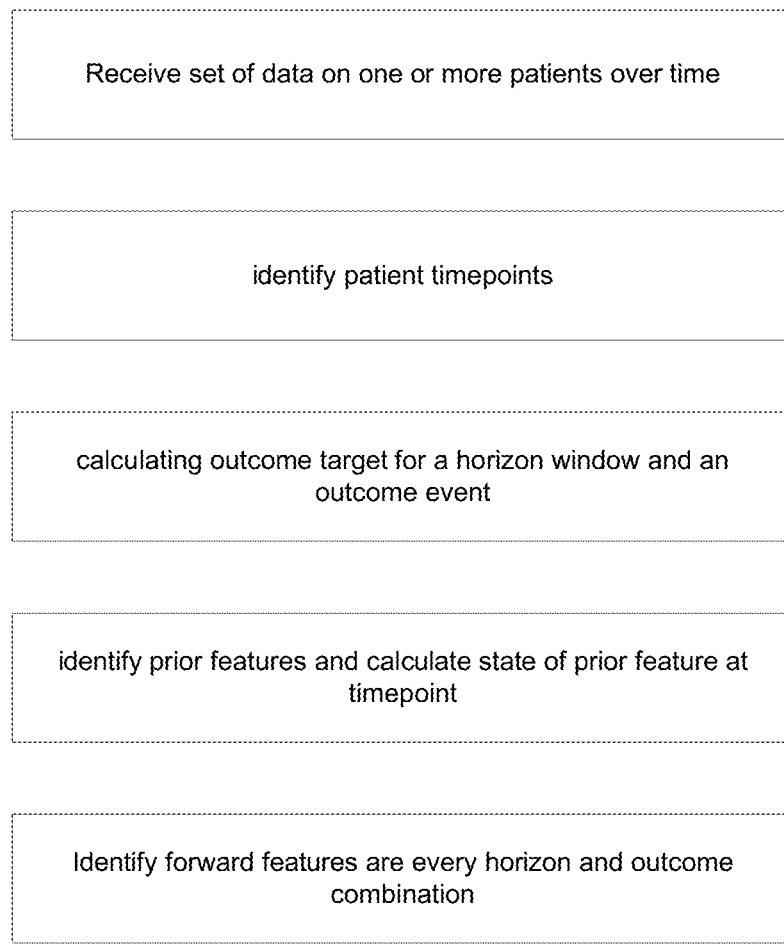
Figure 210:
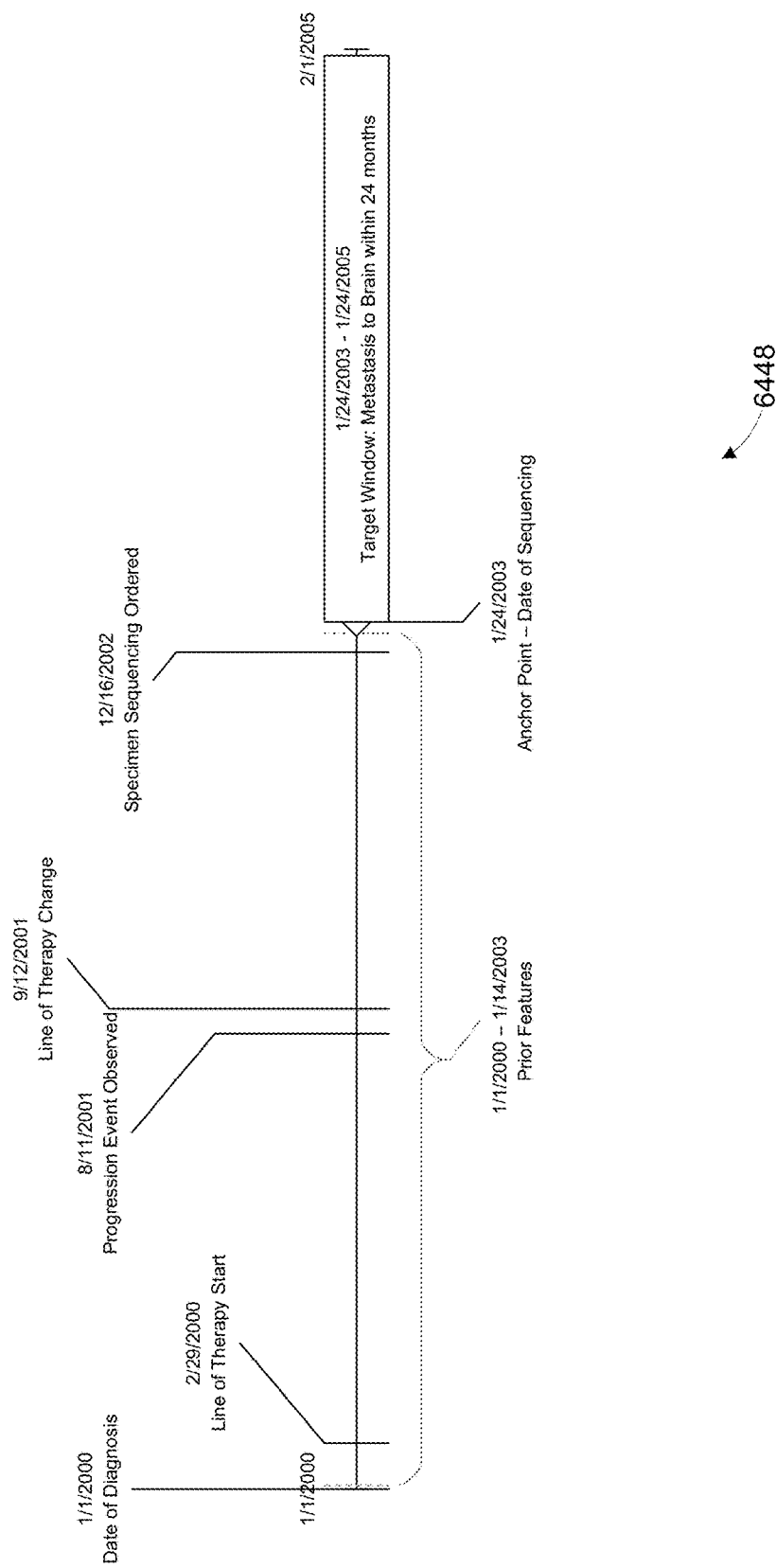
Figure 212:
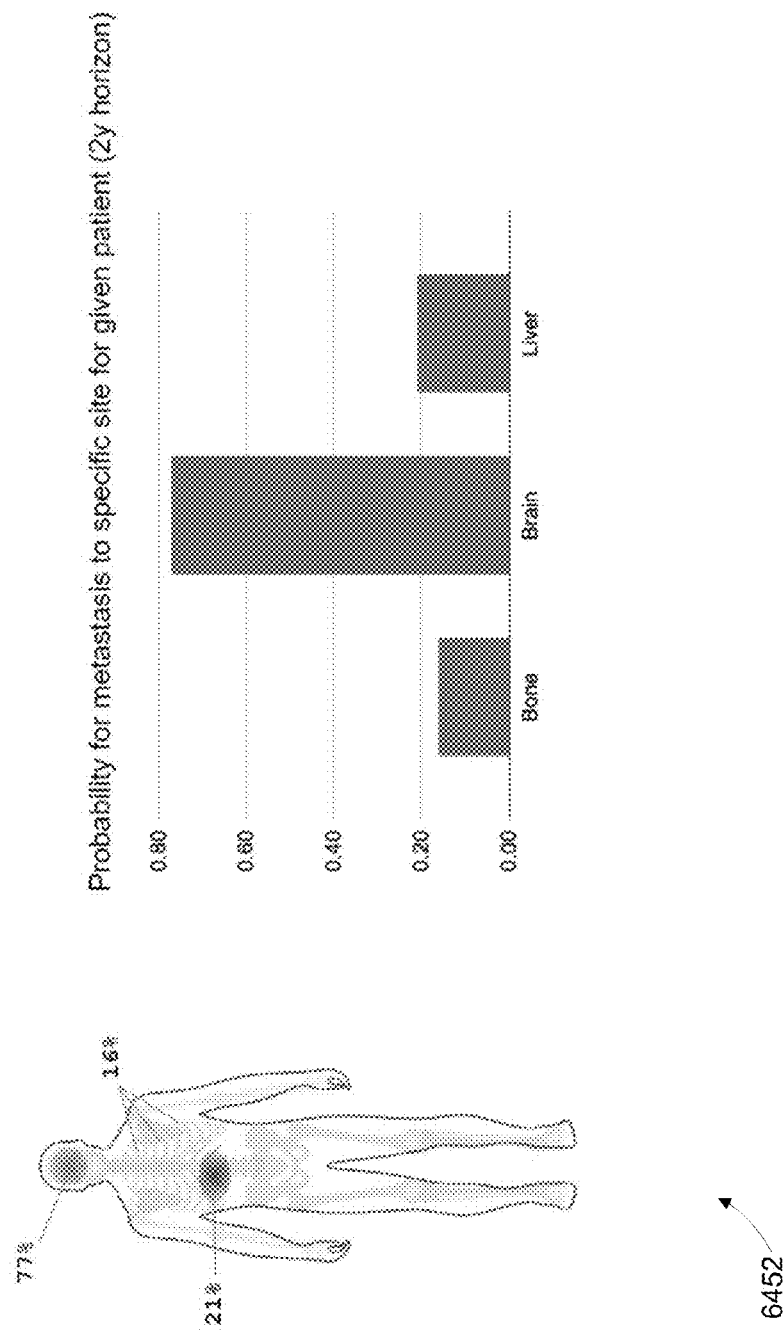
Figure 213:
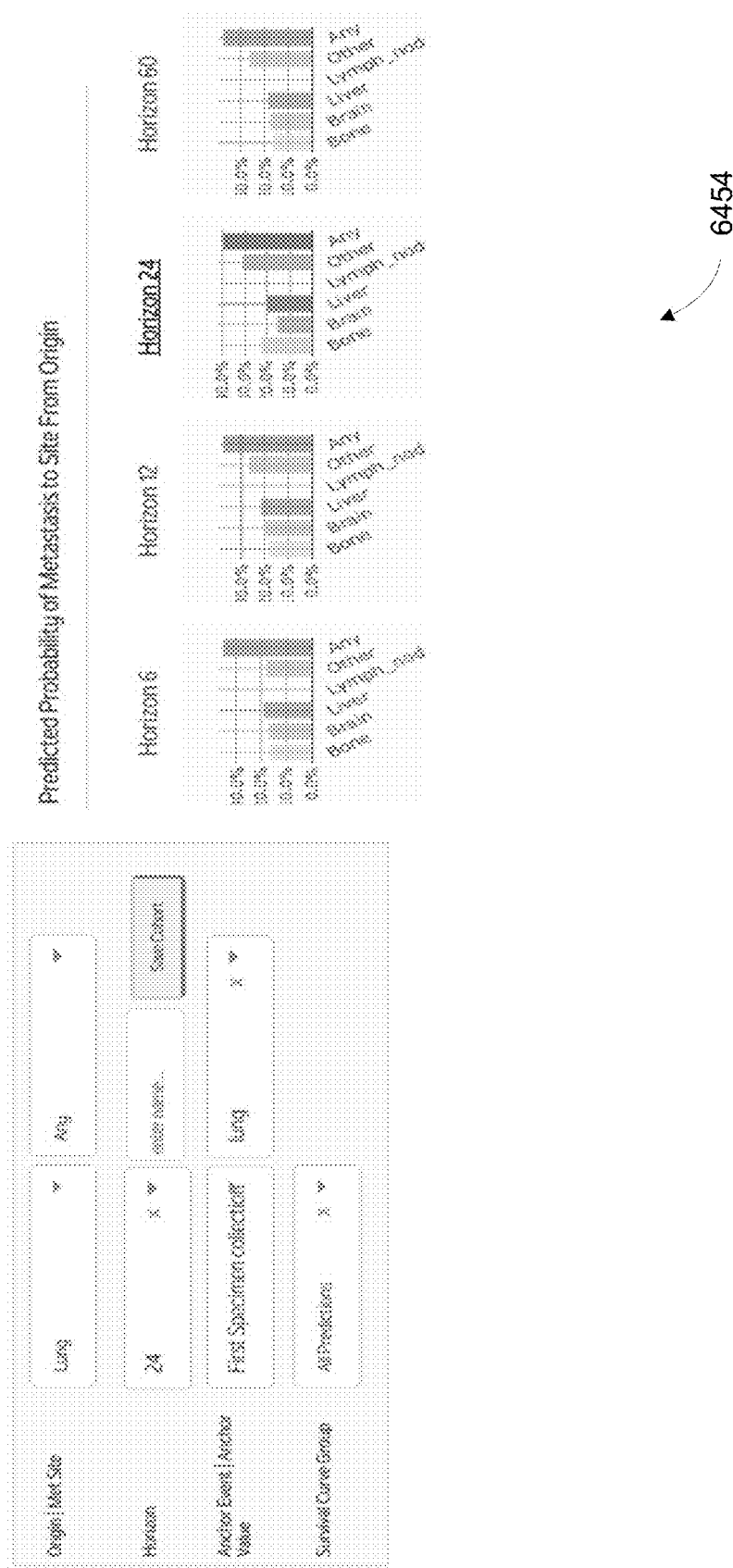
Figure 214:
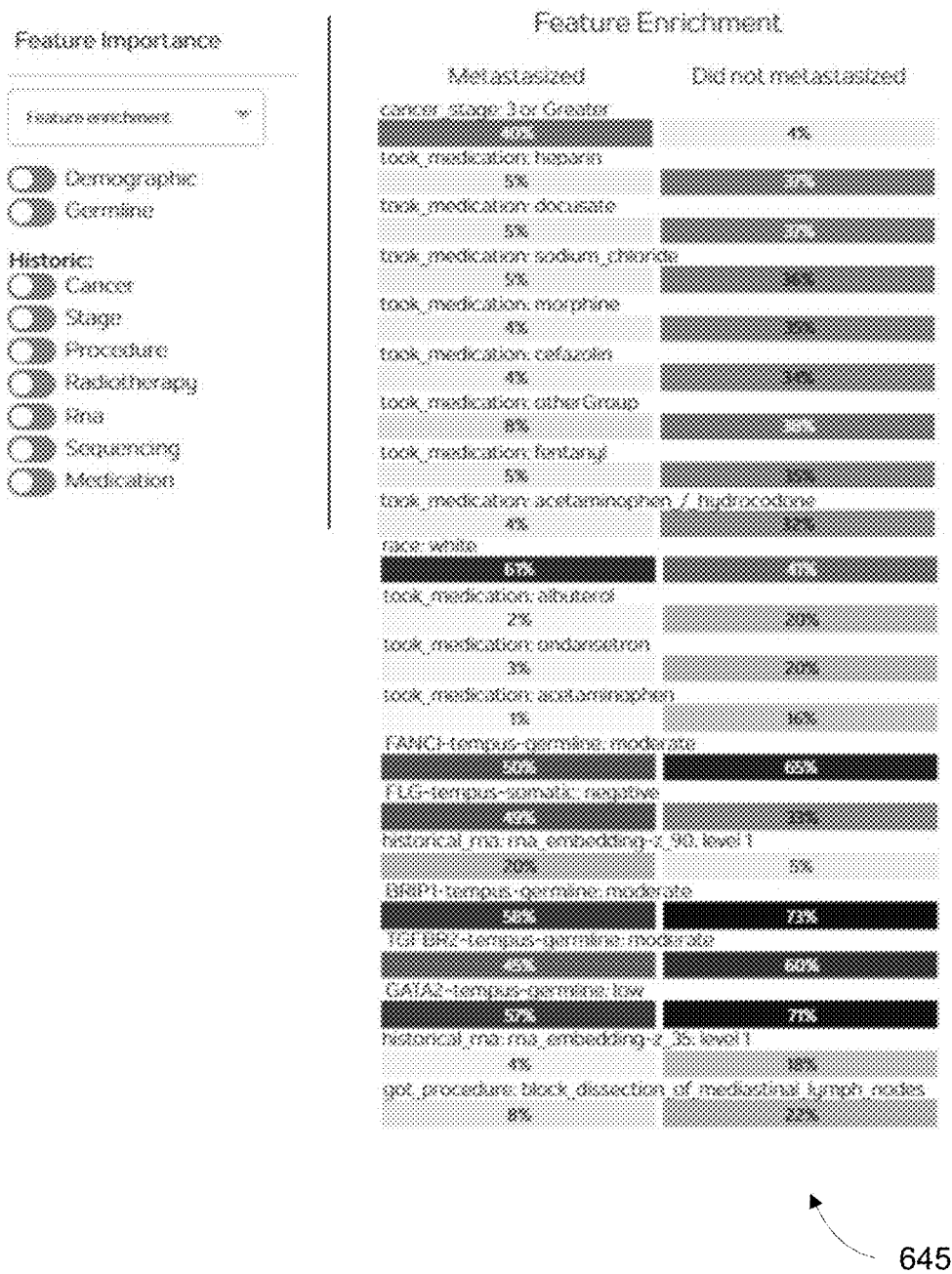
Figure 215:
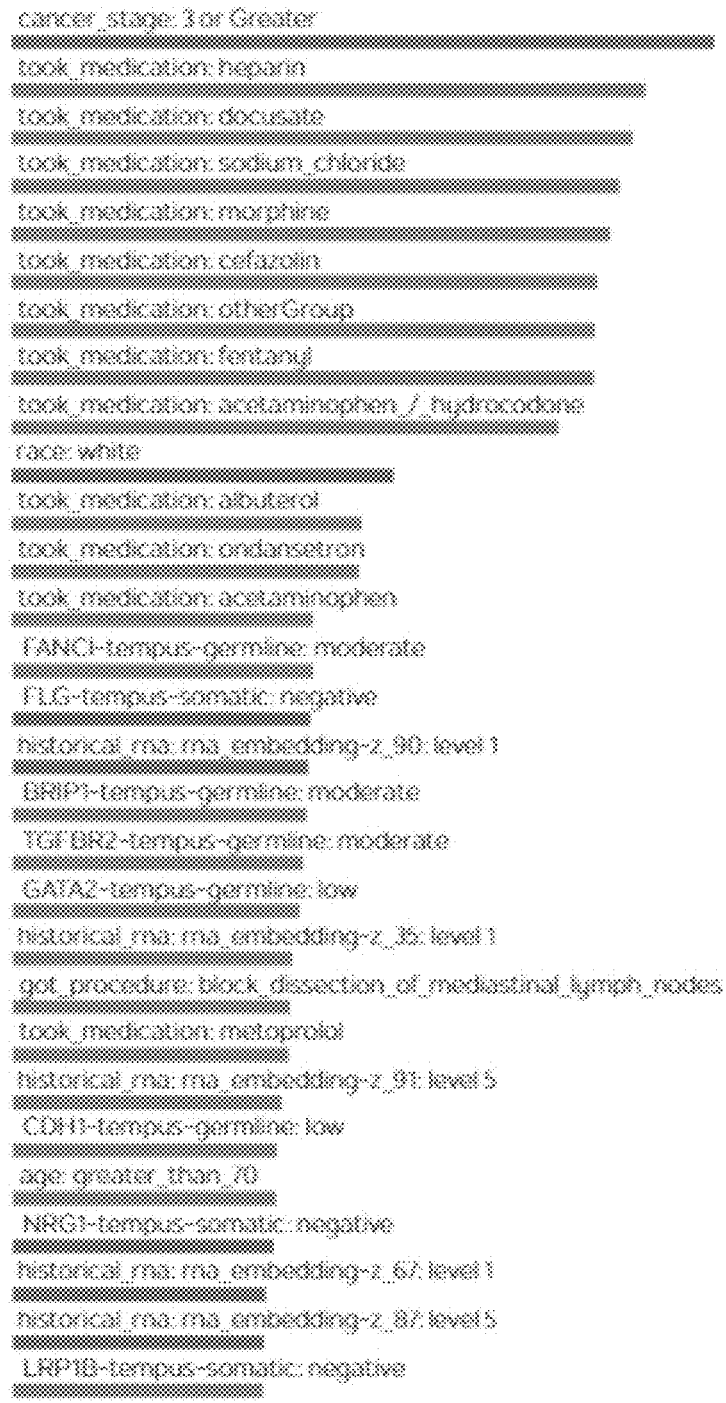
Figure 216:
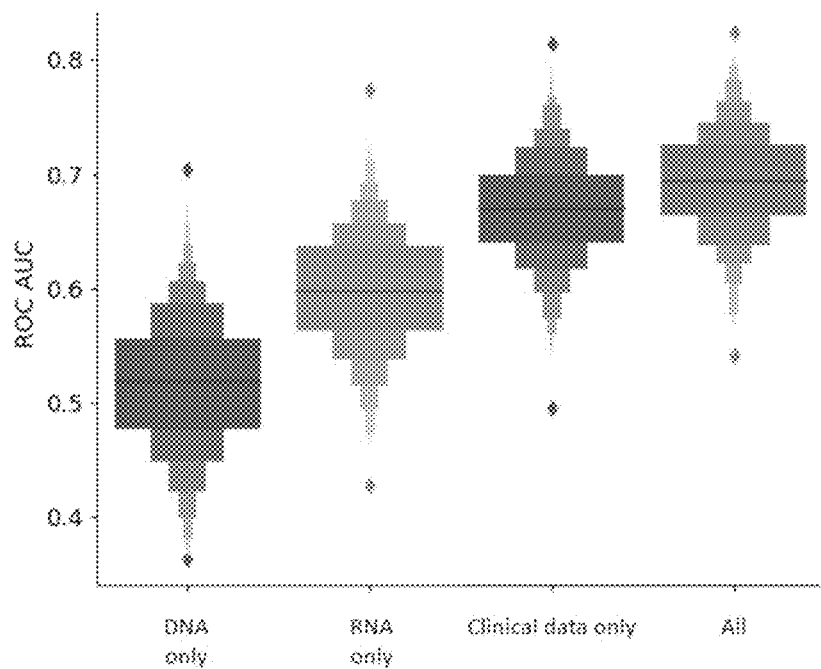
Figure 217:
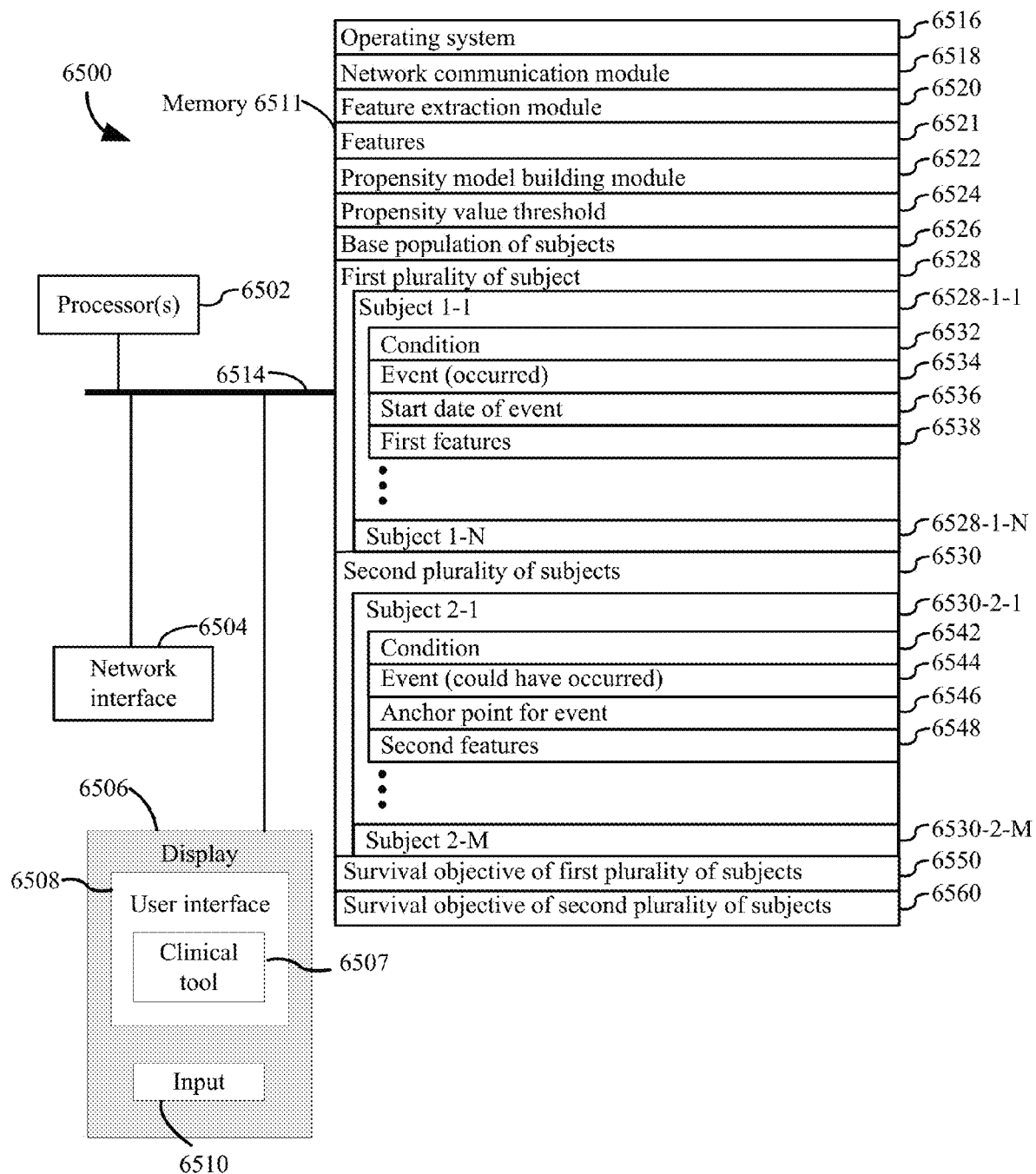
Figure 218:
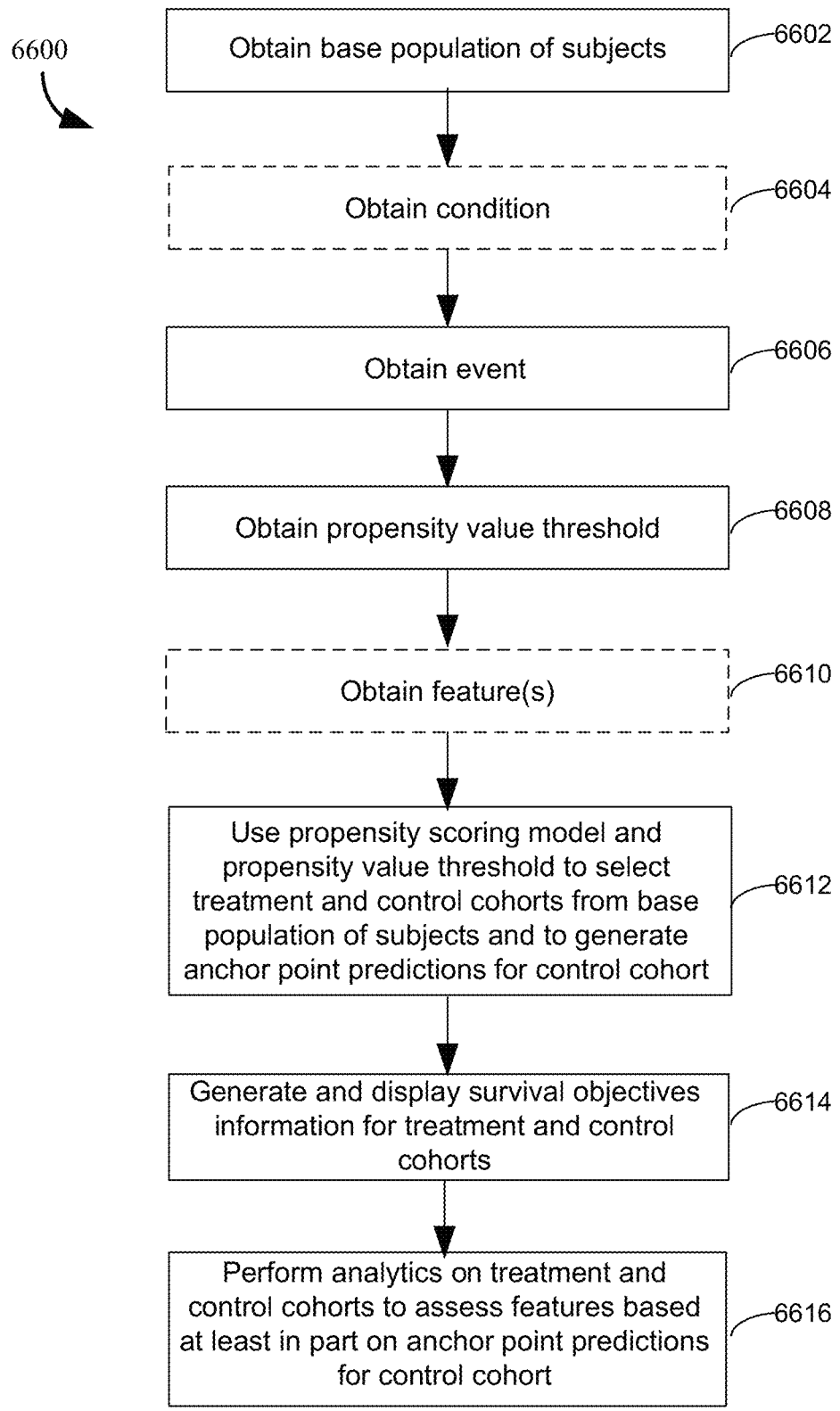
Figure 219:
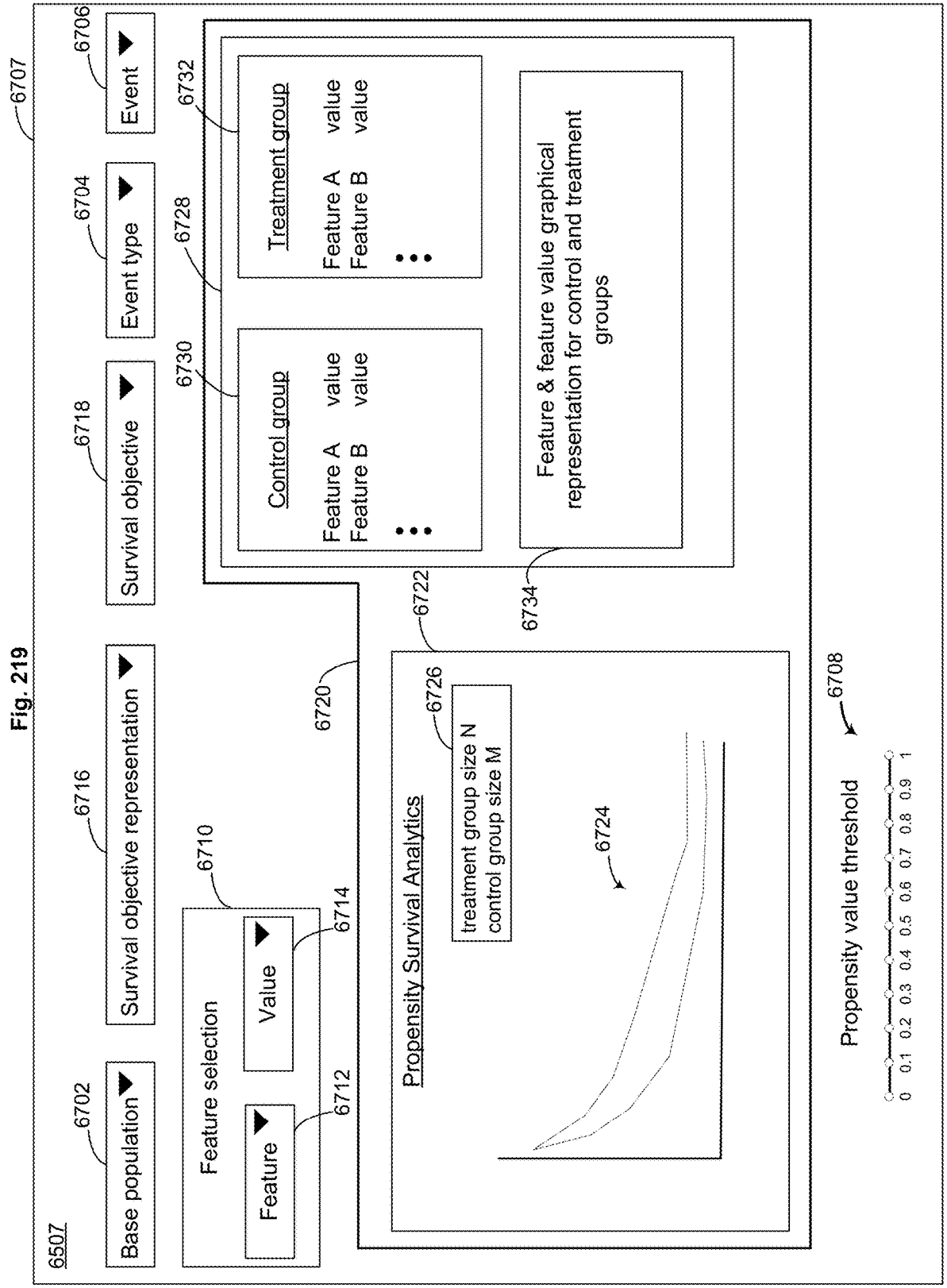
Figure 220A:
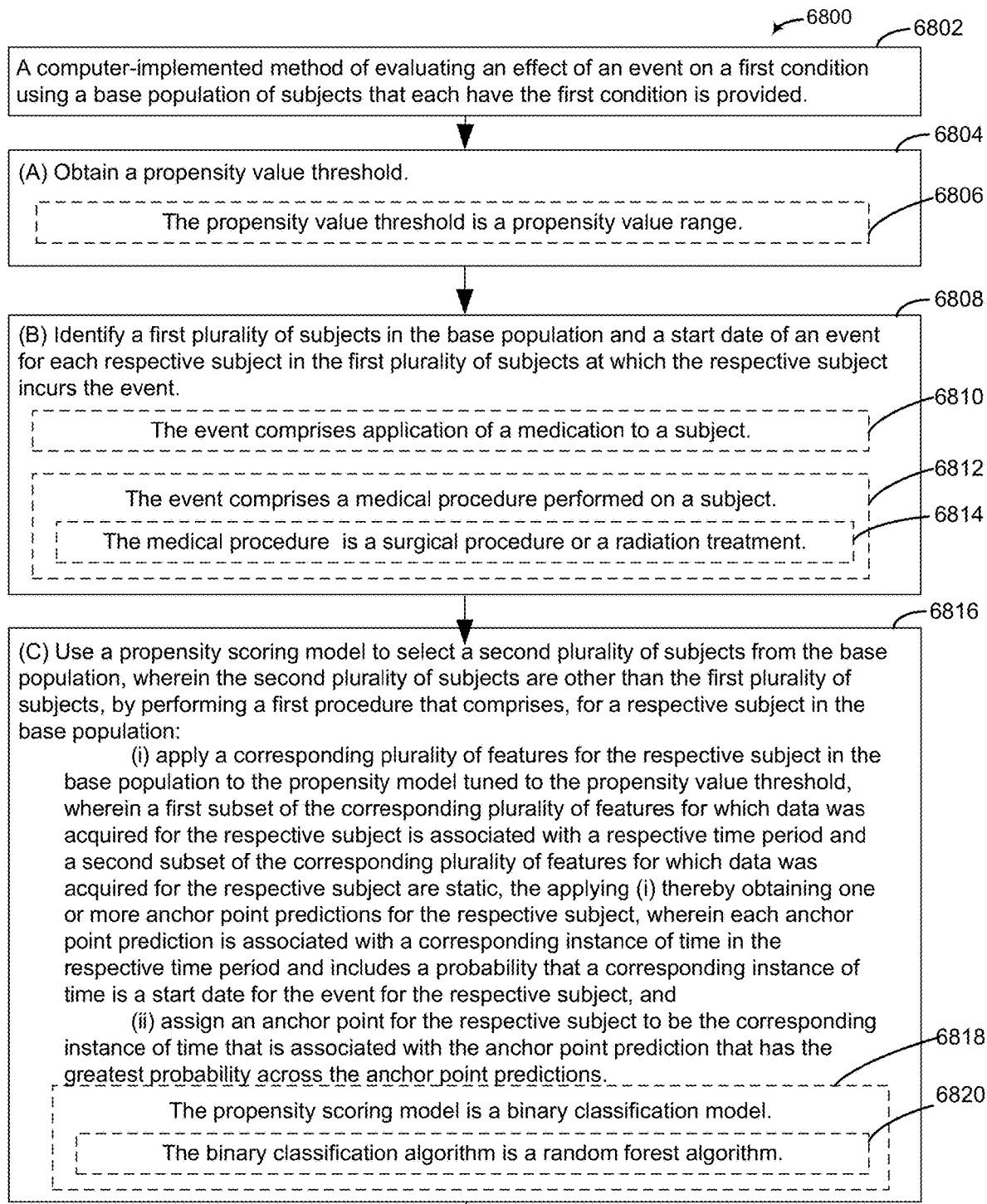
Figure 220B:
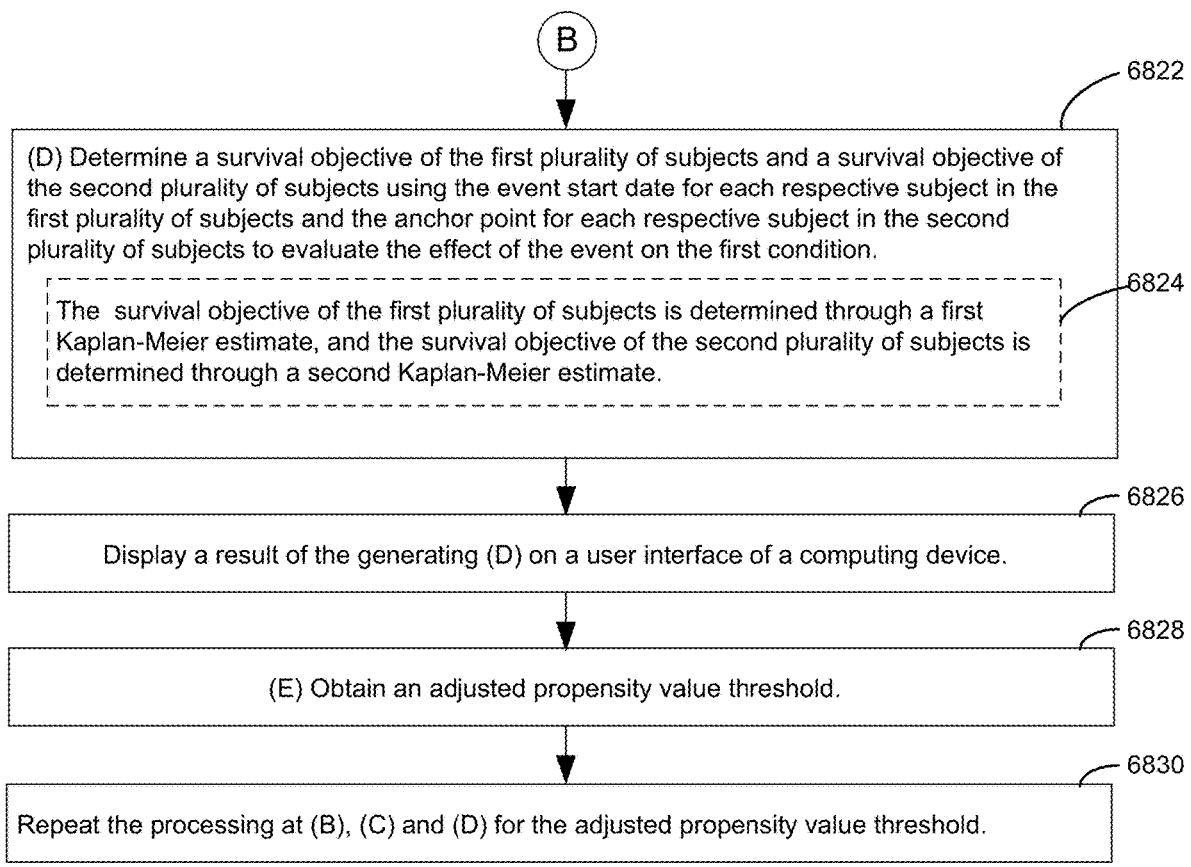
Figure 222A:
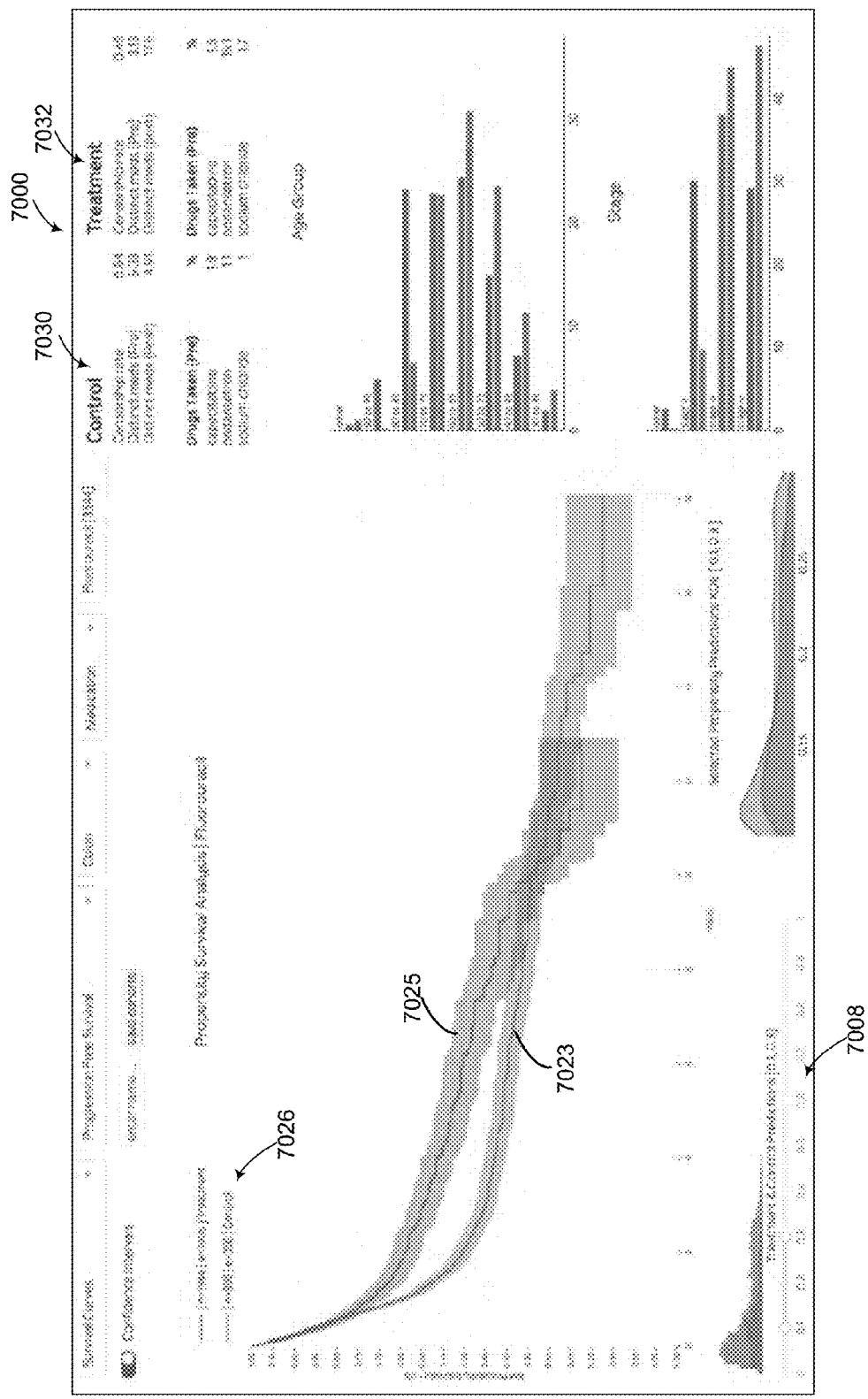
Figure 222B:
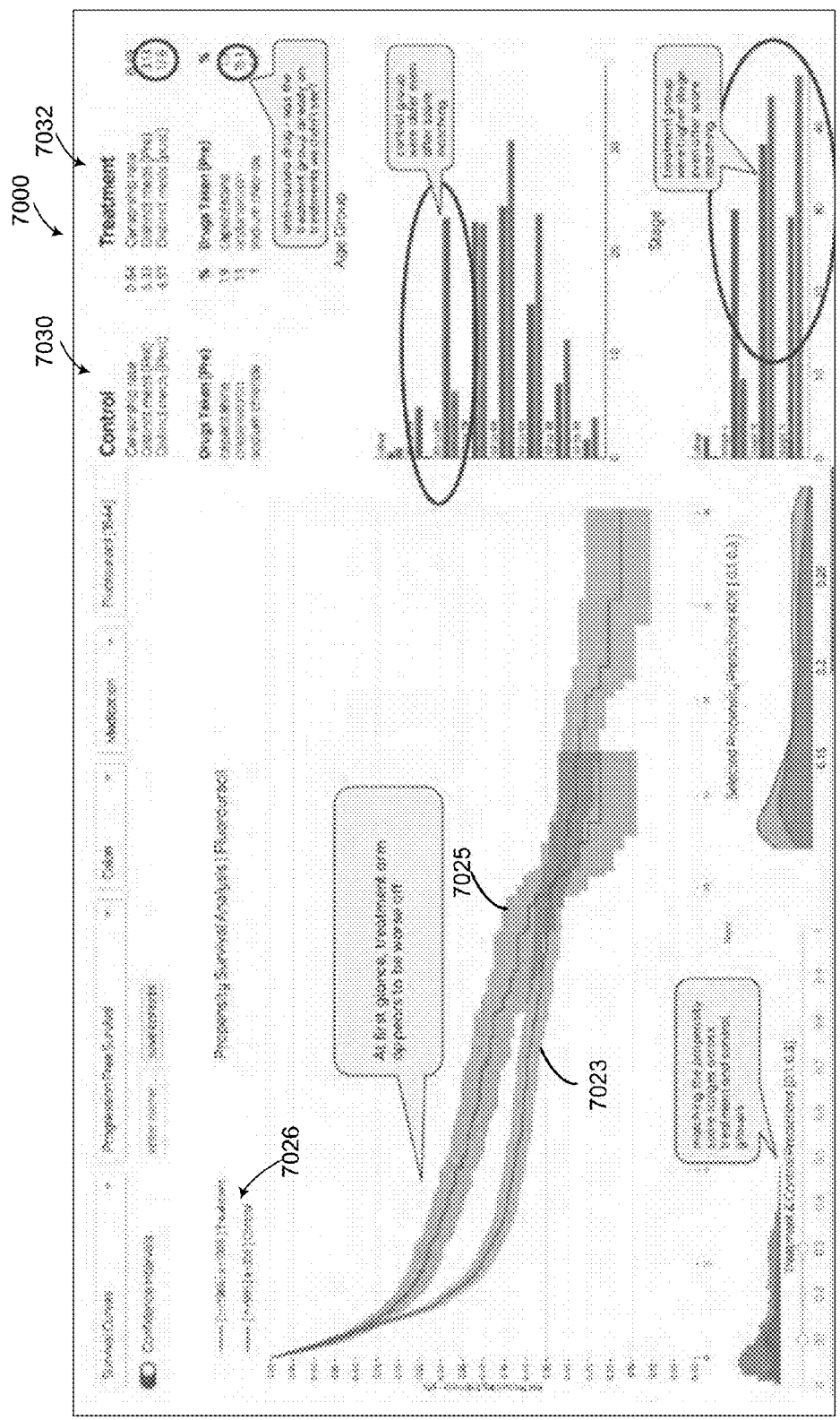
Figure 222C:
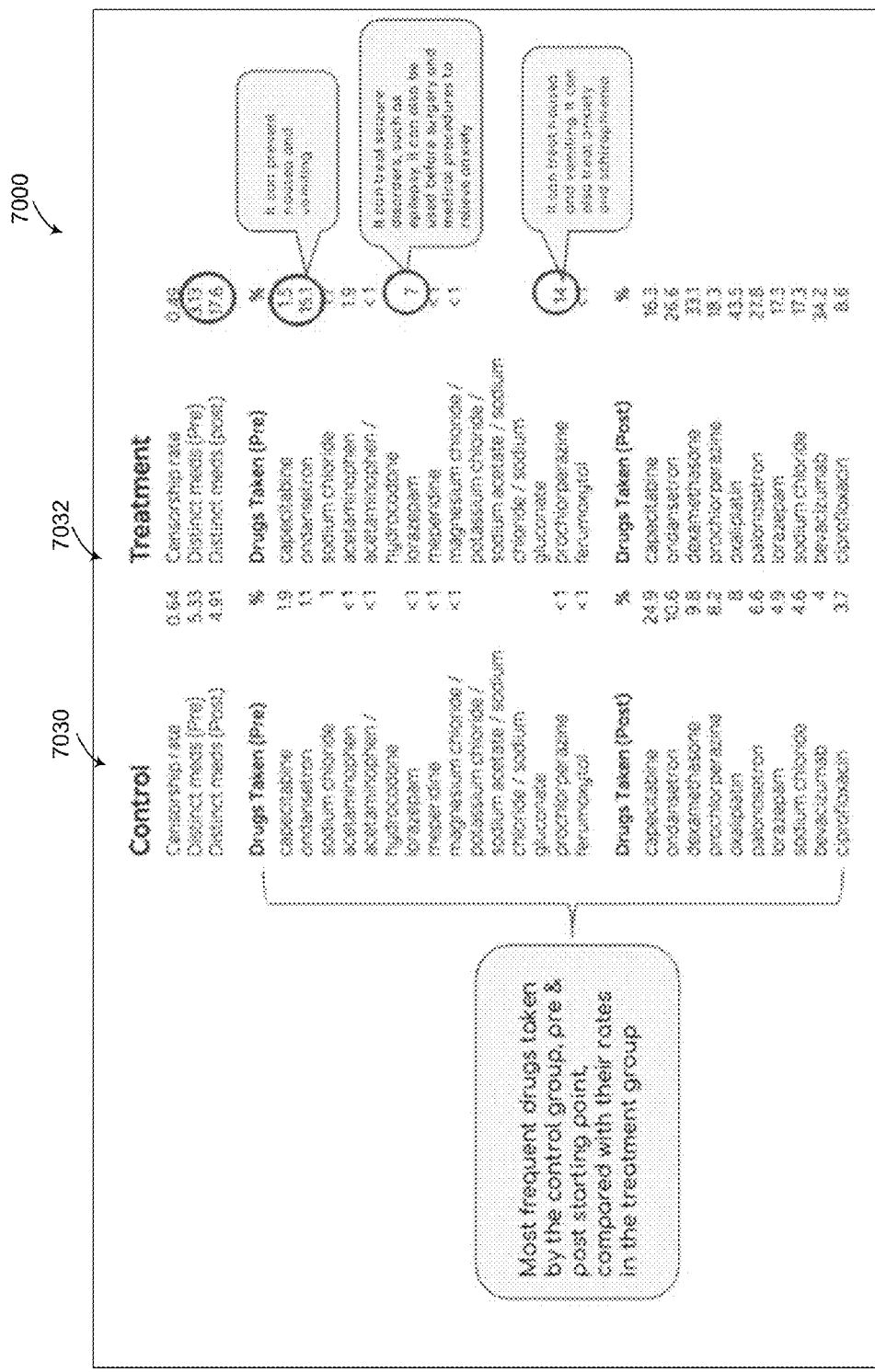
Figure 223:
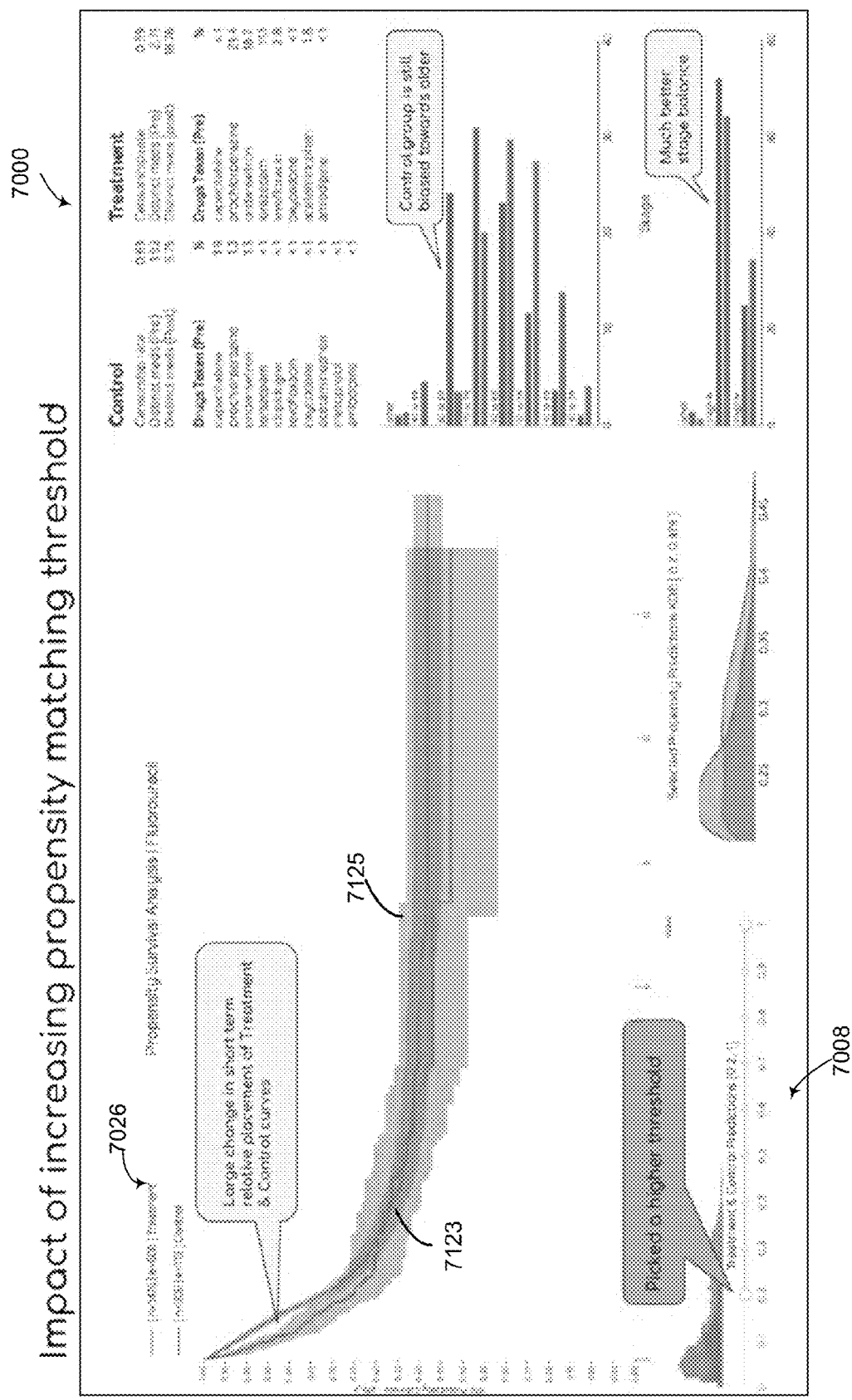
Figure 224A:
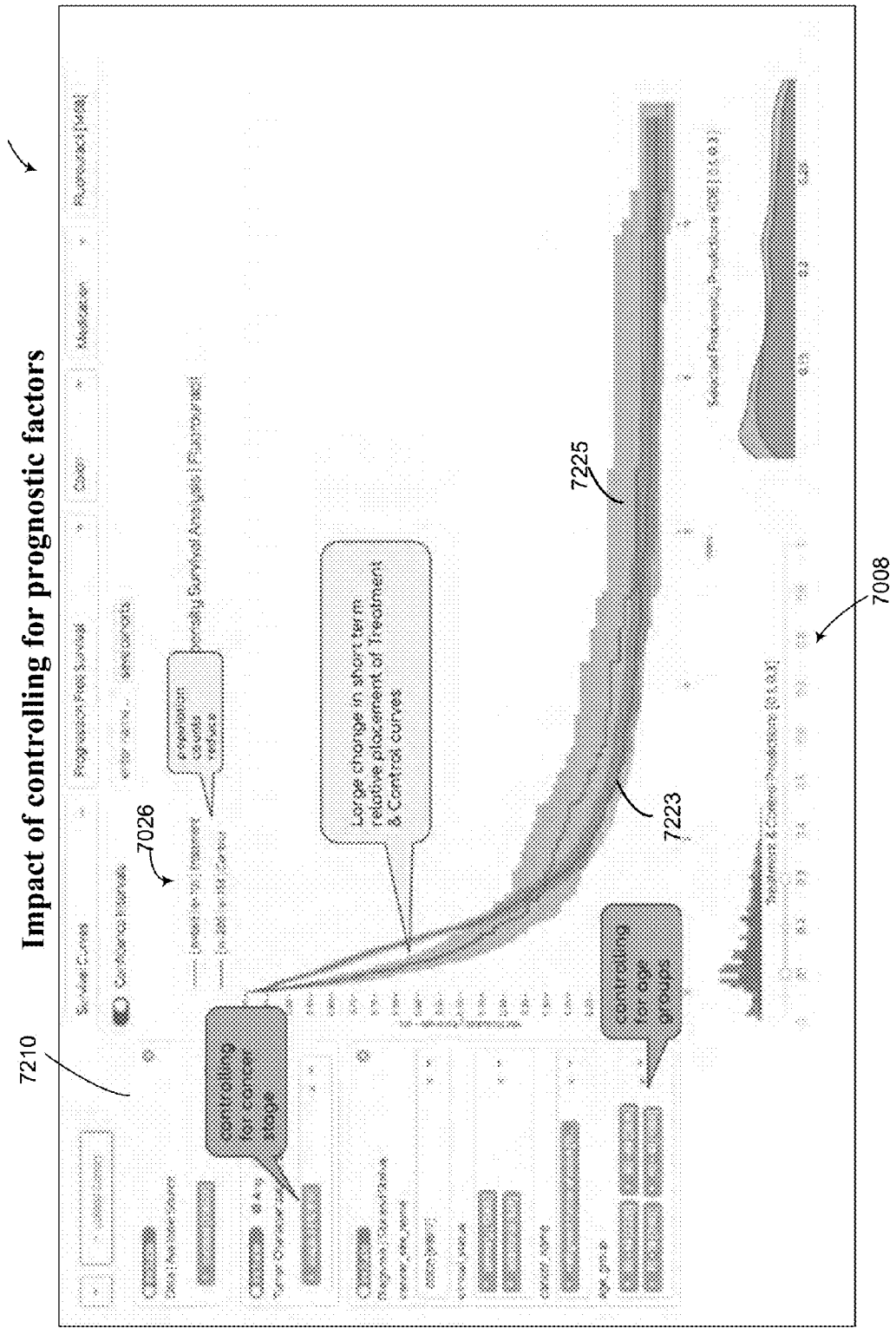
Figure 224B:
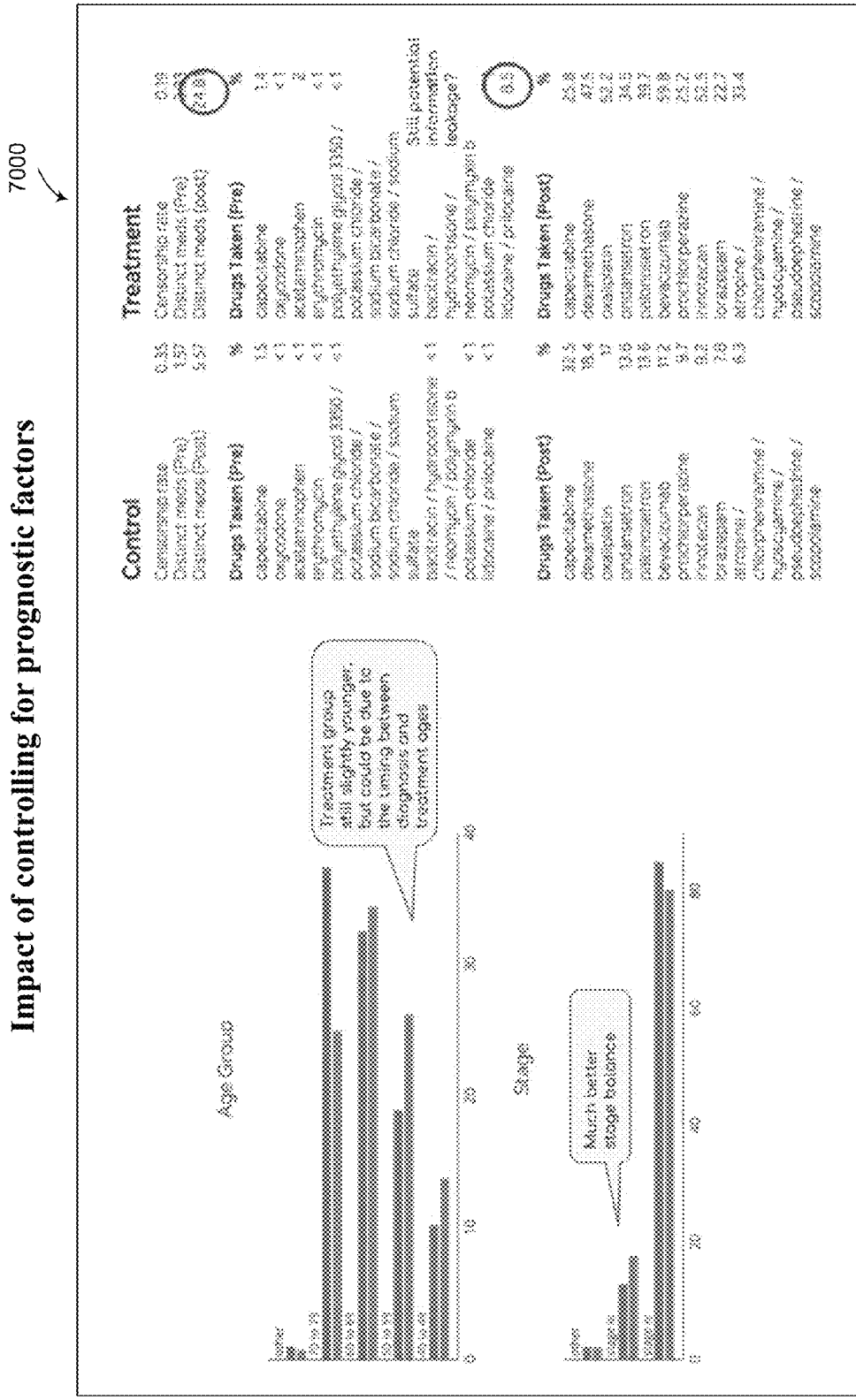
Figure 225A:
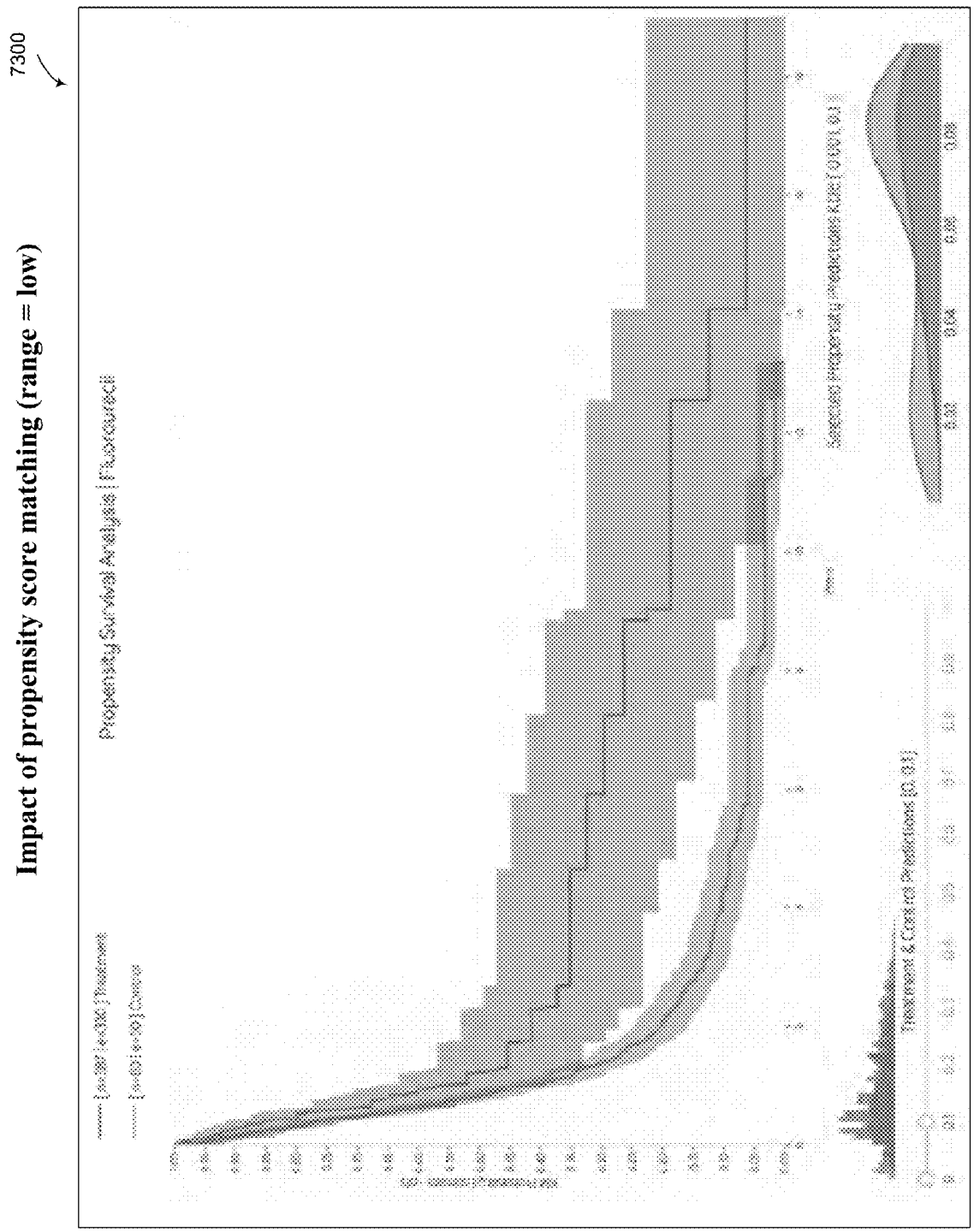
Figure 225B:
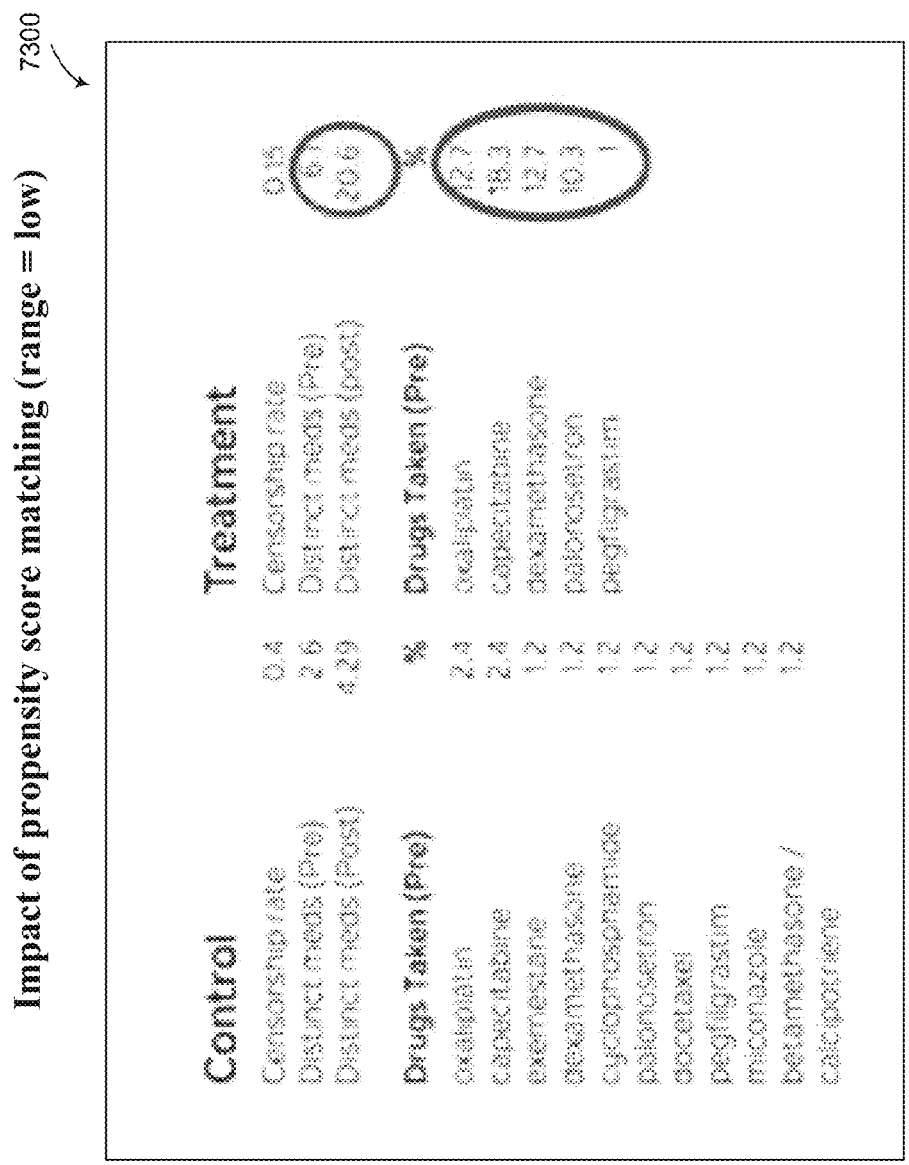
Figure 226A:
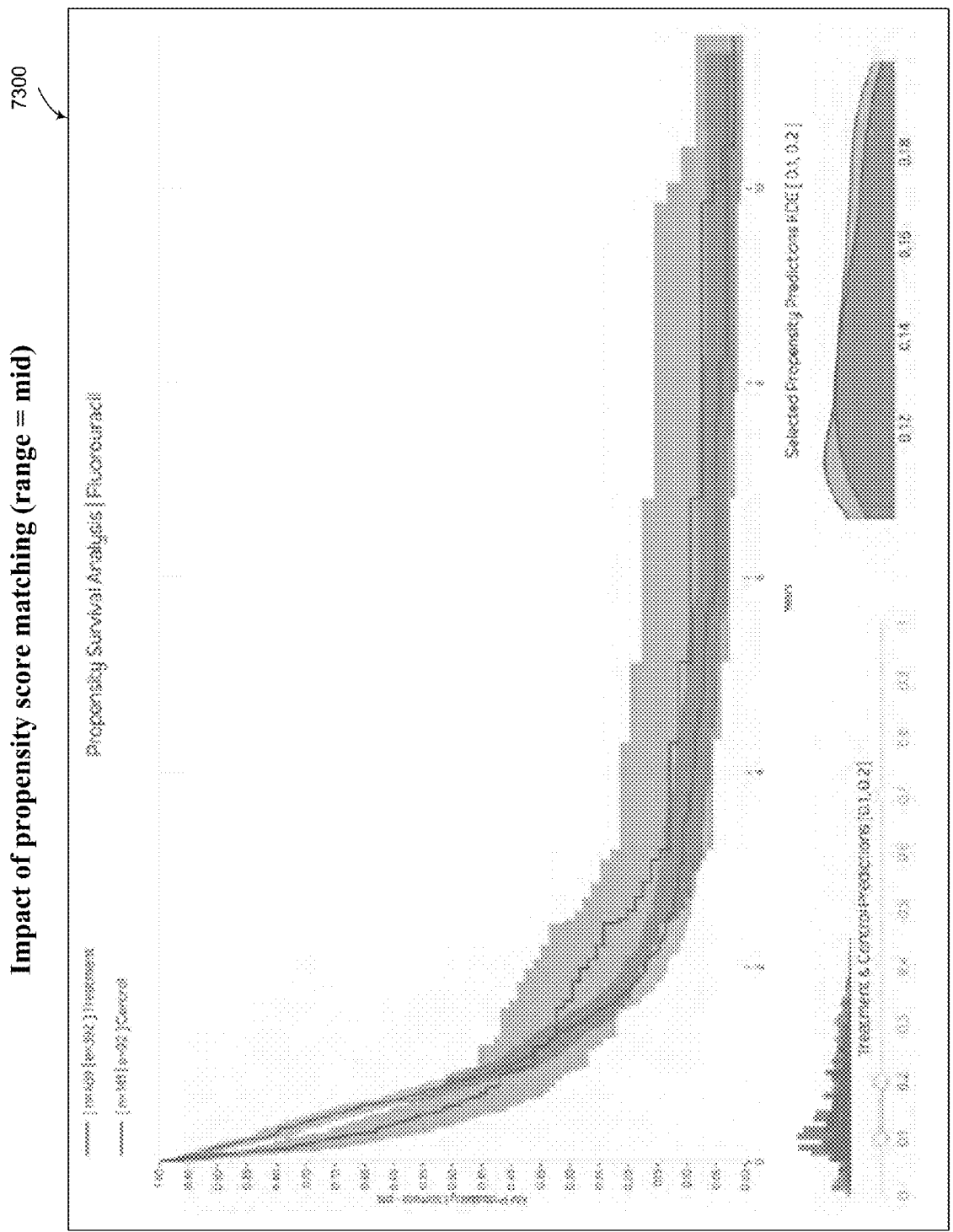
Figure 226B:
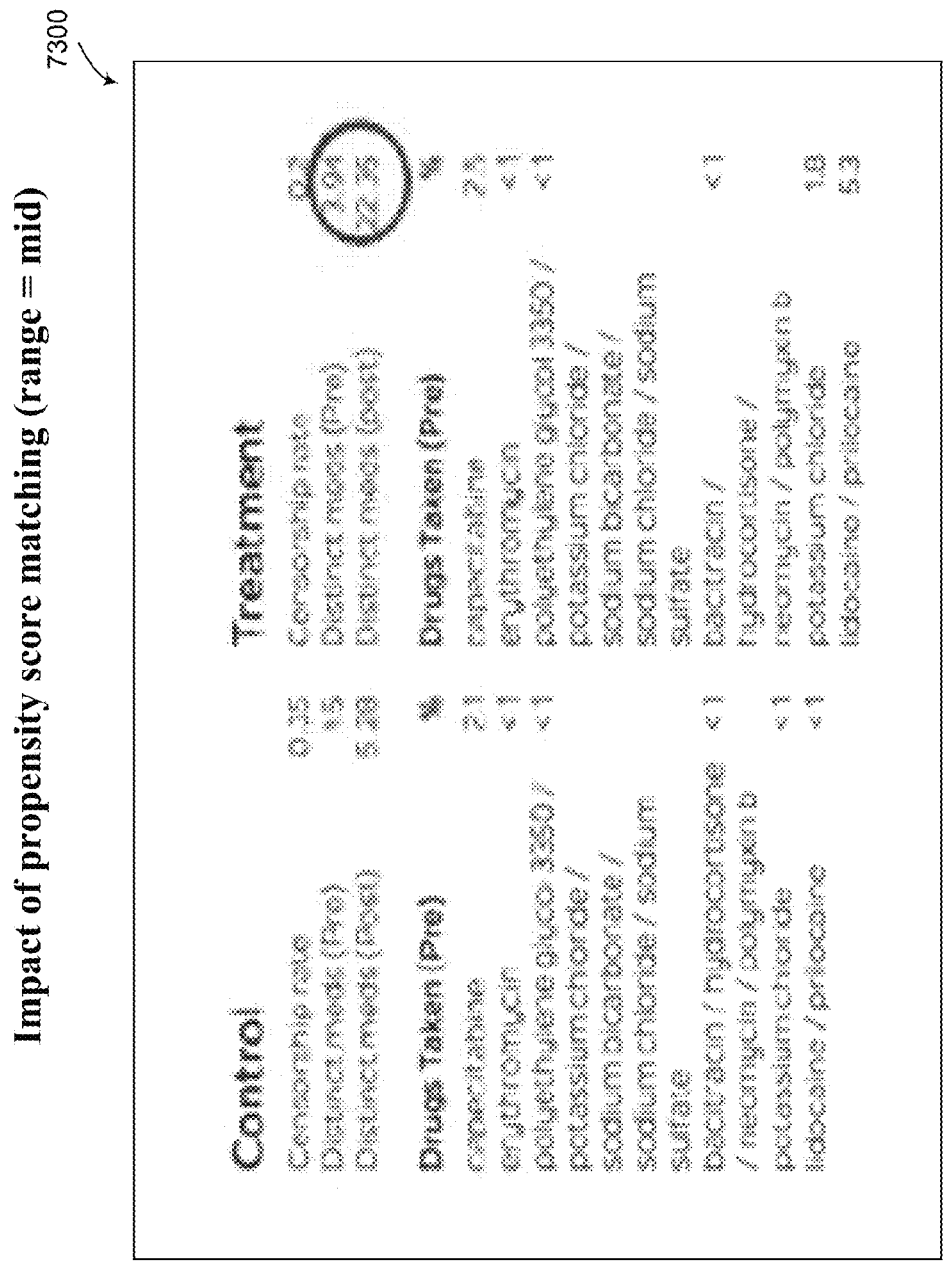
Figure 227A:
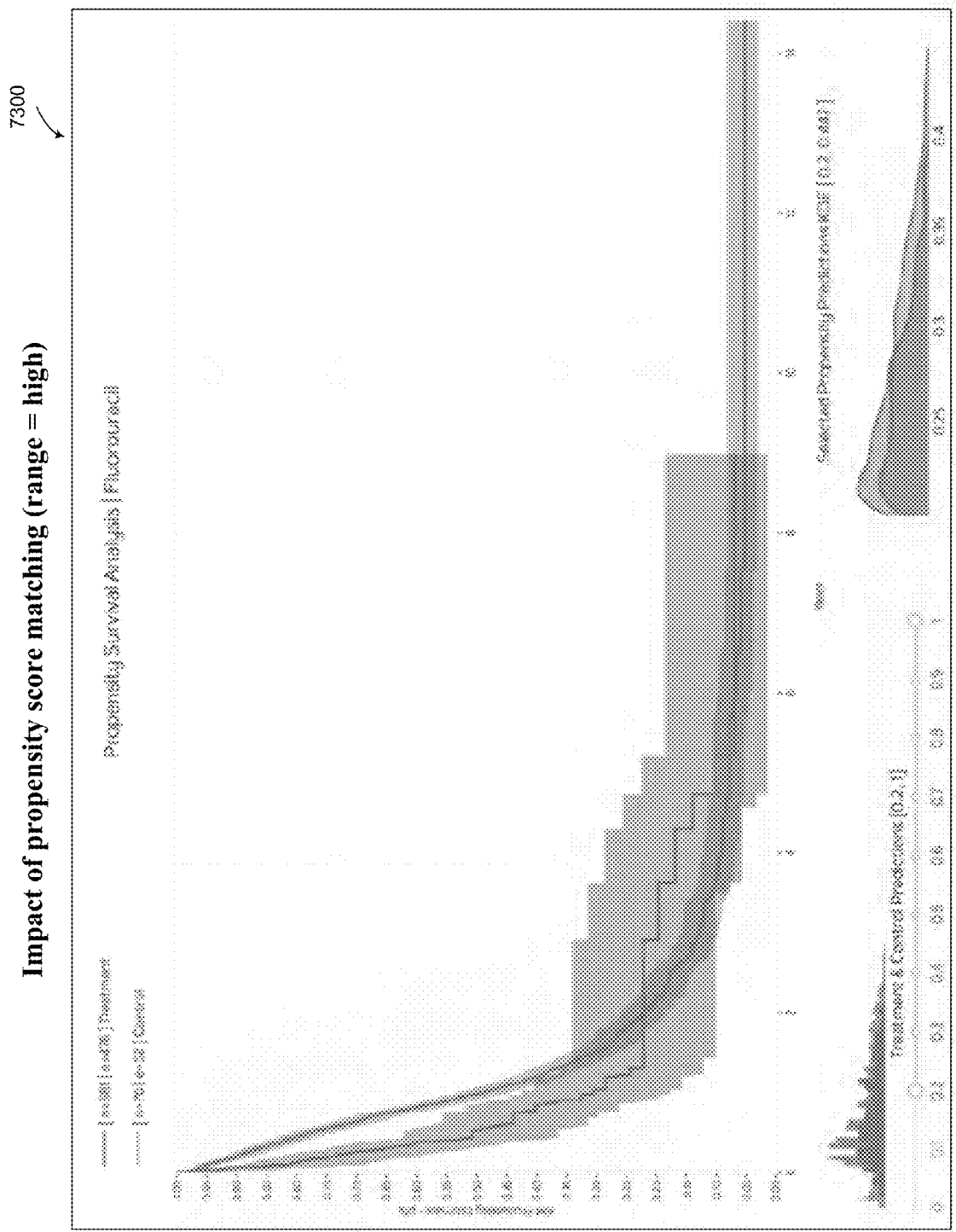
Figure 228:
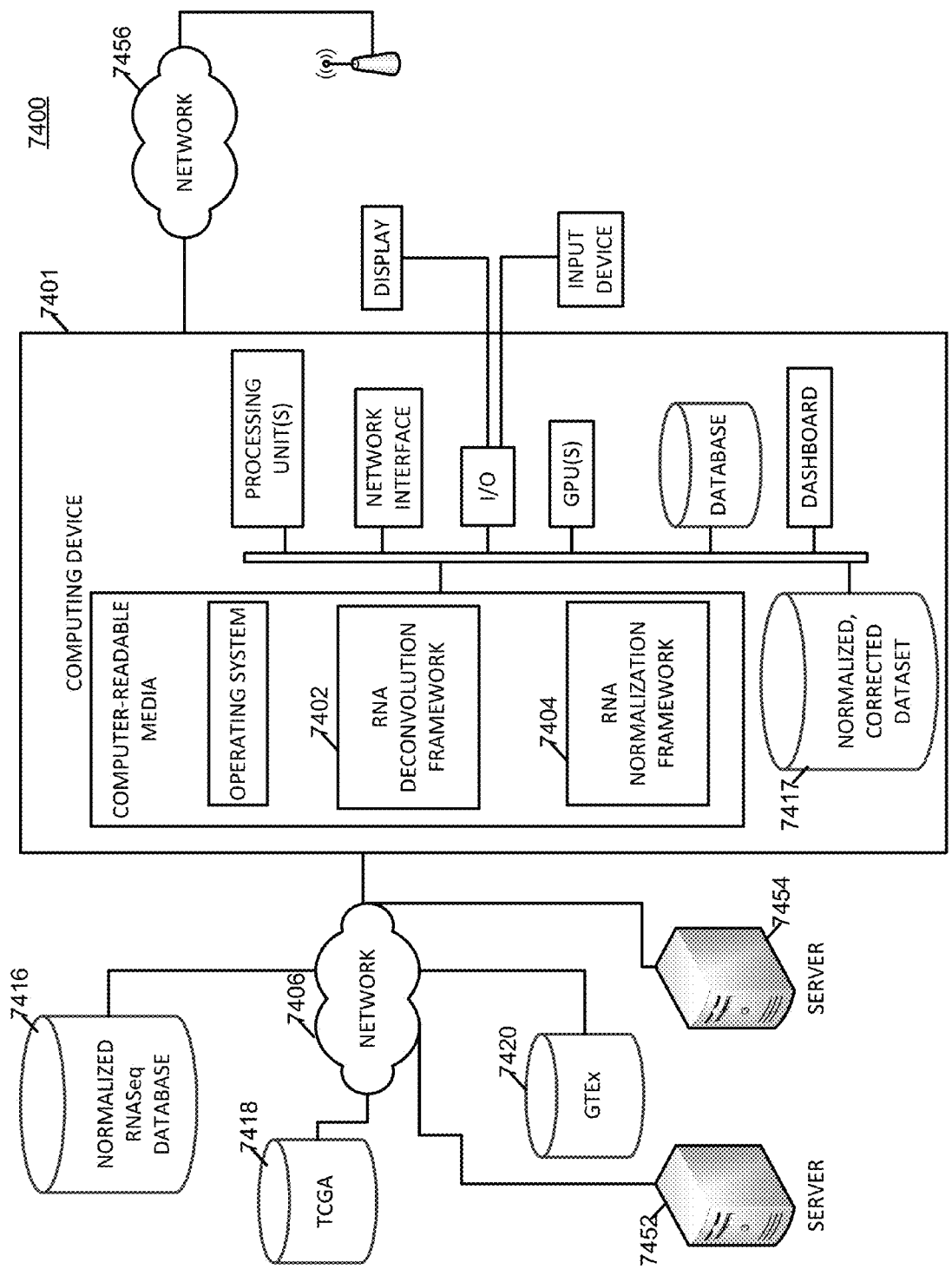
Figure 229:
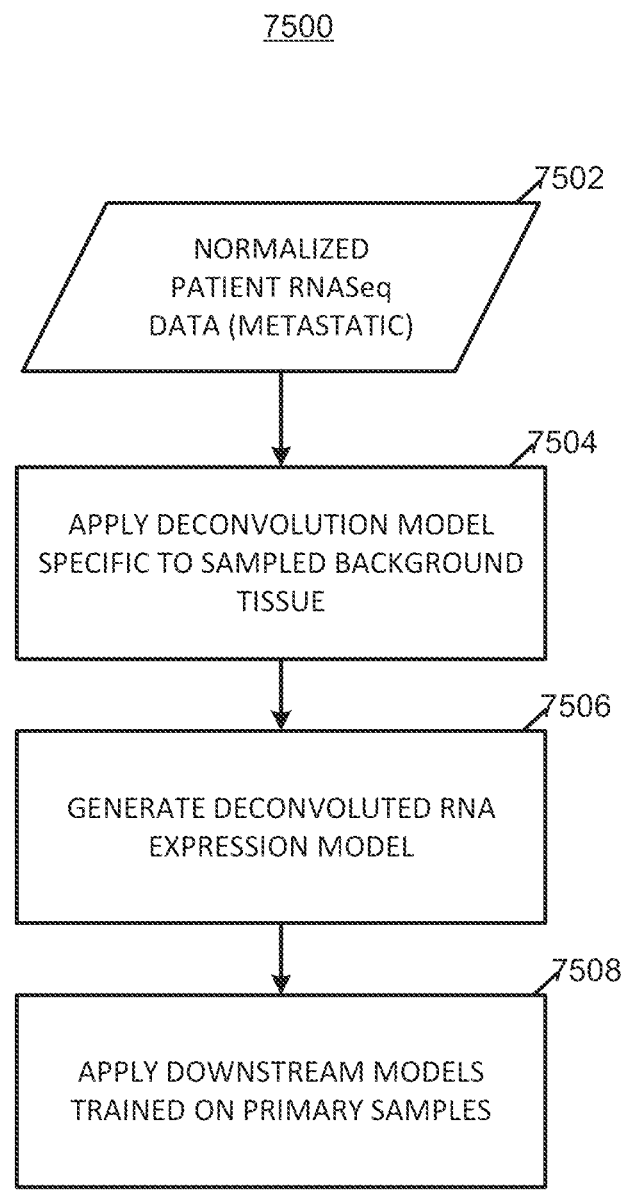
Figure 230:
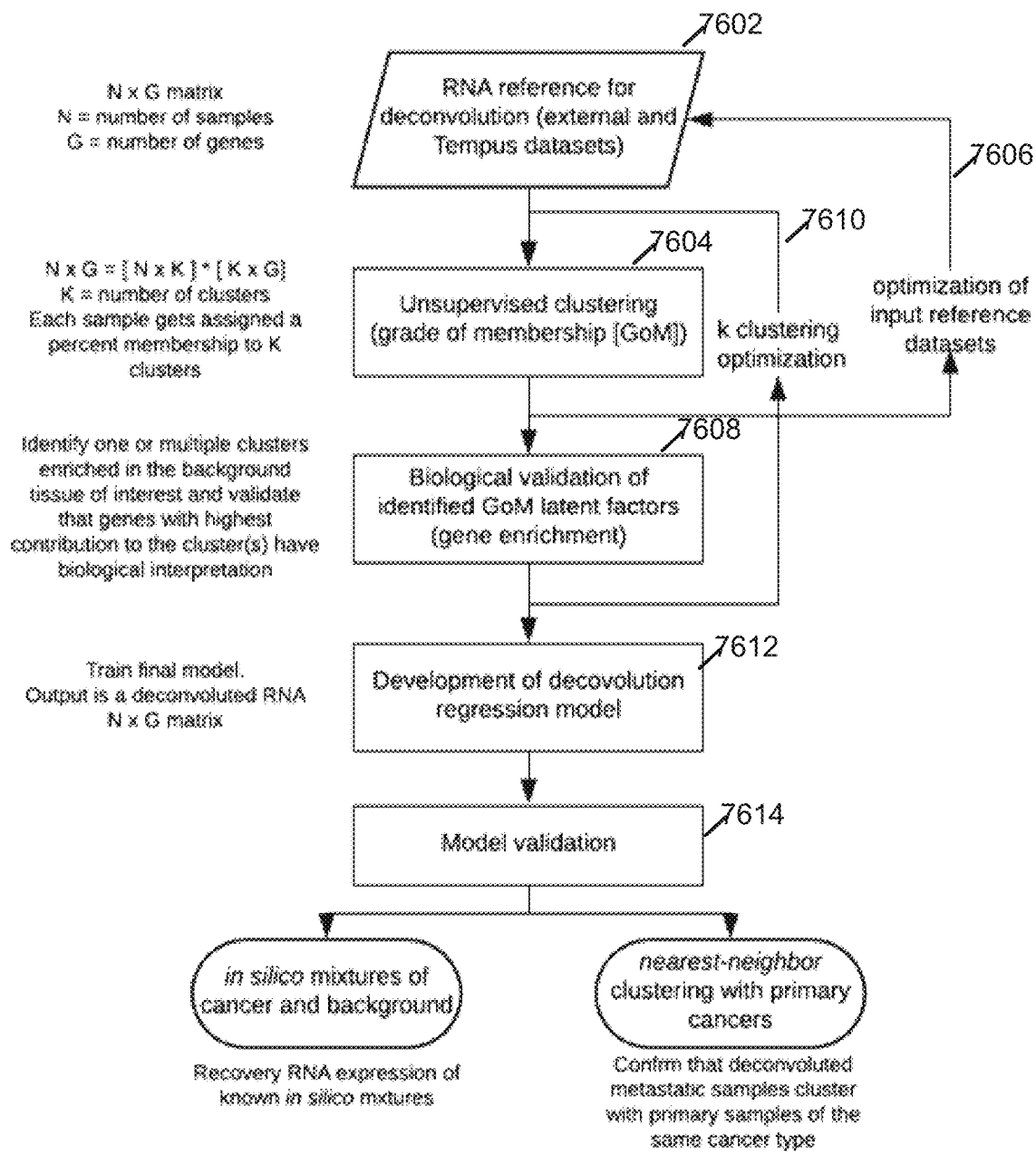
Figure 231:
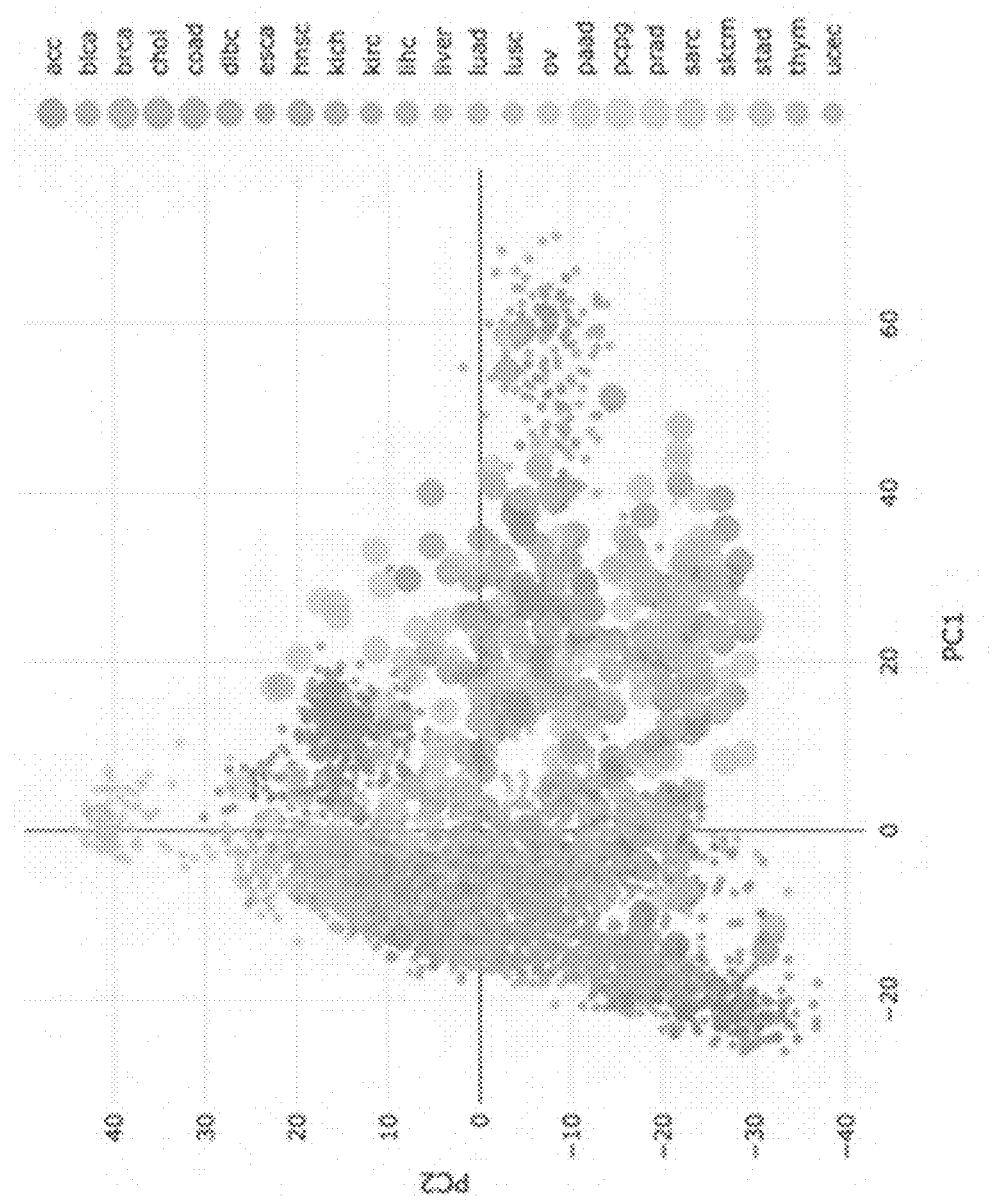
Figure 232:
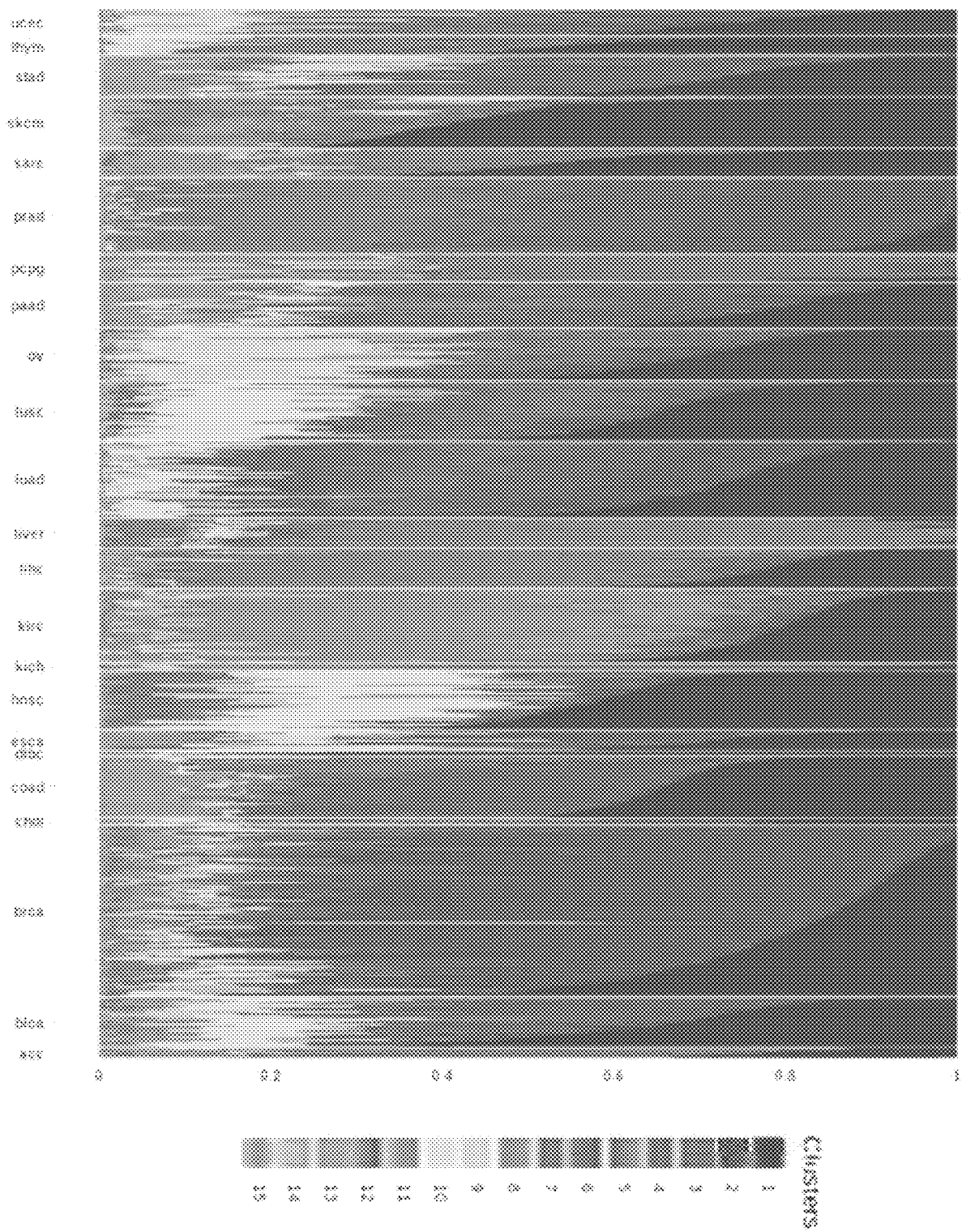
Figure 233:
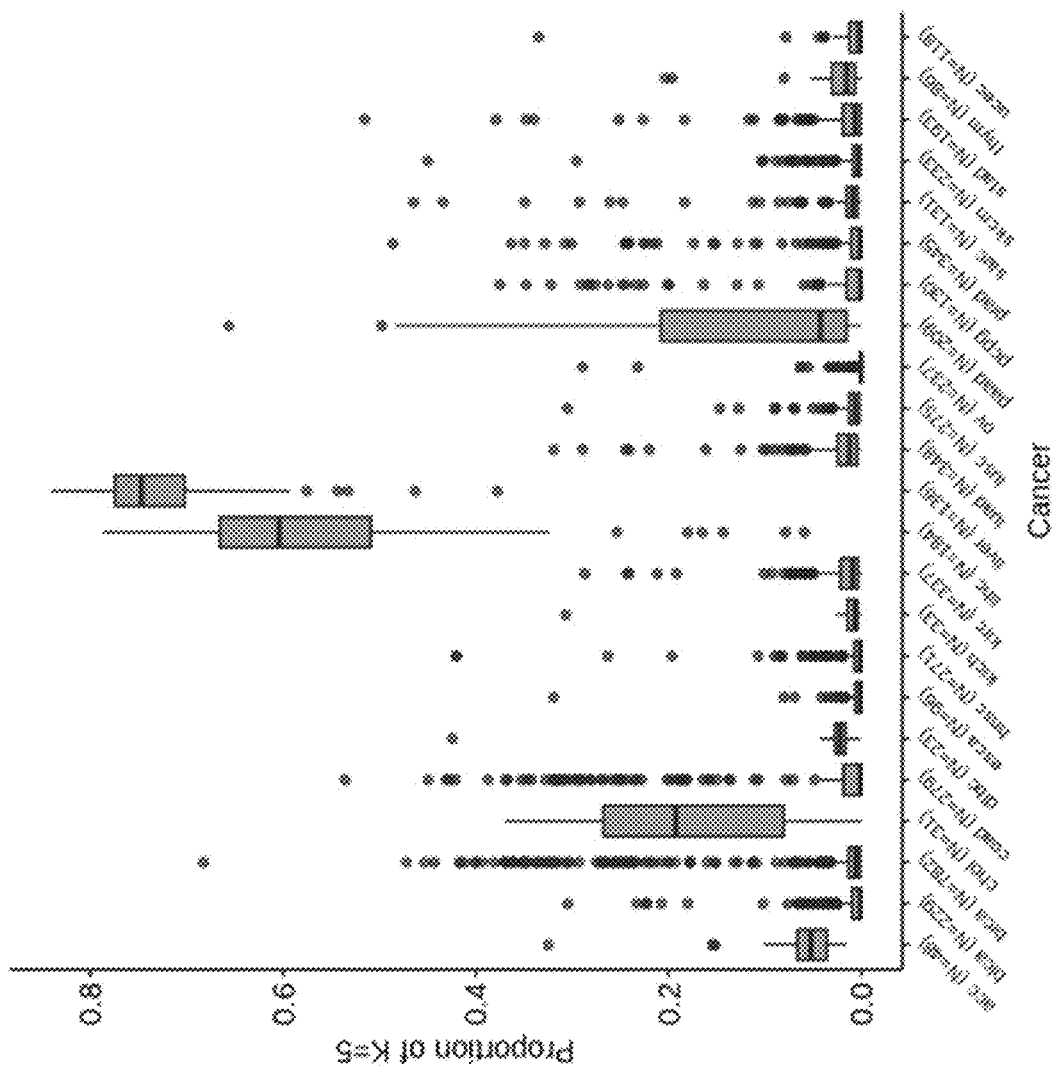
Figure 234:
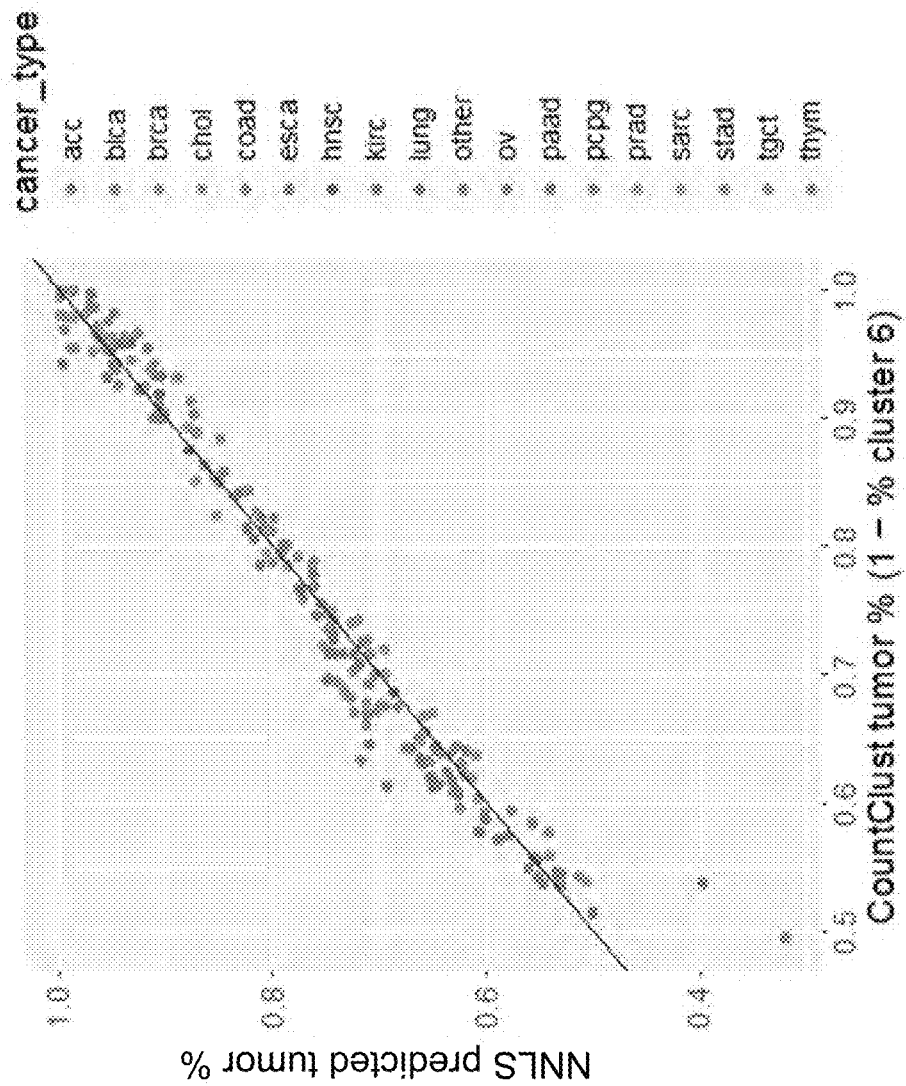
Figure 235:
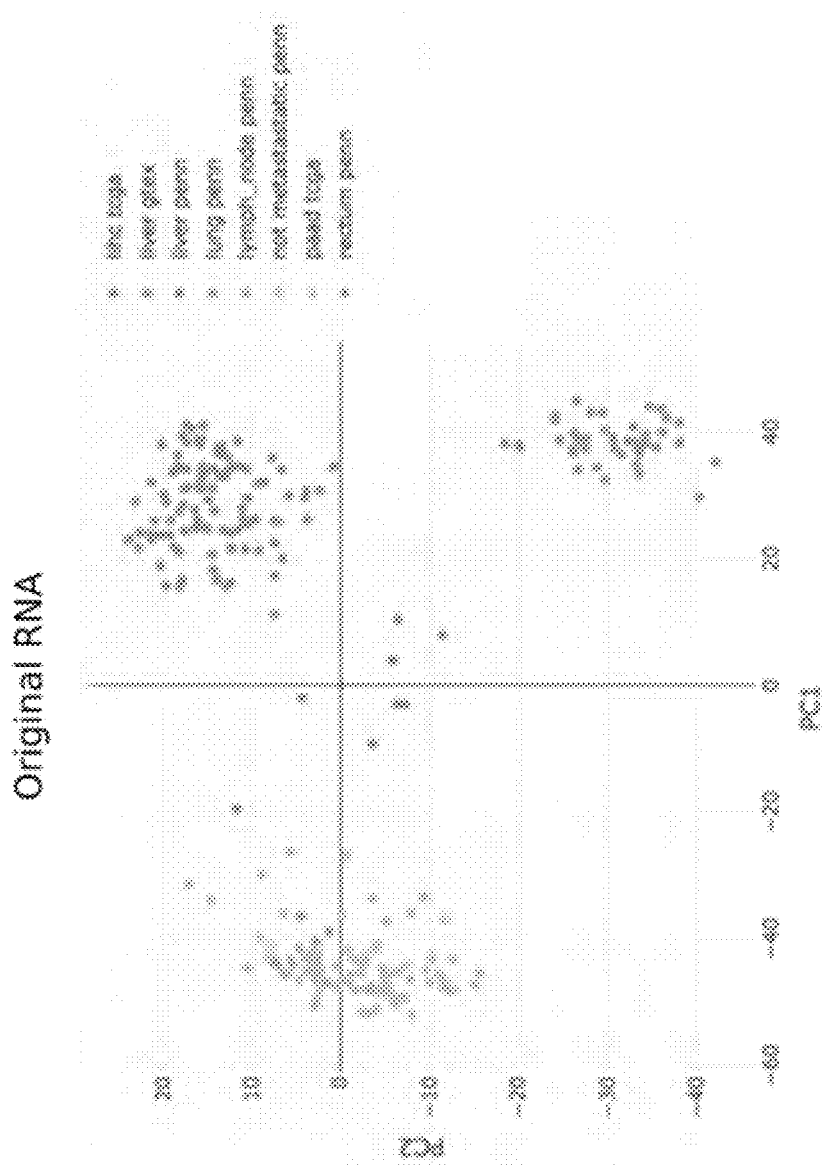
Figure 236:
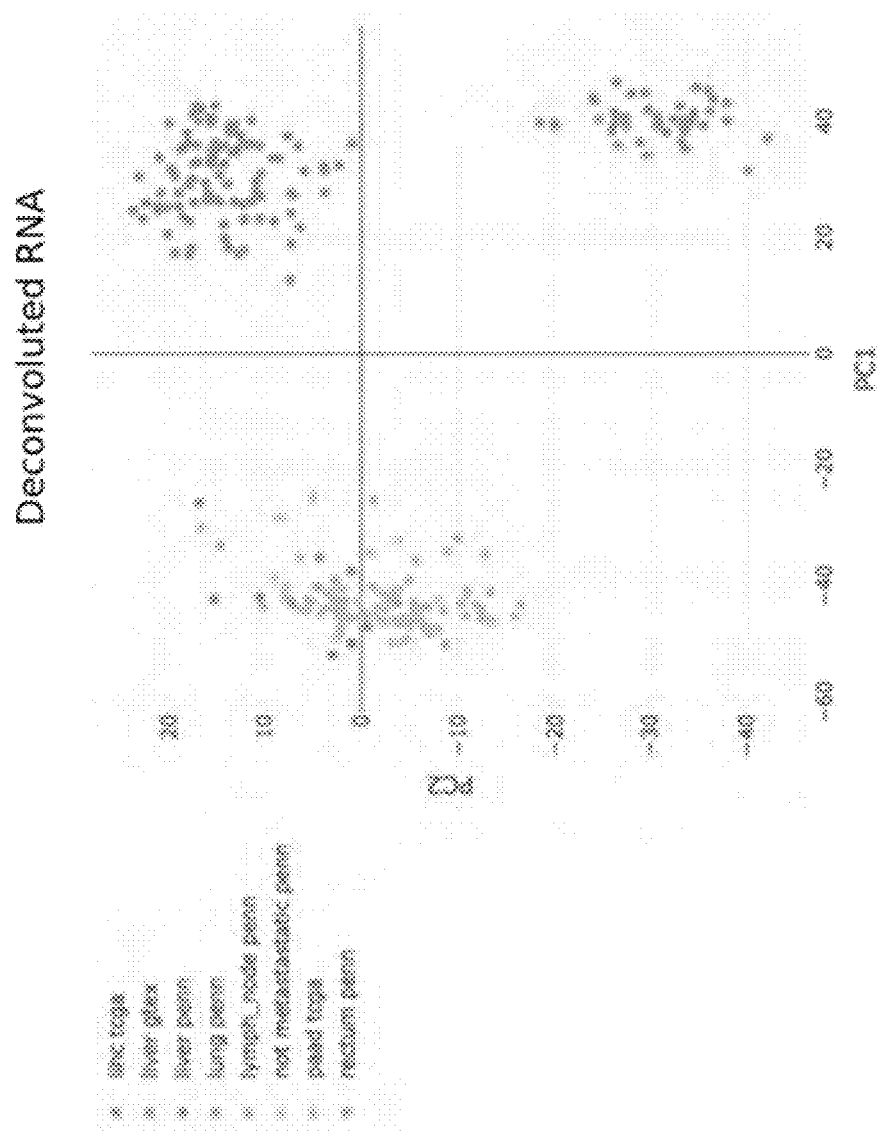
Figure 236A:
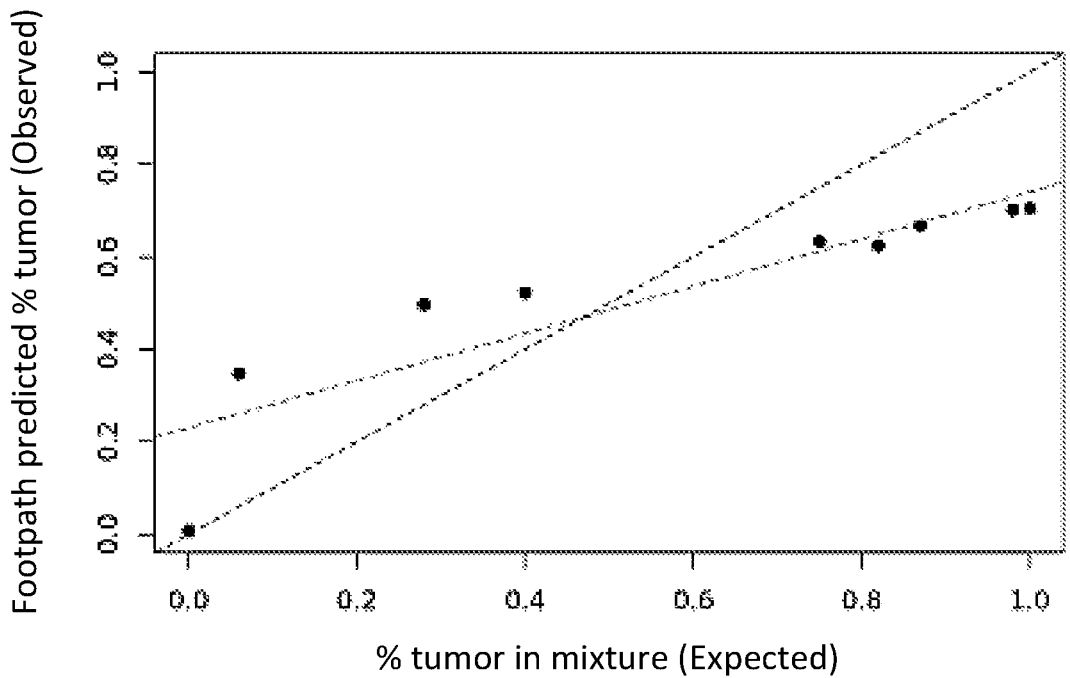
Figure 236B:
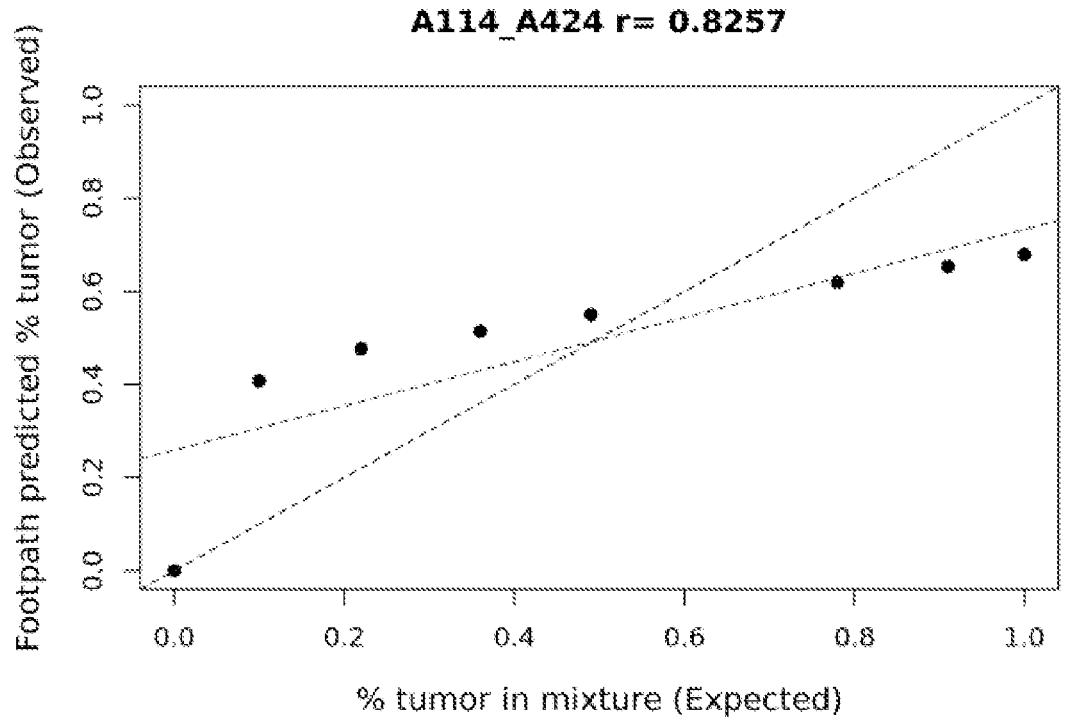
Figure 237A:
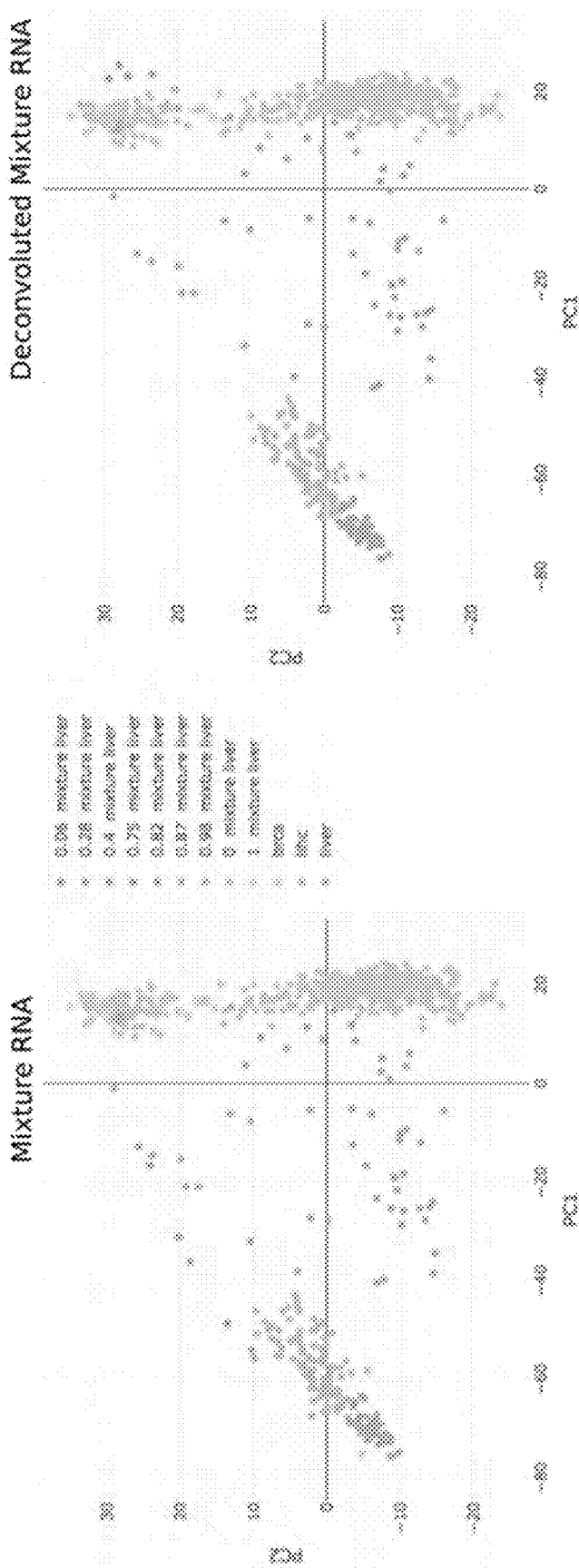
Figure 237B:
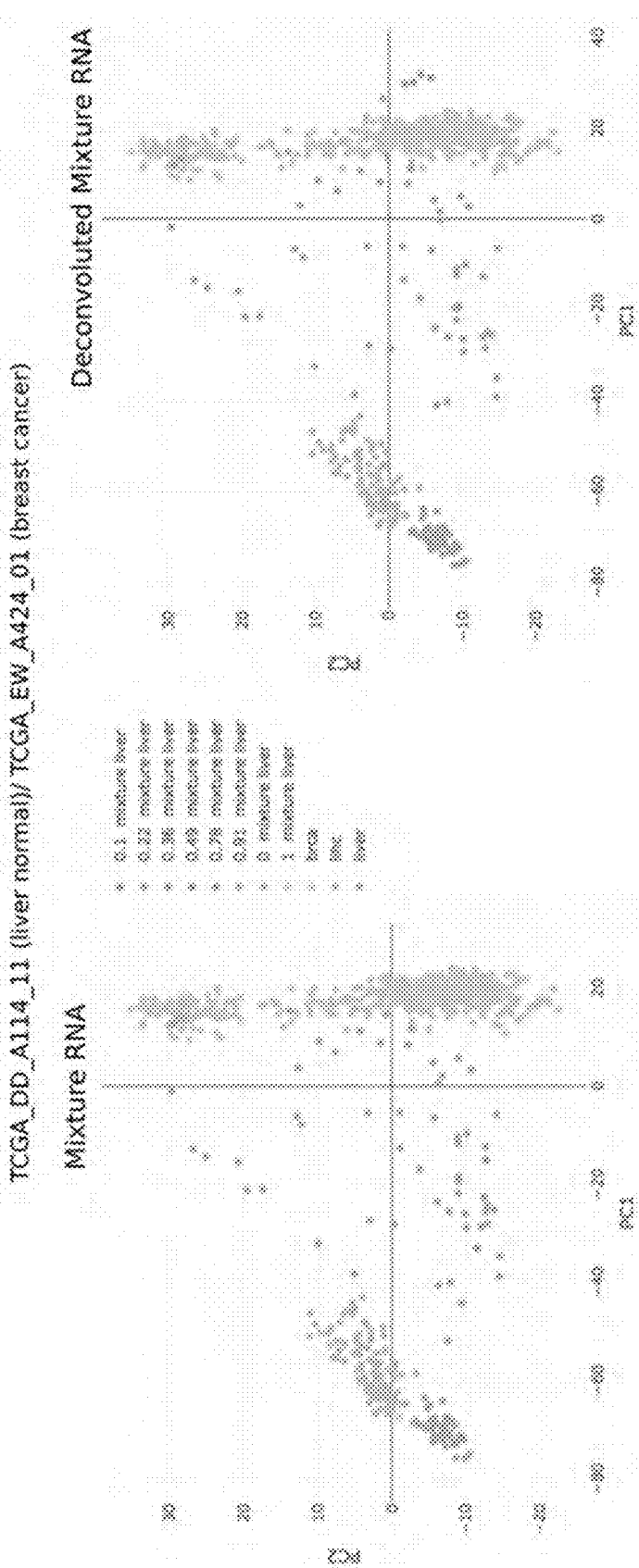
Figure 238:
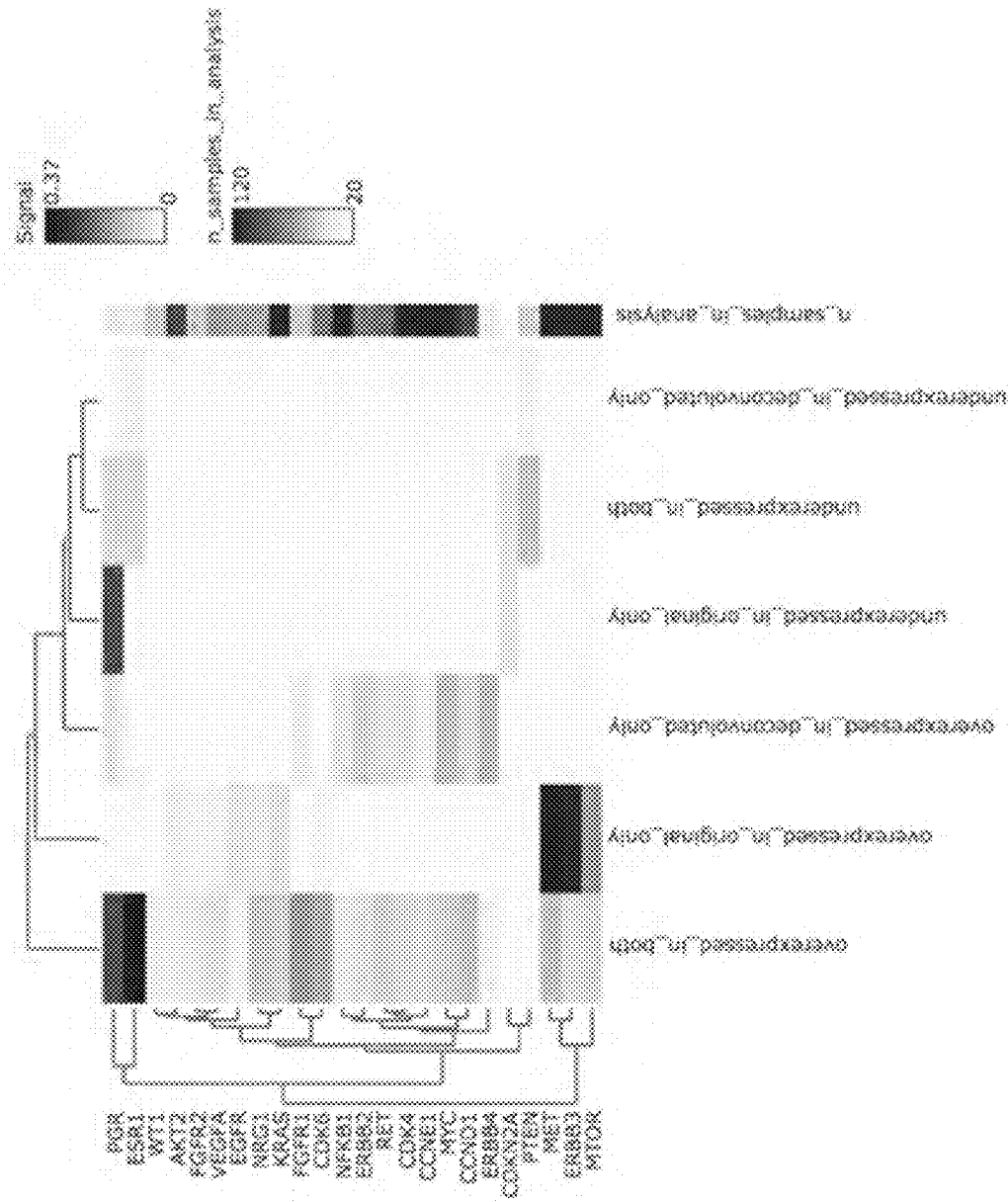
Figure 239A:
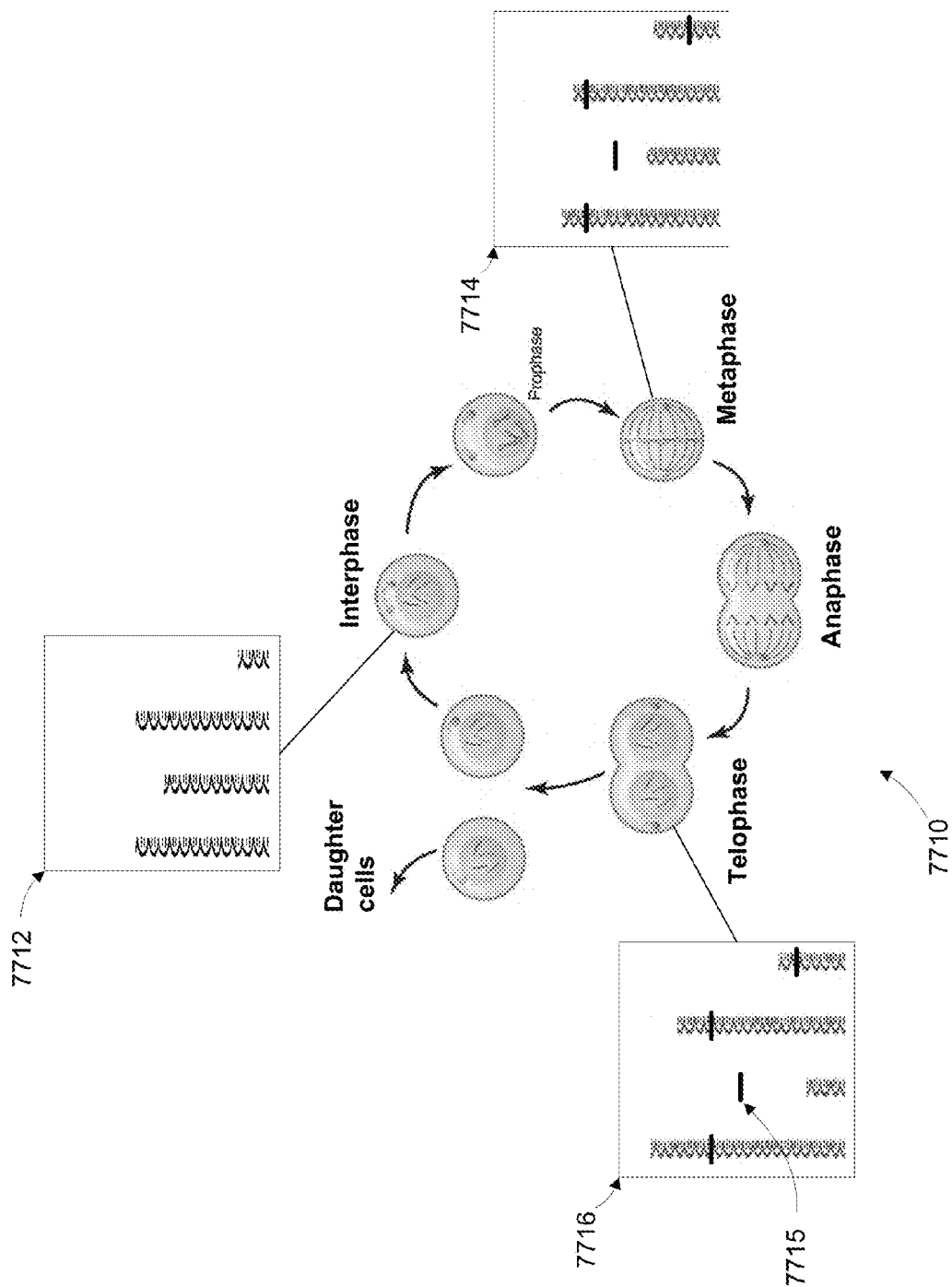
Figure 239B:
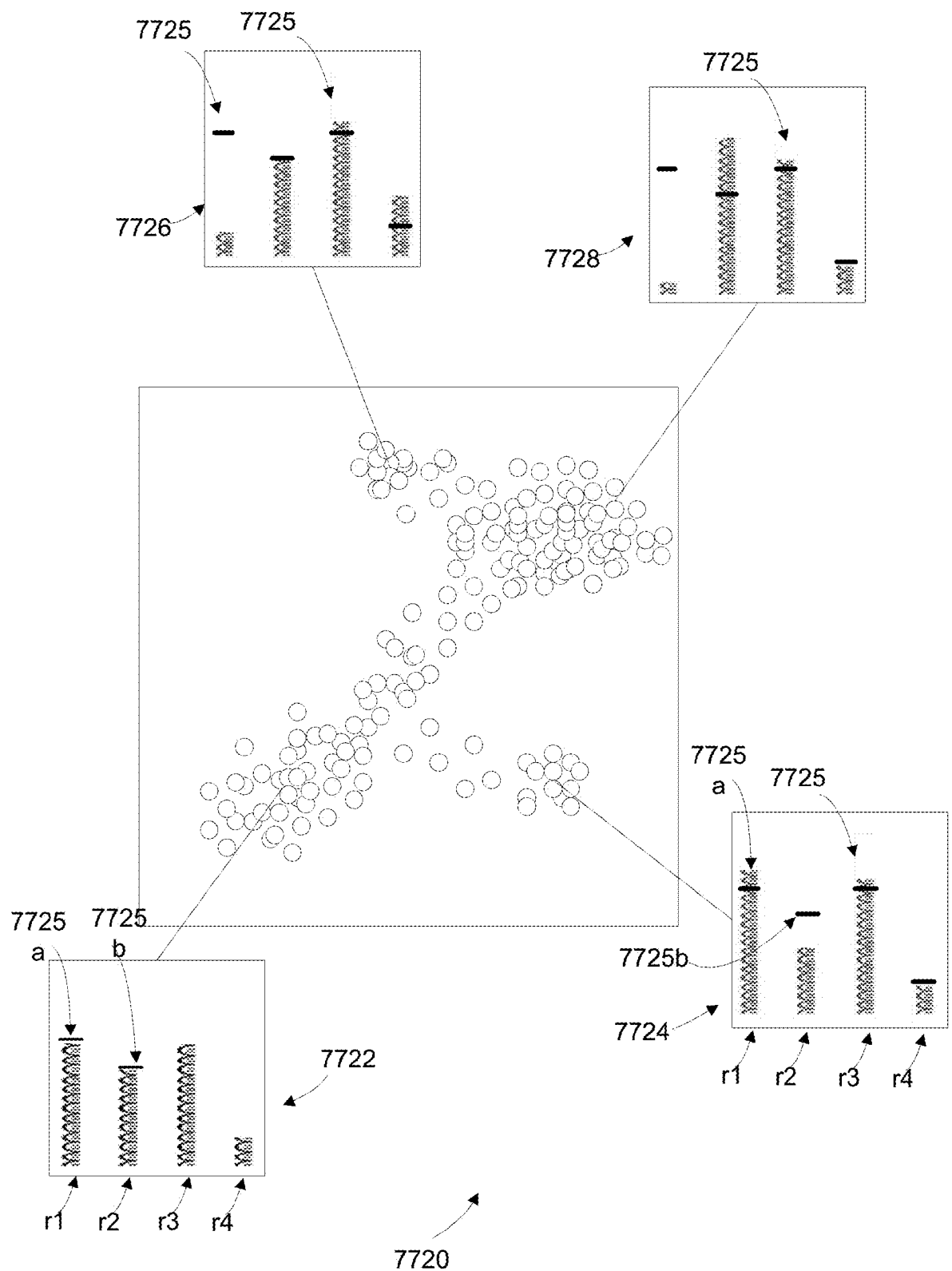
Figure 240:
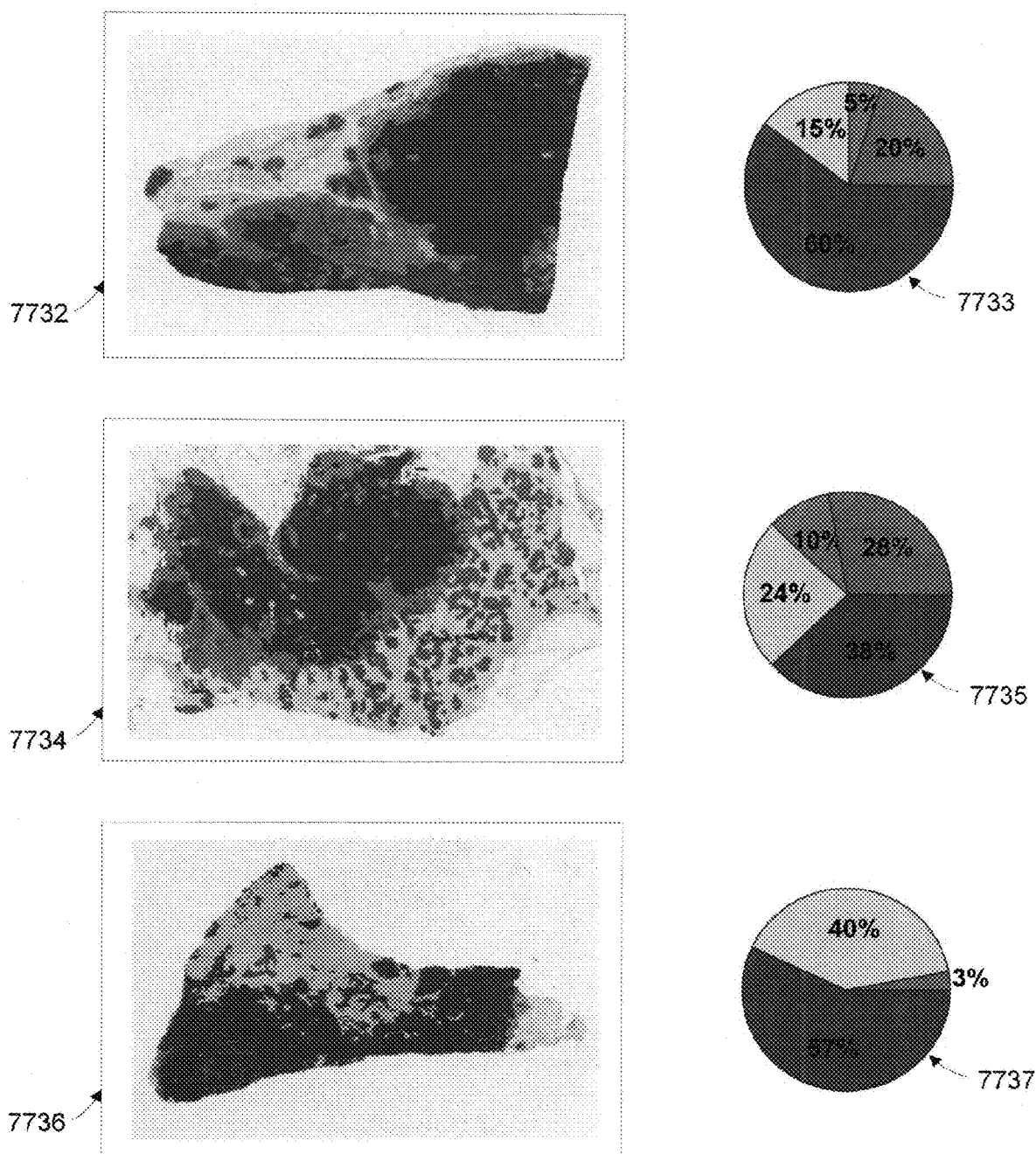
Figure 241:
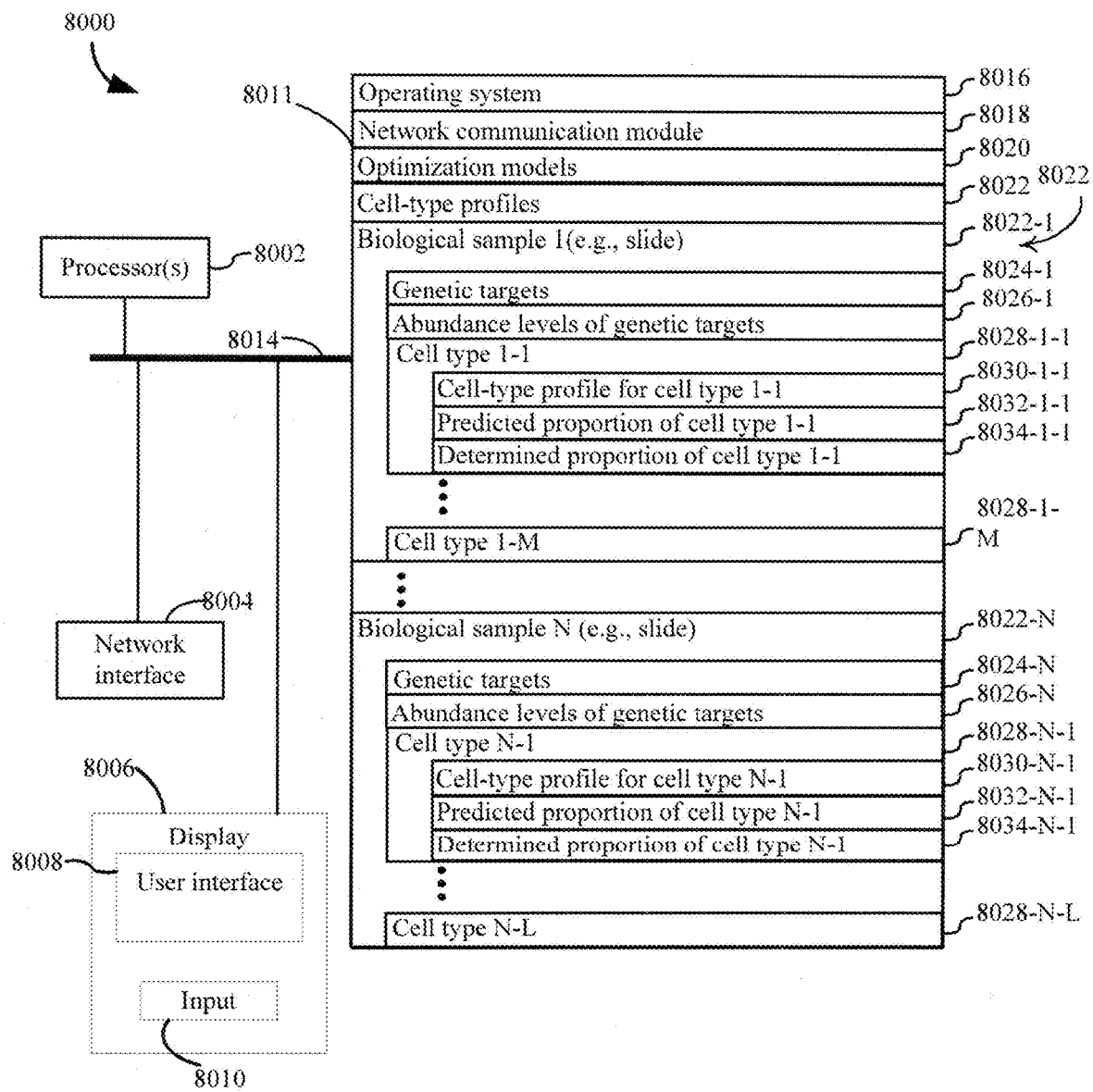
Figure 243:
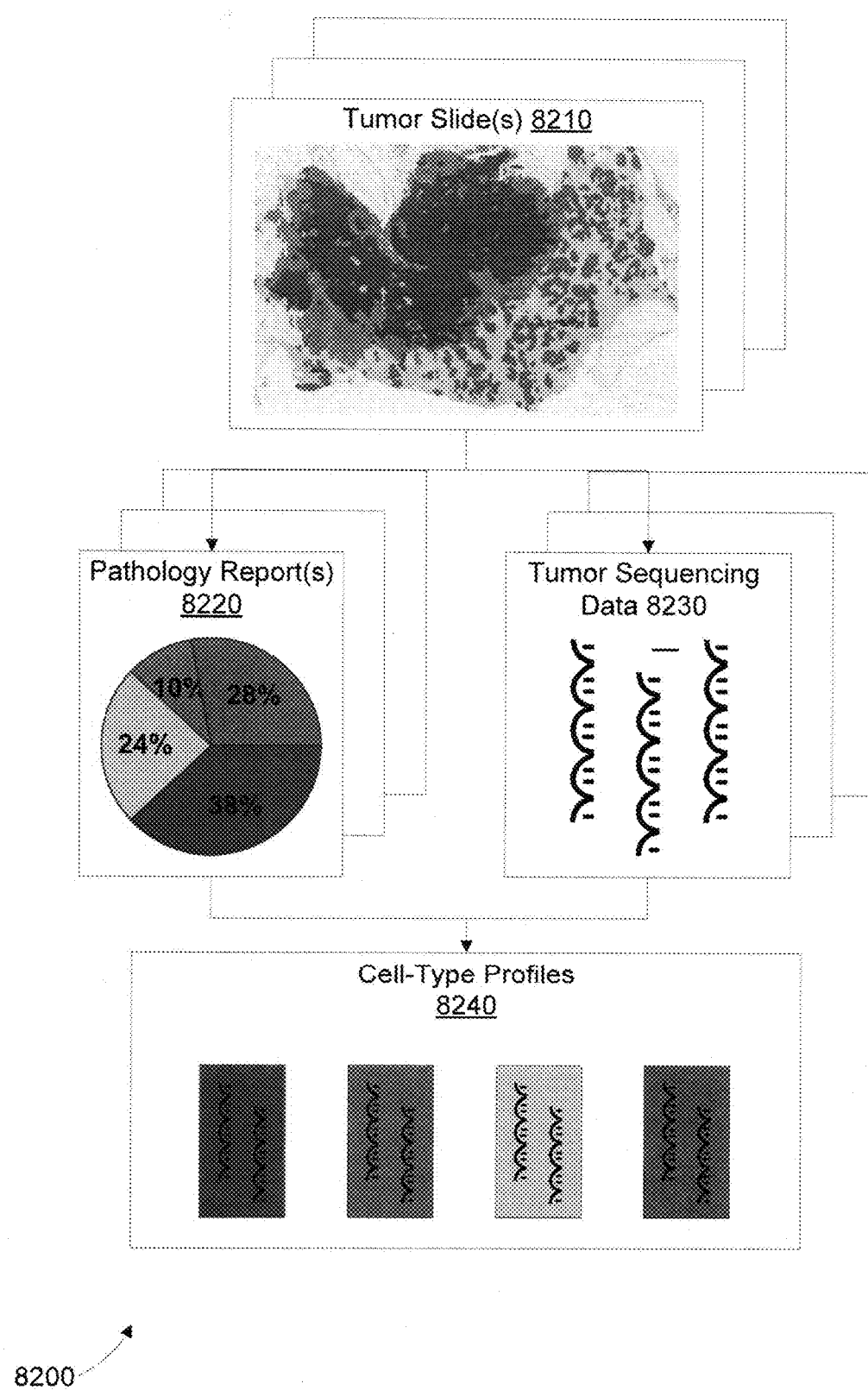
Figure 244:
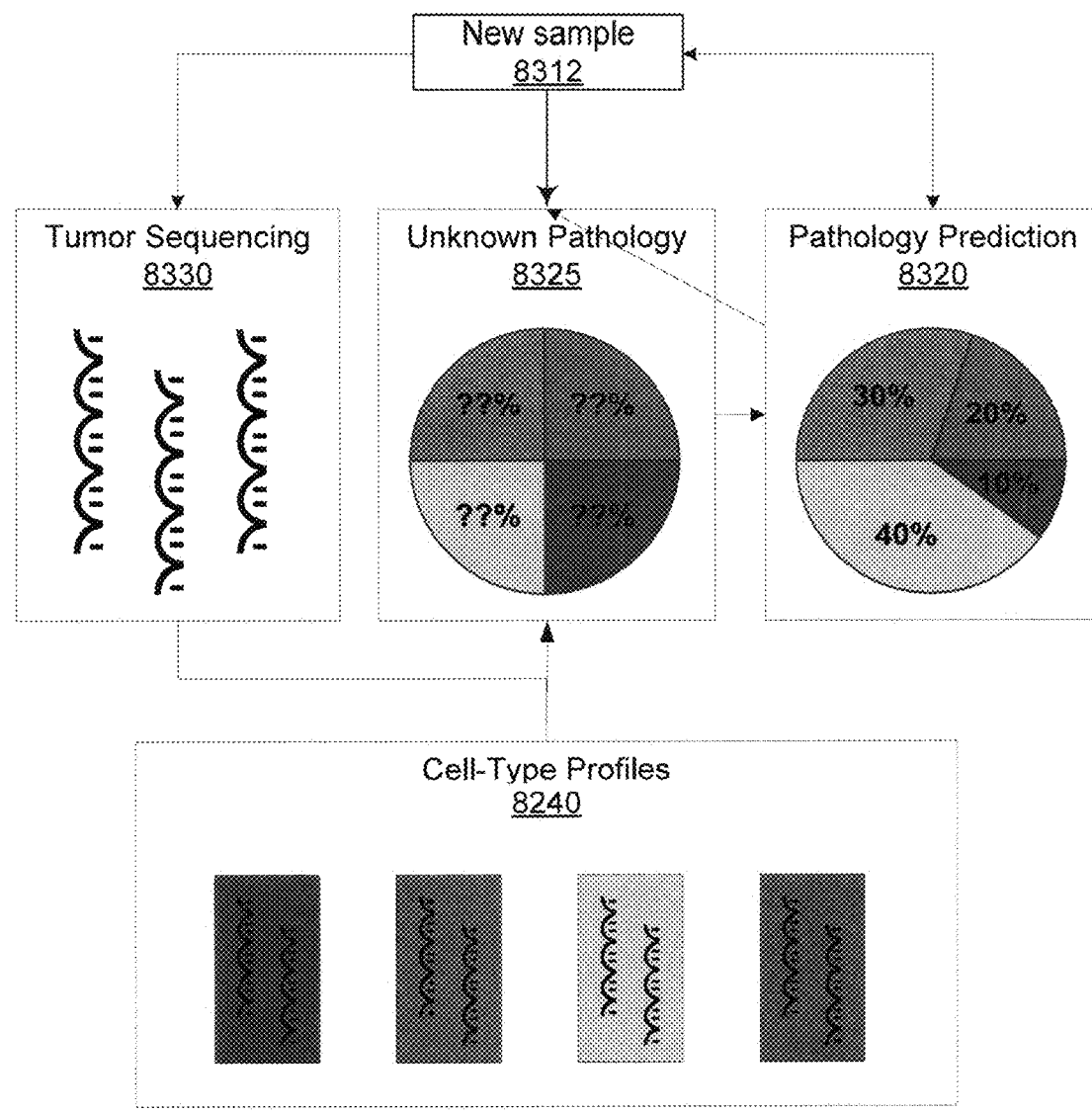
Figure 245:
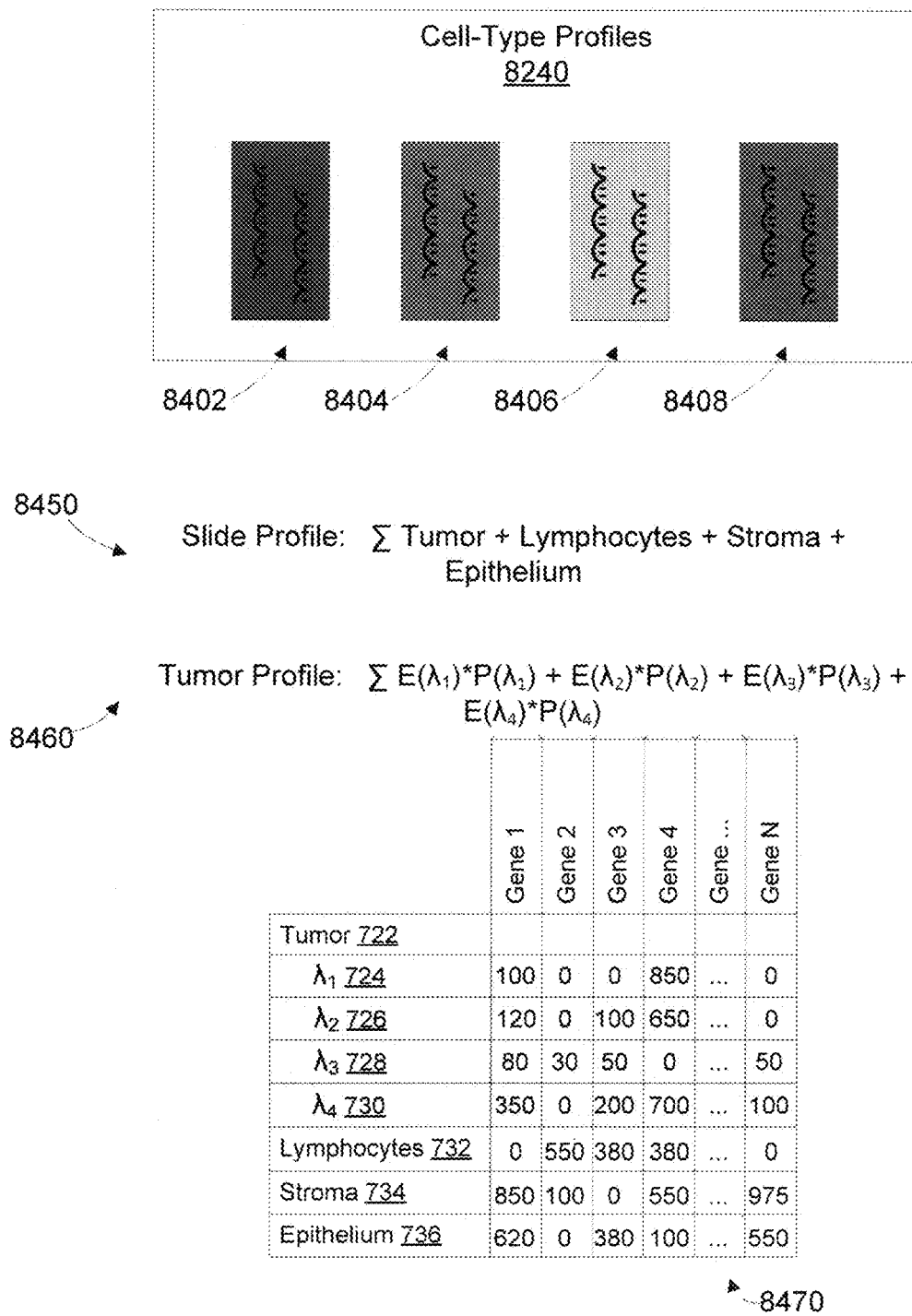
Figure 246:
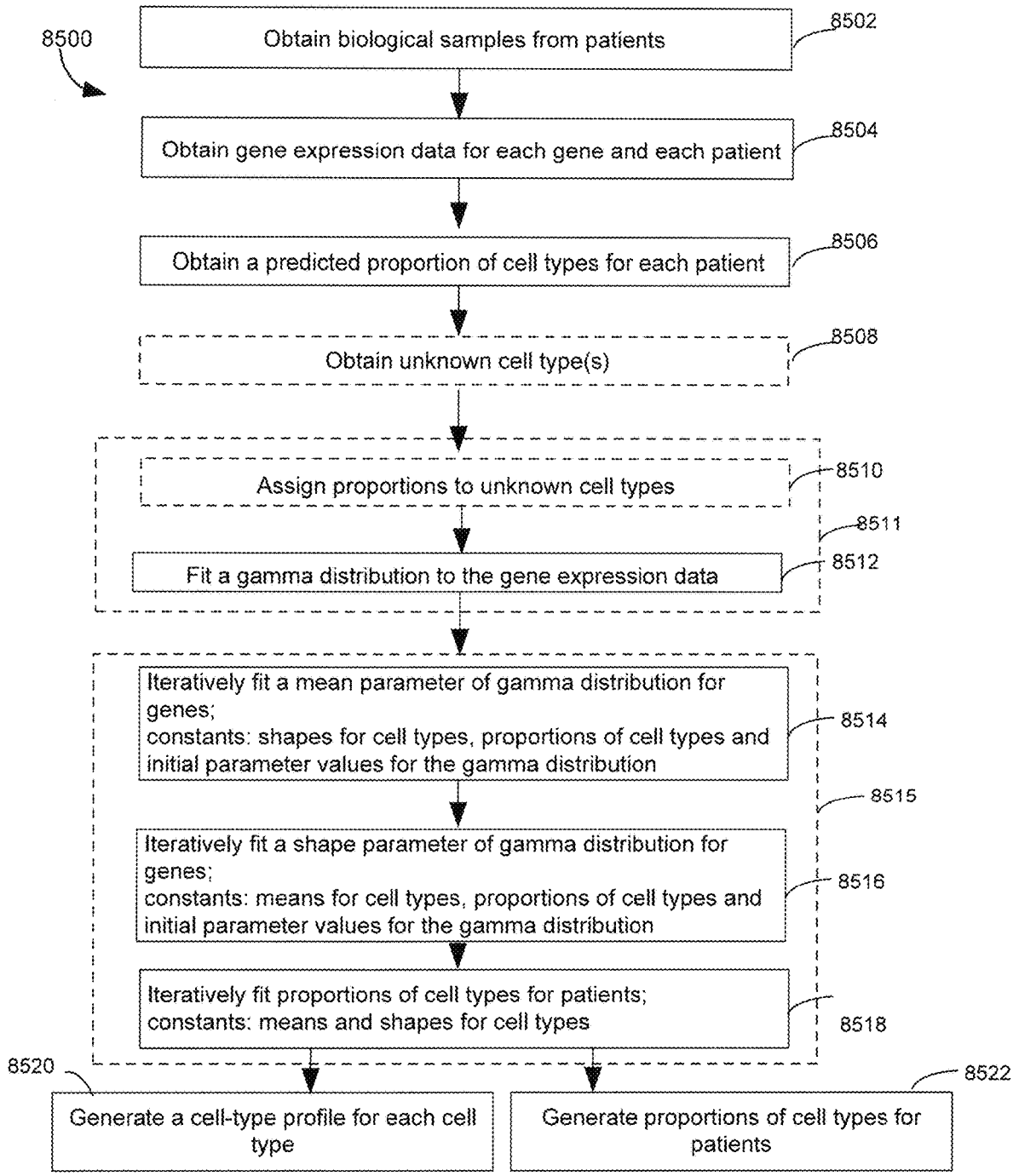
Figure 248A:
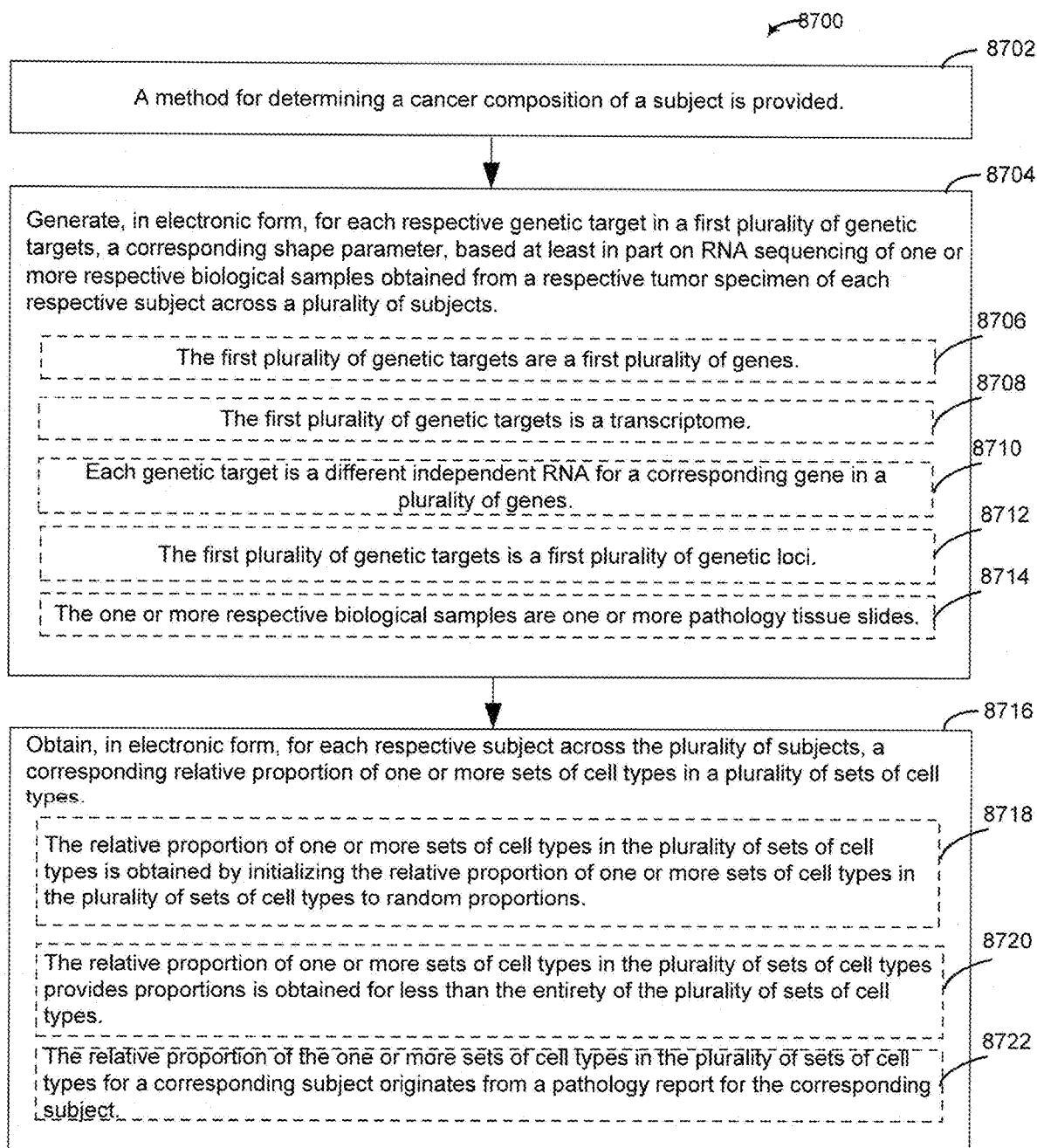
Figure 248B:
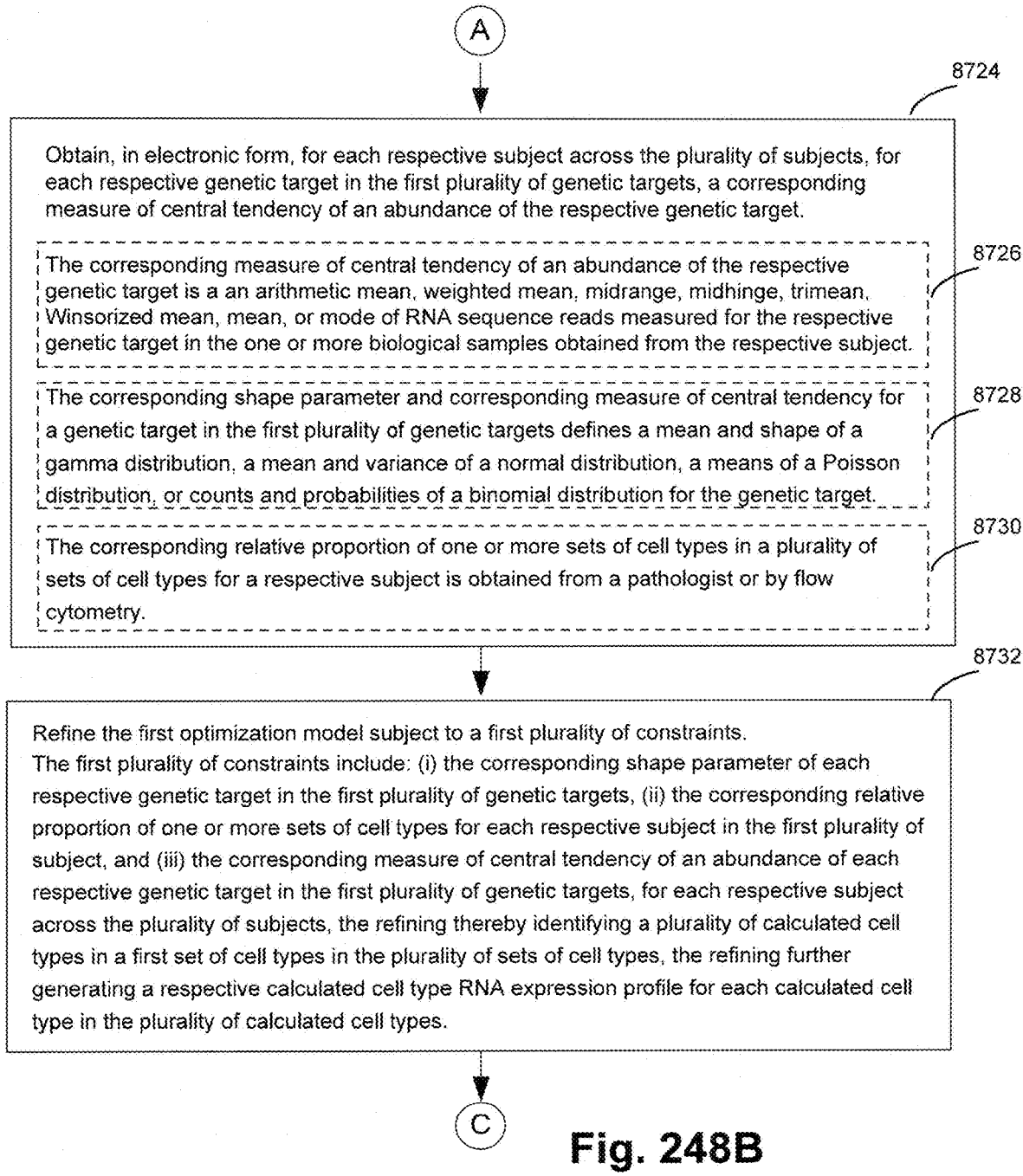
Figure 248C:
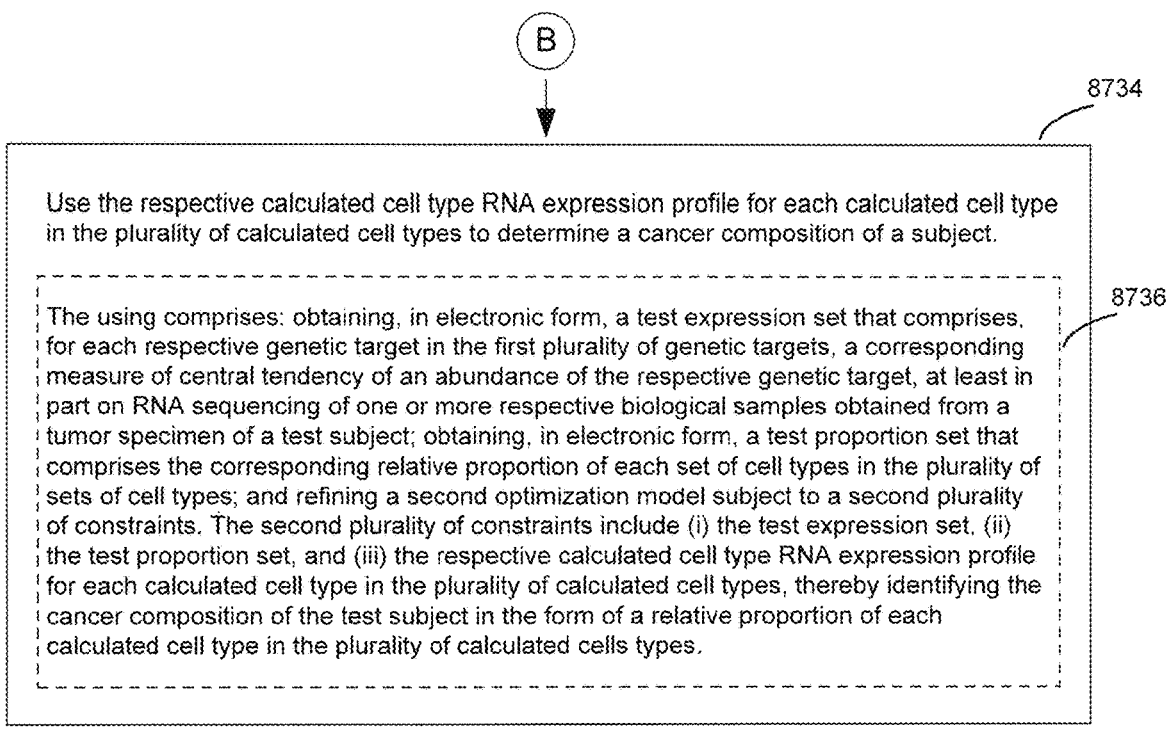
Figure 249:
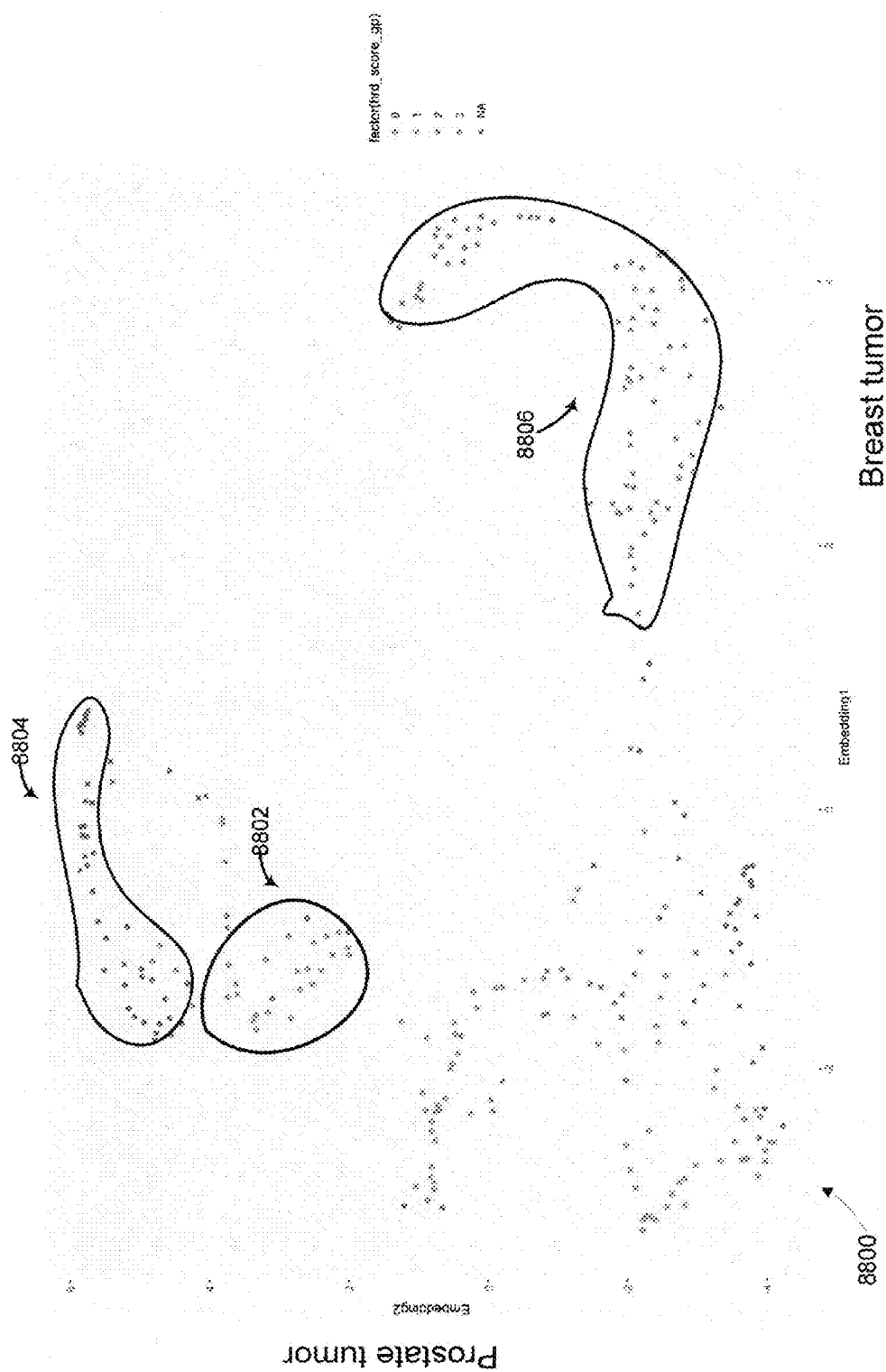
Figure 250:
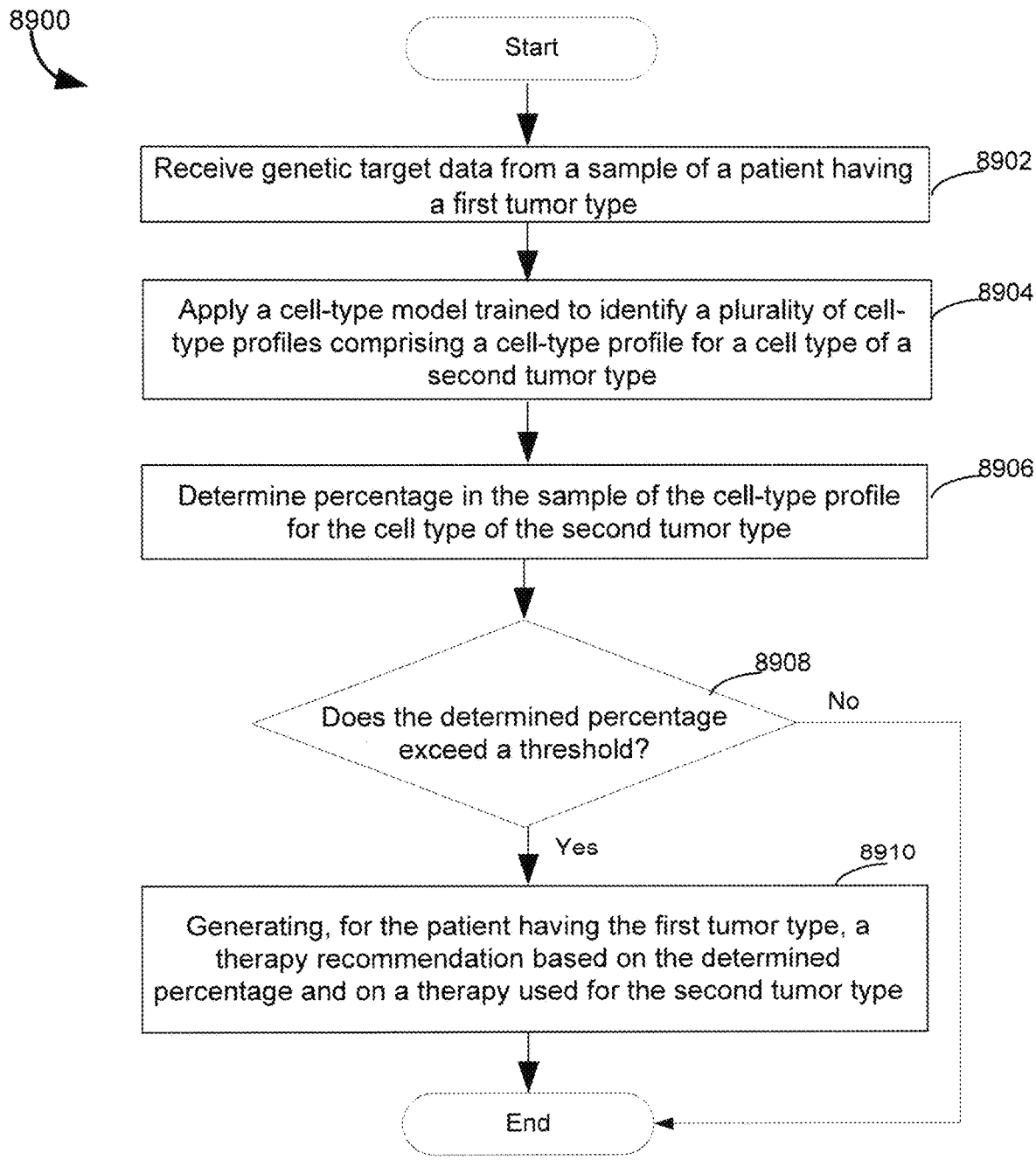
Figure 252:
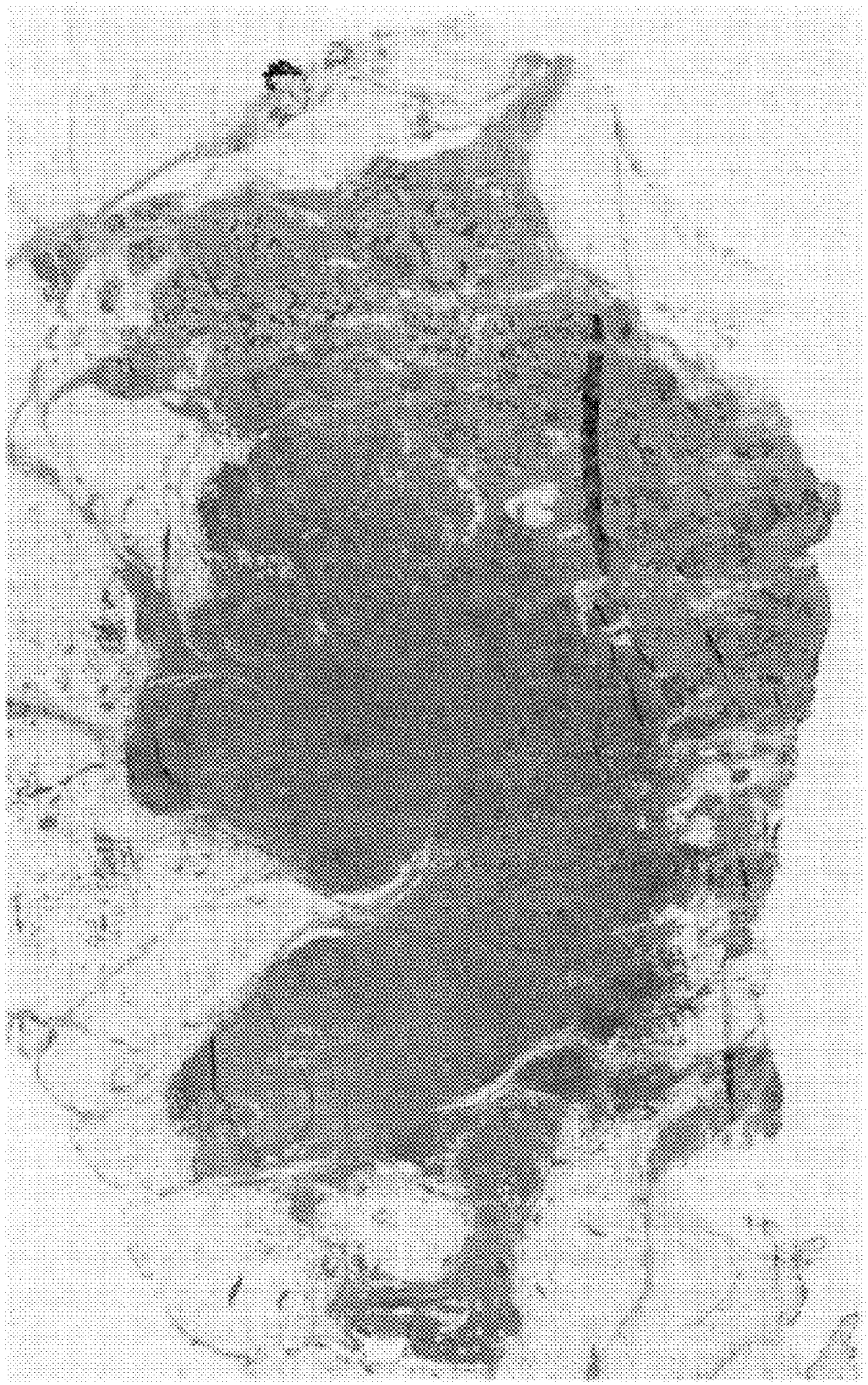
Figure 253:
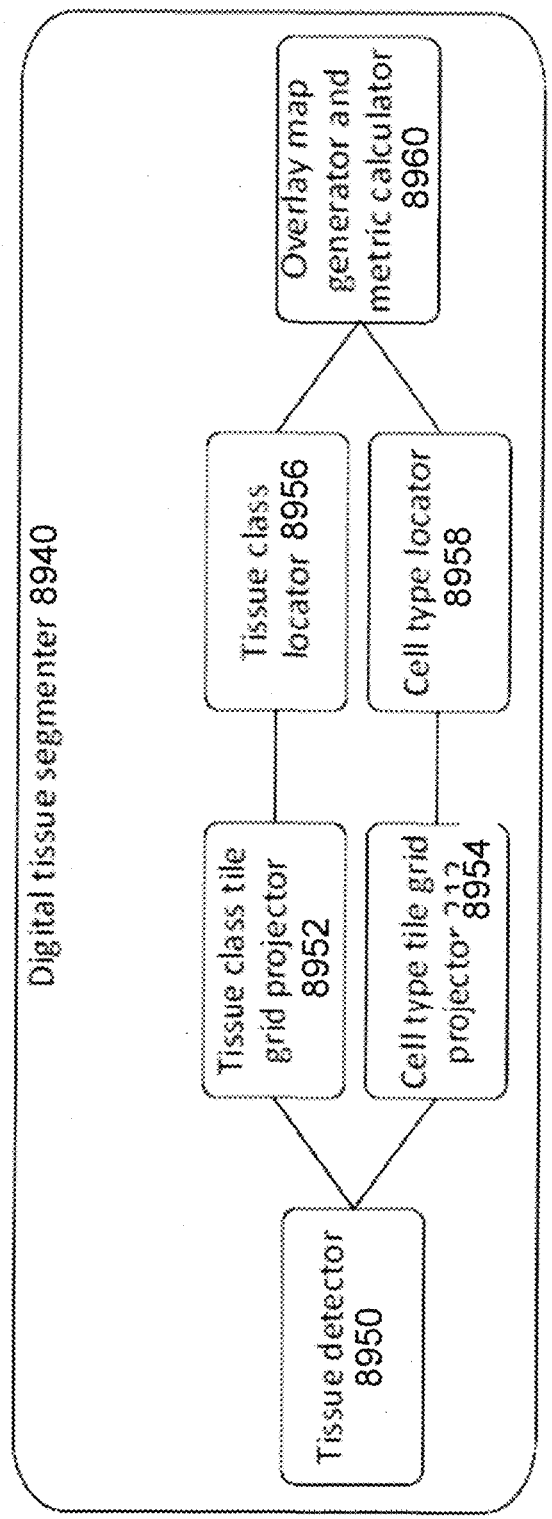
Figure 254B:
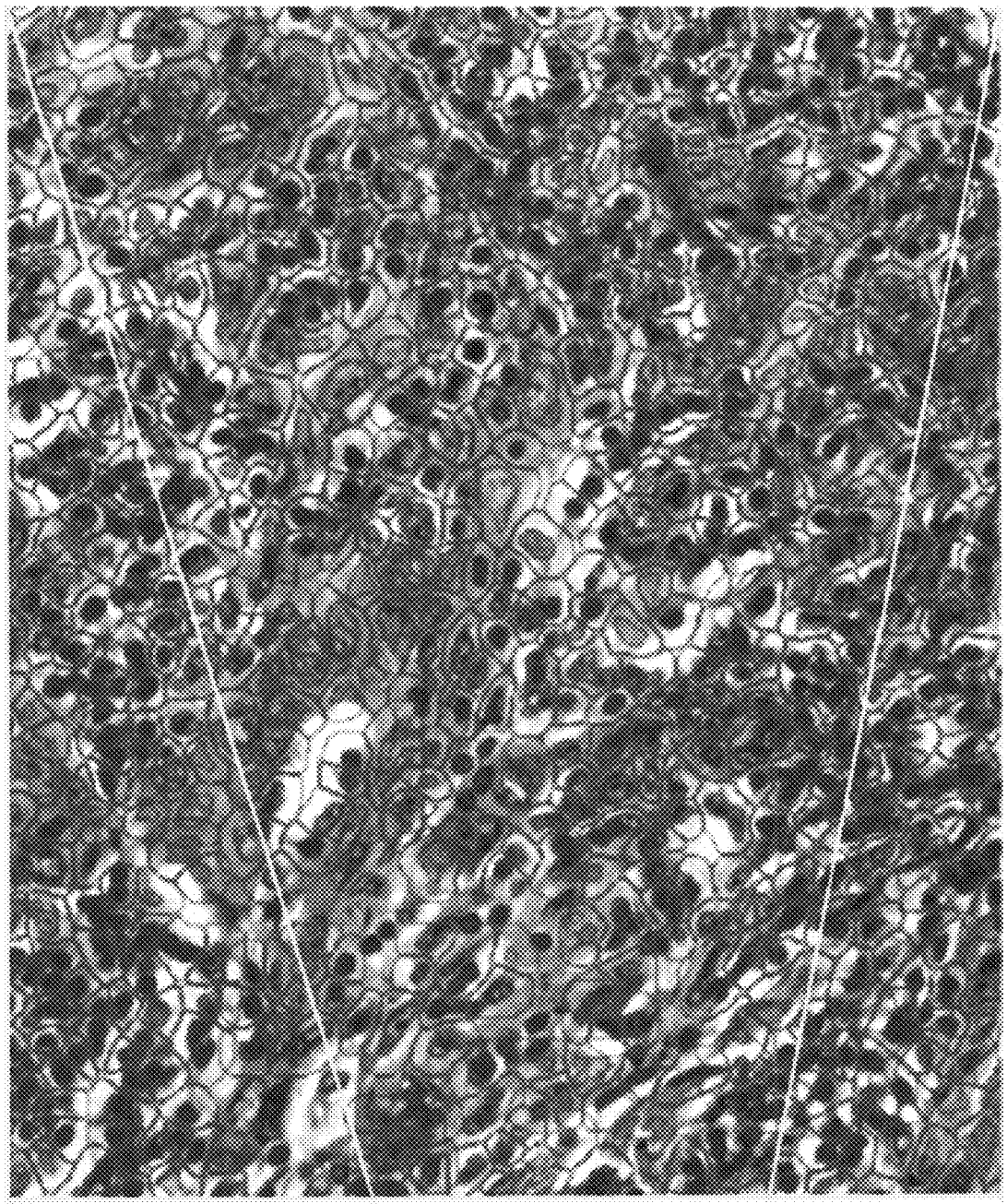
Figure 255:
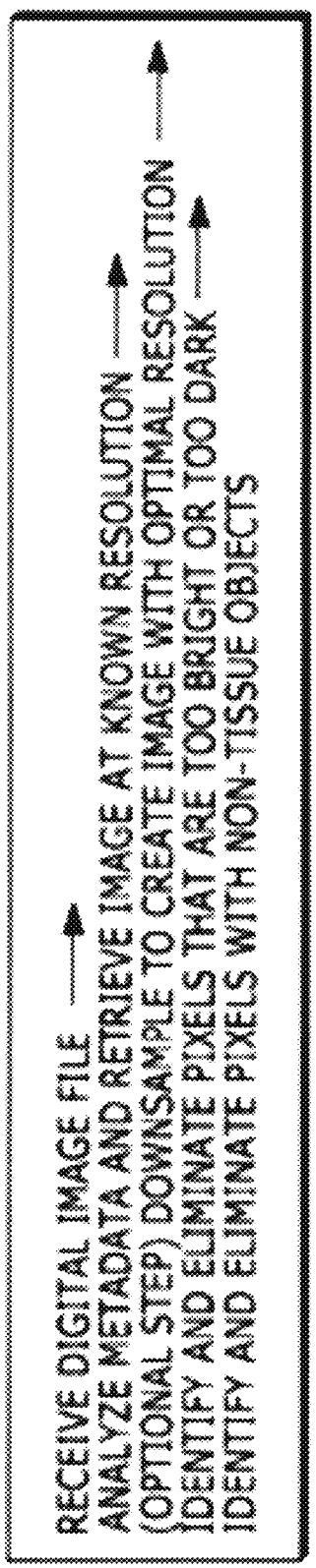
Figure 256B:
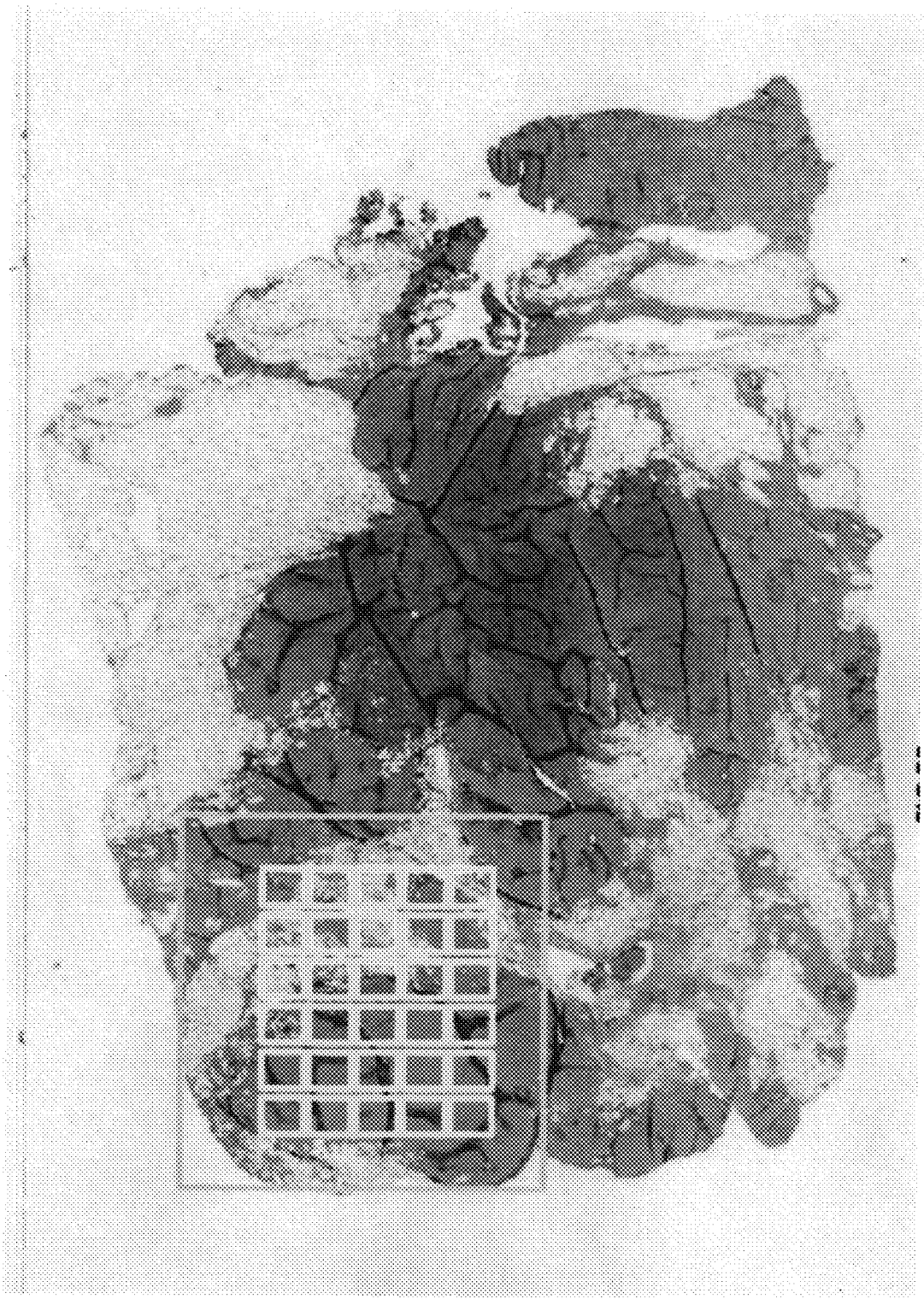
Figure 256C:
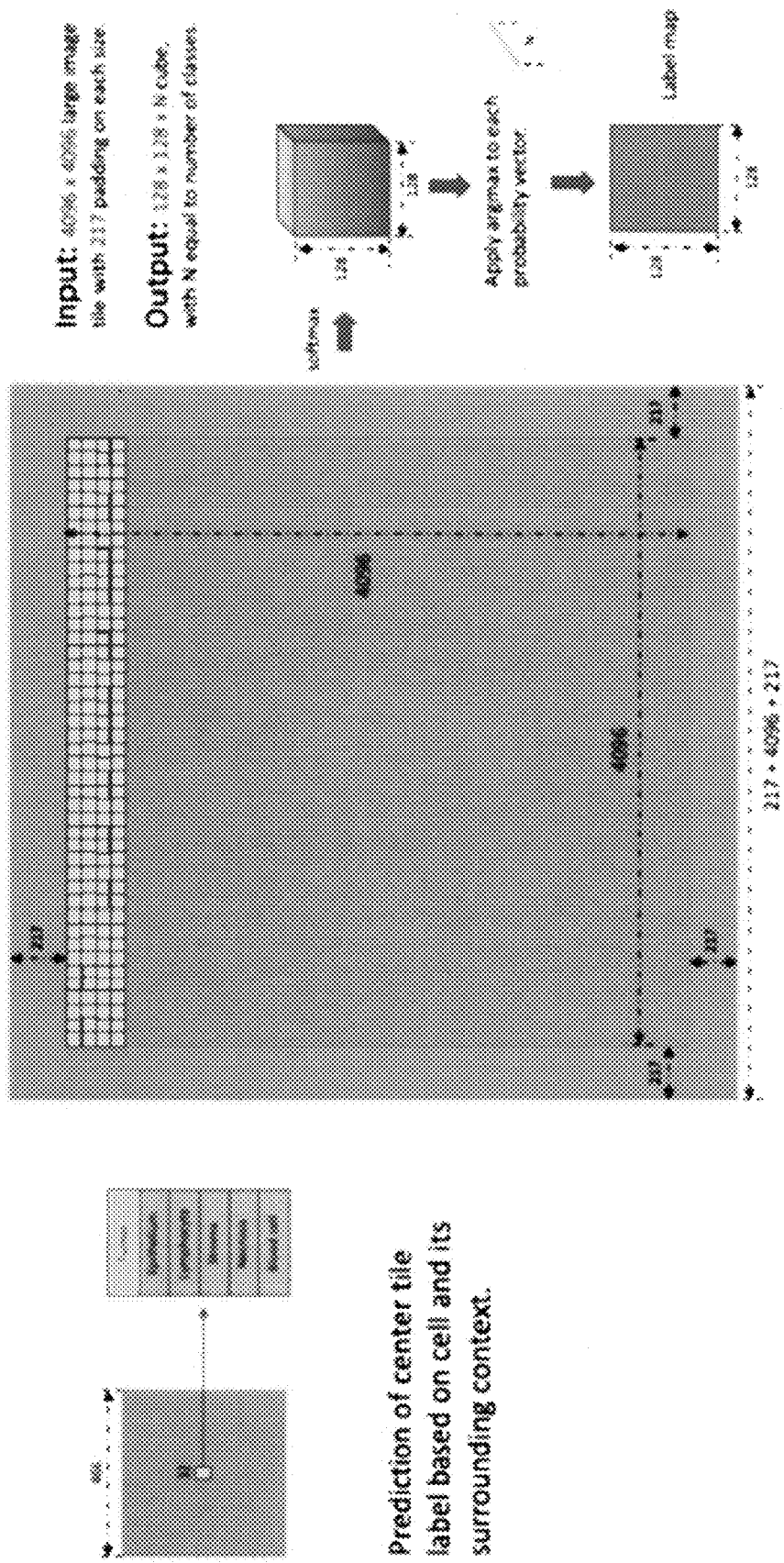
Figure 257A:
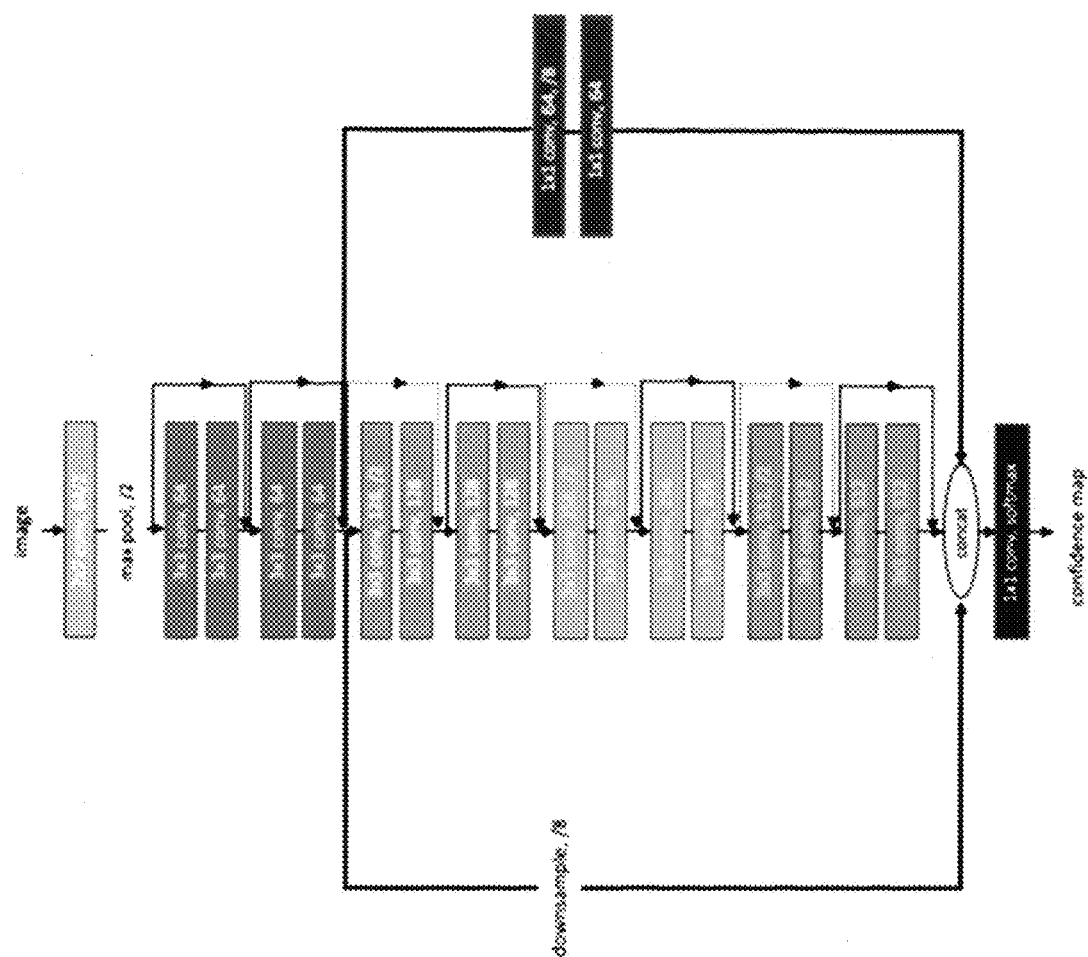
Figure 257C:
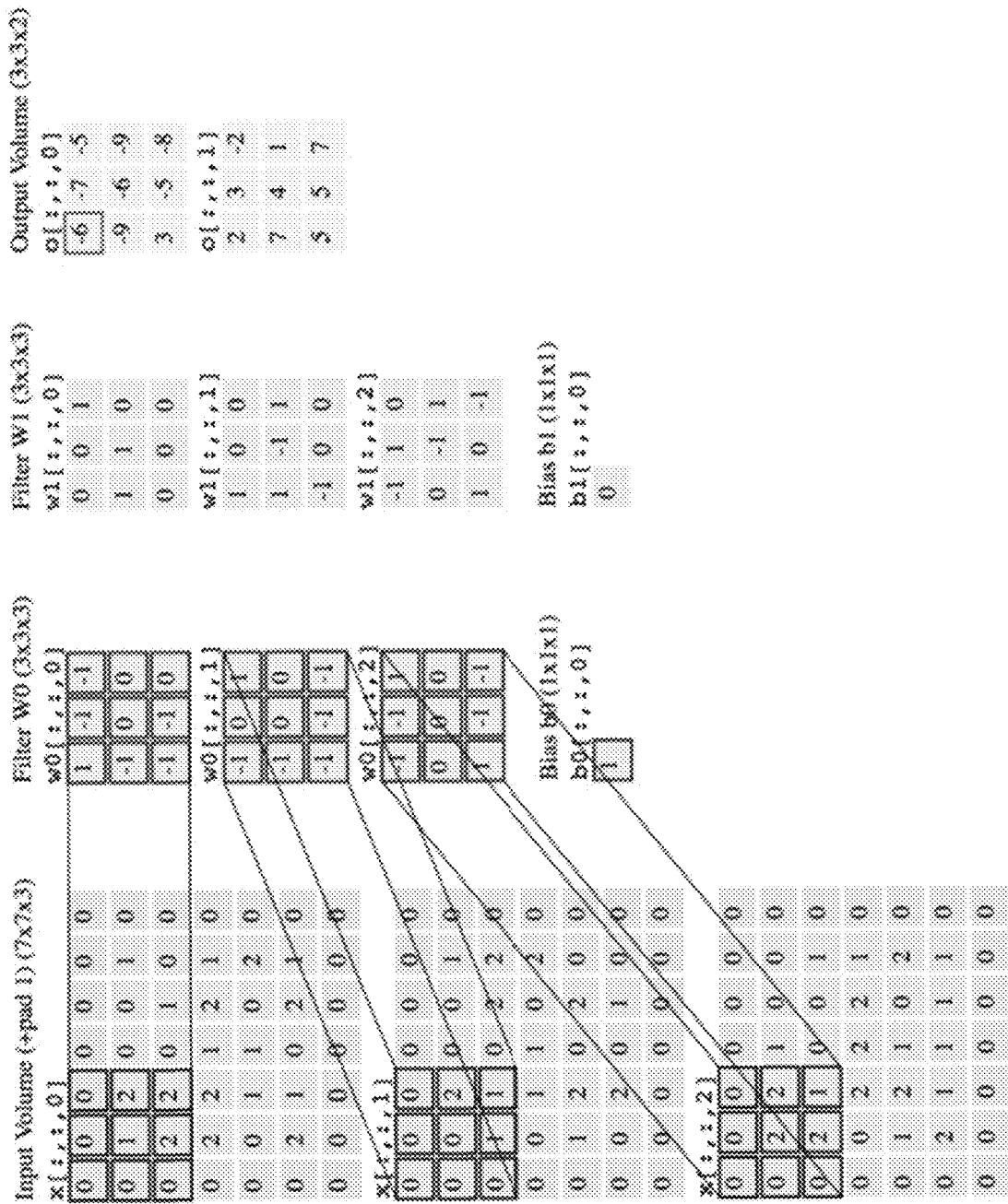
Figure 258:
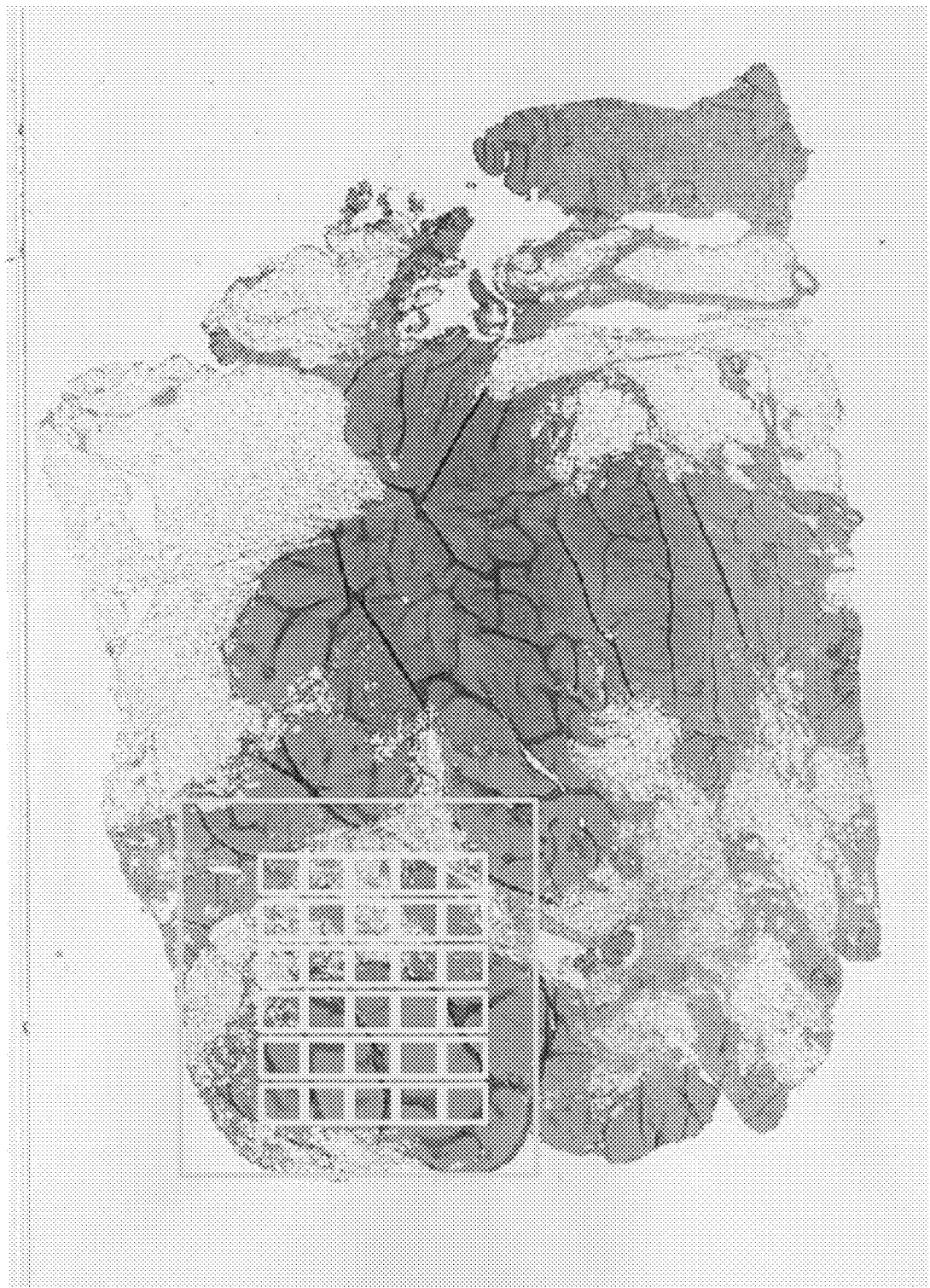
Figure 260A:
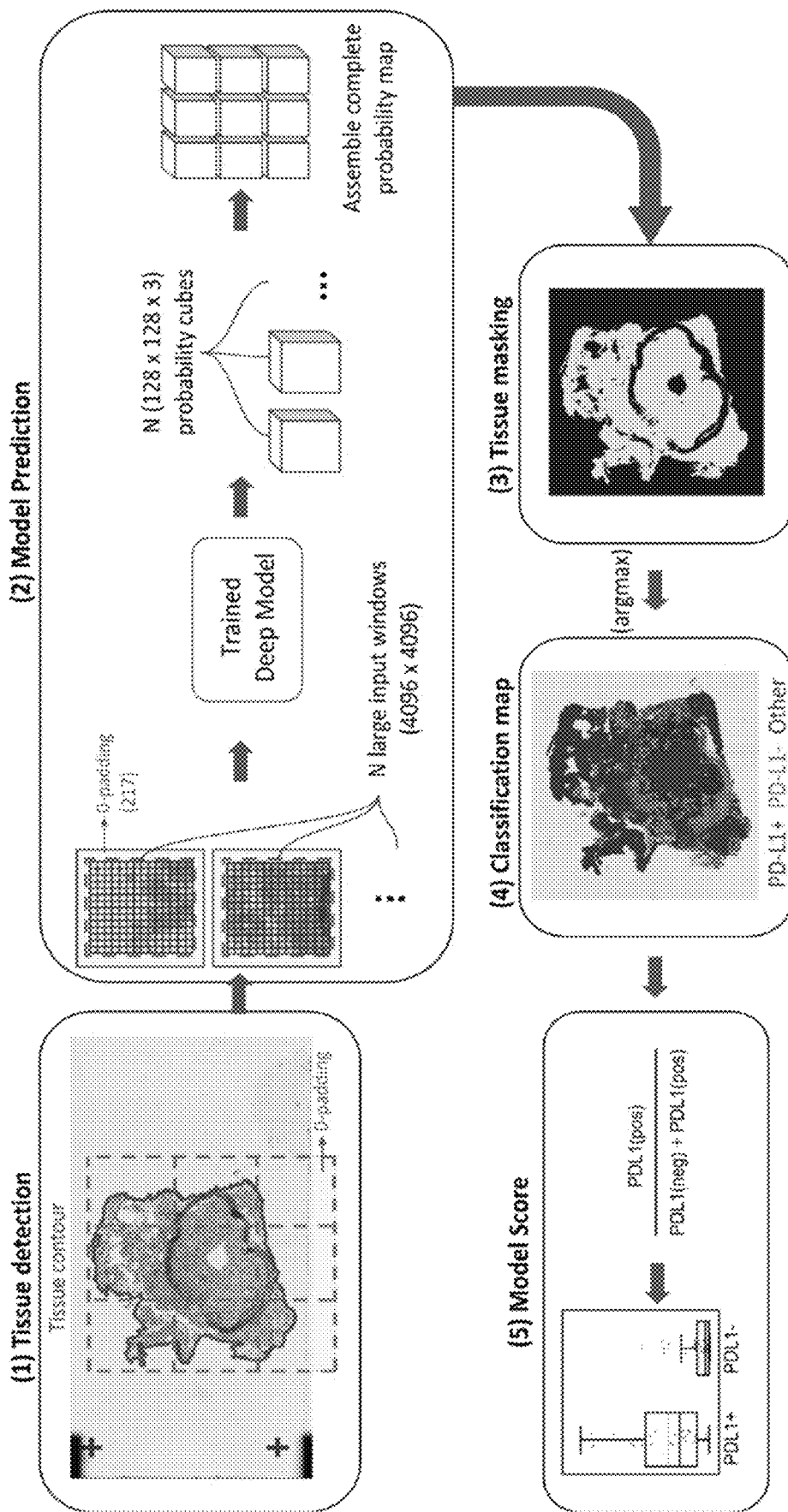
Figure 260B:
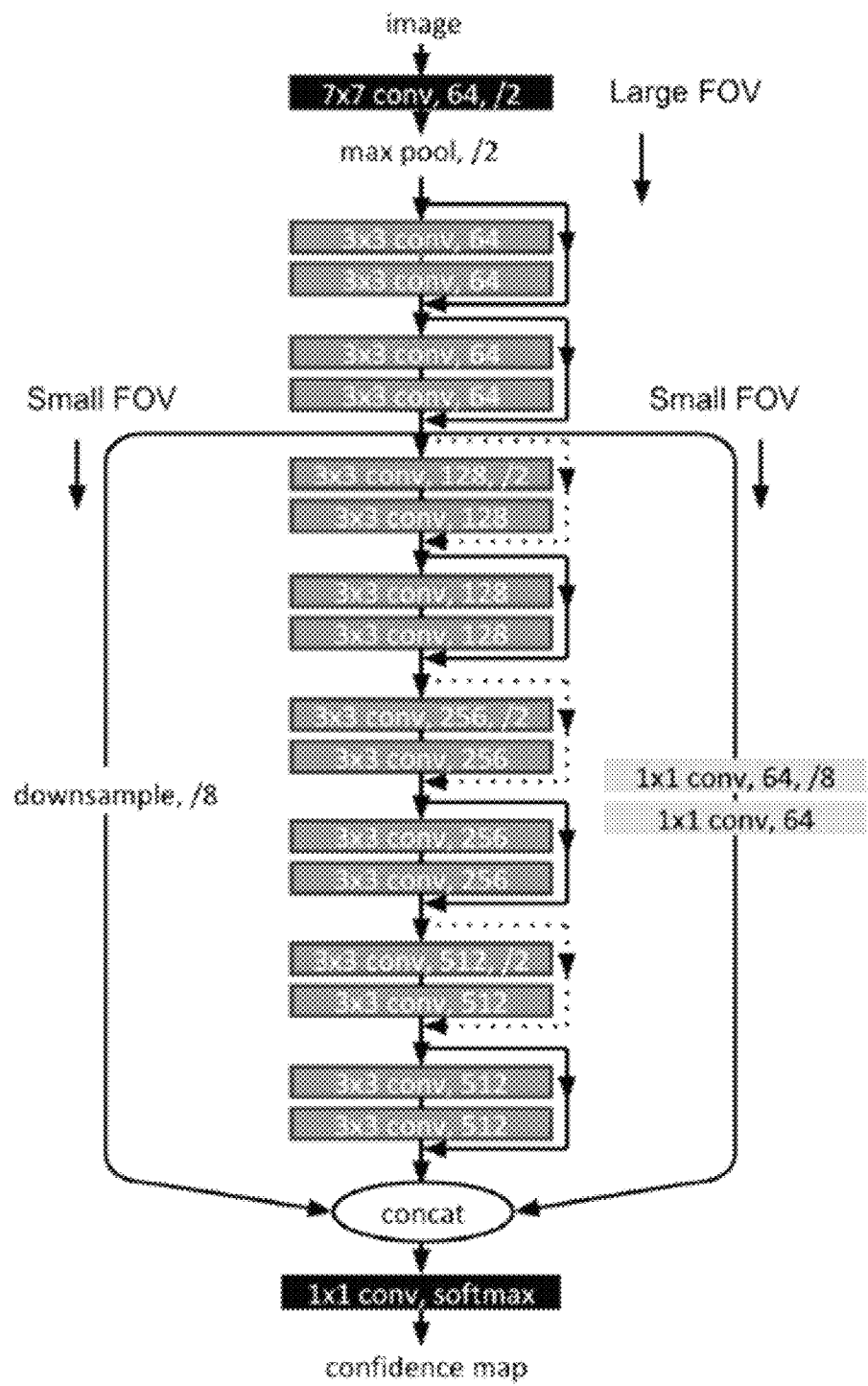
Figure 260C:
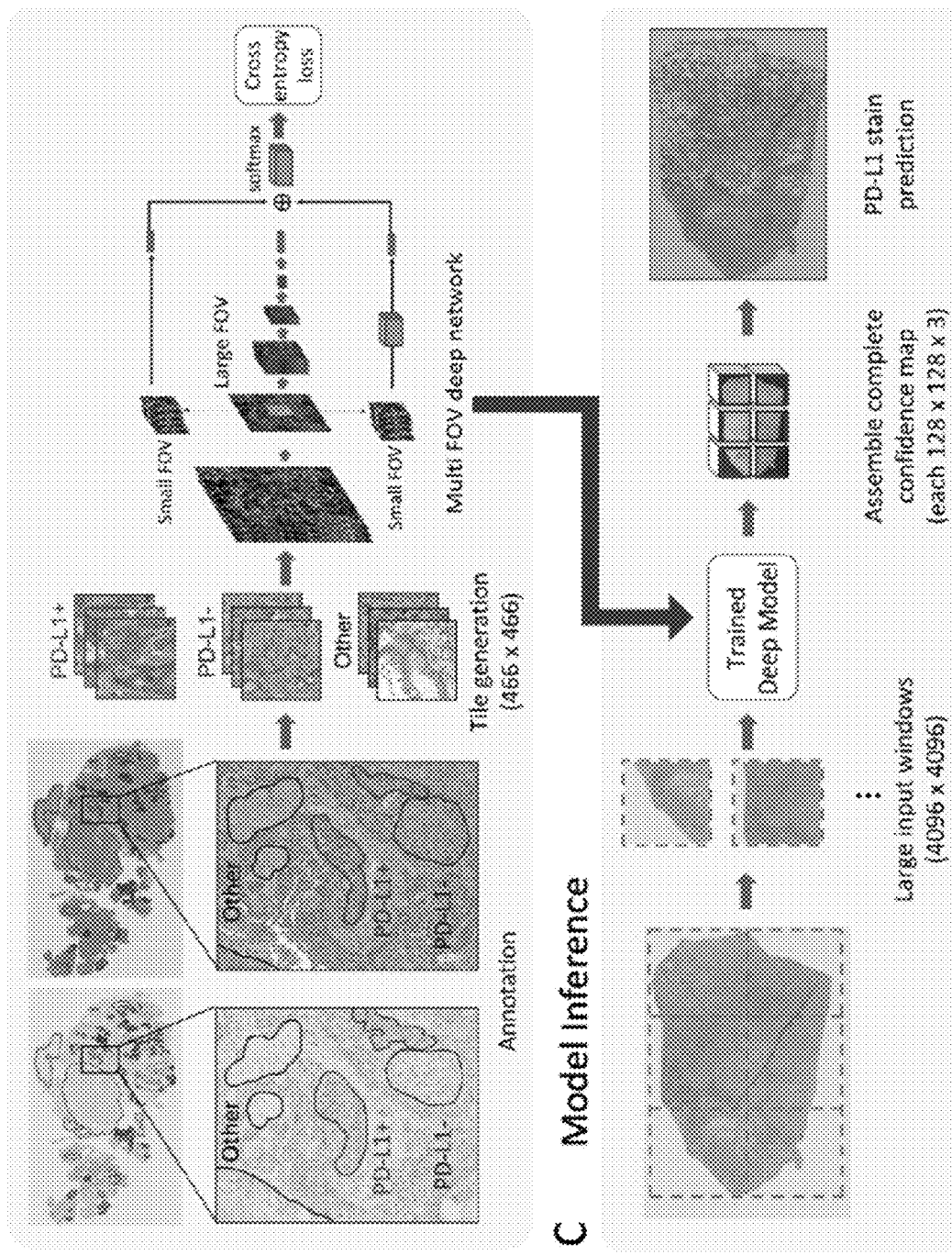
Figure 263B:
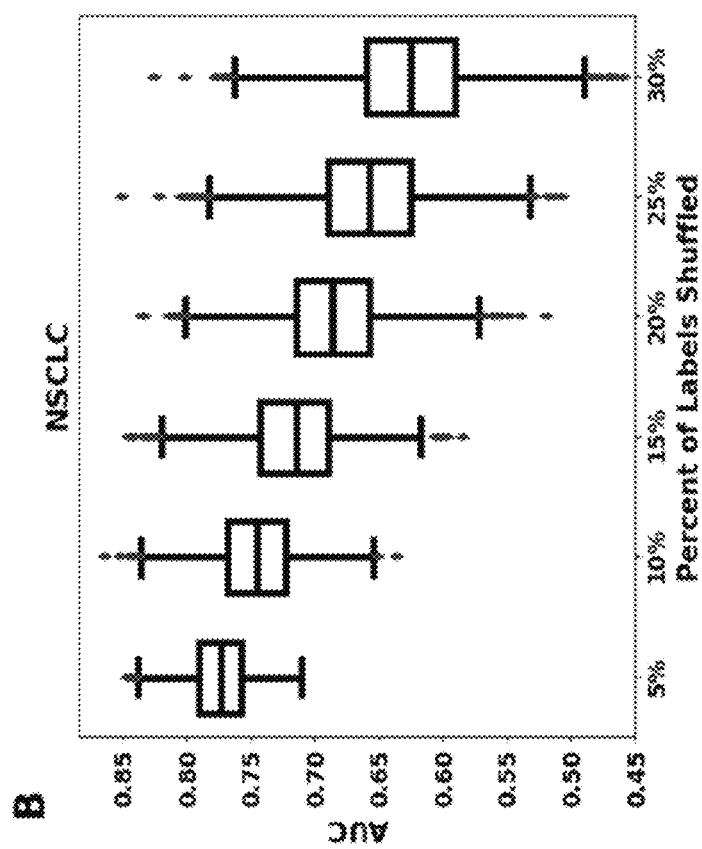
Figure 263A:
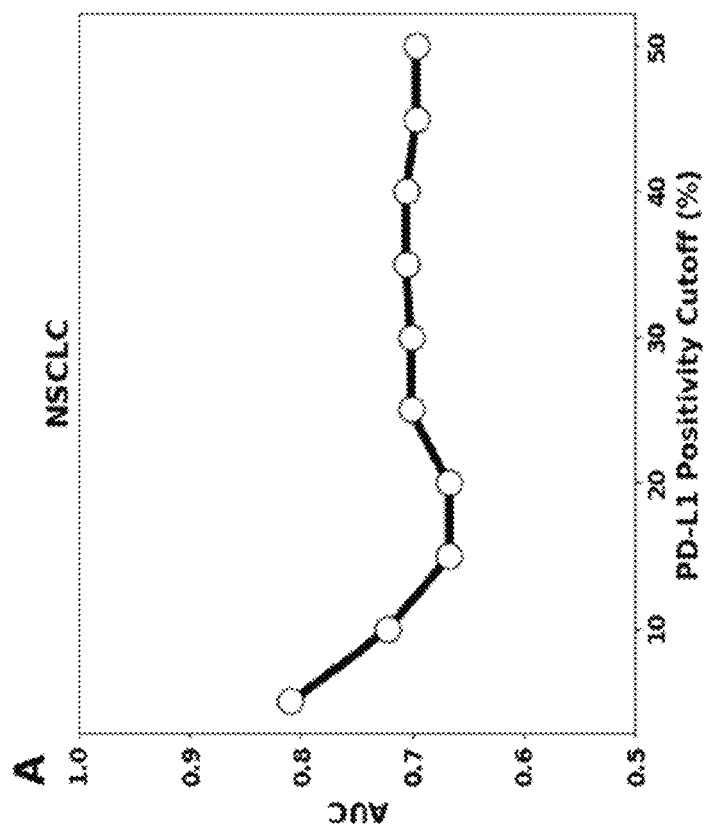
Figure 265:
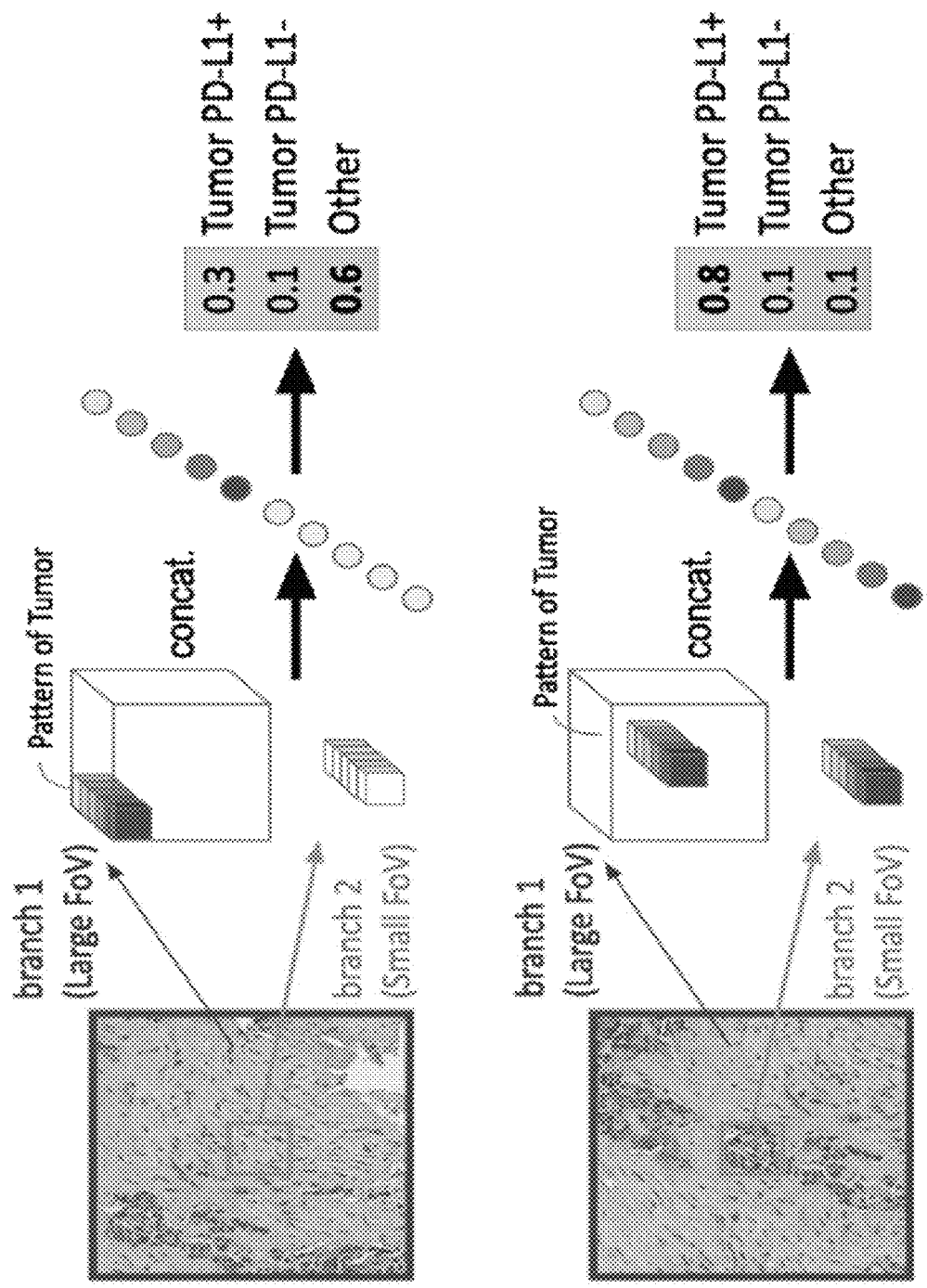
Figure 266:
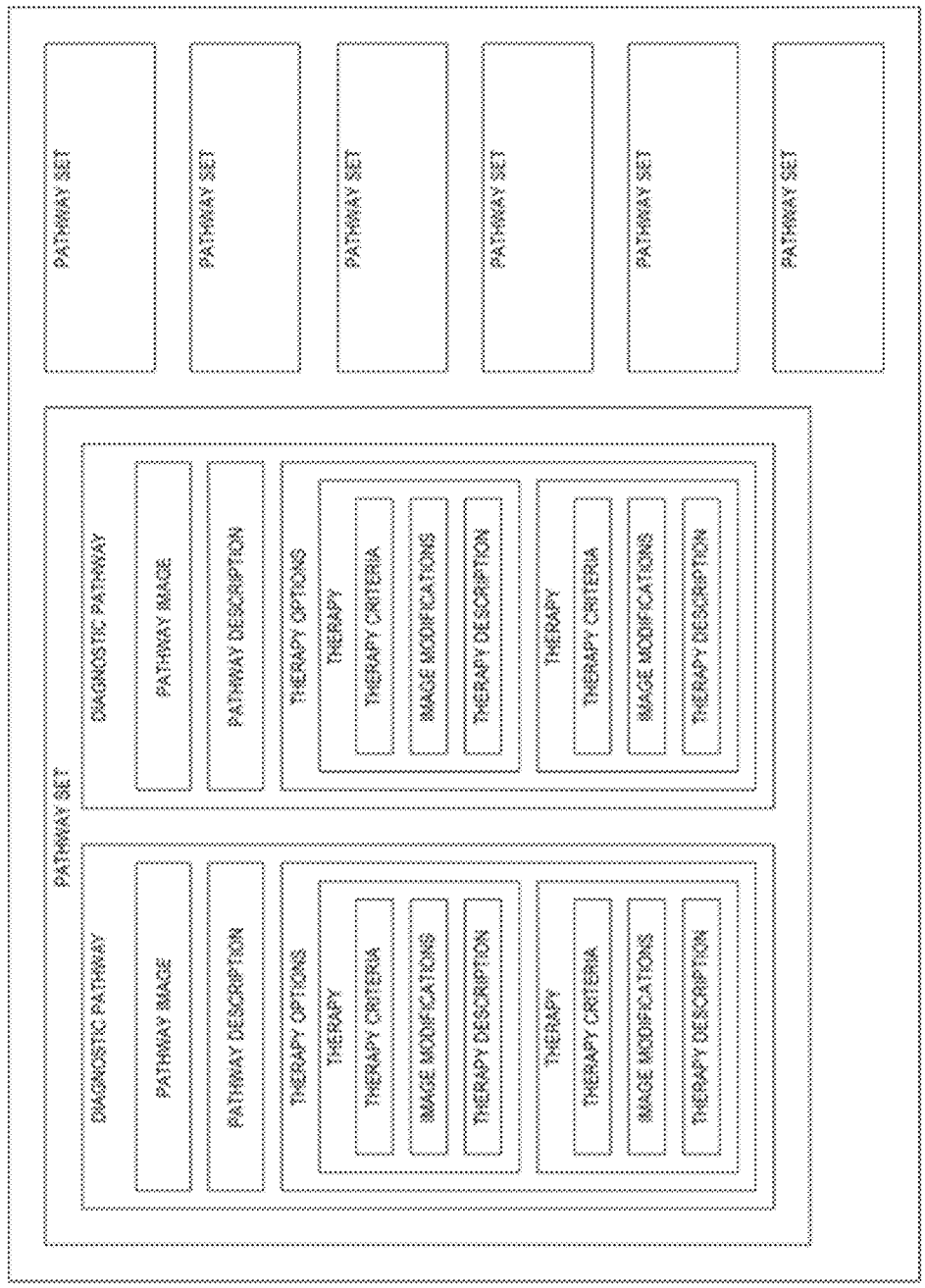
Figure 267:
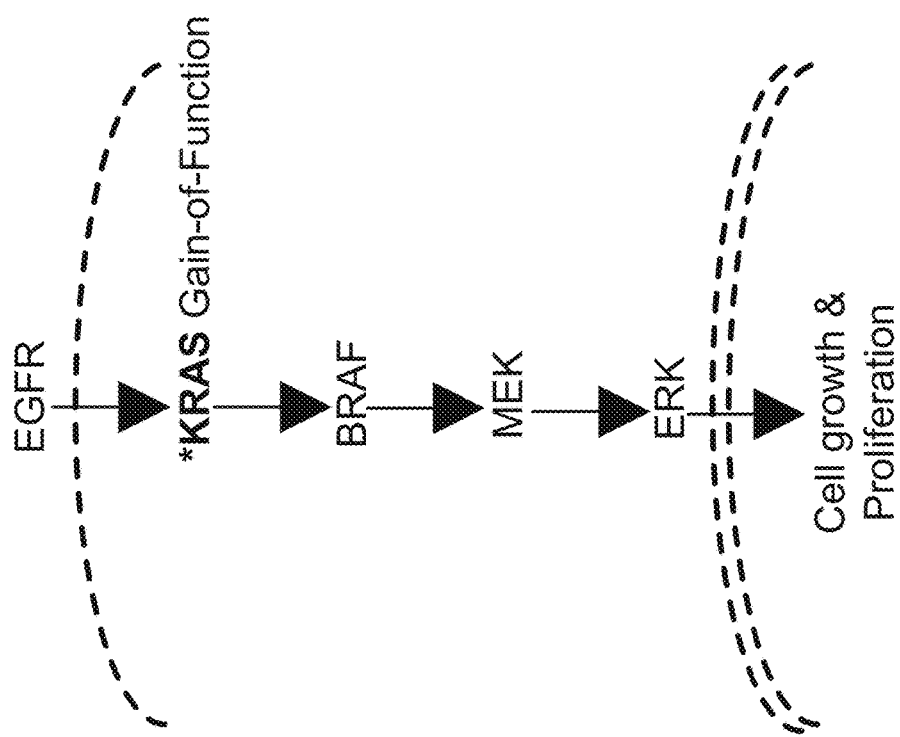
Figure 268:
Figure 269A:
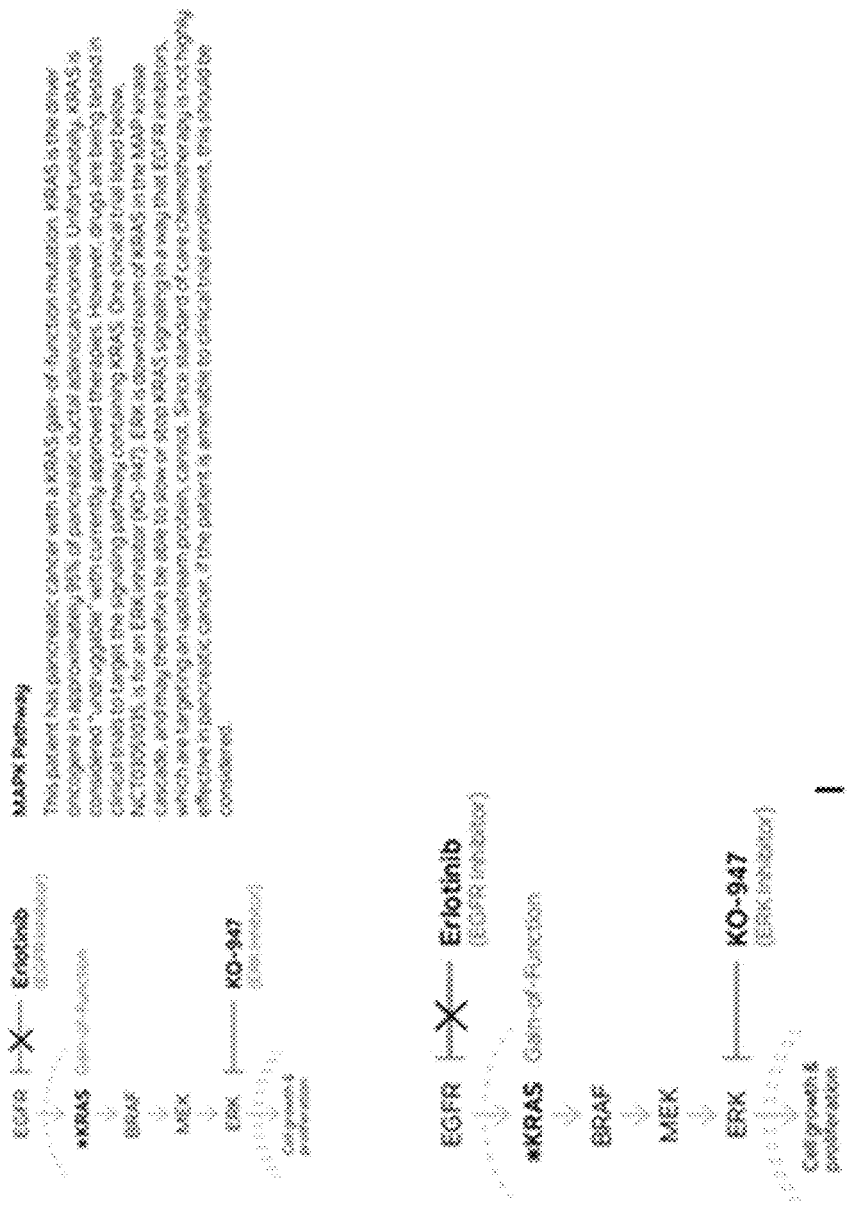
Figure 270:
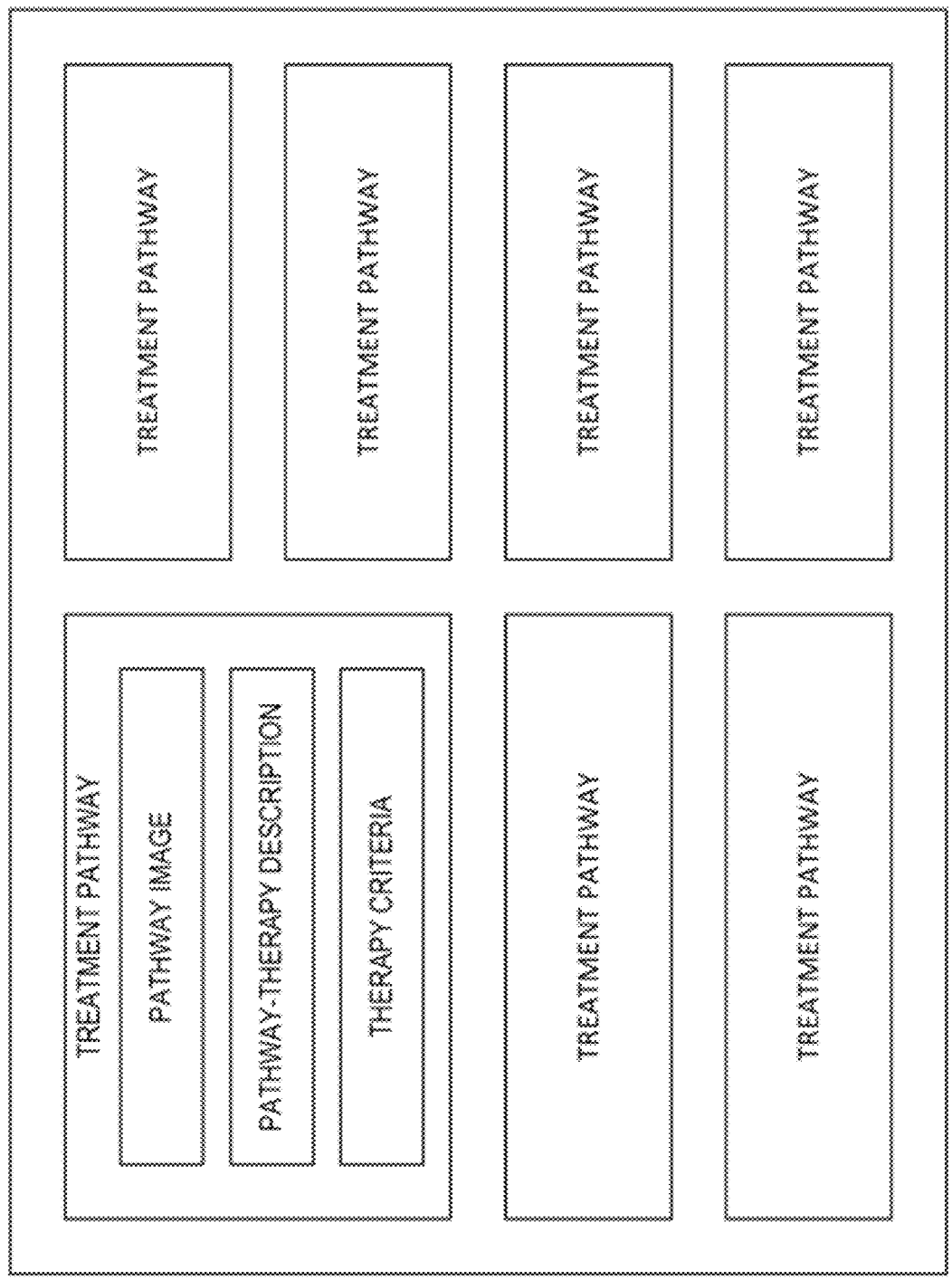
Figure 271:
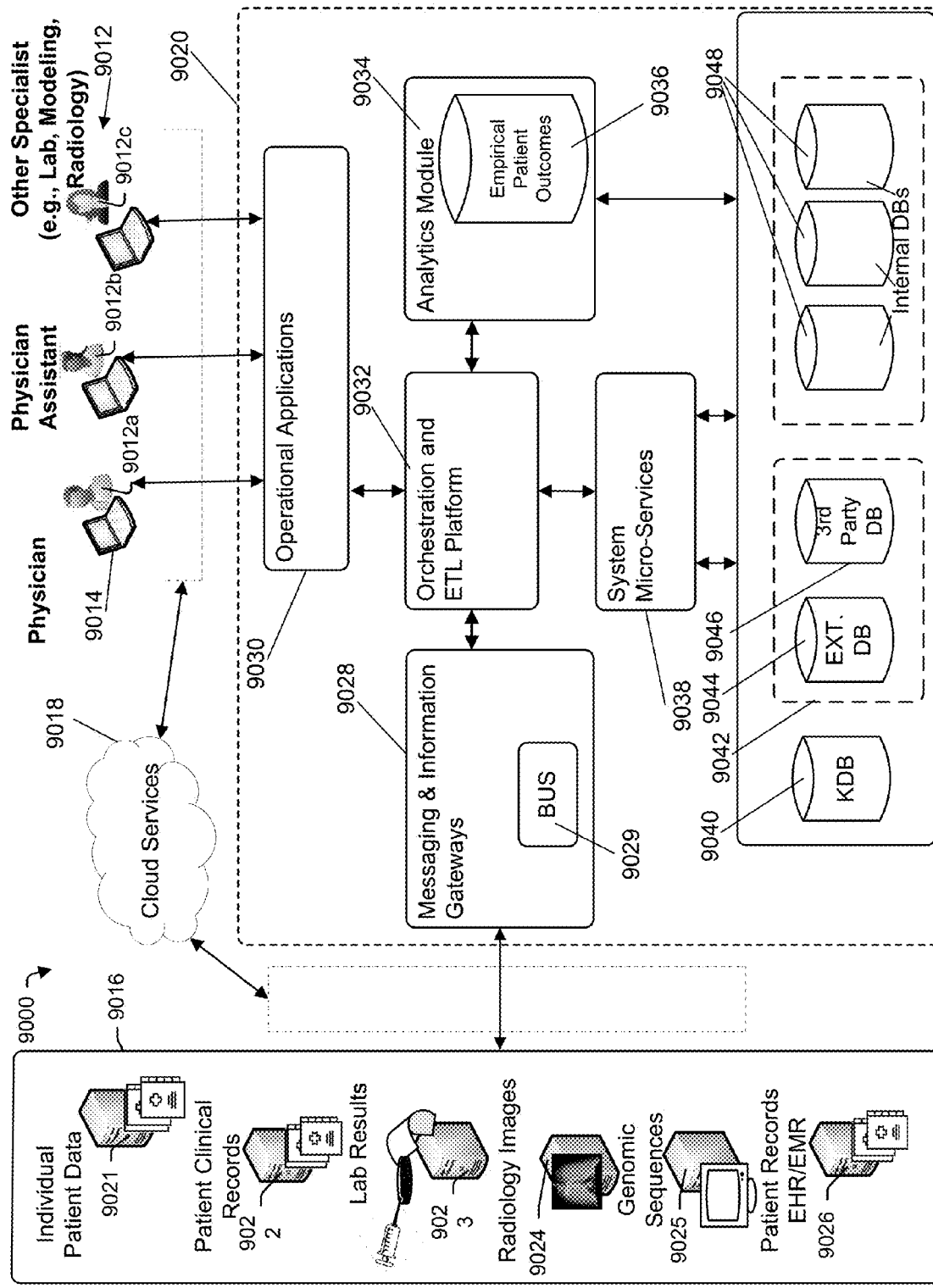
Figure 272:
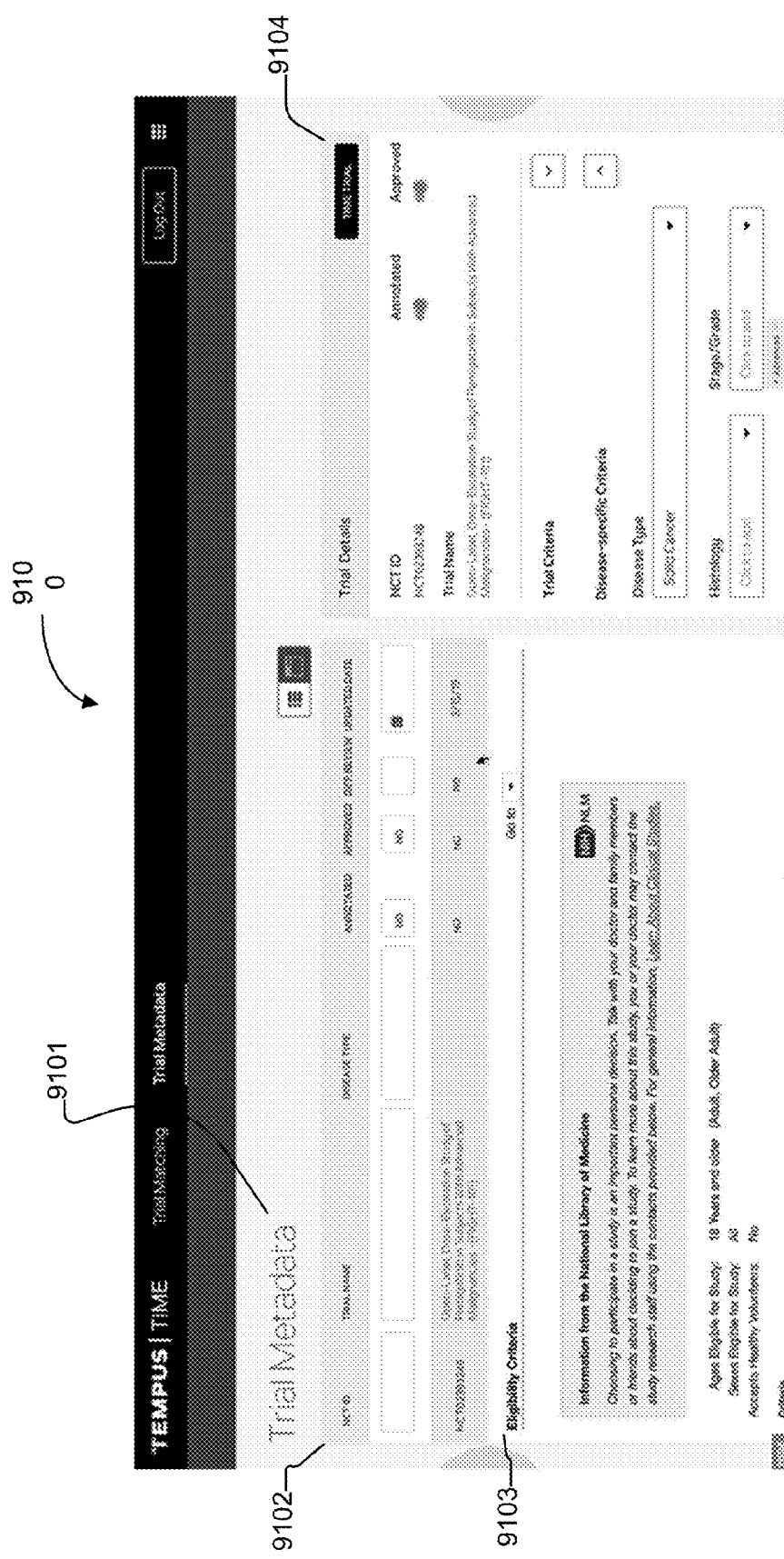
Figure 273:
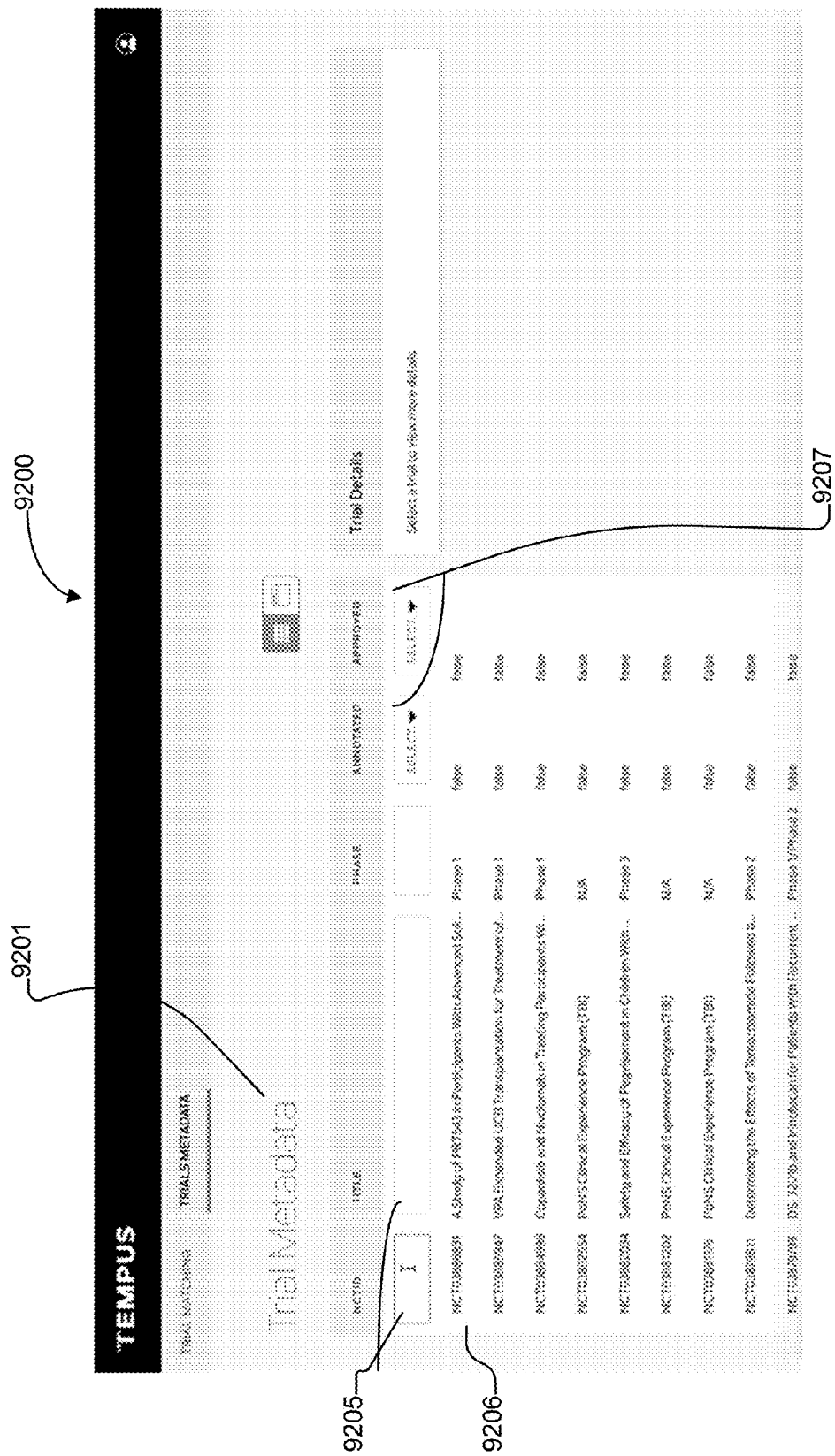
Figure 274:
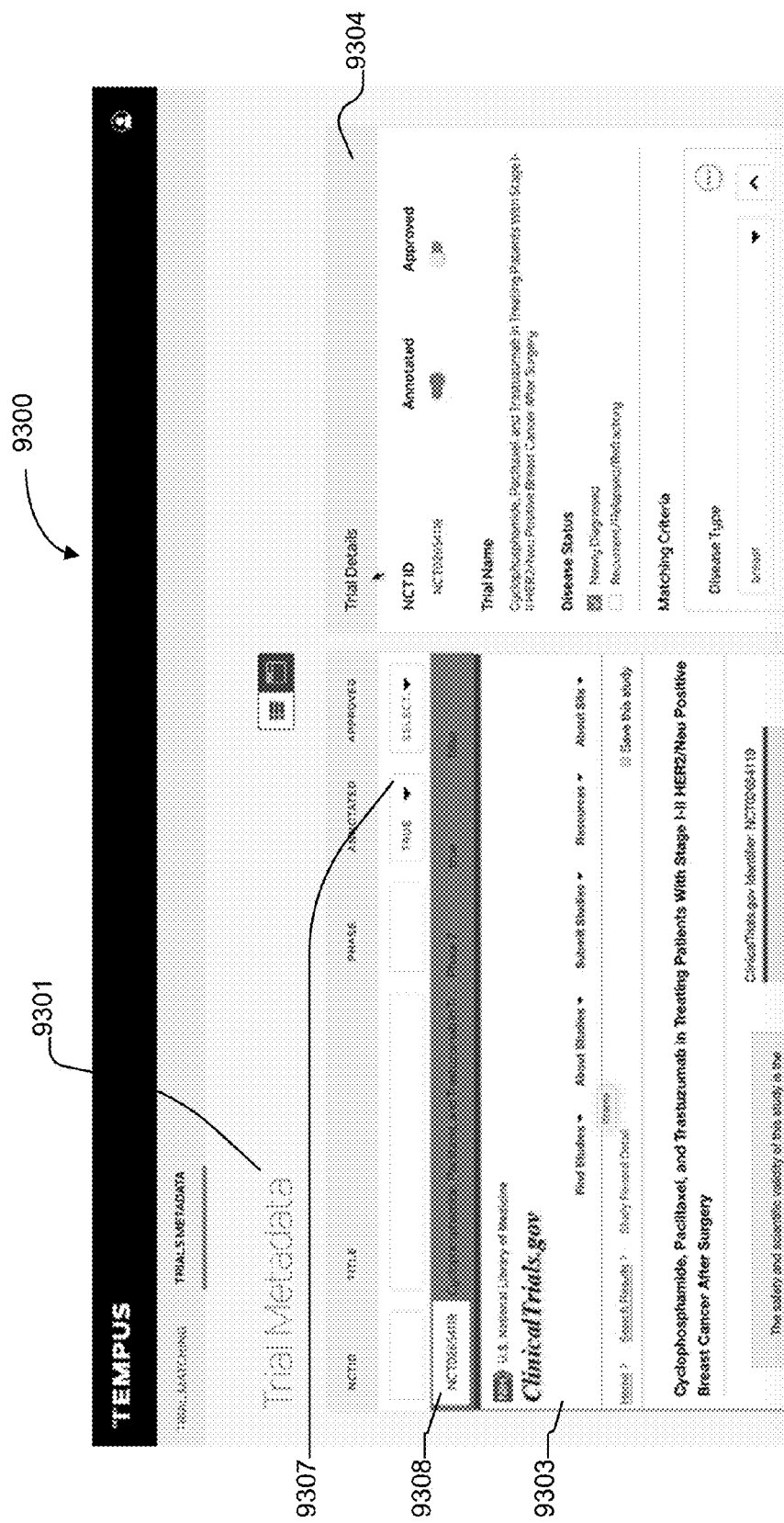
Figure 275:
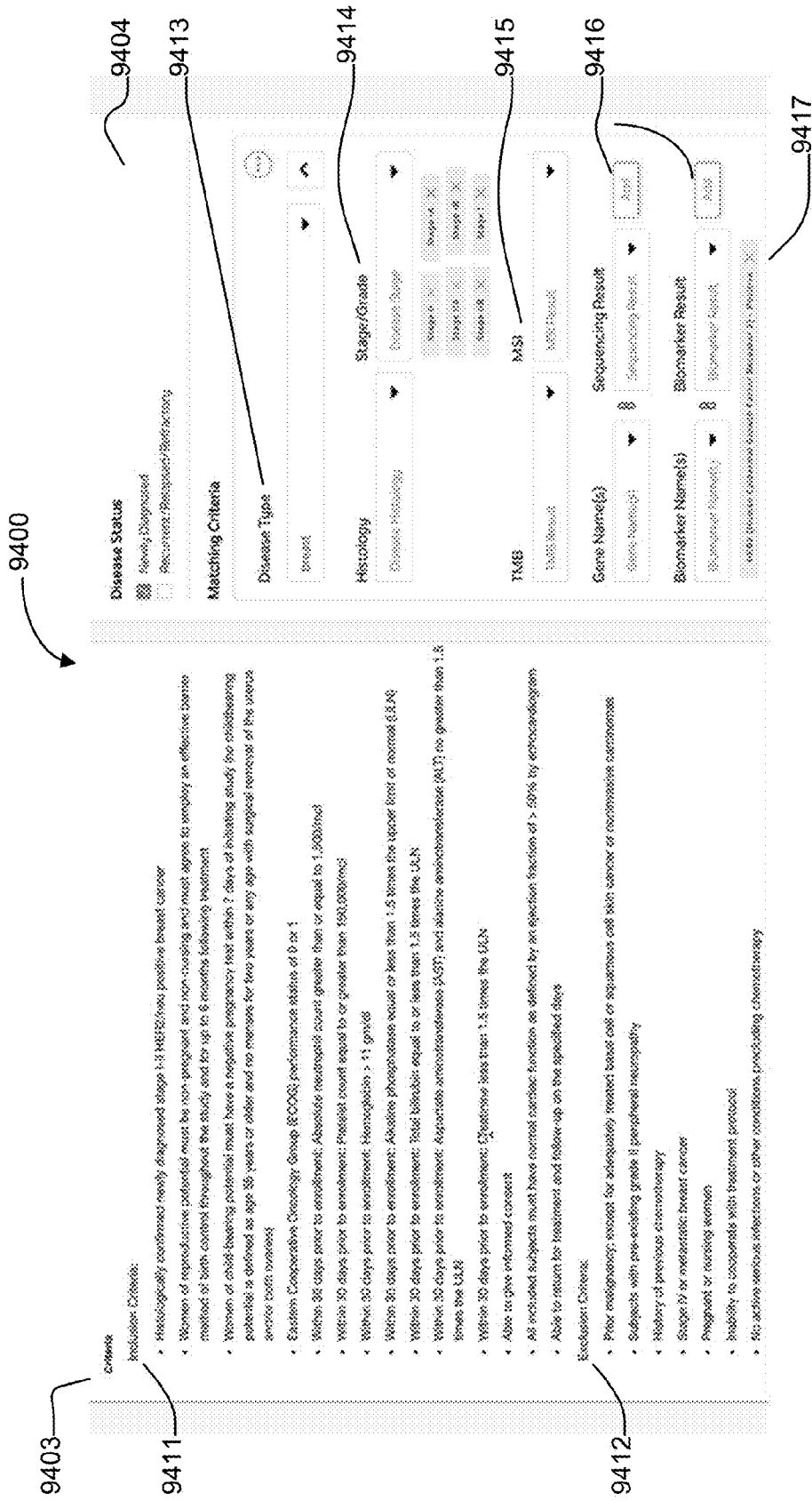
Figure 276:
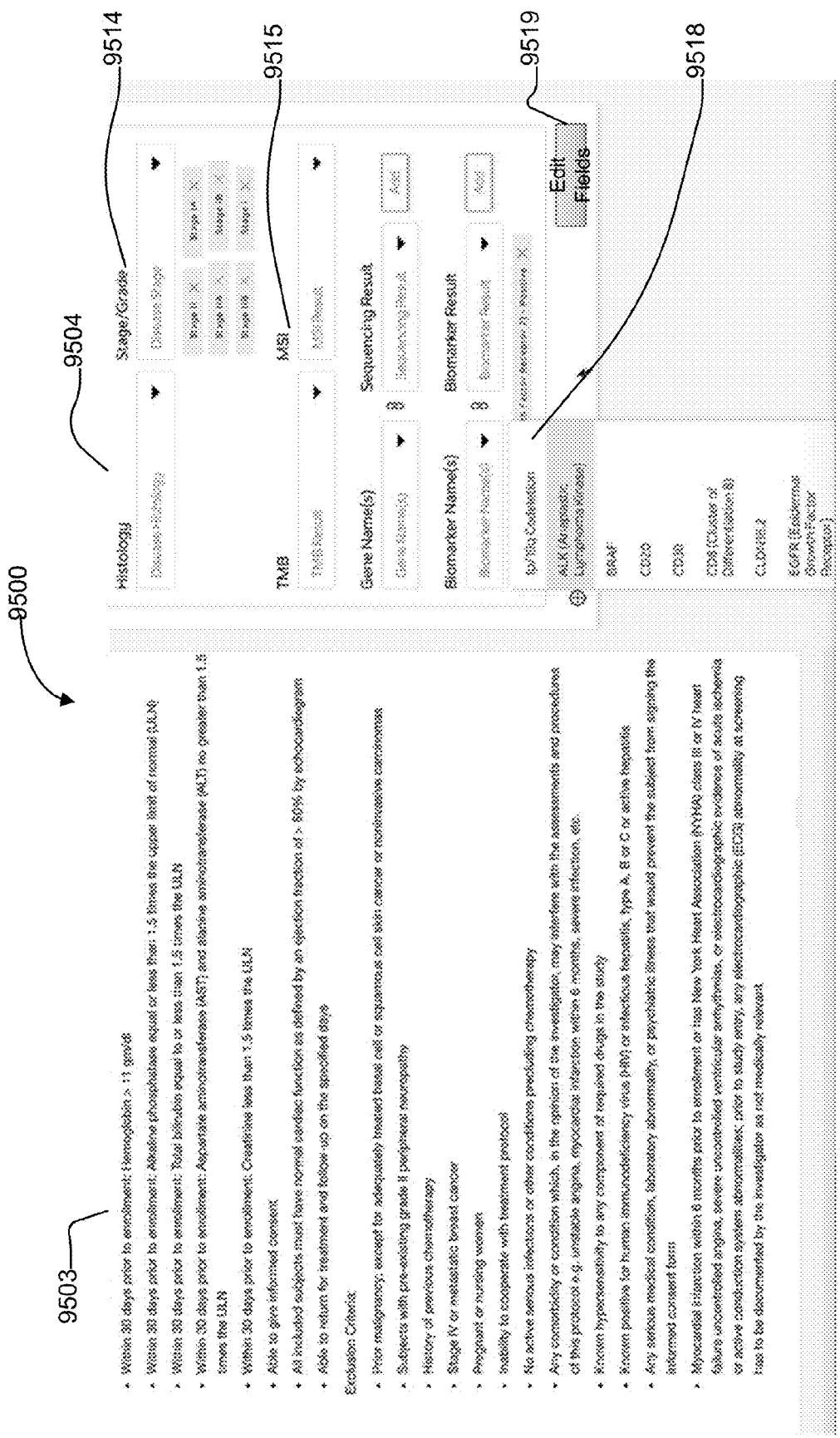
Figure 277:
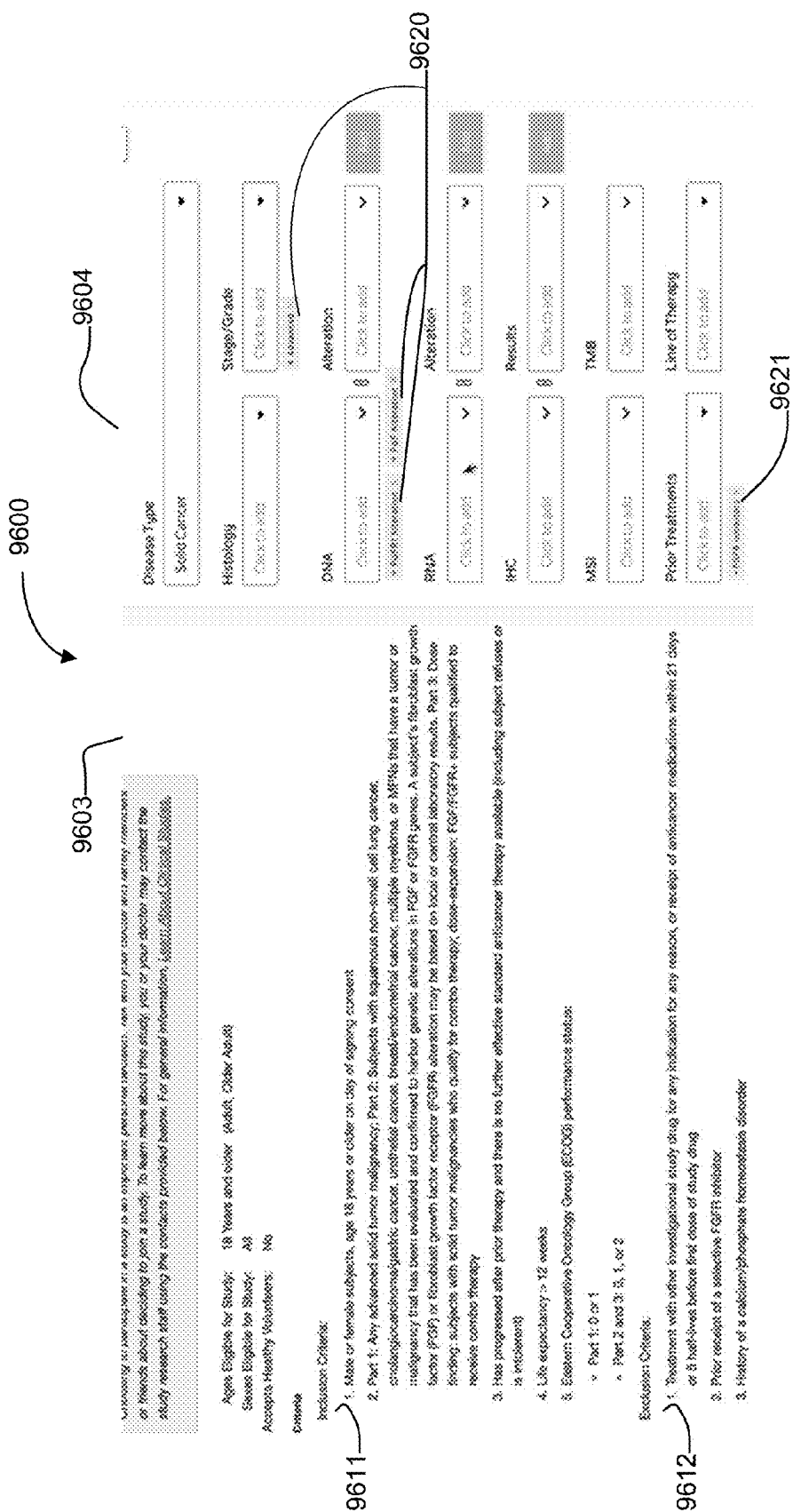
Figure 278:
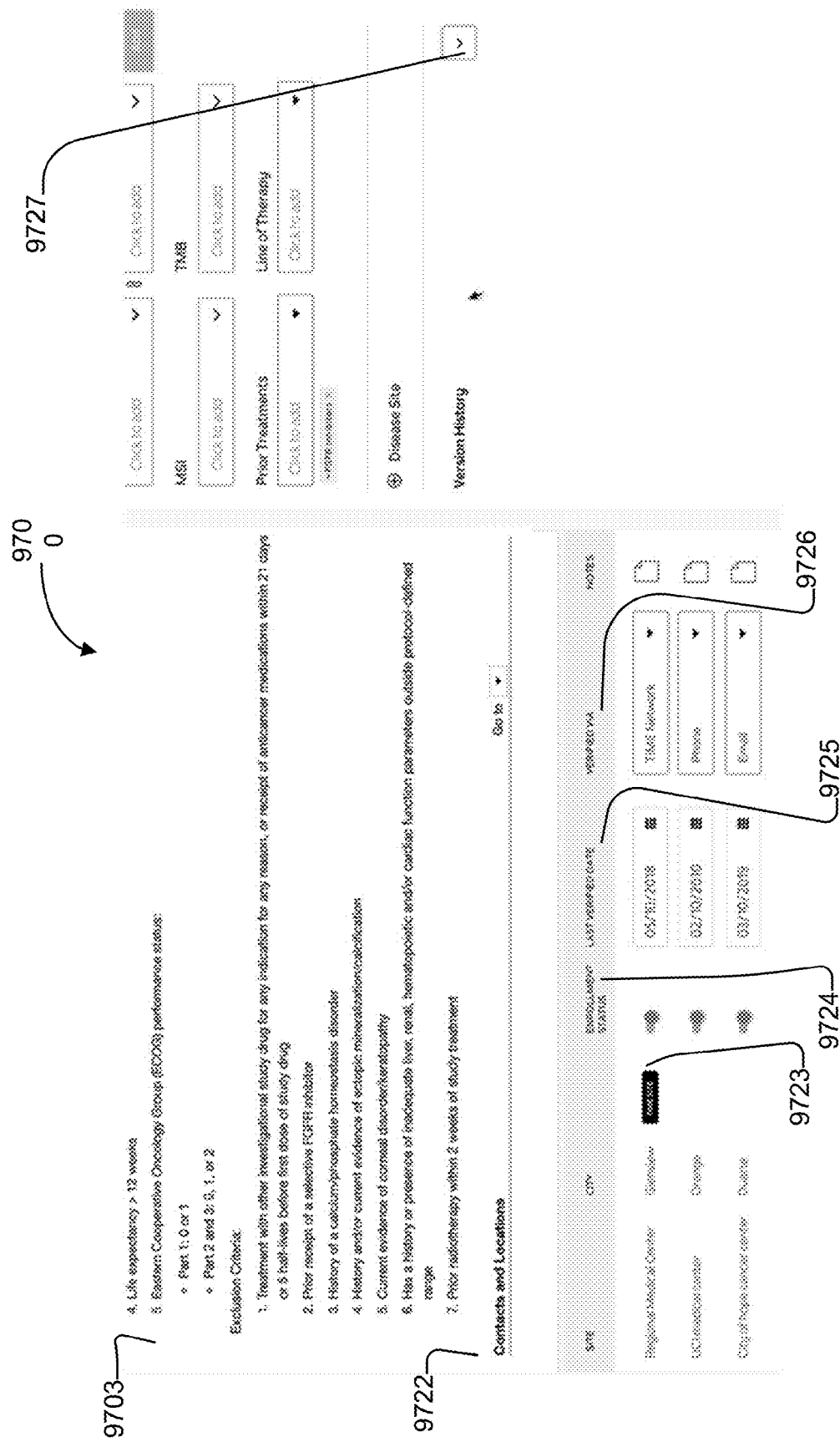
Figure 279:
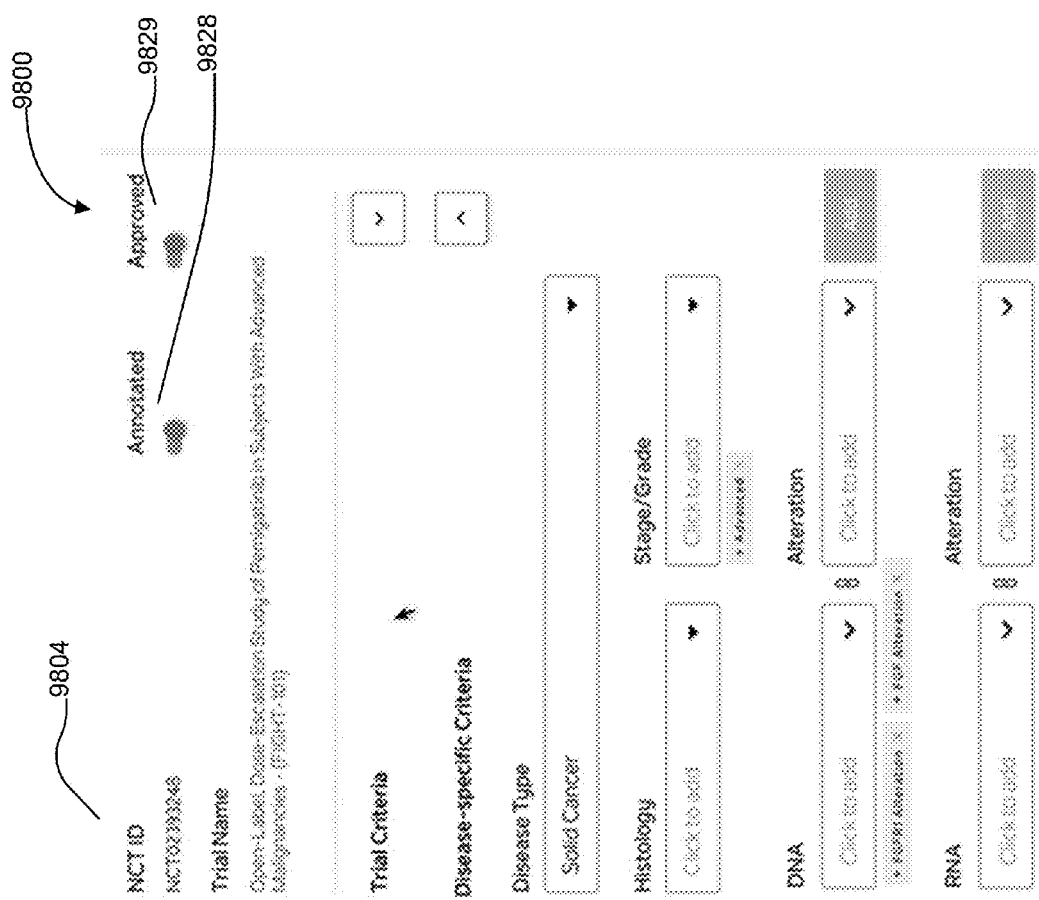
Figure 280:
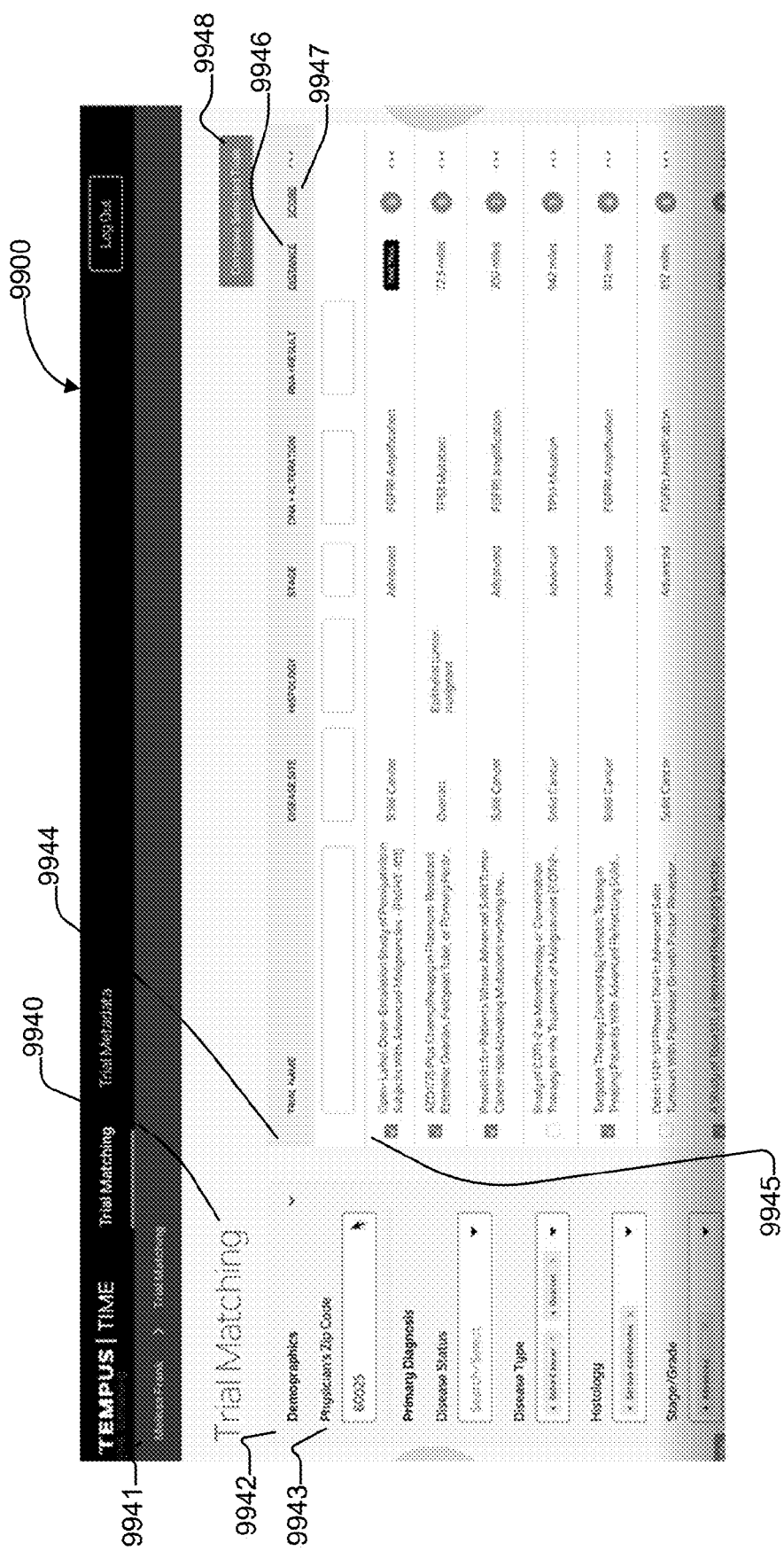
Figure 281:
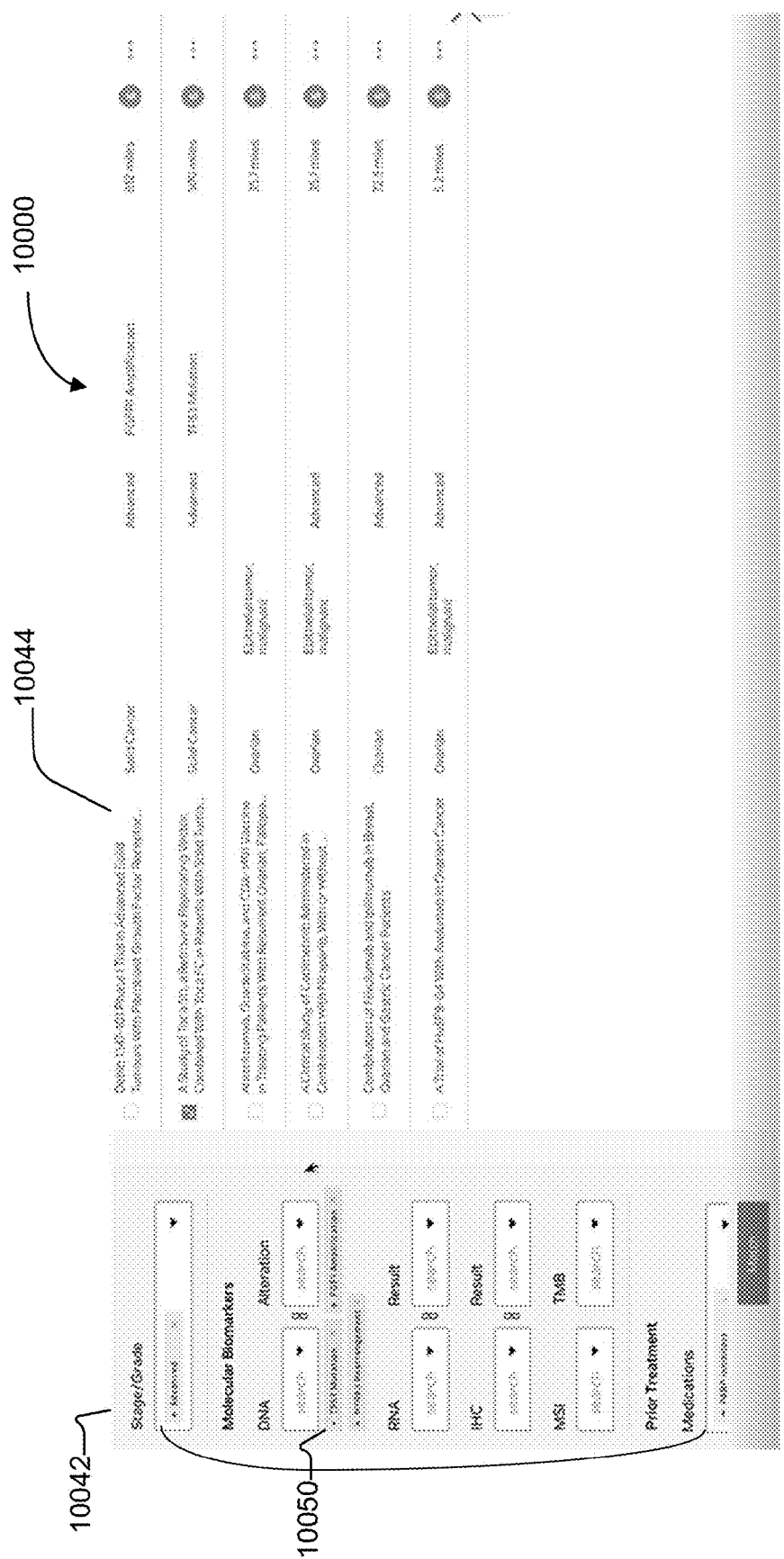
Figure 282:
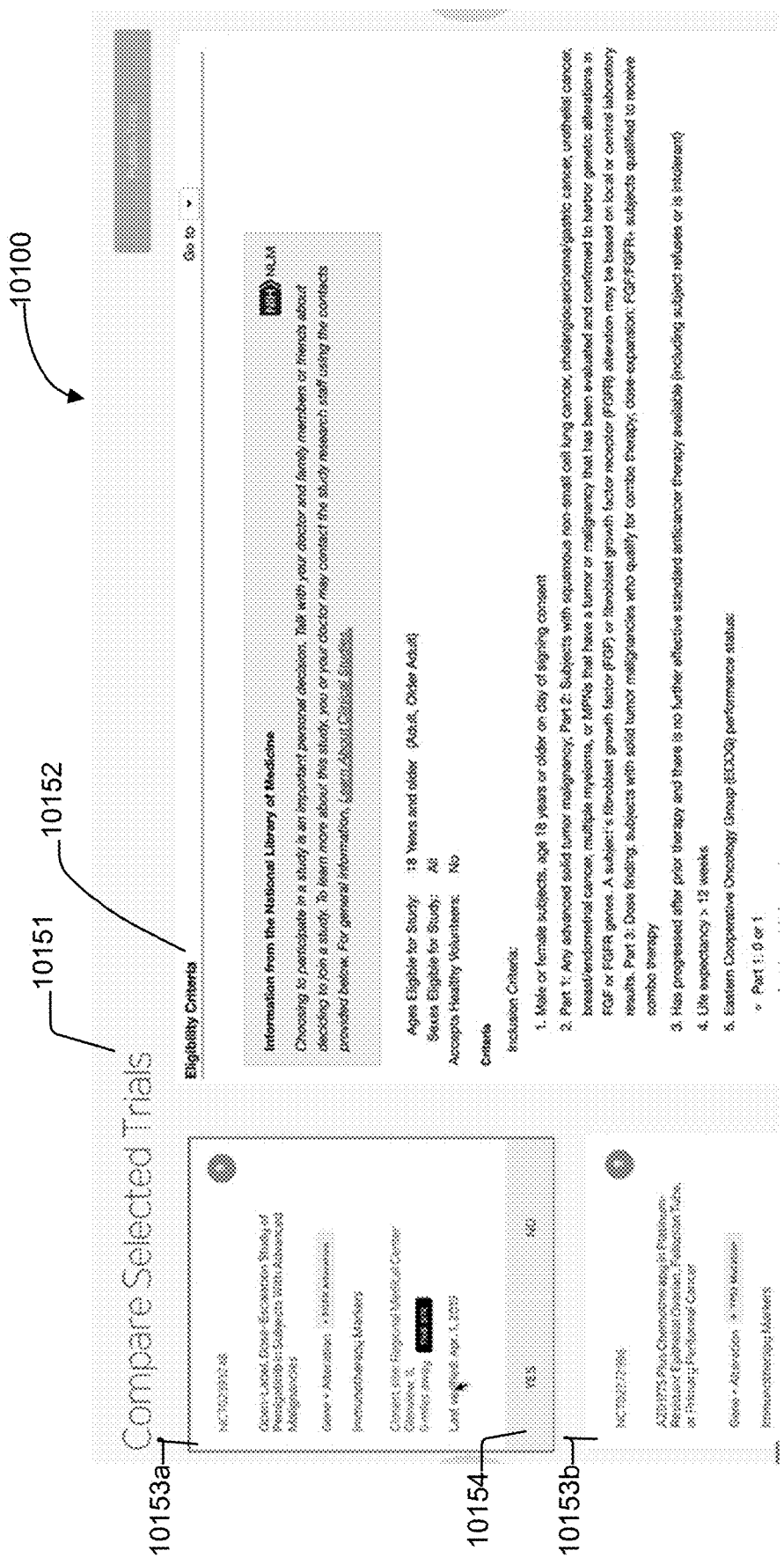
Figure 283:
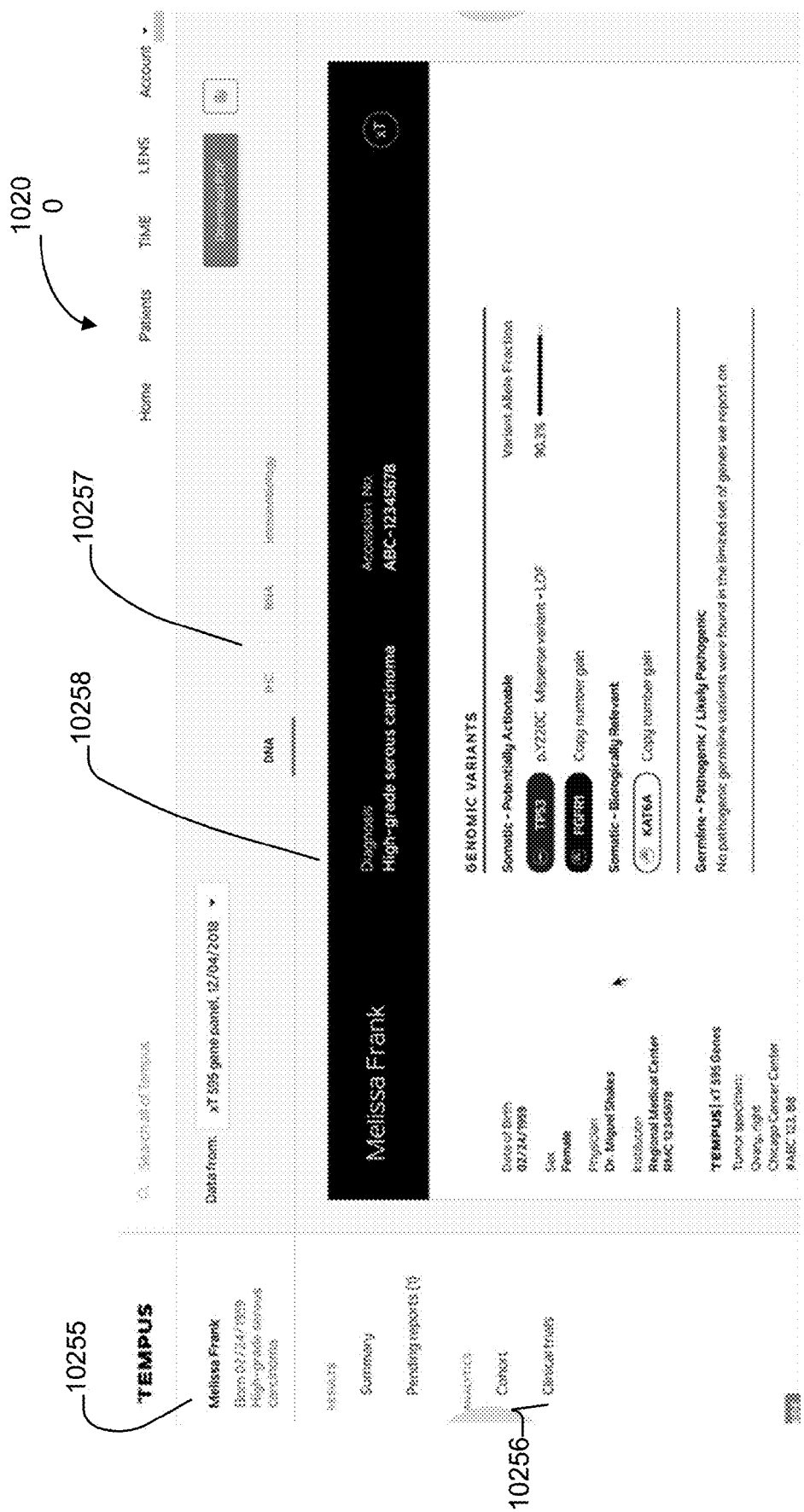
Figure 284:
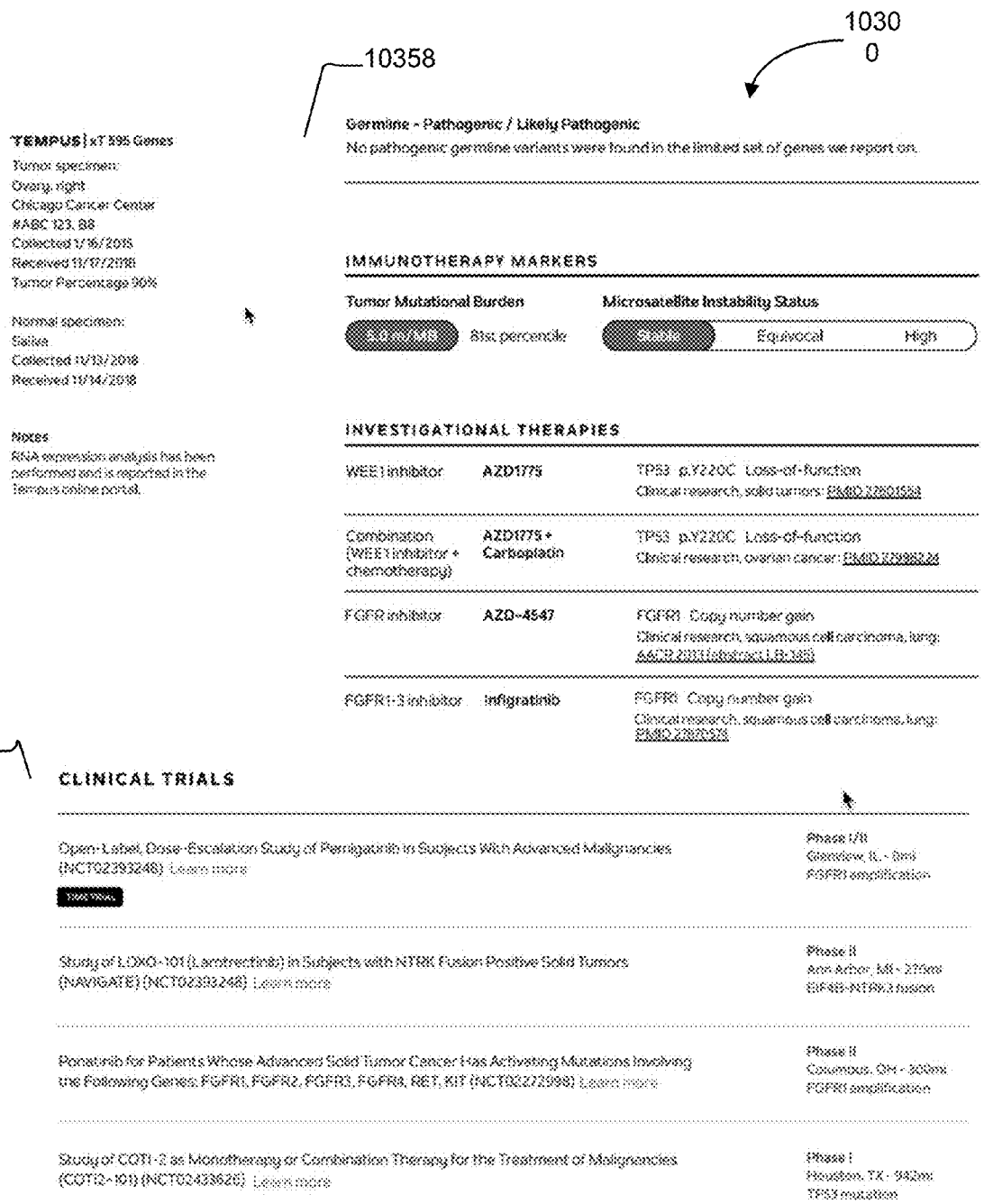
Figure 285:
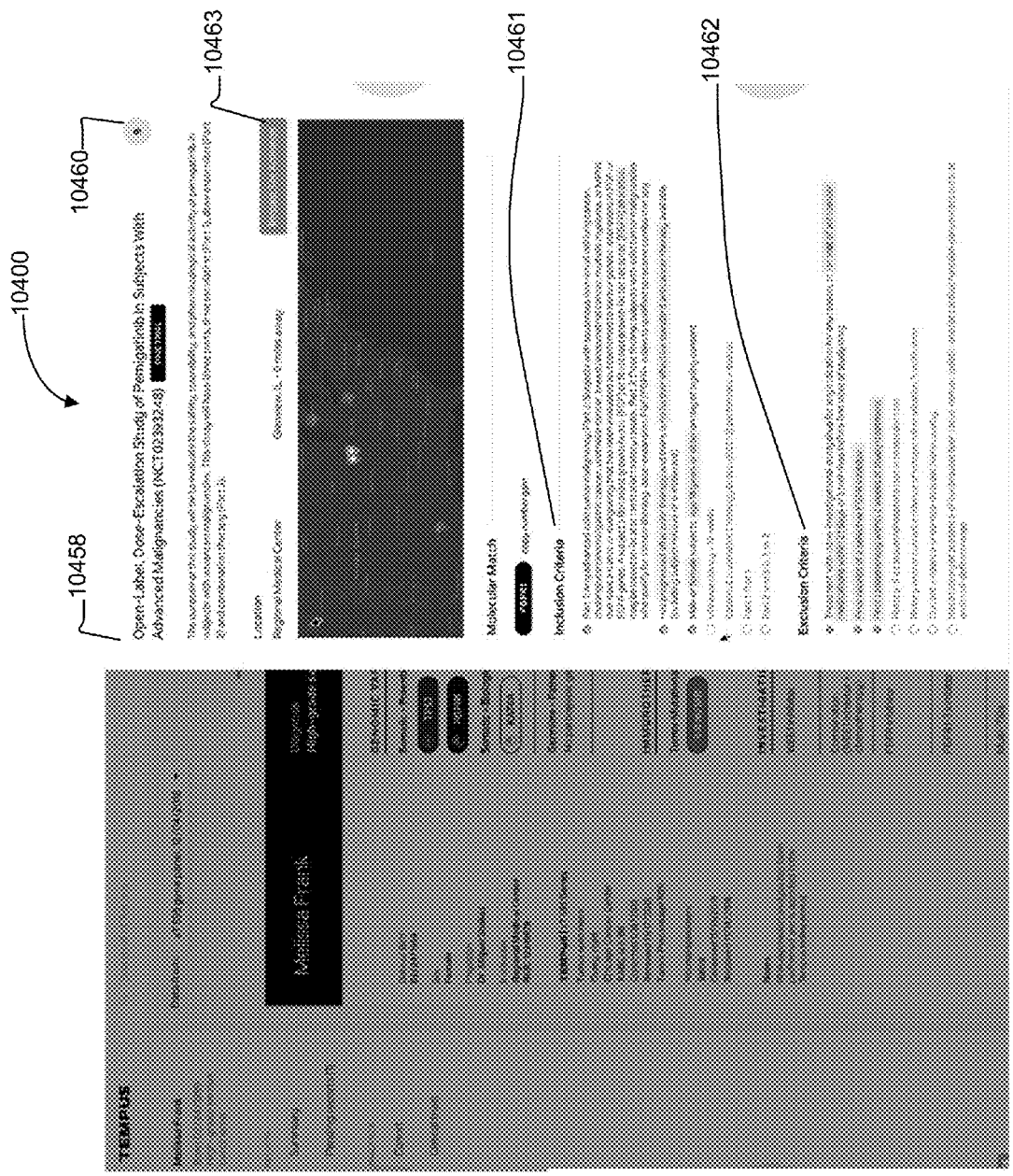
Figure 286:
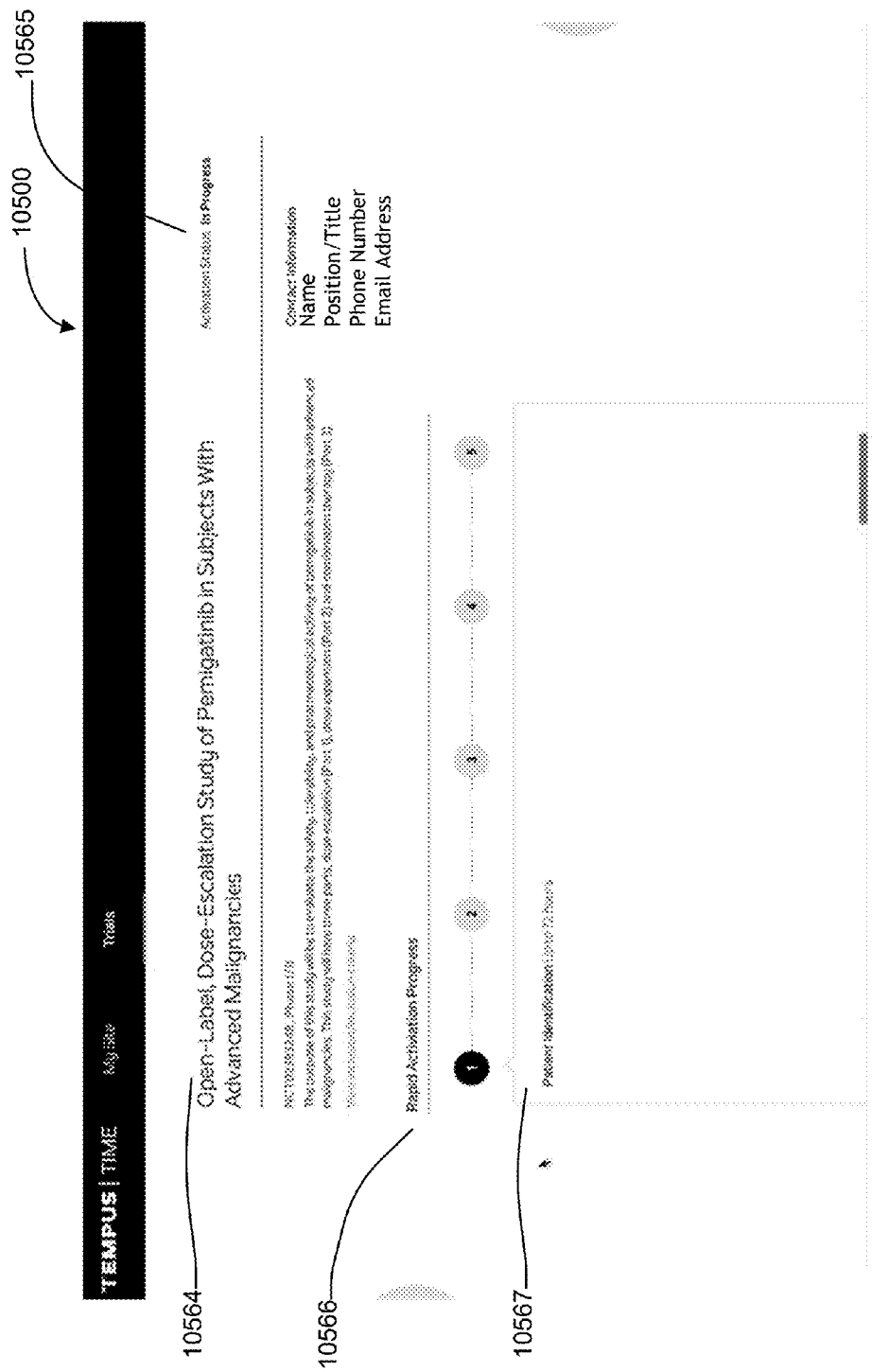
Figure 287:
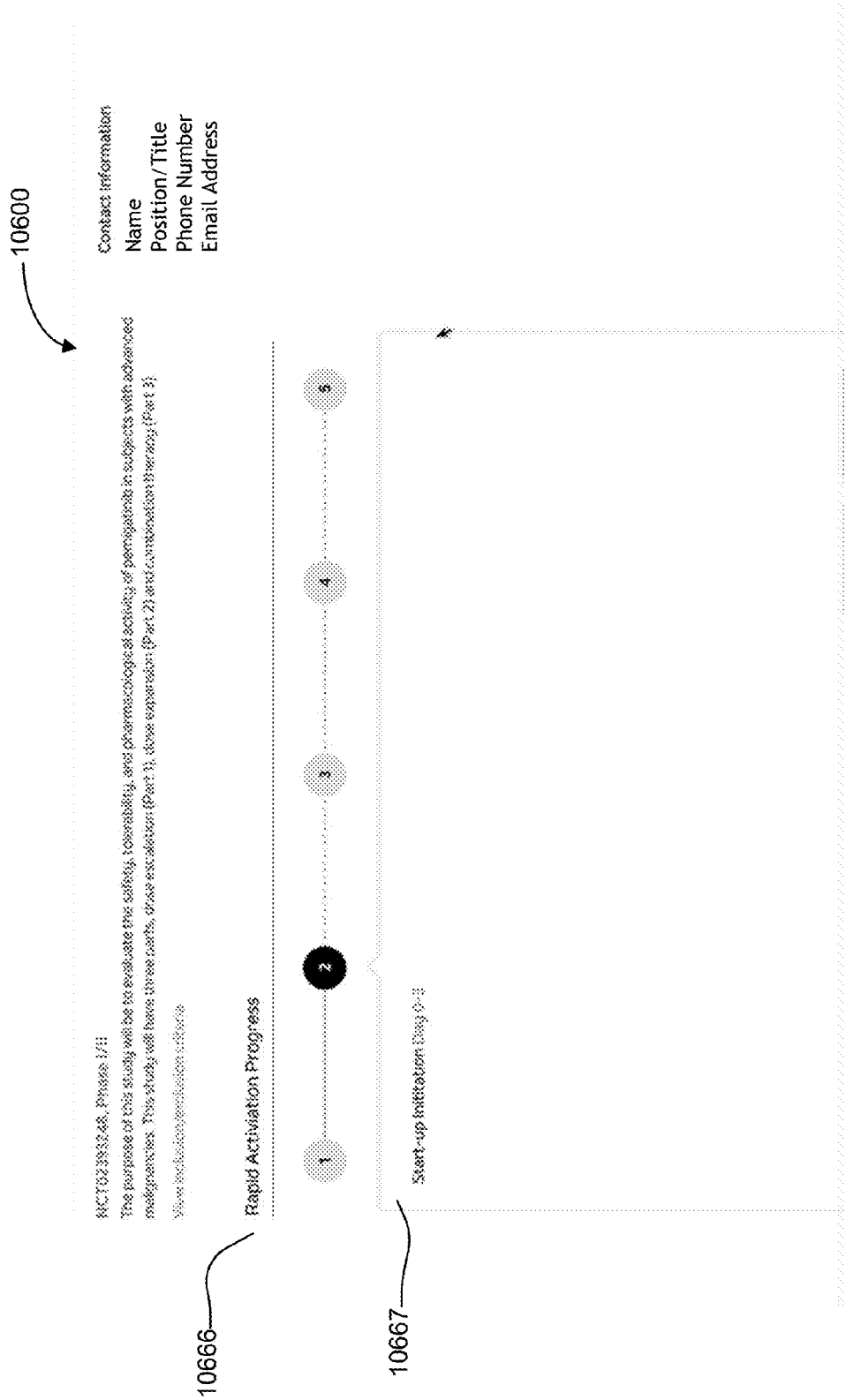
Figure 288:
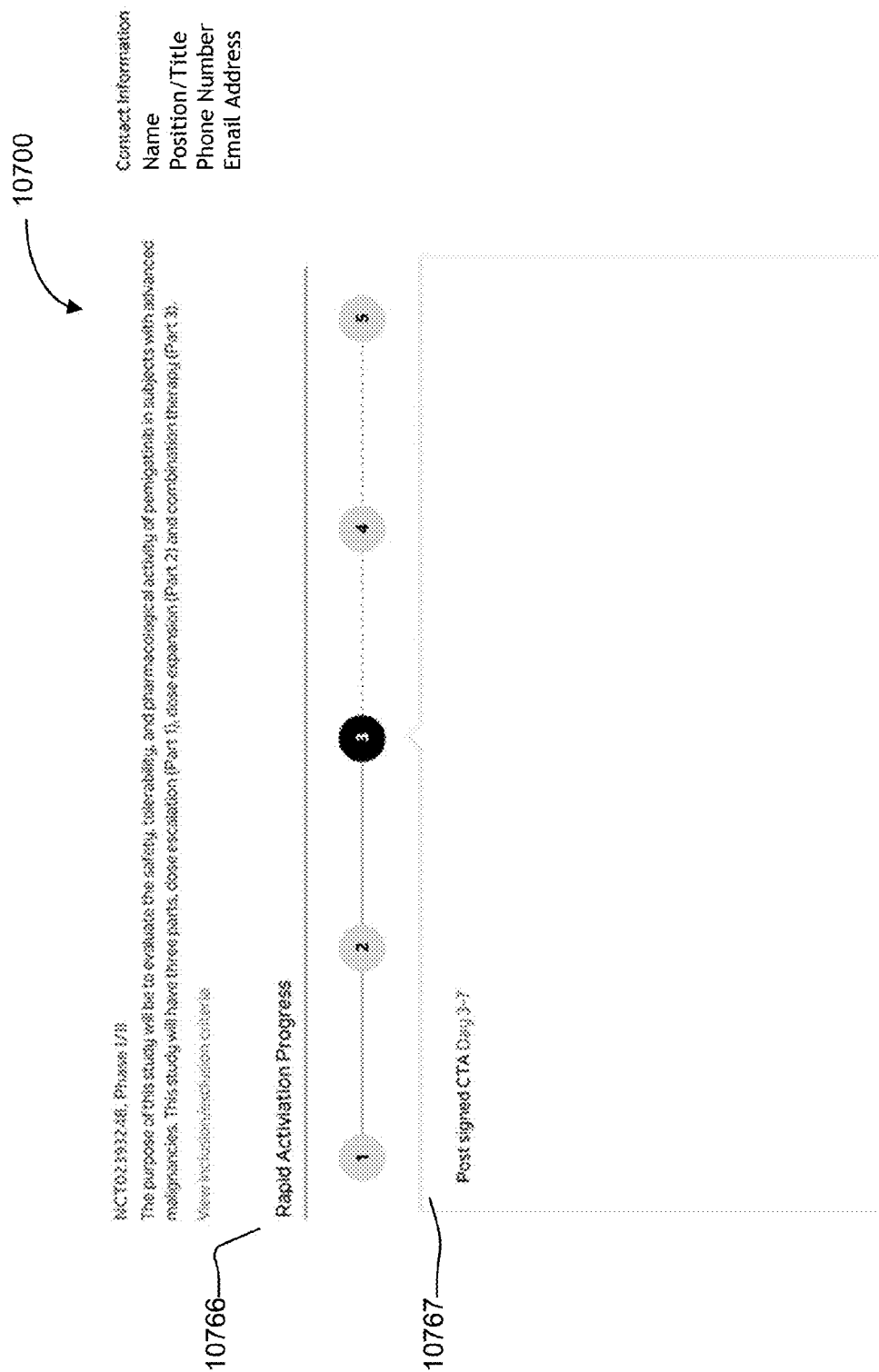
Figure 289:
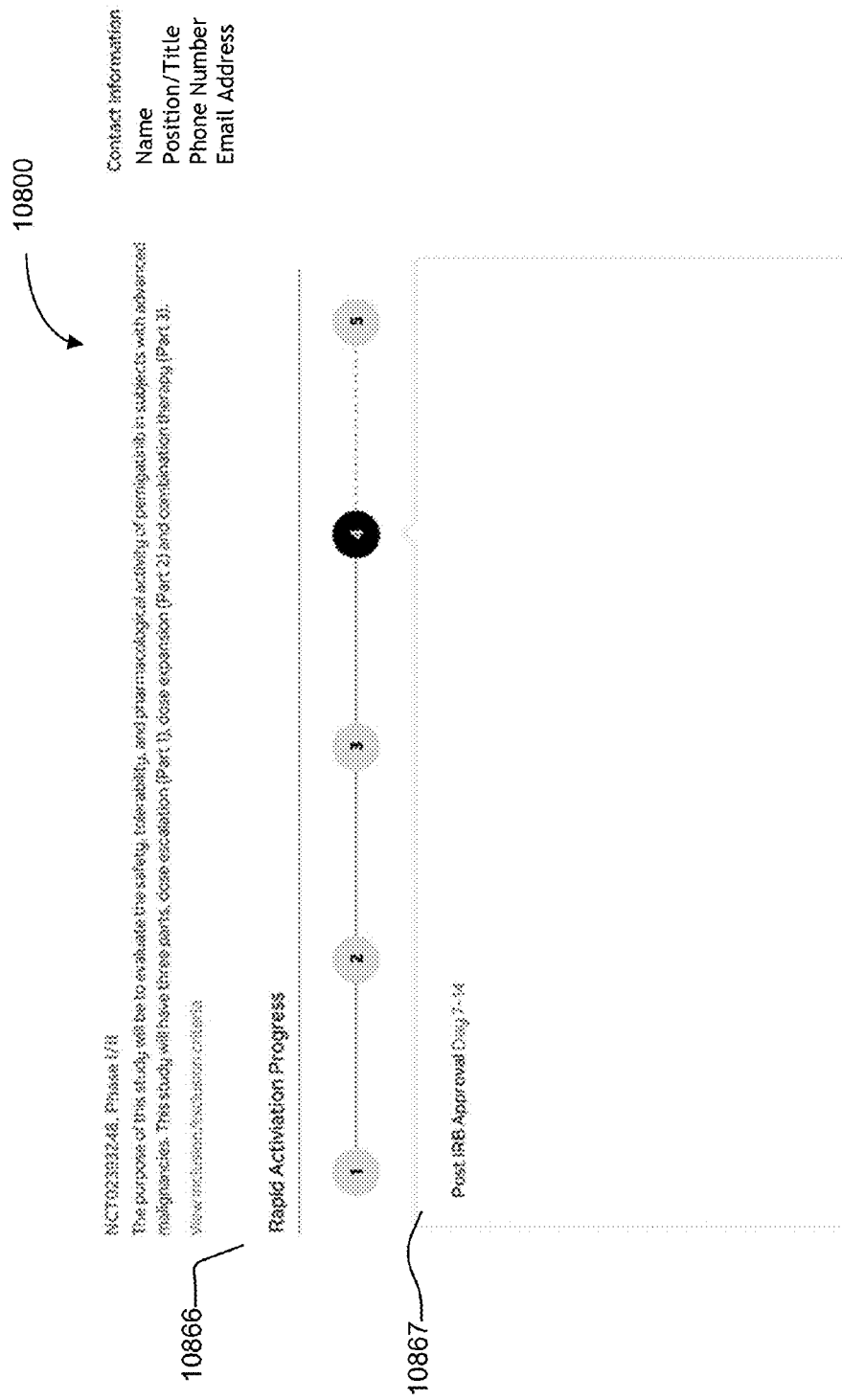
Figure 290:
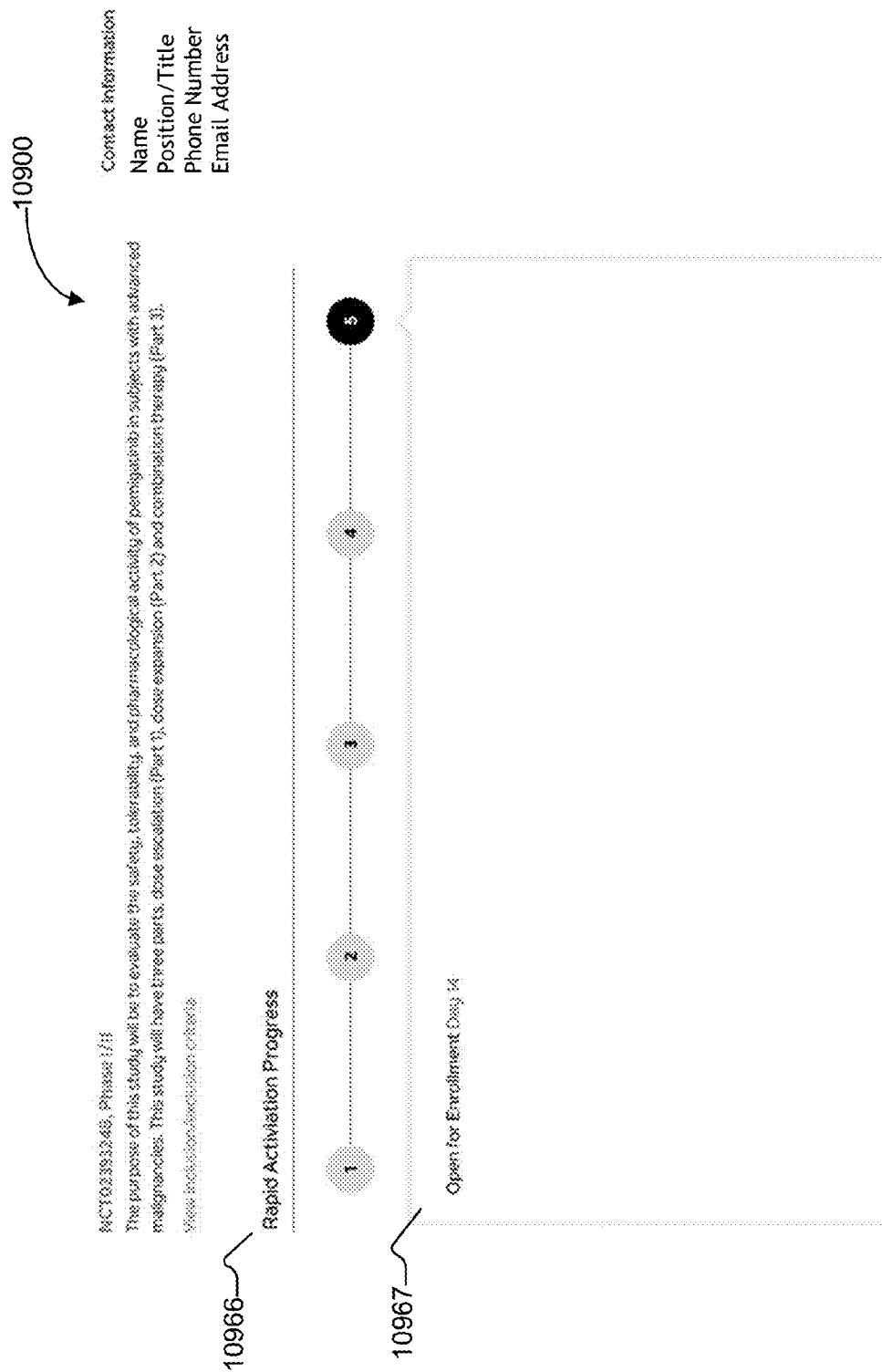
Figure 291:
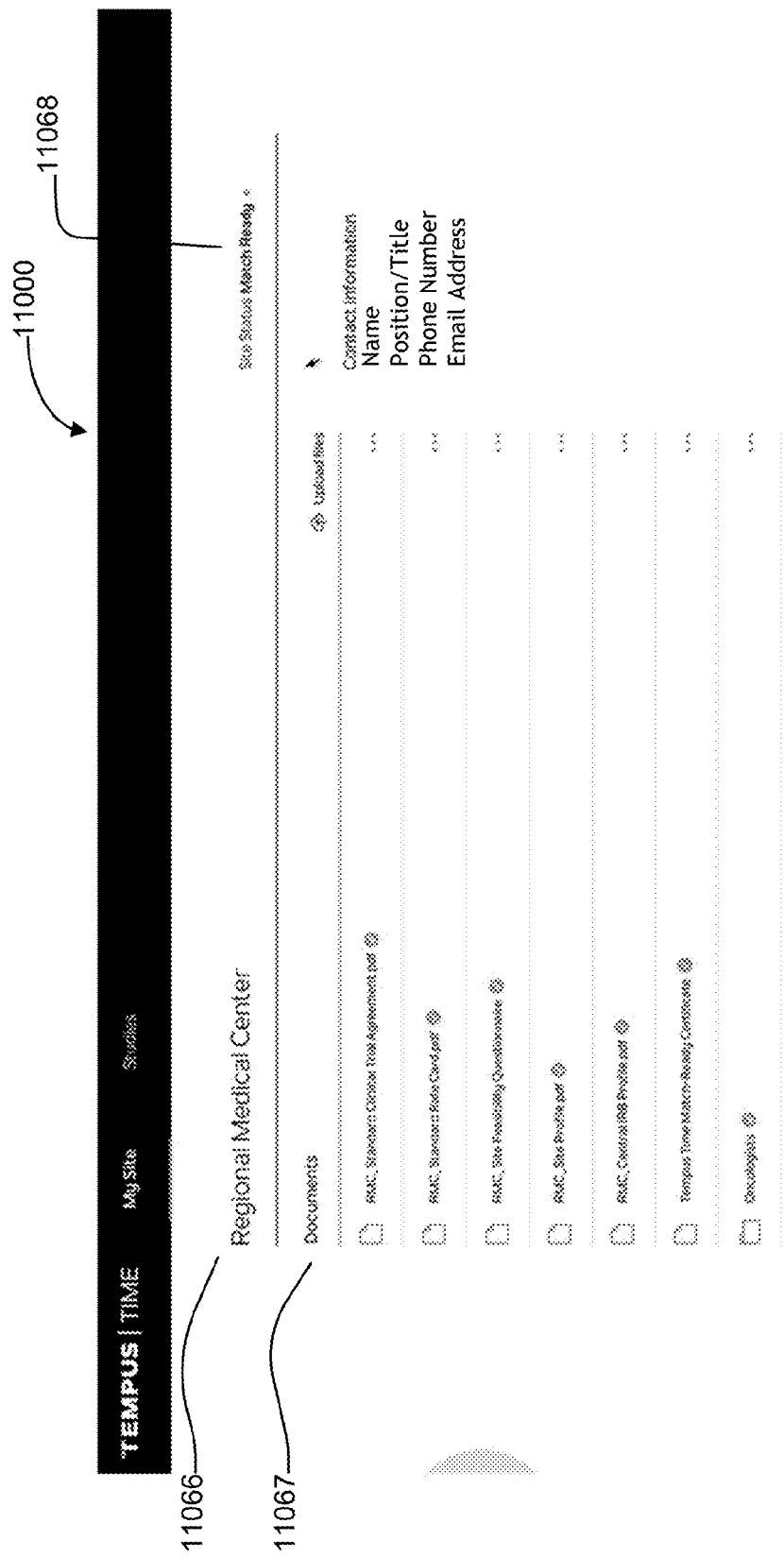
Figure 293:
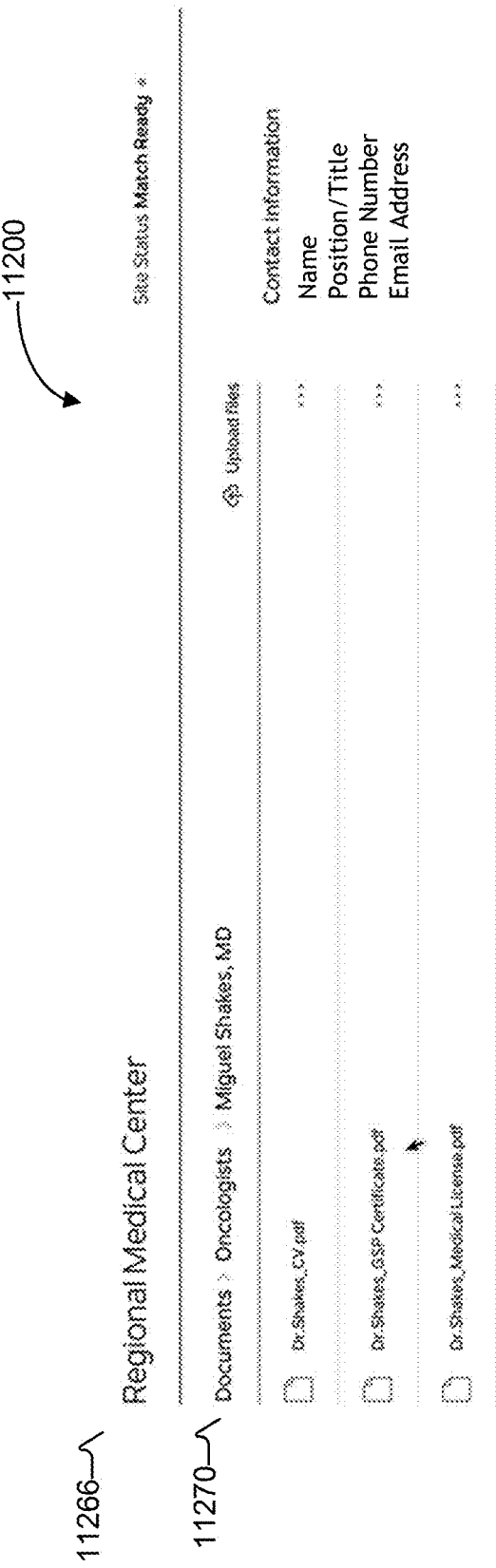
Figure 301A:
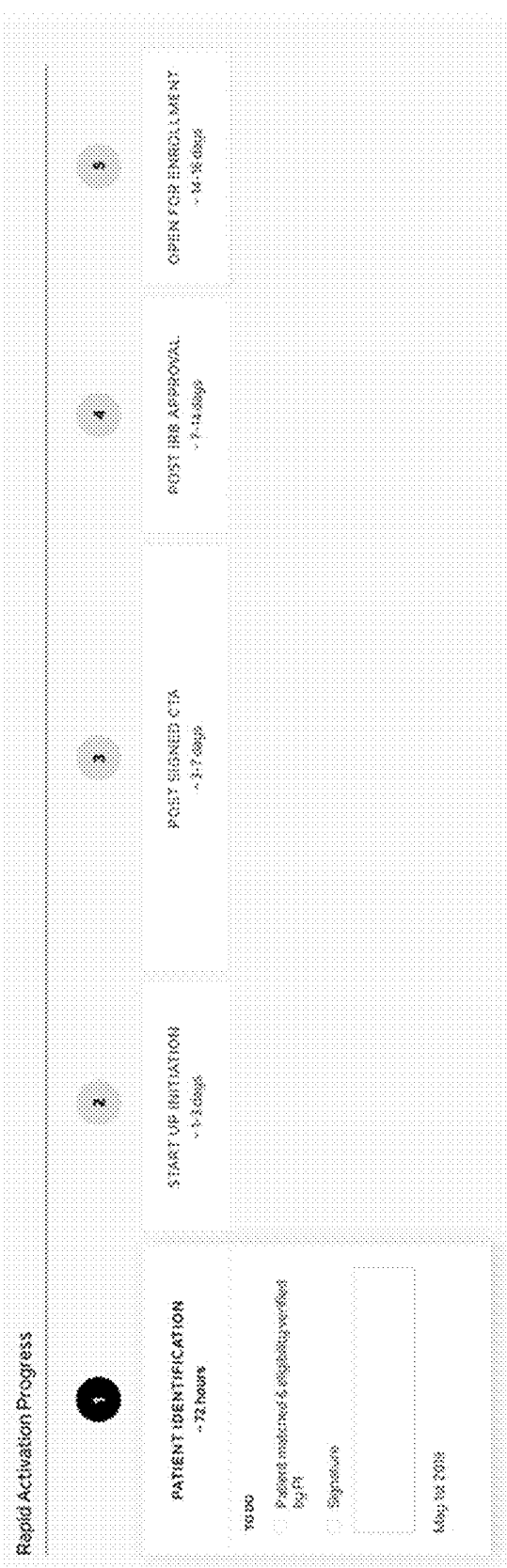
Figure 301B:
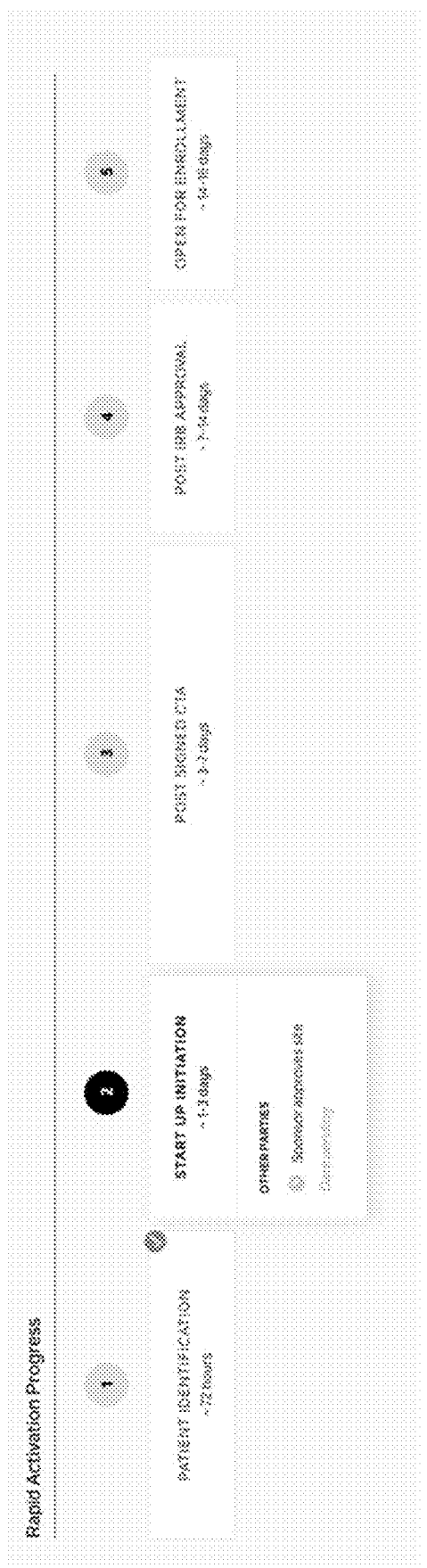
Figure 301C:
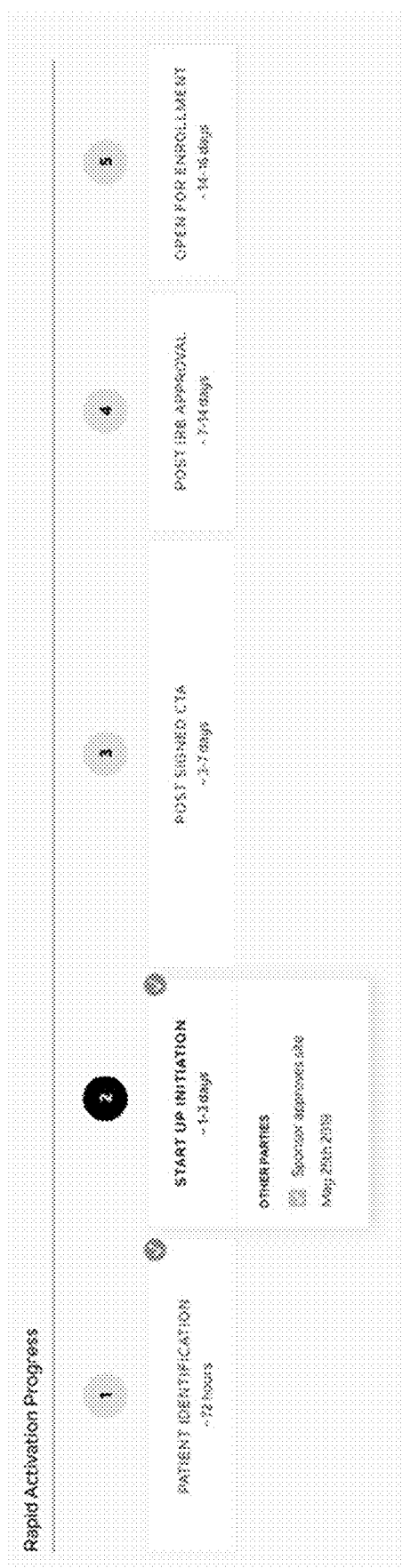
Figure 301D:
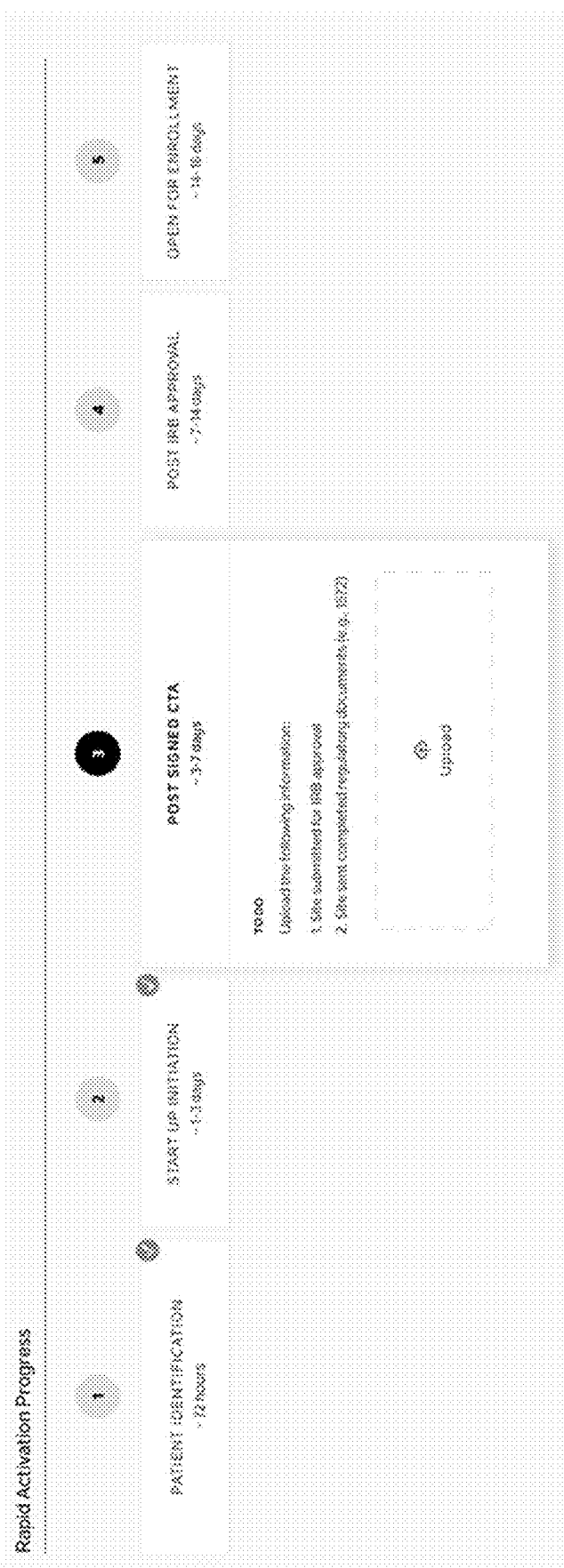
Figure 301E:
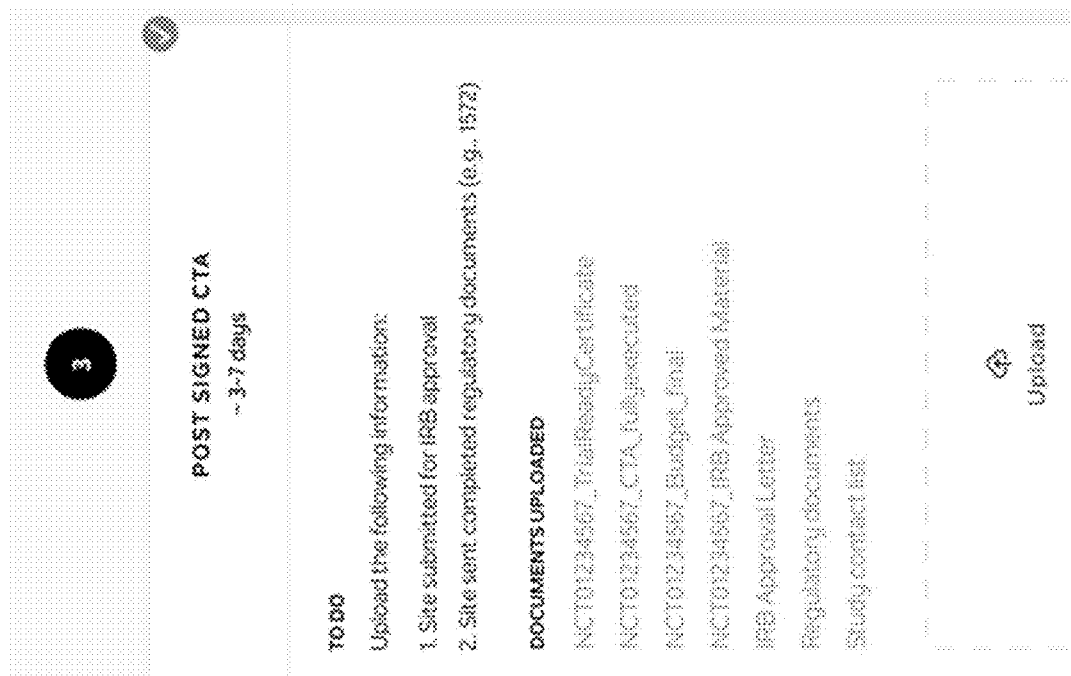
Figure 301F:
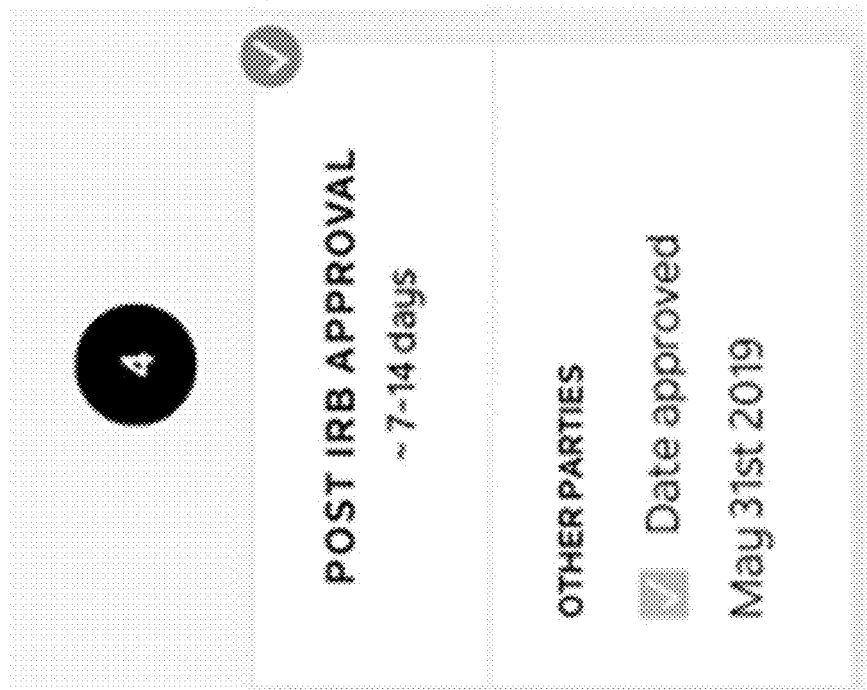
Figure 301G:
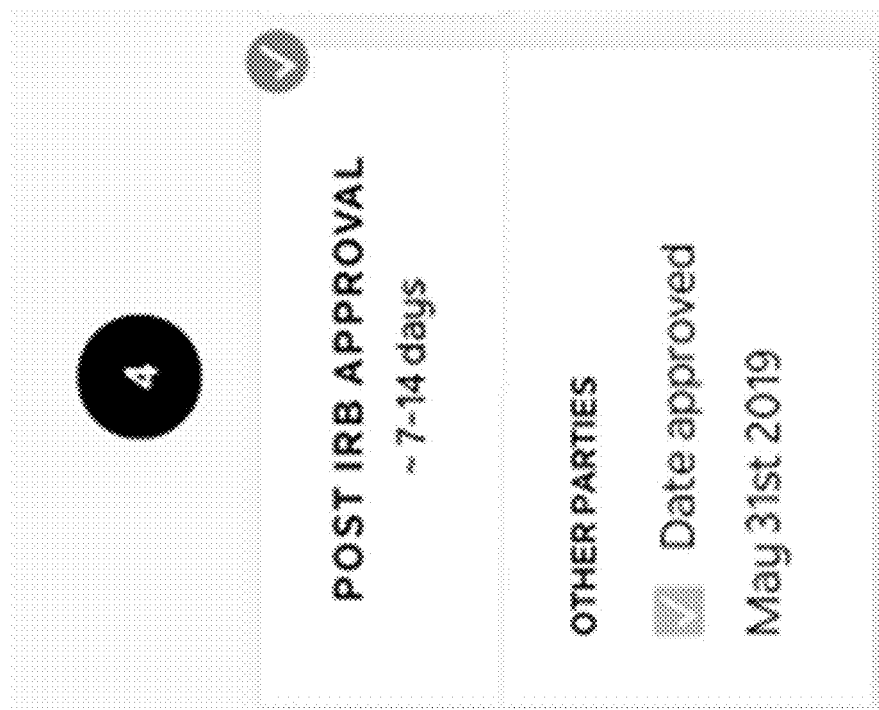
Figure 301H:
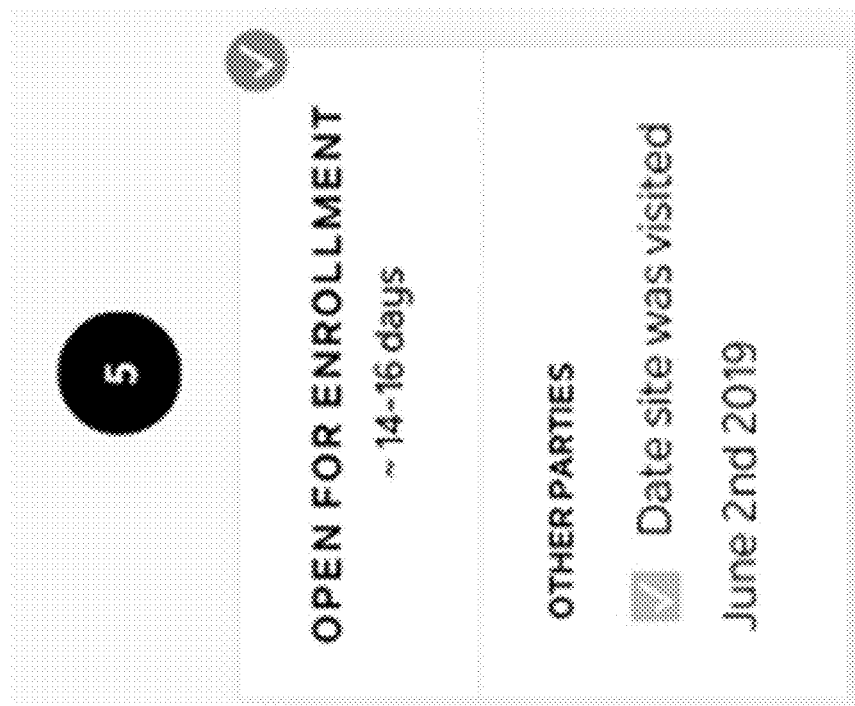
Figure 302:
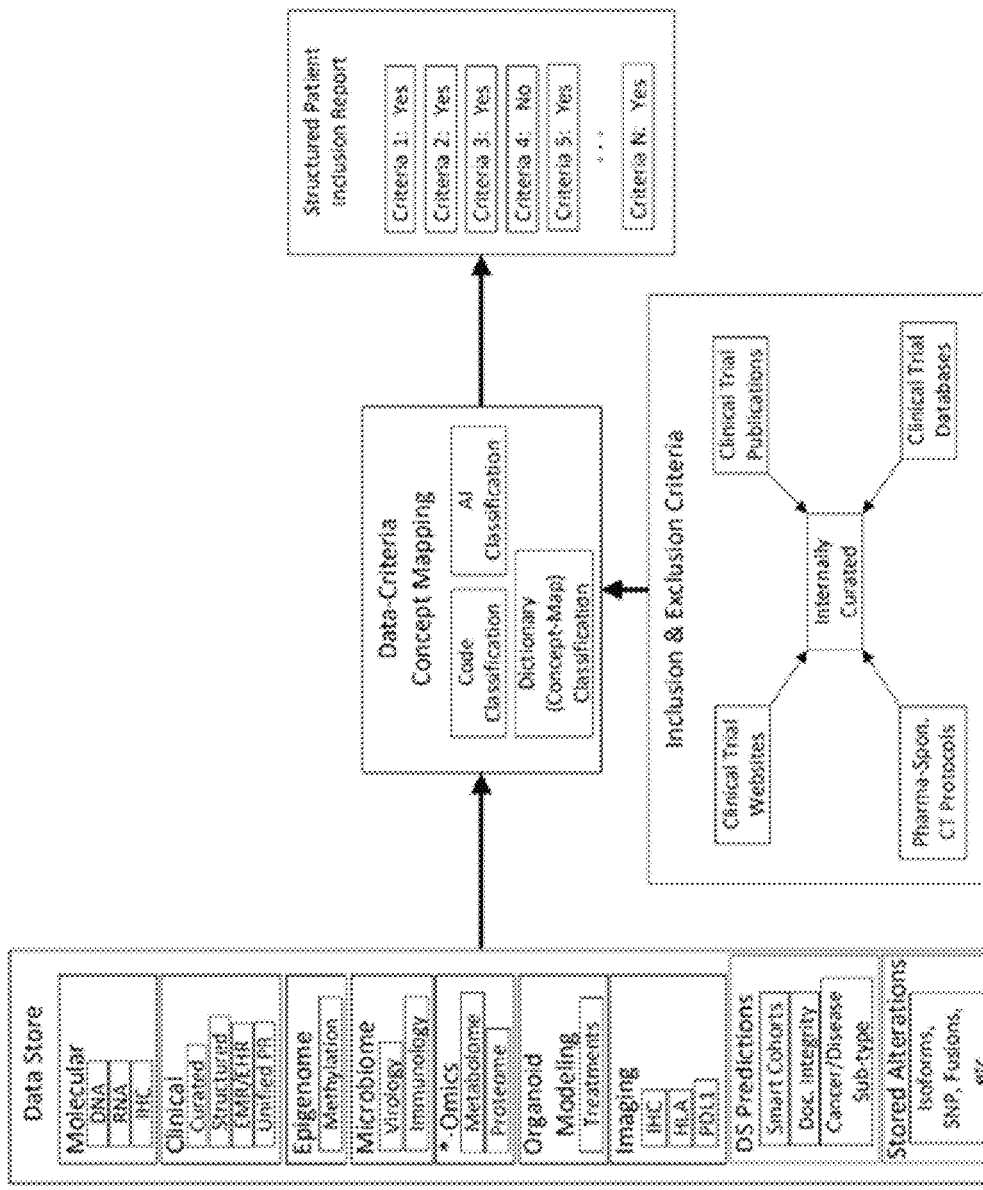
Figure 303:
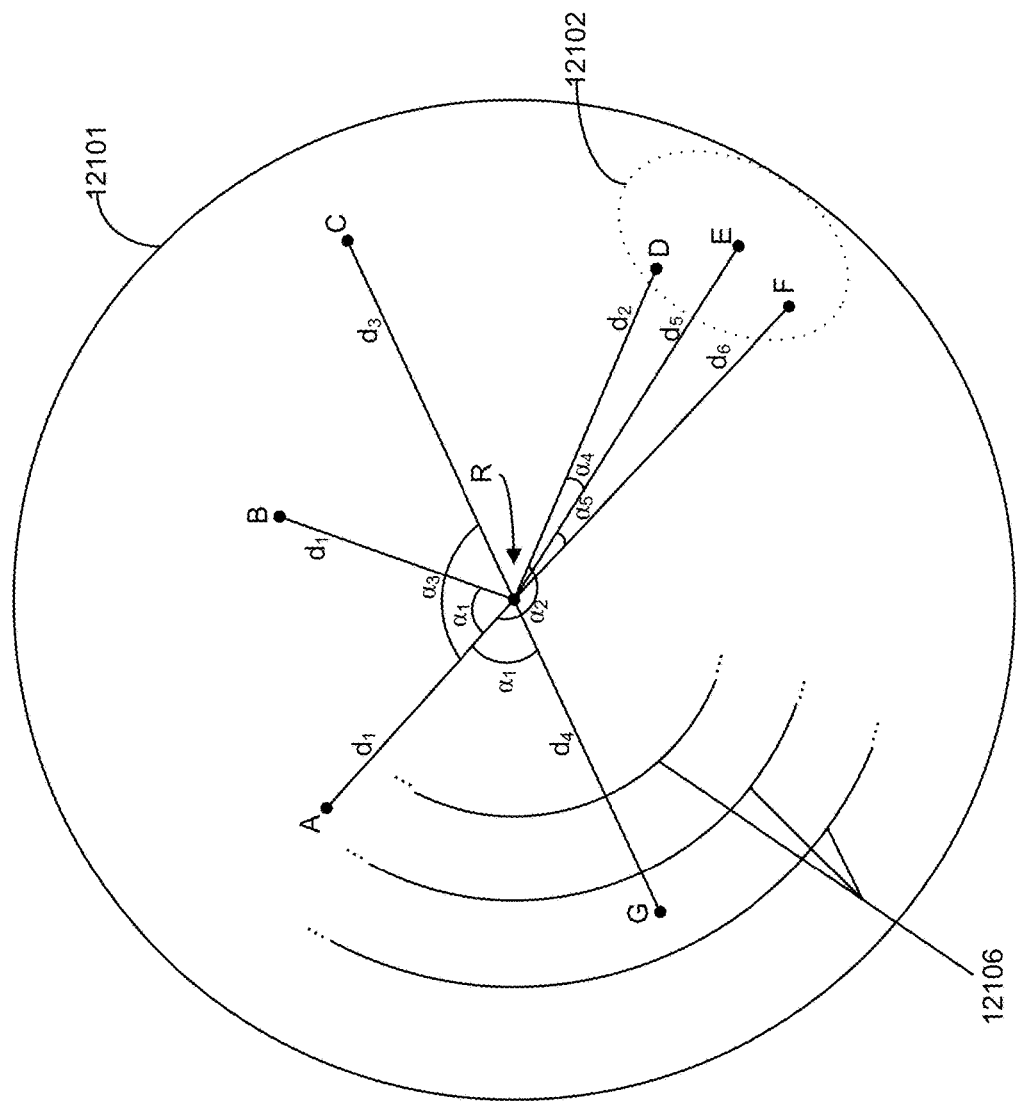
Figure 304A:
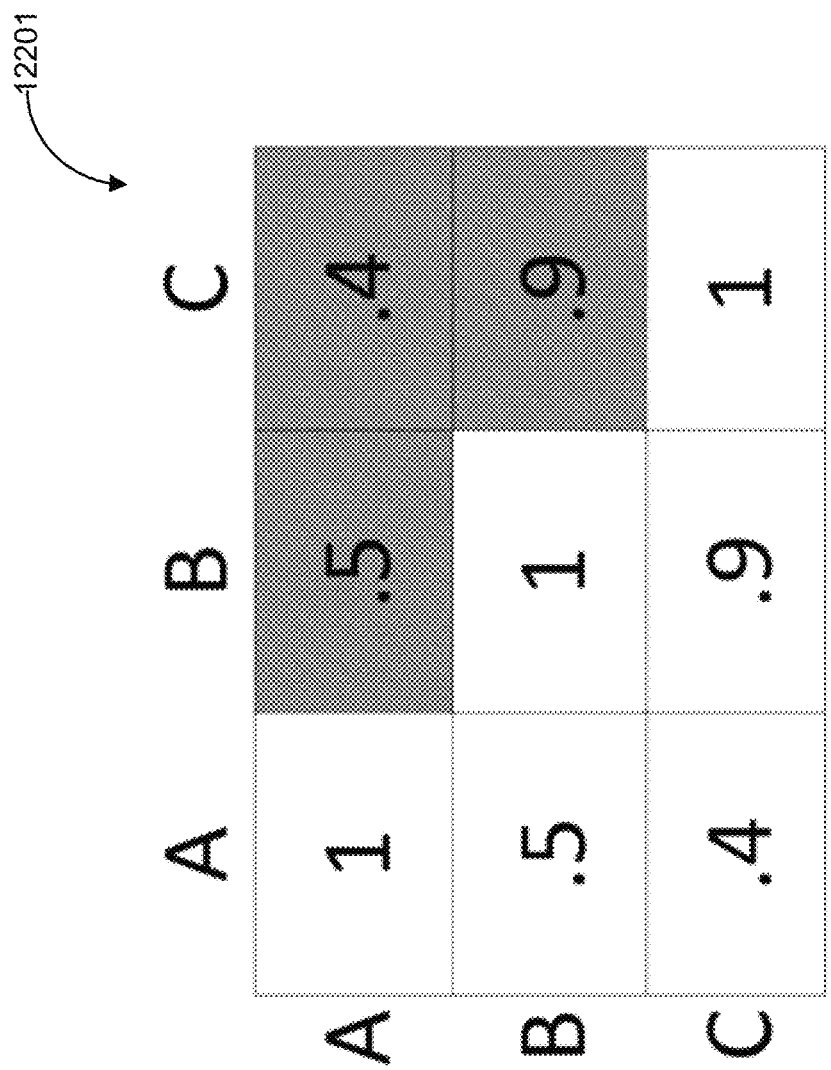
Figure 304B:
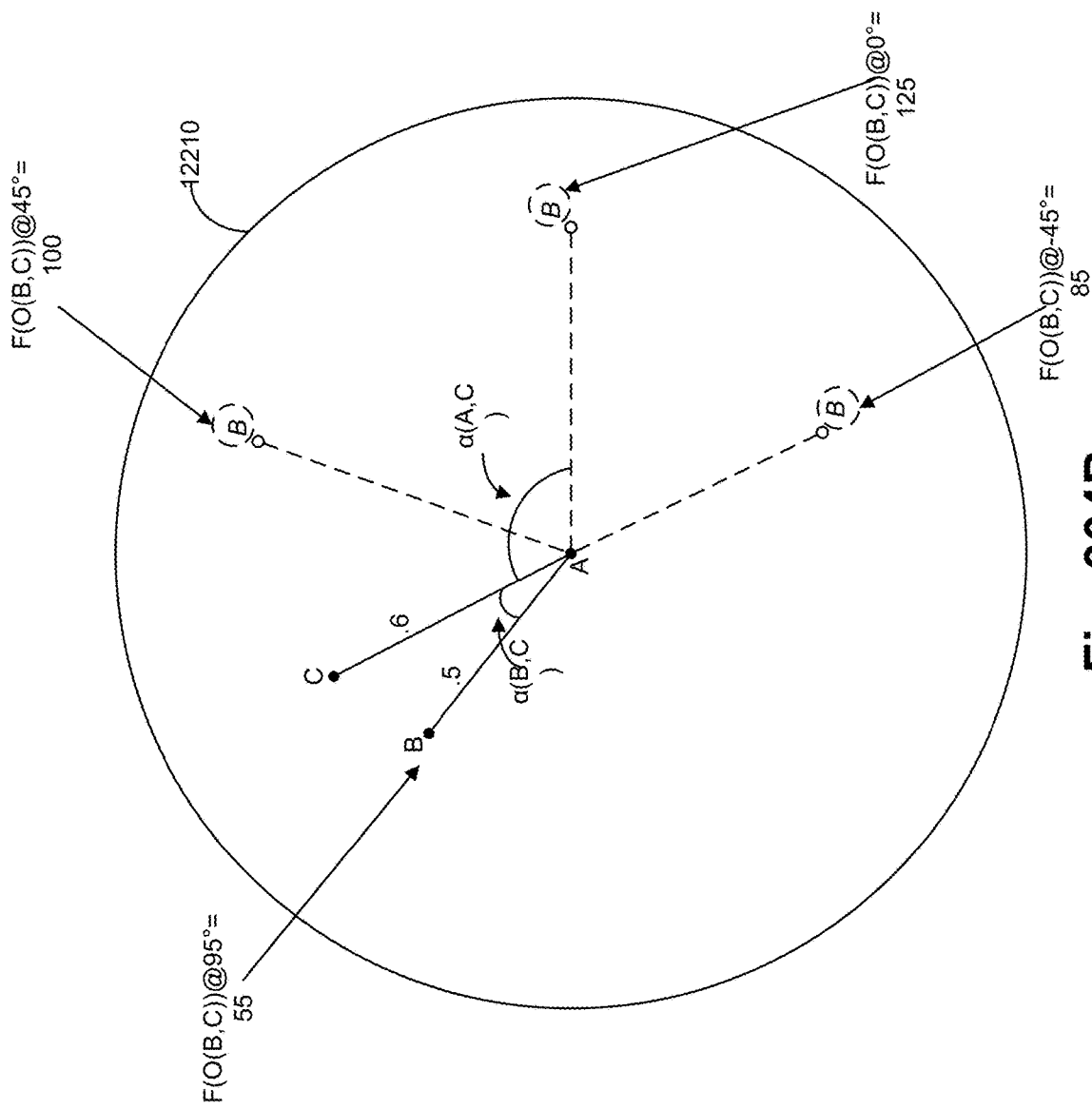
Figure 305:
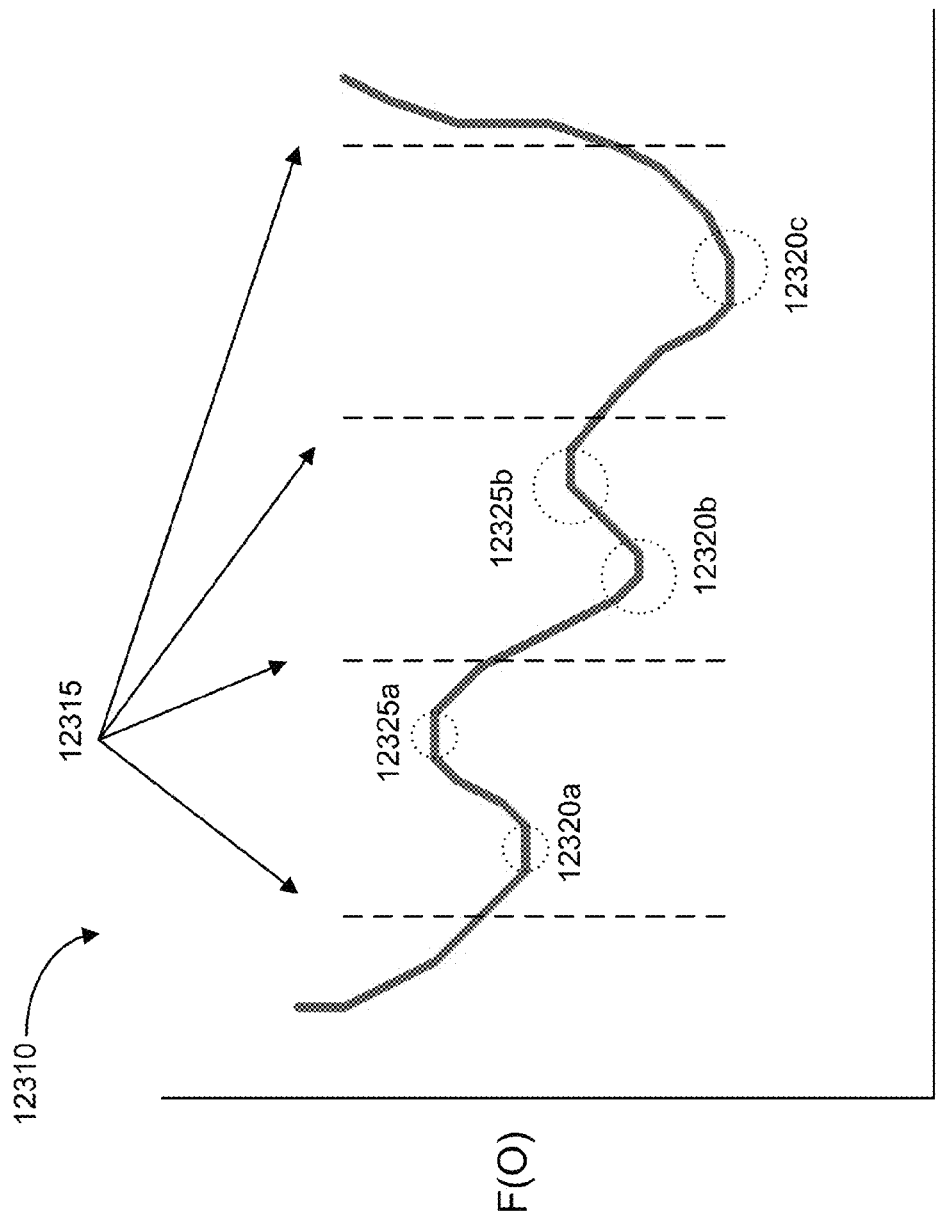
Figure 306A:
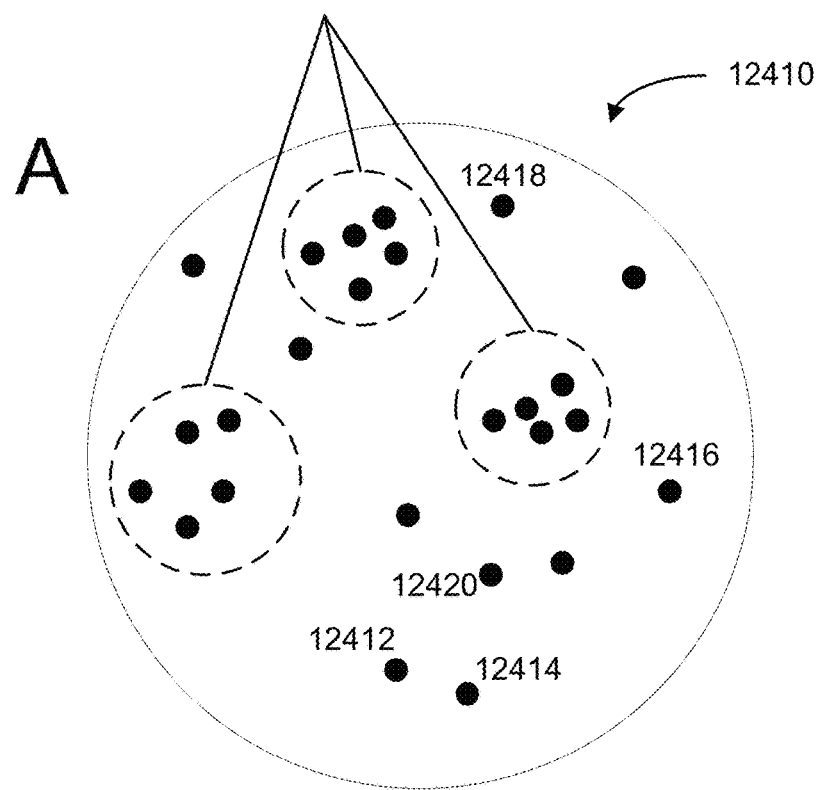
Figure 306B:
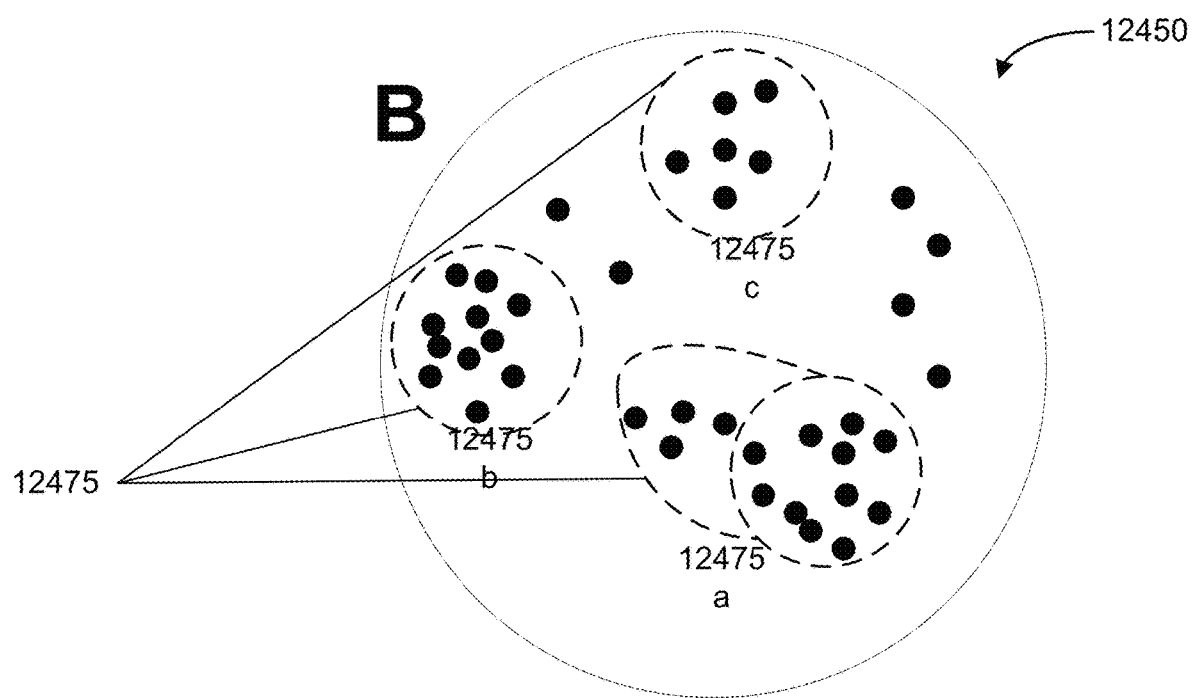
Figure 307B:
Figure 307C:
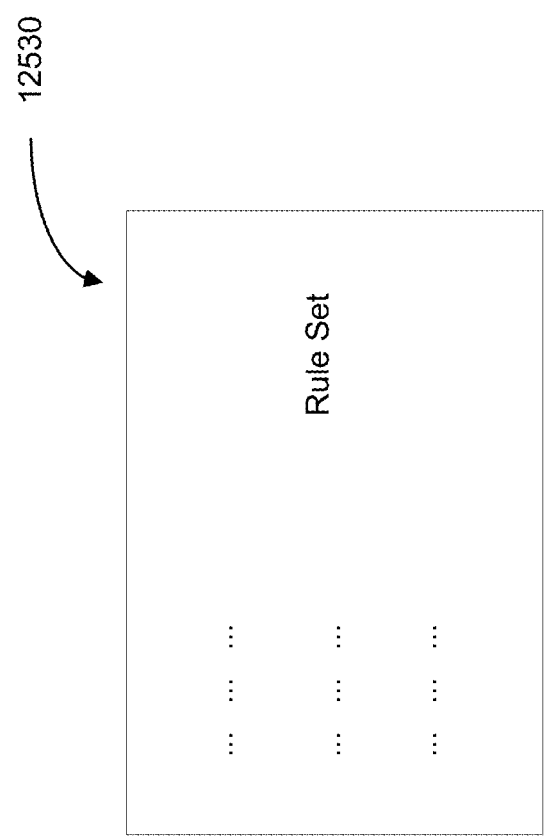
Figure 308:
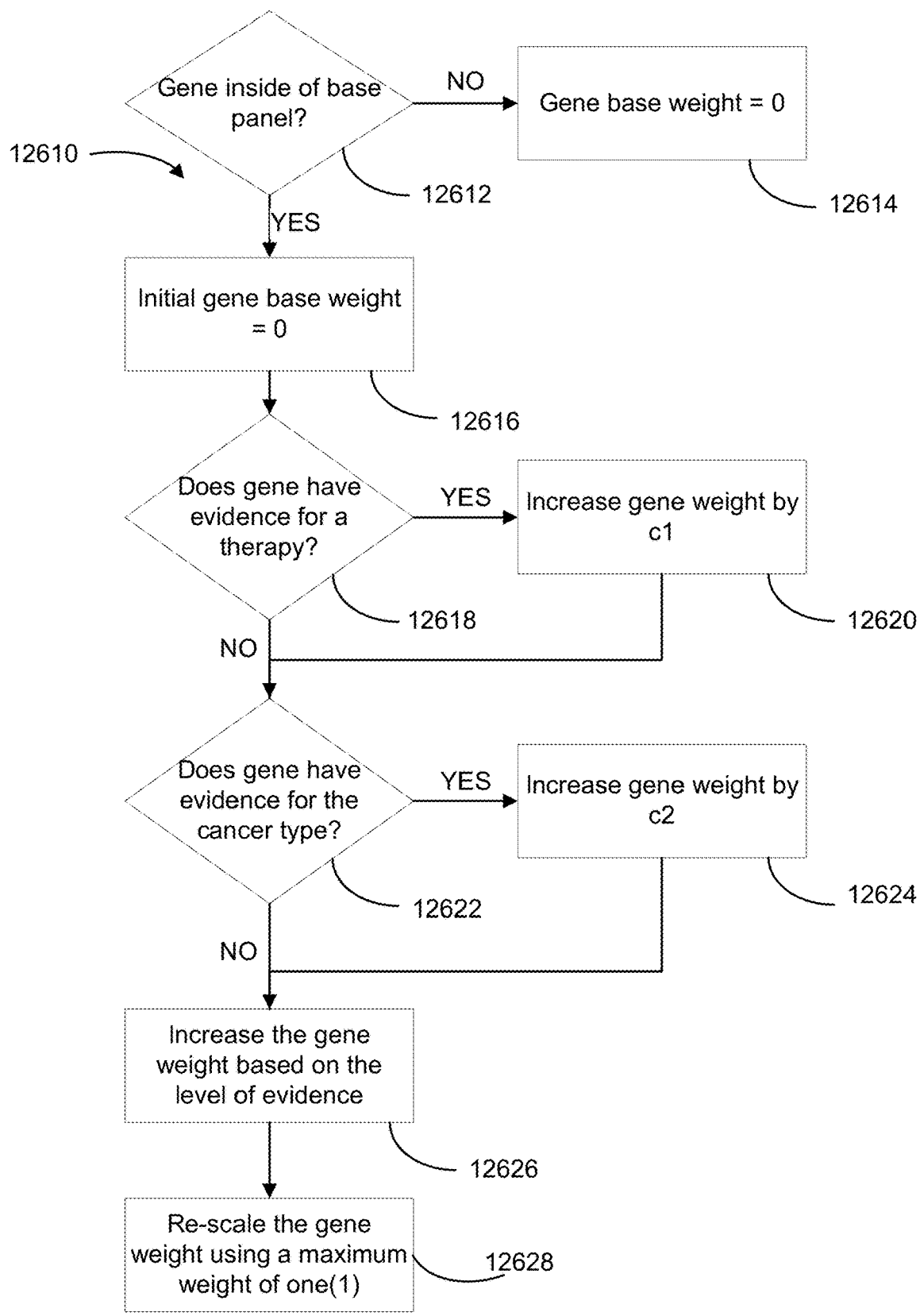
Figure 309:
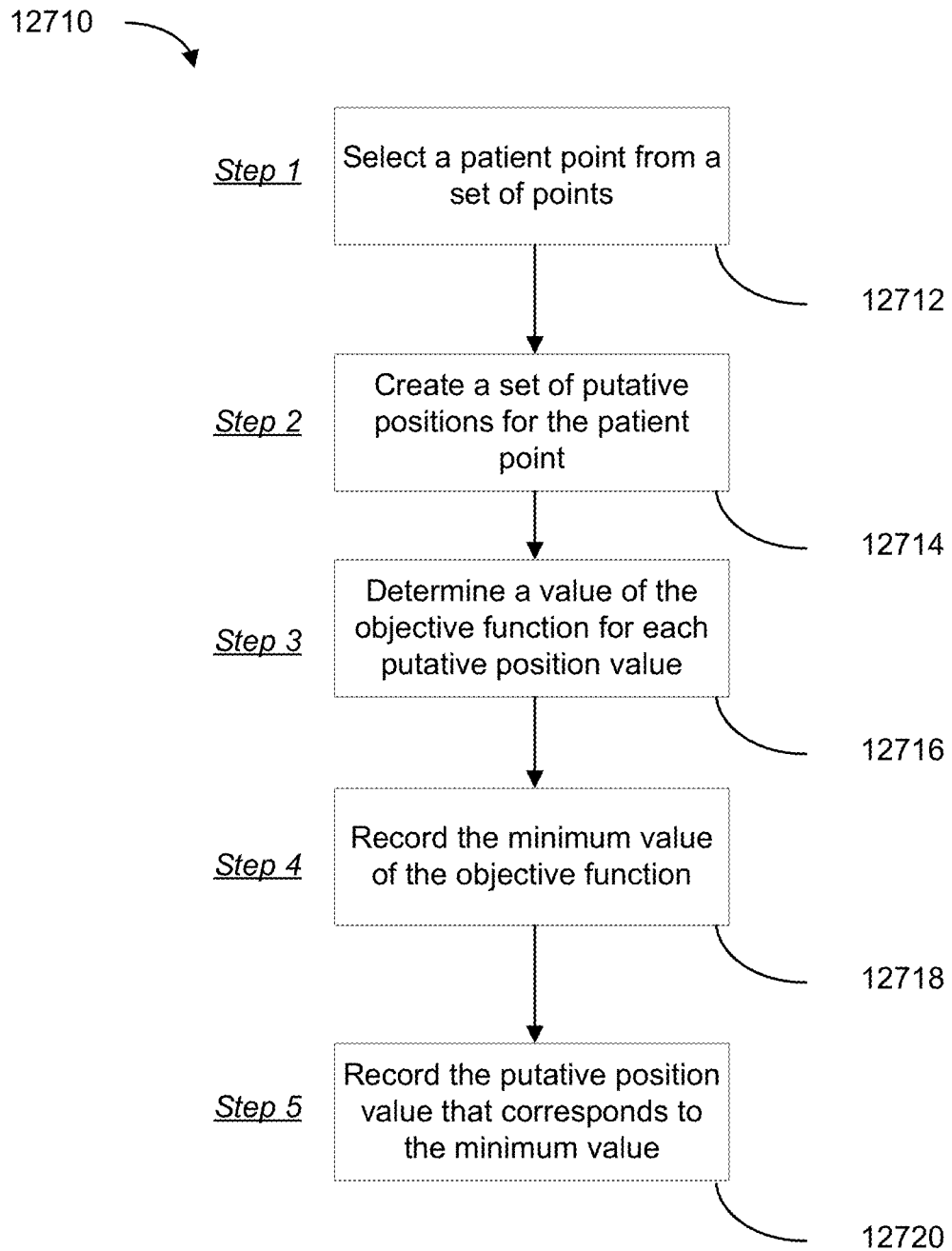
Figure 310:
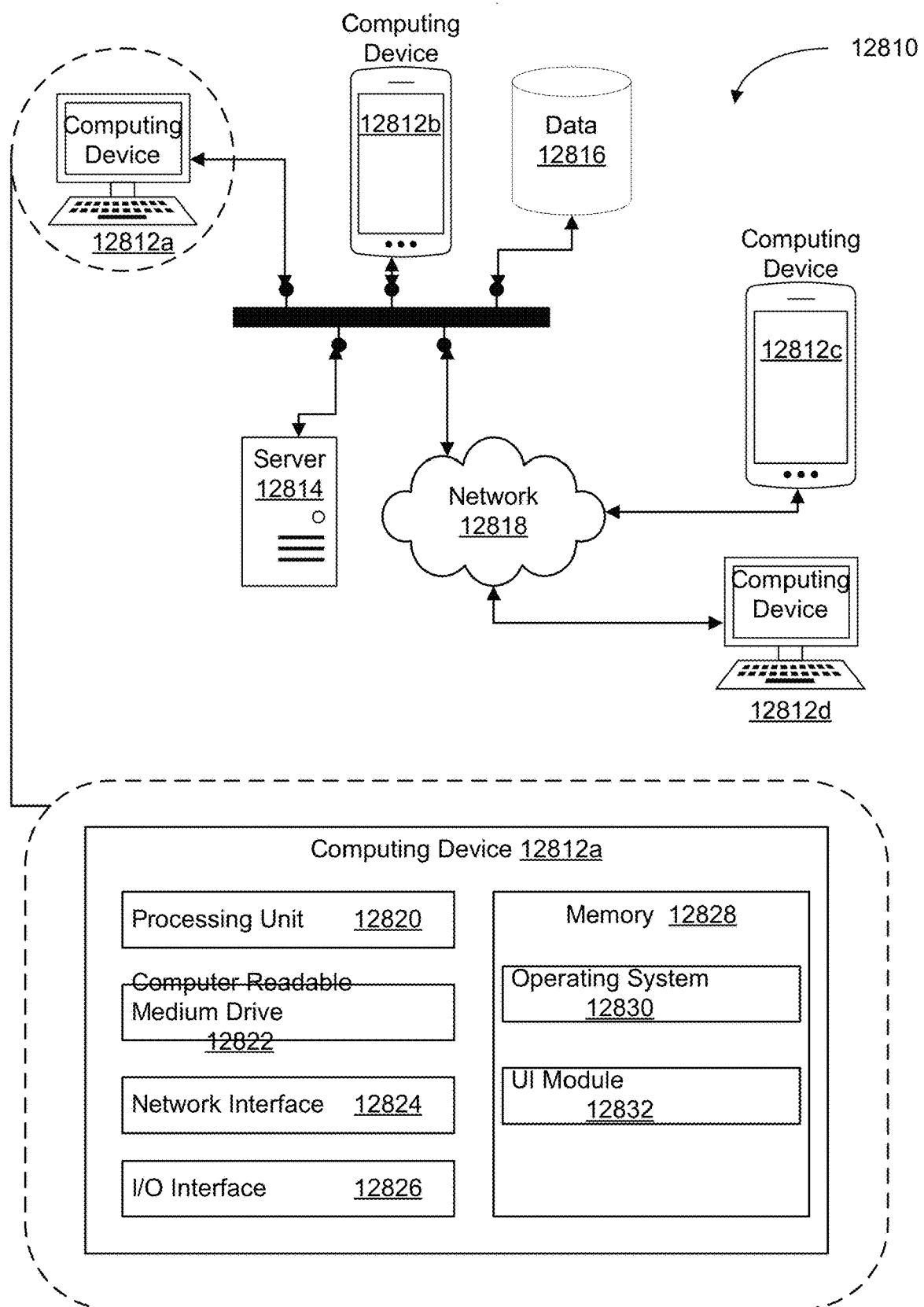
Figure 312:
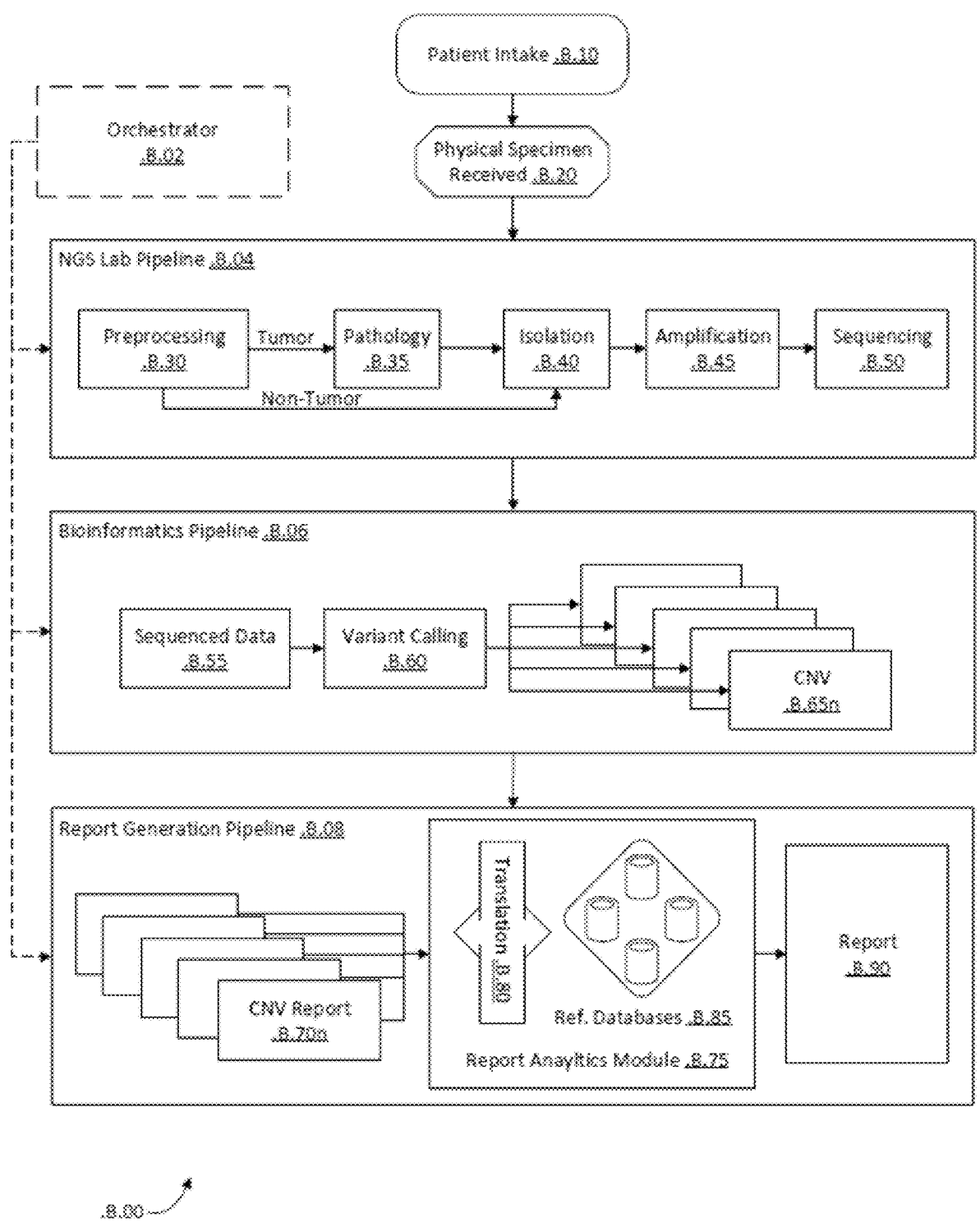
Figure 313:
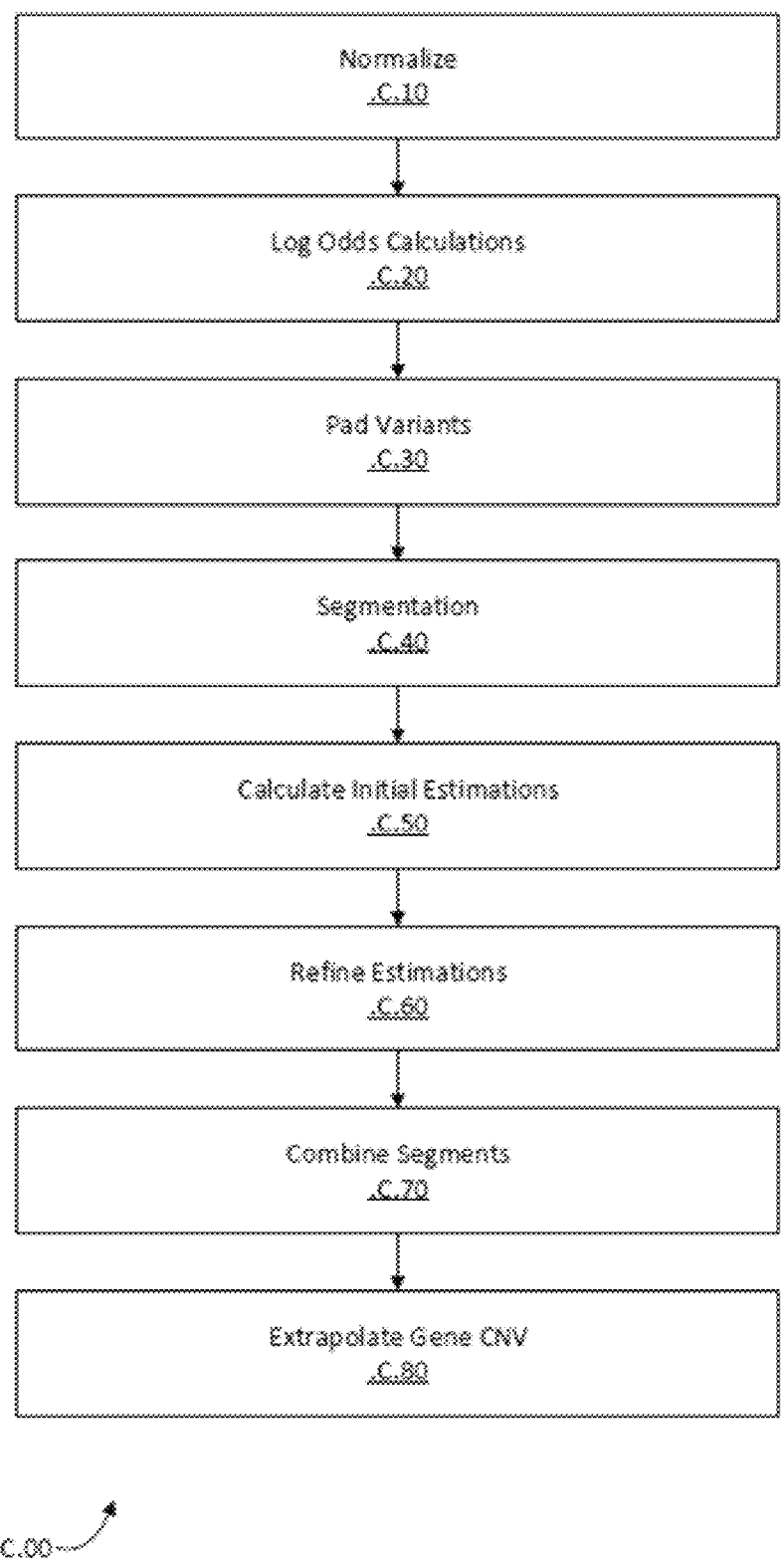
Figure 314:
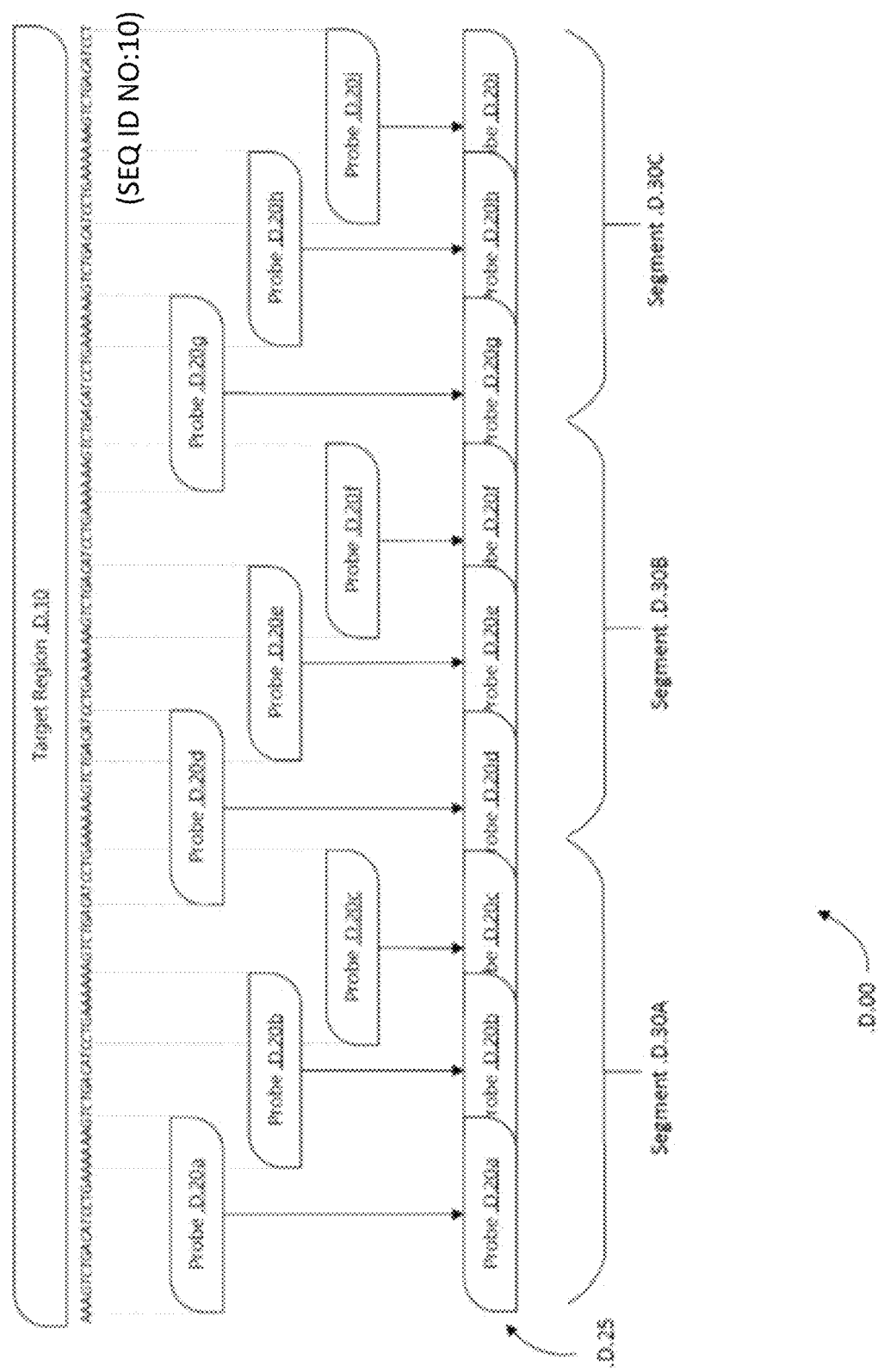
Figure 315:
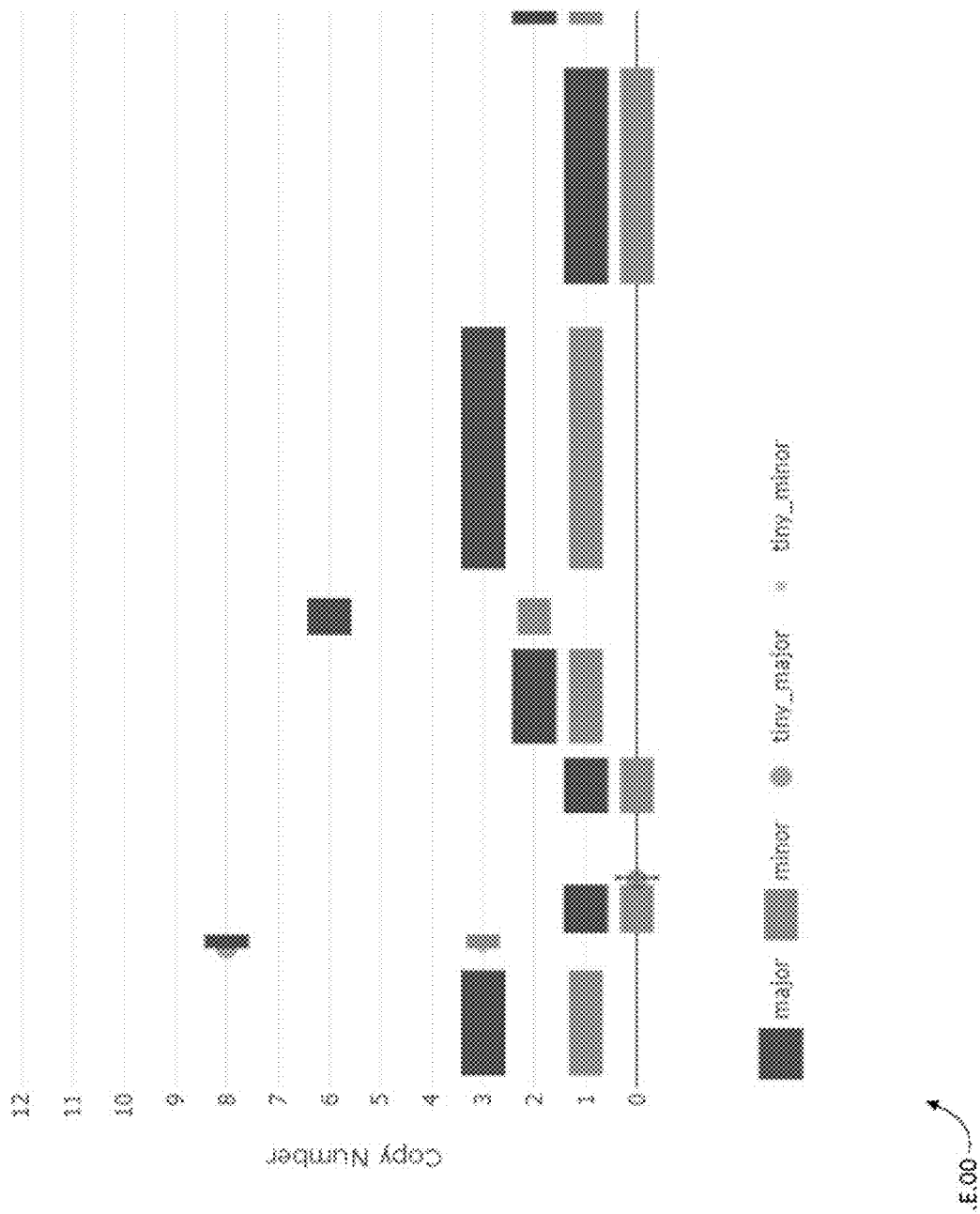
Figure 316:
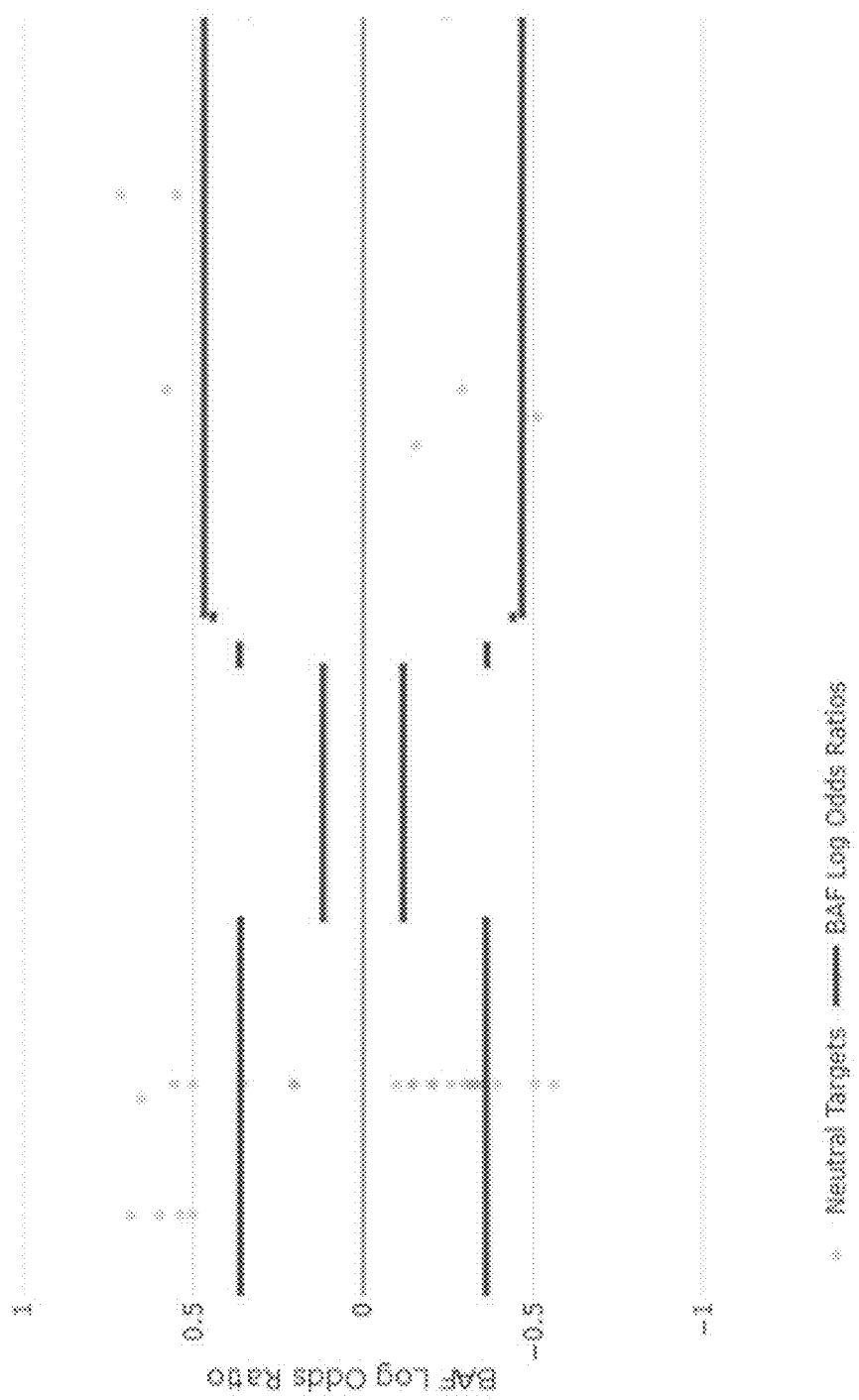
Figure 317:
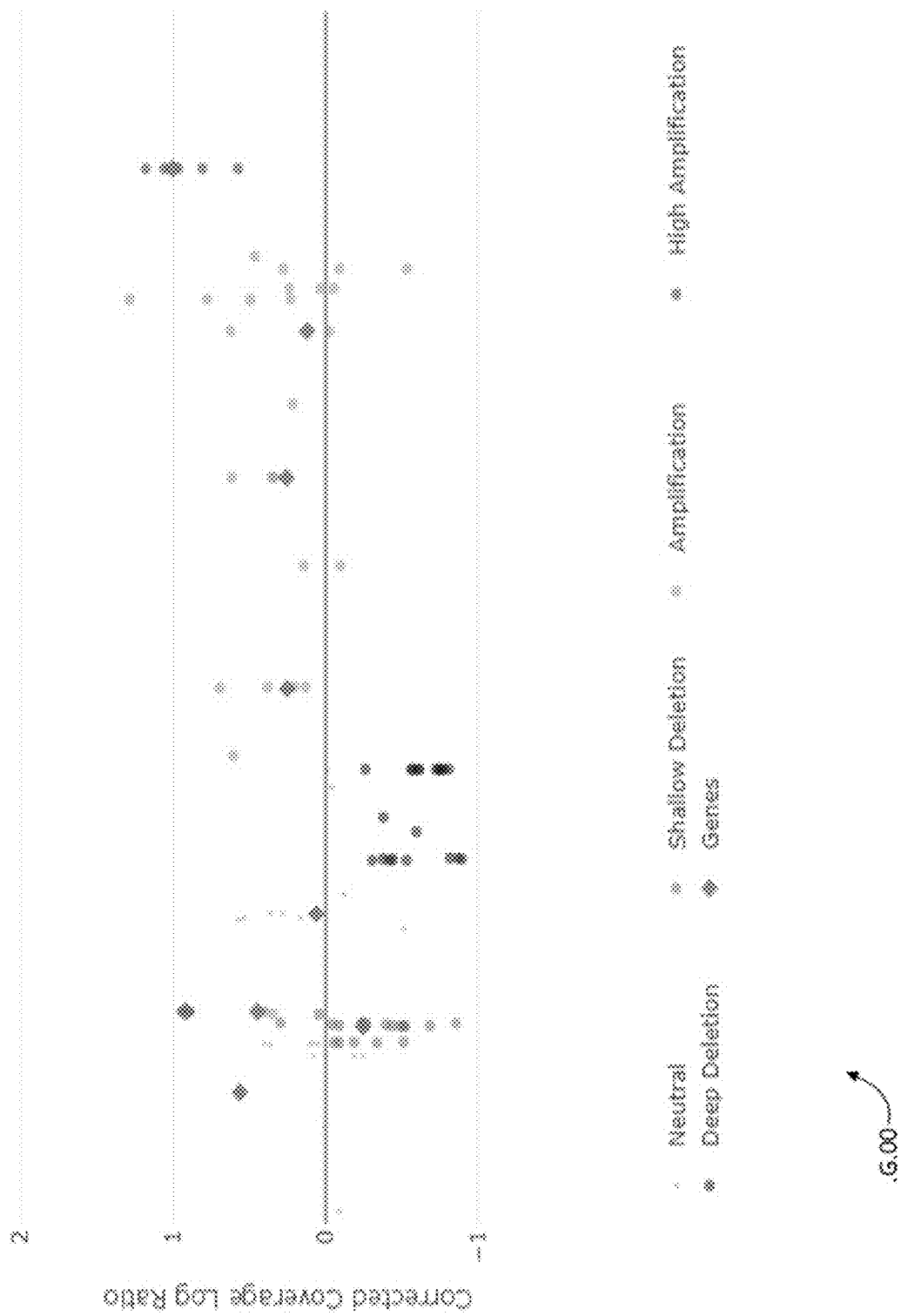
Figure 318:
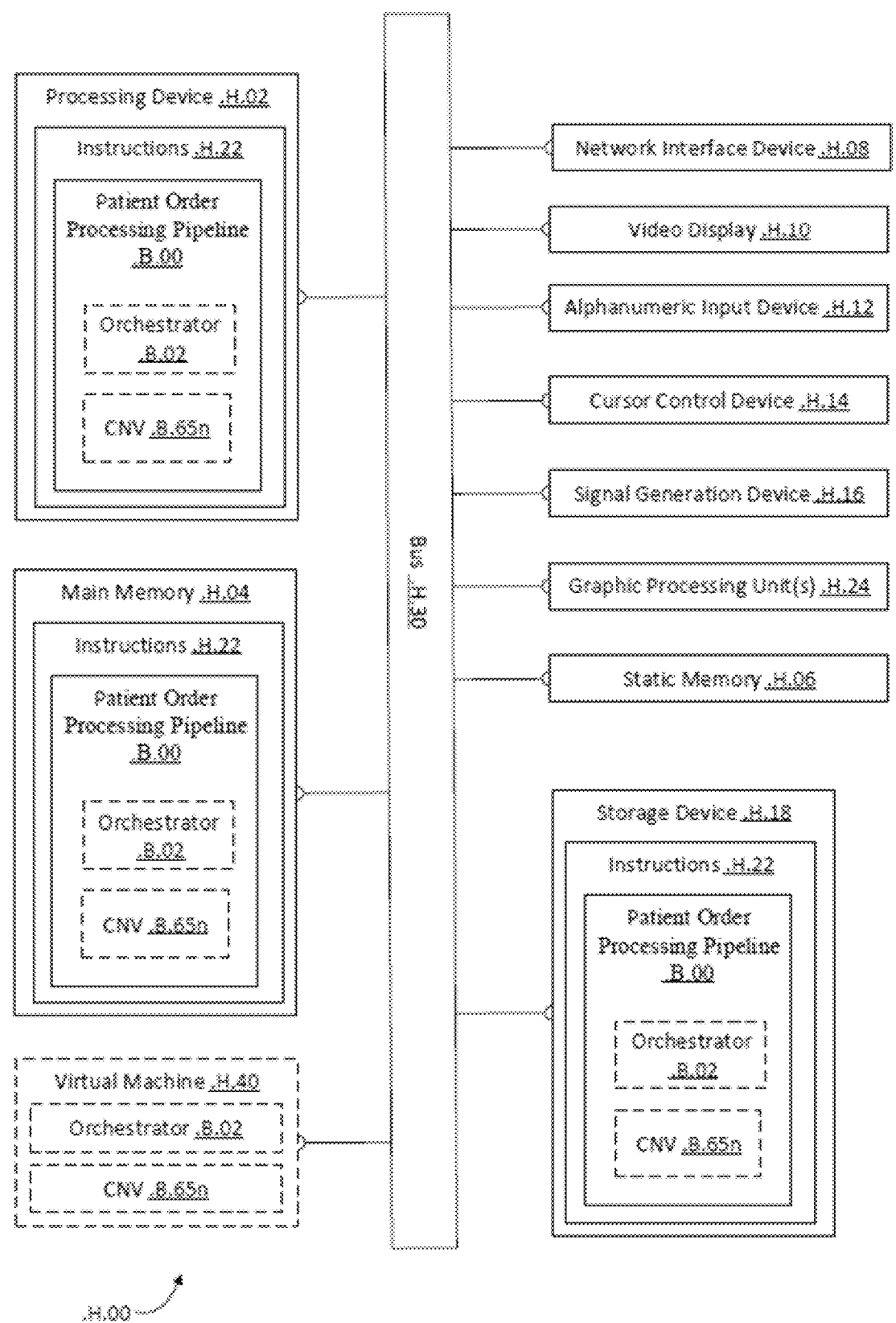
Figure 319:
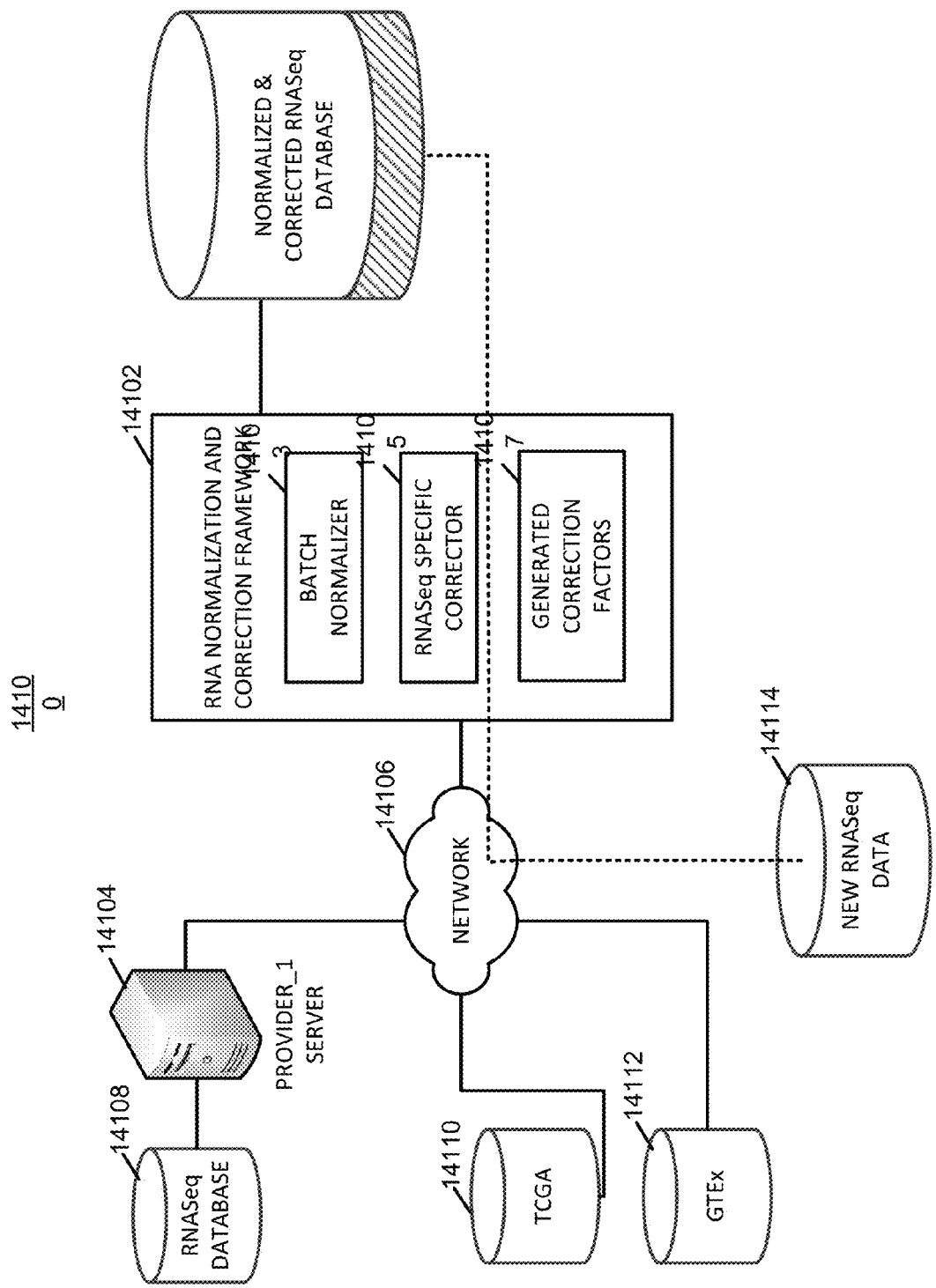
Figure 320:
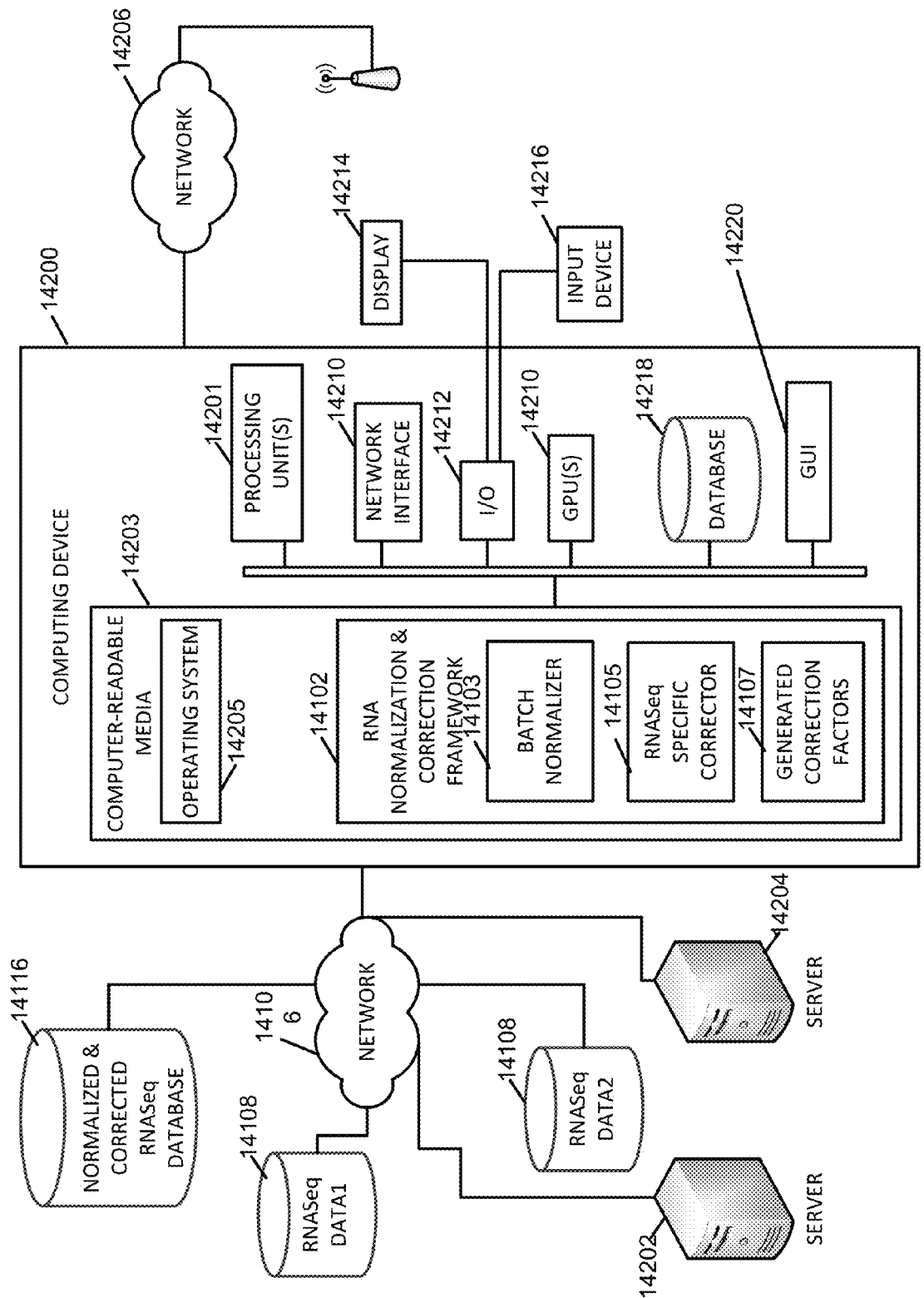
Figure 321:
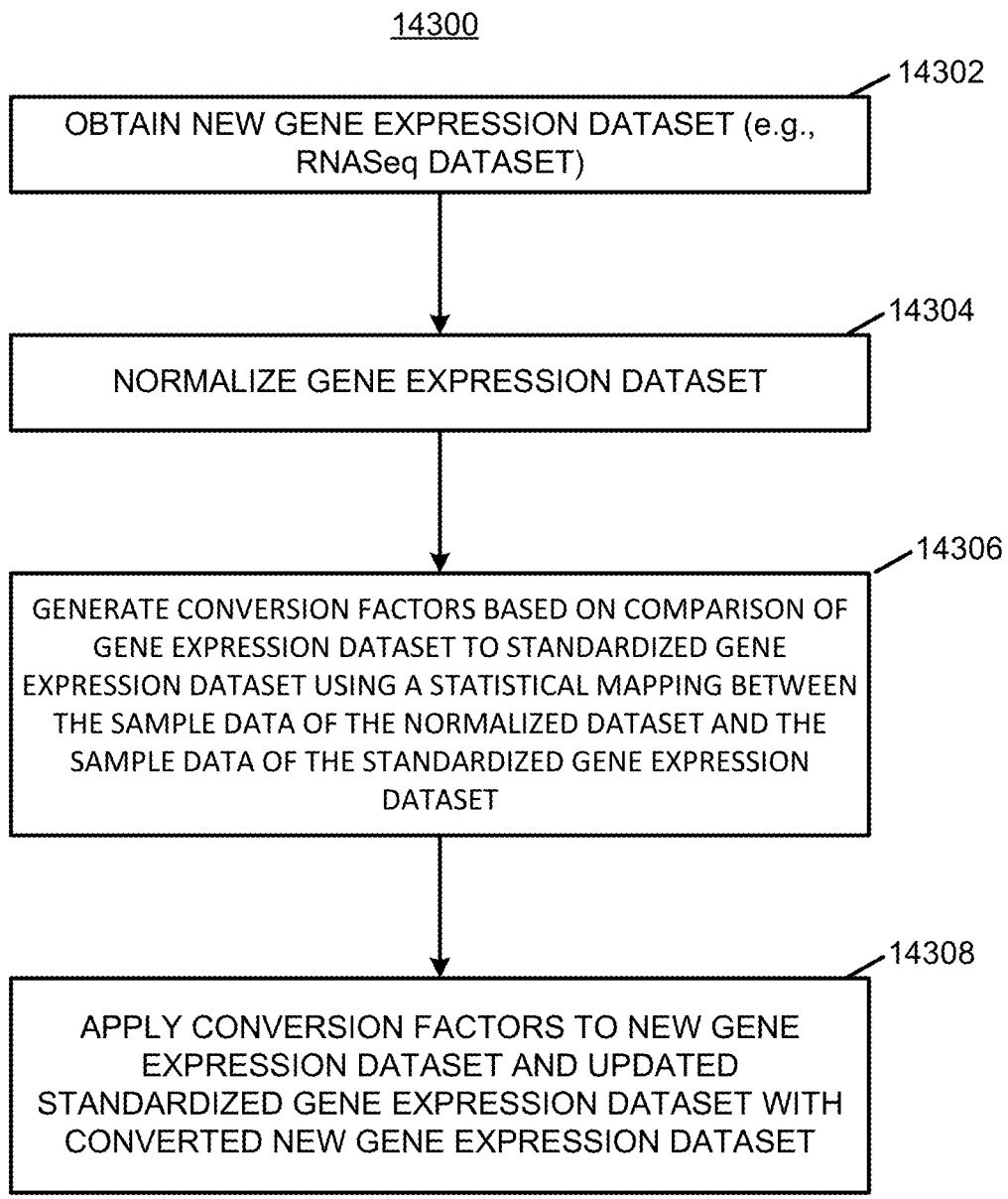
Figure 322:
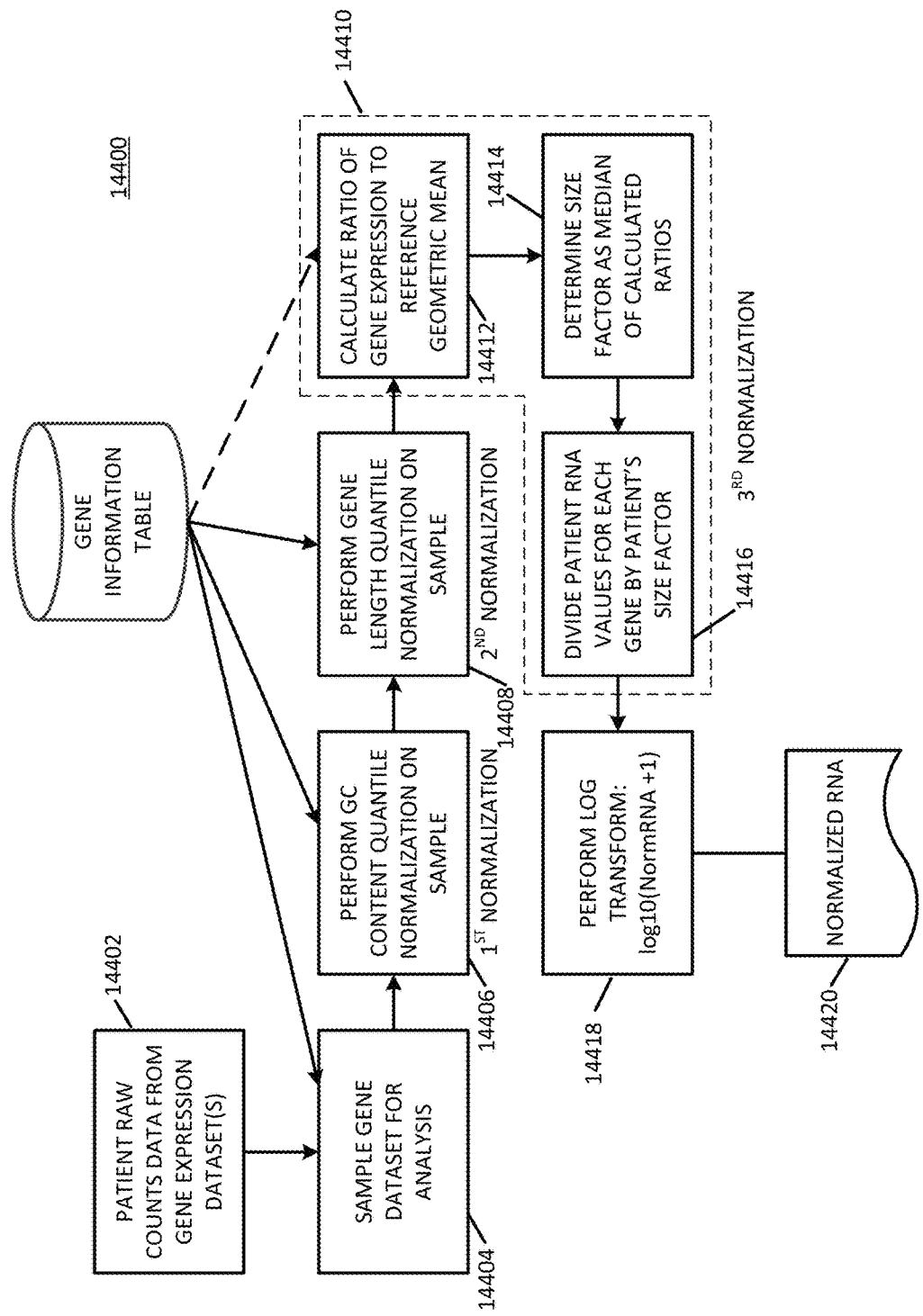
Figure 323:
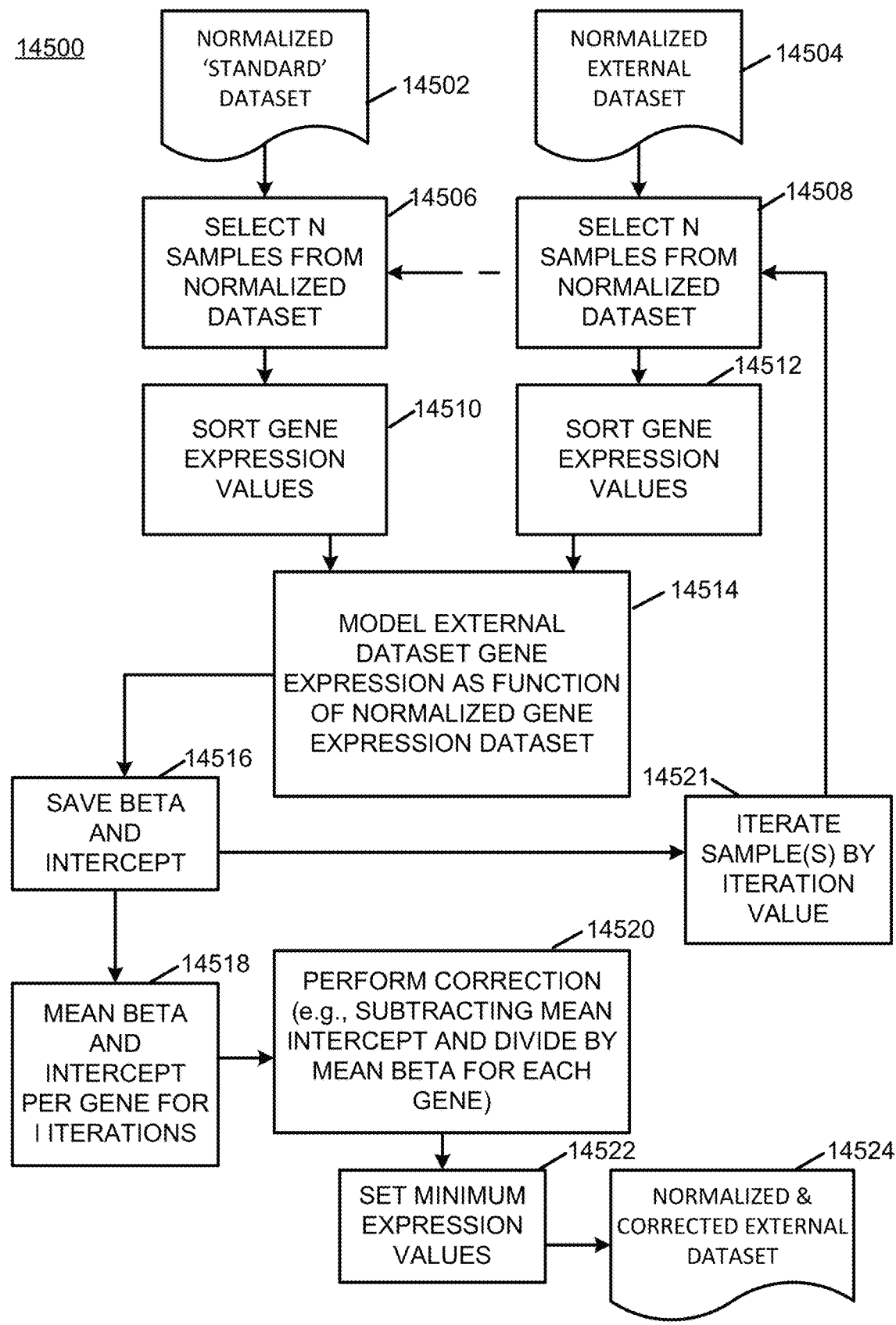
Figure 324:
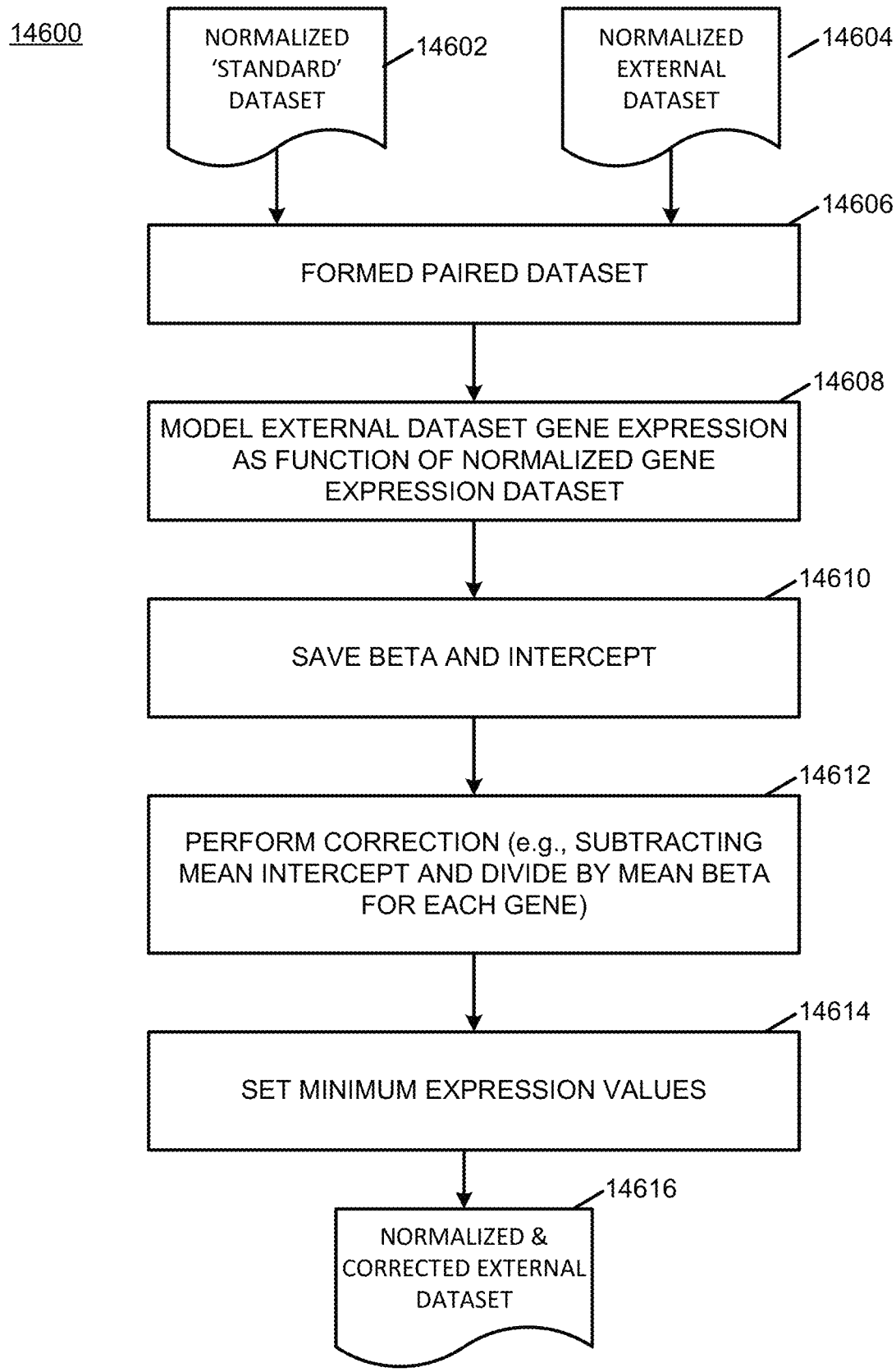
Figure 325:
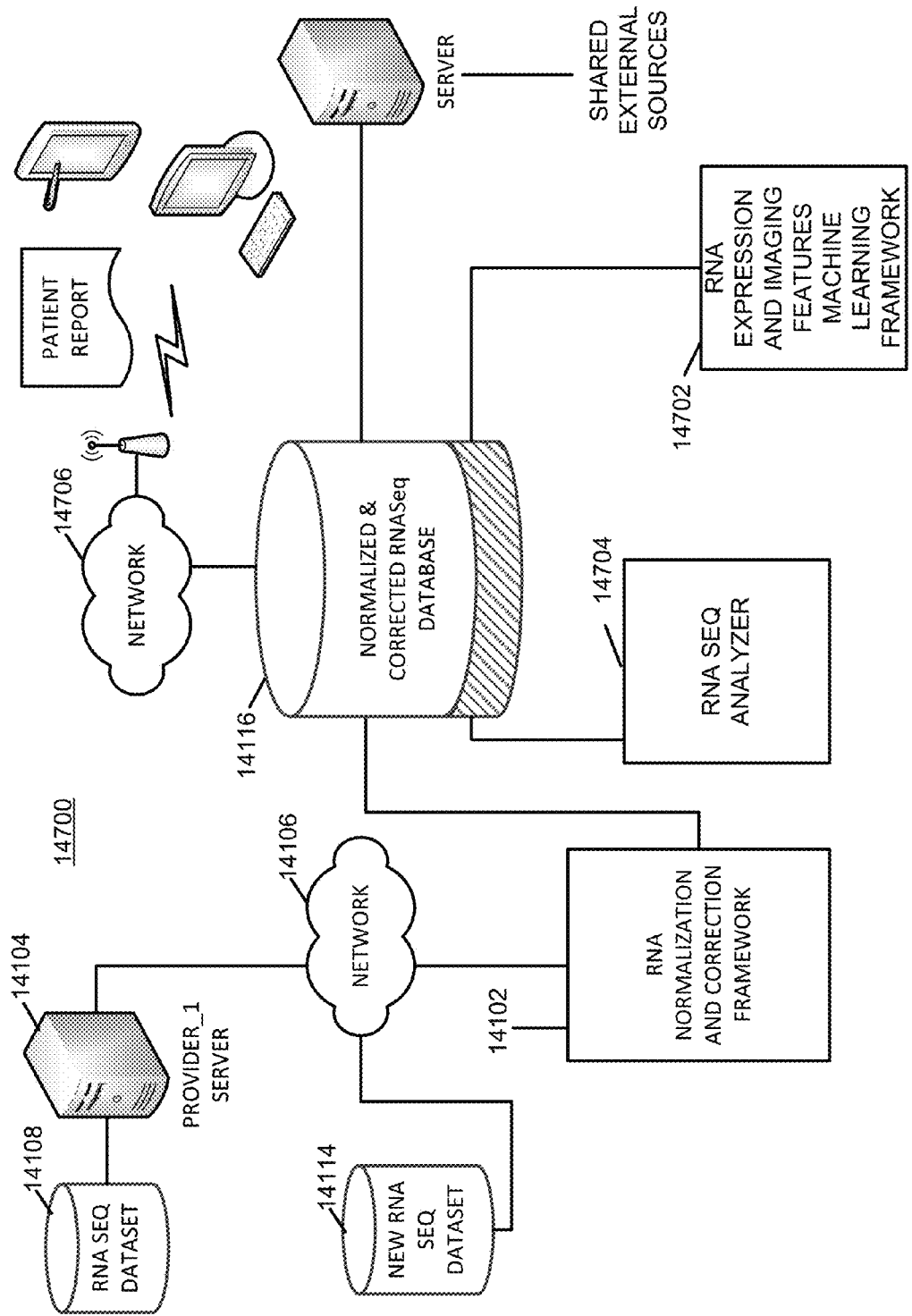
Figures 8, 326:
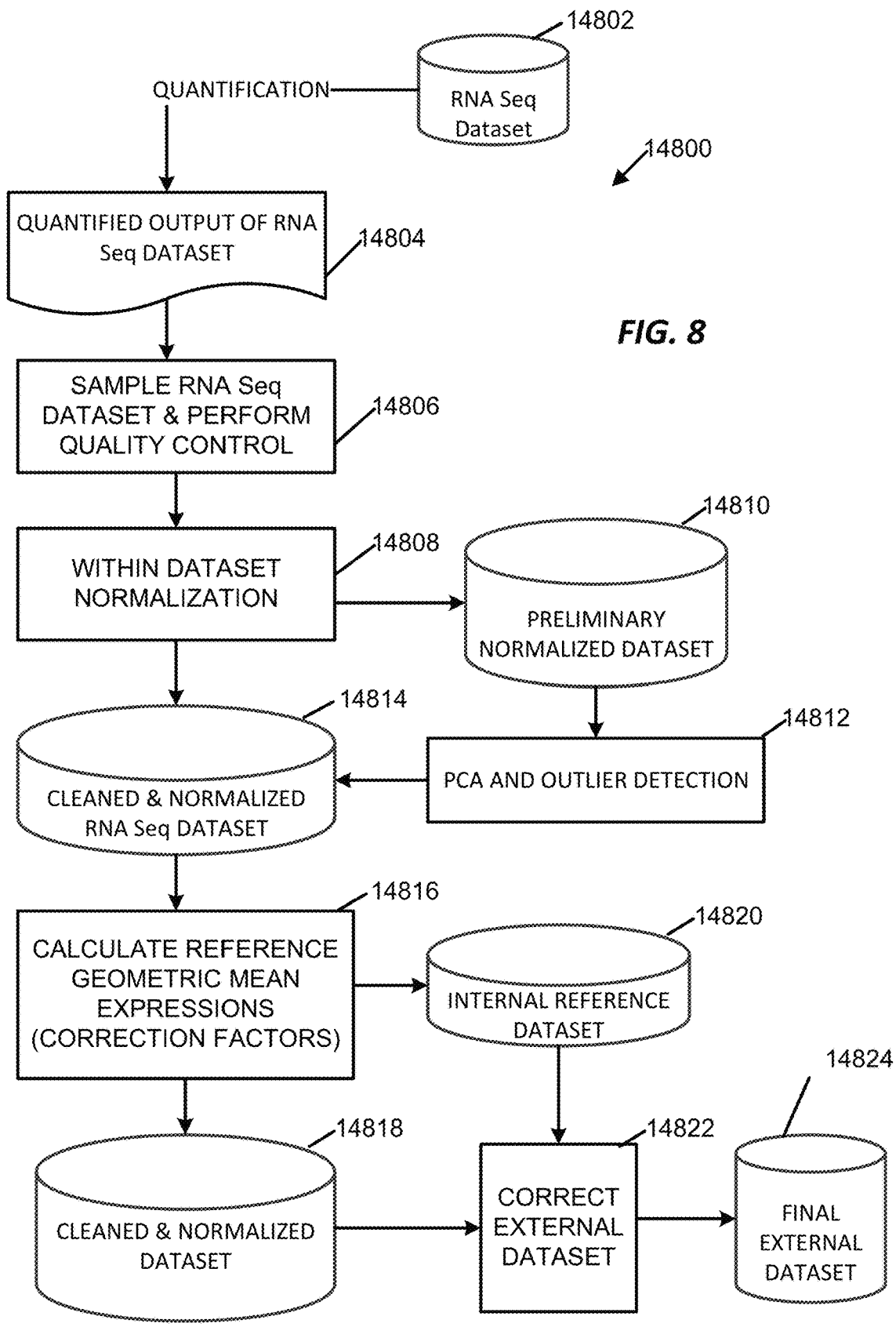
Figure 327:
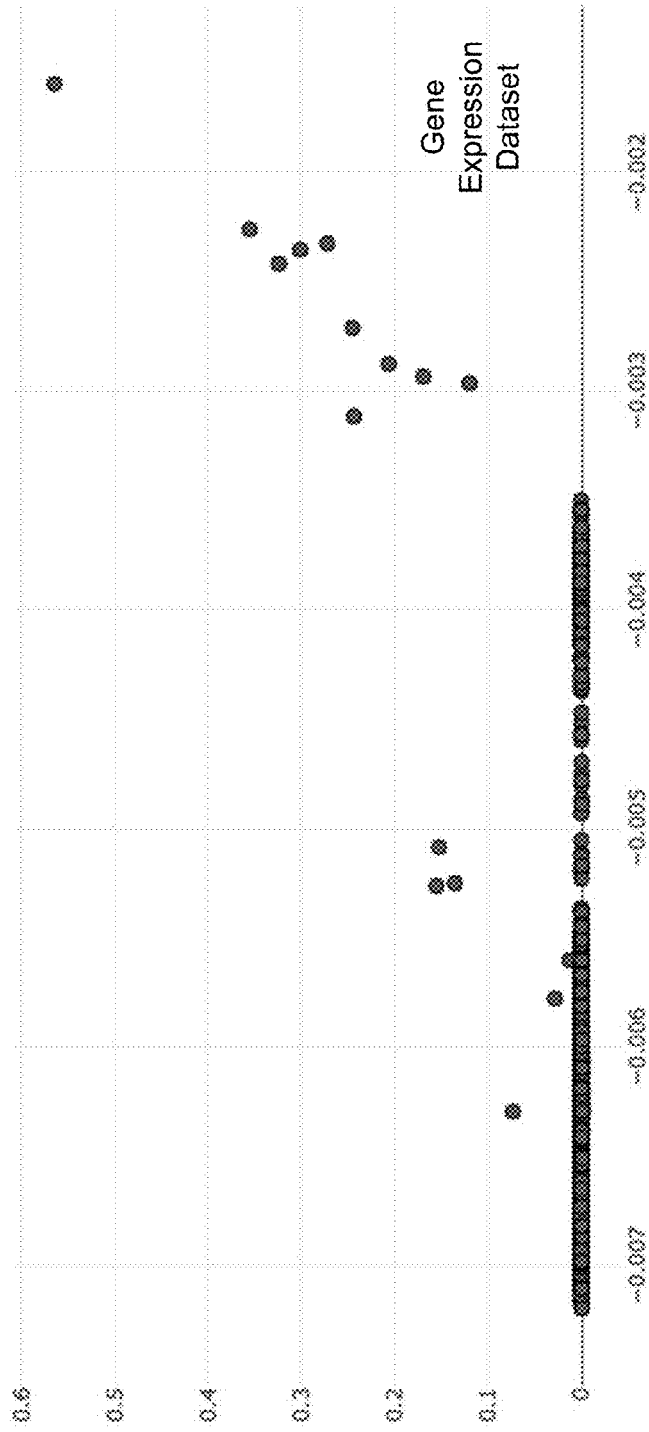
Figure 328:
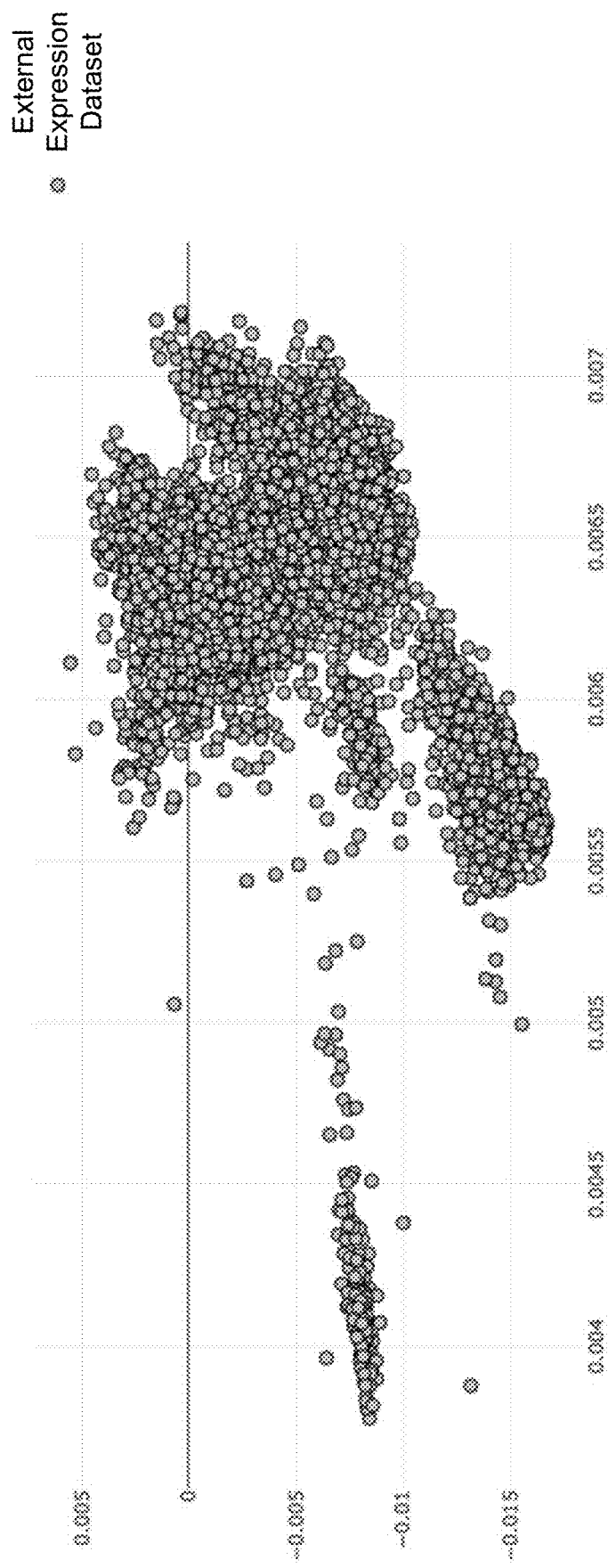
Figure 329A:
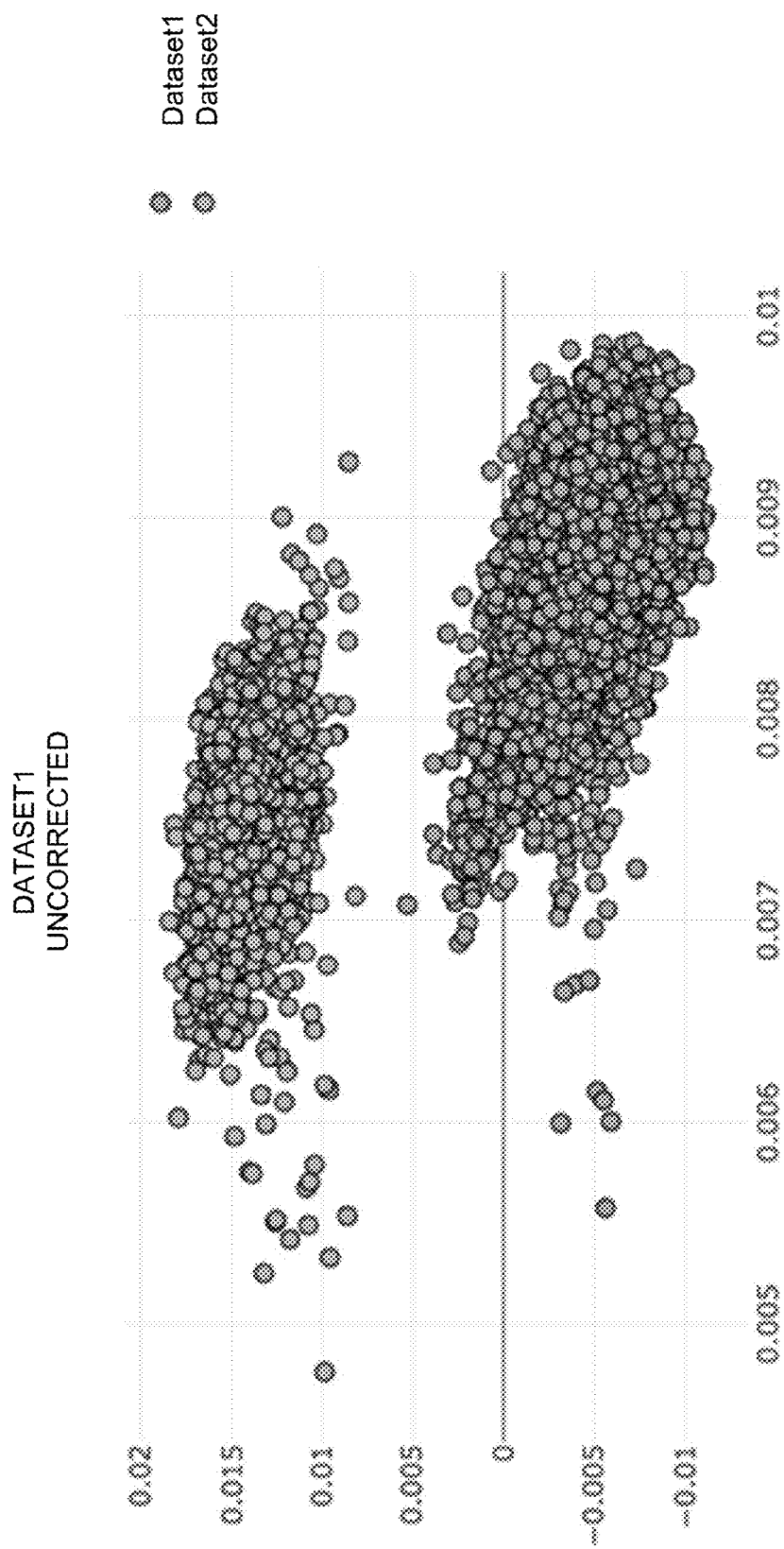
Figure 329B:
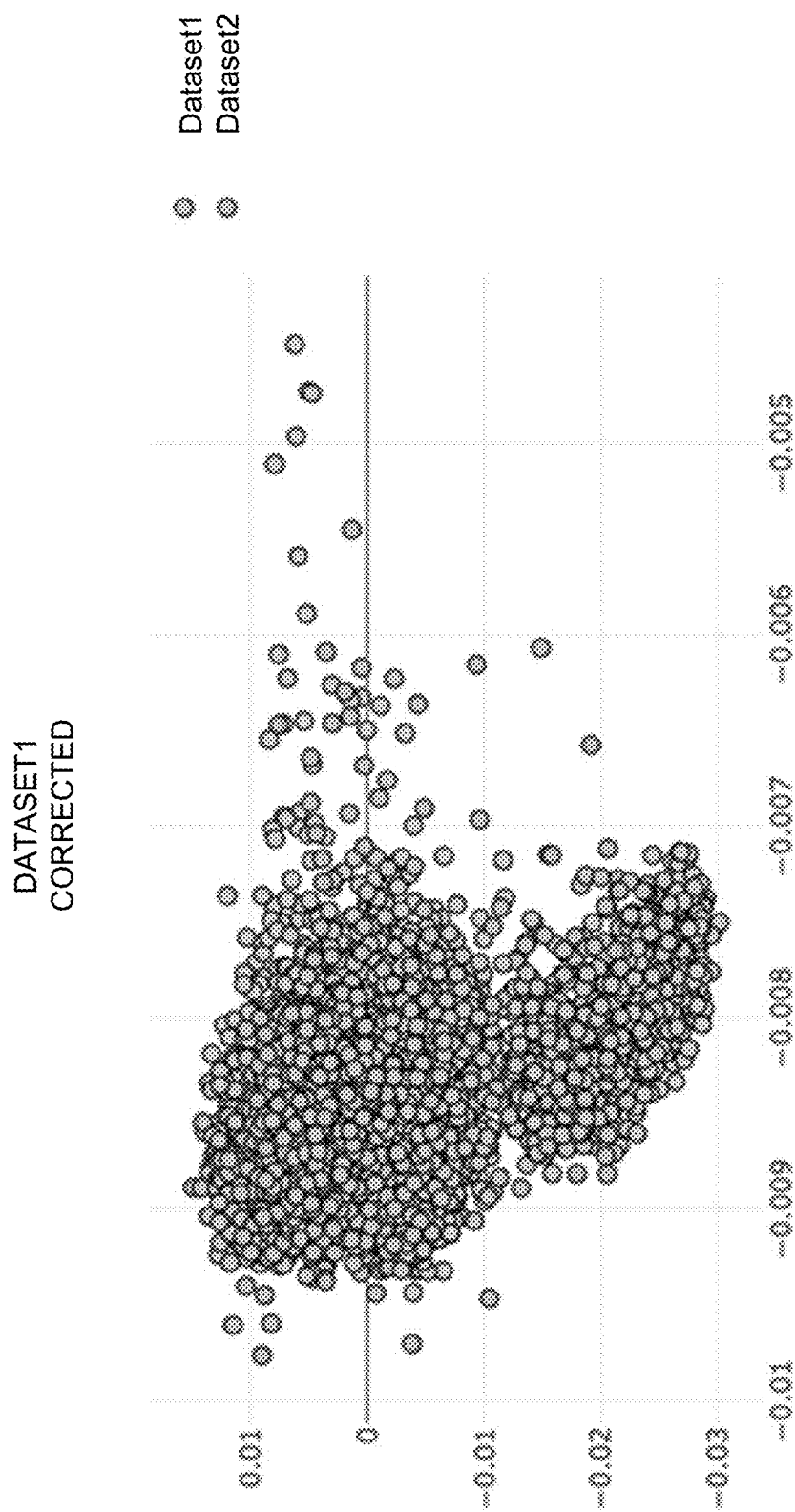
Figure 330:
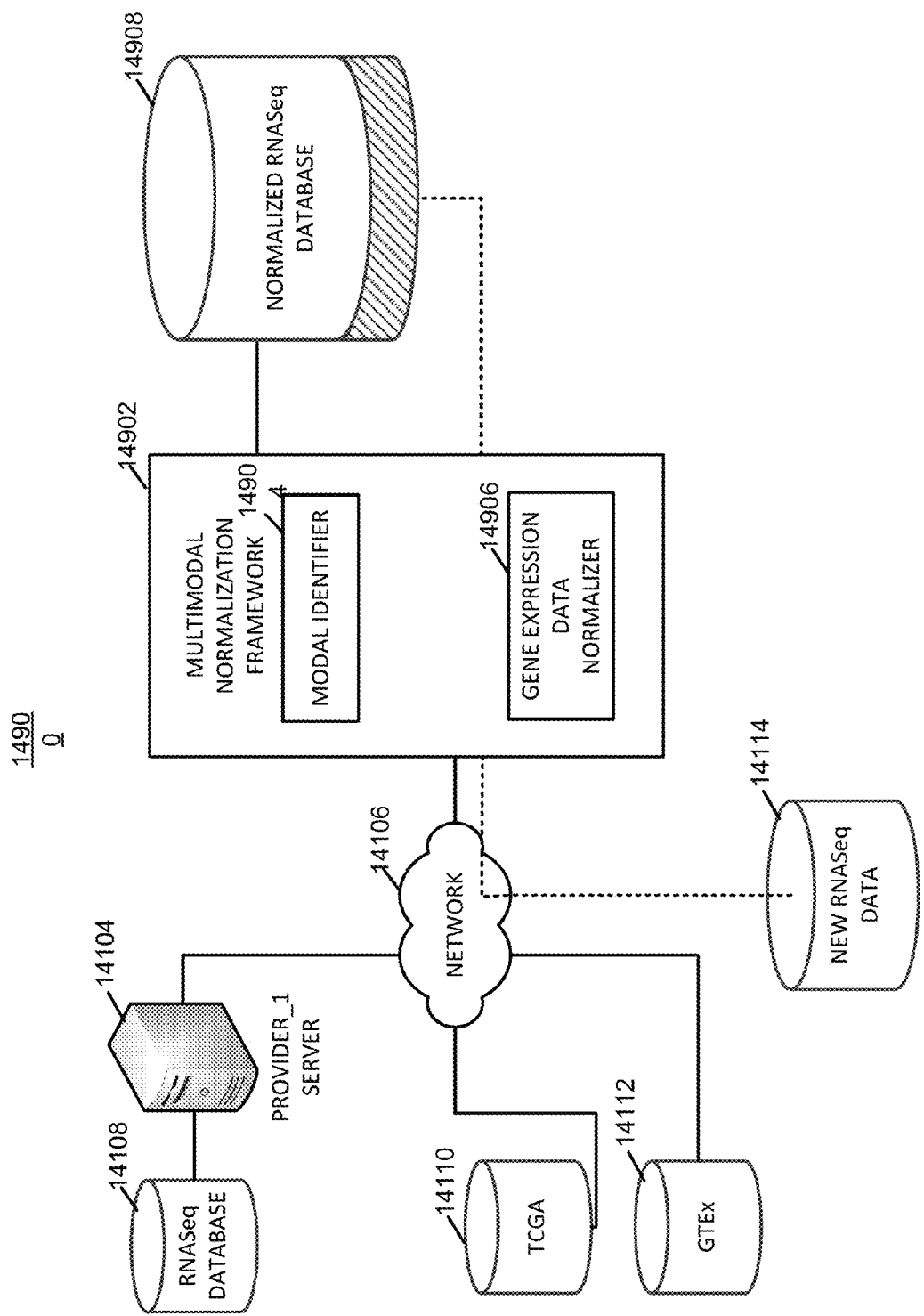

FIG. 195B illustrates an example CRC sample slide with patch-level classification visualized. We infer slide-level MSI status by vote, where the most frequent patch classification is used to predict slide-level status;

FIGS. 196A and 196B are plots illustrating t-SNE projection of 1,000 MSI-H, MSI-L, and MSS image embeddings from UCEC and CRC validation samples. Projection illustrates that embeddings learned by the adversarial deep learning framework are primarily clustered by (A) MSI status instead (FIG. 196A) and by (B) cancer type (FIG. 196B);

FIG. 197 illustrates representative histopathology slides from CRC and UCEC tumors with MSI-H and MSS classifications. Infiltrating lymphocytes are identified as activated features in both MSI-H CRC and UCEC. These cells are characterized by condensed nuclei and a small cytoplasmic halo, which shows distinct observable activation by a model interpreter (indicated by green arrows). Analysis of MSS CRC and UCEC cases showed non-specific morphologic feature activation identifying glandular structures and tissue interfaces;

FIG. 198 illustrates an example computing device for implementing the systems of FIGS. 189-191 and the processes of FIGS. 193 and 194, in accordance with an example implementation;

FIG. 199 is a block diagram of an example method of MSI Detection and classification in a paired mode using tumor and normal matched samples, in accordance with an example implementation;

FIG. 200 is a block diagram of an example method of MSI Detection and classification in an unpaired mode using tumor-only samples, in accordance with an example implementation;

FIG. 201 is a plot of validation results for microsatellite status classification from a genomic sequencing assay on a set of tumor samples, in accordance with an example implementation. The plot displays the count of samples (y-axis) and exemplary thresholds of MSI-H, MSE, and MSS (x-axis);

FIG. 202 is a screenshot of an example clinical reporting of MSI status, in accordance with an example implementation;

FIG. 203 illustrates an example computing device for implementing the processes of FIGS. 199 and 200, in accordance with an example implementation;

FIG. 204 is an illustration of a system for generating predictions of an objective from a selection of patient features;

FIG. 205 is an illustration of a system for performing the selection, alteration, and calculation of additional features from the patient features;

FIG. 206 is an illustration of a system for selecting a feature set for generating prior features and forward features based from a target/objective pair;

FIG. 207 is an illustration of a system for selecting a feature set for generating prior features based from <objective> in accordance with an example;

FIG. 208 is an illustration of a system for selecting a feature set for generating prior features based from <objective> in accordance with an example;

FIG. 209 is a flowchart of a method for generating and providing prior features to a model for predicting <objective> in a patient in accordance with an example;

FIG. 210 is an illustration of a patient timeline having events determining prior and forward features;

FIG. 211 is a flowchart of a method for performing analytics on a model for predicting site-specific metastasis in a patient in accordance with an example;

FIG. 212 is an illustration of elements of a webform for viewing site-specific predictions of metastasis in a patient in accordance with an example;

FIG. 213 is an illustration of elements of a webform for viewing site-specific predictions of metastasis in a cohort of patients in accordance with an example;

FIG. 214 is an illustration of elements of a webform for viewing feature importance rankings of site-specific predictions of metastasis in a cohort of patients in accordance with an example;

FIG. 215 is an illustration of elements of a webform for viewing feature importance rankings of site-specific predictions of metastasis in a cohort of patients in accordance with an example;

FIG. 216 is an illustration of exemplary aggregate measures of performance across possible classification thresholds of input data sets according to an objective of <objective>;

FIG. 217 is an illustration of an exemplary system for implementing the systems of FIGS. 204-208, and 210, the methods of FIGS. 209 and 211, and user interfaces of FIGS. 212-215;

FIG. 218 is a flow chart illustrating a process of evaluating an effect of an event on a condition, in accordance with some embodiments of the present disclosure;

FIG. 219 is a diagram illustrating an example of a user interface of a tool for evaluating an effect of an event on a condition, in accordance with some embodiments of the present disclosure;

FIGS. 220A and 220B collectively provide a flow chart of processes and features for evaluating an effect of an event on a condition, in which optional blocks are indicated with dashed boxes, in accordance with some embodiments of the present disclosure;

FIGS. 221A, 221B, 221C and 221D are diagrams collectively illustrating an example of a user interface of a tool for evaluating an effect of an event on a condition, in accordance with some embodiments of the present disclosure;

FIGS. 222A, 222B, and 222C are diagrams collectively illustrating another example of a user interface of a tool for evaluating an effect of an event on a condition, in accordance with some embodiments of the present disclosure;

FIG. 223 is a diagram illustrating the user interface of FIGS. 222A-222C where a higher propensity value threshold is obtained, in accordance with some embodiments of the present disclosure;

FIGS. 224A and 224B are diagrams collectively illustrating the user interface of FIGS. 222A-222C where features for a propensity scoring model are obtained based on user input, in accordance with some embodiments of the present disclosure;

FIGS. 225A and 225B are diagrams collectively illustrating an example of a user interface of a tool for evaluating an effect of an event on a condition, where a low propensity value threshold is obtained, in accordance with some embodiments of the present disclosure;

FIGS. 226A and 226B are diagrams collectively illustrating the user interface of FIGS. 225A and 225B where a mid-range propensity value threshold is obtained, in accordance with some embodiments of the present disclosure;

FIGS. 227A and 227B are diagrams collectively illustrating the user interface of FIGS. 225A and 225B where a high propensity value threshold is obtained, in accordance with some embodiments of the present disclosure;

FIG. 228 is a schematic illustration of an example computer processing system having a deconvolution framework for performing deconvolution on RNA expression data, in accordance with an example;

FIG. 229 is a block diagram of an example process for generating deconvoluted RNA expression data from normalized, metastatic sample RNA expression data as may be performed by the system of FIG. 228, in accordance with an example;

FIG. 230 is a block diagram of an example implementation of the deconvoluted RNA expression data generating process of FIG. 229, in accordance with an example;

FIG. 231 is a plot of principal component analysis (PCA) of gene expression profiles of reference tissue samples;

FIG. 232 is a plot of proportions for a Grade of Membership (GoM) model with K=15 clusters, in an example implementation of the deconvolution framework of FIG. 228. The K=15 clusters were fit to 4,754 samples from 22 cancers and normal liver. Each sample is represented as a horizontal bar plot of membership proportions to the 15 clusters. Samples are ordered by cancer/tissue type and sorted by cluster proportions of K=1 within each group;

FIG. 233 illustrates a distribution of the GoM cluster K=5 by cancer and tissue type for the 4,754 samples example of FIG. 232. As shown, normal liver GTEx and TCGA lihc samples have the highest proportion of the K=5 latent factor, while TCGA primary cancers have the lowest;

FIG. 234 illustrates results of a leave one out validation of the deconvolution frame, specifically a liver deconvolution model generated by the framework, in accordance with an example. A non-negative least squares (NNLS) model of tumor estimates is shown to be highly correlated to the GoM proportion (r=0.98) of the present techniques;

FIGS. 235 and 236 are plots of principal component analysis of a pancreatic cohort before (FIG. 235) and after (FIG. 236) deconvolution of liver metastases, in accordance with an example. The PCA analysis included 65 pancreatic samples (labelled by their background tissue site) along with TCGA primary liver (lihc) and pancreatic (paad) samples and GTEx normal liver samples. After deconvolution (FIG. 236), liver metastatic samples form a group with all other pancreatic cancer samples;

FIGS. 236A and 236B are plots of non-negative lease squares (NNLS) model results on two breast cancer and liver normal TCGA mixture samples. FIG. 236A shows mixed raw sequence reads for two pairs of samples from TCGA_DD_A118_11 (liver normal) with TCGA_EW_A3U0_01 (breast cancer). FIG. 236B shows mixed raw sequence reads for two pairs of samples from TCGA: TCGA_DD_A114_11 (liver normal) with TCGA_EW_A424_01 (breast cancer);

FIGS. 237A and 237B are plots of PCA analysis of breast and liver in silico mixtures and deconvoluted modelling results, for two different samples. As shown, after deconvolution is applied to the liver mixture RNA expression data, the proper grouping of liver samples occurs;

FIG. 238 is a summary of expression call results in original RNA expression data and in deconvoluted RNA expression data, in accordance with an example. Values are the proportion of samples with calls in each of the groups among the cancers where that gene had at least one sample called;

FIG. 239A is a diagram illustrating a challenge in RNA profiling of multi-cell sequence information;

FIG. 239B is another diagram illustrating a challenge in RNA profiling of multi-cell sequence information;

FIG. 240 is a further diagram illustrating a challenge in RNA profiling of multi-cell sequence information;

FIG. 241 is a block diagram illustrating an example computing device, in accordance with some embodiments of the present disclosure;

FIG. 242 is an illustration of an example of a statistical analysis approach in RNA profiling;

FIG. 243 is a diagram illustrating an example of generating cell-type RNA profiles, in accordance with some embodiments of the present disclosure;

FIG. 244 is a diagram illustrating an example of application the cell-type RNA profiles of FIG. 243 to identify cell-types and their proportions in a biological sample, in accordance with some embodiments of the present disclosure;

FIG. 245 is a diagram illustrating a method of generating of cell-type RNA profiles from information on a pathology slide, in accordance with some embodiments of the present disclosure;

FIG. 246 is a flow chart illustrating a process of generating cell-type profiles, in accordance with some embodiments of the present disclosure;

FIG. 247 is a diagram illustrating three gamma distributions that may be used to model gene expression data, in accordance with some embodiments of the present disclosure;

FIGS. 248A, 248B, and 248C collectively provide a flow chart of processes and features for determining a cancer composition of a subject, in accordance with some embodiments of the present disclosure;

FIG. 249 is a plot of breast and prostate cell types according to similarity and latent factors, in accordance with some embodiments of the present disclosure;

FIG. 250 is a flow chart illustrating a process of generating a therapy recommendation for a patient, in accordance with some embodiments of the present disclosure;

FIGS. 251A and 251B collectively provide a list of example genes that are informative for determining a cancer composition of a subject, in accordance with some embodiments of the present disclosure;

FIG. 252 illustrates an example of a digital image of a histology slide;

FIG. 253 is an overview of a digital tissue segmenter;

FIG. 254A illustrates a tissue segmentation overlay map created by the digital tissue segmenter;

FIG. 254B illustrates a cell outer edge overlay map created by the digital tissue segmenter;

FIG. 255 is a flowchart of a method for preparing digital images of histology slides for tissue segmentation and mapping analysis;

FIGS. 256A, 256B, and 256C each illustrate an exemplary grid overlay used for tissue segmentation on a digital image of a histology slide;

Figure 257B:
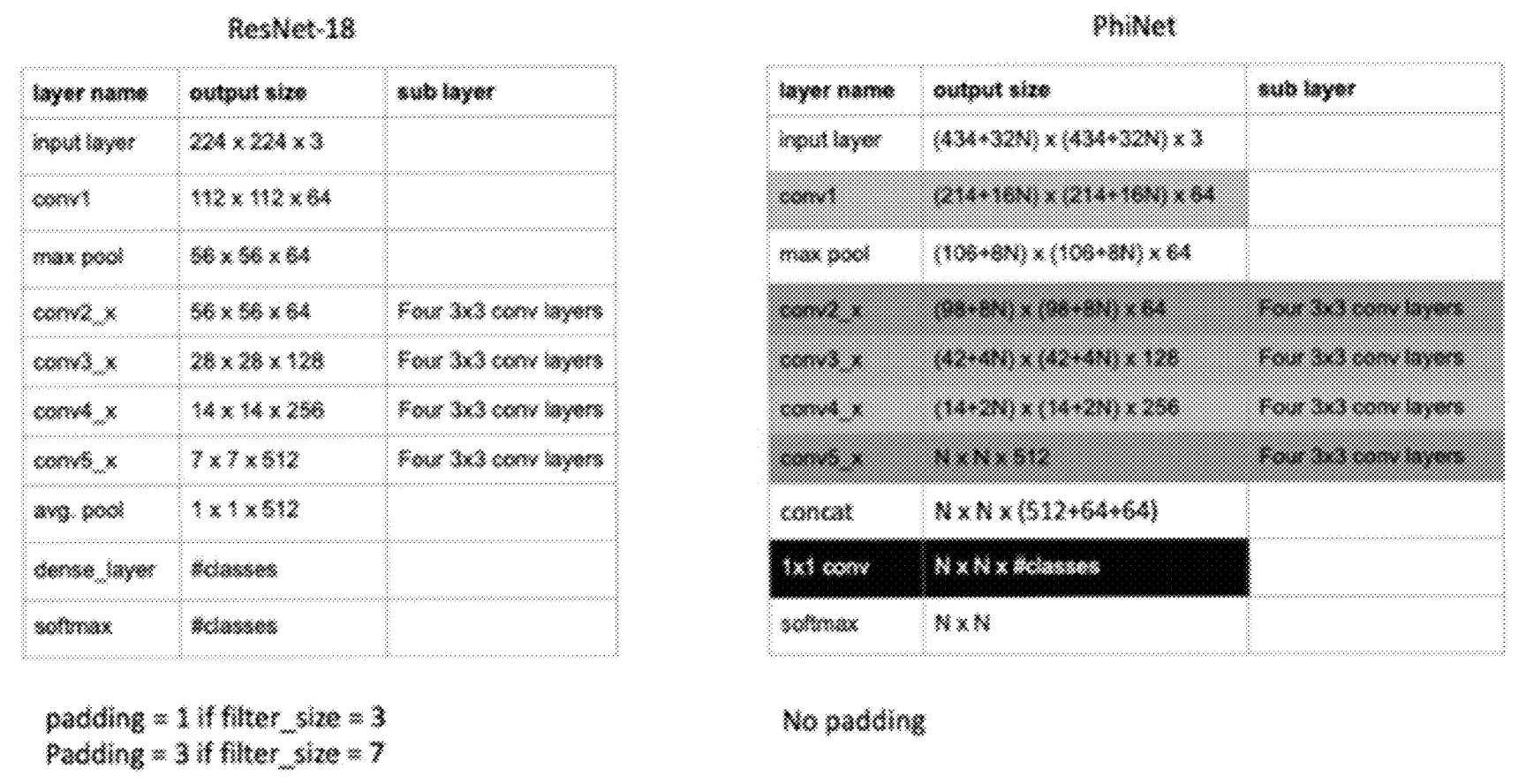

FIG. 257A illustrates the layers of an exemplary tissue segmentation algorithm;

FIG. 257B compares the layers of a known image classification algorithm with an exemplary tissue segmentation algorithm;

FIG. 257C is a visualization of the layers of an exemplary 3-dimensional input image matrix being convoluted by two exemplary 3-dimensional filter matrices;

FIG. 258 illustrates an exemplary grid overlay used for cell outlining on a digital image of a histology slide;

FIG. 259 illustrates exemplary training set images for the cell type locator;

FIG. 260A illustrates an overview of an exemplary digital tissue segmenter;

FIG. 260B illustrates an exemplary network architecture for a tissue class locator;

FIG. 260C illustrates exemplary training of digital tissue segmenter and generation of an overlay map output, predicting the location of IHC PD-L1 staining;

FIG. 260D is a table illustrating characteristics of exemplary training data for a digital tissue segmenter;

FIGS. 261A through 261F illustrate input H and E stained tissue images received by an exemplary digital tissue segmenter, corresponding overlay maps generated by an exemplary digital tissue segmenter to predict the location of IHC PD-L1 staining, and corresponding IHC stained tissue images used as references to determine the accuracy of overlay maps;

FIGS. 262A through 262F illustrate boxplots and receiver operating characteristic (ROC) curves, demonstrating the PD-L1 status prediction accuracy of an exemplary digital tissue segmenter;

FIG. 263A illustrates the effect of the PD-L1 status threshold value on the PD-L1 status prediction accuracy of an exemplary digital tissue segmenter;

FIG. 263B illustrates the effect on the PD-L1 status prediction accuracy of an exemplary digital tissue segmenter after reversing PD-L1 status labels in a percentage of testing data;

FIGS. 264A through 264F illustrate the accuracy of an exemplary digital tissue segmenter for all test data, for test data classified as stage I or stage II cancer cases, or for test data classified as stage III or stage IV cancer cases;

FIG. 265 illustrates how using multiple fields of view improves the accuracy of the exemplary digital tissue segmenter;

FIG. 266 illustrates a database that stores a setoff pathway options with associated data that may be used to modify and/or present options for diagnostic or treatment pathways that is consistent with at least some aspects of the present disclosure;

FIG. 267 is an exemplary image for a MAPK pathway set that is consistent with at least some aspects of the present disclosure;

FIG. 268 includes an image modification including metadata indicating where modifications would be placed relative to a diagnostic pathway;

FIG. 269A shows an exemplary treatment pathway report that is consistent with at least some aspects of the present disclosure, FIGS. 269B through 269E show insight images that are consistent with at least some aspects of the present disclosure;

FIG. 270 is a schematic illustrating an exemplary database that stores treatment pathways separate from diagnostic pathways;

FIG. 271 is a block diagram of a data-based healthcare system, according to aspects of the present disclosure;

FIG. 272 is an image of an example graphical user interface (GUI), according to aspects of the present disclosure;

FIG. 273 is an image of an example graphical user interface (GUI), according to aspects of the present disclosure;

FIG. 274 is an image of an example graphical user interface (GUI), according to aspects of the present disclosure;

FIG. 275 is an image of an example graphical user interface (GUI), according to aspects of the present disclosure;

FIG. 276 is an image of an example graphical user interface (GUI), according to aspects of the present disclosure;

FIG. 277 is an image of an example graphical user interface (GUI), according to aspects of the present disclosure;

FIG. 278 is an image of an example graphical user interface (GUI), according to aspects of the present disclosure;

FIG. 279 is an image of an example graphical user interface (GUI), according to aspects of the present disclosure;

FIG. 280 is an image of an example graphical user interface (GUI), according to aspects of the present disclosure;

FIG. 281 is an image of an example graphical user interface (GUI), according to aspects of the present disclosure;

FIG. 282 is an image of an example graphical user interface (GUI), according to aspects of the present disclosure;

FIG. 283 is an image of an example graphical user interface (GUI), according to aspects of the present disclosure;

FIG. 284 is an image of an example graphical user interface (GUI), according to aspects of the present disclosure;

FIG. 285 is an image of an example graphical user interface (GUI), according to aspects of the present disclosure;

FIG. 286 is an image of an example graphical user interface (GUI), according to aspects of the present disclosure;

FIG. 287 is an image of an example graphical user interface (GUI), according to aspects of the present disclosure;

FIG. 288 is an image of an example graphical user interface (GUI), according to aspects of the present disclosure;

FIG. 289 is an image of an example graphical user interface (GUI), according to aspects of the present disclosure;

FIG. 290 is an image of an example graphical user interface (GUI), according to aspects of the present disclosure;

FIG. 291 is an image of an example graphical user interface (GUI), according to aspects of the present disclosure;

Figure 292:
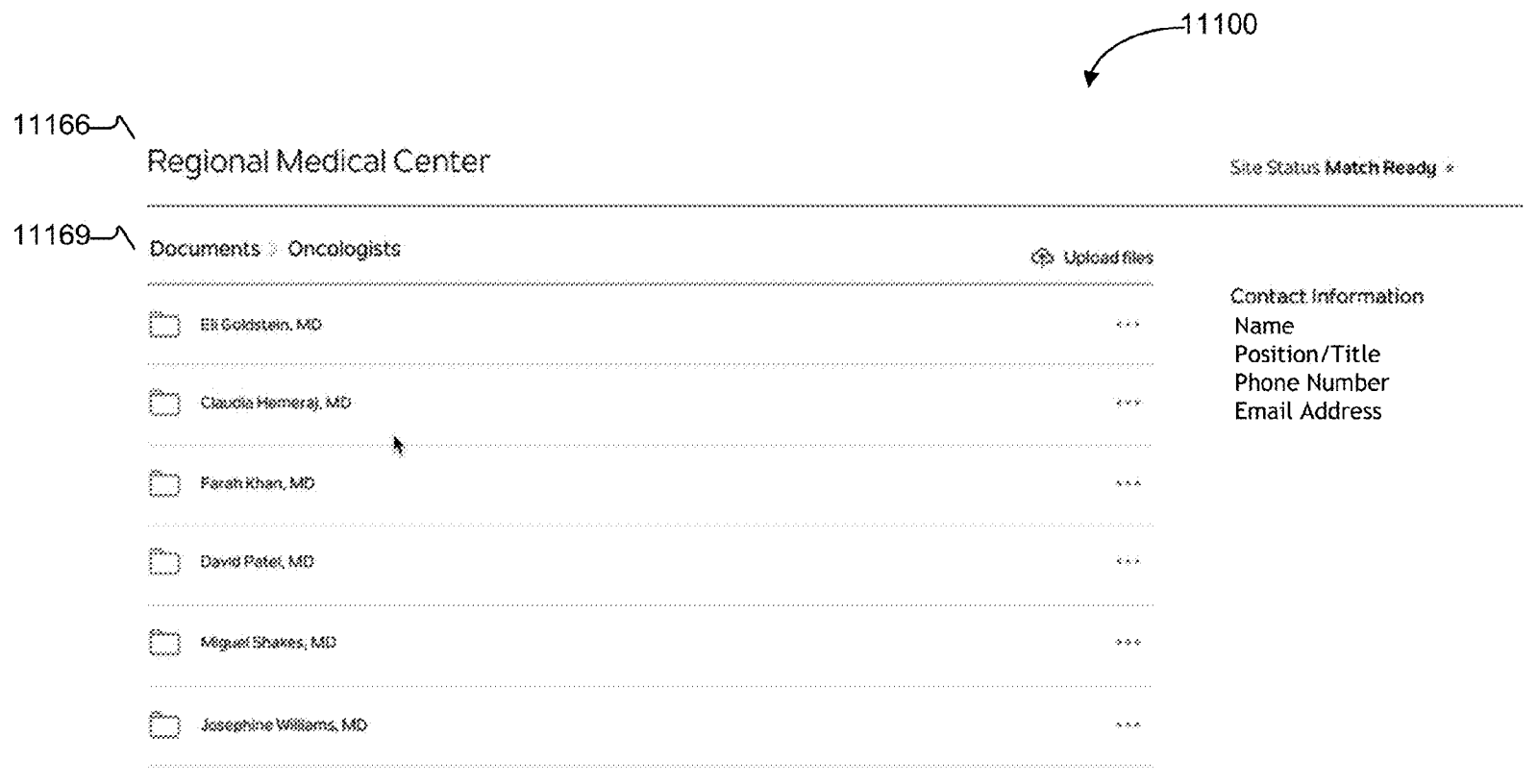

FIG. 292 is an image of an example graphical user interface (GUI), according to aspects of the present disclosure;

FIG. 293 is an image of an example graphical user interface (GUI), according to aspects of the present disclosure;

Figure 294:
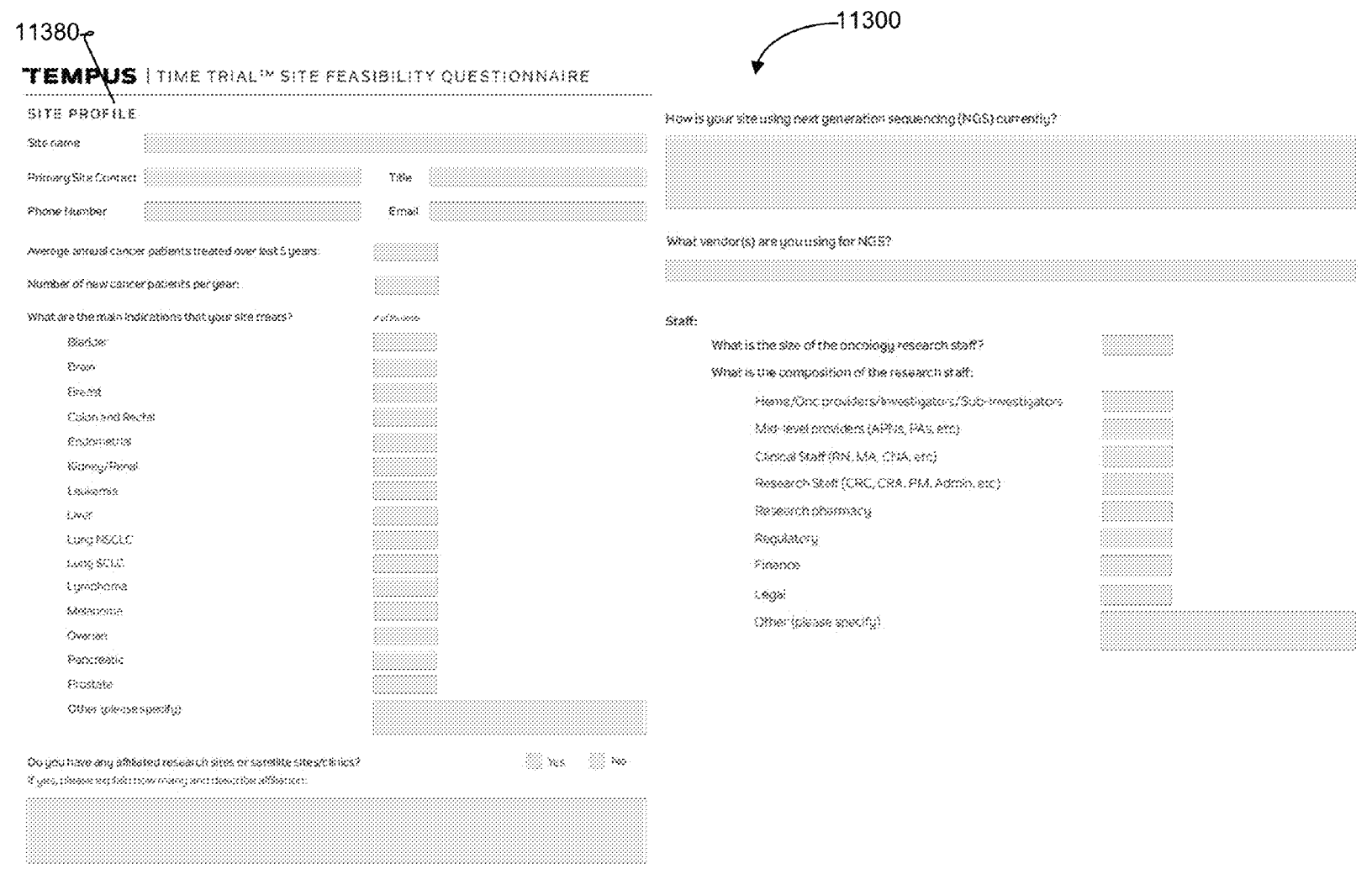

FIG. 294 is an image of an example graphical user interface (GUI), according to aspects of the present disclosure;

FIG. 295A is an image of an example graphical user interface (GUI), according to aspects of the present disclosure;

FIG. 295B is another image of the example GUI of FIG. 295A, according to aspects of the present disclosure;

FIG. 296 is an image of an example graphical user interface (GUI), according to aspects of the present disclosure;

FIG. 297 is an image of an example graphical user interface (GUI), according to aspects of the present disclosure;

FIG. 298A is an image of an example graphical user interface (GUI), according to aspects of the present disclosure;

FIG. 298B is another image of the example GUI of FIG. 298A, according to aspects of the present disclosure;

FIG. 298C is another image of the example GUI of FIG. 298A, according to aspects of the present disclosure;

FIG. 299 is an image of an example graphical user interface (GUI), according to aspects of the present disclosure; and FIG. 300 is an image of an example graphical user interface (GUI), according to aspects of the present disclosure;

FIG. 301A is an image of an example graphical user interface (GUI), according to aspects of the present disclosure;

FIG. 301B is an image of an example graphical user interface (GUI), according to aspects of the present disclosure;

FIG. 301C is an image of an example graphical user interface (GUI), according to aspects of the present disclosure;

FIG. 301D is an image of an example graphical user interface (GUI), according to aspects of the present disclosure;

FIG. 301E is an image of an example graphical user interface (GUI), according to aspects of the present disclosure;

FIG. 301F is an image of an example graphical user interface (GUI), according to aspects of the present disclosure;

FIG. 301G is an image of an example graphical user interface (GUI), according to aspects of the present disclosure;

FIG. 301H is an image of an example graphical user interface (GUI), according to aspects of the present disclosure;

FIG. 302 illustrates an embodiment for mapping clinical trial inclusion and exclusion criteria to features included in a patient data store;

FIG. 303 is an exemplary image of a polar coordinate, similarity plot;

FIG. 304A is a comparison matrix with example normalized similarity values for comparing a plurality of members of a data set;

FIG. 304B is a second exemplary image of a similarity plot;

FIG. 305 is an example of a hypothetical non-convex graph applying a minimum sum of squared error optimization function;

FIG. 306A is an example of an image incorporated into a user interface for visually examining similarity within a patient cohort;

FIG. 306B is an examine of an image incorporated into a user interface for visually examining similarity within a finance cohort;

FIG. 307A is a table of exemplary mutation states for a plurality of genes for multiple patients;

FIG. 307B is a table of exemplary weights to apply to each of the genes identified in FIG. 307A, reflecting an appreciation that certain gene mutations are more significant than others when comparing patients;

FIG. 307C is a depiction of an exemplary rule set, such as the rule set provided in FIG. 308, to be determine the gene weighting of FIG. 307B;

FIG. 307D is a table representing an exemplary DNA comparison matrix for a plurality of patients;

FIG. 308 is a flowchart depicting a rule set for determining weights for a plurality of gene mutations;

FIG. 309 is a flowchart depicting a rule set for determining angular distances between points in a similarity plot;

FIG. 310 is an exemplary diagram of a system for carrying out the method and generating the user interfaces described herein;

FIG. 311 is an illustration of the various types of CNV that occur in the human genome (SEQ ID NO:3-9);

FIG. 312 is a block diagram illustrating a patient order processing pipeline in which embodiments of the present invention may operate;

FIG. 313 is a block diagram illustrating a CNV Pipeline within the bioinformatic pipeline in which embodiments of the present invention may operate;

FIG. 314 is an illustration of a panel of probes for sequencing a target region (SEQ ID NO:10);

FIG. 315 is an illustration of a copy number plot for reporting CNV states;

FIG. 316 is an illustration of a b-allele fraction log odds ratio plot for reporting CNV states;

FIG. 317 is an illustration of a coverage log ratio plot for reporting CNV states;

FIG. 318 is an illustration of a block diagram of an implementation of a computer system in which some implementations of the disclosure may operate;

FIG. 319 is a schematic illustration of an example computer processing system for normalizing and correcting RNA expression data, in accordance with an example;

FIG. 320 illustrates an example computing device for implementing the systems of FIG. 319 and the processes of FIGS. 321-324, in accordance with an example;

FIG. 321 is a block diagram of an example process for updating a standard gene expression dataset with new gene expression data using one or more conversion factors, in accordance with an example;

FIG. 322 is a block diagram of an example process for performing RNA seq normalization, as may be implemented by the process of FIG. 323, in accordance with an example;

FIG. 323 is a block diagram of an example process for generating conversion factors and performing RNA seq correction on unpaired normalized RNA datasets, produced by the process of FIG. 322, in accordance with an example;

FIG. 324 is a block diagram of an example process for performing correction on a paired dataset formed from multiple normalized gene expression datasets, in accordance with an example;

FIG. 325 is a schematic illustration of an RNA normalization and correction framework interfacing to provide normalized and corrected RNA seq data to a multi-model RNA seq, imaging features machine learning framework, and/or other framework, in accordance with an example;

FIG. 326 illustrates an example workflow for implementing a two-step normalization process and correction process on an external gene expression dataset, in accordance with an example;

FIG. 327 is a plot of a linear mapping performed on gene expression data to identifier outliers to clean from the gene expression dataset, in accordance with an example;

FIG. 328 is a plot of a linear mapping performed on an external gene expression data to identify outliers to clean from the external gene expression dataset, in accordance with an example;

FIG. 329A is a plot of an uncorrected exemplary gene expression dataset. FIG. 329B is a plot of the exemplary gene expression dataset normalized and corrected, in accordance with an example;

FIG. 330 is a schematic illustration of a multimodal normalization framework for normalization of gene expression data, in accordance with an example.

Figure 331:
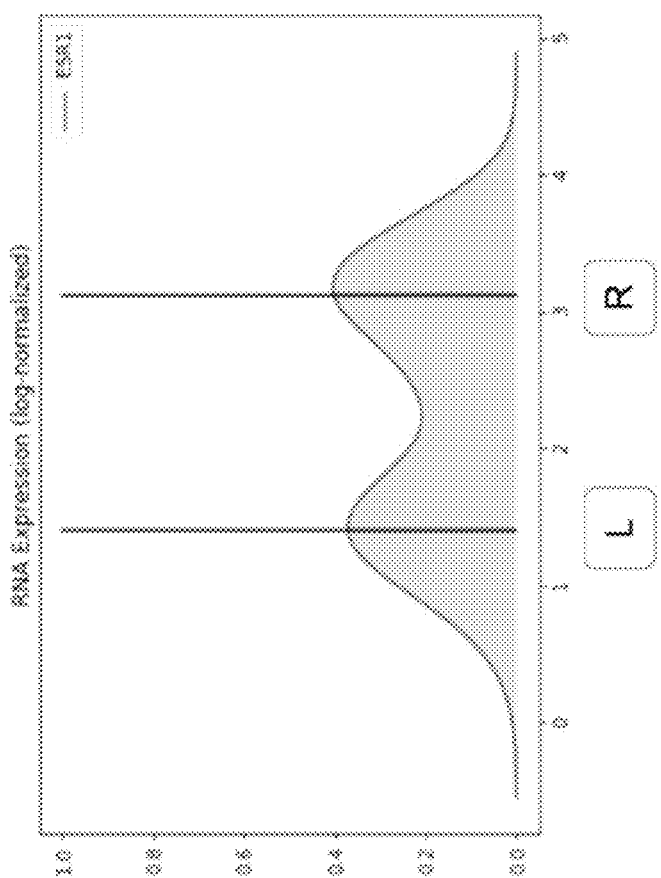

FIG. 331 is a plot of RNA expression data for ESR1, where that data exhibits a bimodal distribution prior to normalization, in accordance with an example.

Figure 332:
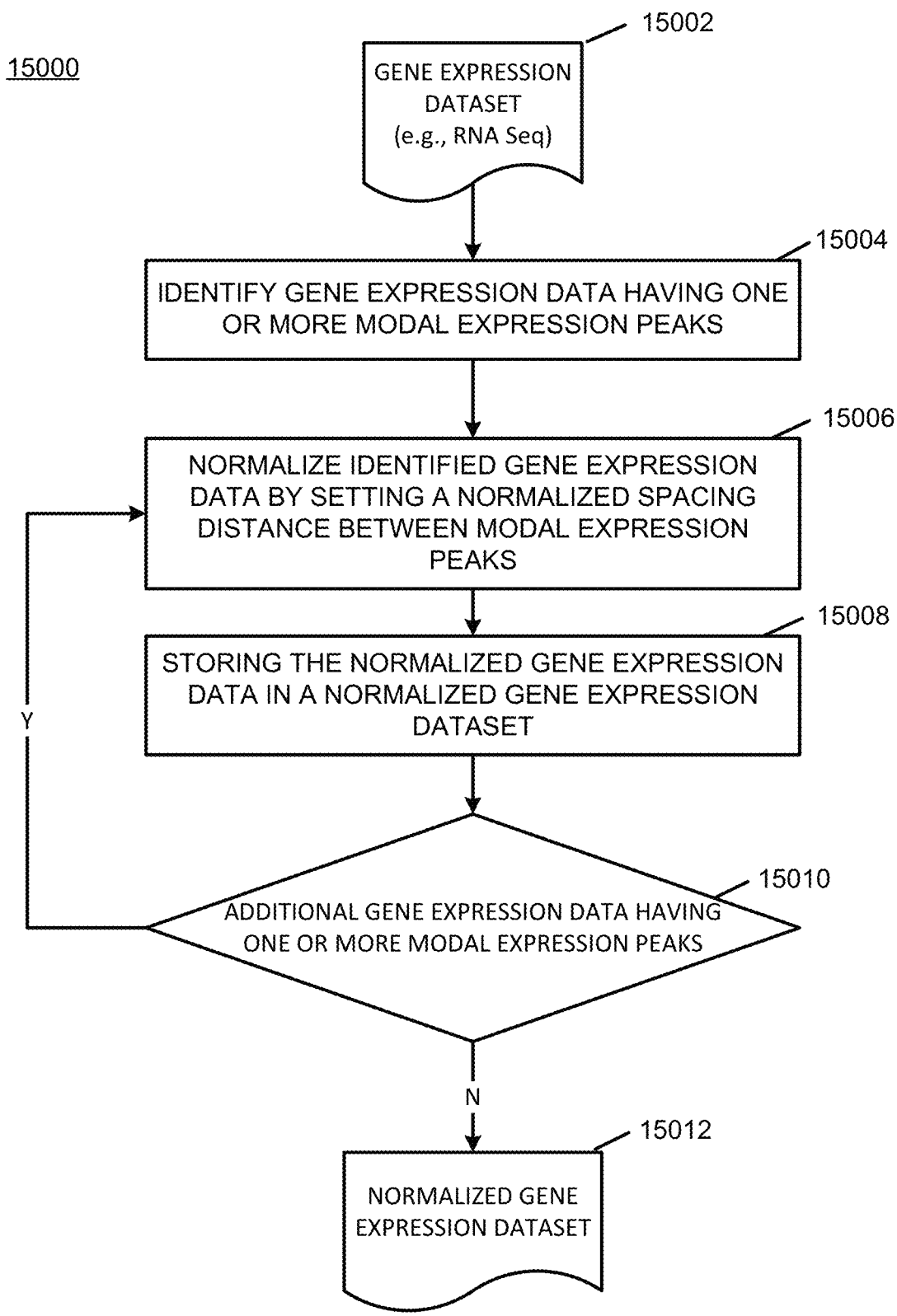

FIG. 332 is a block diagram of an example process for performing correction a multimodal gene expression data, such as the bimodal data of FIG. 331, in accordance with an example.

Figure 333:
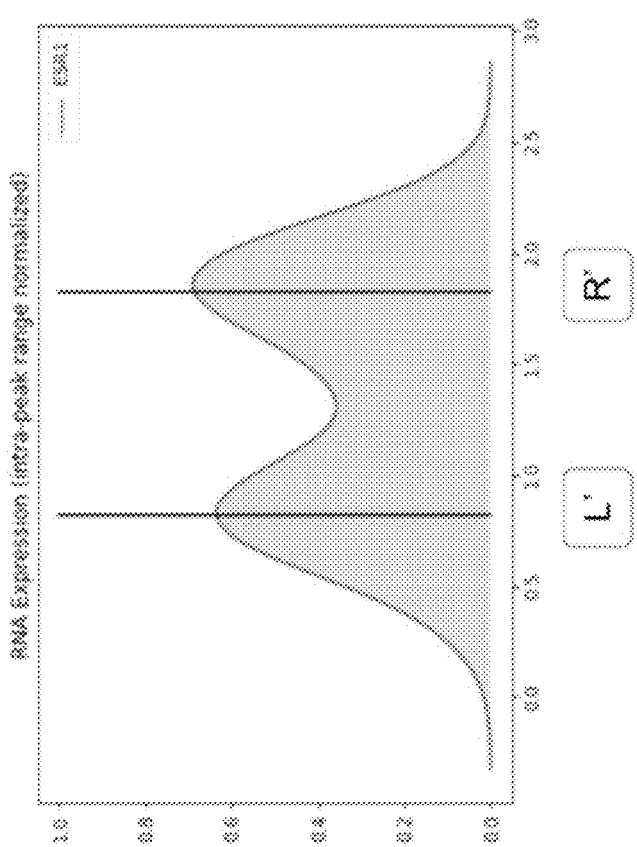

FIG. 333 is a plot of the RNA expression data for ESR1 from FIG. 331, after an intra-peak normalization of the bimodal distribution, in accordance with an example.

Figure 334:
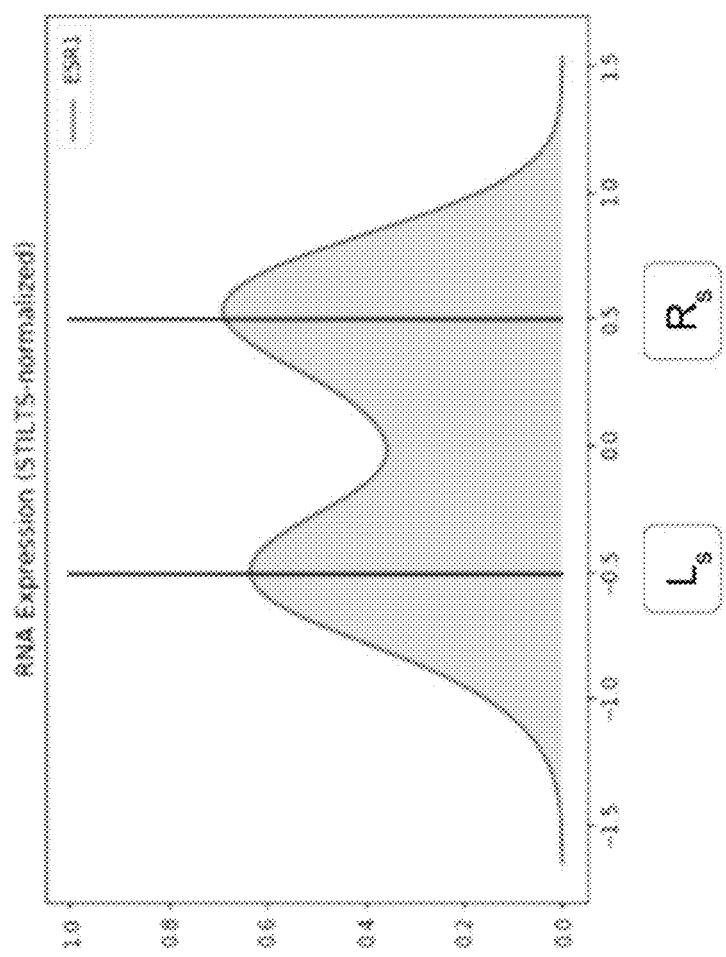

FIG. 334 is a plot of the normalized RNA expression data for ESR1 from FIG. 333, after a shift of the normalized peaks is performed, in accordance with an example.

Figure 335:
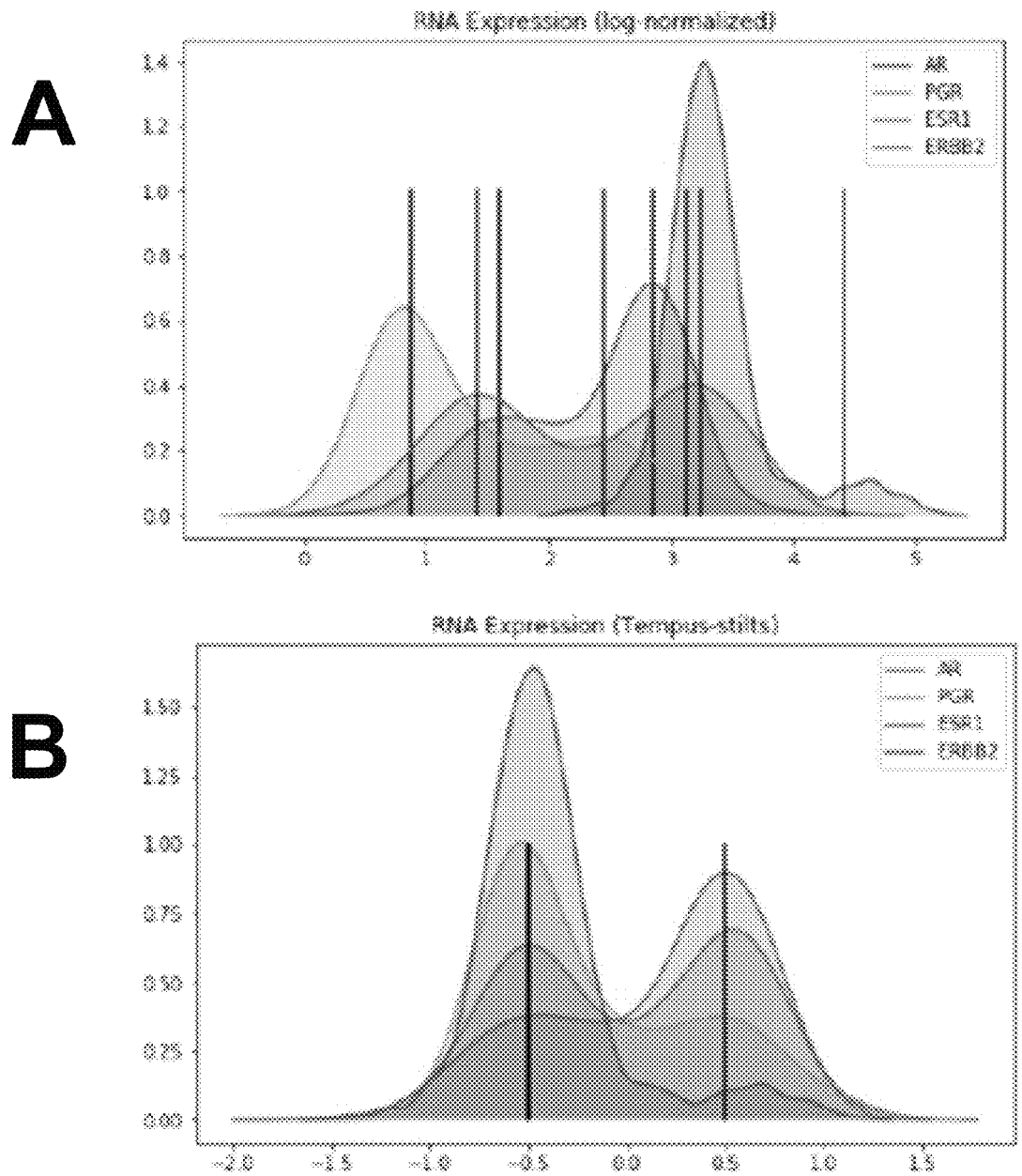

FIG. 335A is a plot of bimodal RNA expression data for multiple different genes (AR, PGR, ESR1, ERBB2), prior to normalization, and FIG. 335B is a plot of that RNA expression data after normalization showing aligned peaks for the bimodal distributions of the data, in accordance with an example.

Figure 336:
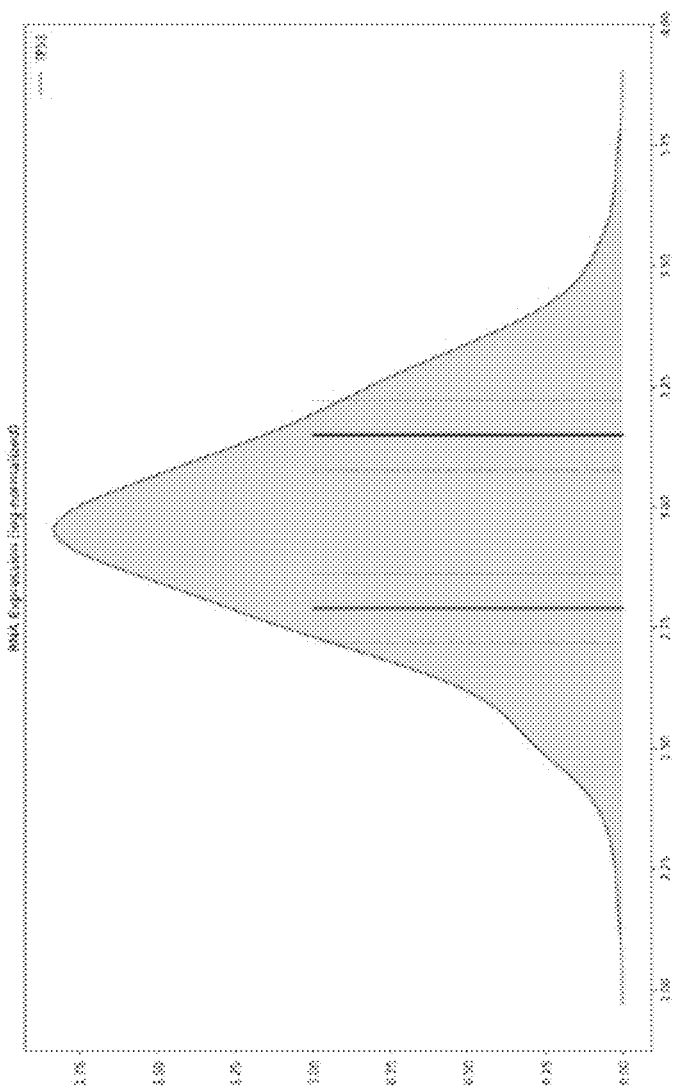

FIG. 336 is a plot of the RNA expression data for TP53 which exhibits a uni-modal distribution, showing a bimodal peak normalization process in progress, in accordance with an example.

FIG. 337A is a plot of uni-modal RNA expression data for multiple different genes (BRCA1, BRCA2, PIK3CA), prior to normalization, and FIG. 337B is a plot of that uni-modal RNA expression data after normalization showing alignment resulting a bimodal peak normalization process, in accordance with an example.

FIG. 338A is a plot of Uniform Manifold Approximation and Projection (UMAP) of ESR1 gene expression data prior to normalization, and FIG. 338B is a plot of UMAP for that RNA expression data after normalization, in accordance with an example.

Figure 339:
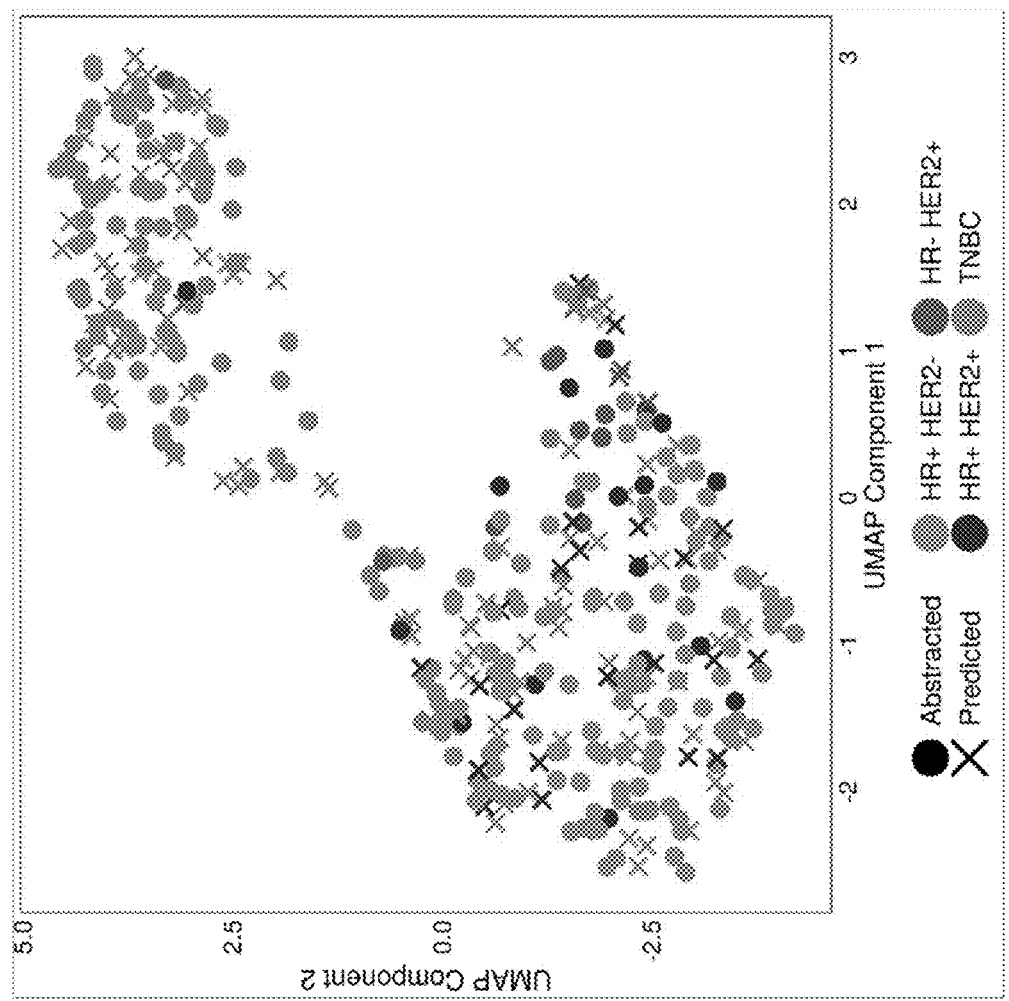

FIG. 339 displays a UMAP plot of a cohort of patient specimens with one cluster of triple negative breast cancer specimens.

Figure 340A:
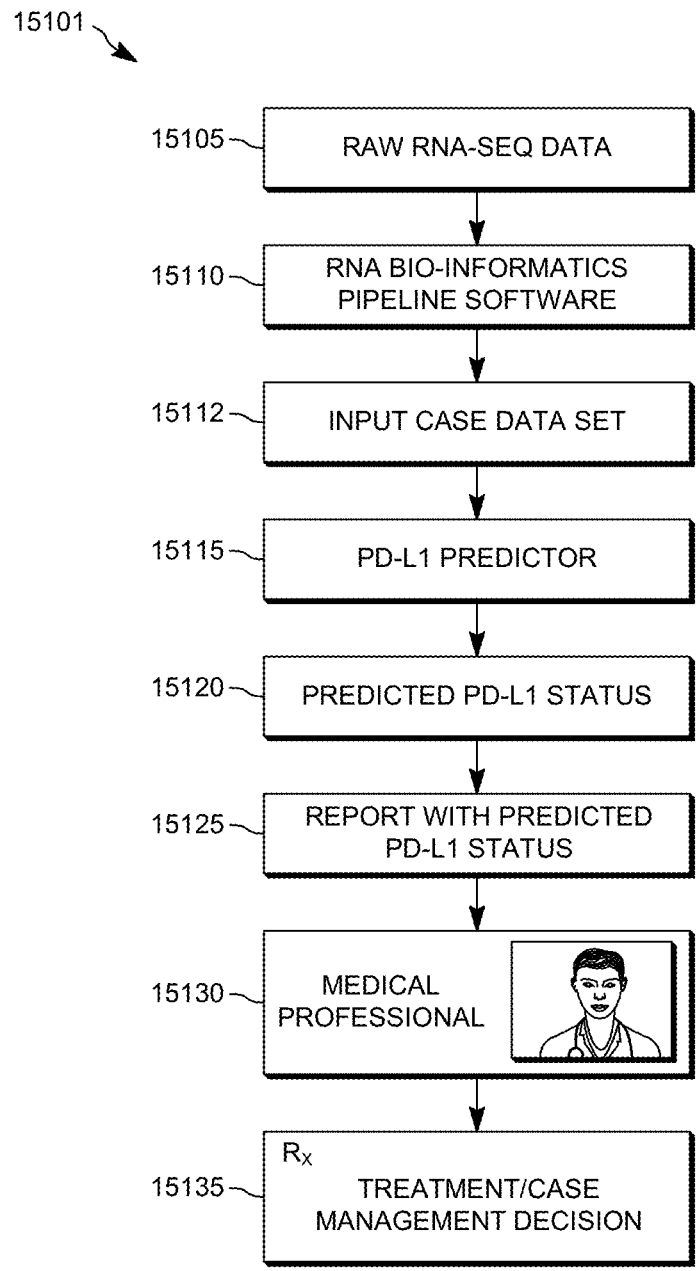

FIG. 340A illustrates an example use case of a PD-L1 status predictor.

Figure 340B:
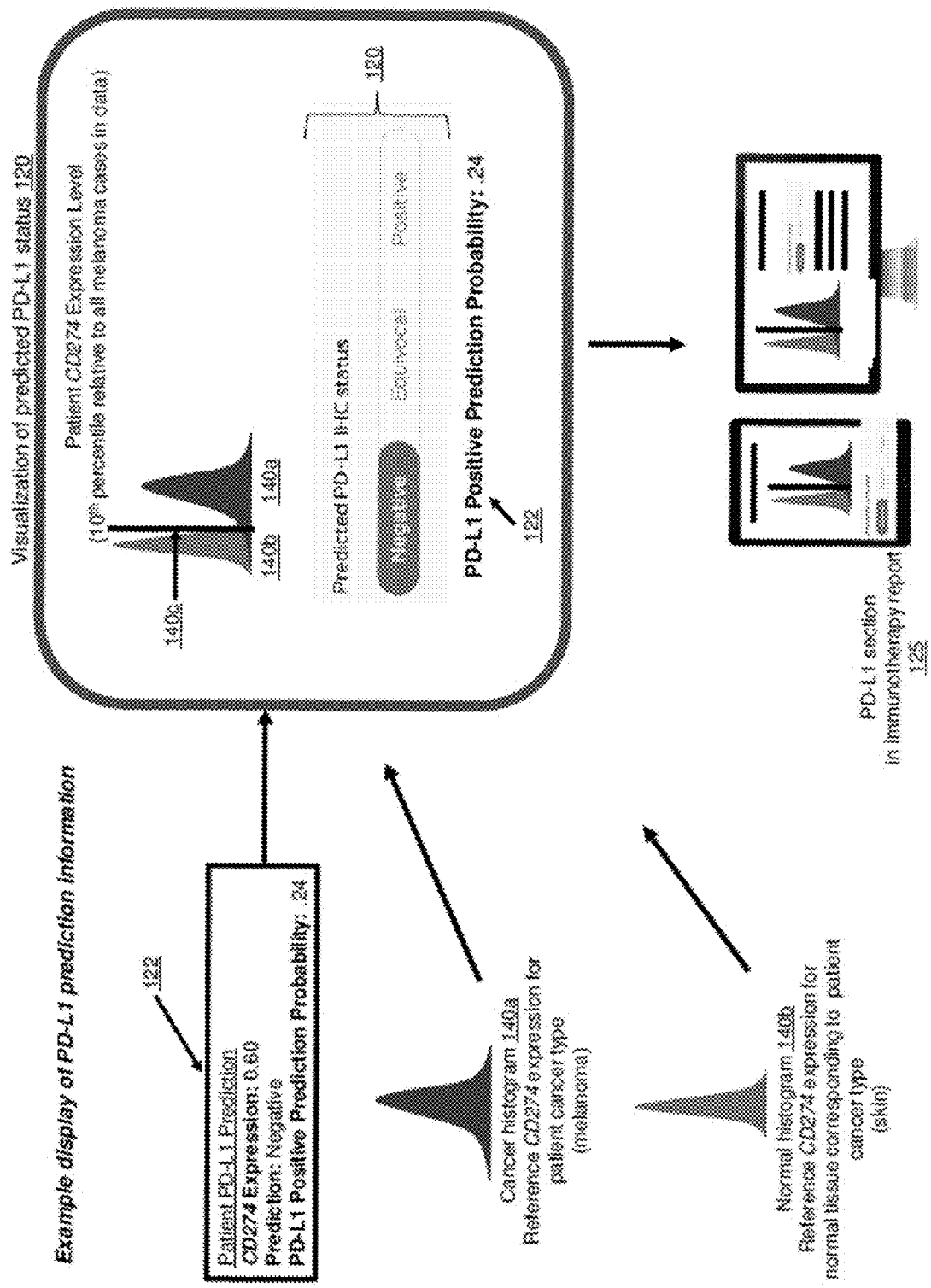

FIG. 340B illustrates an exemplary predicted PD-L1 status as it may appear on a report.

Figure 341A:
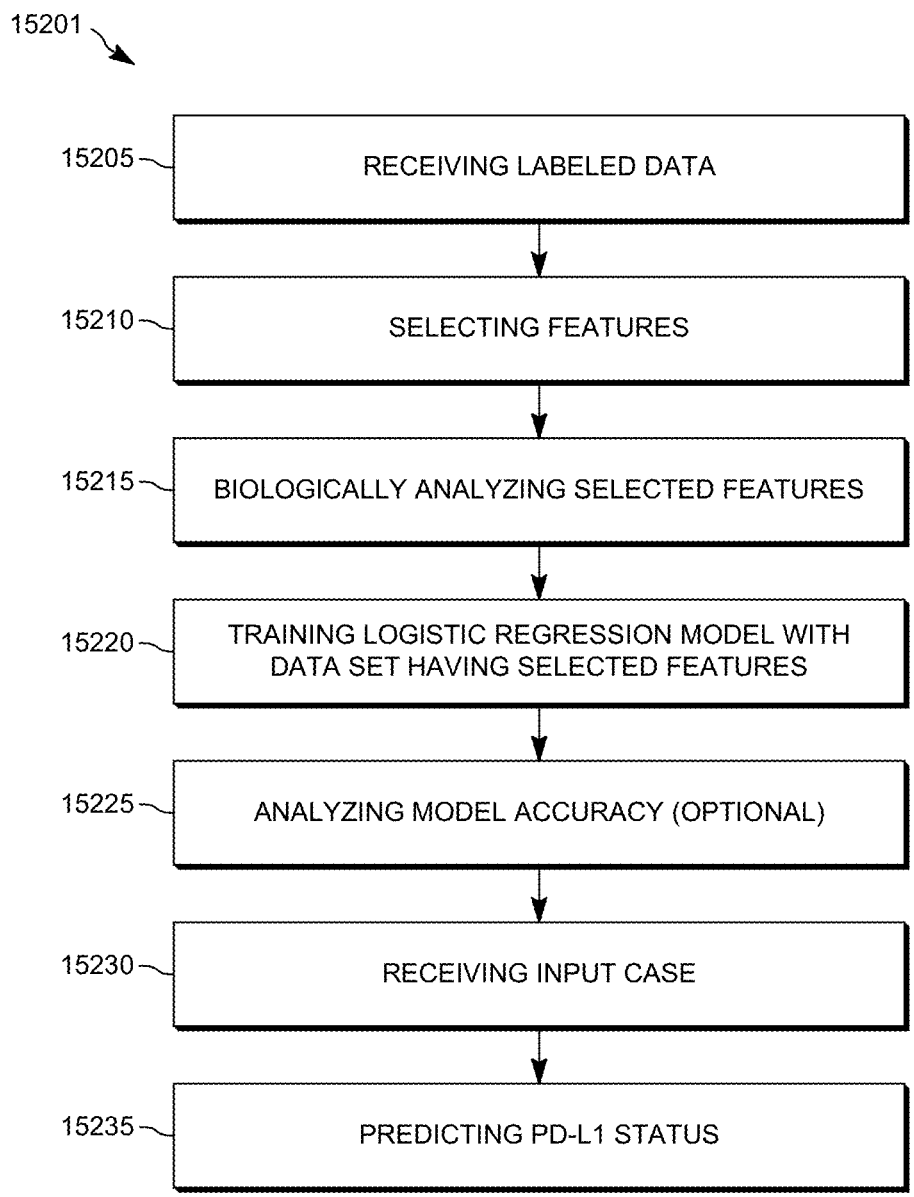

FIG. 341A illustrates a method for training a PD-L1 status predictor and predicting a PD-L1 status using a PD-L1 status predictor.

Figure 341B:
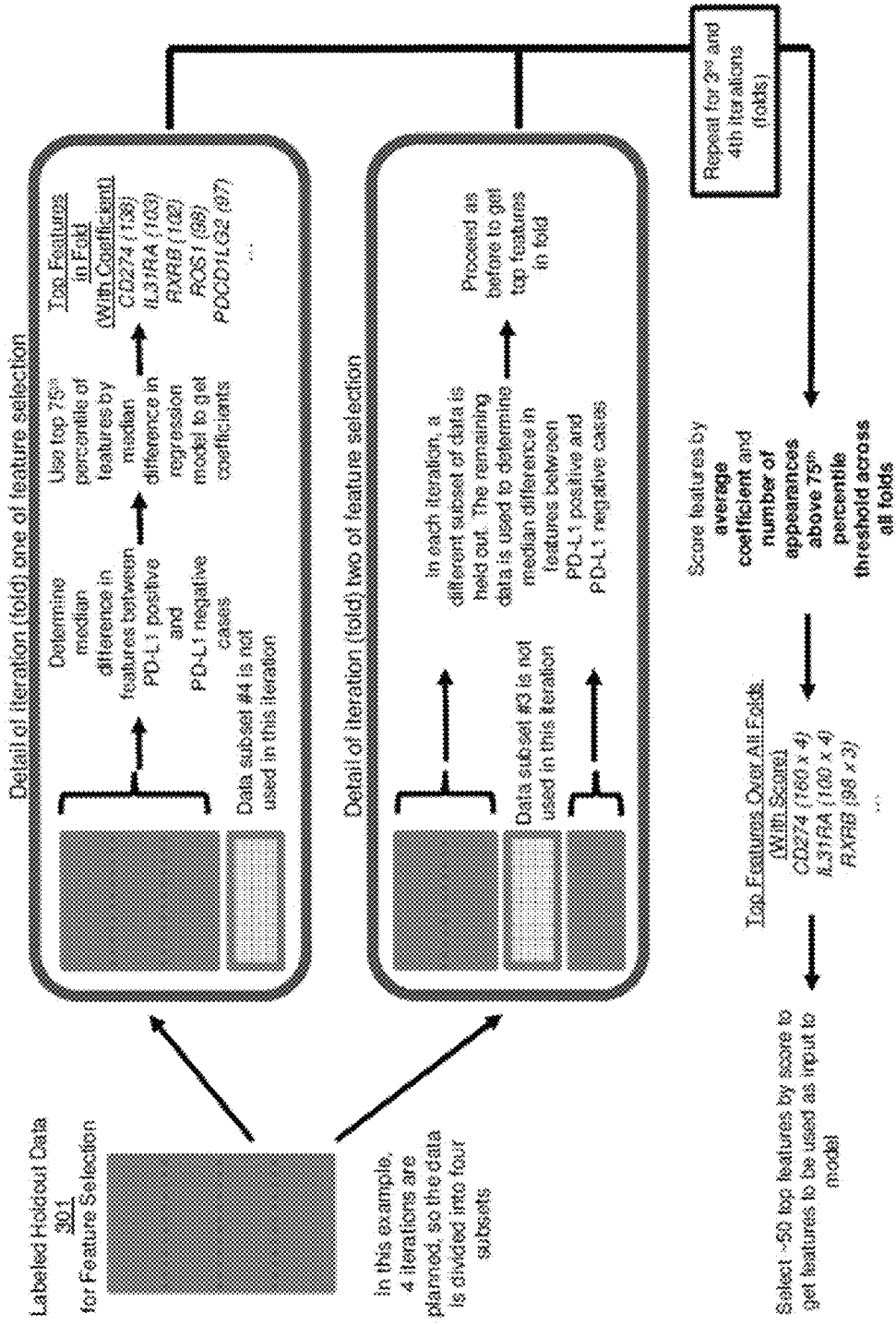

FIG. 341B illustrates an exemplary method for selecting features for a PD-L1 status predictor.

Figure 341C:
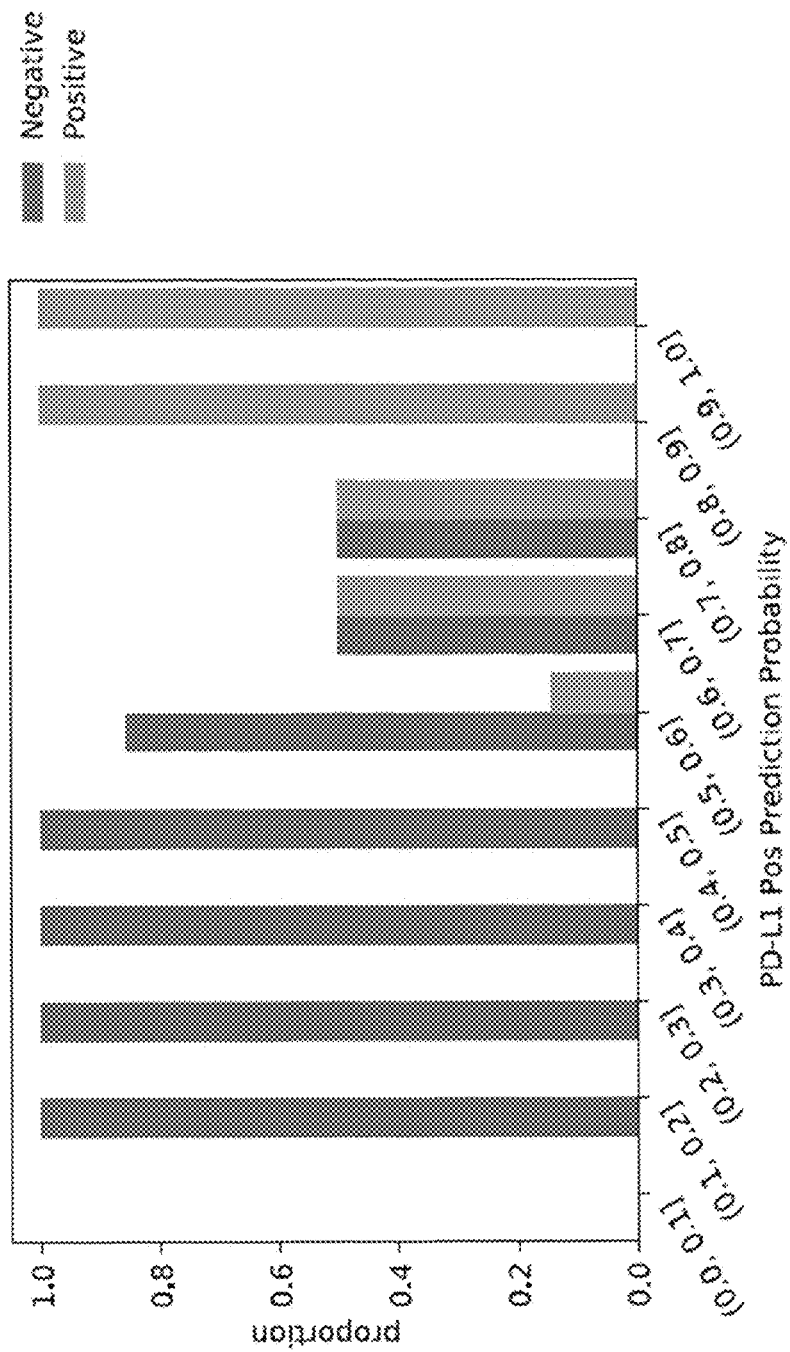

FIG. 341C illustrates an analysis used to select thresholds for classifying a PD-L1 prediction probability as negative, equivocal, or positive.

Figure 342:
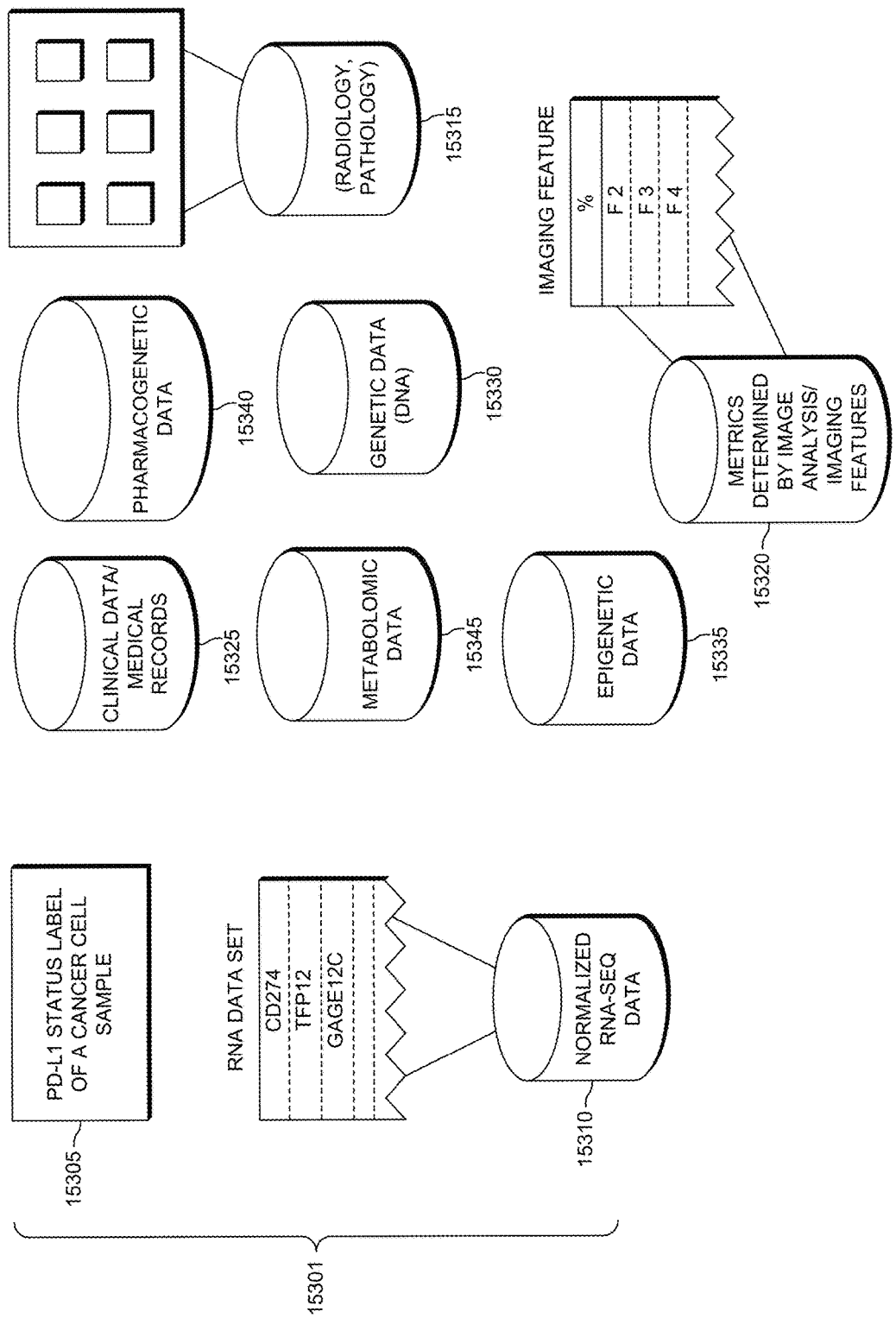

FIG. 342 illustrates example labeled data that may be included in a training data set.

Figure 343:
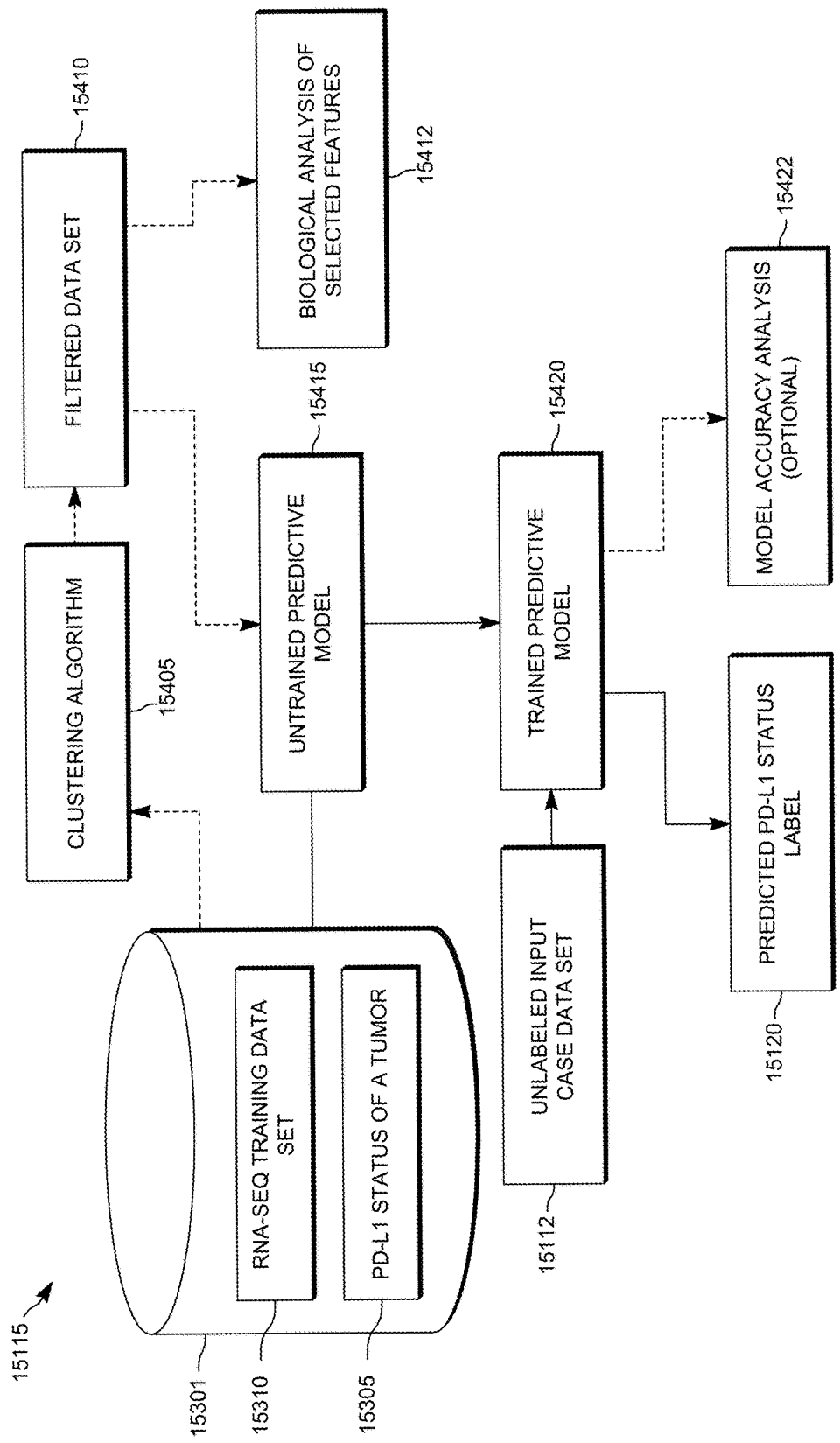

FIG. 343 illustrates an example PD-L1 status predictor.

Figure 344:
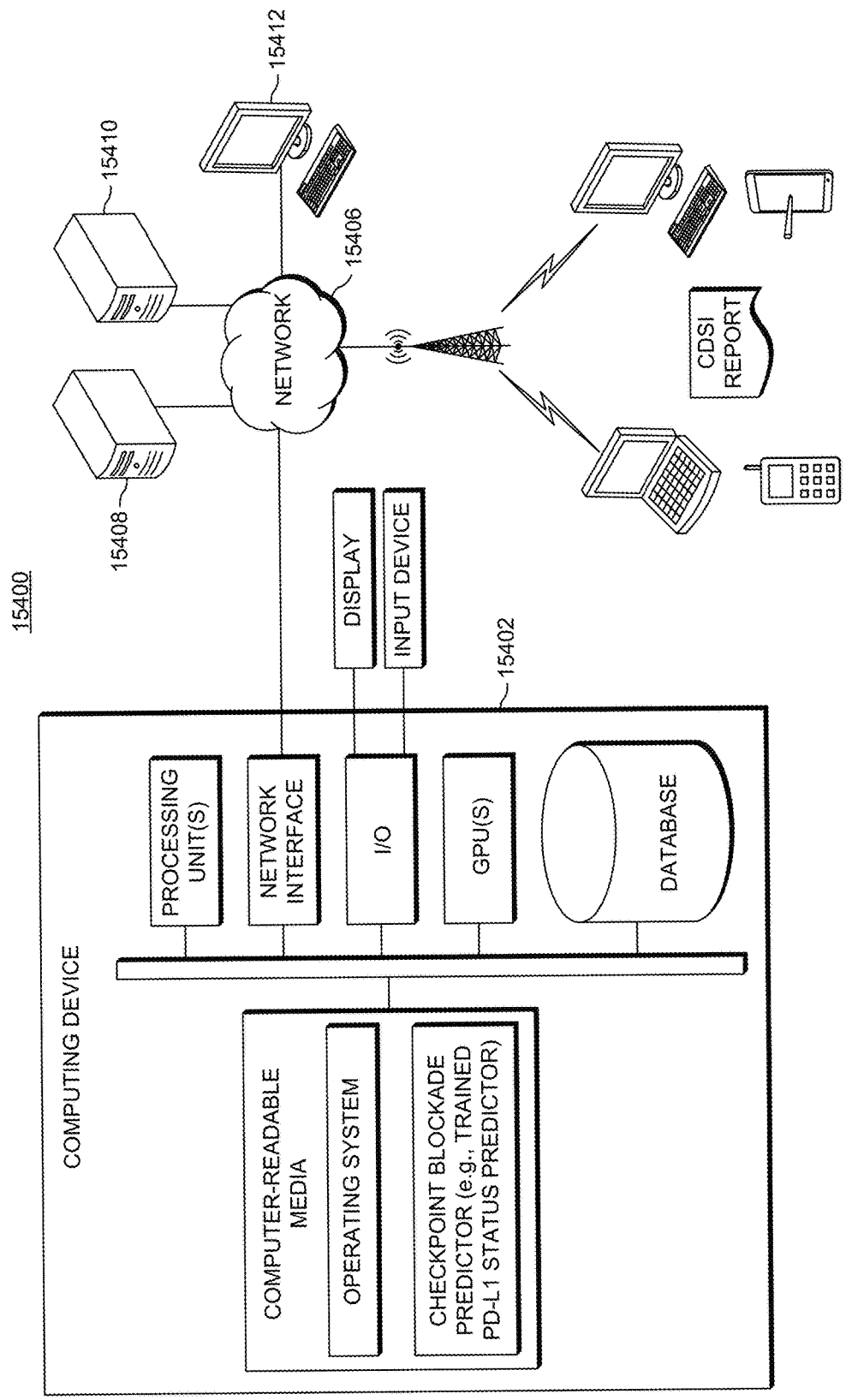

FIG. 344 illustrates a genetic sequence analysis system, in accordance with an example.

Figure 346:
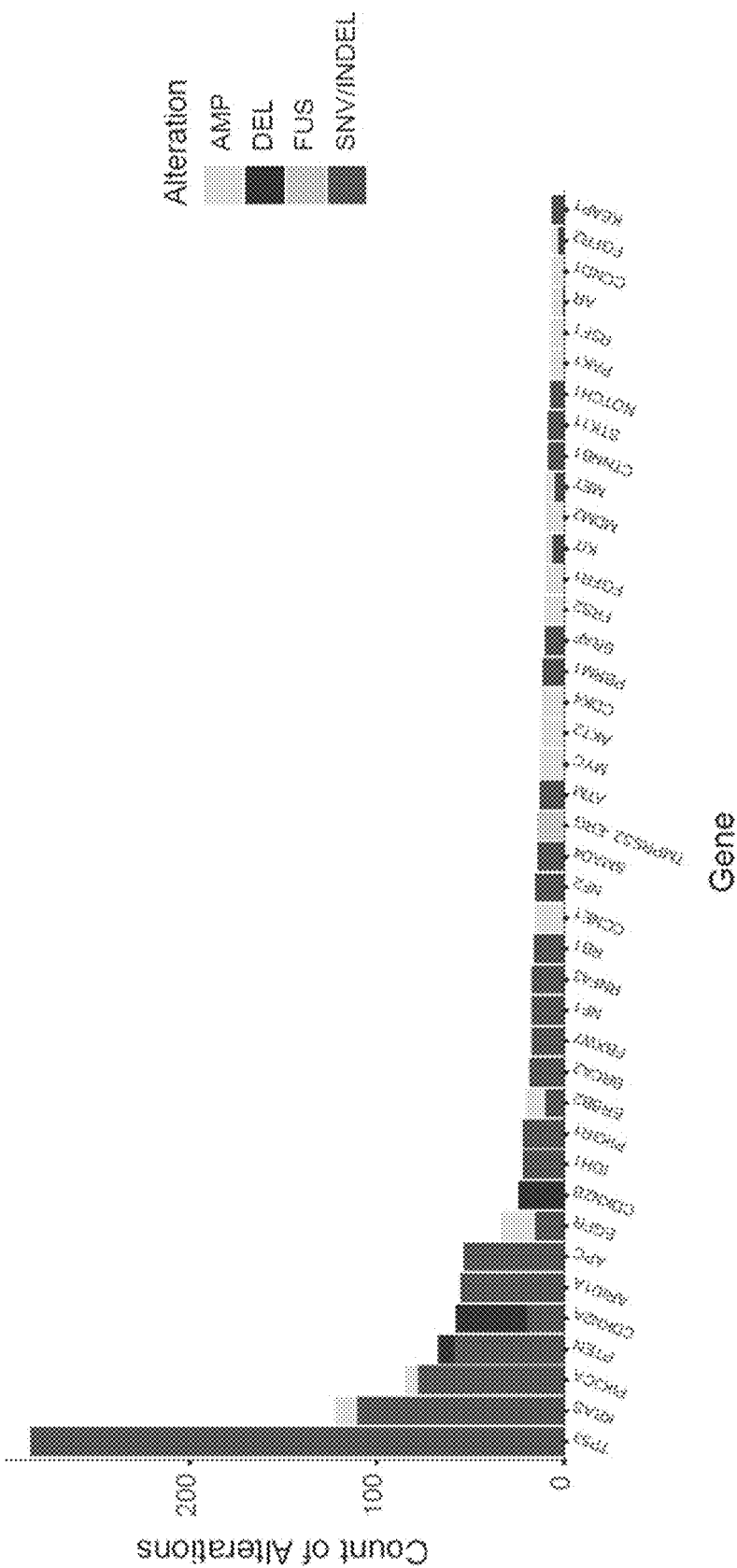
Figure 347:
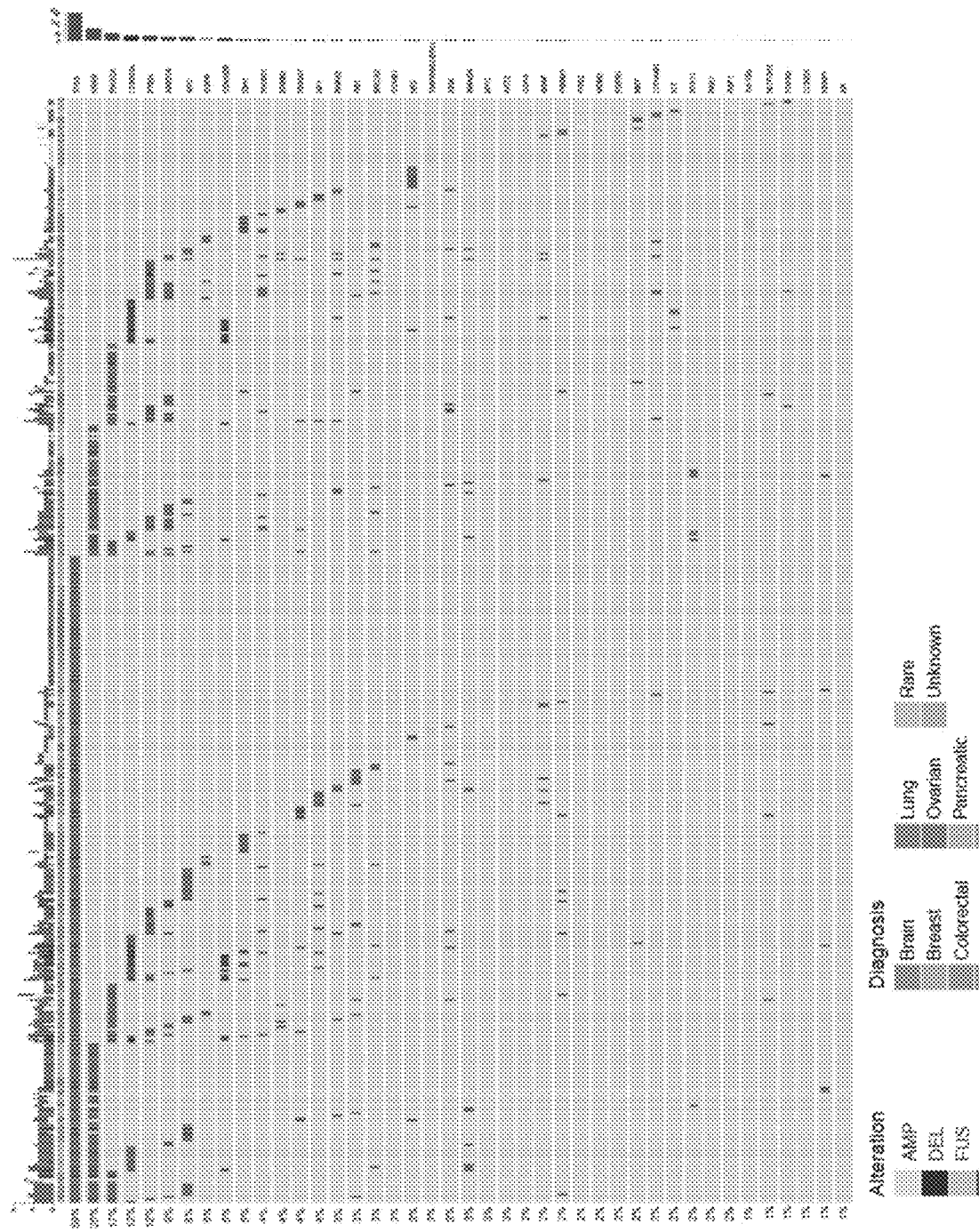
Figure 348:
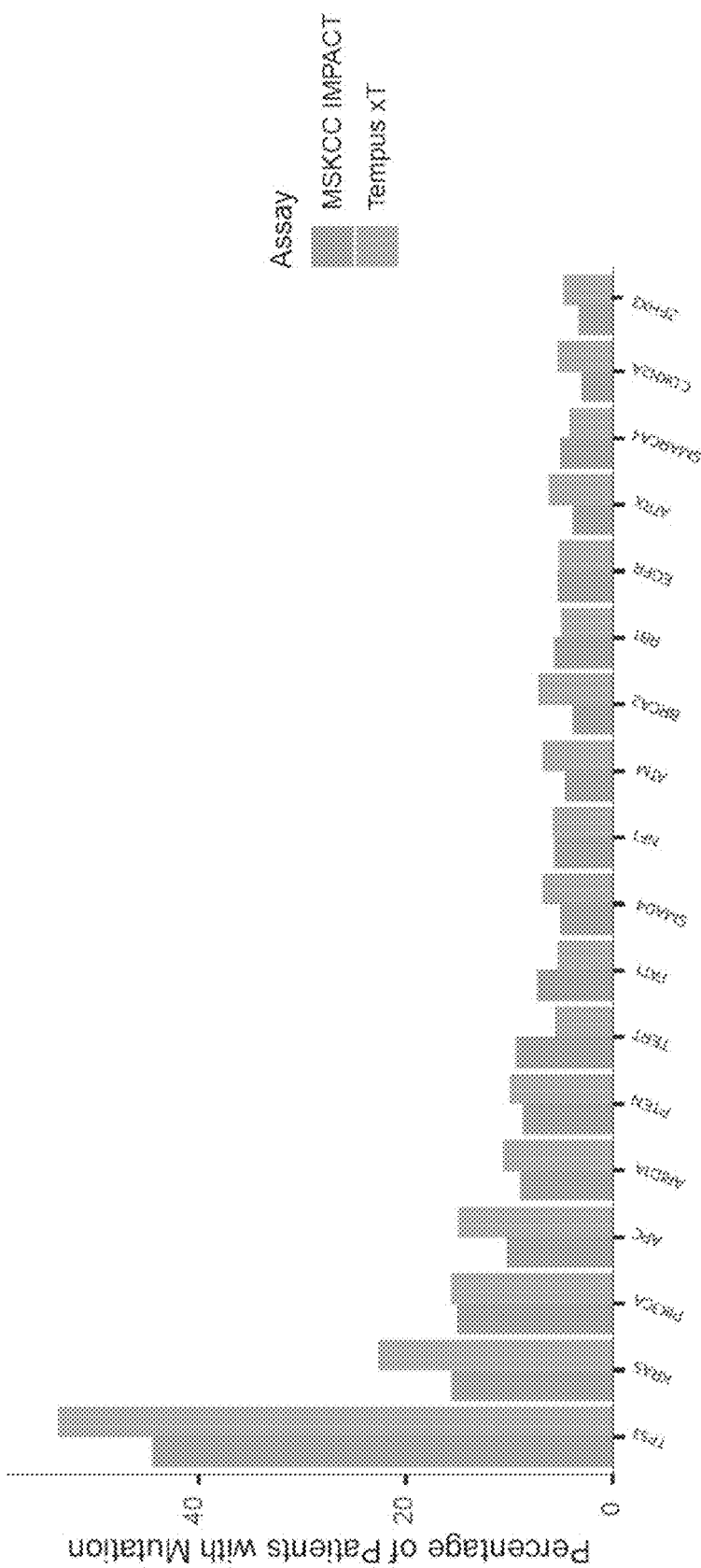
Figure 349:
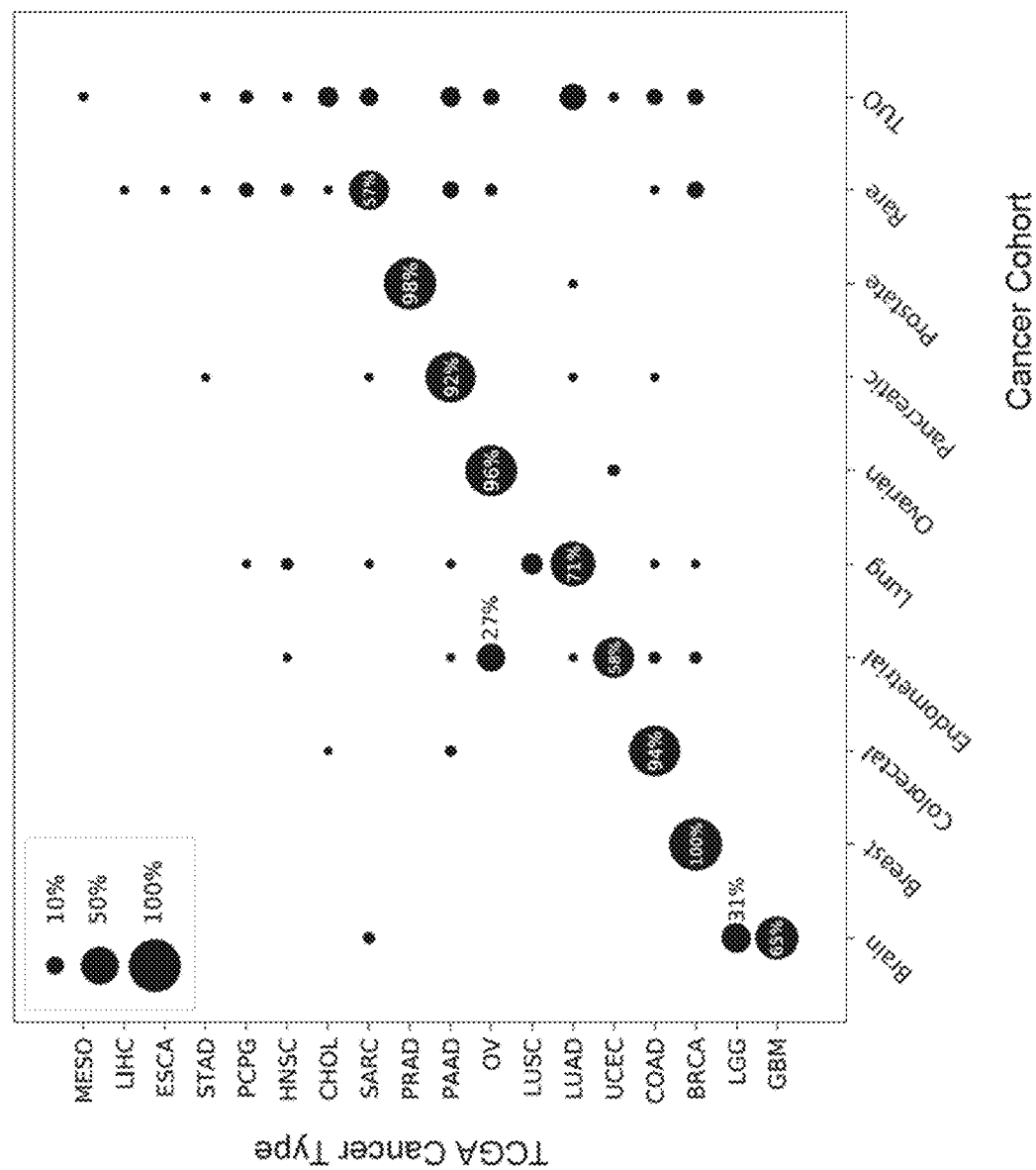
Figure 350:
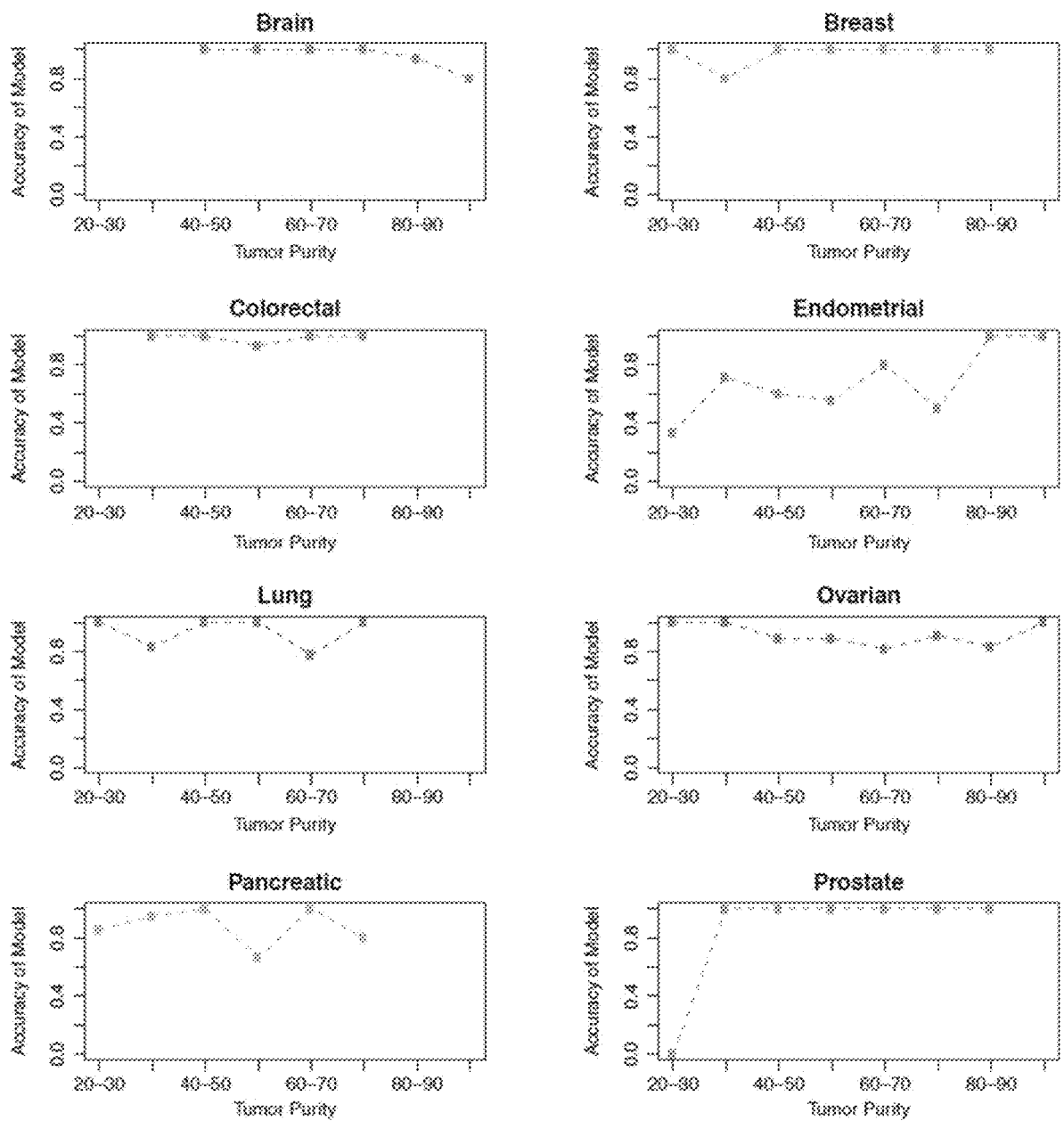
Figure 351:
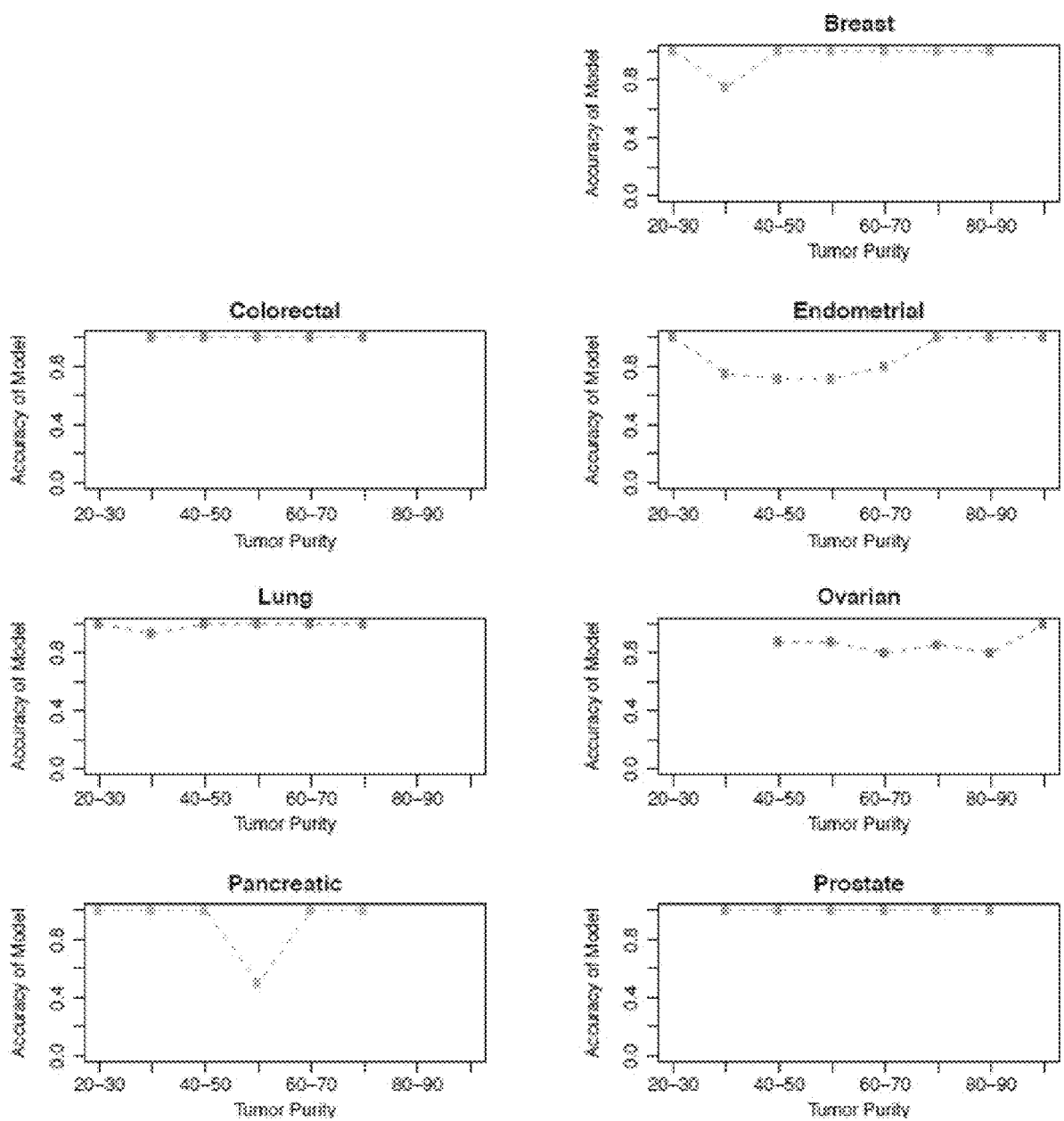
Figure 352:
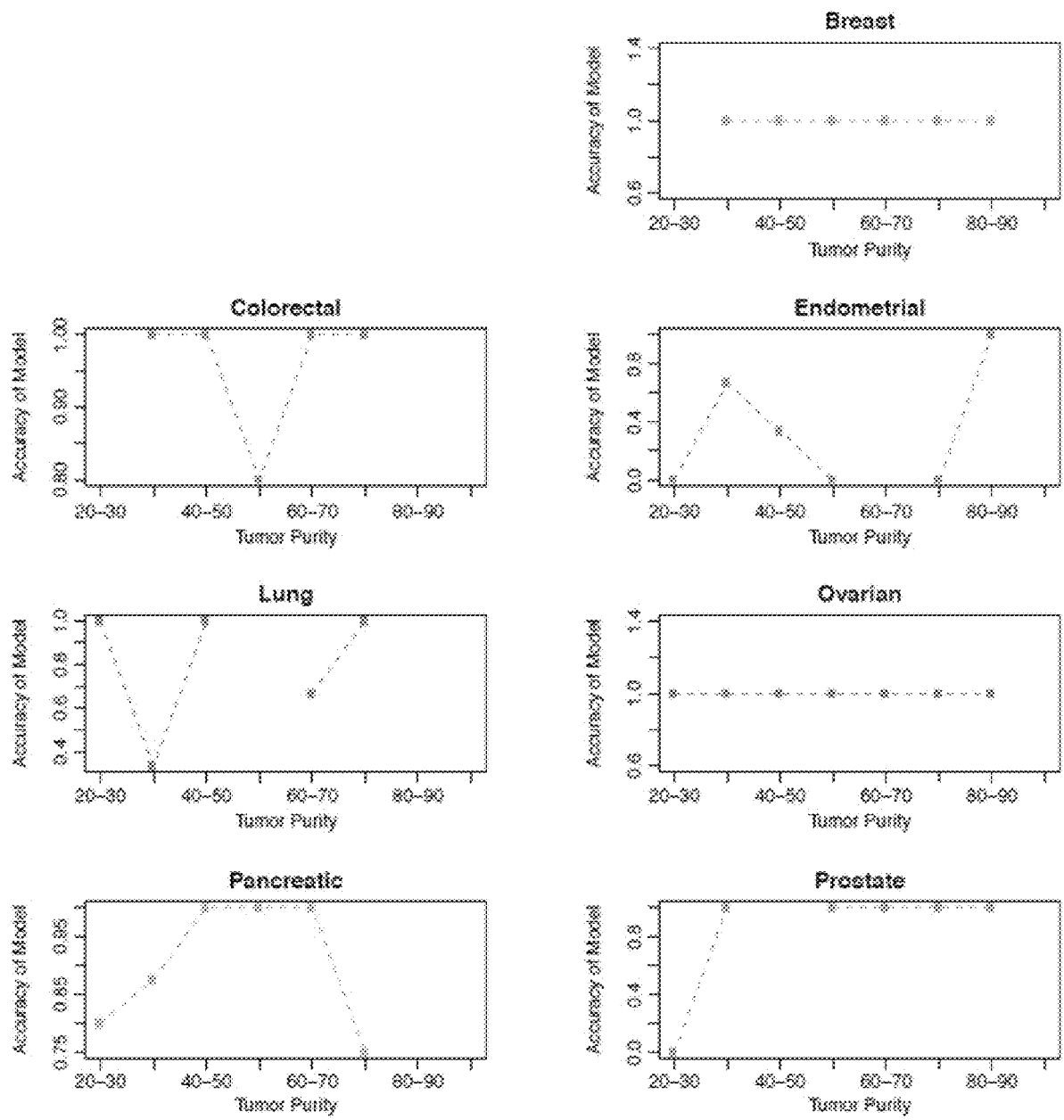
Figure 353:
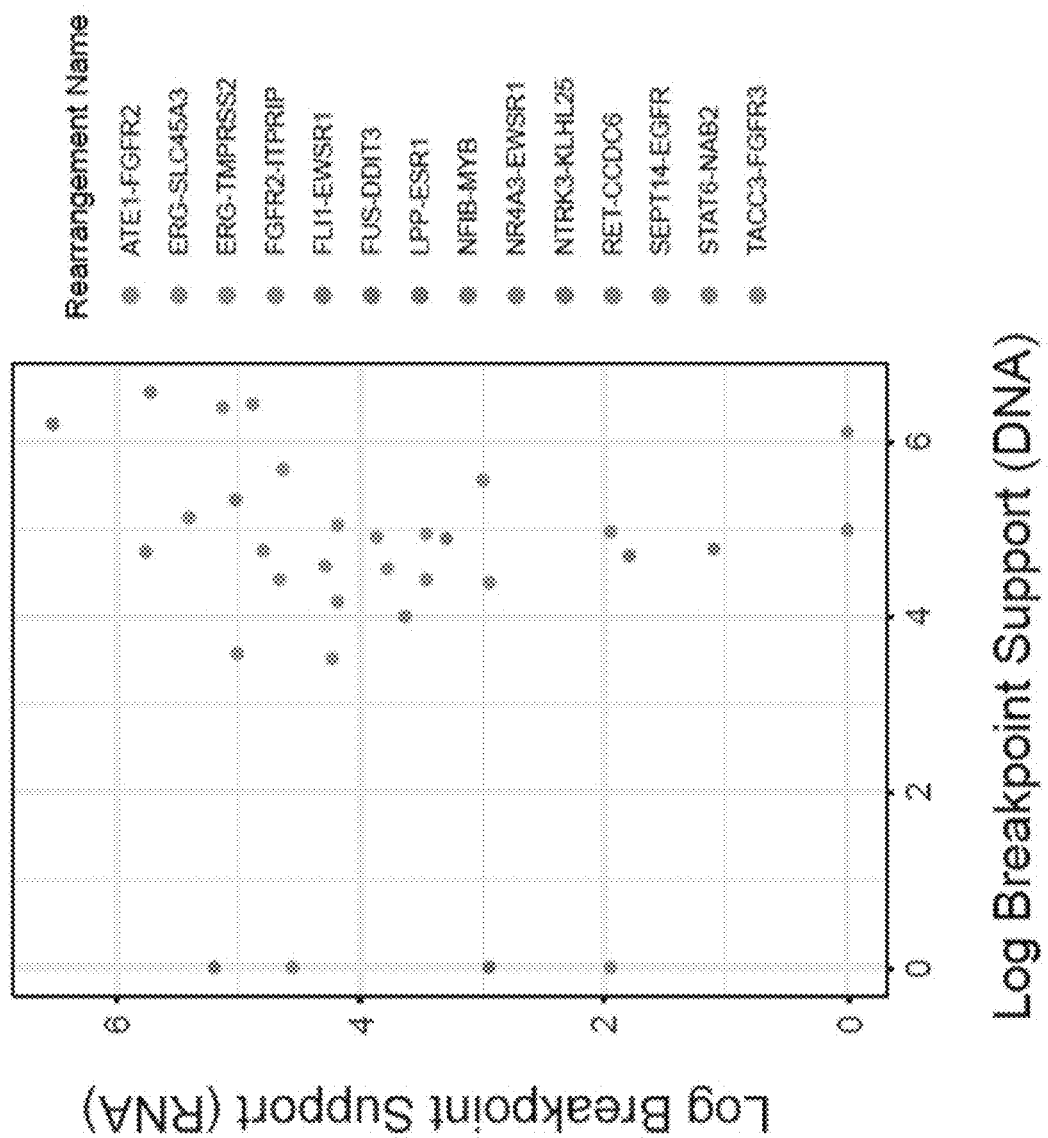
Figure 354:
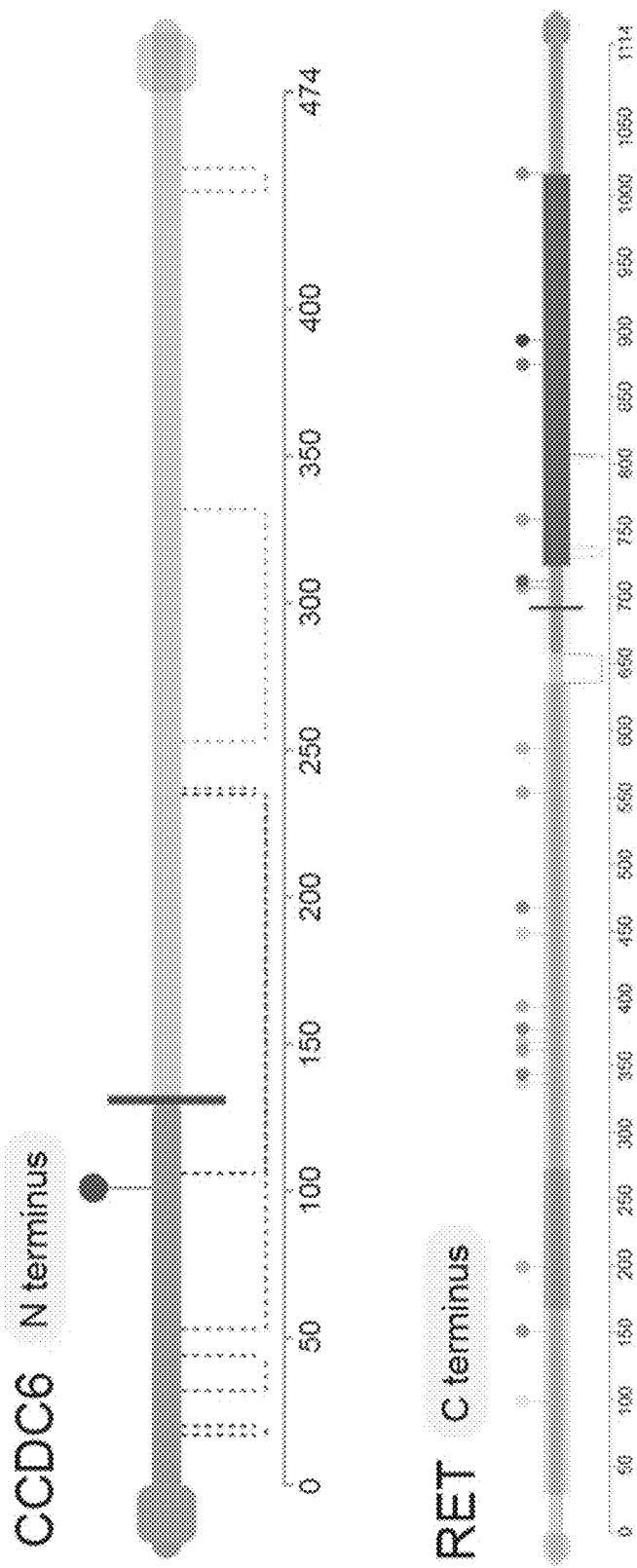
Figure 355:
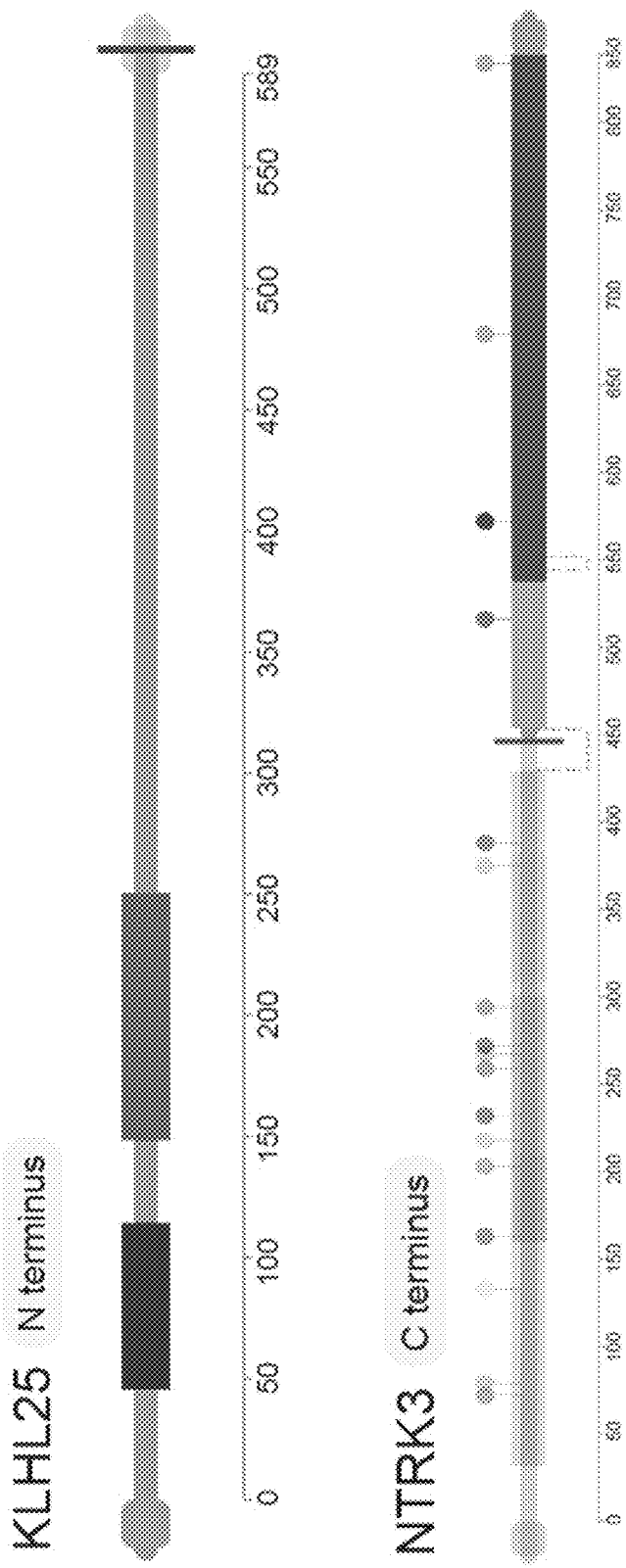
Figure 356:
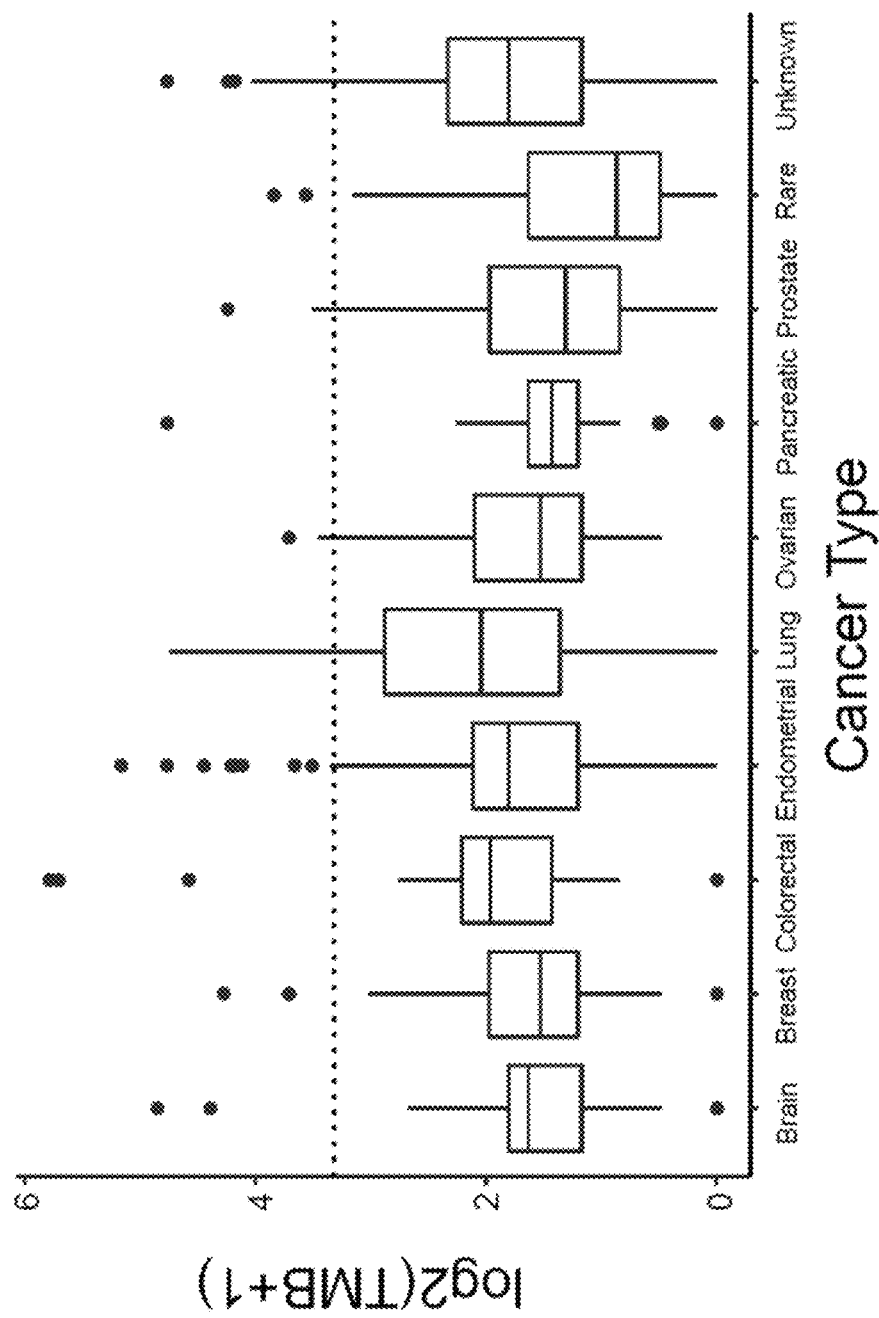
Figure 357:
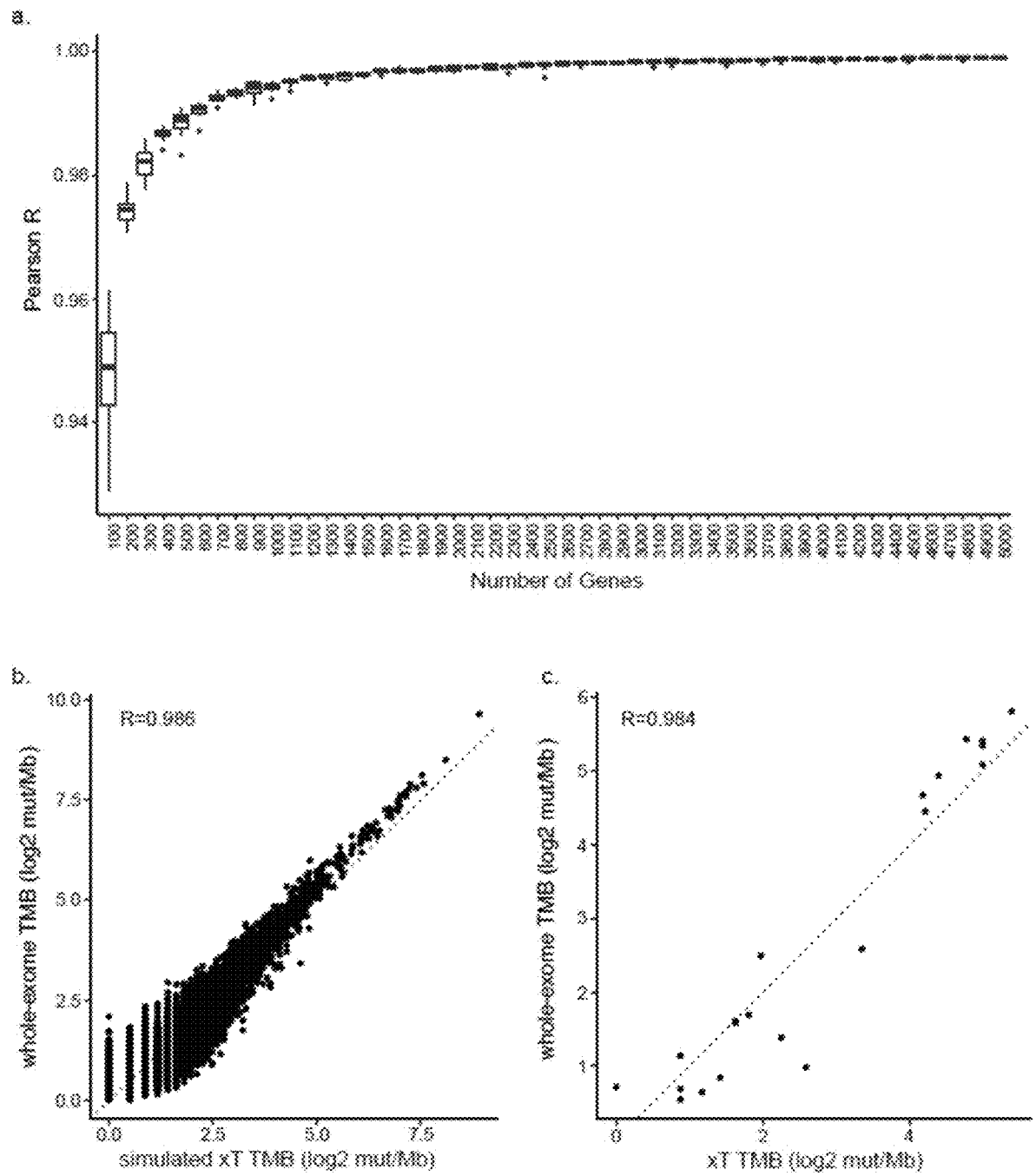
Figure 358:
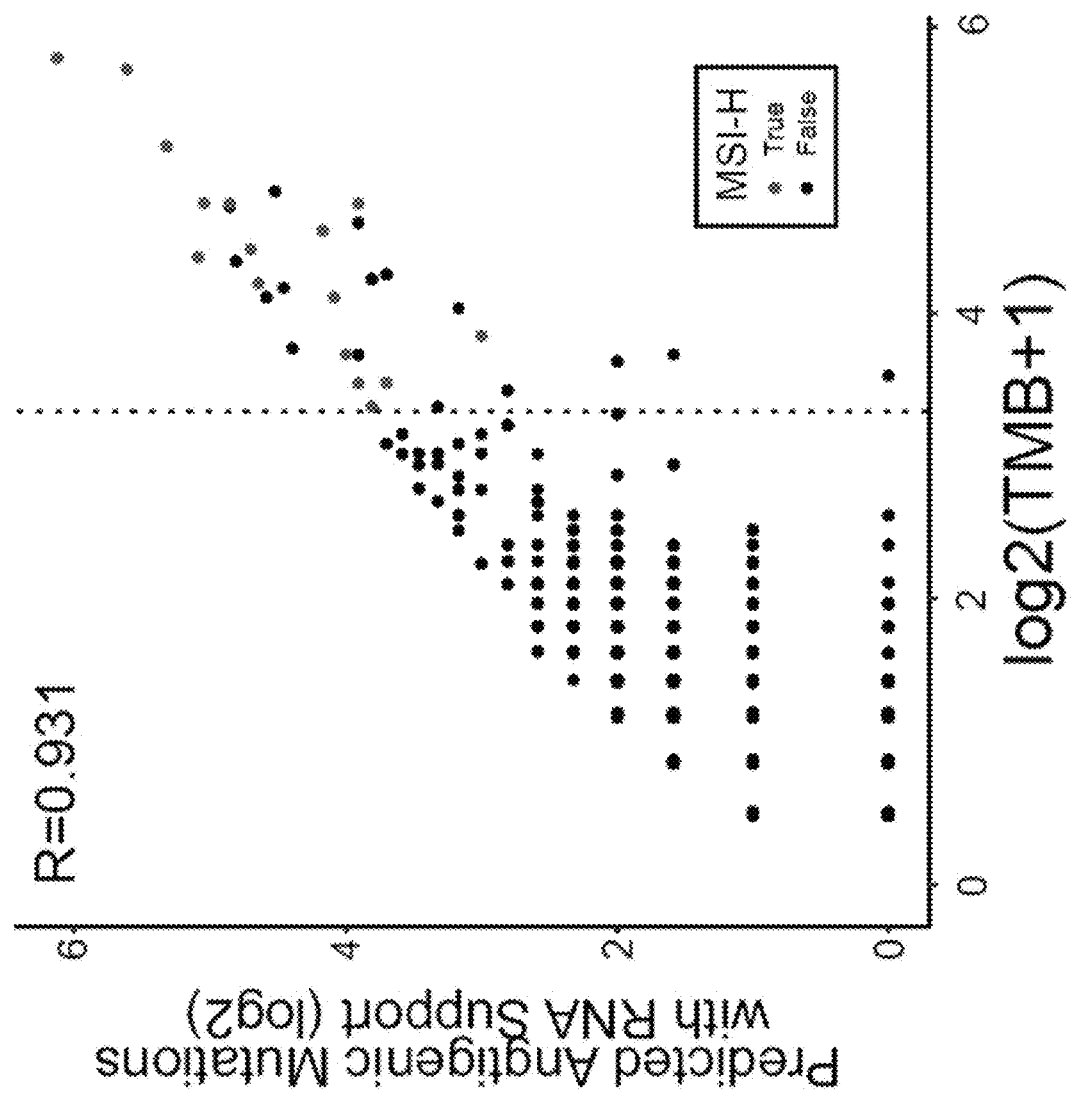
Figure 359:
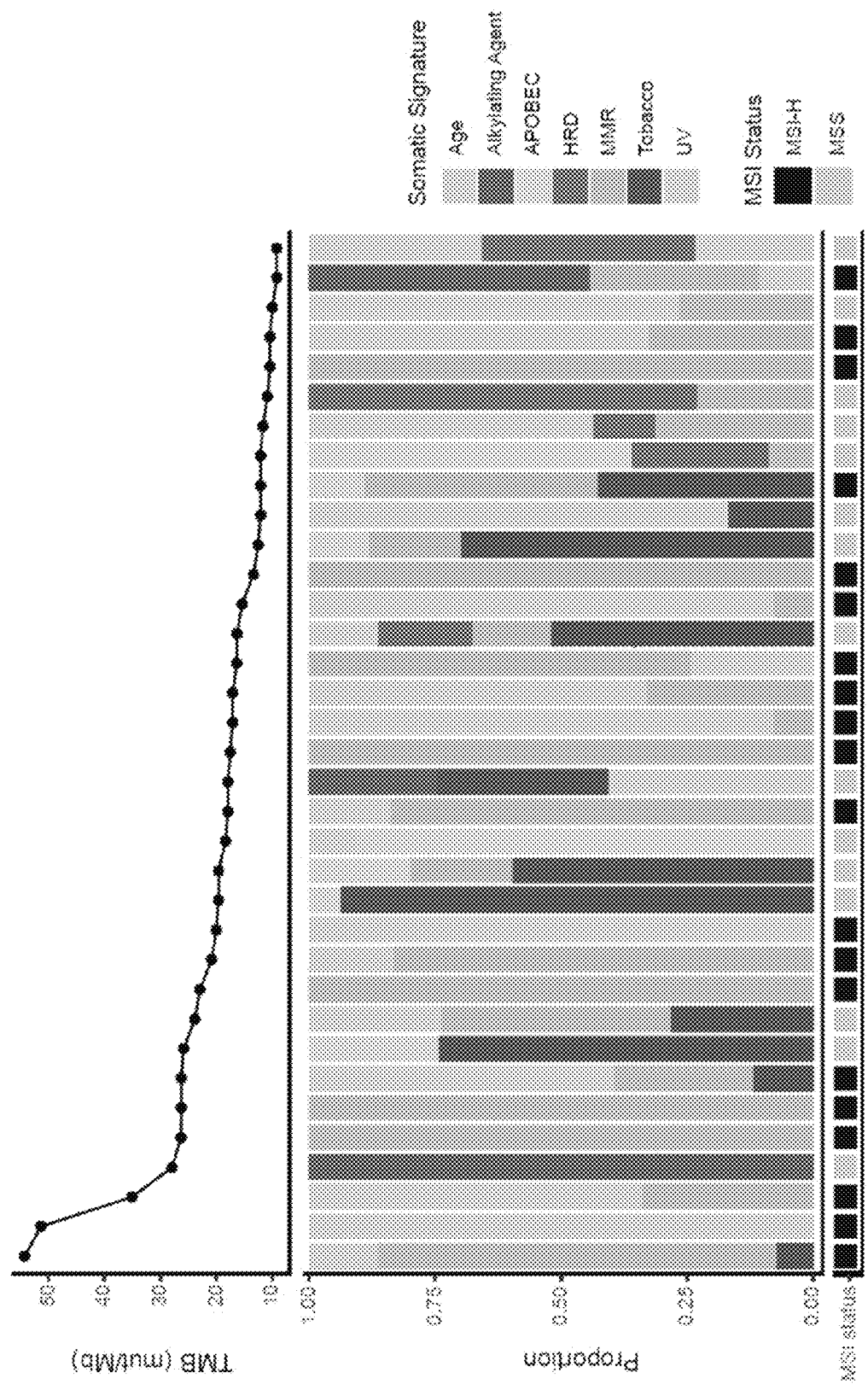
Figure 360:
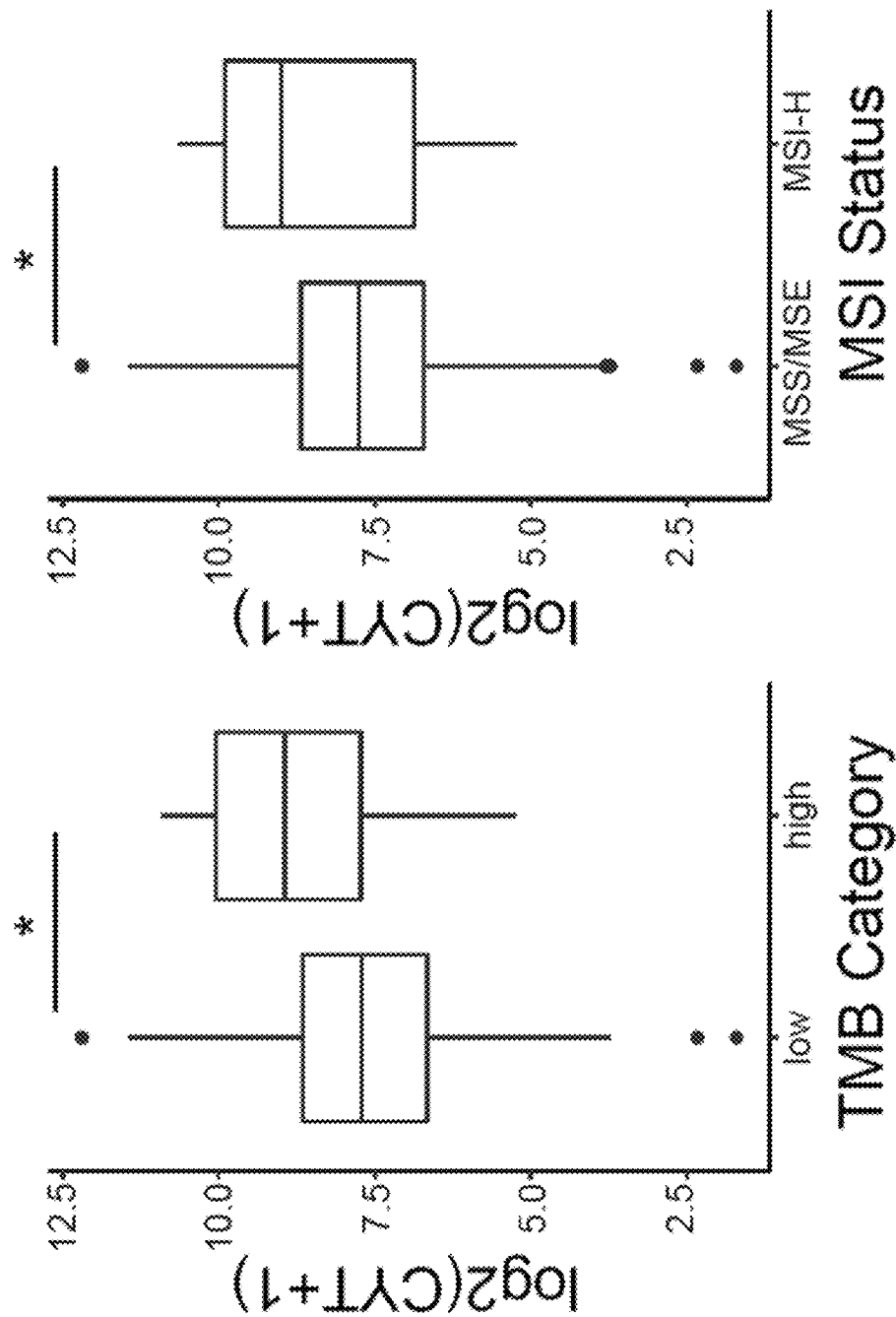
Figure 361:
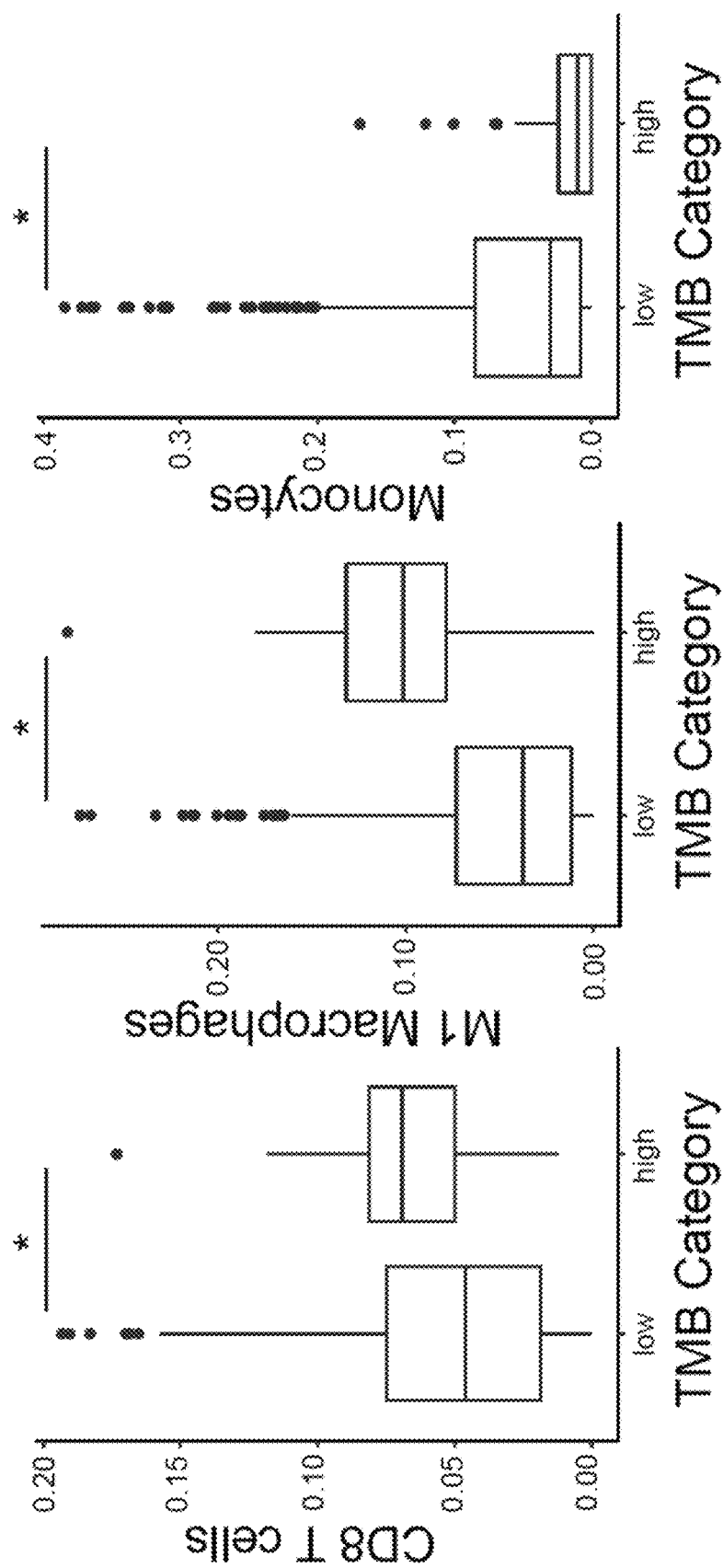
Figure 362:
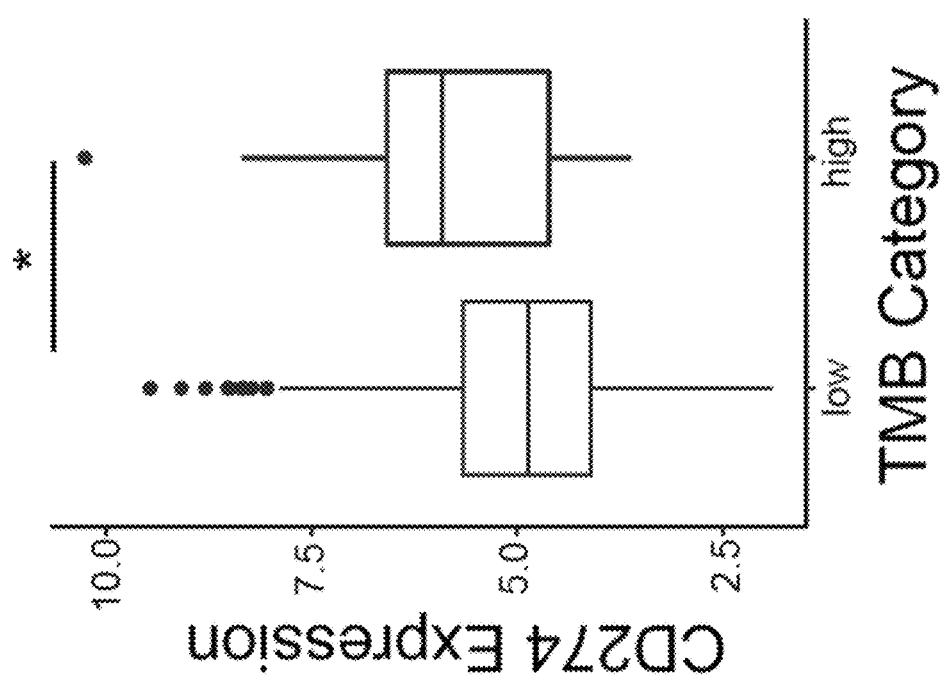
Figure 363:
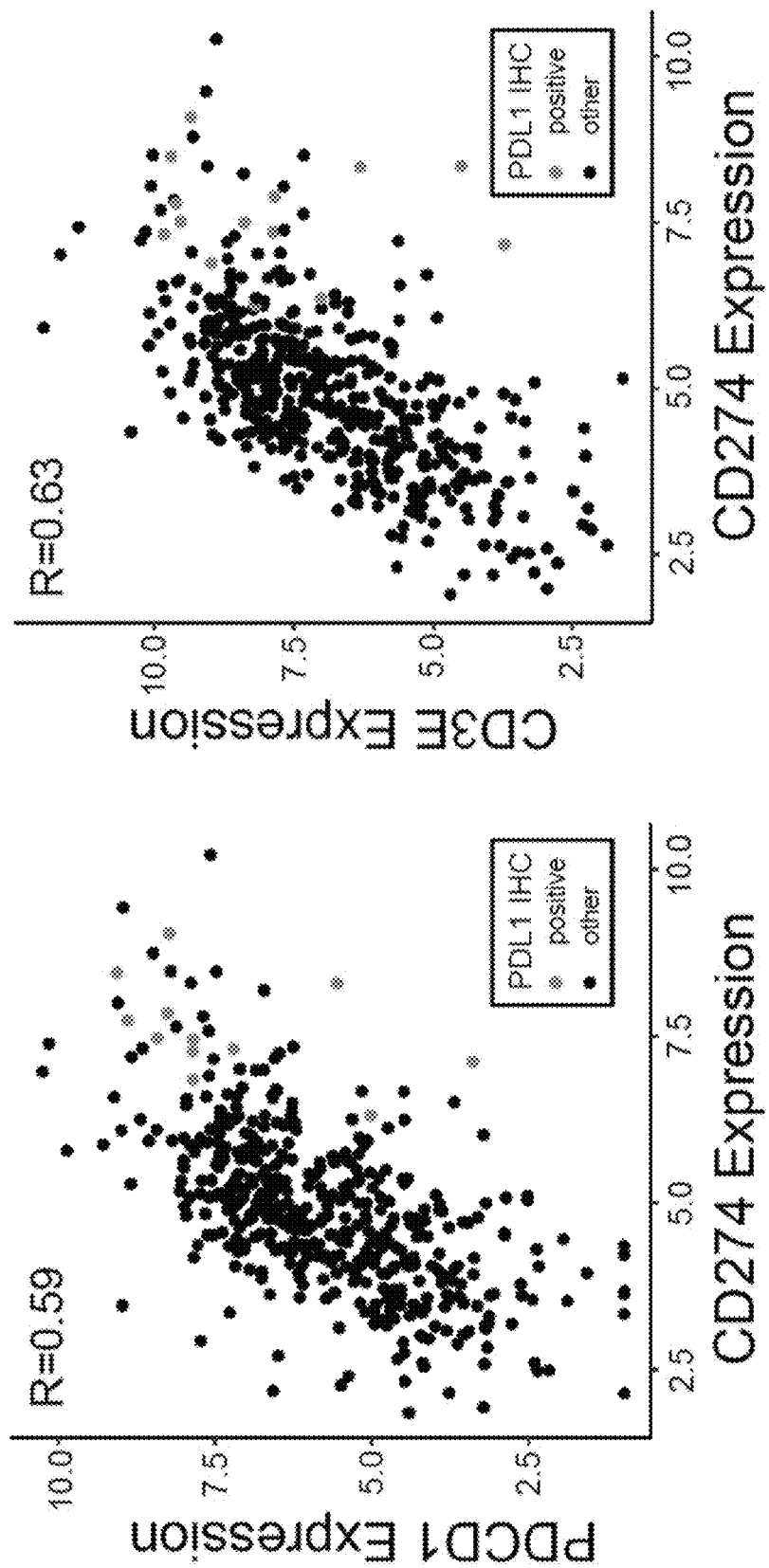
Figure 364:
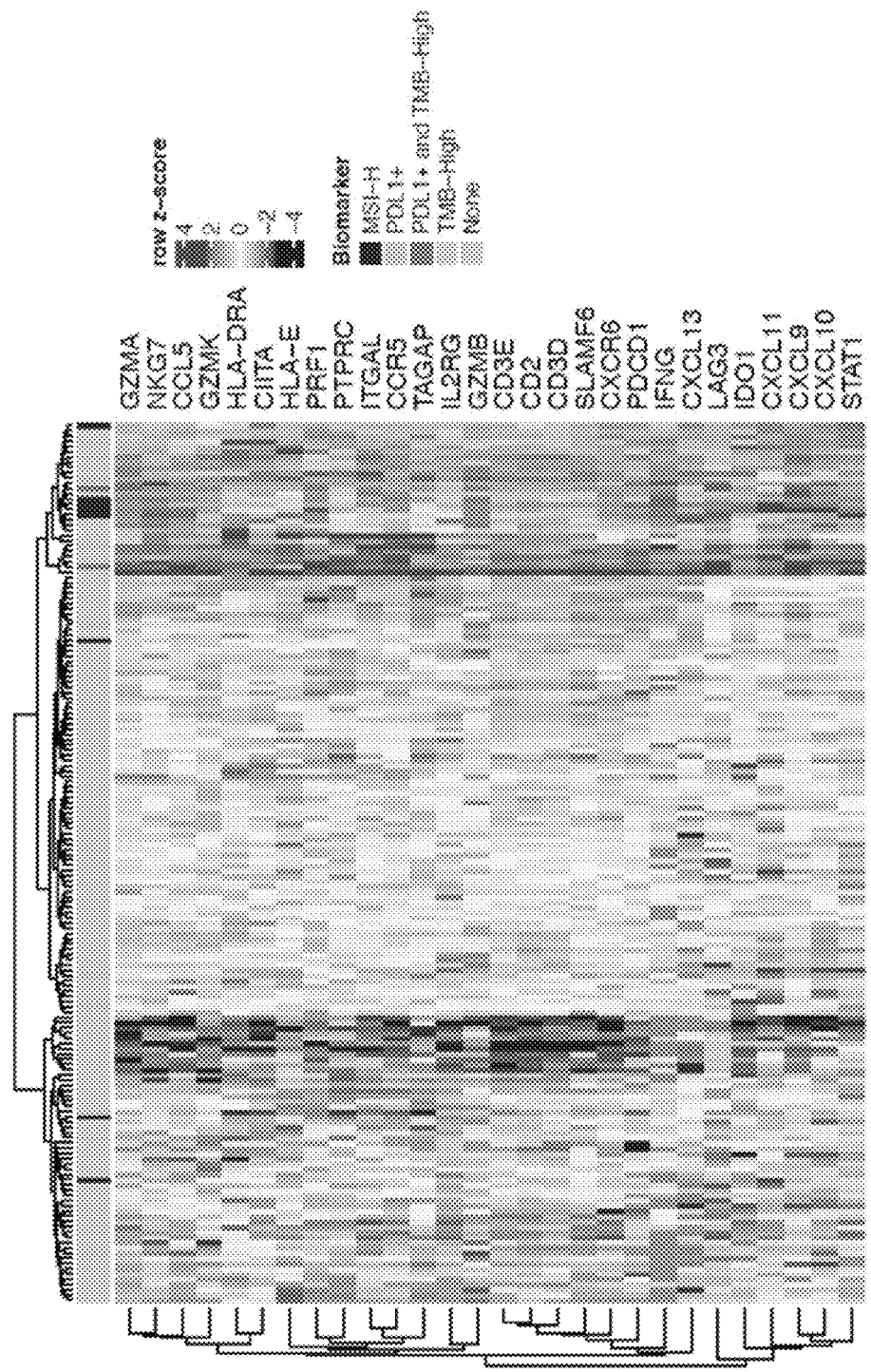
Figure 365:
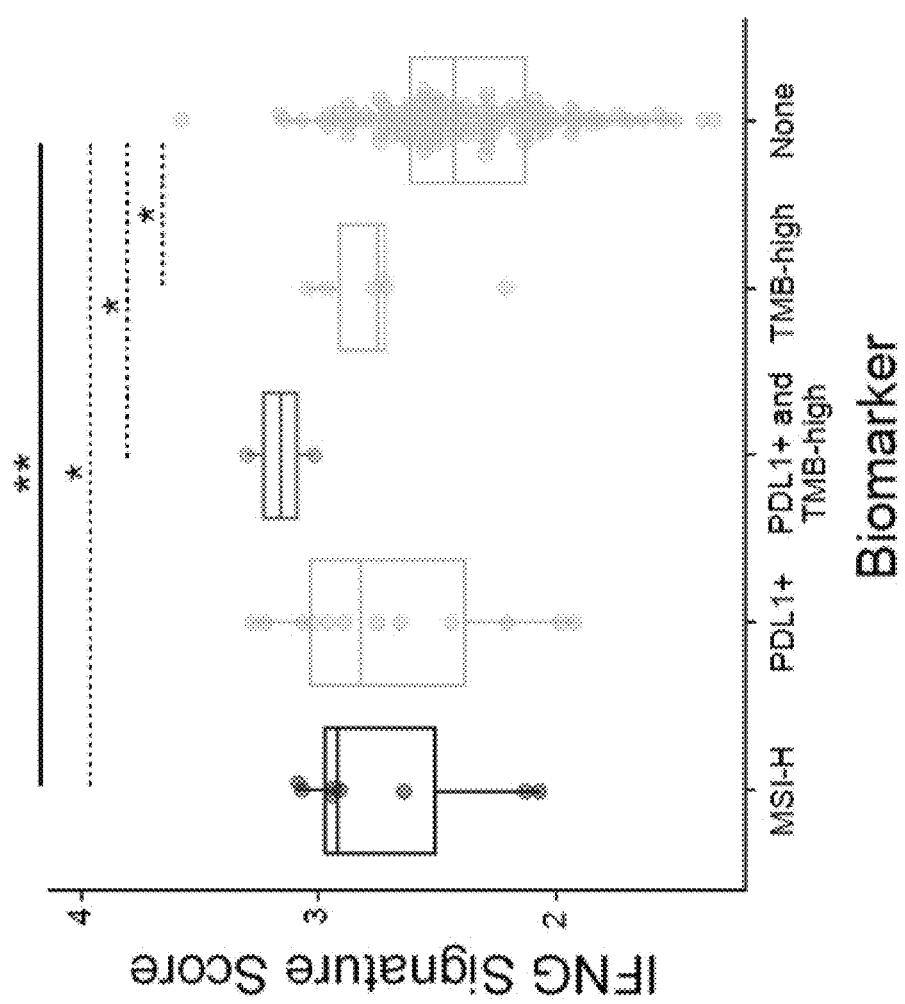
Figure 366:
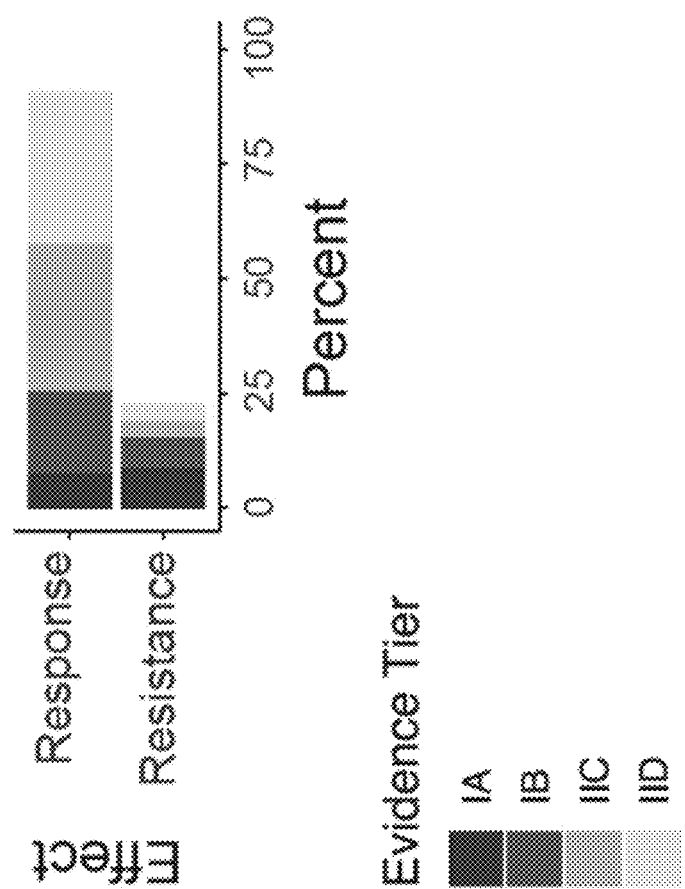
Figure 368:
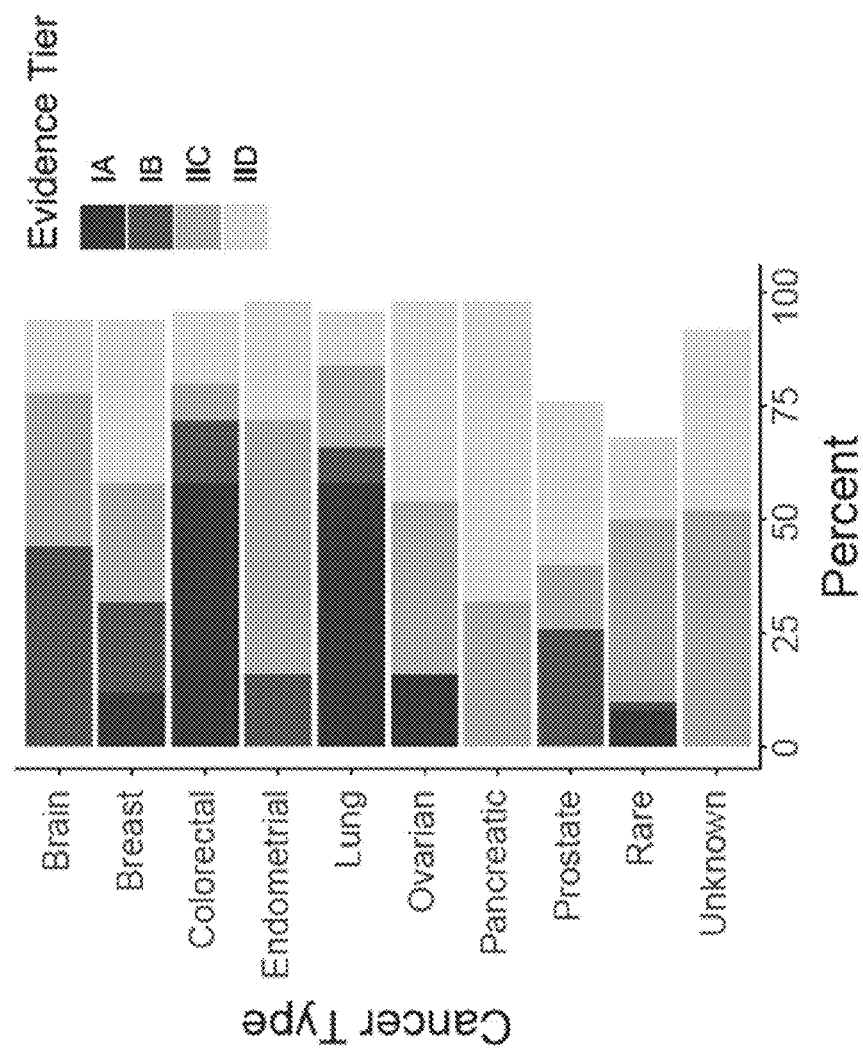
Figure 369:
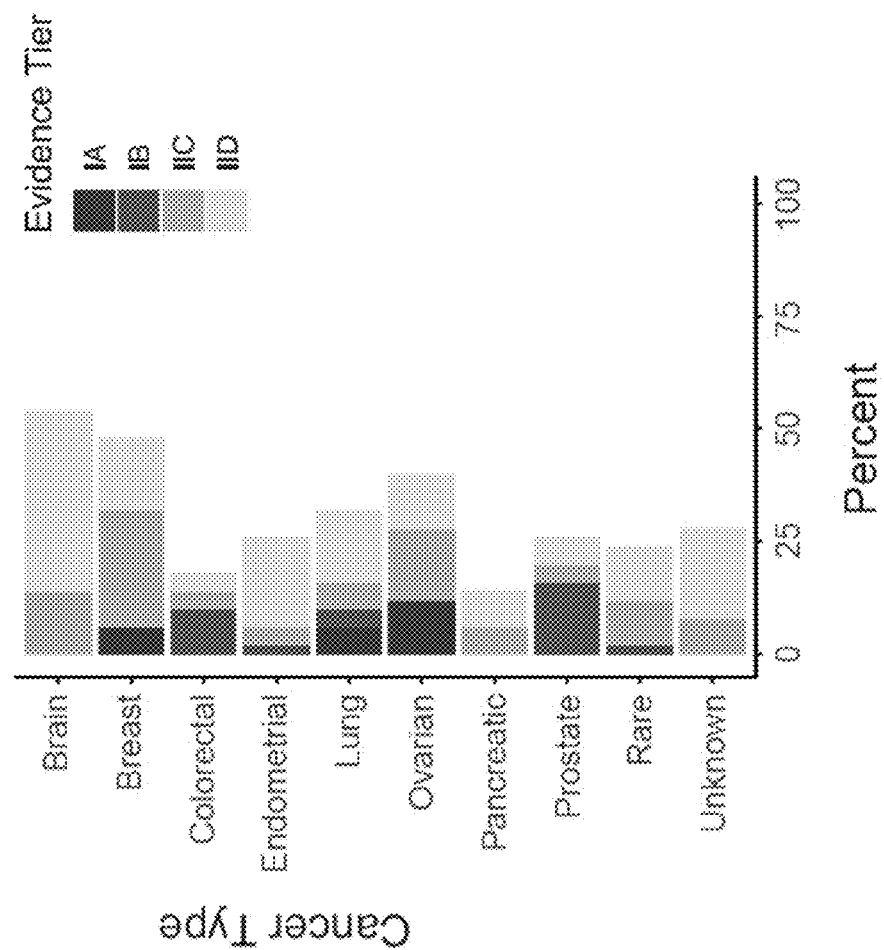
Figure 370:
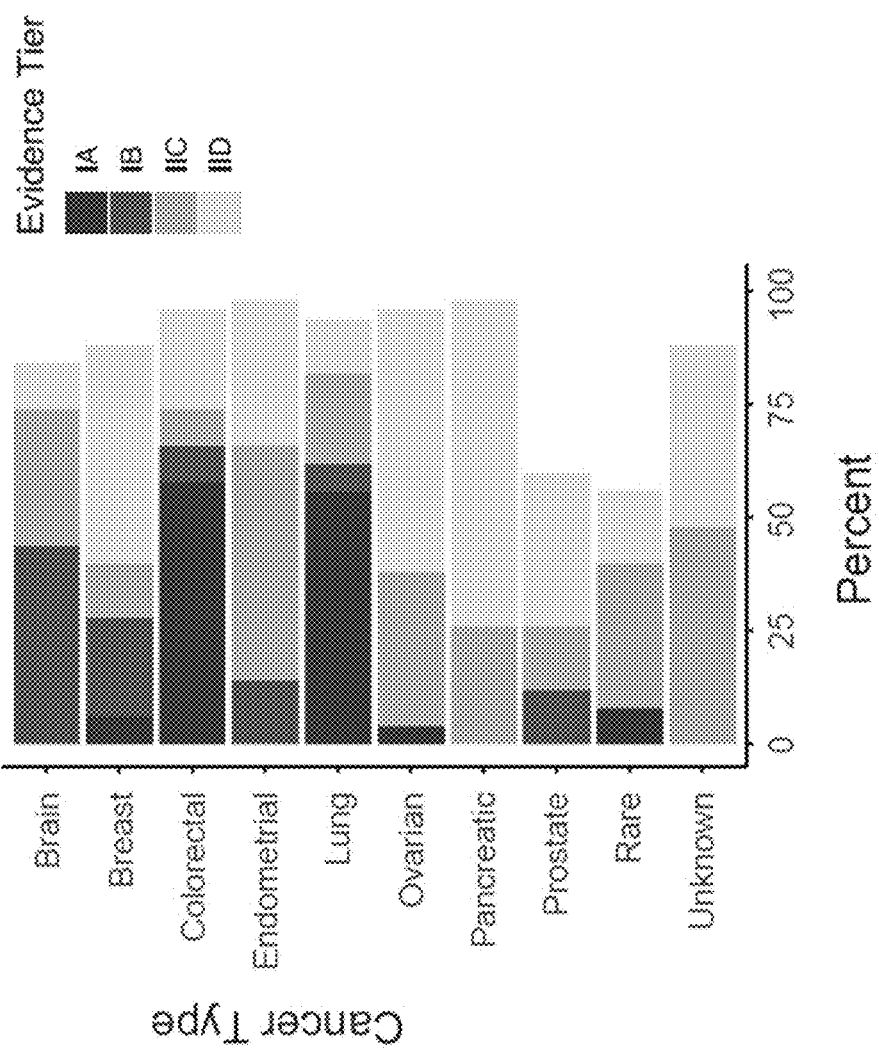
Figure 371:
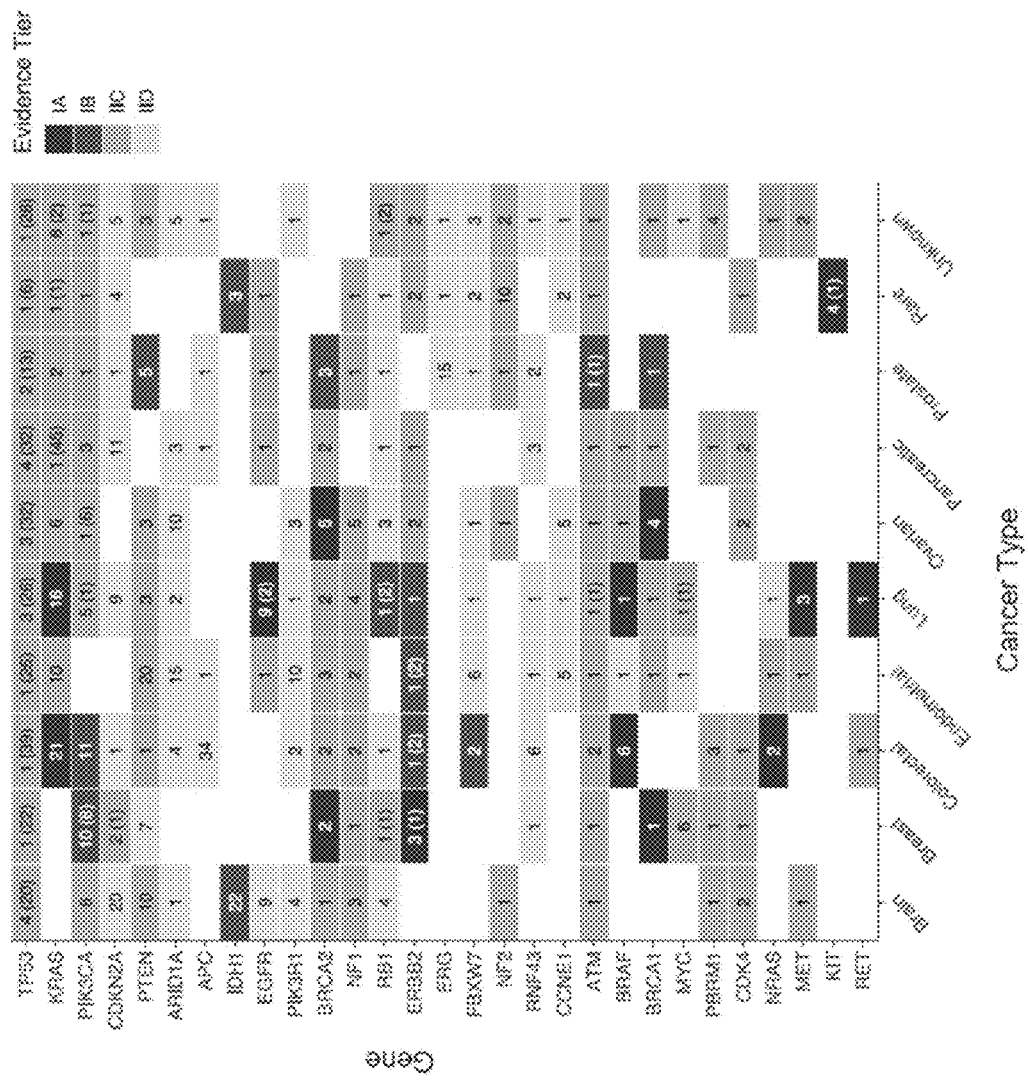
Figure 372:
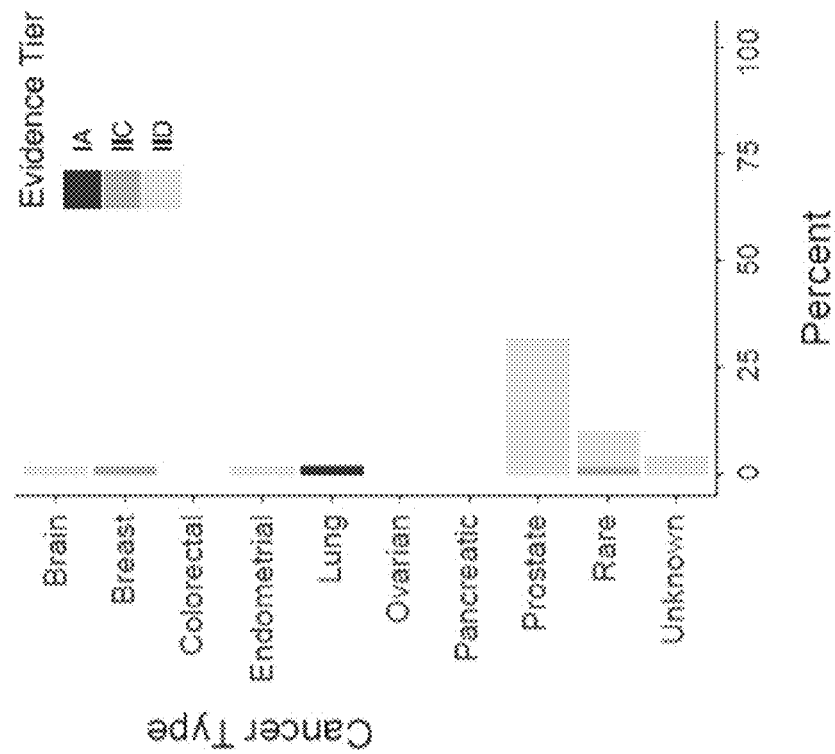
Figure 373:
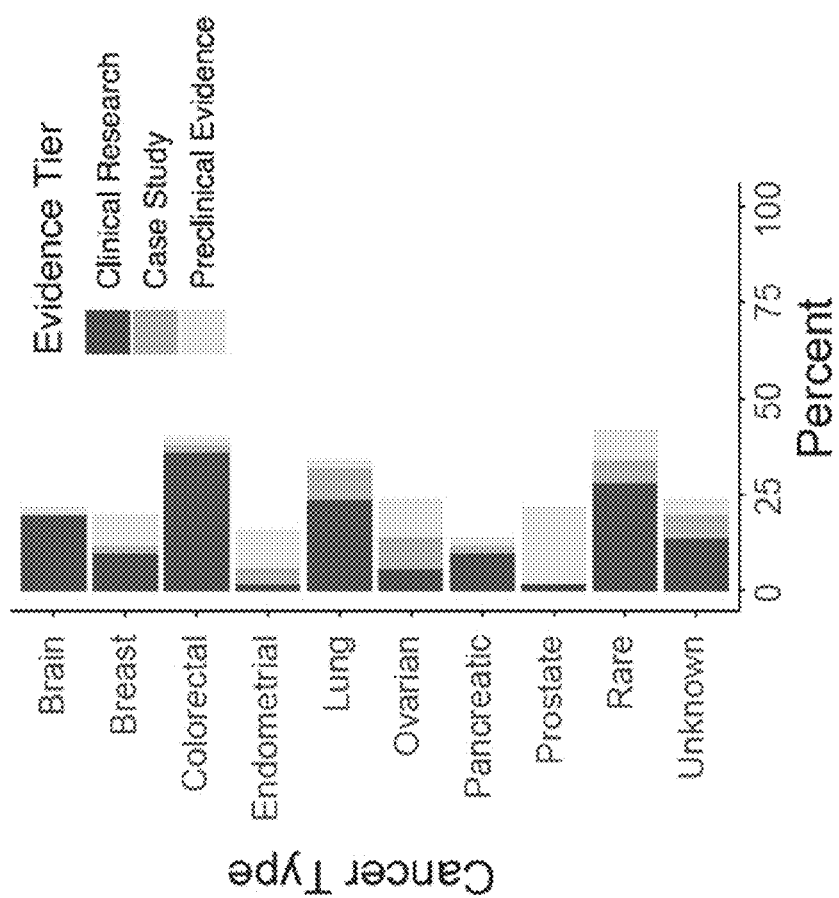
Figure 374:
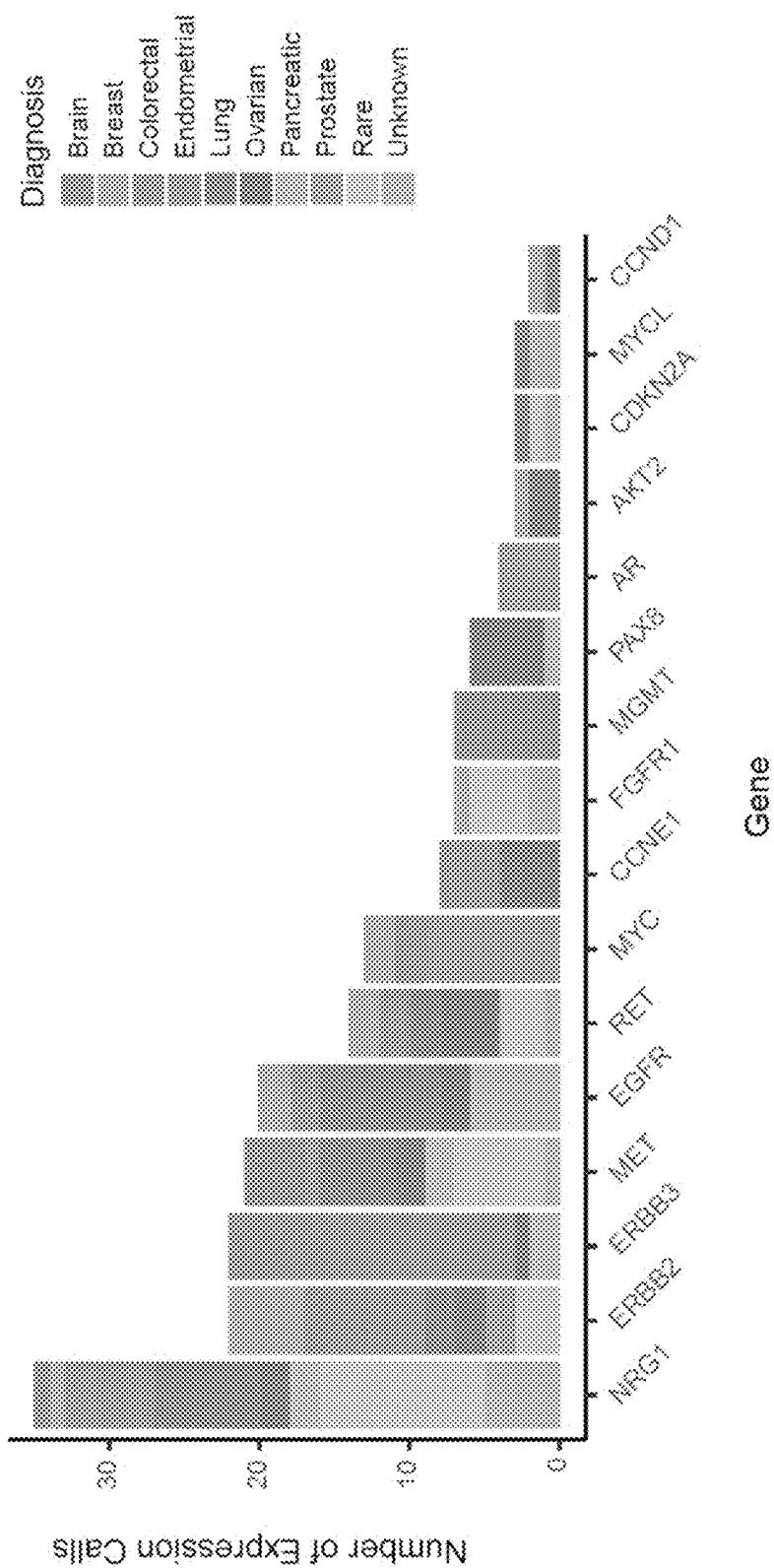
Figure 376:
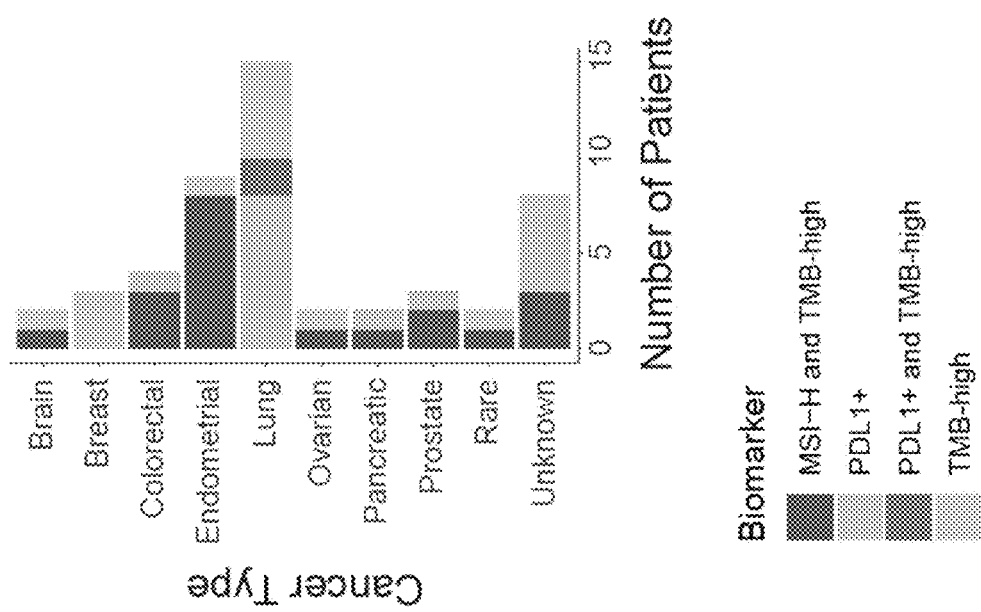
Figure 377:
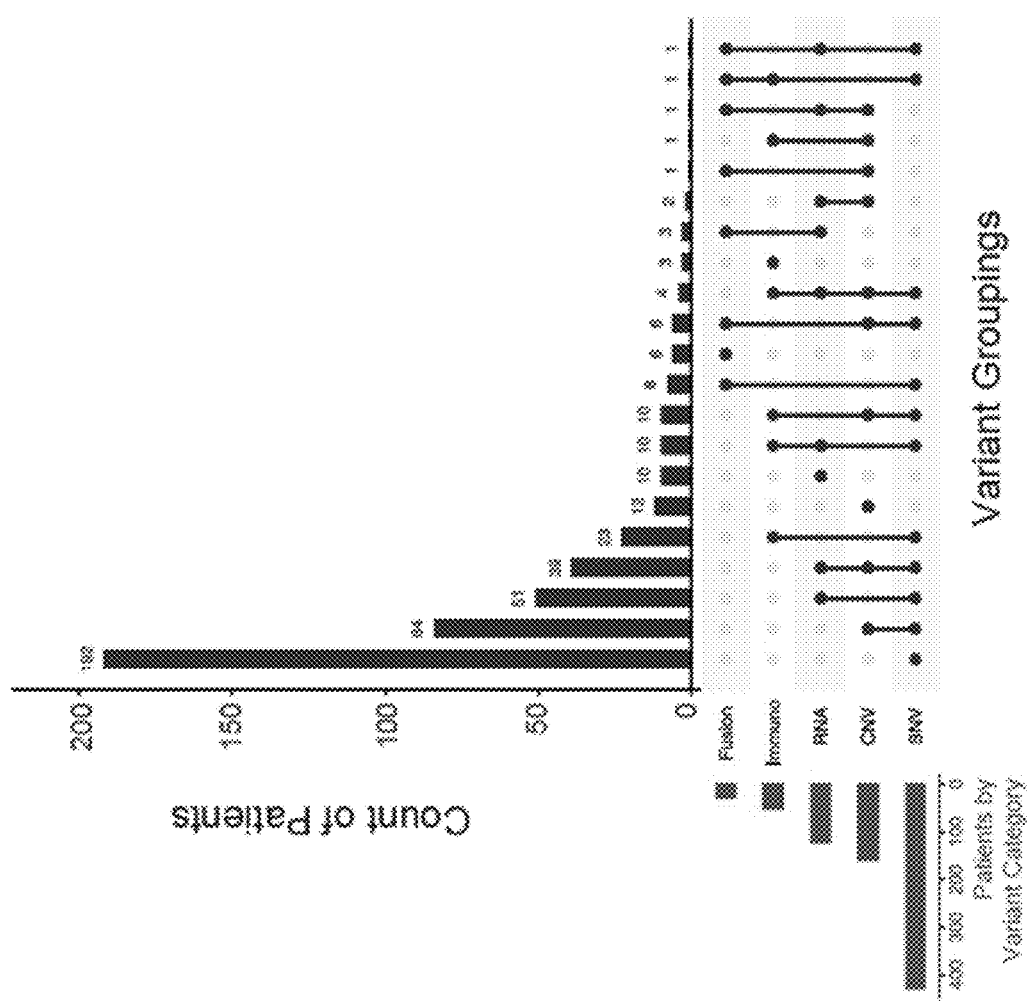
Figure 378:
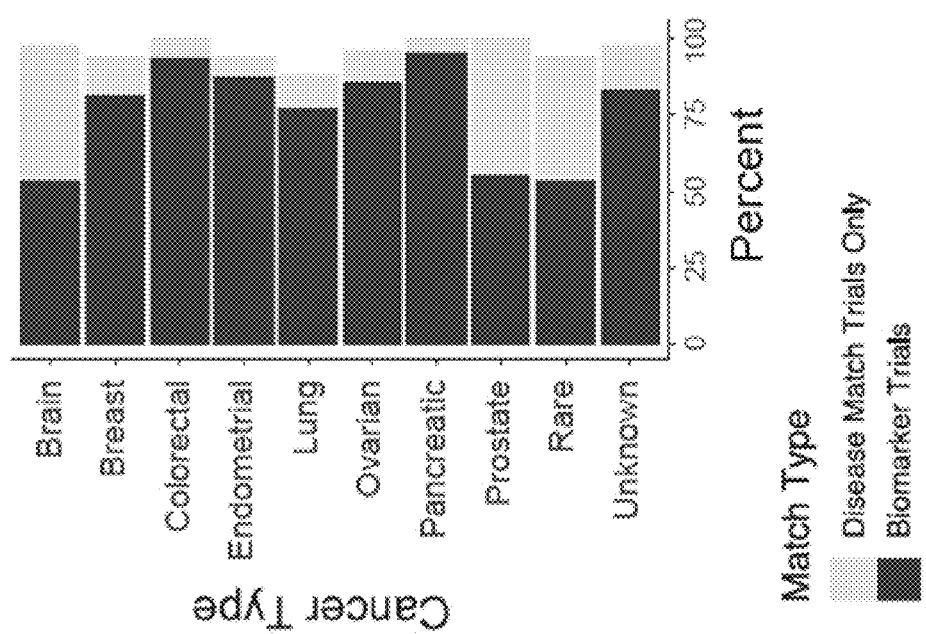
Figure 379:
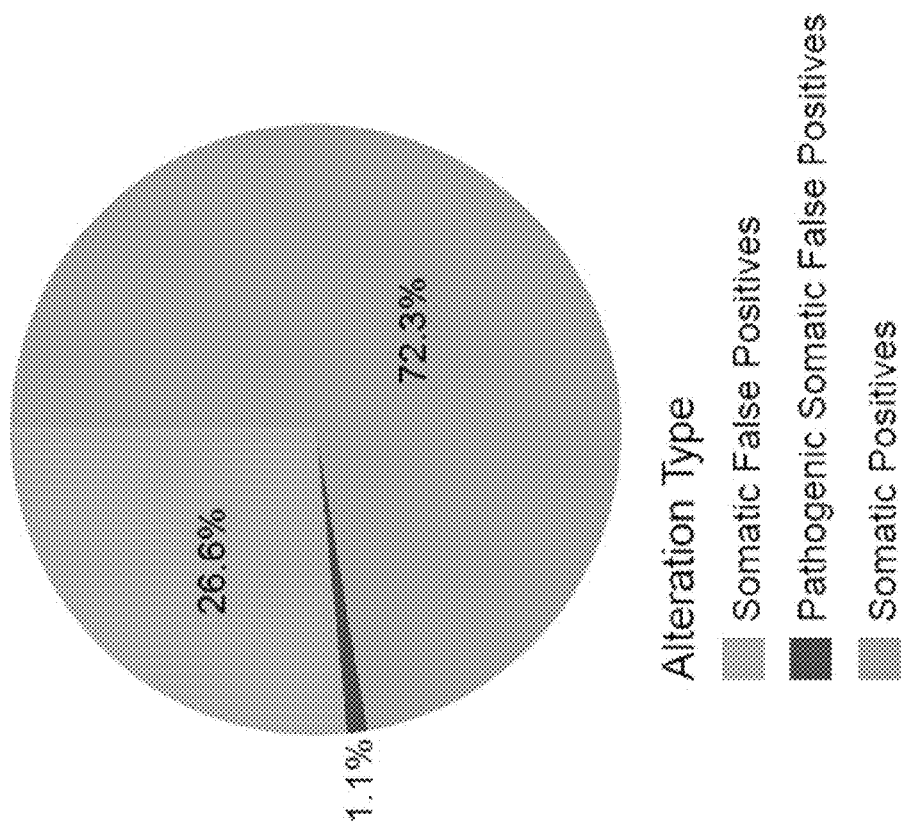
Figure 380:
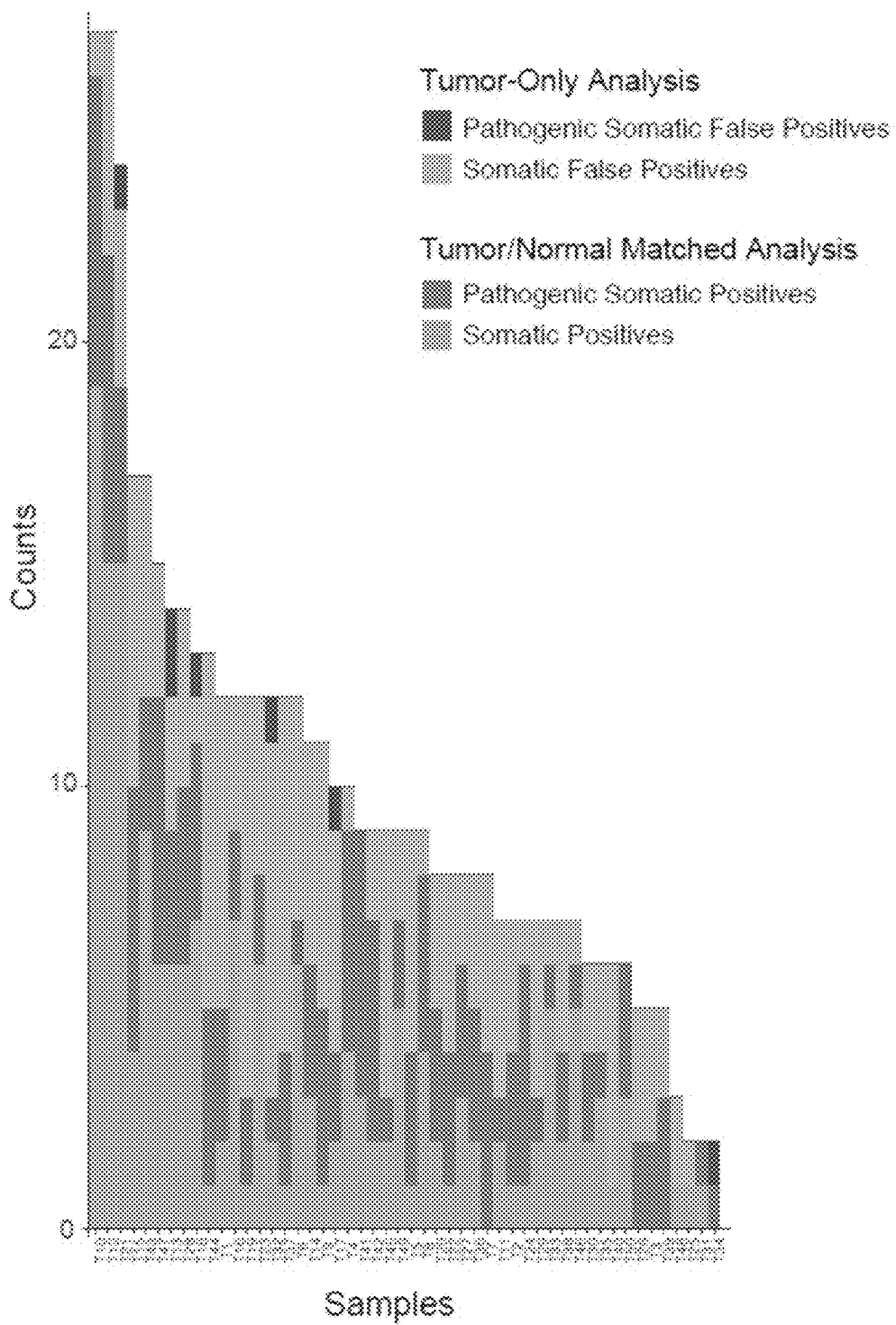

FIG. 345 is a table showing cancer type, primary versus metastatic recurrence at time of sequencing, sex and racial demographics of the xT 500 cohort. The values represent the number of patients belonging to each characteristic;

FIG. 346 is a mutational spectrum of the xT 500 cohort. Alteration types among the xT 500 cohort for the most commonly mutated genes. Alterations including single nucleotide variants (SNVs/indels), fusions (FUS), and a subset of copy number variants (CNVs), amplifications (AMP), and deletions (DEL) were grouped. Those appearing in at least five patients were plotted (1% prevalence);

FIG. 347 is a mutational landscape of the xT 500 cohort. Single nucleotide variants (SNVs), indels, genomic rearrangements, and copy number variants (CNV) classified as alterations were grouped, and those appearing in at least five patients were plotted (1% prevalence). Somatic alteration counts per patient are plotted at the top by cancer type. In the matrix below, per patient mutational profile percentages are plotted by each gene on the y-axis and sorted by prevalence in descending order. Patients were clustered by the overall correlation between mutations. Alteration counts per gene are also displayed on the right-hand side of the matrix;

FIG. 348 is a graph showing alteration types among the xT 500 cohort for the most commonly mutated genes. Alterations including single nucleotide variants (SNVs/indels), fusions (FUS), and a subset of copy number variants (CNVs), amplifications (AMP), and deletions (DEL) were grouped. Those appearing in at least five patients were plotted (1% prevalence). b: Comparison of an xT SNV/indel detection assay against the MSKCC IMPACT study plotted by the prevalence of altered genes commonly known to be hallmarks of cancer;

FIG. 349 is a graph showing Predicted TCGA cancer types for samples within each xT 500 cohort cancer type. Cancer type predictions are based on a random forest model trained on an internal reference dataset. Bubble size corresponds to the percentage of samples from the cohort predicted to have a given TCGA cancer type. Bubbles representing ≥25% of samples are labeled. BRCA: Breast Invasive Carcinoma, COAD: Colon Adenocarcinoma, CHOL: Cholangiocarcinoma, ESCA: Esophageal Carcinoma, GBM: Glioblastoma Multiforme, HNSC: Head and Neck Squamous Cell Carcinoma, LGG: Brain Lower Grade Glioma, LIHC: Liver Hepatocellular Carcinoma, LUAD: Lung Adenocarcinoma, LUSC: Lung Squamous Cell Carcinoma, MESO: Mesothelioma, OV: Ovarian Serous Cystadenocarcinoma, PAAD: Pancreatic Adenocarcinoma, PCPG: Pheochromocytoma and Paraganglioma, PRAD: Prostate Adenocarcinoma, SARC: Sarcoma, STAD: Stomach Adenocarcinoma, UCEC: Uterine Corpus Endometrial Carcinoma;

FIG. 350 is a plot showing Cancer type prediction accuracy stratified by cancer cohort and binned by pathologist tumor purity estimates for all text samples;

FIG. 351 is similar to FIG. 350, albeit showing a cancer type prediction accuracy stratified by cancer cohort and binned by pathologist tumor purity estimates for primary cancers;

FIG. 352 is similar to FIG. 350, albeit showing cancer type prediction accuracy stratified by cancer cohort and binned by pathologist tumor purity estimates for metastatic cancers. Metastatic stratification was not applied to the brain cancers. Rare and unknown cancers were excluded from this analysis. Overall, metastatic samples had slightly lower cancer predictor confidence than primary or brain cancers (n=234 primary, n=107 metastatic, and n=49 rare or brain cancers). A significant association between lower tumor purity and lower cancer prediction confidence was identified in the endometrial cancer group;

FIG. 353 is a plot showing DNA and RNA fusion detection including a comparison between DNA and RNA fusion detection events in the xT 500 cohort;

FIG. 354 is a RET-CCDC1$_6$ fusion detected by both DNA and RNA analyses illustrates a canonical tyrosine kinase activating-type fusion with the C-terminus of RET lost and the tyrosine kinase domain (blue) fully intact;

FIG. 355 is a KLHL25-NTRK3 fusion detected by both DNA and RNA analyses illustrates an intact NTRK3 kinase domain (green) fused to the C-terminal region of KLHL25;

FIG. 356 is a graph showing Immunogenomic landscape of solid tumors in the xT 500 cohort where Tumor mutational burden (TMB) is shown by cancer type (n=50 per group) and plotted on a log 2(TMB+1) scale;

FIG. 357 is related to a whole-exome and xT assay tumor mutational burden concordance. Sub-a shows a tumor mutational burden (TMB) calculated from whole-exome TCGA data is highly correlated with TMB calculated from smaller gene panels. The Pearson correlation coefficients for each TMB simulation are shown. Sub-b shows TMB calculated using the genes in the xT panel is highly correlated with TMB calculated from whole-exome TCGA data (R=0.986, P<2.2×10-16). xT TMB was simulated from the same TCGA variant data in (a) and compared to whole-exome TMB. Sub-c shows TMB is highly correlated between the xT panel and the whole-exome panel (R=0.984, P<2.2×10-16; n=23 samples sequenced with each panel);

FIG. 358 shows a plot where Neoantigen predictions generated for each patient (n=493) are plotted against TMB (Pearson's R=0.931, P=8.20×10$^{-199}$). The Pearson correlation coefficient is shown and the dotted line in (a, b) denotes the TMB-high threshold;

FIG. 359 shows data representing somatic signatures in TMB-high patients. The relative contribution of key somatic signatures to the mutational landscape is displayed. The somatic mutational landscape of all tumor mutational burden (TMB)-high patients (TMB >9 mut/Mb) in the cohort was analyzed and is displayed above the somatic signature proportions. TMB in this patient population ranged from 9.17 to 54.2 mut/Mb and is plotted by decreasing size, with each dot representing one patient. xT microsatellite instability (MSI) status is also displayed for each patient;

FIG. 360 shows a distribution of cytolytic index (CYT) by TMB category (TMB-high n=35, TMB-low n=439) and MSI status (MSI-H n=20, MSS/MSE n=454). Statistical significance was determined using a two-sided Wilcoxon Rank Sum Test (TMB P=1.95×10$^{-4}$, MSI P=2.50×10$^{-2}$);

FIG. 361 shows data where the composition of the immune cell infiltrate was estimated using a support vector regression model. The distribution of the estimated percentage of selected immune cell types is shown by TMB category. Statistical significance was determined using a two-sided Wilcoxon Rank Sum Test and P-values were adjusted for multiple testing using the Benjamini-Hochberg method (CD8 P=4.9×10$^{-4}$, M1 P=1.4×10$^{-7}$, monocyte P=2.0×10$^{-4}$);

FIG. 362 shows expression of CD274 (PD-L1) in log 2(TPM+1) by TMB category. Statistical significance was determined using a two-sided Wilcoxon Rank Sum Test (P=6.69×10$^{-4}$);

FIG. 363 shows plots of Expression of CD274 compared to expression of PDCD1 (PD-1) and CD3E (n=474). Samples that stained positive for PD-L1 IHC are shown in blue. Other samples either stained negative for PD-L1 IHC or were not tested. The Pearson correlation coefficients are shown (PDCD1 P<2.2×10$^{-16}$, CD3E P<2.2×10$^{-16}$);

FIG. 364 includes a heatmap of the 28 interferon gamma (IFNγ)-related genes in the cohort. Patients with RNA data and complete biomarker testing were categorized into the following groups: PD-L1-positive IHC (n=15), TMB-high (n=6), PD-L1-positive IHC and TMB-high (n=2), MSI-high (n=8), and None (n=150);

FIG. 365 illustrates an IFNγ score as calculated by the arithmetic mean of the 28 genes compared between patient groups. Statistical significance was determined using the Kruskal-Wallis test (P=3.77×10$^{-4}$) followed by Dunn's test for multiple comparisons (MSI-H P=0.024, PD-L1-positive P=0.066, PD-L1-positive and TMB-high P=0.037, TMB-high P=0.029). * denotes P≤0.05, ** denotes P<0.01. In the boxplots, the upper and lower hinges represent the first and third quartile. The whiskers extend to the most extreme value within 1.5× interquartile range on either end of the distribution. The center line represents the median;

FIG. 366 is a graph showing evidence-based therapy and clinical trial matching. And specifically the distribution of samples with matched evidence for response or resistance to a therapeutic option;

FIG. 367 includes a table that show the number and percentage of patients matched to therapies within each evidence tier based on tumor and normal matched DNA-seq data analysis. The evidence tiers contain somatic biomarker information related to therapeutic response and/or resistance and are divided into four categories: tier I level A (IA), tier I level B (IB), tier II level C (IIC), and tier II level D (IID). Tiers are ranked according to biomarker evidence strength, ranging from consensus clinical guidelines to case reports and preclinical evidence;

FIG. 368 shows data that represents the distribution of samples with matched therapeutic evidence tiers by cancer types;

FIG. 369 shows data that represents the distribution of samples matched to therapeutic evidence tiers based on detected copy number variations (CNVs) (n=160 patients);

FIG. 370 shows data that represents the distribution of samples matched to therapeutic evidence tiers based on detected single nucleotide variants (SNV) and/or indels by cancer type (n=429 patients);

FIG. 371 shows a chart indicating counts of therapeutic evidence tiers matched to genes and cancer type. Counts are colored by each evidence tier, with the highest level of evidence being IA. Counts in parentheses reflect cases in which patients were also matched to lower evidence tiers;

FIG. 372 shows data that represents the distribution of samples matched to evidence tiers based on detected genomic fusions by cancer type (n=29 patients);

FIG. 373 shows the distribution of samples with reportable gene expression calls and therapeutic evidence by cancer type;

FIG. 374 is a graph illustrating the distribution of gene expression calls with reported therapeutic evidence. Frequency of expression calls by reportable gene matched to therapeutic evidence, stratified by cancer cohort (n=133 patients). Therapeutic evidence for the genes represented on this plot are provided in the table shown in FIG. 367;

FIG. 375 includes a table showing therapeutic evidence for the 16 genes with over- or underexpression calls reported. Consensus evidence level corresponds to NCCN Clinical Practice Guidelines in Oncology;

FIG. 376 is a graph showing the number of patients positive for immunotherapy-relevant biomarkers;

FIG. 377 includes an UpSetR plot of the number of patients for whom therapeutic options were reported based on five variant categories: single nucleotide variants (SNVs)/indels, copy number variants (CNVs), RNA sequencing (RNA-seq) gene expression calls, immunotherapy biomarkers, and fusions. The horizontal blue bars on the left of the matrix represent the total number of patients who had at least one matched therapy reported based on each variant category. The black vertical bars represent the total counts of patients with matched therapies reported based on groupings of variant categories. The matrix with connected filled circles represents the groupings of variant categories that correspond to the counts for the black vertical bars;

FIG. 378 is a graph showing counts of the most common biomarker-based trial matches versus disease-based trial matches for each cancer type;

FIG. 379 includes data comparing tumor-only versus tumor-normal analyses and specifically percentage of somatic false positives (germline in origin) detected in the tumor-only analyses of 50 patient samples; and FIG. 380 shows a graph illustrating germline detection in tumor-normal matched DNA sequencing versus tumor-only sequencing. Tumor-normal counts of true somatic variants (orange and purple bars) were included for reference.

Figure 381:
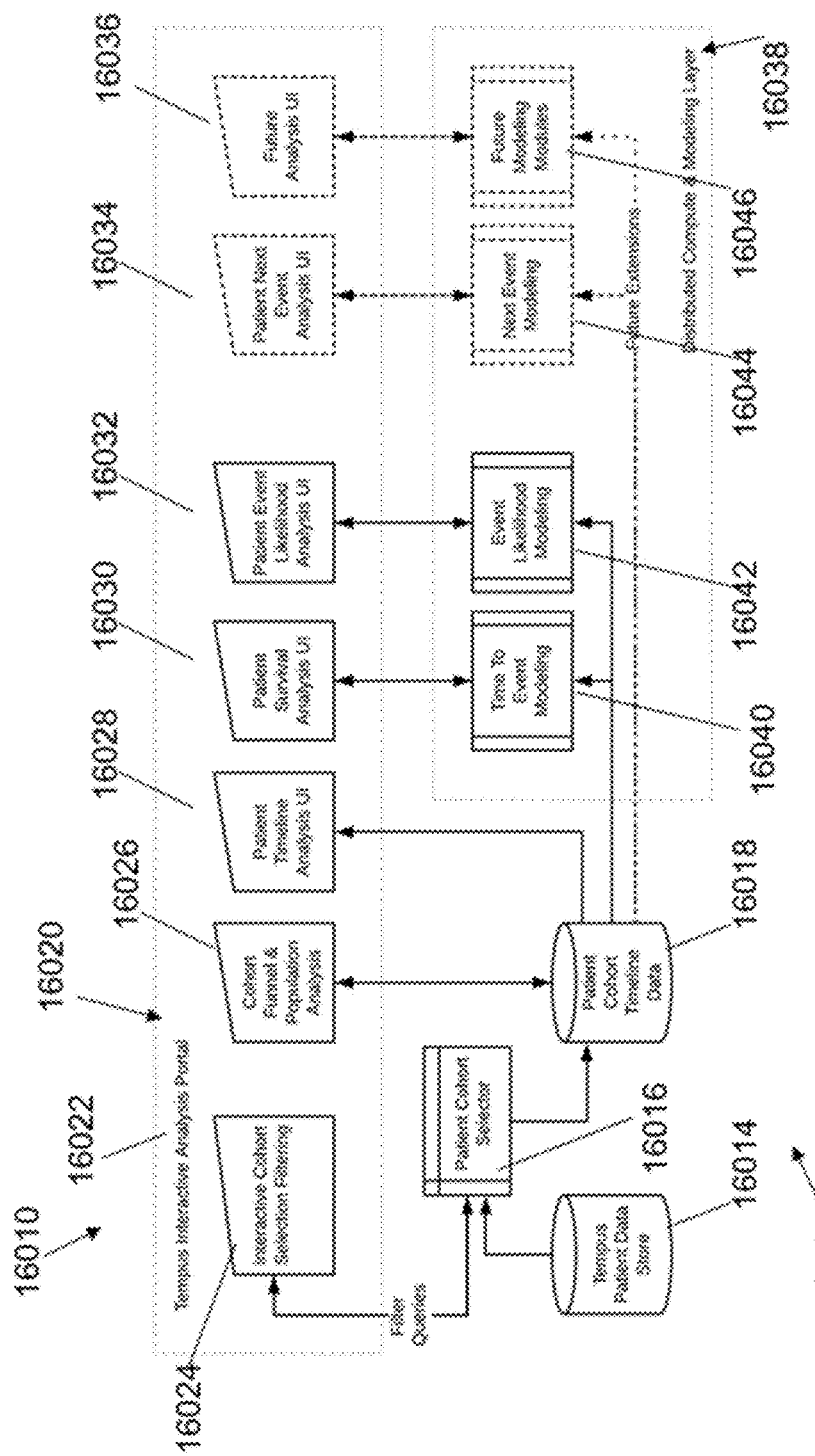
Figure 382:
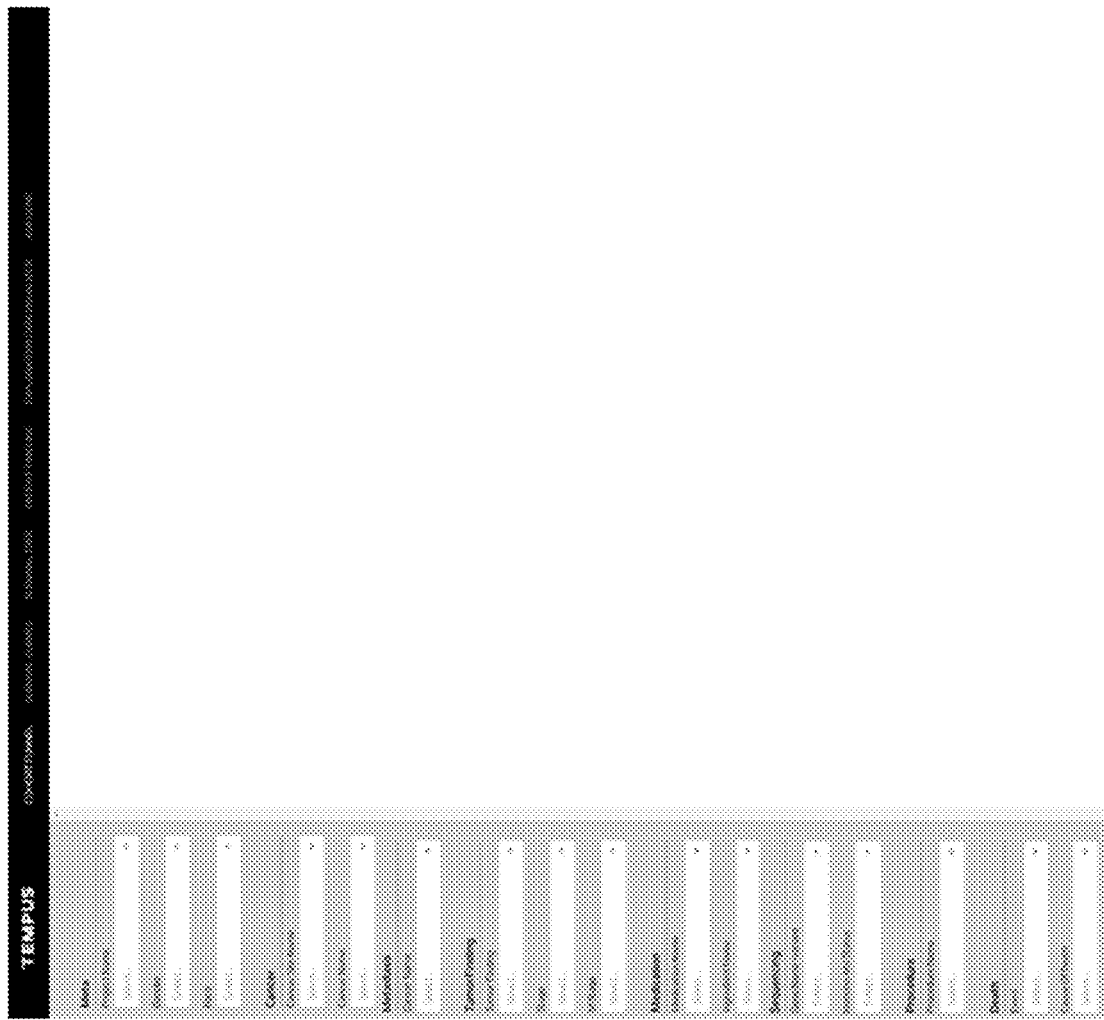
Figure 383:
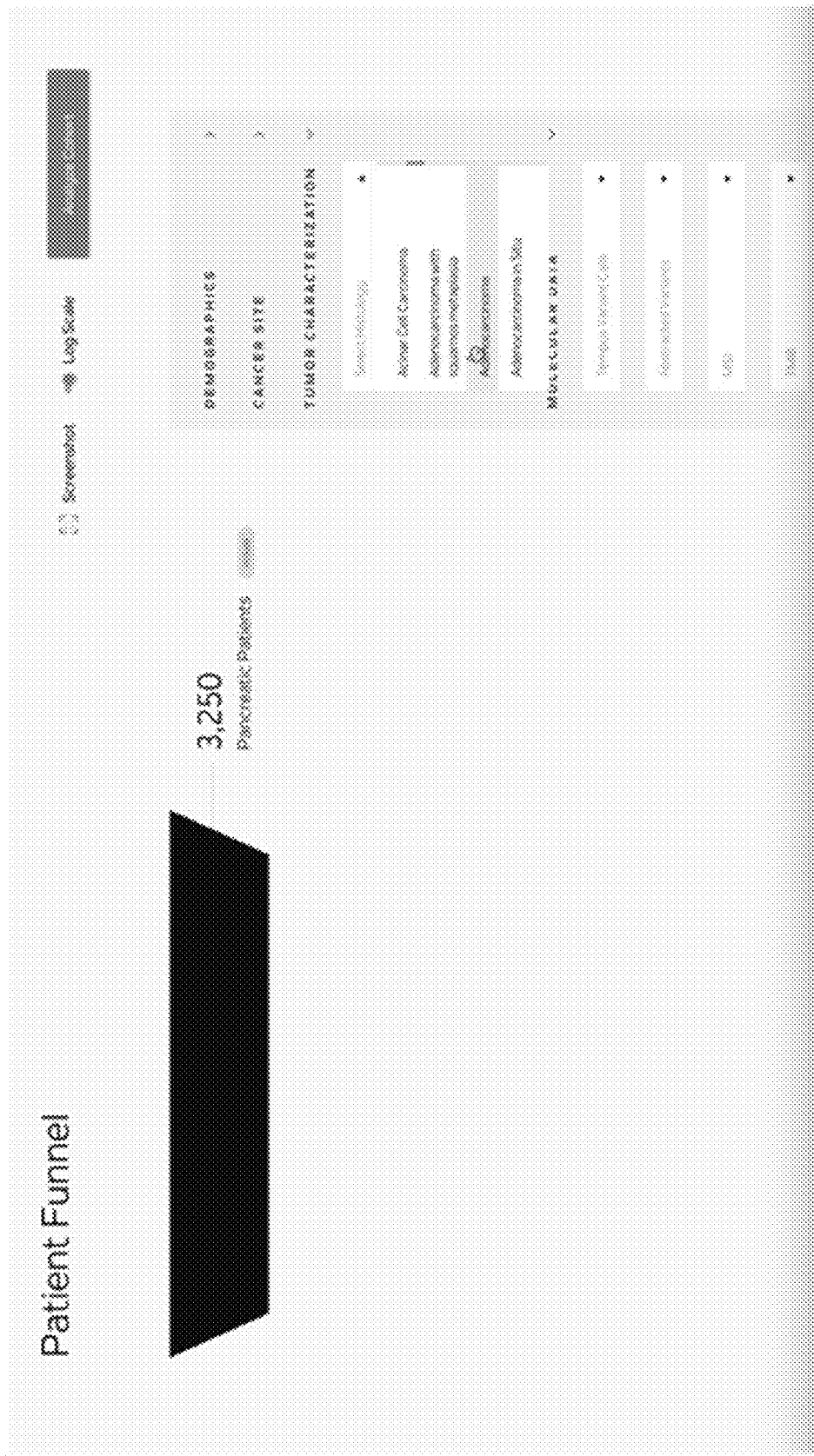
Figure 384:
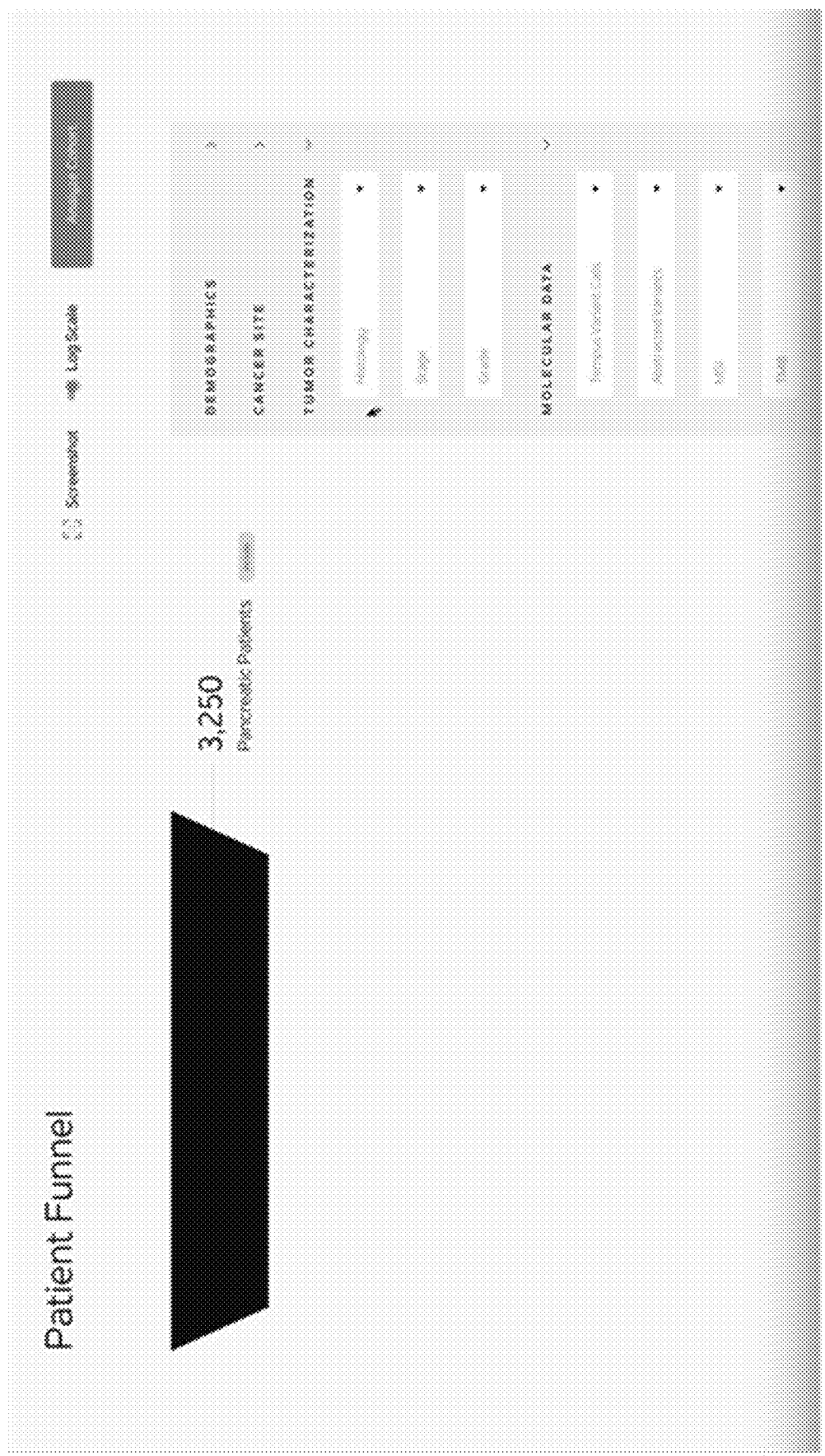
Figure 385:
Figure 386:
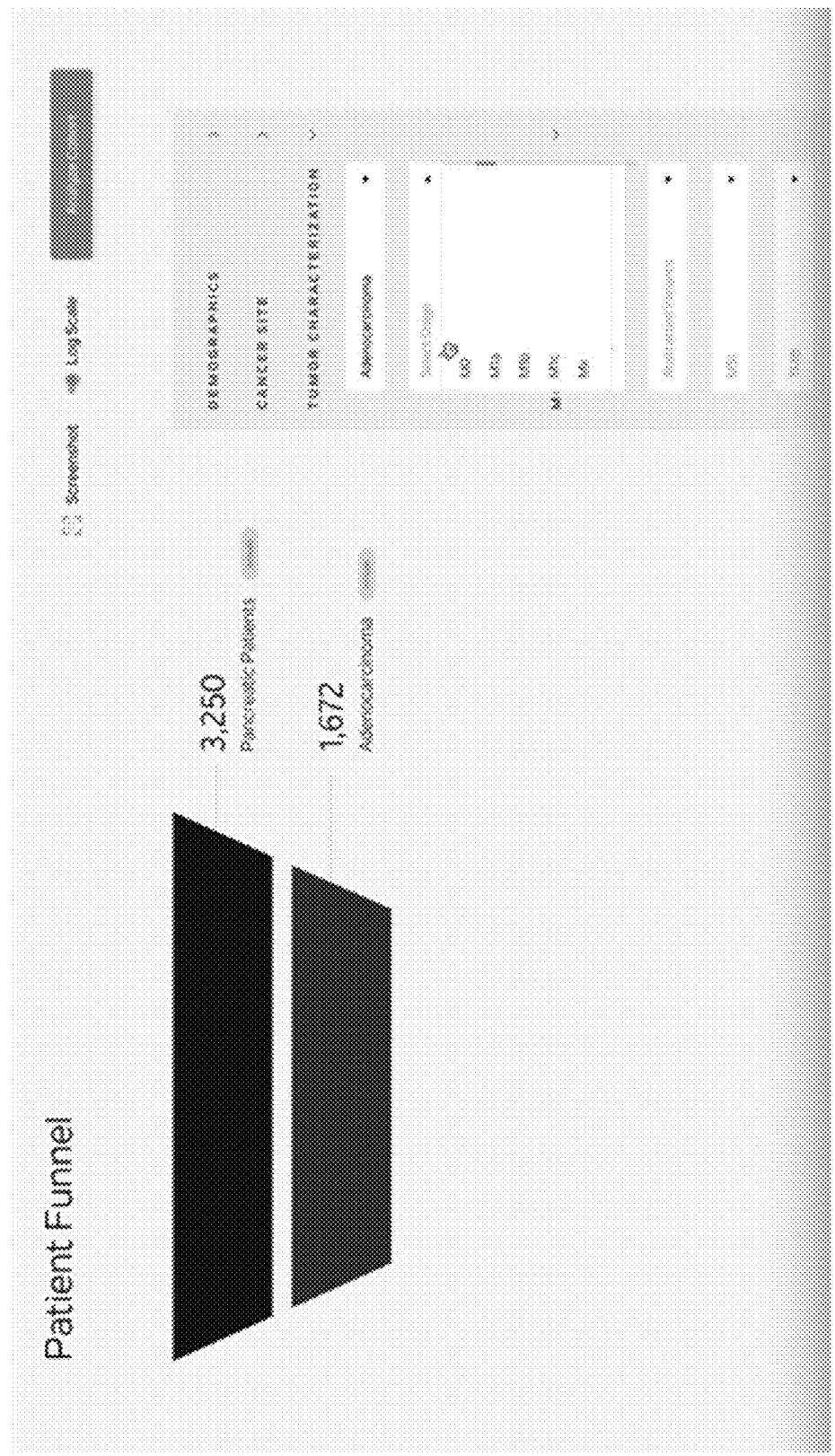
Figure 387:
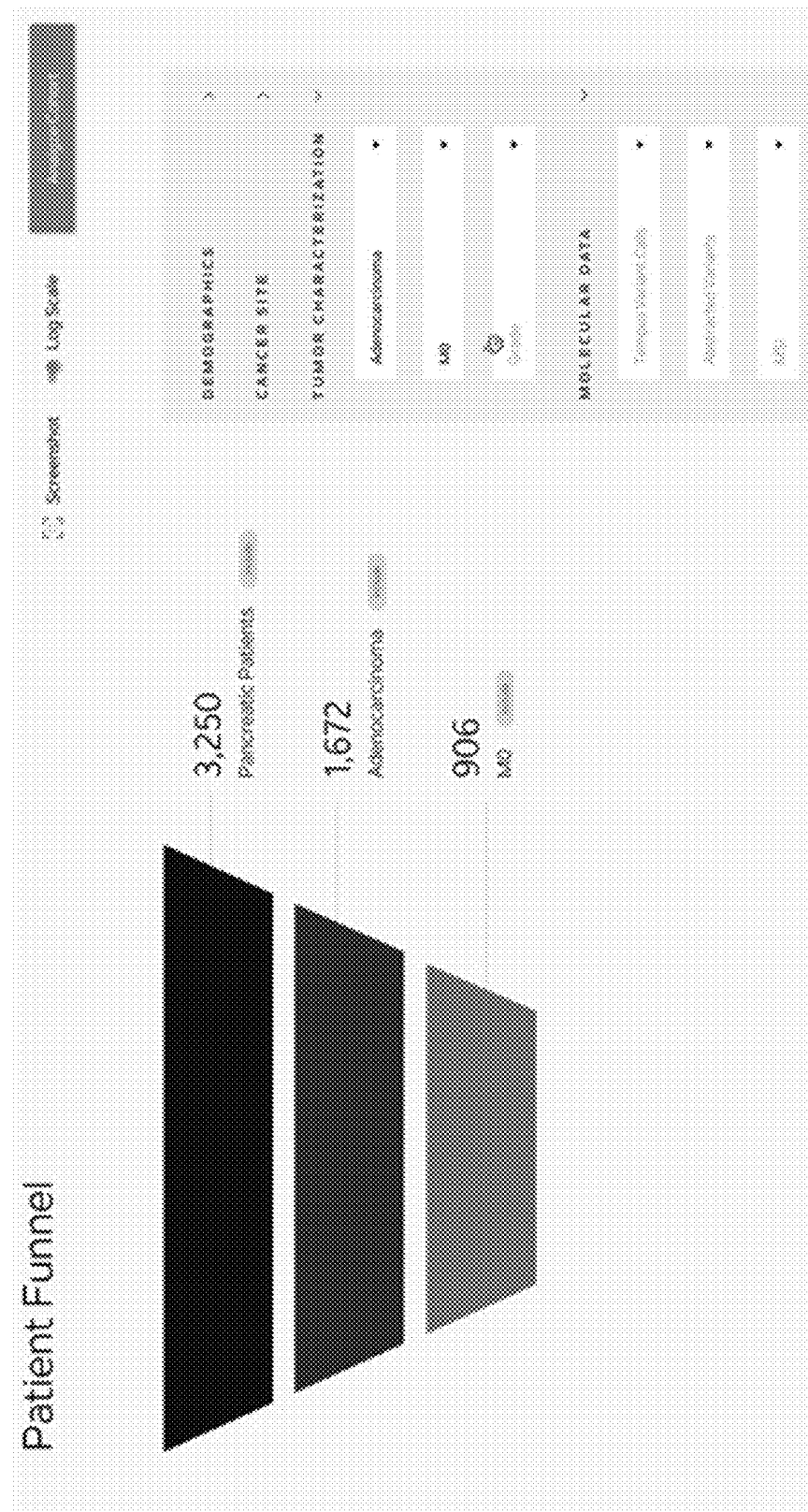
Figure 388:
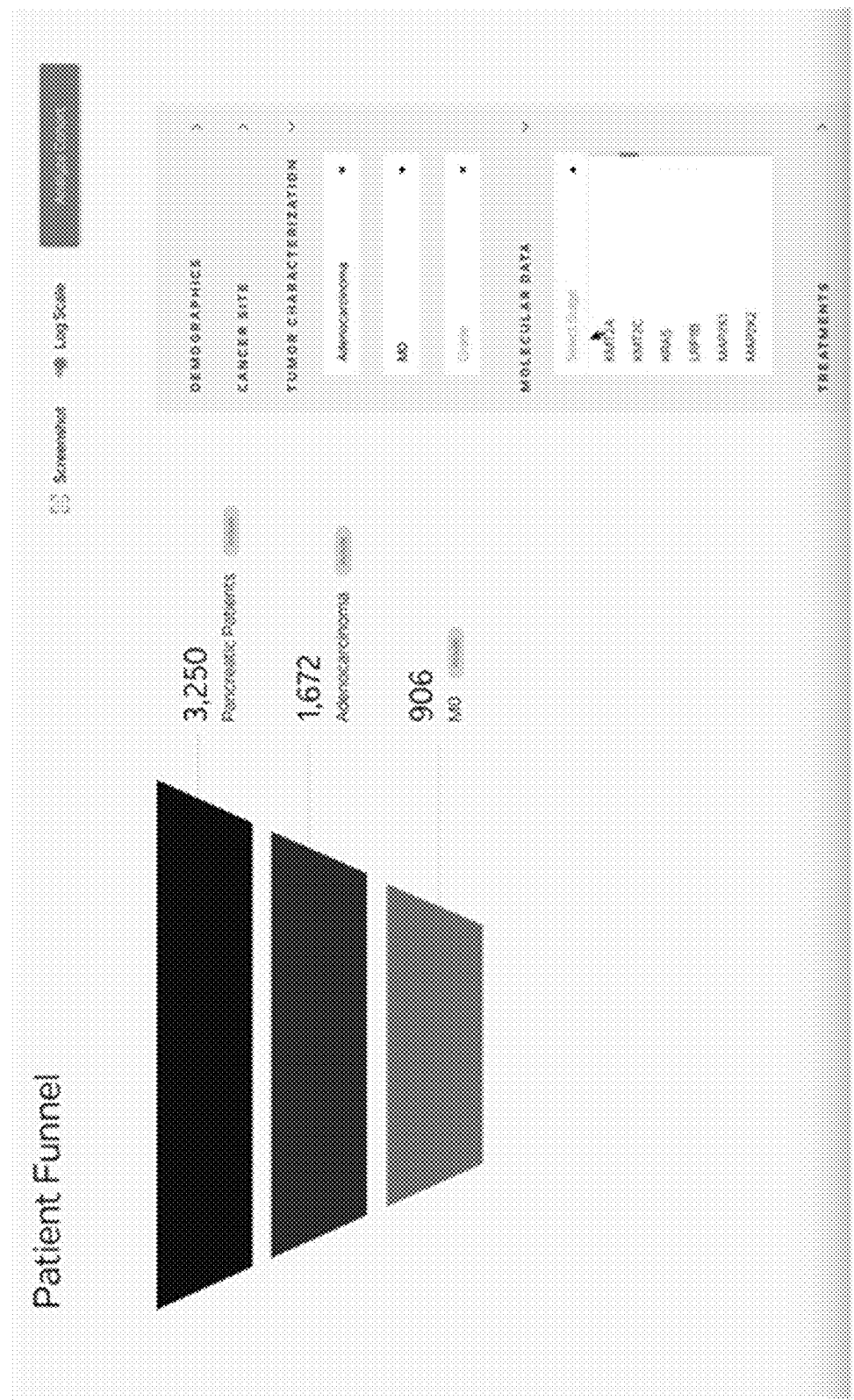
Figure 389:
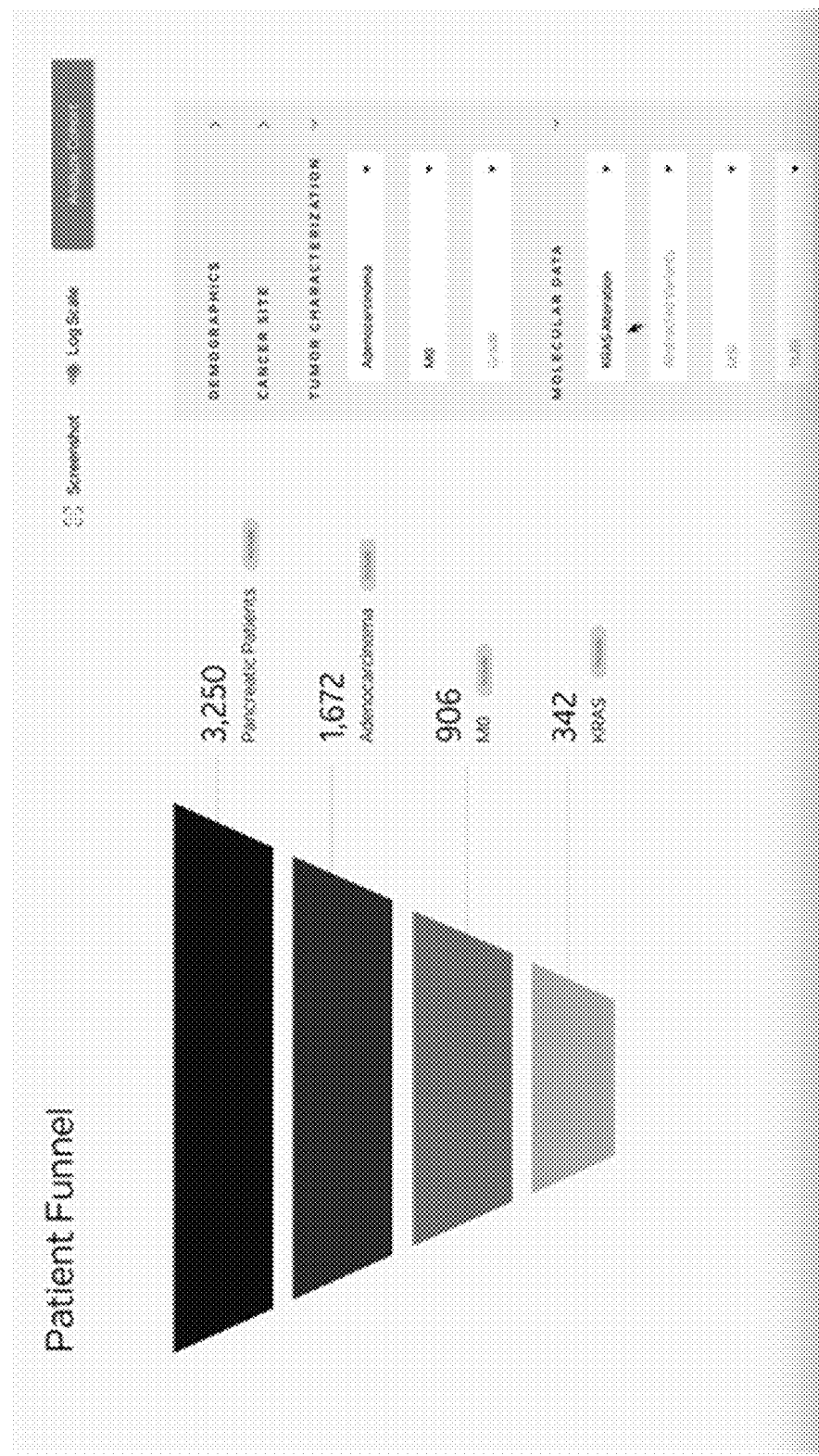
Figure 390:
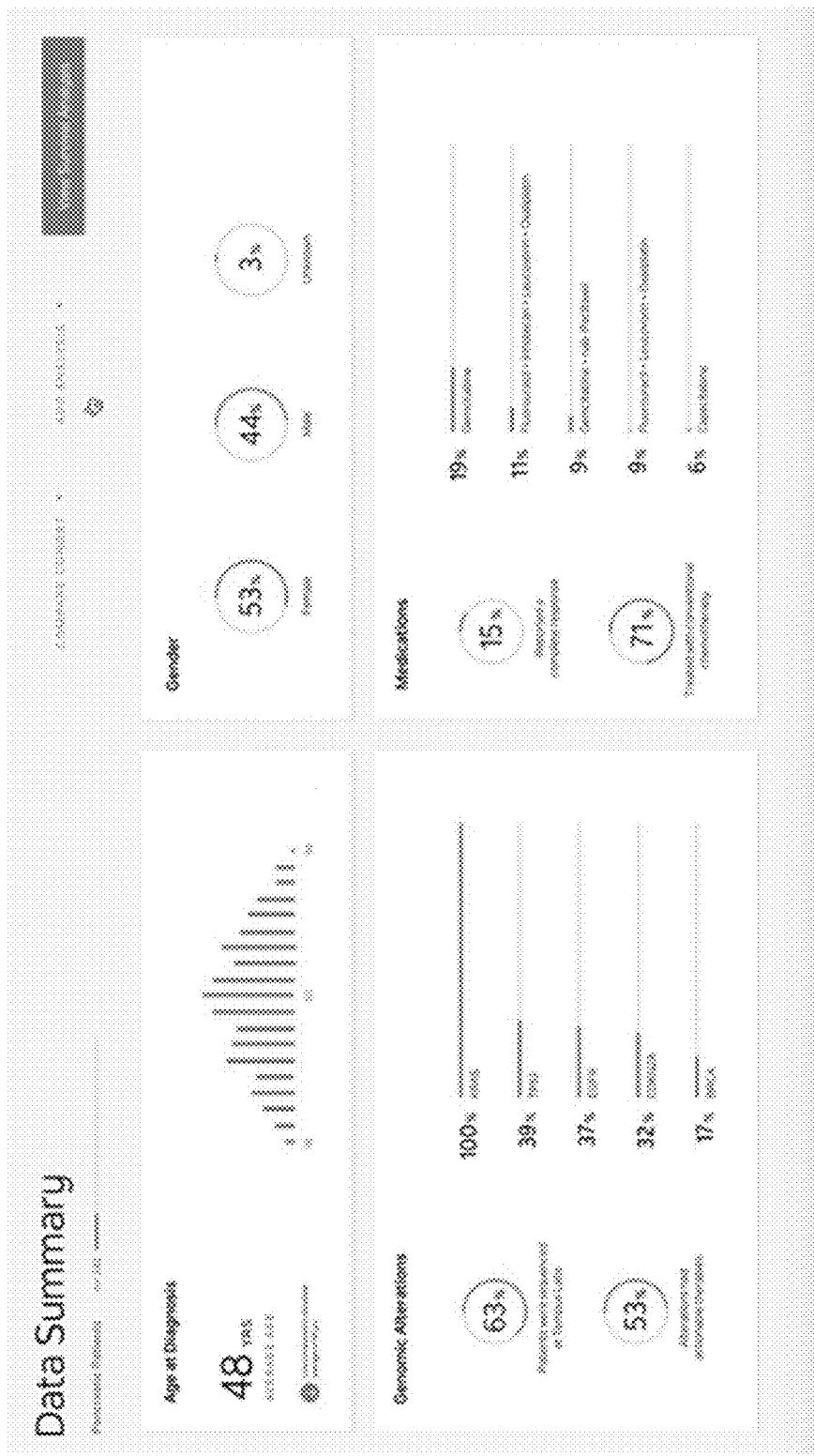
Figure 391:
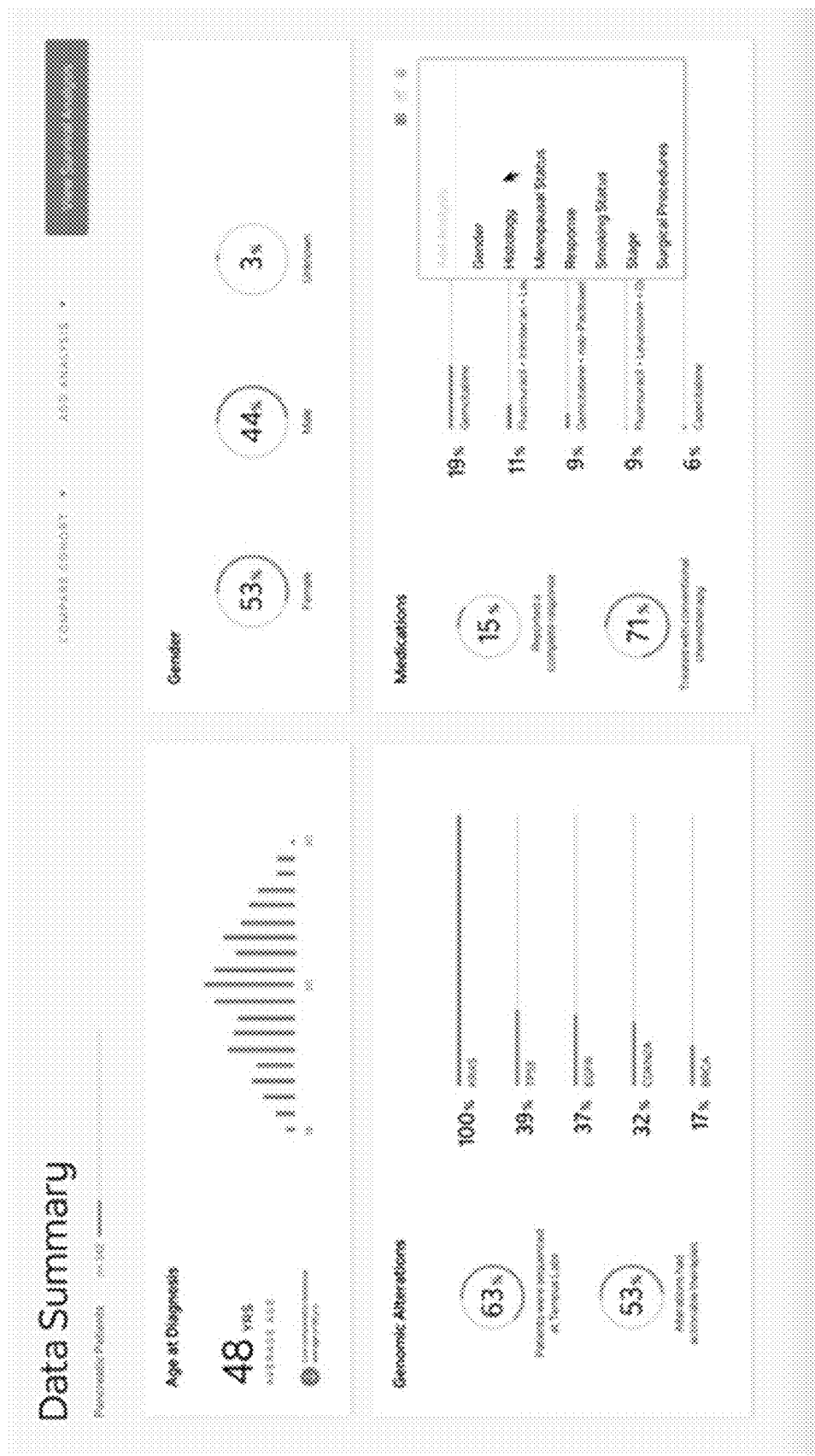
Figure 392:
Figure 393:
Figure 394:
Figure 395:
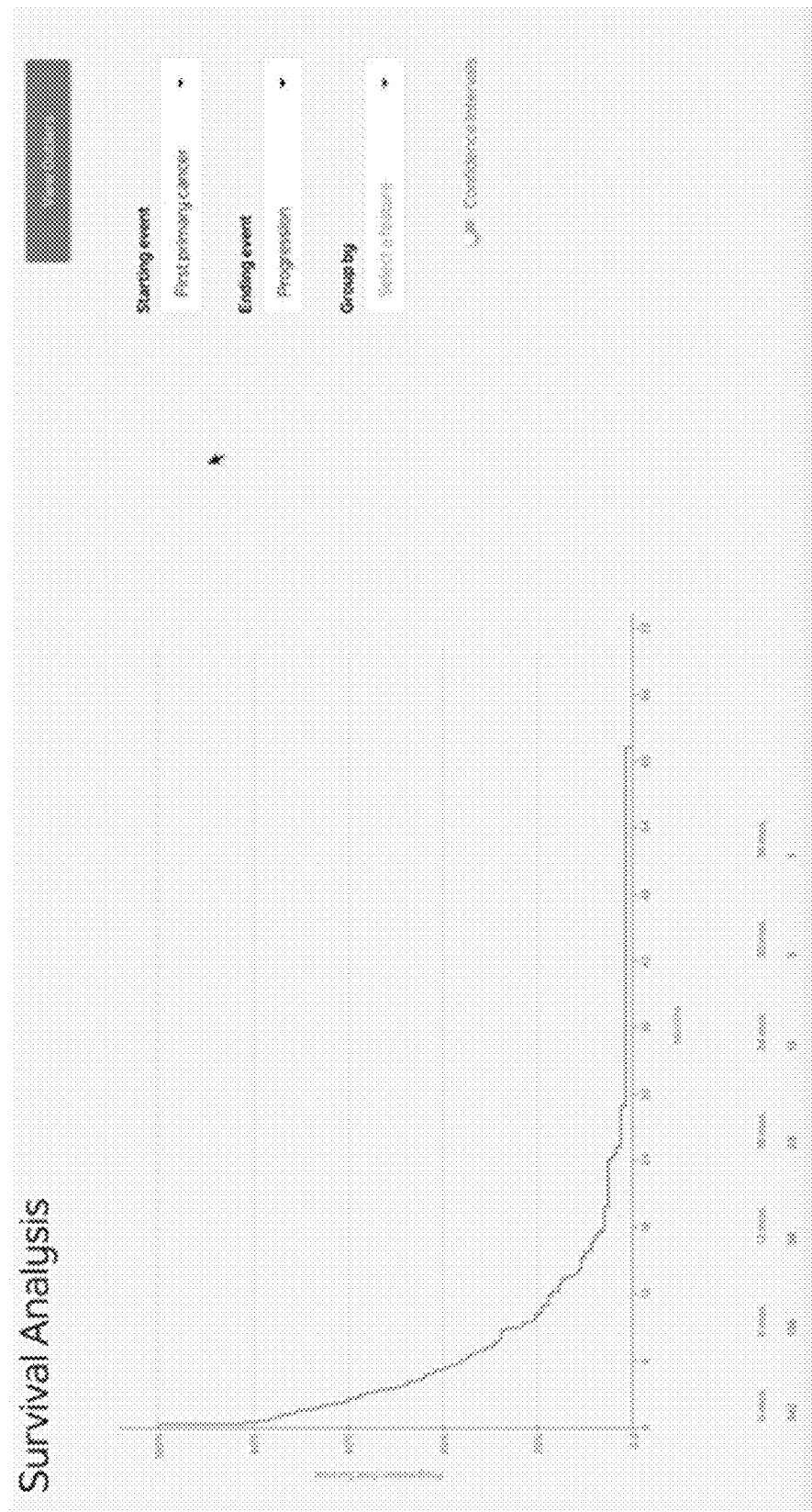
Figure 396:
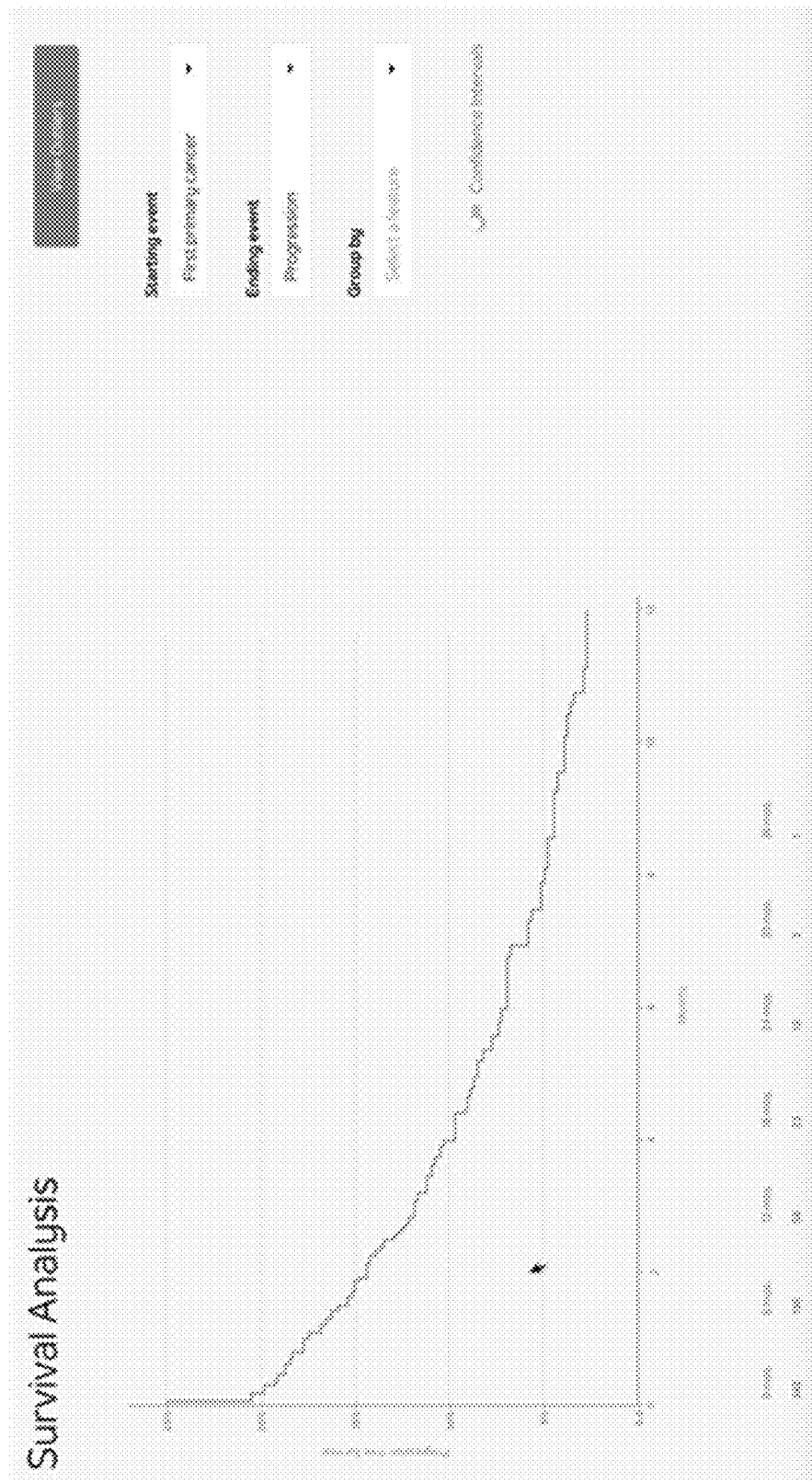
Figure 397:
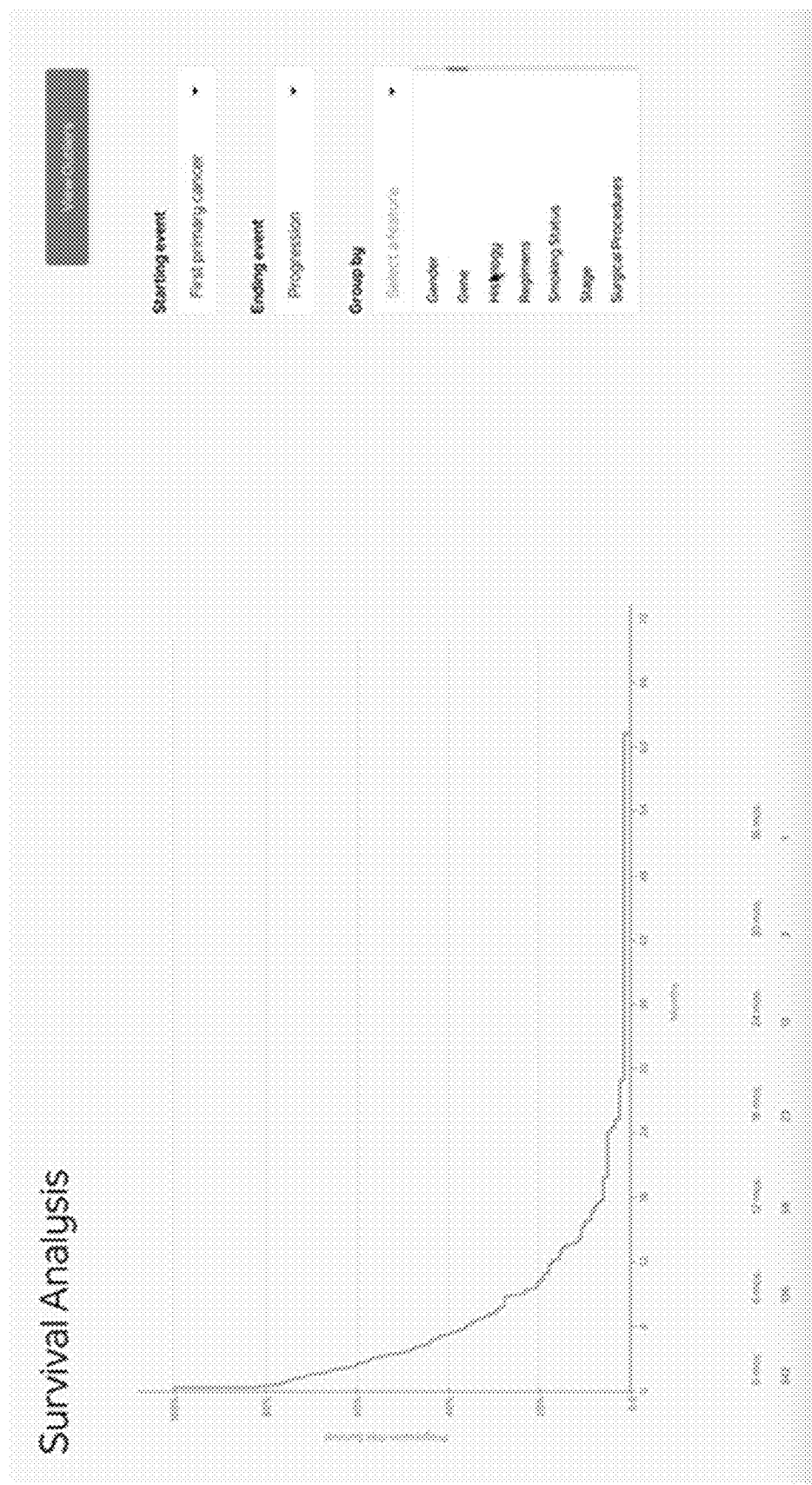
Figure 398:
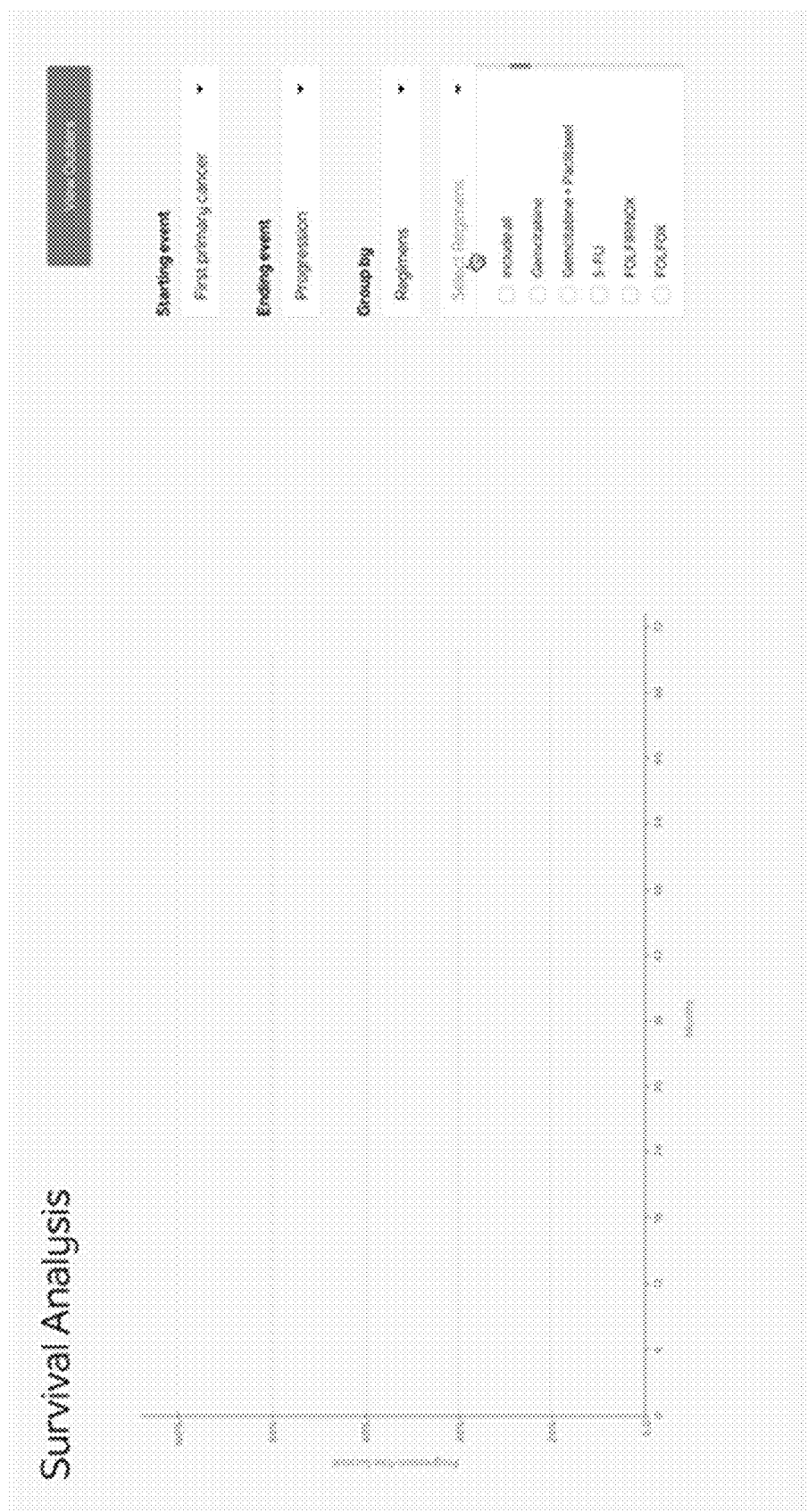
Figure 399:
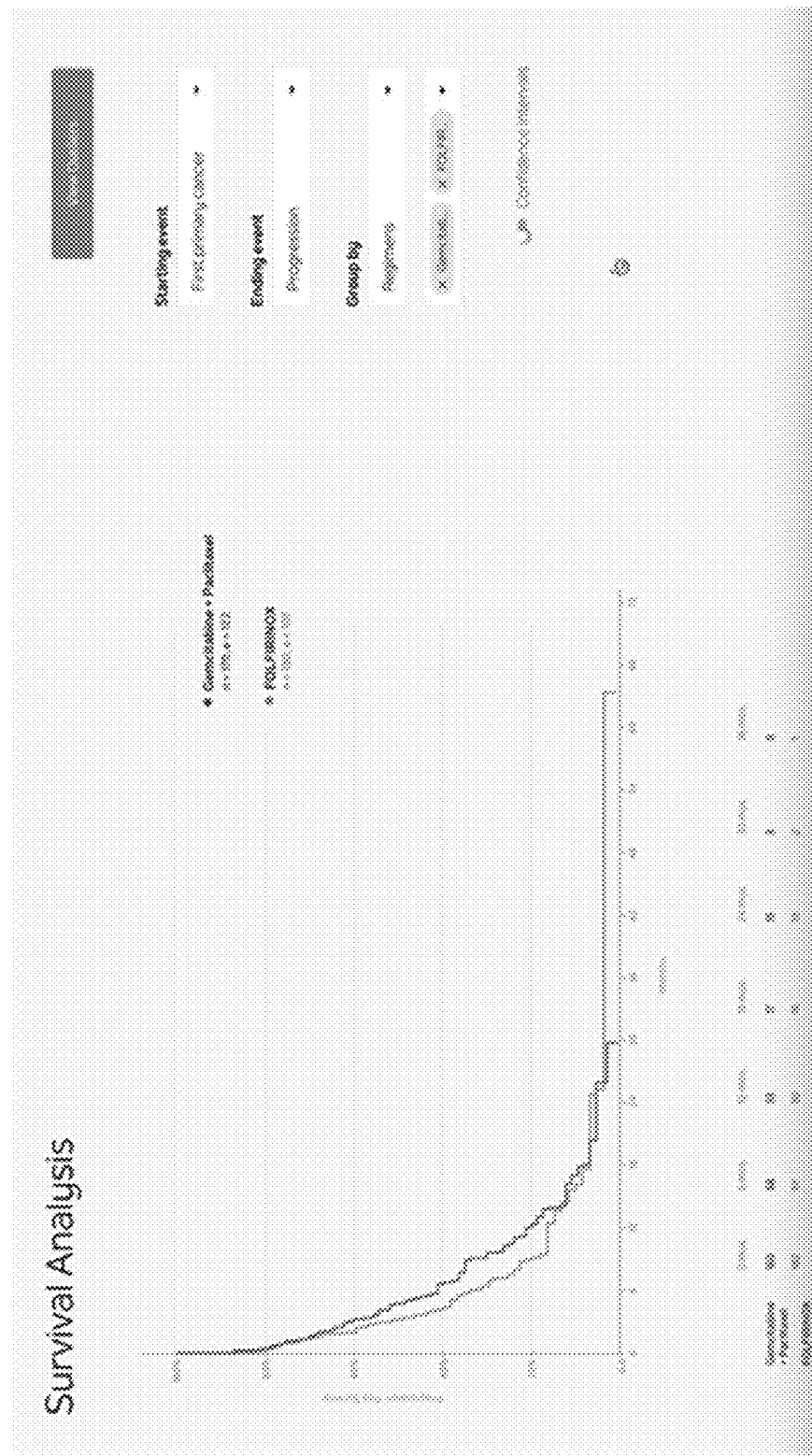
Figure 400:
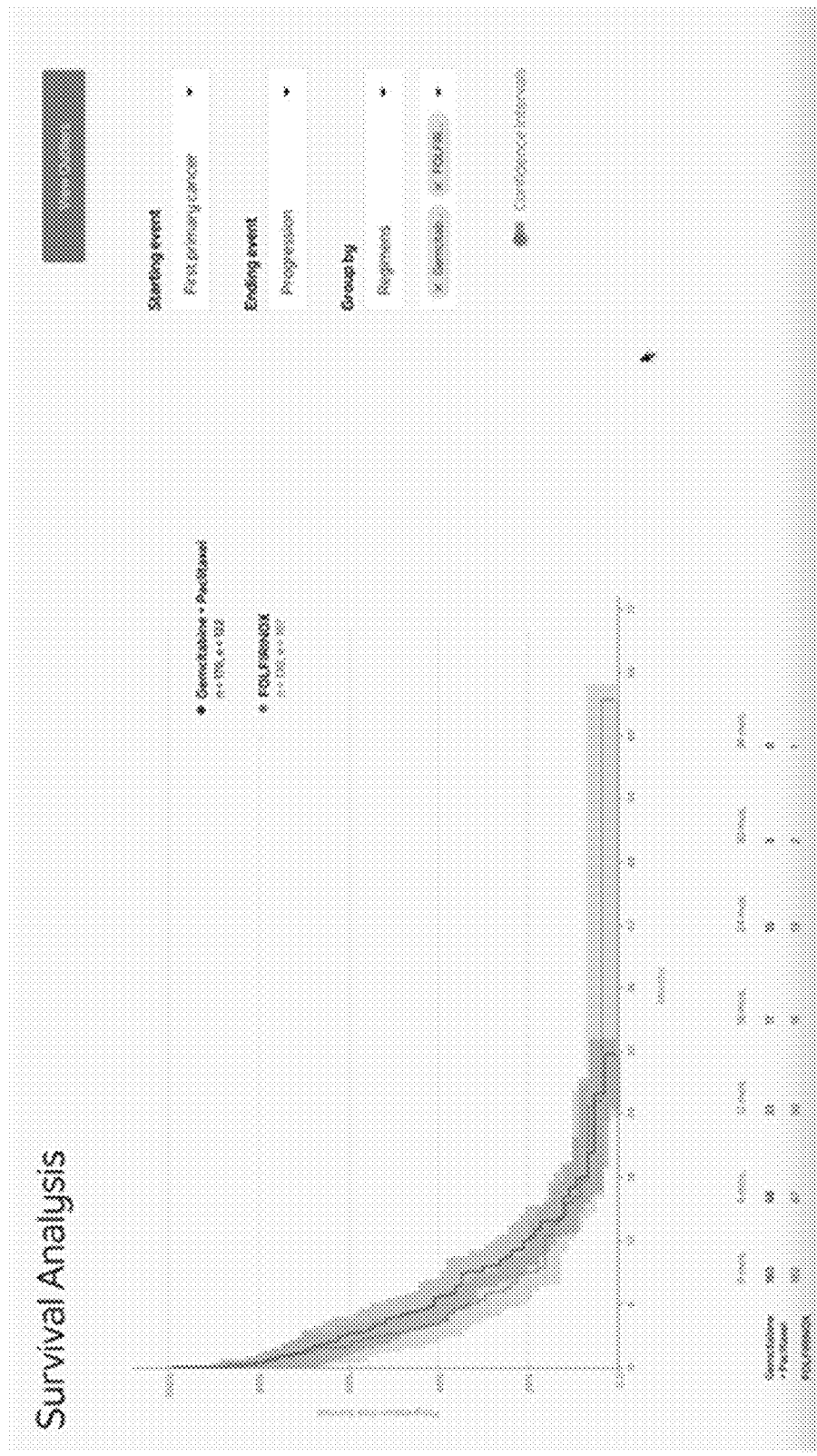
Figure 401:
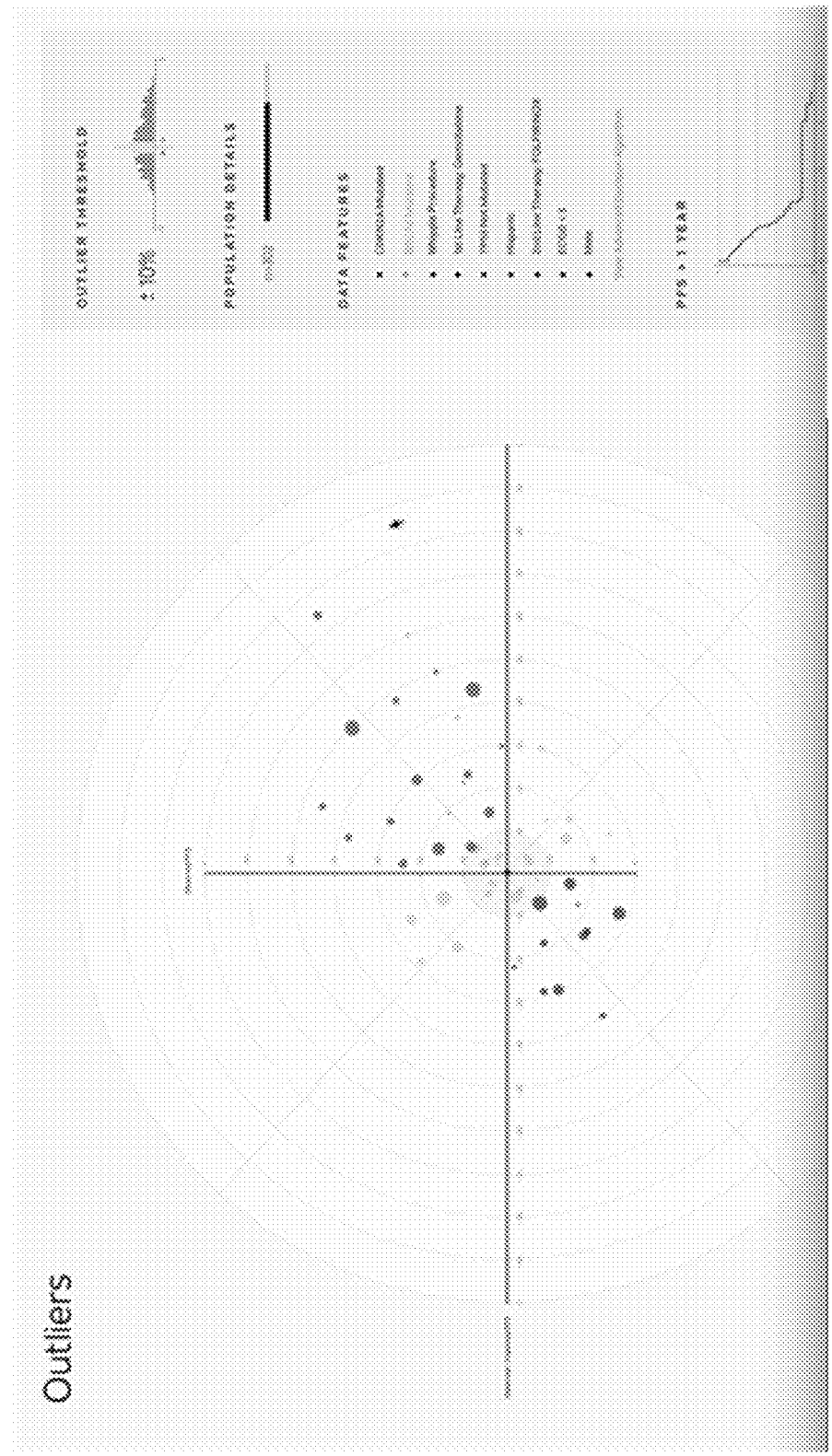
Figure 402:
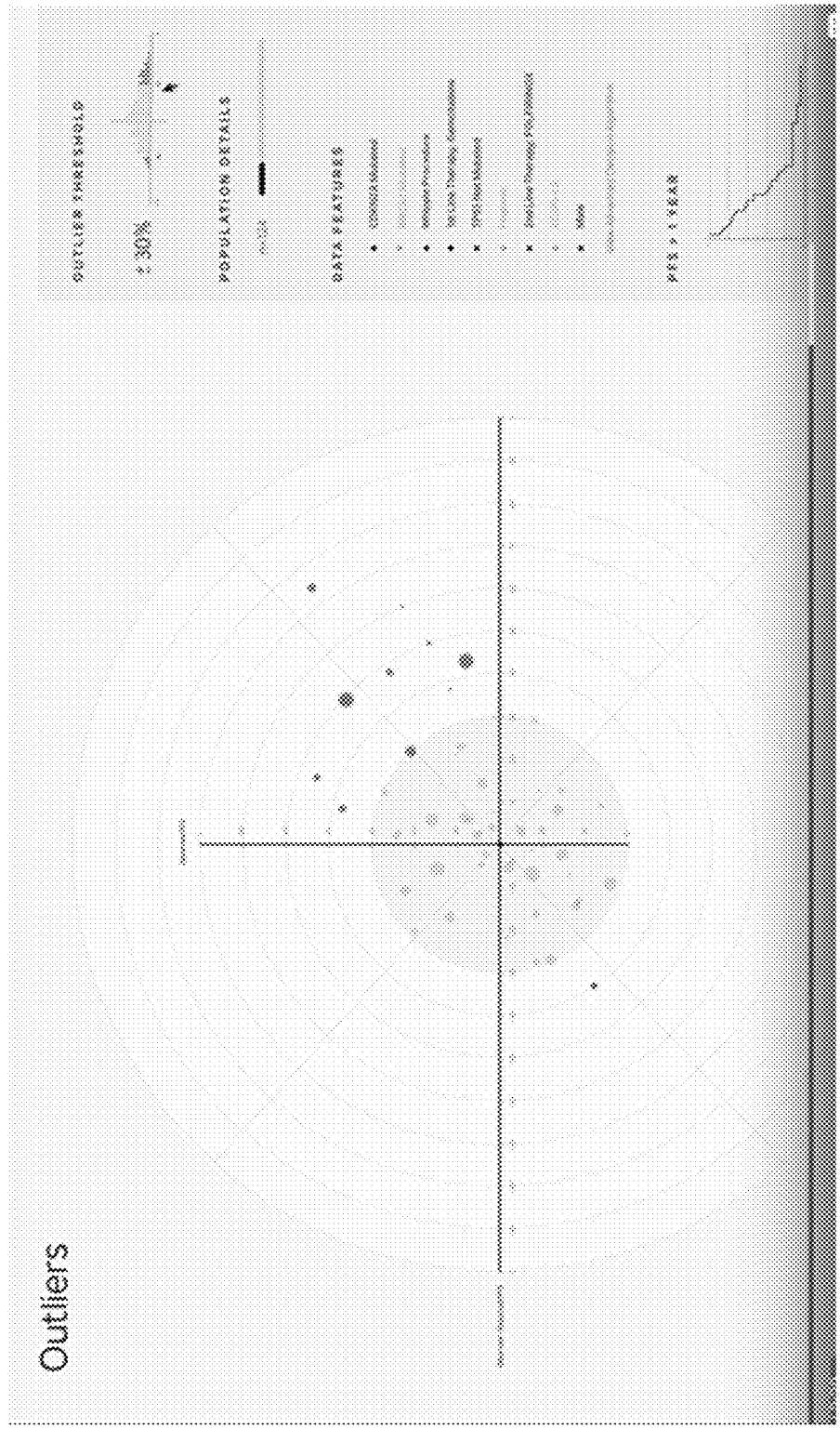
Figure 403:
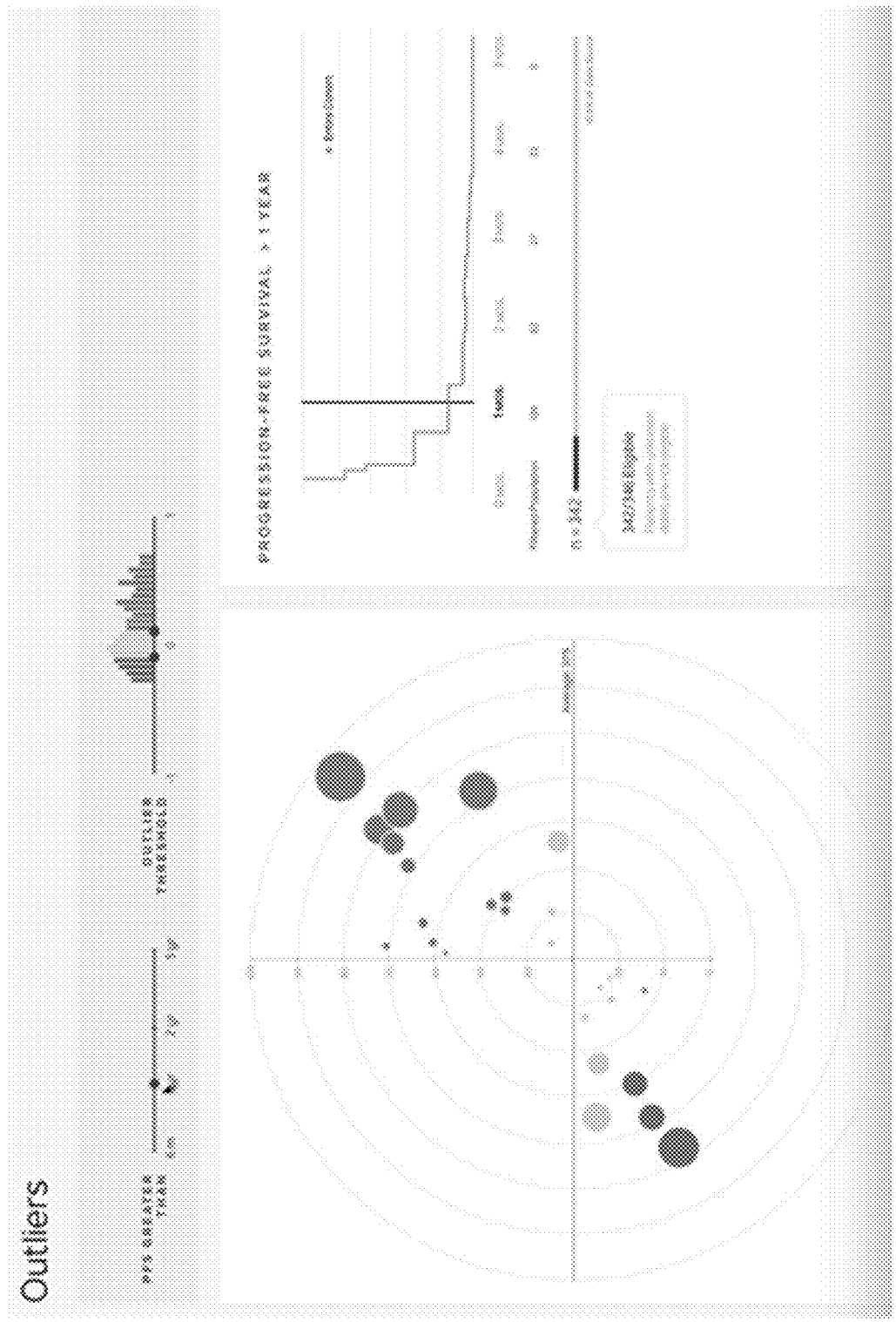
Figure 404:
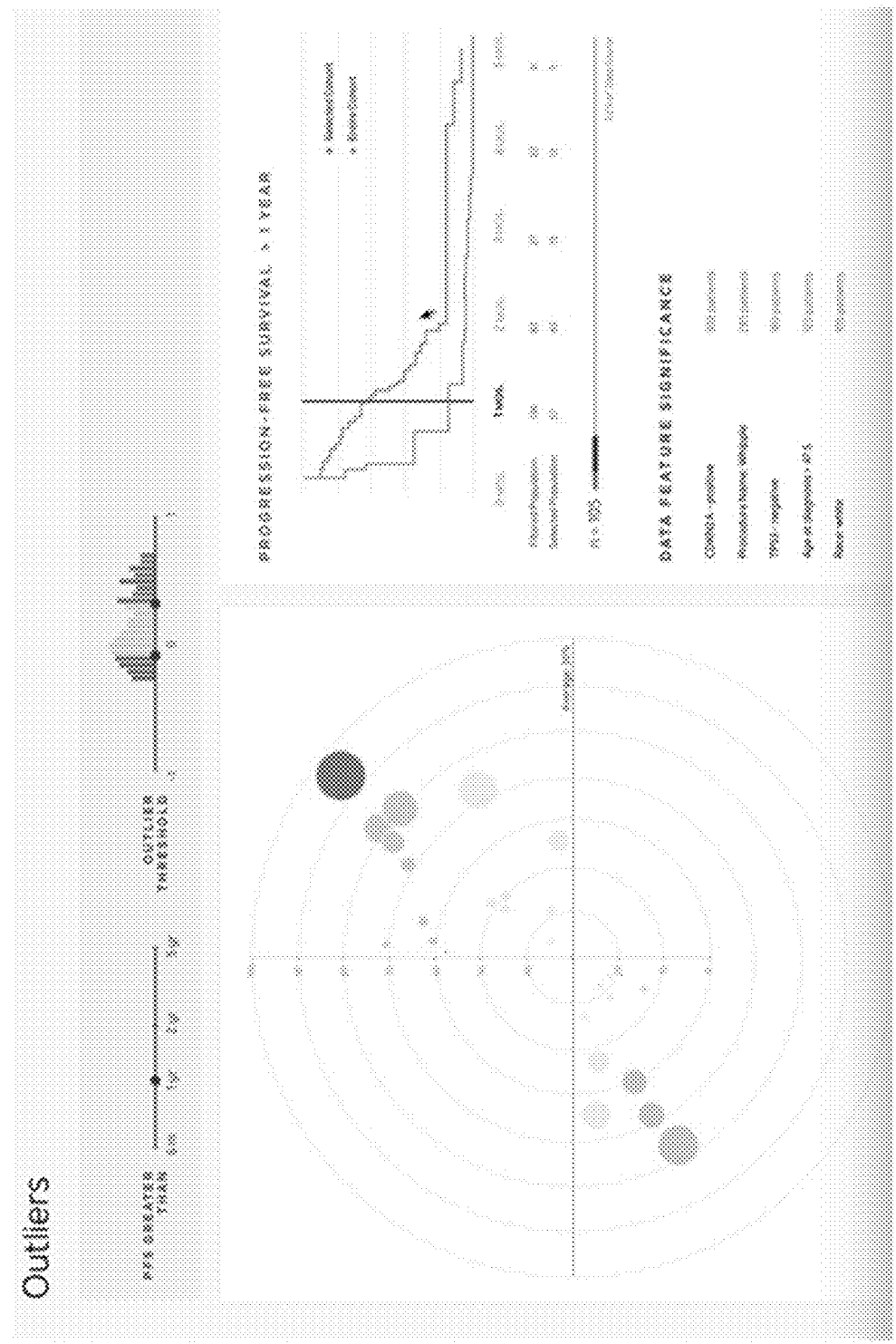
Figure 405:
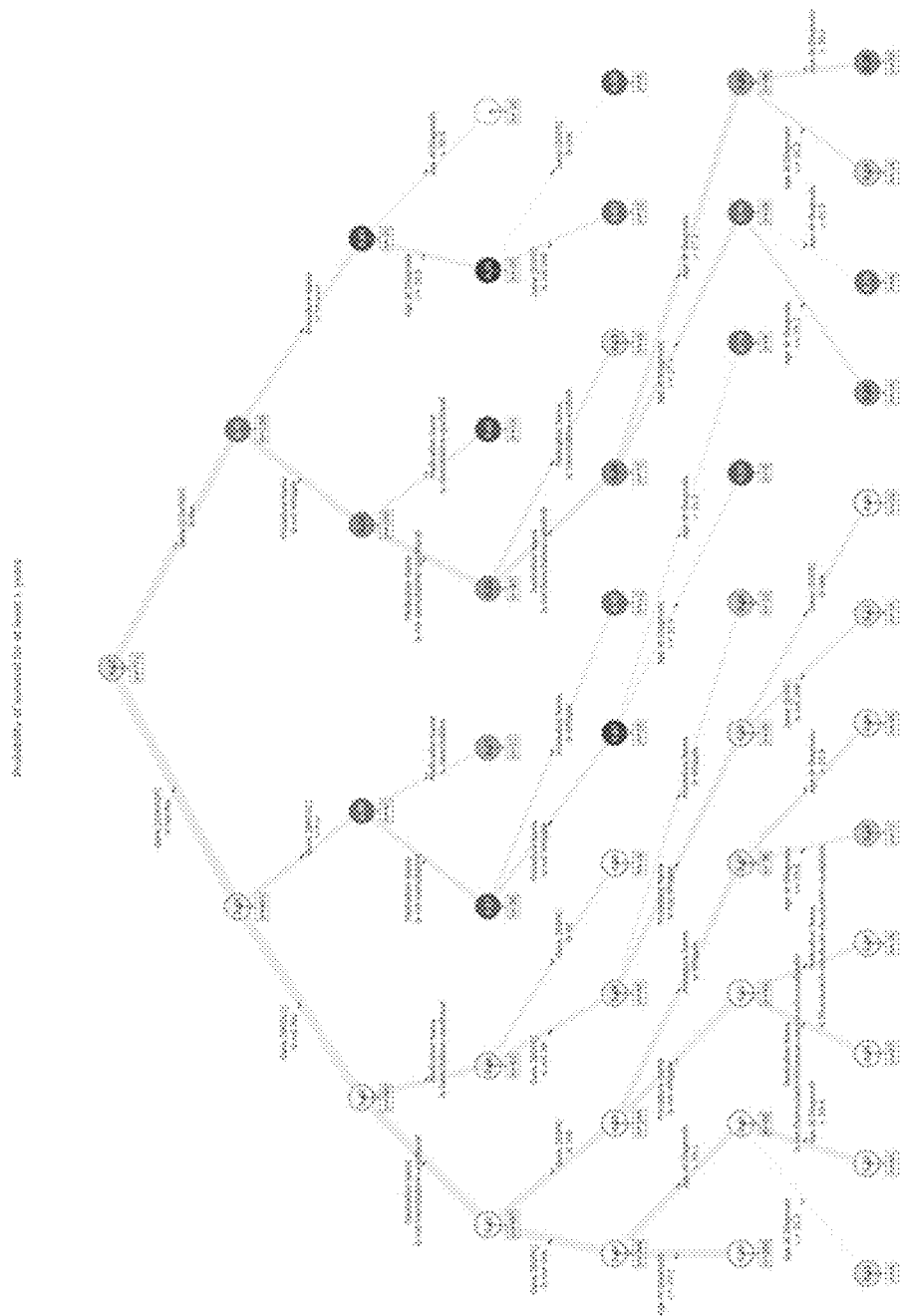

FIG. 381 is an exemplary system diagram of back end and front end components for predicting and analyzing patient cohort response, progression, and survival;

FIG. 382 is one example of a patient cohort selection filtering interface;

FIG. 383 is one example of a cohort funnel & population analysis user interface;

FIG. 384 is another example of a cohort funnel & population analysis user interface;

FIG. 385 is another example of a cohort funnel & population analysis user interface;

FIG. 386 is another example of a cohort funnel & population analysis user interface;

FIG. 387 is another example of a cohort funnel & population analysis user interface;

FIG. 388 is another example of a cohort funnel & population analysis user interface;

FIG. 389 is another example of a cohort funnel & population analysis user interface;

FIG. 390 is one example of a data summary window in a patient timeline analysis user interface;

FIG. 391 is another example of a data summary window in a patient timeline analysis user interface;

FIG. 392 is another example of a data summary window in a patient timeline analysis user interface;

FIG. 393 is another example of a data summary window in a patient timeline analysis user interface;

FIG. 394 is another example of a data summary window in a patient timeline analysis user interface;

FIG. 395 is one example of a patient survival analysis user interface;

FIG. 396 is another example of a patient survival analysis user interface;

FIG. 397 is another example of a patient survival analysis user interface;

FIG. 398 is another example of a patient survival analysis user interface;

FIG. 399 is another example of a patient survival analysis user interface;

FIG. 400 is another example of a patient survival analysis user interface;

FIG. 401 is an example of a patient event likelihood analysis user interface;

FIG. 402 is another example of a patient event likelihood analysis user interface;

FIG. 403 is another example of a patient event likelihood analysis user interface;

FIG. 404 is another example of a patient event likelihood analysis user interface; and FIG. 405 is an example of a binary decision tree for determining outliers usable with respect to the patient event likelihood analysis user interface.

Figure 406:
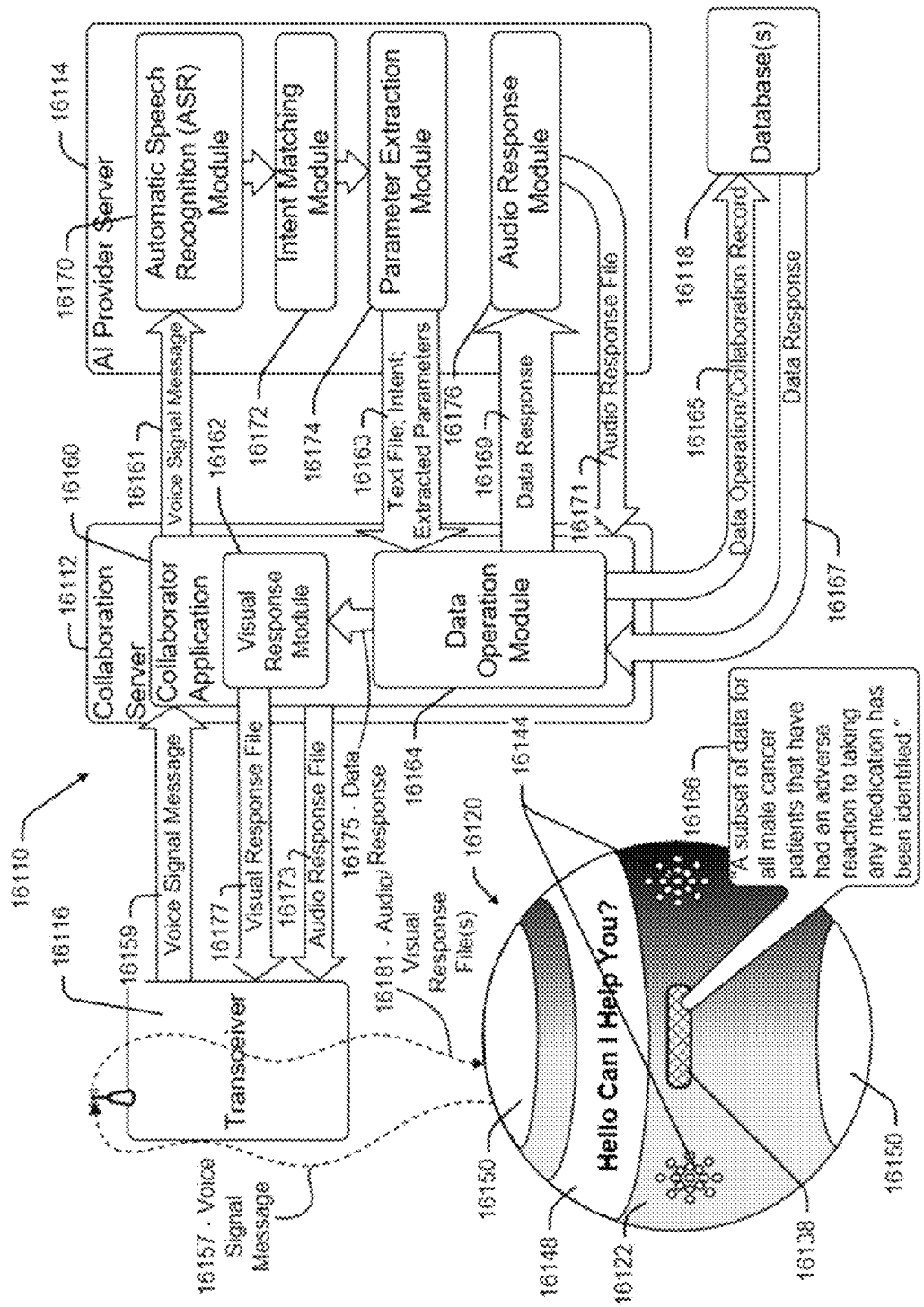
Figure 407:
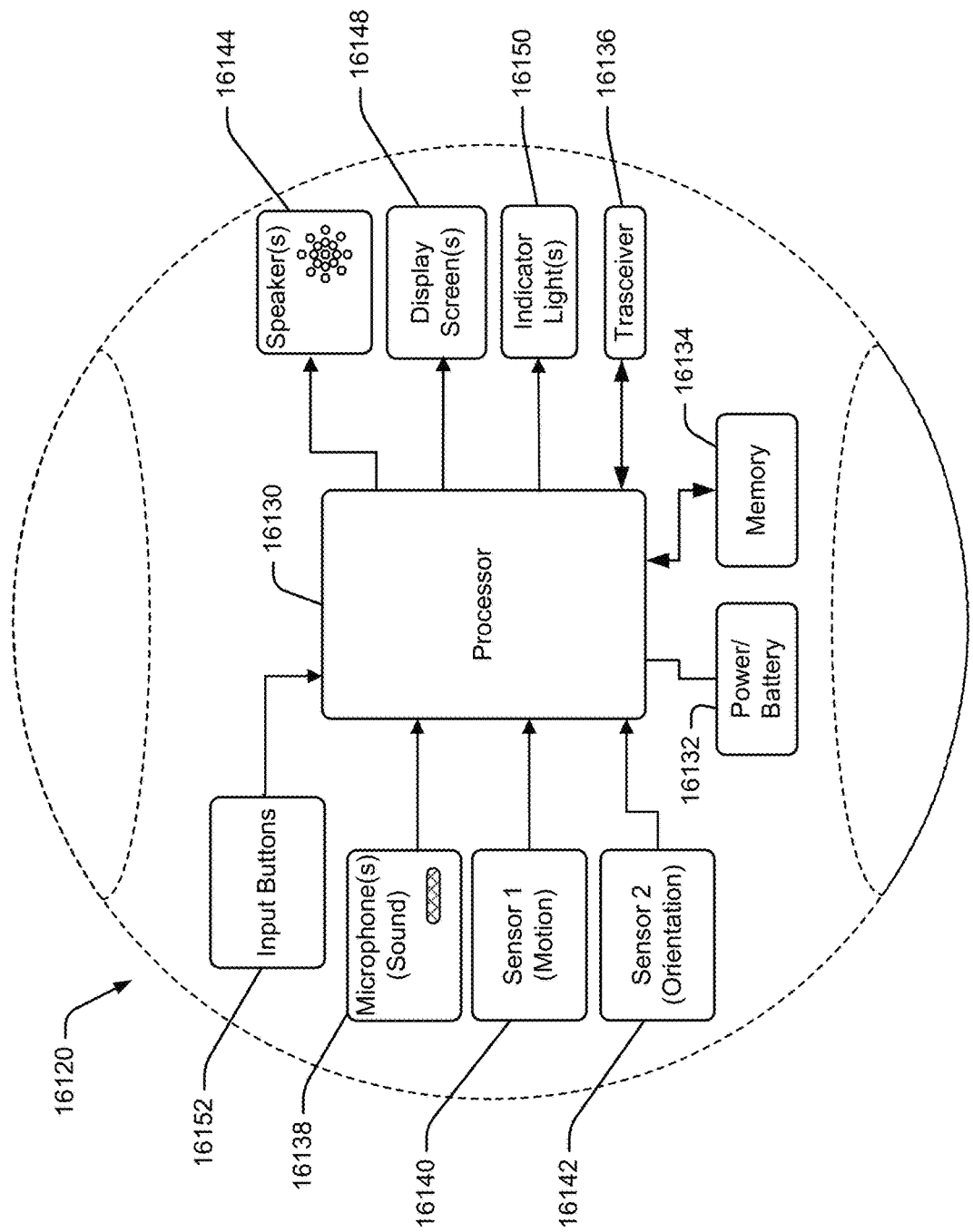
Figure 408:
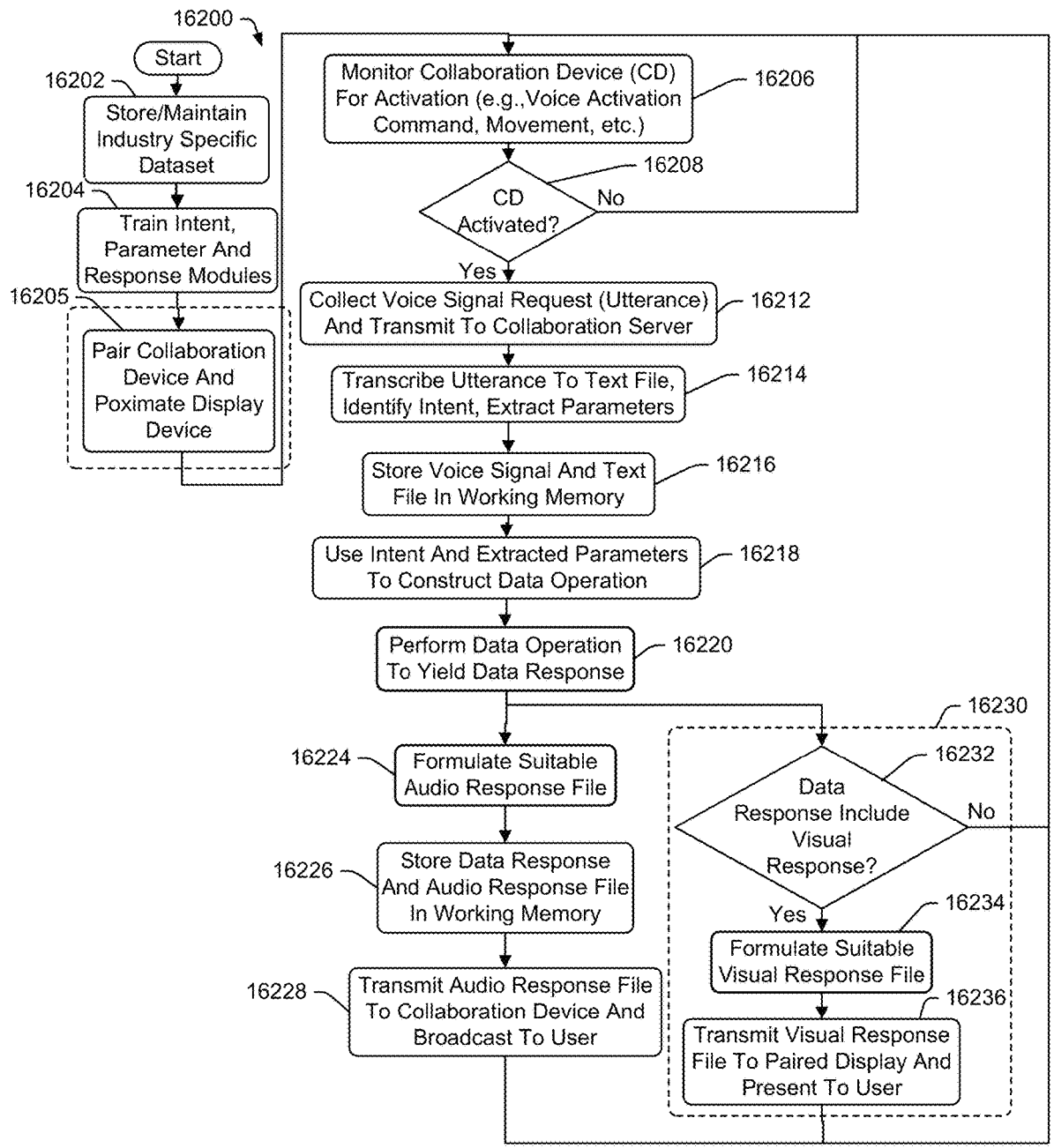
Figure 409:
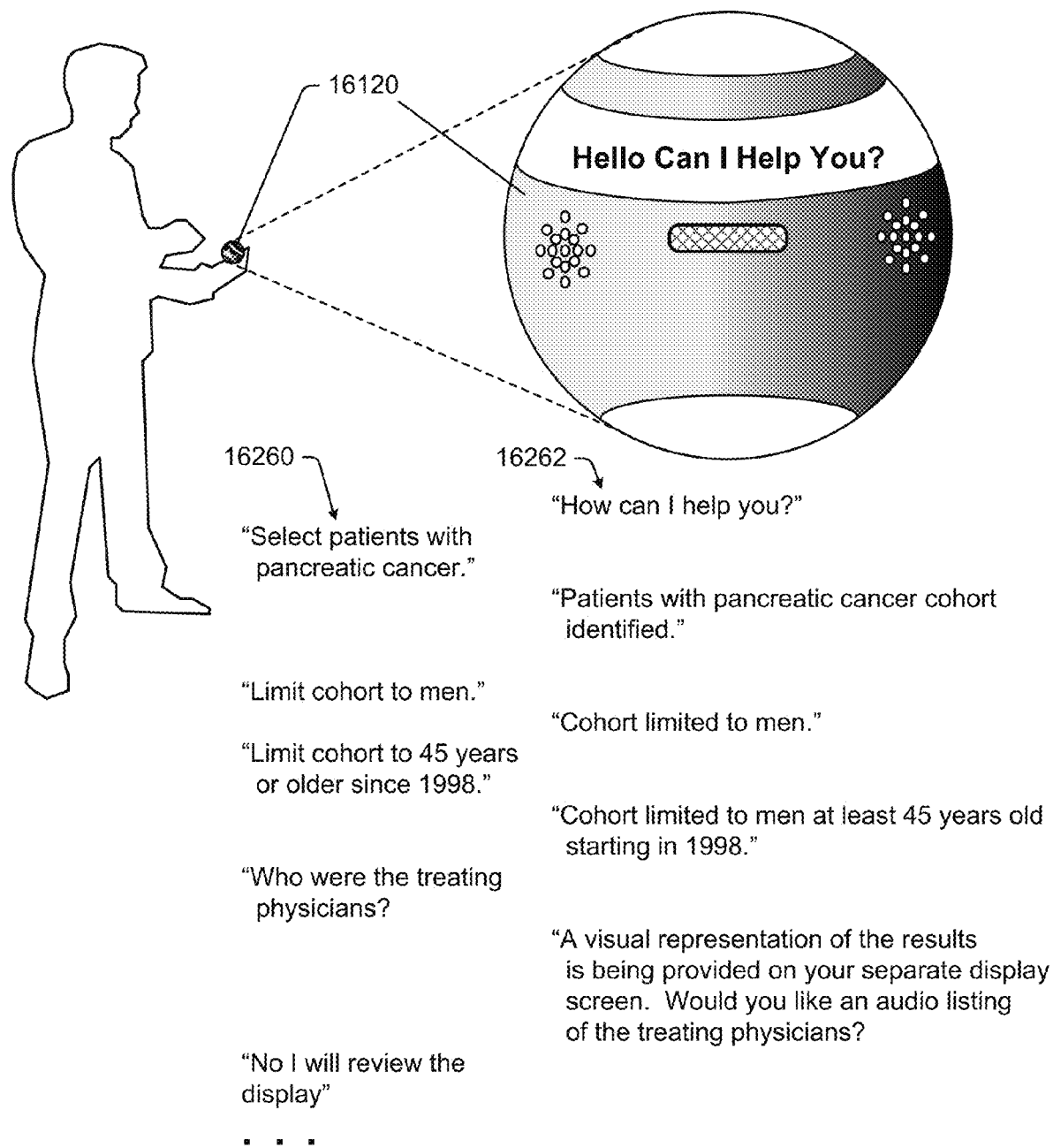
Figure 410:
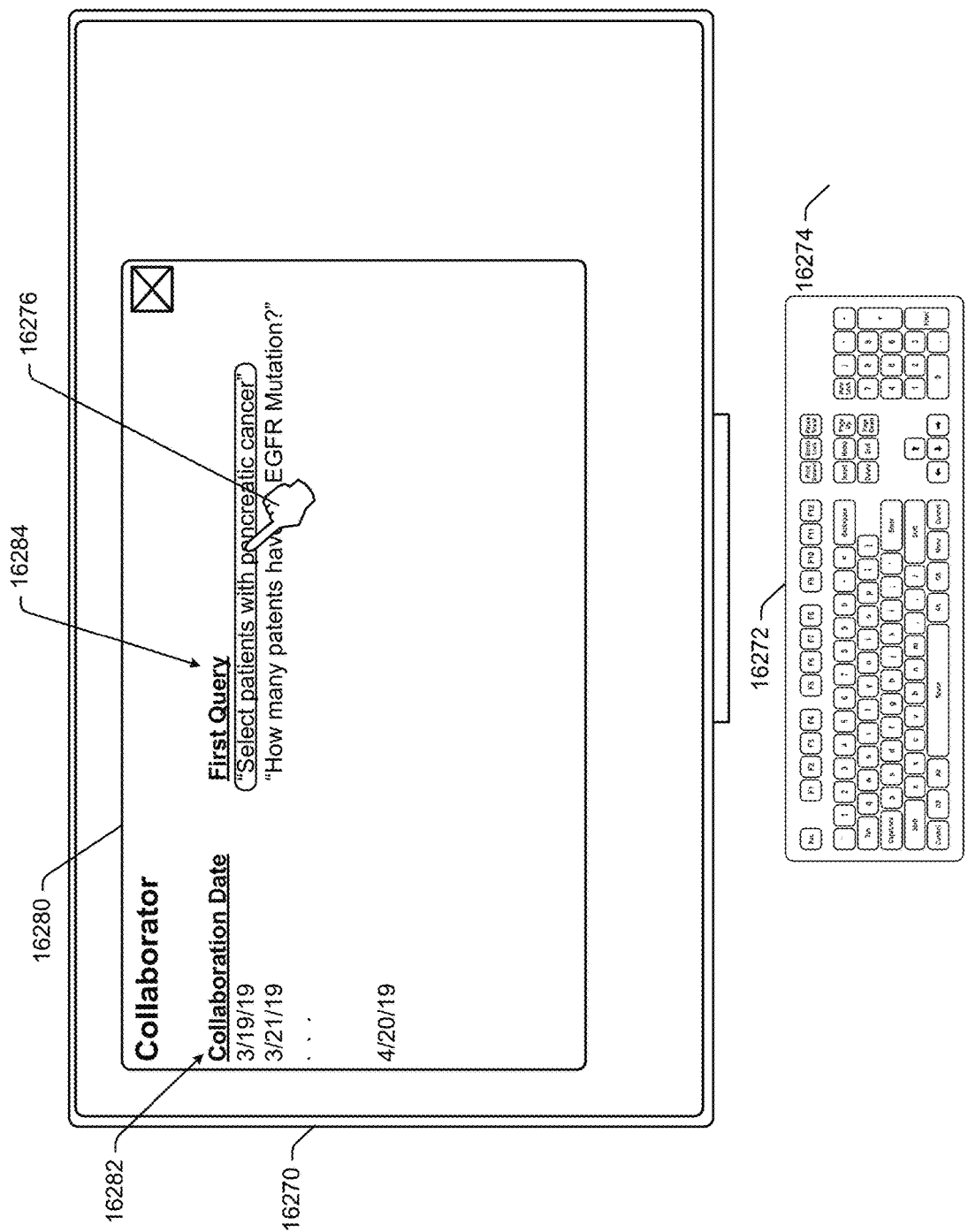
Figure 411:
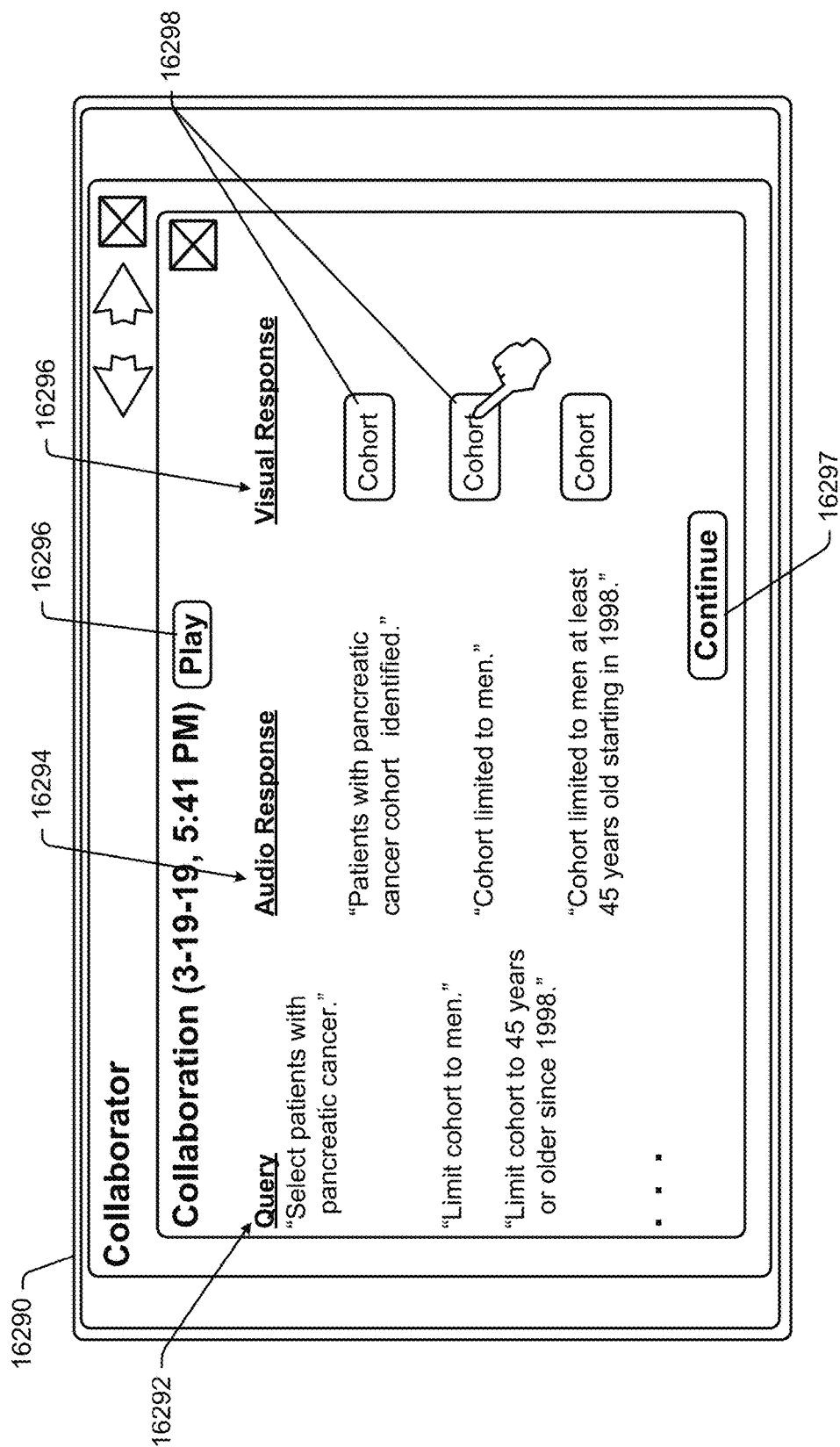
Figure 412:
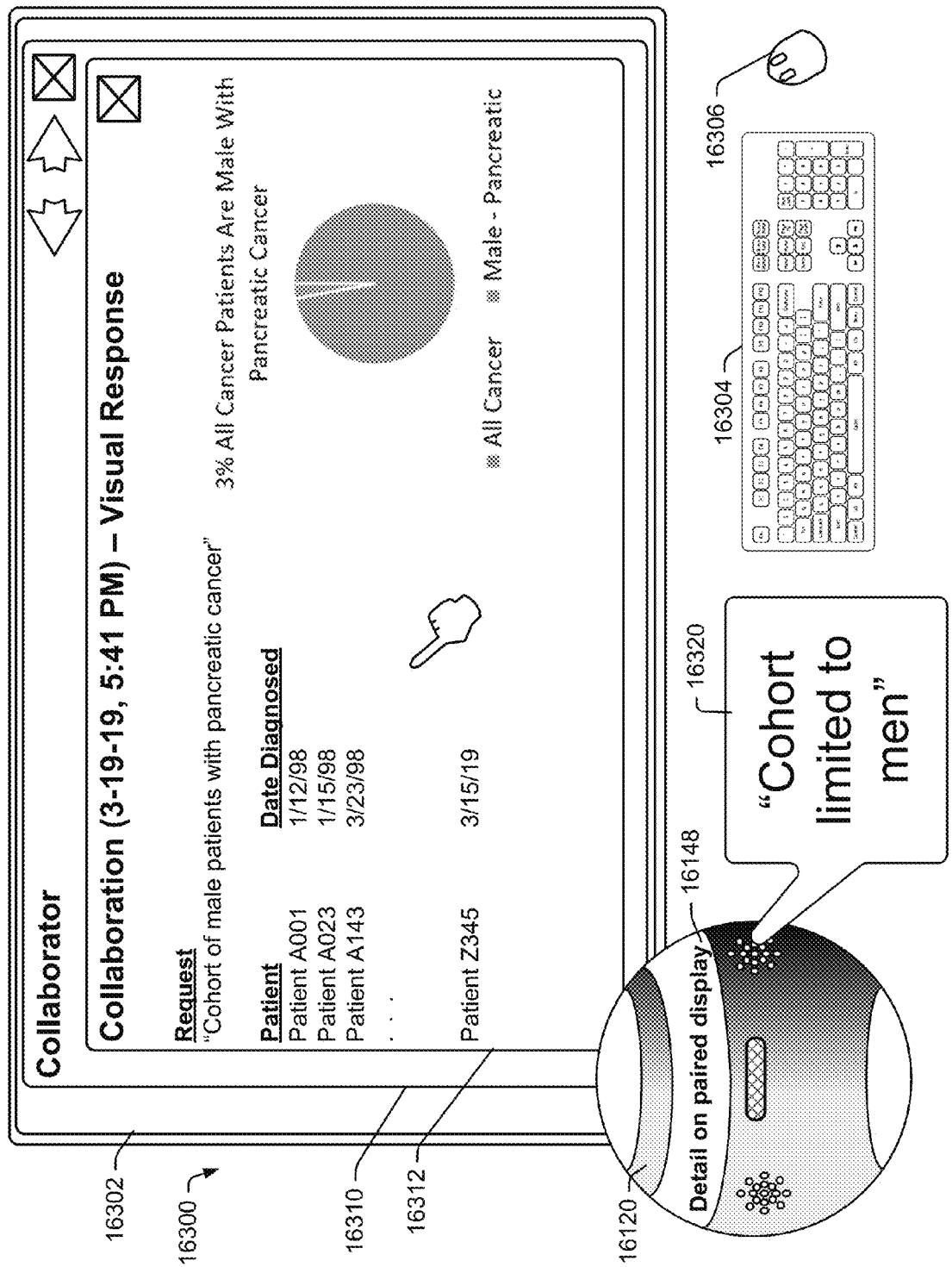
Figure 413:
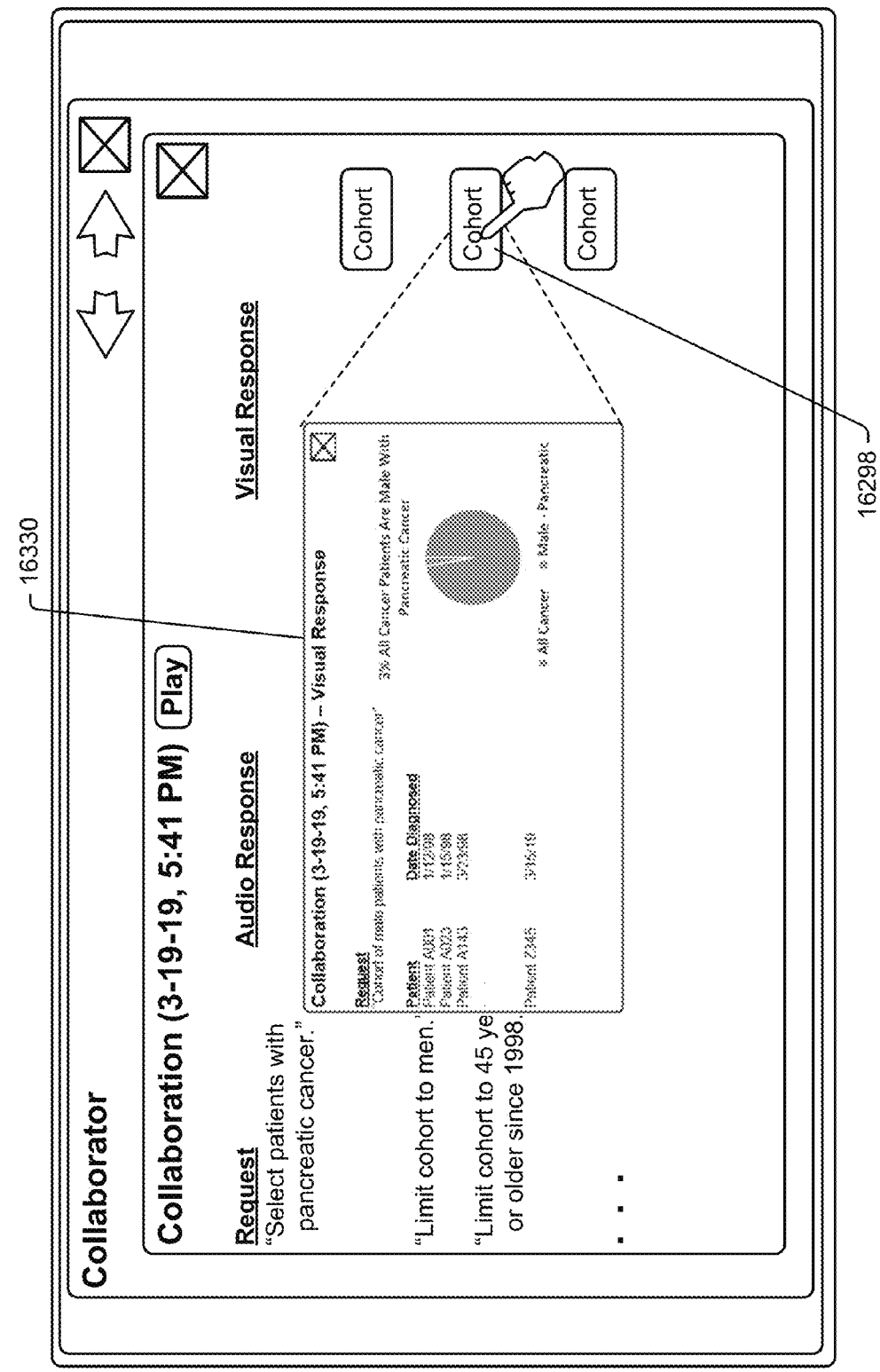
Figure 414:
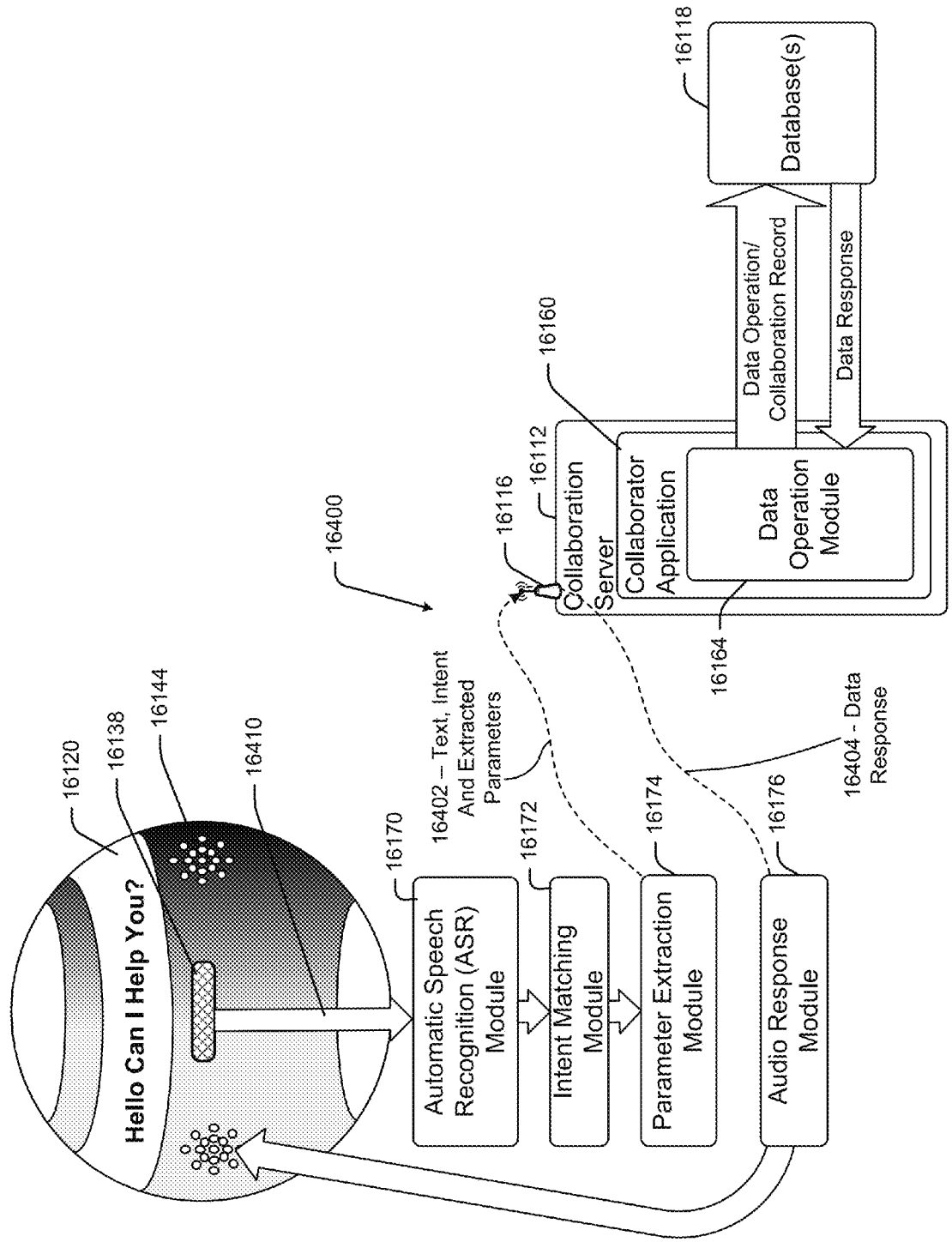
Figure 415:
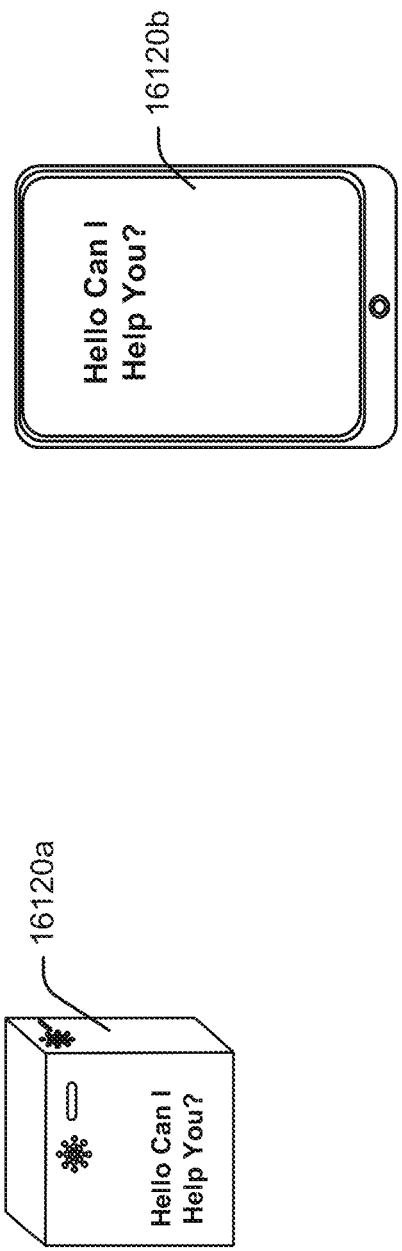
Figure 416:
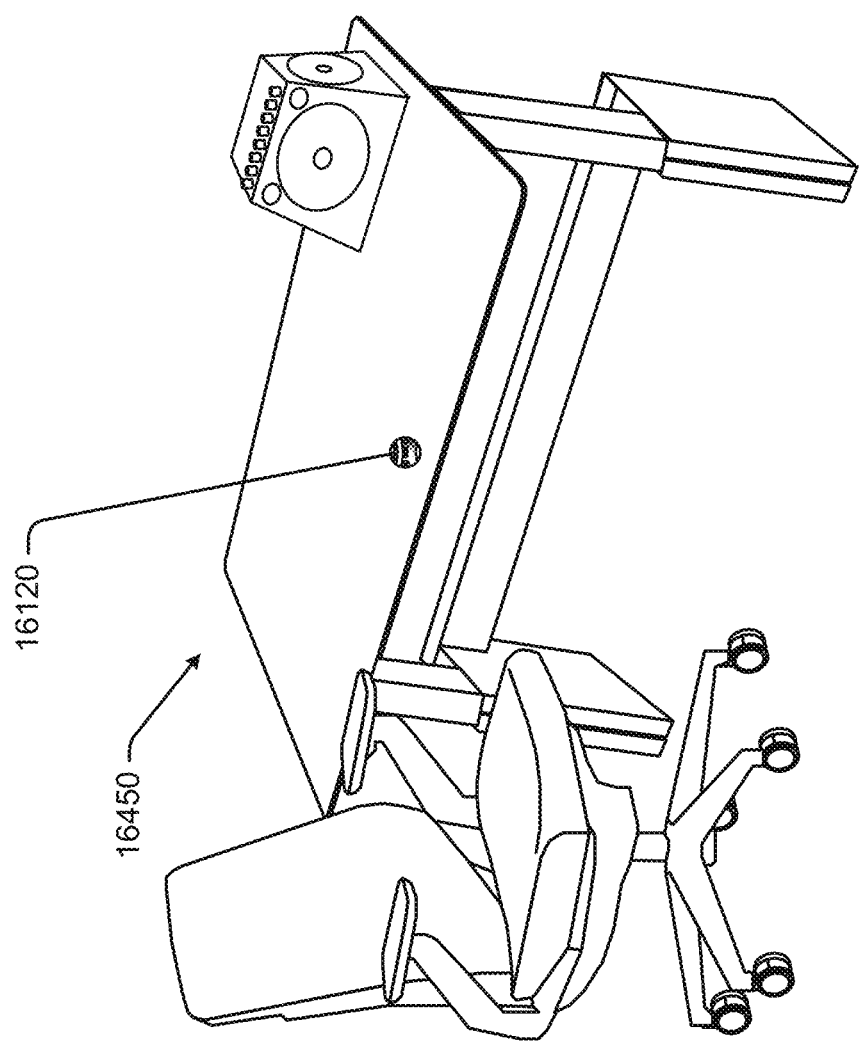
Figure 417:
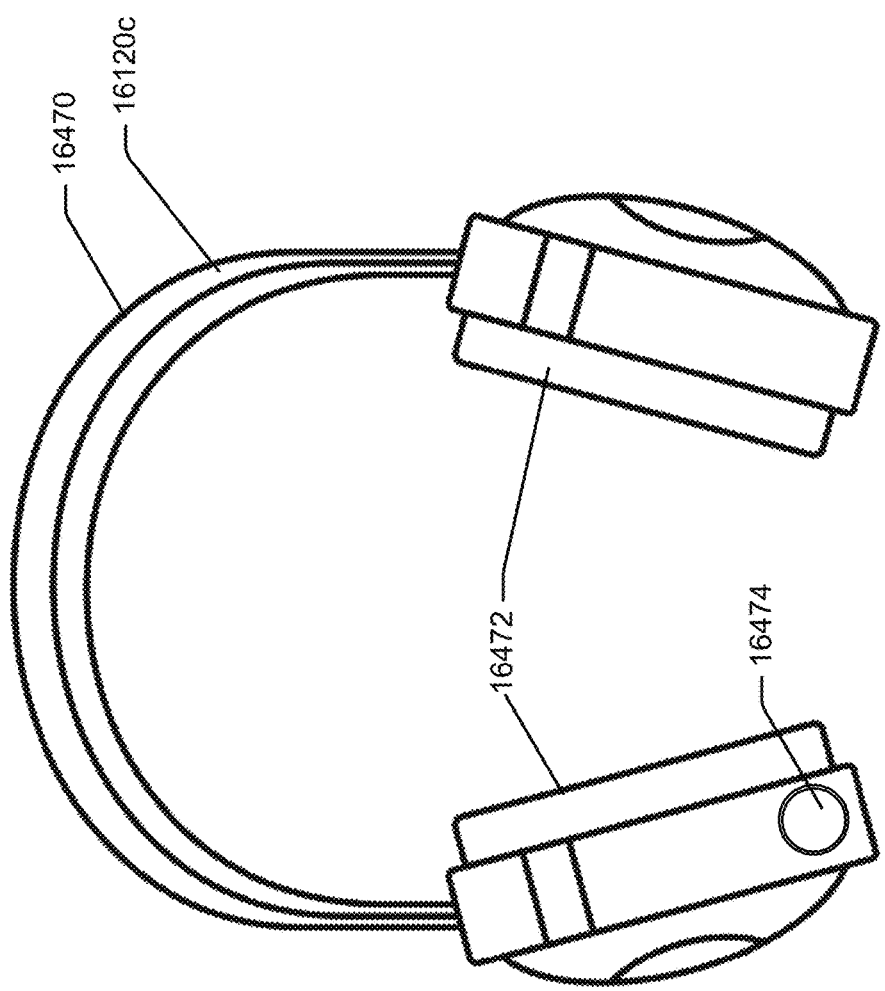
Figure 418A:
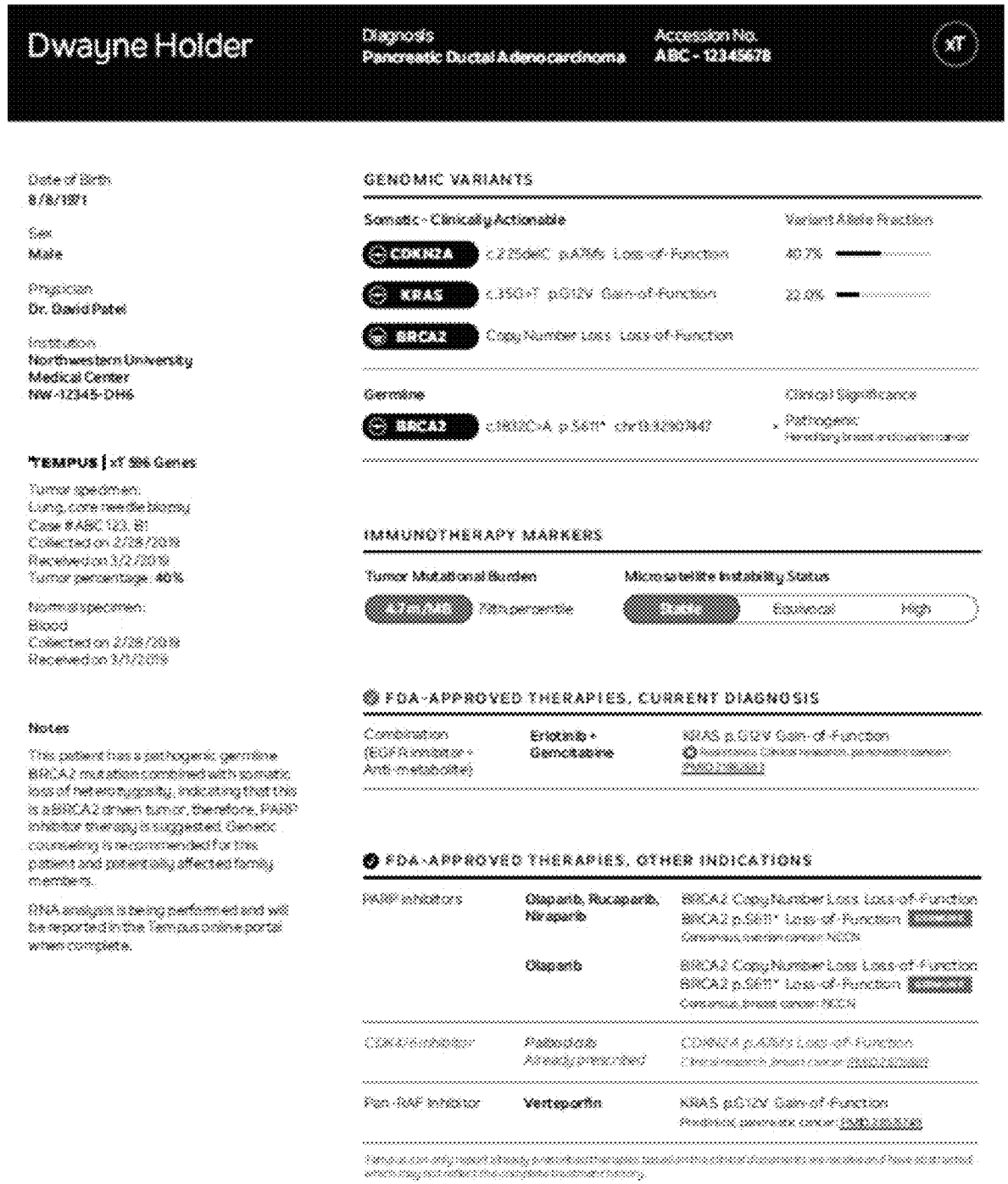
Figure 418C:
Figure 419:
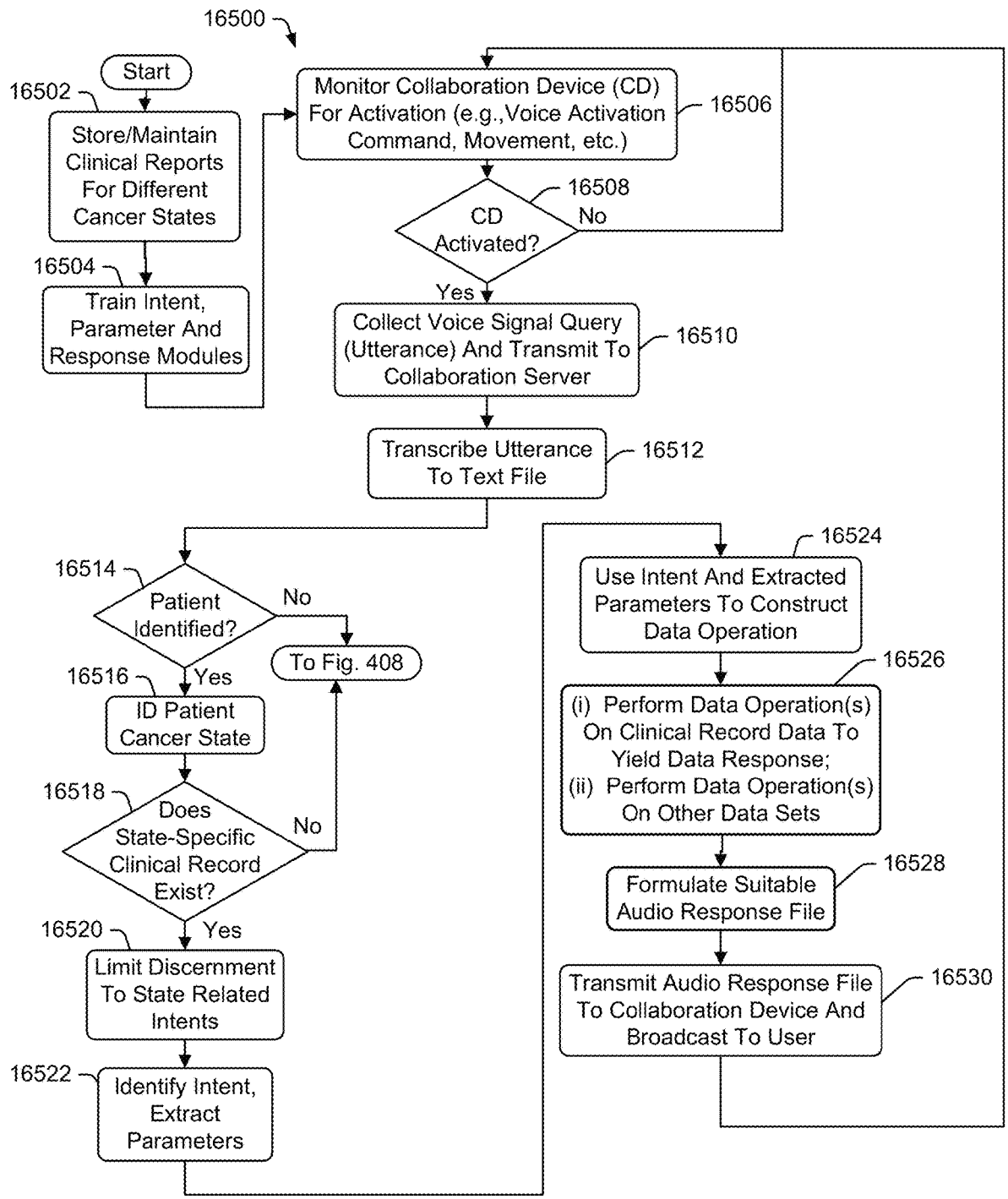
Figure 420:
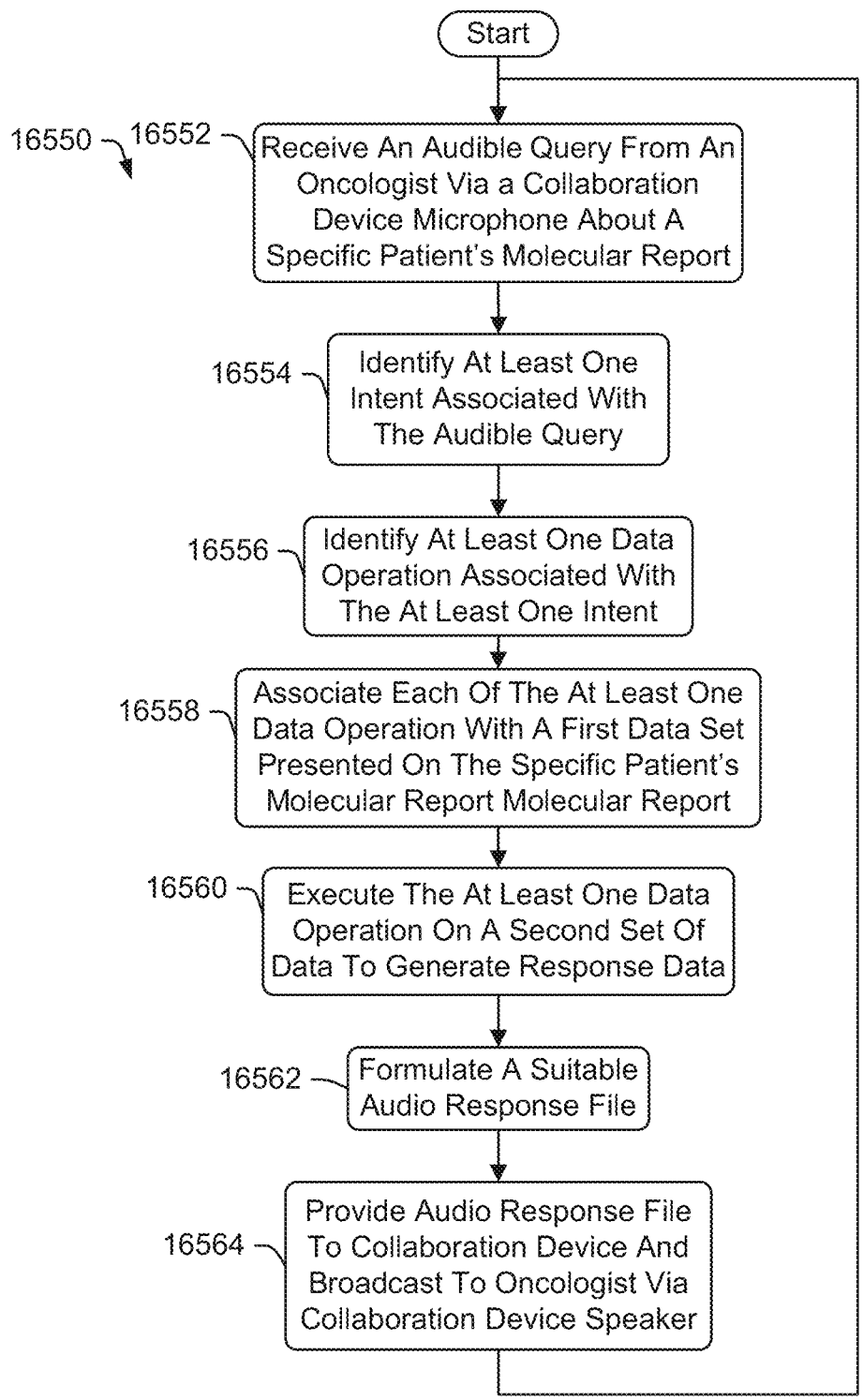
Figure 421:
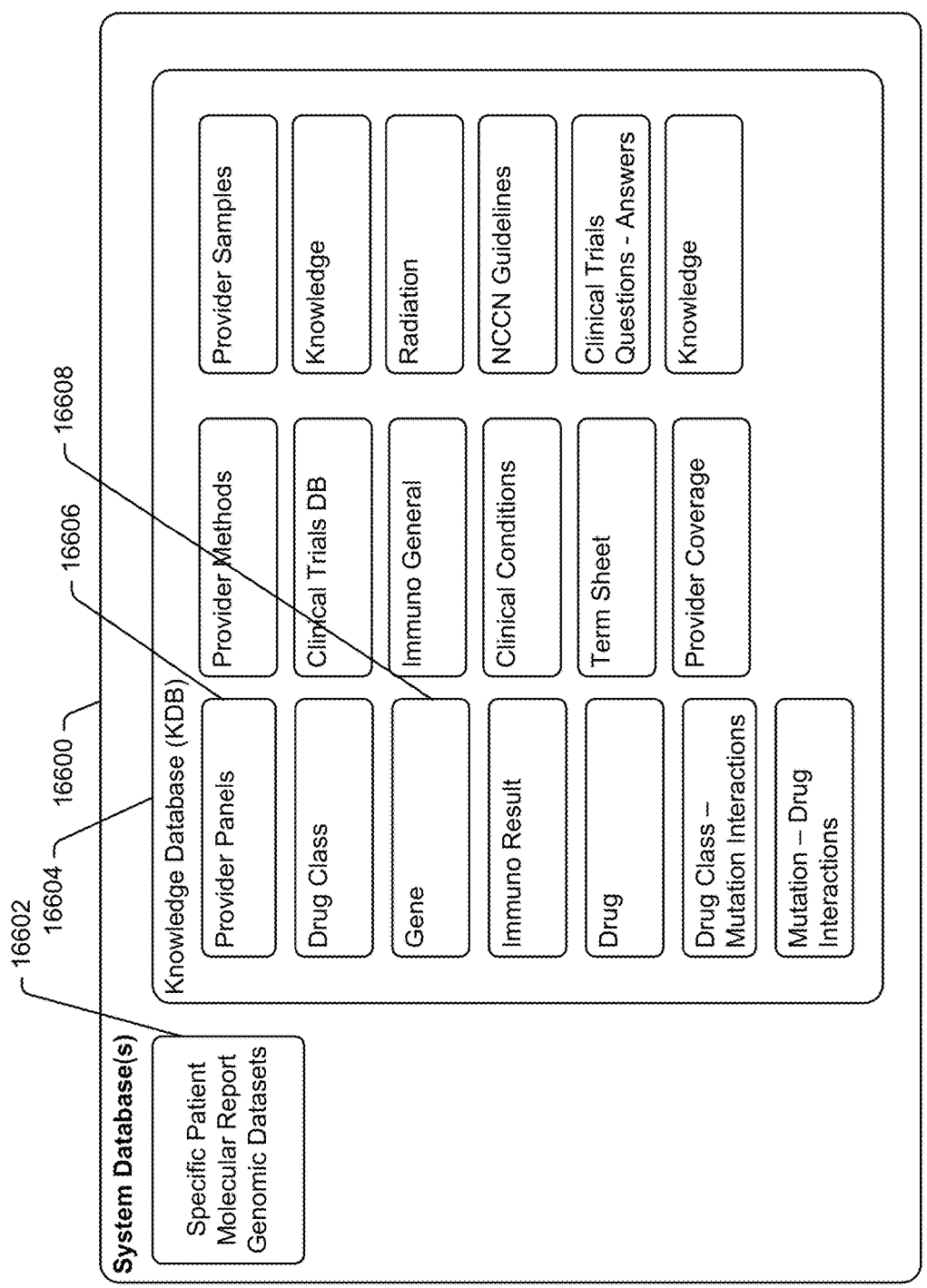
Figure 422:
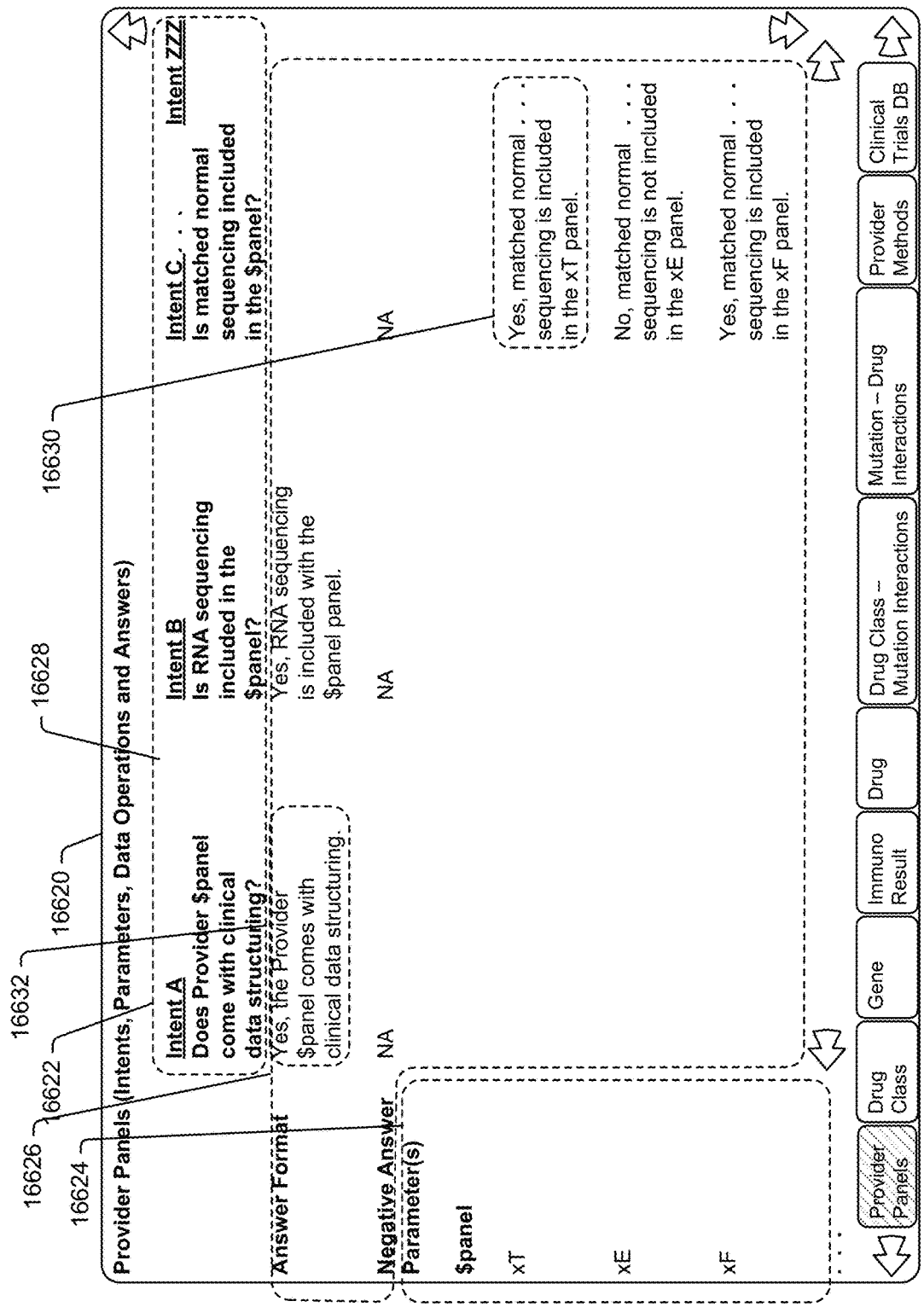
Figure 423:
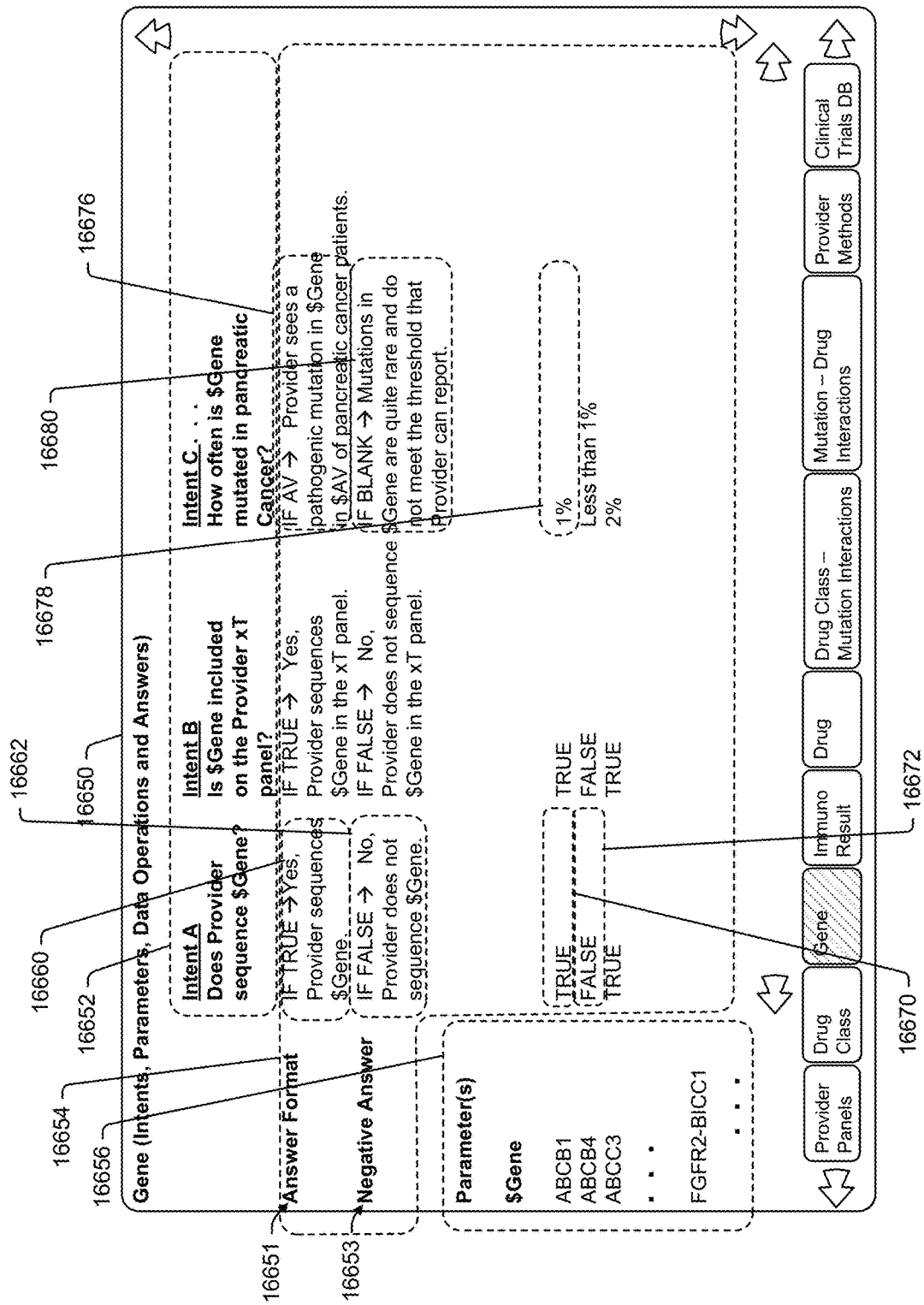
Figure 424:
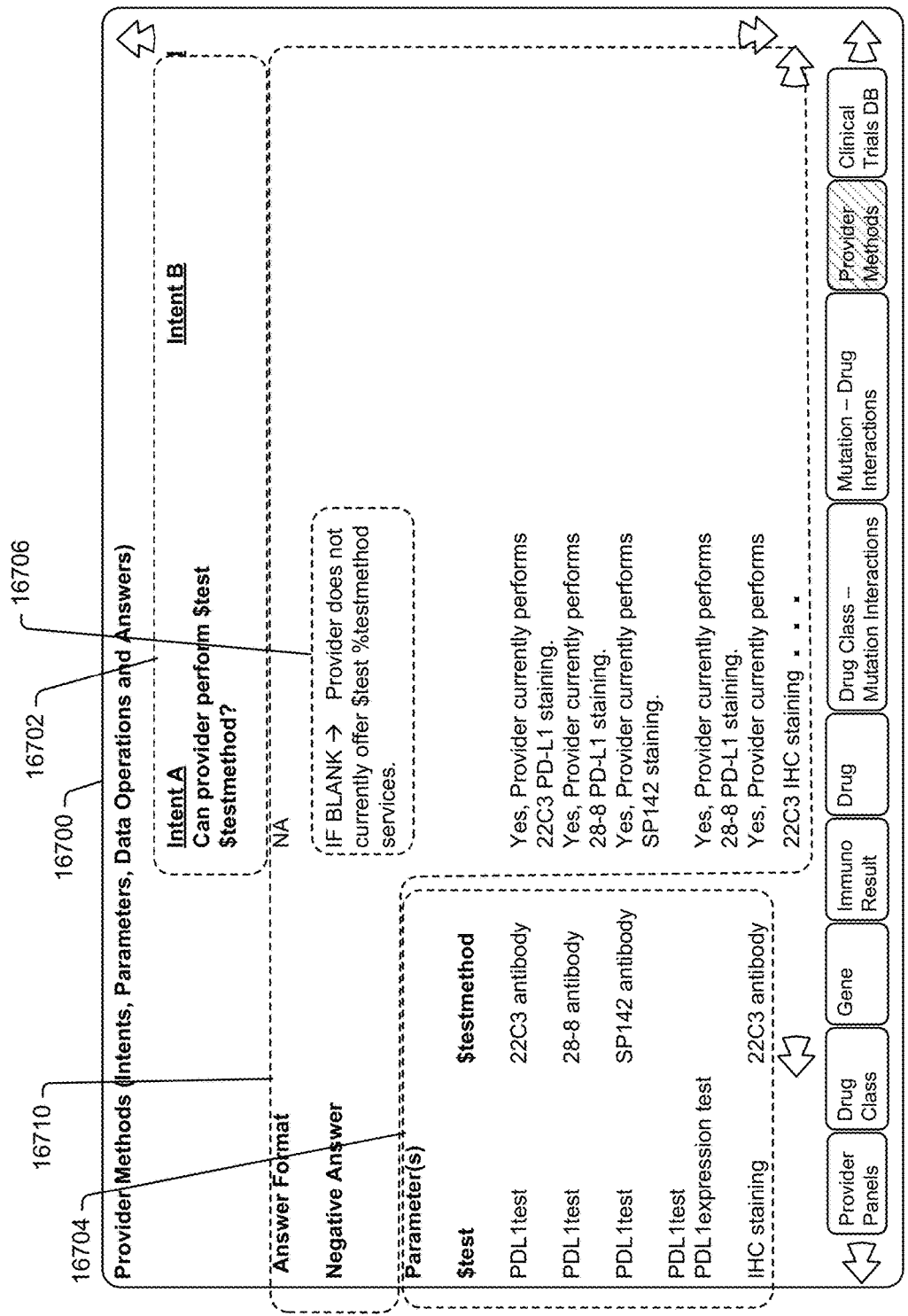
Figure 425:
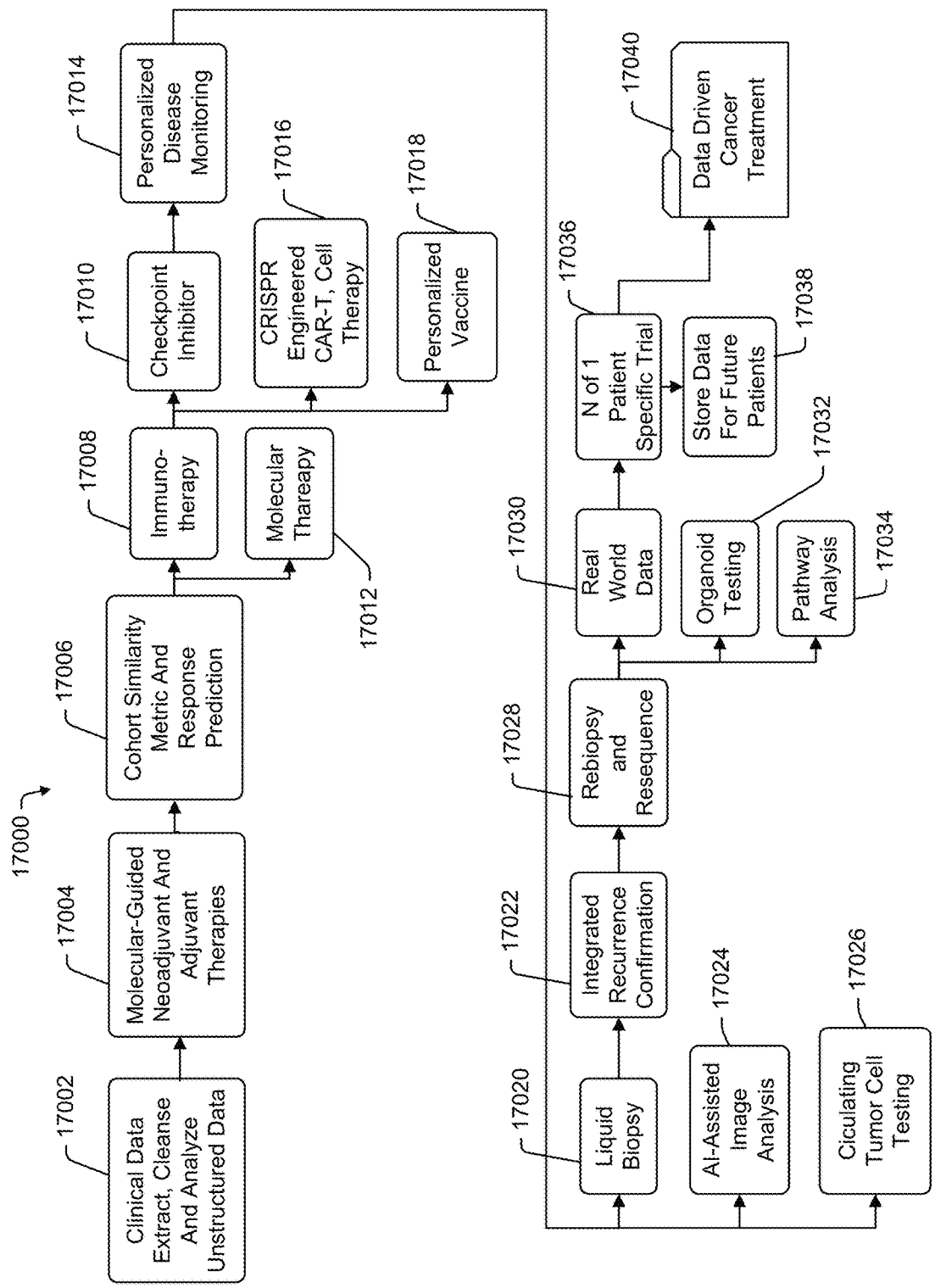
Figure 426:
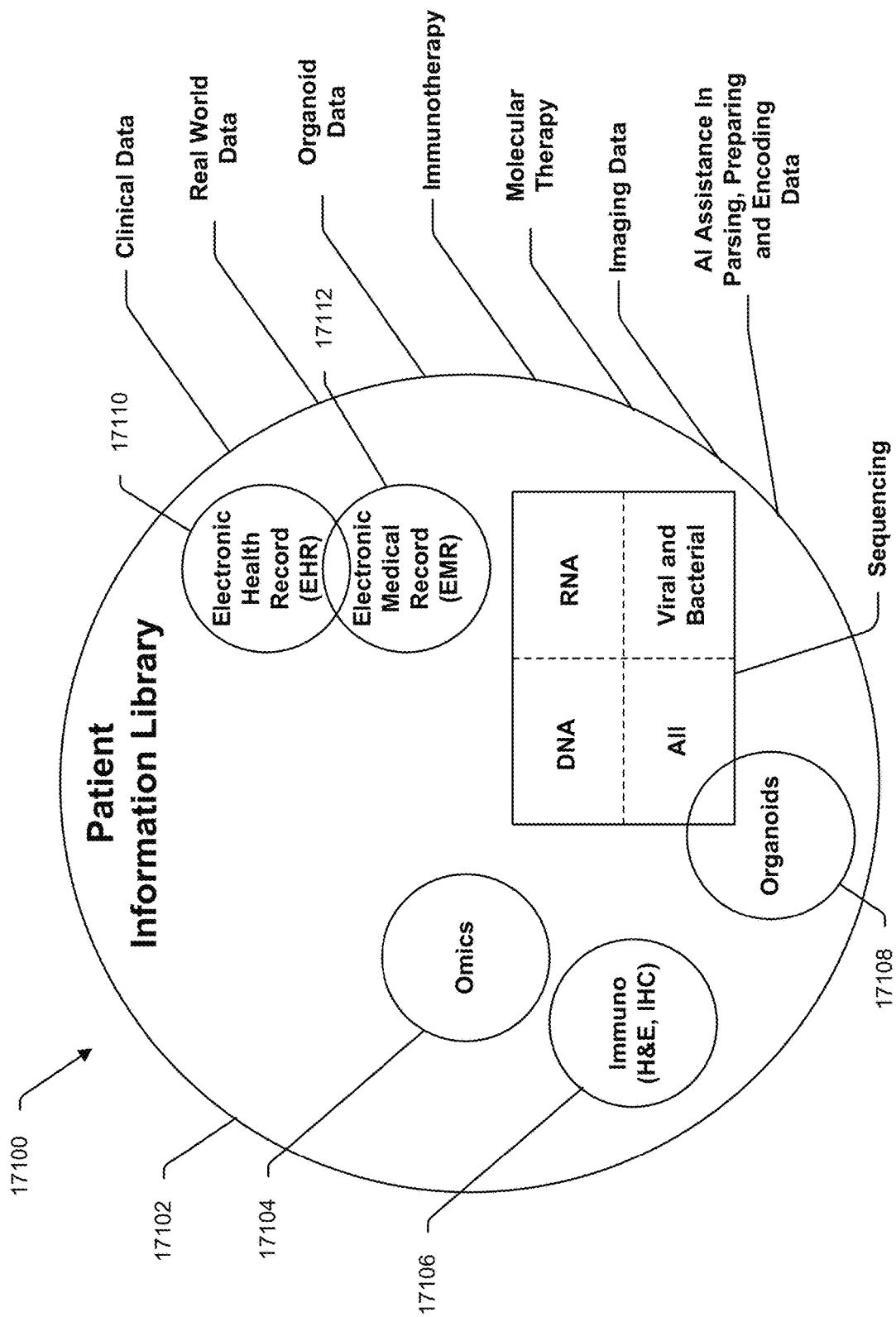
Figure 427:
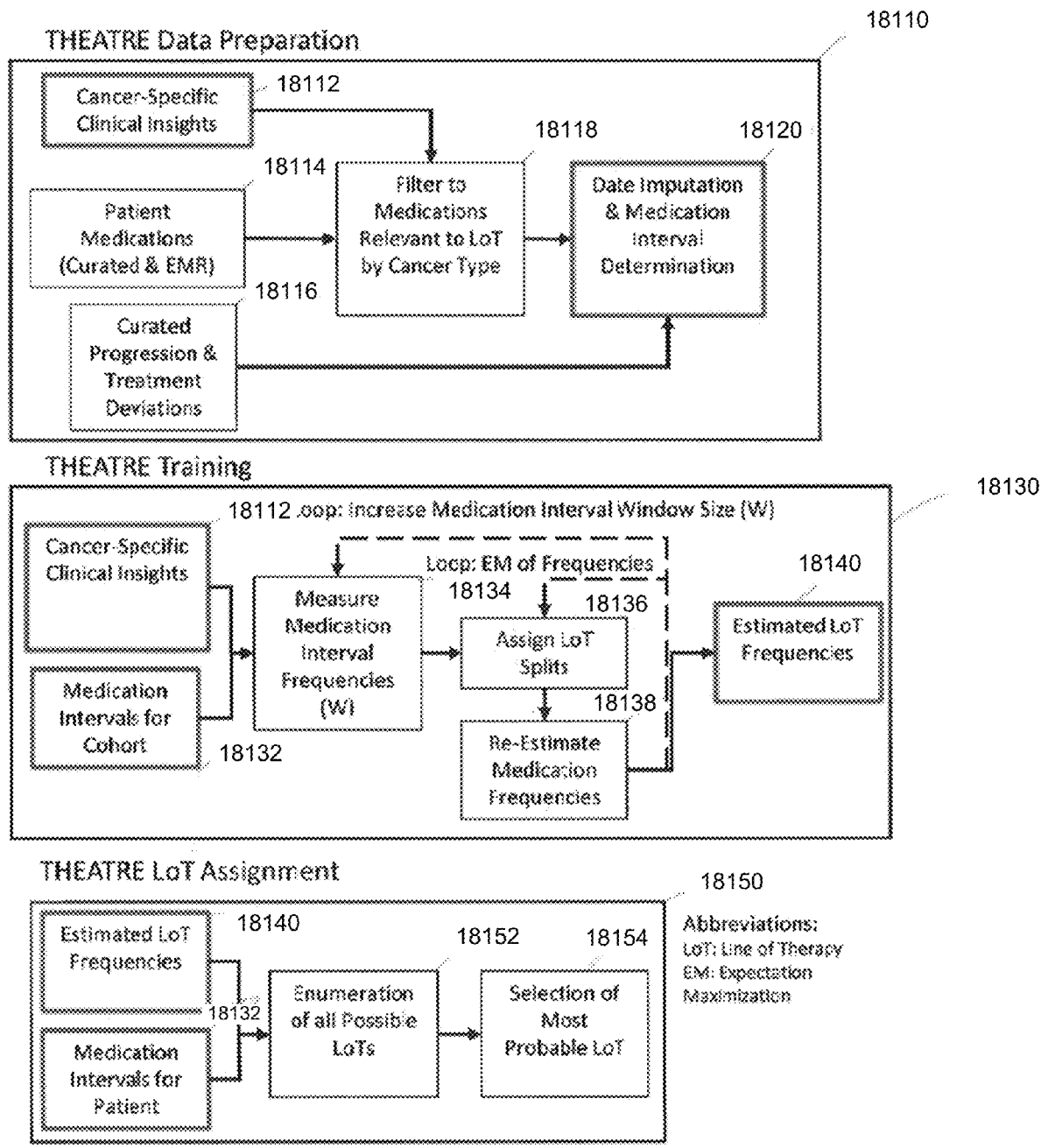
Figure 428:
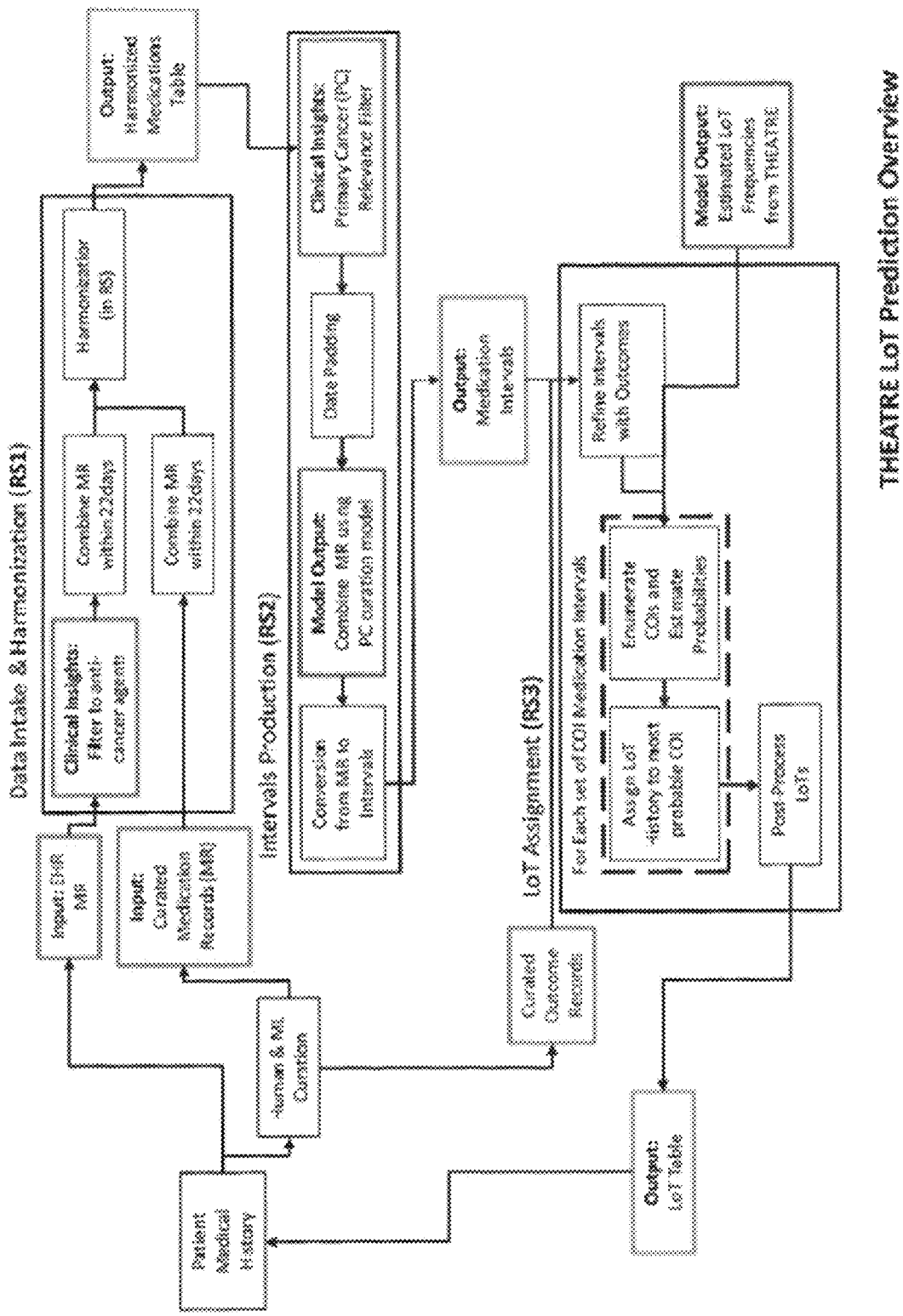
Figure 429:
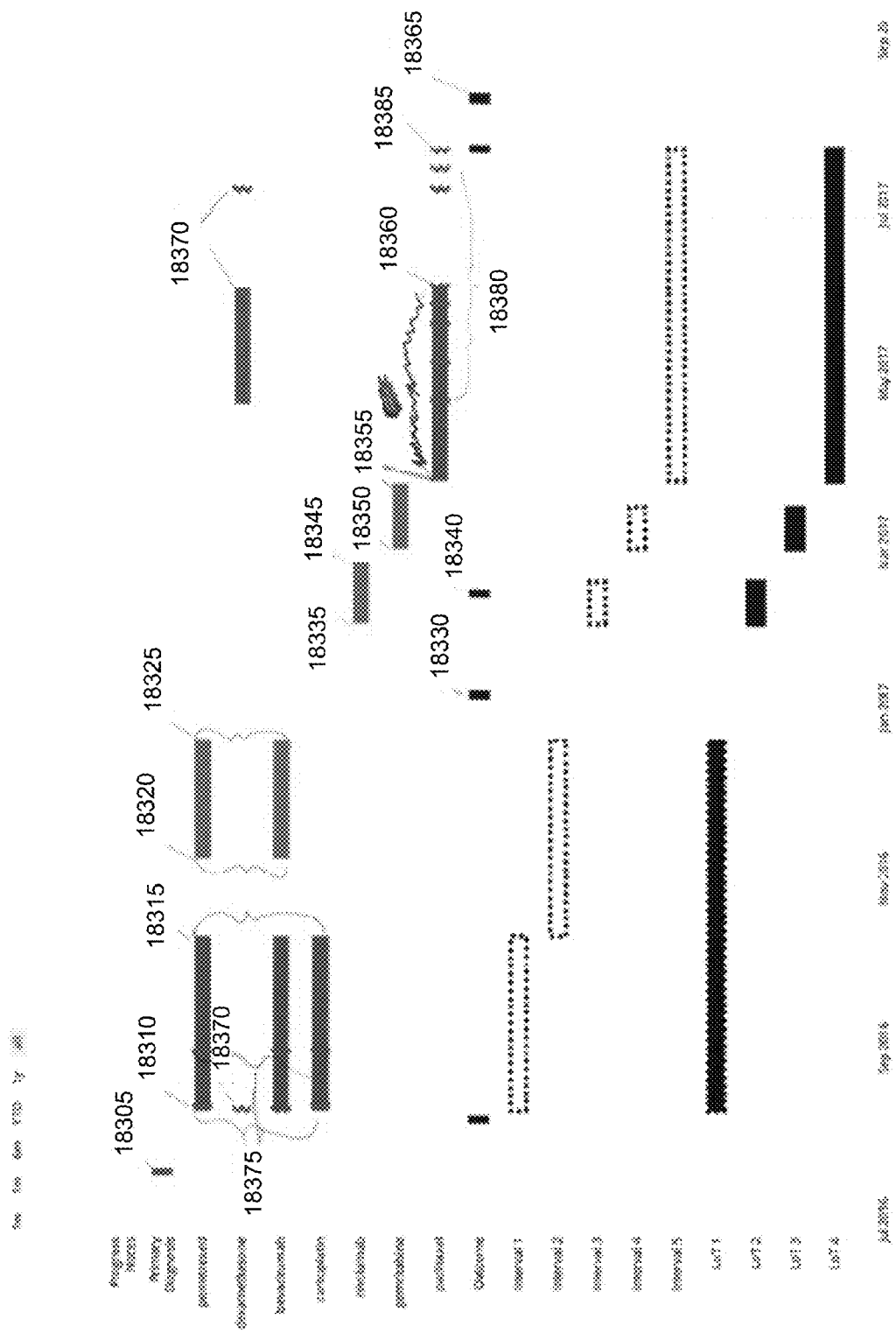
Figure 430:
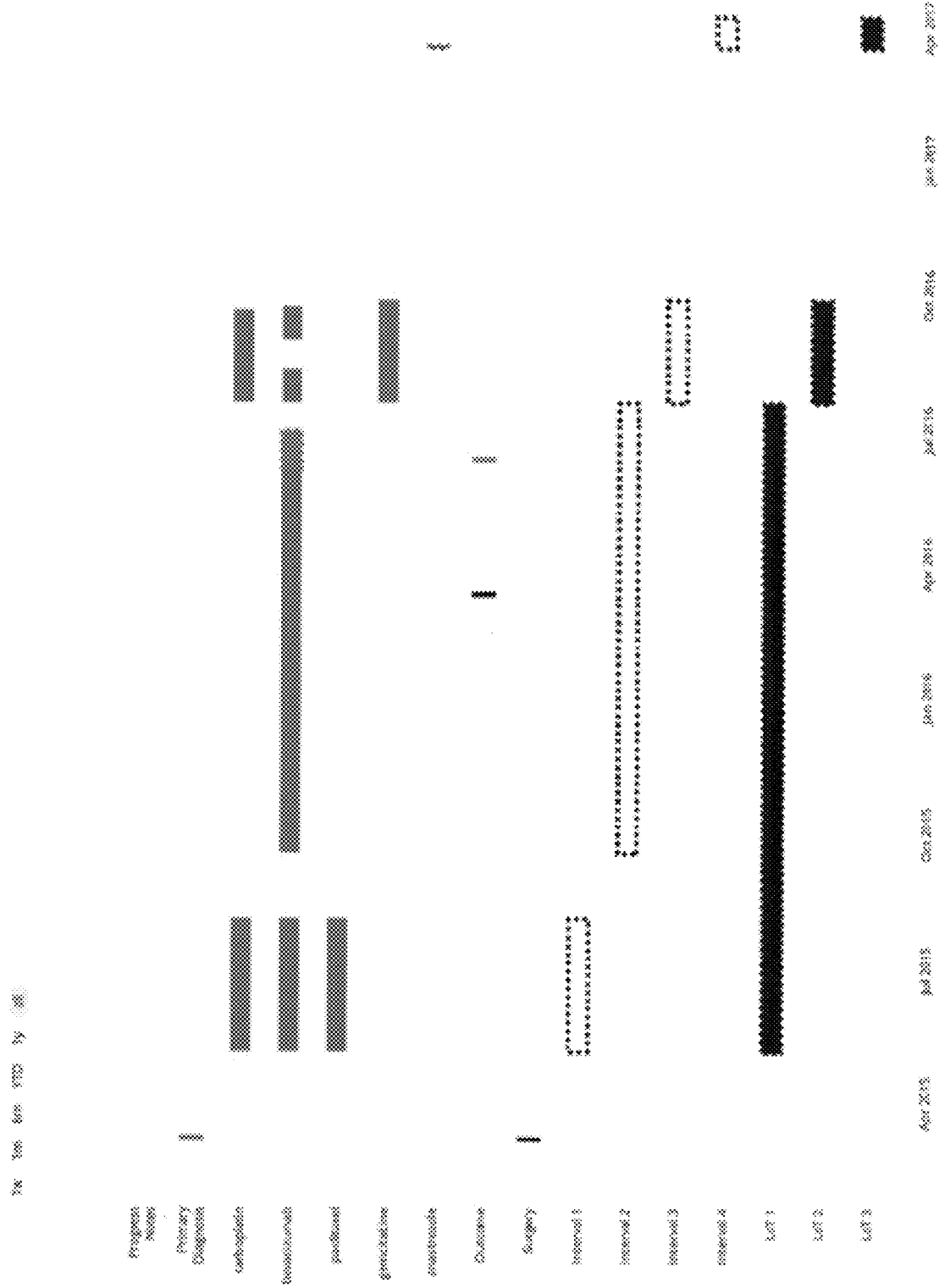
Figure 431:
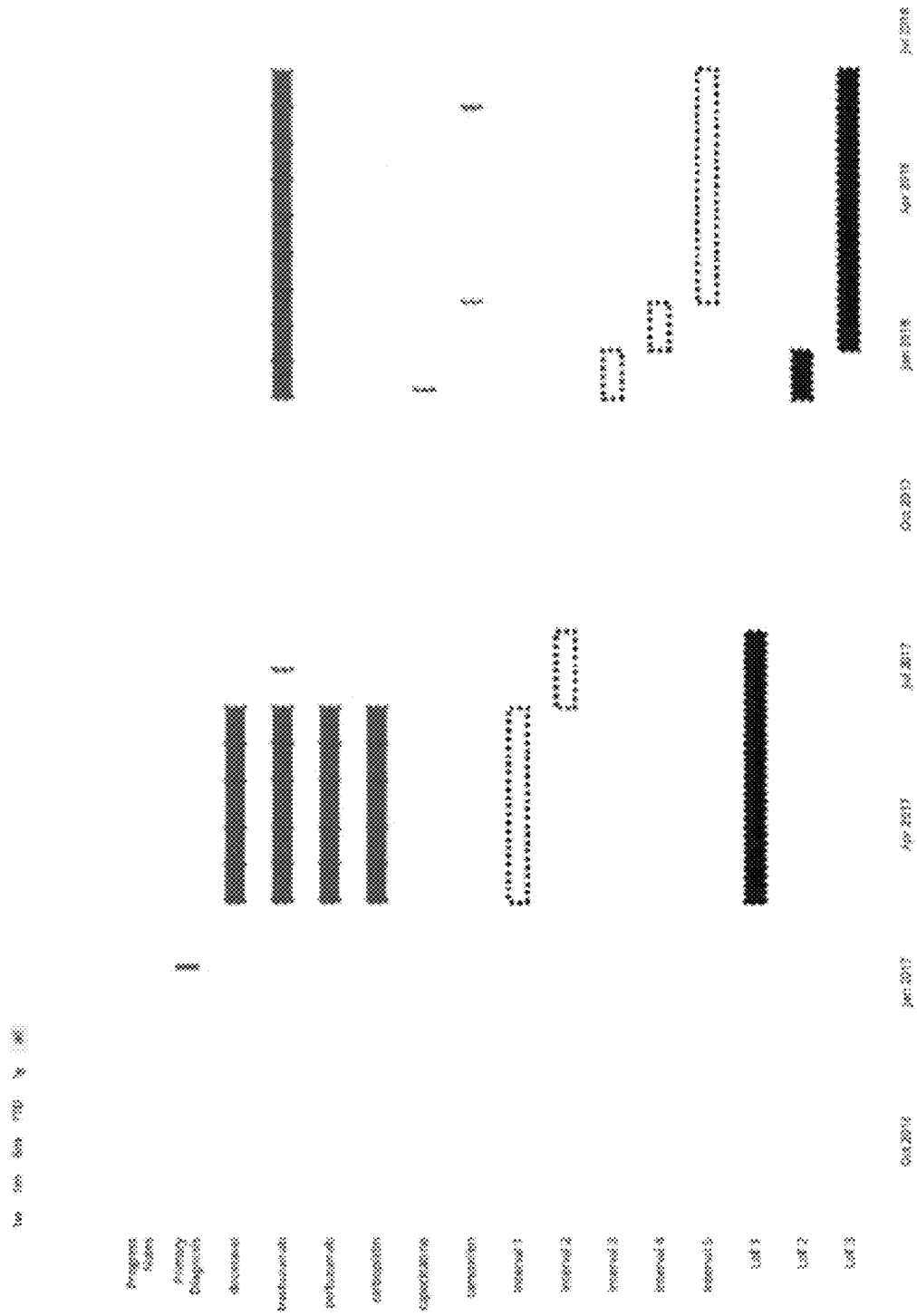

FIG. 406 is a schematic diagram illustrating a collaboration system that is consistent with at least some aspects of the present disclosure that includes a portable wireless collaboration device;

FIG. 407 is a schematic illustrating components of the exemplary collaboration device shown in 1;

FIG. 408 is a flow chart illustrating a collaboration process that is consistent with at least some aspects of the present disclosure;

FIG. 409 is a schematic illustrating a collaboration device user having a conversation with the system of claim 1;

FIG. 410 is a schematic illustrating a workstation usable to access stored collaboration session data;

FIG. 411 is similar to FIG. 410, albeit illustrating another screen shot;

FIG. 412 is a schematic illustrating a portable audible collaboration device being used in conjunction with a workstation including a display;

FIG. 413 is a schematic illustrating another screen shot that is similar to the FIG. 411 view; and FIG. 414 is a schematic illustrating a second collaboration system that is consistent with at least some aspects of the present disclosure, albeit where a portable collaboration device runs AI applications to generate seed data for data operations and also converts data responses to audio response files to be broadcast via the collaboration device;

FIG. 415 shows two additional collaboration device configurations including a cube shaped configuration and a table type configuration;

FIG. 416 is a schematic illustrating a workstation that includes various types of input/output collaboration devices;

FIG. 417 illustrates a headset that may operate as yet another type of input/output audio interface that is consistent with at least some aspects of the present disclosure;

Figure 418B:
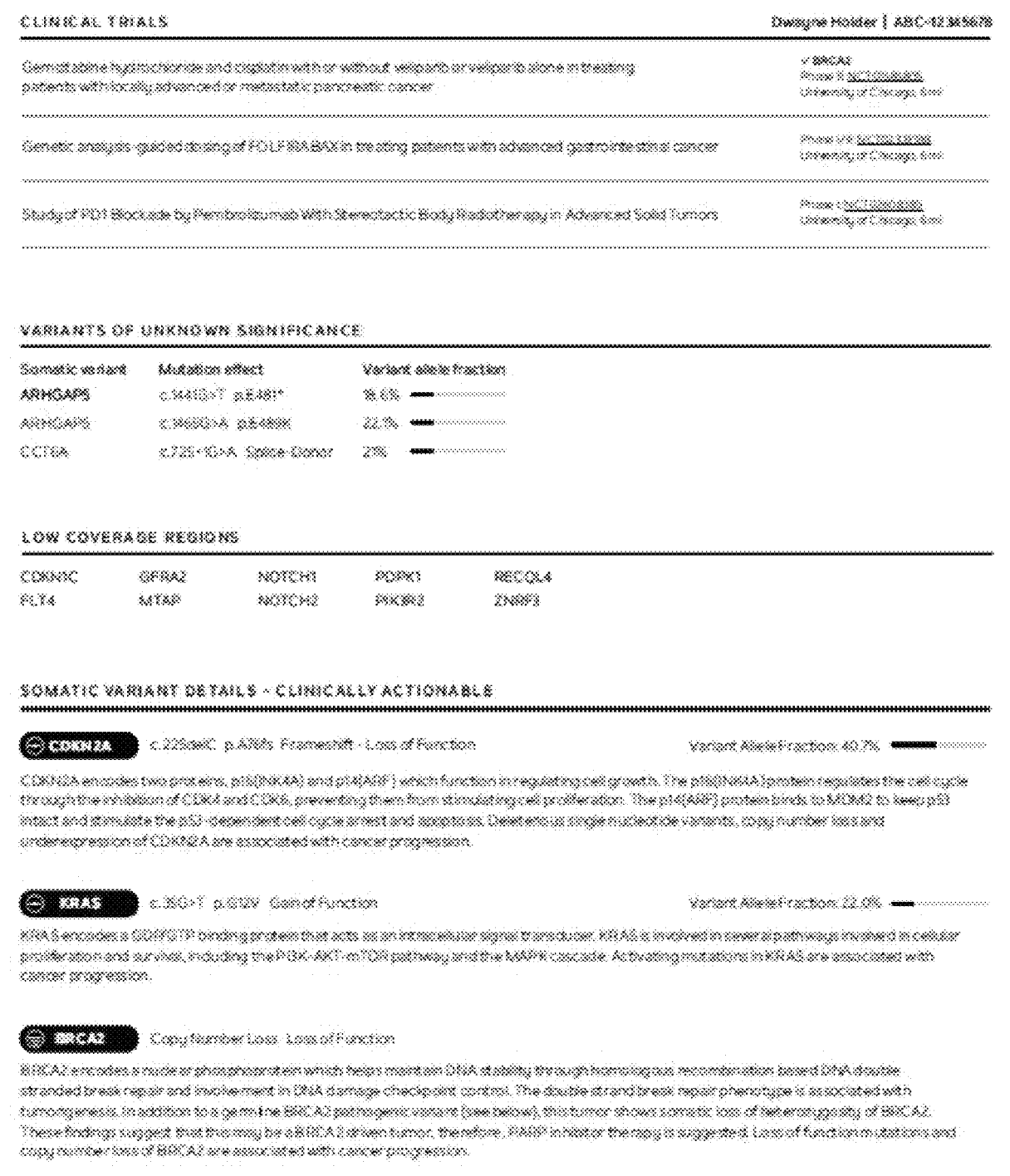

FIGS. 418A-418C are schematics showing a first through third pages of a pancreatic clinical report that may be printed in hardcopy or accessed electronically via a workstation, pad or smart phone device, etc.;

FIG. 419 is a flowchart similar to the chart shown in FIG. 408, albeit where a state-specific clinical record and related intents are used to drive a query process;

FIG. 420 is an audio response process that is consistent with at least some aspects of the present disclosure;

FIG. 421 is a system database that is consistent with at least some aspects of the present disclosure;

FIG. 422 is a screen shot for use by a system administrator for specifying system intents, intent parameters and answer formats for provider panel types that is consistent with at least some aspects of the present disclosure;

FIG. 423 is similar to FIG. 422, albeit including a screen shot for specifying gene specific system information;

FIG. 424 is similar to FIG. 423, albeit including a screen shot for specifying provider methods;

FIG. 425 is a schematic illustrating an exemplary system that connects different data, medical and diagnostic ecosystems that is consistent with at least some aspects of the present disclosure;

FIG. 426 is a schematic illustrating a patient information sphere model of a database that is consistent with at least some aspects of the present disclosure;

FIG. 427 is a flowchart depicting an embodiment of preparing, training, and generating Line of Therapy (LoT) predictions;

FIG. 428 is a flowchart depicting an embodiment of preparing, training, and generating Line of Therapy (LoT) predictions using a MLA approach with rule-based pre-processing;

FIG. 429 is an illustration of a LoT prediction for a first patient diagnosed with metastatic non-small cell lung cancer;

FIG. 430 is an illustration of a LoT prediction for a second patient diagnosed with ovarian cancer;

FIG. 431 is an illustration of a LoT prediction for a third patient diagnosed with breast cancer; and FIGS. 432A through 432D includes lists of exemplary physician questions and answers that may be supported by a collaboration device that is consistent with at least some aspects of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE DISCLOSURE

I. Data Based Cancer Research and Treatment Systems and Methods

The various aspects of the subject invention are now described with reference to the annexed drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

The phrase "Allelic Fraction" or "AF" will be used to refer to the percentage of reads supporting a candidate variant divided by a total number of reads covering a candidate locus.

The phrase "base pair" or "bp" will be used to refer to a unit consisting of two nucleobases bound to each other by hydrogen bonds. The size of an organism's genome is measured in base pairs because DNA is typically double stranded.

The phrase "Single Nucleotide Polymorphism" or "SNP" will be used to refer to a variation within a DNA sequence with respect to a known reference at a level of a single base pair of DNA.

The phrase "insertions and deletions" or "indels" will be used to refer to a variant resulting from the gain or loss of DNA base pairs within an analyzed region.

The phrase "Multiple Nucleotide Polymorphism" or "MNP" will be used to refer to a variation within a DNA sequence with respect to a known reference at a level of two or more base pairs of DNA, but not varying with respect to total count of base pairs. For example an AA to CC would be an MNP, but an AA to C would be a different form of variation (e.g., an indel).

The phrase "Copy Number Variation" or "CNV" will be used to refer to the process by which large structural changes in a genome associated with tumor aneuploidy and other dysregulated repair systems are detected. These processes are used to detect large scale insertions or deletions of entire genomic regions. CNV is defined as structural insertions or deletions greater than a certain base pair ("bp") in size, such as 500 bp.

The phrase "Germline Variants" will be used to refer to genetic variants inherited from maternal and paternal DNA. Germline variants may be determined through a matched tumor-normal calling pipeline.

The phrase "Somatic Variants" will be used to refer to variants arising as a result of dysregulated cellular processes associated with neoplastic cells. Somatic variants may be detected via subtraction from a matched normal sample.

The phrase "Gene Fusion" will be used to refer to the product of large scale chromosomal aberrations resulting in the creation of a chimeric protein. These expressed products can be non-functional, or they can be highly over or under active. This can cause deleterious effects in cancer such as hyper-proliferative or anti-apoptotic phenotypes.

The phrase "RNA Fusion Assay" will be used to refer to a fusion assay which uses RNA as the analytical substrate. These assays may analyze for expressed RNA transcripts with junctional breakpoints that do not map to canonical regions within a reference range.

The term "Microsatellites" refers to short, repeated sequences of DNA.

The phrase "Microsatellite instability" or "MSI" refers to a change that occurs in the DNA of certain cells (such as tumor cells) in which the number of repeats of microsatellites is different than the number of repeats that was in the DNA when it was inherited. The cause of microsatellite instability may be a defect in the ability to repair mistakes made when DNA is copied in the cell.

"Microsatellite Instability-High" or "MSI-H" tumors are those tumors where the number of repeats of microsatellites in the cancer cell is significantly different than the number of repeats that are in the DNA of a benign cell. This phenotype may result from defective DNA mismatch repair. In MSI PCR testing, tumors where 2 or more of the 5 microsatellite markers on the Bethesda panel are unstable are considered MSI-H.

"Microsatellite Stable" or "MSS" tumors are tumors that have no functional defects in DNA mismatch repair and have no significant differences in microsatellite regions between tumor and normal tissue.

"Microsatellite Equivocal" or "MSE" tumors are tumors with an intermediate phenotype that cannot be clearly classified as MSI-H or MSS based on the statistical cutoffs used to define those two categories.

The phrase "Limit of Detection" or "LOD" refers to the minimal quantity of variant present that an assay can reliably detect. All measures of precision and recall are with respect to the assay LOD.

The phrase "BAM File" means a (B)inary file containing (A)lignment (M)aps that include genomic data aligned to a reference genome.

The phrase "Sensitivity of called variants" refers to a number of correctly called variants divided by a total number of loci that are positive for variation within a sample.

The phrase "specificity of called variants" refers to a number of true negative sites called as negative by an assay divided by a total number of true negative sites within a sample. Specificity can be expressed as (True negatives)/(True negatives+false positives).

The phrase "Positive Predictive Value" or "PPV" means the likelihood that a variant is properly called given that a variant has been called by an assay. PPV can be expressed as (number of true positives)/(number of false positives+number of true positives).

The disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Unless indicated otherwise, while the disclosed system is used for many different purposes (e.g., data collection, data analysis, treatment, research, etc.), in the interest of simplicity and consistency, the overall disclosed system will be referred to hereinafter as "the disclosed system".

A. System Overview

Referring first to FIG. 425, a high level system functions diagram 17000 that is consistent with at least aspects of the present disclosure is shown. As illustrated, an initial system function 17002 includes extracting, cleansing and analyzing unstructured clinical patient data. Referring also to FIG. 426, the patient data is stored in a library 17100 and includes Omics 17104, Immuno 17106 and organoid data 17108 as well as genomic sequencing data, electronic health records 17110 and electronic medical records 17112. All data generated by the functions shown in FIG. 425 is stored in the library 17102 for subsequent system access.

Referring again to FIG. 425, at 17004 a system processor uses molecular data to assess likely efficacy of neoadjuvant (i.e., administered prior to main therapy) and adjuvant (i.e., administered in parallel with main therapies) therapies for a patient and may use the Tempus COHORT system at 17006

(described hereafter) to predict responses to different therapies based on efficacy with prior patients that had a similar cancer state and to present results to an attending physician.

At 17008 and 17012 immunotherapy and molecular therapies are administered to a patient, respectively. At 17010 checkpoint inhibitors are administered. At 17016 XRISPR engineered CAR-T (Chimeric antigen receptor T cell) and other cell therapies are applied and at 17018 patient personalized vaccine is administered. At 17014, disease monitoring takes place including imaging, biopsy studies and cancer state detection and analysis.

Referring still to FIG. 425 at 17020, a liquid biopsy is obtained, at 17024 AI assisted image analysis is performed and at 17026 circulating tumor cell testing (e.g., testing for cells that have shed into the vasculature or lymphatics from a primary tumor and are carried around the body in circulating blood) is performed.

At 17022 a patient's recurring cancer state is assessed. At 17028 a tumor and healthy tissue are re-biopsied and resequenced. At 17030, real world data is collected about the patient's cancer state. At 17032 organoids (e.g., grown tumor sections from the biopsy) are grown and tested and at 17034 pathway analysis is performed. At 17036, for a specific patient, an N of 1 trial is performed and resulting data is stored for use in helping dial future treatments in for future patients with similar cancer states. At 17040 a patient specific data driven cancer treatment is prescribed for a specific patient.

Figure 1:
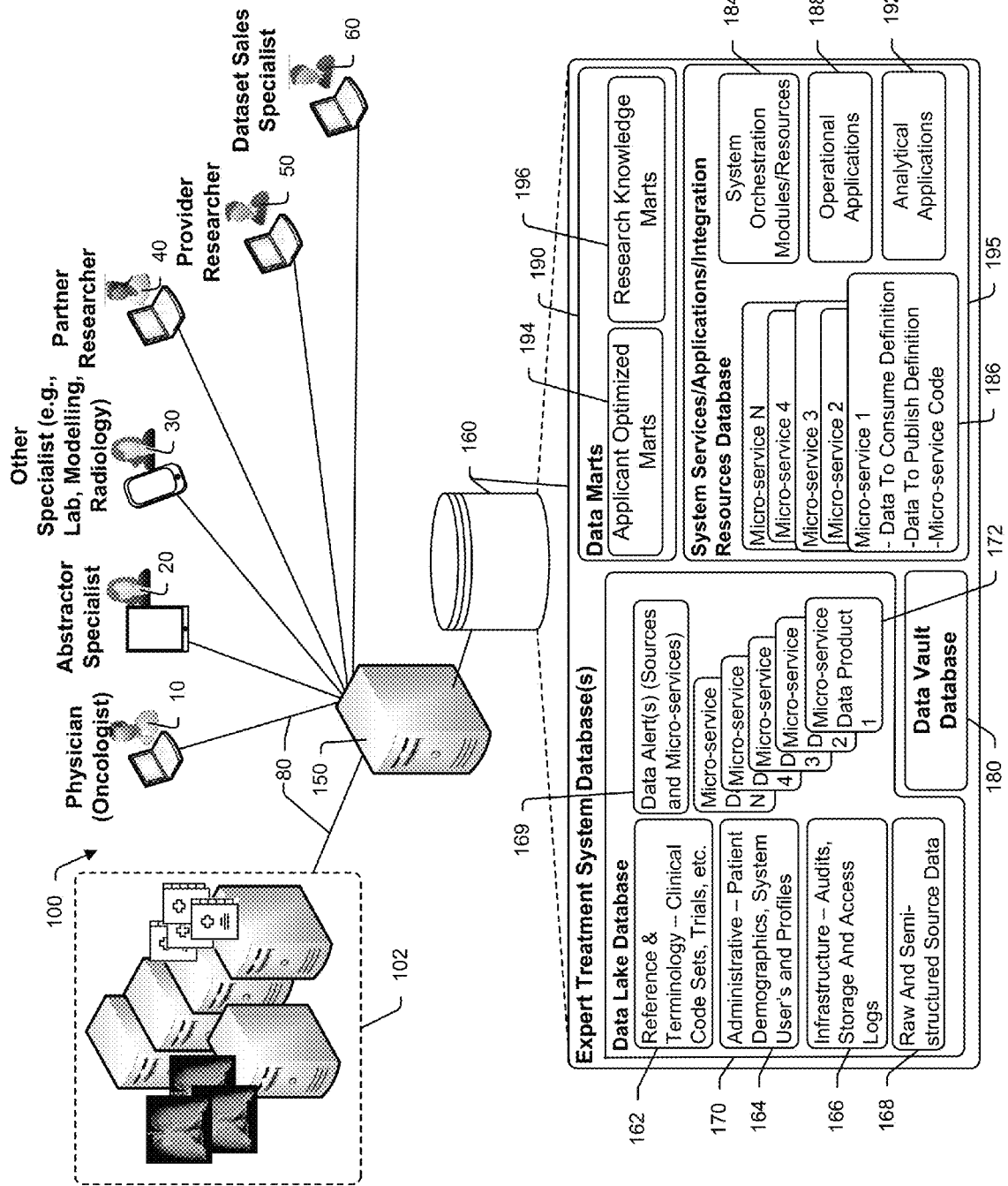
FIG. 1 is a schematic diagram illustrating a computer and communication system that is consistent with at least some aspects of the present disclosure.

Referring now to the figures that accompany this written description and more specifically referring to FIG. 1, the present disclosure will be described in the context of an exemplary system 100 where data is received at a system server 150 from many different data sources 102, is stored in a database 160, is manipulated in many different ways by internal system micro-service programs to condition or "shape" the data to generate new interim data or to structure data in different structured formats for consumption by user application programs and to then drive the user application programs to provide user interfaces via any of several different types of user interface devices. While a single server 150 and a single database 160 are shown in FIG. 1 in the interest of simplifying this explanation, it should be appreciated that in most cases, the system 100 will include a plurality of distributed servers and databases that are linked via local and/or wide area networks and/or the Internet or some other type of communication infrastructure. An exemplary simplified communication network is labelled 80 in FIG. 1. Network connections can be any type including hard wired, wireless, etc., and may operate pursuant to any suitable communication protocols.

The disclosed system 10 enables many different system clients to securely link to server 150 using various types of computing devices to access system application program interfaces optimized to facilitate specific activities performed by those clients. For instance, in FIG. 1 a physician 10 is shown using a laptop computer (not labelled) to link to server 150, an abstractor specialist 20 is shown using a tablet type computing device to link, another specialist 30 is shown using a smartphone device to link to server 150, etc. Other types of personal computing devices are contemplated including virtual and augmented reality headsets, projectors, wearable devices (e.g., a smart watch, etc.). FIG. 1 shows other exemplary system users linked to server 150 including a partner researcher 40, a provider researcher 50 and a data sales specialist 60, all of which are shown using laptop computers.

In at least some embodiments when a physician uses system 100, a physician's user interface(s) is optimally designed to support typical physician activities that the system supports including activities geared toward patient treatment planning. Similarly, when a researcher like a pathologist or a radiologist uses system 100, interfaces optimally designed to support activities performed by those system clients are provided.

System specialists (e.g. employees of the provider that controls/maintains overall system 100) also use interface computing devices to link to server 150 to perform various processes and functions. In FIG. 1 exemplary system specialists include abstractor 20, the dataset sales specialist 60 and a "general" specialist 30 referred to as a "lab, modeling, radiology" specialist to indicate that the system accommodates many different additional specialist types. Different specialists will use system 100 to perform many different functions where each specialist requires specific skill sets needed to perform those functions. For instance, abstractor specialists are trained to ingest clinical records from sources 102 and convert that data to normalized and system optimized structured data sets. A lab specialist is trained to acquire and process non-tumorous patient and/or tumor tissue samples, grow organoids, generate one or both of DNA and RNA genomic data for one or each of non-tumorous and tumorous tissue, treat organoids and generate results. Other specialists are trained to assess treatment efficacy, perform data research to identify new insights of various types and/or to modify the existing system to adapt to new insights, new data types, etc. The system interfaces and tool sets available to provider specialists are optimized for specific needs and tasks performed by those specialists.

Referring yet again to FIG. 1, system database 160 includes several different sub-databases including, in at least some embodiments, a data lake database 170 (hereinafter "the lake database"), a data vault database 180, a data marts database 190 and a system services/applications and integration resource database 195. While database 195 is shown to includes several different types of information as well as system programs, in other cases one or each of the sets of information or programs in database 195 may be stored in a different one of the databases 170, 180 or 190. In general, data lake database 170 is used to store several different data types including system reference data 162, system administration data 164, infrastructure data 166, raw source data 168 and micro-service data products 172 (e.g., data generated by micro-services).

Reference data 162 includes references and terminology used within data received from source devices 102 when available such as, for instance, clinical code sets, specialized terms and phrases, etc. In addition, reference data 162 includes reference information related to clinical trials including detailed trial descriptions, qualifications, requirements, caveats, current phases, interim results, conclusions, insights, hypothesis, etc.

In at least some cases reference data 162 includes gene descriptions, variant descriptions, etc. Variant descriptions may be incorporated in whole or in part from known sources, such as the Catalogue of Somatic Mutations in Cancer (COSMIC) (Wellcome Sanger Institute, operated by Genome Research Limited, London, England, available at https://cancer.sanger.ac.uk/cosmic). In some cases, reference data 162 may structure and format data to support clinical workflows, for instance in the areas of variant assessment and therapies selection. The reference data 162 may also provide a set of assertions about genes in cancer and evidence-based precision therapy options. Inputs to reference data 162 may include NCCN, FDA, PubMed, conference abstracts, journal articles, etc. Information in the reference data 162 may be annotated by gene; mutation type (somatic, germline, copy number variant, fusion, expression, epigenetic, somatic genome wide, etc.); disease; evidence type (therapeutic, prognostic, diagnostic, associated, etc.); and other notes.

Referring still to FIG. 1, reference data 162 may further comprise gene curation information. A sequencing panel often has a predetermined number of gene profiles that are sequenced as part of the panel. For instance, one type of sequencing panel in the market (i.e., xT, Tempus Labs, Inc, Chicago, Ill.) makes use of 595 gene profiles (see tables in FIG. 27 series of figures) while another makes use of 1711 gene profiles (see tables in FIG. 22 series of figures). Reference data 162 may store a centralized gene knowledge base and comprise variant prioritization and filtering information that may be utilized for Gain of Function (GOF), Loss of Function (LOF), CNV, and fusions. For purposes of precision care, evidence may be annotated based on mutation type and disease; therapeutic evidence may include drug(s) and effect (response, resistance, etc.); prognostic effect may include outcome (favorable, unfavorable, etc.). Therapeutic evidence and prognostic evidence may include evidence source level (preclinical, case study, clinical research, guidelines, etc.). Preclinical information may be from mouse models, PDX, cell lines, etc. Case study information may be from groups of one or more patients. Clinical research may be information from a larger study or results from clinical trials. Guideline information may come from NCCN, WHO, etc.

The administrative data 164 includes patient demographic data as well as system user information including user identifications, user verification information (e.g., usernames, passwords, etc.), constraints on system features usable by specific system users, constraints on data access by users including limitations to specific patient data, data types, data uses, time and other data access limits, etc.

In at least some cases system 100 is designed to memorialize entire life cycles of every dataset or element collected or generated by system 100 so that a system user can recreate any dataset corresponding to any point in time by replicating system processes up to that point in time. Here, the idea is that a researcher or other system user can use this data re-creation capability to verify data and conclusions based thereon, to manipulate interim data products as part of an exploration process designed to test other hypothesis based on system data, etc. To this end, infrastructure data 166 includes complete data storage, access, audit and manipulation logs that can be used to recreate any system data previously generated. In addition, infrastructure data 166 is usable to trace user access and storage for access auditing purposes.

Referring still to FIG. 1, lake database 170 also includes raw unmodified data 168 from sources 102. For instance, original clinical medical records from physicians are stored in their original format as are any medical images and radiology reports, pathology reports, organoid documentation, and any other data type related to patient treatment, treatment efficacy, etc. In addition the raw original data, metadata related thereto is also identified and stored at 168. Exemplary metadata includes source identity, data type, date and time data received, any data formatting information available, etc. The metadata listed here is not exhaustive and other metadata types may also be obtained and stored. Raw sequencing data, such as BAM files, may be stored in lake database 170. Unless indicated otherwise hereafter, the data stored in lake database 170 will be referred to generally as "lake data".

It has been recognized that a fulsome database suitable for cancer research and treatment planning must account for a massive number of complex factors. It has also been recognized that the unstructured or semi-structured lake data is unsuitable for performing many data search processes, analytics and other calculations and data manipulations that are required to support the overall system. In this regard, searching or otherwise manipulating a massive database data set that includes data having many disparate data formats or structures can slow down or even halt system applications. For this reason the disclosed system converts much of the lake data to a system data structure optimized for database manipulation (e.g., for searching, analyzing, calculating, etc.). For example, genomic data may be converted to JSON or Apache Parquet format, however, others are contemplated. The optimized structured data is referred to herein as the "data vault database" 180.

Thus, in FIG. 1, data vault database 180 includes data that has been normalized and optimally structured for storage and database manipulation. For instance, raw original clinical medical records stored at 168 in lake database 170 may be processed to normalize data formats and placed in specific structured data fields optimized for data searching and other data manipulation processes. For instance, raw original clinical medical records, such as progress notes, pathology reports, etc. may be processed into specific structured data fields. Structured data fields may be focused in certain clinical areas, such as demographics, diagnosis, treatment and outcomes, and genetic testing/labs. For instance, structured diagnosis information may include primary diagnosis; tissue of origin; date of diagnosis; date of recurrence; date of biochemical recurrence; date of CRPC; alternative grade; gleason score; gleason score primary; gleason score secondary; gleason score overall; lymphovascular invasion; perineural invasion; venous invasion. Structured diagnosis information may also include tumor characterization, which may be described with a set of structured data, including the type of characterization; date of characterization; diagnosis; standard grade; AJCC values such as AJCC status, AJCC status T, AJCC status N, AJCC Status M, AJCC status stage, and FigO status stage. Structured diagnosis information may also include tumor size, which may be described with a set of structured size data, including tumor size (greatest dimension), tumor size measure, and tumor size units. Structured diagnosis information may also include structured metastases information. Each metastasis may be described with a set of structured data, including location, date of identification, tumor size, diagnosis, grade, and AJCC values. Structured diagnosis information may also include additional diagnoses. Additional diagnoses may be described with a set of structured data, including tissue of origin, date of diagnosis, date of recurrence, date of biochemical recurrence, date of CRPC, tumor characterizations, and metastases.

Figure 2:
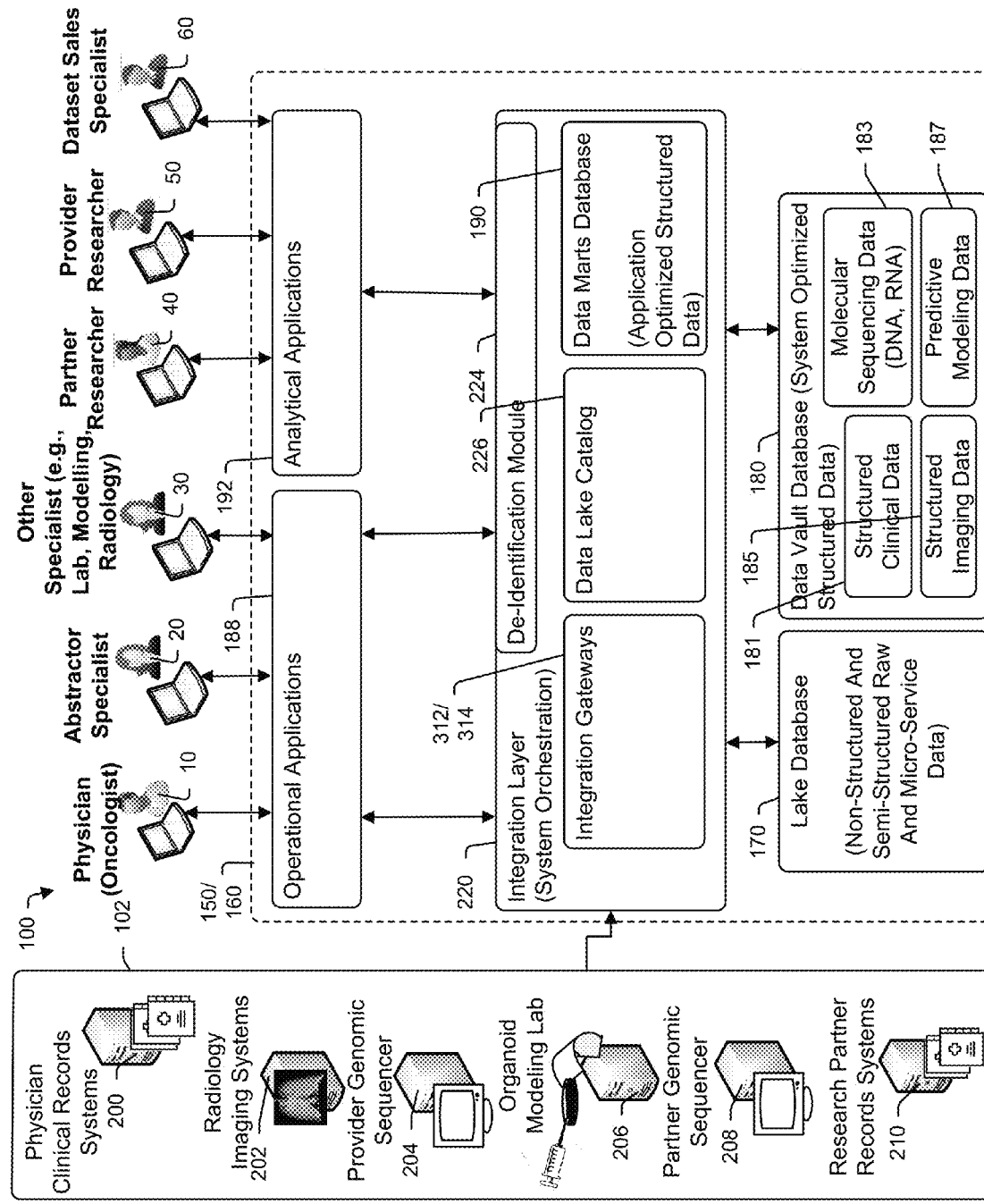
FIG. 2 is a schematic diagram illustrating another view of the FIG. 1 system where functional components that are implemented by the FIG. 1 components are shown in some detail.

As another instance, 2 dimensional slice type images through a patient's tumor may be used to generate a normalized 3 dimensional radiological tumor model having specific attributes of interest and those attributes may be gleaned and stored along with the 3D tumor model in the structured data vault for access by other system resources. In FIG. 2, the data vault database 180 is shown including a structured clinical database 181 for storage of structured clinical data, a molecular sequencing database 183 for storage of molecular sequencing data, a structure imaging database 185 for storage of imaging data, and a predictive modeling database 187 for storage of organoid and other modeling data. Additional databases for specific lines of data may also be added to the data vault database 180. RNA sequencing data in the molecular sequencing data may be normalized, for instance using the methods disclosed in U.S. Provisional Patent App. No. 62/735,349, METHODS OF NORMALIZING AND CORRECTING RNA EXPRESSION DATA, incorporated by reference herein in its entirety. Unless indicated otherwise hereafter, the phrase "canonical data" will be used to refer to the data vault data in its system optimized structured form.

It has further been recognized that certain data manipulations, calculations, aggregates, etc., are routinely consumed by application programs and other system consumers on a recurring albeit often random basis. By shaping at least subsets of normalized system data, smaller sub-databases including application and research specific data sets can be generated and published for consumption by many different applications and research entities which ultimately speeds up the data access and manipulation processes.

Thus, in FIG. 1, data marts database 190 includes data that is specifically structured to support user application programs 194 and/or specific research activities 196. Here, it is contemplated that different user application programs may require different data models (e.g., different data structures) and therefore data marts 190 will typically include many different application or research specific structured data sets. For instance, a first data mart data set may include data arranged consistent with a first data structure model optimized to support a physician's user interfaces, a second data mart data set may include data arranged consistent with a second data structure model optimized to support a radiologist specialist, a third data mart data set may include data arranged consistent with a third data structure model optimized to support a partner researcher, and so on. A single user type may have multiple data mart data sets structured to support different workflows on the same or different raw data.

Similarly, in the case of specific research activities, specific data sets and formats are optimal for specific research activities and the data marts provide a vehicle by which optimized data sets are optimally structured to ensure speedy access and manipulation during research activities. Unless indicated otherwise hereafter, the phrase "mart data" will be used to generally refer to data stored in the data marts 190.

In most cases mart data is mined out of the data vault 180 and is restructured pursuant to application and research data models to generate the mart data for application and research support. In some embodiments, system orchestration modules or software programs that are described hereafter will be provided for orchestrating data mining in the system databases as well as restructuring data per different system models when required.

Referring still to FIG. 1, the system services/applications/integration resources database 195 includes various programs and services run by system server 150 to perform and/or guide system functions. To this end, exemplary database 195 includes system orchestration modules/resources 184, a set of first through N micro-services collectively identified by numeral 186, operational user application programs 188 and analytical user application programs 192.

Orchestration modules/resources 184 include overall scheduling programs that define workflows and overall system flow. For instance, one orchestration program may specify that once a new unstructured or semi-structured clinical medical record is stored in lake database 170, several additional processes occur, some in series and some in parallel, to shape and structure new data and data derived from the new data to instantiate new sets of canonical data and mart data in databases 180 and 190. Here, the orchestration program would manage all sub-processes and data handoffs required to orchestrate the overall system processes. One type of orchestration program that could be utilized is a programmatic workflow application, which uses programming to author, schedule and monitor "workflows". A "workflow" is a series of tasks automatically executed in whole or in part by one or more micro-services. In one embodiment, the workflow may be implemented as a series of directed acyclic graphs (DAGs) of tasks or micro-services.

Micro-services 186 are system services that generate interim system data products to be consumed by other system consumers (e.g., applications, other micro-services, etc.). In FIG. 1, first through Nth micro-service data products corresponding to micro-services 186 are shown stored in lake database 170 at 172. When a micro-service data product is published to lake database 170, a data alert or event is added to a data alerts list 169 to announce availability of the newly published data for consumption by other micro-services, application programs, etc. Micro-services are independent and autonomous in that, once a service obtains data required to initiate the service, the service operates independent of other system resources to generate output data products.

In many cases micro-services are completely automated software programs that consume system data and generate interim data products without requiring any user input. For instance, an exemplary fully automated micro-service may include an optical character recognition (OCR) program that accesses an original clinical record in the raw source data 168 and performs an OCR process on that data to generate an OCR tagged clinical record which is stored in lake database 170 as a data product 172. As another instance, another fully automated micro-service may glean data subsets from an OCR tagged clinical record and populate structured record fields automatically with the gleaned data as a first attempt to convert unstructured or semi-structured raw data to a system optimized structure.

In other cases a micro-service requires at least some system user activities including, for instance, data abstraction and structuring services or lab activities, to generate interim data products 172. For instance, in the case of clinical medical record ingestion, in many cases an original clinical record will be unstructured or semi-structured and structuring will require an abstractor specialist 20 (see again FIG. 1) to at least verify data in structured data record fields and in many cases to manually add data to those fields to generate a completely instantiated instance of the structured record as a data product 172. As another instance, in the case of genetic sequencing, a lab technician is required to obtain and load sample tumor or other tissue into a sequencing machine as part of a sequencing process. In cases where a service requires at least some user activities, the service will typically be divided into separate micro-services where a user application operates on a micro-service data product to queue user activities in a user work queue or the like and a separate micro-service responds to the user activity being completed to continue an overall process. While this disclosure describes a small set of micro-services, a working system 100 will typically employ a massive number (e.g., hundreds or even many thousands) of micro-services to drive all of the system capabilities contemplated. It is possible that in the life cycle of analysis for a patient that hundreds or thousands of executions of micro-services will be performed.

In an embodiment, a micro-service creates a data product that may be accessed by an application, where the application provides a worklist and user interface that allows a user to act upon the data product. One example set of micro-services is the set of micro-services for genomic variant characterization and classification. An exemplary micro-service set for genomic variant characterization includes but is not limited to the following set: (1) Variant characterization (a data package containing characterized variant calls for a case, which may include overall classification, reference criteria and other singles used to determine classification, exclusion rules, other flags, etc.); (2) Therapy match (including therapies matched to a variant characterization's list of SNV, indel, CNV, etc. variants via therapy templates); (3) Report (a machine-readable version of the data delivered to a physician for a case); (4) Variants reference sets (a set of unique variants analyzed across all cases); (5) Unique indel regions reference sets (gene-specific regions where pathogenic inframe indels and/or frameshift variants are known to occur); (6) DNA reports; (7) RNA reports; (8) Tumor Mutation Burden (TMB) calculations, etc. Once genomic variant characterization and classification has been completed, other applications and micro-services provide tools for variant scientists or other clinicians or even other micro-services to act upon the data results.

Referring still to FIG. 1, each micro-service includes a service specification including definitions of data that the specified service is to consume, micro-service code defining the service to be performed by the specific micro-service and a definition of the data that is to be published to the lake as an interim data product 172. In each case, the service to be performed includes monitoring the data alerts list 169 or published data on the system communication network for data to be consumed (e.g., monitor for data that fits subscriptions associated with the microservice) by the service and, once the service generates a data product, publishing that data product to the data lake and placing an alert in alerts list 169 or publishing that data. In operation, when a micro-service is to consume a published data product, the service obtains the data product, consumes the product as part of performing the service, publishes new data product(s) to lake database 170 and then places a new data alert in list 169 to announce to other system consumers that the new data is ready for consumption.

Another system for asynchronous communication between micro-services is a publish-subscribe message passing ("pub/sub") system which uses the alerts list 169. In this system type, alerts list 169 may be implemented in the form of a message bus. One example of a message bus that may be utilized is Amazon Simple Notifications Service (SNS). In this system type, micro-services publish messages about their activities on message bus topics that they define. Other micro-services subscribe to these messages as needed to take action in response to activities that occur in other micro-services.

In at least some embodiments, micro-services are not required to directly subscribe to SNS topics. Rather, they set up message queues via a queue service, and subscribe their queues to the SNS Topics that they are interested in. The micro-services then pull messages from their queues at any time for processing, without worrying about missing messages. One example of a queue service is the Amazon Simple Queue Service (SQS) although others are contemplated.

Granularity of SNS topics may be defined on a message subject basis (for instance, 1 topic per message subject), on a domain object basis (for instance, one topic per domain object basis), and/or on a per micro-service basis (for instance, one topic per micro-service basis). Message content may include only essential information for the message in order to prioritize small message size. In at least some cases message content is architectured to avoid inclusion of patient health information or other information for which authorization is required to access.

Different alerts may be employed throughout the system. For instance, alerts may be utilized in connection with the registration of a patient. One example of an alert is "services-patients.created", which is triggered by creation of a new patient in the system. Alerts may be utilized in connection with the analysis of variant call files. One example is "variant-analysis_staging", which is triggered upon the completion of a new variant calling result. Another example is "variant-analysis_staging.ready", which is triggered upon completed ingestion of all input files for a variant calling result. Another example is "case_staging.ready", which is triggered when information in the system is ready for manual user review. Many other alerts are contemplated.

Both orchestration workflows and micro-service alerts may be employed in the system, either alone or in combination. In an example, an event-based micro-service architecture may be utilized to implement a complex workflow orchestration. Orchestrations may be integrated into the system so that they are tailored for specific needs of users. For instance, a provider or another partner who requires the ability to provide structured data into the lake may utilize a partner-specific orchestration to land structured data in the lake, pre-process files, map data, and load data into the data fault. As another example, a provider or other partner who requires the ability to provide unstructured data into the lake may utilize a partner-specific orchestration for pre-processing and providing unstructured data to the data lake. As another example, an orchestration may, upon publishing of data that is qualified for a particular use case (such as for research, or third-party delivery), transform the data and load it into a columnar data store technology. As another example, a "data vault to clinical mart" orchestration may take stable points in time of the data published to data vault by other orchestrations; transform the data into a mart model, and transform the mart data through a de-identification pipeline. As another example, a "commercial partner egress file gateway" may utilize a cohort of patients whose data is defined for delivery, sourcing the data from de-identified data marts and the data lake (including molecular sequencing data) and publish the same to a third-party partner.

Referring still to FIG. 1, operational and analytical applications 188 and 192, respectively, are application programs that provide functionality to various system user types as well as interfaces optimized for use by those system users. Operational applications 188 include application programs that are primarily required to enable cancer state treatment planning processes for specific patients. For instance, operational applications include application programs used by a cancer treating physician to assess treatment options and efficacy for a specific patient. As another instance, operational applications also include application programs used by an abstractor specialist to convert unstructured raw clinical medical records or semi-structured records to system optimized structured records. As another instance, operational applications may also include application programs used by bioinformatics scientists or molecular pathologists to annotate variants. As another instance, operational applications also include application programs used by clinicians to determine whether a patient is a good match for a clinical trial. As yet one other instance, operational applications may include application programs used by physicians to finalize patient reports.

Analytical applications 192, in contrast, include application programs that are provided primarily for research purposes and use by either provider client researchers or provider specialist researchers. For instance, analytical applications 192 include programs that enable a researcher to generate and analyze data sets or derived data sets corresponding to a researcher specified subset of de-identified (e.g., not associated with a specific patient) cancer state characteristics. Here, analysis may include various data views and manipulation tools which are optimized for the types of data presented. Some applications may have features of both analytical applications 192 and operational applications 188.

B. System Database Architecture and General Data Flow

Referring now to FIG. 2, a second representation of disclosed system 100 shows many of the components shown in FIG. 1 in an operational arrangement. The FIG. 2 system includes system data sources 102 and operational system components including an integration layer 220 in addition to the lake database 170, data vault database 180, operational applications 188 and analytical applications 192 that are described above. Exemplary data sources 102 include physician clinical records systems 200, radiology imaging systems 202, provider genomic sequencers 204, organoid modeling labs 206, partner genomic sequencers 208 and research partner records systems 210. The source data types are only exemplary and are not intended to be limiting. In fact, it is contemplated that many other data source types generating other clinically relevant data types will be added to the system over time as other sources and data types of interest are identified and integrated into the overall system.

Referring again to FIG. 2, integration layer 220 includes integration gateways 312/314, a data lake catalog 226 and the data marts database 190 described above with respect to FIG. 1. The integration gateways receive data files and messages from sources 102, glean metadata from those files and messages and route those files and messages on to other system components including data lake database 170 and catalog 226 as well as various system applications. New files are stored in lake database 170 and metadata useful for searching and otherwise accessing the lake data is stored in catalog 226. Again, non-structured and semi-structured raw and micro-service data is stored in lake database 170 and system optimized structured data is stored in vault database 180 while application optimized structured data is stored in data marts database 190.

Referring again to FIG. 2, system users 10, 20, 30 40, 50 and 60 access system data and functionality via the operational and/or analytical applications 188 and 192, respectively. In some instances, in order to protect patient confidentiality, the system user cannot have access to patient medical records that are tied to specific and identified patients. For this reason, integration layer 220 may include a de-identification module which accesses system data, scrubs that data to remove any specific patient identification information and then serves up the de-identified data to the application platform. In other examples, the data vault database may have its structure duplicated, such that a de-identified copy of the data in the data vault database 180 is retained separately from the non de-identified copy of the data in the data vault database. Data in the de-identified copy may be stripped of its identifiers, including patient names; geographic subdivisions smaller than a state, including street address, city, county, precinct, ZIP code, and their equivalent geocodes, except for the initial three digits of the ZIP code if, according to the current publicly available data from the Bureau of the Census: (1) The geographic unit formed by combining all ZIP codes with the same three initial digits contains more than 20,000 people; and (2) The initial three digits of a ZIP code for all such geographic units containing 20,000 or fewer people is changed to 000; elements of dates (except year) for dates that are directly related to an individual, including birth date, admission date, discharge date, death date, and all ages over 89 and all elements of dates (including year) indicative of such age, except that such ages and elements may be aggregated into a single category of age 90 or older; Telephone numbers; Vehicle identifiers and serial numbers, including license plate numbers; Fax numbers; Device identifiers and serial numbers; Email addresses; Web Universal Resource Locators (URLs); Social security numbers; Internet Protocol (IP) addresses; Medical record numbers; Biometric identifiers, including finger and voice prints; Health plan beneficiary numbers; Full-face photographs and any comparable images; Account numbers and other unique identifying numbers, characteristics, or codes; and Certificate/license numbers. Because data in the data vault database 180 is structured, much of the information not permitted for inclusion in the de-identified copy is absent by virtue of the fact that a structured location does not exist for inclusion of such information. For instance, the structure of the data vault database for storing the de-identified copy may not include a field for storing a social security number. As another example, data in the data vault database may be segregated by customer. For example, if one physician 10 wishes for his or her patients to have their data segregated from other data in the data lake database 170, their data may be segregated in a single tenant data vault, such as the single tenant data vault arrangement shown in FIG. 3a.

Many users employing the operational applications 188 do have physician-patient relationships, or otherwise are permitted to access records in furtherance of treatment, and so have authority to access patent identified medical, healthcare and other personal records. Other users employing the operational applications have authority to access such records as business associates of a health care provider that is a covered entity. Therefore, in at least some cases, operational applications will link directly into the integration layer of the system without passing through de-identification module 224, or will provide access to the non de-identified data in the database 160. Thus, for instance, a physician treating a specific patient clearly requires access to patient specific information and therefore would use an operational application that presents, among other information, patient identifying information.

In some cases, users employing operational applications will want access to at least some de-identified analytical applications and functionality. For instance, in some cases an operational application may enable a physician to compare a specific patient's cancer state to multiple other patient's cancer states, treatments and treatment efficacies. Here, while the physician clearly needs access to her patient's identifying information and state factors, there is no need and no right for the physician to have access to information specifically identifying the other patients that are associated with the data to be compared. Thus, in some cases one operational application will access a set of patient identified data and other sets of patient de-identified data and may consume all of those data sets.

Figure 3:
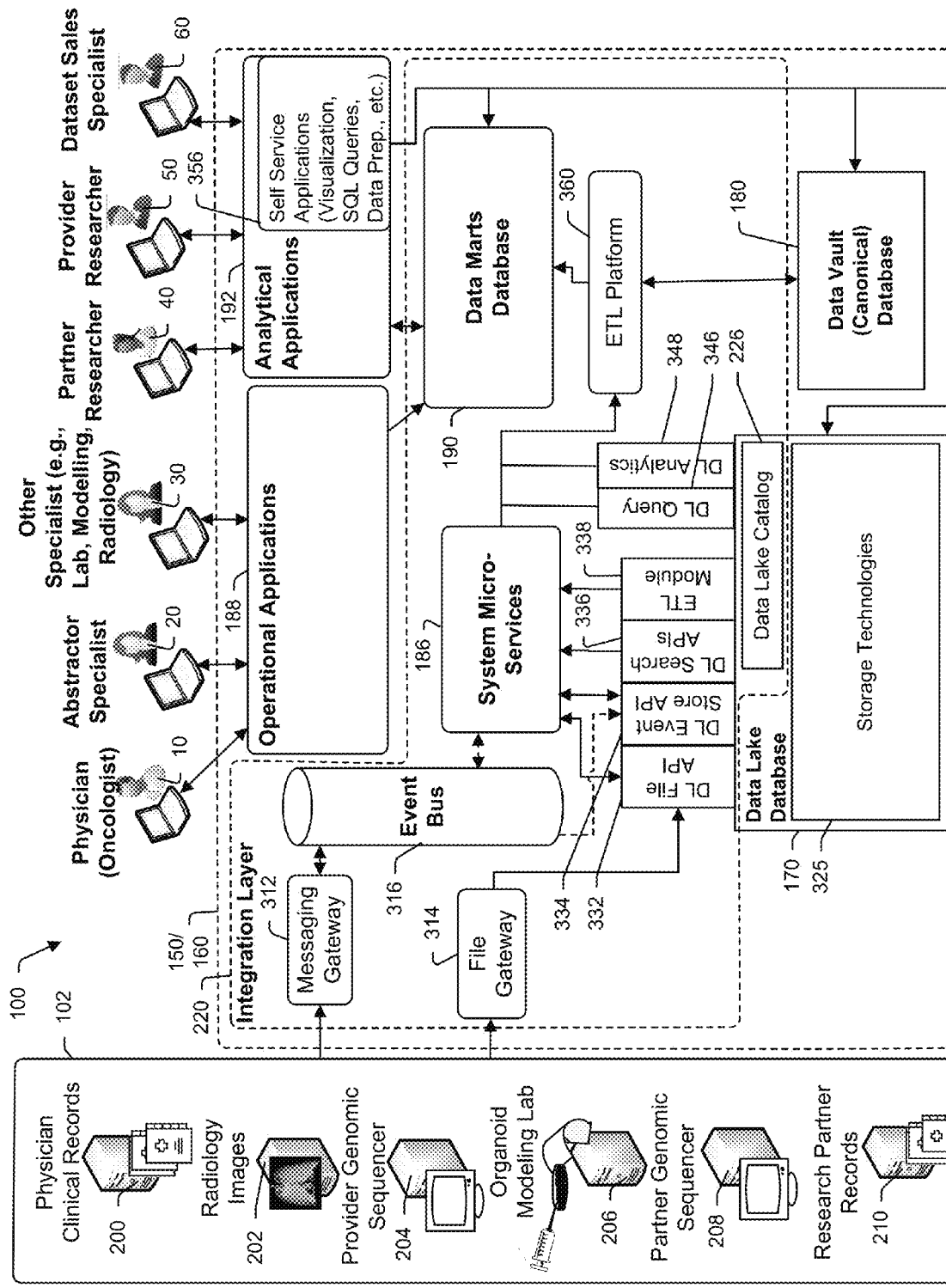
FIG. 3 is a schematic diagram illustrating yet another view of the FIG. 1 system where additional system components are illustrated.

Referring now to FIG. 3, a system representation 100 akin to the one in FIG. 2 is shown, albeit where the FIG. 3 representation is more detailed. In FIG. 3 integration layer 220 includes separate message and file gateways 312 and 314, respectively, an event reporting bus 316, system microservices 186, various data lake APIs 332, 334 and 336, an ETL module 338, data lake query and analytics modules 346 and 348, respectively, an ETL platform 360 as well as data marts database 190.

Referring to FIG. 3, sources 102 are linked via the internet or some other communication network to system 100 via message gateway 312 and file gateway 314. Messages received from data sources 102 at gateway 312 are forwarded on to event bus 326 which routes those messages to other system modules as shown. Messages from other system modules can be routed to the data sources via message gateway 312.

File gateway 314 receives source files and controls the process of adding those files to lake database 170. To this end, the file gateway runs system access security software to glean metadata from any received file and to then determine if the file should be added to the lake database 170 or rejected as, for instance, from an unauthorized source. Once a file is to be added to the lake database, gateway 314 transfers the file to lake database 170 for storage, uses the metadata gleaned from the file to catalog the new file in the lake catalog 226 and posts an alert in the data alert list 169 (see again FIG. 1) announcing that the new data has been published to the lake for consumption.

Referring still to FIG. 3, a subset of micro-services monitoring alert list 169 for data of the type published to lake database 170 access the new data or consume that data when published to the network, perform their data consumption processes, publish new data products to lake database 170 and post new data alerts in list 169 or publish the new data on the network per the publication-subscription architecture described above. In cases where system user activities are required as part of a micro-service, the service schedules those activities to be completed by provider specialists when needed and ingests data generated thereby, eventually publishing new data products to the lake database 170.

The orchestration modules and resources monitor the entire data process and determine when data lake data is to be replicated within the data vault and/or within the data marts in different system or application optimized model formats. Whenever lake data is to be restructured and placed in the data vault or the data marts, ETL platform 360 extracts the data to restructure, transforms the data to the system or application specific data structure required and then loads that data into the respective database 180 or 190. In some cases it is contemplated that ETL platform may only be capable of transforming data from the data lake structure to the data vault structure and from the data vault structure to the application specific data models required in data marts 190.

Referring still to FIG. 3, analytical applications 192 are shown to include, among other applications, "self-service" applications. Here, the phrase "self-service" is used to refer to applications that enable a system user to, in effect, use query tools and data visualization tools, to access and manipulate data sets that are not optimally supported by other user applications. Here, the idea is that, especially in the context of research, system users should not be constrained to specific data sets and analysis and instead should be able to explore different data sets associated with different cancer state factors, different treatments and different treatment efficacies. The self-service tools are designed to allow an authorized system user to develop different data visualizations, unique SQL or other database queries and/or to prepare data in whatever format desired. Hereinafter, unless indicated otherwise, the term "explore" will be used to refer to any self-service activities performed within the disclosed system.

Referring still to FIG. 3, self-service applications 356 enable a system user to explore all system databases in at least some embodiments including the data marts 190, the lake database 170 and the data vault database 180. In other embodiments, because lake database 170 data is either unstructured or only semi-structured, self-service applications may be limited to exploring only the data mart database 190 or the data vault database 180.

C. Data Ingestion, Normalization and Publication

Figure 4:
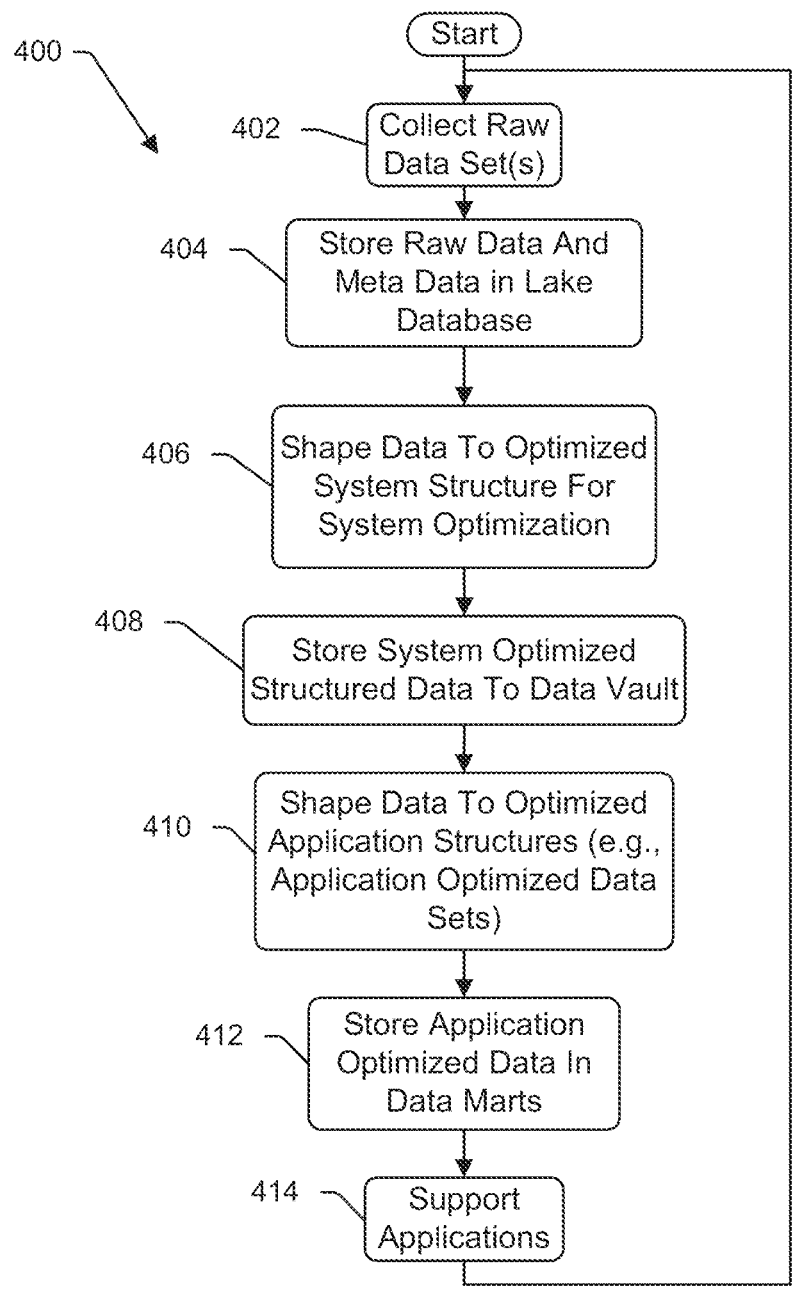
FIG. 4 is a data handling flow chart that is consistent with at least some aspects of the present disclosure.

Referring to FIG. 4, a high level data distribution process 400 is illustrated that is consistent with at least some aspects of the present disclosure. At process block 402, data is collected from various data sources 102 (see again FIGS. 1 through 3) and at block 404, assuming that data is to be ingested into the system 100, the data is stored in lake database 170. Here, data collection is continual over time as more and more data for increasing the system knowledge base is generated regularly by physicians, provider and partner researchers and provider specialists. Specific steps in at least some exemplary data collection processes are described hereafter. The collected original data is stored in the lake database 170 as raw original data (e.g., documents, images, records, files, etc.).

At process block 406, at least a subset of the collected data is "shaped" or otherwise processed to generate structured data that is optimal for database access, searching, processing and manipulation. Here, the data shaping process may take many forms and may include a plurality of data processing steps that ultimately result in optimal system structured data sets. At step 408 the database optimized shaped data is added to similarly structured data already maintained in data vault database 180.

Continuing, at block 410, at least a subset of the data vault data or the lake data is "shaped" or otherwise processed to generate structured data that is optimal to support specific user application programs 188 and 192 (see again FIG. 2). Here, again, the data shaping process may take many forms and may include a plurality of data processing steps that ultimately result in optimal application supporting structured data sets. At step 412 the optimized application structured data is added to similarly structured data already maintained in data marts database 190.

Referring again to FIG. 4, at block 414, system users employ various application programs to access and manipulate system data including the data in any of the lake database 170, data vault database 180 and data marts 190. At block 212, as users use the system, data related to system use is collected after which control passes backup to block 206 where the collected use data is shaped and eventually stored for driving additional applications.

Figure 5:
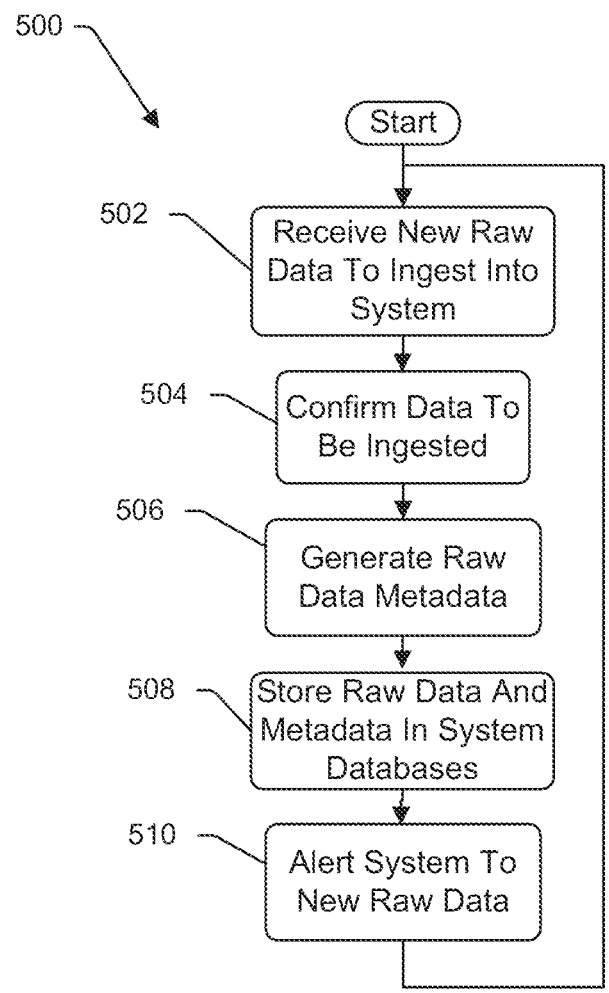
FIG. 5 is a flow chart that shows a process for ingesting raw data into the system and alerting other system components that the raw data is available for consumption.

FIG. 5 includes a flow chart illustrating a process 500 that is consistent with at least some aspects of the present disclosure for ingesting initial raw data into the disclosed system. At process block 502 new raw data is received at the file gateway 314 (see FIG. 2) which, at block 504, determines whether or not the data should be rejected or ingested based on the data source, data format or other transport data used to transmit the received data to the gateway. If the data is to be ingested, gateway 312 gleans metadata from the received data at block 506 which is stored in the data lake catalog 226 (see FIG. 2) while the received data set is stored in data lake 170 at 508. At block 510, an alert is added to the alert list 169 indicting the new data is available to be consumed along with a data type so that other data consumers can recognize when to consume the newly stored data. Control passes back up to block 502 where the process described above continues.

Figure 6:
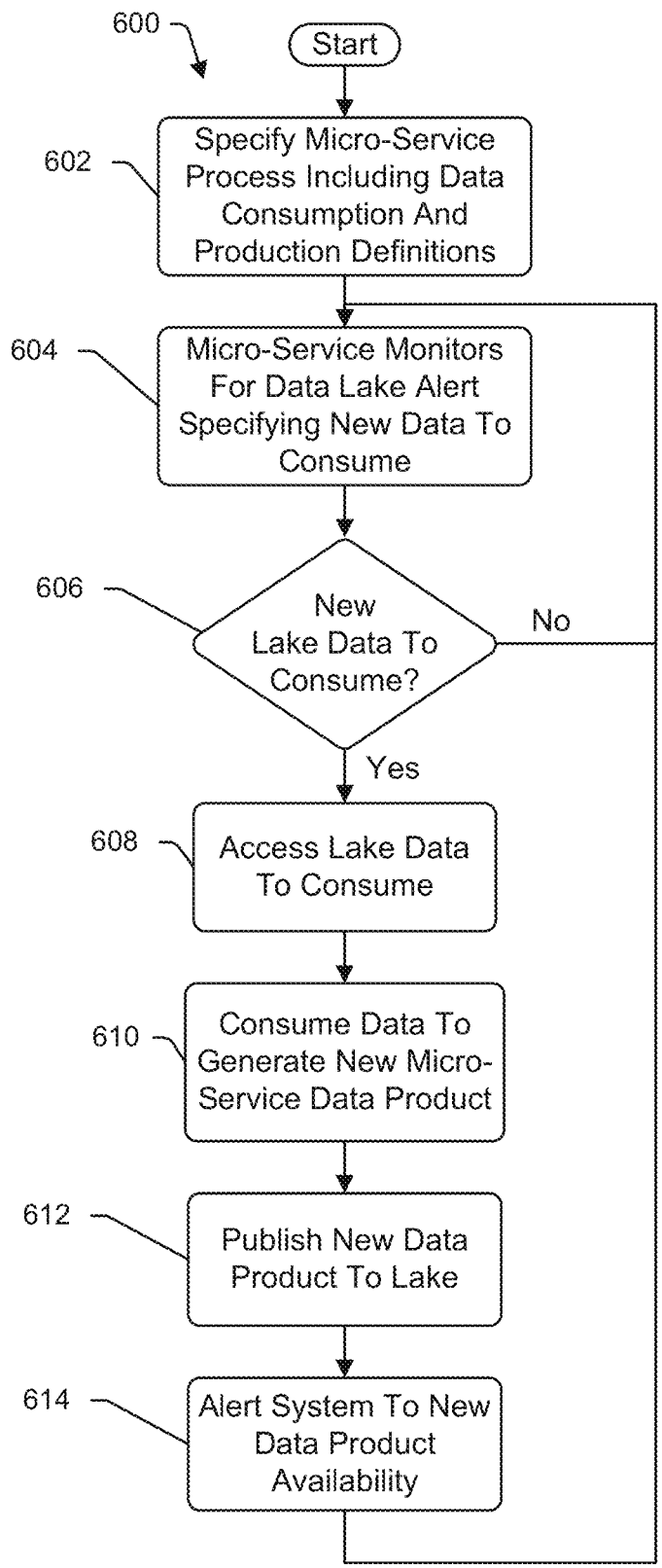
FIG. 6 is a flow chart that shows a micro-service based process for retrieving data from a database, consuming that data to generate new data products and publishing the new data products back to a database while publishing an alert that the new data products are available for consumption.

FIG. 6 is a flow chart illustrating a general process 600 by which system micro-services consume lake data and generate micro-service data products that are published back to the lake database for further consumption by other micro-services. At process block 602 a micro-service process is specified that includes data consumption and data product definitions as well as micro-service code for carrying out process steps. At block 604 the micro-service monitors the data lake 170 for alerts specifying new data that meets the data consumption definition for the specific micro-service. At block 606, where new lake data alerts do not specify data that meets the data consumption definition, control passes back up to block 604 where steps 604 and 606 continue to cycle.

Referring still to FIG. 6, once an alert indicates new data that meets the micro-service data consumption definition, control passes to block 608 where the micro-service accesses the lake data to be consumed and that data is consumed at block 610 which generates a new data product. Continuing, at block 612, the new data product is published to data lake database 170 and at 614 another alert is added to the data alert list 169.

Referring still to FIG. 6, process 600 is associated with a single system micro-service. It should be understood that hundreds and in some cases even thousands of micro-services will be performed simultaneously and that two or more micro-services may be performed on the same raw data or using prior generated micro-service data product(s) at the same time. In many cases a micro-service will require two or more data sets at the same time and, in those cases, a micro-service will be programmed to monitor for all required data in the data lake and may only be initiated once all required data is indicated in the alerts list 169.

Figure 7:
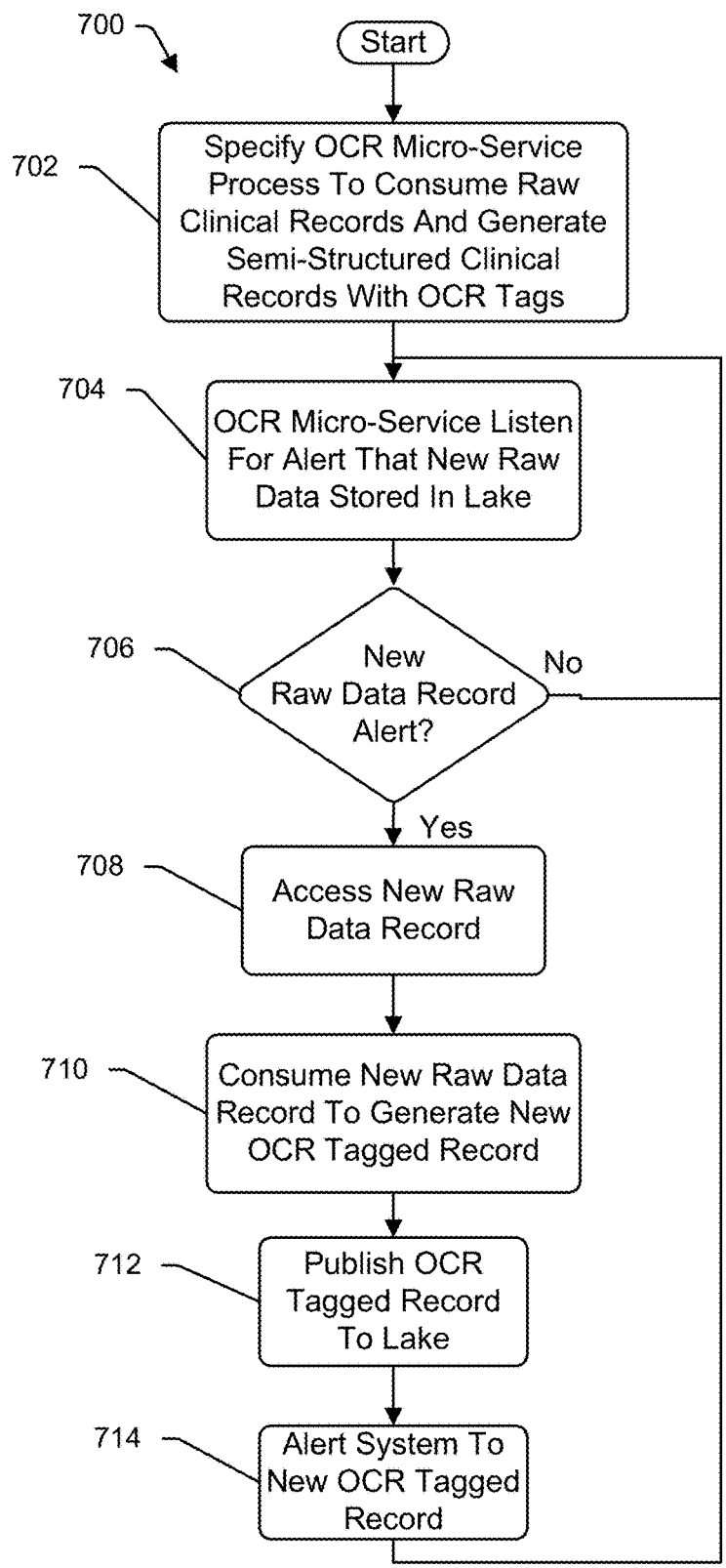
FIG. 7 is a flow chart illustrating a process similar to the FIG. 6 process, albeit where the micro-service is an OCR service.

As described above, some micro-services will be completely automated, so that no user activities are required, while other micro-services will require at least some user activities to perform some service steps. FIG. 7 illustrates a simple fully automated micro-service 700 while FIG. 8 illustrates a micro-service 800 where a user has to perform some activities. In FIG. 7, at process block 702, an OCR micro-service is specified that requires consumption of raw clinical medical records to generate semi-structured clinical medical records with OCR tags appended to document characters. At block 704 the OCR micro-service monitors the system alert list 169 for alerts indicating that new raw clinical records data is stored in the data lake.

At block 706, where there is no new clinical record to be ingested into the system, control passes back up to block 704 and the process 700 cycles through blocks 704 and 706. Once a new clinical record is saved to lake database 170 and an alert related thereto is detected by the OCR micro-service, the micro-service accesses the new raw clinical record from the data lake at 708 and that record is consumed at block 710 to generate a new OCR tagged record. The new OCR tagged record is published back to the lake at 712 and an alert related thereto is added to the data alert list 169 at 714. Once the OCR tagged record is stored in lake database 170, it can be consumed by other micro-services or other system modules or components as required.

The FIG. 8 process 800 is associated with a micro-service for generating a system optimized structured clinical record assuming that an unstructured clinical medical record that has already been tagged with medical terms, phrases and contextual meaning has been generated as a micro-service data product by a prior micro-service. At process block 802, the record structuring micro-service process is defined and includes a data consumption definition that requires OCR, NLP records to be consumed and a data production definition where the system optimized data structure is generated as a micro-service data product. At block 804 the structuring micro-service listens for alerts that new records to consume have been stored in lake database 170. At block 806, where new data to consume has not been stored in the lake database 170, control cycles back through blocks 804 and 806 continually. Once new data to consume has been stored in lake database 170, control passes to block 808 where the micro-service places an alert in an abstractor specialist's work queue identifying the record to consume as requiring specialist activities to complete the micro-service.

Referring still to FIG. 8, at block 810, the system monitors for specialist selection of the queued record for consumption and the system cycles between blocks 808 and 810 until the record is selected. Once the record is selected by the abstractor specialist at 810, control passes to block 812 where the record to be consumed is accessed in database 170. At block 814, the micro-service accesses a structured clinical record file which includes data fields to be populated with data from the accessed clinical record. The micro-service attempts to identify data in the clinical record to populate each field in the structured record at 814 and populates fields with data whenever possible to generate a structured clinical record draft.

Continuing, at block 816 a micro-service presents an abstractor application interface to the abstractor specialist that can be used to verify draft field entries, modify entries or to aid the abstractor specialist in identifying data to populate unfilled structured record fields. To this end, see FIG. 9 that shows an exemplary abstractor interface screenshot 914 that may be viewed by an abstractor specialist which includes an original record in an original record field 900 on the right hand side of the shot and a structured record area 902 on the left hand side of the screenshot. The structured record in area 902 includes a set of fields to be populated with information from the original record or in some other fashion to prepare the structured record for use by system applications. The structured record shown in area 902 only shows a portion of the structured record that fits within area 902 and in most cases the structured record will have hundreds or even thousands of record fields that need to be populated with data. Exemplary structured record fields shown include a site field 904, year fields 905 and a histology field 906.

Figure 9:
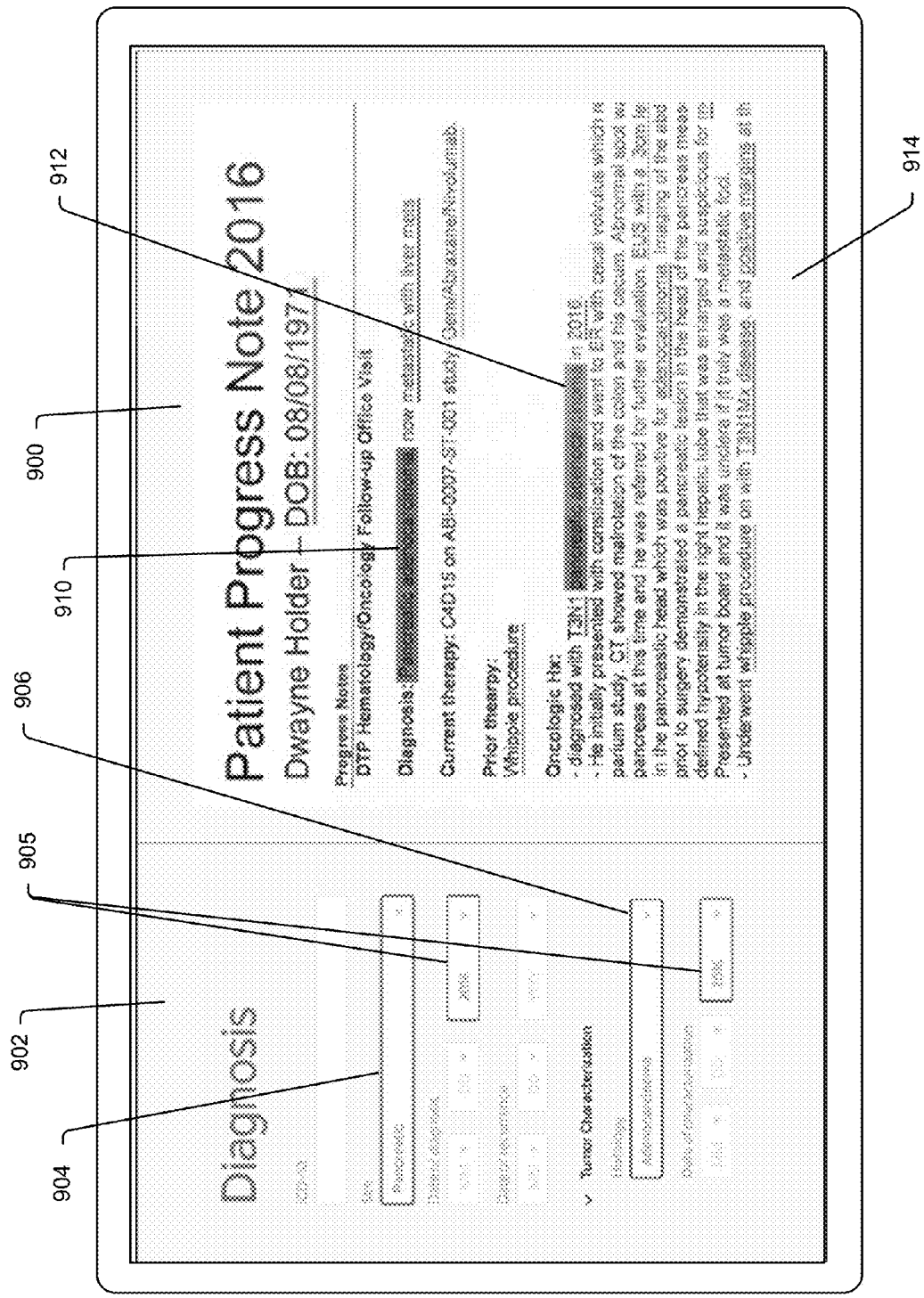
FIG. 9 is a schematic view of an abstractor's display screen used to generate a structured data record from data in an unstructured or semi-structured record.

Referring still to FIG. 9, the original record shown in field 900 has already been subjected to OCR and NLP so that words and phrases have been recognized by a system processor and the text in the document is associated with specific medical words and phrases or other meaning (e.g., dates are recognized as dates, a "Patient's Name" label on an original record is recognized as the phrase "patient's name" and an adjacent field is recognized as a field that likely includes a patient's name, etc.). Again, the processor examines the original record for data that can be used to populate the structured record fields in order to create at least a partially complete draft of the structured record for consideration and completion by the abstractor specialist.

Data in the original record used to populate any field in the structured record is highlighted (see 910, 912) or somehow visually distinguished within the original record to aid the abstractor specialist in located that data in the original record when reviewing data in the structured record fields. The specialist moves through the structured record reviewing data in each field, checking that data against the original record and confirming a match (e.g., via selection of a confirmation icon or the like) or modifying the structured record field data if the automatically populated data is inaccurate (see block 818 in FIG. 8).

In cases where the processor cannot automatically identify data to populate one or more fields in the structured record, the specialist reviews the original record manually to attempt to locate the data required for the field and then enters data if appropriate data is located. Where the micro-service fills in fields that are then to be checked by the specialist, in at least some cases original record data used to populate a next structured record field to be considered by the specialist may be especially highlighted as a further aid to locating the data in the original record. In some cases the micro-service will be able to recognize data in several different formats to be used to fill in a structured record field and will be able to reformat that data to fill in the structured record field with a required form.

Referring again to FIG. 8, at block 820, once the structured clinical record has been completed, the complete system optimized structured clinical record is stored in lake database 170 and then a new data alert is added to alert list 169 at 822 to alert other micro-services and orchestration resources that the complete record is available to be consumed.

In at least some cases it is contemplated that an order management system referred to in some parts of this application as an Orderhub, may automate or at least semi-automate the process of order intake and microservice mapping as well as map modifications to ensure optimized and fulsome patient treatment. To this end, see the exemplary Orderhub system described hereafter in relation to FIGS. 59-68.

In some cases a system micro-service will "learn" from specialist decisions regarding data appropriate for populating different structured data sets. For instance, if a specialist routinely converts an abbreviation in clinical records to a specific medical phrase, in at least some cases the system will automatically learn a new rule related to that persistent conversion and may, in future structured draft records, automatically convert the abbreviation to its expanded form. Many other system learning techniques are contemplated.

In cases where a system micro-service can confirm structured record field information with high confidence, the micro-service may reduce the confirmation burden on the specialist by not highlighting the accurate information in the structured record. For instance, where a patient's date of birth is known, the micro-service may not highlight a patient DOB field in the structured record for confirmation.

Figure 10:
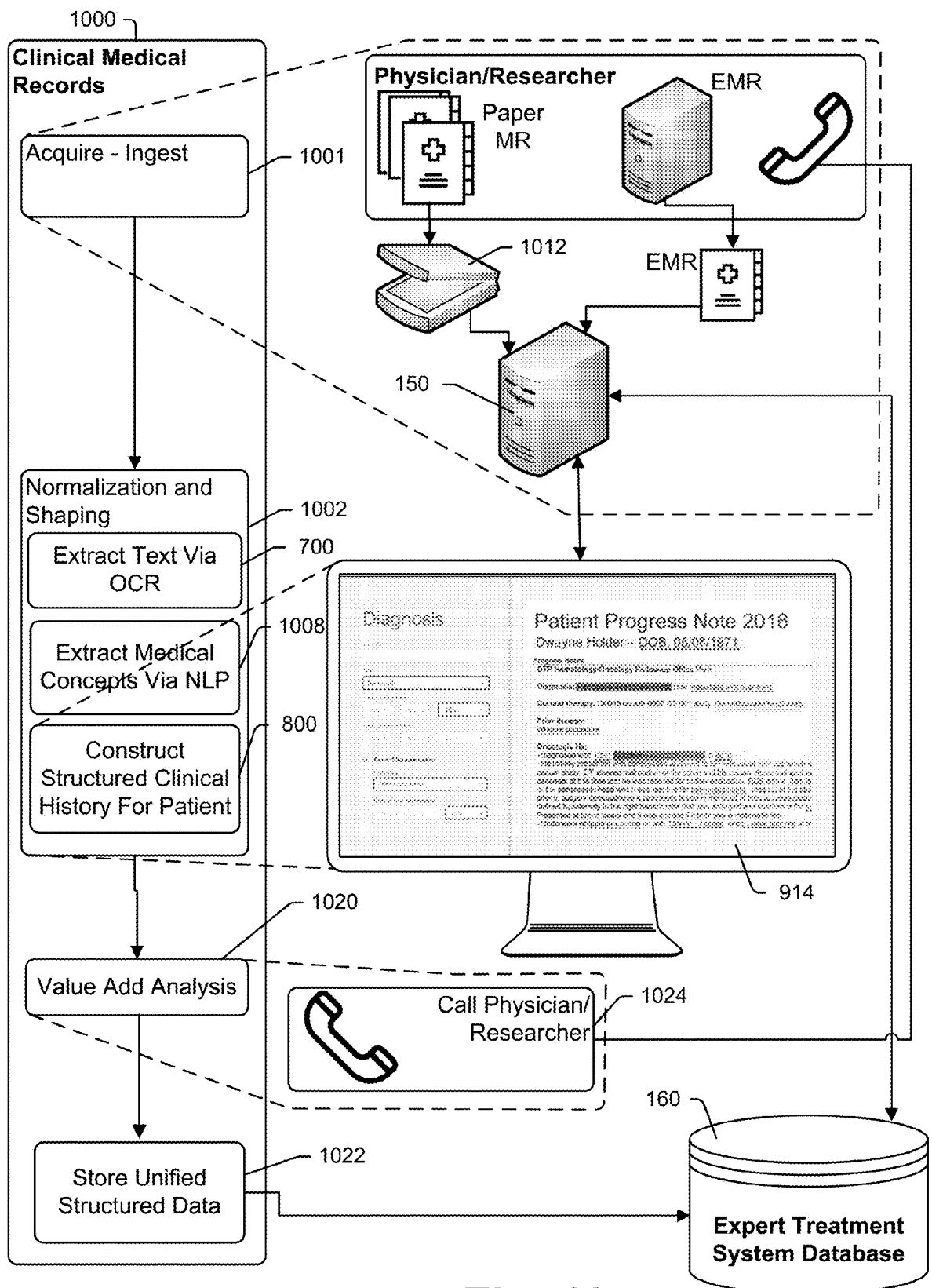
FIG. 10 is a schematic illustrating a multi-micro-service process for ingesting a clinical medical record into the system of FIG. 1.

Referring now to FIG. 10, an exemplary multi-micro-service process 1000 for ingesting a clinical medical record and structuring the record optimally for database activities is illustrated. At step 1001, a medical record is acquired in digital form. Here, where an original record is in paper form, acquiring a digital record may include scanning that record into the system via a scanner 1012 to generate a PDF or other digital representation which is then provided to a system server 150 for storage in database 160. In other cases where the record is already in digital form (e.g., an EMR), the digital record can simply be stored by server 150 in database 160.

A data normalization and shaping process is performed at 1002 that includes accessing an original clinical record from database 160 and presenting that record to a system specialist 40 as shown in FIG. 9. As the original record is accessed or at some other prior time, an OCR micro-service 700 (see again FIG. 7) is used to tag letters in the record. The tagged record is stored in the data lake and an alert is added to the alert list 169. Next, an NLP micro-service 1008 accesses the OCR tagged record and performs an NLP process on the text in that record to generate an NLP processed record which is again stored in the data lake and another alert is added to the alert list 169.

At 800 (see FIG. 8), a draft structured clinical medical record is generated for the patient and is presented to an abstractor specialist via an interface as in FIG. 9 so that the specialist can correct errors.

Referring again to FIG. 10, once the structured record has been filled in to the extent possible based on an original medical record, at block 1020 the specialist may perform some task to attempt to complete record fields that have not been filled. For instance, in a case where a specific structured record field cannot be filled based on information from the original record, the specialist may attempt to track down information related to the field from some other source. For example, in a simple case the specialist may call 1024 a physician that generated the original record to track down missing information. As another example, the specialist may access some other patient record (e.g., an insurance record, a pharmacy record, etc.) that may include additional information useable to populate an empty field. Once the structured record is as complete as possible, that record is stored at 1022 back to the system database 160.

Figure 11:
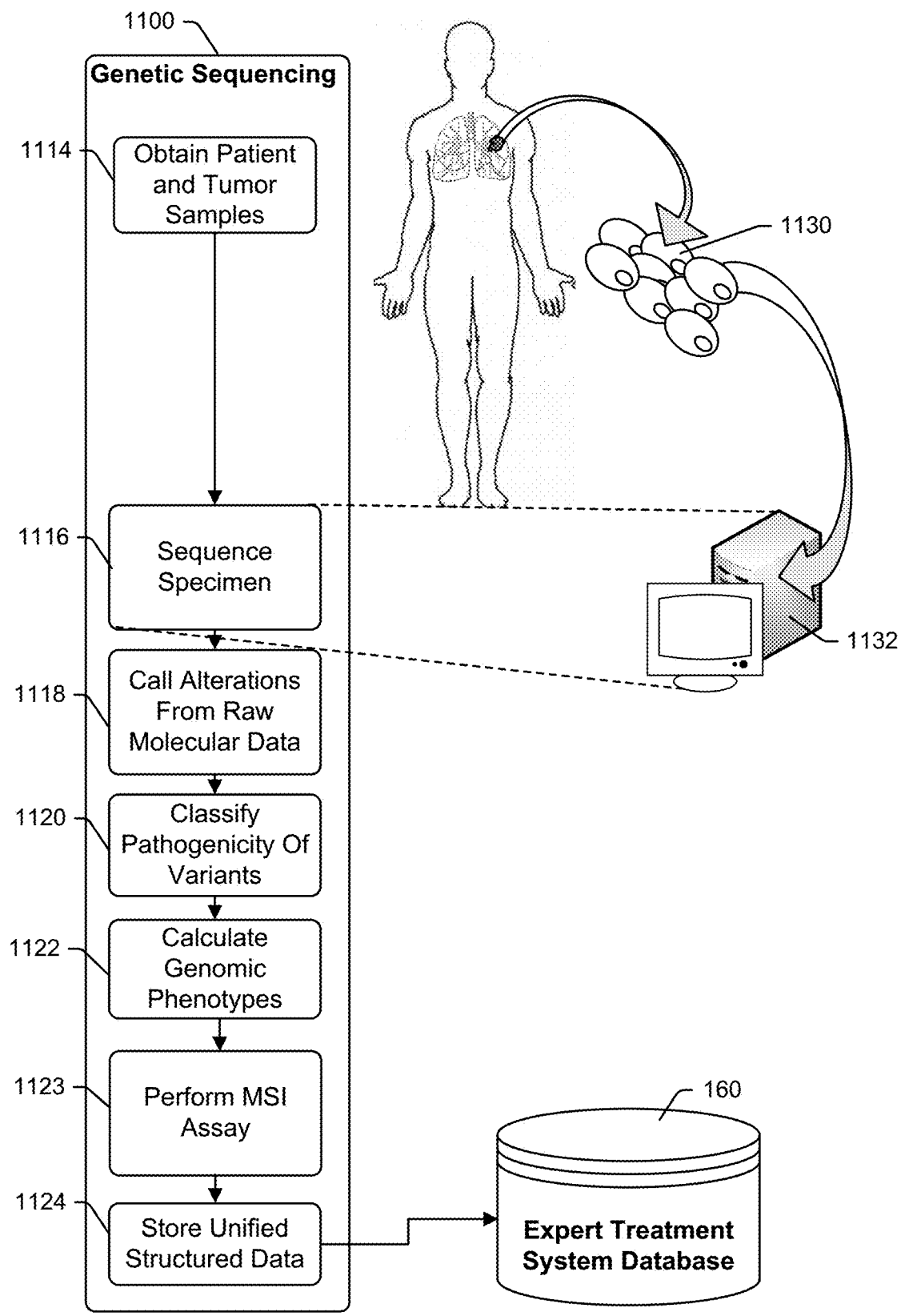
FIG. 11 is a schematic illustrating a multi-micro-service process for generating genomic sequencing and related data that is consistent with at least some aspects of the present disclosure.

Referring now to FIG. 11, an exemplary process 1100 for generating genomic patient and tumor data is illustrated. Robust nucleic acid extraction protocols and sequencing library construction protocols may be applied, and appropriately deep coverage across all targeted regions and appropriately designed analysis algorithms may be utilized. Prior to process 1100, a genomic sequencing order may be received at file gateway 314 and, once ingested, may be stored in lake database 170 for subsequent consumption. Here, when a tumor sample corresponding to the sequencing order is received 1114, the sample is associated with the order and process 1100 continues with the order being assigned to a lab technician's work queue to commence specimen sequencing 1116. At 1116 the specimens are subjected to a genetic sequencing process using sequencing machine 1132 to generate genomic data for both the patient and the tumor specimens. At 1118 alterations from raw molecular data are called and at block 1120 pathogenicity of the variants is classified. At 1122 genomic phenotypes may be calculated. At 1123 an MSI assay may be performed. At 1124 at least a subset of the genomic data and/or an analysis of at least the subset of the genomic data is stored in system database 160.

Referring still to FIG. 11, different approaches may be utilized to implement the genetic sequencing process at 1116. In one example, an oncology assay may be implemented that interrogates all or a subset of cancer-related genes in matched tumor and normal tissue. As used herein, "tumor" tissue or specimen refers to a tumor biopsy or other biospecimen from which the DNA and/or RNA of a cancer tumor may be determined. As used herein, "normal" tissue or specimen refers to a non-tumor biopsy or other biospecimen from which DNA and/or RNA may be determined. As used herein, "matched" refers to the tumor tissue and the normal tissue being correlated at the same position in a DNA and/or RNA sequence, such as a reference sequence. The assay may further provide whole transcriptome RNA sequencing for gene rearrangement detection. The assay may combine tumor and normal DNA sequencing panels with tumor RNA sequencing to detect somatic and germline variants, as well as fusion mRNAs created from chromosomal rearrangements.

The assay may be capable of detecting somatic and germline single nucleotide polymorphisms (SNPs), indels, copy number variants, and gene rearrangements causing chimeric mRNA transcript expression. The assay may identify actionable oncologic variants in a wide array of solid tumor types. The assay may make use of FFPE tumor samples and matched normal blood or saliva samples. The subtraction of variants detected in the normal sample from variants detected in the tumor sample in at least some embodiments provides greater somatic variant calling accuracy. Base substitutions, insertions and deletions (indels), focal gene amplifications and homozygous gene deletions of tumor and germline may be assayed through DNA hybrid capture sequencing. Gene rearrangement events may be assayed through RNA sequencing.

In one example, the assay interrogates one or more of the 1711 cancer-related genes listed in the tables shown in FIG. 22a-22j (referred to herein as the "xE" assay). This targeted gene panel may be divided into a clinically actionable tier, wherein 130 tier 1 genes (see table in FIG. 23) that can influence treatment decisions are assayed with an assigned detection cutoff of 5% variant allele fraction (VAF) i.e. the limit of detection is 5% VAF or lower, and a secondary tier, wherein an additional 1,581 genes (e.g., the difference between the gene set in FIGS. 22a-22j and FIG. 23) are assayed for analytical purposes with an assigned detection cutoff of 10% VAF (limit of detection 10% VAF or lower). The RNA based gene rearrangement detection may also be divided into a primary clinically-actionable tier containing 41 rearrangements (See table in FIG. 24), and a secondary tier that may contain some or all known fusions within the wider literature or novel fusions of putative clinical importance detected by the assay. "Tier 1" genes are genes linked with response or resistance to targeted therapies, resistance to standard of care, or toxicities associated with treatment. The VAF cutoff percentages described herein are exemplary and other cutoff values may be utilized. Reads may be mapped to a human reference genome, such as hg16, hg17, hg18, hg19, etc. (available from the Genome Reference Consortium, at https://www.ncbi.nlm.nih.gov/grc). In another example, the assay may interrogate other gene panels, such as the panels listed in the tables shown in FIGS. 27a, 27b1, 27b2, 27c1 and 27c2 and 27d (herein "the xT panel") or the panel listed in the table shown in FIGS. 28a and 28b.

Figure 11A:
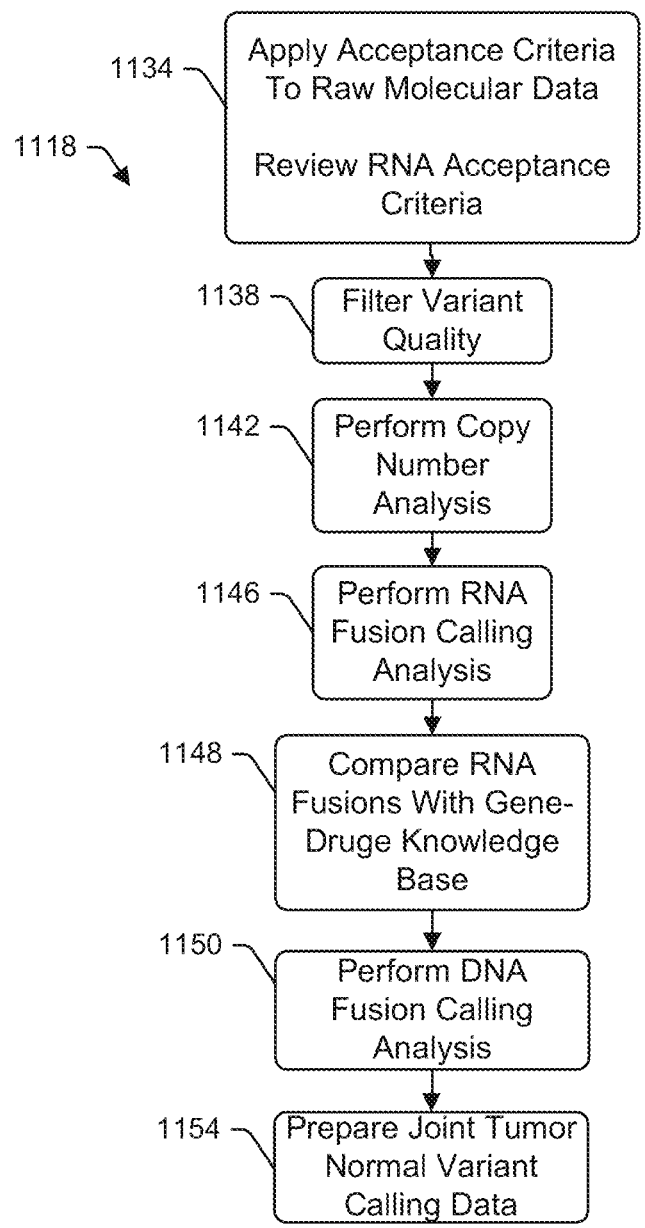
FIG. 11a is a flow chart illustrating an exemplary variant calling process that is consistent with at least some aspects of the present disclosure.

Referring still to FIG. 11, the alterations called in subprocess 1118 may be called through a clinical variant calling process. An exemplary variant calling process is shown in FIG. 11a. At 1134 acceptance criteria are applied to the raw molecular data for clinical variant calling. There may be one or more acceptance criteria, and multiple acceptance criteria may be applied.

One type of acceptance criteria is that a certain percentage of loci assay must exceed a certain coverage. For instance, a first percentage of loci must exceed a certain first coverage and a second percentage of loci must exceed a second coverage. The first percentage of loci may be 60%, 65%, 70%, 75%, 80%, 85%, 80%, 95%, etc. and the first coverage level may be 150×, 200×, 250×, 300×, etc. The second percentage of loci may be 60%, 65%, 70%, 75%, 80%, 85%, etc. and the second coverage level may be 150×, 200×, 250×, 300×, etc. The first percentage of loci assayed may be lower than the second percentage of loci assayed while the first coverage level may be deeper than the second coverage level.

Another type of acceptance criteria may be that the mean coverage in the tumor sample meets or exceeds a certain coverage threshold, such as 300×, 400×, 500×, 600×, 700×, etc.

Another type of acceptance criteria may be that the total number of reads exceeds a predefined first threshold for the tumor sample and a predefined second threshold for the normal sample. For instance, the total number of reads for the tumor sample must exceed 5 million, 10 million, 15 million, 20 million, 25 million, 30 million, 35 million, 40 million, etc. reads and the total number of reads for the normal sample must exceed 5 million, 10 million, 15 million, 20 million, 25 million, 30 million, 35 million, 40 million, etc. reads. In one example, the threshold for the total number of the reads for the tumor sample may be greater than the total number of reads for the normal sample. For instance, the threshold for the total number of the reads for the tumor sample may be greater than the total number of reads for the normal sample by 5 million, 10 million, 5 million, 10 million, 15 million, 20 million, 25 million, 30 million, 35 million, 40 million, etc. reads.

Another type of acceptance criteria is that reads must maintain an average quality score. The quality score may be an average PHRED quality score, which is a measure of the quality of the identification of the nucleobases generated by automated DNA sequencing. The quality score may be applied to a portion of the raw molecular data. For instance, the quality score may be applied to the forward read. Another type of acceptance criteria is that the percentage of reads that map to the human reference genome. For instance, at least 60%, 65%, 70%, 75%, 80%, 85%, 80%, 95%, etc. of reads must map to the human reference genome.

Still at 1134, RNA acceptance criteria may additionally be reviewed. One type of RNA acceptance criteria is that a threshold level of read pairs will be generated by the sequencer and pass quality trimming in order to continue with fusion analysis. For instance, the threshold level may be 5 million, 10 million, 15 million, 20 million, 25 million, 30 million, 35 million, 40 million, etc. Another type of acceptance criteria is that reads must maintain an average quality score. The quality score may be an average RNA PHRED quality score, which is a measure of the quality of the identification of the nucleobases generated by automated RNA sequencing. The quality score may be applied to a portion of the raw molecular data. For instance, the quality score may be applied to the forward read.

Yet another type of acceptance criteria is that the percentage of reads that map to the human reference genome. For instance, at least 60%, 65%, 70%, 75%, 80%, 85%, 80%, 95%, etc. of reads must map to the human reference genome.

If RNA analysis fails pre or post-analytic quality control, DNA analysis may still be reported. Due to the difficulties of RNA-seq from FFPE, a higher than normal failure rate is expected. Because of this, it may be standard to report the DNA variant calling and copy number analysis section of the assay, no matter the outcome of RNA analysis.

At 1138, the step of variant quality filtering may be performed. Variant quality filtering may be performed for somatic and germline variations. For somatic variant filtering, the variant may have at least a minimum number of reads supporting the variant allele in regions of average genomic complexity. For instance, the minimum number of reads may be 1, 2, 3, 4, 5, 6, 7, etc. A region of the genome may be determined free of variation at a percentage of LLOD (for instance, 5% of LLOD) if it is sequenced to at least a certain read depth. For instance, the read depth may be 100×, 150×, 200×, 250×, 300×, 350×, etc.

The somatic variant may have a minimum threshold for SNPs. For instance, it may have at least 20×, 25×, 30×, 35×, 40×, 45×, 50×, etc. coverage for SNPs. The somatic variant may have a minimum threshold for indels. For instance, at least 50×, 55×, 60×, 65×, 70×, 75×, 80×, 85×, 90×, 95×, 100×, etc. coverage for indels may be required. The variant allele may have at least a certain variant allele fraction for SNPs. For instance, it may have at least 1%, 3%, 5%, 7%, 9%, etc. variant allele fraction for SNPs. The variant allele may have at least a certain variant allele fraction for indels. For instance, it may have a 6%, 8%, 10%, 12%, 14%, etc. variant allele fraction for indels.

The variant allele may have at least a certain read depth coverage of the variant fraction in the tumor compared to the variant fraction in the normal sample. For instance, the variant allele may have 4×, 6×, 8×, 10× etc. the variant fraction in the tumor compared to the variant fraction in the normal sample. Another type of filtering criteria may be that the bases contributing to the variant must have mapping quality greater than a threshold value. For instance, the threshold value may be 20, 25, 30, 35, 40, 45, 50, etc.

Another type of filtering criteria may be that alignments contributing to the variant must have a base quality score greater than a threshold value. For instance, the threshold value may be 10, 15, 20, 25, 30, 35, etc. Variants around homopolymer and multimer regions known to generate artifacts may be filtered in various manners. For instance, strand specific filtering may occur in the direction of the read in order to minimize stranded artifacts. If variants do not exceed the stranded minimum deviation for a specific locus within known artifact generating regions, they may be filtered as artifacts.

Variants may be required to exceed a standard deviation multiple above the median base fraction observed in greater than a predetermined percentage of samples from a process matched germline group in order to ensure the variants are not caused by observed artifact generating processes. For instance, the standard deviation multiple may be 3×, 4×, 5×, 6×, 7×, etc. For instance, the predetermined percentage of samples may be 15%, 20%, 25%, 30%, 35%, etc.

Still at 1138, for germline variant filtering, the germline variant may have a minimum threshold for SNPs. For instance, it may have at least 20×, 25×, 30×, 35×, 40×, 45×, 50×, etc. coverage for SNPs. The germline variant may have a minimum threshold for indels. For instance, at least 50×, 55×, 60×, 65×, 70×, 75×, 80×, 85×, 90×, 95×, 100×, etc. coverage for indels may be required. The germline variant calling may require at least a certain variant allele fraction. For instance, it may require at least 15%, 20%, 25%, 30%, 35%, 40%, 45% etc. variant allelic fraction.

Another type of filtering criteria may be that the bases contributing to the variant must have mapping quality greater than a threshold value. For instance, the threshold value may be 20, 25, 30, 35, 40, 45, 50, etc. Another type of filtering criteria may be that alignments contributing to the variant must have a base quality score greater than a threshold value. For instance, the threshold value may be 10, 15, 20, 25, 30, 35, etc.

At 1142, copy number analysis may be performed. Copy number alteration may be reported if more than a certain number of copies are detected by the assay, such as 3, 4, 5, 6, 7, 8, 9, 10, etc. Copy number losses may be reported if the ratio of the segments is below a certain threshold. For instance, copy number losses may be reported if the log 2 ratio of the segment is less than −1.0.

At 1146, RNA fusion calling analysis may be conducted. RNA fusions may be compared to information in a gene-drug knowledge database 1148, such as a database described in "Prospective: Database of Genomic Biomarkers for Cancer Drugs and Clinical Targetability in Solid Tumors." Cancer Discovery 5, no. 2 (February 2015): 118-23. doi: 10.1158/2159-8290.CD-14-1118. If the RNA fusion is not present within the gene-drug knowledge database 1148, the RNA fusion may not be presented. RNA fusions may not be called if they display fewer than a threshold of breakpoint spanning reads, such as fewer than 2, 3, 4, 5, 6, 7, 8, 9, 10, etc. breakpoint spanning reads. If an RNA fusion breakpoint is not within the body of two genes (including promotor regions), the fusion may not be called.

At 1150, DNA fusion calling analysis may be performed. At 1154, joint tumor normal variant calling data may be prepared for further downstream processing and analysis. Germline and somatic variant data are loaded to the pipeline database for storage and reporting. For example, for both somatic and germline variations, the data may include information on chromosome, position, reference, alt, sample type, variant caller, variant type, coverage, base fraction, mutation effect, gene, mutation name, and filtering. FIG. 25 shows an exemplary data set in table form that is consistent with at least some embodiments of the above disclosure.

Copy Number Variant (CNV) data may also be loaded to the pipeline database for downstream analysis. For example, the data may include information on chromosome, start position, end position, gene, amplification, copy number, and log 2 ratios. FIG. 26 includes exemplary CNV data.

Disclosed concepts related to identifying the location, length, and quantity of CNVs in a patient's genome for analysis to improve the patient's subsequent treatment selections and standards of care and, in particular, to the treatment selections and standards of care for oncological diagnosis are described hereafter with reference to FIGS. 311 through 318.

Following analysis, a workflow processing system may extract and upload the variant data to the bioinformatics database. In one example, the variant data from a normal sample may be compared to the variant data from a tumor sample. If the variant is found in the normal and in the tumor, then it may be determined that the variant is not a cause of the patient's cancer. As a result, the related information for that variant as a cancer-causing variant may not appear on a patient report. Similarly, that variant may not be included in the expert treatment system database 160 with respect to the particular patient. Variant data may include translation information, CNV region findings, single nucleotide variants, single nucleotide variant findings, indel variants, indel variant findings, and variant gene findings. Files, such as BAM, FASTQ, and VCF files, may be stored in the expert treatment system database 160.

Referring again to FIG. 11, at 1123, an MSI assay may be performed as a next generation sequencing based test for microsatellite instability. The MSI assay may comprise a panel of microsatellites that are frequently unstable in tumors with mismatch repair deficiencies to determine the frequency of DNA slippage events. Using the assay methods, tumors may be classified into different categories, such as microsatellite instability high (MSI-H), microsatellite stable (MSS), or microsatellite equivocal (MSE). The assay may require FFPE tumor samples with matched normal saliva or blood to determine the MSI status of a tumor. MSI status can provide doctors with clinical insight into therapeutic and clinical trial options for patient care, as well as the need for further genetic testing for conditions such as Lynch Syndrome. The MSI algorithm may be initiated after the raw sequencing data is processed through the bioinformatics pipeline. Upon completion of the MSI algorithm, results may be stored in the expert treatment system database 160. U.S. Prov. Pat. App. No. 62/745,946, filed Oct. 15, 2018, incorporated by reference in its entirety, describes exemplary systems and methods for MSI algorithms.

Referring still to FIG. 11, sub-processes 1116 through 1123 may be substantially or, in some cases even completely automated so that there is little if any lab technician activity required to complete those processes. In other cases each of the sub-processes 1116 through 1123 may include one or more lab technician activities and one or more automated micro-service steps or calculations. Again, in cases where a lab technician performs service steps, the micro-service may present instructions or other interface tools to help guide the technician through the manual service steps. At the end of each manual step some indication that the step has been completed is received by the micro-service. For instance, in some cases a system machine (e.g., the sequencing computer 1132) may provide one or more data products to the micro-service that indicate completion of the step. As another instance, a technician may be queried for specific data related to the stage of the service. As yet one other instance, a technician may simply enter some status indication like, step completed, to indicate that process 1100 should continue.

Figure 11B:
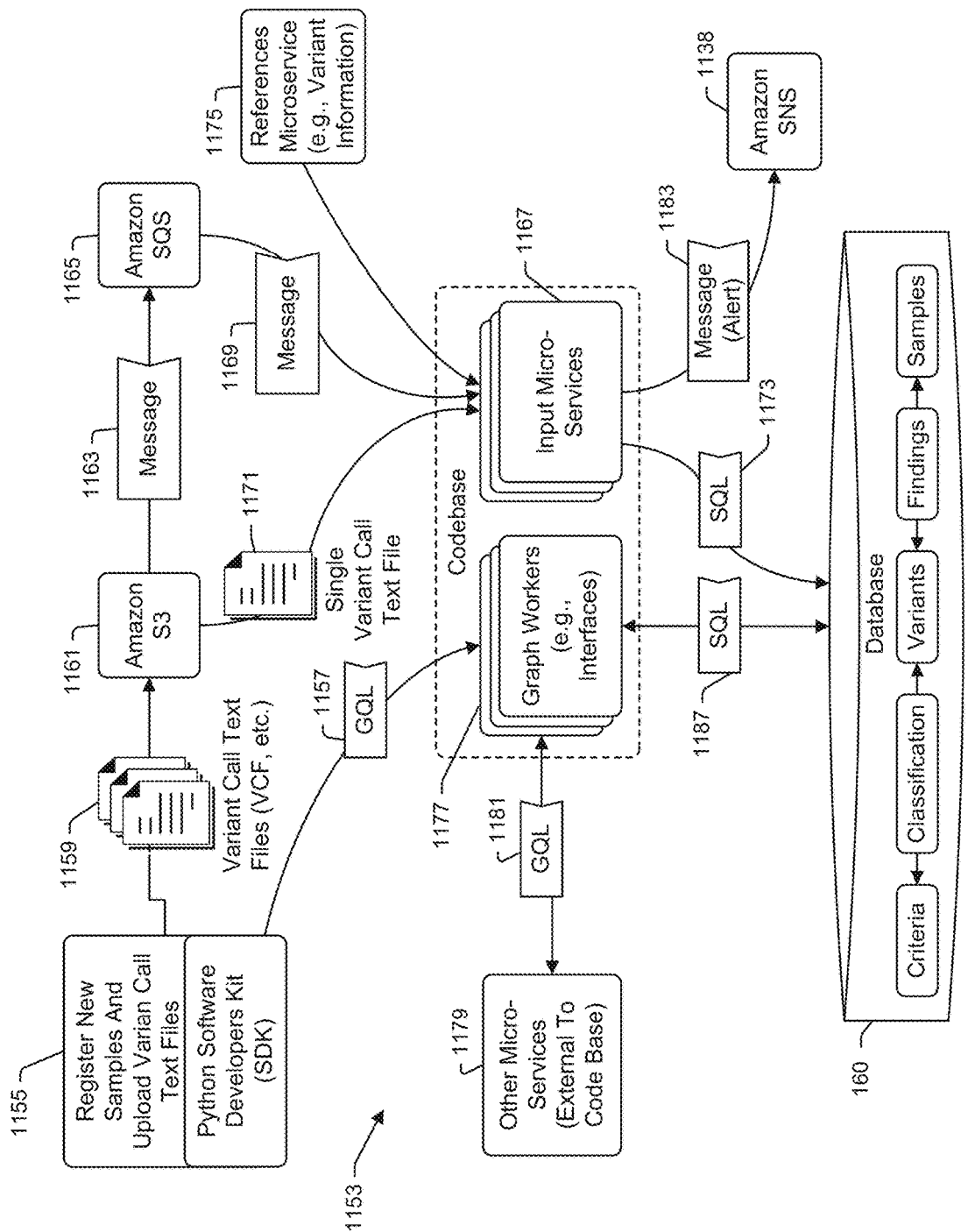
FIG. 11b is a schematic illustrating an exemplary bioinformatics pipeline process that is consistent with at least some embodiments of the present disclosure.
Figure 11C:
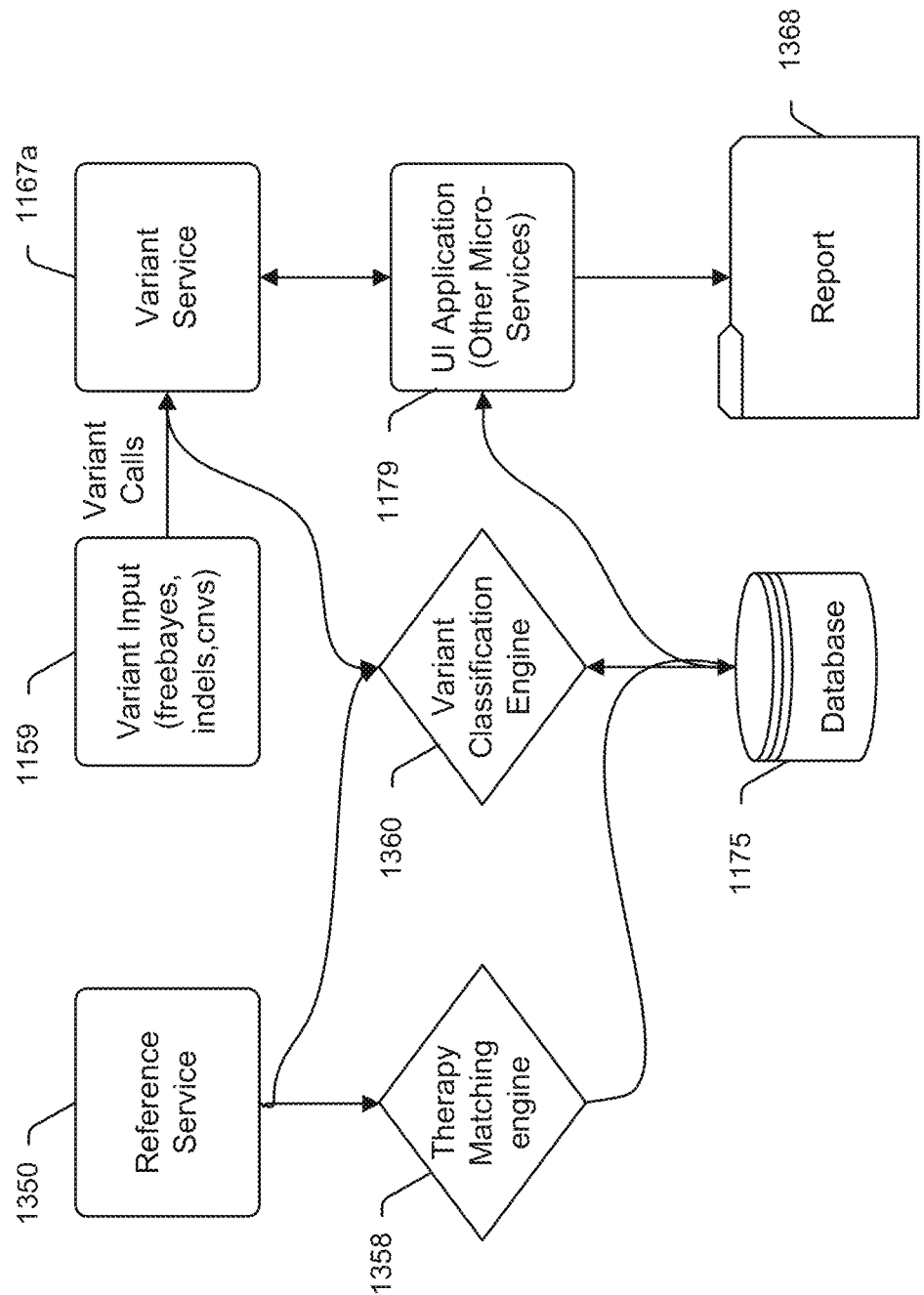
FIG. 11c is a schematic illustrating various system features including a therapy matching engine.

One exemplary workflow 1153 with respect to the bioinformatics pipeline is shown in FIG. 11b. Referring also to FIG. 11c, a client, such as an entity that generates a bioinformatics pipeline, can register new samples 1157 and upload variant call text files 1159 for processing to a cloud service 1161. The cloud service 1161 may initiate an alert by adding a message 1163 to a queue service 1165 (e.g., to an alert list) for each uploaded file. Input micro-services 1167 (1167 in FIG. 11c) receive messages 1169 about each incoming file and process each of those files one at a time (see 1171) as they are received to process and validate each file. The input micro-services 1167 may run as separate node processes and, in at least some cases, generate SQL insertion statements 1173 to add each validated file to the expert treatment system database 160.

Referring still to FIGS. 11b and 11c, the input micro-services 1167 may also run a variant classification engine 1360 on the variant files utilizing a knowledge database of variant information 1175 to calculate many different types of variant criteria, further classification and addition database insertion. The variant micro-service 1167 may publish an alert 1183 when a key event occurs, to which other services 1179 can subscribe in order to react. After a variant call text file is parsed, the variant micro-service may insert variant analysis data into the expert treatment system database 160 including criteria, classifications, variants, findings, and sample information.

Other micro-services 1179 can query 1181 samples, findings, variants, classifications, etc. via an interface 1177 and SQL queries 1187. Authorized users may also be permitted to register samples and post classifications via the other micro-services.

Figure 12:
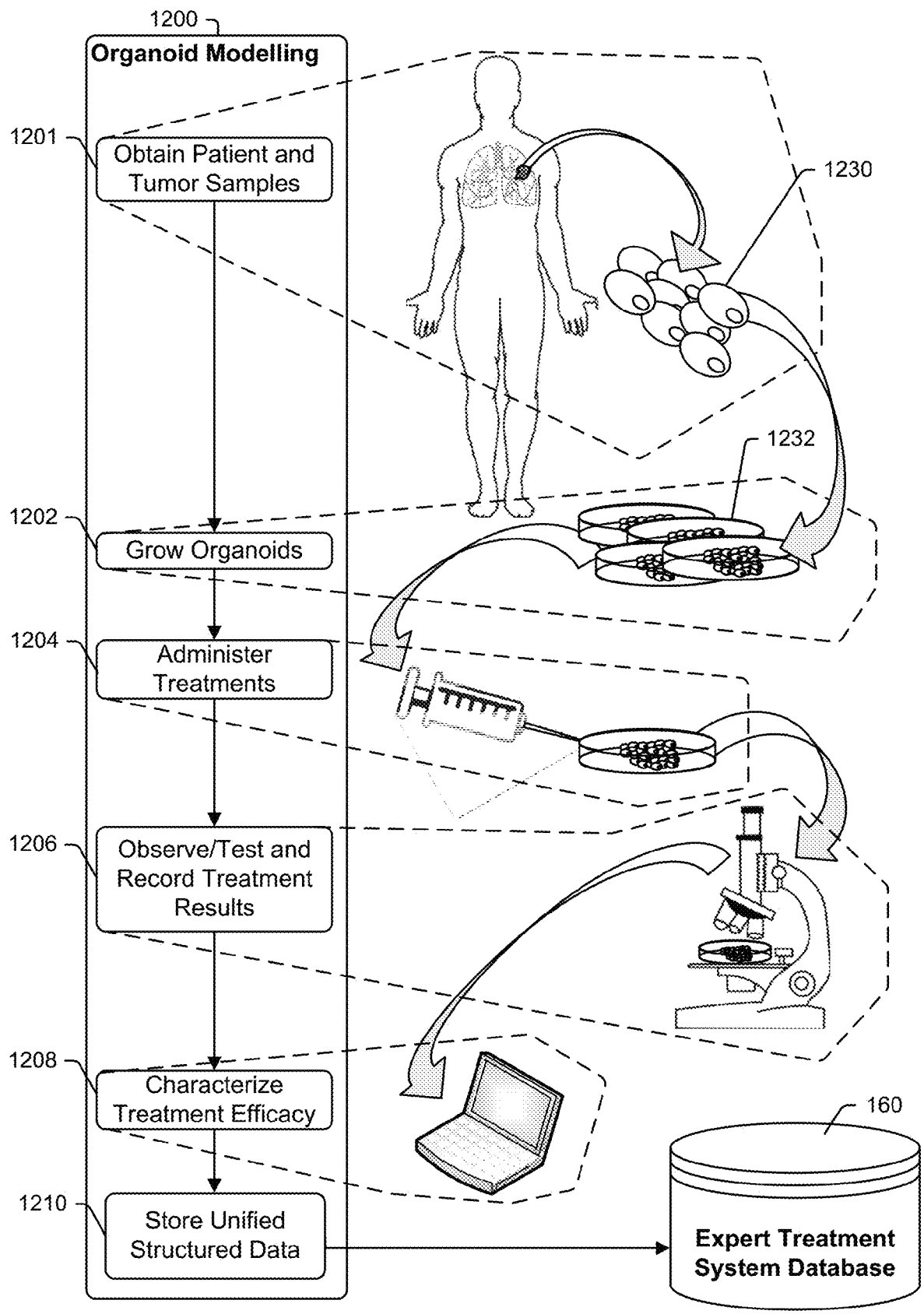
FIG. 12 is a schematic illustrating a multi-micro-service process for generating organoid modelling data that is consistent with at least some aspects of the present disclosure.

Referring to FIG. 12, an organoid modelling process 1200 is illustrated that is consistent with at least some aspects of the present disclosure. At 1201 a tumor specimen 1230 is obtained which is divided into multiple specimens and each specimen is then grown 1202 as a 3D organoid 1232 in a special growth media designed to promote organoid development. At 1204 different cancer treatments are applied to each of the organoids to elicit responses. At 1206 a provider specialist observes the treatment results and at 1208 the results are characterized to assess efficacy of each treatment. At 1210 the results are stored in the system database 160 as part of the unified structured data set for the patient.

Figure 13:
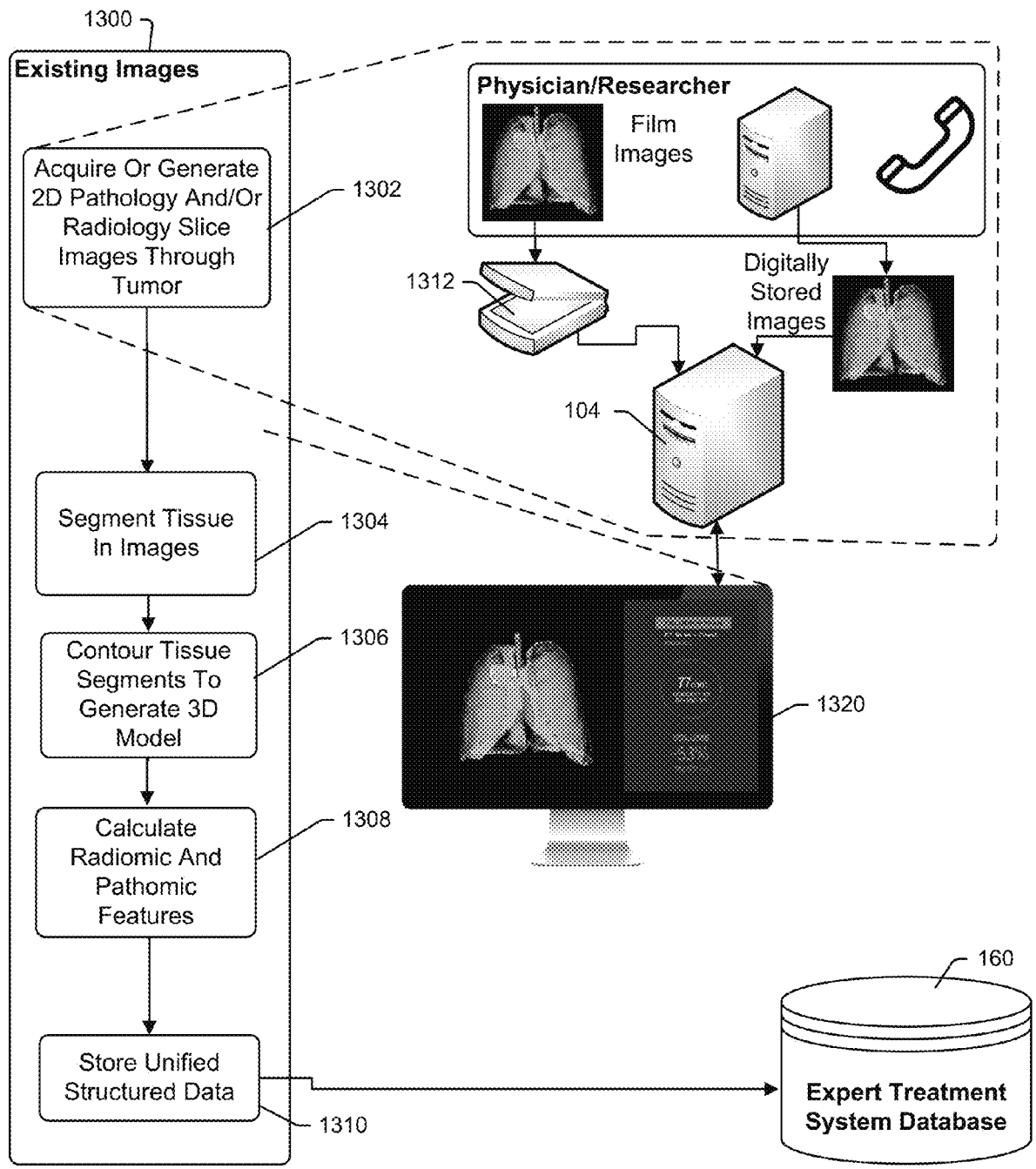
FIG. 13 is a schematic illustrating a multi-micro-service process for generating a 3D model of a patient's tumor as well as identifying a large number of tumor features and characteristics that is consistent with at least some aspects of the present disclosure.

Referring to FIG. 13, a process 1300 for ingesting radiological images into the disclosed system and for identifying treatment relevant tumor features is illustrated. At 1302 a set of 2D medical images including a tumor and surrounding tissue are either generated or acquired from some other source and are stored in system database 160 (e.g., as unaltered images in the lake database). In many cases the 2D images will be in a digital format suitable for processing by a system processor. In other cases the 2D images will be in a format that has to be converted to a data set suitable for system analysis. For instance, in some cases the original images may be on film and may need to be scanned into a digital format prior to creating a 3D tumor model. In some cases original images may not be useable to generate a 3D tumor model and in those cases additional imaging may be required to generate the model.

At 1304 tumor tissue is detected and segmented within each of the 2D images so that tumor tissue and different tissue types are clearly distinguished from surrounding tissues and substances and so that different tumor tissue types are distinguishable within each image. At 1306 the tissue segments within the 2D images are used as a guide for contouring the tissue segments to generate a 3D model of the tumor tissue. At 908 a system processor runs various algorithms to examine the 3D model and identify a set of radiomic (e.g., quantitative features based on data characterization algorithms that are unable to be appreciated via the naked eye) features of the segmented tumor tissue that are clinically and/or biologically meaningful and that can be used to diagnose tumors, assess cancer state, be used in treatment planning and/or for research activities. At 1310 the 3D model and identified features are stored in the system database 160.

While not shown, in some cases a normalization process is performed on the medical images before the 3D model is generated, for example, to ensure a normalization of image intensity distribution, image color, and voxel size for the 3D model. In other cases the normalization process may be performed on a 3D model generated by the disclosed system. In at least some cases the system will support many different segmentation and normalization processes so that 3D models can be generated from many different types of original 2D medical images and from many different imaging modalities (e.g., X-ray, MRI, CT, etc.). U.S. provisional patent application No. 62/693,371 which is titled "3D Radiomic Platform For Managing Biomarker Development" and which was filed on Jul. 2, 2018 teaches a system for ingesting radiological images into the disclosed system and that reference is incorporated herein in its entirety by reference.

An exemplary system for relatively rapidly analyzing H&E and/or IHC slides is described hereafter with reference to FIGS. 252 through 265.

Referring again to FIG. 11c, a therapy matching engine 1358 may match therapies based on the information stored in database 160. In one example, the therapy matching engine 1358 matches therapies at the gene level and uses variant-level information to rank the therapies within a case. For each variant in a case, the therapy matching engine 1358 retrieves therapies matching a variant gene from an actionability database 1350. The actionability database 1350 may store a variety of information for different kinds of variants, such as somatic functional, somatic positional, germline functional, germline positional, along with therapies associated with SNVs and indels.

Therapy matching engine 1358 may rank therapies for each gene based on one or more factors. For instance, the therapy matching engine may rank the therapies based on whether the patient disease (such as pancreatic cancer) matches the disease type associated with the therapy evidence, whether the patient variant matches the evidence, and the evidence level for the therapy. For CNVs, the therapy matching engine may automatically determine that the patient variant matches the evidence. For SNVs or indels, the therapy matching engine may evaluate whether the therapy data came from a functional input or a positional input. For positional SNV/indels, if a variant value falls within the range of the variant locus start and variant locus end associated with the evidence, the therapy matching engine may determine that the patient variant matches the evidence. The variant locus start and variant locus end may reflect those locations of the variant in the protein product (an amino acid sequence position).

For functional SNV/indels, if a variant mechanism matches the mechanism associate with the evidence, the therapy matching engine may determine that the patient variant matches the evidence. Therapies may then be ranked by evidence level. The first level may be "consensus" evidence determined by the medical community, such as medical practice guidelines. The next level may be "clinical research" evidence, such as evidence from a clinical trial or other human subject research that a therapy is effective. The next level may be "case study" evidence, such as evidence from a case study published in a medical journal. The next level may be "preclinical" evidence, such as evidence from animal studies or in vitro studies. Ultimately, pdf or other format reports 1368 are generated for consumption.

While a set of data sources and types are described above, it should be appreciated that many other data sets that may be meaningful from a research or treatment planning perspective are contemplated and may be accommodated in the present system to further enhance research and treatment planning capabilities.

Figure 3A:
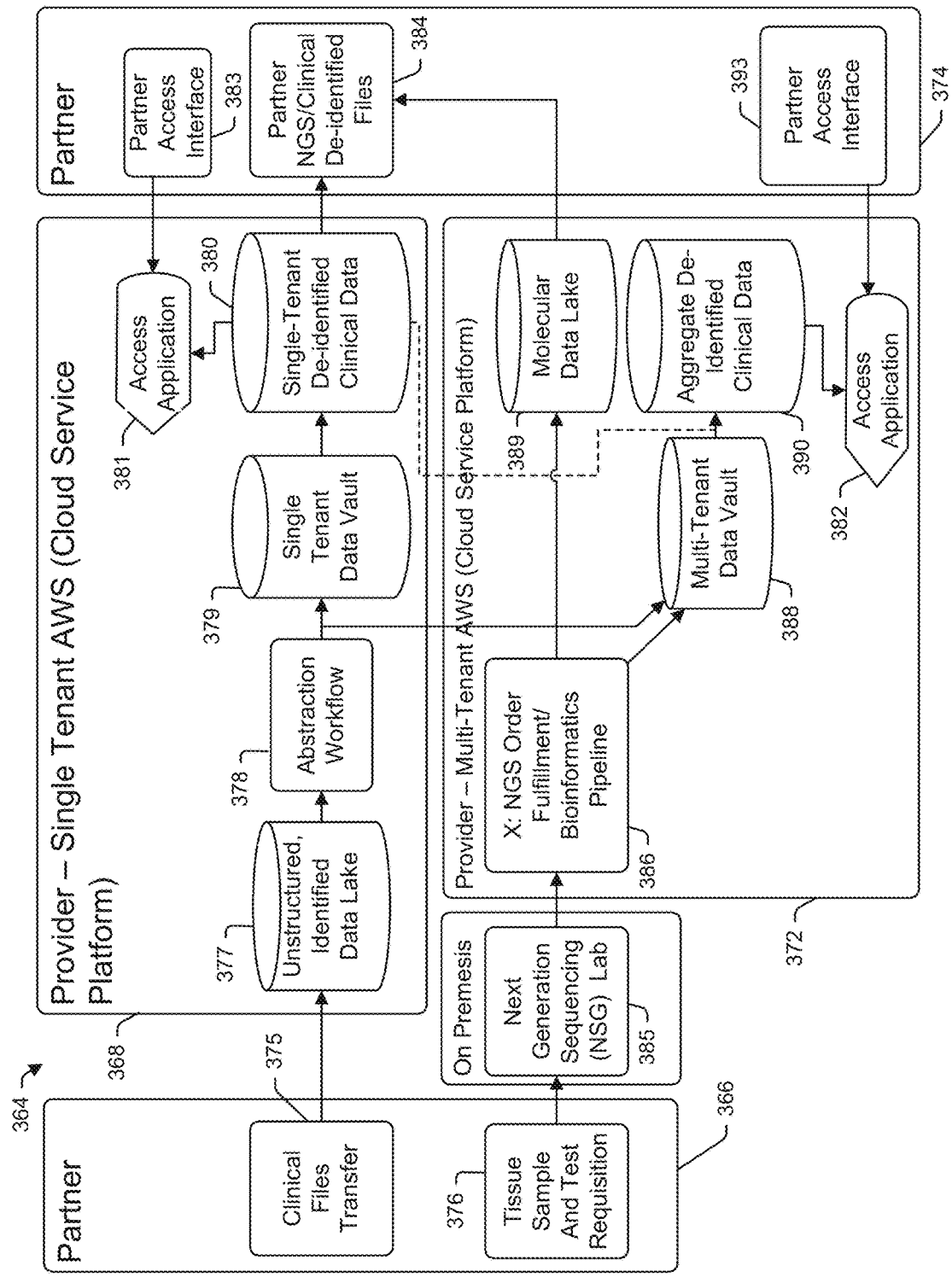
FIG. 3a is a schematic diagram showing a data platform that is consistent with at least some aspects of the present disclosure.

Referring now to FIG. 3a, a schematic is shown that represents an exemplary data platform 364 that is consistent with at least some aspects of the present disclosure. The exemplary platform shows data, information and samples as they exist throughout a system where different system processes and functions are controlled by different entities including an overall system provider that operates both single tenant and multi-tenant cloud service platforms 368 and 372, respectively, partners 366 that provide clinical files as well as tissue samples and related test requisition orders as well as other partners 374 that access processed data and information stored on the service platforms 368 and 372. Partners 366 provide secure clinical files 375 via a file transfer to the single tenant cloud platform 368 and are stored as unstructured and identified files in the lake database. Those files are abstracted and shaped as described above to generate normalized structured clinical data that is stored in a single tenant data vault as well as in a multi-tenant data vault 388. The data from the vault is then de-identified and stored in a de-identified clinical data database which is accessible to authorized partners 374 via system interfaces 383 and applications 381 as described herein.

Referring still to FIG. 3a, partners 366 also provide tissue samples and test requisition orders that drive next generation sequencing lab activity at 385 to generate the bioinformatics pipeline 386 which is stored in both a molecular data lake database 389 and the multi-tenant data vault 388. The data in vault 388 is de-identified and stored in an aggregate de-identified clinical data database 390 where it is accessible to authorized partners via system interfaces 393 and applications 382 as described herein. In addition, the molecular lake data 389 and the de-identified single tenant files 380 are accessible to other authorized partners via other interfaces 384.

D. User Interfaces

Referring again to FIG. 3, the disclosed system 100 is accessible by many different types of system users that have many different needs and goals including clinical physicians 10 as well as provider specialists like data abstractors 20, lab, modeling and radiology specialists 30, partner researchers 40, provider researchers 50 and dataset sales specialists 60, among others. Because each user type performs different activities aimed at achieving different goals, the application suites 188, 192 and associated user interfaces employed by each user type will typically be at least somewhat if not very different. For instance, a physician's application suite may include 9 separate application programs that are designed to optimally support many oncological treatment consideration and planning processes while an abstractor specialist's application suite may include 5 application programs that are completely separate from the 9 programs in the physician's suite and that are designed to optimally facilitate record abstraction and data structuring processes.

In some cases a system user's program suite will be internally facing meaning that the user is typically a provider employee and that the suite generates data or other information deliverables that are to be consumed within the system 100 itself. For instance, an abstractor application program for structuring data from a raw data set to be consumed by micro-services and other system resources is an example of an internally facing application program. Other system user programs or suites will be externally facing meaning that the user is typically a provider customer and that the suite generates data or other information deliverables that are primarily for use outside the system. For instance, a physician's application program suite that facilitates treatment planning is an example of an externally facing program suite.

Referring now to FIGS. 14 through 21, screenshots of an exemplary physician's user interface that include a series of hyperlinked user interface views that are consistent with at least some aspects of the present disclosure are shown. The screenshots show one natural progression of information consideration wherein each interface is associated with one of the physician's program suite applications 188. While some of the illustrated screenshots are complete, others are only partial and additional screen data would be accessible via either scrolling downward as well known in the graphical arts or by selection of a hyperlink within the presented view that accesses additional information related to the screenshot that includes the selected hyperlink.

Figure 14:
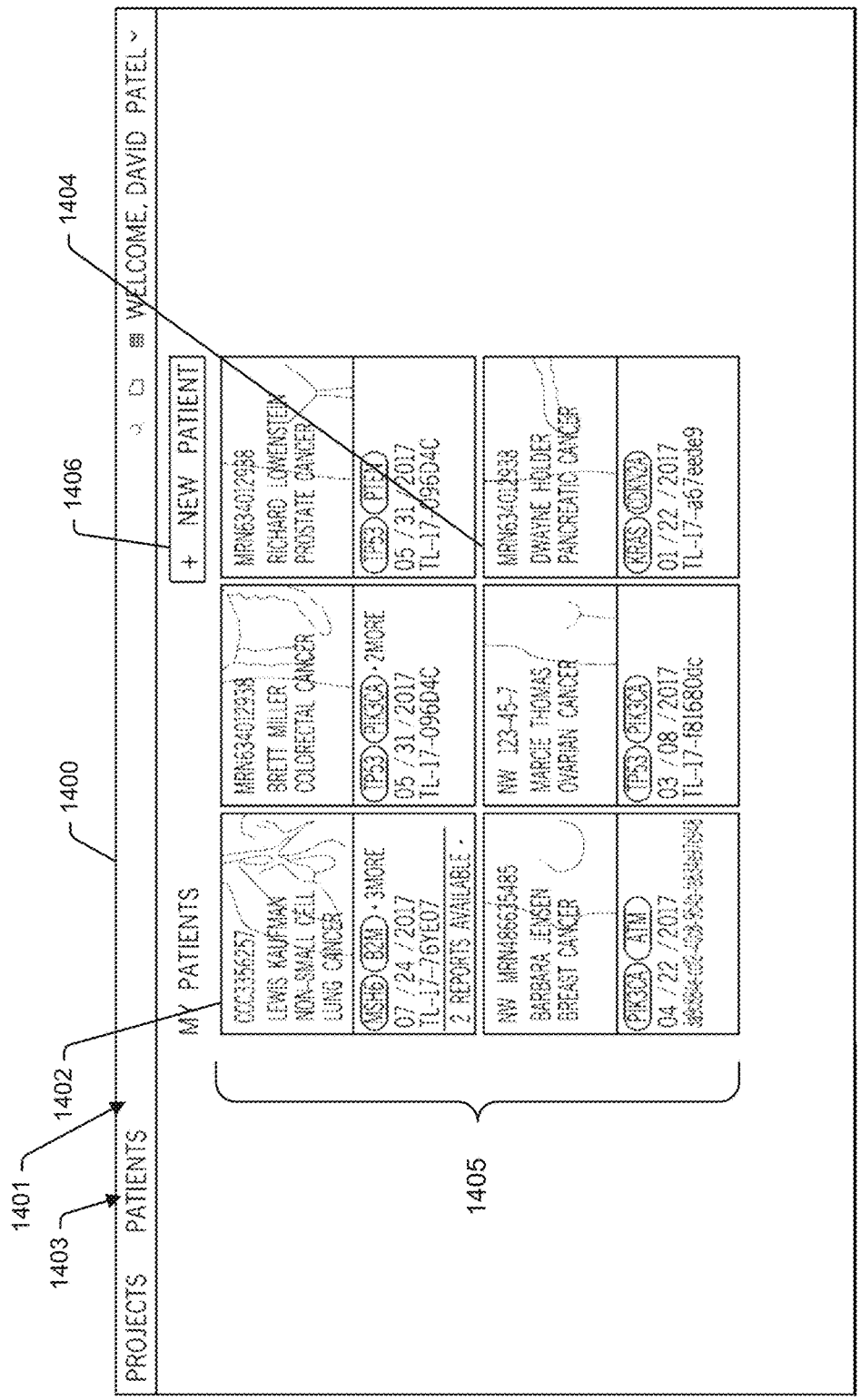
FIG. 14 is a screenshot illustrating a patient list view that may be accessed by a physician using the disclosed system to consider treatment options for a patient.

Referring to FIG. 14, once a physician logs onto system 10 via entry of a username and password or via some other security protocol, the physician is either presented with a patient list screen 1400 or can navigate to that screen. The patient list screen 1400 includes a first navigation bar or ribbon that extends along an upper edge of the view as well as a patient list area 1405 that includes a separate cell or field (two labelled 1402 and 1404) for each of the physician's patients for which the system 100 stores data. Each patient cell (e.g., 1404) includes basic patient information including the patient's name, an identification number and a cancer type and operates as a hyperlink phrase for accessing applications where the system loads data for the patient indicated in the cell. The screen 1400 also includes a "New Patient" icon 1406 that is selectable to add a new patient to the physician's view. The screen 1400 may display all patients of the physicians who have received genomic testing. Each patient cell can represent one or more reports created based on tissue samples. Physicians can also see in-progress patients along with a status indicating an order's progress, such as if the sample has been received. Some physicians may be provided with an additional section displaying reference patients. In these cases, the physician signed into the system 10 is not the patient's ordering physician, but has some other reason to access the patient information, such as because the ordering physician indicated he or she should receive a copy of the report and be permitted other appropriate access. Certain users of the system 10, such as administrators, may have access to browse all patients within their institution.

Figure 15:
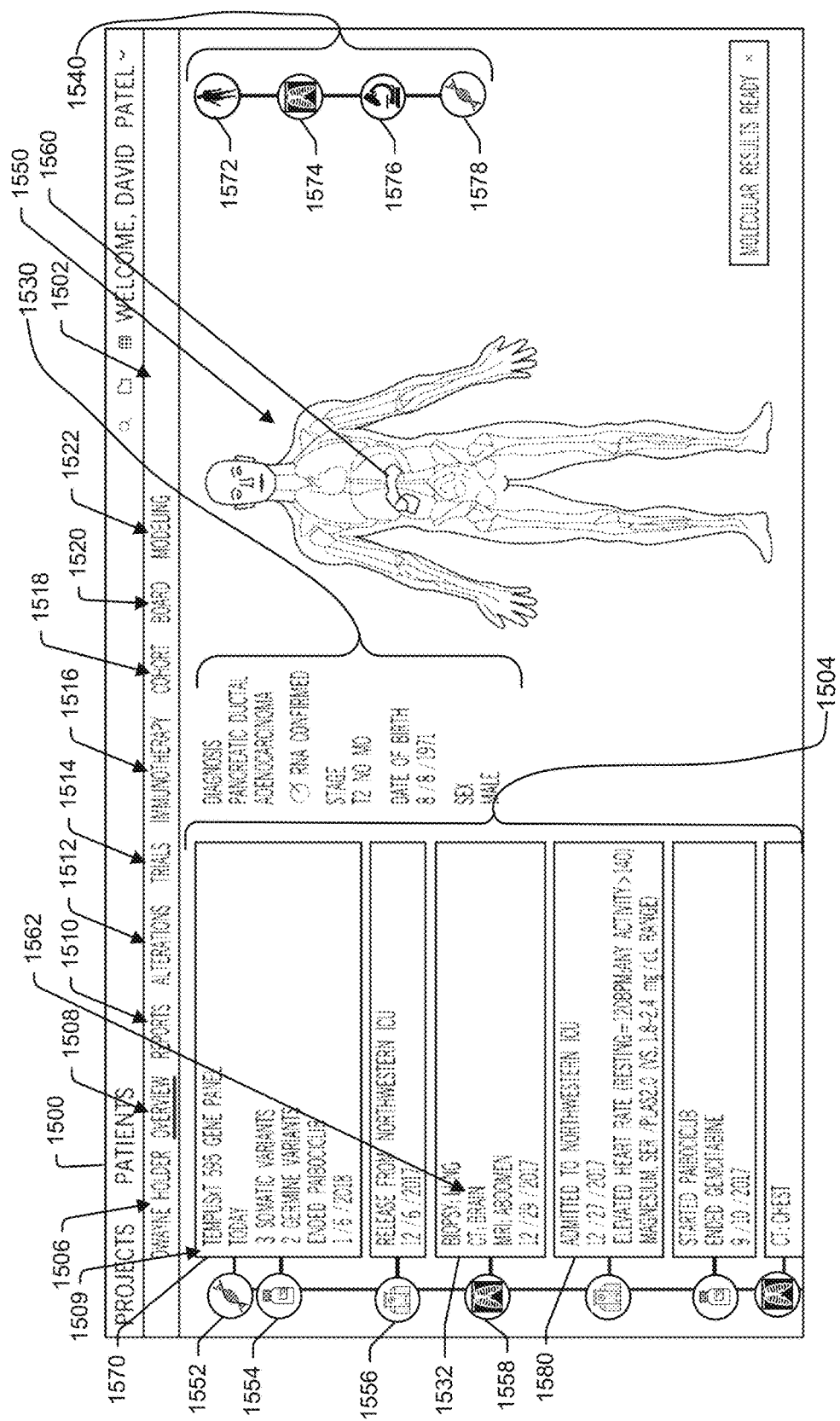
FIG. 15 is a screenshot illustrating an overview view that may be accessed by a physician using the disclosed system to review prior treatment or case activities related to the patient.

Referring again to FIG. 14, upon selecting cell 1404 associated with a patient named Dwayne Holder, the system presents the screenshot 1500 shown in FIG. 15 that includes a second level navigation bar 1502 near the top of the screen 1500 and a workspace 1504 below bar 1502. Navigation bar 1502 persistently identifies the patient 1506 associated with the data currently being viewed by the physician throughout the screenshots illustrated and also includes a separate hyperlink text term for each of several system data views or application programs that can be selected by the physician. In FIG. 15 the view and applications options include an "Overview" option 1508, a "Reports" option 1510, an "Alterations" option 1512, a "Trials" option 1514, an "Immunotherapy" option 1516, a "Cohort" option 1518, a "Board" option 1520 and a "Modelling" option 1522. Many other options will be added to bar 1502 over time as they are developed. A view or application currently accessed by the physician is underlined or otherwise visually distinguished in bar 1502. For instance, in FIG. 15 the overview icon 1508 is shown highlighted to indicate that the information presented in workspace 1504 is associated with the overview data view.

Referring still to FIG. 15, the exemplary overview view includes a patient care timeline 1509 along a left edge of workspace 1504, high level patient cancer state information 1550 in a central portion of workspace 1504 and view selection icons 1540 along a right edge of workspace 1504. Timeline 1509 includes a set of patient care cells 1570, 1580, etc., each of which corresponds to a meaningful care related event associated with treatment of the patient's cancer state. The cells are vertically stacked with earliest cells in time near the bottom of the stack and more recent cells near the top of the stack. Each cell is typically restricted to activities or information associated with a specific date and, in addition to the associated date, may include any subset of several different information types including hospital or clinic admission and release dates, medical imaging descriptors, procedure descriptors, medication start and end dates, treatment procedure start and end descriptors, test descriptors, test or procedure results descriptors and other descriptors. This list is exemplary and not intended to be exhaustive. For instance, cell 1532 that is dated Dec. 29, 2017 indicates that a lung biopsy occurred as well as a brain CT imaging session and an MRI of the patient's abdomen. Information in the timeline 1509 may be loaded from the structured data that results from using the systems and methods described herein, such as those with reference to FIG. 10. Information in the timeline 1509 may also include references to genomic sequencing tests ordered for a patient.

Referring still to FIG. 15, in addition to including the patient care cell stack, the care timeline 1509 includes a vertical activity icon progression 1534 that extends along the left edge of the cell stack. The activity icons in progression 1534 are horizontally aligned with associated textual descriptions of care events in the cell stack. Each activity icon is designed to glanceably indicate an activity type so that a physician can quickly identify activities of specific types within the stacked cells by simply viewing the icons and associated stack event descriptors. For instance, exemplary activity icons include a gene panel publication icon 1552, a medication start/stop icon 1554, a facility admit/release icon 1556 and an imaging session icon 1558. Other icons corresponding to surgery, detected patient medical conditions, and other procedures or important medical events are contemplated.

Referring still to FIG. 15, in at least some cases detailed data related to a care event will be further accessible by selecting one of the activity icons along the left of the cells or events in a cell to hyperlink to the additional information. For instance, the "CT:Brain" text at 1662 may be selectable to link to a CT image viewer to view CT images of the patient's brain that correspond to the event. Other links are contemplated.

Referring again to FIG. 15, general cancer state and patient information at 1550 includes diagnosis, stage, patient date of birth and gender information 1530 as well as an anatomical image that shows a representation of a tumor within a body that is generally consistent with the patient's cancer state. In some cases the tumor representation is just representative of the patient's condition as opposed to directly tied to actual tumor images while in other cases the tumor representation is derived from actual medical images of the patient's tumor.

Referring again to FIG. 15, the patient body image 1550 may be overlaid with structured contours 1560 from the patient's radiology imaging. Represented structures may include primary or metastatic lesions, organs, edema, etc. A physician may click each structured contour to obtain an additional level of detail of information. Clicking the structured contour may isolate it visually for the physician. In the case of a tumor contour, the additional level of detail may include supporting information such as tumor volume, longest 3D diameter, or other features. Certain radiomic features that may be presented to the physician are described in further detail in, for instance, U.S. Provisional Patent Application No. 62/693,371, titled 3D Radiomic Platform for Imaging Biomarker Development, which has been incorporated herein by reference in its entirety.

From this detailed view, the physician may further drill down to an additional, microscopic level of detail. Here, a patient's histopathology results may be displayed. Clinical interpretations are shown, where available from an issued report. The microscopic detail may also display thumbnail images of microscope slides of a patient's specimens.

View selection icons 1540 include a set of icons that allow the physician to select different views of the patient's cancer condition and are progressively more granular. To this end, the exemplary view icons include a body view icon 1572 corresponding to the body view shown in FIG. 15, a medical imaging view icon 1574 for accessing medical X-ray, CT, MRI and other images, a cellular view icon 1576 that shows cellular level images and genomic sequencing data icon 1578 for accessing genomic data views.

Figure 16:
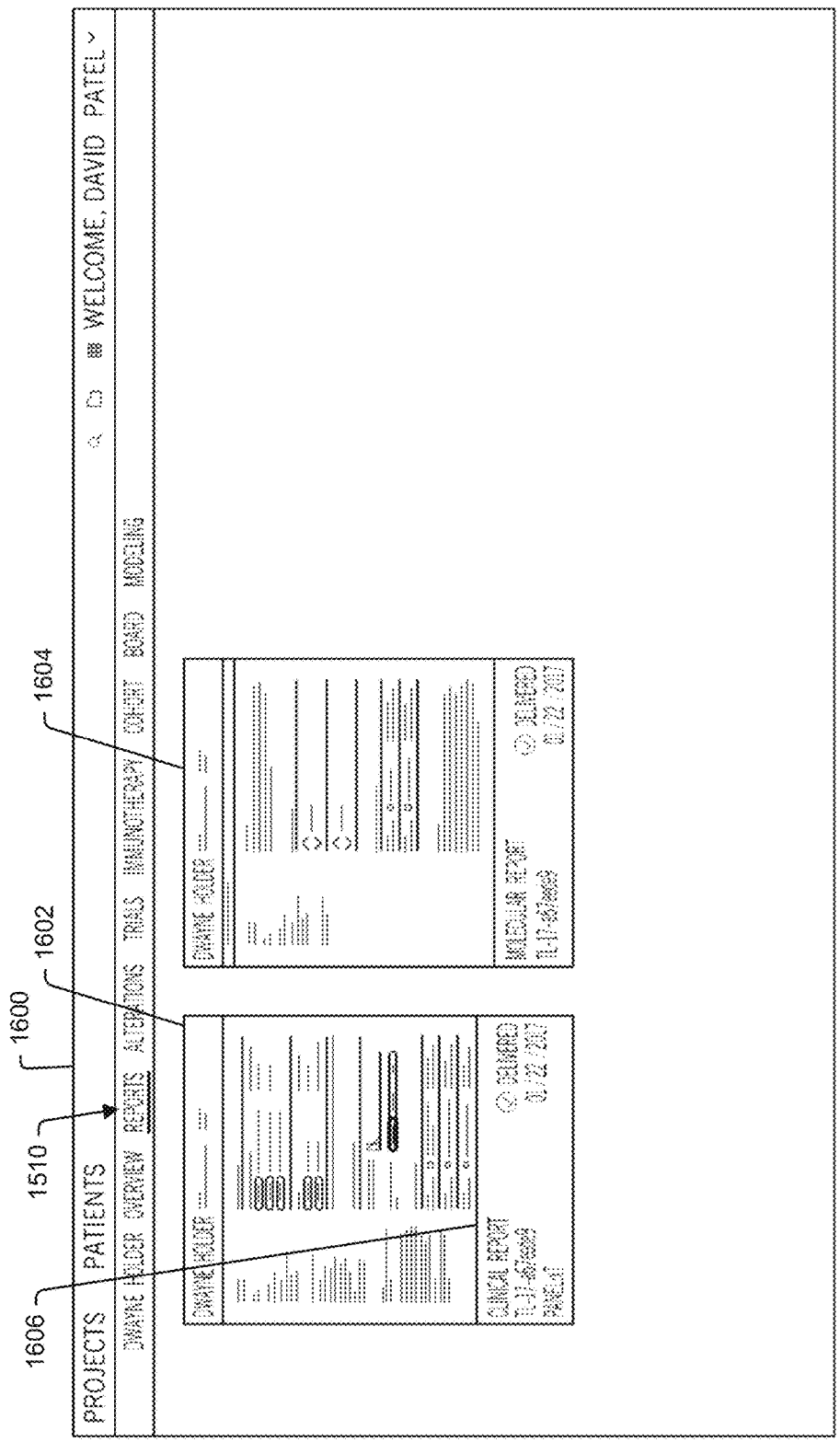
FIG. 16 is a screenshot illustrating screenshot illustrating a reports view that may be used to access patient reports generated by the system 100.

Referring again to FIG. 15, to access specific issued reports associated with the patient the physician selects reports icon 1510 to access a reports screen 1600 shown in FIG. 16. Reports screen 1600 shows the reports icon 1510 highlighted to help orient the physician and includes a report list indicating all reports stored in the system that are associated with the patient. In the exemplary reports view, each report is represented in the list by a reduced size image of the first page of the report and with a general report description field near the bottom of the image. For exemplary report images are shown at 1602 and 1604 and a general report description of the report associated with image 1602 is provided at 1606 indicating report type, date and other characterizing information.

Figure 17:
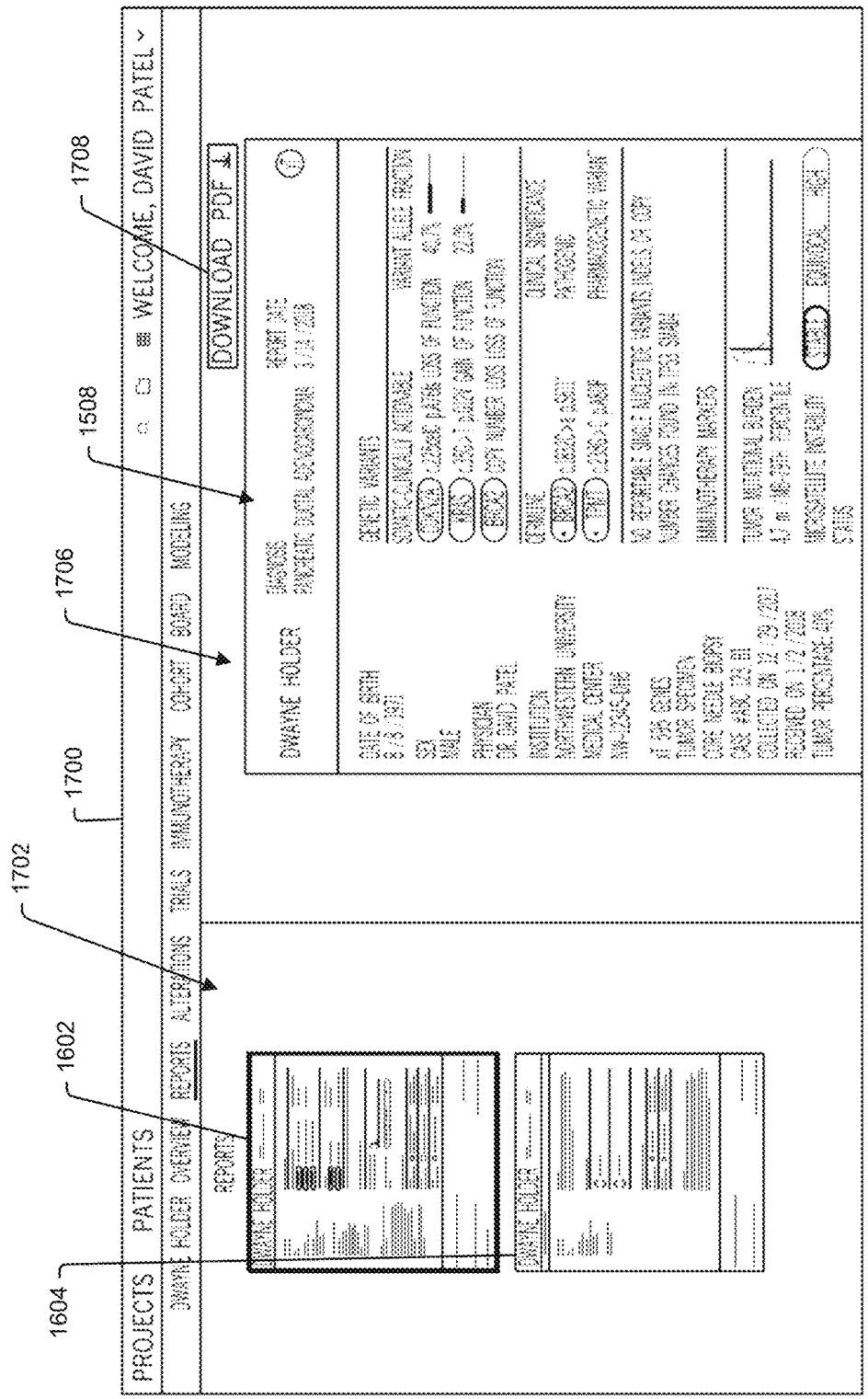
FIG. 17 is a screenshot illustrating a second reports view that shows one report in a larger format.

The physician can select one of the report images to access the full report. For instance, if the physician selects image icon 1602, the screenshot 1700 shown in FIG. 17 is presented that splits the display screen into a report list section 1702 along the left edge of the screen and an enlarged report section 1704 that covers about the right two thirds of the screen where the selected report is presented in a larger format for viewing. The report presents clinically significant information and may take many different forms. Each report is listed again in section 1702 as a reduced size hyper linkable image as shown at 1602 and 1604 where the currently selected report 1602 is highlighted or otherwise visually distinguished. The physician can select a PDF icon 1708 to download a copy of the report to the physician's computer.

As an order is being processed, in at least some embodiments a system processor will monitor microservice progress and automatically continue moving an order through a fulfillment process. In many cases a microservice map will need to be modified midstream during processing. For instance, in some cases an order may be modified prior to completion. In other cases one or more microservices will fail to generate useful information for any of several different reasons (e.g., lab mistake, sequencing error, a machine gets hung up for some reason and cannot complete a service, etc.). In these cases, the system may be programmed to sort of self-heal by assessing instantaneous order processing status and re-mapping a modified path toward order completion. In this regard, see FIGS. 70 through 72 hereafter and associated description of an order management system that can automatically remap microservices as orders progress.

Figure 80:
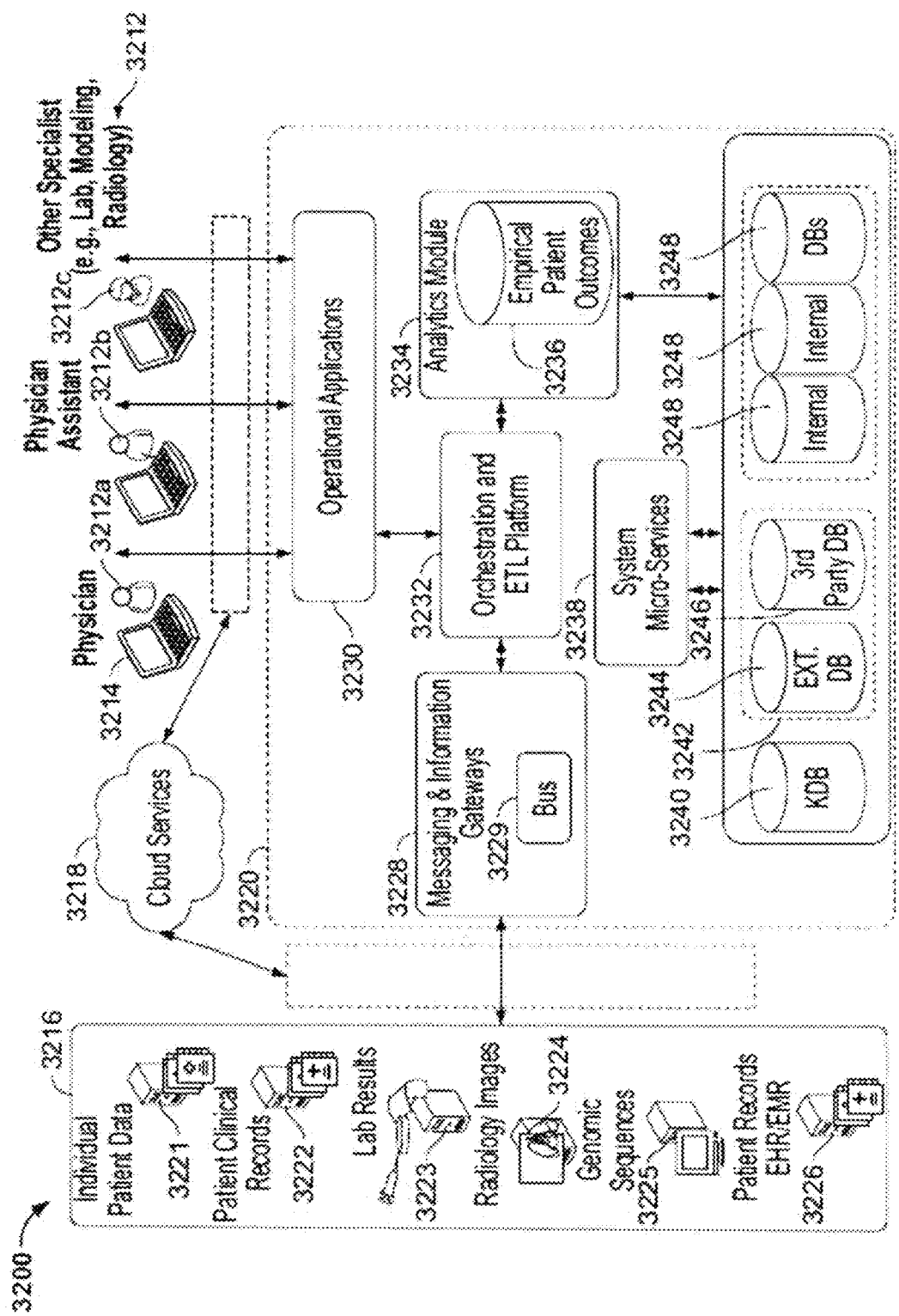
FIG. 80 is a block diagram of a data-based healthcare system, according to aspects of the present disclosure.

A workbench toolset for abstracting data from unstructured or semi-structured prior data records are described hereafter with reference to FIGS. 80 through 138. Purpose-specific functionality and enhancements have been incorporated within the core Workbench toolset to help accelerate clinical data abstraction, streamline case management tasks, facilitate operational workflows and improve quality assurance and overall data integrity.

See also the description hereafter associated with FIGS. 158 through 186 which describe other abstracting systems and features as well as mobile device systems that can capture medical records for system ingestion and that can provide mobile system interfaces of different types to physicians. Another system toolset for automated quality assurance of abstracted data is described with reference to FIGS. 139 through 157 hereafter.

E. Artificial Intelligence for Predicting Events Based on Patient Records

Extracting meaningful medical features from an ever expanding quantity of health information tabulated for a similarly expanding cohort of patients having a multitude of sparsely populated features is a difficult endeavor. Identifying which medical features from the tens of thousands of features available in health information are most probative to training and utilizing a prediction engine only compounds the difficulty. Features which may be relevant to predictions may only be available in a small subset of patients and features which are not relevant may be available in many patients. In at least some embodiments the system is capable of ingesting a comprehensive scope of available data across entire populations or subsets of patients to identify features which apply to the largest number of patients and establish a model for prediction of an objective. In cases where there are multiple objectives to choose from, the system may curate the medical features extracted from patient health information to a specific model associated with the prediction of the desired objective. FIGS. 187A through 187C and 188 describe AI systems that are capable of performing various AI tasks.

Figure 18:
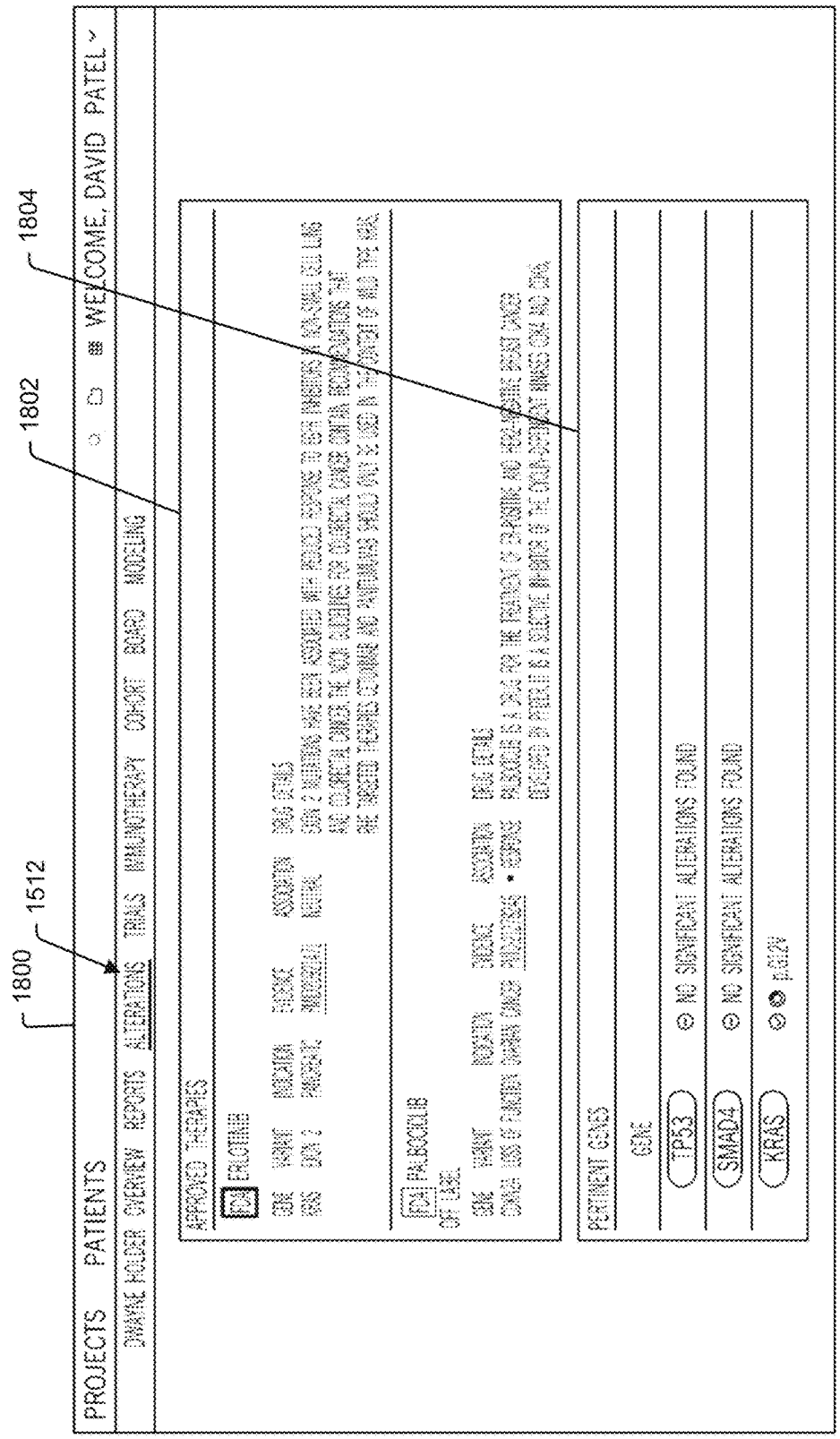
FIG. 18 is a screenshot illustrating an alterations view accessible by a physician to consider molecular tumor alterations.

To examine information related to a patient's genomic tumor alterations and possible treatment options, the physician selects alterations icon 1512 to access screen 1800 shown in FIG. 18. Screen 1800 includes an approved therapies list 1802 and a pertinent genes list 1804. The therapies list 1802 includes a list of genes for which variants have been identified and for each gene in the list, the associated variant, how the variant is indicated and other information including details regarding considerations corresponding to the associated therapy option. Other screens for considering alterations are contemplated to enable a physician to consider many aspects of treatment efficacy. Additional details may be provided to add context to alterations, such as gene descriptions, explanation of mutation effect, and variant allelic fraction. Alterations may be reported by category, ranging from highly relevant genes to variants of unknown significance.

Figure 18A:
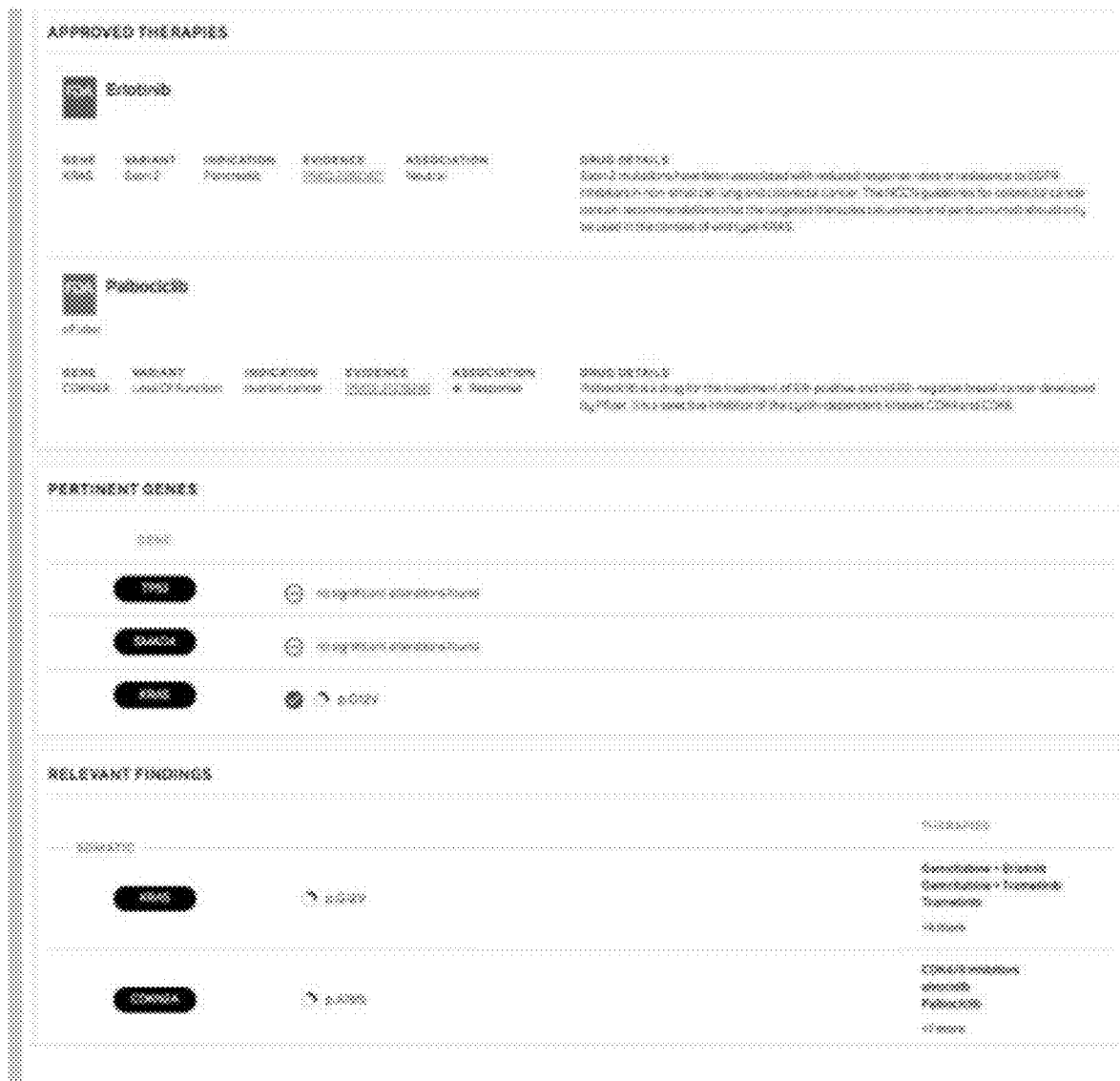
FIG. 18a is an exemplary top portion of a screenshot of a user interface for reporting and exploring approved therapies.
Figure 18B:
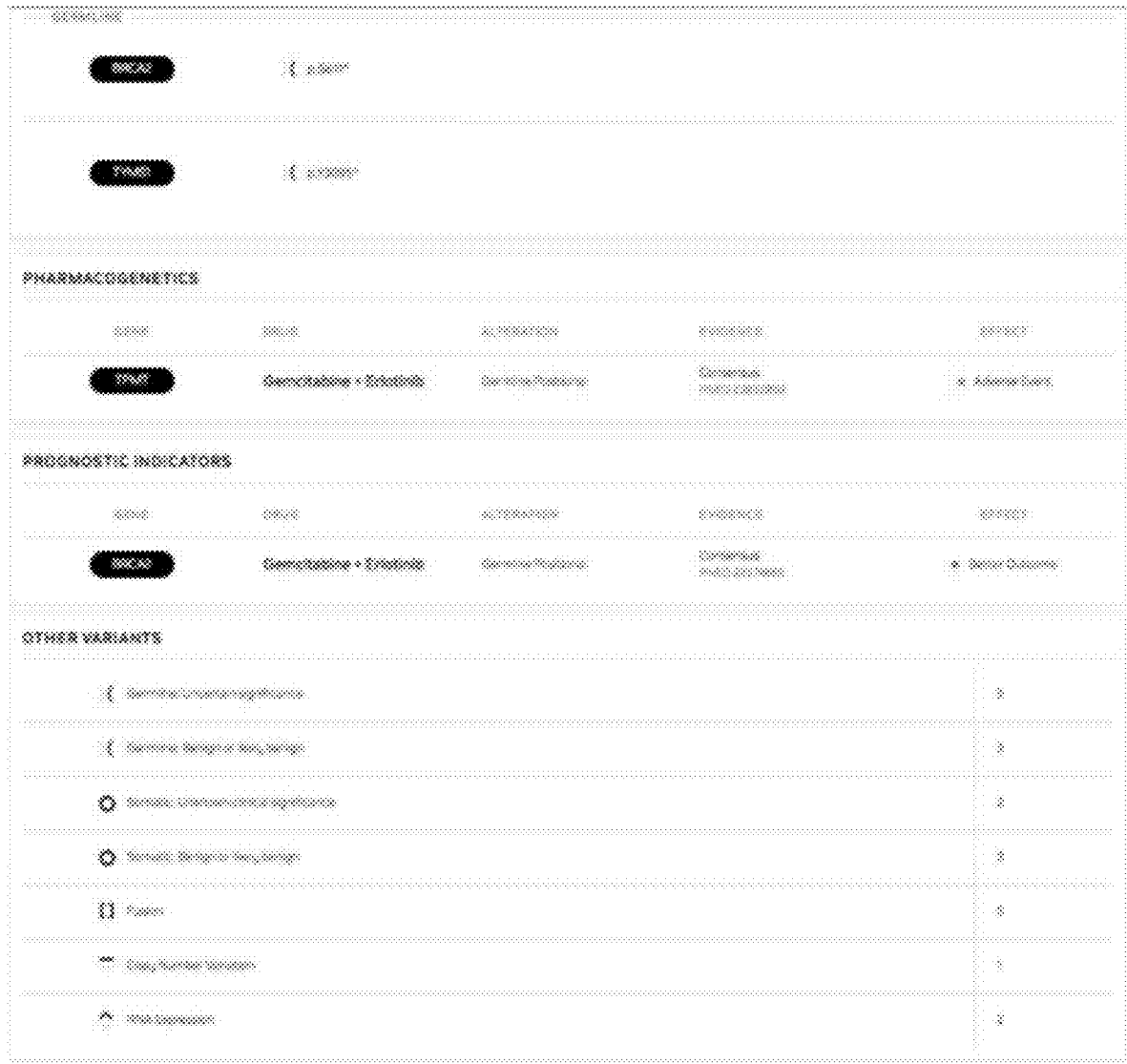
FIG. 18b shows the lower portion of the FIG. 18a screenshot.
Figure 19:
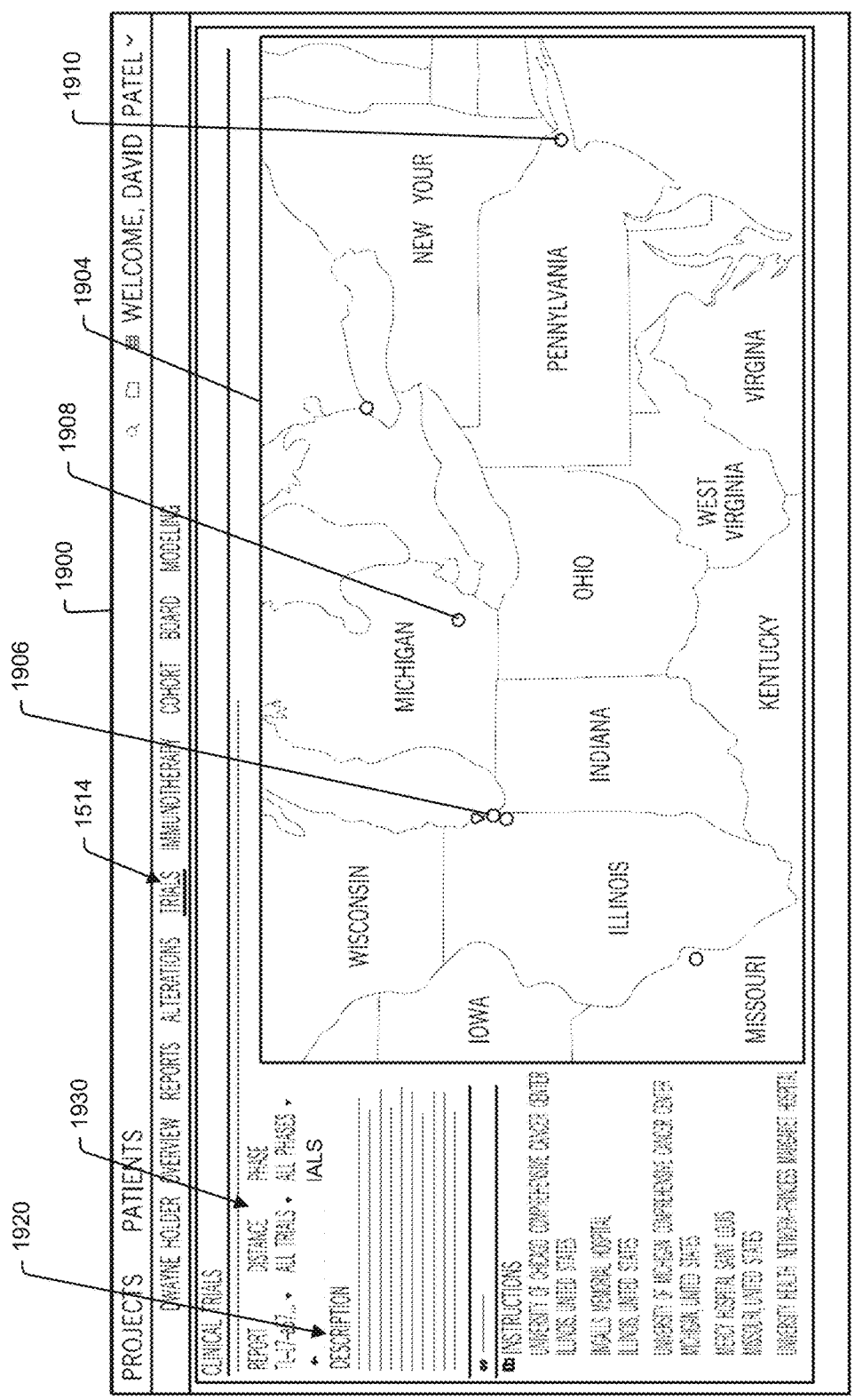
FIG. 19 is a screenshot illustrating a trials view in which a physician views information related to clinical trials on conjunction with considering treatment options for a patient.

Selecting an alteration may take the physician to an additional view, shown at FIGS. 18a and 18b (showing different scrolled sections of one view in the two figures), where the physician can delve deeper into the alteration's effect, with supporting data visualizations. Germline alterations associated with diseases may be reported as incidental findings. In FIG. 18a, approved therapies are listed with relevant related information including a gene and variant indicator along with hyperlinks to evidence associated with the therapy and details about each of the therapies.

In at least some disclosed embodiments the system will be capable of creating and presenting diagnostic and/or treatment pathways and options to physicians, including potential treatment options specifically tailored to a particular patient's cancer state. To this end, a system for identifying treatment pathways is described hereafter in relation to FIGS. 266 through 270. While FIGS. 266 through 270 describe a pathway identifying system in the context of cancer states, it should be appreciated that the system is also applicable to other diseases such as, for instance, depression, Parkinson's disease, Alzheimer's disease, etc.

The physician application suite also provides tools to help the physician identify and consider clinical trials that may be related to treatment options for his patient. To access the trials tools, the physician selects trials icon 1514 to access the screen (not shown) that lists all clinical trials that may be of any interest to the physician given patent cancer state characteristics. For instance, for a patient suffering from pancreatic cancer, the list may indicate 12 different trials occurring within the United States. In some cases the trials may be arranged according to likely most relevant given detailed cancer state factors for the specific patient. The physician can select one of the clinical trials from the list to access a screen 1900 like the one shown in FIG. 19. Screen 1900 includes a map 1904 with markers (three labelled 1906, 1908 and 1910) at map locations corresponding to institutions are participating in the selected trial as well as a general description 1920 of the trial. Screen 1900 also provides a set of filtering tools 1930 in the form of pull down menus the physician can use to narrow down trial options by different factors including distance from the patient's location, trial phase (e.g., not yet initiated, progressing, wrapping up, etc.), and other factors. Here, the idea is that the physician can explore trial options for specific patient cancer states quickly by focusing consideration on the most relevant and convenient trial options for specific patients.

In at least some cases the system will include a tool suite for ingesting clinical trial information into a normalized dataset which then drives a trial matching subsystem and presents matching trial output via user interfaces. One exemplary trial ingestion, matching and interface system is described hereafter with respect to FIGS. 271 through 302.

Figure 20:
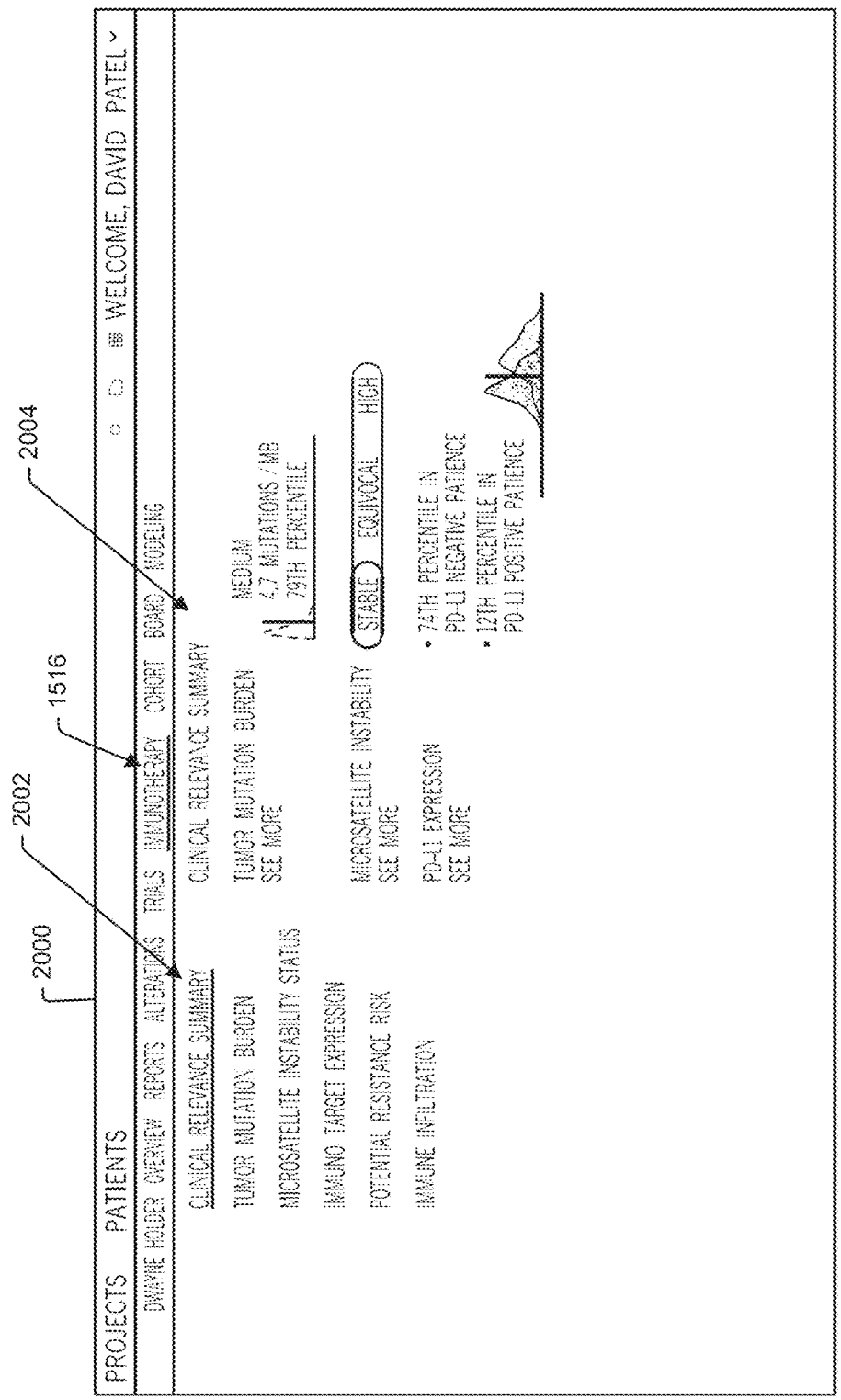
FIG. 20 is a screenshot illustrating an immunotherapy screenshot accessible to a physician for considering immunotherapy efficacy options for treating a patient's cancer state.

The physician application suite provides tools for the physician to consider different immunotherapies that are accessible by selecting immunotherapy icon 1516 from the navigation bar. When icon 1516 is selected, an exemplary immunotherapy screenshot 2000 shown in FIG. 20 is presented. Screenshot 2000 includes a menu of immunotherapy interface options 2002 extending vertically along a left area of the screen and a detailed information area 2004 to the right of the options 2002. In at least some cases the immunotherapy options 2002 will include a summary option, a tumor mutation burden option, a microsatellite instability status option, an immune resistance risk option and an immune infiltration option where each option is selectable to access specific immunotherapy data related to the patient's case. Immunotherapy options 2002 may provide the physician with an indication that an immunotherapy, such as an FDA approved immunotherapy, may be appropriate to prescribe the patient. Examples may include dendritic cell therapies, CAR-T cell therapies, antibody therapies, cytokine therapies, combination immunotherapies, adoptive t-cell therapies, anti-CD47 therapies, anti-GD2 therapies, immune checkpoint inhibitors, oncolytic viruses, polysaccharides, or neoantigens, among others. Area 2004 shows summary information presented when the summary option is selected from the option list 2002. When other list options are selected, related information is used to populate area 2004 with additional related information.

Figure 21:
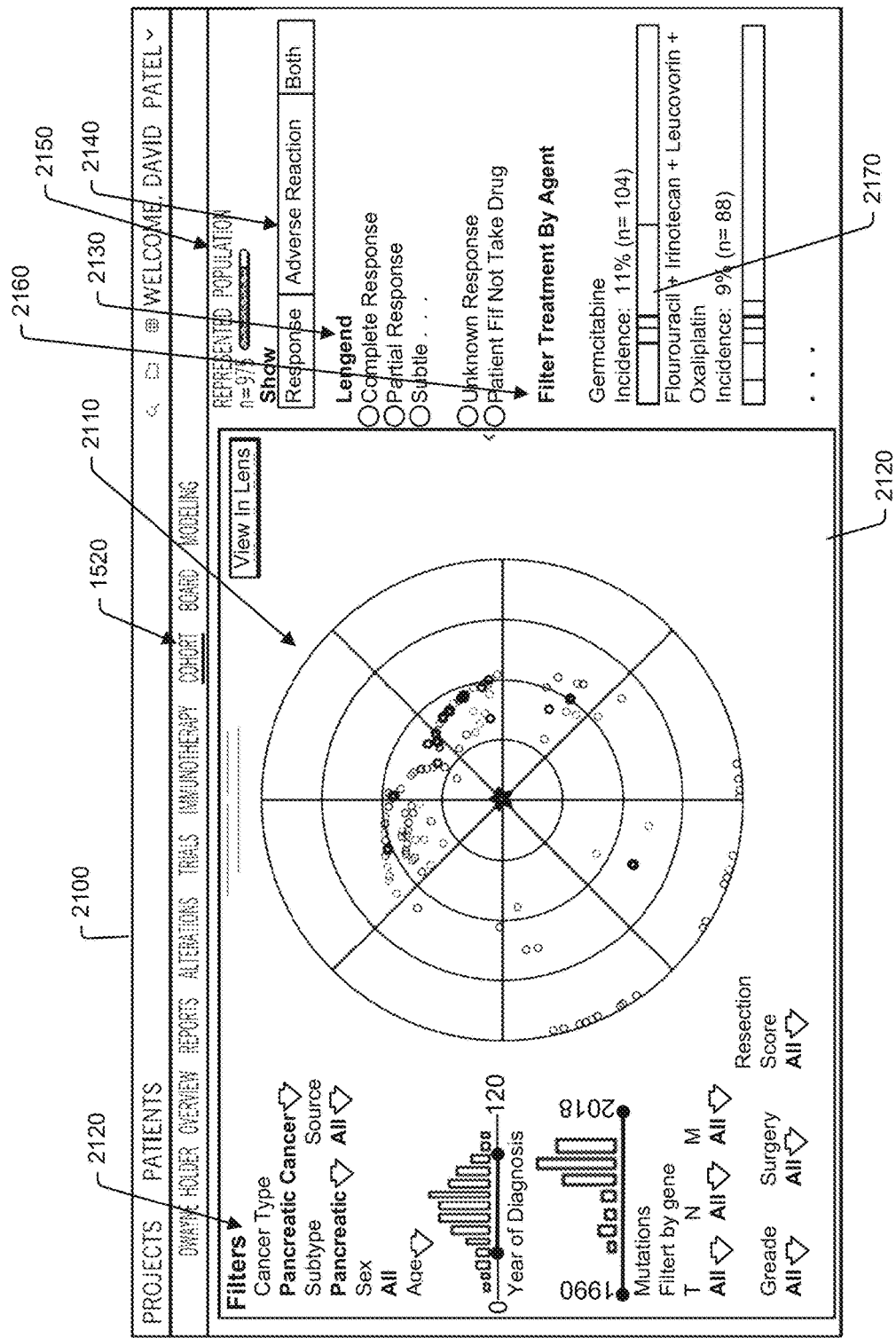
FIG. 21 is a screenshot illustrating an efficacy exploration view where molecular differences between a patient's tumor and other tumors of the same general type are used a primary factor in generating the illustrated graph.

Referring to FIG. 21, the cohort option 1518 can be selected to access an analytical tool that enables the physician to explore prior treatment responses of patients that have the same type of cancer as the patient that the physician is planning treatment for in light of similarities in molecular data between the patients. To this end, once genomic sequencing has been completed for each patient in a set of patients, molecular similarities can be identified between any patients and used as a distance plotting factor on a chart 2110. In FIG. 21, the screen 2100 includes a graph at 2110, filter options at 2120, some view options 2140, graph information at 2150 and additional treatment efficacy bar graphs at 2160.

Referring still to FIG. 21, the illustrated graph presents a tumor associated with the patient for which planning is progressing at a center location as a star and other patient tumors of a similar type (e.g., pancreatic) at different radial distances from the central tumor where molecular similarity is based on distance from the central location so that tumors more similar to the central tumor are near the center and tumors other than the central tumor are located in proximity to one another based on their respective similarity. Angular displacements between the other tumors represented indicate dissimilarity or similarity between any two tumors where a greater angular distance between two tumors indicates greater dissimilarity. Except for the central tumor (e.g., indicated via the star), each of the other tumors is color coded to indicate treatment efficacy. For instance, a green dot may represent a tumor that completely responded to treatment, a yellow dot may indicate a tumor that responded minimally while a red dot indicates a tumor that did not respond. An efficacy legend at 2130 is provided that associates tumor colors with efficacies "e.g., "Complete Response", "Partial Response", etc.). The physician can select different options to show in the graph including response, adverse reaction, or both using icons at 2140.

Referring still to FIG. 21, an initial view 2110 may include all patient tumors that are of the same general type as the central tumor presented on the graph 2110, regardless of other cancer state factors. In FIG. 21, a number "n" is equal to 975 indicating that 975 tumors and associated patients are represented on graph 2110. Filters at 2120 can be used by the physician to select different cancer state filter factors to reduce the n count to include patients that have other factors in common with the patient associated with the central tumor. For instance, patient sex or age or tumor mutations or any factor combination supported by the system may be used to filter n down to a smaller number where multiple factors are common among associated patients.

Referring again to FIG. 21, the efficacy bar graphs 2160 present efficacy data for different treatment types. To this end, screen area 2160 presents a list of medications or combinations thereof that have been used in the past to treat the tumors represented in graph 2110. A separate bar graph is provided for each of the treatment medications or combinations where each bar graph includes different length color coded sub-sections that show efficacy percentages. For instance, for Germcitabine, the bar graph 2170 may include a green section that extends 11% of the length of the total bar graph and a blue section that extends 5% of the length of the total bar graph to indicate that 11% of patients treated with Germcitabine experienced a complete response while 5% experienced only a partial response. Other color coded sections of bar 2170 would indicate other efficacies. The illustrated list only includes two treatment regimens but in most cases the list would be much longer and each list regimen would include its own efficacy bar graph.

F. Automated Cancer State-Treatment-Efficacy Insights Across Patient Populations Referring again to FIG. 21, the cohort tool shown allows a physician to select different cancer state filters 2120 to be applied to the system database thereby changing the set of patients for which the system presents treatment efficacy data to help the physician explore effects of different factors on efficacy which is intended to lead to new treatment insights like factor-treatment-efficacy relationships. While powerful, this physician driven system is only as good as the physician that operates it and in many cases cancer state-treatment-efficacy relationships simply will not even be considered by a physician if clinically relevant state factors are not selected via the filter tools. While a physician could try every filter combination possible, time restraints would prohibit such an effort. In addition, while a large number of filter options could be added to the filter tools 2120 in FIG. 21, it would be impractical to support all state factors as filter options so that some filter combinations simply could not be considered.

To further the pursuit of new cancer state-treatment-efficacy exploration and research, in at least some embodiments it is contemplated that system processors may be programmed to continually and automatically perform efficacy studies on data sets in an attempt to identify statistically meaningful state factor-treatment-efficacy insights. These insights can be confirmed by researchers or physicians and used thereafter to suggest treatments to physicians for specific cancer states.

A more fulsome description of the cohort tool suite and spatial projecting relationships of multidimensional data is described below with reference to FIGS. 303 through 310.

G. Exemplary System Techniques and Results

The systems and methods described above may be used with a variety of sequencing panels. One exemplary panel, the 595 gene xT panel referred to above (See again the FIG. 27 series of figures), is focused on actionable mutations. An exemplary 650 gene solid tumor XT panel is shown at Appendix E. Hereafter we present a description of various techniques and associated results that are consistent with aspects of the present disclosure in the context of an exemplary xT panel.

Techniques and results include the following. SNVs (single nucleotide variants), indels, and CNVs (copy number variants) were detected in all 595 genes. Genomic rearrangements were detected on a 21 gene subset by next generation DNA sequencing, with other genomic rearrangements detected by next generation RNA sequencing (RNA Seq). The panel also indicated MSI (microsatellite instability status) and TMB (tumor mutational burden). DNA tumor coverage was provided at 500× read sequencing depth. Full transcriptome was also provided by RNA sequencing, with unbiased gene rearrangement detection from fusion transcripts and expression changes, sequenced at 50 million reads.

In addition to reporting on somatic variants, when a normal sample is provided, the assay permits reporting of germline incidental findings on a limited set of variants within genes selected based on recommendations from the American College of Medical Genetics (ACMG) and published literature on inherited cancer syndromes.

H. Mutation Spectrum Analysis for Exemplary 500 Patient xT Group

Subsequent to selection, patients were binned by pre-specified cancer type and filtered for only those variants being classified as therapeutically relevant. The gene set was then filtered for only those genes having greater than 5 variants across the entire group so as to select for recurrently mutated genes. Having collated this set, patients were clustered by mutational similarity across SNPs, indels, amplifications, and homozygous deletions. Subsequently, mutation prevalence data for the MSKCC IMPACT data were extracted from MSKCC Cbioportal (http://www.cbioportal.org/study?id=msk_impact_2017#summary) in order to compare the xT assay variant calls against publicly available variant data for solid tumors. After selecting for only those genes on both panels, variants with a minimum of 2.5% prevalence within their respective group were plotted.

I. Detection of Gene Rearrangements from DNA by the xT Assay

Gene rearrangements were detected and analyzed via separate parallel workflows optimized for the detection of structural alterations developed in the JANE workflow language. Following de-multiplexing, tumor FASTQ files were aligned against the human reference genome using BWA (Li et al., 2009). Reads were sorted and duplicates were marked with SAMBlaster (Faust et al., 2014). Utilizing this process, discordant and split reads are further identified and separated. These data were then read into LUMPY (Layer et al., 2014) for structural variant detection. A VCF was generated and then parsed by a fusion VCF parser and the data was pushed to a Bioinformatics database. Structural alterations were then grouped by type, recurrence, and presence within the database and displayed through a quality control application. Known and previously known fusions were highlighted by the application and selected by a variant science team for loading into a patient report.

J. Detection of Gene Rearrangements from RNA by the xT Assay

Gene rearrangements in RNA were analyzed via a separate workflow that quantitated gene level expression as well as chimeric transcripts via non-canonical exon-exon junctions mapped via split or discordant read pairs. In brief, RNA-sequencing data was aligned to GRCh38 using STAR (Dobin et al., 2009) and expression quantitation per gene was computed via FeatureCounts (Liao et al., 2014). Subsequent to expression quantitation, reads were mapped across exon-exon boundaries to unannotated splice junctions and evidence was computed for potential chimeric gene products. If sufficient evidence was present for the chimeric transcript, a rearrangement was called as detected.

K. Gene Expression Data Collection

RNA sequencing data was generated from FFPE tumor samples using an exome-capture based RNA seq protocol. Raw RNA seq reads were aligned using CRISP and gene expression was quantified via the RNA bioinformatics pipeline. One RNA bioinformatics pipeline is now described. Tissues with highest tumor content for each patient may be disrupted by 5 mm beads on a Tissuelyser II (Qiagen). Tumor genomic DNA and total RNA may be purified from the same sample using the AllPrep DNA/RNA/miRNA kit (Qiagen). Matched normal genomic DNA from blood, buccal swab or saliva may be isolated using the DNeasy Blood & Tissue Kit (Qiagen). RNA integrity may be measured on an Agilent 2100 Bioanalyzer using RNA Nano reagents (Agilent Technologies). RNA sequencing may be performed either by poly(A)+ transcriptome or exome-capture transcriptome platform. Both poly(A)+ and capture transcriptome libraries may be prepared using 1~2 ug of total RNA. Poly(A)+ RNA may be isolated using Sera-Mag oligo(dT) beads (Thermo Scientific) and fragmented with the Ambion Fragmentation Reagents kit (Ambion, Austin, Tex.). cDNA synthesis, end-repair, A-base addition, and ligation of the Illumina index adapters may be performed according to Illumina's TruSeq RNA protocol (Illumina). Libraries may be size-selected on 3% agarose gel. Recovered fragments may be enriched by PCR using Phusion DNA polymerase (New England Biolabs) and purified using AMPure XP beads (Beckman Coulter). Capture transcriptomes may be prepared as above without the up-front mRNA selection and captured by Agilent SureSelect Human all exon v4 probes following the manufacturer's protocol. Library quality may be measured on an Agilent 2100 Bioanalyzer for product size and concentration. Paired-end libraries may be sequenced by the Illumina HiSeq 2000 or HiSeq 2500 (2×100 nucleotide read length), with sequence coverage to 40-75M paired reads. Reads that passed the chastity filter of Illumina BaseCall software may be used for subsequent analysis. Further details of the pipeline raw read counts may be normalized to correct for GC content and gene length using full quantile normalization and adjusted for sequencing depth via the size factor method (see Robinson, D. R. et al. Integrative clinical genomics of metastatic cancer. Nature 548, 297-303 (2017)). Normalized gene expression data was log, base 10, transformed and used for all subsequent analyses.

L. Reference Database

Gene expression data generated (as previously described) was combined with publicly available gene expression data for cancer samples and normal tissue samples to create a Reference Database. For this analysis, we specifically include data from The Cancer Genome Atlas (TCGA) Project and Genotype-Tissue Expression (GTEx) project. Raw data from these publically available datasets were downloaded via the GDC or SRA and processed via an RNAseq pipeline (described above). In total 4,865 TCGA samples and 6,541 GTEx samples were processed and included as part of the larger Reference Database for this analysis. After processing, these datasets were corrected to account for batch effect differences between sequencing protocols across institutions (i.e. TCGA & and the Reference Database). For example, TCGA and GTEx both sequenced fresh, frozen tissue using a standard polyA capture based protocol.

M. Gene Expression Calling

For each patient, the expression of key genes was compared to the Reference Database to determine overexpression or underexpression. 42 genes for over- or underexpression based on the specific cancer type of the sample were evaluated. The list of genes evaluated can vary based on expression calls, cancer type, and time of sample collection. In order to make an expression call, the percentile of expression of the new patient was calculated relative to all cancer samples in the database, all normal samples in the database, matched cancer samples, and matched normal samples. For example, a breast cancer patient's tumor expression was compared to all cancer samples, all normal samples, all breast cancer samples, and all breast normal tissue samples within the Reference Database. Based on these percentiles criteria specific to each gene and cancer type to determine overexpression was identified.

N. t-Distributed Stochastic Neighbor Embedding (t-SNE) RNA Analysis

The t-SNE plot was generated using the Rtsne package in R [R version 3.4.4 and Rtsne version 0.13] based on principal components analysis of all samples (N=482) across all genes (N=17,869). A perplexity parameter of 30 and theta parameter of 0.3 was used for this analysis.

O. Cancer Type Prediction

A random forest model was used to generate cancer type predictions. The model was trained on 804 samples and 4,526 TCGA samples across cancer types from the Reference Database. For the purposes of this analysis, hematological malignancies were excluded. Both datasets were sampled equally during the construction of the model to account for differences in the size of the training data. The random forest model was calculated using the Ranger package in R [R version 3.4.4 and ranger_0.9.0]. Model accuracy was calculated within the training dataset using a leave-one-out approach. Based on this data, the overall classification accuracy was 81%.

P. Tumor Mutational Burden (TMB)

TMB was calculated by determining the dividend of the number of non-synonymous mutations divided by the megabase size of the panel (2.4 MB). All non-silent somatic coding mutations, including missense, indel, and stop loss variants, with coverage greater than 100× and an allelic fraction greater than 5% were included in the number of non-synonymous mutations.

Q. Human Leukocyte Antigen (HLA) Class I Typing

HLA class I typing for each patient was performed using Optitype on DNA sequencing (Szolek 2014). Normal samples were used as the default reference for matched tumor-normal samples. Tumor sample-determined HLA type was used in cases where the normal sample did not meet internal HLA coverage thresholds or the sample was run as tumor-only.

R. Neoantigen Prediction

Neoantigen prediction was performed on all non-silent mutations identified by the xT pipeline. For each mutation, the binding affinities for all possible 8-11aa peptides containing that mutation were predicted using MHCflurry (Rubinsteyn 2016). For alleles where there was insufficient training data to generate an allele-specific MHCflurry model, binding affinities were predicted for the nearest neighbor HLA allele as assessed by amino acid homology. A mutation was determined to be antigenic if any resulting peptide was predicted to bind to any of the patient's HLA alleles using a 500 nM affinity threshold. RNA support was calculated for each variant using varlens (https://github.com/openvax/varlens). Predicted neoantigens were determined to have RNA support if at least one read supporting the variant allele could be detected in the RNA-seq data.

S. Microsatellite Instability (MSI) Status

The exemplary xT panel includes probes for 43 microsatellites that are frequently unstable in tumors with mismatch repair deficiencies. The MSI classification algorithm uses reads mapping to those regions to classify tumors into three categories: microsatellite instability-high (MSI-H), microsatellite stable (MSS), or microsatellite equivocal (MSE). This assay can be performed with paired tumor-normal samples or tumor-only samples.

MSI testing in paired mode begins with identifying accurately mapped reads to the microsatellite loci. To be a microsatellite locus mapping read, the read must be mapped to the microsatellite locus during the alignment step of the exemplary xT bioinformatics pipeline and also contain the 5 base pairs in both the front and rear flank of the microsatellite, with any number of expected repeating units in between. All the loci with sufficient coverage are tested for instability, as measured by changes in the distribution of the number of repeat units in the tumor reads compared to the normal reads using the Kolmogorov-Smirnov test. If $p<=0.05$, the locus is considered unstable. The proportion of unstable loci is fed into a logistic regression classifier trained on samples from the TCGA colorectal and endometrial groups that have clinically determined MSI statuses.

MSI testing in unpaired mode also begins with identifying accurately mapped reads to the microsatellite loci, using the same requirements as described above. The mean number of repeat units and the variance of the number of repeat units is calculated for each microsatellite locus. A vector containing the mean and variance data for each microsatellite locus is put into a support vector machine classification algorithm trained on samples from the TCGA colorectal and endometrial groups that have clinically determined MSI statuses.

Both algorithms return the probability of the patient being MSI-H, which is then translated into a MSI status of MSS, MSE, or MSI-H.

T. Cytolytic Index (CYT)

CYT was calculated as the geometric mean of the normalized RNA counts of granzyme A (GZMA) and perforin (PRF1) (Rooney, M. S., Shukla, S. A., Wu, C. J., Getz, G. &

Hacohen, N. Molecular and Genetic Properties of Tumors Associated with Local Immune Cytolytic Activity. Cell 160, 48-61 (2015)).

U. Interferon Gamma Gene Signature Score

Twenty-eight interferon gamma (IFNG) pathway-related genes (Ayers M., J Clin Invest 2017) were used as the basis for an IFNG gene. Hierarchical clustering was performed based on Euclidean distance using the R package ComplexHeatmap (version 1.17.1) and the heatmap was annotated with PD-L1 positive IHC staining, TMB-high, or MSI-high status. IFNG score was calculated using the arithmetic mean of the 28 genes.

V. Knowledge Database (KDB)

In order to determine therapeutic actionability for sequenced patients, a KDB with structured data regarding drug/gene interactions and precision medicine assertions is maintained. The KDB of therapeutic and prognostic evidence is compiled from a combination of external sources (including but not exclusive to NCCN, CIViC{28138153}, and DGIdb{28356508}) and from constant annotation by provider experts. Clinical actionability entries in the KDB are structured by both the disease in which the evidence applies, and by the level of evidence. Therapeutic actionability entries are binned into Tiers of somatic evidence by patient disease matches as laid out by the ASCO/AMP/CAP working group {27993330}. Briefly, Tier I Level A (IA) evidence are biomarkers that follow consensus guidelines and match disease type. Tier I Level B (IB) evidence are biomarkers that follow clinical research and match disease type. Tier II Level C (IIC) evidence biomarkers follow the off-label use of consensus guidelines and Tier II Level D (IID) evidence biomarkers follow clinical research or case reports. Tier III evidence are variants with no therapies. Patients are then matched to actionability entries by gene, specific variant, patient disease, and level of evidence.

W. Alteration Classification, Prioritization, and Reporting

Somatic alterations are interpreted based on a collection of internally weighted criteria that are composed of knowledge of known evolutionary models, functional data, clinical data, hotspot regions within genes, internal and external somatic databases, primary literature, and other features of somatic drivers {24768039}{29218886}. The criteria are features of a derived heuristic algorithm that buckets them into one of four categories (Pathogenic/VUS/Benign/Reportable). Pathogenic variants are typically defined as driver events or tumor prognostic signals. Benign variants are defined as those alterations that have evidence indicating a neutral state in the population and are removed from reporting. VUS variants are variants of unknown significance and are seen as passenger events. Reportable variants are those that could be seen as diagnostic, offer therapeutic guidance or are associated with disease but are not key driver events. Gene amplifications, deletions and translocations were reported based on the features of known gene fusions, relevant breakpoints, biological relevance and therapeutic actionability.

For the tumor-only analysis germline variants were computationally identified and removed using by an internal algorithm that takes copy number, tumor purity, and sequencing depth into account. There was further filtering on observed frequency in a population database (positions with AF>1% ExAC non-TCGA group). The algorithm was purposely tuned to be conservative when calling germline variants in therapeutic genes minimizing removal of true somatic pathogenic alterations that occur within the general population. Alterations observed in an internal pool of 50 unmatched normal samples were also removed. The remaining variants were analyzed as somatic at a VAF>=5% and Coverage>=90. Using normal tissue, true germline variants were able to be flagged and somatic analysis contamination was evaluated. The Tumor/Normal variants were also set at the Tumor-only VAF/Coverage thresholds for analysis.

Clinical trial matching occurs through a process of associating a patient's actionable variants and clinical data to a curated database of clinical trials. Clinical trials are verified as open and recruiting patients before report generation.

X. Germline Pathogenic and Variants of Unknown Significance (VUS)

Alterations identified in the Tumor/Normal match samples are reported as secondary findings for consenting patients. These are a subset of genes recommended by the ACMG (Richards, S. et al. Standards and guidelines for the interpretation of sequence variants: a joint consensus recommendation of the American College of Medical Genetics and Genomics and the Association for Molecular Pathology. Genet. Med. 17, 405-24 (2015)) and genes associated with cancer predisposition or drug resistance.

In an example patient group analysis, a group of 500 cancer patients was selected where each patient had undergone clinical tumor and germline matched sequencing using the panel of genes at FIGS. 27a, 27b, 27c1, 27c2, and 27d (known herein as the "xT" assay). In order to be eligible for inclusion in the group, each case was required to have complete data elements for tumor-normal matched DNA sequencing, RNA sequencing, clinical data, and therapeutic data. Subsequent to filtering for eligibility, a set of patients was randomly sampled via a pseudo-random number generator. Patients were divided among seven broad cancer categories including tumors from brain (50 patients), breast (50 patients), colorectal (51 patients), lung (49 patients), ovarian and endometrial (99 patients), pancreas (50 patients), and prostate (52 patients). Additionally, 48 tumors from a combined set of rare malignancies and 51 tumors of unknown origin were included for analyses for a total of nine broad cancer categories. These patients were collated together as a single group and used for subsequent group analyses.

Figure 29:
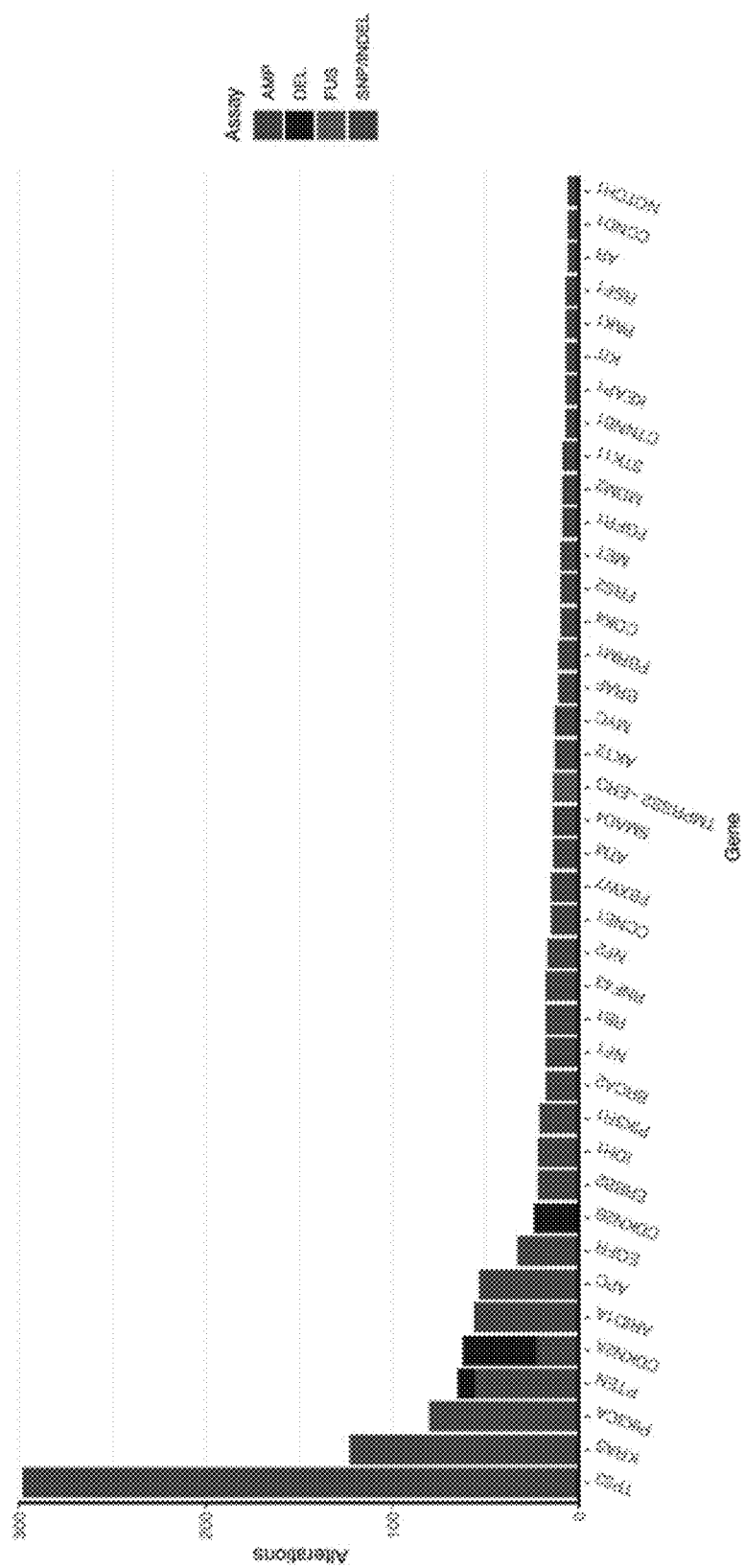
FIG. 29 is a bar chart illustrating data for a 500 patient group that clusters mutation similarities for gene, mutation type, and cancer type derived for an exemplary xT panel using techniques that are consistent with aspects of the present disclosure.

The mutational spectra for the studied group was compared with broad patterns of genomic alterations observed in large-scale studies across major cancer types. First, data from all 500 patients was plotted by gene, mutation type, and cancer type, and then clustered by mutational similarity (FIG. 29). The most commonly mutated genes included well-known driver mutations, including mutations in more than 5% of all cases in the group for TP53, KRAS, PIK3CA, CDKN2A, PTEN, ARID1A, APC, ERBB2, EGFR, IDH1, and CDKN2B. These genes are known hallmarks of cancer and commonly found in solid tumors. Of these genes, CDKN2A, CDKN2B, and PTEN were most commonly found to be homozygously deleted, indicating loss-of-function mutations likely coinciding with loss of heterozygosity. These data demonstrate expected molecular signatures commonly seen in clinical solid tumor samples.

Figure 30:
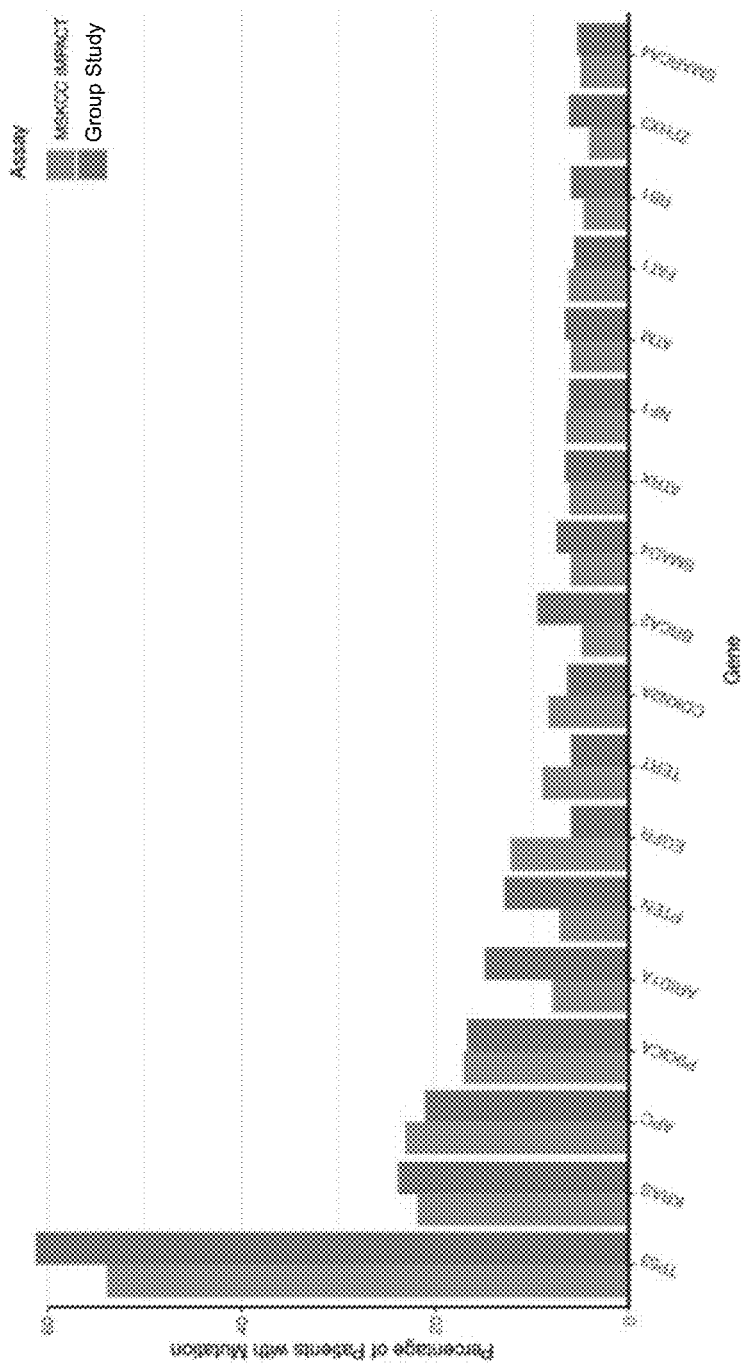
FIG. 30 is a bar chart comparing study results generated for the exemplary xT panel using at least some processes described in this specification with previously published pan-cancer analysis using an IMPACT panel.

Previous pan-cancer mutation analyses have established mutational spectra within and across tumor types, and provide context to which the study group sequencing data may be compared. In FIG. 30, the study group results were compared to a previously published pan-cancer analysis using the Memorial Sloan Kettering Cancer Center (MSKCC) IMPACT panel (Zehir, A. et al. Mutational landscape of metastatic cancer revealed from prospective clinical sequencing of 10,000 patients. Nat. Med. 23, 703-713 (2017)). In both datasets, we observed the same commonly mutated genes, including TP53, KRAS, APC and PIK3CA.

These genes were observed at similar relative frequencies compared to the MSKCC group. These results indicate the mutation spectra within the study group is representative of the broader population of tumors that have been sequenced in large-scale studies.

Because both tumor and germline samples were sequenced in the group, the effect of germline sequencing on the accuracy of somatic mutation identification could be examined. Fifty-one cases were randomly selected from the study group with a range of tumor mutational burden profiles. Their variants were re-evaluated using a tumor-only analytical pipeline. After filtering the dataset using a population database and focusing on coding variants from the 51 samples, 2,544 variants were identified that had a false positive rate of 12.5%. By further filtering with an internally developed list of technical artifacts (e.g., artifacts from DNA sequencing process), an internal pool of matched normal samples, and classification criteria, 74% of the false somatic variants (false positive rate of 2.3%) were removed while still retaining all true somatic alterations.

Hereafter the disclosure related to FIGS. 319 through 339 describes systems and methods for normalizing and correcting gene expression data and, more particularly, to normalizing and correcting gene expression data across varied gene expression databases.

Figure 31:
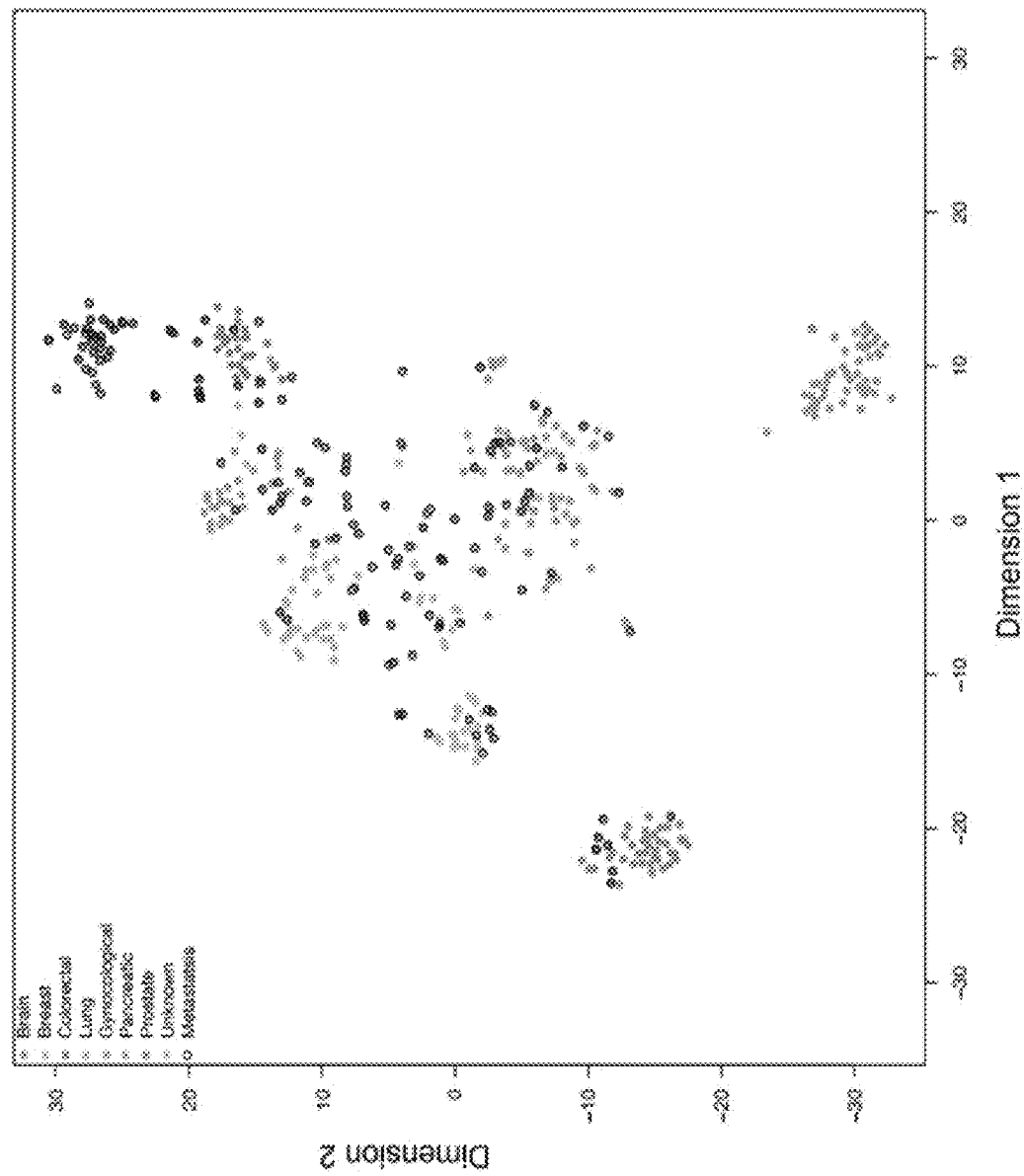
FIG. 31 is a graph illustrating expression profiles for tumor types related to the exemplary xT panel described in the present disclosure.

To further characterize the tumors in the study group, RNA expression profiles for patients in the group were examined. Similar tumor types tend to have similar expression profiles (FIG. 31). On average, samples within a cancer type as determined by pathologic diagnosis showed a higher pairwise correlation within the corresponding TCGA cancer group compared to between TCGA cancer groups (p-values=$10^{-6}$-$10^{-16}$). This clustering of samples by TCGA cancer group is observed in the t-SNE plot shown in FIG. 32. For some tumor types, such as prostate cancer, metastatic samples cluster very closely to non-metastatic tumor samples. However other cancer types, most notably pancreatic cancer and colorectal cancer, form a distinct metastatic tumor cluster that also contains breast tumors and tumors of unknown origin. This effect is likely due to the effect of the background tissue on the expression profile of the tumor sample. For example, metastatic samples from the liver frequently, but not always, cluster together. This effect can also depend on the level of tumor purity within the sample.

Figure 32:
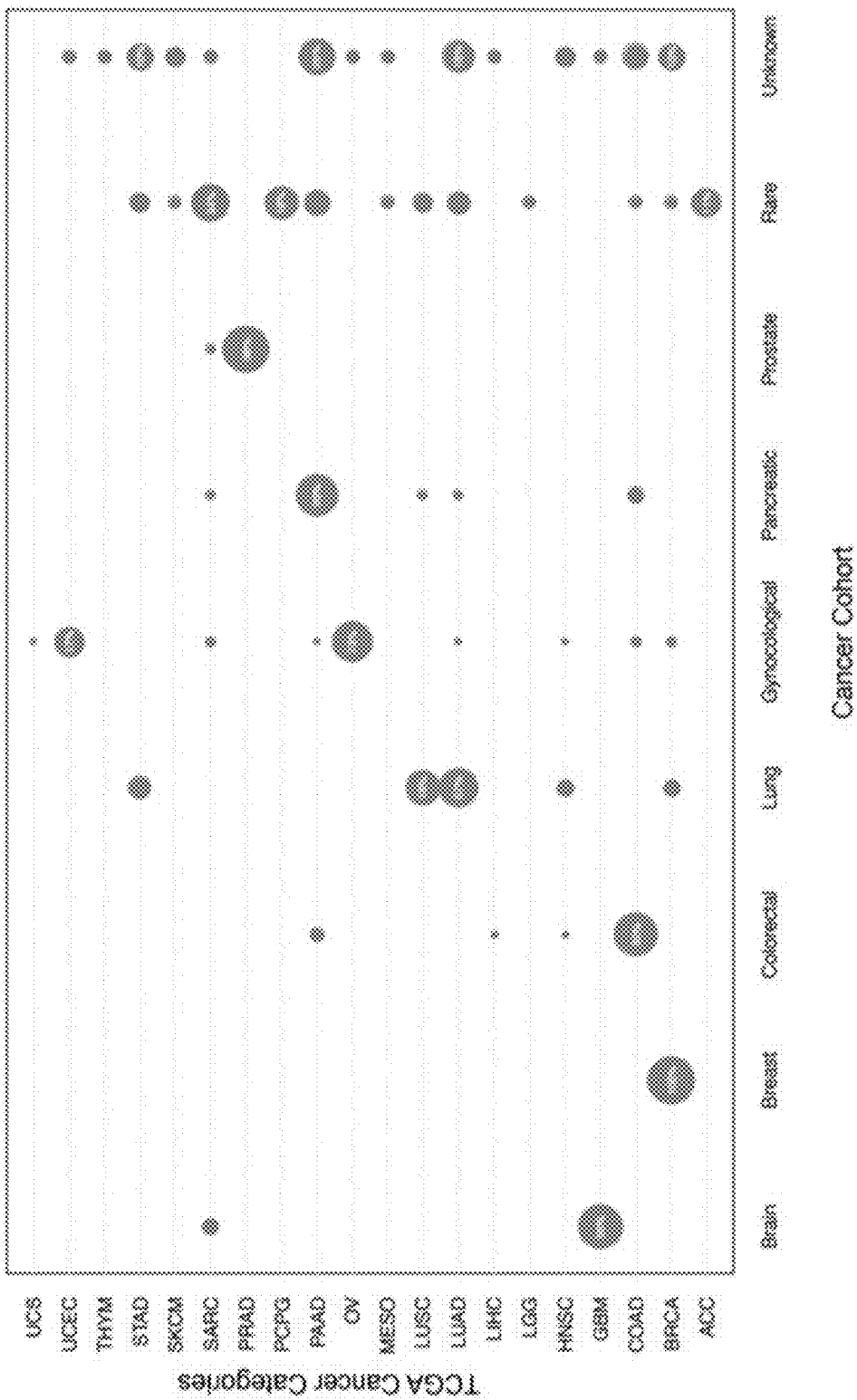
FIG. 32 is a graph illustrating clustering of samples by TCGA cancer group in a t-SNE plot for the exemplary xT panel.

Given the high-dimensionality of the data, we sought to determine whether we could predict cancer types using gene expression data. We developed a random forest cancer type predictor using a combination of publically available TCGA expression data and expression data generated at Tempus Labs. TCGA cancer type predictions compared to the xT group samples are shown in FIG. 32. For example, 100% of breast cancer samples were correctly classified. Interestingly, using this method we are able to accurately classify these tumors even when the samples are biopsied from metastatic sites.

Additionally, it is notable that some of the "misclassified" samples may actually represent biologically and pathologically relevant classifications. For example, of the 50 brain tumors in our dataset, 48 (96%) were classified as gliomas, while 2 were classified as sarcomas.

One of these tumors carries a histopathologic diagnosis of "solitary fibrous tumor, hemangiopericytoma type, WHO grade III", which is indeed a sarcoma. The other was diagnosed as "glioblastoma, WHO grade IV (gliosarcoma), with smooth muscle and epithelial differentiation". The immunohistochemical profile is GFAP negative with desmin and SMA focally positive, supporting the diagnosis of gliosarcoma. It can be argued that the algorithm classified this tumor correctly by grouping it with sarcomas, and in fact, gliosarcomas carry a worse prognosis and have the ability to metastasize, differentiating them clinically from traditional glioblastoma.

Similarly, a case with a histopathologic diagnosis favoring carcinosarcoma was identified by the model as SARC in a patient with a history of prostate cancer presenting with a pelvic mass five years after surgery. The immunohistochemical profile of the tumor showed it was negative for the prostate markers prostatic acid phosphatase (PSAP) and prostatic specific antigen (PSA) and positive for SMA, consistent with sarcoma, which was thought to be secondary to prostate fossa radiation treatment. However, gene rearrangement analysis identified a TMPRSS2-ERG, suggesting that the tumor was in fact recurrent prostate cancer with sarcomatoid features.

The constellation of gene rearrangements and fusions in the study group were also examined. These types of genomic alterations can result in proteins that drive malignancies, such as EML4-ALK, which results in constitutive activation of ALK through removal of the transmembrane domain.

Figure 33:
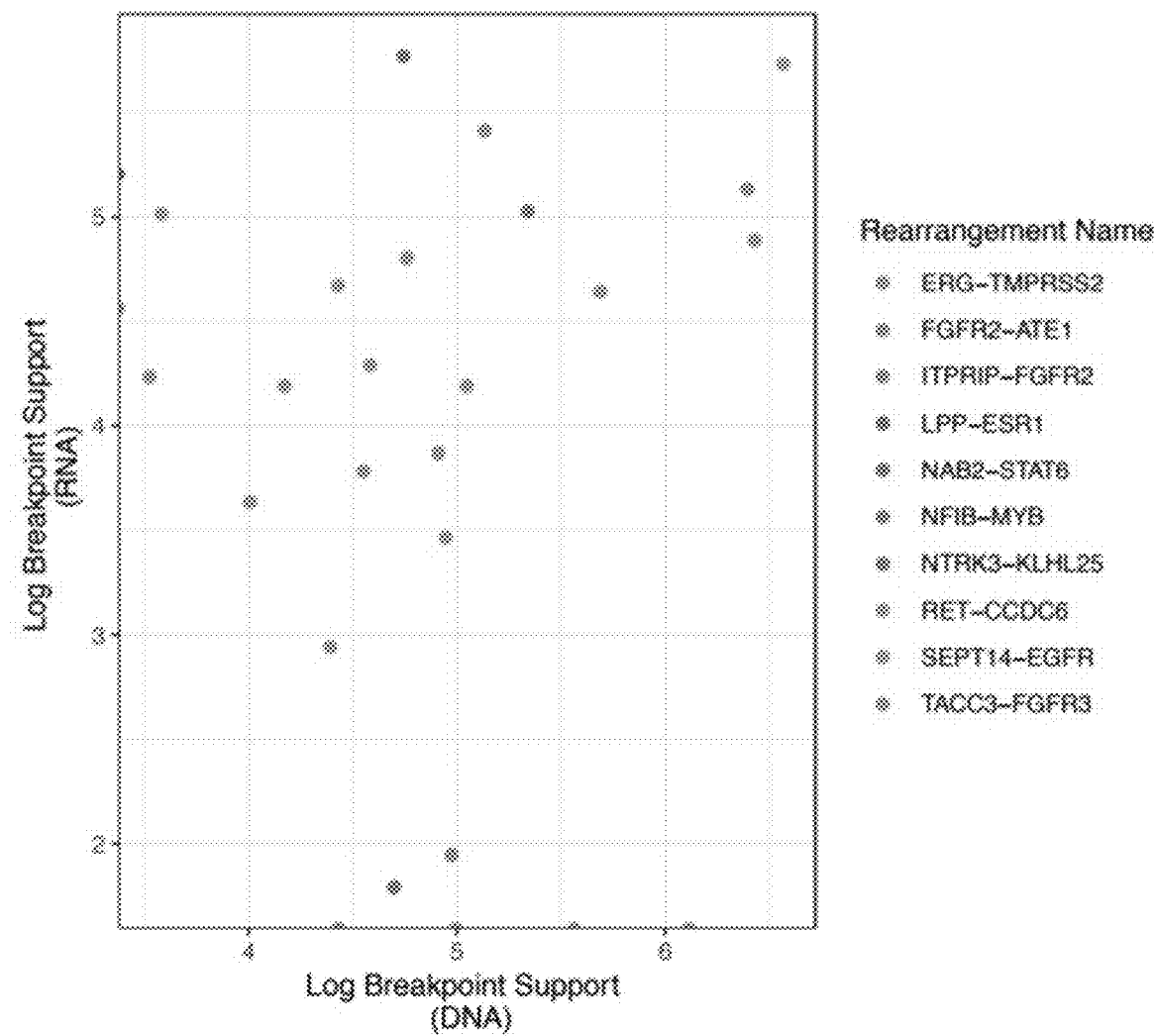
FIG. 33 is a plot of genomic rearrangements using DNA and RNA assays for the exemplary xT panel.
Figure 34:
FIG. 34 is a schematic illustrating data related to one rearrangement detected via RNA sequencing related to the exemplary xT panel.
Figure 35:
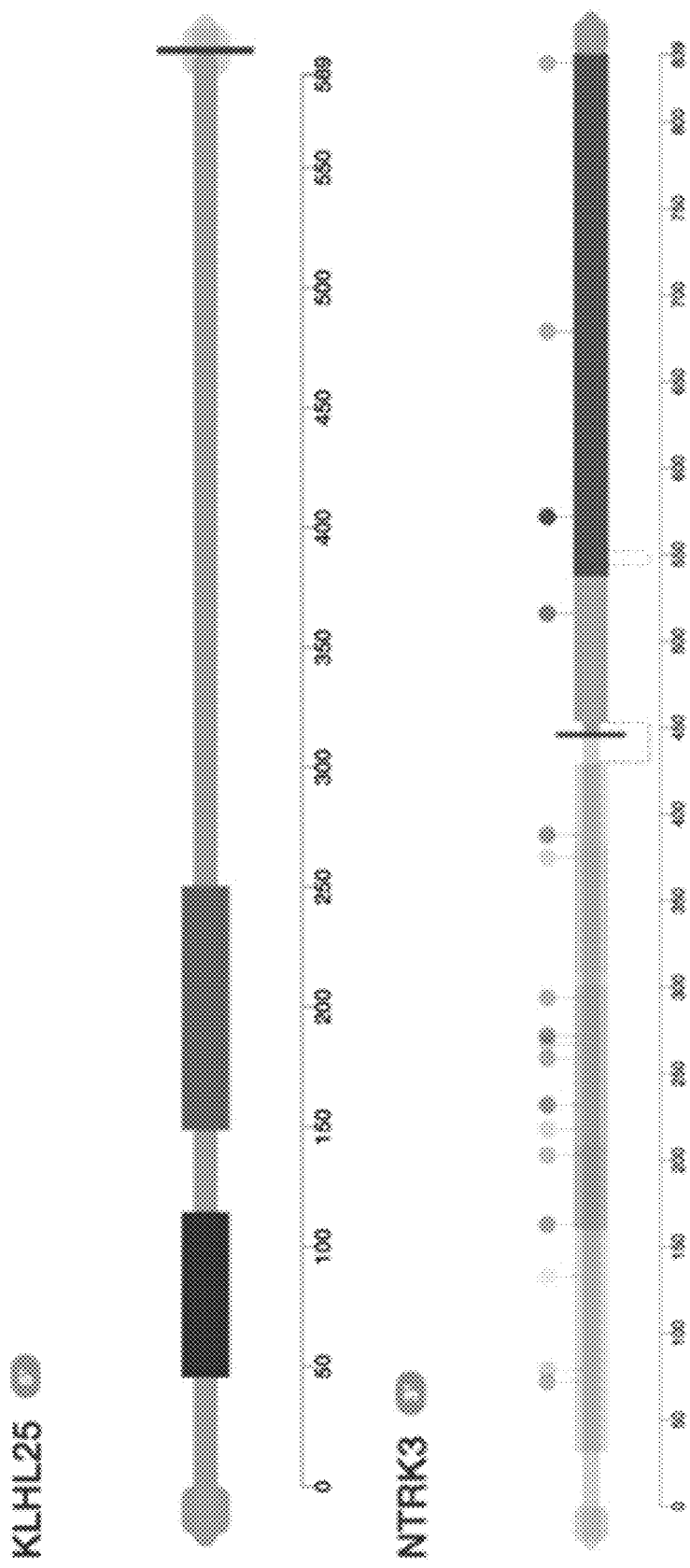
FIG. 35 is a schematic illustrating data related to a second rearrangement detected via RNA sequencing related to the exemplary xT panel.

In order to assess assay decision support for clinically relevant genomic rearrangements, alterations detected using DNA or RNA sequencing assays were compared across assay type and for evidence matching them to therapeutic interventions. Overall, 28 total genomic rearrangements resulting in chimeric protein products were detected in the study group. 22 rearrangements were concordantly detected between assay type, four were detected via DNA-only assay, and two were detected via RNA-only assay (FIG. 33). Of the three rearrangements detected via RNA sequencing, two of the three were not targets on the DNA sequencing assay and thus not expected to be detected via DNA sequencing. The functionality of these fusions were further analyzed via their predicted structures (FIGS. 34 and 35). In all cases, algorithms predicted fully intact tyrosine kinase domains for RET and NTRK3 exemplar rearrangements, which may be potential therapeutic targets for tyrosine kinase inhibitors. This analysis indicates the utility of genomic rearrangement analyses as a source of clinically relevant information for therapeutic interventions.

To characterize the mutational landscape in all patients, the distribution of the mutational load across cancer types was analyzed. The median TMB across the study group was 2.09 mutations per megabase (Mb) of DNA with a range of 0-54.2 mutations/Mb.

Figure 36:
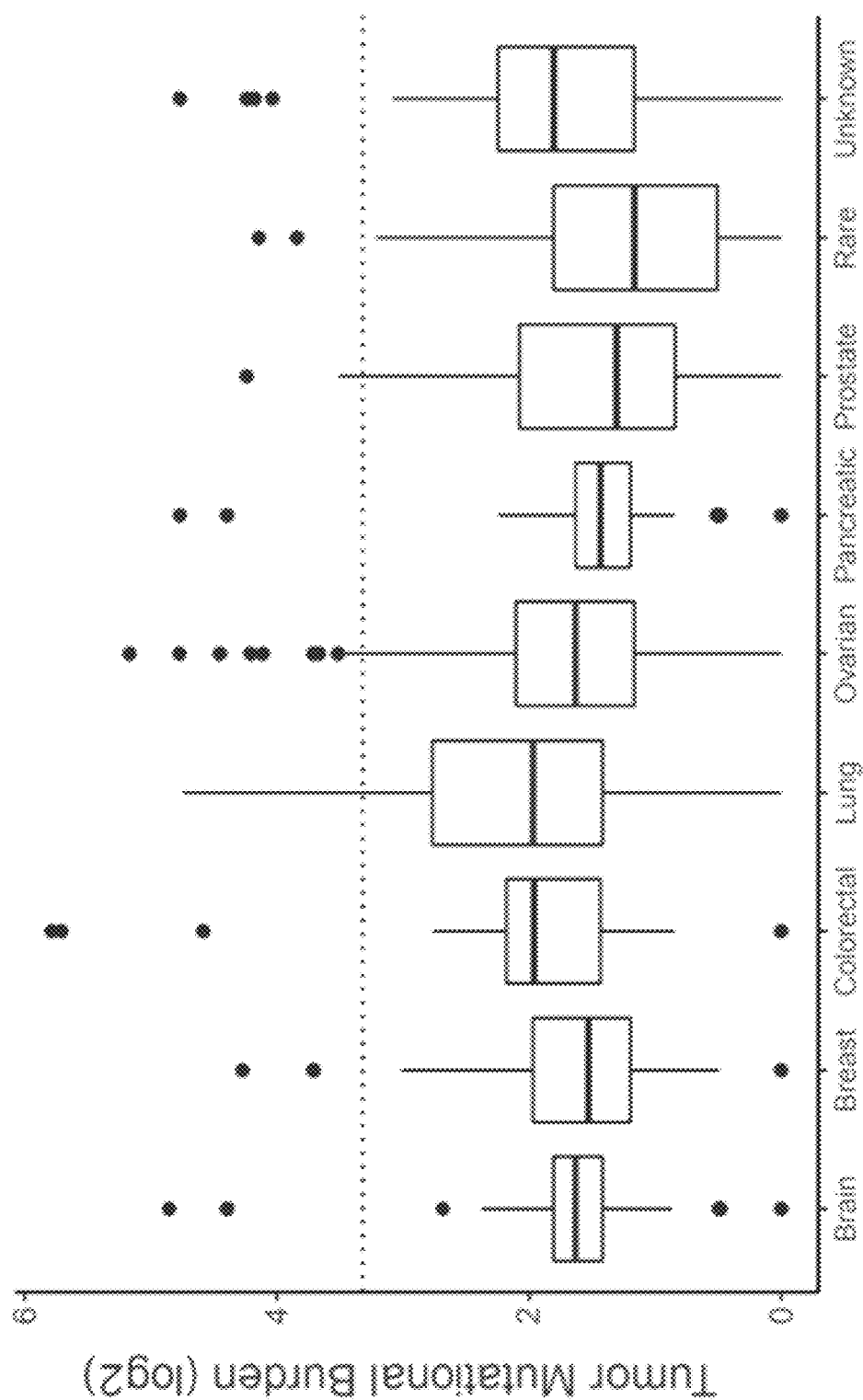
FIG. 36 includes a chart that illustrates the distribution of TMB varied by cancer type identified using techniques that are consistent with at least some aspects of the present disclosure related to the exemplary xT panel.
Figure 37:
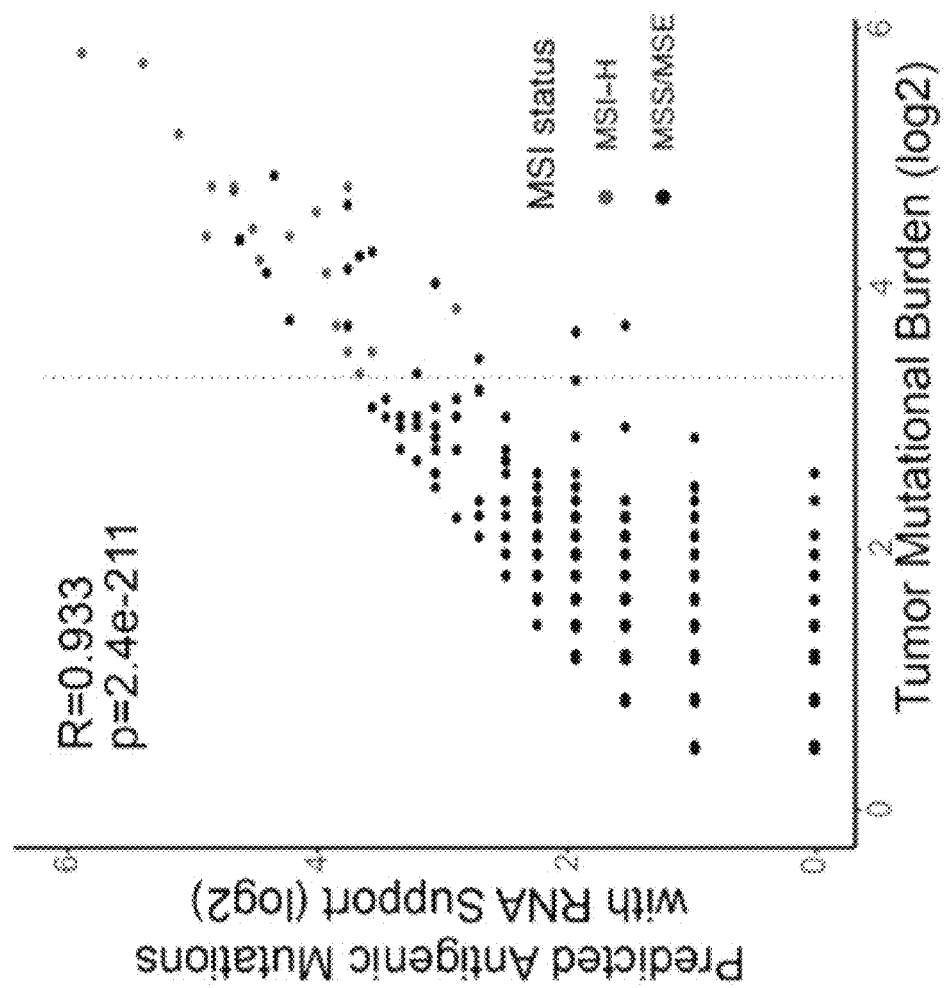
FIG. 37 includes data represented on a two dimensional plot showing TMB on one axis and predicted antigenic mutations with RNA support on the other axis that was generated using techniques that are consistent with at least some aspects of the present disclosure related to the exemplary xT panel.
Figure 38:
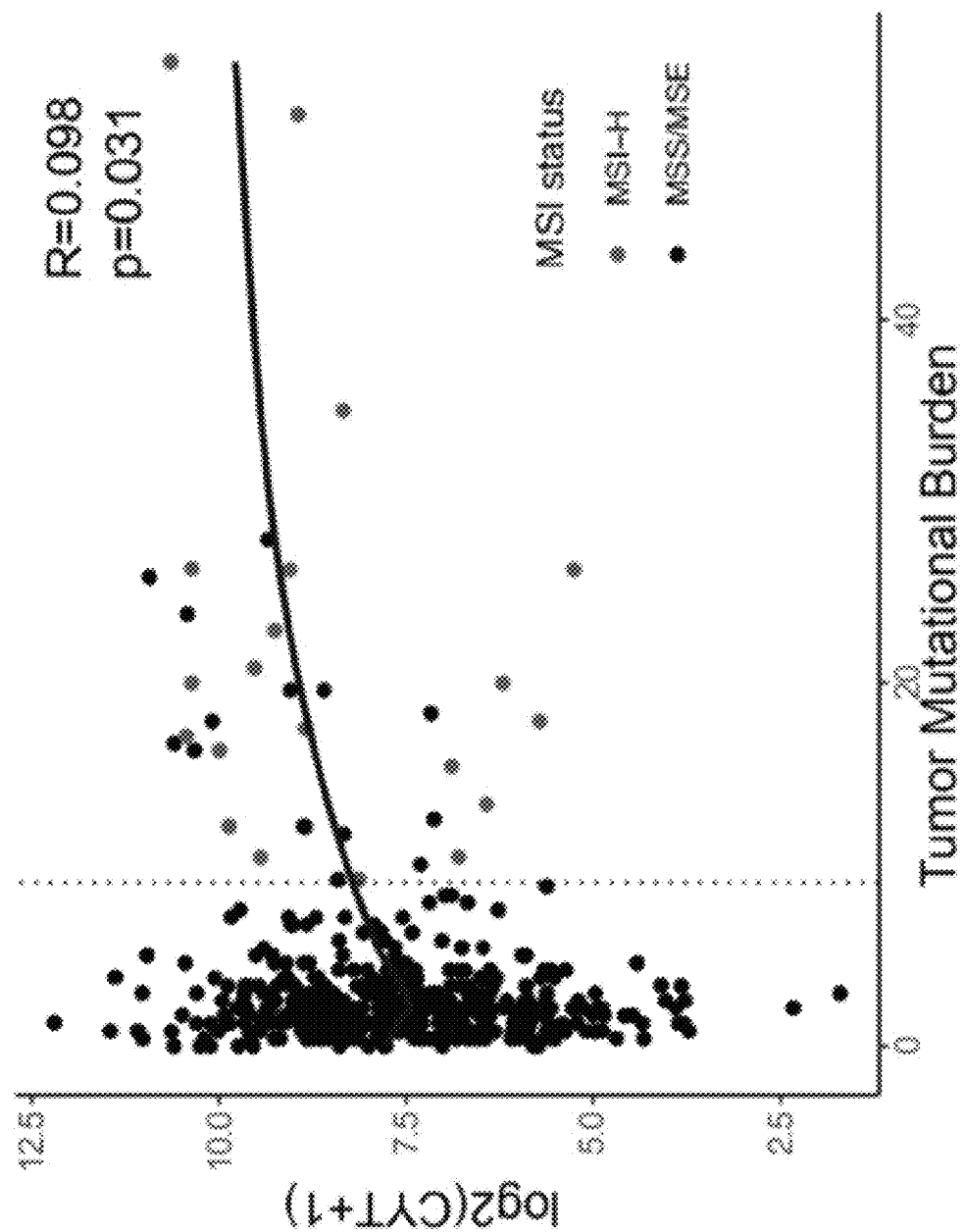
FIG. 38 includes additional data related to TMB generated using techniques that are consistent with at least some aspects of the present disclosure related to the exemplary xT panel.

The distribution of TMB varied by cancer type. For example, cancers that are associated with higher levels of mutagenesis, like lung cancer, had a higher median TMB (FIG. 36). We found that there is a population of hypermutated tumors with significantly higher TMB than the overall distribution of TMB for solid tumors. These hypermutators are found in all cancer types, including cancers typically associated with low TMB, like glioblastoma (FIG. 36). These hypermutated tumors are referred to as TMB-high, which are defined as tumors with a TMB greater than 9 mutations/Mb. This threshold was established by testing for the enrichment of tumors with orthogonally defined hypermutation (MSI-H) in a larger clinical database using the hypergeometric test. In this group, all MSI-H samples are in the TMB-high population (FIGS. 37 and 38). The high mutational burdens from the remaining TMB-high samples were primarily explained by mutational signatures associated with smoking, UV exposure, and APOBEC mediated mutagenesis.

While TMB is a measure of the number of mutations in a tumor, the neoantigen load is a more qualitative estimate of the number of somatic mutations that are actually presented to the immune system. We calculated neoantigen load as the number of mutations that have a predicted binding affinity of 500 nM or less to any of a patient's HLA class I alleles as well as at least one read supporting the variant allele in RNA sequencing data. TMB was found to be highly correlated with neoantigen load (R=0.933, p=2.42×10$^{-211}$) (FIG. 37). This suggests that a higher tumor mutational burden likely results in a greater number of potential neoantigens.

The association of high TMB and MSI-H status with response to immunotherapy has been attributed to the greater immunogenicity of these highly mutated tumors. We used whole transcriptome sequencing to measure whether greater immunogenicity results in higher levels of immune infiltration and activation.

Figure 39:
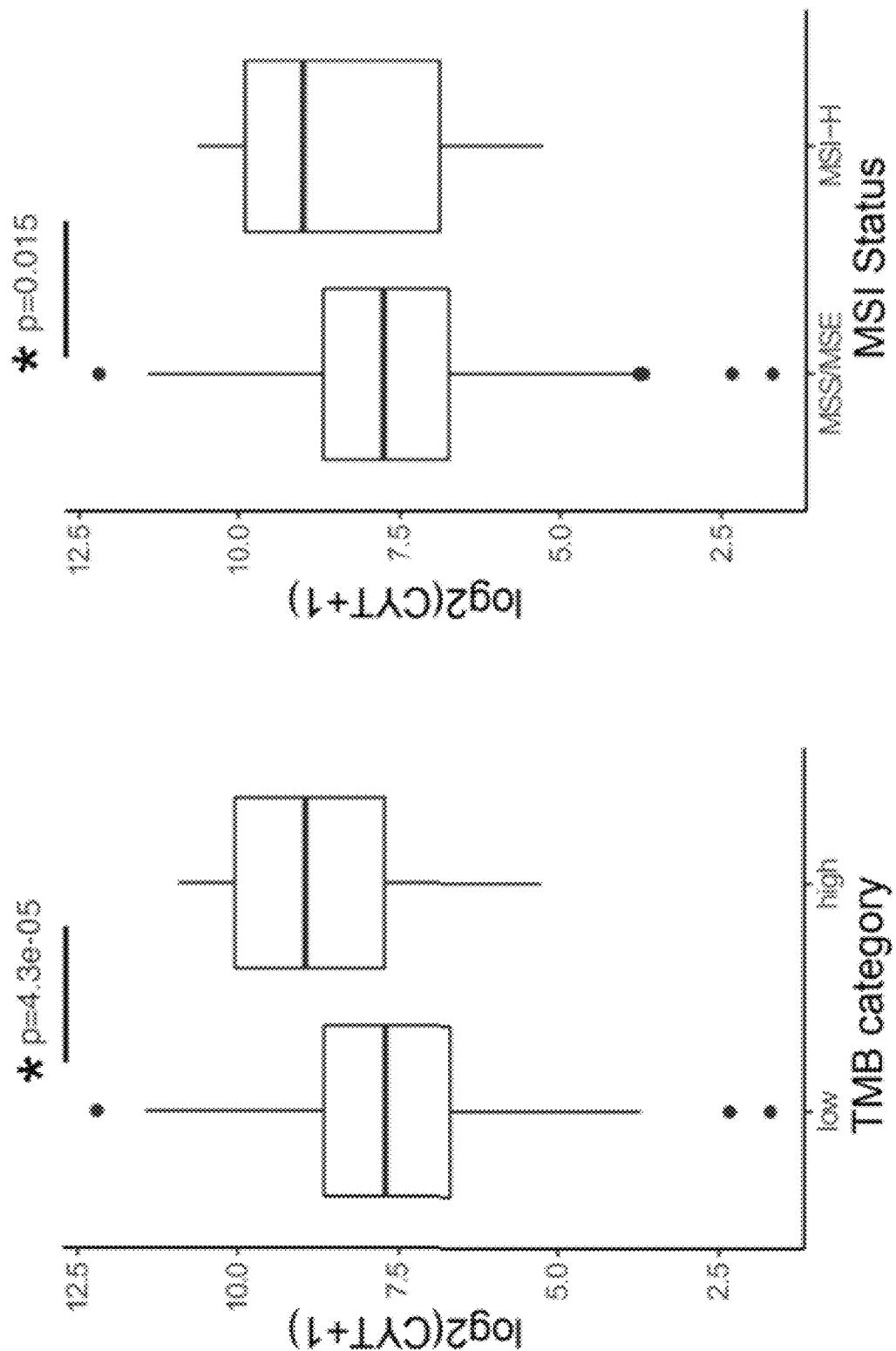
FIG. 39 includes two schematics illustrating two gene expression scores for low and high TMB and MSI populations generated using techniques that are consistent with at least some aspects of the present disclosure related to the exemplary xT panel.

To test this, we assessed the relative levels of cytotoxic immune activity using a gene expression score, cytolytic index (CYT) (Rooney, M. S., Shukla, S. A., Wu, C. J., Getz, G. & Hacohen, N. Molecular and Genetic Properties of Tumors Associated with Local Immune Cytolytic Activity. Cell 160, 48-61 (2015)). We found that this two gene expression score is significantly higher in our TMB-high and MSI-high populations (p=4.3×10-5 and p=0.015, respectively) (FIG. 39). This result demonstrates that even in patients with heavily pre-treated and advanced stage disease, a hypermutator status is strongly associated with greater cytotoxic immune activity.

Figure 40:
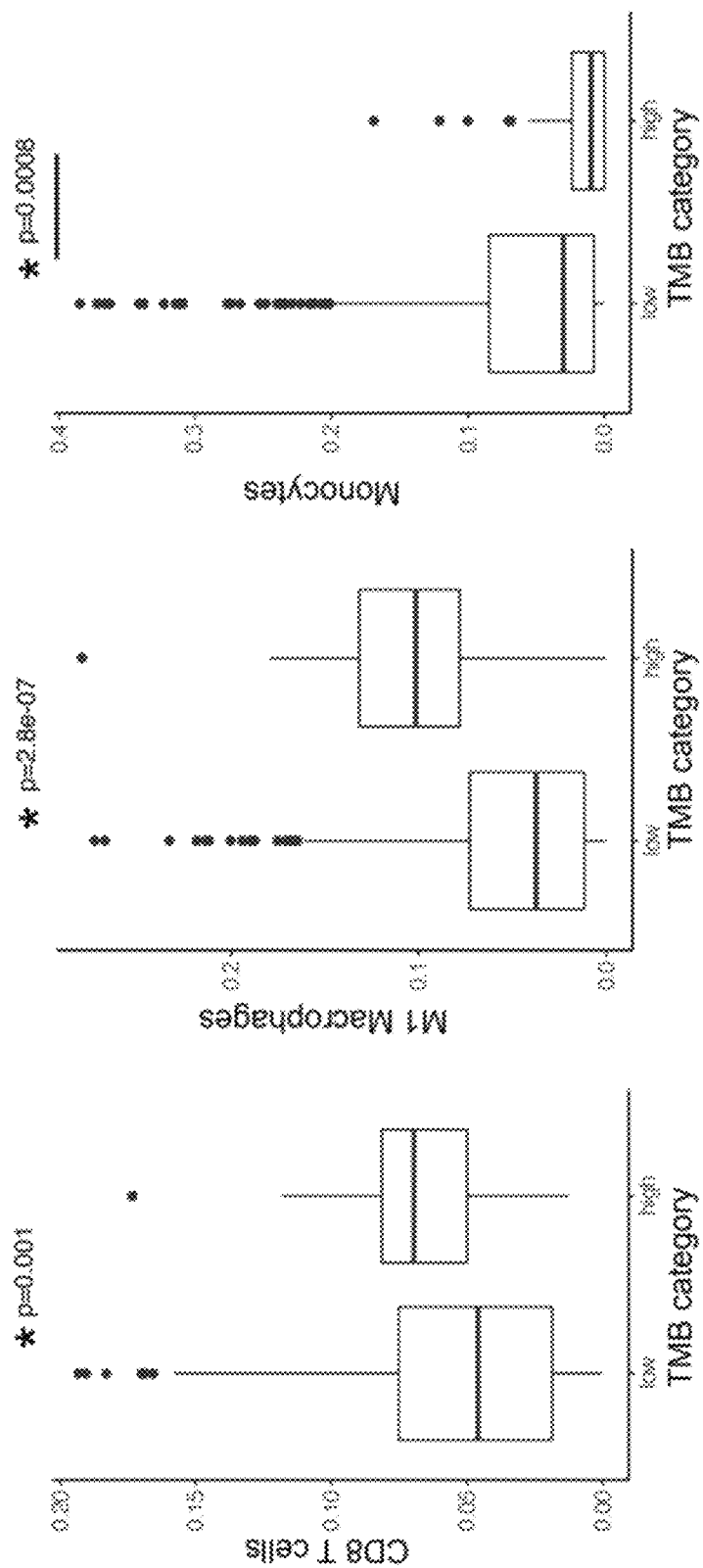
FIG. 40 includes three schematics illustrating data related to propensity of different types inflammatory immune and non-inflammatory immune cells in low and high TMB samples generated for the related xT panel.

Next, whether specific immune cell populations were differentially represented in the immune cell composition of TMB-high tumors compared to TMB-low was analyzed. We implemented a support vector regression-based deconvolution model to computationally estimate the relative proportion of 22 immune cell types in each tumor (Newman, A. M. et al. Robust enumeration of cell subsets from tissue expression profiles. Nat. Methods 12, 453-7 (2015)). In accordance to our cytolytic index analysis, we also found that inflammatory immune cells, like CD8 T cells and M1 polarized macrophages, were significantly higher in TMB-high samples, while non-inflammatory immune cells, like monocytes, were significantly lower in TMB-low samples (p=0.0001, p=2.8×10-7, p=0.0008) (see FIG. 40).

Figure 41:
FIG. 41 includes a schematic illustrating data related to prevalence of CD274 expression in low and high TMB samples generated using techniques consistent with at least some aspects of the present disclosure generated for the related xT panel.
Figure 42:
FIG. 42 includes two schematics illustrating correlations between CD274 expression and other cell types generated using techniques consistent with at least some aspects of the present disclosure generated for the related xT panel.

Increased immune pressure, like infiltration of more inflammatory immune cells, can lead tumors to express higher levels of immune checkpoint molecules like PD-L1 (CD274). These immune checkpoints function as a brake on the immune system, turning activated immune cells into quiescent ones. Accordingly, whole transcriptome analysis determined CD274 expression is significantly higher in the more immune-infiltrated TMB-high tumors (p=0.0002) (FIG. 41). CD274 expression is also highly correlated with the expression of its binding partner on immune cells, PDCD1 (PD-1), as well as other T cell lineage-specific markers like CD3E (FIG. 42). Furthermore, samples that stained positive for PD-L1 protein via clinically-validated IHC tests cluster with higher CD274 RNA expression levels (FIG. 42), suggesting the expression of CD274 may be used as a proxy for protein levels of PD-L1.

A system, methods and model for predicting PD-L1 status of a cancer cell sample using RNA expression data and other patient data is described hereafter with reference to FIGS. 340A through 344 which should be referred to for more detail.

Figure 43:
FIG. 43 is a schematic illustrating data generated via a 28 gene interferon gamma-related signature that is consistent with at least some aspects of the present disclosure.
Figure 44:
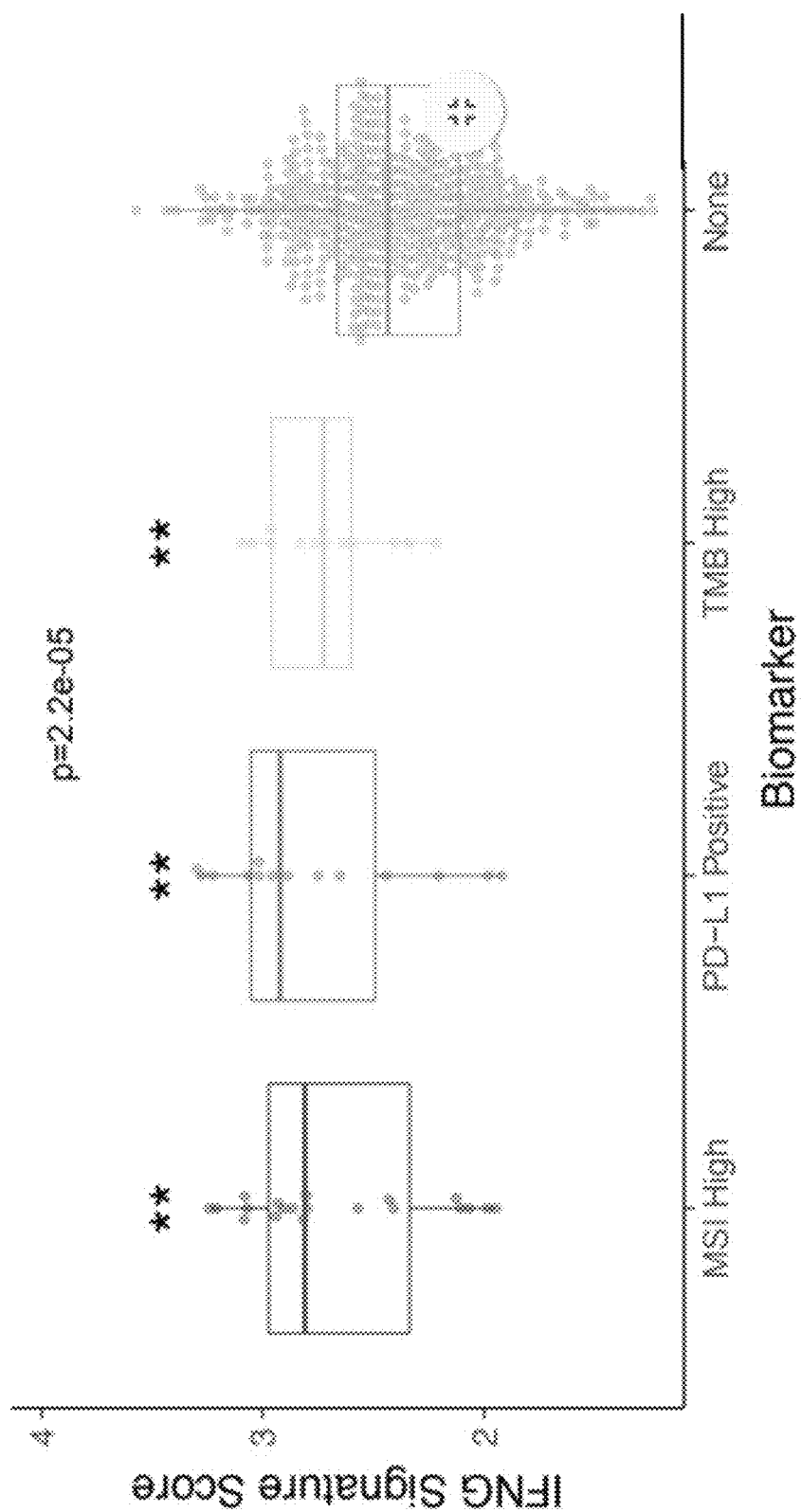
FIG. 44 includes data shown as a graph illustrating levels of interferon gamma-related genes versus TMB-high, MSI-high and PDL1 IHC positive tumors generated using techniques consistent with at least some aspects of the present disclosure.

Transcriptomic markers were utilized to further determine whether patients that lack classically defined immunotherapy biomarkers still exhibited immunologically similar tumors. Using a 28 gene interferon gamma-related signature, it was found that tumor samples could be broadly categorized as either immunologically active "hot" tumors or immunologically silent "cold" tumors based on gene expression (FIG. 43). The 28-gene set encompassed genes related to cytolytic activity (e.g., granzyme A/B/K, PRF1), cytokines/chemokines for initiation of inflammation (CXCR6, CXCL9, CCL5, and CCR5), T cell markers (CD3D, CD3E, CD2, 1L2RG [encoding IL-2Ry]), NK cell activity (NKG7, HLA-E), antigen presentation (CIITA, HLA-DRA), and additional immunomodulatory factors (LAG3, IDO1, SLAMF6). Results support this stratification, with the immunologically "hot" population enriched for samples that were TMB-high, MSI-high or PDL1 IHC positive. Furthermore, TMB-high, MSI-high, or PD-L1 IHC positive tumors expressed higher levels of interferon gamma-related genes versus tumors without any of those biomarkers (p=2.2×10-5) (FIG. 44). Hence, patients within this immunologically active cluster that lack traditional immunotherapy biomarkers represent an interesting patient population that may potentially benefit from immunotherapy.

Figure 56:
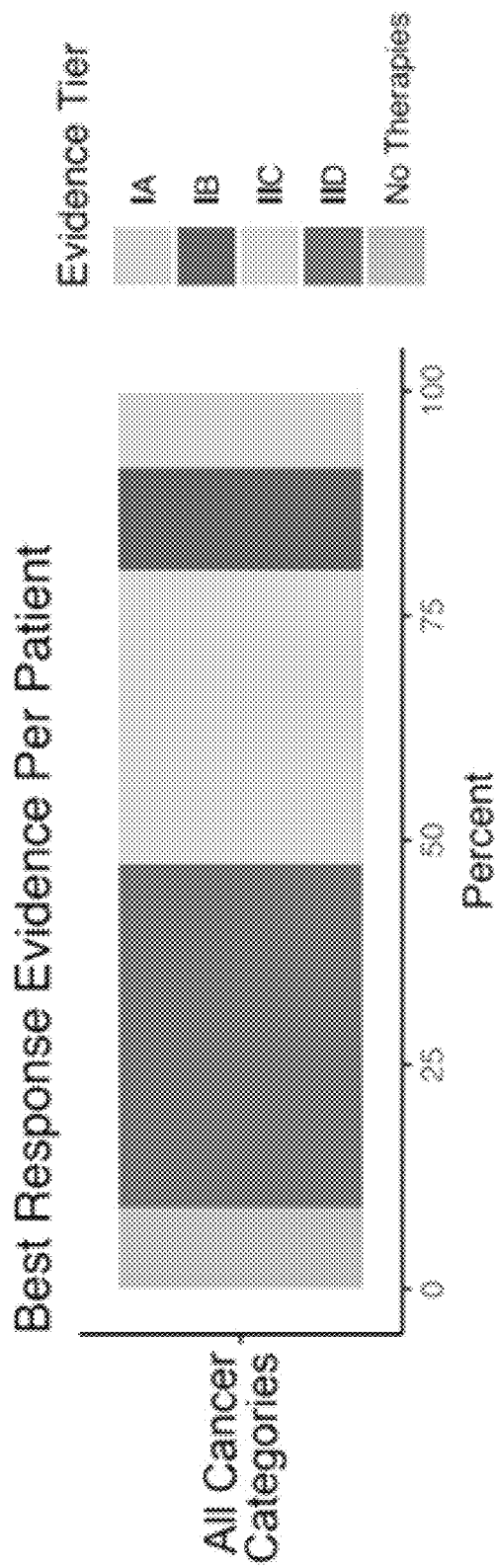
FIG. 56 includes a graph illustrating response evidence to therapies across all cancer types in an exemplary study using techniques consistent with at least some aspects of the present disclosure.
Figure 57:
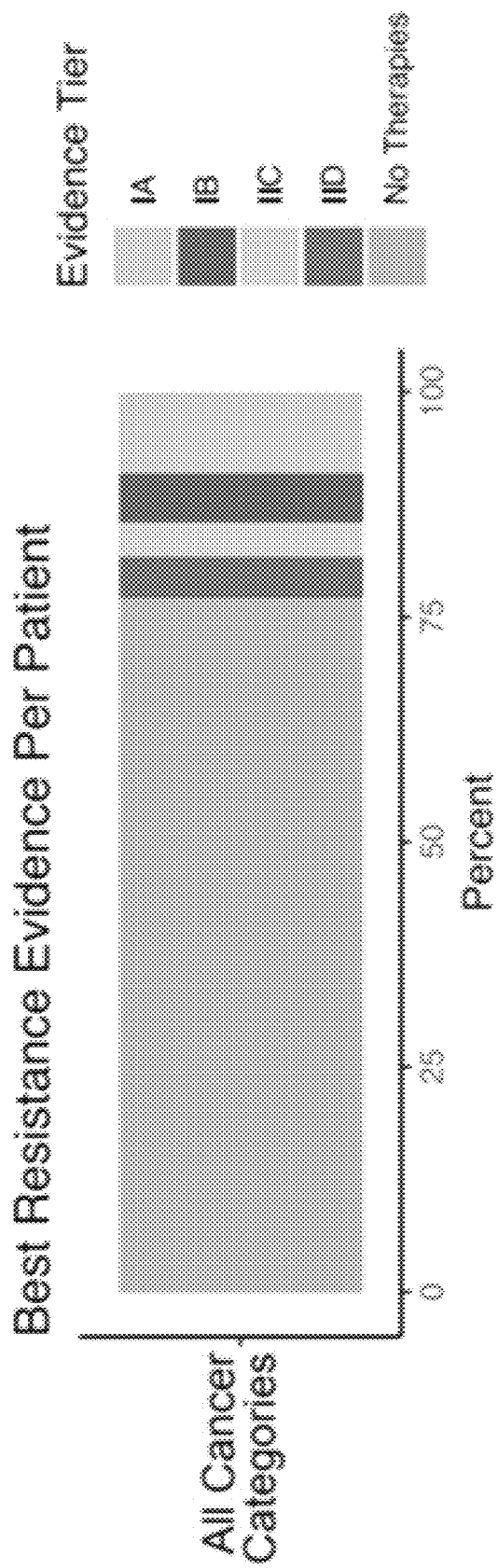
FIG. 57 includes a graph illustrating evidence of resistance to therapies across all cancer types in an exemplary study using techniques consistent with at least some aspects of the present disclosure.

The ultimate goal of the broad molecular profiling done in the xT assay is to match patients to therapies as effectively as possible, with targeted or immunotherapy options being the most desirable. We evaluated whether patients in the xT group matched to response and resistance therapeutic evidence based on consensus clinical guidelines by cancer type (see KDB in Methods). Across all cancer types, 90.6% matched to therapeutic evidence based on response to therapy (FIG. 56), and 22.6% matched to evidence based on resistance to therapy (FIG. 57).

Figure 45:
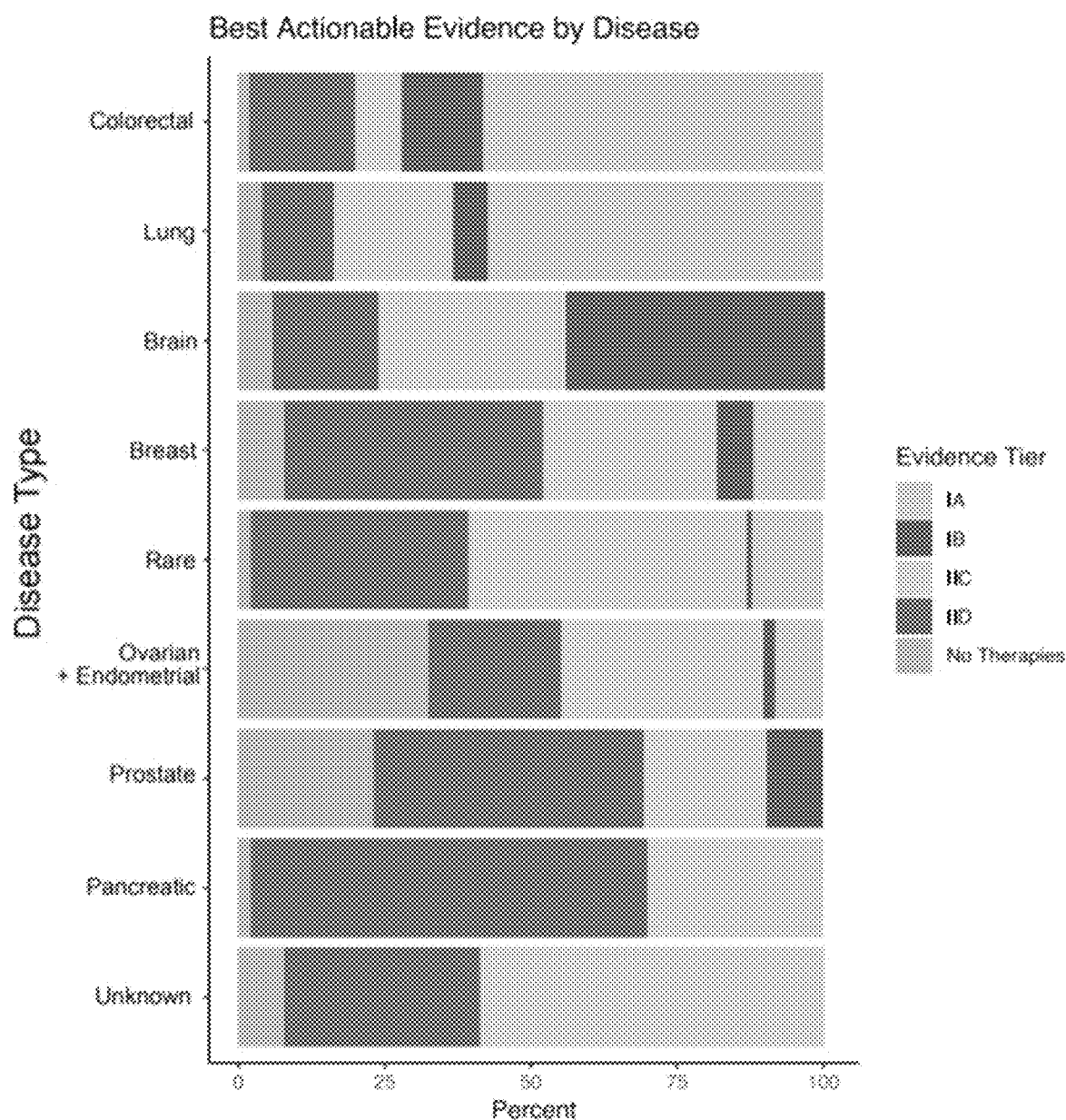
FIG. 45 includes a bar graph illustrating data related to therapeutic evidence as it varies among different cancer types generated using techniques consistent with at least some aspects of the present disclosure.
Figure 46:
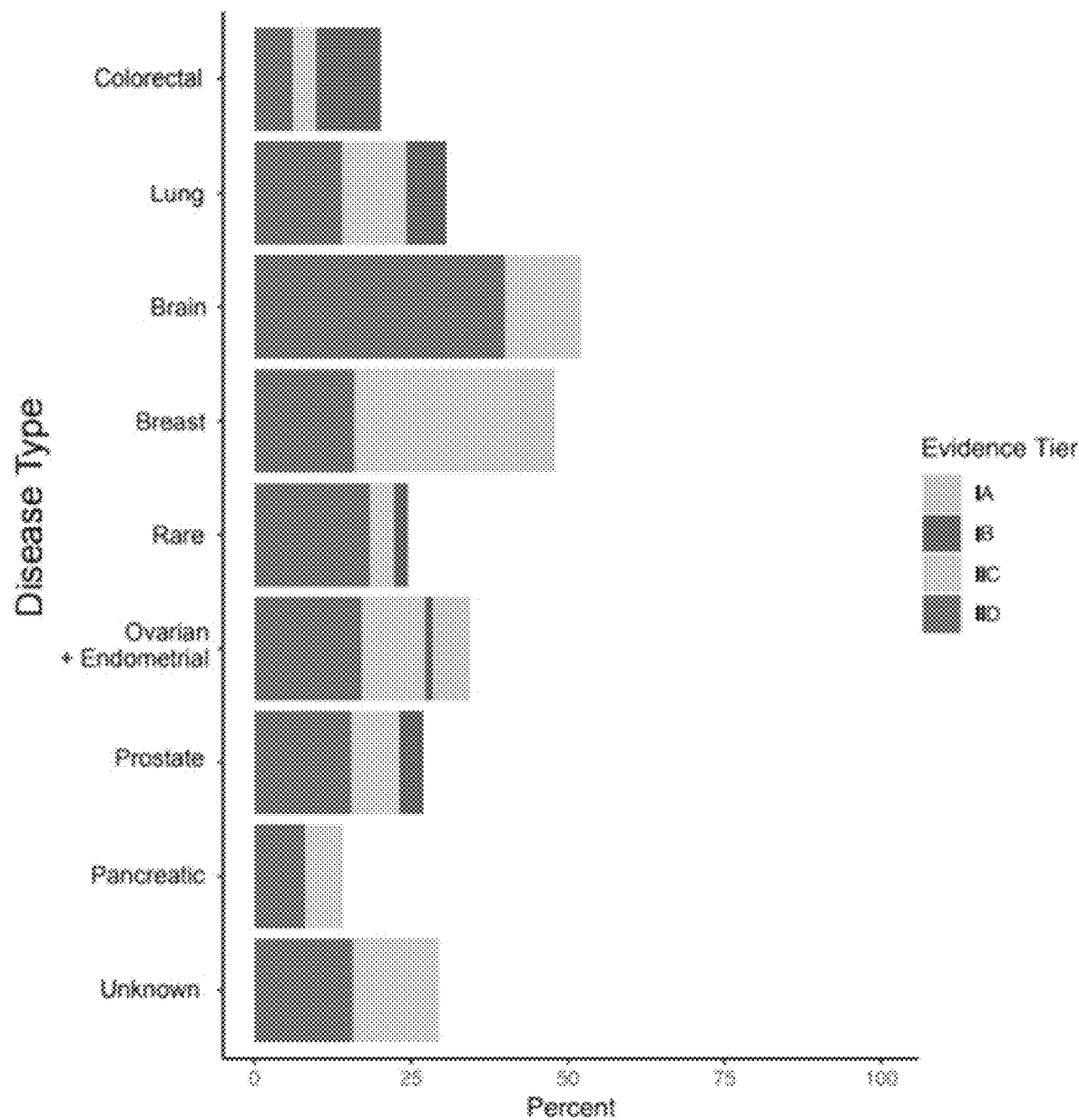
FIG. 46 includes a bar graph illustrating data related to specific therapeutic evidence matches based on copy number variants generating using techniques consistent with at least some aspects of the present disclosure.
Figure 47:
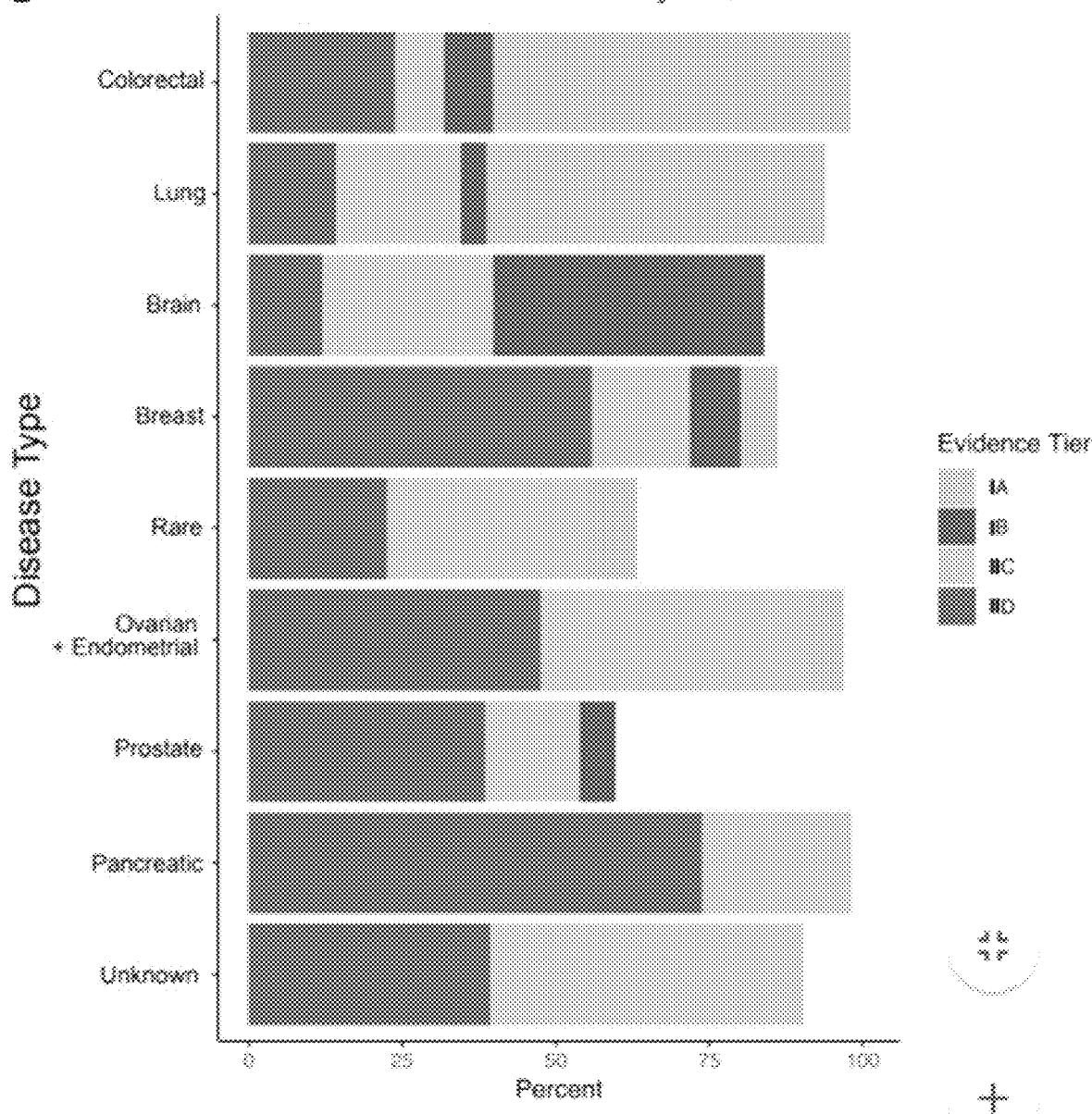
FIG. 47 includes a bar graph illustrating data related to specific therapeutic evidence matches based on single nucleotide variants and indels generating using techniques consistent with at least some aspects of the present disclosure.
Figure 58:
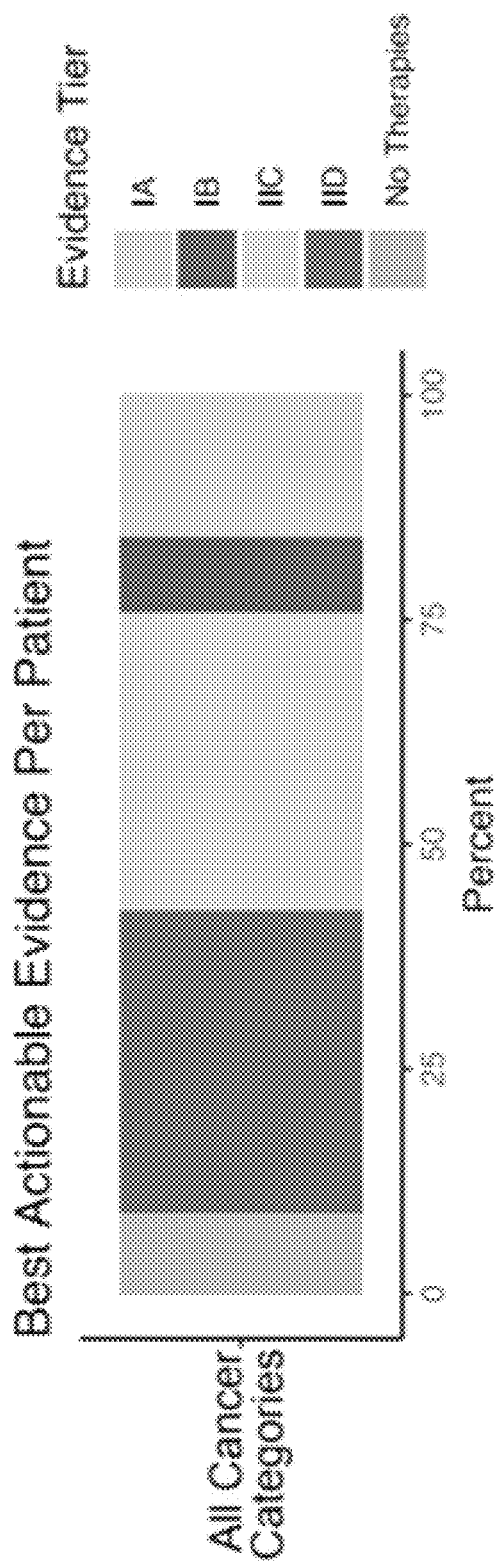
FIG. 58 includes a graph illustrating therapeutic evidence tiers for all cancer types in an exemplary study using techniques consistent with at least some aspects of the present disclosure.

For both response and resistance therapeutic evidence, approximately 24% of the group could be matched to a precision medicine option with at least a tier IB level. In particular, tier IA therapeutic evidence, as defined by joint AMP, ASCO, and CAP guidelines, was returned for 15.8% of patients (FIG. 58). The maximum tier of therapeutic evidence per patient varied significantly by cancer type (FIG. 45). For example, 58.0% of colorectal patients could be matched to tier IA evidence, the majority of which were for resistance to therapy based on detected KRAS mutations; while no pancreatic cancer patients could be matched to tier IA evidence. This is expected, as there are several molecularly based consensus guidelines in colorectal cancer, but fewer or none for other cancer types. Additionally, specific therapeutic evidence matches were made based on copy number variants (CNVs) (FIG. 46) and single nucleotide variants (SNVs) and indels (FIG. 47) for each cancer category.

Figure 48:
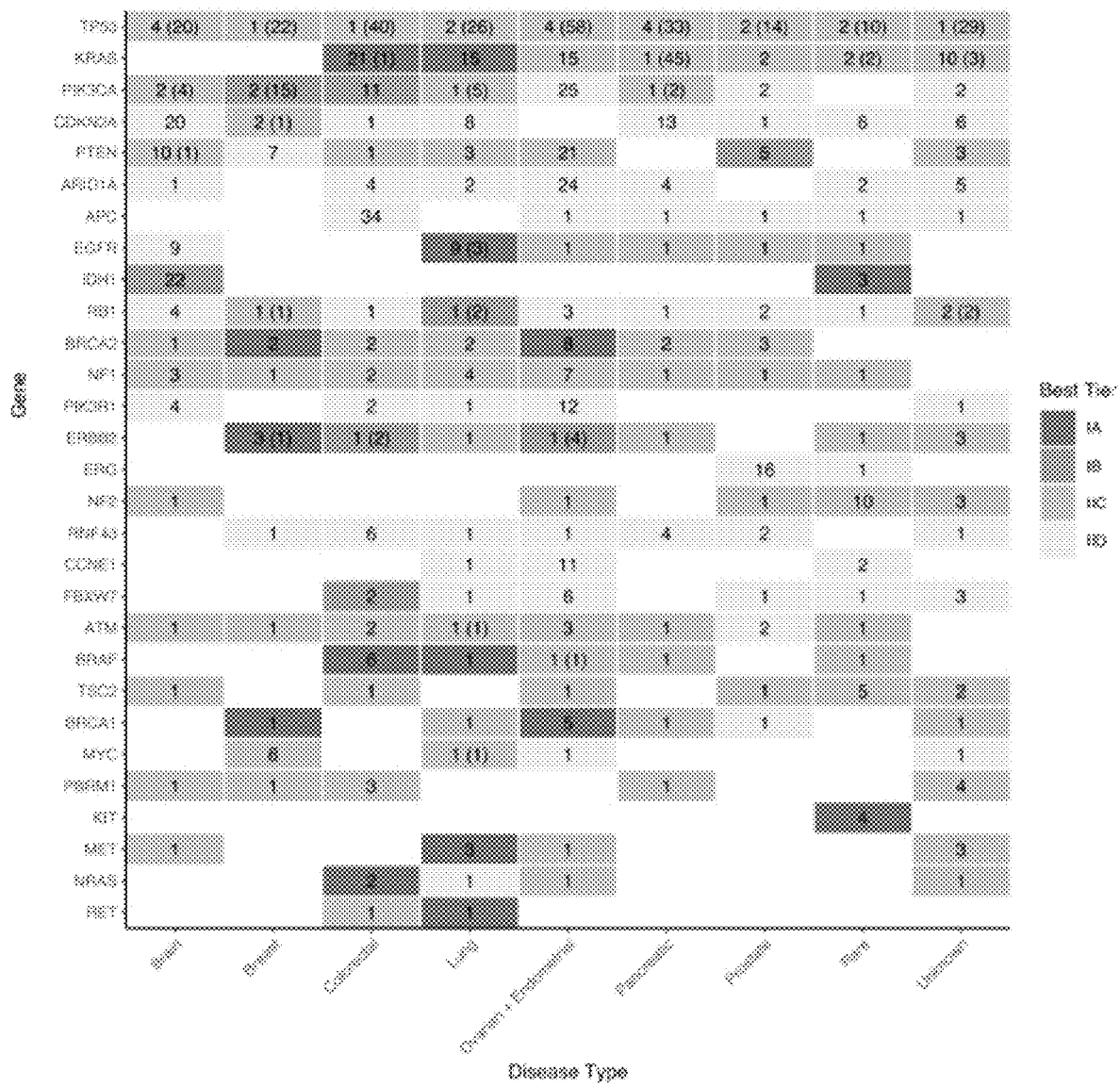
FIG. 48 includes a plot illustrating data related to single nucleotide variants and indels or CNVs by cancer type generating using techniques consistent with at least some aspects of the present disclosure.

Therapies were also matched to single gene alterations, either SNVs and indels or CNVs, and plotted by cancer type (FIG. 48). Unfortunately, the two most commonly mutated genes in cancer are TP53 and KRAS, with TP53 only having Tier IIC evidence and drugs in clinical trials, and KRAS having Tier 1A evidence, but as resistance to therapies targeting other proteins (36 patients). However, many less commonly mutated genes have Tier 1A evidence for targeted therapies across a variety of cancer types. Notable in this category are the PARP inhibitors for BRCA1 and BRCA2 mutated breast and ovarian cancer (16 patients), which are currently also in clinical trials or being used off-label in other disease types harboring BRCA mutations, such as prostate and pancreatic cancer. The majority of the remaining targetable mutations with Tier 1A evidence are from the druggable portions of the MAP kinase cascade (MAPK/

ERK pathway), including EGFR, BRAF and NRAS across colorectal and lung cancer (18 patients).

Therapeutic options were further matched based on RNA sequencing data. We focused on the expression of 42 clinically relevant genes selected based on their relevance to disease diagnosis, prognosis, and/or possible therapeutic intervention. Over or underexpression of these genes may be reported to physicians.

Figure 49:
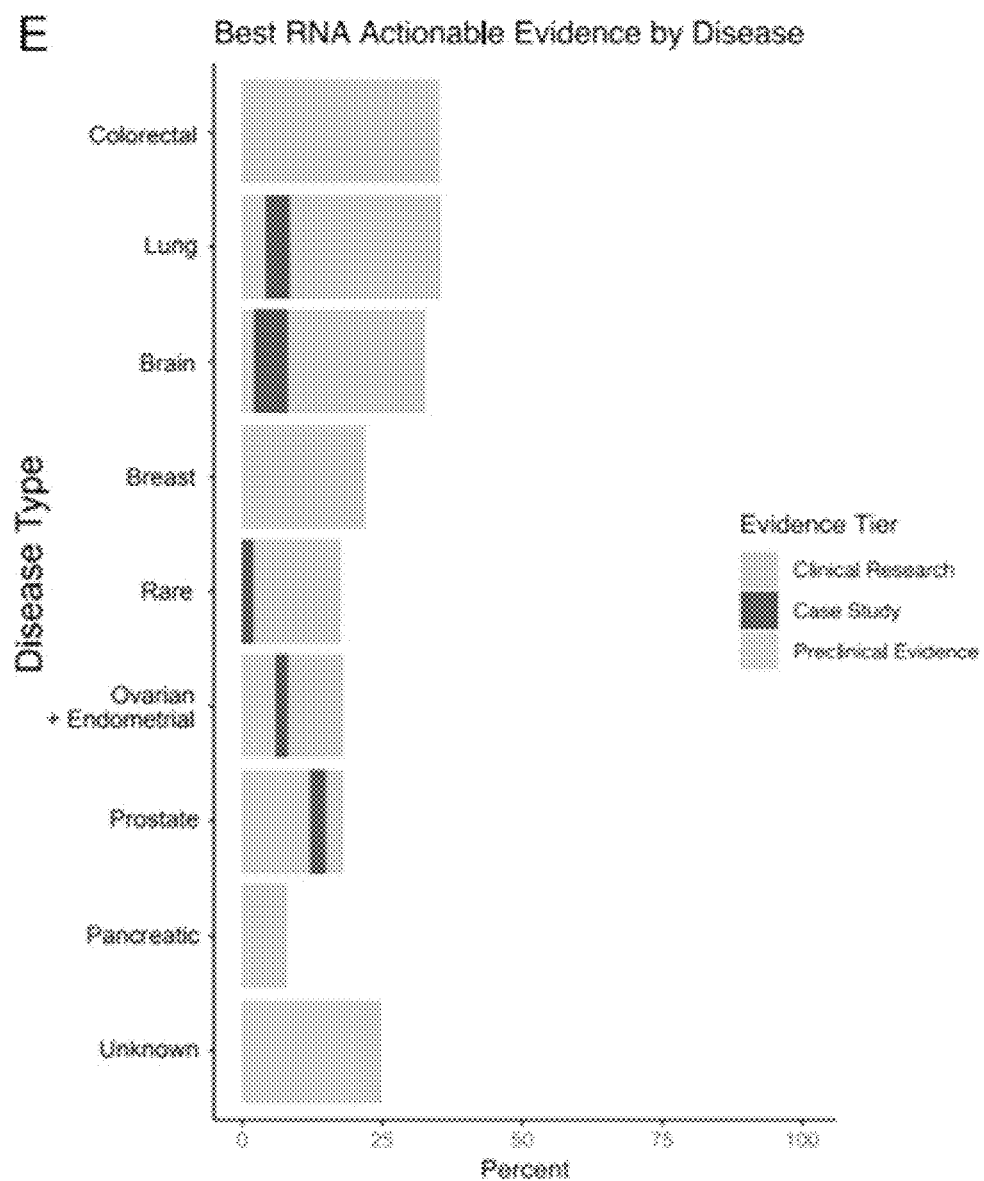
FIG. 49 includes a bar graph illustrating data that shows percent of patients with gene calls and evidence for association between gene expression and drug response where the data was generated using techniques consistent with at least some aspects of the present disclosure.
Figure 54:
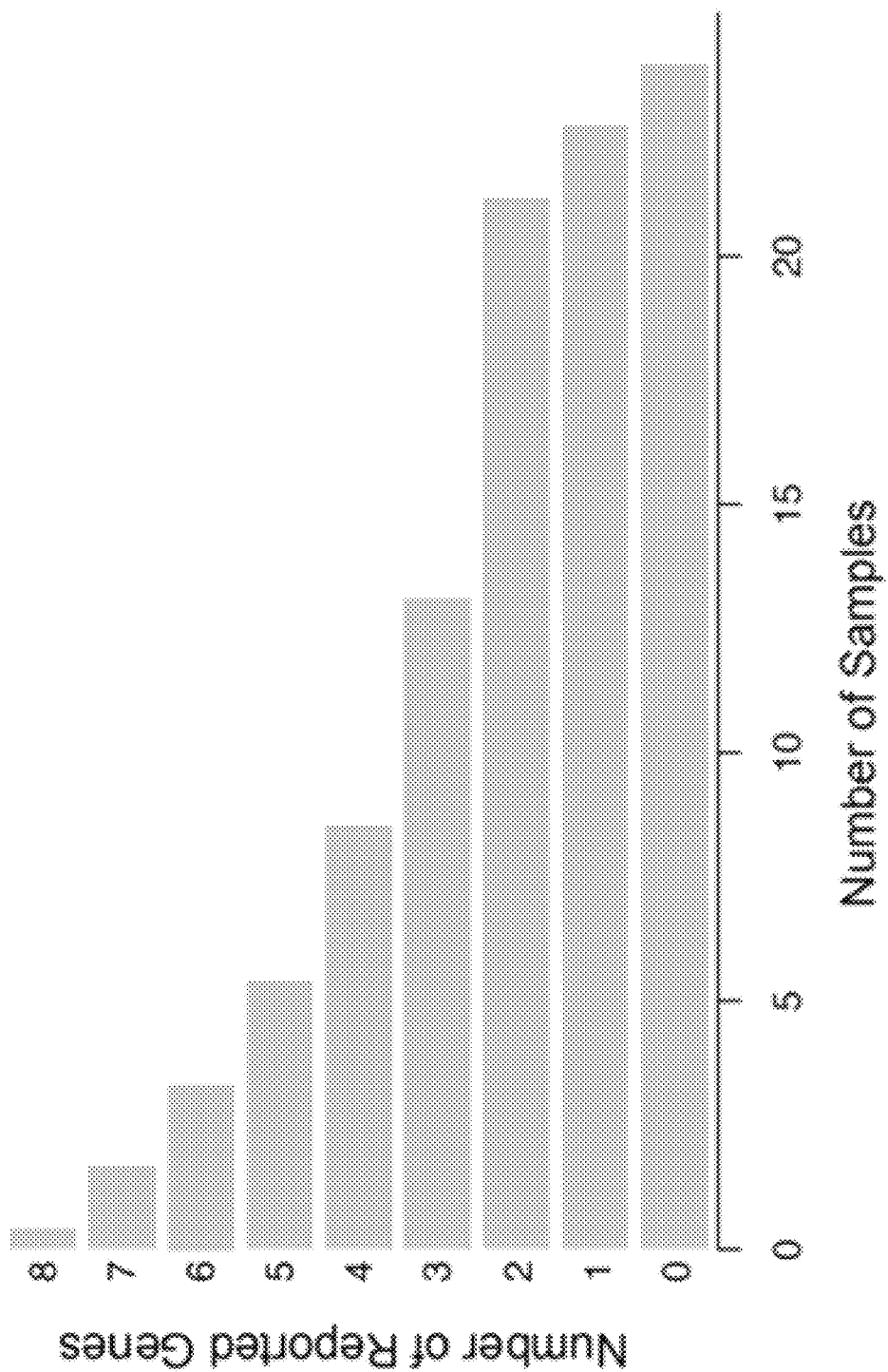
FIG. 54 includes a bar graph including data that shows exemplary distribution of expression calls by sample that was generated using techniques that are consistent with at least some aspects of the present disclosure.
Figure 55:
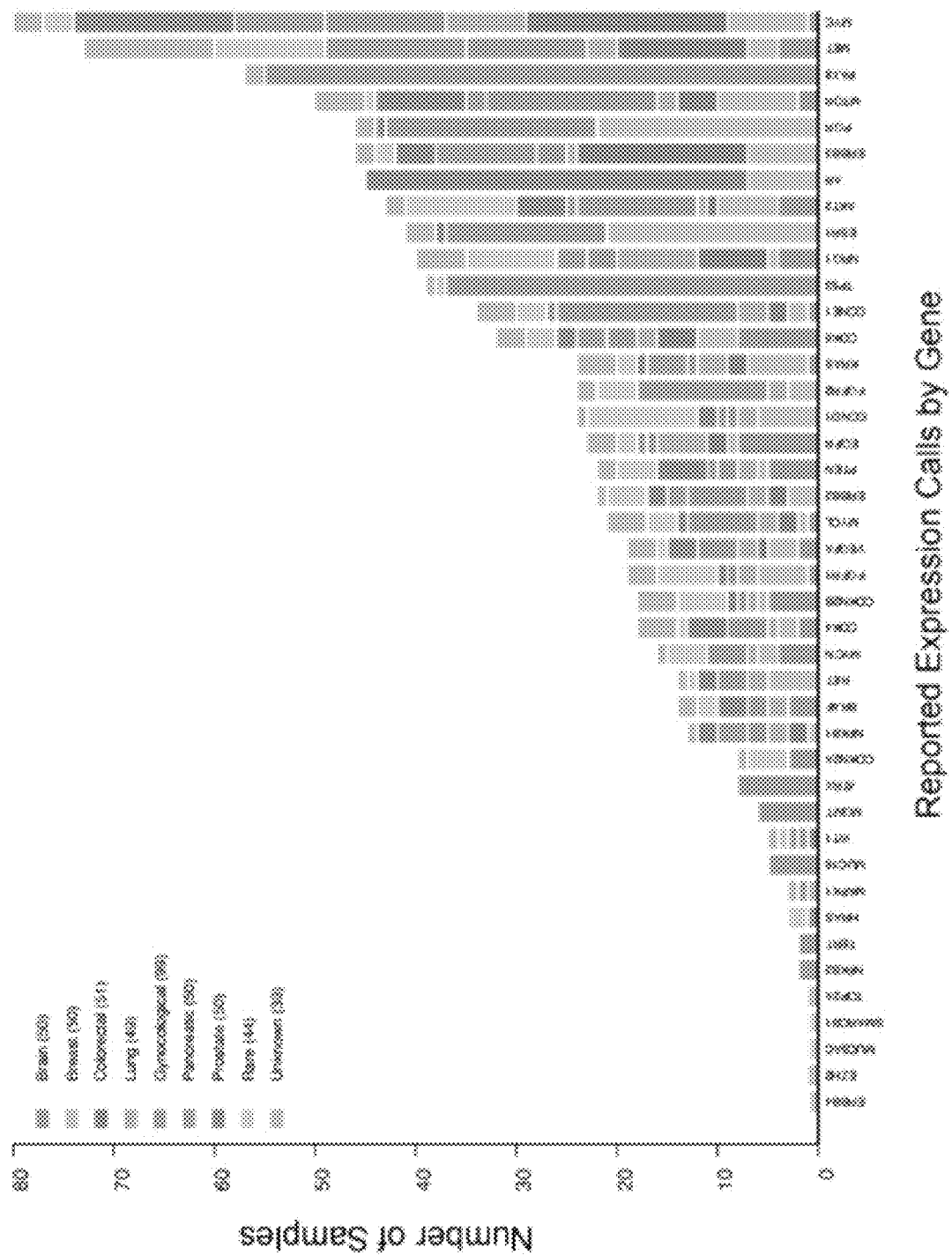
FIG. 55 includes a bar graph including data that shows exemplary distribution of expression calls by gene that was generated using techniques consistent with at least some aspects of the present disclosure.

Expression calls were made by comparison of the patient tumor expression to the tumor and normal tissue expression in the data vault database 180 based on overall comparisons as well as tissue-specific comparisons. For example, each breast cancer case was compared to all cancer samples, all normal samples, all breast cancer samples, and all normal breast samples. At least one gene in 76% of patients with gene expression data was reported. The distribution of expression calls is shown by sample (FIG. 54) and by gene (FIG. 55). It was found that metastatic cases are equally as likely to have at least one reportable expression call compared to non-metastatic tumors (79% vs 75%, p-value=0.288). The most commonly reported gene is overexpression of MYC, which was seen in 80 (17%) patient tumors across the group. Next, the percent of patients with gene expression calls was determined and evidence for the association between gene expression and drug response (FIG. 49) was identified. Among the cases with reported expression calls, 25% of cases across cancer types included evidence based on clinical studies, case studies, and preclinical studies reported in the literature.

Figure 50:
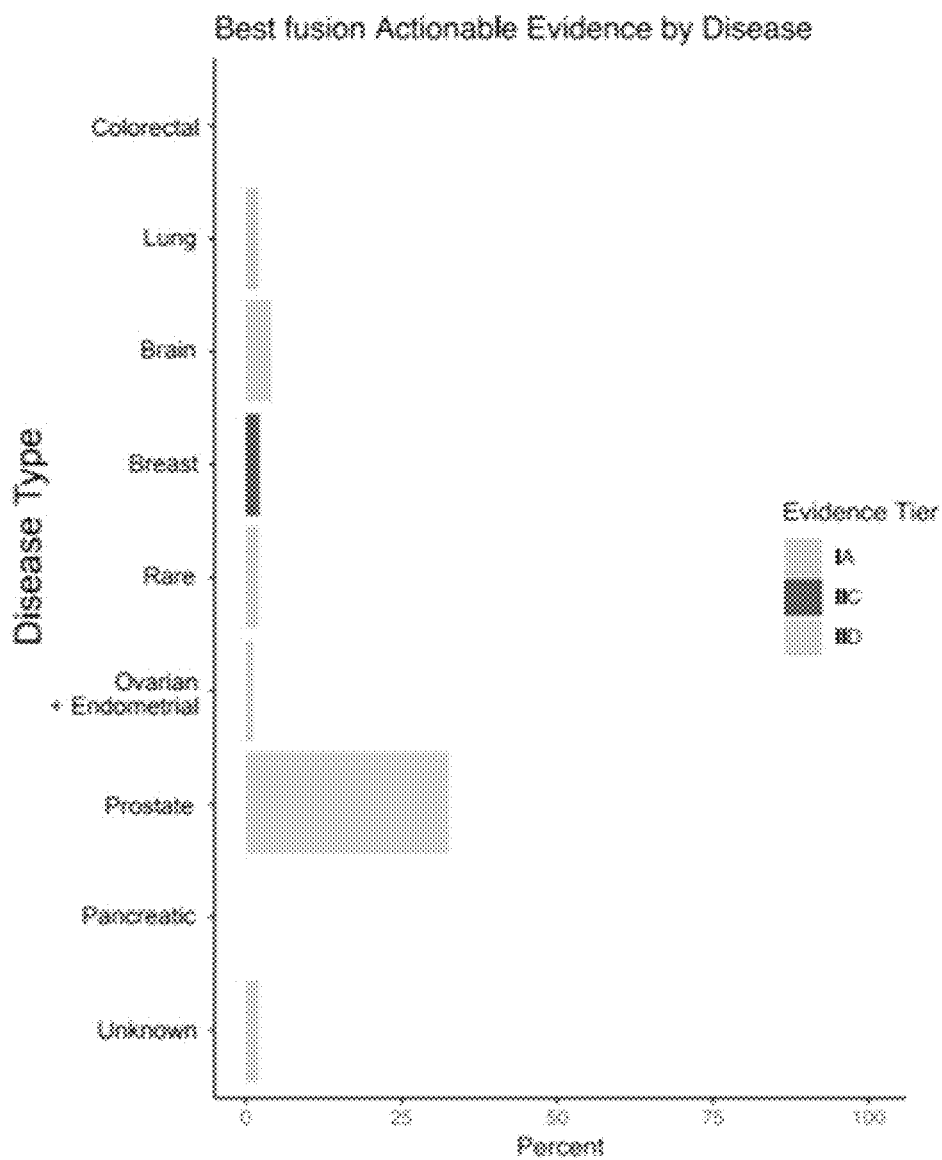
FIG. 50 includes a bar graph illustrating response to therapeutic options based on evidence tiers and broken down by cancer type.

Fusion proteins are proteins made from RNA that has been generated by a DNA chromosomal rearrangement, also known as a "fusion event." Fusion proteins can be oncogenic drivers that are among the most druggable targets in cancer. Of the 28 chromosomal rearrangements detected in the study group, 26 were associated with evidence of response to various therapeutic options based on evidence tiers and cancer type (FIG. 50). The majority of fusion events were TMPRSS-ERG fusions within prostate cancer patients in the group. TMPRSS-ERG fusions in prostate cancer were given an IID evidence level due to the early evidence around therapeutic response. Of the seven non-prostate cancer fusions, one was rated as evidence level IA, one was rated as IIC and five were rated evidence level IID. These detected fusions are clear drivers of cancer, part of consensus therapeutic guidelines and shown to be present with high sensitivity by the xT assay referred to herein.

Figure 51:
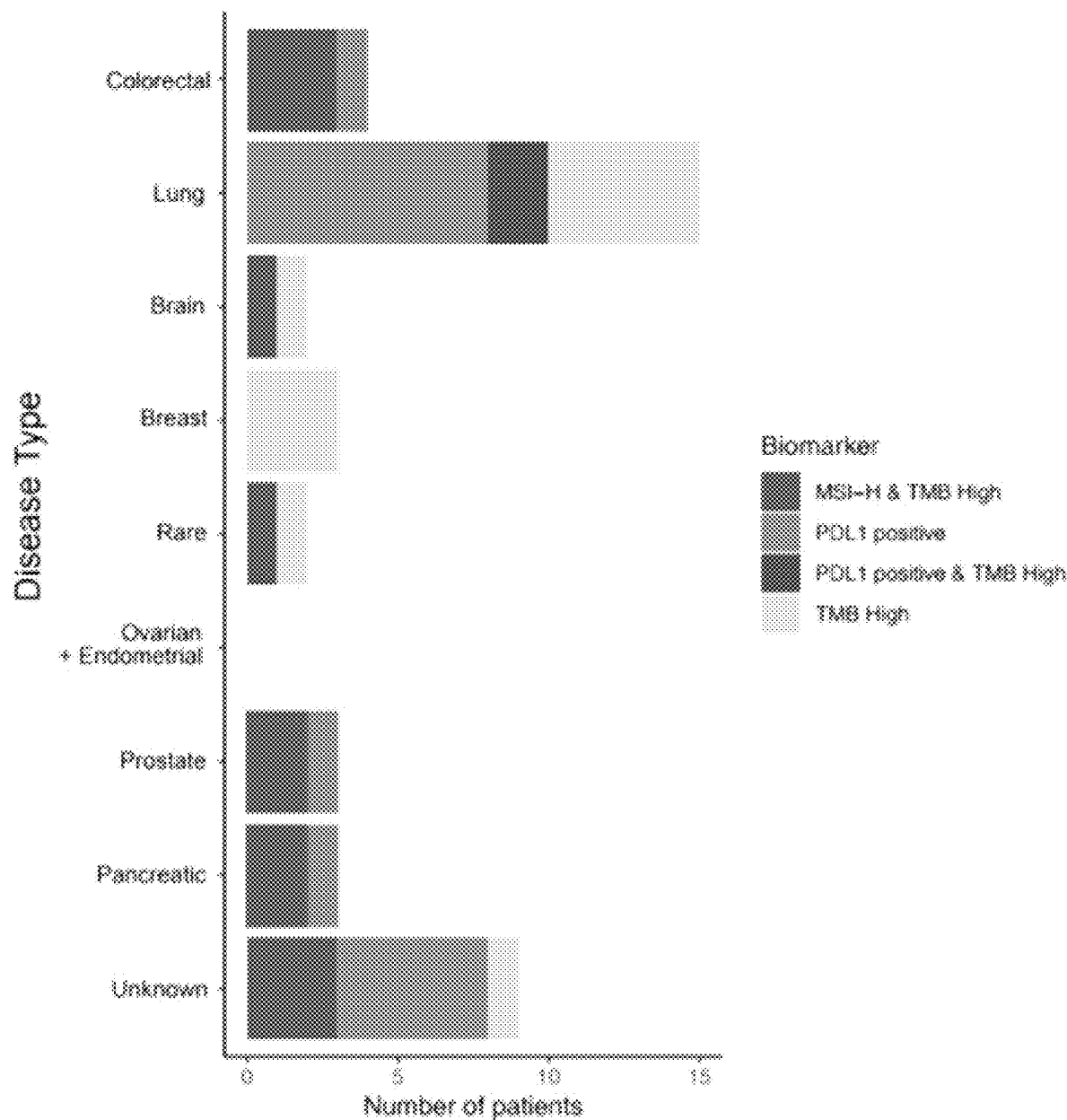
FIG. 51 includes a bar graph showing data related to patients that are potential candidates for immunotherapy broken down by cancer type where the data is based on techniques consistent with the present disclosure.

Based on the immunotherapy biomarkers identified by the xT assays, we investigated what percentage of the group would be eligible for immunotherapy. We discovered 10.1% of the xT group would be considered potential candidates for immunotherapy based on TMB, MSI status, and PD-L1 IHC results alone (FIG. 51). The number of MSI-high and TMB-high cases were distributed among cancer types. This represents the most common immunotherapy biomarkers measured in the group with 4% of patients positive for both TMB-high and MSI-high status. PD-L1 positive IHC alone were measured in 3% of the eligibility group, and was found to be the highest among lung cancer patients. TMB-high status alone was measured in 2.6% of the eligibility group, primarily in lung and breast cancer cases. PD-L1 positive IHC and TMB-high status was the minority of cases and measured in only 0.4% of the eligibility group.

Figure 52:
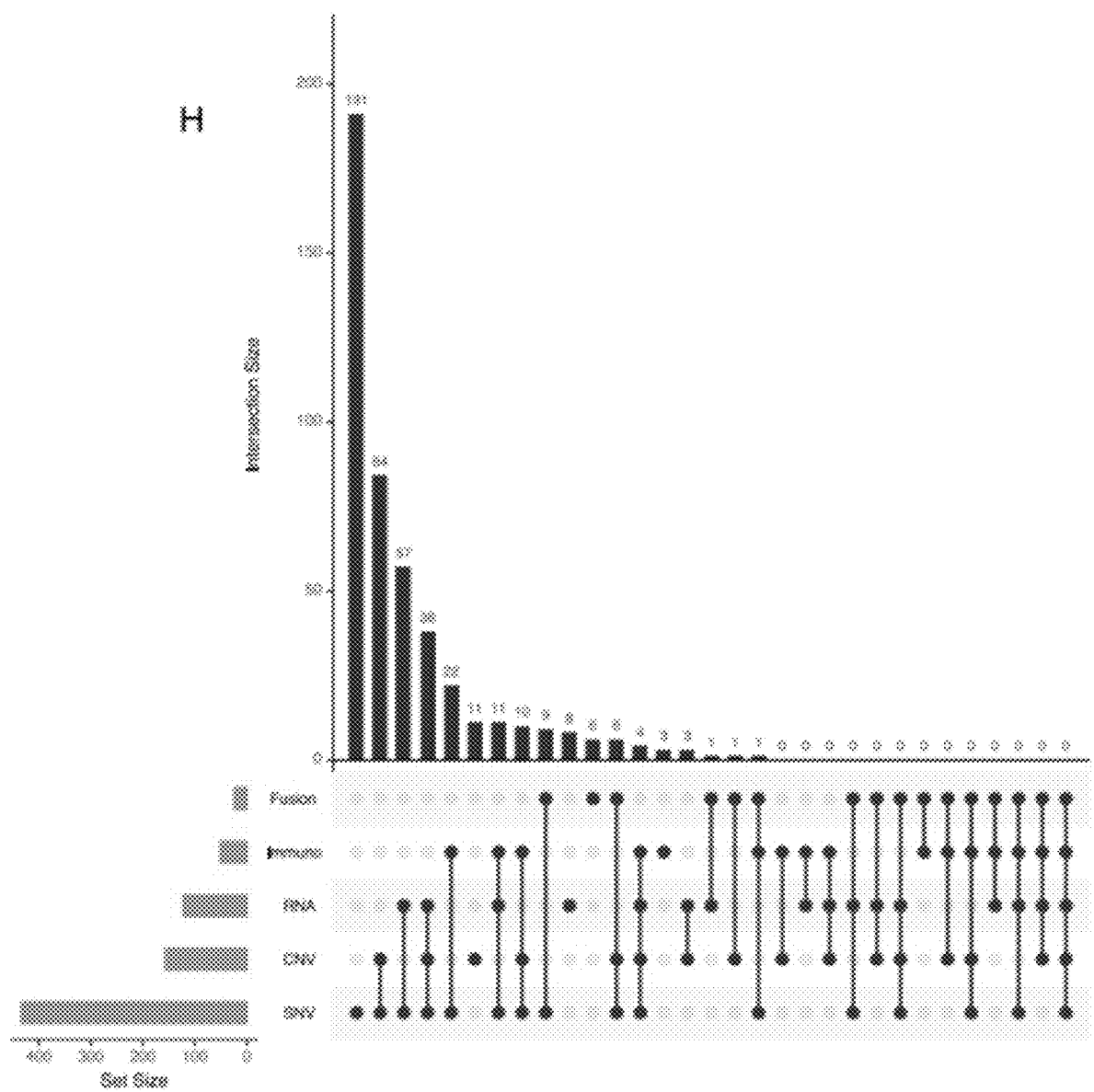
FIG. 52 is a bar graph presenting data related to relevant molecular insights for a patent group based on CNVs, indels, CNVs, gene expression calls and immunotherapy biomarker assays where the data was generated using techniques that are consistent with various aspects of the present disclosure.

Overall, clinically relevant molecular insights were uncovered for over 90% of the group based on SNVs, indels, CNVs, gene expression calls, and immunotherapy biomarker assays (FIG. 52). The majority of therapeutic matches to patients were based on clinically relevant xT findings reported on SNVs and indels. This was followed by matches based on CNVs, gene expression calls, fusion detection, and immunotherapy biomarkers. In addition to therapeutic matching, we determined clinical-trial matching for the group based on molecular insights from the xT assay.

Figure 53:
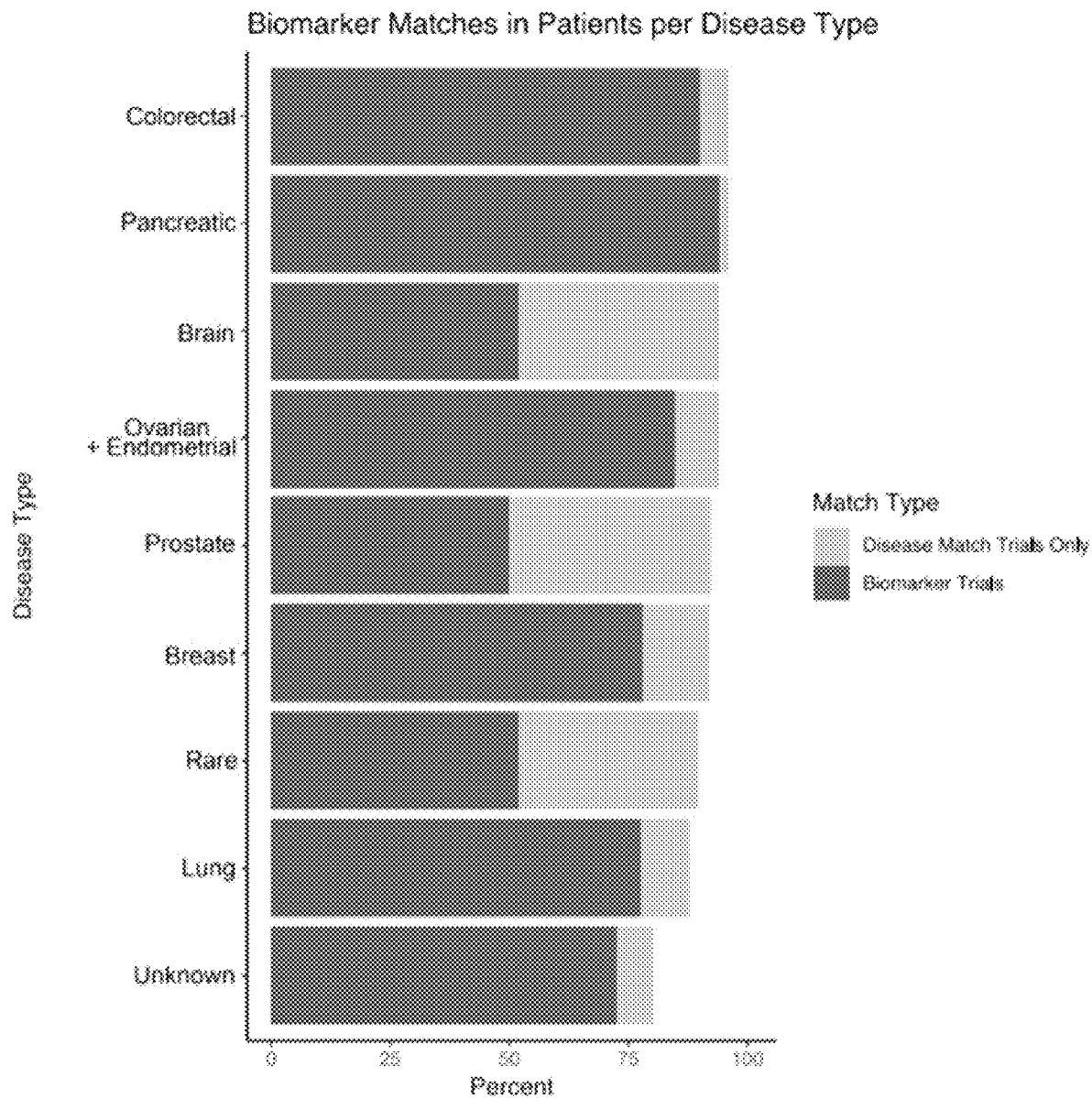
FIG. 53 includes a bar graph illustrating disease-based trial matches and biomarker based match percentages based that reflect results of techniques that are consistent with at least some aspects of the present disclosure.

In total, 1952 clinical trials were reported for the xT 500 patient group. The majority of patients, 91.6%, were matched to at least one clinical trial, with 73.6% matched with at least one biomarker-based clinical trial for a gene variant on their final report. The frequency of biomarker-based clinical trial matches varied by diagnosis and outnumbered disease-based clinical trial matches (FIG. 53). For example, gynecological and pancreatic cancers were typically matched to a biomarker-based clinical trial; while rare cancers had the least number of biomarker-based clinical trial matches and an almost equal ratio of biomarker-based to disease-based trial matching. The differences between biomarker versus disease-based trial matching appears to be due to the frequency of targetable alterations and heterogeneity of those cancer types.

A system and methods that use genomic sequence profiling to expand and optimize treatment options for cancer patients in more detail is describe hereafter with reference to FIGS. 345 through 380.

A system and methods that facilitate discovery of insights of therapeutic significance, through the automated analysis of patterns occurring in patient clinical, molecular, phenotypic and response data, and enabling further exploration via a fully integrated, reactive user interface is described hereafter with reference to FIGS. 381 through 405.

A system and methods for accessing and manipulating large complex data sets in ways that enable system users to develop new insights and conclusions with minimal user-interface friction and, more specifically via verbal dialog, is described hereafter in relation to FIGS. 406 through 424.

II. Adaptive Order Fulfillment and Tracking Methods and Systems

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithms acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium or media. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Referring now to the drawings wherein like reference numerals correspond to similar elements throughout the several views and, more specifically, referring to FIG. 59, the present disclosure will be described in the context of an exemplary adaptive order processing system 2380 that is consistent with at least some aspects of the present disclosure. Processing system 2380 includes several subsystems or functional components including a service request intake system 2320, an "order hub" 2330, a publication/subscription mechanism 2350 and a plurality of microservices collectively identified by numeral 2360. The intake system 2320 receives service requests from physicians and converts those requests to system orders that specify system processes required to generate data products needed to fulfill the requests, ultimately generating one or more final reports that are delivered to the requesting physician. The service orders are provided to order hub 2330 and specifically to an order hub server 2332 which stores the orders in a database 2334 and runs application code 2338 to manage tasks associated with each order by notifying microservices 2360 when tasks are to be performed and tracking task execution and completion. Order hub 2330 also facilitates an archiving or audit log function whereby order changes (e.g., modifications including a new order and order changes as well as order item status changes including pending, in progress, complete, failed, paused and cancelled) are tracked and stored where a system user can access the audit log information to assess current status of order tasks as well as to see a current or historical (e.g., at a specific point in time) visual representation of order item statuses and an order item map.

Referring again to FIG. 59, request intake system 2320 includes an order intake server 2329, a template database 2328 and sub-systems for receiving and manipulating received service requests including an automated entry sub-system 2326 and an abstractor specialist interface 2322. Service requests can be received in several different ways including, for instance, a fax requisition system 2312, an online service request system 2314, or an EMR service request system 2316. Other ways of acquiring service requests are contemplated.

In some cases requested services will require system 2380 to acquire or access detailed patient clinical or medical history records and in these cases a service request will include the required record data or some way to access or obtain to that data. For instance, in some cases a service request will include a copy of a patient's clinical records or a link to a records server that can be used to access those records.

System 2380 requires data and information in a defined or normalized format. In some cases service requests and clinical records are received in the normalized format required by system 2380 and in those cases the requests and clinical records are consumed by server 2329 as received. For instance, in the case of a service request received from an EMR system, the EMR system may be programmed to generate clinical data in the normalized format required by system 2380. In other cases, service requests and clinical records may not be in the normalized format but may be in a format that can be automatically converted to the normalized format via automated entry subsystem 2326. In other cases clinical data may be generally unstructured or in a format that cannot be automatically converted to the normalized format and in that case an "abstractor" specialist (e.g., service provider employee charged with converting requests and clinical records to the normalized formats) manually converts a received order and records to the system required format. For instance, where an unstructured service request is received via facsimile, an abstractor specialist may glean request information therefrom and enter order information in via interface 2322 in the normalized format for consumption by the system 2380. In still other cases automated entry system 2326 may be capable of converting at least some request and record information into the normalized formats and an abstractor specialist may be charged with confirming accuracy of that information as well as filling in any information that cannot be automatically converted. Abstractor software programs/interfaces have been specially designed to facilitate abstraction.

A typical service request will identify a specific set of tests or other procedures to be performed by the service provider. In at least some cases specific physicians or institutions (e.g., medical facilities at which physicians work) have preferences for test types, test sub-processes, report types, report formats, etc. Referring still to FIG. 59, in addition to receiving service requests, intake system 2320 has access to institution preferences 2318 which may specify any of specific test types, sub-processes, report types and formats. In FIG. 59, the phrase "institution preferences" is used generally to refer to specific physician preferences as well as general institutional preferences. In at least some cases it is envisioned that there will be a hierarchy of preferences where a specific physician's preferences may take precedence over institutional preferences or vice versa. In a case where no preferences exist, the system will implement a set of default preferences for any received order or may have a feedback mechanism whereby any required preference is sought from an ordering physician or institution.

Referring again to FIG. 59, intake system 2320 converts a service request and institution preferences into a system service order (hereinafter "order") that includes a plurality of business processes or discrete tasks that can be completed to generate data or information needed to prepare one or more final reports. Hereinafter, unless indicated otherwise, a system business process will be referred to as an "item" and therefore an order may be represented as a series of consecutive items and parallel items. Hereinafter, when an item is complete, the item is said to be "fulfilled" and, in most cases that means that the item has generated one or more data products that have been stored in a system database for subsequent access by other items that comprise a common service order.

Figure 59:
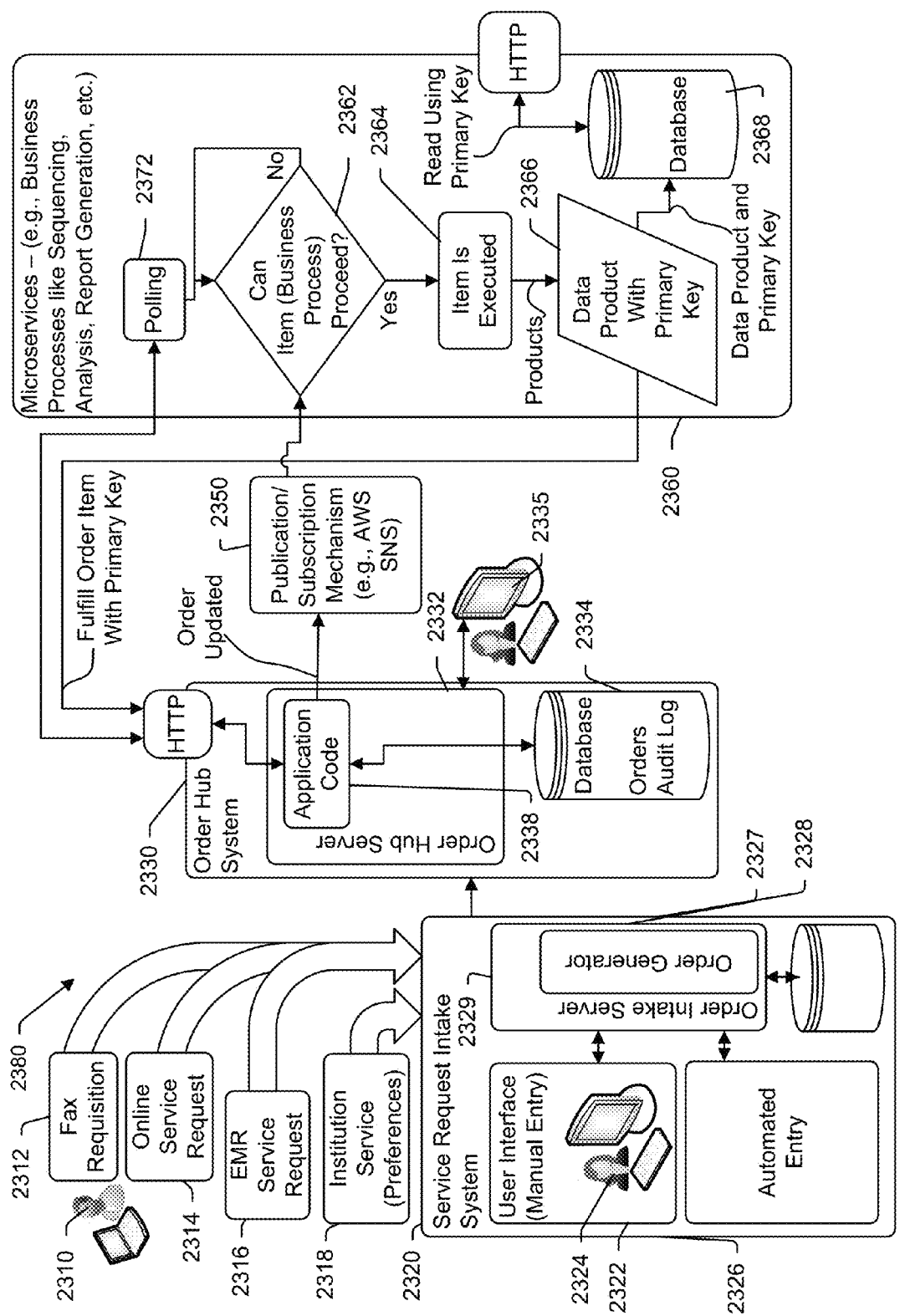
FIG. 59 is a schematic illustrating a genomic order processing system that is consistent with at least some aspects of the present disclosure.
Figure 60:
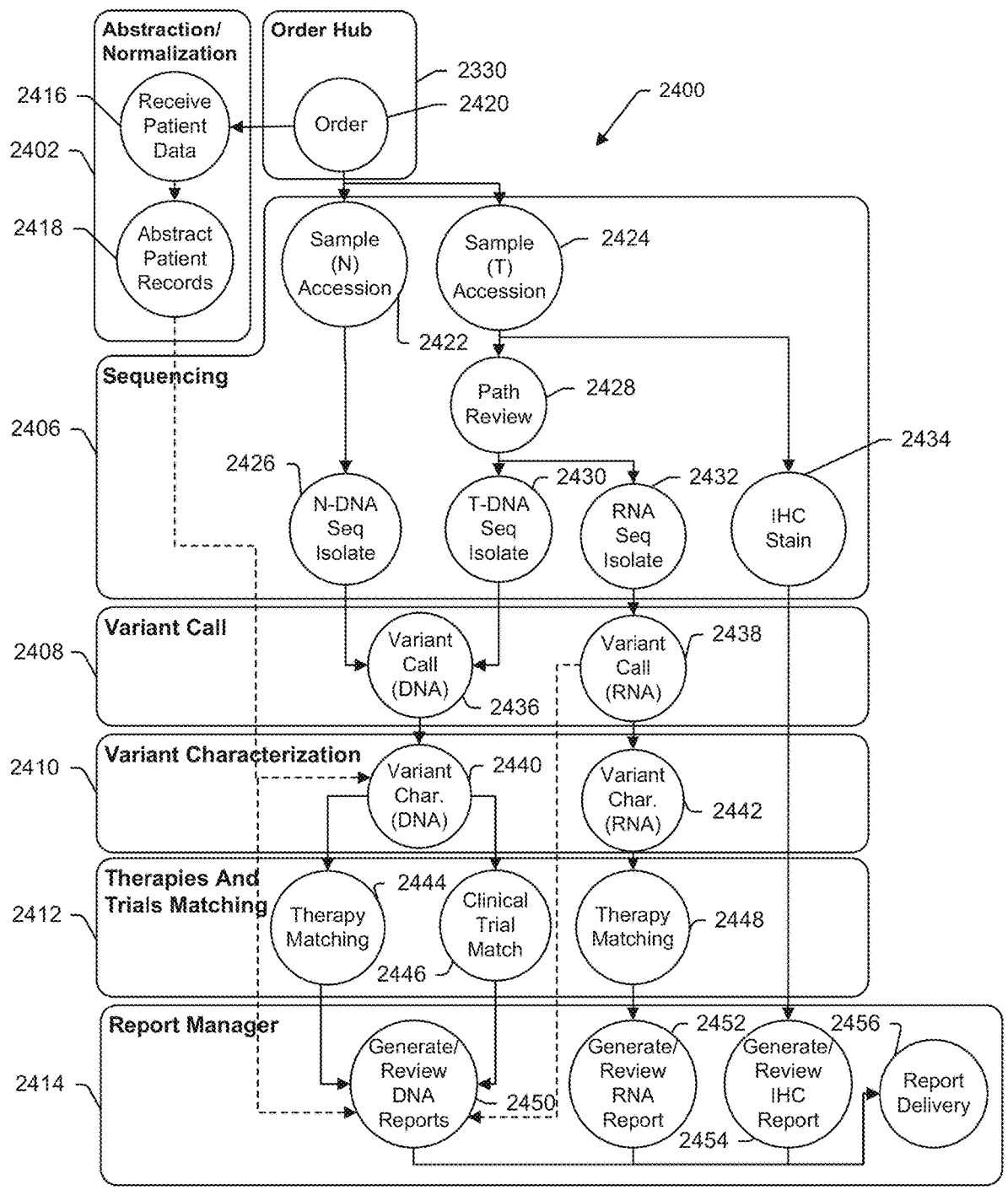
FIG. 60 is a schematic illustrating an exemplary order map and system sub-processes that is consistent with at least some aspects of the present disclosure.

Referring now to FIG. 60, an exemplary and simplified order map 2400 is illustrated that includes items related to an exemplary set of genetic tests and report generation tasks. The ordered map 2400 is related to a specific order 2420 generated by intake system 2320 and stored in order hub database 2334 (FIG. 59) and includes items that are grouped into item subsets that together define order sub-processes geared toward partial completion of the service order. To this end, see that the order items in FIG. 60 are grouped together by sub-processes including an abstraction/normalization sub-process 2402, a sequencing sub-process 2406, a variant calling sub-process 2408, a variant characterization sub-process 2410, a therapies and trials matching sub-process 2412 and a report management sub-process 2414.

The arrows between items in FIG. 60 indicate order flow and item dependencies where any item immediately downstream of any other item can only be initiated once the prior item(s) has been completed (e.g., downstream items are "dependent"). In at least some cases hereafter the relationship between any item and an immediate downstream item will be referred to as a parent-child relationship where immediately adjacent upstream and downstream items are parent and child items, respectively. All child items are "dependent" on their directly linked parent items and child items "depend" on or from their parent items while parent items are "dependencies" of their directly linked child items.

Referring again to FIGS. 59 and 60, order hub 2330 tracks progress and completion of each item in each system order, determines when all dependencies for each item are complete and, when all dependencies for an item are complete, publishes an "item ready" notification on a system network shared with microservices 2360 indicating that the item is ready to be initiated.

Each microservice 2360 includes resources that are capable of completing at least one and in many cases several different types of order items. For example, a sequencing lab may comprise a microservice where the lab is capable of generating many different sequence panels for many different sample types including human normal, human tumor, mouse normal, mouse tumor, fluid, etc. In these cases the lab may be capable of performing one or more items of different types for sample and panel pairs. As another example, a bioinformatics lab that performs variant call items may be capable of performing many different item types depending on sequencing lab tests, institutional preferences, etc.

Each microservice may be fully automated or may include automated and manual resources. For instance, in many cases automated systems generate intra-item data products that a pathology or other system specialist need to consider, confirm and in some cases modify, as part of the item process. In at least some cases on microservice may use other microservices as resources to perform various tasks.

In some embodiments a single service provider provides all microservice resources and handles all order items. In other cases, one service provider may provide order hub 2330 and a subset or none of the microservice resources while other service providers provide other microservices required by the system. Thus, for instance, a first service provider may manage order hub 2330 at a first location while NGS sequencing items may be performed by microservices at a hospital or pathology lab at a second location, bioinformatics processing items may be performed by microservices operated by a bioinformatics service provider and/or automated bioinformatics method(s) operating at a third location, and variant calling and characterization items may be performed by microservices operated by a variant science service provider and/or variant method(s) operating at a fourth location. Other permutations are also possible (e.g. NGS sequencing at one location and everything else at a second location). In each case each location uses the same order hub information to assist in the automatic processing of information in order to complete testing processes. For instance if sequencing and bioinformatics are conducted at different locations, order hub 2330 "listens" on the network for sequencing items to be complete before triggering child bioinformatics items.

Referring still to FIG. 59, microservices 2360 subscribe to the order hub publications and listen on the network for "item ready" notifications and, when an item is ready to be initiated, if a specific microservice is capable of executing the item, initiates the item and sends an "in progress" status notification to order hub 2330. Order hub 2330 retransmits the "in progress" notification to other system microservices so that other microservices similarly capable of executing the item stand down to avoid item duplication. Thus, the exemplary FIG. 60 order map 2400 can be thought of as a set of tasks to perform or, from the perspective of order hub 2330, a map of order items to be tracked.

Referring again to FIG. 60, abstraction and normalization sub-process 2402 includes items for receiving patient data 2416 (e.g., tracking receipt of clinical or medical record data for a patient) and abstracting 2418 and normalizing that data (e.g., tracks completion of extracting details about a patient from clinical documents) to generate data in a normalized or structured, system-useable format. The abstracted data is stored in a system database and is rendered accessible to other downstream system items via the internet or other communication network.

Exemplary sequencing sub-process 2406 includes seven items and commences with tumor and normal sample accession items 2424 and 2422, respectively. Normal sample accession item 2422 tracks receipt of a patient's normal physical specimen from a physician. In some cases the sample may be a tissue sample and in other cases the sample may be a substance refined from a tissue or fluid specimen, the tissue, fluid specimen, or refined substance may be referred to as an "isolate". This process includes receiving and accessioning a sample into the lab and includes categorization (e.g., tumor or normal) and source (human/mouse) of the expected sample as well as collection of case specific sample information (e.g., Institution ID, patient info, case #, sample block #, sample ID, order information (Tumor/Normal, DNA, RNA, Immuno tests, etc.). Tissue sample accession item 2424 tracks receipt of a patient's tumorous physical specimen from a physician.

Path review item 2428 tracks completion of a pathological review of a tumor sample (e.g., tissue or isolate) where the review entails diagnosis of the accessioned tumor sample and is fulfilled with storage of a diagnosis record. More specifically, a hemotoxylin and eosin (H&E) slide deck is collected, slides are verified to ensure that what is reported on the pathology report is what is shown in the slides. A pathology specialist updates diagnosis (e.g., refines from cancer or breast cancer to Invasive ductal carcinoma) and adds tumor cell counts and tumor purity metrics to the data set. The pathology specialist maps the pathology report data and the added information to an internal structured data format for internal records.

The sequencing items tracks sequencing of a specific sample. Each sequencing item causes a lab to load a sequencer with samples scraped from slides which have been RNA/DNA separated and amplified and with controls (controls testing for contamination, biases, etc., for quality control). Controls are tested to conform with required accuracy for identifying a corresponding variant call in the control sample to ensure successful sequencing in each batch.

Regarding the specific sequencing items, the N-DNA Seq Isolate item 2426 tracks that sequencing of a patient's normal physical sample is imminent. Here, an isolate is prepared from a patient's normal sample for a specific panel (e.g., exemplary whole exome NGS panel; exemplary solid tumor NGS panel; exemplary liquid biopsy NGS panel, etc.) and DNA combination and for a specific coverage depth (e.g., high/low) and is placed in a flow cell destined for a service provider's genomic sequencers. This item is fulfilled with microsevice storage of a sequencer isolate record and raw sequencer output files. Similarly, T-DNA Seq Isolate item 2430 tracks that sequencing of a patient's tumorous physical sample is imminent. In this case, an isolate is prepared from a patient's tumorous sample for a specific panel and DNA combination and is placed in a flow cell destined for a service provider's genomic sequencers. RNA Seq Isolate item 2432 tracks that sequencing of an isolate from a patient for a specific panel and RNA combination is imminent and that an isolate is likewise placed in a flow cell for sequencing. IHC stain item 2434 tracks completion of a staining of slides for an IHC report, scanning and uploading the slide and pathological review of the slide.

Referring again to FIG. 60, variant call sub-process 2408 includes two items including a variant call DNA item 2436 and a variant call RNA item 2438. Item 2436 tracks completion of a DNA pipeline that is managed by a bioinformatics team and, as known in the industry, is completed using the sequencer outputs related to the Isolate items 2426 and 2430. This item analyzes the upstream sequence isolate fulfillments and sequencer output files and is fulfilled (e.g., is completed so that a data product is stored and available for use by other order items) by an analysis which describes any mutations in a patient's DNA and the RNA variant call is fulfilled in a similar fashion. Item 2438 tracks completion of an RNA pipeline and is completed using the sequencer output related to isolate items 2432.

Variant characterization sub-process 2410 includes two items including a variant characterization DNA item 2440 and a variant characterization RNA item 2442. Item 2440 tracks completion of a DNA variant characterization analysis which analyzes the upstream variant call fulfillment and is fulfilled with an analysis which describes the pathology of the mutations in a patient's DNA. Item 2442 tracks completion of an RNA variant characterization. RNA variant characterization is completed using the variant calls produced by item 2438. Several characterization processes are associated with items 2440 and 2442. Exemplary characterization processes include S/M(NP) processes to identify single and multiple nucleotide polymorphisms (e.g., variations), an InDels process to detect insertions in and deletions from the genome, a CNV process to detect copy number variations, a fusions process to detect gene fusions, a TMB process to calculate tumor mutational burden, an MSI process to calculate microsatellite instability, and an IHC process. Once variants are characterized, each variant is then classified by the characterization item as benign, likely benign, pathogenic, likely pathogenic or VUS (e.g., variant of unknown significance). Each item 2440 and 2442 stores characterized variants along with the classifications at which point the variant classification process is complete.

Therapies and Trials Matching sub-process 2412 includes three items in the FIG. 60 map including a DNA related therapy matching item 2444, a clinical trial matching item 2446 and an RNA related therapy matching item 2448. The therapy matching items 2444 and 2448 track completion of DNA and RNA based therapy recommendations in which detected variants are matched with therapies that specifically treat those variants. Trials matching item 2446 analyzes upstream variant categorization fulfillment and is itself fulfilled with storage of recommendations of clinical trials that may benefit a patient. Trial matching involves matching detected variants to clinical trials that have inclusion criteria for the specific variants.

Report manager sub-process 2414 includes items that, in general, generate a final report, check quality of the report, facilitates a signout process for the report and delivers the report to an ordering physician. More specifically, the report manager sub-process brings together the results from each order "branch" (e.g., RNA, IHC, DNA, etc.) and causes references from one branch to the other where appropriate to generate data needed to develop a final report. Report manager sub-process 2414 then facilitates data error checking to ensure that all needed report branches exist and have passed quality control. The manager sub-process creates an unpopulated shell report based on order objectives, test types performed, etc.

An artificial intelligence program auto-populates the shell based on rulesets and information curated via machine learning. Sub-process 2414 enables a pathology specialist to confirm or modify AI populated report information and add additional information derived during review. Once done reviewing and supplementing the report, the pathology specialist signs and time stamps the report and then a PDF of the report is generated, structured data from the report is made available in an online portal display, etc. In some cases sequencing reports for variant calls and characterizations are made independently available in both machine and human readable forms. In some cases treatment reports are generated as a clinical trial reports. Sub-process 2414 may also facilitate report deliveries via e-mail, posting of alerts, etc.

In FIG. 60, report manager sub-process 2414 includes four items. A first item 2450 is a generate/review DNA reports item which tracks consumption of upstream variant categorization, match clinical trials, match therapies, path review and sequence isolates fulfillments, generation of a report and sign-off by a pathology specialist and is fulfilled with a final report. Similarly, items 2452 and 2454 track completion and sign-off of an RNA sequencing report and an IHC report as well as generation of PDF reports and uploading of those reports to an attachments service. Once a report PDF has been generated, that PDF must be delivered to an order management team and the report delivery item 2456 tracks status of that delivery. Report delivery item 2456 is fulfilled with a delivery confirmation ID.

Referring still to FIG. 60, the microservice executing each item completes or fulfills the item by generating a database storage location or "address" at which to store item data product(s), storing the data product(s) at the generated address and then transmitting the address as a fulfillment ID to order hub 2330. Here, in at least some cases the address is based on a system wide address format so that other items that have access to information that populates the address can independently resolve the address without requiring information from the order hub. For this reason, "item ready" notifications can be extremely simple and only need to identify limited information useable to distinguish one order item from other items queued at the hub for execution.

Figure 61:
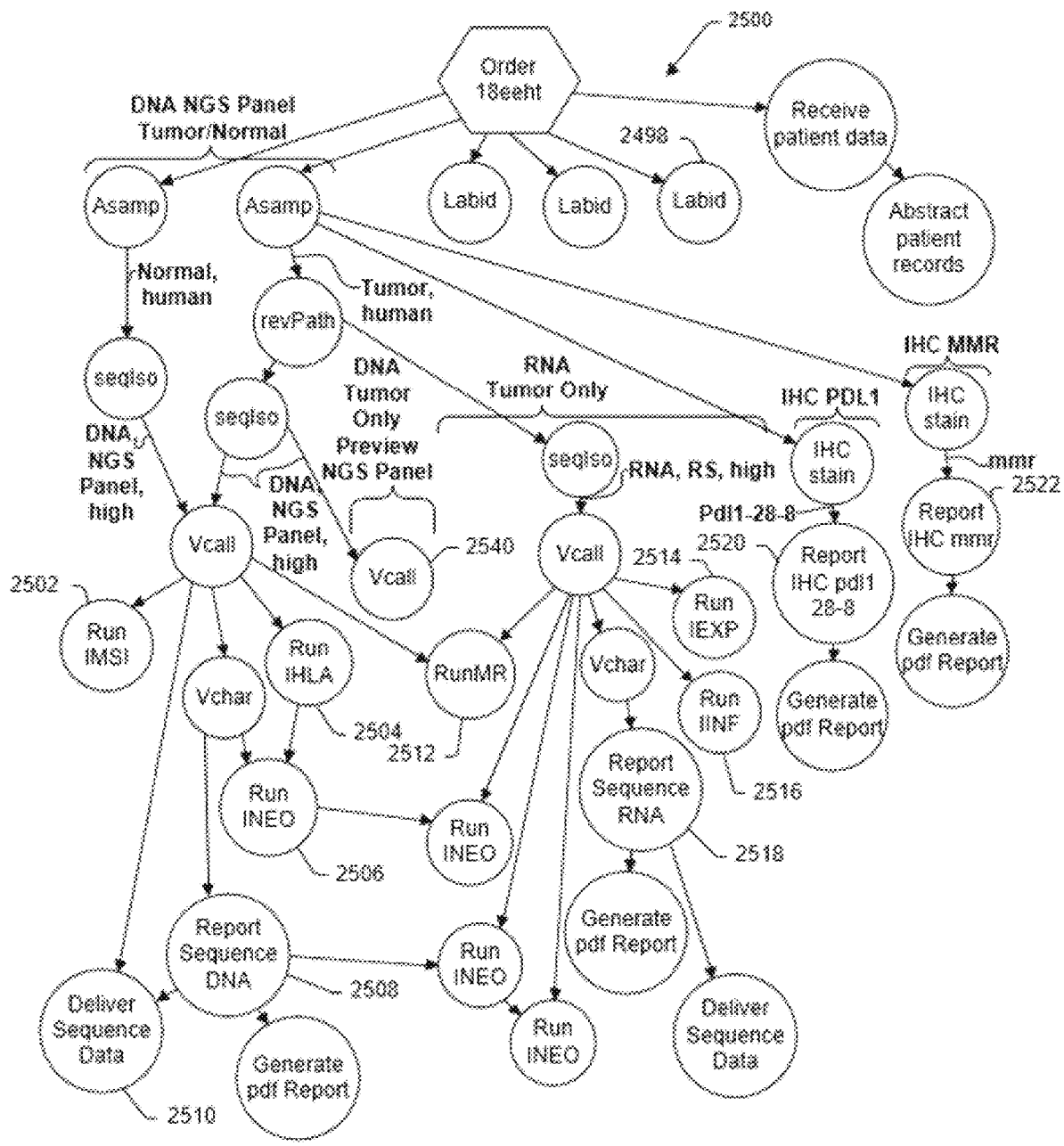
FIG. 61 is similar to FIG. 60, albeit showing a more complex order map that include additional order items.

Referring now to FIG. 61, a more complex service order 2500 is illustrated that again includes a circular representation for each item in the order. In FIG. 61, some of the item labels are identical to the FIG. 60 item labels and refer to the same items. Because the illustrated order 2500 includes many more items than shown in FIG. 60, several abbreviated item labels are used in FIG. 61 so that the entire order map can be shown. To be clear, label "Asamp" in FIG. 61 corresponds to "Sample Accession" in FIG. 60, "seqIso" in FIG. 61 corresponds to "Seq Isolate" in FIG. 60, "revPath" in FIG. 61 corresponds to "Path Review" in FIG. 60, "Vcall" in FIG. 61 corresponds to "Variant Call" in FIG. 60, "Vchar" in FIG. 61 corresponds to "Variant Char" in FIG. 60, and "Generate pdf Report" in FIG. 61 corresponds to "Generate/Review Reports" in FIG. 60.

FIG. 61 includes other common order items including a "lab identification" item 2498 that tracks a lab identification process to identify the lab from which a sample is received as well as any special steps that need to be taken with respect to the identified lab which could affect the order map, a "Run IMSI" item 2502 (e.g., tracks execution of an Immunotherapy MSI analysis module), a "Run IHLA" item 2504 (e.g., tracks execution of an Immunotherapy HLA analysis module), several "Run INEO" item 2506 (e.g., each tracks execution of an Immuno-neoantigen analysis module), a "Report Sequence DNA" item 2508 (tracks completion and sign-out of a DNA sequencing report), several "Deliver Sequence Data" items 2510 (e.g., each tracks delivery of raw sequencing data results to a client), a "Run MR" item 2512 (e.g., tracks execution of an MR analysis module), a Run IEXP item 2514 (e.g., tracks execution of an Immunotherapy Expression Targets analysis module), a "Run IINF" item 2516 (e.g., tracks execution of an Immunotherapy Infiltration), a "Report Sequence RNA" item 2518 (tracks completion and sign-out of an RNA sequencing report), a "Report IHC pdl1 28-8" item 2520 (tracks completion and sign-out of an Immunohistochemistry Report using PDL1 28-8 stain) and a "report IHC mmr" item 2522 (tracks completion and sign-out of an IHC report for mismatch repair detection. While the map in FIG. 61 includes several order item types, many more item types are contemplated, some of which are described hereafter in more detail. In addition, while order 2500 is somewhat complex, far more complex orders including hundreds of items are contemplated.

Referring again to FIG. 59, to simplify the process of converting a service request into a system order including a mapped set of items, item mapping templates have been developed that encapsulate item sequences that commonly appear within order maps. To this end, most service requests specify sequencing tests to be performed where the test set is selected from a small set. The tasks or items associated with each of the tests are typically duplicated each time the test is performed and therefore, templates have been developed for a small set of archetypes of tests. For example, in a particularly advantageous system there are four main archetypes of tests and each can be represented by an archetype specific item sequence. The four archetypal tests include DNA solid tumor sequencing (each of a whole exome NGS panel, a solid tumor NGS panel and another exemplary NGS panel), DNA liquid biopsy sequencing (liquid biopsy NGS panel), RNA sequencing and an IHC test.

Figure 62:
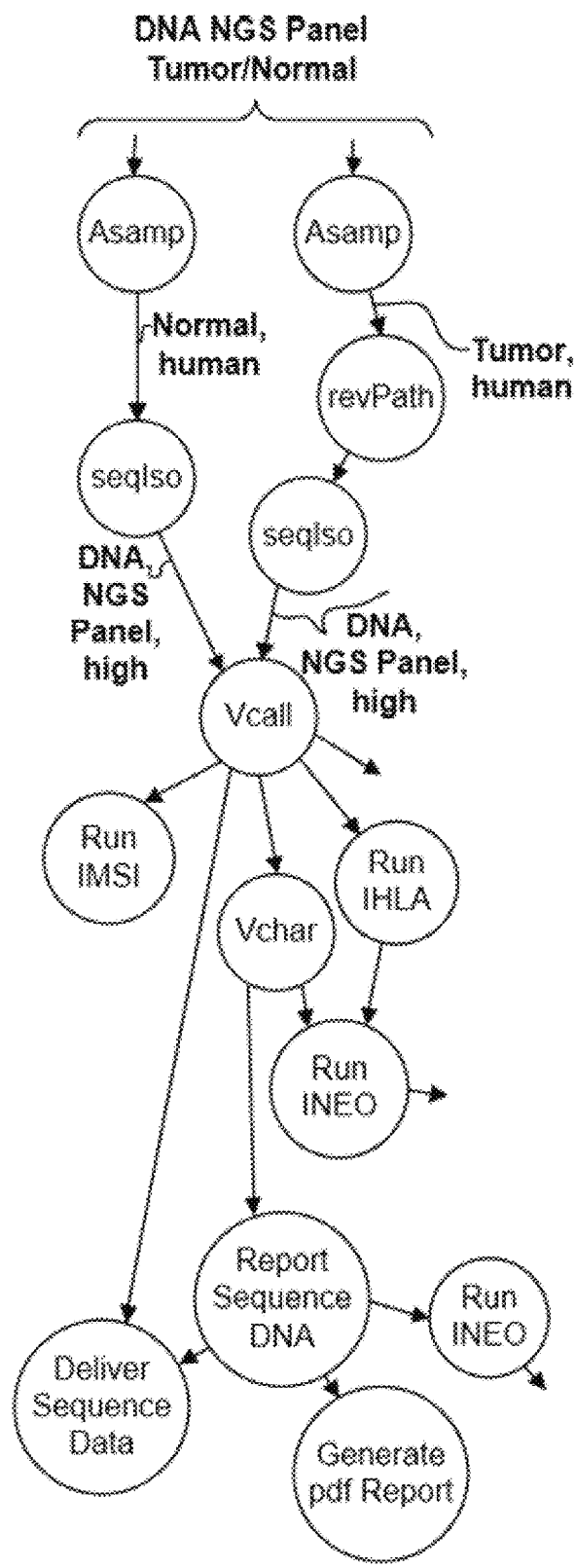
FIG. 62 is a schematic illustrating a DNA NGS tumor/normal template item sequence that is used to instantiate new item based orders that is consistent with at least some aspects of the present disclosure.
Figure 63:
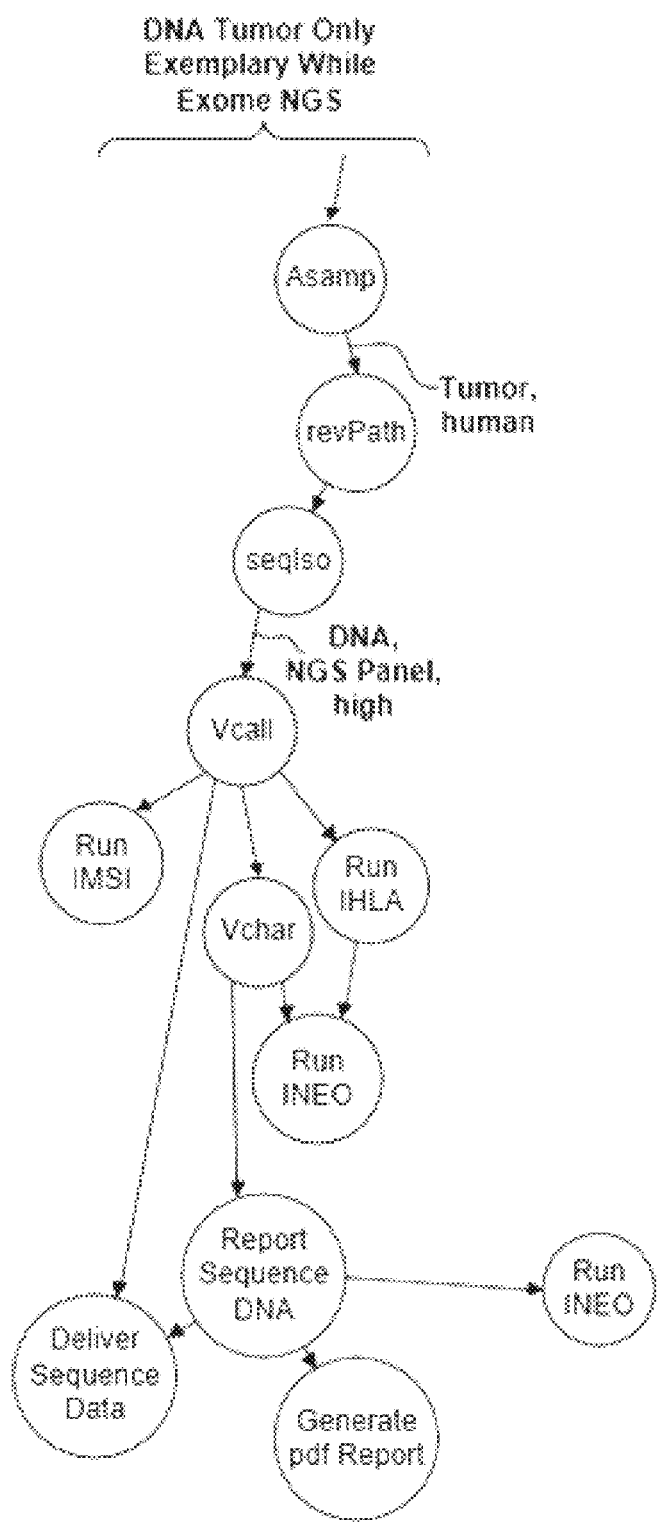
FIG. 63 is similar to FIG. 62, albeit showing a DNA tumor only exemplary whole exome NGS panel template.
Figure 64:
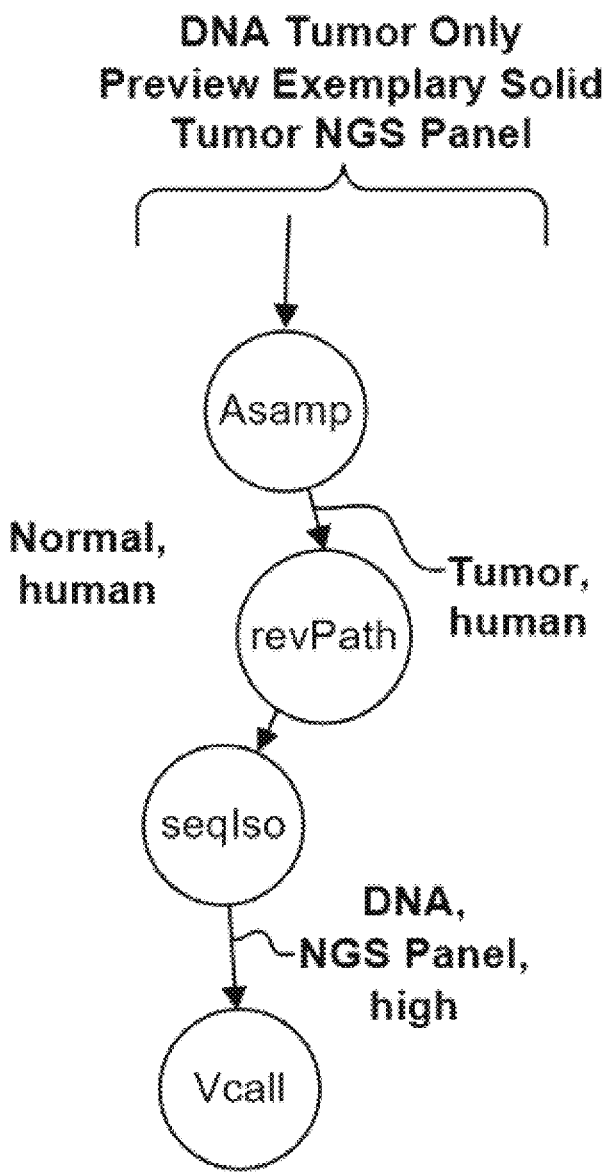
FIG. 64 is similar to FIG. 62, albeit showing a DNA tumor only preview exemplary solid tumor NGS panel template.
Figure 65:
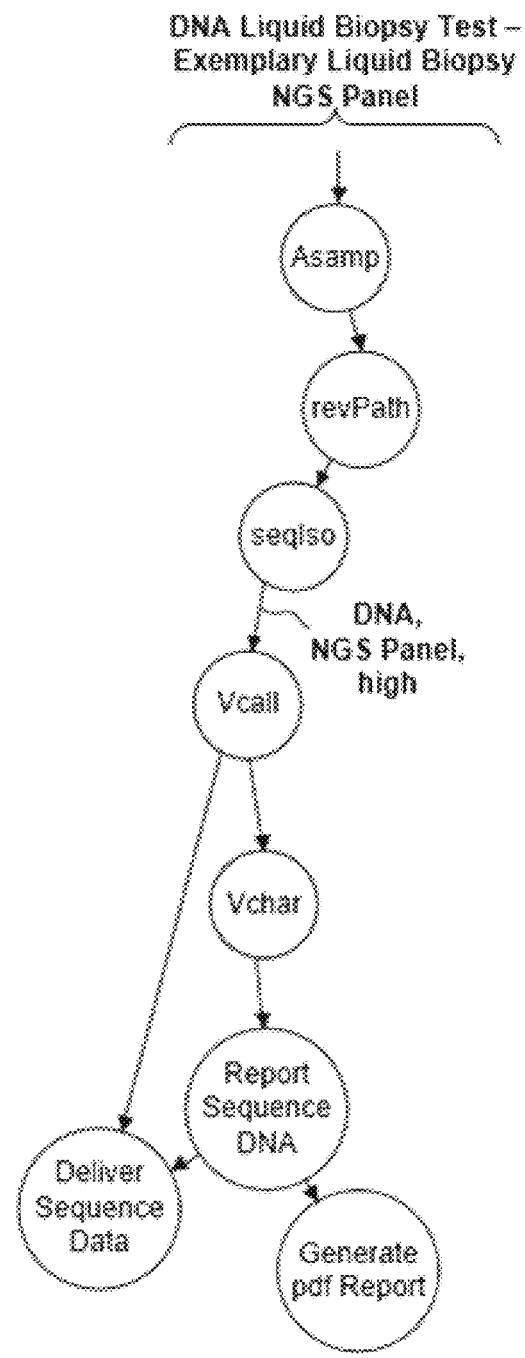
FIG. 65 is similar to FIG. 62, albeit showing a DNA liquid biopsy exemplary liquid biopsy NGS panel template.
Figure 66:
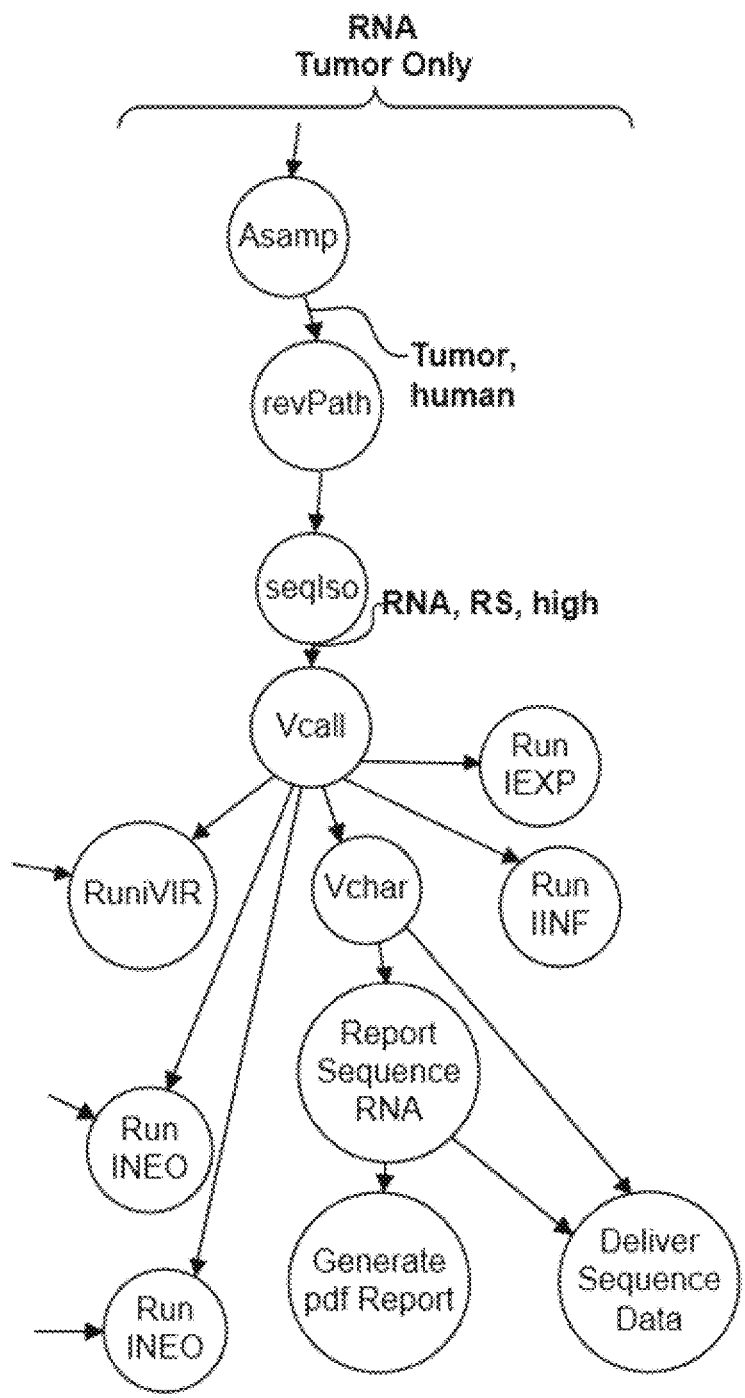
FIG. 66 is similar to FIG. 62, albeit showing an RNA tumor only template.
Figure 67:
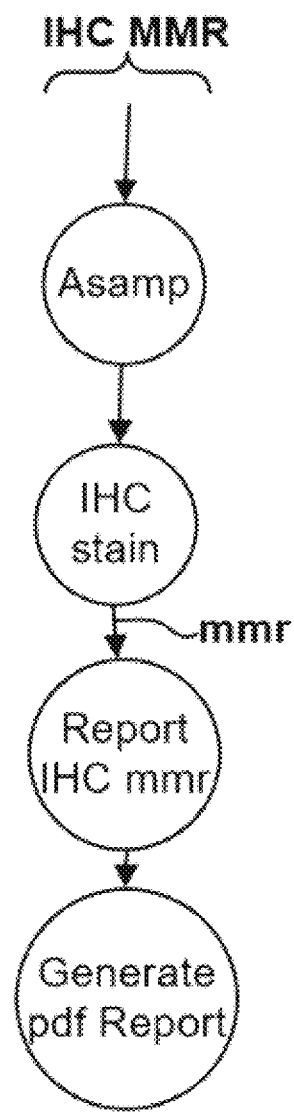
FIG. 67 is similar to FIG. 62, albeit showing an immunohistochemistry (IHC) mismatch repair (MMR) template.

Referring now to FIG. 62, an exemplary item sequence template that corresponds to a DNA NGS tumor/normal match panel is illustrated which includes normal and tumor sample accession items, a pathology review item, two sequence isolate items, a variant call item, a variant characterization item Run IMSI, IHLA and INEO items and a set of reporting items. FIG. 63 shows an exemplary item sequence template that corresponds to a DNA tumor only whole exome NGS panel and FIG. 64 shows an exemplary item sequence template that corresponds to a DNA tumor only preview NGS panel. FIG. 65 shows an exemplary DNA liquid biopsy NGS panel. FIG. 66 shows an RNA test item sequence and FIG. 67 shows an exemplary IHC test item sequence.

Comparing the template item sequence from FIG. 62 to the left portion of FIG. 61 (see portion labelled DNA NGS Panel Tumor/Normal) it should be appreciated that the entire FIG. 62 sequence is included in FIG. 61. The replication of FIG. 62 in FIG. 61 is because the FIG. 62 template was used along with other test templates to generate the multi-test FIG. 61 order map. In fact, each of the FIG. 62, FIG. 64, FIG. 66 and FIG. 67 templates was used by an operating service 2320 request intake system to generate the FIG. 61 order map. Comparing the FIG. 64 template item sequence to map 2500 in FIG. 61 it should be appreciated that only a portion of the template sequence persists in map 2500. To this end see that the only FIG. 64 template item that is reflected in map 2500 is a "Vcall" item 2540 which is labelled "DNA tumor Only Preview NGS panel". Similarly, several of the items in the FIGS. 65 and 66 templates are missing in map 2500. FIGS. 64, 66 and 67 template items are missing in map 2500 because they were duplicative with other items that occur as part of the DNA NGS Panel Tumor/Normal item mapping from the FIG. 62 template. Thus, upon receiving a service request, order intake server 2327 identifies requested tests, accesses an item template for each archetypal test, then identifies duplicative items among test templates and links child items together through a single duplicative parent item whenever possible in order to eliminate duplicative system processes and tasks in the final order map.

Referring again to FIG. 61, another test type referred to as an IHC PDL1 is included in exemplary order map 2500 which is not associated with any one of the exemplary archetypal templates in FIGS. 62 through 66. Here, the IHC PDL1 test item sequence may be defined by institutional preferences or may be specified by an abstractor specialist or other system administrator based on service request requirements.

In at least some embodiments other factors in addition to requested tests and institutional or physician preferences are used by intake system 2322 to generate an order map. For instance, in at least some cases the intake system will discern whether or not clinical data for a patient associated with a received service request exists within the system databases and will add items to an order map required to create a new patient and abstract required data when that data does not exist within the system databases. In addition, information on a requisition form may be used to add items to an order, to delete items from a template item sequence or to modify default template items. Moreover, in at least some cases billing details for an institution or physician may be obtained and used to modify order items.

In many cases institutional preferences indicate if an order is for research or clinical use which influences whether report items like "report sequence DNA", "report sequence RNA", "report IHC-mmr", etc., and related items are added to an order map. Institutional preferences also may specify tests that an ordering physician can add to a service request which limits possible template item sequences that can be added to an order map. Institutional preferences also specify if raw sequencing data should be delivered to an institution which determines if a "deliver sequence data" item will be added to a map for an institution and parameters for that item. Institutional preferences also may specify if RNA and DNA tumor samples will be received separately which influences whether RNA and DNA tests will share the same "accession sample" item or if a separate accession sample item will be created for each test. Other institution preferences may be considered and appropriately handled by the order hub system.

Ordering physician preferences may specify contact preferences and a care team which affects what is reported out to a client, the manner of report (e.g., e-mail, facsimile, other) and to whom reports are sent. Other physician preferences may specify default tests typically ordered for patients (e.g., NGS panel matching+MMR+PDL1). Another preference may indicate if raw sequencing data should be delivered to an ordering physician which determines if a "deliver sequence data" item is added for the physician as well as parameters for that item.

While only four archetypal test templates are described above, it is contemplated that a system may include tens if not hundreds of item sequence templates for different purposes or functions. For instance, another simple exemplary item sequence template may be provided to help manage patient record ingestion and abstraction processes. Here, an exemplary sequence of template items may include "Receive patent data" (e.g., receipt of clinical patient documents/records), "Abstract patient" (e.g., abstract patient timeline) and "Quality review patient" (e.g., patient record is reviewed by a manager, may result in further actions being created for the patient). As another instance, an item sequence template may be provided to collect and optionally backfill (e.g., full or partial re-run of bioinformatics or variant science) data for a specific patient test that is part of a pharma deliverable. Here, an exemplary template item sequence may include "Identify asset and test", "Capture variant call", "Capture variant characterization" and "Collect Pharma Data".

Figure 68:
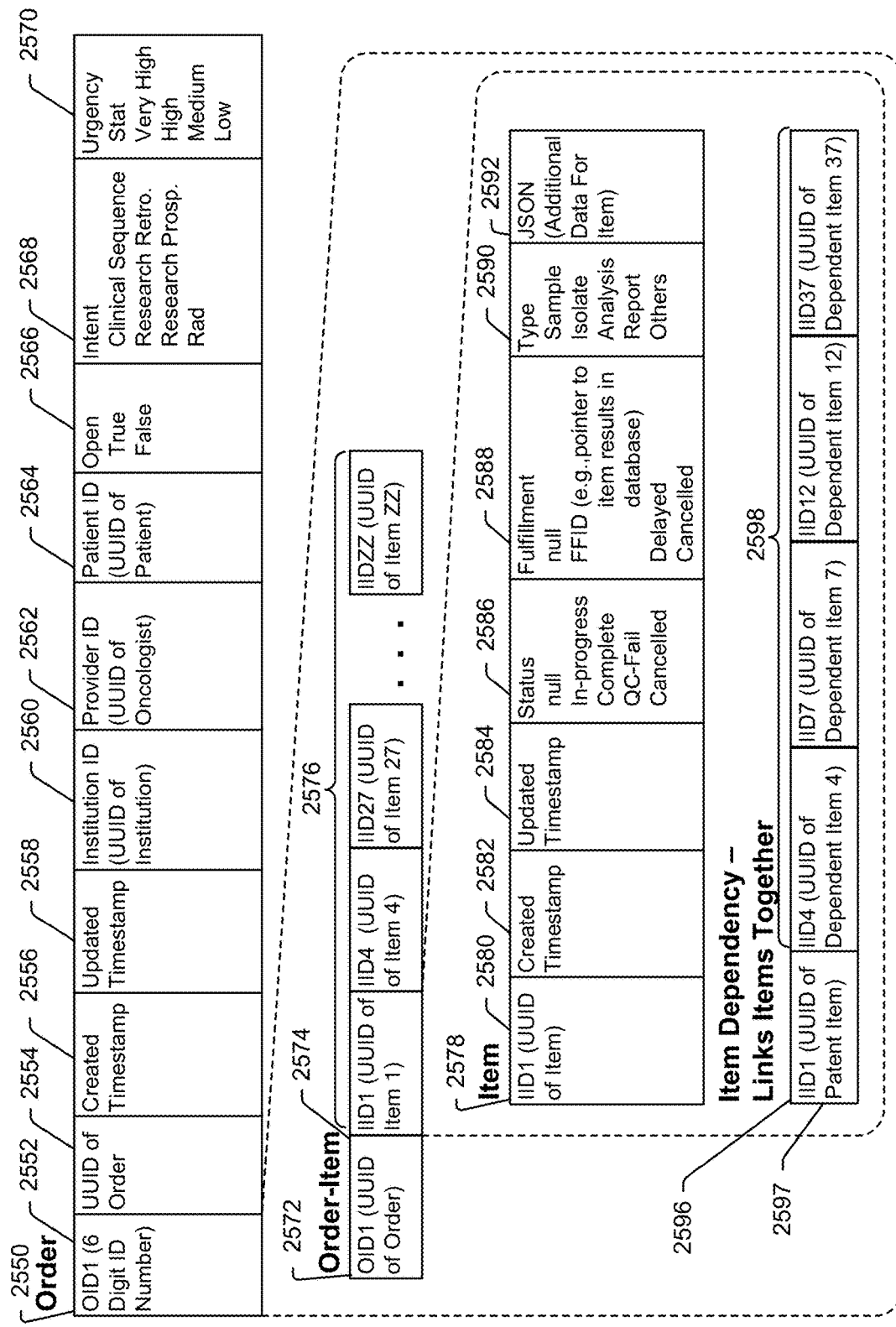
FIG. 68 is a schematic illustrating exemplary order, order-item, item and item dependency format specifications that are consistent with at least some embodiments of the present disclosure.

Referring again to FIG. 59, order hub 2330 stores received orders in database 2334. Referring also to FIG. 68, in the disclosed system an exemplary system order includes a set of related data constructs including an order specification 2550 (hereafter an "order"), an order-item specification 2572 (hereinafter an "order-item list" or simply "item list"), an item specification 2578 (hereafter an "item") and an item dependencies specification 2596 (hereafter a "dependencies list"). Exemplary order 2550 includes a data format including ten information fields 2552 through 2570. Each system order is assigned a human-readable unique identifier which, in the disclosed system, is a 6 character value like "18eeft" (see again the order at the top of FIG. 61) and that unique identifier is placed in the first order field 2550 for uniquely identifying the order. A second field 2552 is populated with an assigned 4 character universal unique identifier (UUID) which is used as an internal system key and which is guaranteed by the system to be immutable.

Referring again to FIG. 68, a third field 2556 includes a "created timestamp" that indicates the time at which an order was initially created and fourth field 2558 includes an "updated timestamp" indicating the most recent update to an order or execution of any item associated with the order. Fifth field 2560 includes an institution ID which is also a 4 character UUID that uniquely identifies the institution with which a requesting physician is associated, sixth field 2562 includes a provider ID which includes a 4 character UUID that uniquely identifies the service provider that manages the order processing system 2380, and seventh field 2584 includes a 4 character patient UUID identifying the patent associated with the order. Eighth field 2566 includes an order "open" status indicating whether or not an order is completed where possible field values include "True" (e.g. that the order is not complete) and "False" (e.g., that the order is not open and therefore has been completed). Ninth field 2568 includes an "intent" field in which a value indicates an intended use of an order. Intent values may be any one of clinical sequence, research retrospective, research prospective and radiation. The intent is not used for order prioritization in at least some system embodiments. Tenth field 2570 is an "urgency" field and is used to indicate a desired order processing speed and is used to prioritize system orders. Exemplary urgency field 2570 values arranged from highest to lowest include stat, very-high, high, medium, low, and very-low. Order hub 2330 uses a triage process to control order and order item sequences among all pending and in progress orders based on the urgency values.

As described above each system order includes an item map (see exemplary map 2500 in FIG. 61) that includes a plurality of items. A separate order-item list 2572 is provided for each order 2550 and includes a list of items to be executed to complete the order. The list 2572 includes a specific order UUID in a first field 2574 and a separate item in each of a second through N fields collectively labelled 2576. Each item in one of the second through N fields is identified by its unit UUID.

Each item is defined by a separate item specification. In FIG. 68 one exemplary item specification is shown at 2578 for the first item in the order-item list 2572. Exemplary item specification 2578 includes seven fields. An item's UUID is placed in the first item specification field 2580 and created and updated timestamps are placed in second and third fields 2582 and 2584, respectively. The fourth field 2586 operates as an item status field where one value selected from a list including null, in-progress, complete, delayed, QC-fail and cancelled is placed in the field to specify a current item status. In-progress, complete, delayed (e.g., that the item is taking longer to complete than expected or is waiting for something to occur to continue execution), and cancelled status values should be understood. A null value indicates that an item has not been initiated (e.g., either item dependencies have not been completed or no microservice has indicates an in-progress status). A QC-fail status is related to quality control and indicates that the system or a system administrator has determined that an item has failed for some reason. In the case of a failed item, the system may automatically attempt to complete the failed item again once or several times or may perform some type of administrator notice process so that an administrator can address the failure.

Referring still to FIG. 68, fifth item specification field 2588 is a "fulfillment" field which indicates if a task has been completed and may have any of null, cancelled, or a fulfillment ID, values. "Null" means an item has yet to be fulfilled and "cancelled" means the item has been cancelled for some reason. A fulfillment ID indicates that the item has been completed. The fulfillment ID includes a database pointer address (e.g., specifies a database location) indicating a location at which data products associated with completion of an item have been stored.

Sixth field 2590 is a "type" field indicating a type of an associated item. The type defines many aspects about an order item, such as additional fields that may be populated within an item specification, types of item fulfillment(s) allowed, and a number and type of items that may be present in the dependencies list (see 2597 in FIG. 68). JSON field 2592 is an additional item data field that is optional in at least some embodiments.

Item dependencies list 2597 defines item dependencies for an associated item (e.g., parent items/tasks within a common order that need to be completed prior to commencement of another item). In list 2597, an item identified in a first list field 2596 is dependent on completion of all of the items in the second through N fields collectively labelled 2598. Thus, in FIG. 68, there is a separate order-item specification 2572 for each order specification 2550, a separate item specification 2578 for each item listed in specification 2572 and also a separate item dependency specification 2597 for each item listed in specification 2572.

Table 1 in Appendix A presents a list of item types and related information. Some of the listed item types are referenced above in the context of the order maps in FIGS. 60 and 61 and others are described in Table 1 for the first time. For each item type the Table 1 information indicates how the item needs to be fulfilled, required dependencies (e.g., a minimum set of other items that need to be completed to execute a specific item type), an exemplary item type data format and additional information required to instantiate an item of the specific type. For example, for the third item type (3) accession sample in Table 1, the item is only completed once a fulfillment ID that points to a database record for a sample is placed within the item fulfillment field 2588 in an associated item specification 2578 (see again FIG. 68), the accession sample item type has no dependencies but requires additional information to define the item including tissue classification, tissue source, slide count and slide stain information. While Table 1 includes many different item types, the list is not intended to be exhaustive and the disclosed system is extendable to support other kinds of work. For instance, other items may track any process that includes multi-team item coordination.

It should be appreciated that in the disclosed system, a system order contains only data that is necessary to indicate precisely what items need to be completed to complete the order, the status of those items, and a way to reference ultimate item data products. Completion status and an output reference for each item are encapsulated in a fulfilment ID placed in an item fulfillment field 2588. Thus, an order and associated order items do not include details about item data products which intentionally limits the scope of knowledge that order hub 2330 has about outside systems. The only knowledge contained in order hub about item data product is the fulfillment ID that points to the data product in a database.

Referring again to FIG. 59, and now more specifically to the microservices 60, each microservice that has subscribed to publication mechanism 2350 "listens" for notifications indicating that an item that can be executed by the specific microservice is ready to be executed. Here, again, an item is ready to be executed when all other items from which the specific item depends have been completed. At decision block 2362 a microservice determines if a received notification indicates a ready item that the microservice can execute. Where no notification indicates a ready item that the microservice can execute, control simply continually loops through block 2362. If a notification indicates a ready item that at least one microservice can execute, at some point a microservice that can execute the item initiates execution 2364 of that item. Upon initiating execution of an item, the executing microservice transmits an "in progress" notice back to order hub 2330 which then notifies the other system microservice that the ready item is in progress by another microservice to avoid a case where one item is inadvertently duplicated by other microservices. Once an item is completed, a data product and primary key (e.g., database address) for that data product 2366 are stored in database 2368 for subsequent access by other order items via an HTTP link or the like. In addition, once an item is completed, the microservice transmits the item primary key (e.g., a fulfillment ID in the form of the database address of the associated data product) is transmitted to order hub 2330 where it is used to populate the item fulfillment field 2328 shown in FIG. 68. Here, the primary key may be transmitted via email, a messenger service, SMS, MMS, broadcast to a but/network, etc. In at least some cases a microservice is also able to poll 2372 order hub data to check item statuses and access other information needed for various purposes.

Figure 69:
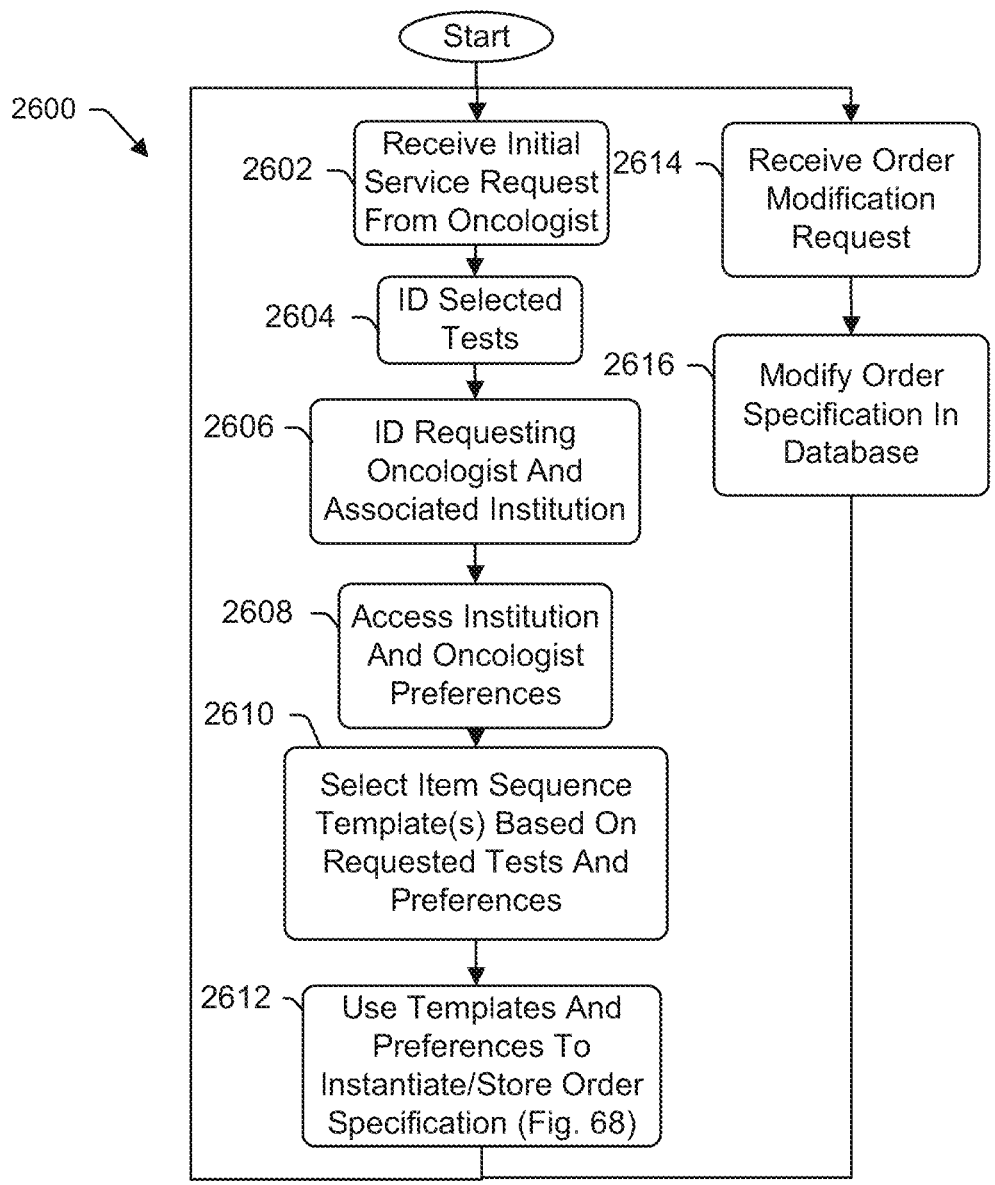
FIG. 69 includes a flowchart that shows an order instantiation process performed by the intake system shown in FIG. 59.

Referring now to FIG. 69 an exemplary process 2600 performed by service request intake system 2320 (see also again FIG. 59) that is consistent with at least some aspects of the present disclosure for generating a service order is illustrated. At block 2602 a physician 2310 sends and intake system 2320 receives a service request. At block 2604 intake server 2329 identifies requested tests. At block 2606 server 2329 identifies the requesting physician and associated institution and at block 2608 server 2329 accesses institutional and physician preferences. At process block 2610 server 2329 selects one or more item sequence templates from database 2328 based on the requested test, institutional preferences and physician preferences. Here, templates may also in part be based on other information in a requisition form that more specifically define request limitations. At block 2612 the templates, preferences and other requisition limitations are used to instantiate and then store an order specification (see again FIG. 68) in order hub database 2334 after which control passes back to block 2602 where intake system waits to receive another service request.

Referring still to FIG. 69, in at least some embodiments, intake system 2320 performs a parallel process including blocks 2614 and 2616 to receive and consume order changes requested by a physician or a system administrator (e.g., an abstractor specialist). To this end, at block 2614 a modification to an existing order is received by the intake system 2320. Here, the modification may include cancelling one or more order items, modifying an existing item, adding one or more order items, eliminating an order test or tests, adding a new order test or tests, etc.

At block 2616, intake system 2320 changes an existing order based on a service request modification. Here, if an order has not commenced prior to reception of a service request modification, the intake system may simple generate a completely new order specification (see FIG. 68) by working through process steps 2602 to 2612 and then swap the new order specification for the original order specification.

In a case where an original order has been initiated and at least some order items have been completed, intake system 2320 may be programmed to assess if any of the completed items and associated data products can be used to fulfill similar items in a modified order. For instance, in at least some cases when a service request modification is received, the intake server may be programmed to execute many of the process steps including blocks 2602 through 2612 in FIG. 69 anew to generate a completely modified order specification and associated order map. The intake server may then compare the modified order specification with the original order specification to identify identical or common order items and different order items. For order items that appear in the original order specification but not in the modified order specification, the intake server may simply change statuses of those items to "cancelled". In some cases where one of these cancelled items was previously completed, any fulfillment ID in an item fulfillment field may remain to memorialize that the item was completed and so that the data product associated with that item can be subsequently accessed by other order items.

For order items that appear in the original order specification and are also replicated in the modified order specification, the intake server 2329 would leave those item specifications unchanged. Thus, for instance, for an item common between the original and modified order specifications that has already been completed by a microservice, that item would remain fulfilled with a fulfillment ID in the modified order specification. Once an order specification is modified, hub server 2332 again commences item management to pick up where execution of the old order left off and to fulfill each of the modified order items.

In other cases when an order amendment is received, intake server 2329 may access an original order map (see FIG. 61) and simply amend that map by adding complete item sequences or separate items to the map or by deleting existing item sequences or separate items from the map. In some cases order map amendments may have to be scrutinized by a system administrator prior to reinitiating execution while in other cases execution may be initiated immediately after an amended order map is stored in the order database.

In still other cases a system administrator using an intake system user interface 2322 (e.g., a web based computer interface) may be able to access any system order stored in database 2334 and modify that order by adding or deleting order items, selecting or cancelling different order tests or other processes, analysis or procedures, changing task parameters, etc. In these cases order changes would be handled in a fashion similar to that described above where a physician makes a service request modification.

Figure 70:
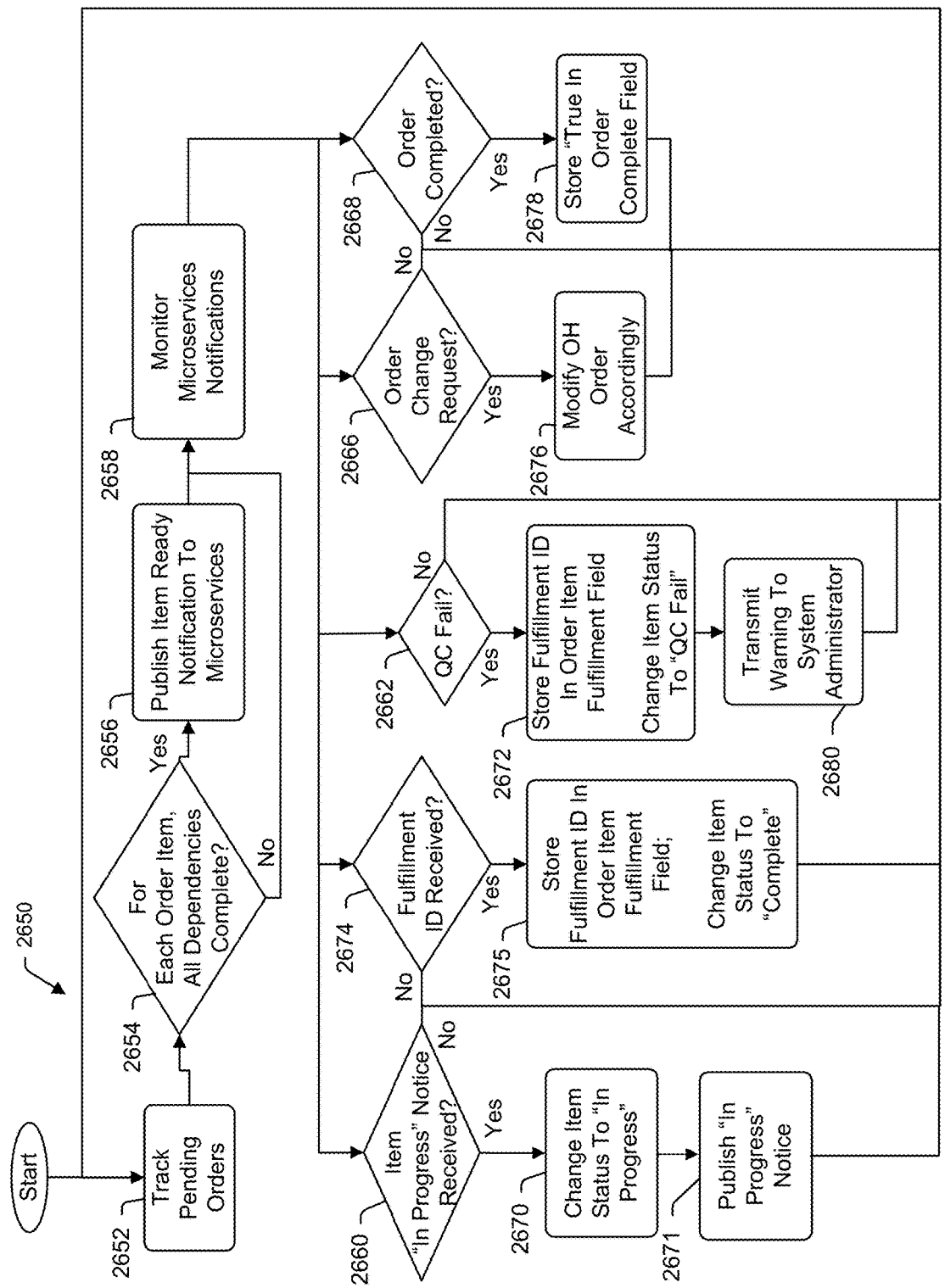
FIG. 70 is a flowchart illustrating an order management process that is performed by the order hub server shown in FIG. 59.
Figure 71:
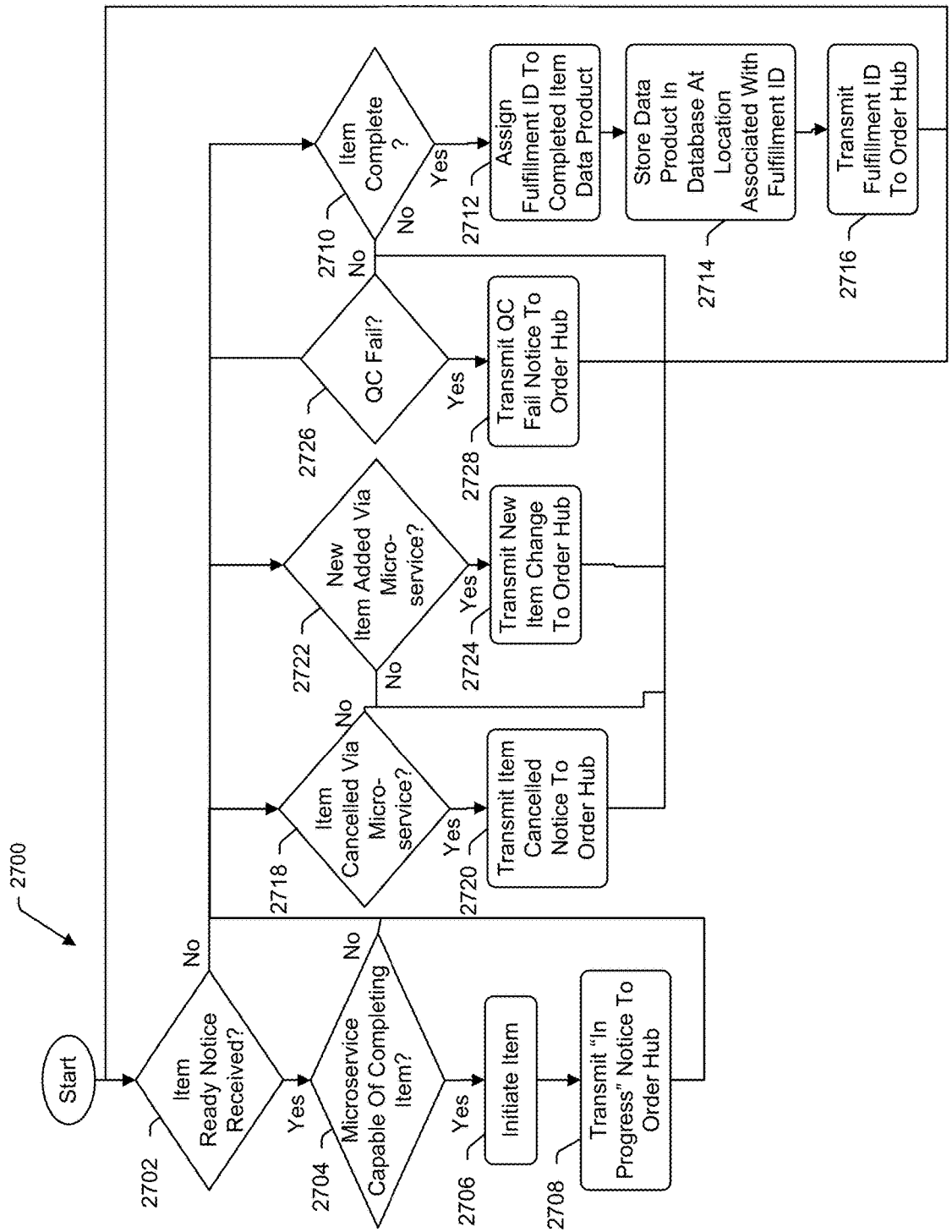
FIG. 71 is a flowchart illustrating an item processing process that is performed by one of the microservices that is shown in FIG. 59.

Referring now to FIG. 70, an order hub process 2650 for tracking and managing order items performed by microservices is illustrated. FIG. 71 shows a microservice process 2700 that operates in parallel at each system microservice 2360. FIGS. 70 and 71 will be described together. In FIG. 70, at block 2652 the order hub server 2332 tracks all pending system service orders and more specifically, all items in all service orders, to assess the status of each item in each order. At block 2654, for each item in each order, server 2332 determines if all items from which an item depends have been fulfilled (e.g., are complete). If all items from which a specific item depends are complete, control passes to process block 2656 where server 2332 publishes an "item ready" notification on the network including system microservices 2360 after which control passes to block 2658 where server 2332 monitors for microservice notifications (e.g., notices of item status changes). Referring again to decision block 2654, if all items from which a specific item depends are not complete, control passes from block 2654 to block 2658.

Referring now to FIG. 71 which shows a microservice process 2700, at decision block 2702 a microservice determines if an "item ready" notification has been received from order hub 2330. If an item ready notification has not been received, control passes to other decision blocks as illustrated that are described hereafter. If an "item ready" notification is received, at decision block 2704 the microservice determines if the microservice is capable of completing the ready item. If the microservice cannot complete the ready item the microservice simply ignores the "item ready" notification and control passes on to other decision blocks as illustrated. If the microservice can complete the ready item, control passes to block 2706 where the microservice initiates the item. At block 2708 the microservice transmits an "in progress" notice to order hub 2330.

Referring again to FIG. 70, one notification type that may be received at block 2658 is an "in progress" notice from a microservice that recently initiated an item. At decision block 2660, when an "in progress" notice is received, order hub server 2332 control moves to block 2670 where the server 2332 changes the item status in field 2586 (FIG. 68) to "in-progress". At block 2671 sever 2332 publishes an "in progress" notification to the microservices indicating that one microservice has started the in progress item and therefore that no other microservice should start a duplicative item. After block 2671 control loops back up to block 2652 where the process described above continues to cycle.

Referring again to FIG. 71, at block 2710 the microservice determines if an in process item executed by the microservice has been completed and if so, control passes to block 2712. At block 2712, the microservice assigns a fulfillment ID to a completed item data product which indicates a system database location/address at which the data product is stored at block 2714. At block 2716 the fulfillment ID is transmitted to order hub 2330.

Referring back to FIG. 70, at decision block 2674, order hub server 2332 determines if a fulfillment ID has been received from any of the microservices indicating that an item has been completed. Where a fulfillment ID has been received control passes to block 2675 where server 2332 stores the fulfillment ID in the fulfillment field 2588 (see again FIG. 68) and changes the item status in field 2586 to complete. After block 2671 control loops back up to block 2652 where the process described above persists.

In at least some cases some aspect of an item will fail during execution so that an item fails to generate expected data products or so that data products associated therewith are not reliable. In some cases, a pathology specialist or other service provider specialist that performs at least some steps associated with an item may recognize item failure and simply indicate failure via a computer or other type of user input device associated with a microservice. In other cases a system server may be programmed to automatically recognize item failure and flag that failure within the system. For instance, where a data product generated by an item is outside a possible value range, a system processor may recognize the errant value and automatically indicate a QC fail.

In some cases when an item failure occurs, the item and associated order may simply be delayed in a queue until a system administrator can access the item and associated order and address the failure in some fashion such as, for instance, initiating duplicated item. In other cases when an item failure occurs, a microservice may be programmed to automatically initiate a new item of the same type in a second attempt to successfully complete the item. In some cases if item failure persists after a second attempt, a third attempt may occur and so on until a threshold maximum number of attempts result in failure at which point an administrator could be notified.

Where an item fails, a microservice may transmit a "QC fail" notice to order hub 2330 so that the hub can memorialize the failure. Similarly, when a duplicative item is initiated, the microservice may transmit a change request to order hub 2330 so that hub 2330 can memorialize the change. In at least some cases order changes are memorialized within an order. For instance, in the case of an added item, referring again to FIG. 68, the new item may be added to the order-item specification 2572 and an item specification akin to specification 2578 and an item dependency list akin to 2596 may be generated for the new item. As another instance, where an item fails (e.g., a QC fail notice is generated), order hub 2330 may place a QC fail status value in the item status field 2586 (see FIG. 68) and, where the item generated a data product, may store the data product in a system database and store a fulfilled ID in the item field 2588 to memorialize the data result.

In at least some cases a microservice (e.g., automatically or a person affiliated with a microservice) will cancel an order item for some reason. Where an item is cancelled, the microservice may transmit a "cancelled" notice to hub 2330 and the hub may memorialize the cancellation. Referring again to FIG. 68, a cancellation is memorialized by changing the status of an item to "cancelled" in field 2586 and also by placing a "cancelled" designation in the fulfillment field 2588.

Referring again to FIG. 71, an exemplary microservice monitors in progress items at the microservice for any QC fail conditions at block 2726 and if a fail condition occurs, control passes to block 2728 where the microservice transmits a QC fail notice to order hub 2330. Similarly the microservice monitors in progress items at the microservice for any newly added item at block 2722 and transmits a new item notice to order hub 2330 whenever a new item occurs at block 2724 and monitors in progress items at the microservice for any cancelled item at block 2718 and transmits a cancelled item notice to hub 2330 at 2720 whenever any item is cancelled. After blocks 2720, 2724 and 2728 control passes back up to block 2702 where the process described above continues to cycle.

Exemplary errors for some of the main order sub-processes shown in FIG. 60 are instructive. To this end, an exemplary sequencing error may involve running a wrong assay through a sequencer, using a wrong sample, a tumor without normal or a normal without tumor situation, etc. In variant calling a common error may be that a data dependency does not exist even if a system generating the dependency indicates that an item has been fulfilled. Similarly, a common variant characterization error may be that a data dependency does not exist even if a system generating the dependency indicates that an item has been fulfilled. A quality control error may occur when a variant calling process detects an error that a sample sequence that was expected in not available. Here, a microservice or provider specialist may request an item to rerun for that sample sequencing and in this case, the system would revise the order map to add additional items into the map to track the modified order items.

In cases where the system or a provider specialist identify errors in a report, those errors may trigger a QC error message to order hub 2330 again causing items to be added to a flow for correcting the errors.

In some cases a template error may occur such as, for instance, where tumor and normal branches of an order should have been created but an error caused only the tumor branch to be instantiated in the order map. Here, a normal item sequence would have to be added to the order map. In some cases an order branch has to be completely cancelled from an order map.

Referring again to FIG. 70, QC fails notifications are tracked at block 2666 and when one is received hub 2330 memorializes the item failure in the item specification (see again item specification 2578 in FIG. 68) by storing any fulfillment ID in field 2588 for any data product that was generated by the microservice as well as by placing a QC fail indicator in field 2586 as indicate data block 377. In addition, in at least some cases a warning signal may be transmitted to an administrator as indicated at block 2680 indicating the item that failed.

At block 2666 hub server 2332 monitors for any order changes (e.g., cancelled items, newly added items, modified items, etc.) and, when an order change is received from one of the microservices, server 2332 uses the change information in the notice to modify the order at block 2676 by either changing item status to "cancelled", by adding new items to an order specification, or by amending item characteristics if appropriate.

Referring yet again to FIG. 70, at decision block 2668, hub server 2332 determines if all items associated with an order have been completed and if so, stores a "True" value in the order specification open field 2566 (see FIG. 68 again).

Figure 72:
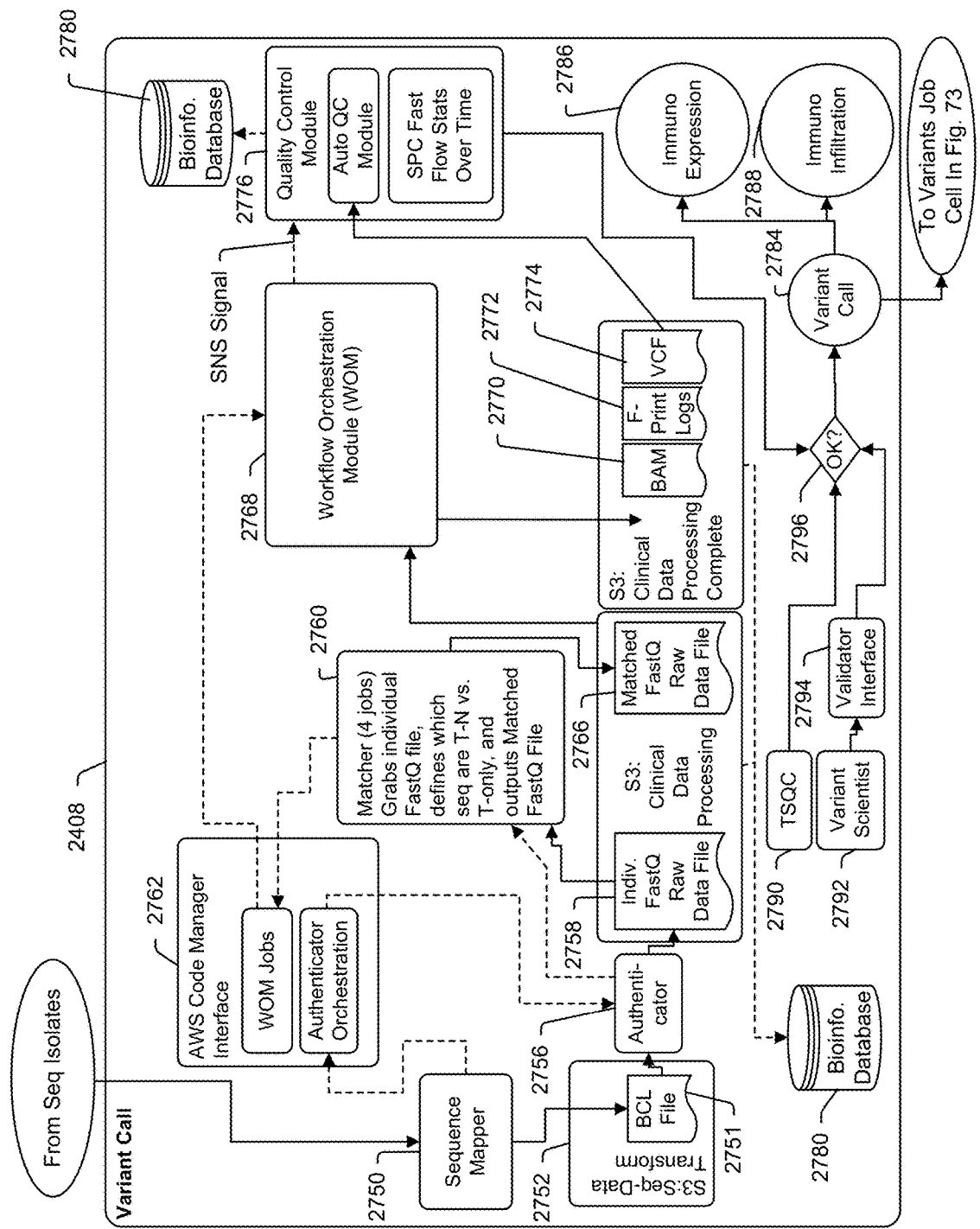
FIG. 72 is a schematic that illustrates the FIG. 60 variant calling process in more detail.

Referring once again to FIG. 60, order map 2400 is presented in an extremely simple format in the interest of simplifying this explanation and each of the order sub-processes is fairly complex requiring activities and tasks by many different microservices and provider specialists. For example, the variant call sub-process 2406 takes advantage of many different microservices to complete items 2440 and 2442 shown in FIG. 60. Referring now to FIG. 72, an exemplary more complex variant call and characterization sub-process is illustrated.

Referring to FIG. 60, after sequence data has been stored as data products by each of items 2426, 2430 and 2432 and fulfillment IDs have been added to item specifications for each of those items, order hub 2330 initiates the variant call sub-process 2408. Referring also to FIG. 72, initially a sequencing mapper 2750 accesses the sequencing data for a multiple sample (e.g., 55 samples, 45 samples with an additional 10 control samples for QC validation) workflow (hereinafter a "flowcell") and mapper 2750 maps subsets of the sequence data to specific samples to generate sample based raw sequencing data as a base call (BCL) file 2751 that is stored in the AWS S3 cloud storage system (hereafter S3). An AWS code manager interface module 2762 is a system that allows code to be deployed to AWS repositories for execution. The code manager 2762 essentially validates system code is in good condition to run, deploys to AWS, monitors deployment until complete, and provides status info at each stage of deployment. More specific code manager tasks include setting up data dependencies for an authenticator, downloading data from AWS, authenticating sample sheets for each sequence result, indicates which sample is processed from which lane of the sequencer, identifies which files/indices are assigned to different samples, etc.

An authenticator module 2756 converts the BCL file to a FASTQ file which is stored in S3. Module 2756 also compares the raw sequencing data to sample sheets to determine, for each sample dataset, if the set is related to tumor-only or tumor-normal matched testing. Where a dataset is related to matched testing, module 2756 calls on a Matcher module 2760 to match the sequencing results from a tumor sample to the sequencing results from a normal sample of the same patient and stores a matched FASTQ file in S3 or similar cloud or internal data storage.

Referring again to FIG. 72, once sequencing data is in the FASTQ format and tumor-normal matching is complete, a workflow orchestration software module 2768 initiates and manages a set of bioinformatics workflows which are executed for each genetic sequencing panel. (Exemplary liquid biopsy NGS panel, exemplary whole exome NGS panel, exemplary solid tumor NGS panel, xG, etc.) In one embodiment the workflows occur in parallel and facilitate DNA Variant detection, DNA Fusion detection, and Meta-genomics detection. Other characteristic detections are contemplated and will be added to the system as further developments occur. In general module 2768 performs alignment, normalization, sorting and variant calling functions. Module 2768 aligns DNA/RNA strands to begin identifying where they appear in the genome and then normalizes the data by removing duplicates corresponding to over amplified regions. Module 2768 separates human from viral/bacterial/non-human data to ensure that only human DNA/RNA is processed. Next module 2768 pairs sequenced strands with a human reference genome and compares strands to identify variants in the tumor sample.

An exemplary bioinformatics workflow may include the following. First, module 2768 accesses the FASTQ file and runs an aligner software program (e.g., a Burrows-Wheeler Aligner (BWA)) to align a patient's sequence data and stores the results in a BAM file 2770 in S3. Next, module 2768 uses various software programs to call variants including, for instance, Freebayes and Pindel and in the case of exemplary liquid biopsy NGS panel, Vardict. Module 2768 stores a Variant Call Format (VCF) file 2774 in S3 with corresponding variant-allele-fraction (VAF) and coverage/equality metrics that are distinct from VAF. Module 2768 filters out artifact noise and then uses CONA library & SNP-eff to identify copy number variants (CNVs), single nucleotide polymorphisms (SNPs), insertions and deletions (InDels) and Fusions. Module 2768 next generates fingerprint logs 2768 memorializing DNA and RNA match as well as if tumor-normal and tumor-only match. Finally, module 2768 formulates and transmits an SNS signal to indicate that variant calling is complete.

Referring still to FIG. 72, once module 2768 generates and stores variant calls, a quality control module 2776 initiates quality control processes to identify any irregularities in the VCF data results. Some quality control processes are automated. For instance, one simple automated process may check if matched tumor and normal data are both associated with the same gender. Another automated process may check if a variant was identified in all samples in a common workflow (e.g., all 55 samples in a flow) which would be highly irregular. At another instance, module 2776 may track flowcell statistics over time to identify any irregularities or drift in results. Where quality is suspect, module 2776 memorializes QC data in a bioinformatics database 2780 and may initiate some corrective or notification process. As yet another instance, module 2776 may check operational statistics including runtime, auto notification of delays, auto verification that data dependencies are satisfied when an "item complete" message is received, etc.

Referring still to FIG. 72, other quality control functions are contemplated like a trade standards QC module 2790 that compares call results to standards within the industry and a manual process performed by a variant scientist 2792 using a validator interface 2794. Once at least a minimum set of quality controls are met (see decision block 2796), the variant call process is complete as indicated by variant call item 2784. Immuno expression and Immuno Infiltration items 2786 and 2788 are performed based on the variant call data products. At this point the variant call data is stored in a system database and the call sub-process is completed when a fulfillment ID is placed in the variant call item fulfillment field (see again FIG. 68). Once the variant call item is complete, order hub 2330 publishes a notification indicating that the variant characterization sub-process 2410 (see again FIG. 60) can be initiated.

In at least some embodiments order hub 2330 maintains an audit log in database 2334 that includes an order history. In general, each time any event occurs that is related to a system order, an event description referred to hereinafter as an "audit record" is stored within the audit log along with a timestamp indicating when the event occurred. The audit log is useful to analyze time series of changes that occur to an order. Several useful metrics can be extracted from the log data such as rates of exceptions within various systems, time to completion of each item and execution time distribution of order items. Order events that are tracked by the audit log include events that change the items tracked by order hub 2330 such as (i) order creation and (i) order modification like adding an item to the order, cancelling an item from an order, adding an item sequence to support an additional test to an order, etc. In addition, events tracked by the log also include order and item status events such as item "in progress", item "QC fail", item "complete", item "cancelled", item "pause" and item "stop". Other order and item related events may be memorialized in the log as well. In at least some cases the log will also include modifications to existing items within an order map (e.g., changing a physician's preferences related to a specific item).

Referring now to FIG. 73, an exemplary audit record specification or data format 2850 is illustrated that includes seven format fields including an audit ID field 2852, an order ID field 2854, an item ID field 2856, a created timestamp 2858, an event type field 2860, a JSON field 2862 and a comments field 2864. A separate 4 character UUID that uniquely corresponds with a specific audit record is placed in field 2852. Unique order and item UUIDs corresponding to an order and item that are affected by an event that is memorialized by an audit record are placed in fields 2854 and 2856, respectively. A time stamp corresponding to an event is placed in field 2858. An event type is placed in field 2860 and, as described above, may have any of several different values related to order item changes or item statuses.

A JSON in field 2862 includes a representation of a new order after the event in field 2860 has occurred. Here, the JSON reflects order item changes like new items added to an initial order and items deleted from an order that persist at the time indicated by the timestamp in field 2858. In addition, in some cases the JSON may include information indicating the immediate status of each order item at the timestamped time including information indicating that an item is in progress, has been cancelled, has failed or is in a paused state. In other cases the JSON will not include all item status information and instead the system will access that information in other audit records corresponding to other order items when needed. Optional comments may be placed in field 2862.

Figure 74:
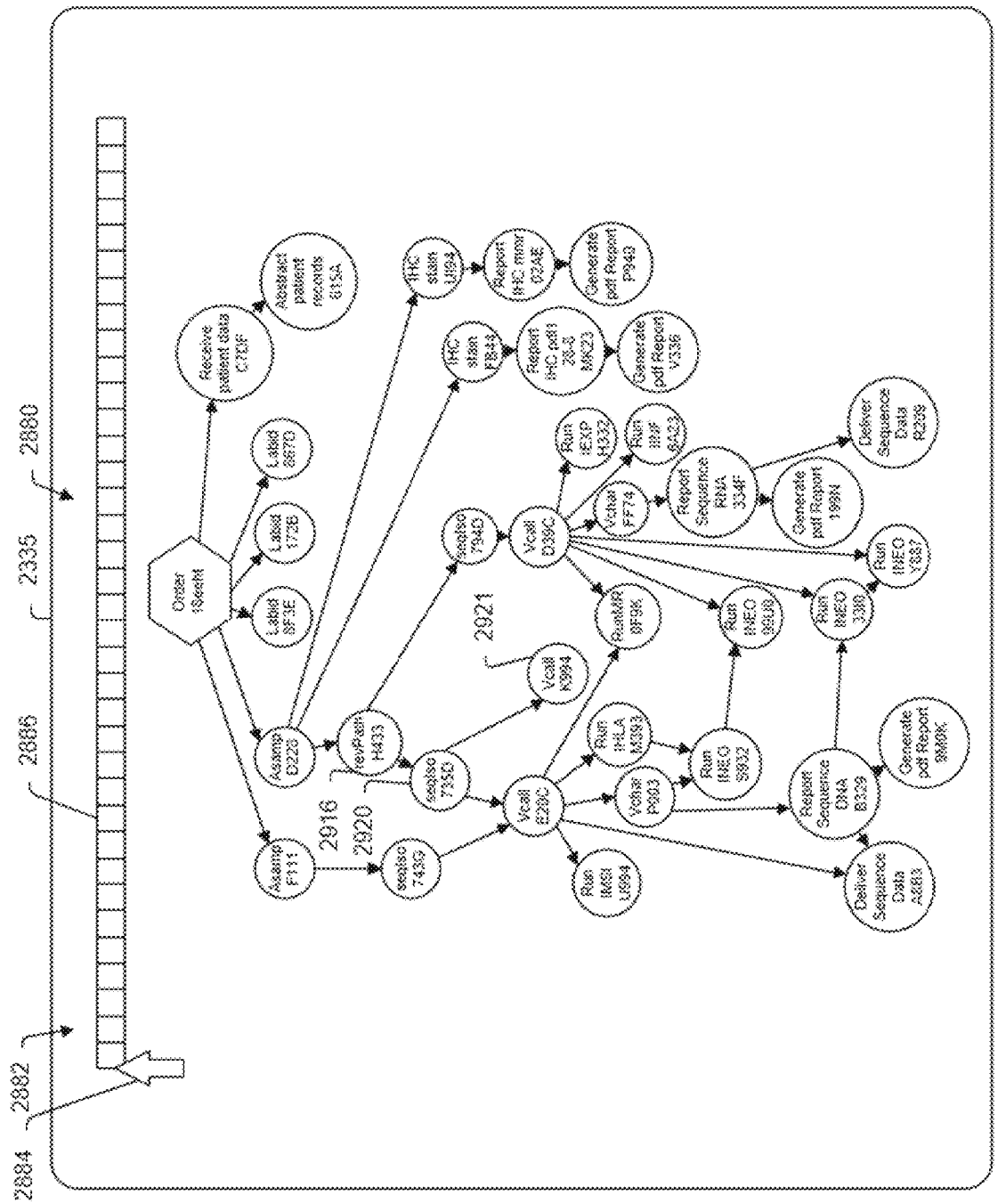
FIG. 74 is a schematic illustrating a user interface screen shot and a visualization tool that enables a user to view a current or historical order map and order item statuses.

In addition to driving statistical analysis of various system operations, an order map and the audit record can be used to generate a detailed visual representation of a pending order or a completed order or a real time representation showing instantaneous status of an order currently in progress. To this end, see FIG. 74 that shows a screen shot 2880 on an interface display screen 2335 (see also FIG. 59) that shows a replication of the order map 2500 from FIG. 61. A sliding control tool 2882 includes a timeline 2886 and a moveable pointer icon 2884 that can be moved to different locations along the timeline 2886 to select different points in time. After an order is stored in the order database 2334 shown in FIG. 60, a system user may access a visual representation of that order as shown in FIG. 74 via display 2335. The FIG. 74 map includes circular item representations that are all non-hatched meaning that none of the order items have been completed. The FIG. 74 representation corresponds to a time prior to order initiation when pointer icon 2884 is far to the left on the timeline and no items are complete or even in-progress. Order hub 2330 generates the FIG. 74 representation by converting a JSON file from an "order create" audit record into a DAG image.

Figure 75:
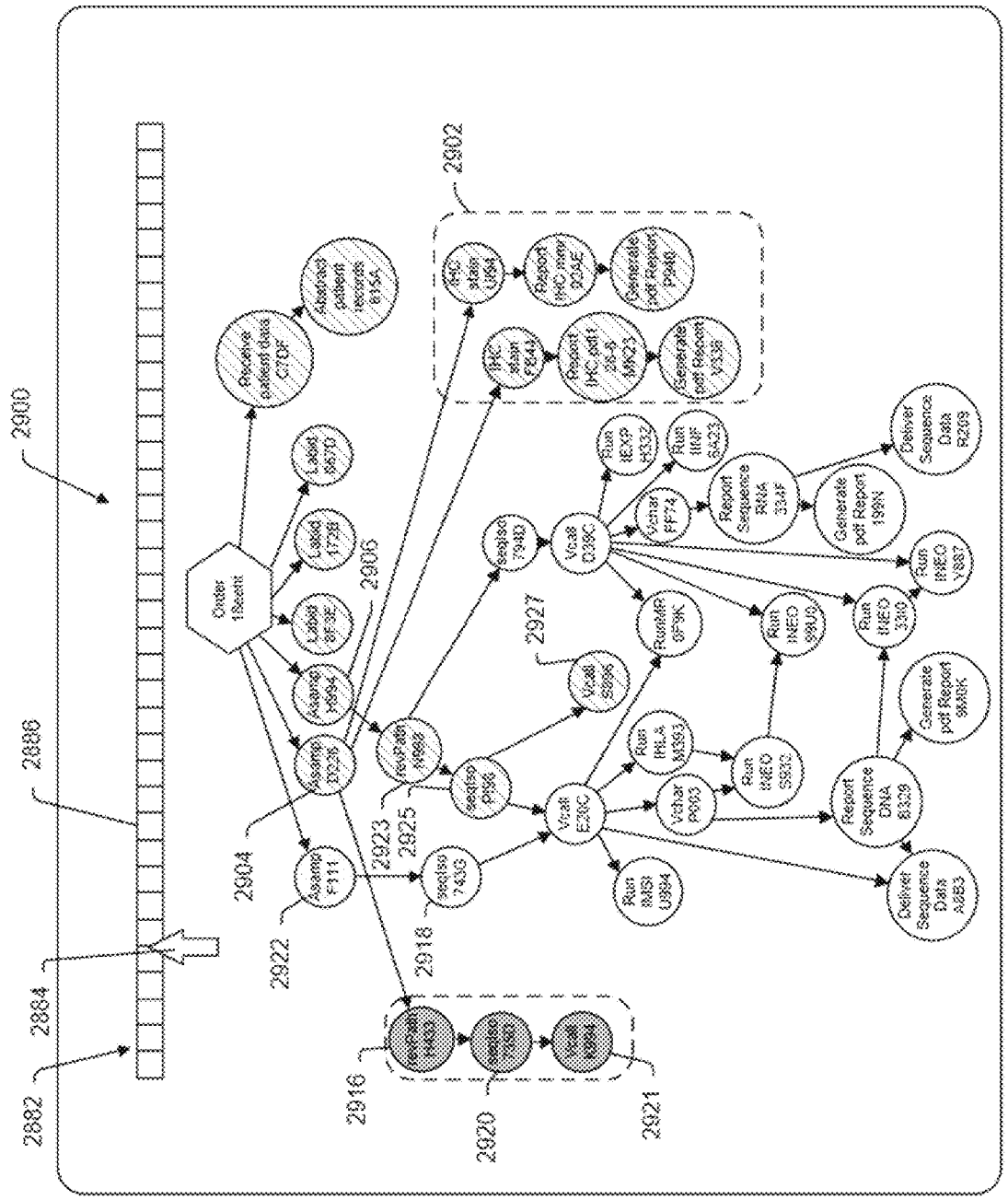
FIG. 75 is similar to FIG. 74, albeit showing the order map at a later point in time.

Referring to FIG. 75, a screenshot 2900 similar to the screen shot 2880 in FIG. 74 is shown, albeit where an associated order has commenced as indicated by the location of pointer icon 2884 on timeline 2886. In FIG. 75, many of the item icons are shown cross hatched left up to right, one 2922 is shown double cross hatched ad three 2916, 2920 and 2921 are shown shaded dark to indicate different item statuses. In FIG. 75 and subsequent figures, left up to right hatching will be used to indicate that an item has been completed and double diagonal cross hatching will be used to indicate that an item is currently in-progress. In addition, dark shading will be used to indicate that a quality control fail status has been assigned to an item and left down to right hatching will be used to indicate that an item has been cancelled. Thus, in FIG. 75, left up to right cross hatched items are completed, item 2922 is in-progress and items 2916, 2920 and 2921 have failed during some quality check.

Status map 2900 is generated using the audit record that corresponds to an audit record timestamp that occurred just prior to the time selected on timeline 2886, accessing the JSON representation of the order in the JSON field 2862 associated with the identified audit record and converting the JSON representation to a DAG image as shown at 2900. In cases where the JSON includes status information on all persisting order items, the JSON to DAG conversion can be direct. In cases where the JSON does not include all item statuses, order hub server 2332 may access most recent audit records for each of the order map items that persists in the JSON to identify current statuses of each of those items and use that information to visually distinguish different item statuses on the DAG image.

Up to the time represented by the FIG. 75 DAG image what has happened is as follows. A tumor sample was received and processed. IHC PDL1 and MMR tests were completed (see box 2902). At Vcall item 2921 a tumor only preview was identified as incorrectly prepared for sequencing, and no sample from item 2904 remained. Items 2916, 2920 and 2921 were identified as QC fail (hence are shown as dark shaded) and a new sample accession item 2906 was added to the order map along with new items 2923, 2925 and 2927 to replicate the failed items 2918, 2920 and 2921, respectively. The new sample was obtained and items 2923, 2925 and 2927 have been successfully completed. Item 2922 is in progress. IHC stains are of good quality, no change needed for those delivered tests.

Figure 76:
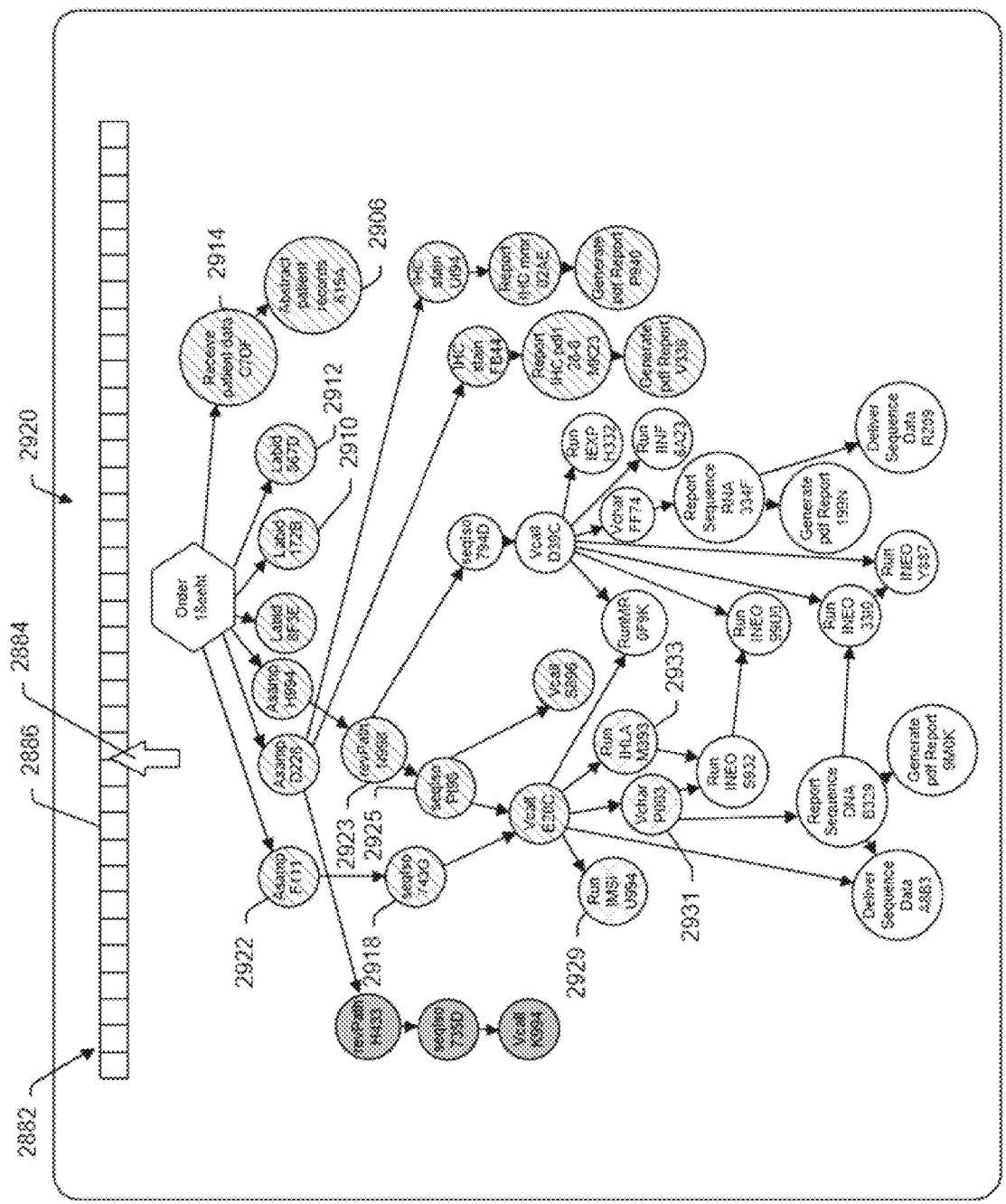
FIG. 76 is similar to FIG. 75, albeit showing the order map at a later point in time.

Referring to FIG. 76, a screen shot 2920 similar to the screen shot 2900 in FIG. 75 is shown, albeit where time has progressed further as indicated by the location of pointer icon 2884 on timeline 2886. In FIG. 76, many of the item icons are shown cross hatched left up to right indicating completion, several are shown shaded dark indicating QC fail status and items 2929, 2931 and 2933 are double hatched indicating that each in progress. No further QC failures occurred as of the time shown in FIG. 76.

Figure 77:
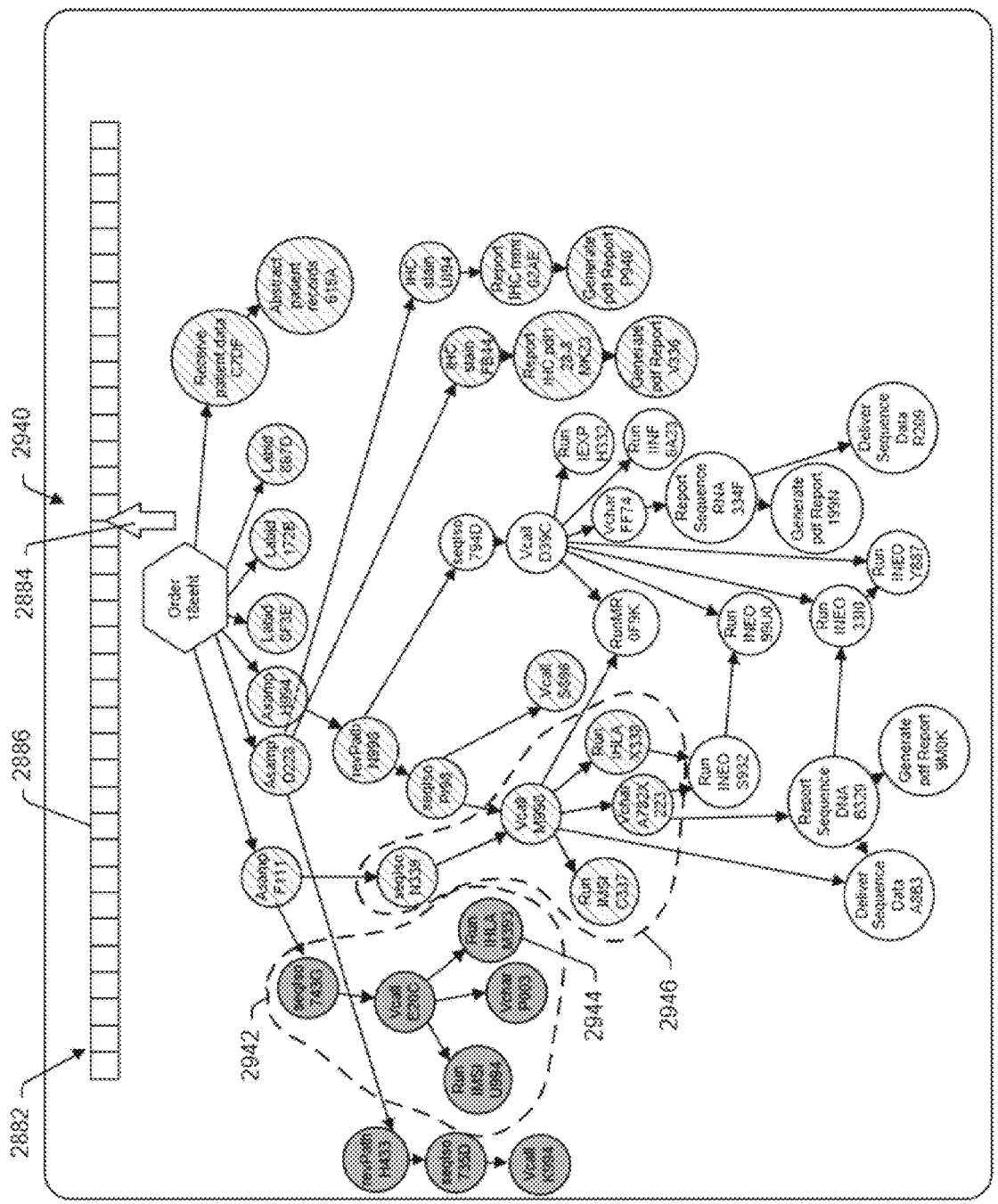
FIG. 77 is similar to FIG. 76, albeit showing the order map at a later point in time.

Referring to FIG. 77, a screen shot 2940 similar to the screen shot 2920 in FIG. 76 is shown, albeit where time has progressed further as indicated by the location of pointer icon 2884 on timeline 2886. Up to the time represented by the FIG. 77 DAG image what has happened is as follows. Items in set 2942 excluding item 2944 were completed at item 2944 issues were identified with the Normal sample sequencing output and therefore the normal sample sequencing had to be re-executed. To cause re-execution, items in set 2946 were added to the order map to replace items in set 2942. The normal sample sequence was completed.

Figure 78:
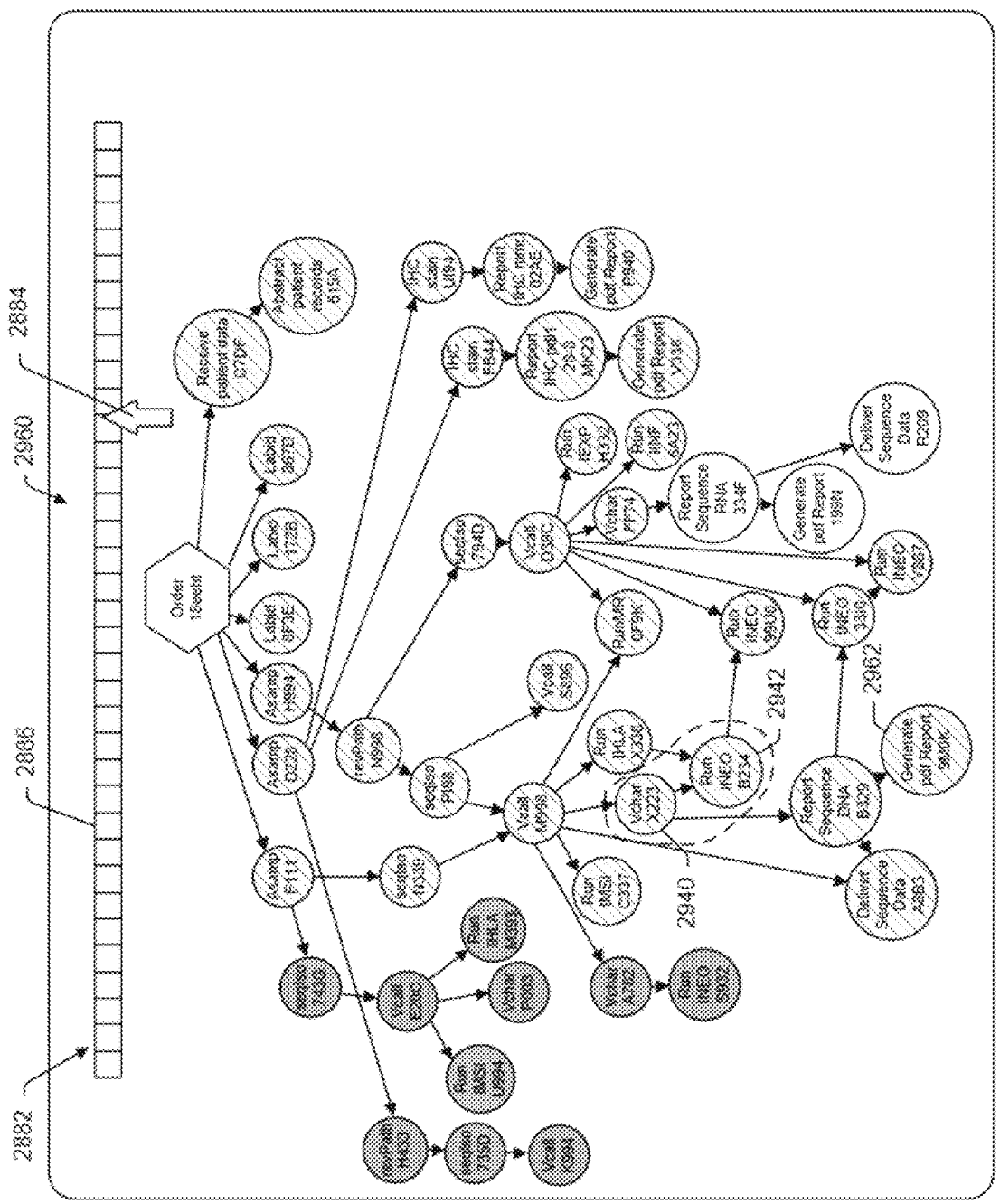
FIG. 78 is similar to FIG. 77, albeit showing the order map at a later point in time.

Referring to FIG. 78, a screen shot 2960 similar to the screen shot 2940 in FIG. 77 is shown, albeit where time has progressed further as indicated by the location of pointer icon 2884 on timeline 2886. Up to the time represented by the FIG. 78 DAG image what has happened is as follows. An AI variant science auto-categorization program was run which generated a notification requiring manual review. Manual variant science was performed and a report signed out as indicated by item 2962. The deliver sequence data item at 2964 encountered an error so that item was temporarily delayed (not shown in FIGS. but "delay" status would be shown visually distinguished from other DAG image statuses). A provider specialist identified the source of the item 2964 error, corrected it, and restarted the item 2964 which completed. Most of the other items in the order are shown as complete. RHA sequencing commenced once DNA tests were complete.

Figure 79:
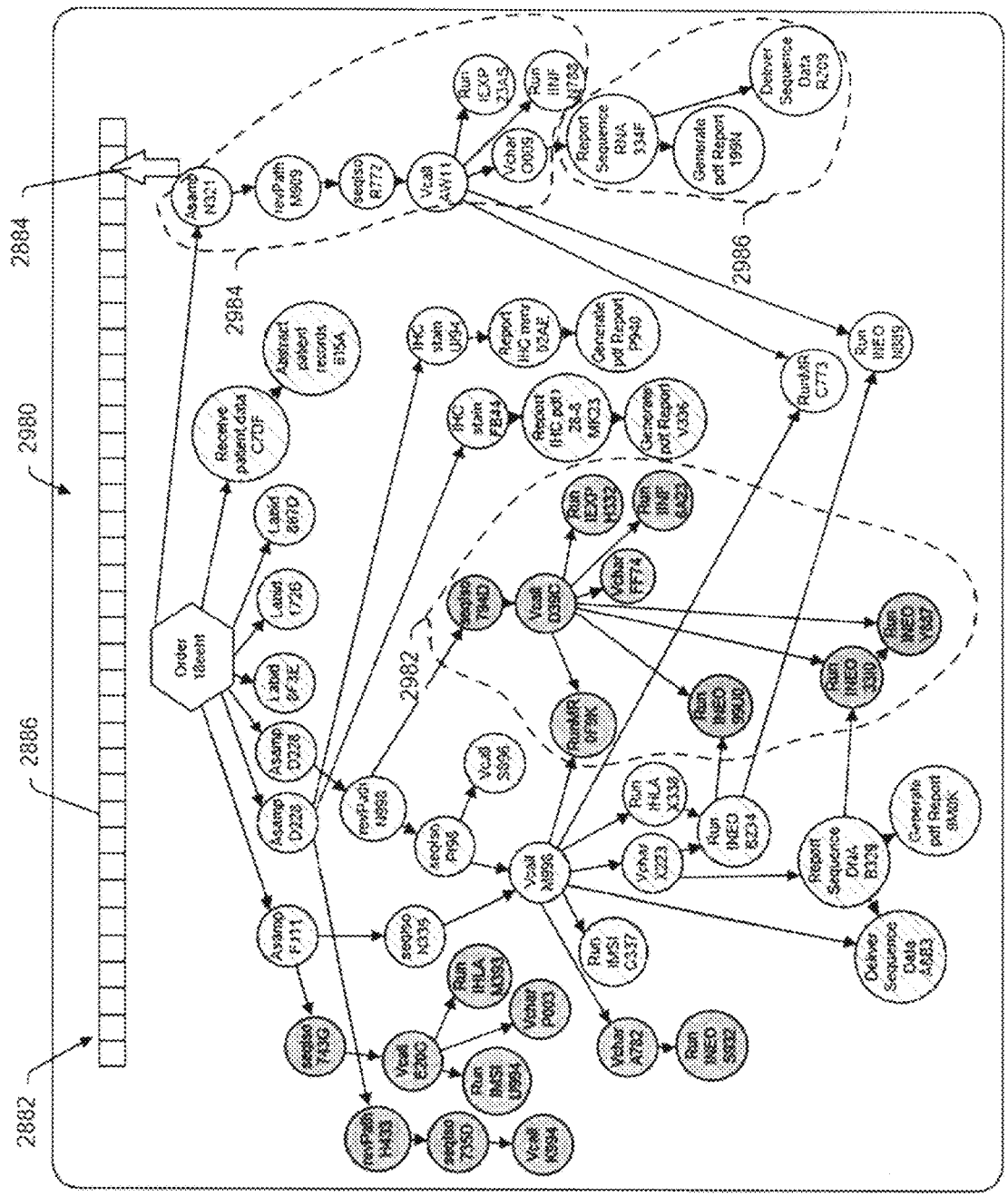
FIG. 79 is similar to FIG. 78, albeit showing the order map at a later point in time.

Referring to FIG. 79, a screen shot 2980 similar to the screen shot 660 in FIG. 78 is shown, albeit where time has progressed further as indicated by the location of pointer icon 2884 on timeline 2886. Up to the time represented by the FIG. 78 DAG image what has happened is as follows. After many RNA items were completed (see again FIG. 77), report review identified that an inadvertent sample swap occurred during RNA sequencing in the lab, and no additional sample remains. Again, a new sample is required and the RNA testing items have to be re-executed. To this end, prior completed RNA items in set 2982 are all set to a QC fail status (as indicated by the dark shading in the DGA image) and a new set of RNA test items 2984 is added to the order map starting with a new sample accession item. The original report sequence RNA, Generate pdf Report and Deliver Sequence Data items in set 2986 remain and are simply fitted onto the new RNA test set 2984. The DNA report from the same sample is unaffected by the RNA swap. After the time corresponding to the FIG. 79 DAG image it is assumed the remainder of the order processes without any QC fail issues.

III. Systems and Methods for Interrogating Clinical Documents for Characteristic Data The various aspects of the subject invention are now described with reference to the annexed drawings. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (such as hard disk, floppy disk, and magnetic strips), optical disks (such as compact disk (CD), digital versatile disk (DVD)), smart cards, and flash memory devices (such as card, stick). Additionally it should be appreciated that a carrier wave can be employed to carry computer-readable electronic data such as those used in transmitting and receiving electronic mail or in accessing a network such as the Internet or a local area network (LAN). Transitory computer-readable media (carrier wave and signal based) should be considered separately from non-transitory computer-readable media such as those described above. Of course, those skilled in the art will recognize many modifications may be made to this configuration without departing from the scope or spirit of the claimed subject matter.

Unless indicated otherwise, while the disclosed system is used for many different purposes (such as data collection, data analysis, data display, treatment, research, etc.), in the interest of simplicity and consistency, the overall disclosed system will be referred to hereinafter as "the system."

The methods and systems described herein may be used on information generated from NGS techniques. The field of NGS for genomics is new and faces significant challenges in managing relations between sequencing, bioinformatics, variant calling, analysis, and reporting data. NGS involves using specialized equipment such as a next generation gene sequencer, which is an automated instrument that determines the order of nucleotides in DNA and RNA. The instrument reports the sequences as a string of letters, called a read, which the analyst may compare to one or more reference genomes of the same genes. A reference genome may be compared to a library of normal and variant gene sequences associated with certain conditions. With no settled NGS standards, different NGS providers have different approaches for sequencing patient genomics; and, based on their sequencing approaches, generate different types and quantities of genomics data to share with physicians, researchers, and patients. Different genomic datasets exacerbate the task of discerning and, in some cases, render it impossible to discern, meaningful genetics-treatment efficacy insights as required data is not in a normalized form, was never captured or simply was never generated.

Extracted DNA from blood or saliva samples are single or paired-end sequenced using an NGS platform, such as a platform offered by Illumina.

The results of sequencing (herein, the "raw sequencing data") may be passed through a bioinformatics pipeline where the raw sequencing data is analyzed. After sequencing information is run through the bioinformatics pipeline, it may be evaluated for quality control, such as through an automated quality control system. If the sample does not pass an initial quality control step, it may be manually reviewed. If the sample passes an automated quality control system or is manually passed, an alert may be published to a message bus that is configured to listen for messages from quality control systems. This message may contain sample identifiers, as well as the location of BAM files. A BAM file (.bam) is the binary version of a SAM file. A SAM file (.sam) is a tab-delimited text file that contains sequence alignment data (such as the raw sequencing data). When a message notifying the topic is received, a service may be triggered to evaluate the sequencing data for pharmacogenomics factors.

The bioinformatics pipeline may receive the raw sequencing results and process them to identify genetic variants that are expressed in the patient's DNA or RNA. An identified variant may be referred to as a variant call. Once a variant has a sufficient number of reads from the raw sequencing results to qualify as a variant call, a variant characterization may be performed on that variant call. Variant characterization may include searching published variant datasets identifying variants of pharmacogenomic importance, searching FDA publications on therapies and their targeted variants, or comparing the variant calls to an internally curated list of variants having pharmacogenomic importance. Any variant calls with pharmacogenomic importance may be flagged for inclusion in a report, such as the reports described in more detail below.

A knowledge database may be generated for accumulating a cohort of patient NGS results and clinical information. The accumulated patient information may be analyzed to identify insights such as potential biomarkers or trends in pharmacogenomics.

The analytic power of NGS stands out above conventional methods of processing genetic variants or alleles which have pharmacogenetic importance. Because the entirety of the normal human genome may be referenced for each of the targeted genes (described in more detail below), NGS may identify previously unobserved variant calls even if the variant was not targeted by the NGS panel. For example, if the normal genome is ATTACCA for a given region of the chromosome, but an untargeted and/or previously undocumented variant exists such that a variant sequence is identified as ATTATCA in that same region, an allele mismatch indicating detection of a new allele spanning that region may be detected merely from the absence of an expected variant call. For example, alleles may be identified from a sequence of nucleotides that match the normal sequence, a sequence of nucleotides that match the sequence of any known allele variation from normal, or by identifying a new sequence which is not a match to any of the known alleles.

Furthermore, because NGS probe reads include the sequence of the DNA molecule that extended from each probe and not just the probe, probe reads from upstream in a DNA molecule which also encompass an untargeted downstream variant may be reported by the NGS sequencer. Confirmed detection of an untargeted variant may be made after analysis in the bioinformatics pipeline, based upon new research or published data. Additionally, sequence coverage over the whole genome allows for research to be performed across aggregated sequencing results and enables the identification of new biomarkers which were previously unknown. An exemplary system that provides a foundation to capture the above benefits, and more, is described below.

System Overview

The present architecture is designed such that system processes may be compartmentalized into loosely coupled and distinct micro-services for defined subsets of system data, may generate new data products for consumption by other micro-services, including other system resources, and enables maximum system adaptability so that new data types as well as treatment and research insights can be rapidly accommodated. Accordingly, because micro-services operate independently of other system resources to perform defined processes where development constraints relate to system data consumed and data products generated, small autonomous teams of scientists and software engineers can develop new micro-services with minimal system constraints that promote expedited service development.

This system enables rapid changes to existing micro-services as well as development of new micro-services to meet any data handling and analytical needs. For instance, in a case where a new record type is to be ingested into an existing system, a new record ingestion micro-service can be rapidly developed resulting in that addition of a new record in a raw data form to a system database as well as a system alert notifying other system resources that the new record is available for consumption. Here, the intra-micro-service process is independent of all other system processes and therefore can be developed as efficiently and rapidly as possible to achieve the service specific goal. As an alternative, an existing record ingestion micro-service may be modified independent of other system processes to accommodate some aspect of the new record type. The micro-service architecture enables many service development teams to work independently to simultaneously develop many different micro-services so that many aspects of the overall system can be rapidly adapted and improved at the same time.

A messaging gateway may receive data files and messages from micro-services, glean metadata from those files and messages and route those files and messages on to other system components including databases, other micro-services, and various system applications. This enables the micro-services to poll their own messages as well as incoming transmissions (point-to-point) or bus transmissions (broadcast to all listeners on the bus) to identify messages that will start or stop the micro-services.

Referring now to the figures that accompany this written description and more specifically referring to FIG. 80, the present disclosure will be described in the context of an exemplary disclosed system 3200 where data is received at a server 3220 from many different data sources (such as database 3232, clinical record 3224, and micro-services (not shown)). In some aspects, the server 3220 can store relevant data, such as at database 3234, which is shown to include empirical patient outcomes. The server 3220 can manipulate and analyze available data in many different ways via an analytics module 3236. Further, the analytics module 3236 can condition or "shape" the data to generate new interim data or to structure data in different structured formats for consumption by user application programs and to then drive the user application programs to provide user interfaces via any of several different types of user interface devices. While a single server 3220 and a single internal database 3234 are shown in FIG. 80 in the interest of simplifying this explanation, it should be appreciated that in most cases, the system 3200 can include a plurality of distributed servers and databases that are linked via local and/or wide area networks and/or the Internet or some other type of communication infrastructure. An exemplary simplified communication network is labeled 3218 in FIG. 80. Network connections can be any type, including hard wired, wireless, etc., and may operate pursuant to any suitable communication protocols. Furthermore, the network connections may include the communication/messaging gateway/bus that enables micro-services file and message transfer according to the above system.

The system 3200 enables many different system clients to securely link to server 3220 using various types of computing devices to access system application program interfaces optimized to facilitate specific activities performed by those clients. For instance, in FIG. 80 a provider 3212 (such as a physician, researcher, lab technician, etc.) is shown using a display device 3216 (such as a laptop computer, a tablet, a smart phone, etc.) to link to server 3220. In some aspects, the display device 3216 can include other types of personal computing devices, such as, virtual reality headsets, projectors, wearable devices (such as a smart watch).

In at least some embodiments, when a physician uses system 3200, a physician's user interface (such as on display device 3216) is optimally designed to support typical physician activities that the system supports including activities geared toward patient treatment planning. Similarly, when a researcher (such as a radiologist) uses system 3200, user interfaces optimally designed to support activities performed by those system clients are provided. In other embodiments, the physician's user interface, software, and one or more servers are implemented within one or more microservices. Additionally, each of the discussed systems and subsystems for implementing the embodiments described below may additionally be prescribed to one or more micro-systems.

System specialists (such as employees that control/maintain overall system 3200) also use interface computing devices to link to server 3220 to perform various processes and functions. For example, system specialists can include a data abstractor, a data sales specialist, and/or a "general" specialist (such as a "lab" specialist). Different specialists will use system 3200 to perform many different functions, where each specialist requires specific skill sets needed to perform those functions. For instance, data abstractor specialists are trained to ingest clinical records from various sources (such as clinical record 3224) and convert that data to normalized and system optimized structured data sets. A lab specialist is trained to acquire and process patient and/or tissue samples to generate genomic data, grow tissue, treat tissue and generate results. Other specialists are trained to assess treatment efficacy, perform data research to identify new insights of various types and/or to modify the existing system to adapt to new insights, new data types, etc. The system interfaces and tool sets available to provider specialists are optimized for specific needs and tasks performed by those specialists.

Referring again to FIG. 80, server 3220 is shown to receive data from several sources. According to some aspects, clinical trial data can be provided to server 3220 from database 3232. Further, patient data can be provided to server 3220. As shown, patient 3214 has corresponding data from multiple sources (such as lab results 3226 will be furnished from a laboratory or technician, imaging data 3228 will be furnished from a radiologist, etc.). For simplicity, this is representatively shown in FIG. 80 as individual patient data 3222. In some aspects, individual patient data 3222 includes clinical record(s) 3224, lab results 3226, and/or imaging data 3228. Further, in some aspects, clinical record(s) 3224 may include longitudinal data, which is data collected at multiple time points during the course of the patient's treatment.

The individual patient data 3222 can be provided to server 3220 by, for example, a data abstractor specialist (as described above). Alternatively, electronic records can be automatically transferred to server 3220 from various facilities and practitioners, where appropriate. As shown in FIG. 80, patient data communicated to server 3220 can include, but is not limited to, treatment data (such as current treatment information and resulting data), genetic data (such as RNA, DNA data), brain scans (such as PET scans, CT, MRI, etc.), and/or clinical records (such as biographical information, patient history, family history, comorbid conditions, etc.).

Still referring to FIG. 80, server 3220 is shown to include analytics module 3236, which can analyze data from database 3234 (empirical patient outcomes), and individual patient data 3222. Database 3234 can store empirical patient outcomes for a large number of patients suffering from the same or similar disease as patient 3214. For example, "individual patient data" for numerous patients can be associated with each respective treatment and treatment outcomes, and subsequently stored in database 3234. As new patient data and/or treatment data becomes available, database 3234 can be updated. As one example, provider 3212 may suggest a specific treatment for patient 3214, and individual patient data 3222 may then be included in database 3234.

Analytics module 3236 can, in general, use available data to indicate a diagnosis, predict progression, predict treatment outcomes, and/or suggest an optimized treatment plan (such as a medication type, an available clinical trial) based on the specific disease state of each patient. Exemplary analytics may include machine learning algorithms or neural networks. A machine learning algorithm (MLA) or a neural network (NN) may be trained from a training data set. For a disease state, an exemplary training data set may include the clinical and molecular details of a patient such as those curated from the Electronic Health Record or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where certain features/classifications in the data set are annotated) using generative approach (such as mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, long short term memory networks, or other neural models where the training data set includes a plurality of samples and RNA expression data for each sample. While MLA and neural networks identify distinct approaches to machine learning, the terms may be used interchangeably herein. Thus, a mention of MLA may include a corresponding NN or a mention of NN may include a corresponding MLA.

Training may include identifying common clinical traits or genetic traits that patients of the overall cohort or patient database may exhibit, labeling these traits as they occur in patient records, and training the MLA to identify patterns in the outcomes of patients based on their treatments as well as their clinical and genetic information. Outputs from analytics module 3236 can be provided to display device 3211 via communication network 3218. Further, provider 3212 can input additional data via display device 3216 (such as a prescribed treatment), and the data can be transmitted to server 3220.

Display device 3216 can provide a graphical user interface (GUI) for provider 3212. The GUI can, in some aspects, be interactive and provide both comprehensive and concise data to provider 3212. As one example, a GUI can include intuitive menu options, selectable features, color and/or highlighting to indicate relative importance of data, and sliding-scale timelines for the viewing of disorder progression. The GUI can be tailored to the type of provider, or even customized for each individual user. For example, a physician can change a default GUI layout based on individual preferences.

Figure 81:
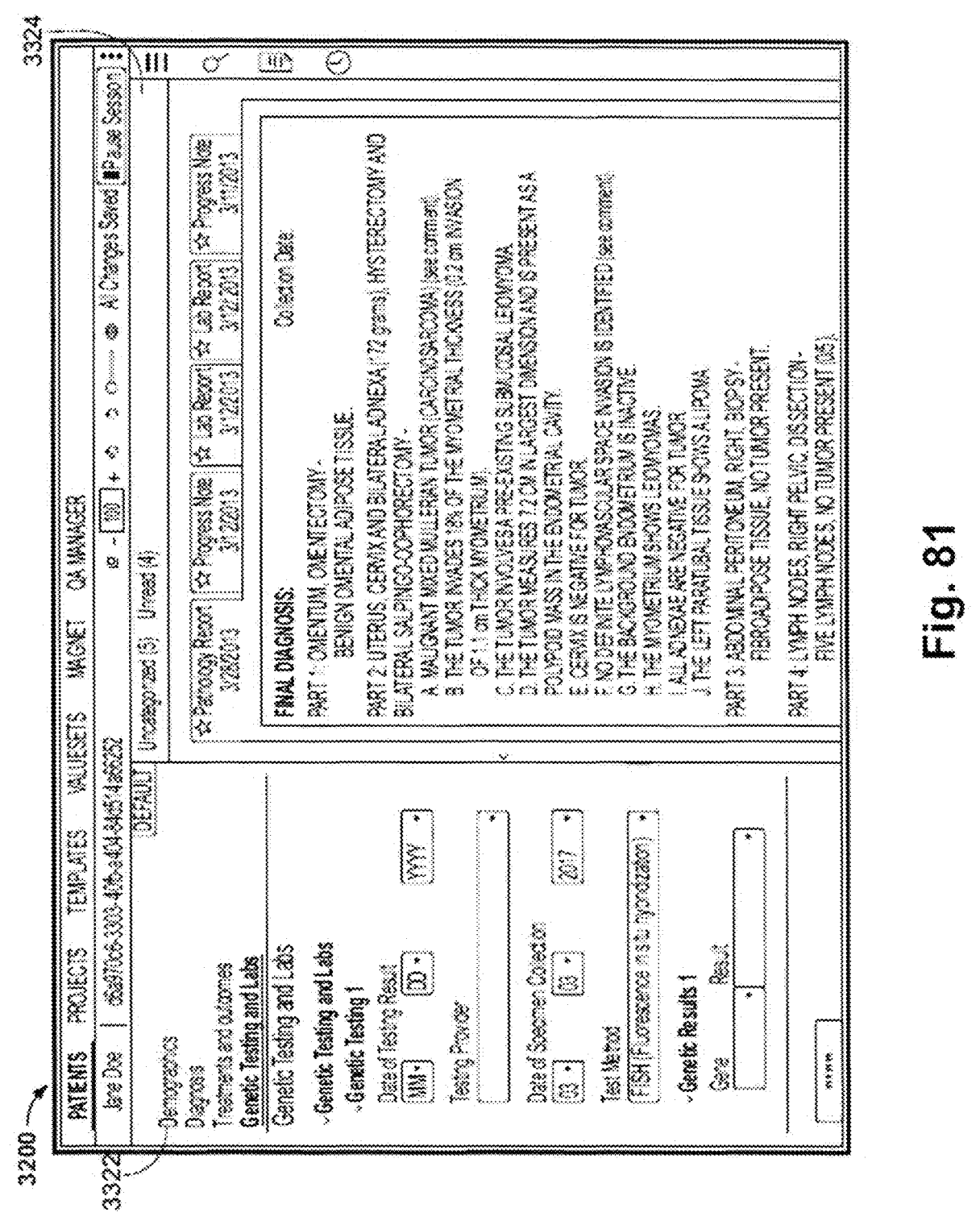

Further aspects of the disclosed system are described in detail with respect to FIGS. 81-138. In particular, an interactive GUI that can be displayed on display device 3216, is shown and described.

Graphical User Interface

In some aspects, a graphical user interface (GUI) can be included in system 3200. Advantageously, the GUI can provide a single source of information for providers, while still encompassing all necessary and relevant data. This can ensure efficient analysis, searching, and summary of health data. System specialists (e.g., data abstractors), can input patient health data into system 3200 via the GUI. For instance, a data abstractor can ingest clinical records from various sources (such as clinical record 3224) and convert that data to normalized and system optimized structured data sets. An exemplary GUI is shown and described with respect to FIGS. 81-138.

In some embodiments, system 3200 can query relevant data sets. As additional source documents are provided to the system 3200, quick search functionality and document management/indexing can improve user interaction with the system 3200, as well as limit the amount of manual review and/or searching that occurs. In some embodiments, raw clinical documents and data can be injected into the system 3200. A workflow management system/software can be configured to pull in new data and documents, according to some embodiments.

FIG. 81 is a graphical user interface (GUI) 3320 that can be implemented in system 3200 to enable clinical data structuring and abstraction work on a large scale. In some embodiments, GUI 3320 can include several modules as part of a workflow management system. In particular, GUI 3320 can include a "Patients" module, a "Projects" module, a "Templates" module, a "Valuesets" module, a "Magnet" module, a "QA Manager" module, and/or a "Validations Manager" module. The modules shown via GUI 3320 can communicate data with one another (e.g., patient data, system rules regarding data input, etc.).

Referring broadly to FIGS. 81-86, GUIs 3320-700 show details corresponding to the "Patients" module. In some embodiments, a data abstractor can use GUI 3320 to enter patient health data from raw third party data. As shown in FIG. 81, GUI 3320 can provide a split view, with a first panel 3322 configured to accept input data from a user (e.g., data abstractor), and a second panel 3324 configured to display raw documents corresponding to a patient. In some embodiments, for example, documents can include scanned forms and/or handwritten comments from a provider. Additionally, documents can include third party genetic sequencing reports. As shown by FIG. 81, the first panel 3322 can include a data section corresponding to genetic testing and labs, with a plurality of data entry fields available. The first panel 3322 is selectable by the user, so that different data fields are displayed depending on the item selected from the first panel 3322. For instance, as shown in FIG. 81, the "Genetic Testing and Labs" item has been selected, and so the data fields for Genetic Testing and Labs are displayed, such as date of testing results, testing provider, date of specimen collection, test method, results, and so forth. Each data entry field may have a drop-down menu that lists a plurality of options for the user to select. For instance, "FISH (Fluorescence in situ hybridization)" has been selected in the "Test Method" field in FIG. 81. Other options may be selected from a drop-down menu that has been populated with different test methods. Similarly, the other data fields may be populated with lists. Different types of user interface elements may be utilized in the first panel 3322, such as expansion lists (indicated in first panel 3322 by a plus sign within a square), dropdown lists (indicated in first panel 3322 by a rectangular box with a downward pointing triangular arrow on the right-hand side), free text boxes, and other input elements from the user interface arts.

The GUI may be arranged so that the first panel 3322 remains on the screen while the user views different original medical records. Tabs for example original medical records are shown in FIG. 81, namely, a pathology report, a progress note, a first lab report, a second lab report, and a progress note. Each tab may also indicate the date of the record, as is shown in FIG. 81. The pathology report is displayed; however, the user may select one of the other records to display by selecting (via mouse click or other known methods) it's associated tab. Selecting a different record while keeping the first panel 3322 on the screen allows the user to more easily develop a comprehensive set of structured data about a patient based on review of multiple medical records.

Figure 82:
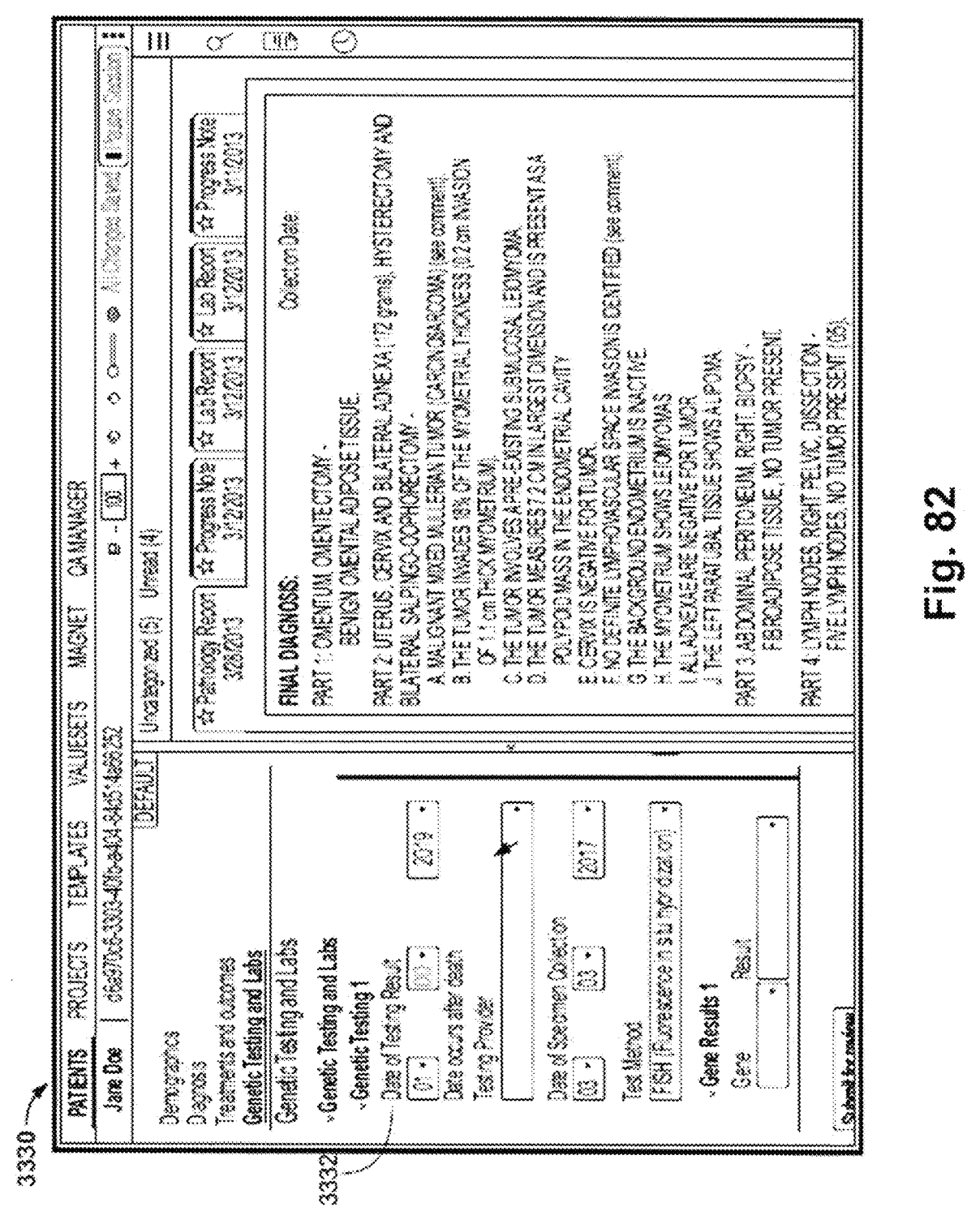

In some embodiments, system 3200 (via GUI 3320) can include two warning modes with respect to data entry. Colored text and/or a colored outline corresponding to the text field can provide a visual indication of a warning to the user. A first warning mode can be a "soft" warning mode, which can correspond to a first color indicator (e.g., yellow). A soft warning may permit the user to submit the data as-is, but can still provide an indication of sub-optimal data entry. A second warning mode can be a "hard" warning mode, which can correspond to a second color indicator (e.g., red). A hard warning may prevent the user from submitting the data as-is, and additional data or revised data may be required before system 3200 allows the user to continue with submission. As shown by FIG. 82, for example, a hard warning 3332 indicates that the entered "date of testing result" occurs after the instant patient's date of death. Accordingly, a data abstractor can be prevented from submitting this patient's data, until the "date of testing result" warning is reconciled. The warning modes may be designed in advance of a user operating the GUI in order to abstract health information from an original medical record.

Figure 83:
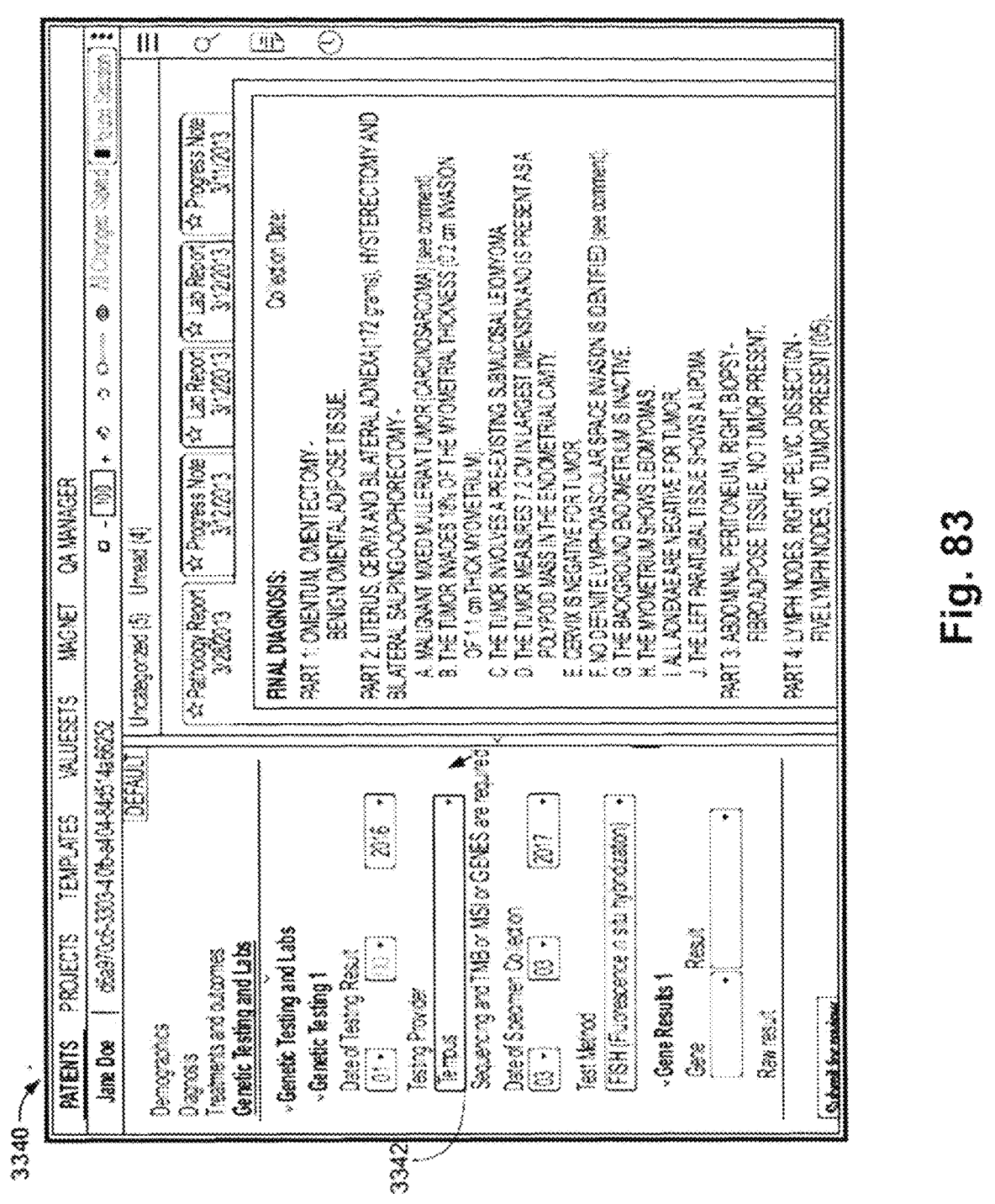
Figure 84:
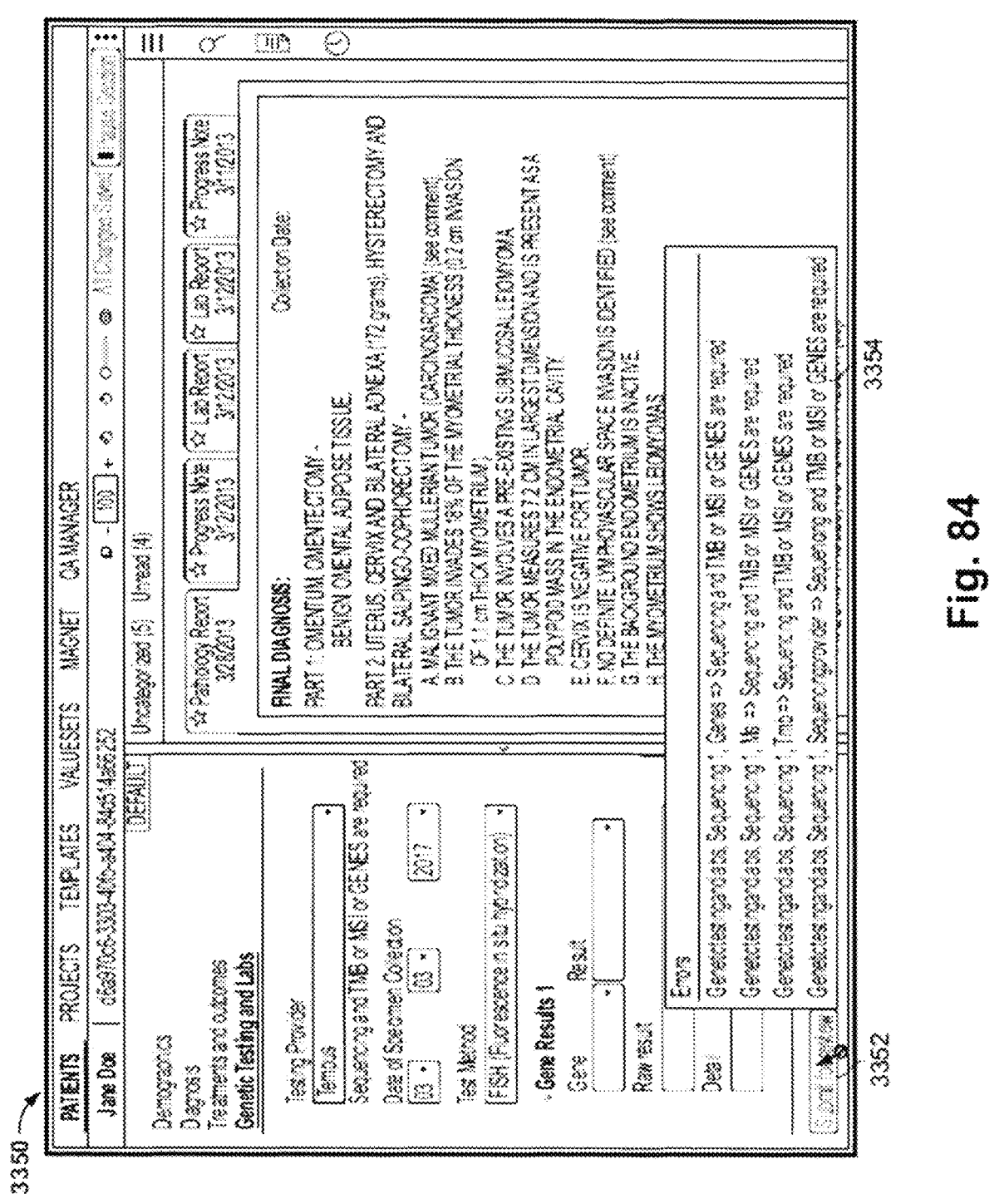
Figure 85:
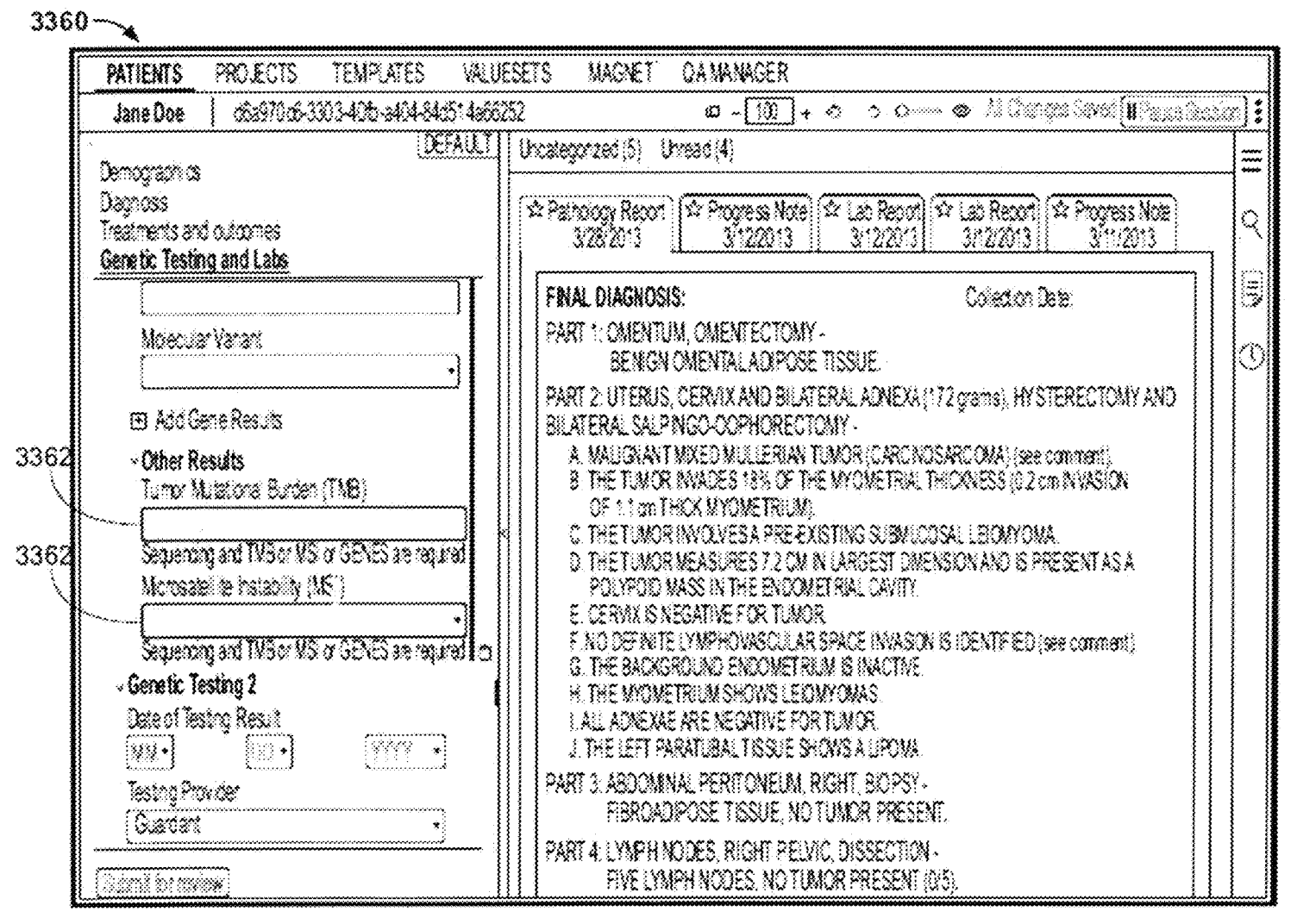

Referring now to FIGS. 83-85, another hard warning example is provided via GUIs 3340-600. As shown, entering the testing provider "Tempus" can generate a hard warning 3342. System 3200 can recognize that "Tempus" testing reports can have a number of attributes (e.g., TMB, MSI, IHC, etc.), and accordingly, an error/warning state can occur when system 10 detects that the entered data is insufficient. As shown by FIG. 84, the selection button "submit for review" 3352 can appear grayed out if certain data (e.g., genetic data) is missing and/or insufficient. Hovering over the "submit for review" button 3352 can trigger an error pop-up window 3354, which can list each outstanding error in the current data entry form. As indicated above, based on the testing provider ("Tempus"), system 3200 is looking for specific information before the abstractor is permitted to submit the data form. As indicated by the red warning boxes 3362 shown by FIG. 85, TMB and MSI data has not been entered. The data, in some embodiments, cannot be properly structured and stored without one or more of the TMB and MSI options filled in. In other embodiments, the data can be properly structured and/or stored without such options, with the approval of a designated individual (such as the user's manager).

Figure 86:
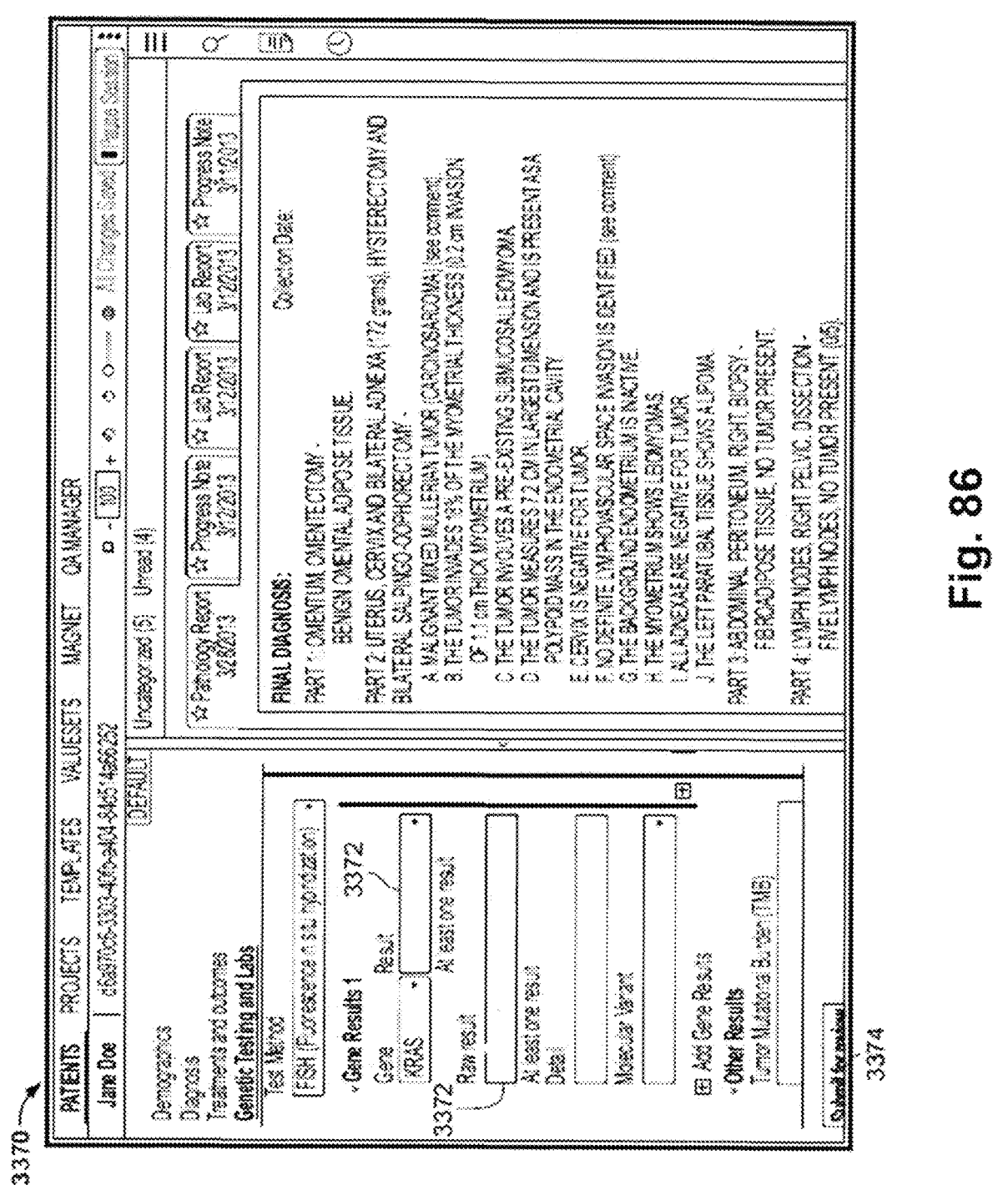

Referring to FIG. 86, as an example, the gene "KRAS" can be input into the gene results portion of the data form. As shown, new warnings occur; for instance, the data entry element may be outlined with a warning color (such as red). For instance, entering "KRAS" as the Gene may cause outline of the result entry box 3372 to change color to red. A written warning (such as "At least one result") may also automatically be displayed in proximity to the result entry box 3372. Similarly, hovering over or selecting the "submit for review" selection button 3374 can trigger an error pop-up window with new outstanding errors corresponding to the data entry form. Selecting a "result" that corresponds to the gene can eliminate the outstanding error warning, and the user (e.g., data abstractor) can now successfully select the "submit for review" button 3374.

Referring now to FIGS. 87-96, the "Validations Manager" module can be an administrative module where validations can be contained, revised, authored, etc. FIG. 87 shows an example table 3382 via GUI 3380 within Validations Manager that contains multiple exemplary validations and test validations that can produce some of the soft and hard warnings as described above. Some example validations include "immunophenotyping result text is a number" 3384 (i.e., text entries are not permitted for immunophenotyping results), "heme additional diagnosis date of recurrence" 3386 (i.e., date entries before the date of diagnosis are not permitted), and "date validations after birth" 3388 (i.e., date entries that occur before birth are not permitted). In some embodiments, the various validations can ensure that only quality data is accepted into the system 3200. Each validation can be represented with a name, description, date of creation, a user ID corresponding to the validation author, a level (e.g., error, warning), and the option to edit the validation. Additional disclosure relating to validations may be found in U.S. Provisional Patent Application No. 62/787,249, titled "Automated Quality Assurance Testing of Structured Clinical Data", filed Dec. 31, 2018, the contents of which are incorporated by reference in their entirety, for all purposes.

Figure 88:
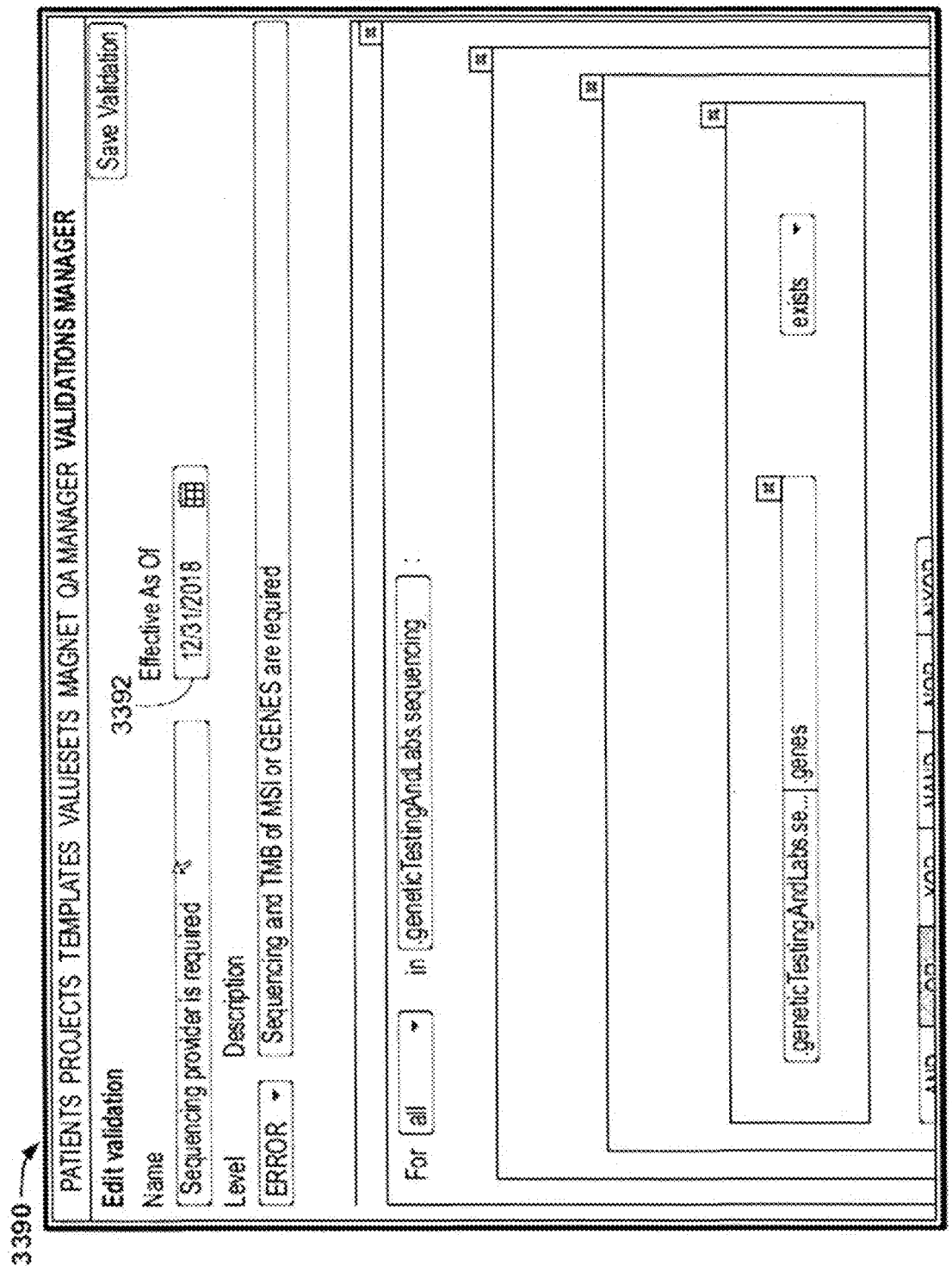
FIG. 88 is another image of an example graphical user interface (GUI), according to aspects of the present disclosure.
Figure 89:
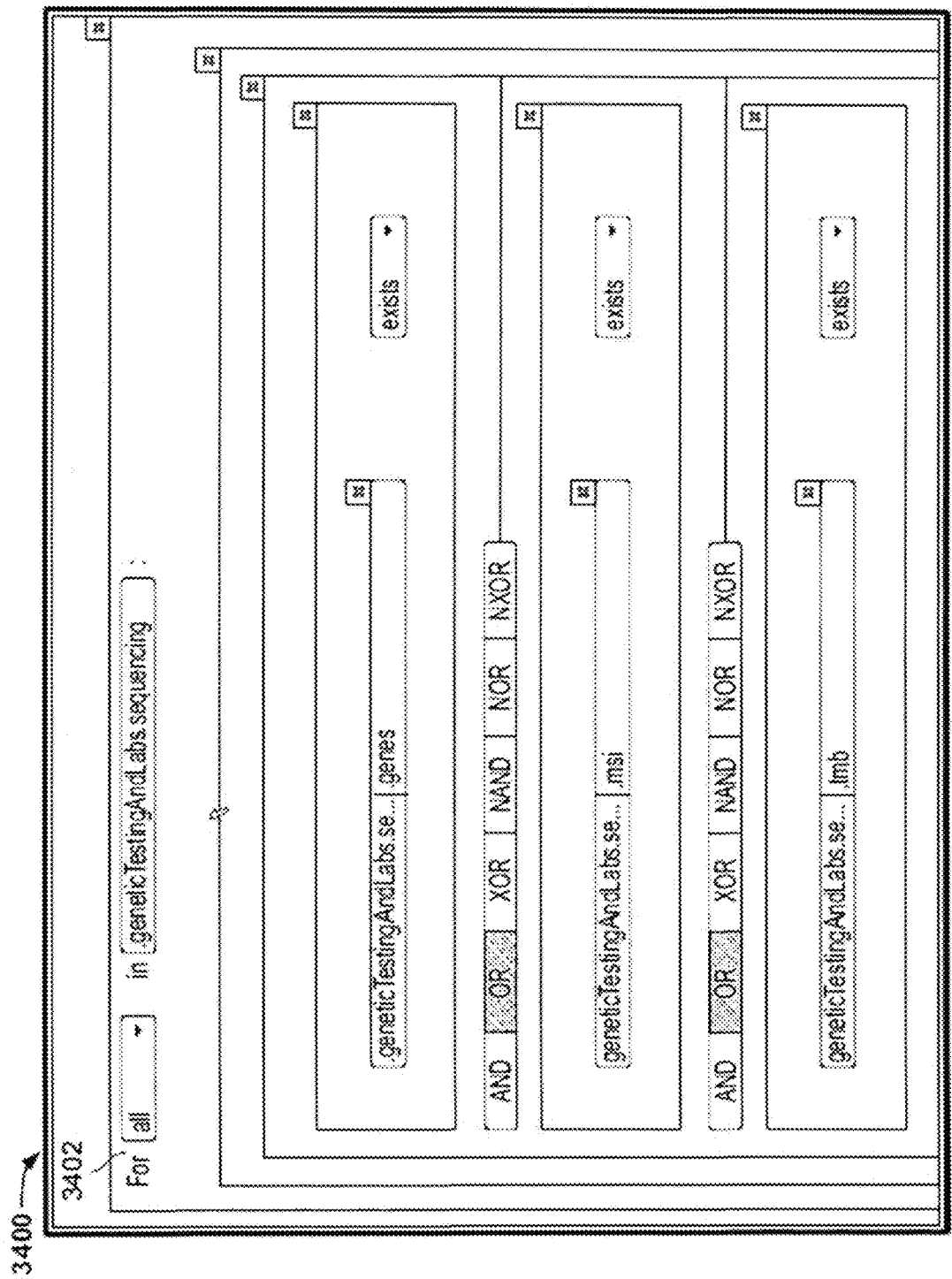
FIG. 89 is another image of an example graphical user interface (GUI), according to aspects of the present disclosure.

As shown by FIG. 88, a user can edit existing validations via GUI 3390. In some embodiments, the effective date can be set to a future date using an input such as a calendar dropdown menu 3392, and the validation will not activate until that future date. In the lower portion of the window, a dropdown menu is displayed that has been selected to an "all" value. This selection reflects that FIG. 89 shows a rule authoring system that can be configured to create rules for each validation via GUI 3400, according to some embodiments. Various combinations can be created using conditional statements (e.g., AND, OR, NOT, etc.). In some embodiments, multiple data sets can correspond to a single patient. As one example, a patient can have a first genetic test and a second genetic test. The rules for each validation can, for example, apply to each instance of data (e.g., validation can occur for both the first genetic test data and the second genetic test data). This can be configured and/or changed using the rule authoring system, and specifically, the "For" dropdown menu 3402 which is shown as "For" "all." As shown by FIG. 89, each gene report for this sequencing provider requires a gene, or MSI, or TMB data.

Figure 90:
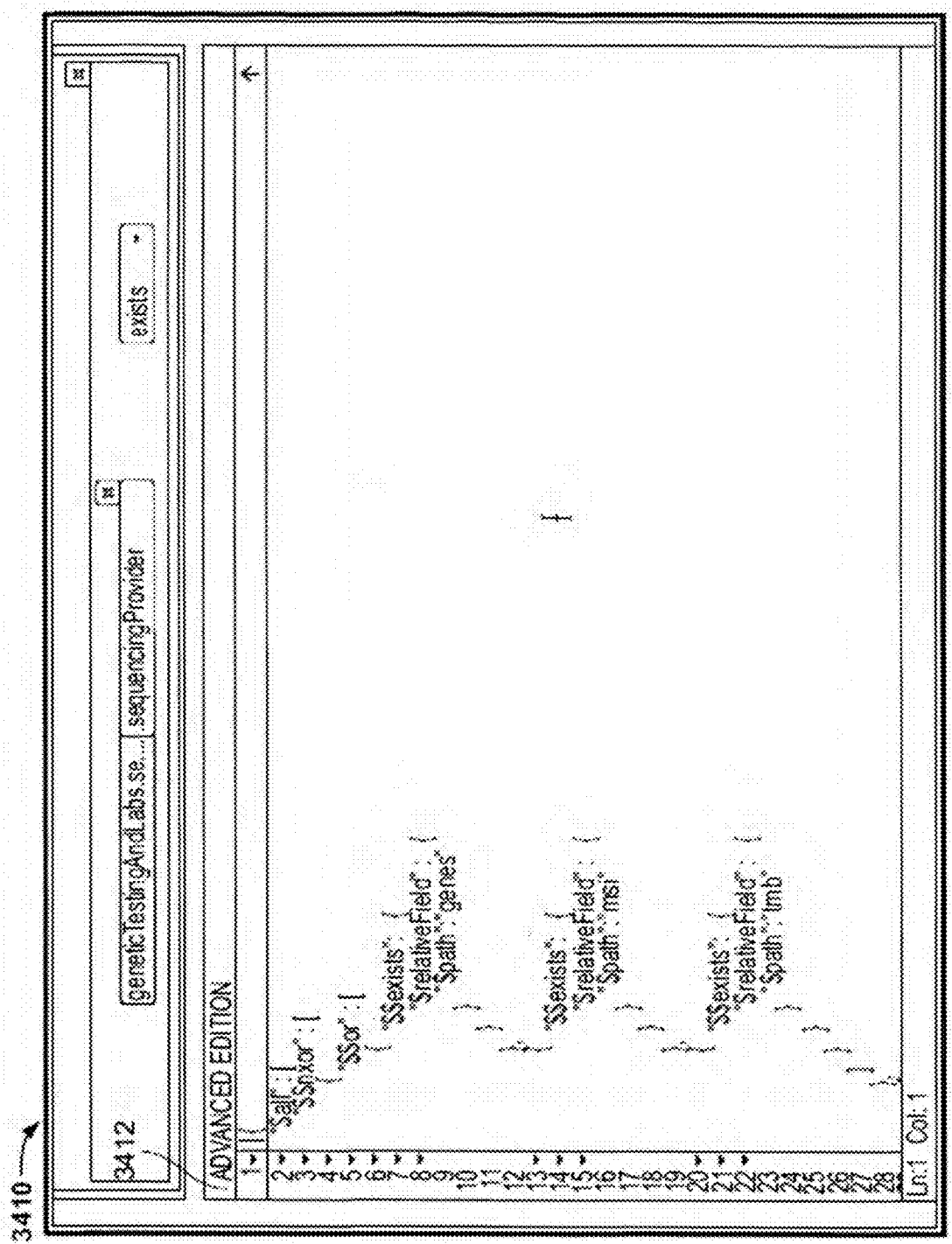
FIG. 90 is another image of an example graphical user interface (GUI), according to aspects of the present disclosure.

As shown by FIG. 90, via GUI 3410, the rule authoring system can include a validation language that can take rules authored in the user interfaces of FIGS. 88-89, and translate the rules to corresponding code 3412 for implementation in system 3200. In some embodiments, a new rule can be applied retroactively to existing patient data, such that new insights can be gleaned without being restricted to patient data entered moving forward. In some embodiments, the ability to add new rules to existing validations may be restricted to certain authorized users. However, a broader class of authorized users can still create new validations with new rules.

In some embodiments, the ability to add new and manage existing rules can be performed programmatically in the absence of a GUI (e.g., GUI 3410). In some situations, this can help with the composition of bulk validation checks that, for example, can assess the validity of reported AJCC cancer staging by cancer and its corresponding sub-type. Additionally, in some embodiments, programmatic rule management can enable, accelerate and/or help to manage various validation checks within and across systems (e.g., system 3200), tools and applications, such as clinical trial matching, the management of lab specimens in a Laboratory Information Management System (LIMS) solution, the information stored in a patient electronic health record, or the information stored in medical coding and billing systems.

Figure 91:
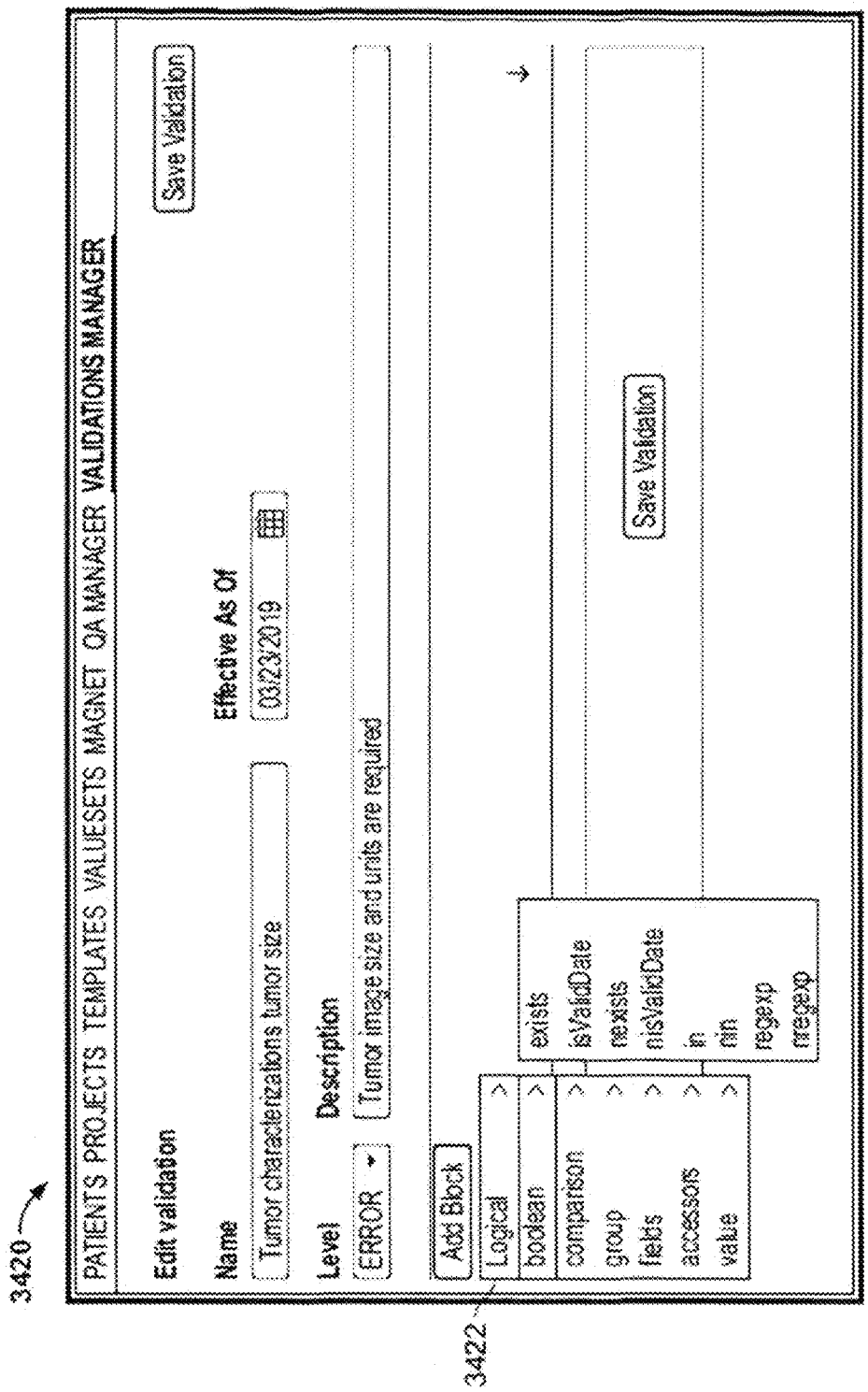
FIG. 91 is another image of an example graphical user interface (GUI), according to aspects of the present disclosure.

Referring now to FIG. 91, a new validation can be created by a user via GUI 3420, according to some embodiments. In contrast to editing existing validations (which can be restricted to certain authorized users), creating a new validation can now provide a user with an "add block" function. As shown, GUI 3420 can display a dropdown menu 3422 of selectable functions that can be customized for the specific validation.

Figure 94:
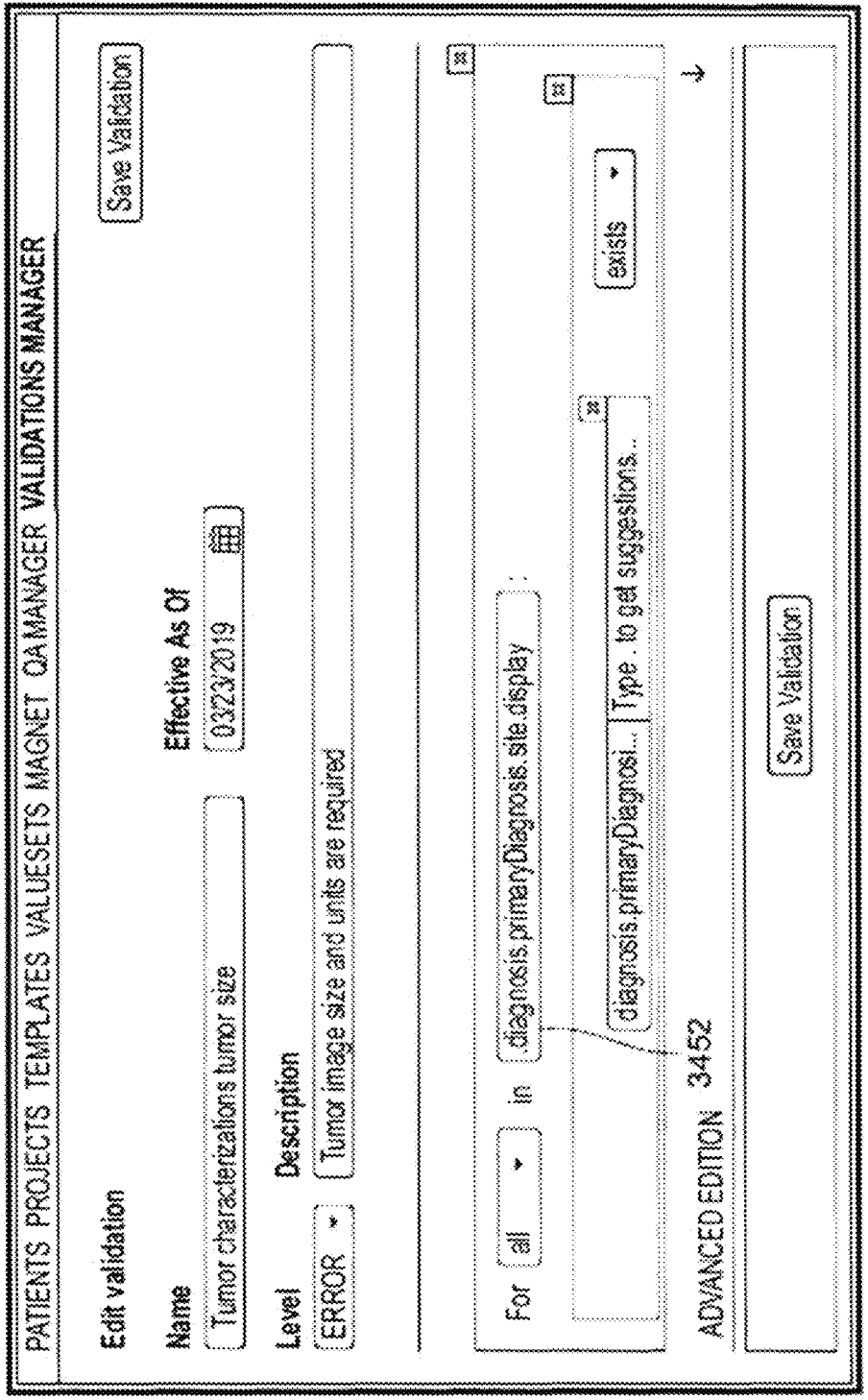
FIG. 94 is another image of an example graphical user interface (GUI), according to aspects of the present disclosure.

FIGS. 92-94 show the development of a new validation via GUIs 3430-3450. A new validation may enable the utilization of a template that permits the grouping of patients into one or more distinct cohorts. Such a grouping may be valuable for a variety of purposes, such as being able to search the one or more cohorts for certain health criteria, such as clinical, molecular, genetic, or imaging criteria. In other use cases, the system 3200 can find all sites for all patients where an indicated diagnosis exists.

In some embodiments, the validation may be developed using a selection tool such as a search bar 3432, that may receive a search term from a user and display a suggestion menu 3442 based on the search term in order to reduce user search time. The suggestion menu 3442 may be populated from the one or more templates associated with the validation. As an example, the four categories displayed in suggestion menu 3442 may be matched back to the list of items displayed in panel 3322. After a category 3452 from suggestion menu 3442 has been selected, the rule authoring system can create the corresponding system code for the new validation. For example, the selection of the category 3452 may trigger the appearance of sub-level data entry elements tied to the selected category 3452. As shown in FIG. 94, for example, the selection of .diagnosis.primaryDiagnosis.site.display as category 3452 populates the rule displays shown below the label. The field ".diagnosis.primaryDiagnosis.site.display" refers to the text that is in a set of structured data that reflects the primary diagnosis of a tumor at a site of biopsy. For example, the value of that text entry may be "breast cancer," "prostate cancer," or the like. However, it should be understood that in the examination of a patient's medical record, particularly the medical record of a medically complex patient such as a metastatic cancer patient, there is a substantial amount of information in the record that may suggest the factual primary diagnosis of a cancer at a site. In addition, because medical records are updated over a period of many years and many clinical visits, it is often the case that information collected in the medical record over time may be inconsistent—that is to say, records from a first clinical visit may indicate that the size of the tumor is 5 cm while records from a second clinical visit may indicate that the size of the tumor is 6 cm. This may be because the size of the tumor has changed between appointments. Or, it may be a data entry error that was not corrected in the medical record. For this reason, a validation may be set up to check one or more structured data fields for internal value consistency as a condition to ensuring that the primary diagnosis text can be relied on with a high level of confidence, given the extensive and sometimes contrary information in a medical record.

Referring back to FIG. 94, an entry field may receive input related to the selected category 3452. As shown in FIG. 94, the entry field is in the form of a text box with the informational label "Type. to get suggestions . . . ". This indicates to the user that she/he may start typing in this text box in order to get suggestions about rule items, such as the rule items shown in FIG. 96 labeled 3474.

Figure 95:
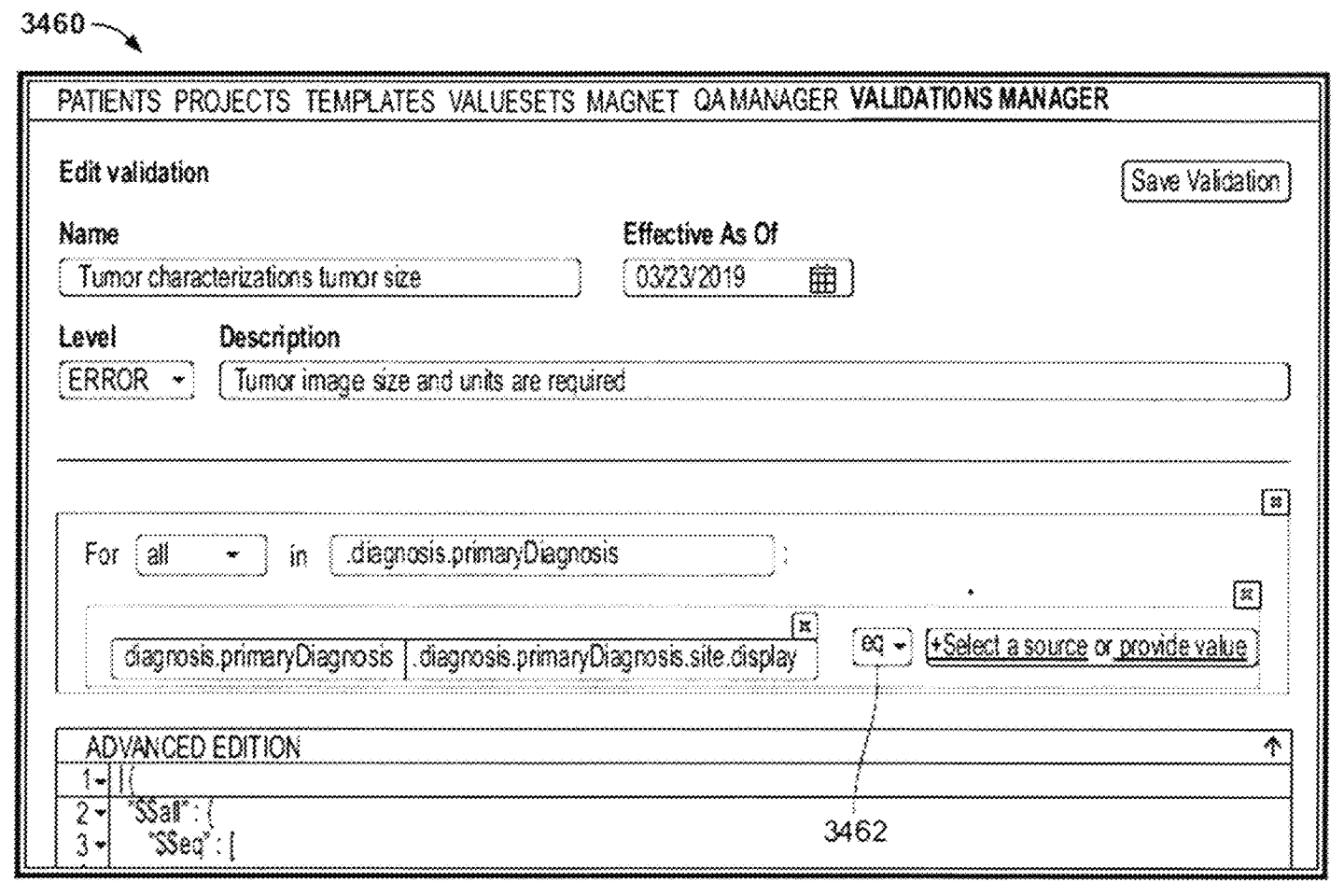
Figure 96:
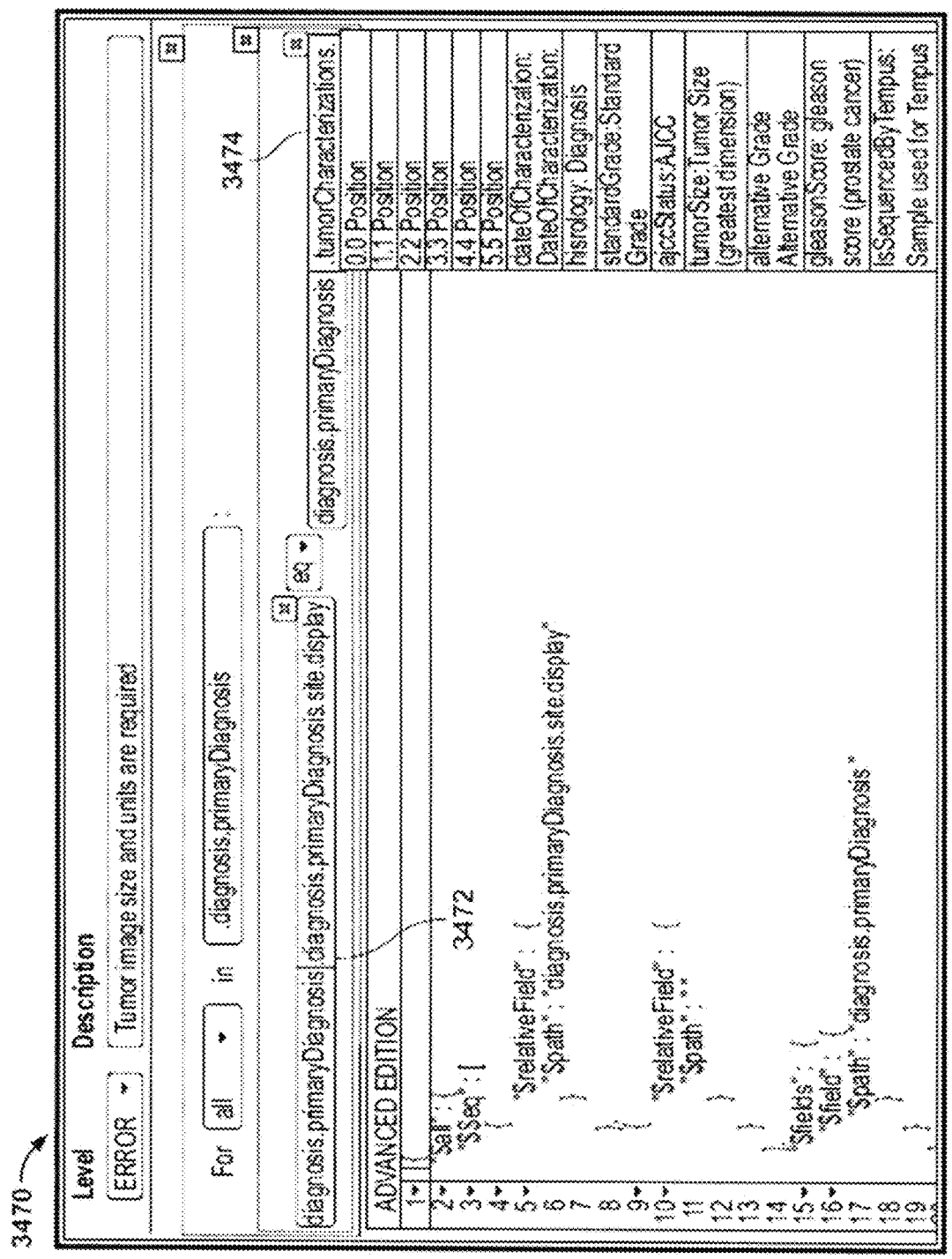
FIG. 96 is another image of an example graphical user interface (GUI), according to aspects of the present disclosure.
Figure 97:
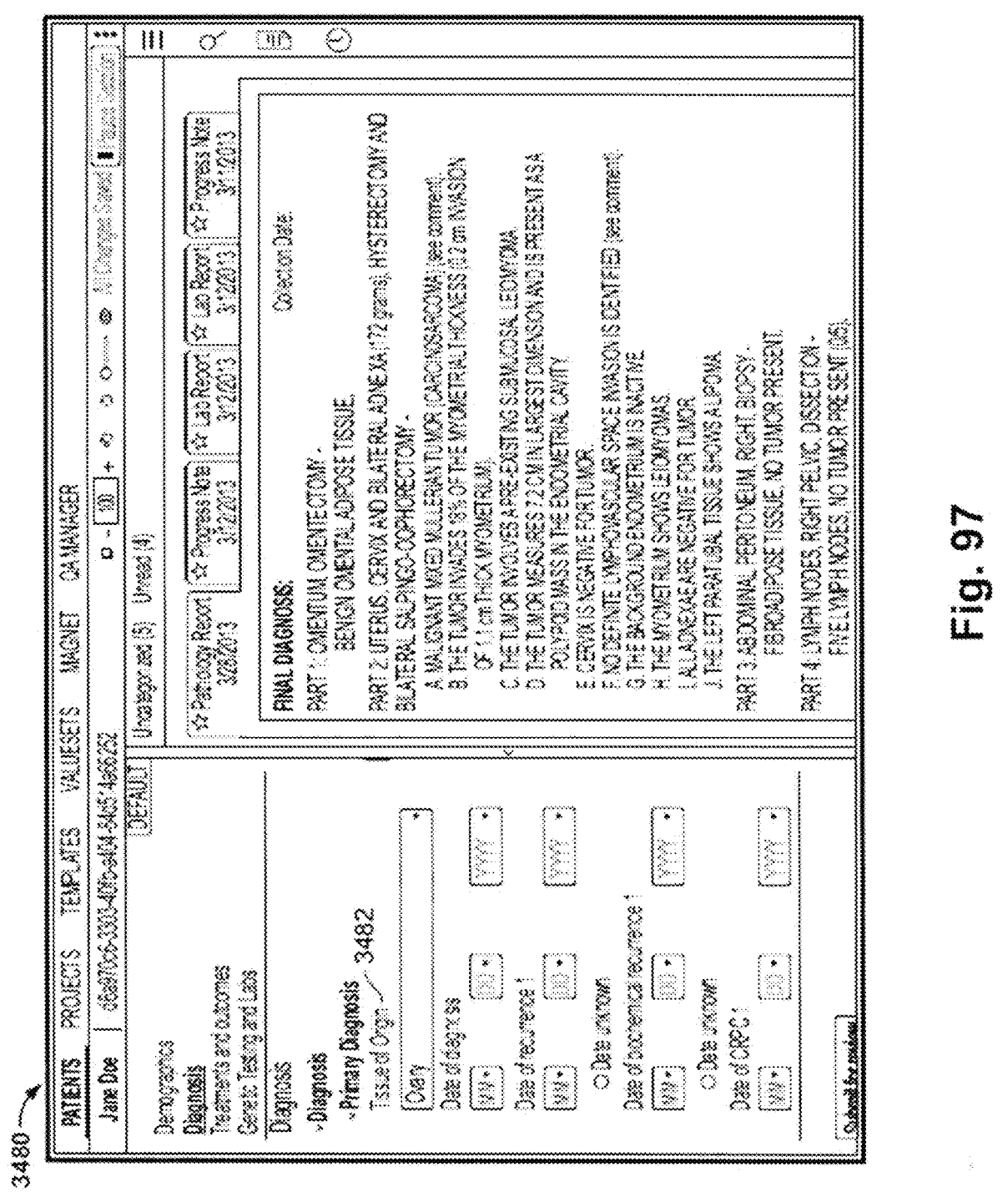
Figure 98:
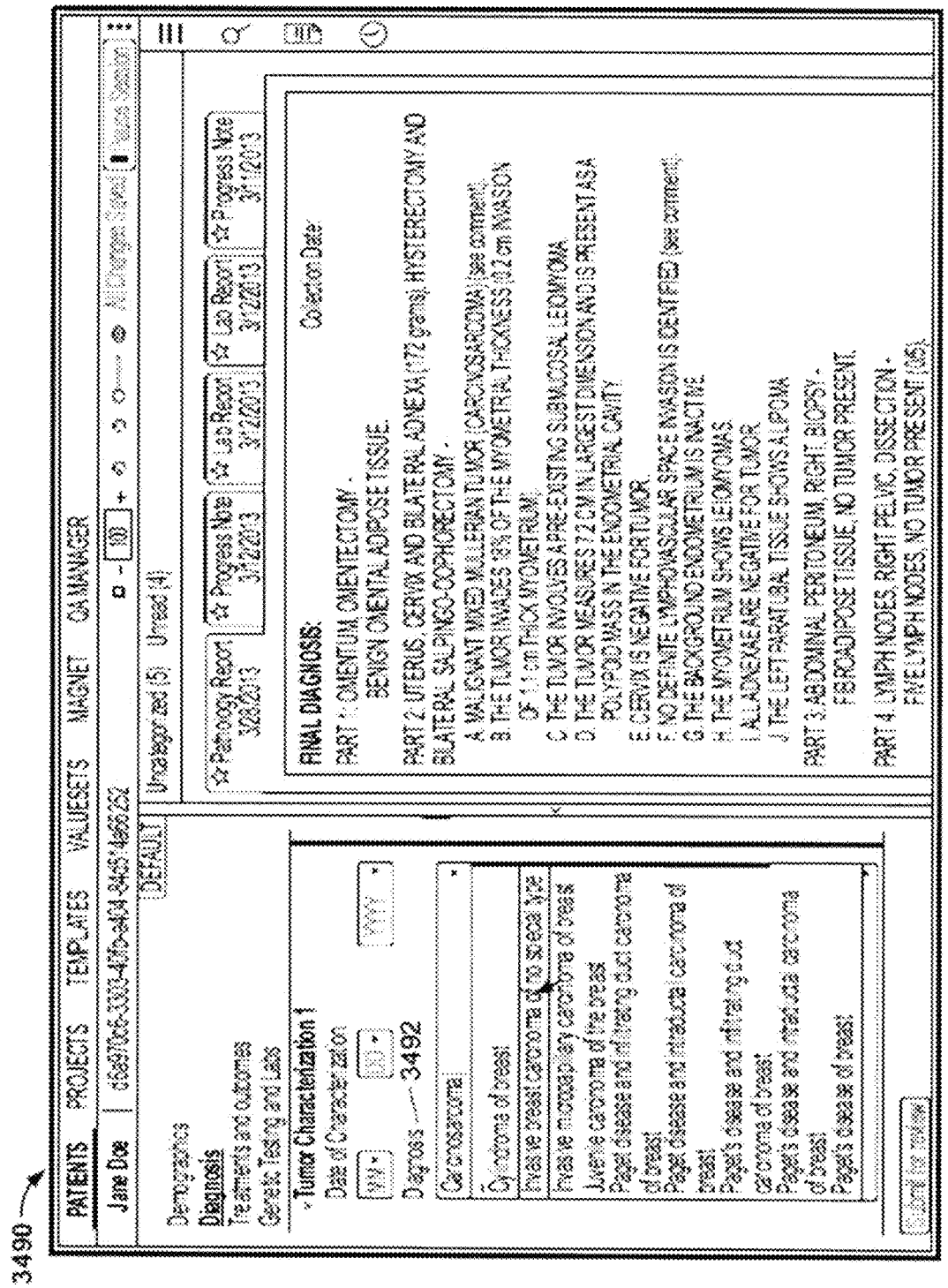
FIG. 98 is another image of an example graphical user interface (GUI), according to aspects of the present disclosure.

As shown by FIGS. 95-96, additional rules can be added to the new validation via GUIs 3460-3470. As an example, a comparison can be added as a rule using a selection tool such as a dropdown menu 3462. In this comparison, the query starts with primary diagnosis and the display text for the primary site As shown, system 3200 can consider every single diagnosis for a patient, and enforce the equality between the site display text for the primary diagnosis 3472 (e.g., "breast," "lung"), and any tumor characteristic 3474 that has been entered with a histology. As an example, FIGS. 97-98 show, via GUIs 3480-3490, a tissue of origin text 3482 corresponding to "ovary," and a diagnosis text 3492 that includes "carcinosarcoma." Accordingly, the equality of the new rule can be satisfied, and no new errors/warnings would result from the instant patient data.

Figure 99:
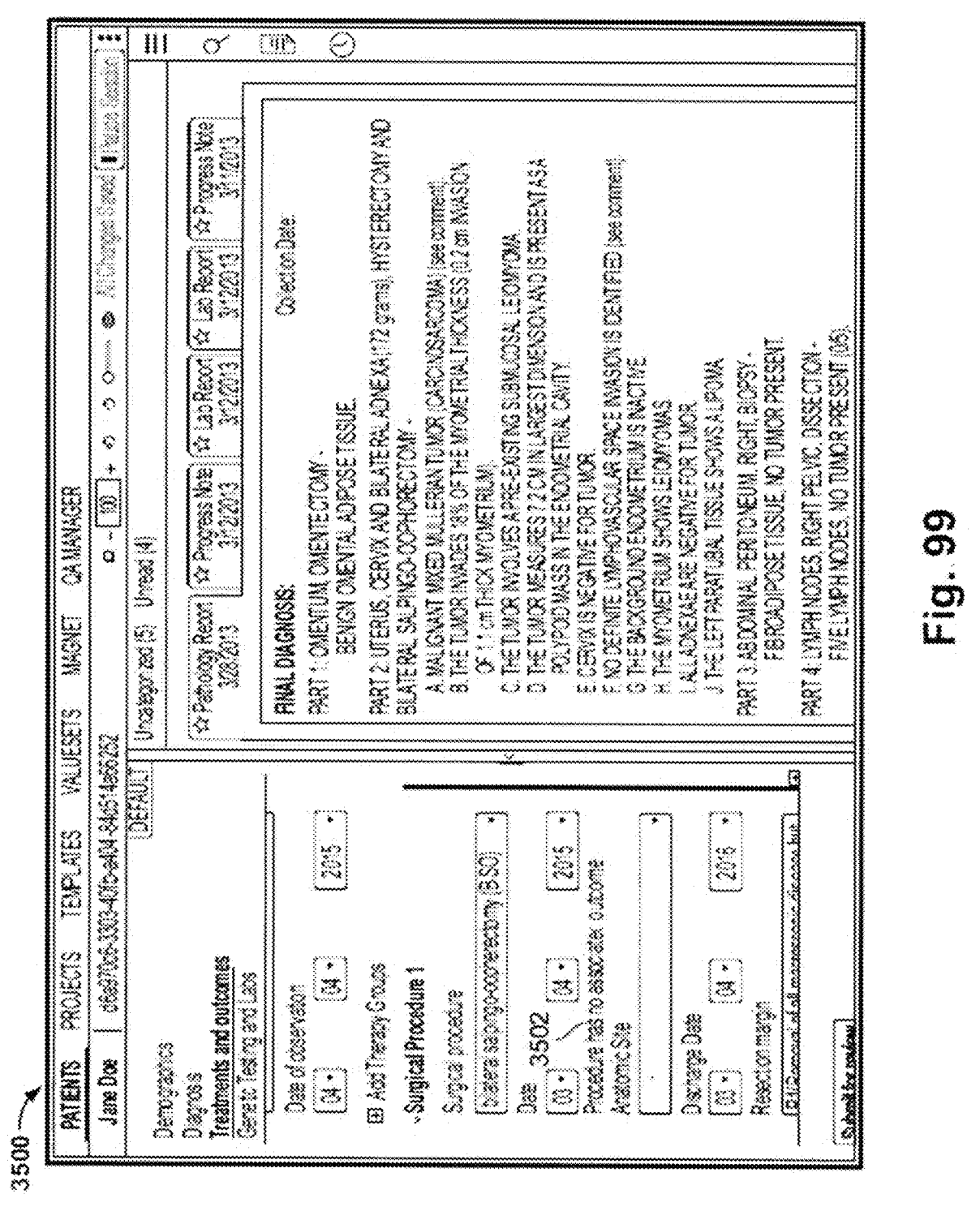

Referring now to FIG. 99, an example of a "soft" warning is shown, according to some embodiments. GUI 3500 can display a yellow warning text 3502, such as the text shown in FIG. 99. As shown, system 3200 expects a procedure outcome due to the input surgical procedure "bilateral salpingo-oopherectomy (BSO)." Notably, a user (e.g., a data abstractor) may still submit the patient data without resolving the soft warning, and the GUI 3500 may continue displaying the yellow warning text 3502.

Figure 104:
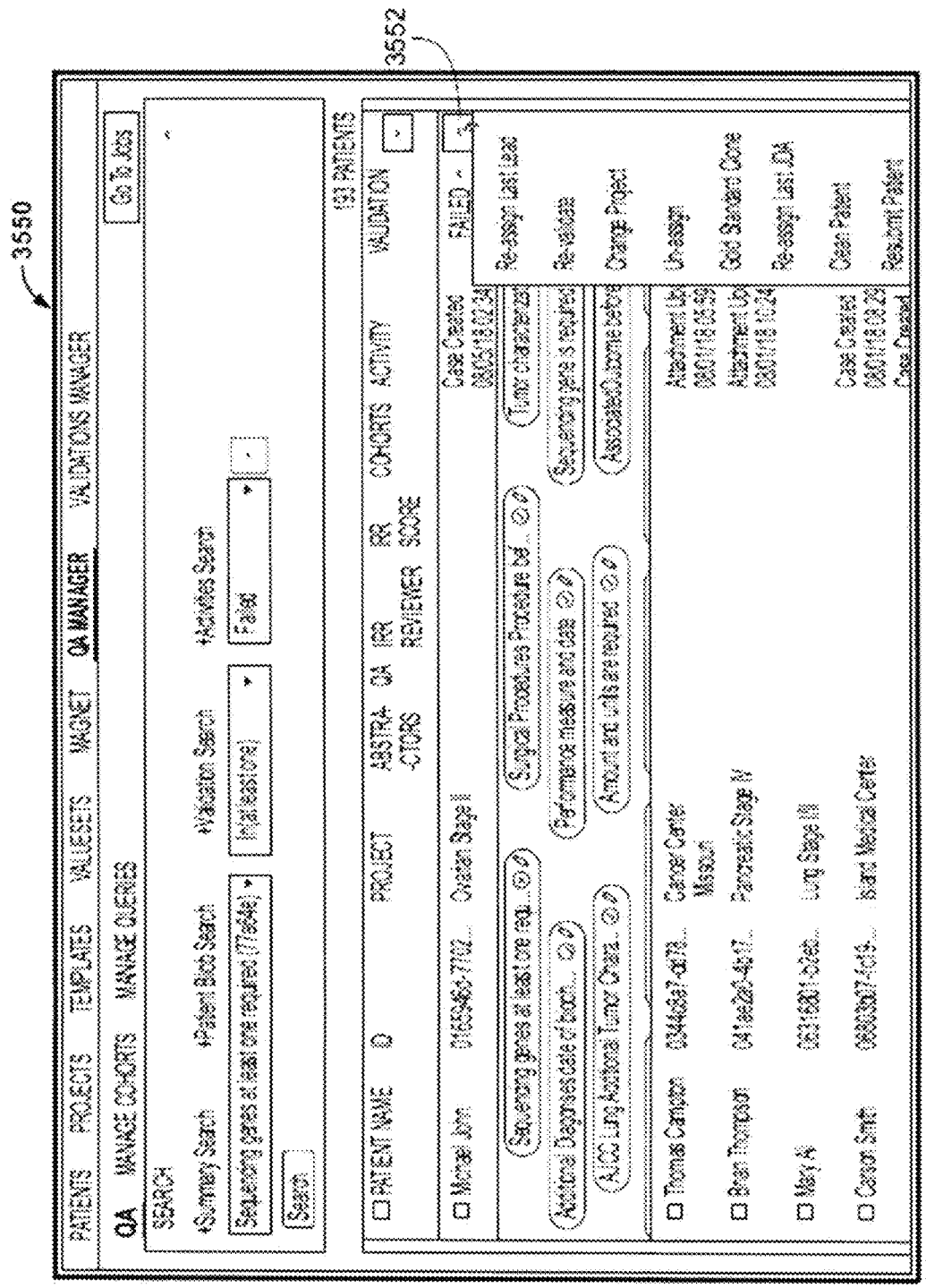
FIG. 104 is another image of an example graphical user interface (GUI), according to aspects of the present disclosure.
Figure 102:
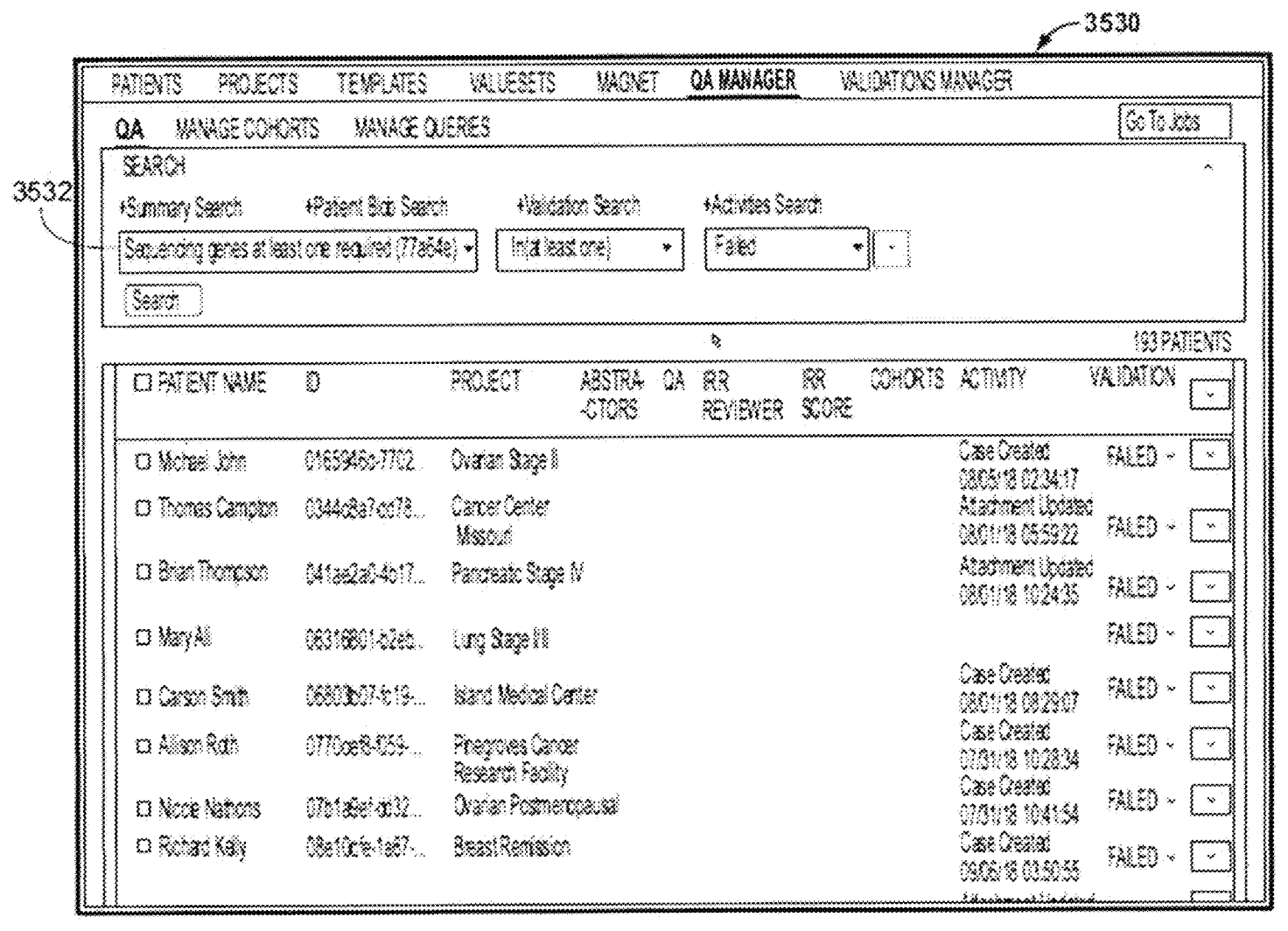
Figure 103:
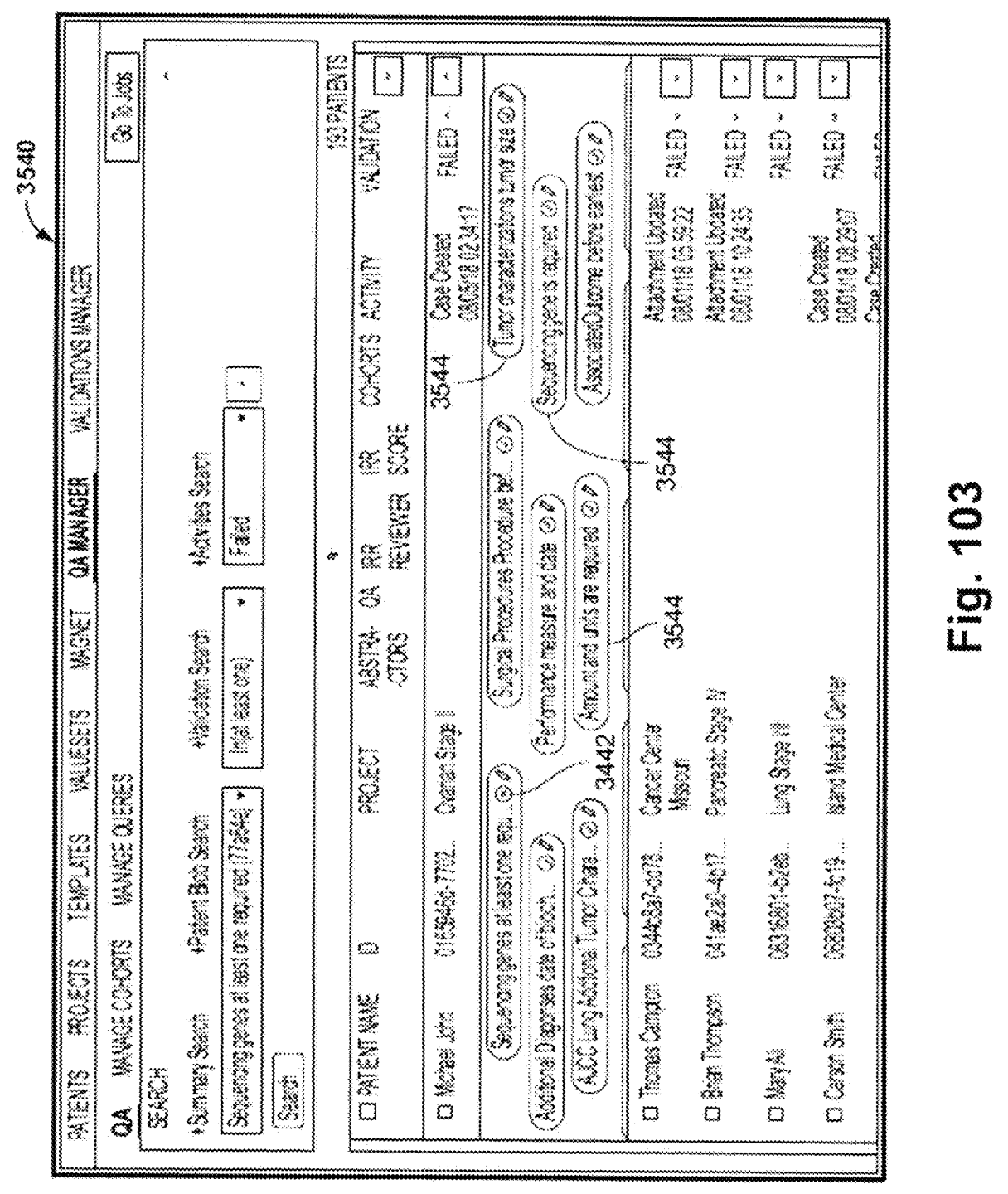

Referring now to FIGS. 100-104, a "QA Manager" module is shown, via GUIs 3510-3550, according to some embodiments. In some embodiments, the QA Manager can include a number of controls that allow users to find matching patient cases based on certain criteria. The controls may include one or more add search buttons 3512, which may be used to create one or more search rows 3522 corresponding to a search type such as a summary search, a patient search, a validation search, an activities search, or another applicable search type. Each search type may have one or more dropdown menus, search bars, or other input selectors to receive one or more search parameters. A search may permit the selection of a particular validation for further analysis. For instance, as shown in FIG. 102, the exemplary validation "sequencing genes at least one required (77a64e)" can be selected from a dropdown menu 3532 of existing validations. A user can, for example, search for all patients from one or more cohorts where that selected validation has "failed." In some situations, this search functionality can be used to efficiently resolve errors across many patients. Cases that are in a "failed" state can quickly be identified based on this status within system 3200, and action can be taken to resolve each case. As shown by FIG. 103, a user (via GUI 3540) can select individual patients, and a dropdown summary can be displayed. As an example, an error identifier 3542 indicates that the selected patient data failed the validation "sequencing genes at least one required." As shown, other identifiers 3544 indicate data types that were successfully validated. In some embodiments, a dropdown menu 3552 (as shown by FIG. 104) can provide several options for the selected case/patient. In particular, the case/patient can be reassigned to a different abstractor (or "JDA"), assigned to a new manager (or "Lead"), moved to a different project, or resubmitted, among other things.

In some embodiments, role-specific errors and/or warnings can be included within system 3200. This can include, for example, requiring a user (such as a data abstractor) to acknowledge a soft warning before submitting the patient data for review. In some embodiments, this can further include prompting a user to provide a rationale for ignoring the soft warning. Advantageously, this can ensure that users are at least aware of the soft warnings prior to submitting the patient data.

In some embodiments, the workflow management system can accommodate not only written patient documents, but also electronic medical records (EMRs). For example, the workflow management system may be integrated into an existing EMR platform, such as the EMRs offered by companies like Epic, Cerner, or other providers. When integrated into an existing EMR platform, the workflow management system can, according to some embodiments, automatically pre-populate data fields within system 3200. Accordingly, data abstractors can verify/correct pre-populated data as opposed to exclusively performing manual data entry.

Additionally, in some embodiments, optical character recognition (OCR) and natural language processing (NLP) can be implemented to pre-populate data fields from written/scanned patient documents. Once pre-populated, the data fields may be displayed to a user for manual approval, or the data fields may be automatically approved based on predetermined criteria, such as a threshold that indicates the probability that the pre-populated information is in error is less than an error rate for manual data entry.

Referring broadly to FIGS. 105-120, GUIs 3560-3720 show details corresponding to the "Templates" module, according to some embodiments. A user can utilize a template created in the "Templates" module in order to allow a data abstractor to ingest clinical records from various sources (such as a clinical record) and convert that data to normalized and system optimized structured data sets specified in part by the template, according to some embodiments.

Figure 105:
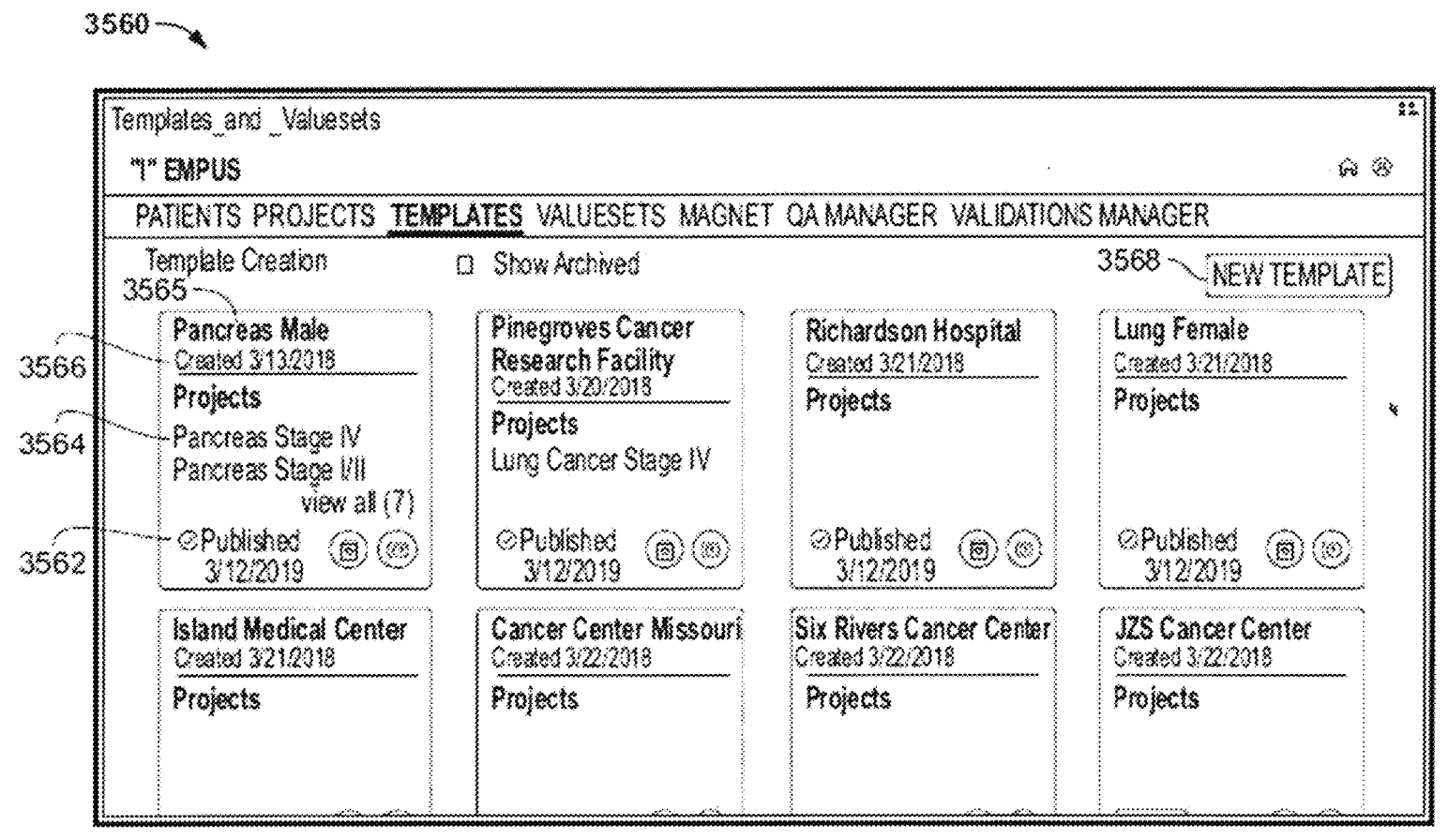

Referring to FIG. 105, GUI 3560 shows details corresponding to the "Templates" module. A template 3562 can be linked to one or more projects, and can specify what types of data fields can be input for patients in each linked project, as will be explained below. Each project linked to the template 3562 can be shown in a project list 3564. Each template can have a name 3565 and a "date created" 3566 displayed. Each template 3562 can be used to quickly and dynamically change data fields of each patient case belonging to a given project. A new template can be created by selecting a "new template" button 3568.

Figure 106:
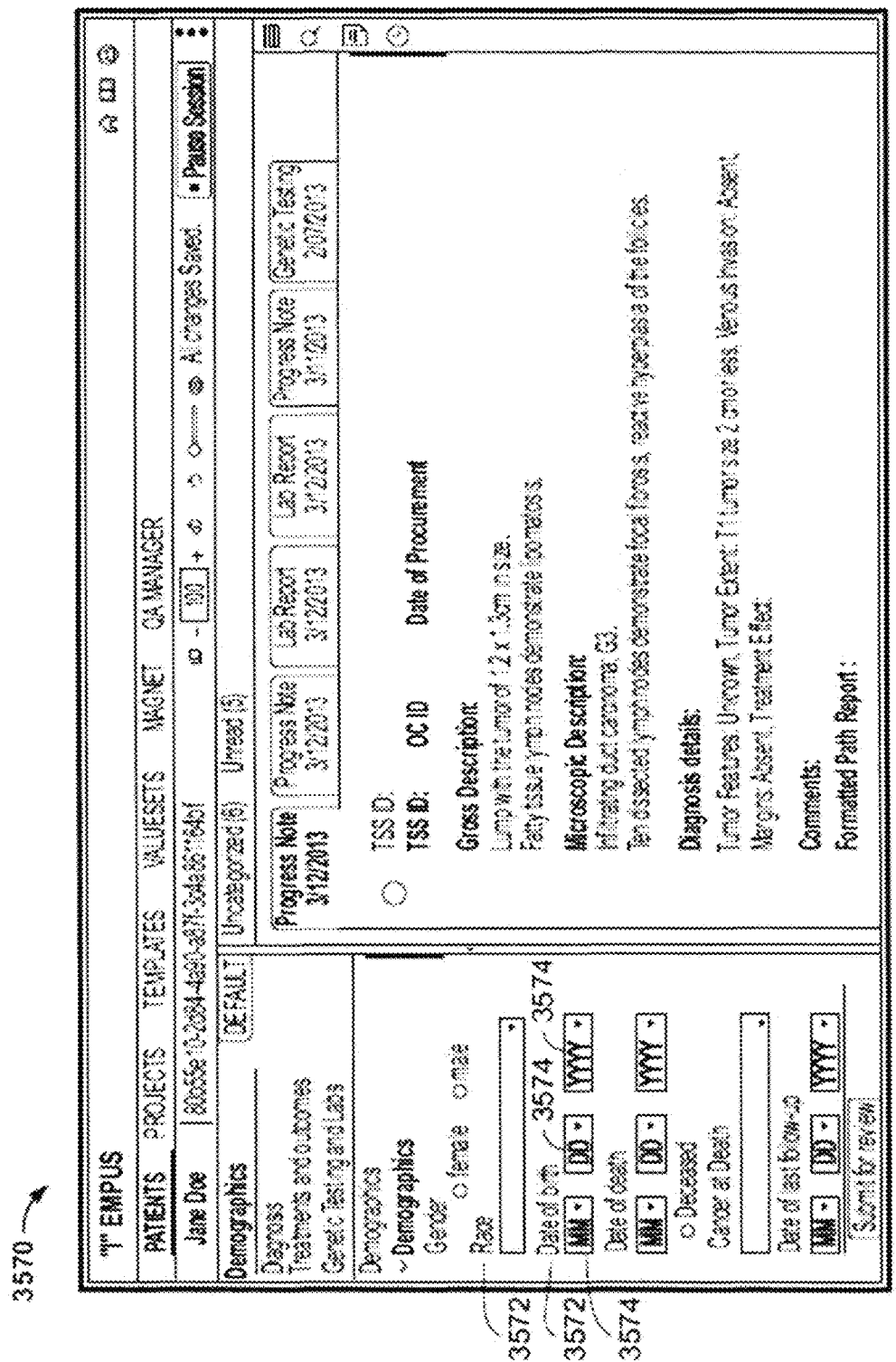
FIG. 106 is another image of an example graphical user interface (GUI), according to aspects of the present disclosure.

Referring to FIG. 106, GUI 3570 shows details corresponding to the "Patients" module. The template (e.g., template 3562) can be used to set one or more data fields that are enabled for use by the abstractors in the "Patient" module for each patient case in the project. In some embodiments, a data field 3572 may have one or more nested elements 3574, such as in the case of the data field "Date of birth," which can have nested elements "Month," "Date," and/or "Year." A client such as a hospital can provide raw data in the form of clinical documents, pathology reports, progress notes, testing data, electronic medical records (EMRs), or other relevant medical history data for each patient. A client can have any number of projects, and some projects may have the same template. In some embodiments, the same template may be used across multiple projects and/or multiple clients. For instance, if Hospital A and Hospital B each require services to structure their clinical data for stage III ovarian cancer, one template may be prepared with the data fields most relevant to stage III ovarian cancer and then utilized for Hospital A's project and for Hospital B's project. In some embodiments, each data field or nested element can have a data type such as repeatable, select, text, row, text, dropdown, date, Boolean, or combinations thereof such as dropdown and date. Some data fields in each patient case may be pre-populated depending on the type of raw data containing the relevant information for the data field. For example, optical character recognition (OCR) may be run on certain file types, and the data extracted using OCR can be used to pre-populate certain data fields 3572 and/or nested elements 3574.

Figure 107:
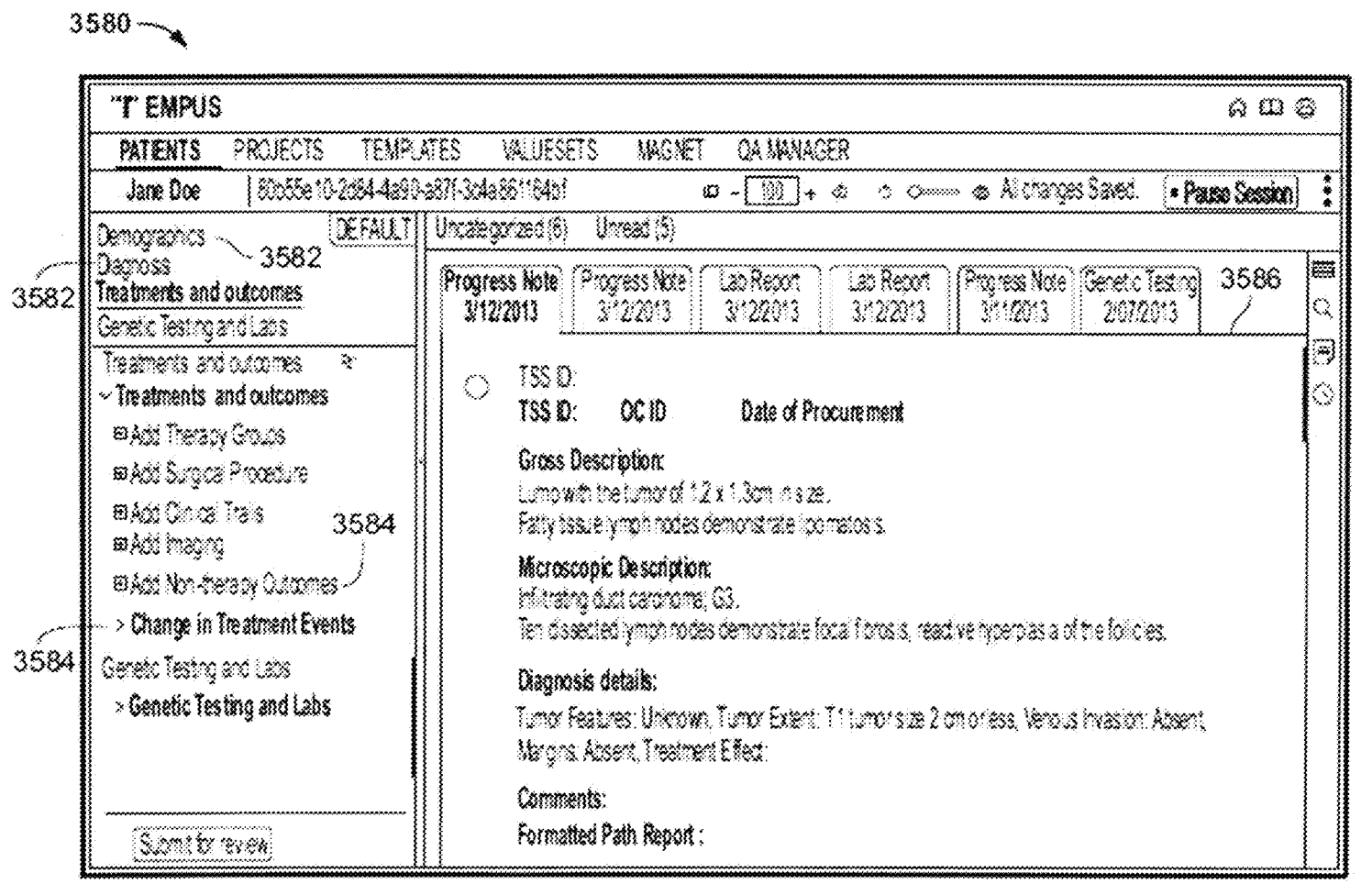
Figure 108:
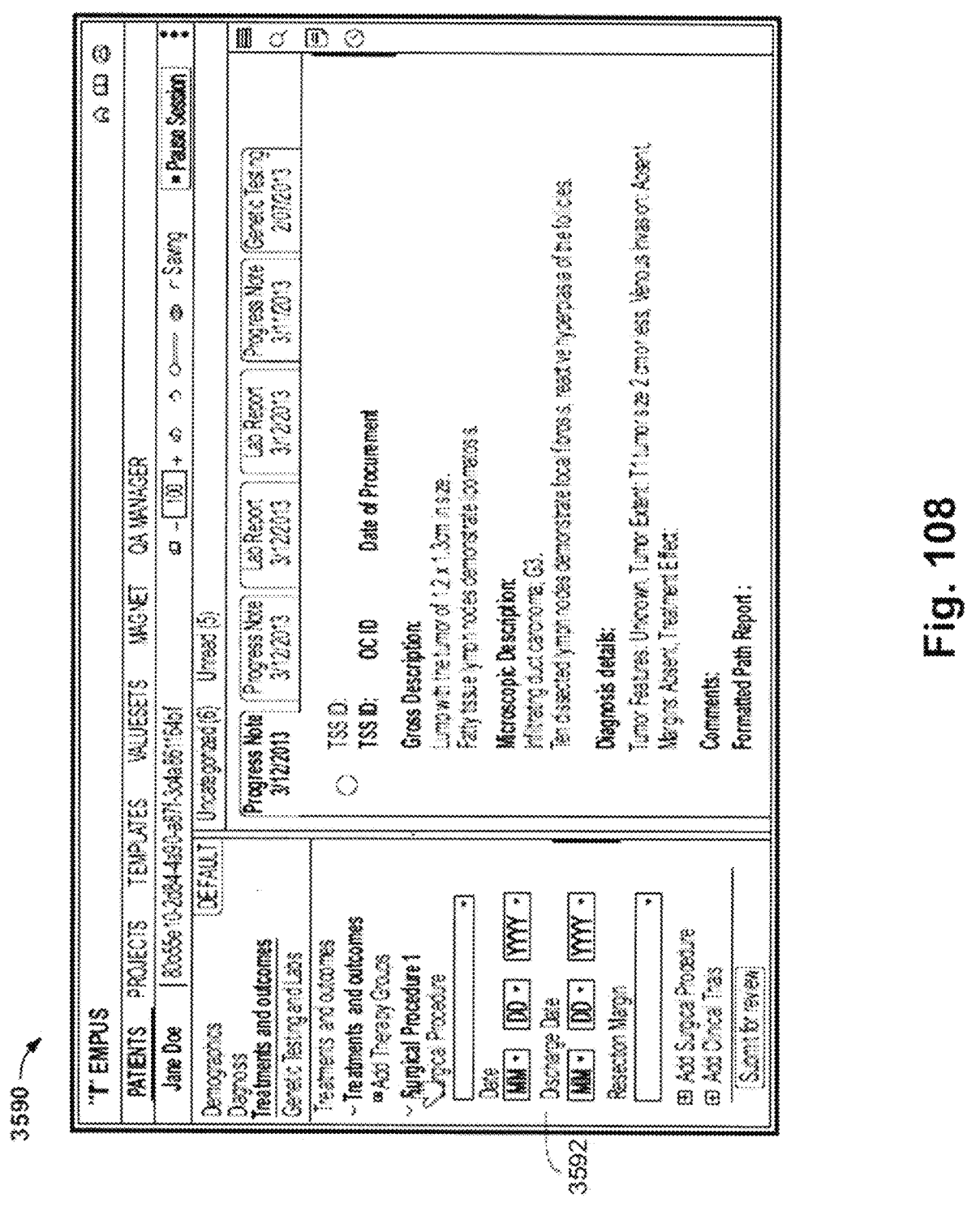
Figure 109:
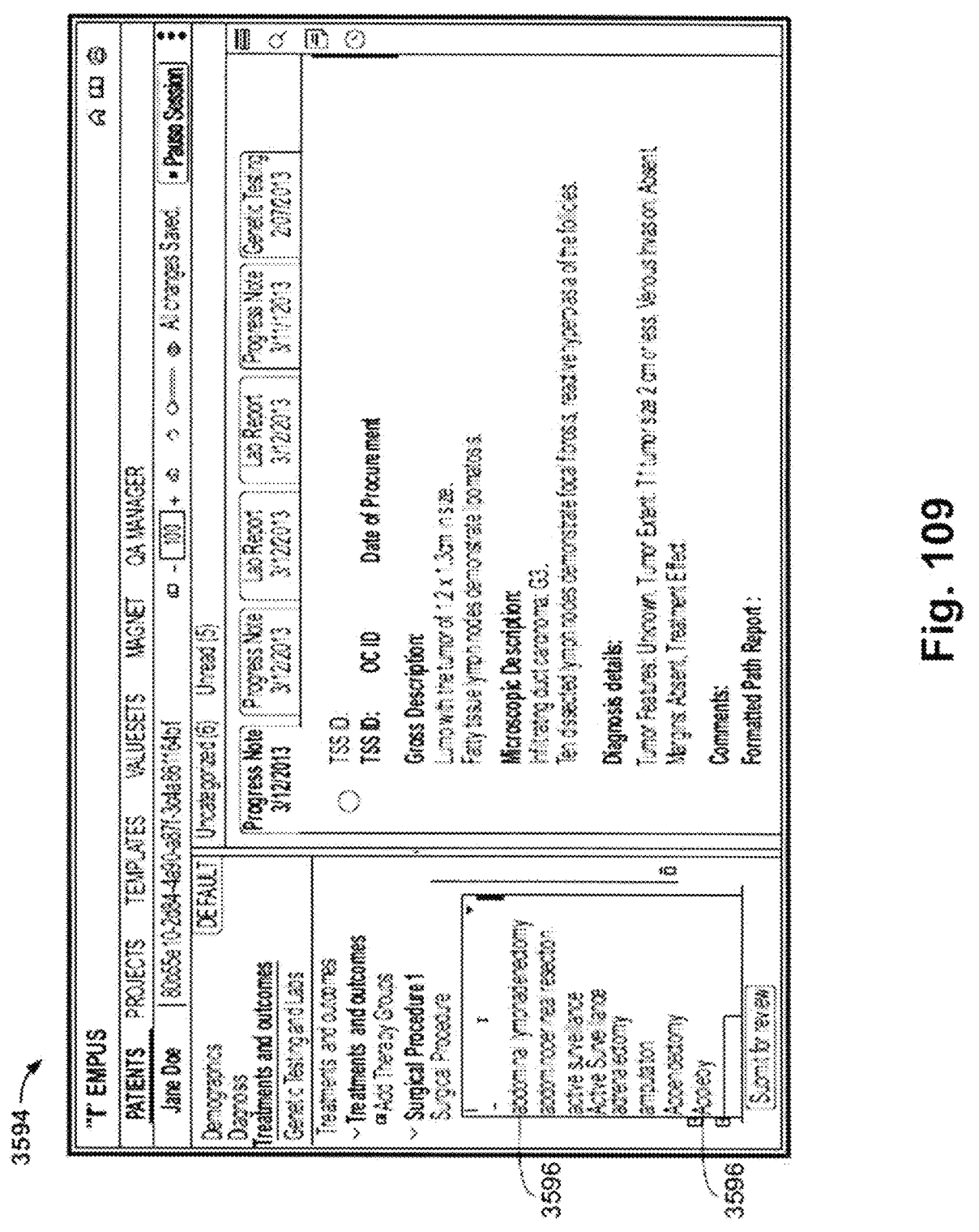

Referring broadly to FIGS. 107-109, GUIs 3580-3594 show details corresponding to the "Patients" module. For each patient case in a project, abstractors can view the data fields 3582 of the template corresponding to the project. The abstractors can then populate any unpopulated data fields 3582 in the patient case when extracting information from the raw data (e.g. progress notes, lab reports, genetic testing results, and so forth) of the patient case. Some data fields 3582 can be populated using a dropdown menu containing one or more field values 3596. The field values 3596 can be selected or set in the "Templates" module and/or the "Valuesets" module, as will be explained below.

One or more patient documents 3586 from the data provided by the client can also be viewed simultaneously, in tabbed fashion as shown in the figures, along with the data fields 3592 to allow the abstractor to efficiently populate the data fields 3592 and any required nested elements (e.g., nested elements 3574) of the data fields, according to some embodiments. The system 3200 can load the patient documents 3586 using a patient identification code of the patient case. The data fields may be categorized by a root category 3582 such as demographics, diagnosis, treatment and outcomes, genetic testing and labs, or any other category that may help better organize the data fields.

Each root category 3582 can have one or more sub-categories 3586 to further organize the data fields. Some root categories 3582, sub-categories 3584, and/or data fields 3592 can be related to oncology, diabetic disorders, neurological disorders, or any other branch of medicine. The root and/or sub-categories of each data field can be changed depending on the project using the "Templates" module. For example, a data field such as "diabetes" may be categorized in the "demographics" category for one project while being categorized in the "diagnosis" category in another project. The enabled data fields from the project's template can be shown to the abstractor.

Referring to FIGS. 110 and 111, GUIs 3600 and 3620 show details corresponding to the "Patients" module. Certain data fields can have one or more soft warning messages 3610 and/or one or more hard warning messages 3622 that the system 3200 displays based on a set of rules for the data fields stored in the template. Each rule can prevent the abstractor from entering improper data and/or the abstractor from saving a patient case if the rule is violated, as described in detail above with respect to FIGS. 81-104.

Figure 112:
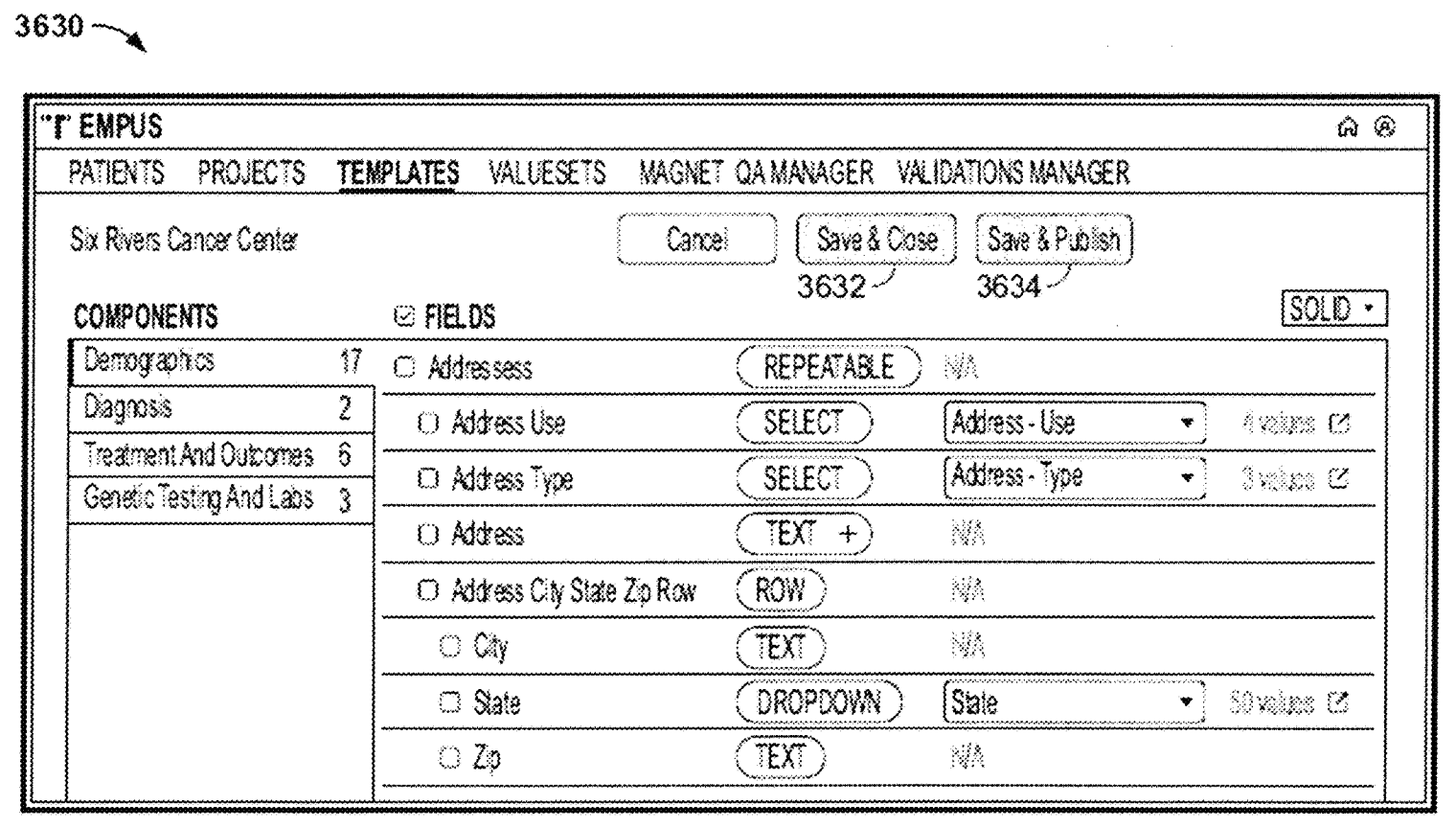
Figure 113:
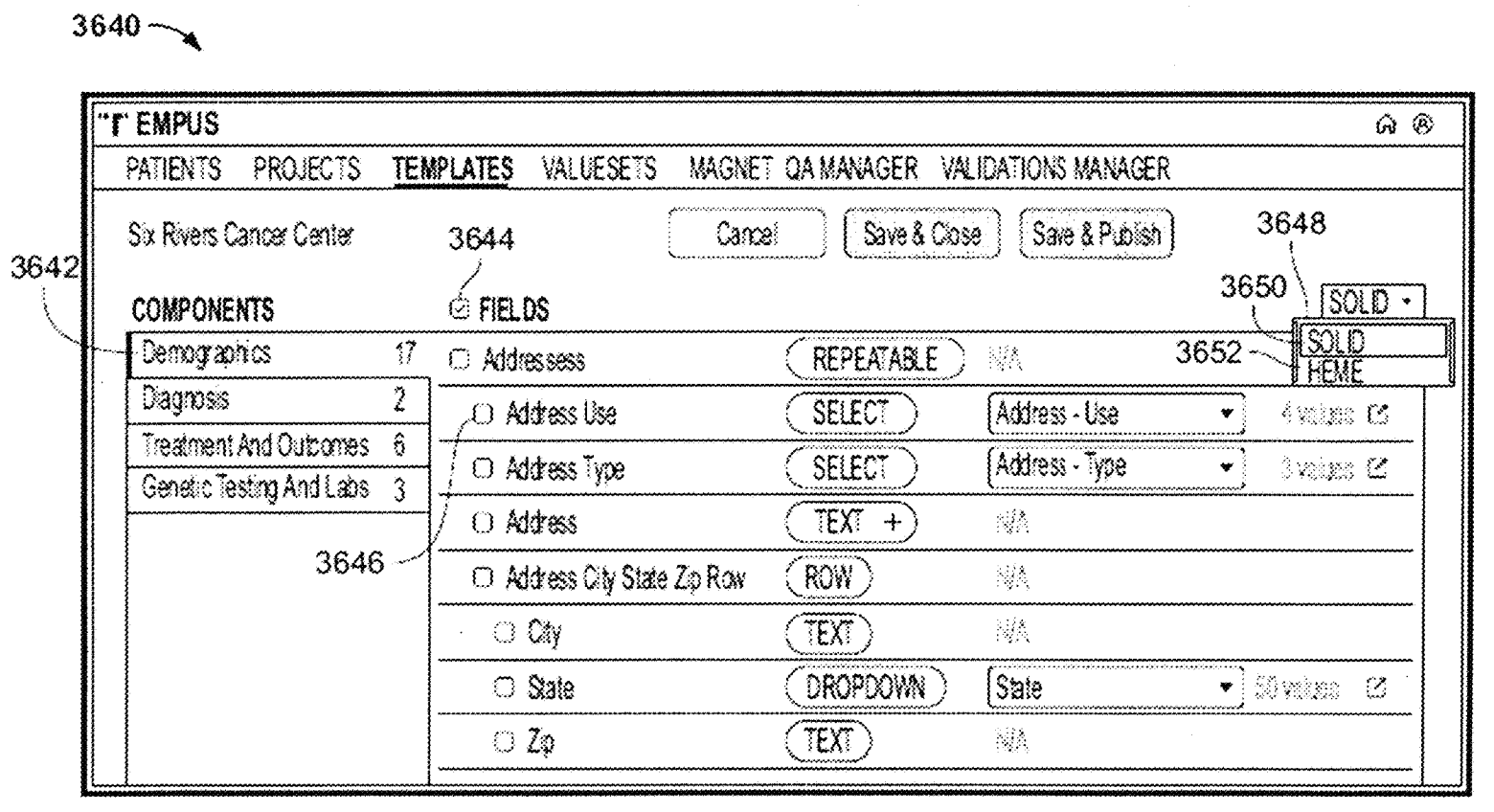
Figure 114:
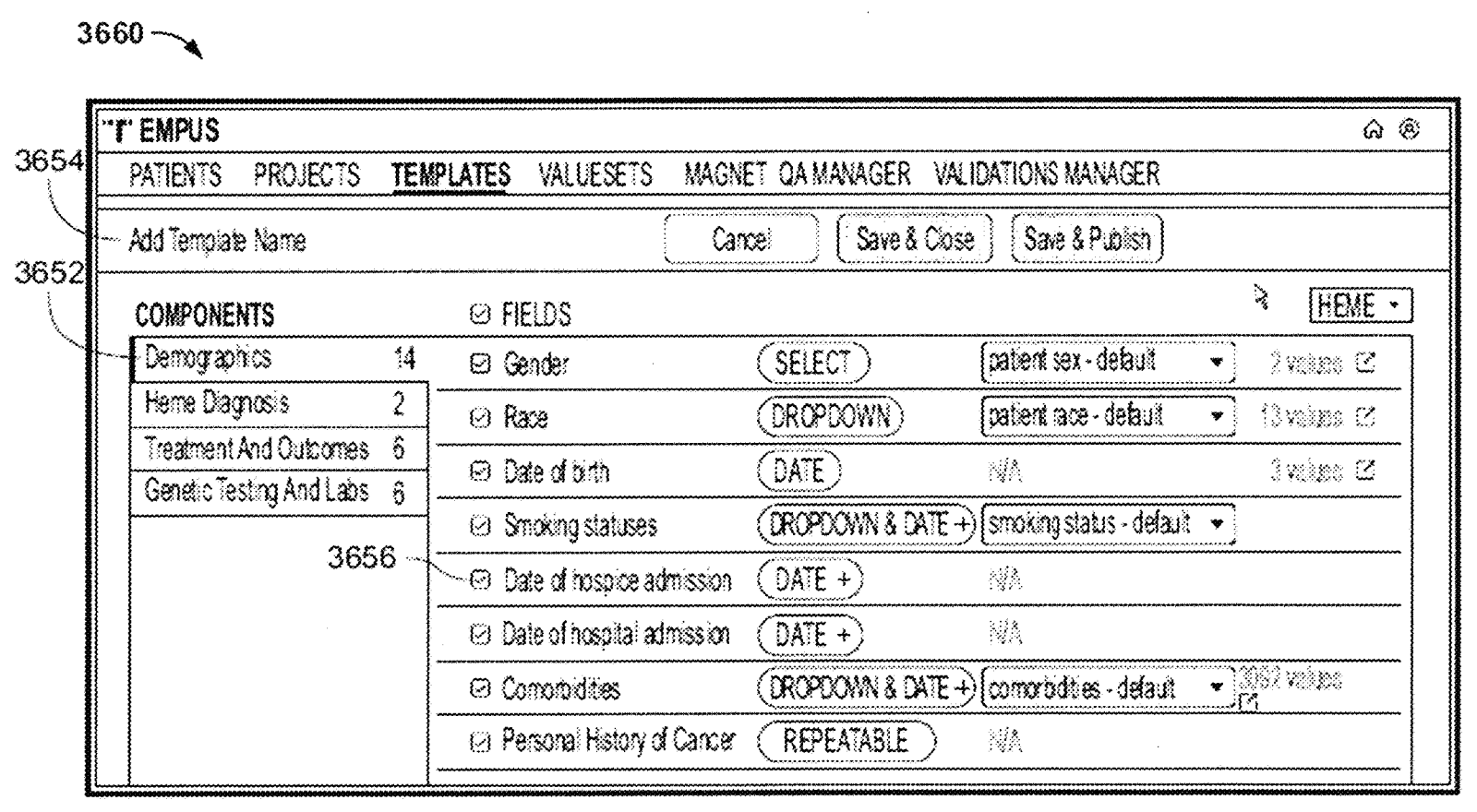

Referring broadly to FIGS. 112-114, GUIs 3630-3660 show details corresponding to the "Templates" module. A user can save a template using a save and close option 3632, which can allow the template to be saved but not published. When the template is published, any projects using the template (i.e. linked projects) will be updated by the system 3200 to have the data fields of the new template available in the "Patients" module and, in some examples, elsewhere throughout the system. If the template is saved but not published, the abstractor working on a patient case in a project may not see any changes to the data fields of the template, such as updates to the data fields and/or added or removed data fields. In some embodiments, the system 3200 may periodically save the template without publishing.

Alternatively, a user can save the template using a save and publish option 3634, which can allow the template to be published to projects and/or patient cases using the template. In other words, the abstractors or end users of projects and/or patient cases will see all updated, added, or removed data fields of the template. In some embodiments, the user may be prevented from removing or modifying any active fields, i.e. fields that have a checked box, in order to preserve data from being lost and/or protect the template. In some embodiments, the user may be allowed to add more active fields after publishing. In some embodiments, the template may be published, but only with respect to projects selected by the user.

Each category and/or data field may be defined and stored within a database associated with the system 10, and re-used as needed for individual templates. Each category and/or data field can belong to one or more template medical groups corresponding to various branches of medicine, conditions, diseases, or disorders that can be selected from medical group dropdown menu 3648. For example, there may be a solid tumor group 3650 of categories and data fields and a heme group or blood cancer group 3652 of categories. In some embodiments, the solid tumor group 3650 may include a diagnosis category, while the heme group 3652 may have a heme diagnosis category. Some categories may have a different number of data fields in different template medical groups, for example the solid tumor group 3650 may have seventeen data fields in the demographics category 3642, while the heme group 3652 may have fourteen data fields in the demographics category 3662. The categories and data fields of the medical group can be selected by a user to be present or not present.

After a template has been named and/or saved, the "Templates" module may prevent the user from switching the medical group of the template in order to prevent templates from overlapping and/or loss of data populated in the data fields. The system 3200 may display a warning such as a red box 3664 in response to a user attempting to change the template's medical group after naming and/or saving the template. A dropdown menu of valueset options of some data fields may change between template medical groups. In some embodiments, the "Templates" module may allow cross population of data fields and/or categories between multiple template medical groups. In these embodiments, the data fields may be labeled and/or grouped by template medical group. For example, data fields unique to the solid tumor group 3650 would be marked to clearly differentiate from the data fields of the heme group 3652. As templates are improved or revised, the system may save each separate version so that a user can revert to a prior template version. Each version may store the content of the template, including the enabled data fields, the types of each field, the valuesets related to each data field, and the values related to each valueset.

Once the template medical group has been selected, the user can choose which of the data fields and/or nested elements of the data fields to present or not present in the template and to show or not show in the "Patient" module by checking or not checking a box 3646 by each data field name. Active fields can be marked by a checked box such as box 3530. A user may select or deselect all data fields in a category or template by checking or unchecking a select all box 3644.

Figure 116:
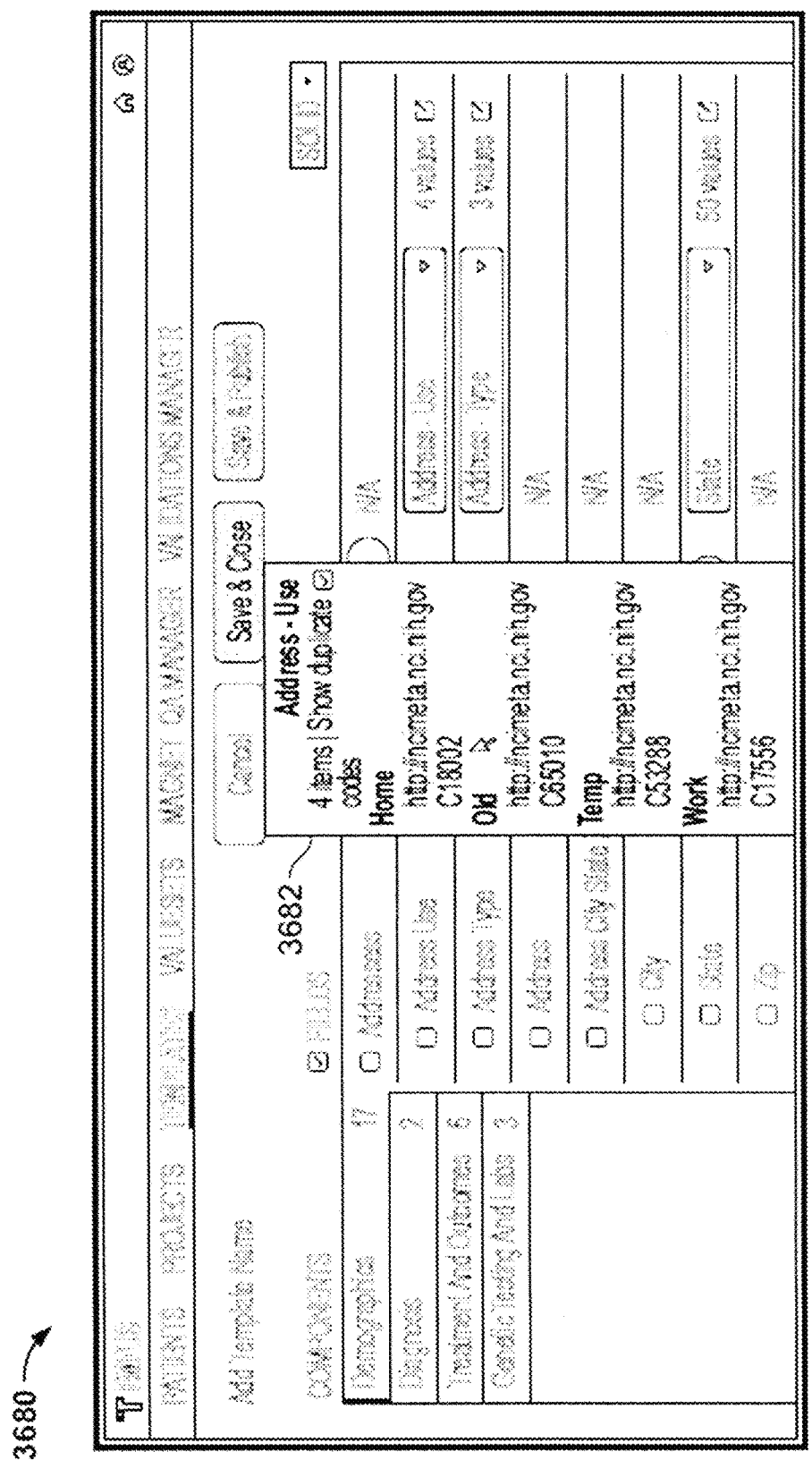
Figure 115:
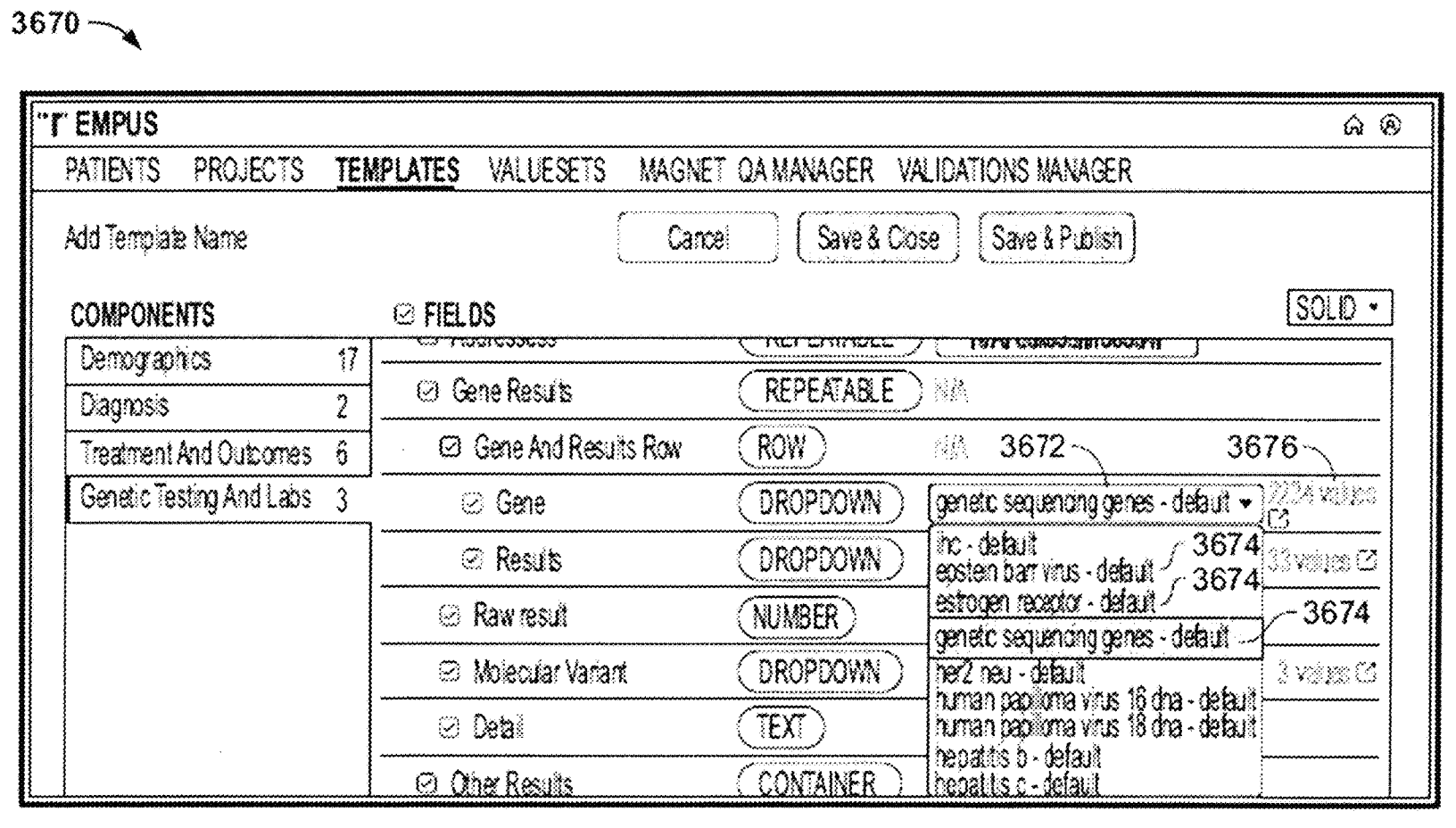
Figure 117:
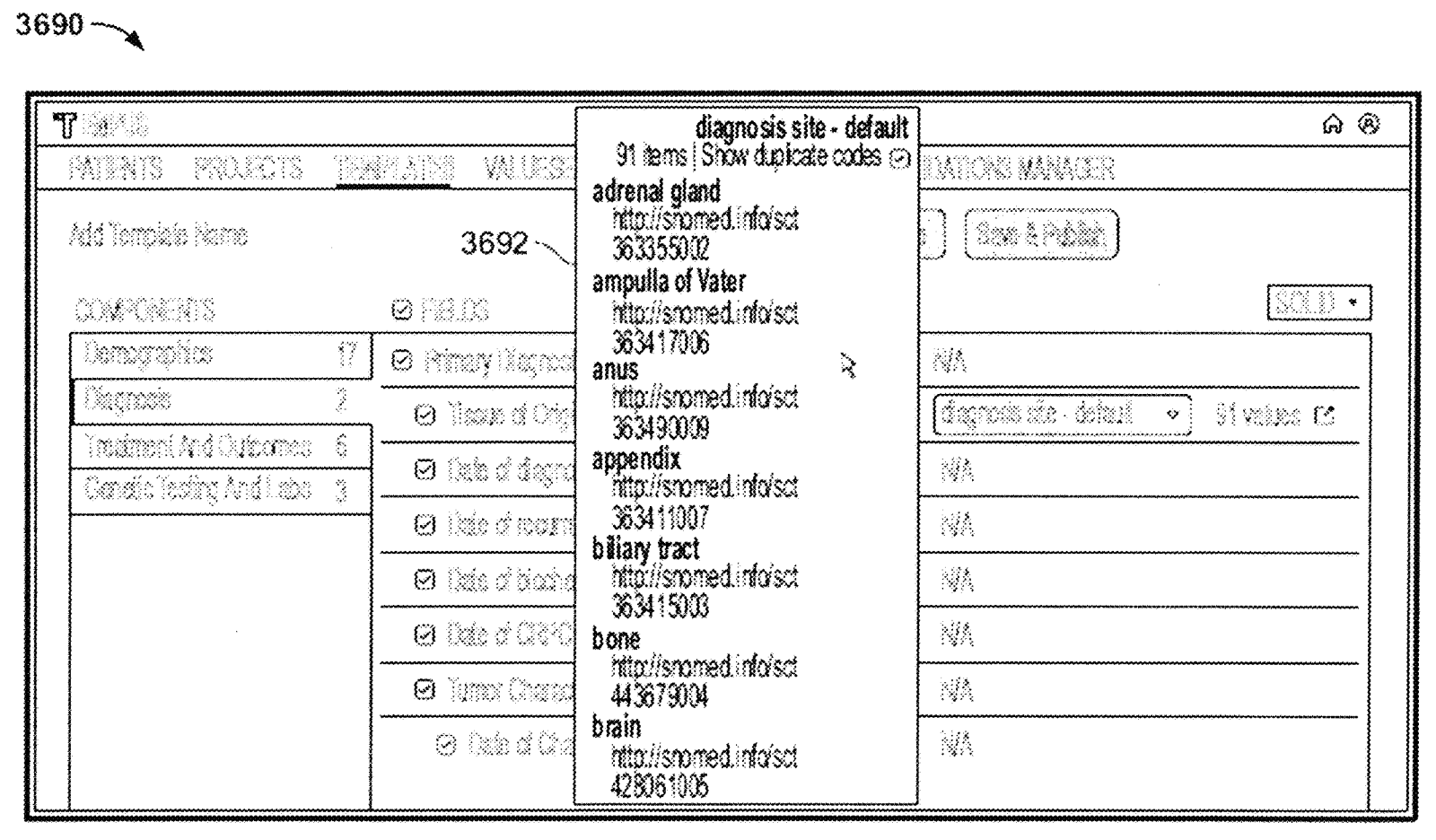

Referring broadly to FIGS. 115-117, GUIs 3670-3690 show details corresponding to the "Templates" module. Some data fields and/or nested elements such as the address use field may have a valueset dropdown menu 3672 with a one or more valuesets 3674, each valueset 3674 having a set of values for populating the data fields that an abstractor can select from when populating the data field using the "Patients" template. A valueset size 3676 of the selected valueset 3674 can be displayed near the valueset dropdown menu 3672. The actual values 3682, 3692 of the selected valueset 3674 may be viewed by a user by selecting the valueset size 3676 on the GUI (e.g., GUI 3670, 3680, 3690).

With respect to FIG. 115, the "genetic sequencing genes—default" valueset is selected. This valueset has 2234 values, with each value representing a specific gene that may be abstracted from a medical record, such as a genomic sequencing report. Valuesets may be amended to add, subtract, or modify their associated values, and re-saved with the modified values for further use throughout the system.

For instance, as shown in FIG. 117, a portion of values in the "diagnosis site—default" valueset are displayed in a pop-up window. The values include a description of the diagnosis site and an associated URL with a SNOMED code associated to the diagnosis site. It should be apparent that the values may contain more than as many type or quantity of data fields in order to sufficiently characterize the value, including but not limited to text descriptors, number descriptors, URLs, FHIR elements, and so forth.

A valueset can be selected for certain data fields and/or nested elements in order to help the abstractor find values more efficiently. Some values in data fields or nested elements such as a gene nested element can be associated with one or more other data field values such as a testing provider or test method, which can be used to filter the number of gene options available to the abstractor using the "Patients" module. Certain genes may only be associated with certain testing methods, and eliminating non-associated genes reduces the lookup time for the abstractor.

Figure 118:
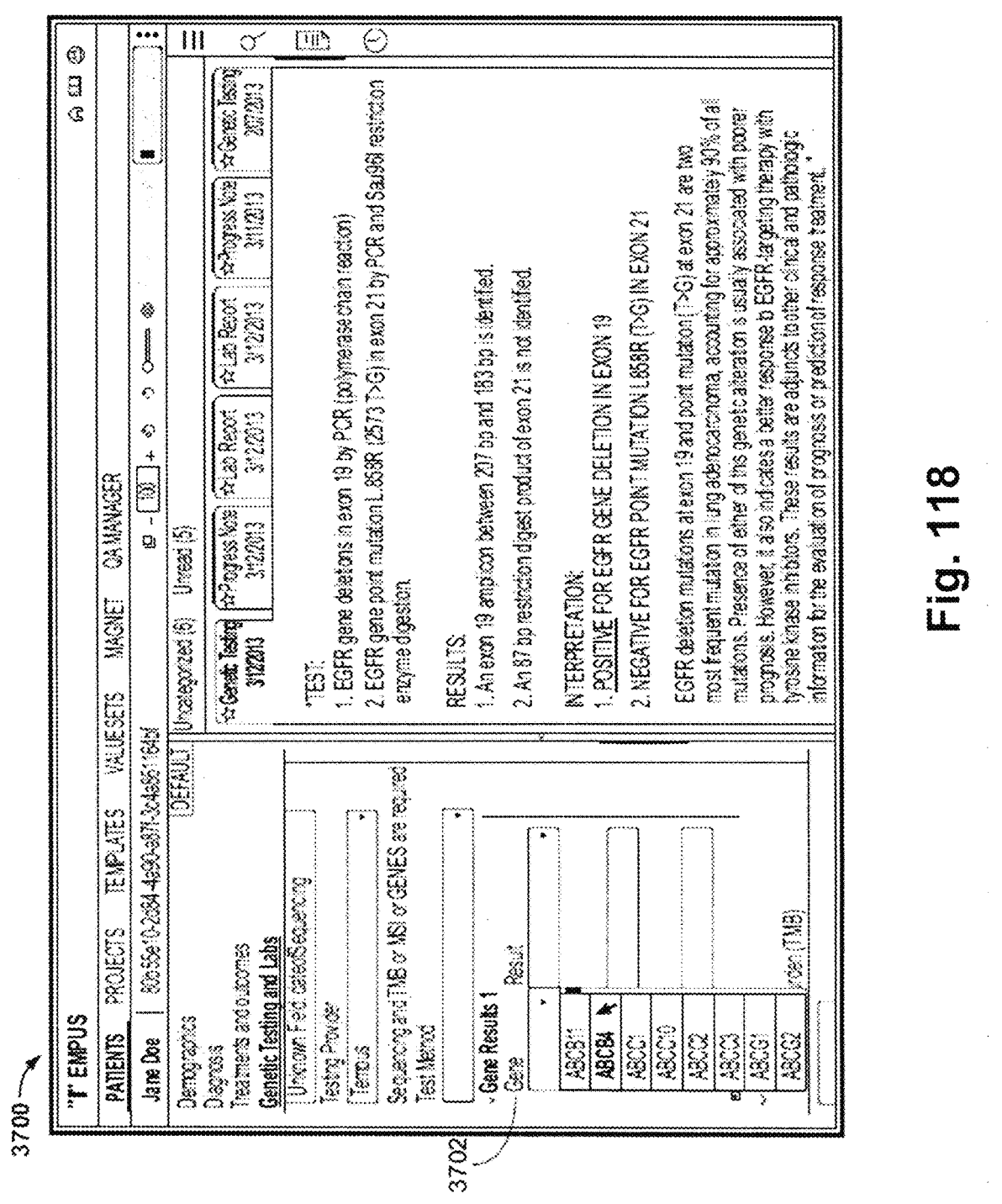

Referring to FIG. 118, GUI 3700 can display the values of the chosen valueset for certain data fields using the "Patient" module. Some data fields 3702 such as the gene data field may have over two-thousand values in a given valueset, as one example. A user with proper access to editing valuesets can select the values available for the data field or nested element by modifying a valueset associated with the data fields using the "Valuesets" module. Certain users such as administrators with sufficient privileges may be able to add new fields and/or modify the corresponding attributes of the valueset associated with the field. Different valuesets can be selected in order to reduce the number of options available for the abstractor for certain data fields and/or nested elements such as the gene nested element.

Figure 119:
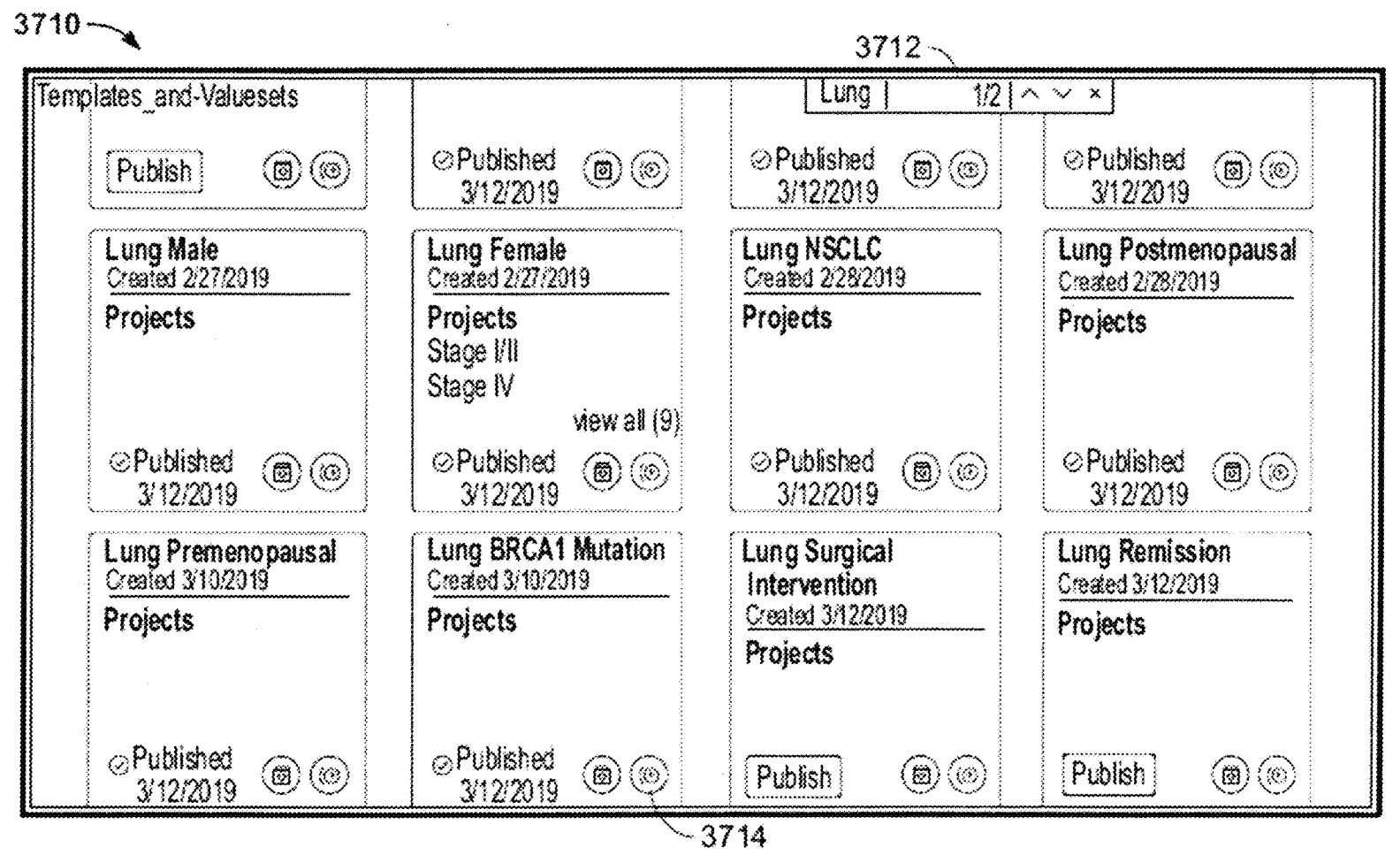
Figure 120:
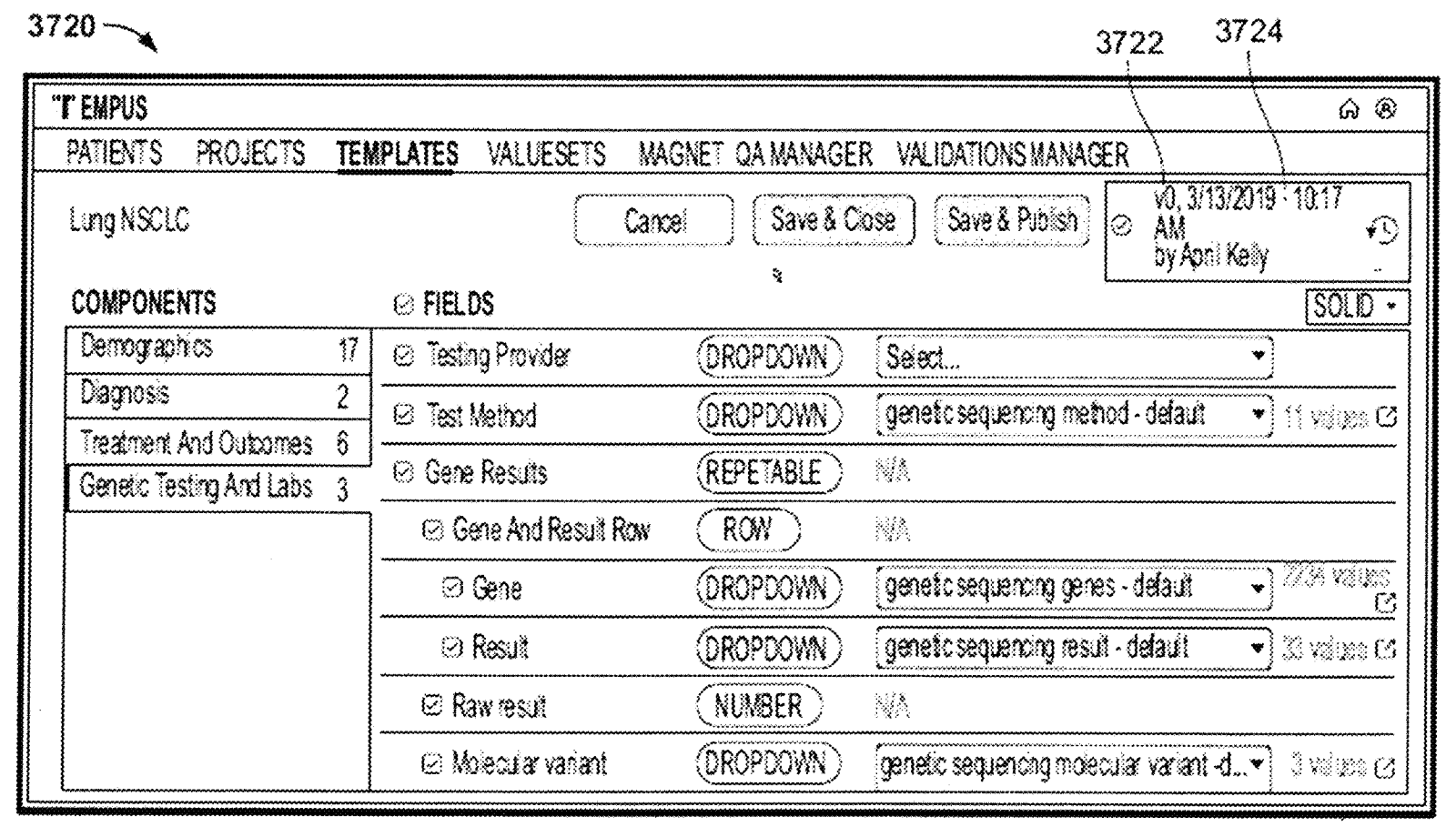

Referring broadly to FIGS. 119-120, GUIs 3710, 3720 can have a search function box 3712 in the template module to better find module, data fields, or another item of interest in the module more quickly. Templates may have a clone button 3714 to copy the template's data fields and other characteristics to a new template and thus create the new template more quickly. Multiple versions of the template can be automatically or manually saved during the modification of the template in order to preserve a history of the modification of the template. A version number 3722 of the most recently saved version of the template and/or a time 3724 that the version was saved may be displayed. Each template may displayed in a manner that shows projects which rely on that template. For instance, the "Lung Female" template has a "Stage I/II" project, a "Stage IV" project, and nine other projects that utilize the template.

Templates can be stored within an open source platform (e.g., FHIR), and can generally be accessible by URL. The platform can be used to represent molecular and clinical data in a uniform, consistent, and portable manner. Each template can have a corresponding URL, and can include related code definitions. This can allow templates to be shared with any number of third parties that uses the open source resource, allowing secure sharing of templates. Templates may comply with multiple open source platforms in order to be shared with even more third parties.

Figure 121:
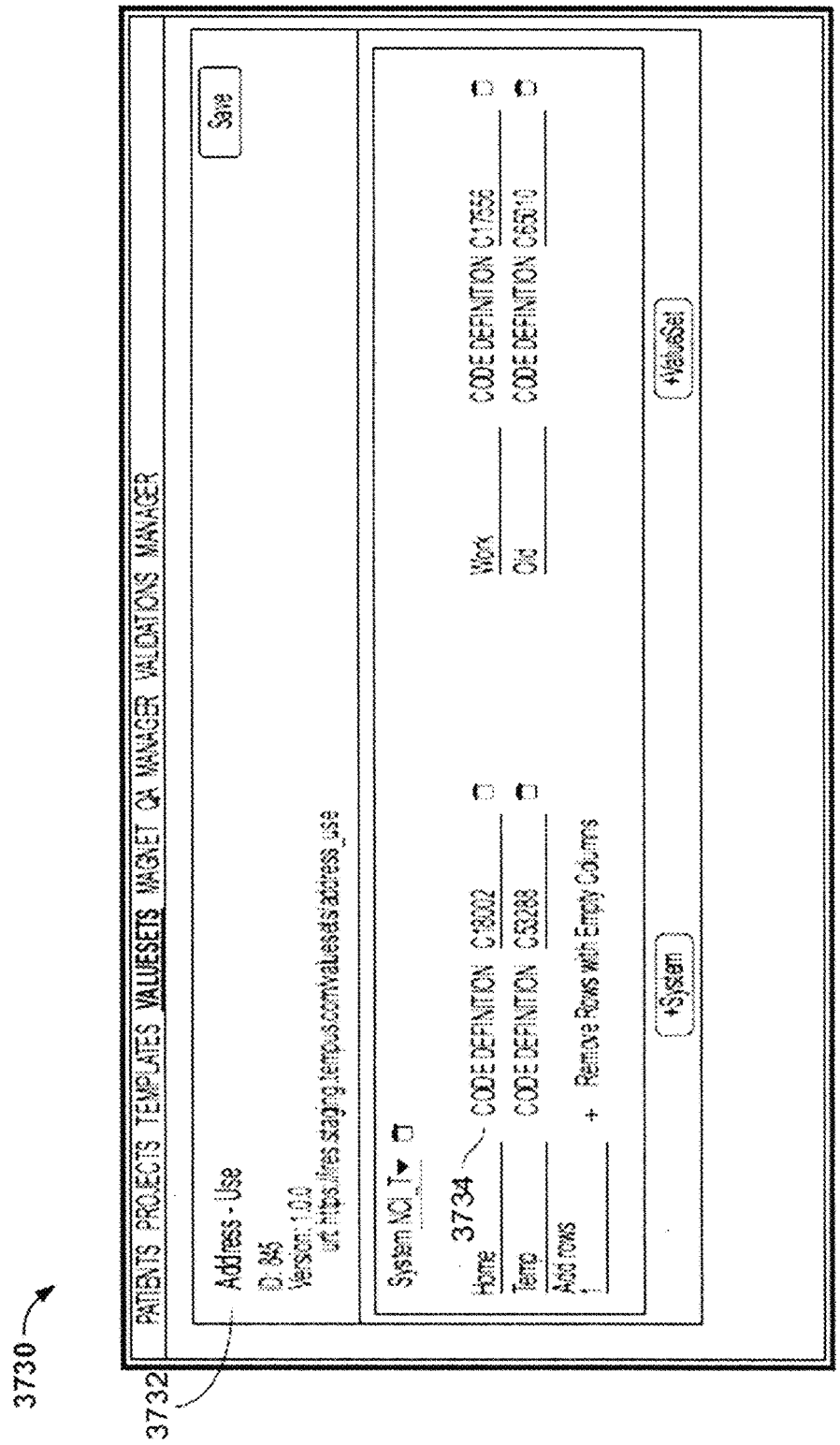
Figure 122:
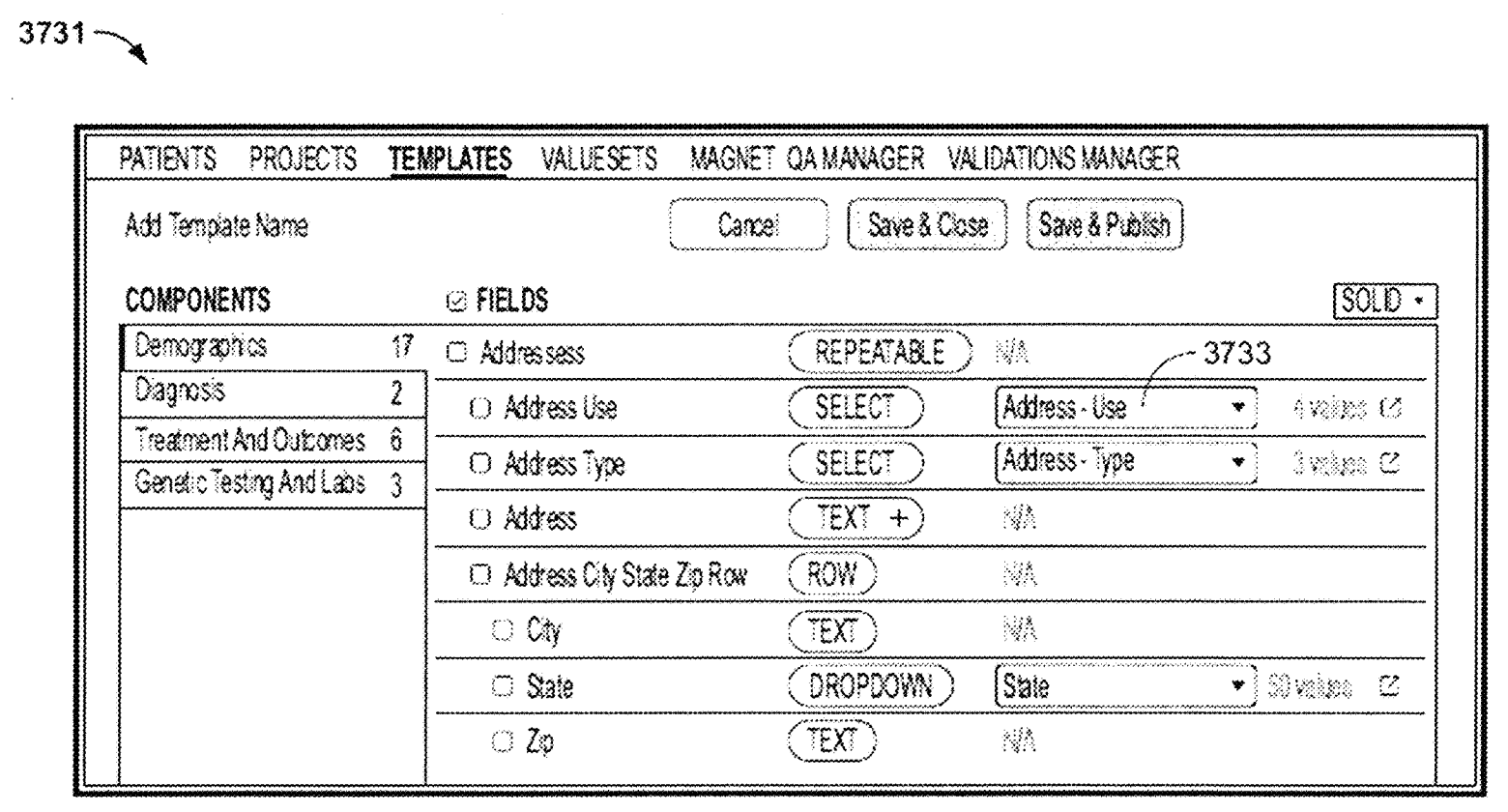

Referring broadly now to FIGS. 121-127, GUIs 3730-3742 show details corresponding to the "Valuesets" module, according to some embodiments. FIG. 121 shows an example valueset 3732 entitled "Address-Use," according to some embodiments. Address-Use 3732 can, for example, be stored within an open source platform (e.g., FHIR), and can generally be accessible by URL. The platform can be used to represent molecular and clinical data in a uniform, consistent, and portable manner. Each valueset can have a corresponding URL, and can include related code definitions 3732b. As shown, for example, "Address-Use" 3732a includes code definitions related to home, work, old, and "temp," all within the context of addresses. Every valueset can have a distinct ID. Adding a code to a valueset can retroactively make all new entries available in every instance of the valueset call from the abstraction portal (e.g., via a template). In some embodiments, the code can be associated with an external system (such as a dictionary from SNOMED, GCNU, etc.) or a custom and proprietary system as in TEMPUS. These entries are visible in a dropdown from the abstraction portal for that particular field. As shown by FIG. 122, the "Address-Use" valueset 3733 can be included in a listing of demographics-related templates. Notably, the valueset 3733 is indicated as having "4 values"—which aligns with the four codes (home, work, old, temp) shown in FIG. 121.

In some embodiments, multiple systems can be combined to create a robust valueset. Abstraction could include, for example, genes from HUGO, TEMPUS, COSMIC, etc. By allowing the integration of all systems in one valueset, system 3200 can provide quality, meaningful results without having to maintain convoluted combined datasets, or require unique fields associated with only a single dataset from a single system. System 3200 can include valuesets for every data field, and not all have an external database. Accordingly, valuesets without an external database can be assigned an internal representation with unique codes.

Figure 123:
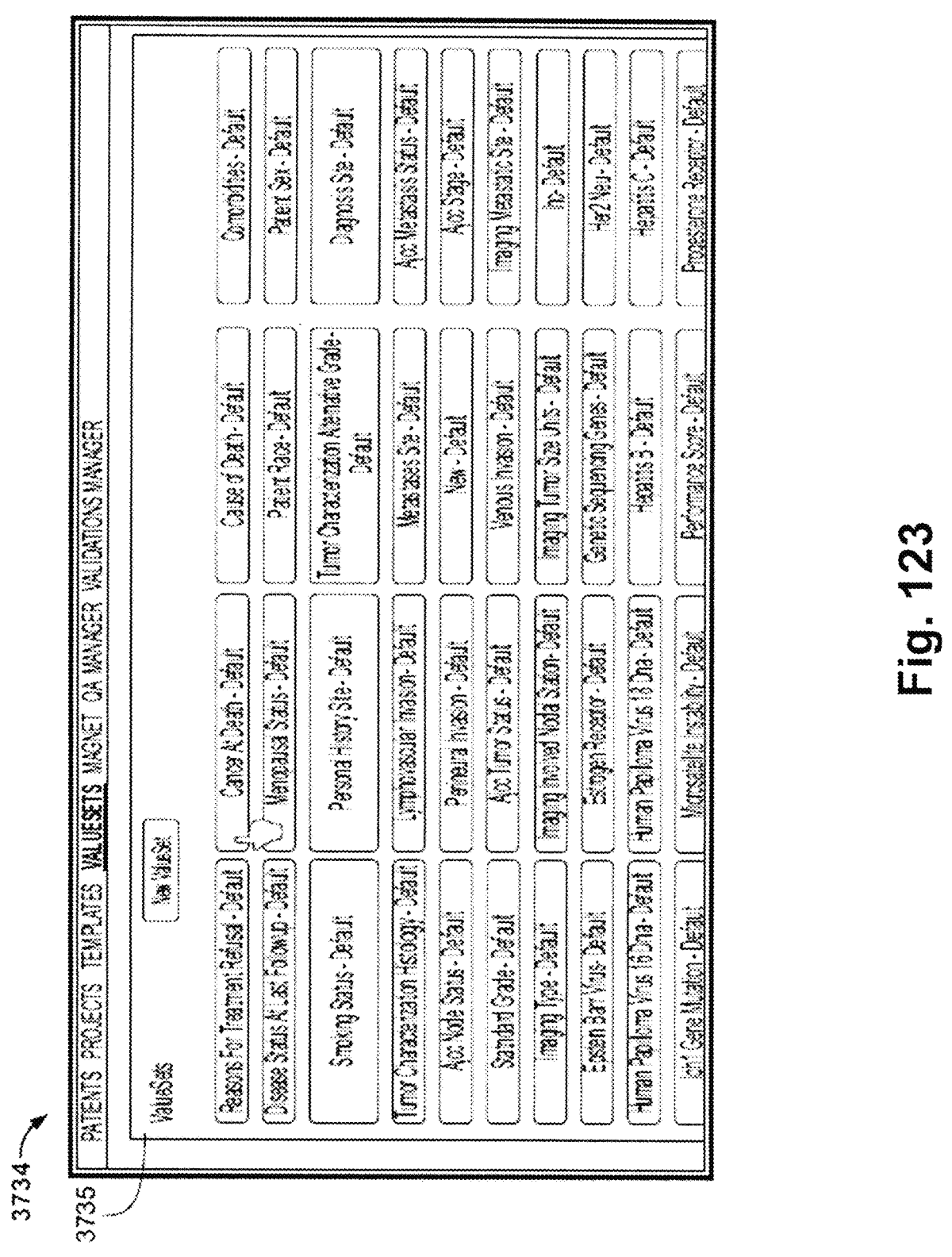
Figure 124:
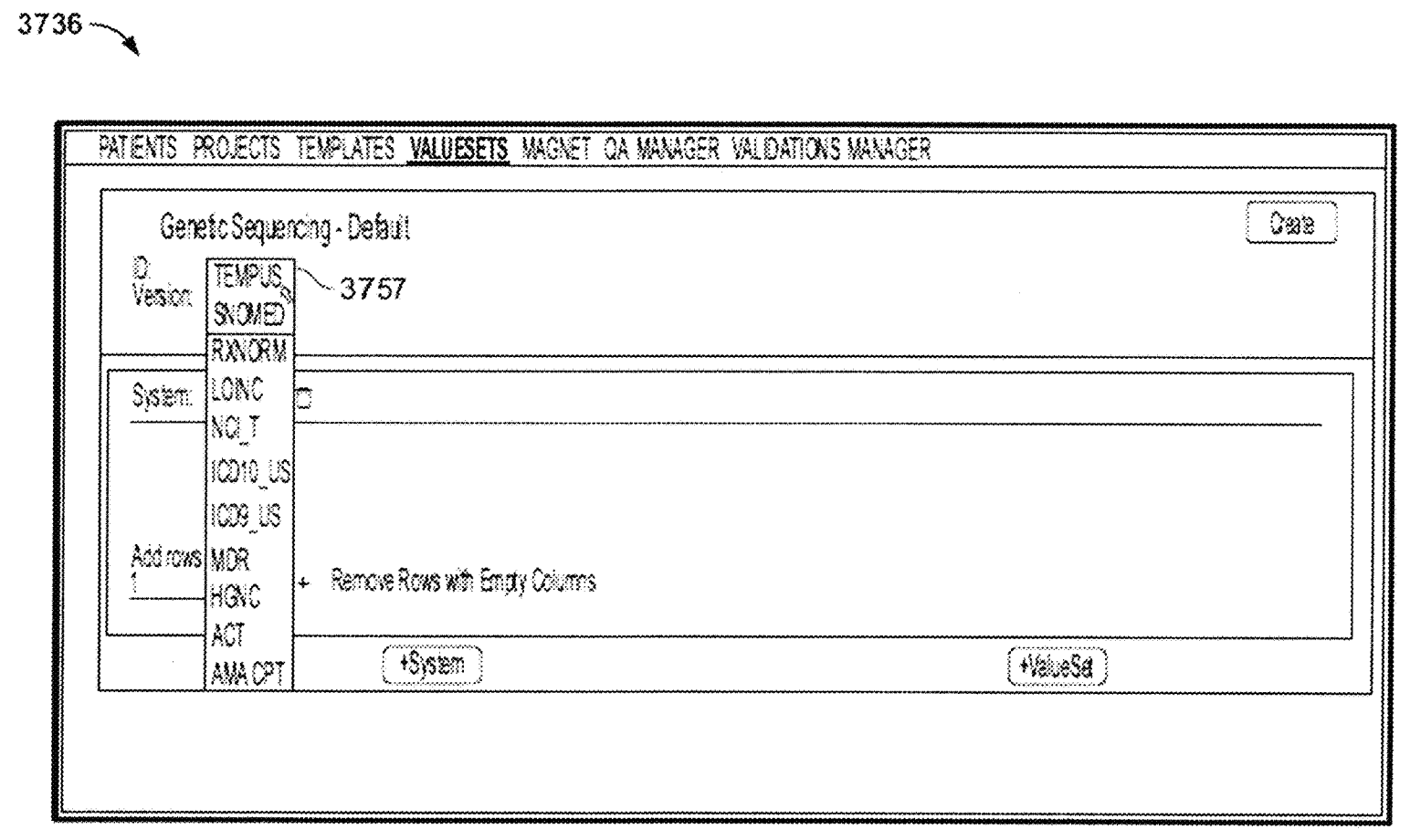

Referring to FIG. 123, a list 3735 of exemplary existing valuesets within system 3200 is shown via GUI 3734. Selecting a valueset can show additional details for that particular valueset. Additionally, new valuesets can be created by system users. A user can create a valueset, and when a system (e.g., a third party data system) is subsequently selected, all codes tied to that system may be imported to memory. As an example, FIG. 124 shows a new valueset entitled "Genetic Sequencing-Default" with a dropdown menu 3737 of various known systems. A user can select a desired system, such as HUGO, for example.

Referring now to FIG. 125, a user can add rows 3739 within the valueset. In some embodiments, a user can input a common term into each row 3739 (here, ABCB1, corresponding to a specific gene). As shown by FIG. 126, system 3200 can output a corresponding code definition 3741 that relies on the user's input, as well as the desired system (e.g., HUGO). As an example, system 3200 is shown to output "HGNC:40," which corresponds to HUGO's nomenclature for ABCB1. In some embodiments, system 3200 can import all codes from an external system without the user having to type each entry. Further, in some embodiments, system 3200 can provide dynamic representation of codes, meaning, auto-population of the name, the ID, or both from a partial name or partial ID can occur.

Accordingly, in some embodiments, the valueset, the codes, internal name, and a reference name from any external source of the dataset can by synced within system 3200. This enables efficient assignment of human readable values in the valueset to the system-important code designation that can be meaningful to data curation, abstraction, analysis and research, and/or algorithms.

Still referring to FIG. 126, a user can save the new valueset, which can prompt system 3200 to assign a new valueset ID, set the version to 0.0.0 (or as appropriate based on major/minor version changes), and assign a URL to the valueset based on the valueset name. The saved valueset can be added to the template system for selection, and any changes to the valueset can be propagated to all templates that utilize that valueset. As shown by FIG. 127, the new valueset "Genetic Sequencing-Default" can now be accessed via the system templates. When selected, the corresponding data 4810 can be displayed (e.g., which genes are included, code, name, etc.).

As described above, a workflow management system/software can do the orchestration of file upload and saving files to storage (e.g., a permanent document storage). There can be a number of metadata tags that come along with new documents, for example, file type, file extension, file size, etc. Once the document(s) are communicated to storage, additional processing can occur. In some embodiments, the workflow management system/software can determine if each document should be converted to a particular format, if optical character recognition (OCR) can be utilized, etc. Once this optional formatting occurs, the output can be provided to a search/analytics engine. In some embodiments, the search/analytics engine can be a commercially available product, such as Elasticsearch®.

The search/analytics engine can store each document, all of the related insights, all of the known information about each document, and/or scoring certain criteria for the attributes in the clinical text. In some embodiments, raw data content can be provided into a main element of the search/analytics engine, with metadata then stored on top. In some embodiments, words extracted from the document during OCR can be stored in a list, array, or other data structure, alongside the document in the search/analytics engine, which can allow searches to be run on the documents more quickly as will be explained below.

In some embodiments, access to the search/analytics engine can be limited to application accounts. Authorization service can be used, and access restrictions can be enforced at the user role level. The search activity, and even the ability to see the GUI can be controlled by various permissions at the application level. Accordingly, system 3200 can't perform the look up by responding to actuation of the run button, unless the application and/or the user is sufficiently credentialed.

FIG. 129 is a graphical user interface (GUI) 3750 that can be implemented in system 3200 to manage a number of operational tasks, and specifically, to enable clinical data structuring and abstraction work on a large scale. In some embodiments, GUI 3750 can include several modules as part of a manager console. As shown, the GUI 3750 can include a module that enables user search of a large repository of protected health information documents. In some embodiments, the GUI 3750 (within, for example, system 3200), can provide for searching particular keywords or other phrases, and subsequently return a list of patients whose documents potentially match the search terms. In some embodiments, the returned documents can be analyzed by a person (e.g., a data abstractor) for further analysis, data structuring, and other purposes.

In some embodiments, the GUI 3750 (e.g., via the system 3200) can identify patient cases of interest, before any structuring of clinical data occurs. In particular, system 3200 can identify cases that match certain criteria, and then perform a responsive action. In some embodiments, the action can be extracting patient ID's for the purposes of analytics. Alternatively, in some embodiments, the action can be extracting patient ID's for clinical data structurers and abstractors. The data structurers and/or abstractors can subsequently review the specific cases that match the search criteria, and select a subset of cases for abstraction. Previous systems and methods required manual review of all clinical documents, typically one document at a time, with a user personally identifying patient ID's to include in relevant analytics.

Healthcare providers, in some embodiments, may supply large data sets for analysis via the system 3200. Often, a subset of the larger data set needs to be structured. As one non-limiting example, a healthcare provider can supply all of their electronic health records, with the request for a data structure corresponding to a certain type of mutation. The mutation can be called out and/or described within unstructured or structured patient records. Additionally, the healthcare providers may request an analysis based off of the unstructured medical records. Such an analysis can identify patients who might be eligible for a clinical trial. Accordingly, the system 3200 can conduct a first data search of unstructured documents within electronic health records. The GUI 3750 can output a patient list, for example, of patients who are likely eligible for the clinical trial.

Referring again to FIG. 129, a query homepage 3752 can include a plurality of query tiles 3754, 3756 that each represent an existing search query. Notably, queries can be re-run over time, and the search results can change based on new clinical documents, new notes, etc. Additionally, in some embodiments, a user can create a new query by selecting button 3758 ("Create New Query"). As shown, each query tile 3754, 3756 can include a query title (shown in bold), a creation date, and "batch" filtering data (when desired).

As used herein, the term "batch" can generally be defined as a subset of a complete dataset. As an example, implementing a "batch" search can provide an additional layer of filtering. In some embodiments, when there is no defined batch, the corresponding query can search all available data (e.g., across all patients, providers, facilities, etc.). Alternatively, when a batch is selected/defined, the data that is subsequently searched can be limited to that data subset ("batch"). A batch can be, for example, data received on a specific date, data received from a specific provider, input type (e.g., FHIR, HL7), source institution, integration type, trust level of the data, and/or score carding of the data. As shown in FIG. 129, a user can view all batches by selecting button 3760 ("List All Batches").

In some embodiments, the query title can be indicative of the characteristics that are being searched for. As one example, a query title can be "RET Fusion," and the query can search for RET fusion characteristics—characteristics of cancer that are found in a small minority of cancer patients, making clinical trial enrollment expensive and difficult. As another example, a query title can be "PIK3CA KRAS Mutations," which can be tied to pancreatic cancer. As another example, a user may input a query title corresponding to a key phrase which may be found within clinical documents or notes (e.g., "minimal residual disease"). In some embodiments, a user can nest and/or combine search terms to yield further focused results. Further, in some embodiments, the query title can correspond to a certain combination of drugs, or name associated with a drug regimen. A user can title queries as being focused on one or more particular biomarkers for one or more particular disease characteristics (e.g., HRD status), which might be indicated in the underlying unstructured medical record.

Referring now to FIGS. 130-135, additional illustrations of GUIs 3770-3840 are shown, according to embodiments of the present disclosure. User selection of the button 3758 can initiate the GUI 3770 to display a new query, via query tile 3774. In some embodiments, selecting a refresh button on GUI 3770 can allow a user to fill in a new query title. When saved, via selection of a button 3786, the new query tile 3774 can appear on the query homepage 3752. In some embodiments, a user can import previous query criteria, if desired. As shown, an example query title 3772 can be the name of the health care provider whose records are being searched, such as "JZS Cancer Center." The query tile 3774 can include a group tile 3780, a selection button 3784, and/or a query list 3782. The group tile 3780 can include a group name ("Drug Name"), a batch ID 3798, and the query list 3782. The query list 3782 can have one or more query entries that correspond to a search term/phrase. The batch ID 3798 can be blank, which can indicate that the full data set will be searched. Alternatively, a selected batch ID 3798 can indicate a subset of data that will be searched. Some projects may only have a single batch, which can allow the user to easily search for documents relevant to the project using the batch ID 3798 of the single batch. In some embodiments, a user can press the selection button 3784 to add a new group tile. Accordingly, each group can have multiple search phrases, and each query tile can have multiple groups, if desired.

Additionally, each query entry can include a slop number and/or a fuzziness number. As used herein, the term "slop" can generally be defined as how far apart words within search terms are allowed to be while still considering the document a "match," while "fuzziness" is how far letters within the search term are. For example, a search query with the search phrase "Aug. 1, 1991" may return a document with the phrase "August 1" or "August 1991" with a certain slop number. In another example, a search query with the search phrase "Aug. 1, 1991" may return a document with the phrase "Aug. 1, 1992" with a certain fuzziness number. In some embodiments, the selection button 3784 can perform a live call against a system data set (e.g., a search/analytics engine data set). Additionally, in some embodiments, a user can select an upload/download button 3776. The system 3200 can upload existing search queries, if desired. Similarly, the system 3200 can download queries to save for future reuse.

Each query entry may also include a maximum patient number. The maximum patient number can be used to limit the number of results returned by the search to no more than the specified maximum patient's number. A batch may have thousands of documents containing the search phrase, and a user may wish to limit the results to a fraction of the documents.

Each query entry may provide a search language to the search/analytics engine in order to refine the results returned from the search/analytics engine. The search language may include a subset of words from a written language such as English, Spanish etc. The subset of words may include medical terms commonly used in documents about a certain medical disorder. For example, a search language used for a blood disorder may have words such as "hemophilia" or "von Willebrand" that may be commonly used in describing blood disorders but less common in everyday use. The query entry can select the search language based on a batch number, as the batch number may correspond to a project with a specific medical focus, or by the search term. For example, the query entry may provide a search language related to blood disorder if the search term is "von Willebrand." The search language can then be used by the search/analytics engine to adjust internal search parameter to return more relevant results to the user.

As shown, the group tile 3780 can have a query that includes a search "phrase" 3792. As one example, the search phrase 3792 can be "Herceptin." In some embodiments, using quotation marks within the search phrase 3792 can result in a system output corresponding to documents having an exact match to the search phrase 3792. Alternatively, using a search phrase 3792 without quotation marks can broaden the number of documents that will match. As one non-limiting example, the term "perception" may flag a document for review, simply based on the number of shared letters with the search phrase 3792 "Herceptin." In some embodiments, a certain character such as a "$" inserted at the start of the search phrase 3792 can result in a search being conducted with no fuzziness. Running searches without fuzziness may be desired when searching for specific stages of cancer, such as when documents related to "Stage III" are desired but documents related to "Stage II" are not.

In some embodiments, the query tiles, for example query tiles 3774 and 3794, can include a run button 3778, a results list 3796, and a save button 3797. When a user selects the run button 3778, the system 3200 can run the search query and display the results list 3796. As shown, 89 patients have documents corresponding to the search phrase 3792. If a user wants to save a portion or the entirety of the results list 3796, they can select the save button 3797. As shown, the results list 3796 can include one or more search results 3810, which can provide additional detail when selected. As an example, FIG. 132 shows the GUI 3800 with the search result 3810 selected. In some embodiments, upon selection, a patient window 3808 can open. The GUI 3800 can include the query tile 3802, query list 3804, and/or results list 3806. The patient window 3808 can display high level information such as the query title, project name, status, document number(s), etc. In some embodiments, the system can run a separate search for each group tile.

As shown in FIG. 133, each result in the results list 3822 can include a selection box 3824. In some embodiments, an assignment button 3826 can be used to assign selected (e.g., via selection box 3824) results to a project. When a result is selected via the selection box 3824, inspection data 3828 can be displayed via the GUI 3820. The inspection data 3828 can include a document portion corresponding to the matched search phrase. In some embodiments, the desired search term/phrase can be shown in the inspection data 3828 using bold text, highlight, a different font size, etc. As shown, each entry within the inspection data 3828 can display identifying parameters, such as document number, file size, number of pages, document type (progress note, pathology report, etc.) page number (of the relevant document portion), and/or relevant phrase text. Notably, in some embodiments, a patient's data may be represented in the results list 3822 by a single entry. In contrast, a single patient may correspond to multiple documents shown in the inspection data 3828. Each document can be tied to a patient via a patient ID.

The system 3200 may sort the results list 3822 by putting the most relevant documents at the beginning of the results list 3822 before displaying. In some embodiments, the system 3200 may run separate searches for each group tile and then compare document ranks between group tile search results before displaying a final results list. In some embodiments, the system 3200 may average the ranks of each document across multiple group tile searches and then order the documents by the determined average rank in the results list 3822. For example, the system may determine a document ranked first in a first group tile search and third in a second group tile search, and place the document second on the final results list. Polling search results from multiple group tile searches can normalize and/or better rank the results, as documents that consistently rank highly in various group tile searches will be displayed near the top of the final results list while documents that ranked highly in one group tile search but lower in many other group tile searched will not be ranked near the top of the final results list. In other words, this approach can help prevent outlier documents that may be less relevant from being displayed to a user.

In some embodiments, selection of the assignment button 3826 can prompt a new data window within the GUI. As shown by FIG. 134, an assignment window 3832 can be displayed in response to selection of the assignment button 3826. Once a project is identified, each selected result from the results list 3822 can be added to the corresponding project workspace. In some embodiments, the assignment window 3842 can include a project search field 3844, which can update suggested projects as the user types out a search. A user can select a listed project via the assignment window 3842. As one non-limiting example, if a user were to select the "Cancer Center Lung" project, 89 new cases would then become available immediately for abstraction to clinical data structurers, and abstractors on their interface. In some embodiments, abstractors can then manually look at the documents that are in the project, followed by the actual work of data structure. Project types can include, for example, abstract patients for clinical pipeline, institution specific projects, and institutions that identify specific research areas.

Referring now to FIGS. 136-138, additional illustrations of the GUIs 3850-3880 are shown, according to embodiments of the present disclosure. As one non-limiting example, the query tile 3858 can be directed to searching for a type of ovarian cancer. The group tile 3852 can include a title "Ovarian." The query list 3854 can include multiple phrases for searching. In some embodiments, phrases can include "ovarian cancer," "fallopian tube cancer," and variations thereof. FIG. 137 is shown to include a second group tile 3874. The group tile 3874 can include a title "Stage II-IV." In some embodiments, search phrases corresponding to group tile 3874 can include "stage $ii," and "stage $iia." Notably, within group tiles 3872, 3874, phrases are not within quotations, which can allow for non-exact matches within searched documents. As shown, slop numbers 3860 can be set to 0. In some embodiments, the results list 3856, 3876 can include each patient with at least one document that indicates ovarian cancer stages II-IV (i.e., conditions of both group tiles 3872, 3874 are satisfied). It should be understood that dozens or more of different phrases may be included in a single query, providing a powerful and flexible tool to permit differentiated searching of records. In other examples, the record set to be searched may be from a plurality of health care providers.

As shown by FIG. 138, the inspect data 5920 can include documents that potentially discuss ovarian cancer stages II-IV. In some embodiments, system 3200 can provide an average order 3310. The average order 3310 can rank patient results based on defined search parameters. As one example, the search/analytics engine can perform scoring and/or ranking of results. The average order 3310 can provide an indication of result quality. In some embodiments, for example, the average order calculation can consider the frequency of phrase appearance within documents, and/or the overall number of matching phrases within documents.

Thus, as described herein, system 3200 is capable of efficiently capturing all treatment relevant data including disease state factors, treatment decisions, treatment efficacy and exploratory factors (such as factors that may have a causal relationship to treatment efficacy) and structuring that data to optimally drive different system activities including memorialization of data and treatment decisions, database analytics and user applications and interfaces. In addition, system 3200 is highly and rapidly adaptable so that it can be modified to absorb new data types and new treatment and research insights, as well as to enable development of new user applications and interfaces optimized to specific user activities.

IV. Automated Quality Assurance Testing of Structured Clinical Data

A comprehensive data integrity evaluation and validation system is described herein, the system usable, e.g., to generate a definitive clinical record for a patient or consistency among groups, projects, or cohorts of patients. Due to the quantity and varying intricacy or elements of a clinical record, multiple categories of basic and complex validations may be needed to provide the requisite completeness and accuracy. In the functionality described below, various authors use software tools to compose validation rules that can be run independently on one or more patient records or applied in aggregate to all patient records comprising a given grouping, project or defined cohort.

These validations can be applied to a specific attribute (e.g. gender) or to a combination of attributes (e.g. gender and primary diagnosis) that results in the authoring of basic and advanced rule-based logic. In particular, the system may include a dynamic user interface enabling a user to design and build a new query by selecting one or more attributes represented in the system and then associating a desired rule (e.g. is present, is above/below/within a certain threshold value or range, etc.) with those attributes. Validation rules can operate in a stand-alone fashion or can be chained and/or linked together at a project and/or patient cohort level.

The construction of these validations is performed through the selection of one or more existing query sets as part of a validation query and/or through the design of a new query. Alternatively, validation checks can also be grouped and bundled into query sets or used individually as part of an ad-hoc quality assurance check initiated either manually or automatically upon delivery of a cohort of patient data. Still further, the system may maintain the ability to programmatically seed and/or populate a predefined set of validation rules that may be applicable to one or more streams.

A validation rule may be composed of a seeded set of rules and/or checks that enable data integrity. From a system perspective, a series of API endpoints await a sufficiently articulated and valid rule definition as well as a corresponding validation rule name. The API for the service may enable the creation, update, and/or deletion of the validations; alternatively, the validations may be managed in an administrative user interface or directly via database queries.

In a separate transaction, the rule can be associated with a query set (a combination of validation queries) and/or a specific cohort of patients where it can be run automatically to detect data inconsistencies and anomalies. Query sets may be groupings of validation rules and checks that are grouped as a result of similarity in the types of checks performed and/or the needs of a quality assurance ("QA") user wanting to identify the integrity of patient records via use of bulk and/or combined validation rules and checks.

Applying a query set to a patient record or a portion thereof may result in the system verifying an accuracy of the data structuring within an acceptable system- or user-defined threshold level, in which case the structured data may be deemed accepted and the patient record may be amended to include that structured data. In another instance, the query set result may indicate the presence of one or more errors in the data structuring, requiring further review and/or modifications to the structured data, and the patient record then may be amended to include the modified structured data.

Structuring Data

In order to properly apply the validation rules, it may be necessary to standardize, normalize, or otherwise structure the input data. Thus, systems and methods are described herein that permit the automatic analysis of different types of structured clinical data. The structured clinical data may differ on the basis of the types of data elements within each list of structured clinical data, the organization of data elements within a structured clinical data schema, or in other ways.

Within the context of the present disclosure, the following terms may be understood to have the following meanings:

"Structured" clinical data refers to clinical data that has been ingested into a structured format governed by a data schema. As one simple example, structured clinical data may be patient name, diagnosis date, and a list of medications, arranged in a JSON format. It should be understood that there are many, more complicated types of structured clinical data, which may take different formats.

"Data schema" means a particular set of data attributes and relationships therein that comprise a set of structured data to be used for various purposes (e.g. internal analysis, integration with purpose-built applications, etc.).

"Data element" means a particular clinical and/or phenotypic data attribute. For instance, a comorbidity (e.g. acute myocardial infarction), adverse event (e.g. conjunctivitis), performance score (e.g. ECOG score of 3), etc.

"Data value" means the value of the data in a data element. For instance, in a "Diagnosis Date" data element, the data value may be "Oct. 10, 2016".

Certain systems and methods described herein permit a patient's structured clinical record to be automatically evaluated and scored in a consistent manner, while also simultaneously allowing for the determination of data integrity across various data sources. In some aspects, inter-rater reliability and a comprehensive clinical data validation system facilitate the identification and resolution of gaps in a patient's record when abstracted across multiple disparate streams.

Certain systems and methods may be utilized within an overall clinical data structuring platform. The platform may include a workflow tool and an administrative user interface for querying, reporting, and output tagging.

In one aspect, the system may support externally sourced data validations and/or edit checks corresponding to custom data science analysis workflows as well as data integrity enforcement for various purposes, such as for clinical trial management. In this context, "externally sourced" may refer to validation rules or checks authored by one or more external parties, e.g., health systems, clinical trial management services, etc., importable and ingestible into the present validation system, for use and integration with other rules and/or validation checks. "Externally sourced" also may refer to ingestion of other validations originated by other individuals or applications other than the present validation system while still internal to the entity employing the present system.

Additionally or alternatively, the system may compare multiple sets of structured clinical data for a single patient, select the most correct data element for each of the structured data elements, and return a new list of structured clinical data containing the most correct data element value for each data element. The new list reflects a single "source of truth" for a patient based on the raw clinical data for that patient.

Certain systems and methods may make use of various systematic validation checks at multiple stages in a process that commences with raw data input and ends with the data being curated, including at a data abstraction stage and/or a quality assurance stage. Additional stages in this timeline may include a data sufficiency score-carding stage in which the raw inputs are analyzed to determine whether they contain a sufficient amount of clinical data to proceed with the abstraction stage, and a downstream stage in which validation checks are used for patient cohorts.

In certain embodiments, the structured clinical data may be merged into a larger dataset. The larger dataset may have the same or a similar data schema to the structured clinical data. The larger dataset may be used for the conduct of research, may be associated with published research or clinical guidelines, and may be provided to third parties for their own research and analysis.

Turning now to FIG. 139, an exemplary user interface that a clinical data analyst may utilize to structure clinical data from raw clinical data is depicted.

In one aspect, the input data may be abstracted data that signifies a comprehensive, dynamic representation of a patient's clinical attributes across multiple categories, e.g., demographics, diagnosis, treatments, outcomes, genetic testing, labs, etc. Within each of these categories, attributes may be repeated to reflect multiple instances of a particular clinical data attribute present in multiple locations within the patient data.

In a second aspect, patient data can be extracted from source records, research projects, tracking sheets and the like. For example, sample source fields from unstructured flat files may include: enrollment_date, age_at_enrollment, sex, race, marital_status, gravidity, menopause, cancer status, age_at_diagnosis, laterality, T_stage_clinical, T_stage_pathological, histology, grade, etc., and the system may extract both the source fields as well as their respective data values.

In both aspects, the form of this input data often is inconsistent and dynamic to the principal investigator, researcher and/or partnering organization providing the patient data. As a result, a mapping exercise may be required to relate information from unstructured data originating in flat files into a canonical schema, format and/or model for evaluation purposes. In particular, the mapping exercise may identify source data fields and attributes from the data provider, e.g., a third party organization or researcher, and analyze that data in its raw form in order to determine linkages between the data and medical concepts or terminology reflected by the data and a data model used by the system. Such concept mapping may be performed manually by specially-trained informatics engineers or other specialists or one or more software applications specifically designed to undertake such mapping, as would be appreciated by one of ordinary skill in the relevant art.

In a third aspect, patient data may be Electronic Medical Record (EMR)-extracted structured data. This data can include a set of text strings representing various clinical attributes but may also include various ontological code systems and concepts to represent each text string in a way that can be compared against other data sets and/or validations. As a result of this structuring, the data mapping exercise may be significantly more straightforward than the exercise required for either of the other two instances. FIG. 140 depicts one example of EMR-extracted structured data that includes a payload of diagnosis-related data, specifically, data pertaining to a diagnosis of Malignant neoplasm of larynx, unspecified. Similarly, FIG. 141 depicts one example of EMR-extracted structured data relating to the medication Paclitaxel, provided intravenously.

In a fourth aspect, patient data may be extracted through a clinical concept identification, extraction, prediction, and learning engine such as the one described in the commonly-owned U.S. provisional patent application Ser. No. 62/774,854, titled "System and Method Including Machine Learning for Clinical Concept Identification, Extraction, and Prediction," the contents of which are incorporated herein in their entirety. The output of this engine may be a configurable and extensible set of predictions about a given patient's clinical attributes across a variety of content types. These types may include (but may not be limited to) primary diagnosis & metastases sites, tumor characterization histology, standard grade, tumor characterization alternative grade, medication/ingredient, associated outcomes, procedures, adverse events, comorbidities, smoking status, performance scores, radiotherapies, imaging modality, etc.

Triggering Analysis Once Data is Structured

In order to make use of data from one or more of these streams, the system may be configured to automatically initiate the evaluation of both partial and fully structured patient clinical records across multiple sources and/or streams through a variety of triggering events. Such events may include, e.g.: (1) receiving an on-demand request, e.g., via an Administrator-driven user interface that can initiate the process programmatically, (2) via a background service triggered upon receipt of new software code commits or corresponding application build phases, (3) when new data is either received or ingested across sources and streams, (4) upon achieving a sufficient inter-rater or intra-rater reliability scoring system, which is run automatically on a configurable percentage of patient records as part of a project or batch, (5) upon completion of either a case abstraction and/or QA activity, (6) upon receipt of clinical data and/or records for patients participating in an institution's clinical trial, which may be obtained via a site coordinator, via EMR or source records, or (7) real-time analysis during creation of a patient note or other clinical data. Each of these trigger events is discussed in greater detail, as follows.

Trigger #1 (on-demand): a user with appropriate authorization can manually initiate one or more distinct tests to support the evaluation of one or more patient clinical records. In its default state, this functionality manifests itself as part of a graphical user interface presented after entering in a specific request for one or more tests at a terminal window command line.

Trigger #2 (on receipt of code commits): tests can be initiated en masse via a background service or selectively when only a subset of tests are required to validate specific patient clinical data and/or attributes. In this aspect, validation may take advantage of "continuous integration," or the practice of integrating new code with existing code while embedding automated testing and checks into this process to minimize and/or eliminate gaps and issues in production-level software and applications. As part of this process, new code commits are made, reviewed, approved and merged into various code branches for subsequent application build phases while intermediate software (e.g. Jenkins) maintains responsibility for running one or more test suites programmatically and recording their output (e.g. failed, pending and passed) as well as collecting details, stacktraces and/or screenshots resulting from these tests.

Trigger #3 (new data ingested): an integration engine and/or intermediate data lake receives and processes new structured data which may also initiate corresponding tests to evaluate and score the data as its own distinct stream as well as comparatively to any existing data received for the patient. In one possible implementation, an integration engine may receive a stream of XML and/or JSON content comprising structured data and corresponding ontological code systems and concepts as extracted from a health system's EMR at a single point in time. Upon receipt, this data would be evaluated against one or more test suites for accuracy, coverage and/or insufficiency. It may also be compared and evaluated relative to other patient record data received via other sources and similarly run through one or more test suites. In another possible implementation, the system may receive a FHIR-compliant payload from partners that contains one or more genetic/genomic testing results for one or more patients. In this example, the test suite for genetic testing referenced above may be run programmatically to evaluate the integrity of this data and may also be compared and evaluated relative to other genetic testing content already ingested and/or abstracted as part of one or more patient records.

Trigger #4A (inter-rater reliability): the system will evaluate two instances of a patient's abstracted clinical data and compose a score at both the case and field-levels to determine a level of agreement between the a plurality of abstractors (or "raters") in order to determine whether to automatically begin the evaluation process. In this example, "automatically" may refer to a systematic assignment of a subset of patient cases that will be abstracted by two distinct individuals in a "double-blind" manner where the reviewer may also be unaware of participant identities. Further, a scoring scheme is used to calculate the proficiency and accuracy of each submission by taking into account the modifications and updates made by a conflict resolution user.

The system may assign a first version or instance of a case or data stream to a first rater and a second version or instance of the case or data stream to a second rater, i.e., the plurality of raters may review the same subset of cases or records, after which the system may determine whether there is a sufficiently high degree of overlap and/or agreement between each rater's abstraction. When the requisite threshold is not met, a third-party conflict resolver may review the raw clinical data and each rater's abstraction content in order to generate a de facto or "best" abstraction of the patient record. In one aspect, the conflict resolver may select from among the abstractions provided by the other raters. In another aspect, the conflict resolver additionally or alternatively may provide its own abstraction and select the "best" abstraction from the group that includes its own abstraction and those of the other raters.

With regard to this trigger, FIG. 142 illustrates one of the steps to be performed by a conflict resolution user when a complex disagreement is identified for a patient record. In this example, a conflict resolver must evaluate the radiotherapies cited by the two abstractors and determine which are in fact appropriate for the "de facto" patient clinical record by moving the most correct items to therapy groups.

Conversely, FIG. 143 illustrates one of the steps to be performed by a conflict resolution user when a basic disagreement is identified for a patient record. In this example, a conflict resolver must evaluate the demographic data cited by the two abstractors and determine which are in fact appropriate for the "de facto" patient clinical record by selecting the correct "race" clinical data value.

Trigger #4B (intra-rater reliability): like the previously-disclosed trigger, the system also may be used to evaluate a plurality of abstractions from a single rater, in order to determine how consistent the rater is in his or her efforts. The notes or other clinical data reviewed by the rater may relate to the same patient, e.g., different portions of a patient's record, or they may be similar or distinct portions of raw clinical data from multiple patients.

Trigger #5 (case abstraction completion and/or quality assurance completion): clinical data attributes for the patient record may be evaluated systematically for gaps in logic through the use of a clinical data validation service that centralizes a number of rules (see below for details) and works in conjunction with a cohort sign-out process.

Trigger #6 (upon receipt of clinical data and/or records for patients participating in an institution's clinical trial): clinical data attributes for a patient potentially eligible for participation in a clinical trial may be evaluated on-demand or as part of a broader batch of patients from that institution on a rolling basis. With regard to this workflow, the present system and method may support the workflow's ability to identify gaps in clinical attributes that may be required for inclusion/exclusion criteria evaluation and matching.

Trigger #7 (on-demand analysis): structured data may be extracted, either directly or via a mapping procedure, from a clinical note while that note is being created or dictated by a physician or other clinician. The structured data is analyzed, and errors, incomplete information, or conflicting information in the underlying data are reported back to the clinician in real time.

Analysis Following Triggering Event

Regardless of the choice of triggering event, the default set of evaluation criteria (e.g. test suites) may be composed at a category-level (e.g. demographics, diagnosis, genetic testing and labs, treatments and outcomes) along with nested sub-groupings that allow for granular and precise evaluation of clinical patient attributes by type. For example, and with regard to the depiction in FIG. 144 of a list of test suites within a "demographics" root level category, a test may be written to determine whether a record of ovarian cancer was a correctly structured instance:

Primary tumor instance identified as part of a patient record

Tissue of origin identified for a corresponding primary tumor instance e.g. Ovary Date of diagnosis identified for a primary diagnosis e.g. Dec. 15, 2015

Date of recurrence identified for a primary diagnosis e.g. Mar. 5, 2016

Diagnosis (e.g. histology) identified for the corresponding primary diagnosis e.g. Ovarian stromal tumor Standard grade identified for the corresponding primary diagnosis e.g. Grade 2 (moderately differentiated)

AJCC staging identified for the corresponding primary diagnosis e.g. T1B, N0, M0 (Stage 1B)

In this example, a determination that the record was structured "correctly" may mean more than simply determining whether there are data values in each of the specified fields and attributes. Instead, correct structuring also may signify that all of the attributes listed were adequately provided and mapped to accepted and/or preferred medical concepts, i.e., that the requisite data was provided, represented, and properly fulfilled all validation checks managed by the system. Mapping may relate to both a system-defined data model as well as one or more external models, such as the Fast Healthcare Interoperability Resources ("FHIR") specification. In this regard, the system may include one or more test suites that define the criteria for the relevant categories and nested sub-groupings and then may execute relevant validation checks to carry out those test suites.

Medical concepts can span numerous dictionaries, vocabularies and ontologies, and data elements within structured data generally conform to a specific system, concept code and preferred text descriptor. For instance, in the example discussed above, for "Ovary," i.e., the tissue of origin identified for a corresponding primary tumor instance, the system may determine whether that data instance is mapped to the "SNOMED" code of 93934004 with a preferred text descriptor of "Primary malignant neoplasm of ovary (disorder)" in order to comply with a test suite that includes the same relationship.

In a second example, and with regard to FIG. 145, the test suite for determining sufficiency of a structured and/or abstracted instance of genetic testing may include evaluating whether values for the following criteria are present and accurately structured:

Initial genetic testing instance identified and/or added to a patient record

Date identified for an instance of genetic testing
e.g. Jan. 1, 2017

Testing provider identified for an instance of genetic testing
e.g. Tempus

Test method identified for an instance of genetic testing
e.g. Mutation analysis Gene result detail identified for an instance of genetic testing
e.g. Gene: KRAS
e.g. Result: Amplification
e.g. Raw Result: 100
e.g. Detail: N/A Tumor mutational burden identified for an instance of genetic testing
e.g. 10

Microsatellite instability identified for an instance of genetic testing
e.g. High In a third example, and with regard to FIG. 146, a test suite for determining sufficiency of a structured and/or abstracted instance of genetic testing may include the following criteria:

Initial genetic testing instance identified and/or added to a patient record

Date identified for an instance of genetic testing
e.g. Jan. 1, 2017

Testing provider identified for an instance of genetic testing
e.g. Tempus

Test method identified for an instance of genetic testing
e.g. Mutation analysis Gene result detail identified for an instance of genetic testing
e.g. Gene: KRAS
e.g. Result: Amplification
e.g. Raw Result: 100
e.g. Detail: N/A Tumor mutational burden identified for an instance of genetic testing
e.g. 10

Microsatellite instability identified for an instance of genetic testing
e.g. High In one aspect, the evaluation and/or analysis performed as part of the system referenced above may comprise a combination of several of the trigger mechanisms discussed above. For example, the system may include: (1) automated and continuously maintained test suites specific to one or more clinical attributes and/or content types, (2) clinical data validation processes performed at run-time during abstraction as well as quality assurance activities, and (3) inter-rater reliability (IRR). Additionally, the triggers may evolve or be revised over time to generate a more robust, more complete quality assurance system. For example, test suites may grow continuously to support more templates or later-generated abstraction fields for clinical data structuring. Similarly, the clinical data validations (errors, warnings, etc.) may be maintained in a library programmatically via web service endpoints or a user interface that supports the addition of new validations and corresponding definitions of rules, e.g., using a rule builder. The system may generate multiple streams of abstracted clinical data that can be evaluated and re-assigned to a more sophisticated user with deeper clinical background to help resolve any conflicts, thereby producing a de facto "source of truth" for a given patient's clinical record.

In still another example, the system may rely on data from other patients to determine whether the data in a target patient's record appears correct or whether it may warrant an alert signifying a potential error or an otherwise unexpected finding. For example, a patient record may include both clinical and molecular data, where the molecular data may include data reflecting a "new" gene, in that there may not be much, if any, clinical knowledge regarding the medical effects of having the gene. In that case, the system may search its data store for indications of other patients with that gene. The system then may search for similarities in clinical data among those other patients in order to develop a template test suite. Thus, the system may assume that the other patients' clinical data is accurate, such that deviations from that data when a validation check is performed on a subject patient's data may trigger an alert to the provider or reviewer as to either an error in the subject patient's data or, alternatively, to an unexpected result that may warrant further investigation.

In one instance, validations may be fairly straightforward, e.g., when comparing different portions of a patient record, is the system able to extract a patient's gender from more than one location and do those gender-based attributes match up? In those instances, a test suite that instructs the system to query one or more known portions of a record for gender-identifying information, review that information for internal consistency (if more than one portion of the record is considered), and to return that gender as an attribute for the patient may be usable for multiple use cases as a fairly generic test suite. In another example, the test suite may seek to compare the structured patient data against a set of one or more guidelines, e.g., clinical trial inputs or metrics reflecting general patient population results (e.g., survival, progression, etc.), to determine whether the patient's data is in-line with those guidelines or reflects a potential error or outlier.

In another instance, validations may be specific to certain use cases based, e.g., on other data extracted from a patient record. For example, certain types of cancer are gender-specific. Thus, a quality assurance validation or rule that says "if structured data extracted from the patient record includes an attribute for prostate cancer, then a patient gender of 'female' represents an error" is useful for prostate cancer use cases but not for other cancers or diseases.

In still another instance, validations may be multi-variable or require more than a simple cross-check of two fields against one another. For example, with regard to lung or breast cancer, a patient record may document scenarios that reflect valid or invalid staging, and the relevant cancer also may have subtypes that vary based on staging. Thus, a complete validation check of a test suite may require that the system evaluate all of the possibilities at each stage to determine whether the structured data is complete and internally consistent.

Still further, the system may include an automated process for evaluating each test suite to determine whether it represents an accurate test. That process may require running through each of the possibilities that are queried in the test suite and determining that none of the tests conflict with other tests in the suite. Thus, e.g., the system may assume that a first test yields a "true" or valid result. Then, given that result, the system determines whether it is possible for a second test to also yield a "true" or valid result. The system continues in that process until a "false" or invalid result is reached or until all tests have been evaluated. In the latter case, the system may recognize that the test suite does not include any failures and may publish the test suite for actual implementation. In the former case, once an invalid result is determined, the system may flag the test suite for further review and either amendment or definitive approval, despite the invalid result.

One objective of the system is to allow for the creation, management and assignment of specific clinical data fields and their corresponding attributes via a single user interface. A dynamic management and rendering engine for template-specific fields enables the system to achieve this objective by permitting different classes of users to rapidly configure new templates with custom field configurations in minutes without code by employing a user interface that permits those users to select both the fields, as well as the hierarchy among the fields, that are desired for a given clinical data structuring project or use case. Templates may drive a determination of what content from the raw data is available to an abstractor. Finally, the system maintains a version history of every template modification made by authorized users for auditing purposes.

In addition to the single-user-centric analysis described above, in another aspect, validations can be leveraged at a more granular project-specific level (rather than at an individual level or a cohort level), which may allow for the evaluation and scoring of specific template configurations as well as their corresponding data fields. Thus, rather than running validations against a single patient's clinical data elements and content generally, the validation service also may be run with a batch or bulk set of patient clinical data elements that correspond to one or more projects. Data may be sourced from one or more sources, including upstream abstracted patient content (e.g., prior to structuring) or from more finalized versions of the data (e.g., from a downstream data warehouse in a structured format). Like the single-user-centric analysis described above, these bulk or test validation service checks may be configured to run either sequentially or simultaneously. The system may be configured to perform these validation checks on patients associated with projects that have been configured to these templates to ensure that data has been abstracted, captured and/or encoded properly.

Results of the foregoing validations may be output as structured code, e.g., in a JSON file format. The file may include one or more indicators describing which clinical data attributes passed or failed a particular validation. Similarly, results of a test suite processing all clinical data attributes may produce a result output as structured code, e.g., also in a JSON format, that describes which particular test(s) within the suite passed or failed for one or more given patient records passed to it.

Various System-Supported User Roles or Use Cases

The system may usable by a plurality of different users having distinct roles. For example, the following list describes various user roles or use cases, the corresponding actions each user may take, and one or more benefits that may result from use of the system as a result of those actions:

A clinical manager may want to evaluate a single patient, a project, an in-progress or completed cohort or one or more patients abstracted and/or QA'ed by a specific abstractor or lead user for accuracy. Additionally, this user may want to obtain an analysis of a data stream sourced externally (e.g. via EMR or structured data extract) to determine the need for further incremental abstraction of a patient's clinical record.

A single abstracted patient can be evaluated for accuracy through the use of the clinical data validation service either upon request, when the corresponding patient case is being submitted via Workbench or when clinical attributes are modified. Validation rules are run atop all structured clinical data for a single abstracted patient and pass/fail assignments are made as a result. The clinical data validation service also maintains an "effective as of" timestamp that ensures that only appropriate validations are run on a single abstracted patient at that point in time.

A project can be evaluated for accuracy through the use of the clinical data validation service either upon request or when the project is used as a filter within the QA Manager Console user interface. At this point in time, validation rules will have already been run atop all structured clinical data for all completed and submitted patients within the given project and pass/fail assignments are retrieved as a result. The clinical data validation service also maintains an "effective as of" timestamp that ensures that only appropriate validations are run on abstracted patients within a project at that point in time.

A cohort can similarly be evaluated for accuracy through the use of the clinical data validation service either upon request or when the cohort is used as a filter within the QA Manager Console. At this point in time, validation rules will have already been run atop all structured clinical data for all completed and submitted patients with the given cohort and pass/fail assignments are retrieved as a result. The clinical data validation service also maintains an "effective as of" timestamp that ensures that only appropriate validations are run on abstracted patients within a cohort at that point in time.

Externally sourced data streams may first be ingested and mapped to a source-specific schema by a member of an integrations team. Subsequently, the schema may be aligned to a clinical data model by a member of an informatics team that allows for mapping of concepts to a canonical set of systems, codes, and values. After the schema mapping and concept mapping steps, the clinical data validation service can evaluate an externally sourced patient record upon request by using the default set of validations checks. Further, source-specific custom rules and validations may be authored within the QA Manager Console to ensure proper coverage of all desired data integrity checks.

A clinical abstraction lead may want to identify gaps in abstraction for a patient and/or project assigned to their abstraction team, perhaps specific to a cancer type (e.g. colorectal team). In this instance, the clinical abstraction lead may want to obtain the IRR score for a project, manually initiate a test suite for one or more clinical data attributes as well as perform various validation checks. IRR scores at a project-level are aggregated and averaged across all eligible and completed IRR cases within that project. As a reminder, IRR case agreement thresholds and case eligibility percentage are configurable at the project level and will vary. A global set of validation checks are available via the clinical data validation service and can be run atop one or more patient records corresponding to a project.

A clinical data abstractor may want to preview content ingested from third party sources into various data streams and obtain a report consisting of quantitative insights specific to clinical data attributes (e.g. medications, procedures, adverse events, genetic testing, etc.) that will help them to more fully abstract a patient's clinical record from various disparate sources.

An operational lead may want to better understand data coverage and quality gaps specific to one or more patients or in aggregate across specific projects/cohorts. Further, they may want to receive automated notifications and warnings that will alert them to take action directly with health system content partners when data validations fail and/or the automated evaluation and scoring for various clinical data streams is insufficient.

A data scientist may want to integrate with the system to better train machine learning models based on various levels of priority and/or a trust scale for various clinical data ingested and/or structured across clinical data streams. For example, a project or cohort with a high IRR score, near-perfect clinical data validation checks and automated test suites passing may be treated preferentially to other unstructured or semi-structured clinical data with lower scores.

An integration and/or infrastructure engineer may want to monitor various clinical data streams being ingested from external sources to verify connectivity, data sufficiency as well as quality over time.

A quality assurance engineer may want to compare the output of their manually maintained clinical data test suites against externally sourced content programmatically or on an ad-hoc basis.

A product manager may want to better understand the project, cohort and/or field level scoring of either/both abstracted and structured data to determine further improvements to various workflows, user interfaces and design patterns to accelerate and further streamline the data structuring operation.

For each of the triggers discussed above, as well as for other events that may trigger the quality assurance testing disclosed herein, the system maintains a continuously growing set of stream-specific validations, warnings, and errors that help proactively inform and/or alert administrators of patient data quality and integrity issues. By making a request to the clinical data validation service, a supported application and any of its users can quickly identify whether a patient case, either individually or one within a specific cohort, has passed or failed one or more validation checks.

Validations may be managed through a QA Manager Console user interface where they are constructed and/or grouped for use as part of quality assurance activities (at a batch and/or cohort level) and as part of on-demand evaluation criteria for one or more patient records. These validations are also useful when accounting for inclusion and exclusion criteria specific to patient cohorts for research and/or clinical trial consideration purposes.

FIGS. 147-150 depict one example of the user interface through which a manager-level user can view and maintain these validations, quickly determine which patient cases have passed or failed, obtain the specific detail about any failed validation, and quickly re-assign cases for further manual QA and issue resolution prior to clinical sign-out and approval. In particular, FIG. 148 depicts an exemplary user interface for performing quality assurance testing based on generic abstractions from raw documents. FIG. 149 depicts an exemplary user interface that is used to provide abstraction across multiple streams of raw clinical data and documents. FIG. 150 depicts an exemplary user interface for performing an inter-rater reliability analysis.

In another aspect, FIGS. 151 and 152 show a second exemplary user interface that a clinical data analyst may utilize to compare, merge and generate a "single source of truth" patient record across multiple data schemas, sources and/or streams.

Turning now to FIGS. 153-156, the system additionally may output and/or deliver various metrics and reports that provide insight into the accuracy and/or completeness of patient clinical records specific to a project as well as across selected projects for comparative and benchmarking purposes. Reporting data may include rankings and scores at both the patient record and clinical data attribute/field grain, indicative of data source/stream quality, completeness and integrity. This information becomes available to clinical data abstractors within a data curation, abstraction, and/or structuring toolset and user interface to aid in their desire to generate a "single source of truth" consolidated patient record atop various sources. It can also be used by clinical data managers to ensure a high quality data product deliverable for partners. As seen in these figures, the system may generate outputs permitting a user to visualize the IRR scoring and conflict resolution processes, as well as to review the subsequent reporting and insights generated afterwards. Additionally, a sample visualization describing data quality across various clinical data attributes and types is included for reference.

With regard to the analytical tools described above, validation rules may be composed of hard, blocking errors (e.g., an indication of a new problem emerging after a recorded date of death) and loose warning notifications (e.g., an indication from one portion of the patient's record that the patient has stage 2 lung cancer while a second portion of the record indicates that the cancer is stage 3) that help to improve the integrity of a patient record during the clinical data structuring process as well as afterwards during subsequent QA activities. Because the system may include a "sliding scale" of error severity, the results of the data quality tests may not be an "all-or-nothing" situation. Instead, as seen in FIG. 155, the system may generate quantitative metrics such as a "% success" indicator to measure the accuracy of the data structuring. This indicator also may account for the fact that a test suite may comprise dozens, if not hundreds, of different validation checks and that some may return acceptable results while others may indicate errors, missing information, or incomplete information.

Finally, FIG. 157 depicts one exemplary process flow of the present disclosure. In that figure, external data is received by the system, where it is ranked, scored, or otherwise structured, either on its own or in consideration with other data streams from the same patient. The structured data then is run through one or more QA Automation processes, such as the processes discussed herein in order to generate metrics and reports that can be output, e.g., to an administrative user or to the institution providing the external data.

V. Mobile Supplementation, Extraction, and Analysis of Health Records

With reference to FIG. 158, the present disclosure describes an application interface 4010 that physicians can reference easily through their mobile or tablet device 4012. Through the application interface 4010, reports a physician sees may be supplemented with aggregated data (such as de-identified data from other patients' reports) to provide critical decision informing statistics or metrics right to their fingertips. While a mobile or tablet device 4012 is referenced herein throughout for the sake of simplicity and consistency, it will be appreciated that the device running the application interface 4010 may include any device, such as a personal computer or other hardware connected through a server hosting the application, or devices such as mobile cameras that permit the capturing of digital images for transfer to another hardware system connected through a server hosting the application.

An exemplary device may be any device capable of receiving user input and capturing data a physician may desire to compare against an exemplary cohort to generate treatment recommendations. An exemplary cohort may be a patient cohort, such as a group of patients with similarities; those similarities may include diagnoses, responses to treatment regimens, genetic profiles, and/or other medical, geographic, demographic, clinical, molecular, or genetic features.

Generating a report supplement may be performed by a physician by opening or starting-up the application, following prompts provided by the applications to capture or upload a report or EMR, and validating any fields from the report that the application automatically populated for accuracy. Once captured, the patient's data may be uploaded to server and analyzed in real time; furthermore, cohort statistics relating to the patient's profile may be delivered to the application for the physician's reference and review. The details of this implementation, and more, will be discussed with reference to the Figures below.

In one embodiment, as seen in FIG. 158, a home screen 4014 of a mobile application is displayed on the mobile device 4012. The home screen 4014 may provide access to patient records through a patient interface 4018 that may provide, for one or more patients, patient identification information 4020, such as the patient's name, diagnosis, and record identifiers, enabling a user (physician or staff) to identify a patient and to confirm that the record selected by the user and/or presented on the mobile device 4012 relates to the patient that the user wishes to analyze. In the event that a desired patient is not displayed on the patient interface 4018, the home screen 4014 may also include a search indicator 4016 that, upon selection by the user, receives text input such as a patient's name, unique identifier, or diagnosis, that permits the user to filter the patients by the search criteria of the text input to search for a specific patient. The mobile device 4012 may include a touch screen, through which a user may select a desired patient by touching the area on the application interface that includes the desired patient identification information 4020. A cursor (not shown) may appear on the screen where the user touches to emphasize touch or gestures received.

Alternative home screens may be implemented that provide a user with options to perform other functions, as well as to access a patient identification information screen, and it will be appreciated that exemplary embodiments referenced herein are not intended to limit the interface 4010 of the application in function or design.

Staying with FIG. 158, a user may add a new patient by selecting a corresponding "add patient" icon 4022 on the application or through gesture recognition. Exemplary gestures may include swiping across the screen of the mobile device 4012 to the left or right, using several fingers to scroll or swipe, tapping or holding down on a portion of the patient interface 4018 not occupied by patient identification 4020, or any other designated gesture. Alternatively, if no patient data is present in the patient interface 4018, the interface may default to adding a user once active. Adding a patient may either be performed manually, by entering patient information into the application, or automatically by uploading patient data into the application. Furthermore, automatic uploading may be implemented by capturing an image of patient data at the mobile device 4012, such as from a report, as disclosed below with reference to FIG. 159.

Turning to FIG. 159, once a user has selected a patient, completed adding a new patient, or is adding a new patient from a report, an electronic document capture screen 4024 may appear. The system may be configured to capture images of documents that are saved in a plurality of different formats. Exemplary electronic document captures may include a structured data form (such as JSON, XML, HTML, etc.), an image (such as JPEG, PNG, etc.), a PDF of a document, report, or file, or a typeface or handwritten copy of a document, report, or file.

In order to electronically capture a physical copy of a document, the user may place the document on a surface, such as a surface that provides a contrasting color or texture to the document, and aim the mobile device's camera at the document so that an image of the document appears in the document capture screen 4024. The user then may select a document capture icon 4026 to begin a document capture process. In an alternative embodiment, an automatic capture may be generated once capture criteria are met. Exemplary capture criteria may include that the document bounds are identifiable and/or that the document is in focus.

During the capture process, or once the document capture icon 4026 has been selected, the application 4010 may launch a document sensing engine that applies an algorithm to scan incoming image data from the device's camera and overlays a document highlight, such as a border or shaded region 4028 on top of the document to visually indicate to the user the bounds of the report currently being captured. The document sensing engine may request that the document be placed on a contrasting surface so that the edges of the document, such as the borders of an 8"×10" or 8.5"×11" sheet of paper, are detectable in the camera frame as well as on the electronic document capture screen 4024. Upon detecting a document, the application also may request that the user hold the device 4012 steady, or still, so a capture may be processed of the document. After the document is captured, the application may prompt the user to take one of a plurality of additional actions, including, for example, recapturing the image, capturing additional images from the document, or indicating that the user is done with the document capture.

In an alternative embodiment, the application may provide an icon on the capture screen or the home screen to upload an electronic data capture, image, or digitized file that is already present on the mobile device. A user may then navigate to the folder on the device containing the document and select it for upload. Part of the upload process may include converting the uploaded file into a preferred format for an electronic data capture.

In one embodiment, an electronic document capture may be generated in black and white, grayscale, or color. If necessary, the electronic document capture may be pre-processed to perform text cleaning and error detection, such as format conversion, resolution conversion, skew detection/correction, or batch sizing, resizing, or processing using document processing tools. Once pre-processed, the document may be submitted for optical character recognition (OCR) on the document to convert the text into a machine-readable format, such as text, html, JSON, or XML using other document processing tools. Once in a machine-readable format, error correction, such as spell checking, noise removal, or context based correlation may be performed on the now-machine-readable text using still other document processing tools. It should be appreciated that the document processing tools may be a single tool or may be a collection of tools from which the requisite tool for the processing task is selected in turn. When processing electronic document captures, many document formats may require format conversion from an unsupported format to a supported format. Exemplary conversions may take documents of a variety of formats, including, for example, XML, HTML, rich text, PDF, PNG, or JPG, and convert them to a format that a respective OCR service accepts, such as JPG or PNG. During format conversion, additional processing may be performed for parameter optimization for each respective document to achieve the best results from the OCR service selected, for example, by converting documents from a source resolution, or dots per inch (dpi), to a resolution best supported or by combining multiple requests into one to optimize batch processing. Furthermore, another advantage of batch processing is discussed below with respect to FIG. 160.

In another embodiment, additional pre-processing may be performed after submitting an image to OCR to determine whether the detected text is "reasonable" before outputting final results. In one example, the word "beast" may rarely occur in an a patient report, for example, as "patient was mauled by unknown beast;" however, "breast" may occur more frequently, for example, as "patient expresses concern re: lump in breast," "breast cancer," "stage iv breast cancer," or "patient's breast recovered from surgery," giving "breast" a much higher probability of occurrence weighting than "beast." As a result, a reasonability determination may replace "beast" with "breast," and indicate that the resulting OCR text is reasonable. While some OCR technologies may perform their own reasonability determination, it may be necessary to further improve upon the quality of the OCR output by performing a text cleaning algorithm on the OCR output.

In one embodiment, a document classifier may process the OCR output of the electronic document capture to recognize document identifiers which are linked to features of the document stored in a predefined model for each document. Predefined models may also be referred to as predetermined models. Document identifiers may include Form numbers (such as Form CA217b, Patient Report Rev 0.17, AB12937, etc.) indicating a specific version of a document which provides key health information in each of the respective document's features. Features of a document may include headers, columns, tables, graphs, and other standard forms which appear in the document.

Exemplary predefined models may be a JSON file, HTML, XML, or other structured data. Predefined models may store a list of features that are derived from the document based on MLA processing. The processing may occur over a plurality of MLA processing steps and/or sub-steps, each of which may output certain features to the predefined model after each processing step as discussed in further detail below. Each of these features may additionally have a required or optional tag identifying whether the feature must be present or may be present. Furthermore, each feature may have a list of expected key health information types. For example, a header may expect a patient name, a patient date of birth, an institution name, a report date, a diagnosis, etc. The list of features and corresponding expected key health information may be encoded into the predefined model. Furthermore, a mask, natural language processing model, and other extraction guidelines may be stored in the predefined model. Extraction guidelines may include reliability checks to ensure that the information is correct. For example, a diagnosis date may not occur before birth, or a treatment date may not occur after death. Masks, natural language processing models, and other extraction guidelines are discussed in further detail below and, in addition, with respect to FIG. 160. Predefined models may be the result of a machine learning algorithm (MLA) or may be curated by hand for each report type. It should be appreciated that a predefined model may include or exclude additional criteria and/or differing levels of the above criteria, in addition to other unmentioned criteria based upon the report type, the curating method, or user preference.

In another embodiment, document identifiers may be generated from the MLA. A MLA may not generate easily human recognizable patterns, such as the form numbers above. Instead a MLA may identify a document by pixel arrangements, locations, colors, or other features. For example, a standard report may have a test provider's logo in the top left hand corner of the first page and a header encased in a solid black border after the logo. The MLA may identify distinguishing characteristics, pixels, or colors from the logo and the thickness of the border of the header a seemingly random placement as a unique document identifier which is consistent between reports. Furthermore, even if a document is identified as "Form CA217b", the MLA may not use the text for identification purposes but instead identify, for example, that the pixels of the "F" are in a slanted line.

As a result of the OCR output, the application also may identify medical data present in the document. Medical data, or key health information, may include numerous fields including, but not limited to, patient demographics (such as patient name, date of birth, gender, ethnicity, date of death, address, smoking status, diagnosis dates, personal medical history, or family medical history), clinical diagnoses (such as date of initial diagnosis, date of metastatic diagnosis, cancer staging, tumor characterization, or tissue of origin), treatments and outcomes (such as therapy groups, medications, surgeries, radiotherapy, imaging, adverse effects, associated outcomes, or corresponding dates), and genetic testing and laboratory information (such as genetic testing, performance scores, lab tests, pathology results, prognostic indicators, or corresponding dates).

Each of the fields, for example the address, cancer staging, medications, or genetic testing may also have a plurality of subfields. The address field may have subfields for type of use (personal or business), street, city, state, zip, country, and a start or end date (date that residency at the address begins or expires). Genetic testing may have subfields for the date of genetic testing, testing provider used, test method, such as genetic sequencing method or gene panel, gene results, such as included genes, variants, expression levels/statuses, tumor mutational burden, and microsatellite instability. One type of genetic testing may be next-generation sequencing (NGS). The above-provided examples, enumerations, and lists are not intended to limit the scope of the available fields and are intended to be representative of the nature and structure that fields may take.

In some instances, the application may direct a user to scan additional pages of the document based on the predefined model associated with the recognized document identifier. For example, if a 20-page report features key health information on pages 1-5 and 17, the application may determine the format of the report and request the user to process an electronic document capture on each of pages 1-5 and 17 before performing additional data extraction. In another example, if a report has a non-standard page layout, the application may request the user to skip background sections, waivers, privacy notices, or other pages which do not contain key health information when capturing pages of the document. Exemplary key health information may be found in features of the document such as headers and tables. An exemplary header may include a standardized format with key health information such as a patient's name, date of birth, age, gender, diagnosis, treating facility, and other medical data detailed above. An exemplary table may also include key health information in the form of report summary information such as mutations or genetic variants identified during sequencing of a patient's DNA or gene expression counts identified during sequencing of a patient's RNA. Extraction techniques are discussed in more detail below.

In another embodiment, the electronic document capture may reference the predefined model to identify the region of the electronic document capture containing key health information and extract the identified region for further processing. A region (such as a header, table, graphic, or chart) may be identified by utilizing a stored feature list for the document, or each page of the document, that identifies features present in the page along with their corresponding locations in the page. For example, the model may indicate that a page should expect to present a patient header, two tables, a chart, and a graph. A region mask may be applied to the capture to verify that any regions expected to be present are actually within the capture. A region to extract may be identified by the region mask and, upon verifying that the region is present, the region may be extracted. Text may be identified from the extracted region and provided to a natural language processing (NLP) algorithm to extract patient information, such as patient name, diagnosis, notable genetic mutations, or gene expression count information including count values representing the number of times the RNA sequence occurs in sequencing and/or deviation in gene expression counts compared to the gene expression counts of normal samples that may be labeled over or under expressed. More details for feature/region detection and extraction are discussed below with respect to tabular extraction.

Each field of the extracted region may have a plurality of enumerated values, or, if an enumerated list of values is unavailable may be limited to a certain type of value. For example, if the field relates to patient diagnosis, it may have a corresponding enumerated list of all diagnoses that may be provided in the report. If the field relates to a treatment, it may have all known treatments and further parse the field to identify and enumerate unknown treatments. Alternatively, if the field is a medication that the patient was prescribed, it may be limited to a type, so that data parsed will be checked against known medications and, if necessary, add the parsed text to a medications database as a new entry of type medications. The types of field, their enumerated values, or the classification associated with unknown values may be stored as part of the predefined model.

In an alternate embodiment, a tabular extraction method may be performed on the OCR output of the electronic document capture. Where the above method requires that each document type has a predefined model in-place to capture specific elements from the document, a tabular extraction approach may process a document type without a predefined model and generate a model as an output of an algorithm, described in more detail with respect to FIG. 160, below. For example, every report may include patient information or demographics such as the patient's name, date of birth, diagnosis, or institution which may be automatically parsed without particular knowledge of the specific report. In addition, specific reports may be discernible contextually, for example, a genetic sequencing report may include listing of genes, mutations, variants, and expressions which would indicate that the report may provide certain classifications of patient information that should be extracted. A gene field may be tagged as required, as any sequencing report may present this information and a mutation, variant, or expression field may be tagged as optional as different sequencing reports may present differing types of information (such as a DNA report may include mutations, but not expression).

FIG. 160 depicts an exemplary tabular extraction approach involving masks 1-3. In this example, the document 4030 being extracted may be a standardized report, such as a report used by a physician or group of physicians, including patient onboarding forms, progress notes, pathology reports, and other standard documents. Standardization in this situation may indicate that the reports are presented in a general format with regularly occurring fields (permanent or optional) populated specific to a patient. For example, a patient onboarding form may have a header 4032 (as shown in FIGS. 161A-B) which lists patient information such as name, address, symptoms, medications. A progress note may have a table that allows the physician to catalog treatment options recommended to the patient, treatment options which were pursued from a previous visit, and any updates to the status of the patient relating to the treatment options pursued. A pathology report may include a first section 4034 listing a plurality of genetic variants that may be tested in a specific pathology assay and a second section 4036, which may be distinct from the first section, providing sequencing results for each corresponding genetic variant of the first section at a spatially corresponding location to the first section. Furthermore, some reports may feature tables, charts, or other sections 4038 that may expand or be split across multiple pages, similar to section 4 of Mask 3 (also shown in FIGS. 161A-B).

In this context, a MLA or a deep learning neural network (DLNN) may be utilized. The MLA may have been trained with a training dataset that comprises annotations for types of classification that may be performed. It should be understood that the terms MLA and DLNN are interchangeable throughout this disclosure. Thus, a mention of MLA may include a corresponding DLNN or a mention of DLNN may include a corresponding MLA. A resulting ruleset or neural network may identify or recognize a plurality of features across a standardized report or other template signifying that a classification may be extracted from a specific section of a particular report based at least in part on that extraction ruleset. Exemplary metrics and features that may be applied are discussed in more detail below.

As noted above, one type of document that the system may be configured to capture is a genetic testing report and, in a particular aspect, a next generation sequencing (NGS) report. For example, once the mobile device captures the NGS report about a sequenced patient (for example, by generating an electronic document capture), the system may extract some or all of the NGS medical information (such as patient information, genes, mutations, variants, or expression data) contained in the document. Using various OCR, MLA, and DLNN techniques, such as those described herein, that extracted information then may be stored in a database or other data repository, preferably in a structured format.

The system may be configured to recognize various types of NGS medical information from the captured report. For example, the system may be configured to extract and recognize NGS medical information relevant to one or more diseases, including: cancer, diabetes, depression, cardiovascular disease, neurological disorders, infectious diseases, lupus, or endocrinology-related diseases. The NGS medical information additionally may include one or more of: somatic variants, germline variants, tumor mutation burden (TMB) values, microsatellite instability (MSI) values, therapy resistance values, organoid response values, epigenetic values, RNA expression values, locus-based somatic variants, and/or gene-based somatic variants. Still further, the NGS medical information may focus on specific genetic mutations, such as a KRAS mutation, a BRCA mutation, an EGFR mutation, a CYP2C19 mutation or other mutations, such as any of the genes referenced below.

Once the system extracts the NGS medical information, the system then may classify or correlate that information to other medical data, based, e.g., at least in part on the feature(s) from which it is extracted. For example, the system may correlate the NGS medical information to prior treatment data, including medication and/or chemotherapy data. The system also may correlate the NGS medical information to prior outcomes data, including survival, remission, and/or tumor progression data. It will be appreciated that the prior treatment and/or prior outcomes data may be from the patient to whom the NGS medical information relates or from patients other than the sequenced patient.

Turning to FIGS. 161A-B, an exemplary NGS report featuring Sections 1-4 as described in FIG. 160 may be processed by an MLA or DLNN to identify Section 1 as a header 4032 which lists a plurality of features 4040, such as a patient's name, date of birth, and diagnosis; the institution's name and location; and the date of report, of data collection, etc. The MLA may also identify extraction techniques to apply, such as use sentence splitting algorithms to parse a plurality of sentences and then regular expressions to match "Patient Name:", "D.O.B.:", "Diagnosis:", "Collection Date:", and "Institution:" or alternatively splitting the sentences on the colon (":") character and applying the first results to a patient name field, second results to a date of birth field, third result to a diagnosis field, fourth result to a collection date field, and fifth result to institution name and location fields.

The MLA may identify Section 2 as a region 4034 including a plurality of features 4042, such as a listing of genetic mutations which are linked to Section 3. For example, within this other region 4036, the MLA may enumerate additional features 4044, including all possible genetic mutations or variants that may occur in Section 2. Additionally or alternatively, the MLA may be trained to identify the word "Mutation" and then determine that the text immediately preceding or following that word is a candidate for a possible mutation. In this regard, the system may utilize the nature of mutation descriptions, namely that many mutations are represented by unique alphanumeric phrases, such as "KRAS," "BRAF," and "PIK3CA" in FIG. 161A. Thus, when the MLA identifies these phrases, it may compare them against a database or dictionary or known mutations such that, when one or more matches are found, the MLA may be able to conclude with a high degree of confidence that the match corresponds to a possible mutation, in other words, a risk of a false positive is low. Still further, because the mutations of Section 2 are linked to the variants in Section 3, the MLA may perform a two-way cross-check against the dictionary or database in the event that the text extracted does not correspond to a known mutation or variant. A two-way cross-check may also be performed to another section within the report such as an appendix or glossary. For example, if the system read the mutation "KRAS" as "RRAS," it would not find the latter mutation in its database or dictionary. At that point, the system may check its corresponding variant—in this case, "Exon 2 100C→A," determine that there is a match in the database or dictionary for that variant, and determine that the mutation corresponding to that variant is "KRAS." At that point, the MLA may either accept the change automatically, or it may do a comparison between the extracted term, such as "RRAS," and this matching term, "KRAS." The MLA may rely on various comparators, such as the number of characters in each term, the number of matching characters in each term (such as the second character in each term is an "R," the third character in each term is an "A," and the fourth character in each term is an "S"), a comparability score between the non-identical characters (such as "K" and "R" may be given a higher comparability score than "K" and "Q," as the former set of characters more closely resemble one another than the latter), or other comparators, in order to determine a likelihood of match. If the match likelihood is above a certain threshold, the MLA then may conclude that the extracted term should be modified to the matching term and will replace the term accordingly.

Furthermore, the MLA may identify a number of fields that may be extracted in this section as a range of values. For example, if there is always at least 1 mutation listed but never more than 9, the MLA may identify a range from 1-9 for extraction, similarly, if there are no mutations listed, the MLA may "tag," or annotate, this field as optional and include a range of 0-9 mutations for extraction.

The MLA may identify each row in Section 3 as a corresponding sequencing result to the genetic mutation of Section 2 in the same row. For example, if there are three rows in Section 2 identifying KRAS, BRAF, and PIK3CA mutations, there should exist at least three rows in Section 3 which feature corresponding variants to the KRAS, BRAF, and PIK3CA mutations, respectively. The MLA may identify column and row numbers or just row numbers for the number of genetic mutations, variants, or expressions to extract based upon the detected structure during processing. It is possible that there may be more than one variant detected for a given mutation. In that regard, different document types may report that information differently. For example, one type of document may provide the information in a 1:1 fashion, such that there may be two rows in Section 2 with the same mutation listed, each row corresponding to a unique variant in Section 3. Alternatively, a different document type may group all variants for a given mutation in the same box in Section 2, those different variants separated by some kind of indicator, such as a comma, semicolon, colon, slash, backslash, new line, etc.

Lastly, the MLA may identify Section 4 as a region 4038A a multi-page table in which its features 4046A include summaries of conclusions made from the sequencing results of Sections 2 and 3. In this example, Section 4 spans multiple pages, and the system may recognize that the portion 4038B of Section 4 on the second page (FIG. 161B) is a continuation of the portion of Section 4 on the first page, with additional features 4046B. For example, the MLA may recognize a width of the columns in both of the portions and determine that the widths of the respective portions of each column are the same, the first column in Section 4 in FIG. 161A is the same width as the first column in FIG. 161B. In another instance, the portion at the top of the second page may include one or more headers, which the MLA may recognize as the same header(s) as the portion of Section 4 at the bottom of the first page. In still another instance, the MLA may recognize other text (such as "Continued" or "Cont'd" or " . . . "), signaling that the portion at the top of the second page is a continuation of Section 4.

The MLA may identify a column and row structure where column 1, rows 1-N correspond to Rows 1-N of Section 2. The MLA may further indicate that OCR results of the previous Sections may be verified by comparing with the current section and vice versa. Furthermore, the MLA may identify that Column 2 of Rows 1-N correspond to therapies of genetic mutations detected in Section 2 and that Column 3 or Rows 1-N identify whether the therapies are approved for other cancer types. For example, if there are three rows, an exemplary model may identify that for N rows, column-row pair 1-1, 1-2, . . . 1-N, each identify a mutation; column-row pair 2-1, 2-2, . . . 2-N, each identify a therapy for that mutation; and column-row pair 3-1, 3-2, . . . 3-N, each identify if alternate carcinomas may be treated with the therapy. Just as there may exist N rows there may also exist some number, M, of columns such that column-row pairs M-1, M-2, . . . M-N exist and relationships between the columns and rows may be represented.

Alternatively, the discrete elements in one or more of the columns may span more than one row. For example, in FIGS. 161A-B, the therapies may be presented as a class of therapy on a first row, such as "PI3K Inhibitors;" followed by one or more specific therapies within that class, such as "Erlotinib" and "Gefitinib," on separate, successive rows. The MLA may be trained to recognize that an indentation from one row to the next may indicate such group/instance relationships, that successive lines with no indentation may signify a continuation of the text of the first line, and/or that a certain minimum amount of white space between lines may signify a break from one class of therapies to the next.

Each of the above identifications, validity checks, or other determinations made by the MLA may be encoded and stored in the predetermined model (or predefined model as discussed above) for reference during processing of a report sharing the same template. In this regard, the model may be considering an overarching rule set used to identify a report or other document. The model may be generated from the MLA, from a human curation, or a combination thereof (such as an MLA model supplemented with additional human curation). Templates for each document may be one component of the model, along with identifiers for each template, regions or masks, features or fields and tools or instructions for how to extract those features or fields and verify the accuracy of that extraction, associated sub-fields, and rules for normalization of those fields and sub-fields.

One exemplary technique to access the data within each of the identified sections may be to generate a mask which "outlines" the section, apply the mask to the document to extract each section in turn, and then provide the section to an OCR algorithm, such as an OCR post-processing optimized to extracting information from the respective section type.

As discussed above, exemplary masks for extracting each of the Sections 1-4 are disclosed in FIG. 160. Mask 1 may identify the bounds of Section 1, for example, by identifying a size (such as number of pixels, width, length, diameter, etc.), shape (such as square, rectangle, or other shape), and origin point (such as a pixel X,Y pair) for a mask 4050A or by identifying a starting (such as the pixel location of the top, left side) and ending point (such as a pixel location of the bottom, right side) of a rectangular mask. Other field designations may be useful for other shapes, for example, a circle may have an origin and a diameter, or any enclosed shape (polygonal or combinations of shapes), such as an L shaped box may have multiple corner points outlining the exterior of the mask in a node/edge graph relationship establishing nodes, edges shared between nodes, and the location of each node. The mask may be a numerical 1 for the white region or 0 for the black region. Alternatively, the mask may be 1 for a pixel intensity value greater than/ greater than or equal to a certain threshold and 0 for a pixel intensity less than or equal to/less than a certain threshold. The pixel values of the document then may be multiplied with the corresponding mask value to apply the mask or may be applied in a binary fashion such as a logical AND operation. For example, only the region of the image which is multiplied, or logical AND operation, with a 1 are kept for OCR; the region that is multiplied, or logical AND operation, with a 0 is lost. Once the mask is applied, an exemplary optimized OCR post-processing for that section may include a regular expression, such as a regular expression or matching a string "Name:" or "DOB:", and/or a column, row pair(s) which contains key health information, for example, a cell located at Column 2, Row 2 may provide a patient name, or a cell located at Column 2, Row 3 may provide a patient date of birth. In a similar fashion, Section 2 may be extracted next using a second mask 4050B and Section 3 may be extracted using a third mask 4050C. Sections 2 and 3 may then be supplied to OCR post-processing for linking the results of Section 3 to the enumerated content of Section 2. In an alternate embodiment, Sections 2 and 3 may be extracted at the same time using a combined mask 4050D. Section 4 may similarly be extracted at the same time using a combined mask 4050E by appending/concatenating the image of page 1 and page 2 together or may be masked individually for each page and the resulting masked sections may be appended/concatenated for post processing. In other alternative embodiments, masking may be performed by cropping the image, extracting only the image along a bounded box, or other image segmentation techniques.

As discussed above, the MLA may search for one or more keywords or phrases identifying the entity generating the document, such as the "Institution:" keyword in Section 1 may trigger the MLA to understand that the word or words following the ":" are an indicator of document source. The MLA then may use that information, alone or in combination with other extracted data such as the Collection Date value, a Version No., etc., to access a stored library of templates. For example, with regard to FIG. 161, the system may include one or more stored document templates for documents created by "ABC Labs," and the Oct. 20, 2018, collection date may inform the MLA as to which document to use when there are multiple documents.

The MLA or DLNN performing tabular extraction may be implemented as a single training set for all documents, or it may be segmented into one or more layers to improve processing speed of the each stage of the extraction process and to allow modular improvements to be incorporated without retraining the entire process at once. An exemplary multi-layer extraction may be performed through a template-based approach using a supervised or semi-supervised training set or may be performed through a fully tabular approach using an unsupervised or semi-supervised training set. In an exemplary template-based approach, an MLA may be provided with specific forms containing a standardized layout for each document type commonly found in electronic document captures. Additional information on how to identify the form may be provided (such as a location/bound to OCR and a text string to match a document name). In another embodiment, the MLA may train to discern how to identify the form and may train to recognize concept candidates in the specific form document provided. The template-based approach (as described above) may further incorporate the methods and processes of the instant tabular approach to operate consistent with the below description.

In an exemplary tabular approach, a first layer of a multi-layered MLA may process (in training) electronic medical record (EMR) and electronic health record (EHR) documents to identify documents of similar form, layout, or structure. For example, in an EMR of a 1000 documents, the first layer MLA may identify that 400 of the documents follow a first similar form (such as the document in FIG. 161 for the form in FIG. 160), 300 follow a second similar form different from the first, and the remaining documents do not follow a similar form. The MLA may identify one or more of a first subset of masks for the 400 documents of first similar form (such as Sections 1-4 of FIG. 160) and may identify one or more of a second subset of masks for the 300 documents of a second similar form. An output of the MLA from the first layer may be a series of masks for each of the identified similar forms. In another embodiment, the first layer may be broken up into a series of MLA; for example, the processing flow of the first layer may be arranged to divide the tasks of recognizing similar documents to identify a potential template and then process each template to generate masks for each of the identified templates as two or more operations. The results of each layer of the MLA processing may be encoded into the predefined model for retrieval during processing or may be encoded in the neural network of the DLNN.

A second layer of a multi-layered MLA then may utilize the resulting masks from the first layer to process the training data set by identifying regions of interest in a document, identifying a corresponding mask for each identified region of interest, and applying the mask to each document to extract and process the region of interest. An exemplary intermediary processing step of the second layer MLA may identify, for each region of interest, which type of feature the region of interest may contain (such as a table, header, graph, etc.). An output of the MLA from the second layer may be a series of masked images for each of the regions of interest and an indicator for the type of feature that exists in the region of interest.

In another embodiment, the second layer may be broken up (or consolidated) into a different series of MLA; for example, the processing flow of the second layer may be arranged to divide the tasks of applying each mask to each region of interest and identifying the features of the region of interest into a single operation or further subdivide the processing into further operations.

A third layer of a multi-layered MLA may utilize the resulting masked regions of interest and identified features for each region to select an optimized OCR post-processing to extract the text from the region of interest. An exemplary optimized OCR post-processing for that section may include a regular expression, such as a regular expression or matching a string "Name:" or "DOB:", and/or a column, row pair(s) which contains key health information, for example, a cell located at Column 2, Row 2 may provide a patient name, or a cell located at Column 2, Row 3 may provide a patient date of birth. Further post processing of the OCR text may identify that regions of interest are related to one another. For example, a first region of interest may provide a series of gene variants while a second region of interest may provide the expression level/status of those gene variants. In this example, there are a known number of genes, each having a plurality of possible variants, and a query to a molecular pathology service may be initiated to validate whether a recognized gene and variant combination is valid/known or if the combination is actually an unrecognized variant, an OCR introduced error, or if the unknown combination originated from the document. The MLA may detect that regions are related and assign a corresponding concept candidate using both of the regions of interest together. By utilizing relationships between regions of interest in the document, the MLA may provide a more robust classification and provide a more detailed error checking than an algorithm that analyzes portions of the document in isolation. Related regions may further be used to provide error correction or OCR validation. For example, certain reports may include a feature that includes genetic variations that have been overexpressed in an RNA report. A second feature nearby may represent the same overexpressed genetic variants but further provide therapies targeting these genetic variants, and potential clinical trials that may be relevant. The reuse of data in subsequent features provides an opportunity for validating correct OCR results by comparing the results from each of these respective features. In another example, an appendix may be included at the end of the report that provides all variants which may be included. If an OCR error of a variant has occurred, then that result may not match any entry in the appendix, and may be corrected.

An unrecognized variant is one that has not been identified, sufficiently classified, or expertly-curated by the scientific community. Generally, reports include only known variants and publish updated documentation for any newly supported variants for each test/report offered. An output of the MLA from the third layer may be a collection of concept candidates or classifications for the document/patient. In another embodiment, the third layer may be broken up (or consolidated) into different a series of MLAs; for example, the processing flow of the third layer may be arranged to divide the tasks of text extraction, classification, and identifying relationships between regions of interest into a single operation or further subdivide the processing into further operations.

While the instant embodiments are described as including three layers with respective intermediate processing steps, it should be understood that each layer and the included intermediate processing steps may be reordered, combined, or skipped based on the layout of the training documents and configuration of the MLA. Therefore embodiments having fewer or extra layers may be realized without departing from the spirit of the disclosure. Furthermore, the outputs of each layer of the MLA may be encoded as rules in the predefined model for retrieval during processing of a new document.

Identifying regions of interest, features within the region of interest, or relationships between regions may be performed from the OCR text itself or processed from the image itself prior to OCR. For example, identifying a region of interest may be performed by identifying a border (such as a black box) that encapsulates some segment of text. In some instances, a border may actually be identified using the negative space (such as the white space) around a text by observing that the white space is of at least a uniform distance all around a segment of text and creating a natural boundary. For example, white space that also borders an edge of a paper may be several times as thick as the white space above and below the segment of text, but there will be at least a uniform white space of the width above and below, that is also present in the larger section on the border. Other distinctions may be observed and utilized as well based on the MLA applied. For example, a table may be identified by observing two or more intersecting lines. Similarly, lines segmenting the columns and rows of a table may be solid, dashed, or even extrapolated from the negative space between the words. Additionally or alternatively, OCR post-processing may recognize text which is presented in columns to combine the text in the correct order. Certain features may be identified based on the image of the text prior to OCR. For example, text in all capital letters may be identified by having more straight lines than typical text, bold text may be identified by having thicker letters than typical text, or italicized text may be identified by have angled lines more frequently than typical text. These features of text may be applied in determining regions of interest, related regions, or concept candidates from each region of interest. Furthermore, features of text may be identified by both image details (such as pixel density, pixel chroma, etc.) and text (such as the OCRed words themselves are shared between documents). It is appreciated that MLA and DLNN may identify features, relationships, and masks using any number of techniques which may not be easily predicted or explained herein, the above examples are merely exemplary, and easily identified/understood to illustrate the types of features that may be important to the MLA and DLNN but are not a full accounting of the possibilities.

An exemplary natural language processing (NLP) algorithm may receive as an input, a region of the electronic document capture which has had optical character recognition (OCR) performed on the extracted region to identify if the text of the region corresponds to the value type expected in that extracted region where the mask was applied. For example, if the region was expected to provide treatment information, the NLP algorithm may attempt to classify the extracted text as treatment information based off of the NLP algorithm training data set. Furthermore, the patient information being extracted, such as patient name, diagnosis, treatment, or sequencing information, may be associated with a respective field in the application. Extracted patient information may then be populated into the mobile application for review by the user, as seen in FIG. 173 and as discussed in greater detail below. The user may correct any errors by selecting the data field in the application corresponding to the information. These errors may be stored and/or sent to a training engine to improve upon the extraction algorithms and techniques. The training engine may generate a new extraction algorithm to use in future extractions based from detected errors. More information is disclosed below with respect to FIGS. 165 and 168, below. For text based fields, a text editor/keyboard may be displayed for the user to provide text corrections. Additionally, suggested replacements may also appear in a dropdown list in addition to or in place of the text editor. For date based fields, a calendar may be displayed to select the correct date, or for diagnosis, a drop down featuring diagnoses supported by the document type, report type, or even the database may be enumerated for selection. The field types listed above are merely representative and are not intended to limit fields to the specific type of data associated in the above description, for example, date based fields may also be populated using text input. The predefined model that is associated with each of the templates may contain reference fields to identify each of the fields that may be extracted to generate the extracted patient information. For example, a feature corresponding to the informational header may have a corresponding field in the predefined model which lists a location the patient name is expected, a location the patient date of birth is expected, and a location of the diagnosis (such as cancer type) is expected as described above.

In an alternative embodiment, a MLA may receive as an input, a region of the electronic document capture which has had optical character recognition (OCR) performed on the extracted region to identify if the text of the region corresponds to the value type expected in that extracted region where the mask was applied. For example, if the region was expected to provide treatment information, the MLA may attempt to classify the extracted text as treatment information based off of the MLA training set. Furthermore, the patient information being extracted, such as a patient name, diagnosis, treatment, or sequencing information, may be associated with a respective field in the application. Extracted patient information may then be populated into the mobile user interface for review by the user. Other information that may be extracted may include: gene(s) (such as TP53, NF1, or PDL1); gene expression count information (such as over/under expressed or count values representing the number of times the expression occurs in sequencing); respective gene variants (such as Q192 or E496); gene variant calls (such as "4724+1G>A", "Q192*", or "c.380C>A"); depth of sequencing (such as occurrences of chromosome hits per number of DNA reads); scope of sequencing (such as panel type: whole genome or targeted panels); proteomics (such as protein based assertions: counts and shapes); epigenetics; RNA expressions (such as over-expression or under-expression); organoids (such as chemical/medical responses organoids experienced in a lab setting); germline (such as mutations present in healthy cell DNA); immunotherapies (such as engineered immune receptors such as CAR-T, cancer vaccines, checkpoint blockades, etc.); and tumor-normal (such as a comparison of RNA and/or DNA sequencing results of tumor tissue with RNA and/or DNA sequencing results of a non-tumor sample, such as non-tumor tissue, blood, or saliva). Features of the electronic data capture may also be directed to clinical trials, for example, by listing details associated with the name of the clinical trial, geographic location of the facilities administering the trial, treatments associated with the trial, inclusion/exclusion criteria for patients who may participate in the trial, and other relevant information.

Information that is extracted may be from various disease states and relate to various genes or locus/loci (a fixed position on a chromosome, such as the position of the gene or genetic marker). For instance, on a report providing genetic sequencing information that may help a clinician make a decision about which medication to prescribe for a patient's depression, the genes related to the information on the report may include one or more of CYP2C19, CYP2D6+ DEL/DUP, CYP1A2, CYP2B6, CYP2C9, CYP3A4, HLA-A, HLA-B, HTR2A, SLC6A4, or UGT1A4. In other examples, the genes related to the information on the report may include one or more of 5HT2C, ABCB1 (MDR1), ABCG2, ACE, ADRA2A, ADRB1, ADRB2, AGT, ANKK1, ANK3, APOE, BDNF, CACNA1C, CES1, COMT, CYP3A5, CYP4F2, DPYD, DRD1, DRD2, DRD3, EDN1, ERCC1, FCGR2A, FCGR3A, F2, F5, G6PD, GNB3, GRIK1, GRIK4, GSTP1, HNF4A, HSD3B1, HTR2C, HTR1A, IFNL3, IL28B (IFNL4), KCNIP1, KCNJ11, KCNQ1, LDLR, LIPC, MC4R, MTHFR, MTRR, NEU-ROD1/BETA2, NQO1, NR1H3, NUDT15, OPRM1, PAX4, POLG, PPARA, PPARG2, PPARGC1A, PRKAA1, PRKAB2, PTPRD, RBP4, SLC6A2, SLC22A1 (OCT1), SLC22A2 (OCT2), SLC30A8, SLC49A4 (PMAT), SLC47A1 (MATE1), SLC47A2 (MATE2-K), SLCO1B1, SOD2, STK11, TCF7L2, TPMT, TYMS, UCP2, UGT1A1, UGT1A9, UMPS, or VKORC1.

In other examples, the genes related to the information on the report may include one or more of AATK, ABCA1, ABCB1, ABCB11, ABCB4, ABCC1, ABCC2, ABCG1, ABCG2, ABI1, ABL1, ABL2, ACE, ACSL6, ACTA2, ACTC1, ACVR1, ACVR1B, ACVR2A, ACVR2B, ADAM17, ADAMTS20, ADGRA2, ADGRB3, ADGRL2, ADGRL3, ADRB1, ADRB2, AFF1, AFF2, AFF3, AHR, AIP, AJUBA, AKAP9, AKT1, AKT2, AKT3, ALK, ALKBH6, ALOX12B, ALOX5, AMER1, APC, APEX1, APH1A, APOA1, APOB, AR, ARAF, AREG, ARFRP1, ARHGAP10, ARHGAP26, ARHGAP35, ARID1A, ARID1B, ARID2, ARID5B, ARNT, ARNT2, ARPC1A, ARPC1B, ARTN, ARX, ASCL1, ASCL2, ASCL3, ASCL4, ASCL5, ASH1L, ASH2L, ASPSCR1, ASXL1, ASXL2, ASXL3, ATAD2, ATAD2B, ATF1, ATM, ATR, ATRX, AURKA, AURKB, AURKC, AXIN1, AXIN2, AXL, B2M, BABAM1, BACH1, BACH2, BAG4, BAP1, BARD1, BAX, BAZ1A, BAZ1B, BAZ2A, BAZ2B, BBC3, BCAR3, BCL10, BCL11A, BCL11B, BCL2, BCL2A1, BCL2L1, BCL2L11, BCL2L2, BCL3, BCL6, BCL7A, BCL9, BCLAF1, BCOR, BCORL1, BCR, BDNF, BID, BIRC2, BIRC3, BIRC5, BIRC8, BLK, BLM, BLNK, BMI1, BMPR1A, BMPR1B, BMX, BPTF, BRAF, BRCA1, BRCA2, BRD1, BRD2, BRD3, BRD4, BRD7, BRD8, BRD9, BRDT, BRIP1, BRPF1, BRPF3, BRWD1, BRWD3, BTC, BTG1, BTG2, BTG3, BTK, BTRC, BUB1, BUB1B, BUB3, CACNA1C, CACNA1S, CACNB2, CADM2, CALR, CAMTA1, CAPRIN2, CARD10, CARD11, CARD6, CARDS, CARM1, CASC11, CASP8, CBFA2T2, CBFA2T3, CBFB, CBL, CBLB, CBLC, CBX1, CBX2, CBX3, CBX4, CBX5, CBX6, CBX7, CBX8, CCDCl$_6$, CCNB3, CCND1, CCND2, CCND3, CCNE1, CCNE2, CCNL1, CD1D, CD22, CD274, CD276, CD28, CD40, CD40LG, CD44, CD70, CD79A, CD79B, CD80, CD86, CDC14A, CDC20, CDC25A, CDC25B, CDC25C, CDC42, CDC6, CDC73, CDH1, CDH10, CDH11, CDH2, CDH20, CDH3, CDH5, CDH7, CDK1, CDK10, CDK11A, CDK11B, CDK12, CDK13, CDK14, CDK15, CDK16, CDK17, CDK18, CDK19, CDK2, CDK20, CDK3, CDK4, CDK5, CDK6, CDK7, CDK8, CDK9, CDKN1A, CDKN1B, CDKN1C, CDKN2A, CDKN2B, CDKN2C, CDKN3, CDX1, CDX2, CEBPA, CEBPB, CEBPD, CEBPE, CEBPG, CEBPZ, CECR2, CENPE, CES1, CES2, CHD1, CHD1L, CHD2, CHD3, CHD4, CHD5, CHD6, CHD7, CHD9, CHEK1, CHEK2, CHIC1, CHIC2, CHUK, CIC, CIITA, CKS1B, CKS2, CLIP1, CMPK1, CNKSR1, CNOT3, CNTFR, COL3A1, COMT, COPS3, CRBN, CREB1, CREB3L1, CREB3L2, CREB3L4, CREBBP, CREM, CRHR1, CRK, CRKL, CRLF2, CRTC1, CRTC2, CRTC3, CSF1, CSF1R, CSF2RA, CSF2RB, CSF3R, CSK, CSNK1D, CSNK1E, CTCF, CTCFL, CTLA4, CTNNA1, CTNNA2, CTNNA3, CTNNB1, CTNND1, CTSD, CTSL, CTSS, CUL3, CUL4A, CUL4B, CUX1, CYLD, CYP17A1, CYP1A2, CYP21A2, CYP2A6, CYP2B6, CYP2C19, CYP2C8, CYP2C9, CYP2D6, CYP2J2, CYP2R1, CYP3A4, CYP3A5, CYP4F2, DACH1, DACH2, DAXX, DBH, DCC, DCUN1D1, DCUN1D2, DDB2, DDIT3, DDR1, DDR2, DDX3X, DDX5, DDX6, DEK, DHFR, DHH, DIAPH1, DIAPH2, DIAPH3, DICER1, DIRAS3, DIS3, DKC1, DMXL1, DNM2, DNMT1, DNMT3A, DNMT3B, DNMT3L, DOCK2, DOT1L, DPYD, DRD1, DRD2, DSC2, DSG2, DSP, DUSP22, DVL1, DVL2, DVL3, DYRK2, E2F1, E2F3, E2F5, E2F6, E2F7, EBF1, ECT2L, EED, EGF, EGFR, EGR1, EGR2, EHF, EHMT1, EHMT2, EIF1AX, ELANE, ELF1, ELF2, ELF3, ELF4, ELF5, ELK1, ELK3, ELK4, ELP3, EML4, EMSY, EP300, EPCAM, EPGN, EPHA1, EPHA2, EPHA3, EPHA4, EPHA5, EPHA6, EPHA7, EPHA8, EPHB1, EPHB2, EPHB3, EPHB4, EPHB6, EPOR, ERBB2, ERBB3, ERBB4, ERCC1, ERCC2, ERCC3, ERCC4, ERCC5, EREG, ERF, ERG, ESCO1, ESCO2, ESPL1, ESR1, ESR2, ESRRA, ETS1, ETS2, ETV1, ETV2, ETV3, ETV3L, ETV4, ETV5, ETV6, ETV7, EWSR1, EXT1, EXT2, EXTL1, EZH1, EZH2, FADD, FAM175A, FAM46C, FANCA, FANCB, FANCC, FANCD2, FANCE, FANCF, FANCG, FANCI, FANCL, FANCM, FAS, FASLG, FAT1, FAT2, FAT3, FAT4, FBN1, FBXO11, FBXO8, FBXW11, FBXW7, FEN1, FER, FES, FEV, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFR1, FGFR2, FGFR3, FGFR4, FGR, FH, FHIT, FigF, FKBP10, FKBP5, FKBP9, FLCN, FLI1, FLT1, FLT3, FLT3LG, FLT4, FOLH1, FOS, FOSB, FOSL1, FOSL2, FOXA1, FOXA2, FOXA3, FOXG1, FOXL1, FOXL2, FOXM1, FOXN3, FOXO1, FOXO3, FOXO4, FOXP1, FOXP2, FOXP3, FOXP4, FOXQ1, FRK, FRS2, FRS3, FSHR, FUBP1, FUS, FYN, FZR1, G6PC3, G6PD, GAB1, GAB2, GABPA, GALNT12, GATA1, GATA2, GATA3, GATA5, GATA6, GDNF, GFI1, GFI1B, GFRA4, GGCX, GHR, GID4, GLA, GLCCI1, GLI1, GLI2, GLI3, GLIS1, GLIS2, GLIS3, GNA11, GNA13, GNAQ, GNAS, GNRHR, GOT1, GPC3, GPC5, GPS2, GRB10, GRB2, GRB7, GREM1, GRIN2A, GRK4, GRK5, GRM3, GRM8, GSK3A, GSK3B, GSTT1, GTPBP4, GUCY1A2, H3F3A, HAX1, HBEGF, HCK, HDAC1, HDAC10, HDAC11, HDAC2, HDAC3, HDAC4, HDAC5, HDAC6, HDAC7, HDAC8, HDAC9, HDGF, HELLS, HES1, HES2, HES4, HEY1, HEY2, HGF, HIF1A, HIF1AN, HIST1H1E, HIST1H3B, HIST1H4E, HLA-A, HLA-B, HLF, HLTF, HMGA1, HMGA2, HMGCR, HNF1A, HNF1B, HNRNPA3, HOXA10, HOXA11, HOXA13, HOXA3, HOXA9, HOXB13, HOXB3, HOXC10, HOXC11, HOXC13, HOXD10, HOXD11, HOXD13, HOXD3, HOXD4, HR, HRAS, HSD11B2, HSD3B1, HSP90AA1, HSP90A131, HSPBAP1, HTR1A, HTR2A, ICK, ICOS, ICOSLG, ID1, ID2, ID3, ID4, IDH1, IDH2, IFNLR1, IGF1, IGF1R, IGF2, IGF2R, IHH, IKBIP, IKBKAP, IKBKB, IKBKE, IKZF1, IKZF2, IKZF3, IL10RA, IL10RB, IL11RA, IL12RB1, IL12RB2, IL13RA1, IL15RA, IL17RA, IL17RB, IL17RC, IL18R1, IL18RAP, UM, IL1R2, IL1RAP, IL20RA, IL20RB, IL21R, IL22RA1, IL22RA2, IL23R, IL2RA, IL2RB, IL2RG, IL3, IL3RA, IL4R, IL5RA, IL6R, IL6ST, IL7R, IL9R, ING1, ING4, INHBA, INPP4B, INSR, INSRR, INTS12, IQGAP1, IQGAP2, IQGAP3, IRAK1, IRF4, IRF5, IRF6, IRS1, IRS2, IRS4, ITK, ITPKB, JADE1, JAK1, JAK2, JAK3, JARID2, JAZF1, JMJD1C, JMJD4, JMJD6, JMJD7, JMJD8, JUN, JUNB, JUND, JUP, KAT2A, KAT2B, KAT5, KAT6A, KAT6B, KAT7, KATE, KCNH2, KCNJ5, KCNQ1, KDM1A, KDM1B, KDM2A, KDM2B, KDM3A, KDM3B, KDM4A, KDM4B, KDM4C, KDM4D, KDM5A, KDM5B, KDM5C, KDM5D, KDM6A, KDM6B, KDM7A, KDM8, KDR, KDSR, KEAP1, KEL, KHSRP, KIF1B, KIT, KITLG, KLF12, KLF4, KLF5, KLF6, KLF8, KMT2A, KMT2B, KMT2C, KMT2D, KMT2E, KRAS, LATS1, LATS2, LCK, LDB1, LDLR, LEF1, LEPR, LGR4, LGR5, LGR6, LHCGR, LIFR, LMNA, LMO1, LMO2, LMO7, LMTK2, LMTK3, LPP, LRP1B, LRP5, LRP6, LRRK2, LSM1, LTK, LYL1, LYN, LZTR1, MAD1L1, MAD2L1, MAD2L2, MAF, MAFB, MAGED1, MAGI2, MAK, MALT1, MAML1, MAML2, MAML3, MAMLD1, MAOA, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K3, MAP3K4, MAP3K5, MAP3K6, MAP3K7, MAP3K8, MAP3K9, MAP4, MAP4K1, MAP4K2, MAP4K3, MAP4K4, MAP4K5, MAPK1, MAPK10, MAPK11, MAPK12, MAPK13, MAPK14, MAPK15, MAPK3, MAPK4, MAPK6, MAPK7, MAPK8, MAPK9, MAST1, MAST2, MATK, MAU2, MAX, MBD1, MBD3, MC1R, MCL1, MCPH1, MDM2, MDM4, MDS2, MECOM, MED12, MED12L, MED29, MEF2B, MEN1, MERTK, MET, MGA, MGMT, MIDI, MINK1, MIPOL1, MITF, MKL1, MKL2, MLF1, MLH1, MLH3, MLLT1, MLLT10, MLLT11, MLLT3, MLLT6, MLST8, MN1, MNX1, MOB1A, MOB1B, MOS, MPG, MPL, MRE11A, MSH2, MSH3, MSH4, MSH6, MSI2, MST1, MST1R, MTAP, MTCP1, MTDH, MTOR, MUSK, MUTYH, MXD1, MYB, MYBL1, MYBL2, MYBPC3, MYC, MYCL, MYCN, MYD88, MYH11, MYH7, MYL2, MYL3, MYLK, MYOD1, NA, NAB1, NAB2, NAT2, NBN, NCK1, NCK2, NCOA1, NCOA2, NCOA3, NCOA4, NCOR1, NCOR2, NCSTN, NDRG1, NEK1, NEK10, NEK11, NEK2, NEK3, NEK4, NEK5, NEK6, NEK7, NEK8, NEK9, NF1, NF2, NFATC1, NFATC2, NFATC3, NFATC4, NFE2L2, NFIA, NFIB, NFIC, NFIX, NFKB1, NFKB2, NFKBIA, NFKBIB, NFKBID, NFKBIE, NFKBIZ, NGF, NHP2, NIPBL, NKX2-1, NKX2-2, NKX2-3, NKX2-4, NKX2-5, NKX2-6, NKX2-8, NKX3-1, NKX3-2, NLRP1, NOD2, NONO, NOP10, NOTCH1, NOTCH2, NOTCH2NL, NOTCH3, NOTCH4, NPM1, NPPB, NPR1, NQO1, NROB1, NR3C1, NR3C2, NR4A1, NR4A2, NR4A3, NRAS, NRG1, NRG2, NRG3, NRG4, NRIP1, NRTN, NSD1, NT5C2, NTF3, NTF4, NTRK1, NTRK2, NTRK3, NUMB, NUMBL, NUP214, NUP93, NUP98, NUTM1, NUTM2A, NUTM2B, NUTM2F, NUTM2G, ODC1, OLIG2, OSMR, PAK1, PAK2, PAK3, PAK4, PAK6, PAK7, PALB2, PALLD, PARK2, PARP1, PARP2, PARP4, PATZ1, PAX1, PAX2, PAX3, PAX4, PAX5, PAX6, PAX7, PAX8, PAX9, PAXIP1, PBRM1, PBX1, PBX2, PBX3, PBX4, PCBP1, PCSK9, PDCD1, PDCD1LG2, PDGFA, PDGFB, PDGFC, PDGFD, PDGFRA, PDGFRB, PDK1, PDPK1, PDS5A, PDS5B, PEAR1, PEG3, PERP, PGF, PGR, PHB, PHF1, PHF2, PHF6, PHF8, PHIP, PHLPP1, PHLPP2, PHOX2A, PHOX2B, PICALM, PIK3C2A, PIK3C2B, PIK3C2G, PIK3C3, PIK3CA, PIK3CB, PIK3CD, PIK3CG, PIK3R1, PIK3R2, PIK3R3, PIK3R4, PIM1, PIM2, PIM3, PKHD1, PKP2, PLA2G2A, PLAG1, PLAGL1, PLAGL2, PLCG1, PLCG2, PLK1, PLK2, PLK3, PLK4, PMAIP1, PML, PMS1, PMS2, PNRC1, POLD1, POLE, POR, POT1, POU2AF1, POU2F2, POU5F1, POU5F1B, POU5F2, POU6F1, POU6F2, PPARA, PPARD, PPARG, PPFIA1, PPM1D, PPP1R1C, PPP2R1A, PPP2R1B, PPP2R2B, PPP6C, PRCC, PRDM1, PRDM10, PRDM11, PRDM12, PRDM13, PRDM14, PRDM15, PRDM16, PRDM2, PRDM4, PRDM5, PRDM6, PRDM7, PRDM8, PRDM9, PREX2, PRF1, PRKACA, PRKACB, PRKAG2, PRKAR1A, PRKAR1B, PRKCI, PRKD1, PRKDC, PRLR, PRMT1, PRMT2, PRMT3, PRMT5, PRMT6, PRMT7, PRMT8, PRPF40B, PRPF6, PRRX1, PRRX2, PRSS1, PRSS3, PRSS8, PSEN1, PSEN2, PSENEN, PSIP1, PSPN, PTCH1, PTCH2, PTEN, PTGIS, PTGS1, PTGS2, PTK2, PTK2B, PTK6, PTK7, PTPN11, PTPN2, PTPN21, PTPN6, PTPRB, PTPRC, PTPRD, PTPRF, PTPRG, PTPRJ, PTPRK, PTPRM, PTPRQ, PTPRR, PTPRT, PTTG1, PVT1, RAB23, RAB25, RABEP1, RAC1, RAC2, RAD21, RAD50, RAD51, RAD51AP1, RAD51B, RAD51C, RAD51D, RAD52, RAD54B, RAD54L, RAF1, RAP1GDS1, RARA, RARB, RARG, RASA1, RB1, RBM10, RBM14, RBM15, RBMX, RBMXL1, RBMXL2, RBPJ, REC8, RECQL4, REL, RELA, RELB, RET, RHEB, RHOA, RHOB, RHOH, RHOT1, RICTOR, RIPK1, RIPK2, RIPK3, RIPK4, RIT1, RNF213, RNF40, RNF43, ROBO2, ROCK1, ROCK2, ROR1, ROR2, ROS1, RPA1, RPL5, RPN1, RPS6KB1, RPS6KB2, RPTOR, RRM1, RSPO2, RSPO3, RUNX1, RUNX1T1, RUNX2, RUNX3, RUVBL1, RXRA, RYK, RYR1, RYR2, SAMD9, SAV1, SBDS, SCN5A, SDHA, SDHAF2, SDHB, SDHC, SDHD, SET, SETBP1, SETD1A, SETD1B, SETD2, SETD3, SETD4, SETD5, SETD6, SETD7, SETD8, SETD9, SETDB1, SETDB2, SETMAR, SF1, SF3A1, SF3B1, SFPQ, SFRP1, SGK1, SGOL1, SGOL2, SH2B3, SH2D1A, SH3GL1, SHB, SHC1, SHC2, SHC3, SHC4, SHFM1, SHH, SHOC2, SKI, SKIL, SKOR1, SKP2, SLC15A2, SLC19A1, SLC22A1, SLC22A2, SLC22A3, SLC22A6, SLC26A3, SLC47A1, SLC47A2, SLC6A3, SLC6A4, SLCO1A2, SLCO1B1, SLCO1B3, SLCO2B1, SLIT2, SLX4, SMAD1, SMAD2, SMAD3, SMAD4, SMAD5, SMAD6, SMAD7, SMAD9, SMARCA1, SMARCA2, SMARCA4, SMARCA5, SMARCB1, SMARCC1, SMARCD1, SMARCD2, SMARCD3, SMARCE1, SMC1A, SMC1B, SMC2, SMC3, SMC4, SMC5, SMC6, SMCHD1, SMO, SMURF1, SMURF2, SMYD1, SMYD2, SMYD3, SMYD4, SMYD5, SOCS1, SOS1, SOS2, SOX1, SOX10, SOX17, SOX2, SOX21, SOX3, SOX8, SOX9, SP100, SP110, SP140, SP140L, SP3, SPDEF, SPEN, SPI1, SPIB, SPIC, SPOP, SPOPL, SPRED1, SPRED2, SPRED3, SPRY2, SPRY3, SRC, SRGAP3, SRMS, SRSF2, SS18, SS18L1, SSTR1, SSTR2, SSTR3, SSTR4, SSTR5, SSX1, SSX2, SSX3, SSX4, STAG1, STAG2, STARD3, STAT1, STAT2, STAT3, STAT4, STAT5A, STAT5B, STATE, STK11, STK19, STK3, STK36, STK4, STYK1, SUFU, SULT1A1, SUV39H1, SUV39H2, SUV420H1, SUV420H2, SUZ12, SYK, SYNE1, TAF1, TAF15, TAF1L, TAU, TAL2, TAOK1, TAOK2, TAOK3, TBC1D12, TBL1X, TBL1XR1, TBP, TBX18, TBX2, TBX22, TBX3, TBXAS1, TCEB1, TCF12, TCF3, TCF4, TCF7, TCF7L1, TCF7L2, TCL1A, TCL1B, TEAD1, TEAD2, TEAD3, TEAD4, TEC, TEF, TEK, TENM2, TERC, TERF1, TERT, TET1, TET2, TET3, TFE3, TFEB, TFEC, TFG, TGFA, TGFB1, TGFB2, TGFBR1, TGFBR2, THPO, TIE1, TINF2, TLK1, TLK2, TLR1, TLR10, TLR2, TLR4, TLR5, TLR6, TLR7, TLR8, TLR9, TLX1, TLX2, TLX3, TMC6, TMC8, TMEM127, TMEM43, TMPRSS2, TNFAIP3, TNFRSF14, TNFRSF17, TNK1, TNK2, TNKS, TNKS2, TNNI3, TNNT2, TOP1, TOP2A, TOP2B, TP53, TP53BP1, TP63, TPM1, TPMT, TPTE, TPTE2, TRAF1, TRAF2, TRAF3, TRAF3IP1, TRAF3IP2, TRAF3IP3, TRAF6, TRAF7, TRIB1, TRIB2, TRIB3, TRIM24, TRIM28, TRIM33, TRIM66, TRIO, TRRAP, TSC1, TSC2, TSHR, TSHZ3, TWIST1, TWIST2, TXK, TYK2, TYRO3, U2AF1, U2AF2, UBE2D1, UBE2D2, UBE2D3, UBE2D4, UBE4A, UBR5, UGT1A1, UGT1A4, UHRF1, UHRF2, USB1, USP9X, USP9Y, UTY, VAV1, VAV2, VAV3, VDR, VEGFA, VEGFB, VEGFC, VGLL1, VGLL2, VGLL3, VGLL4, VHL, VHLL, VKORC1, VTCN1, WAPL, WAS, WASL, WHSC1, WHSC1L1, WIF1, WISP1, WNK1, WNK2, WNK3, WNK4, WNT1, WNT10A, WNT10B, WNT11, WNT16, WNT2, WNT2B, WNT3, WNT3A, WNT4, WNT5A, WNT5B, WNT6, WNT7A, WNT7B, WNT8A, WNT8B, WNT9A, WNT9B, WRN, WT1, WWTR1, XBP1, XIAP, XIRP2, XPA, XPC, XPO1, XRCC2, YAP1, YEATS4, YES1, YWHAB, YWHAE, YWHAH, YWHAQ, YWHAZ, YY1, ZAP70, ZBTB16, ZBTB20, ZBTB33, ZBTB5, ZBTB7B, ZC3H12A, ZC3H12D, ZC3H7B, ZCCHC7, ZEB2, ZFHX3, ZMYM3, ZMYND11, ZMYND8, ZNF217, ZNF384, ZNF423, ZNF444, ZNF471, ZNF521, ZNF607, ZNF639, ZNF668, ZNF703, ZNF704, ZNF750, ZNRF3, or ZRSR2. In other examples, the genes related to the information on the report may include one or more of genes sequenced in a whole exome panel, which is a panel that sequences the whole exome. In other examples, the genes related to the information on the report may include one or more of the genes sequenced in a whole genome panel, which is a panel that sequences the whole genome.

For each feature, the list of fields may be retrieved from the predefined model and candidate extraction may be performed according to the expected field. Each candidate that is extracted using the methods detailed above may have a confidence value identifying an estimated accuracy of the result. In some circumstances, a high level of confidence may not be available. When a level of certainty lies below a threshold value (such as less than 90%), the MLA may output the highest entry with the highest level of certainty calculated identifying, for example, a 60% confidence male and 40% confidence female. In another embodiment, no prediction may be generated when the confidence value is below the threshold and the user may be required to manually populate the associated field in the application.

Extracted candidate concepts may be processed to identify any links between the concepts and known entities, for example, the enumerated list of medical drugs discussed above. Entity linking is the task of determining whether a candidate concept (phrase) is a relevant clinical concept. Relevancy may be determined by the presence of the candidate concept in a medical dictionary. Fuzzy matching may be implemented by an approximate string matching algorithm. For example, in conventional string matching, a string must exactly match, character for character, with a reference string in order to yield a positive match result. In fuzzy string matching a string is still matched character by character; however, for each mismatch in character, operations may be performed to elicit a match. For example, a mismatching character may be deleted, and the next character considered for a hit, which would account for having an extraneous character in a word, a character may be inserted at the mismatching character to provide a match to allow a match to occur even if a character was omitted, a character may be substituted at the mismatching character to allow a match even if the wrong character was inserted, or a character may be transposed at the mismatching character. For each mismatch operation that is performed, a counter may increment to track the number of errors allowed. In an embodiment, the number of errors may be capped to restrict the flexibility of the fuzzy searching algorithm, for example, only three mismatch corrections may be allowed before no match may be identified during processing. Other embodiments may adjust the threshold based upon the length of the word to allow longer words more mismatches than shorter words. For example, if a three letter word is allowed three mismatch operations, then a fuzzy string matching algorithm may generate matches for thousands of concepts from 1-6 characters.

Fuzzy matching is structured around the text concepts included in the medical dictionary and may be applied on a word-by-word basis rather than a letter-by-letter basis. For example, a concept candidate may include the phrase "needle biopsy." An entity matching search may identify entities linked to, for example an exact match "needle biopsy", a reordered match "biopsy needle", or phrase matches of "needle aspiration biopsy of lung" or "breast needle biopsy." Such entity matches may be derived using the same fuzzy matching operations above (deletion, insertion, transcription, etc.), but on the whole word rather than each individual character. Furthermore, in still another embodiment, both fuzzy matching on a character by character basis and word by word basis may be applied concurrently to generate entity matches.

Certain features, such as the TNM Classification of Malignant Tumors (TNM) or genetic variant/mutation results, may be preempted from fuzzy matching because the sequence of the characters are important and any rearrangement or replacement (fuzzy matching) to generate a match may cause the incorrect concept to be matched.

Matched concepts may be normalized to ensure that the concepts that are matched are consistent with the concepts archived in the database (described below in more detail). For example, in a cancer type normalization, there may be numerous candidate matches which reference breast cancer in one form or another that match. A post-processing step to the normalization may be applied which identifies, for example, when a cancer site is designated as breast, and adjusts the final result such that all entries with a breast cancer site share the same cancer site code and same spelling "breast". Other normalized results may include each main cancer site, such as brain, lung, liver, ovary, or bone marrow, a predetermined catch-all for unknown sites, or known codes which are irrelevant and may be filtered.

With regard to both the post-processing of scanned documents discussed above, as well as the analysis and structuring of other aspects of patient EHRs or EMRs, such as next-generation sequencing reports, a system that identifies and processes information in clinical documents or other records is disclosed herein. The system may use a combination of text extraction techniques, text cleaning techniques, natural language processing techniques, machine learning algorithms, and medical concept (Entity) identification, normalization, and structuring techniques. The system also maintains and utilizes a continuous collection of training data across clinical use cases (such as diagnoses, therapies, outcomes, genetic markers, etc.) that help to increase both accuracy and reliability of predictions specific to a patient record. The system accelerates a structuring of clinical data in a patient's record. The system may execute subroutines that highlight, suggest, and pre-populate an electronic medical record ("EHR" or "EMR"). The system may provide other formats of structured clinical data, with relevant medical concepts extracted from the text and documents of record.

The system may include a persistent, stateless service that receives a plurality of queued messages from one or more peripheral services (such as a file conversion service or an optical character recognition service) which may also perform natural language processing (NLP) operations on outputs of those peripheral services. Those NLP operations include machine learning features, as described herein, in order to increase the speed, efficiency, and accuracy of the processing. A persistent, stateless system is a system operating in an asynchronous manner in comparison to a conventional point to point pipeline. For example, the system may be structured in a "pipeline" fashion, but each modular component of the system may retrieve and store exemplary input/output datasets as they become available, without relying on the modular component before or after in the pipeline to initiate or acknowledge availability for a transfer. Such statelessness allows for more advanced parallelization because it reduces inefficiencies at each bottleneck of the pipeline (handshaking to pass data). More detail on the persistent, stateless service is discussed with reference to FIG. 162 below.

The system may include a training service designed to promote user interaction to improve machine learning capabilities. In one aspect, the training service may use a production repository as its input data. In another aspect, the training service may use a data repository separate from the production repository. Additionally, the system may operate in a plurality of manners. In a first manner, the system may be triggered in response to specific queries requesting processing on specific EHR or EMR files. In a second manner, the system may include a backend service that reviews and processes EHR or EMR files continuously (without a need for specific user queries). The backend service may operate asynchronously from user input, such as queries or commands. In such a manner, the system may detect when a patient record has been received, either partially or in full, and begin processing the patient record in aggregate or as a whole to determine relevant medical concepts for entry into the EMR.

In the field of clinical abstraction from EHR and EMR documents, machine learning or deep learning may be combined with NLP techniques to abstract relevant medical concepts. While the detailed implementations of these are disclosed in more detail below, an exemplary abstraction performed on a simple text is now provided to give a general understanding of one aspect of the disclosure. For instance, the simple text "The patient was given Tylenol 50 mg at 10:35 am." may be analyzed using a machine learning algorithm (MLA) trained on EHR and EMR documents relating to thousands of patients to recognize medications that the patient was prescribed in order to generate the table 4052 of FIG. 163, where the MLA may be the same or a different MLA from the one discussed above.

Generating a training set from which to train the MLA involves both enumerating known drugs (which may include thousands or even tens of thousands of drugs) and also maintaining the flexibility to recognize drugs which are not included in the sources of the known drugs. The process of enumerating the known drugs into a list may include identifying clinical drugs prescribed by healthcare providers, pharmaceutical companies, and research institutions. Such providers, companies, and institutions may provide reference lists of their drugs. For example, the US National Library of Medicine (NLM) publishes a Unified Medical Language System (UMLS) including a Metathesaurus having drug vocabularies including CPT®, ICD-10-CM, LOINC®, MeSH®, RxNorm, and SNOMED CT®. Each of these drug vocabularies highlights and enumerates specific collections of relevant drugs. Other institutions such as insurance companies may also publish clinical drug lists providing all drugs covered by their insurance plans. By aggregating the drug listings from each of these providers, companies, and institutions, an enumerated list of clinical drugs that is universal in nature may be generated.

A combination of NLP and supervised, semi-supervised, or unsupervised MLA techniques may be used to generate an intelligent training set of data to recognize entries from the enumerated list of clinical drugs, in order to identify patterns within the text of abstracted documents which typically surround drug entries. The identified patterns may then be applied to unknown drugs to generate new entries which are added to the clinical drug list. An exemplary pattern may be a sentence structure containing "patient was given" or "patient was prescribed." In these examples, the known drugs are the supervised portion of the semi-supervised algorithm while the new entries determined are the unsupervised portion of the semi-supervised algorithm. In this manner, a non-exhaustive listing of drugs may be leveraged to train a MLA to detect drugs based on sentence structure, associated key terms, or other patterns in the text. Once trained, the unsupervised portion of the semi-supervised algorithm will apply the training to detect unclassified words for addition to the classification list. In this manner, a semi-supervised MLA can apply features of NLP to detect and classify unknown and known drug entries in medical texts. While described herein with respect to the medical concept of a drug, this approach may be applied to all medical concept classifications using the techniques described herein. Specific details of the NLP and MLA techniques are discussed in more detail with respect to FIGS. 160 and 164-167, below. Specific details of supervised, semi-supervised, or unsupervised MLA techniques are discussed in more detail below.

As discussed above, medical data may include numerous fields including, but not limited to, patient demographics, clinical diagnoses, treatments and outcomes, and genetic testing and laboratory information, and each of the fields may also have a plurality of subfields. The above provided examples, enumerations, and lists are not intended to limit the scope of the available fields and are intended to convey only the nature and structure that fields within medical data may be represented within a universal EMR. These fields of medical data may also identify concept candidates, discussed in more detail below with respect to FIGS. 160 and 164-167. For example, Tylenol may be a concept candidate relating to medication in treatment and outcomes.

Returning to FIG. 163, the sentence "The patient was given Tylenol 50 mg at 10:35 am." in a document dated Jan. 1, 2001, may be encoded field-by-field into the table 4052 by identifying and populating one or more fields of:

Text: The entirety of the text ("The patient was given Tylenol 50 mg at 10:35 am.").

Medication: Identifying any medication mentioned in the text (Tylenol). Medications may be brand name or generic name. This field does not include information about the dosage or method of administration.

Active Ingredient: Identifying the active ingredients (acetaminophen) of the medication mentioned using a list such as a search table linking drug names to their active ingredients.

Dosage & Dosage Units: The dosage (50 mg) associated with the medication mentioned. In the above example, identifying that the dosage as 50 mg is fairly straightforward by reading the sentence, but clinical data is often printed in tables with a variety of structures that are not easy to infer. As such, normalizing the dosage and dosage units by separating value 50 into the dosage field and string "mg" or by selecting a known value entry for the milligram units within a list may be preferable.

Document & Page: The document and page where the text is found (Progress Note 01_01_01. pdf and page 3).

UMLS_CUI: The Concept Unique Identifier (CUI) field (C1234567) of the UMLS entry corresponding to the medication. The UMLS is a list of medical concepts (described in more detail with respect to FIG. 160, below) and the UMLS_CUI refers to the CUI field, which is UMLS' universal identifier. UMLS is comprised of a number of independently maintained clinical dictionaries and ontologies (such as those for cancer diagnosis & treatment, dentistry, veterinarian medicine, etc.). That is, the CUIs are universal to UMLS, such as there is only one CUI for Tylenol across all of its constituent dictionaries that enables UMLS to unite all of these disparate sources.

UMLS_AUI: The Atom Unique Identifier (AUI) field (RXNORM #12345) is the dictionary-specific identifying code of the UMLS. Where the CUI is universal, and has the same entry across all included sources, the AUI for Tylenol will have different AUIs for each dictionary that it has an entry in.

In one instance, the above fields, both the plurality of features 4054 and their respective feature classifications 4056 may be populated by a data analyst with sufficient medical knowledge and access to the requisite databases. Such an analyst may apply their education and experiences in the field of medicine to identify any medications administered despite confounding factors present in the text (such as shorthand, typos, obscure references), their dosage, and understand the integration of the two in the provided text. However, analysts are constrained by their human limits. Actions such as locating the data, opening it up in either a physical or digital format, reading through documents of 100s or 1000s of pages, etc., all require considerable time. Furthermore, the companies and institutions which hire analysts must invest in considerable financial expenses to hire, train, and maintain teams of analysts. Incorporating a combination of machine learning algorithms (MLA) and natural language processing (NLP) algorithms into this process may substantially improve the efficiency of the analysts or replace them altogether. The MLA and NLP algorithms will be discussed in more details with respect to FIGS. 160 and 163-167, below. Before text may pass through the multiple layers of MLA and NLP algorithms, it must be extracted from the documents using optical character recognition (OCR) and cleaned up through a variety of pre-processing steps.

Returning now to FIG. 162, a high level overview of an exemplary processing pipeline 4060 is provided. An exemplary Intake Pipeline 4062 may be configured to perform the following processing steps: 1. OCR, 2. Pre-processing, 3. Sentence Splitting, 4. Candidate Extraction, 5. Entity Linking, 6. Entity Normalization, and 7. Entity Structuring. Specifically, and with reference to FIG. 162, pipeline stage 4064 for pre-processing may include OCR and text cleaning, stage 4066 for parsing may include NLP algorithms for sentence splitting and candidate extraction, stage 4068 for dictionary lookups may include entity linking, stage 4070 for normalization may include entity normalization, stage 72 for structuring may include entity structuring, and stage 4074 for post-processing may include structuring the data and formatting it into a universal EMR or institution based EMR format. Due to the asynchronous and modular nature of the pipeline stages, each stage may pass data directly to the next stage based on processing availability or may store data in a corresponding portion of a storage component or database. In an exemplary embodiment, a sentence splitting algorithm may be stored in a cloud based server or on a local/remote server 4076 and may be incorporated into the parser at stage 4066, a fuzzy matching algorithm 4078 may be incorporated into the dictionary lookup at stage 4068 and an Ontological graphing algorithm 4080 may be incorporated into the normalization at stage 4070.

For example, upon receiving a record update or a request in the form of a clinical document, a database of multiple documents, or another form of patient record, the request may pass through a pre-processing subroutine 4082, a parsing subroutine 4084, a dictionary lookup subroutine 4086, a normalization subroutine 4088, a structuring subroutine 4090 for filtering and/or ranking, and a post-processing subroutine 4092 in order to generate and serve a response to a remainder of the system. The first four of these subroutines may encompass a first layer, in which the system identifies and structures clinical concepts with corresponding metadata (clinical or medical concepts) extracted from clinical documents.

The intake pipeline 4062 receives a clinical document that may include machine readable text or that may be received as an image file. If necessary, the document may be submitted to a pre-processor stage 4064 that performs text cleaning and error detection (format conversion, resolution conversion, batch sizing, text cleaning, etc.). Once pre-processed, the document may be submitted for OCR on the document to convert the text into a machine-readable format (text document, html, etc.). Once in a machine-readable format, the error correction (such as spell checking, noise removal, context based correlation, etc.) may be performed on the now-machine-readable text. The intake pipeline stages 4064-70 are modular components, which allows for real-time selection of the best processing tools and software depending on the type of document and document content being processed, enabling the processing pipeline to replace/compare algorithms used as necessary. Two examples of OCR software that may be used include Tesseract and Google Cloud Vision API. Tesseract provides high-speed OCR for documents which do not have any artifacting/noise (documents that have been printed to PDF or that had very little noise generated during the scanning process). Google Cloud Vision API, conversely, may be used for documents which have too much noise, as it is well-suited to process old documents or images of documents that have been scanned/faxed many times, introducing extensive artifacting and noise into the image. As a result, Cloud Vision may provide detailed information about the position of paragraphs, words, and documents within the documents processed. Other OCR systems may also be utilized in lieu of or in combination with the two described above.

The modularity of each processing stage requires different pre-processing mechanisms for each OCR service/software implemented. For example, different OCR services support some image formats and resolutions for OCR but may not support others. When processing patient records, many document formats included within the record are unsupported, and may require format conversion from the unsupported format to a supported format, as well as additional processing for parameter optimization for each respective document to achieve the best results from the OCR service selected, as discussed above. For example, when utilizing Google Cloud Vision, images may need to be format-converted to 300 dpi JPG files. Furthermore, Google Cloud Vision API charges for OCR on a per-request basis, but supports requests of up to 4 MB and supports batch requests (as many images as can be fit into one 4 MB request) for no extra cost. Additional processing may be performed to include additional document images into a request to place each request at the maximum file size and use batch processing to decrease costs.

Documents received at the pre-preprocessing stage may be in various text formats (such as DOC, DOCX, RTF, or as values in a spreadsheet/database). For simple documents, pre-processing may be performed by simply extracting any text directly (such as TXT, RTF, etc.), but some require advanced software to parse the file formats (such as DOCX, PDF, ACCDB). Exemplary software for parsing more complex file formats include pandoc and PDFBox.

As with the OCR steps discussed above, in another embodiment, additional pre-processing may be performed after submitting an image to OCR to determine whether the detected text is "reasonable" before outputting final results. While some OCR technologies may perform their own reasonability determination, it may be necessary to further improve upon the quality of the OCR output by performing a text cleaning algorithm on the OCR output. Text cleaning may be implemented by a category of NLP models designed for Language Modeling. Additionally, machine learning algorithms and deep learning algorithms may be utilized to further improve upon the OCR results. Exemplary categories of language models may include: statistical (n-gram), graphical (CRF/HMM), and neural (RNN, LSTM, skip-gram, BOW, etc.). While each category of language model may process datasets of particular structure and content differently, the modular nature of the processing pipeline allows the most appropriate language model to be selected based upon the document being processed. For instance, a first language model may be selected if the document is a progress note while a second language model may be selected if the document is a lab result. As another example, a first language model may be selected if the document is from a first institution and a second language model may be selected if the document is from a second institution. As another example, a first language model may be selected if the document is from a first clinician and a second language model may be selected if the document is from a second clinician.

In one aspect, due to the frequency of tables, charts, structured headers, and other features in medical documents, neural language models may be preferred. Neural networks for language modeling may be trained over millions of sentences and perform best when trained over text from the same domain as they will encounter in a production system. For example, language models trained over medical/clinical text will perform better in medical-based OCR text cleaning tasks than language models trained over online reviews, news articles, or other generic and freely-available sources. Similarly, language models trained over clinical documents that are specific to a particular disease state, such as cancer, may perform better in medical-based OCR text cleaning tasks upon disease state-related clinical documents than language models trained over clinical documents that are not specific to a particular disease state. By providing a training set having millions of clinical documents that are similar to the documents submitted for OCR, an exemplary language model may be trained over in-domain text that many traditional NLP sources do not have access to, resulting in a more robust language model.

Language models may estimate the probability of a given sequence of words or characters (letters, numbers, punctuation, etc.) occurring in a current document based on the frequency of the given sequence of words or characters as they appeared in the original training documents. Language models may identify regions of OCR output that are uncommon in the training text (such as "stage iv beast cancer" is an unlikely sequence of words in medical documents). Language models may also identify which words/characters were most likely to have occurred in each position in text, for example, "stage iv cancer" may have a high probability for "lung" and "breast" filling the blank. By combining a probability distribution over words most likely to fill the blank (such as in this example cancer sites, but may be medications, dates, diagnosis, treatment results, etc.) and words most likely to be OCR as "beast," the system may determine that "beast" was most likely "breast" without having to look at the image itself and only relying on linguistic patterns.

A probability distribution may be generated by applying a neural network for Named Entity Recognition (NER). For example, individual words may be provided a weighting factor for probability of occurrence across a massive training set. Statistical information may be stored that indicate likely phrases, based off a starting word, and any following words of a phrase. Each word, in turn, may be applied a weight about whether it is a starting word or a following word and the likelihood that the word is part of a phrase or standing alone in the text.

In one example, the phrase "stage iv _____ cancer" may be processed. "Stage" may be provided a starting word score of 0.6, a following word score of 0.3, and a standalone score of 0.1 which would account for the entirety of the potential distribution of the word's appearance in the training text. The word "iv" may be provided a starting word score of 0.05, a following score of 0.55, and a standalone score of 0.4. The word "cancer" may be given a starting score of 0.1, a following score of 0.7, and a standalone score of 0.2. A sentence analysis for the exemplary NER may find that because "stage" has a high probability for being a starting word and "iv" has a high probability for being a following word, that "_____" may have a higher probability for being a following word that matches "stage iv _____" or "stage iv _____ cancer" in a phrase.

Additionally, because "cancer" similarly has a high probability for being a following word, NER may predict that the "_____" is either a following word that continues the word beginning at "stage" or may be a beginning word that begins before "cancer". Because the word "beast" has a beginning word score of 0.1, a following score of 0.2 and a standalone score of 0.7, the model may flag that "beast" does not fit within the expected sequence of words. By comparing similar words, (such as breast, feast, rest, roast, wrest, etc.) the NER model may identify that breast has a beginning score of 0.5, a following score of 0.3, and a standalone score of 0.2, making breast fit within two models of the predicted phrases and selecting "breast" to replace "beast" based on the predicted phases alone. The modified phrase then may be further tested, or tested alone using a more generalized probability distribution. For example, the training date may weight the occurrence of words in medical texts. As discussed above, while the word "beast" may rarely occur in a patient report, (such as patient was mauled by unknown beast), "breast" may occur more frequently (such as patient expresses concern re: lump in breast, breast cancer, stage iv breast cancer, patient's breast recovered from surgery, etc.), giving "breast" a much higher probability of occurrence weighting than "beast," such similarity analysis likewise can apply to an EMR/EHR. As a result, the preprocessing stage 4064 may replace "beast" with "breast," terminate preprocessing, and indicate that the resulting text is reasonable.

In an alternate embodiment, a tabular extraction method may be performed across EMR and EHR documents, similar to the tabular extraction method discussed above with regard to the output of the electronic document capture, such as incorporating the exemplary tabular extraction approach involving masks 1-3 of FIG. 161. Tabular extraction involves applying MLA and deep learning algorithms to optimize the OCR process for reports which may have a standardized format.

Returning to FIG. 162, once the pre-processing stage 4064 has completed, the generated OCR output may be stored for later retrieval by the parser stage 4066 of the intake pipeline 4062. In an alternative embodiment, the preprocessing stage may check in with parser 4066 to confirm availability and pass the OCR output to the parser stage directly. Due to the modular nature of the intake pipeline 4062, each processing stage may process their respective data without regard for the specific OCR or pre-processing methods. A modular pipeline approach allows the pipeline to swap in and out the most appropriate OCR and pre-processing technologies to improve the results of the overall processing.

Sentence splitting is a function of NLP that may be incorporated to parse sentences into meaningful structures. Documents may arrive in either plaintext format (containing all text from the document) or in a structured OCR format (including the text as well as bounding boxes for every character, word, and sometimes paragraph if the model is capable of identifying paragraph regions). Conventional sentence splitting may be implemented by many readily available NLP applications, including, such as any of CoreNLP, Spacy, AllenNLP, or NLTK. The system may implement a plurality of NLP applications, and identifying a most appropriate tool for sentence splitting may be depend on the nature of the clinical documents at hand, since clinical documents have a large variety in document layouts and content. Each tool for sentence splitting has advantages for particular types of documents, expected sentence structures, etc. In particular, documents often have headers and footers with useful structured text data, but headers/footers may not be presented in a standard sentence format (such as document citation or quote) and may confound certain sentence splitters. Similarly, doctors may use clinical shorthand which conventional NLP tools are not trained to parse; for example, a doctor may write "pt dx luad 2017" to mean "the patient was diagnosed with lung adenocarcinoma in 2017."

These deficiencies in sentence splitting may be overcome by adding models before this stage to identify whether text is semi-structured data, well-formed text, clinical shorthand, uninformative headers/footers, etc. By creating methods for distinguishing between these types of text, the intake pipeline may use specific models to extract information from each type. For example, complex sentences may be broken down into simple sentences by looking for coordination constructs, adjectival clauses, evaluating parataxis, prepositional phrases, etc., by applying phrase-based or syntax-based machine translation approaches. For sentences which are well-structured (such as following traditional grammar and prose), parse trees or deep semantic representations may be utilized. For sentences which are noisy (such as structured, but with unclear boundaries), a maximum entropy approach may be utilized. In texts which are very specialized in nature (such as medical texts, legal texts, etc.), a tokenization and document segmentation algorithm may be applied. By implementing sentence splitting, the processing pipeline may split the document into sentences for individual parsing.

Candidate extraction may be performed using one of above-referenced approaches. For example, one approach may include a symbolic approach that relies on the structure of the sentence. Relying on the structure means that the sentence may be passed into a dependency parser or constituency parser.

Constituency-based parse tree text analysis systems may incorporate a list of phrase types that are likely to occur in sentences containing medical concepts. A subset of phrase types from the improved list of concepts may include:

CC—Coordinating conjunction, (such as and, but);
CD—Cardinal number, (such as one, two, 1, 2);
DT—Determiner, (such as a, the);
EX—Existential clause, (such as there);
*FW—Foreign word, (such as absentia, nauseam, habeas);
IN—Preposition or subordinating conjunction, (such as although, because);
*JJ—Adjective, (such as wet, fast);
*JJR—Adjective, comparative, (such as -er);
*JJS—Adjective, superlative, (such as -est);
LS—List item marker, (such as numbering, bullets);
MD—Modal, (such as shall, will, might);
*NN—Noun, singular or mass, (such as cell, cancer);
*NNS—Noun, plural, (such as cells, fingers);
*NNP—Proper noun, singular, (such as California, London);
*NNPS—Proper noun, plural, (such as the Joneses, the Bushes);
PDT—Predeterminer, (such as both, a lot);
POS—Possessive ending, (such as 's);
PRP—Personal pronoun, (such as we, she);
PRP$—Possessive pronoun, (such as his, hers);
*RB—Adverb, (such as quite, then);
*RP—Particle, (such as not, to);
*SYM—Symbol, (such as @, &);
*UH—Interjection, (such as ah, oh);
*VB—Verb, base form, (such as run, inject);
*VBD—Verb, past tense, (such as ran, injected);
*VBZ—Verb, 3rd person singular present, (such as runs, injects);
WDT—Interrogative determiner, (such as what, which);
WP—Interrogative pronoun, (such as who, whom);
WP$—Possessive interrogative pronoun, (such as whose);
WRB—Interrogative adverb, (such as where, how); and
. —Period character.

While conventional implementations are not optimized for technical texts (medical texts), the conventional list of phrase types may be augmented to include additional phrase types to optimize sentence splitting for medical-based texts. Such additions have been indicated with an asterisk (*). Conventional implementations that involve constituency-based parse trees include Apache cTAKES™, Stanford Parser, TensorFlow, and Charniak-Johnson.

Turning to FIG. 164, one example of a constituency-based parse tree is depicted. In that example, a constituency-based parse tree may receive a sentence "the patient was given tylenol 50 mg at 11:35 am." from which a parse tree may be generated. As depicted in the tree of FIG. 164, concepts may be identified (such as medical concepts) using different linguistic phrases and parts of speech. An example constituency parser then may generate: (ROOT (S (NP (DT The) (NN patient)) (VP (VBD was) (VP (VBN given) (NP (NP (NNP Tylenol) (CD 50 mg)) (PP (IN at) (NP (CD 11:35 am)))))) ( . . . ))).

In this example, phrase types: S, VP, NP, and PP markers are not in the above list. They represent the top-level sentence, verb phrase, noun phrase, and prepositional phrase, respectively. Furthermore, "patient", "Tylenol", "Tylenol 50 mg", "50 mg", and "11:35 am" may be included in a list of concept candidates 4096 (graphically represented as dotted lines around the words in the parse tree). Concept candidates may be determined by noting important phrase types (such as NP, CD, etc.) and may be further refined by comparing any associated text against a list of weighted words, whereby words which are weighted above a threshold weight may be presented as concept candidates. For example, the word "patient" may be flagged as a concept candidate, but due to its low weighting factor, may be removed from the candidate list.

In another embodiment, an MLA may be utilized to identify concept candidates. An exemplary MLA for identifying concept candidates includes a name entity recognition (NER) model. NERs may be implemented using conditional random fields, convolutional neural networks, attention based neural networks, long short term memory networks, or other neural models.

Language models may vary based upon the type of document being processed, (such as pathology reports, progress notes, and other EHR and EMR documents, etc.), to optimize the type of information which may be extracted from the documents. For example, a whole document classifier may be applied to a progress note (physician generated report of patient status on each checkup), pathology report, or other EHR/EMR documents to identify a patient's gender, cancer types, or other information that may require verification over one or more documents to provide reliable predictions. For a whole document classification, the text of the entire document may be evaluated before the document as a whole is classified (such as male/female, lung/breast cancer, date of birth, etc.). For other types of information, a sequence labeling classifier may be applied to a progress note, pathology report, or EMR/EHR documents to identify, for example, medications taken by a patient, therapies a patient may be undergoing, or other information which may be difficult to extract due to the extensive number of varying entries for each type of class. For a sequence labeling classification, each sentence, or combination of sentences in the document may be evaluated before the document is assigned another classification for identifying a class entry (such as a medication or therapy of the patient). The implementation details of an exemplary whole document classifier and sequence labeling classifier are discussed below.

In one aspect, a whole document classifier may rely on a training model that has been trained on thousands of medical documents found in EMRs and EHRs of patients. The training data may be provisioned with the parts of speech assigned to words and the true classification for each patient (such as male/female, age, ethnicity, etc.). A machine learning algorithm or a neural network may process the training data to generate a rule set or a trained neural network, respectively. In an exemplary rule set, a list of words with corresponding weights may be generated based upon the frequency they appear in text with proper classification vs text without the proper classification. For example, a rule set for determining if a document for a patient is to be classified according to gender may have a list of words including "male", "man", "he", "his", "testicular", "prostate", etc., which are weighted heavily towards identifying gender as male and a list of words including "female", "woman, "her", "she", "breast", "ovaries", "ovulation", "menstrual", etc., which are weighted heavily towards identifying gender as female.

The rule sets may include a vector of, for example, three hundred words and their respective weights, and each rule set may be applied over all words in a sentence to generate weights for every sentence. For example, a sentence "The patient was given prostate exam after he complained about having difficulty urinating in the mornings" may be given a high weight for gender as male because of words "prostate exam" and "he". After each word of each sentence is processed, each respective sentence may be assigned a sentence vector (such as 10% female, 90% male), then each sentence in a document may be processed to assign a document vector, and finally, each document in a patient's EMR or EHR may be processed to assign a patient vector.

At each level of granularity, the whole document classifier may be interrupted, for example, if a sufficient level of certainty has been reached or processing was intended to terminate at that level. For example, if a document has been determined to have a high incidence of accuracy because a table on page 3 of a document may always return the correct gender for the patient, then the algorithm may identify that high accuracy has been provided for the document based on the one sentence of that document and stop processing a gender classification at the sentence level vector for that patient. Furthermore, a patient level vector may not be generated if a document level vector has reached a certain threshold of certainty (such as 95%), or if, for example, only one document is being processed.

FIG. 165 provides a visual representation of word weightings for a sentence 4098 containing "The patient was given Tylenol 50 mg at 11:35 am." At the word level, "the", "was", "given", and "at", may be given low weights, "patient" and "11:35 am" may be given medium weights, and "Tylenol" and "50 mg" may be given high weights. As a result, the overall sentence may be classified with a high weight 4100 (such as 95%) that medication the patient has taken includes Tylenol 50 mg. For this example, because such a high confidence value is determined, the processing may not need to continue to evaluate other sentences in the document to determine that the patient did indeed take Tylenol 50 mg, but each sentence 4102, 4104 will be processed to determine if other concepts are identified (such as to identify gender, other medications, other treatments, or demographic information). In this example, even though only the medication concept is given a high weight, each of the identified concept candidates may be retained for the next stage of the intake pipeline for further processing; alternatively, those identified concept candidates may be dropped from the candidate list.

In some circumstances, a high level of confidence may not be available. For example, a patient who has undergone a gender reassignment surgery may have documents with a high level of confidence for one gender before surgery and a high confidence for another gender after surgery, or a document for a patient of a different gender may have been misfiled in the current patient's file. When a level of certainty lies below a threshold value (such as 90%), the whole document classifier may output the highest level vector calculated identifying, for example, a 60% confidence male and 40% confidence female. The output may also include one or more identifiers for which document, which section of which document, which sentence, or even which word from which the confidence values were calculated. In another embodiment, no prediction may be generated when the confidence value is below the threshold. In still other embodiments, documents which have contention in a prediction may be flagged, a true determination of classification may be obtained, and the documents and the true classification may be provided to a training engine which may retrain the rule set or neural network to further improve accuracy.

As discussed above, in another aspect, a sequence labeling classifier may be implemented. An MLA or neural network may be trained to generate a rule set identifying words and word sequences which are likely to identify concept candidates. Such concept candidates may include stand-alone words such as "patient," "age," or "gender," with a high stand-alone rating. It should be noted that these words may not be commonly coupled with other words in medical text but may still have some word couplings (such as under age). Other concept candidates may include words which are commonly linked to other words in a medical text. Words which commonly begin a multi-word concept include "breast" (such as breast cancer, breast reduction, breast augmentation, breast surgery) and "stage" (such as stage I cancer, stage II cancer, etc.). Other such words may include "high" (such as high blood pressure), "low" (such as low cholesterol), or "heart" (such as heart attack, heart failure). Words which commonly begin a multi-word phrase may feature a high beginning score and a medium stand-alone score. Intermediary words in a multi-word phrase (such as cancer, cell, failure) are words which may have a high intermediary score and a medium stand-alone score). For example, each word in a sentence may be assigned a value for the likelihood that the word is a beginning of a multi-word phrase (such as a "B" value), an intermediary of a multi-word phrase (such as an "I" value), and a standalone word (such as an "O" value), and then each word or collection of words may be evaluated to identify clinical concepts.

Turning to FIG. 166, a sequence labeling classifier 4106 may provide a "BIO" score for each word, where a BIO score (10, 30, 60) would mean that the associated word is the first word in a multi-word phrase in about 10% of its occurrences in the training set, an intermediary word in a multi-word phrase in about 30% of its occurrences in the training set, and a stand-alone word in about 60% of its occurrences in the training set. For example, the word "the" almost always precedes another word and occasionally is an intermediary word of a multi-word phrase, so may be provided a BIO score 4108 of (90, 10, 0). "The" may also be considered an extraneous word, despite almost always preceding other words of importance, so it may be provided a BIO score of (0, 10, 90) to prevent processing, "patient" may be provided a BIO score 4110 of (5, 20, 75), and "was" may be provided a BIO score 4112 of (0, 0, 100). The sequence labeling model may begin processing the sentence at the first word, "the," and then note a high incidence of that word being the beginning value of a multi-word phrase (in the first incidence where BIO score is (90, 10, 0)), process the second word "patient" to note a high incidence of being an intermediary or stand-alone word, and process the third word "was" to note a high incidence of being a stand-alone word. By recognizing a potential beginning of a multi-word concept, a potential intermediary of a multi-word concept, and a distinct non-multi-word entry, the sequence labeling model may identify a first multi-word concept. Therefore the sequence labeling model may indicate "the patient" 4114 as a likely candidate concept for the multi-word label and "patient" 4116 as a likely candidate concept for the stand-alone word label.

Processing may continue word-by-word until another stand-alone word (B, I, or O labels) or multi-word (BIll . . . labels) are detected. In the example of FIG. 166, another multi-word phrase 4118 may be detected at "Tylenol 50 mg," and concepts "Tylenol" and "Tylenol 50 mg" may be generated. A final concept 4120 may be generated at "11:35 am."

A sequence labeling classifier may be able to identify labels with a higher accuracy than a parse tree by linking words together through their labels (such as BI, BII, BIII, etc.) to identify multi-word concepts (such as heart attack, stage IV cancer, medial tibial stress syndrome, etc.) as the totality of their concept rather than each of the words in multi-word concept.

The number of candidate concepts which may be extracted may be needlessly large. For example, in patient file with thousands of documents, a concept candidate for breast cancer may occur hundreds of times, a concept for lung cancer may occur tens of times, and a concept for liver cancer may only occur once. It may be useful to filter/rank the mentions of each concept candidate to reduce repetition in the following stages in the pipeline. For concept candidates which may be consolidated (such as mentions of breast cancer for diagnosis) the concept candidate may be reduced to a single concept with a count field in the hundreds. Furthermore, if concept candidates are competing for the same field, the concept candidate may be coupled with a reliability index based upon the frequency of the concept candidate occurring in relationship to the others (such as 200 mentions of breast cancer, 13 mentions of lung cancer, and 1 mention of liver cancer may be processed to a 200/214 reliability index that the patient has breast cancer). The highest ranked competing concept candidate may be preserved with a reliability index, or a consolidated report of the most frequent competing concept candidates may be preserved along with their count values and/or reliability index.

Using any of the above methods, candidate extraction generates a plurality of candidate concepts which may be evaluated in the following stage for entity linking.

Returning to FIG. 162, the entity linking pipeline stage 4068 receives/retrieves the candidate phrases as a list and may process each candidate to identify any links between the phrases and known entities (such as the enumerated list of medical drugs discussed above). Entity linking is the task of determining whether a candidate concept (phrase) is a relevant clinical concept. Relevancy may be determined by the presence of the candidate concept in any medical dictionary or the universal dictionary described above. Relevancy may also be determined based on proximity to a concept candidate hit. For example, a time "11:35 am" may not result in a hit in any dictionary as a medical concept. However, certain medical concepts, such as medications, may fall within an abstraction category such as treatment. A treatment may have fields such as treatment type (the medicine) and date and time of treatment (11:35 am). By considering proximity to other concept candidates, key information may be retained even if the concept may not exist in the database. The retained candidate concept may not be classified as a linked entity, but may be associated with the linked entity for abstraction purposes.

Within the entity linking pipeline stage 4068, the list of concept candidates generated in the previous pipeline stage may be provided to a dictionary lookup for matches. Conventional dictionary lookup tools may include Elasticsearch, Solr, Algolia, or Sphinx. In one aspect, a direct dictionary lookup may not always result in a database hit (the candidate is in the database) because of typographical errors, OCR errors, shorthand, or other confounding factors. In those situations, candidates which are not an exact match may still be found in the database by applying fuzzy matching logic. For example, the entity linking pipeline stage 4068 may expect to find matches for "Tylenol" and "Tylenol 50 mg" because exemplary queries allow for "fuzzy matching," which will correct potential typographical errors or OCR errors that occur in "Tylenol."

Fuzzy matching may be implemented by an approximate string matching algorithm, such as the exemplary fuzzy matching algorithm discussed above.

Fuzzy matching is structured around the text concepts included in the above enumerated list or the UMLS, including metadata fields CUI (the UMLS unique ID) and AUI (dictionary-specific unique ID), so that an exhaustive search may be performed for all medical concepts. The dictionary search engine may also return metadata about the specific entry detected (such as universal ID assigned in the above enumerated list or the UMLS), which is useful for understanding Tylenol as a medical concept and not just the correct spelling of a drug. At the end of text normalization, some of the extracted candidates may have zero matches but others may have many matches. For example, there are many versions of Tylenol throughout the UMLS database because of the number of dictionaries represented therein. Fortunately, the CUI (the UMLS uuid) provides a generalization to join similar concepts, which reduces the number of matches from one for each potential database to the number of unique CUIs represented. Not all concepts can be simplified so succinctly, though. For example, "Tylenol" is a different concept than "Tylenol 50 mg", which is a dosage-specific version of "Tylenol". Any ambiguation from "Tylenol 50 mg" to "Tylenol" would effectively constitute a loss of information.

As discussed above, fuzzy matching may also apply on a word-by-word basis rather than a letter-by-letter basis. Furthermore, in still another embodiment, both fuzzy matching on a character by character basis and word by word basis may be applied concurrently to generate entity matches.

Certain features, such as the TNM Classification of Malignant Tumors (TNM) is a globally recognized standard for classifying the extent of spread of cancer, must be preempted from fuzzy matching. TNM is a notation system that describes the stage of a cancer, which originates from a solid tumor, using alphanumeric codes: T describes the size of the original (primary) tumor and whether it has invaded nearby tissue; N describes nearby (regional) lymph nodes that are involved; and M describes distant metastasis (spread of cancer from one part of the body to another). For example, T may be designated a value to estimate size or direct extent of the primary tumor (Tx: tumor cannot be assessed, Tis: carcinoma in situ, T0: no evidence of tumor, T1, T2, T3, T4: size and/or extension of the primary tumor), N may be designated based upon the degree of spread to regional lymph nodes (Nx: lymph nodes cannot be assessed, N0: no regional lymph nodes metastasis, N1: regional lymph node metastasis present; at some sites, tumor spread to closest or small number of regional lymph nodes, N2: tumor spread to an extent between N1 and N3 (N2 is not used at all sites), N3: tumor spread to more distant or numerous regional lymph nodes (N3 is not used at all sites), and M may be designated based upon the presence of distant metastasis (M0: no distant metastasis, M1: metastasis to distant organs (beyond regional lymph nodes)). Exemplary TNM codes may be "pT1 pN0 M0" or "pT4 pN2 M1". Due to the importance of the TNM codes being parsed precisely as they appear to maintain the TNM values, fuzzy matching may be disabled for stop words relating to TNM values, for example, "t0", "T1a", "t3", so that fuzzy matching does not change a "t1" into a "t2" to match a database Entity. NLP may be combined with restricted fuzzy matching in certain embodiments to correct OCR errors related to TNM codes. For example, a NLP model may detect that TNM is being referenced by detecting the presence of a T, N, and M code; however, classification may fail due to an OCR of "pT0" with "pTo", by allowing a restricted fuzzy matching of only similar characters (such as an "o" for an "0"), TNM codes may be maintained while still correcting for errors.

Due to the large volume of concept candidates that may exist from the previous pipeline stage, merely searching for a match and terminating the search upon finding a single match may provide a substantial benefit in reducing the processing time spent crawling the relevant databases/dictionaries. However, the best matches may not be the first matches, and if there are multiple matches within a group (such as synonyms which are off by a single word to the concept candidate), it may be necessary to pick the match which has the lowest fuzzy "score" (the value that counts the number of errors corrected to generate the fuzzy match). If there are still ties (such as there are two matches of equal fuzzy "score"), then the tied matches may be sorted based on length of characters or length of words (such as shorter matches with less words/characters score higher than longer matches with more words/characters). Any unresolved matches may then be selected randomly or according to a first-in, first-out FIFO queue of matches, such that the first match is selected.

Templates, Fuzzy Text Matching & Regular Expressions:

Many reports within EMRs and EHR are provided in consistent formatting across institutions for periods of time (such as patient intakes may share the same form for a period of time until the next revision). Relying on this consistency, the system may consider a case where a hospital system prints its pathology reports using the same template and had a different template for any documents that were created before Jan. 1, 2001. If Pathology Reports from this hospital system are identified as frequent documents received in EMR and EHR, optimizations may be applied to processing to create methods for extracting information from known locations within the shared templates of each respective form. An exemplary method (such as the method described above) may also include multiple parts, as follows:

Document classification: The system may generate an image or text classification model to: determine whether a given document belongs to one of the templates that may be extracted from, assign the document an identifier for linking the document to the template, use the identifier to look up the classification model optimized for the document, and classify the document. Exemplary template-based approaches and tabular approaches are discussed above.

Regular Expressions: The system may identify anchor strings regularly occurring in text that identify where key health information may reside. For example, the system may recognize that "DOB" is a string to search for dates of birth and "Pathological Diagnosis" may be a header to a section that provides concepts for linking to a pathological diagnosis.

Fuzzy Text Matching: As discussed above, the system may apply a fuzzy search algorithm to a regular expression in order to allow the application of regular expressions to words which have OCR errors, typographical errors, or are otherwise confounded.

Templates: Once a document has been classified, and regions of text may be determined in advance, an image classification model may leverage the predetermined region locations to identify those same regions within a document image to extract key health information (clinical concepts). For example, document headers may often be visually structured for presenting information to the reader, and that known visual structuring may contain useful demographic information. By identifying a document header, processing may include rotating/skewing the image to line up the template, removing image irregularities, OCR of the text, and applying regular expressions to extract any information from the standardized format. Any concepts extracted from the template may be provided to the entity linking pipeline 4140 and may be processed to identify any respective matching concepts for linking.

Returning to FIG. 162, in another embodiment, entity normalization (such as at step 4070) may be applied to determine which of the entity linked concepts of the previous stage are relevant to abstraction and, if they are relevant, which encoding schema may be applied to encapsulate the abstraction completely. For example, "Tylenol" and "Tylenol 50 mg" may match in the dictionary from UMLS with a concept for "acetaminophen". It may be necessary to explore the relationships between the identified concept from the UMLS dictionary and any other concepts of related dictionaries or the above universal dictionary. Though visualization is not required, these relationships may be visualized through a graph-based logic for following links between concepts that each specific integrated dictionary may provide.

FIG. 167 is an exemplary ontological graph database 4122 for viewing links between different dictionaries (databases of concepts) that may be interlinked through a universal dictionary lookup in order to carry out the normalizing stage 4070 in FIG. 162. Conventional ontological graph databases may include GraphT, Neo4j, ArangoDB, Orient, Titan, or Flockdb. The following references to dictionaries and databases are for illustrative purposes only and may not reflect accurately the concepts/synonyms, entities, or links represented therein. Links between two concepts may represent specific known relationships between those two concepts. For example, "Tylenol" may be linked to "acetaminophen" by a "trade name" marker, and may be linked to "Tylenol 50 mg" by a "dosage of" marker. There may also be markers to identify taxonomic "is a" relationships between concepts. "Is a" markers provide relationships between over some clinical dictionaries (such as SNOMEDCT_US, Campbell W S, Pederson J, etc.) to establish relationships between each database with the others. For example, we can follow "is a" relationships from "Tylenol", "Tylenol 50 mg", or "acetaminophen" to the concept for a generic drug. Such a relationship may not be available for another concept, for example, a match to the dictionary for UMLS to "the patient" or "patient" may not have a relationship to a medication dictionary due to the conceptually distinct natures of each entity. Relationships may be found between drugs that have the same ingredients or are used to treat the same illnesses.

Other relationships between concepts may also be represented. For example, treatments in a treatment dictionary may be related to other treatments of a separate treatment database through relationships describing the drugs administered or the illness treated. Entities (such as MMSL #3826, C0711228, RXNORM # . . . , etc.) are each linked to their respective synonyms, (such as Tylenol 50 mg, Acetaminophen, Mapap, Ofirmev, etc.). Links between concepts (synonyms), may be explored to effectively normalize any matched candidate concept to an RXNORM entity.

Returning to FIG. 167, the concept candidate "Tylenol 50 mg" 4124 may have a hit in the National Library of Medicine Database MMSL. In the preceding stage of the pipeline, "Tylenol 50 mg" may have been linked to the Entity MMSL #3826 4126 as an identifier for the "Tylenol 50 mg" concept in MMSL. The linked Entity, MMSL #3826, may reside in a database which is not a defined database of authority, or, for document classification purposes, MMSL #3826 may not provide a requisite degree of certainty or provide a substantial reference point needed for document/patient classification. Through entity normalization, it may be necessary to explore links to MMSL #3826 until a reference entity of sufficient quality is identified. For example, the RXNORM database may be the preferred authority for identifying a prescription when classifying prescriptions a patient has taken because it provides the most specific references to drugs which are approved by the U.S. Food and Drug Administration (FDA).

Other authorities may be selected as the normalization authority based upon any number of criteria. The exact string/phrase "Tylenol 50 mg" may not have a concept/entity match to the RXNORM database and the applied fuzzy matching may not generate a match with a high degree of certainty. By exploring the links from MMSL #3826, it may be that concept "Tylenol Caplet Extra Strength, 50 mg" 4128 is a synonym to "Tylenol 50 mg" in the MMSL database. Furthermore, concept "Tylenol Caplet Extra Strength, 50 mg" may also be linked to Entity C0711228 4130 of the UMLS database. By exploring the synonyms to "Tylenol 50 mg" 4124 through Entity MMSL #3826 4126, the concept candidate may be linked to the UMLS Entity C0711228 4130. However, the UMLS Entity C0711228 4130 is not the preferred authority for linking prescriptions, so further normalization steps may be taken to link to the RXNORM database. Entity C0711228 4130 may have synonym "Tylenol 50 MG Oral Tablet" 4132 which is also linked to RXNORM #5627 4134. RXNORM #5627 4134 may be a normalization endpoint (once RXNORM #5627 has been identified, normalization may conclude); however, RXNORM #5627 4134 may also represent the Tylenol specific brand name rather than the generic drug name. A degree of specificity may be placed for each source of authority (normalization authority) identifying criteria which may been desired for any normalized entity. For example, a medication may need to provide both a brand drug name and a generic drug name. Links in the RXNORM database may be explored to identify the Entity for the generic drug version of Tylenol. For example, RXNORM #5627 4134 may have an "ingredient of" link to RXNORM #2378 4136 which has a "has tradename" link to RXNORM #4459 4138 with concept acetaminophen. RXNORM #4459 4138 is the Entity within the RXNORM database which represents the generic drug 4140 for Tylenol 50 mg and is selected as the normalized Entity for identifying a prescription in the classification of prescriptions a patient has taken. In this aspect, normalization may first identify an Entity in the dictionary of authority (as defined above) and may further normalize within the dictionary of authority to a degree of specificity before concluding normalization.

For each field of medical data that is abstracted in the intake pipeline, reasonable reference points for normalization may be identified (such as RXNORM for medications, SnoMed for cancers) and which types of relational links may be traversed from matched concepts in the fields of medical data. As described above, medical data may include fields of patient demographics (such as patient name, date of birth, gender, ethnicity, date of death, address, smoking status, diagnosis dates, personal medical history, family medical history, etc.), clinical diagnoses (such as date of initial diagnosis, date of metastatic diagnosis, cancer staging, tumor characterization, tissue of origin, etc.), treatments and outcomes (such as therapy groups, medications, surgeries, radiotherapy, imaging, adverse effects, associated outcomes, and corresponding dates, etc.), and Genetic Testing and Labs (such as genetic testing, performance scores, lab tests, pathology results, prognostic indicators, and corresponding dates, etc.). Each of the fields (such as address, cancer staging, medications, genetic testing, etc.) may also have a plurality of subfields. For example, address may have subfields for type of use (such as personal, business), street, city, state, zip, country, and a start or end date (date that residency at the address begins or expires). Genetic testing may have subfields for the date of genetic testing, testing provider used, test method (such as genetic sequencing method, gene panel), gene results (such as included genes, variants, expressions, etc.), tumor mutational burden, and microsatellite instability. For medications, links as described above, including "has tradename" and "dosage of" relationships from any entity links may be traversed determine if there is a relevant drug related to the candidate concept.

In another embodiment, a linked Entity may be received from the entity linking stage of the intake pipeline. A query may be generated to search over an ontological graph database having relationships including meta-synonymous links, synonymous relationships between links, and other relationships. For example, a linked entity may resolve to Ductal Carcinoma In Situ (DCIS) in the SnoMed dictionary. SnoMed may be the preferred authority for cancers due to degree of comprehension and detailed concepts included in the dictionary, expert opinion identifies SnoMed as the best dictionary, or because SnoMed has the most comprehensive relationships between other dictionaries, is well established, and meets requirements set forth by the institutions managing the EMR/WHR. A desired degree of specificity may have selection criteria for normalized endpoints. For example, the selection criteria of a cancer type may include an Entity which identifies 1) the cancer site (where the cancer is located in the patient) and 2) the cancer type. An entity identifying DCIS may be limited to identifying the cancer type, but may not satisfy the cancer site selection criteria and SnoMed may be searched to identify a normalized Entity which satisfies both criteria.

Normalizing DCIS may include navigating "is a" relationship links within the SnoMed database until an Entity is reached which identifies the cancer site as breast. For example, DCIS may be a tier three entity which "is a" specific type of cancer under "breast cancer." Breast cancer may be a tier two entity which "is a" specific type of cancer under the root "cancer." Breast cancer may have a "has finding site" relationship to breast, which satisfies the selection criteria for identifying the cancer site (breast) and the cancer type (breast cancer). However, to prevent loss of information, both the DCIS Entity and Breast Cancer Entity may be retained for the normalized Entity to aide in Entity Structuring described below. In SnoMed, relationships between cancers are structured such that there is a finite number of jumps that "is a" links may traverse. Upon each traversal, an "is a" link may either result in a leaf node (traversed down), a terminal node (cancer with no further classification), or to the root (cancer). Traversal may stop at the first "is a" link which is encoded as a terminal node (such as based on the tier as described above, based off a relationship that exists in the node as described above, or that is predetermined as a terminal node). Other relationships which may identify terminal nodes include, for example, in a medicine dictionary, Term Types "Ingredient" or "Preferred term" (such as TTY: GN for Generic Drug Name and TY:BD/BN/FBN for Branded Drug/Name or Foreign Brand Name, etc.), or the degree of specificity may be based off of relationships (such as "is a generic", "is a brand name").

Normalization queries are constructed to prevent out of bound searches, spurious results, and infinite searches. A representative normalization query of a medication may include:

MATCH $p$=(start: DICT {code:"DICT #$AUI$"})-[: has_tradename|tradename_of*0 . . . 3]-(end: DICT)-[:has_$umls\_aui$]→($aui2$)←[:has_$aui$]- (descendant_$cui$)

RETURN DISTINCT descendant_cui.cui AS match_cui, length(p) AS graph_distance

This query may return CUI's related to concepts which are linked to ingredients identified in the medications terminal node list by up to 3 trade names or generic names. In one aspect, a limit on the number of links which may be traversed and included in the query results may be included to reduce computational constraints (such as processor and memory reservations). Queries may be optimized to provide both generic and trade name normalization endpoints, for example, by not specifying or restricting the directionality of the [:has_tradename|tradename_of] portion of the query. Alternatively, queries may be directionally limited to only traverse [:has_tradename|tradename_of] in a specified direction to limit the results which are generated as desired. A terminal node entry for an ingredient to be encoded to in the medications valueset and may be encoded by including each respective code's dictionary (DICT above) and AUI into the query so that when a new entity is traversed, the AUI may be referenced with the list of terminal nodes.

A representative normalization query for a cancer type may include:

MATCH $p$=($cui:umls\_cui$)-[:has_$aui$]→ ($aui:umls\_aui$)←[:has_$umls\_aui$]-(descendant: DICT)-[:$isa$*0 . . . ]→(:DICT {{code:"DICT #$AUI$"}})

RETURN DISTINCT cui.cui AS match_cui, length(p)-2 AS graph_distance

This query may return CUI's related to concepts which are lined as "is a" descendants of a given code (node). A terminal node entry for a cancer type may be encoded in the cancer valueset and may be encoded as a primary diagnosis by including each representative code's dictionary (DICT above) and AUI into the query so that when a new entity is traversed, the AUI may be referenced with the list of terminal nodes. For cancer type queries, a return value may include the graph_distance of the path, which provides a qualifier for how many "is a" nodes are in the path between the descendant and the queried code. After processing queries for each node in the primary diagnosis valueset, there may exist many descendants that point to multiple parents. The resulting query response of potential matches may be further curated according to the following logic:

If a descendant D is generated by two ancestors A and B, but A and B are not descendants of each other, then keep the mapping of D to both A and B; OR If a descendant D is generated by two ancestors A and B, but A is also a descendant of B, then discard the mapping of D to B (because A is a nearer ancestor).

In another embodiment, a concept candidate may be explored by more than one query relating to the concept. For example, a concept candidate may be explored/followed until a concept with a related structure (as described in FIG. 163) is linked/normalized, then each of the associated fields are queried in turn (Entity structuring is disclosed in more detail, below).

An aspect of query generation may include tailoring queries to avoid spurious searches. For example, by recognizing directional relationships which preserve the integrity of the source node, queries which prevent erroneous destination nodes from being reached are preferred. For example, normalizing the Brand Name Entity for Tylenol may include traversing the "ingredient of" relationship that Tylenol has. In one direction, drugs for which Tylenol is considered an ingredient of may be safely explored. However, in the other direction, the ingredients of Tylenol may be explored. An ingredient which is shared between Tylenol and another drug may be linked by, for example, magnesium stearate which is shared between Tylenol and Advil. A generic drug ibuprofen may then result from an unbounded query which does not restrict the traversal of "ingredient of" fields to prevent spurious drug hopping.

It may be advantageous to precalculate the results from frequent query searches and cache the query results for speed. Caching precomputed queries represent a tradeoff for the flexibility of results with the speed at which they may be generated. Caches may include a node hop count value that is used to resolve ties for least number of hops. Caching may be performed at the Entity Link stage and the Entity Normalization Stage. In a simplified representation, an Entity Linking Cache may include fields such as: Name of Concept Candidate, Dictionary Candidate Located In, and CU ID. It may further be advantageous to identify a structure category and corresponding fields based from the identified CUID.

Normalization may be directed to generate results which relate to the fields of the structure category identified. In another simplified representation, an Entity Normalization Cache may include fields such as: CUID, Medical Concept Structure, and normalized response for concept (Normalized CUID). Additional fields for either table may include: graph distance (number of hops), preferred dictionary CUID, pre-defined entries (such as names, regions, categories), inferred structure entries (such as diagnosis site, generic drug name), language of text, match type (such as exact, exact but letter case mismatch, fuzzy matched, etc.), text type (TTY, described above), or other fields.

Normalized Entities may be further normalized to reduce known variance in results. For example, in a cancer type normalization, there may be numerous normalization endpoints which reference breast cancer in one form or another that match the selection criteria of the normalization algorithm. A post-processing step to the normalization may be applied which identifies, for example, when a cancer site is designated as breast, and adjusts the final result such that all entries with a breast cancer site share the same cancer site code and same spelling "breast". Other normalized results may include each main cancer site (brain, lung, liver, ovary, bone marrow, etc.), a predetermined catch-all for unknown sites, or known codes which are irrelevant to the normalization results and may be filtered.

Returning to FIG. 162, the Entity structuring pipeline 4072 compiles each of the normalized concepts identified in the previous stage. However, given thousands of pages of documentation within an EMR/EHR for a patient, the number of normalized entities that may be identified and resolved during processing may number in the hundreds of thousands. The abstraction process as described above with reference to FIG. 162, may display information about a normalized concept by providing various identified and populated fields. For example, with reference to the sentence "The patient was given Tylenol 50 mg at 10:35 am.," the entity structuring pipeline 4072 may encode the following fields:

Text: The entirety of the text ("The patient was given Tylenol 50 mg at 10:35 am.").

Medication: Identifying any medication mentioned in the text (Tylenol). Medications may be brand name or generic name. This field does not include information about the dosage or method of administration.

Active Ingredient: Identifying the active ingredients (acetaminophen) of the medication mentioned using a list such as a search table linking drug names to their active ingredients.

Dosage & Dosage Units: The dosage (50 mg) associated with the medication mentioned. In the above example, identifying that the dosage as 50 mg is fairly straightforward by reading the sentence, but clinical data is often printed in tables with a variety of structures that are not easy to infer. As such, normalizing the dosage and dosage units by separating value 50 into the dosage field and string "mg" or by selecting a known value entry for the milligram units within a list may be preferable.

Document & Page: The document and page where the text is found (Progress Note 01_01_01. pdf and page 3).

UMLS_CUI: The CUI field (C0711228) of the UMLS entry corresponding to the medication. The UMLS is a list of medical concepts and the UMLS_CUI refers to the CUI field, which is UMLS' universal identifier. UMLS is comprised of a number of independently maintained clinical dictionaries and ontologies (such as those for cancer diagnosis & treatment, dentistry, veterinary medicine, etc.). That is, the CUIs are universal to UMLS, and there is only one CUI for Tylenol across all of its constituent dictionaries that enables UMLS to unite all of these disparate sources.

UMLS_AUI: The AUI field (RXNORM #4459) is the dictionary-specific identifying code of the UMLS. Where the CUI is universal, and has the same entry across all included sources, the AUI for Tylenol will have different AUIs for each dictionary that it has an entry in.

Various fields, such as UMLS_CUI, UMLS_AUI, Medication, and Active Ingredient may each be determined through the entity normalization process by exploring the links to each of the Entities. The other fields, such as dosage, dosage units, date/time administered, document, and page may not be determined through the normalization process. Instead, these other fields are provided to a Relational Extraction MLA for extracting this information from the surrounding context or document information (such as name, number of pages, etc.). For example, a document named Progress Note 01_01_01 may be presumed to have a date of Jan. 1, 2001. Other concept candidates from the document may be referenced to validate the date/time or select the date absent any other validating/corroborating information. For example, the time 11:35 am may have been provided as a concept candidate spatially near the "Tylenol 50 mg" concept candidate. The Relational Extraction MLA may then identify 11:35 am as the time the medication was administered based on the concept candidate time being the next concept candidate in the list, a spatial proximity of the concept candidate, a new application of NLP to the OCRed text string, or any combination thereof. Additionally, a page number may be identified, for example, in a document that has 5 pages by referencing the page number by performing an OCR of text at the bottom of the page or may be extrapolated by counting the number of pages before the page the concept candidate was extracted from. Once each field of the medical data is identified through either the normalization process or the structuring process and the relational extraction MLA, the patient/document may be ready to be classified according to each normalized and structured entity.

Returning to FIG. 162, the post-processing pipeline stage 4074 may receive a listing of all the structured entities and generate a response/report. For example, a response may be a formatted into an output divided into several sections, each section relating to, for example, the fields of Diagnosis, Procedures, Radiology, etc., as discussed above. Under a Diagnosis header/identifier, structured entities relating to diagnosis may be summarized with the final normalized entity, information from the entity structuring, and any confidence values generated during the classification and/or ranking/filtering. The response may include all of the sections with corresponding structured entities. The response may be generated and output, such as a word document, a spreadsheet, or a JavaScript Object Notation (JSON) file with each of the relevant sections and structured entities encoded therein.

The MLA and DLNN algorithms described herein may be implemented using supervised, unsupervised, and/or semi-supervised approaches. Patient/document classification based off of text classification is the general task of processing text and identifying whether it belongs to one of many pre-defined groups (such as the above-referenced medical fields). For example, supervised machine learning methods may be used to classify patients as Male or Female, because many clinical documents exist for patients whose genders are known. Exemplary non-machine learning ways of determining a gender would be to apply a regular expression for "Gender:" in text or "pt is a ##yo X". It would be an exhausting endeavor to create a regular expression for every potential combination of words or characters that gender may be mentioned in text in order to be able to extract it using simple text matching. Instead, a simple heuristic component for classifying a gender may be to determine the ratio of male vs female pronouns in text, under the assumption that references in medical text are almost entirely describing the patient (as opposed to their family members or medical staff, who are occasionally mentioned as well).

Similarly, a supervised machine learning method may require that the gender is known or provided for some batch of patients. The machine learning method may then extract signals or features from the text that are indicative of the gender. At that point, a Naive Bayes MLA may be utilized to, for example, identify the ratio of male vs female pronouns. The Naive Bayes MLA may determine the frequency of every word that occurs in any clinical document occurs in the male documents vs how often the same words occur in the female documents in terms of probability (such as 'he' is 2% of words in male documents and 0.1% of female documents). Once trained, for each new document to be classified, the Naive Bayes may use the generated probabilities/statistics to determine the likelihood that a document falls within the male linguistic probability distribution or the female distribution. A general threshold value or comparison may be applied to determine whichever probability is higher.

While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. Returning to the example regarding gender, an unsupervised approach may attempt to identify a natural divide of documents into two groups without explicitly taking gender into account. On the other hand, a drawback to a purely unsupervised approach is that there's no guarantee that the division identified is related to gender. For example, the division may be a between patients who went to Hospital System A and those who did not.

As a result, semi-supervised methods may be the most optimal approach whenever there are a large number of unlabeled or unannotated documents as well as labeled documents in the training set. EMRs/EHRs may be particularly well-suited to this approach, because hospitals take care to note key health information for each patient. For example, considering a practical approach to applying a semi-supervised MLA, presume that an exemplary dataset generates a probability distribution such that "he" accounts for 2% of the words in male patients' documents and 0.75% of female patients' documents. If these estimates were taken over a small number of patients (such as 100 pages of text total), but 4080 of these pages are from female patients, the probability distribution may be quite susceptible to noise (erroneous weighing) and may generate wrong or undesirable results.

The unsupervised approach solves this by providing a number of documents from patients whose genders unknown, effectively allowing the MLA to learn something about language in general. Specifically, the MLA determines how frequent "he" may be presented in clinical text in general. If the semi-supervised MLA identifies that "he" only occurs 0.5% of the time, "he" may be occurring unusually frequently in the labeled documents (such as at 2% and 0.75% probability distribution). For example, no ratio of male-to-female patients could balance out to 0.5% given an initial probabilities of 0.75% and 2%. Instead, the MLA corrects for the noise in the data set by applying the information that there were more female patients than male patients and accordingly adjust the probabilities more strongly for the male probability distributions than the female. A scaled probability distribution may indicate that "he" occurs at 0.9% frequency in male patient files and 0.1% in female patient files, so that the average distribution of "he" is 0.5%. The semi-supervised MLA may then accurately apply the heuristic technique as a portion of the classification determination.

Machine learning algorithms and deep learning neural networks tend to provide approximate solutions to any complex problem without a clear set of rules to constrain the problem through. MLA and DLNN are most useful for problems which are too difficult to constrain accurately to a few simple rules/constraints and excel at finding unique solutions to these complex problems. These unique solutions may also include equally unique bugs for edge cases of the unique solution, which may require fine tuning to improve the performance of the MLA by adding better/more accurate/more representative training data, by tuning hyperparameters, or by improving or replacing the MLAs themselves.

In an exemplary model, as described below with reference to FIG. 168, a training feedback loop 4142 operates to improve the training data set by improving the annotations of the edge cases and using the improved training data to refine the MLA model itself. For example, an initial MLA trained on an initial data set may be only 75% accurate at its given task. By directly utilizing the MLA in a platform where humans are entering data based on clinical documents for patients, edge cases (erroneous output) may be identified, the annotations surrounding the documents/patients of the edge case may be improved, and the improvements submitted back into the MLA to further train the model to improve accuracy. Regardless of whether the human agrees or disagrees with the machine learning model's prediction/classification, the human takes into account the prediction as well as other information in the clinical documents before making their final annotation. This final annotation is utilized as the "gold standard" by which the MLA should operate and can immediately add the labeled documents and the corresponding annotation to the training data set to improve the results when the MLA is trained in the future. Each edge case that is corrected by a human, even each additional question that a human answers above and beyond the erroneous outputs may directly help the machine learning model answer the corresponding question correctly in the future.

The feedback process may be improved by adding the ability to collect direct feedback from an annotator. For example, if the annotator agrees with the machine learning model's prediction, then it may be presumed that the prediction was correct. Conversely, if the annotator disagrees with the prediction, it may not be clear why the MLA prediction was wrong. For example, the MLA may make an erroneous prediction if the documents were for the wrong person, if OCR errors exist which confounded the prediction, or if the model simply was not sufficiently trained to make a correct prediction from the data in that instance.

Staying with FIG. 168, an exemplary system architecture is depicted. In particular, FIG. 168 depicts a scenario in which the system receives documents, for example, from a clinical data vault 4144, new documents from an Attach system 4146, or corrected documents via the Workbench 4148 (introduced below), uploads documents, and posts them to a Workflow 4150. Workflow 4150 may be a server that coordinates a number of tasks and manages the intake of documents for the intake pipeline described in FIG. 162.

From there, the documents are posted to Attachments 4146, for example, another server that stores sensitive files and authenticates all access to those files. Concurrently, a copy of each of the documents is sent to a Converter 4152, which patches each document with a viewable image, such as a PDF, of the document. The system calls an OCR service 4154, such as Google Cloud Vision or Tesseract, which runs optical character recognition on the documents. Alternatively, if the system determines that the document was already OCRed, a cached copy of the OCR document is retrieved from a database (S3) 4156. The viewable image file then is transmitted to the Attachments component 4146, which links the original file with the image file. Similarly, a copy of a searchable text version of the document is provided from the OCR service 4154 to the Attachments component 4146 to combine with the original document and the viewable image from the Converter 4152 and, if not previously OCRed, a second copy of the searchable text version is transmitted to the database 4144 where it is cached. The Abstraction Engine 4158 and Abstraction Engine toolbox 4160 components utilize MLA and NLP to generate predictions.

Once the patient documents are processed in Workflow 4150, Workbench 4148, and then processed through OCR 4154, raw OCR information may be pulled from the database. The processing intake pipeline stage for pre-processing and OCR occurs in these servers/processes. The system also may check the database to determine whether improved NLP models have been provided and retrieve any new or updated models. The system then applies the most current NLP algorithms and models to the raw OCR files. In this regard, patient data may be encoded differently depending on the project for which it is being used, so the system may communicate with a service (such as Valuesets 4162 in FIG. 168) that includes one or more templates to set forth how the OCR'd data should be abstracted and which values within that data are displayed for each field. Tabular and template extraction may also be contained within the Valuesets database 4162.

The predictive data is then tailored for the given project from the tabular extraction applied, and those predictions then are posted to a second database (such as the Abstraction Engine toolbox 4164) for use by one or more additional applications. The Valuesets service 4162 may specify a global encoding list for all of the concepts related to each of the dictionaries/databases and the internal universal dictionary (such as medical concepts and fields described above). Using medications as an example, Valuesets 4162 specifies all of the medication ingredients that may be beneficial for analysis.

By narrowing the search to a targeted list of concepts that are important to identify, overall processing speed of the architecture may be improved. For example, UMLS metadata may be applied to determine that "Tylenol" is a brand name drug, "acetaminophen" is a generic ingredient as described above. When "Tylenol" is recognized as a medication, medication-specific queries may be processed to identify normalization candidates, for example, in the Abstraction Engine toolbox 4160. If a query returns that "acetaminophen" is in Valuesets 4162 but "eucalyptus leaves" is not, any medication determined to be eucalyptus-based may be ignored by the system.

Workbench 4148 may represent a server for maintaining a user interface (UI) to implement a patient record analysis system responsible for managing the flow of information between systems of the instant architecture and/or stage of the processing pipeline. An exemplary high-level description of the UI may include three windows/panes, such as a center pane that allows an abstractor to view patient documents for which the other two panes may display information relating to. A left pane may be configured for entering the abstracted information, including fields (drop-down lists that are populated by Valuesets 4162), dates can be entered and subjected to rules for validation (such as DOB must be before date of death), singular fields (such as patient's gender or primary cancer diagnosis), repeatable fields (such as drugs the patient took, surgeries, etc.), fields with subfields (such as medication structured data, cancer diagnoses, etc. as disclosed above with reference to FIG. 163). A right pane may be configured for displaying Abstraction Engine 4158 results. The way these are structured is determined by the Abstraction Engine 4158 configuration. Category groups fields at a high level and specifies, for example, four of them currently: Demographics, diagnosis, treatments, outcomes. Categories have many fields, which are what the abstractors are trying to enter values for. These fields may also be expanded and collapsed. When expanded, a list of values that the Abstraction Engine 4158 predicted for that field (and optionally, a confidence score specified for that value) may be shown. Fields can also have justifications tied to them, which are text snippets that the Abstraction Engine 4158 determines best shows why the given value is correct for the given field. Given that many of the predictions are tied to the intake pipeline stages, the text surrounding the identified concept candidate may be provided as the justification.

Workbench 4148, the patient record analysis system, may access and/or retrieve patient data from a patient record located in the Workflows component 4150, requested from the clinical data vault from the Workflows component 4150, or from the patient record including the documents that were stored in the Attachments storage 4146. For each document, Workbench 4148 may also retrieve the corresponding NLP predictions from Abstraction Engine toolbox 4160. Once abstracted, the final abstraction report and data may be transmitted, via Workflows 4150, to a clinical data vault. For example, the MLAs may have already provided classifications/predictions for the patient that is being abstracted. The Abstraction Engine server 4158 may have already processed all of the documents for the given patient, generated its predictions, and uploaded them to Abstraction Engine Toolbox 4160. The Workbench server 4148 may then retrieve the patient documents as well as Abstraction Engine 4158 predictions for each patient. An abstractor may use an interface of Workbench 4148 for manual abstraction. The Abstraction Engine 4158 pipeline may be further optimized such that the Workbench interface 4148 also includes machine learning predictions for each template's fields and presents them to the abstractors (such as the fields of FIG. 163). Once identifications of relevant metadata for clinical concepts are found in text, Abstraction Engine Toolbox 4160 may generate predictions. Once entity normalization have been completed, a report may be generated and provided to Workflows 4150 for storing in the clinical data vault, for example, in a text file or a JSON format. This information may be populated for every medication that is identified in the patient's clinical documents and may also be provided to the Abstraction Engine Toolbox Service 4160 for storing this information in a protected database. Other services can then query Abstraction Engine Toolbox 4160 by Patient or by Document and determine which clinical predictions Abstraction Engine 4158 has made. Abstraction Engine S3

4156, Abstraction Engine 4158, Abstraction Engine Toolbox 4160, and Valuesets 4162 together implement the parser, entity linking, and entity normalization intake pipelines stages.

As mentioned above, the system periodically checks to make sure that the NLP/MLA models being used are most up-to-date (such as elements 4076, 4078, and 4080 from FIG. 162). The system may include a Bootcamp subroutine 4166 for evaluating and updating the NLP and MLA models. In this subroutine 4166, the system retrieves clinical record documents from the clinical data vault 4144, such as based on one or more unique user id's, on clinical features common to one or more patients, or any other criteria. The subroutine also may communicate with the Abstraction Engine S3 database 4156 to retrieve the raw OCR files corresponding to each of those documents, as well as the current NLP model. The system further may retrieve abstractor feedback (such as the feedback loop's erroneous result corrections/annotations) from the toolbox 4160. Each of these inputs may be used to execute a training script to verify or update the NLP model. At that point, metadata relating to the updated model may be communicated to the Abstraction Engine toolbox database 4164 (such as for later human inspection, model or data provenance, and/or long-term metrics). Workbench 4148 supports the ability for abstractors to tag Abstraction Engine's 4158 incorrect predictions with a predetermined set of issues (such as documents are from wrong patient, OCR errors, wrong entity linked, correct concept candidate, wrong entity linked, correct concept candidate but hypothetical reference in document cannot be construed as haven taken place, etc.). For example, in the case of patients whose predictions are incorrect because 'Documents are for wrong patient', the Abstraction Engine Bootcamp 4166 may ignore these patients when training future MLAs to understand gender or may instantiate a specific training phase to train the current MLAs to predict which patients have documents from multiple patients and exclude from training and/or flag all patients which have documents from wrong patient for independent abstraction.

Similarly, other tags such as 'Bad prediction due to OCR error' may be applied as feedback on a given OCR software/service, which means the system can implement various OCR services and use abstractor feedback to determine the highest quality OCR service 4154 from various competitors. Abstraction Engine toolbox 4160, Workbench 4148, and Workflows 4150 together implement the Entity structuring and post processing intake pipeline stages.

Workbench 4148 facilitates and incorporates human abstraction by providing prediction justifications and confidence metrics alongside the predictions. A number of issues arise when providing an abstractor with only a single list of possible answers and corresponding confidence values. For example, an abstractor may not be provided with any reasoning about how the predictions or confidence values are calculated, or it may not be clear when an abstractor should trust the NLP models and when they should take a deeper look into the patient record because it is difficult to know what confidence level is needed before an output needs to be verified for accuracy. Instead of making this decision the sole responsibility of the abstractor, Abstraction Engine 4158 is designed to provide justifications for its predictions in the form of textual contexts that are determined to indicate that a prediction is correct.

Following the example of structuring a full medication entry that included a Text Context field (FIG. 163), additional processing may determine whether the fully structured concept is a positive mention (such as it is not related to a family member's previous illness or treatments, it is not a hypothetical treatment proposed by a doctor, it is not a diagnosis unrelated to the patient that happens to be mentioned in supplemental literature, etc.) and maintaining links to text context may be a useful justification to the positive mention. This determination may be processed through other text classification algorithms that use the contextual information to identify whether the concept mention is positive or negative. For example, the simplest implementation may include a pattern-based system configured to ignore diagnoses in contexts such as "{mother/father/sister/etc.} has a history of {disease}." While these phrases may be considered in the NLP algorithm itself, error checking may involve repeating the process in low confidence predictions, or providing additional algorithms with text classifiers that utilize the additional textual context. Another embodiment may involve aggregating all of the mentions of a primary cancer site which may also include all or some of the textual contexts for those mentions, which can provide the abstractor with confidence that the prediction was correct without manual intervention.

Turning now to FIG. 169, a patient upload process of the instant architecture is disclosed. In particular, this figure illustrates a process in which Patient documents may be uploaded by Extract, Transform, Load (ETL) Tool or a Q-Manager. Q-Workflows 4150 may post the documents to Attachments 4146. A Converter 4152 may patch the documents with viewable PDFs. OCR 4154 may run either an OCR service such as Google Cloud Vision or Tesseract to OCR documents or, if the document was previously OCRed, it may retrieve a cached copy of the OCR. The system then may receive a response from S3 4156 instead of OCRing it again. OCR 4154 may patch the documents with a searchable text version of the PDFs, and OCR 4154 may cache the raw OCR files to the Abstraction Engine S3 bucket 4156.

Turning now to FIG. 170, a prediction generation process of the instant architecture is disclosed. In this aspect, once the patient documents are processed, the Abstraction Engine 4158 may pull raw OCR files from its S3 bucket 4156, check S3 4156 for improved NLP models and pulls them if necessary, run the documents through its current NLP pipeline and models, pull project-specific templates from Valuesets 4162, tailor its final predictions for the given project, and post those predictions and related metadata to the Abstraction Engine Toolbox 4160. In this regard, patients may be encoded differently in each project, so Valuesets 4162 may be a service that coordinates project encodings (such as which fields are abstracted, which values are displayed for each field).

Turning now to FIG. 171, an abstraction process of the instant architecture is disclosed. In this aspect, when a Q-Workbench user loads a patient, Q-Workbench 4148 may pull the patient record from Q-Workflows 4150 (Q-WF), including patient documents which are passed from Attachments 4146 through Q-WF 4150. Q-Workbench 4148 also may pull the corresponding Abstraction Engine predictions from Abstraction Engine Toolbox 4160 (if the predictions are available). The abstractor may abstract data field by field and pass patient data to Q-WF 4150. Patients may provide direct feedback about specific NLP predictions, which will be passed directly to Abstraction Engine Toolbox 4160. And the abstractor may submit the final abstraction report and data makes its way through Q-WF 4150 to the Clinical Data Vault 4144.

Turning then to FIG. 172, a feedback loop and training process of the instant architecture is disclosed. In this aspect, the Abstraction Engine Bootcamp 4166 may periodically update Abstraction Engine NLP models. Specifically, the Abstraction Engine Bootcamp 4166 may be initialized by a script or a periodic update protocol. The Abstraction Engine Bootcamp 4166 also may pull: clinical records from the Clinical Data Vault 4144 for a list of patient UUIDs specified by script/protocol, the raw OCR files that correspond to each of these patients' documents from the Abstraction Engine S3 bucket 4156, and existing NLP models from S3 4156 (some models can be trained multiple times and improve over many iterations of new data). Abstractor feedback may be pulled from Abstraction Engine Toolbox 4160 into Abstraction Engine Bootcamp 4166 for additional training info. The Abstraction Engine Bootcamp 4166 may execute its training script and post NLP models to S3 and also post model metadata to Abstraction Engine Toolbox 4160 for human inspection, model/data provenance, and long-term metrics.

The systems described above may have multiple uses that are beneficial to clinicians and researchers involved in the treatment of diseases, research into diseases, and data analysis involving disease. One example is in the field of clinical trials. A clinical trial is a research study to determine the safety and efficacy of a drug, device, biologic, or other potential treatment. Clinical trials often have inclusion and exclusion criteria, whereby a patient must meet all of the inclusion criteria and not have any of the exclusion criteria in order to enroll in the study. Many clinical trials have specific criteria that can be determined only after close examination of the medical record. For instance, an example of inclusion criteria for a study of chemotherapy of breast cancer subjects might be postmenopausal women between the ages of 45 and 75 who have been diagnosed with Stage II breast cancer. An exclusion criterion for this study may include a positive identification for abnormal renal function, if, for example, one or more of the drugs used as treatment in the study are nephrotoxic. A medical institution, such as a hospital, may have many patients who are eligible for the study, but require the system described above in order to parse their EHR in order to prepare a list of patients who are eligible to participate in the study.

Another example relates to the development of synthetic control arms for clinical trials. In a clinical trial, a group of patients (called the "control group") receives standard of care treatment while a second group (the "experimental group") receives an experimental treatment (such as a study drug). Often, a study is "blinded" meaning the patients who enroll in the study do not know if they are part of the control group or the experimental group. It can be difficult to recruit patients to clinical trials because many patients wish to ensure they are part of the experimental group. An institution may utilize the systems and methods described herein in order to create a list of structured data from each patient in the EHR who meets the inclusion/exclusion criteria. By leveraging the existing data of patients who do not qualify for the clinical trials, a propensity based model may supplement the clinical trial data as the control arm of the study. These patients may be considered the control group, and their health data as captured in structured format may be utilized as the control arm of the study. In this way, a separate enrolled control group is not needed for the study, and the patients who enroll may all be made part of the experimental group.

Another example relates to data analysis of an institution's EHR. Many institutions, such as hospitals, retain patient health information in free text that is not easily searchable for patterns in treatment or outcomes. Using the systems above, institutions may be able to create structured data sets with data elements that permit the institution to conduct sophisticated data analysis to look for data trends. Such trends may indicate best practices in particular departments, or may indicate areas of concern that require the institution to conduct further investigation. For example, the institution may utilize the systems and methods described above in order to determine which patients are being prescribed which medications at which dosages. The systems and methods may be used periodically (for instance, on a quarterly basis), to analyze utilization rates. As another example, the institution may utilize the systems and methods described above in order to characterize the outcomes of patients with respect to treatments which they have been prescribed and undertook while under the care of the institution. The analysis may be conducted in a way that the structured data generated by the systems and methods described above omits certain data elements in order to ensure that the structured data is de-identified or that protected health information is securely maintained, encoded, or removed. For instance, name, address (all geographic subdivisions smaller than state, including street address, city county, and zip code), elements (except years) of dates related to an individual (including birthdate, admission date, discharge date, date of death, and exact age if over 89), telephone numbers, fax number, email address, Social Security Number, medical record number, health plan beneficiary number, account number, certificate or license number, any vehicle or other device serial number, web URL, Internet Protocol (IP) address, finger or voice print, or photographic image of the patient, may all be omitted from structured data fields. Alternatively, or in addition, the resulting data may be run through a statistical system to ensure there is a very low chance it contains identifiable health information.

In another example, an institution may utilize the systems and methods described above to conduct automatic quality checks on the information contained in its medical record. For instance, the institution may use the systems and methods to compare information in one section of the medical record with information in another section of the medical record to ensure consistency between the records in each section. As an example, imaging reports on cancer tumors can contain radiology information about the tumor (such as its size), while a radiology report prepared by a physician may also contain similar information. The systems and methods described herein may be used to ensure that the imaging report (for instance, the tumor diameter is 2 cm) is consistent with the information as the radiology report (for instance, the tumor diameter is 2 cm). If the information is different, an alert may be triggered to have a clinician review the record further.

In another example, other types of records could be used instead of patient records to create a structured set of data from unstructured information. One type of record that could be analyzed using the systems and methods described above is a scientific journal publication. Many publications disclose information about new and potentially promising treatments in cancer and other diseases. Other publications disclose information about existing treatments that may be useful for newly indicated diseases. The systems and methods described herein may be used to automatically generate a list of structured data from a scientific publication (for instance, it may generate a list of structured data indicating that a certain drug is effective at a certain dosage for a certain class of patients). The list of structured data may be combined in a knowledge database comprising other similar lists of data.

In another example, the systems and methods described herein may produce structured data that can be aggregated, and the results of the aggregation may be analyzed for comparative purposes. One exemplary use is for population health purposes. For instance, the systems and methods described herein may be used to compare aggregated structured data from one institution with aggregated structured data from another institution or another group of institutions. Such comparison may be useful when determining medication utilization rates; duration of inpatient stays; rates of readmission; types and frequencies of diseases, such as cancers; or other indicators. As another example, the systems and methods described herein may be used to compare aggregated structured data from one geographic area with aggregated structured data from another geographic area. Structured data from an institution or a geographic area may be aggregated using methods known in the art.

In exemplary embodiments, processing of the electronic document capture may be performed on the mobile device 4010 or may be sent to a cloud server to reduce the demand on the mobile device's battery and processing resources. For example, the mobile device may obtain an electronic data capture and provide an image of the capture to the cloud server for processing according to the steps disclosed herein. Alternatively, the mobile device may obtain an electronic data capture, perform region capture, and perform OCR on the capture to extract text from the captured region. The mobile application may then provide only the extracted text as well as text identifiers to the cloud server for processing. Exemplary text identifiers may include the Form identifier or document identifiers discussed above as well as a region identifier which identifies which region the extracted text corresponds to. In each of the above embodiments, the cloud server may return the extracted patient information, such as patient name, diagnosis, treatment, or sequencing information, to the mobile application for display and verification by the user.

In one embodiment, the application may include error detection of the electronic document capture. For example, the application may detect that an electronic data capture is of poor quality, and request that the user rescan the page. Such quality detection may be performed by evaluating character quality, for example, comparing density of the solid lines or the fuzziness of lines, checking the whitespace around perceived collection of words for artifact detection. In another embodiment, the application may detect that a page of the document is incorrectly scanned (such as the user either scanned the wrong page of the correct document or a page from a different document). Exemplary detection may be performed by comparing the expected layout of the page (arrangement of document features in the predefined model) with the electronic document capture. For example, if a table is present in the feature list of the identified document, but is not located in the electronic document capture at the expected page, a general error may be flagged to indicate to the user that the expected page was not captured. Furthermore, features which are tagged as optional may be ignored during form verification if they are not present.

Certain error detection may not be easily performed. For example, genes have a plurality of possible variants and each variant further has possible representations. As discussed above, redundant information stored in multiple features of a report, or even report appendices, may be referenced to provide a more robust error detection. However, it may not be possible to automatically detect when a genetic variant is an error from OCR or not.

This problem may be resolved by cultivating a growing set of knowledge and insights around genetic variants and their related attributes. For instance, the application may be able to programmatically differentiate valid vs. invalid variants (correct: EGFR, incorrect: HFGR) by querying a genetic variant database for observed and classified variants for each gene. A database may store knowledge and insights around genetic variants and their related mutation effects currently consists of both internally managed and externally sources, for example, COSMIC (the Catalogue of Somatic Mutations in Cancer), NCI's Clinvar, or gnomAD (the Genome Aggregation Database). This reference data may be used to classify a genetic variant according to data elements such as over or under expression or other deviation in gene expression counts, single nucleotide variants, copy number variants, or coding mutations and fusions. Additionally, various other classifying attributes may be found in the set of knowledge and insights, for example, the chromosome on which the variant was detected, whether a variant is therapeutically actionable, or if it is germline. By using a combination of the redundant features in the electronic document capture and reference data sets, a variant identified in source documents by the application can be evaluated for validity.

In one aspect, the application or a cloud server in communication with the application may query the database via its API to validate whether a recognized gene and variant combination is valid/known or if it is actually an unrecognized variant, an OCR introduced error, or if the unknown combination originated from the clinical documentation and/or text. Known genes and variants have matches, unrecognized variants may not have matches or one that has not been identified, sufficiently classified, or expertly-curated by the scientific community. An OCR error, however, results from imperfect technology for identifying and extracting text from images and/or documents.

Turning to FIG. 173, the user may validate the information captured from a document (such as the document of FIGS. 161A-B) by confirming the patient details are correctly populated in the fields and initiating a query of the patient cohort. For example, the application may include a review interface 4170, through which the physician may confirm that the name populated in text field or drop down 4172 is the patient's and is spelled correctly, the diagnosis in text field or drop down 4174 is the patient's and is spelled correctly, the collection date of the report in date field, text field, or drop down 4176 is the report's, and each of the gene identifiers and corresponding variants in fields 4178A-C are consistent with the report data. In the event that the captured information is inconsistent with the document from which it was captured, the application may permit manual editing of that information. For example, if the patient name was captured as "Jane A. Dot," tapping or pressing and holding the patient name field may open an editor permitting the user to make the necessary changes. Similarly, selecting a gene identifier icon, such as the oval in any of fields 4178A-C may permit the user to modify the mutated gene identified by the MLA in the event it does not match the captured document. Selecting that icon may open a search dialog box and a keyboard on the mobile device in order to receive user input of the specific mutation. If the correct gene was identified as mutated, but the specific variant within the gene does not match that listed on the document, the user may tap or press and hold the portion of field 4178A-C outside the oval. Doing so may open a similar keyboard as for the gene identifier. Alternatively, the application may open a list of possible variants for the identified gene, the list being scrollable in the event that its full contents do not fit on the screen all at once. It should be understood that suggested field types above, including text, drop down, or date are merely representative of the types of fields that may be implemented and should not be construed as limiting each respective field to those types as disclosed above.

A button or gesture may be used to add a field to the data which may have been omitted by the extraction process above. For example, the user may press and hold on the blank space below the last entry to cause a new field to appear, or the user may place a finger on two consecutive fields and spread them apart to cause a new field to appear between them. The newly added field may appear at the bottom of the list and the user may drag and drop the field into the appropriate place on the application interface 4010. The user may confirm the information is correct by selecting button 4180 or by initiating a corresponding gesture (such as using three fingers to swipe interface 4170 to transition to the next window of the app). Upon validation of the information, the application may also store a copy of the data (after deidentification and/or removal of protected health information) to include in future reports. New fields and updated fields may be processed again for entity linking and normalization to ensure that each field is accurately curated for generating the query and storage.

The initiated query may be generated by extracting the data from each field of the application and generating a query with the extracted data. For example, each field may include both the text that has been confirmed by the physician and the entity linking data identifying the match to a concept in the medical dictionary as described above. The fields may be added to a container, object model used by the underlying databases, a nested database/dictionary, or other format before encoding and transmission. Transmission may be received and processed at an endpoint of a cohort repository and engine for processing patients and generating the cohort report.

In another embodiment, the initiated query may be received at a database storing aggregate information from patients of one or more physicians. Fields of the query may be extracted and processed by the database to identify a group, or "cohort", of patients in the database who are similar to the physician's patient. Both the text and the linked entity may be stored to ensure the medical concept/relevance of each entry is accurately recorded. Similar patients having features matching one or more of the features included in the query may be identified and added into a cohort of similar patients. For instance, the initiated query may include a gene identifier that reflects a genomic mutation present on the patient's NGS sequencing report or other document which was initially image captured. A gene identifier may be a gene name, abbreviated gene name, or another label that indicates a specific gene. The cohort of similar patients may be then selected, at least in part, by identifying those patients in the database of aggregate patient information with the same genomic mutation. For example, if a patient's next-generation sequencing report indicates that the patient has a BRAF mutation, the database of aggregate patient information may be queried to identify all patients in the database whose records indicate they also have a BRAF mutation.

The medical information of the cohort of similar patients, or summary analysis thereof, may then be provided to a report generator for processing to identify trends of the patients' case histories during diagnosis and treatment and generate a cohort report. The cohort report may be displayed to the physician, for instance on a screen of the mobile device 4010.

As seen in FIGS. 174-176, the application may display the cohort report of summarized medical information, which that may help the physician make a treatment recommendation to the patient. When the summarized medical information supplements the information on the initial report, it provides new information to the physician, not present in the initial report, which can help the physician make a more informed treatment decision that may result in improvements to the patient's care, such as improved patient outcomes and greater value of care. FIG. 174 depicts a first cohort report 4182 including summarized medical information about the cohort. The summarized medical information includes one or more treatment regimens 4184 administered to patients in the cohort, along with relevant response data 4186 for each regimen. FIG. 175 depicts a second cohort report 4192 including the same treatment regimens 4184 as in the first cohort report 4182, this time with summarized medical information including relevant adverse event data 4194 for each regimen. FIG. 176 depicts a third cohort report 4196 depicting summarized medical information in the form of potential clinical trial matches 4198 for the patient. Each of these cohort reports are discussed in greater detail below. It should be understood that the types of summarized medical information detailed in FIGS. 174-176 are exemplary, and other types of summarized medical information of the cohort may be presented to the clinician, such as immunotherapy results, radiology imaging results (for instance, the average progression of tumor size in patients in the cohort), pathology imaging results, other imaging results, outcomes information (such as survival information), medical billing information (for instance, the cost of care for patients in the cohort), etc.

After data has been validated by a user (a clinical data abstractor, nurse, physician, etc., that has ensured that a patient's information has been accurately extracted from the electronic document capture of one or more patient reports), the extracted patient information may be stored in a common and structured data format either on a mobile device or in the cloud. An example of a structured data format includes FHIR, OMOP and/or other priority data models that support the representation of numerous attributes (such as demographics, diagnosis, treatments and outcomes, genetic testing, assessments and labs, etc.). This structured data may then be shared back with a health system's EMR or EHR as part of a patient's record or with certain third party applications that support the ingestion of this type of data (such as Apple's HealthKit, ResearchKit, CareKit, or internal proprietary format for each database, etc.). More than one database may receive the structured data or a relevant portion thereof. For example, a patient cohort database may receive all of the patient information while a genetic database may only receive the genes expressed by the patient, the diagnosis of the patient, and/or other patient information also included in the genetic database. The structured data may also be provided to a master patient index which may identify if the patient already has entries from prior interaction with the database through either the application or another partnered institution. The new information may be associated with the already existing patient data or if no matching patient is found a new patient may be added. Other exemplary databases include variant databases to store genetic variants, or clinical trial management systems and databases which track patients who are undergoing treatment as part of a given clinical trial. A notification may be provided to the user spanning multiple different delivery mechanisms including a direct push notification to their mobile device, an SMS or text message sent to their mobile device, an in-application notification as part of the application user interface and/or via an accompanying email that may be sent to any associated email address corresponding to their valid user profile. An analytics module may be present and connected to any of the above databases. The analytic module may be the same as described in U.S. Provisional Application No. 62/746,997, incorporated by reference in its entirety, including the analytical tool that enables the oncologist to explore prior treatment responses of patients that have the same type of cancer as the patient that the oncologist is planning treatment for in light of similarities in molecular data between the patients. Furthermore, the cohort analytics identifies different cancer state filters to be applied to the system database thereby changing the set of patients for which the system presents treatment efficacy data to explore effects of different factors on efficacy to lead to new treatment insights like factor-treatment-efficacy relationships. To further the pursuit of new cancer state-treatment-efficacy exploration and research, in at least some embodiments it is contemplated that system processors may be programmed to continually and automatically perform efficacy studies on data sets in an attempt to identify statistically meaningful state factor-treatment-efficacy insights. These insights can be confirmed by researchers or oncologists and used thereafter to suggest treatments to oncologists for specific cancer states. Trends, outliers, insights, and other metrics may be analyzed and stored for later use. Additionally, metrics may include pathogenicity of variants, genomic phenotypes, organoid response to treatment in a laboratory for efficacy calculations, radiomic and pathomic features from an imaging lab, tumor mutation burden, microsatellite instability status, immunological target expression, resistance risks, immune system infiltration, PD-LI expressions, as well as any trends, outcomes, and insights that may be made between them. These metrics, and more, may be provided to the cohort report below for inclusion as additional data. Additional data may be include general NGS medical information or field specific NGS medical information such as oncological NGS medical information for cancer patients. Oncological NGS medical information may include a diagnosis of cancer, metastasis, or other diagnosis, types of treatments including medications and therapies, duration and dosing of treatments, and for tumors, the tumor and/or patients non-tumor molecular structure, genes, variants, fusions, copy number counts. General NGS medical information may include the "normal" genome of a patient molecular structure, genes, variants, fusions, or copy number counts. General NGS medical information may include any details which may be shared between NGS reports for differing illness, disease, and cancers.

FIGS. 174-176 detail different embodiments of the cohort report. FIG. 174 is one aspect of the cohort report and may feature particular treatment regimens 4182 which have been prescribed to similar patients, how frequently the treatment occurs in the subset of similar patients (the "incidence"), and a visual or numerical representation of the patient responses to the treatment 4186. Treatments may include singular drugs, therapies, or combinations of drugs and/or therapies. For example, while FIG. 174 displays five separate regimens comprising singular drugs (vemurafenib, perifosine, miltefosine, erlotinib, and rapamycin), in another instance, a regimen may comprise a combination of two or more of those drugs, or one of those drugs plus radiation or another therapy. In certain embodiments, combinations of drugs and/or therapies may be difficult to display in one line. In such cases, the combination may be terminated early with an ellipsis and the user may expand the combination by selecting it in the application. Upon selection, the corresponding entry may resize to display the full combination. The display of one or more of FIGS. 174-176 may include an information icon 4188 next to one or more of the treatment regimens, the selection of which may launch a web browser on the mobile device 4012 or another screen in the application 4010 to provide more information about the selected regimen. Alternatively, the text of each regimen or the field or row in which the regimen is shown may include an embedded hyperlink, accessible, such as by pressing and holding on the text of the regimen, hovering over the regimen using the cursor discussed above, etc. In either case, selection of the information icon or selecting the field may launch a drop down, a hover menu, a web browser or another screen in the application to provide further information about the selected regimen. For example, FIG. 174 includes a drop down 4190 providing the user with various options related to a selected regimen ("Rapamycin"), including the ability to access select reference materials, to search one or more databases of information (such as PubMed), and/or to edit one or more fields of the captured document (for example, to correct an error if the physician notices during reading the report that treatments shown correspond to the wrong patient information).

The cohort report may contain all resulting treatment regimens from the subset of similar patients, the treatments that have a statistically significant incidence, or all treatments which meet at least a minimum threshold of patients. Such threshold may be based off a predetermined number of patients, or may be based upon the number of patients in each of a plurality of treatment regimens, such that only regimens which have a certain percentage of the patients of the whole cohort are included, for example, by summing the number of patients in the treatment regimens and only displaying treatments with at least 5% or higher of the total patients. The lower (5%) and upper bounds of this threshold may be determined based off of the number of regimens included in the report and their incidence rate as well. In another example, if several regimens have patients by the tens or hundreds, a regimen with only five patients may be excluded from display. The values may use the average, the mean, the average of the mean, or other calculations to identify where the lower and upper threshold cutoffs should be placed. An exemplary numerical description may quantify the number of patients who received the treatment, the number of patients who responded favorably to the treatment, the number of patients who had no change from the treatment, and/or the number of patients who responded unfavorably to the treatment, identified as "Complete Response (CD), Partial Response (PR), Stable Disease (SD), Progressive Disease (PD)", respectively. In an exemplary visual representation, a color coded graph 4186 may be provided to the user to visually represent the same features as the numerical description outlined above. For example, patients who responded favorably may be color coded green and given a distribution of the graphical representation directly proportional to the percentage and patients who responded unfavorably may be color coded red and given a distribution of the graphical representation directly proportional to the percentage.

FIG. 175 is another aspect of the cohort report, with similar layout and information provided as FIG. 174. In FIG. 175, however, the application may provide a therapy response summary conveying adverse event information 4194 for each of the regimens 4184 identified in FIG. 174. In addition to displaying similar patients' responses to treatment regimens the system may return the incidence of adverse events incurred by similar patients respective to those treatments. These adverse events may be categorized by the type of event (such as neutropenia, nausea, headache, hallucinations, fever, fatigue, depression, cardiac disorders, etc.) and/or by the grade of its severity. (Mild, Moderate, Severe, Life-Threatening, Death). There are thousands of classified adverse events, and the application may be configured to display events based on their respective grade of severity, rather than a name-by-name basis. In another embodiment, the user may select the field of the medication to see the adverse events that contributed to the grade of severity displayed alongside the medication along with the number of incidences and the grade of severity associated with the adverse event.

FIG. 176 is still another aspect of the cohort report which may specialize on clinical trials. Based upon the key health information extracted from the electronic document capture, clinical trials that are available to the patient may be identified and displayed. For each clinical trial, details 4198 associated with the name of the clinical trial, geographic location of the facilities administering the trial, treatments associated with the trial, inclusion/exclusion criteria for patients who may participate in the trial, and other relevant information may be included in the report. Additional information may be extracted from the electronic health or medical records associated with the patient when the query is processed that further allow the inclusion and exclusion criteria of a clinical trial to be evaluated. For example, the electronic document capture may be missing key health information pertaining to the patient's medical history, such as medical history relating to whether the patient has taken a drug as part of treatment or has undergone chemotherapy, and the patient's medical history may be referenced to determine eligibility for clinical trial inclusion and exclusion criteria.

Swiping between each report may be performed by pressing the tab associated with the report from the user interface or through gesture controls. For example, a user may swipe the current page to the left or right to swap between respective reports.

The application as described above may be useful in multiple aspects of medical care. For example, the following use cases may be representative of the various ways in which the application may be employed, although it will be understood that the application should not be limited solely to the following use cases.

1: Report Supplementing

Turning to FIG. 177, one method 4200 for implementing the present system is depicted. At step 4202, the mobile device may be used to capture a document such as a NGS report, the document including medical information such as sequencing information about a patient. At step 4204, an entity linking engine may be used to extract at least some of that information, such as using the techniques described above. At step 4206, that information then may be provided to one or more data repositories, such as in a structured format.

Information from the electronic document capture may be supplemented in the cohort report with additional supplemented structured data. For example, a genetic sequencing report such as the report of FIG. 161 may identify a genetic mutation that is present in the patient's DNA and may further list treatments available for the genetic mutation. A new treatment may become available after the report is generated but before the physician meets with the patient to discuss the report results. Notification of that treatment may be received, as at step 4208. At step 4210, the above-described mobile application may supplement the report information and alert the physician to the new treatment for the identified genetic mutation that may have been otherwise overlooked. Additionally, the report may be supplemented by providing access, via hyperlinks or otherwise, to recent articles, publications, or other relevant information that may aid the physician by providing context, background information, or access to recent publications that address details of the report, the other articles, publications, or other relevant information being structured using similar techniques for convenient retrieval. Other medical topics of interest may also be referenced, such as new cell-based therapies (such as immuno, viral, or vector delivery methods) available or new therapies available (such as checkpoint blockades for accelerating immune response, cancer vaccines, etc.). Furthermore, a physician may make treatment decisions and treat the patient according to treatments identified as having a likelihood of success across other patients having similar molecular and clinical features to the patient. Additionally, a physician may identify that a therapy has not had success for the patient and may desire to replace the unsuccessful therapy with one of the report supplemented therapies which is expected to have a likelihood of success. In order to receive preauthorization from or to validate a claim with the patient's insurance (e.g., by indicating the medical necessity of the treatment), the physician may reference the supplementary information, such as the progression free survival rate of similar patients or a publication recently linked on PubMed in their requests to the insurance company. After receiving such pre-authorization or medical necessity indication, the physician then may administer the therapy or other treatment.

2: Training Set Inclusion

The mobile application described above may also be useful when paired with the existing clinical abstraction training sets for machine learning algorithms driving the abstraction process. Thus, turning to FIG. 178, another method 4300 for implementing the present system is depicted. At step 4302, the mobile device may be used to capture a document such as a NGS report, the document including medical information such as sequencing information about a patient. At step 4304, an entity linking engine may be used to extract at least some of that information, such as using the techniques described above. At step 4306, that information then may be provided to one or more data repositories, such as in a structured format. At step 4308, an active learning element of the machine learning engine may identify a section of the electronic document capture for which the algorithm did not have a high confidence of the predicted output. The electronic document capture may then be labeled as a training input and added to a respective training data set, as at step 4310. The improved training set may then be used to train a machine learning algorithm to generate improved results. Many document types (such as genetic sequencing reports) include relevant attributes such as genes, variants, etc., that would normally be abstracted physically by hand may then be automatically extracted according to these characteristics and paired with additional clinical and phenotypic characteristics (such as demographics, diagnosis, assessments, labs, etc.).

3: Database Comprehension Validation

Turning to FIG. 179, another method 4400 for implementing the present system is depicted. At step 4402, the mobile device may be used to capture a document such as a NGS report, the document including medical information such as sequencing information about a patient. At step 4404, an entity linking engine may be used to extract at least some of that information, such as using the techniques described above. At step 4406, that information then may be provided to one or more data repositories, such as in a structured format. Further, the disclosure may also aid in the ability to fully assess the quality of a given structured clinical record by comparing extracted information against other structured data, as at step 4408. For instance, the mobile application may indicate the presence (or absence) of various molecular biomarkers (such as TP53) that indicate whether other various and/or observed clinical attributes are appropriate. For example, molecular biomarkers like KRAS may be present in only a certain subset of cancer types (such as pancreatic cancer). This capability can improve data integrity by identifying unusual and/or incorrect structured clinical data that may have been abstracted and/or ingested directly from third parties via various integration mechanisms, as at step 4410, and by identifying and highlighting discrepancies between the extracted data and other relevant data in the system separate from that extracted data, as at step 4412

4: Radiology Report Supplementing

Turning to FIG. 180, still another method 4500 for implementing the present system is depicted. At step 4502, the mobile device may be used to capture a document such as a NGS report, the document including medical information such as sequencing information about a patient. At step 4504, an entity linking engine may be used to extract at least some of that information, such as using the techniques described above. At step 4506, that information then may be provided to one or more data repositories, such as in a structured format. The extracted data then may also be useful when attempting to determine and/or unite clinical and/or phenotypic attributes with observations from pathological and/or radiological imagery, such that the system may link the extracted data, via its structuring, with structured clinical patient data received from pathology reports, imaging features, and/or other imaging sources, as at step 4508. Often, the ability to obtain more context about a given patient and/or diagnosis is crucial in determining whether imaging is of a sufficient quality for computing radiomic attributes (such as surface area, volume, etc.) as part of contouring efforts. Further, clinical attributes obtained via the disclosure can help to unify disparate sources of data (such as molecular characteristics found on a genetic sequencing report, structured clinical data obtained from pathology reports, imaging features and characteristics extracted from imaging). As a result, radiomic and imaging specific machine learning algorithms can become more robust through the availability of this additional data, such as by using the data linked in step 4508 as inputs to those algorithms at step 4510. Furthermore, the imaging itself may or may not come with diagnosis and/or phenotypic attributes included so the linkage between the imaging data and the related information that can be extracted from source documents via the invention can help resolve gaps in data.

5: Knowledge Database Curation and Additions

Turning to FIG. 181, yet another method 4600 for implementing the present system is depicted. At step 4602, the mobile device may be used to capture a document such as a NGS report, the document including medical information such as sequencing information about a patient. At step 4604, an entity linking engine may be used to extract at least some of that information, such as using the techniques described above. At step 4606, that information then may be provided to one or more data repositories, such as in a structured format. In addition to this patient-specific data, the system also may process journal articles from medical publications by similarly extracting structured medical information from those sources at step 4608 and then adding that structured information to the data repository at step 4610 to curate a knowledge database based upon features of each report which are relevant to each database specialization. For example, a knowledge database for cancer treatments may desire to receive new articles which are relevant by filtering newly published articles to find articles which are oncology and treatment focused which may be added into the knowledge database along with key words, phrases, and other indexable features. The new entry may then be reviewed for curation or automatically entered into the knowledge database.

6: Facility-Based Records Sync for Facilities that do not Easily Share Data

The disclosure above may also serve as a means to easily integrate EMR systems which are not synced. For example, turning to FIG. 182, yet another method 4700 for implementing the present system is depicted. At step 4702, the mobile device may be used to capture a document such as a NGS report, the document including medical information such as sequencing information about a patient. At step 4704, an entity linking engine may be used to extract at least some of that information, such as using the techniques described above. At step 4706, that information then may be provided to one or more data repositories, such as in a structured format. A patient receiving treatment at an institution which is geographically distance from their home may desire to report to a local institution for testing and lab results. The local institution may not sync their EMR with the primary institution and only provide a document with the testing or lab reports to the primary institution. The instant disclosure may allow the primary institution to sync the report with their EMR by quickly scanning the report once received, as at step 4708.

7. Adding to De-Identified Data Sets

A physician may wish to take the information provided on a lab report and ingest it into a data platform that is unconnected from the provider of the lab report. Thus, turning to FIG. 183, yet another method 4800 for implementing the present system is depicted. At step 4802, the mobile device may be used to capture a document such as a NGS report, the document including medical information such as sequencing information about a patient. At step 4804, an entity linking engine may be used to extract at least some of that information, such as using the techniques described above. At step 4806, that information then may be provided to one or more data repositories, such as in a structured format. At step 4808, the data platform may allow the physician to view the patient information from the report in the context of a larger data set of "like" patients, whom may have received NGS from different clinical laboratories.

8. Tumor Board

Turning to FIG. 184, yet another method 4900 for implementing the present system is depicted. At step 4902, the mobile device may be used to capture a document such as a NGS report, the document including medical information such as sequencing information about a patient. At step 4904, an entity linking engine may be used to extract at least some of that information, such as using the techniques described above. At step 4906, that information then may be provided to one or more data repositories, such as in a structured format. At that point, a physician may wish to take the information provided on a lab report and ingest it into a data platform that provides tumor board functionality to the physician, as at step 4908. An exemplary tumor board platform may provide functionality to permit physicians to review the cases of multiple patients, one at a time, and review patient characteristics (such as age, molecular profile, clinical profile, gender, race, and so forth) to determine the most appropriate treatment for the patient. The tumor board platform may permit multiple clinicians to sit in a single location, such as a room, and view the clinical information about each patient, as at step 4910. Or, the platform may be virtual, allowing multiple clinicians to sit in disparate locations while simultaneously reviewing a patient's information, as at step 4912.

9. Alternative Clinical Decision Support

Different clinical laboratories use different bioinformatics platforms, and calling a variant on a gene does not necessarily mean that a clinical laboratory will suggest the same treatment as another clinical lab that calls the same variant. Thus, turning to FIG. 185, still another method 5000 for implementing the present system is depicted. At step 5002, the mobile device may be used to capture a document such as a NGS report, the document including medical information such as sequencing information about a patient, as well as one or more of a type of treatment, dosage of treatment, duration of treatment, immunology markers, potential clinical trial(s) available to the patient, etc. Exemplary immunology markers include, but are not limited to, PD-1 expression, other checkpoint inhibitor indicators (such as CTLA-4), immune cell infiltration, immunohistochemistry (IHC) indicators, tumor infiltrating lymphocyte indicators, monoclonal antibody indicators, vaccine/adjuvant indicators such as tumor cell vaccines, antigen vaccines, dendritic cell vaccines, vector-based vaccines, oncolytic viruses, CAR T-cell therapy, etc. At step 5004, an entity linking engine may be used to extract at least some of that information, such as using the techniques described above. At step 5006, that information then may be provided to one or more data repositories, such as in a structured format, the data repositories including the relevant types of treatment, dosages of treatment, durations of treatment, immunology markers, potential clinical trial(s) available to the patient, etc., for patients with similar sequencing information, where the information presented in the NGS report may be different from the relevant counterparts stored in the data repositories. At step 5008, the system may display a subset of the extracted data, such as the patient's identified mutations and variants. By permitting capture of clinical variants, a physician may be able to get a "second opinion" on the type of treatment, dosage of treatment, duration of treatment, immunology markers, and so forth. Likewise, at step 5010, the system may display one or more clinical trials potentially available to the patient, as discussed above. In this manner, by comparing and displaying the reported information against their potentially available counterparts, the physician may get a "second opinion" on clinical trials that may be appropriate for the patient.

As seen in FIG. 186, a system 5100 may include a server 5102 including or in communication with a first database 5102 and a second database 5104. In one aspect, the first database 5102 may include patient-specific information, such as elements of each patient's EHR or EMR data. The second database 5104 may be a knowledge-database that includes patient-agnostic medical information, such as genetic variants and their related mutation effects for observed and classified variants for each gene, medications or other treatments relevant to the genetic variants, articles relevant to those variants, etc. The second database 5104 further may include mask or template-based information to enable the system to more efficiently extract information from one or more template-style documents. It will be appreciated that the first and second databases may be combined into a single database or, alternatively, that one or both of those databases individually may actually be a plurality of different databases, such as to assist in data segregation or improved processing by optimizing database calls for the requested different types of data.

Staying with FIG. 186 the server 5102 may be in communication with one or more mobile devices, such as smartphones 5108A, 5108B, tablet devices 5108C, 5108D, and laptop or other computing devices 5108E. In one aspect, the server 5102 may be connected directly to one or more of the devices, such as via an Ethernet or other suitable connection. Alternatively, the server 5102 may be connected wirelessly to one or more of the devices, such as via WiFi or another wireless connection, as would be appreciated by those of ordinary skill in the relevant art. As discussed herein, one or more analytical actions described herein may be performed by the mobile devices. Additionally or alternatively, one or more actions may be performed by the server, such as the mobile devices may be used to create new patient records and capture electronic images of documents relating to patients, while the server may be employed to perform the OCR and/or other analytics described above on the captured documents.

VI. Artificial Intelligence and Machine Learning

Referring now to FIG. 187A, one exemplary AI system that is consistent with at least some aspects of the present disclosure is represented at 5200. AI system 5200 include several neural network or other computing modules 5210, 5212, 5214, 5216, Nth 5219, each of which is trained to, given specific inputs, generate information indicating likelihood of a specific medical condition, outcome, event, etc. For instance, a PD-L1 trained model is programmed to predict occurrence of PD-L1 protein from a set of patient H&E slides by presenting a set of slides as input as well as occurrence or not of the PD-L1 protein as output during a network training process. Then, when a new patient's H&E slide set is fed into the trained module, the module predicts occurrence of PD-L1 protein expression within the patient. The other modules are trained in a similar fashion to predict other events or conditions within patients. Software that provides the modules may be stored in a database 5220 either locally or at a remote server run by a third party service provider (e.g., an A1 provider). Many different inputs and outputs are contemplated for training purposes.

Referring still to FIG. 187A, a clinical decision support system 5218 receives output from the prediction modules, uses the output to predict current states and/or future patient outcomes as well as to identify suitable therapies given system predictions, locations for receiving treatments and physicians that have expertise in the predicted cancer states and relevant therapies, all of which are stored in a prediction database 5224.

Referring to FIG. 187B, an exemplary patient order processing pipeline 5300 is illustrated that is consistent with at least some aspects of the present disclosure. The patient order processing pipeline 5300 may facilitate processing flow for a patient order from inception, NGS and variant calling, report processing and generation, through reporting the results of NGS to an ordering physician. An orchestration module or software such as orchestrator 5304 may guide the processing of each of the blocks and elements contained in the pipeline 5300 to ensure efficient processing with little downtime in between stages and no missed steps by providing signals to each of NGS lab pipeline 5308, bioinformatics pipeline 5310, and report generation pipeline 5312 directing current states and processing in each.

A patient may be received, such as from a sequencing order received from a physician, and sent to patient intake 5302, where the patient's clinical data may be entered and information detailing the type of sequencing and reporting that the physician is requesting may be stored in a system. The order as entered into the system may provide the orchestrator 5304 with a series of steps which are to be performed during the processing of the patient sequencing order. The process from which this may be performed may then rely on establishing a sample of the patients DNA. Herein, a sample may be sent to block 5306 when the sample is received at the laboratory performing the sequencing.

For cancer treatment, this may be a cancer sample, such as a sample of tumor tissue, and a sample of the patient's saliva or blood. For treatments of other diseases, this may be a sample of saliva or blood only. For cancer treatments, a sample of a tumor may originate from a biopsy (such as a needle aspiration or physical site extraction). Biopsies are inherently messy affairs where a biopsy may generally acquire an indeterminate proportion of cells, such as healthy cells and tumor cells which are sequenced together.

An NGS Lab Pipeline 5308 may receive the samples and process the samples for sequencing. A pre-processing stage 5314 may include the laboratory identifying each and every sample received for a particular specimen, generating a label for the samples, the slides of those samples, and other accessioning tasks to enable the tracking of the samples through the pipeline 5300.

During preprocessing, some samples may be identified as tumor samples, a pathology stage 5316 may be activated to identify the type of cells in the sample and a proportion of these types of cells to each other. During the pathology stage 5316, a pathologist may review slides of cells extracted from the sample. In another embodiment, a machine learning algorithm which has been trained on the pathology results from similar types of slides may be applied to new slides to either aid the pathologist in making a determination or to replace the pathologist and provide a determination without the oversight of the pathologist. In alternative embodiments, the samples received at stage 5306 may include slides acquired and prepared by the ordering physician.

When preprocessing identifies other samples as non-tumor samples such as a blood or saliva sample for germline sequencing, the pathology stage 5316 may be bypassed all together as the steps of identifying the type of cells and the proportion of those cells on the slide are not necessary. An assumption that non-tumor cells samples are "pure" non-tumor may be made.

An isolation stage 5318 may receive a sample of cells from either the tumor or non-tumor sample and isolate either the DNA or the RNA from the sample. DNA may be isolated by destroying any RNA present in the sample and, similarly, RNA may be isolated by destroying any DNA present in the sample.

An amplification stage 5320 may receive the isolated DNA or RNA and amplify the respective sample such that the provide RNA or DNA is copied over and over to improve the potential read results that may be made by the sequencer. Polymerase chain reaction (PCR) is a method may be employed to make many copies of a specific DNA/RNA segment. Using PCR, a single copy (or more) of a DNA sequence is linearly or exponentially amplified to generate thousands to millions of more copies of that particular DNA segment.

Sequencing may be performed on the amplified samples at the sequencing stage 5322, a NGS sequencing, such as illumina's iSeq, MiniSeq, MiSeq, or NextSeq Systems; Ion PGM, Proton, or GeneStudio Systems; or comparable NGS systems from Pacific Biosciences, Roche 454, or SOLiD may be used. The sequencing stage may output sequencing data containing reads from probes such as in a raw data FASTQ format, raw data FASTA format, a Binary Alignment Map format (BAM), Sequence Alignment Map format (SAM) or other raw or aligned file formats. In one example, the SAM or BAM files may list all genetic sequences identified in a sample, the count for each sequence, and the location of each sequence read with respect the complete genome. In one example, a second set of SAM or BAM files may be included for listing all genetic sequences identified in a normal, non-cancer sample collected from the same patient as the cancer sample. The sequencing stage may further output an index file for each SAM or BAM file, indicating the file location of each read within the SAM or BAM file. In one example, an index file for a BAM file contains a table or list of all reads found in the BAM file and the file location of each read within the BAM file. In one example in the index file, each read may be labeled by a read ID (for example, read A, read B, etc. or read 1, read 2, etc.), by the sequence of the read, or by the chromosome and/or nucleotide position within the chromosome of the sequence of the read. The file location of the read may be listed as a line number within the BAM file.

A bioinformatics pipeline 5310 may receive the sequencing results generated from sequencing stage 5322 or results translated from a raw to an aligned format at sequenced data stage 5324. In another embodiment, sequenced data stage 5324 may receive sequencing results in a raw format and perform filtering and/or alignment to generate an aligned format. Filtering may include detecting spurious or incorrect reads and removing them from the dataset. The bioinformatics pipeline 5310 may access resource files such as one or more pool files containing reads from one or many normal samples.

Resource files may include a published reference genome such as human reference genome 19 (hg19) or human reference genome 38 (hg38), etc. Resource files may further include a blacklist file containing a list of blacklist regions and/or genes in the genome for which CNV calculation is less likely to be accurate or a whitelist file containing a list of whitelist regions and/or genes in the genome which should be incorporated into the CNV analysis. Any decreased accuracy of CNV calculation for blacklisted regions may be due to the genetic analysis technique used to identify genetic sequences in a sample. For example, if the genetic analysis technique requires genetic probes to bind to nucleic acid molecules isolated and/or copied from a sample, the probes binding to a blacklist region may bind in an inconsistent manner. A blacklist region may bind to probes less frequently than a typical region or may be saturated with bound probes. Another reference file may include a target file for enumerating the list of target genes, variants, or regions. The bioinformatics pipeline 5310 may incorporate the enumerated list of targets and implement the pipeline staged for one or more targets in the list of targets.

A variant calling stage may identify variants in the sequencing data of 5324 by identifying reads for each variant based upon variant location, length, and/or depth. Variants may be portions of genetic sequences in the cancer sample which do not exist in the normal sample, and/or which do not exist in a reference genome or database of normal sequences. Variant information for each variant may include the variant's location, the normal nucleotide sequence seen in the reference genome at that position, and the variant nucleotide sequence seen in the sample. The variant location may include a chromosome number and a nucleotide position number to differentiate nucleotide positions that are located in the same chromosome. Reads may be compared to a reference genome to identify normal reads and/or variants. The number of reads for each variant may be counted, and the aggregate count for all identified variants may be stored in a Variant Call Format (VCF) or comma-separated values (CSV) that specifies the format of a text file used in bioinformatics for storing gene sequence variations. By storing the variant calls in VCF only the variations need to be stored and a reference genome may be utilized to identify each variant of the VCF.

A VCF or comparable variant calling output may be provided to one or more stages 5328. Stages 5328 may provide specialized testing for one or more of tumor mutational burden (TMB), microsatellite instability (MSI), gene fusions, single nucleotide variants (SNV) and somatic/indel mutations, and CNV detections. Each of these stages may receive a VCF file and perform analytics of the variants therein to identify the respective TMB, MSI, gene fusion, SNV, Indel, or CNV states and generate output files for report parsing, interpretation, and generation.

Validation may be performed at 5330, validation may be manual review by a variant scientist, or similarly educated and trained personnel or be handled in an automatic fashion. Automation may be performed using a rule set or a machine learning algorithm.

A report generation pipeline 5312 may receive the output files from each of stages 5328 at report stages 5332. Reports 5332 may then be provided to report analytics module 5334 for generating analysis of the respective reports against databases of pharmacogenomic and cohort effects. For example, a cohort of patients may be maintained comprising the clinical and molecular medical information of all patients whose DNA or RNA have been sequenced. This cohort may be filtered according to common features with the instant patient (such as demographic, clinical, or molecular features) and trends within the cohort may be analyzed to generate predictions for the instant patient's pharmacogenomic response to medications/treatments or type of cancer or disease state determination. These predictions may be summarized for inclusion in a report, such as report 5336. Furthermore, for each of the reports 5332, additional databases 5340 may be referenced to identify insights that may be ascertained from the patient's TMB, MSI, gene fusion, SNV, Indel, or CNV states. These additional references databases 5340 may be stored in many different formats depending on the institution that curated the database.

It may be necessary to maintain a translation process 5338 which may recognize key terms from each of reports 5332 and translate these key terms to a format which may be recognized in one or more of the reference databases 5340. A CNV in report 5336, may be referenced according to a table of variants. There are several resources for common gene and variant identifiers, such as the Human Genome Organisation (HUGO) Gene Nomenclature Committee (HGNC) or the National Center for Biotechnology Information (NCBI) with the Entrez list. The HGNC approves a unique and meaningful name for every known human gene. Such a table may include, for each CNV: an identifier to an Entrez Gene or an HGNC Gene or in which the variant was detected; the gene symbol of the gene in which the variant was detected; a copy state indicator of a copy number gain, copy number loss, or conflict; an message-digest checksum (such as MD5) of the values for a string, such as <entrezId><state> or <hgncId><state>, to serve as the primary key of the table; copy number region aggregations that determined the copy state; one or more indicators of a loss of function (LOF), gain of function (GOF), amplification (AMP), or gene fusion (FUS); a flag indicating whether the variant is therapeutically actionable based on known references; an overall reportability classification determined for the CNV such as "Reportable", "Not Reportable", or "Conflicting Evidence"; a unique identifier of the scientist who confirmed the classification of the CNV; a timestamp of when the scientist made the confirmation; and the classification of relevance for the CNV as being in a gene of therapeutic relevance such as "True", "False", or "Indeterminate."

An Entrez Gene Id (GeneID) is a representation of gene-specific information at the. The information conveyed by establishing the relationship between sequence and a GeneID is used by many NCBI resources. For example, the names associated with GeneIDs are used in resource/reference databases HomoloGene, UniGene and RefSeqs. These relationships may further the capabilities of translation 5338 by providing additional reference points between these and other external databases. A loss of function mutation (LOF above), also called inactivating mutations, is the result in the gene product having less or no function whereas the GOF is the opposite result where function is gained due to the gene mutation. A classification of a CNV as "Reportable" means that the CNV has been identified in one or more reference databases as influencing the tumor cancer characterization, disease state, or pharmacogenomics, "Not Reportable" means that the CNV has not been identified as such, and "Conflicting Evidence" means that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV.

For example, a variant may be identified in a CNV report as having a count twenty times that of normal. However, a database in the reference database may not recognize the variant as encoded in the CNV report 5332 and the translation process .B.80 may translate the variant representation from that of the report to one which is recognized by the database to link the report with meaningful analytic information from the database. Report analytics module 5334 may process each of the identified variant calls, TMB, MSI, gene fusion, SNV, Indel, or CNV states through the reference databases 5340 to ascertain report indicia worth reporting to the ordering physician and summarize the report indicia in report .B.90 which is to be provided to the ordering physician.

An orchestrator 5302 may coordinate the timing for each of the above identified steps. For example, NGS pipeline 5308 may not be initiated until patient intake 5302 has been successfully completed, bioinformatics pipeline 5310 may not be initiated until sequencing 5322 has successfully completed, and each of the report analytics for reports 5332 may be started in turn as specialized testing stages each complete. In addition, a notification to the ordering physician that report 5336 is available for view may not be generated until all of reports 5332 have each been successfully analyzed against the reference databases 5340 and the report is completely generated.

With healthcare testing and decision making, it is important that all steps along a texting, diagnosing, prescription and administration of treatments be accurate and correct in order to achieve the best possible outcome for a patient, for this reason, in many cases medical entities (e.g., hospitals, research institutions, etc.) require manual confirmation of almost every task outcome within a patient workflow. While manual confirmation tends to be accurate, it is time consuming and can bog down patient processing appreciably. The slowing effect of manual processes is exacerbated as more and more steps are added to a patient processing system in order to support optimized personal diagnosis and treatments.

For this reason, in at least some disclosed embodiments, the system include a process whereby a processor checks outcomes of various process tasks and, in effect, auto-passes the results so that manual review is not needed when the outcomes are expected or within some expected range of acceptable parameters. Then, if an outcome is not expected or within an expected parameter range, a manual review process is initiated. Here, in at least some cases the expected outcomes may be specified by a system administrator during a system commissioning or maintenance procedure while in other cases, the system may be programmed to identify expected outcomes or ranges from physician use of the system and then either automatically initiate use of those outcomes in new auto-pass rules or suggest high confidence outcomes to be used to create new auto-pass rules.

Referring now to FIG. 187C, an exemplary auto-pass process 5250 that is consistent with at least some aspects of the present disclosure is illustrated. At block 5252 a new case is initiated with reception of a tumor sample in a lab. At decision block 5254, tumor quality is determined and, if the quality is poor, the process 5250 stops and a notification is provided to a lab technician to manually review at 5256. Where the tumor quality is not poor, at decision block 5258 tumor purity is checked to determine if the purity is greater than or equal to 30%. If tumor purity is less than 30% another automatic notification is generated initiating manual review of the tumor sample prior to proceeding. If tumor purity is greater than 30% the process auto-passes the manual review at 5260 and the process control moves to block 5262.

At block 5262, tumor purity difference (e.g., % cancer cells in a solid tumor sample) is compared to a <=30% threshold. Where the different is less than or equal to 30%, another manual review process is initiated at 5264, otherwise process 5264 is auto-passed and control moves on to block 5266. At block 5266, the system determines if the P/LP is in a whitelist (e.g., a list of genes in the genome which should be incorporated into an analysis) and if not, another manual review step occurs at 5258. Else step 5258 is auto-passed and control passes to block 5270.

Referring still to FIG. 187C, at block 5270, the system determines if a variant of uncertain significance (VUS) is identified and listed in a blocking database (e.g., database of curated mutations (DOCM), clinical interpretation of variants in cancer (CIVIC), etc.) and, if it is listed, a notification initiates a manual review at 5276. If no VUS is in the blocking database, control passes to decision block 5274 where the system determines if the cancer state detected is therapeutically actionable. If the state is not actionable, manual review 5278 is initiated. If the state is actionable, control auto-passes to block 5280 where the system determines if a missense variant (e.g., a genetic alteration in which a single base pair substitution alters the genetic code in a way that produces an amino acid that is different from the usual amino acid at a position) or an inframe Indel (e.g., insertion or deletion) that is less than 5aa, and where the conditions are not met, manual review 5282 is initiated, else the system auto-passes to block 5284. At block 5284 the system determines if the Missense or Indel is in a system database (e.g., CIVIC ROI, EXON ROI, Important Indels, COSMIC) and if it is then another manual review process 5286 is initiated, else control passes to block 5288.

At block 5288 the system determines if a CNV was detected and if so, again, a manual process 5290 is initiated. If no CNV is detected control passes to block 5292 where the system determines if any germline mutation has been detected and if so a manual review is imitated at 5294, else control passes to block 5296 where the case is auto-passed without a manual review. Thus, it is conceivable that in some cases the system may not initiated any manual review and may instead auto-pass the case through the entire process 5250.

The auto-pass process described with respect to FIG. 187C is a set, non-evolving process as illustrated. As described above, in other cases the process or at least portions of the process may evolve via machine learning techniques so that the more and more manual review steps are eliminated when appropriate. For instance, in a case where every one of twenty consecutive times a specific condition occurs an oncologist manually confirms that the FIG. 187C process should continue, the system may automatically learn that the next time the condition occurs, the manual review process should be skipped to reduce the manual review burden. In cases where an auto-pass step candidate is identified by the system, instead of automatically implementing the auto-pass step, the system may present that candidate to a system administrator who then has to confirm implementation prior thereto by the system.

Referring now to FIG. 188, an exemplary data collection and analysis system 5408 that is consistent with at least some aspects of the present disclosure is illustrated and includes a feature collection database 5405, an alteration module 5450, a structural variant classification module 5480, other databases including an all patient information database 5600, a knowledge database 5602 and a treatments & outcomes database 5604 and a Cohort interface tool 5610 that is described in greater detail in other parts of this disclosure. In at least some embodiments the bioinformatics pipeline generates and structurally stores all of the information (and more) shown within collection database 5405. Collection 5405 includes data associated with de-identified patients that may come from medical documents which are abstracted and curated, patient EMR/EHR, lab or imaging results, features curated from alteration module 5450, and/or features curated from classification module 5480.

Referring still to FIG. 188, in some cases any combination of the alterations in alteration module 5450 may be selected as inputs to structural variant (SV) classification module 5480 for engine training with one or more classifications as output. Results from SV classification can be visualized in a Cohort analysis for a specific patient. In addition, Cohort analysis may be performed across any of the features in collection 5405, all patient information in database 5600, the system knowledge database 5602, and/or the system treatment/outcomes database 5604 (such as from patients, organoids, or other sources). The similarities in the patient to the patients of the most representative cohort will decide some of the content for a patient report 5620 which goes to a physician and/or a tumor board 5630 to inform treatment decisions for the patient.

Referring still to FIG. 188, exemplary feature collection database 5405 includes the following information types. Genome module 5410—A feature collection associated with the DNA-derived information of a patient. These features may include raw sequencing results, genes, mutations, variant calls, and variant characterizations. Genomic information from a patient's normal sample is stored as germline 5414 and genomic information from a patient's tumor sample are stored as somatic 5412.

Transcriptome module 5416—A feature collection 5418 associated with the RNA-derived information of a patient. These features may include raw sequencing results, transcriptome expressions, genes, mutations, variant calls, and variant characterizations.

Clinical module 5500—A feature collection associated with information derived from clinical records of a patient and records from family members of the patient. These may be abstracted 5502 from unstructured clinical documents, EMR, HER 5504, or other sources of patient history. Information may include patient symptoms, diagnoses, treatments, responses to treatments, laboratory testing results, medical history, geographic locations of each, demographics, or other features of the patient which may be found in the patient's medical record.

Imaging module 5444—A feature collection associated with information derived from imaging records of a patient. Imaging records may include H&E slides, IHC slides 5446, radiology images, PDL1 5448, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers, tumor budding/size/aggressiveness/metastasis/immune state, chromatin morphology, and other characteristics of cells/tissues/tumors for prognostic predictions.

Epigenome module 5420—A feature collection associated with information derived from DNA modifications which are not changes to the DNA sequence which regulate the gene expression. These modifications are frequently the result of environmental factors based on what the patient may breathe, eat, or drink. These features may include DNA methylation 5422, histone modification, or other factors which deactivate a gene or cause alterations to gene function without altering the sequence of the nucleotides in the gene.

Microbiome module 5424—A feature collection associated with information derived from the viruses and bacteria of a patient. These features may include viral infections 5426 which may affect treatment and diagnosis of certain illnesses, the bacteria present in the patient's gastrointestinal tract which may affect the efficacy of medicines ingested by the patient and immunology 5428.

Proteome module 5430—A feature collection associated with information derived from the proteins 5432 produced in the patient. These features may include protein composition, structure, and activity; when and where proteins are expressed; rates of protein production, degradation, and steady-state abundance; how proteins are modified (for example, post-translational modifications (PTMs) such as phosphorylation); the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Omics module(s) 5434—A feature collection associated with all the different field of omics, including 5438:

(i) Cognitive genomics: Study of the changes in cognitive processes associated with genetic profiles.

(ii) Comparative genomics: Study of the relationship of genome structure and function across different biological species or strains.

(iii) Functional genomics: Describes gene and protein functions and interactions (often uses transcriptomics).

(iv) Interactomics: study relating to large-scale analyses of gene-gene, protein-protein, or protein-ligand interactions.

(v) Metagenomics: Study of metagenomes, i.e., genetic material recovered directly from environmental samples.

(vi) Neurogenomics: Study of genetic influences on the development and function of the nervous system.

(vii) Pangenomics: Study of the entire collection of gene families found within a given species.

(viii) Personal genomics: Branch of genomics concerned with the sequencing and analysis of the genome of an individual. Once the genotypes are known, the individual's genotype can be compared with the published literature to determine likelihood of trait expression and disease risk. Helps in Personalized Medicine (ix) Epigenomics: The epigenome is the supporting structure of genome, including protein and RNA binders, alternative DNA structures, and chemical modifications on DNA. Nucleomics: Study of the complete set of genomic components which form "the cell nucleus as a complex, dynamic biological system, referred to as the nucleome".

(x) Lipidomics: The lipidome is the entire complement of cellular lipids, including the modifications made to a particular set of lipids, produced by an organism or system.

(xi) Proteomics: The proteome is the entire complement of proteins, including the modifications made to a particular set of proteins, produced by an organism or system.

(xii) Immunoproteomics: Study of large sets of proteins (proteomics) involved in the immune response.

(xiii) Nutriproteomics: Identifying the molecular targets of nutritive and non-nutritive components of the diet. Uses proteomics mass spectrometry data for protein expression studies (xiv) Proteogenomics: An emerging field of biological research at the intersection of proteomics and genomics. Proteomics data used for gene annotations.

(xv) Structural genomics: Study of 3-dimensional structure of every protein encoded by a given genome using a combination of experimental and modeling approaches.

(xvi) Glycomics: Glycomics is the comprehensive study of the glycome i.e. sugars and carbohydrates.

(xvii) Foodomics: Foodomics was defined in 2009 as "a discipline that studies the Food and Nutrition domains through the application and integration of advanced-omics technologies to improve consumer's well-being, health, and knowledge"

(xviii) Transcriptomics: Transcriptome is the set of all RNA molecules, including mRNA, rRNA, tRNA, and other non-coding RNA, produced in one or a population of cells.

(xix) Metabolomics 5436: The scientific study of chemical processes involving metabolites. It is a "systematic study of the unique chemical fingerprints that specific cellular processes leave behind", the study of their small-molecule metabolite profiles (xx) Metabonomics: The quantitative measurement of the dynamic multiparametric metabolic response of living systems to pathophysiological stimuli or genetic modification.

(xxi) Nutritional genomics: A science studying the relationship between human genome, nutrition and health.

(xxii) Nutrigenetics studies the effect of genetic variations on the interaction between diet and health with implications to susceptible subgroupsCognitive genomics: Study of the changes in cognitive processes associated with genetic profiles.

(xxiii) Pharmacogenomics investigates the effect of the sum of variations within the human genome on drugs;

(xxiv) Pharmacomicrobiomics investigates the effect of variations within the human microbiome on drugs.

(xxv) Toxicogenomics: a field of science that deals with the collection, interpretation, and storage of information about gene and protein activity within particular cell or tissue of an organism in response to toxic substances.

(xxvi) Mitointeractome: Process by which the mitochondria proteins interact.

(xxvii) Psychogenomics: Process of applying the powerful tools of genomics and proteomics to achieve a better understanding of the biological substrates of normal behavior and of diseases of the brain that manifest themselves as behavioral abnormalities. Applying psychogenomics to the study of drug addiction, the ultimate goal is to develop more effective treatments for these disorders as well as objective diagnostic tools, preventive measures, and eventually cures.

(xxviii) Stem cell genomics: Helps in stem cell biology. Aim is to establish stem cells as a leading model system for understanding human biology and disease states and ultimately to accelerate progress toward clinical translation.

(xxix) Connectomics: The study of the connectome, the totality of the neural connections in the brain.

(xxx) Microbiomics: the study of the genomes of the communities of microorganisms that live in the digestive tracts of animals.

(xxxi) Cellomics: the quantitative cell analysis and study using bioimaging methods and bioinformatics.

(xxxii) Tomomics: A combination of tomography and omics methods to understand tissue or cell biochemistry at high spatial resolution, typically using imaging mass spectrometry data (xxxiii) Ethomics: Is the high-throughput machine measurement of animal behavior.

(xxxiv) Videomics: A video analysis paradigm inspired by genomics principles, where a continuous image sequence (or video) can be interpreted as the capture of a single image evolving through time through mutations revealing 'a scene': Study of the effects of foods and food constituents on gene expression.

Organoids module 5440—A feature collection associated with organoids grown from tumor tissue of a patient. These features may include insights derived from an organoid modeling lab from the DNA and RNA sequencing information germane to each organoid and results from treatments applied to those organoids.

Stored alterations module 5506—A feature collection associated with alterations which have been processed through one or more alteration modules. Features include SNP, MNP, Indels, MSI, TMB, CNV, Fusions, IHC, Therapies, VUS, Trials, Amplifications, Isoforms, Raw Counts. For example, the imaging results may need to be combined with MSI information derived from RNA expressions to determine additional further imaging features.

Stored classifications module 5520—A feature collection associated with the variant characterization machine learning models, classification models, or other artificial intelligence derived features.

Referring again to FIG. 188, alteration module 5450 includes one or more servers, scripts, or other executable algorithms which generate alteration features associated with de-identified patient features from feature collection 5405. Recognizable features include the following.

SNP 5452—single-nucleotide polymorphism: is a substitution of a single nucleotide that occurs at a specific position in the genome, where each variation is present to some appreciable degree within a population (e.g. >1%). For example, at a specific base position in the human genome, the C nucleotide may appear in most individuals, but in a minority of individuals, the position is occupied by an A. This means that there is a SNP at this specific position, and the two possible nucleotide variations—C or A—are said to be alleles for this position. SNPs underline differences in our susceptibility to a wide range of diseases (e.g. —sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration.

MNP 5454—Multiple-nucleotide polymorphisms are the substitution of consecutive nucleotides at a specific position in the genome.

Indels 5456—an insertion or deletion of bases in the genome of an organism classified among small genetic variations. While usually measuring from 1 to 10 000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites.

MSI 5458—Microsatellite instability is the condition of genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs).

TMB 5460—Tumor mutational burden is a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials.

CNV 5462—copy number variations result from analyzing genes, variants, alleles, or sequences of nucleotides to identify deviations from the normal genome and any subsequent implications. CNV are the phenomenon in which structural variations may occur in sections of nucleotides, or base pairs, that include repetitions, deletions, or inversions. A classification of a CNV as "Reportable" means that the CNV has been identified in one or more reference databases as influencing the tumor cancer characterization, disease state, or pharmacogenomics, "Not Reportable" means that the CNV has not been identified as such, and "Conflicting Evidence" means that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV.

Fusions 5464—A fusion gene is a hybrid gene formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

IHC 5466—Immunohistochemistry (IHC) is the most common application of immunostaining. It involves the process of selectively identifying antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualising an antibody-antigen interaction can be accomplished in a number of ways. In the most common instance, an antibody is conjugated to an enzyme, such as peroxidase, that can catalyse a color-producing reaction in immunoperoxidase staining. Alternatively, the antibody can also be tagged to a fluorophore, such as fluorescein or rhodamine in immunofluorescence.

Therapies 5468—Researchers have learned about some of the differences in cancer cells (or other cells near them) that help them grow and thrive. This has led to the development of drugs that "target" these differences. Treatment with these drugs is called targeted therapy. For example, many targeted drugs go after the cancer cells' inner workings—the programming that makes them different from normal, healthy cells, while leaving most healthy cells alone. Targeted drugs can work to: Block or turn off chemical signals that tell the cancer cell to grow and divide; Change proteins within the cancer cells so the cells die; Stop making new blood vessels to feed the cancer cells; Trigger your immune system to kill the cancer cells; Carry toxins to the cancer cells to kill them, but not normal cells; Some targeted drugs are more "targeted" than others. Some might target only a single change in cancer cells, while others can affect several different changes. Others boost the way your body fights the cancer cells. This can affect where these drugs work and what side effects they cause. Matching targeted therapies may include identifying the therapy targets in the patients and satisfying any other inclusion or exclusion criteria.

VUS 5470—Variants which are called but we cannot classify as pathogenic or benign are classified as variants of unknown significance. We conduct an internal review of all publications regarding a VUS to identify if they may be classified as benign or pathogenic. We tend to not report VUS unless they are the only variants that are reportable.

Trials 5472—Similar to Therapies, clinical trials exist to identify and test hypotheses for treating cancers having specific characteristics. These trials have inclusion and exclusion criteria that must be matched to enroll. Our methods include ingesting and structuring these trial criteria so that we may match patients to trials.

Amplifications 5474—Some genes increase in count disproportionately to other genes. Amplifications may cause the gene to go dormant, become overactive, or operate in another unexpected fashion. Amplifications may be detected at a gene level, variant level, RNA transcript or expression level, or even a protein level. Detections may be performed across all the different detection mechanisms and validated against one another.

Isoforms 5476—A protein isoform, or "protein variant", is a member of a set of highly similar proteins that originate from a single gene or gene family and are the result of genetic differences. While many perform the same or similar biological roles, some isoforms have unique functions.

A patient may have multiple reports for each specimen or specimen set sequenced. Reports may include DNA sequencing reports, IHC staining reports, RNA expression level reports, organoid growth reports, imaging and/or radiology reports, etc. Each report may contain results of sequencing of the patient's tumor tissue and, where available the normal tissue as well. Normal tissue can be used to identify which alterations, if any, are inherited versus those that the tumor uniquely acquired. Such differentiation often has therapeutic implications.

Figure 17A:
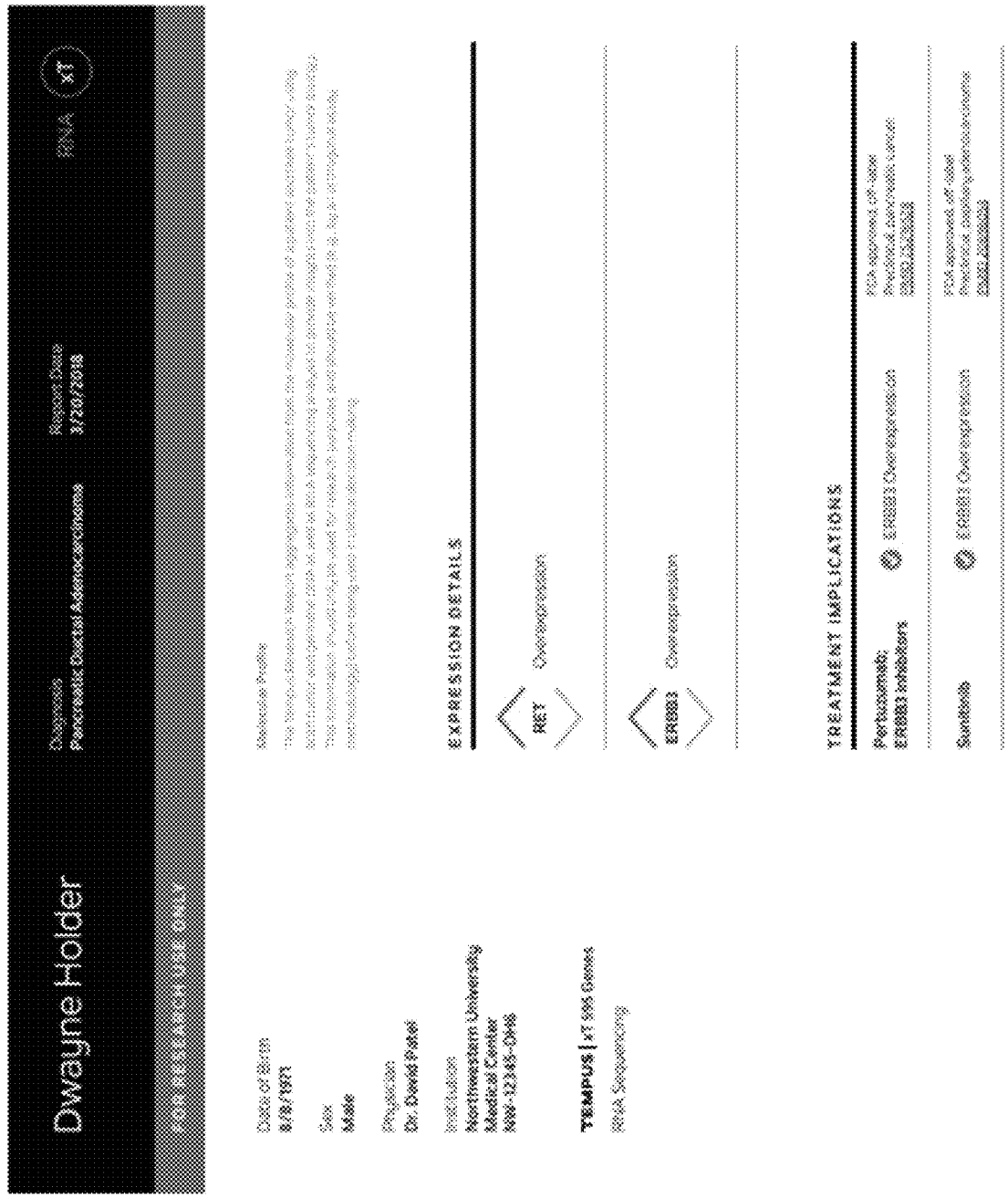
FIG. 17a shows an initial view of an RNA sequence reporting screenshot that is consistent with at least some aspects of the present disclosure.

FIG. 17*a* shows an exemplary first page of a report screenshot indicating the results of one RNA sequencing process. Profiling of whole RNA transcriptome provides molecular information that is complementary to DNA sequencing and can be clinically important to physicians. For example, RNA sequencing can assist in clinically validated unbiased translocation detection. Overexpression and underexpression of certain genes may be presented to the physician as a result of RNA sequencing. Likewise, treatment implications may be provided to the physician which the physician may take into consideration when determining the best type of treatment for a patient.

VII. A Generalizable and Interpretable Deep Learning Framework for Predicting MSI from Histopathology Slide Images The present disclosure is generally related to techniques for providing a generalizable and interpretable deep learning model for predicting microsatellite instability (MSI) directly from medical images, including routine histopathology images. These techniques provide an entirely new and automated modality for MSI testing and MSI status prediction via learned processes. Moreover, these techniques may be implemented in different frameworks, in what we call non-adversarial frameworks and adversarial frameworks, where the former allows for a cancer type-specific bias in a trained deep learning model and the where the later effectively eliminates/reduces cancer type-specific bias in a trained deep learning model.

In some examples, the present techniques provide a system for analyzing medical images to accurately predict MSI status for a patient. Those medical images are histopathology slide images, which under the present techniques, are determined to contain sufficient latent information for accurate prediction of MSI status.

The tumor microenvironment is extremely complex and heterogeneous, containing a diverse mixture of tumor, stromal, and immune cells. Tumors use immune checkpoints in the body to shield themselves from attack by the immune system. These immune checkpoints can be stimulatory or inhibitory, and checkpoint blockade therapies are being developed to stop this tumor shielding process. The success of checkpoint blockade treatment is based, in part, on the activation of infiltrating immune cells present in the tumor microenvironment. Information about infiltrating immune cells in histopathology slides is normally only accessible by overlaying additional multiplexed immunofluorescence or immunohistochemistry stains. But the we reasoned that embedded in common microscopic histopathology slides is fine-grained information about the topology, morphology, and population structure of cells within the tumor-immune microenvironment. We therefore developed frameworks designed to analyze these topology structures, morphology structures, and population structures of the cells in the microenvironment, for predicting MSI status for a patient.

In some examples, the present techniques include processes for training a deep neural network to assess medical images and predict MSI status. Generally speaking, deep neural networks provide a robust and durable approach to solving complex image analysis tasks, especially when specific visual features may be difficult to articulate a priori. The present techniques exploit deep neural networks to assess medical images, e.g., histopathology slide images, by analyzing extremely nuanced and fine-grained nature of features that distinguish certain pathological classifications from others, topology features, morphology features, and/or population features. Conventionally, nuanced analysis has been a long-standing challenge, in particular with regard to visual assessment of histopathology images. Medical professionals would manually identify patterns in medical images, and even then it is virtually impossible for medical professionals to identify features of topology and complex morphology. With the present techniques, however, deep neural networks have been used to learn fine-grained features directly from raw images in a supervised machine learning setting.

The present techniques predict MSI from histopathology slide images by classifying images based on a plurality of MSI states. MSI is a type of genomic instability that results from defects in DNA mismatch repair and can occur in a range of cancers. This mismatch repair defect results in a hyper-mutated phenotype where alterations in the repetitive microsatellite regions accumulate. Microsatellite instability may result in colon cancer, gastric cancer, endometrium cancer, ovarian cancer, hepatobiliary tract cancer, urinary tract cancer, brain cancer, and skin cancers, while MSI is believed to be most prevalent in colon cancers.

In described in examples herein, the present techniques predict MSI states based on three MSI states: Microsatellite-High (MSI-H), Microsatellite Stable (MSS), and Microsatellite-Low (MSI-L). MSI-H tumors are those in which the number of repeats present in microsatellite regions differ significantly from the number of repeats that are in the DNA of a benign cell. By way of example, in clinical MSI PCR testing, tumors with length differences in 2 or more of the 5-microsatellite markers on the Bethesda panel unstable are considered MSI-H. MSS tumors are tumors that have no functional defects in DNA mismatch repair and have no significant differences between tumor and normal in microsatellite regions. MSI-L tumors are tumors with an intermediate phenotype that cannot be clearly classified as MSI-H or MSS based on cut-offs used to define those two categories. Overall, MSI is observed in 15% of sporadic colorectal tumors worldwide and has been reported in other cancer types including uterine and gastric cancers.

In some examples, the present techniques include training a neural network to predict MSI status of histopathology slide images based on a training image sets that include cancer-type specific biases. Because MSI is most prevalent in colon cancer, the training images are colon cancer dominant, which results in a trained deep learning model that is colon cancer sensitive. The trained MSI predictor model in such examples can predict MSI status for images of other cancer types (e.g., Microsatellite gastric cancer, endometrium cancer, ovarian cancer, hepatobiliary tract cancer, urinary tract cancer, brain cancer, and skin cancers), but with lower accuracy, in general, compared to MSI prediction for colon cancer. Such implementations are termed non-adversarial herein.

In some examples, however, the present techniques have been implemented to include adversarial deep learning techniques that, while trained with the same cancer-type specific biases, can predict MSI status across the different cancer types without any (or with a less degree) of bias. Conventional deep learning techniques suffer from selection bias, where a network is trained based on a set of training images that are too similar to one another. The result is a deep learning process trained biased toward certain outcomes. Selection bias, we found, is a particular problem in cancer detection in medical images, especially when trying to predict MSI. The selection bias for MSI is particularly acute, we have found, because the overwhelming majority of medical images exhibiting MSI states correlated to a cancer are medical images of colon cancer. Such bias affects various non-adversarial implementations of the present techniques, for example. Yet, the present techniques include an adversarial deep learning process that determines MSI predictor status in a cancer agnostic manner, thereby allowing for accurate MSI status for different types of cancers, even when the system is trained by a training image set that has a cancer type-specific bias, such as a colon cancer dominant training image set. With the adversarial trained MSI predictor models herein, MSI prediction status is not anatomically restricted to a specific cancer type (or cancer types), and the MSI predictor model is able to predict MSI status across a range of cancer types including, including for cancer types not actually observed in training.

To implement adversarial deep learning, in some examples, the present techniques deploy a framework having two classifiers, one for predicting MSI status and the other predicting tumor type. To retain higher accuracy in MSI prediction, the frameworks may be designed to predict MSI status with a higher degree of accuracy, while allowing for predicting tumor type with a lower degree of accuracy, as any model that successfully predicts tumor type is likely learning features of the anatomical location rather than generalizable, biological features of MSI.

As discussed further in reference to FIG. 191, the two classification outcomes of adversarial deep learning may be accomplished, in some examples, by orienting the tumor type classifier into an adversarial objective, which causes a high-dimensional image embedding to adjust and satisfy the dueling objectives of high MSI prediction accuracy and sufficient tumor prediction. The framework reduces cancer type-specific biases (i.e., selection bias) and instead learns invariant high-dimensional representations of MSI.

FIG. 189 illustrates a deep learning MSI predictor processing system 6200 for predicting MSI state for a patient via analysis of medical image data. As used herein, the terms MSI state, MSI classification, MSI predictor, and MSI prediction are used interchangeably. Furthermore, the plurality of MSI states refers to states MSI-H, MSI-L, and MSS, in various examples herein. In other examples, the MSI predictor processing system 6200 may predict an "Equivocal" MSI state, e.g., an MSI state which is neither MSI-H nor MSS.

The deep learning MSI predictor processing system 6200 is described, in various examples, as trained using histopathology images, in particular H&E (Haematoxylin and Eosin) stained images.

The deep learning MSI predictor processing system 6200 includes an image pre-processing controller 6202 and a deep learning framework 6204. The pre-processing controller 102 is communicatively coupled to a network 6206 to receive medical images (e.g., H&E stained histopathology images) from a variety of different sources, including (i) medical imaging databases of healthcare providers (Provider 1) such as hospitals, physician groups, labs, etc.; (ii) dedicated digital medical image scanners which may be any suitable optical histopathology slide scanner including 20× and 40× resolution magnification scanners; and (iii) histopathology image repositories, such as the Cancer Genome Atlas (TCGA) and NCI Genomic Data Commons. Each of the image sources may present multiple image sources.

The deep learning MSI predictor processing system 6200 may be implemented on a computing device such as a computer, tablet or other mobile computing device, or server. The system 6200 may include a number of processors, controllers or other electronic components for processing or facilitating the image capture, generation, or storage and image analysis, as described herein. An example computing device 6216 for implementing the MSI predictor processing system 6200 is illustrated in FIG. 198. As illustrated, the system 6200 may be implemented on the computing device 6216 and in particular on one or more processing units, which may represent Central Processing Units (CPUs), and/or on one or more Graphical Processing Units (GPUs), including clusters of CPUs and/or GPUs. Features and functions described for the system 6200 may be stored on and implemented from one or more non-transitory computer-readable media of the computing device 6216. The computer-readable media may include, for example, an operating system and the deep learning framework having elements corresponding to that of MSI predictor processing system 6200, including segmentation, MSI classifier module, and a model interpreter. More generally, the computer-readable media may store trained deep learning models, executable code, etc. use for implementing the techniques herein. The computing device 6216 includes a network interface communicatively coupled to the network 6206, for communicating to and/or from a portable personal computer, smart phone, electronic document, tablet, and/or desktop personal computer, or other computing devices. The computing device further includes an I/O interface connected to devices, such as digital displays, user input devices, etc. In the illustrated example, the MSI predictor processing system 6200 is implemented on a single server 6216. However, the functions of the system 6200 may be implemented across distributed devices 6216, 6218, 6219, etc. connected to one another through a communication link. In other examples, functionality of the system 6200 may be distributed across any number of devices, including the portable personal computer, smart phone, electronic document, tablet, and desktop personal computer devices shown. The network 6206 may be a public network such as the Internet, private network such as research institutions or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 6216 may represent a CPU-type processing unit, a GPU-type processing unit, a field-programmable gate array (FPGA), another class of digital signal processor (DSP), or other hardware logic components that can be driven by a CPU.

Returning to FIG. 189, the image processing controller 6202 includes a pre-processing module that may perform initial processes such as image quality assessment and noise filtering. Because medical images such as H&E stained histopathology images may come from different sources, including different scanners and scanner types, in some examples the controller 6202 performs a color normalization to establish a uniform color-scape for the medical images. Additionally, in some examples, the controller 6202 performs a tissue segmentation that identifies target tissue within the received medical images and segments that target tissue for analysis by the framework 6204. In some examples, the controller 6202 deploys a convolutional neural network to perform whole slide image segmentation; although any number of unsupervised or supervised methods of image segmentation may be used.

The tissue segmentation process further identifies a patch that will be used for analyzing by the deep learning framework 6204 in determining MSI status. Patches may be geometric, e.g., a repeating pattern of square or rectangular pixels defined across each medical image and at a pixel size sufficient to analyze changes in topology and morphology in medical images. Example patch sizes include 1000×1000 pixels, although fewer pixels can be used, such as 900×900, 800×800, 700×700, 600×600, 500×500, and so on, down to at least 100×100, and even further, such as 50×50 depending on the application. In other examples, patch type may be non-geometric, also termed herein a "super pixel," where each patch is allowed to vary in shape, but where the super pixels are generated to include a sufficient threshold of imaging information for topology and morphology analysis.

The deep learning framework 6204 may be implemented as a baseline deep learning framework as in framework 6208 of FIG. 190. While in other examples, the deep learning framework 6204 may be implemented as an adversarial deep learning framework as in the framework 6210 of FIG. 191, both discussed further below.

The deep learning framework 6204 includes a training state and a testing state. In the training state, the framework 6204 generates a deep learning MSI predictor model and a deep learning tumor predictor model from trained medical images, such as H&E stained histopathology images, where those models are stored in memory. An example method is described in reference to FIG. 193. In a testing state, the trained deep learning MSI predictor model is applied to received medical images and generates a MSI state prediction for the MSI status values (MSI-H, MSI-L, and MSS). That MSI prediction is a coordinate of probability values (or vectors) for each MSI state [MSI-H, MSI-L, MSS], the sum of which is 1. For example, an MSI state prediction [0.7, 0.2, 0.1] represents a determination that a medical image has a 70% likelihood the patient exhibits MSI-H, a 20% likelihood the patient exhibits MSI-L, and a 10% likelihood the patient exhibits MSS. Corresponding, an MSI state prediction [0.2, 0.2, 0.8] would indicate a 80% likelihood the patient exhibits MSS. The framework 6204 may optionally further include a tumor predictor model that is trained to identify a tumor type for each medical image.

FIG. 190 illustrates an example framework 6208 implementation of the MSI deep learning framework 6204. In the illustrated example, digital H&E slide images are provided (e.g., from the pre-processing controller 6202) to the framework 6208. A deep learning classifier is provided to identify one or more topology, morphology, and population features within the H&E slide images. The deep learning classifier may also use machine learning algorithms capable of being trained by feature selection. The deep learning classifier may employ a convolutional neural network for training. Example convolutional neural networks include VGGNet, GoogLeNet, and ResNET. In examples described herein, Inception v3 was used as the deep learning classifier. Further, the illustrated example included a 1024-dimension embedding layer to predict MSI status.

In an example implementation of the framework 6208, digital H&E stained histopathology slide images and clinically determined MSI status were obtained from The Cancer Genome Atlas (TCGA). Along with MSI status, 585 colorectal carcinoma (CRC), 556 uterine corpus endometrial carcinoma (UCEC), and 209 stomach adenocarcinoma (STAD) whole-slide histopathology images were obtained from the NCI Genomic Data Commons. In this example, the pre-processing controller 6202 was not used, but instead whole-slide images were provided to the deep learning classifier.

In an example, a segmentation process was used to clip the H&E stained histopathology slide images into non-overlapping 1000×1000px sized patches at 20× magnification. Slides with 40× magnification were rescaled to 20× using the Python Imaging Library (version 1.1.7). The segmentation process discarded patches that were >50% empty, and generated nearly 620,833 patches. At runtime patches were resized to input dimensions required for specific deep learning frameworks.

The framework 6208 performs parameter tuning. For example, CRC patches were randomly assigned to non-overlapping training (80%), test (10%), and validation (10%) image sets. Hyper-parameter settings such as learning rate and batch size were tuned for Inception-v3, VGG19, and ResNet-50 classifier architectures using CRC training and test sets. We used the accuracy on the test set to select the best hyper-parameter settings for all subsequent validation results.

In assessing the different classifier architecture, a validation procedure was performed where 10% of the UCEC slide patches (and as previously defined for CRC) were randomly chosen for validation. The other 90% of patches were used for training. All STAD patches were held out and reserved for validation testing only. Patches of different MSI status and different tumor types were sampled with equal probability each step, and each patch was trained at least once in each epoch. Several regularization techniques, including batch normalization and early stopping, were employed to optimize the training process and address overfitting. Prediction accuracy was measured by percent concordance between predicted and clinically determined MSI status (3 classes: MSI-H, MSI-L, and MSS).

In an example, the deep learning classifier was trained as follows. Let $x_I$ be a 1000×1000px patch clipped from a slide. For each image $x_I$, the classifier defined its tumor type $t_I$ and its MSI status $m_I$, such that:

$$t_I = \begin{cases} 0 & \text{if } x_I \text{ belongs to } CRC \\ 1 & \text{if } x_I \text{ belongs to } UCEC \end{cases}$$

and $$m_j = \begin{cases} 0 & \text{if } x_I \text{ belongs to } MSS \\ 1 & \text{if } x_I \text{ belongs to } MSI-L \\ 2 & \text{if } x_I \text{ belongs to } MSI-H \end{cases}$$

In this example, in the final classifier model, the penultimate layer has 1024 variables, although fewer or great numbers of variables could be used. These 1024 variables are used as embeddings for a MSI status predictor classification. In an example, the MSI status predictor classification is implemented with one ReLU (rectified liner units) layer and one 1024×3 fully-connected layer. In other examples, any non-linearity can be introduced into the MSI predictor model, e.g., using any non-linear function such as ReLU, Tanh, or sigmoid to improve accuracy of the MSI predictor model.

In an example of the system 6200, we evaluated pre-existing deep neural network architectures for the deep learning classifier, specifically, Inception-v3, VGG19, and ResNet-50. Before training the dedicated model for classifying MSI status, we initialized the model with parameters pre-trained on ImageNet. And as a result, we developed fully trained models fine-tuned for MSI classification end-to-end. We configured the system 6200 to use the Adam optimization method with learning rate 1e-4 and betas=(0.9, 0.999). And for the examples illustrated, all models were implemented with PyTorch and all experiments were conducted on a GPU cluster.

FIG. 191 illustrates an example framework 6210 implementation of the MSI deep learning framework 6204 with similar elements to that of the framework 6208, but configured in an adversarial deep learning framework, in which training images include digital H&E slide images and cancer type data. Similar deep learning classifier and 1024 variable embedding procedures were used in the framework 6210 to identify one or more topology, morphology, and population features within the H&E slide images for predicting MSI status. However, the 1024 variables are used as embeddings for both MSI status predictor classification and a tumor predictor classification. That is, in addition to embeddings for MSI state, embeddings for tumor type classification, in an example, using a ReLU layer and one 1024×2 fully-connected layer, were used. The tumor predictor classification used a soft-max operation on the output that was interpreted as the probability of the classes. As with the MSI status predictor, other non-linear functions, such as Tanh and sigmoid, could be used in placed of the ReLU, and further a larger or smaller connected layer could be used.

The adversarial framework 6210 was developed to provide MSI status predictor models that are more generalizable and robust to new tumor types, even when trained with cancer type-specific training sets. In design, we sought to eliminate cancer type-specific biases so that the models instead learned invariant high-dimensional representations of MSI.

In an example implementation, the framework 6210 was configured with three components: (i) An embedding for some image patch: $R(x_l)$, (ii) an MSI classifier: $D_{MSI}(R(x_l))$, and (iii) a tumor type classifier: $D_{Tumor}(R(x_l))$. For each mini-batch of samples, we trained the embedding and MSI predictor and tumor classifiers iteratively. We set a scalar weight for tumor type µ=0.1.

First we trained the embeddings (e.g., via Inception v3) according to following conditions:

$$L_{encoder} = L_{MSI} - \mu L_{Tumor}$$

$$L_{MSI} = -\sum_l \sum_m h_m(x_l) \log D_{MSI}(R(x_l))$$

$$L_{Tumor} = -\sum_l \sum_t h_t(x_l) \log D_{Tumor}(R(x_l))$$

Here m is the MSI type and t is the tumor type. $h_m$ and $h_t$ are indicator variables.

$$h_m(x_l) = \begin{cases} 1 & \text{if } x_l \text{ belongs to } m, \\ 0 & o.w. \end{cases}$$

and $$h_t(x_l) = \begin{cases} 1 & \text{if } x_l \text{ belongs to } t, \\ 0 & o.w. \end{cases}$$

Then we train the two classifiers:

$$L_{classifiers} = L_{MSI} + L_{Tumor}$$

As shown, each of the frameworks 6208 and 6210 output an MSI status prediction, reflected as a coordinate of MSI-H (%), MSI-L (%), and MSS (%). As discussed in examples below, the adversarial framework 6210, providing a generalizable and interpretable deep learning mode, is capable of predicting MSI status with more accuracy across a greater number of cancer types, even for cancer types not included in the training image set.

For the baseline non-adversarial framework 6208 and for the adversarial framework 300 MSI predictor status is provided, along with the corresponding medical image, to a model interpreter that may include a guided backpropagation procedure to visualize salient image features associated with predicted MSI status as further discussed herein below. The model interpreter examines an H&E digital image to identify pixels associated with the MSI classification. The interpreter can include for example a Gradient-weighted Class Activation Map. For example, the model interpreter collects from the MSI status predictor the assigned MSI status of the H&E digital image and then identifies those pixels or groups of pixels that correspond to the overall MSI prediction for the whole H&E digital image. The model interpreter then identifies those pixels or groups of pixels that coincide with the overall MSI prediction. We describe this process as a guided backpropagation. FIG. 192 illustrates an example of an H&E digital image in which the model interpreter generates a new rendition of the H&E digital image, with the pixel or pixel group locations associated with the MSI prediction. In this way, the model interpreter provides healthcare professionals with a visual indication of the locations in a medical image where the MSI state is evident.

FIG. 193 illustrates an example process 6212 for performing adversarial training of a deep learning framework to develop an MSI predictor classifier model and a tumor predictor classifier model. As shown, in training state, initially pre-processed medical images (e.g., stained histopathology images with cancer-specific type bias) are received. Then a deep learning framework (e.g., convolutional neural network) is trained to analyze images to generate an MSI state predictor model based on cancer-specific type bias images. Broadly speaking, the deep learning framework may implement any suitable statistical model (e.g., a neural network or other model implemented through a machine learning process) that will be applied to each of the received images. As discussed herein, that statistical model may be implemented in a variety of manners. In some examples, machine learning is used to evaluate training images and develop classifiers that correlate predetermined image features to specific categories of MSI status. For example, image features can be identified as training classifiers using a learning algorithm such as Neural Network, Support Vector Machine (SVM) or other machine learning process. Once classifiers within the statistical model are adequately trained with a series of training images, the statistical model may be employed in real time to analyze subsequent images provided as input to the statistical model for predicting MSI status. In some examples, when statistical model implemented using a neural network, the neural network may be configured in a variety of ways. In some examples, the neural network may be a deep neural network and/or a convolutional neural network. In some examples, the neural network can be a distributed and scalable neural network. The neural network may be customized in a variety of manners, including providing a specific top layer such as but not limited to a logistics regression top layer. A convolutional neural network can be considered as a neural network that contains sets of nodes with tied parameters. A deep convolutional neural network can be considered as having a stacked structure with a plurality of layers. The neural network or other machine learning processes may include many different sizes, numbers of layers and levels of connectedness. Some layers can correspond to stacked convolutional layers (optionally followed by contrast normalization and max-pooling) followed by one or more fully-connected layers. For neural networks trained by large datasets, the number of layers and layer size can be increased by using dropout to address the potential problem of overfitting. In some instances, a neural network can be designed to forego the use of fully connected upper layers at the top of the network. By forcing the network to go through dimensionality reduction in middle layers, a neural network model can be designed that is quite deep, while dramatically reducing the number of learned parameters.

Either simultaneously or iteratively, the method further includes adversarial training of the MSI state predictor model to remove cancer-specific type bias. For example, the method applies equations (1), (2), and (3) in an alternating manner to apply adversarial training. The result is that the method generates adversarial trained convolution neural network for MSI status prediction, i.e., an adversarial trained MSI status predictor model.

FIG. 194 illustrates an example process 6214 for performing MSI prediction and tumor prediction on received testing medical images using the adversarial trained deep learning framework of FIG. 191, e.g., after the process 6212. Initially, pre-processed medical images are received, and each is applied to the adversarial trained convolution neural network, which determines MSI status for each medical image, and which then performs model interpretation and guided backpropagation for each medical image, which may then be displayed to healthcare personal or to a patient directly.

Examples

While the techniques herein may be used with any deep learning framework, we used the processing system 6200 to evaluate multiple deep learning frameworks for MSI classification to identify differences in performance. In particular, we evaluated several deep learning architectures, including VGG19, Inception-v3, and ResNet-50, using colorectal cancer samples as a teaching imaging set. The frameworks have been used for a range of image recognition tasks, with a high level of accuracy, therefore suggesting they might be suitable for implementation into an adversarial deep learning MSI status detection system as described herein. To assess the performance and suitability of these models in predicting MSI status, we evaluated the accuracy in classifying MSI status (MSS, MSI-L, and MSI-H) from colorectal carcinoma (CRC) histopathology slide images during a testing stage. CRC is a useful baseline for evaluating MSI status prediction as it is found in approximately 15% of stage II to III colorectal cancers.

The processing system 6200 was used to fully train each deep learning framework end-to-end on 90% of CRC data and evaluated accuracy on the remaining 10% CRC data as a validation set. We continued training until we observed diminishing improvement in validation accuracy. We found that Inception-v3 and ResNet-50 performed competitively, achieving max accuracy of 92.2% and 91.44% respectively over 40 epochs. Accuracy for VGG19 remained typically below both Inception-v3 and ResNet-50 at every epoch, and was discontinued from further training at epoch 20. In addition, we found GPU memory usage for Inception-v3 (4641 MiB) and ResNet-50 (5441 MiB) to be similar, whereas VGG19 required nearly twice as much memory (9455 MiB) despite the same mini-batch size. Overall, we found Inception-v3 and ResNet-50 both to be efficient and suitable frameworks for MSI prediction.

While any deep learning framework may be used, for the testing examples described further below, the processing system 6200 was configured to use Inception-V3 for our adversarial framework, based on the higher validation accuracy and smaller memory footprint of that framework.

To provide comparisons, we used the framework 6208 of FIG. 190 to characterize how well a naïve deep learning model trained using a single tumor type generalizes to a new, different tumor type when predicting MSI status. MSI has been reported with high incidence in sporadic endometrial carcinoma.

In a first example, we applied the framework 6208 in an example trained on CRC medical image to assess prediction of MSI status on medical images for patients exhibiting uterine corpus endometrial carcinoma (UCEC) (Table 1). In this way, the example demonstrates the effect of cancer type-specific bias when using the framework 6208, i.e., a non-adversarial MSI predictor trained neural network.

In this first example, the processing system 6200 retrained Inception-v3 end-to-end using CRC samples to predict three clinical classes: MSS, MSI-L, and MSI-H. A patch-level accuracy was 91.7% when testing subsequent medical images of patients exhibiting CRC, but only 50.3% accuracy when testing medical images of patients exhibiting UCEC (with a patch being defined as a non-overlapping 1000× 1000px region at 20× magnification). We also calculated a new slide-level accuracy by polling all patches in a specific slide to determine a slide-level classification (FIGS. 195A and 195B). The model achieved 98.3% accuracy at the slide-level for CRC. As a comparison, a purely random MSI predictor would have accuracy near ~33%. The patch- and slide-level accuracies for the UCEC samples was ~50%, suggesting that some transfer learning exists between training MSI classification in one cancer type and then predicting status in a different cancer type.

TABLE 1

| Non-adversarial training on CRC images | | |
|---|---|---|
| Validation set | Patch-level accuracy | Slide-level accuracy |
| CRC | 91.7% | 98.3% |
| UCEC | 50.3% | 53.7% |

In a second example, we examined how training the framework 6208 with both UCEC and CRC examples changed MSI classification accuracy and generalizability. This example provided a comparison for non-adversarial MSI predictor trained neural network based on two different cancer type-specific training images. Consistent with the first example, we trained Inception-v3 end-to-end using now both CRC and UCEC images to predict three clinical classes: MSS, MSI-L, and MSI-H (Table 2). We determined that, including UCEC examples during training improves model accuracy for predicting MSI status in the UCEC validation set (~70% vs. ~50% accuracy at patch-level; ~80% vs. ~50% accuracy at slide-level). However, these improvements came at the cost of relatively reduced accuracy for CRC tumors (60% and ~70% accuracy for patch and slide-level accuracies, respectively).

TABLE 2

Non-adversarial training on CRC and UCEC images

| Validation set | Patch-level accuracy | Slide-level accuracy |
|---|---|---|
| CRC | 60.1% | 72.3% |
| UCEC | 73.2% | 84.2% |
| STAD | 31.8% | 34.9% |

As shown in Table 2, we also evaluated MSI prediction accuracy on stomach adenocarcinoma (STAD) samples. Strikingly, we observed approximately random performance in predicting MSI status in the STAD test samples (~33%).

Collectively, these results show that while naïve deep learning models can provide a useful approach for predicting MSI status using the framework 6208, the generalizability of these models comes at the cost of the "no free lunch" theorem. Although these models perform well when trained and evaluated on the same tumor types, they pay a price with degraded performance on new and all remaining unseen cancer types, thereby reducing their clinical application potential.

We then tested the framework 6210 is an example adversarial MSI predictor trained neural network. Specifically, the framework 6210 was used to eliminate cancer type-specific biases (CRC, UCEC, etc.). Our intuition was that similar to the shared genomic and clinical assays used to determine MSI status across different cancer types, predictive and useful latent image features associated with MSI status should be common regardless of cancer type. Therefore, by developing a framework that removes tumor specific biases, we can create a model to learn better, invariant high-dimensional representations of MSI from medical images across cancer types.

In this third example, that of the framework 6210, we retained Inception-v3 end-to-end with CRC and UCEC images, i.e., with the same cancer type-specific images in example 2 above (see, Table 3). We verified that the adversarial objective of the framework 6210 was effective by calculating the training accuracy for classifying tumor types to be 51.1% at 20 epochs. We then evaluated MSI prediction accuracy for UCEC and CRC validation samples.

TABLE 3

Adversarial training on CRC and UCEC images

| Validation set | Patch-level accuracy | Slide-level accuracy |
|---|---|---|
| CRC | 77.6% | 85.0% |
| ITU | 85.9% | 94.6% |
| STAD | 56.7% | 57.4% |

As shown in Table 3, the adversarial MSI predictor trained configuration generated a substantial increase in MSI classification accuracy for both CRC and UCEC cancer types. Comparing Table 3 to Table 2, our use of adversarial training increased patch-level accuracies by an average of 18.4%. Our slide-level accuracies similarly improved by 15.2%. In particular we note that the largest gain occurred for STAD, which improved by nearly 25% at patch-level and approaches ~60% accuracy for MSI prediction at slide-level. In sum, these results demonstrate that adversarial training substantially improves the generalizability of deep learning models in complex digital pathology tasks, such as MSI prediction.

We further used the framework 6210 to provide a visual indication of the MSI predictions. Broadly, while the visual indications can be achieved in different ways, in these particular examples, visual indications were generated to understand what components of the medical images are used by an adversarial trained model when deciding on MSI status. In an example, the guided backpropagation controller was used to generate these visual indications and to demonstrate how different features and details on images influence MSI predictions.

In an example, the high-dimensional space of embeddings learned by the framework 6210 is trained using CRC and UCEC in an adversarial manner. The embeddings were visualized using t-SNE to project 1024-dimensional embeddings from 1,000 MSI-H, MSI-L and MSS patches from UCEC and CRC training medical image samples into two-dimensions, as shown in FIGS. 196A and 196B. FIG. 196A illustrates a two-dimensional plot of t-SNE 1 vs. t-SNE 2 showing MSI status predictions (MSI-H, MSI-L, MSS) and showing that the framework 6210 places embeddings belonging to the same MSI class close together, in high-dimensional space as observed by the distinct clustering of MSI-H, MSI-L and MSS. Furthermore, when viewing the SNE projection through the lens of cancer type (UCEC vs. CRC), as shown in FIG. 196B, we demonstrate a lack of distinct tumor specific clustering, or certainly to a lesser extent. These results suggest that the image embeddings learned by the framework 6210 in this example are primarily clustered by MSI status.

The guided backpropagation controller was configured to connect MSI prediction to specific features and details on test medical images, e.g., in histopathology images. The guided backpropagation controller was used to reveal the gradient of the first layer in the adversarial trained MSI predictor model. In particular, the guided backpropagation controller was used to visualize activations of specific pixels associated with MSI status, and therefore to provide medical practitioners a high level understanding of what features and details on images influence MSI predictions For example, we sampled multiple UCEC and CRC based medical images, from the MSI-H and MSS clusters. MSI-H and MSS are clinically well defined, whereas MSI-L is thought be an intermediate or equivocal state. We present representative patches in FIG. 197. We observed that MSI-H patches show activations around potential patterns of infiltrating immune cells. Here a distinct activation (white) around a round cell with large nucleus (black) suggests instances of lymphocytic infiltrate. Tumors with MSI-H are often characterized by strong infiltration of the tumor microenvironment with lymphocytes such as CD8+ cytotoxic T cells, CD4+T helper 1 cells and natural killer cells. In contrast, for MSS patches we observed activation of larger tissue level, morphological features, such as glandular structures and non-specific tissue interfaces and voids within tumors. These features are generalizable across adenocarcinomas and may represent the identification of common features in MSS cases for these disease types.

Overall, the visualization of our adversarial learned embeddings demonstrates shared feature representations within MSI classes. Furthermore, the inspection of histopathology images associated with MSI classes through guided backpropagation implicates clinically interpretable class-discriminative features, such as immune infiltration.

For more than half a century, manual evaluation of histopathology slides by experienced pathologists has remained the standard for identifying potential clinically actionable pathologic features for different cancers. With the present disclosure, we introduce a novel deep learning framework that predicts MSI status directly from haematoxylin and eosin stained histopathology slide images. The result is generalizable and interpretable framework for modeling histopathology slide images, and which holds the potential for substantial clinical impact, including broadening access to MSI testing by "pre-screening" for MSI cancers, with a follow-up screen made with either IHC or DNA analysis.

As shown, our results demonstrate that a deep learning framework can be used to determine MSI status in a tumor specific manner, and importantly, we provide an approach to identify pathologic features such as immune infiltrate that are clinically interpretable by pathologists. The identification of clinically interpretable and biologically supported features is a valuable for the widespread adoption of deep learning models in clinical medicine.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. For example, references and illustrates herein to a "motion capture device," motion capturing hardware device, and the like, include references to multiple ones of these devices as may be used attached to and/or separately spaced from a user. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

VIII. Microsatellite Instability Determination System and Related Methods

The present application presents techniques for determining microsatellite instability (MSI) directly from microsatellite region mappings for specific loci in the genome. In some examples, a MSI assay is disclosed. The assay may be a tumor-normal MSI assay. The MSI assay may refer to specific loci in the genome. The MSI assay may employ a support vector machine (SVM) classifier. For a tumor-normal MSI assay, instability may be tested at each locus by comparing the distributions of the repeat length of the tumor and normal sample. The proportion of unstable loci may then be fed into a logistic regression classifier.

In exemplary embodiments, the techniques for determining MSI include a sequencing data pre-processing process and an MSI status calling process. These processes may be applied to specific microsatellite regions, in particular a specific panel chromosomes with identified microsatellite regions.

In exemplary embodiments, an initial procedure includes sequencing data pre-processing. In particular, the methods and systems described herein may be used on information generated from next generation sequencing (NGS) techniques. Extracted DNA from tumor tissue is single or paired-end sequenced using a NGS platform, such as a platform offered by Illumina. Methods for sequencing using an NGS platform are described in further detail in, for instance, U.S. Patent Publication No. US20160085910A1, which is incorporated by reference in its entirety.

The results of sequencing (herein, the "raw sequencing data") may be passed through a bioinformatics pipeline where the raw sequencing data is analyzed. After sequencing information is run through the bioinformatics pipeline, the sequencing information may be evaluated for quality control, e.g., through use of an automated quality control system. If the sample does not pass an initial quality control step, it may be manually reviewed. If the sample passes an automated quality control system or is manually passed, an alert may be published to a message bus that is configured to listen for messages from quality control systems. This message may contain sample identifiers, as well as the location of BAM files, i.e. a binary format for storing sequence data. When a message notifying that the topic is received, an MSI micro-service may be triggered. In one embodiment, the MSI micro-service launches a Jenkins job, which deploys an EC2 instance with an MSI Algorithm Docker image that may be stored in in an elastic container repository, such as the web server AWS ECR.

In exemplary embodiments, the techniques for determining MSI further include a process of MSI calling. In an example, a plurality of microsatellites is analyzed to determine the frequency of DNA slippage events. A "DNA slippage event" is a change in the length of repetitive regions in the genome, like microsatellites, due to local mismatches between DNA strands during replication. When the mismatch repair machinery is defective, these slippage events accumulate throughout the genome, particularly in microsatellite regions. For MSI testing, microsatellites may be selected on the basis of their instability in tumors with mismatch repair deficiencies, where microsatellites with greater instability are better candidates for selection.

In an example, the frequency of microsatellite instability is measured by obtaining the lengths of the microsatellite repeats for all reads that map to each locus and comparing that distribution of repeat lengths to the distribution of repeat lengths obtained from a matched normal sample at each locus using a statistical method, such as Kolmogorov-Smirnov test. A threshold of significance number is set, such as a false discovery rate of <=0.05, for the locus to determine whether it is considered unstable versus stable.

In an example, some or all of the 43 microsatellites listed in Table 1 may be used to determine the frequency of DNA slippage events. The information detected is provided to an MSI classification algorithm, described herein below, which then classifies tumors into three categories: microsatellite instability high (MSI-H), microsatellite stable (MSS), or microsatellite equivocal (MSE). Table 1 illustrates the chromosome number, start and end position of the microsatellite, and the nucleotide or nucleotides repeated in that region of DNA (repeat unit).

Table 1 lists chromosomes with identified microsatellite regions. The first column lists the chromosome name. The second column lists the start position (genomic coordinates) of the microsatellite region (locus) within the chromosome. The third column lists the end position (genomic coordinates) of the microsatellite region (locus) within the chromosome. The fourth column lists the unit(s) that repeat throughout the microsatellite region.

TABLE 1 xT Microsatellite Regions

| Chromosome | MS start | MS end | Repeat unit |
|---|---|---|---|
| chr18 | 649879 | 649893 | T |
| chr14 | 73959703 | 73959718 | T |
| chr8 | 23712066 | 23712077 | T |
| chr3 | 71008341 | 71008353 | T |
| chr4 | 39501722 | 39501739 | A |
| chr3 | 113377481 | 113377491 | T |
| chr14 | 53513439 | 53513450 | A |
| chr19 | 14104688 | 14104701 | T |
| chr11 | 63149670 | 63149680 | A |
| chr6 | 11714639 | 11714652 | A |
| chr1 | 47325299 | 47325311 | A |
| chr3 | 130733046 | 130733056 | T |
| chr3 | 30691871 | 30691880 | A |
| chr13 | 58299434 | 58299444 | A |
| chr11 | 115047032 | 115047045 | T |
| chr1 | 149900985 | 149901000 | A |
| chrX | 101409254 | 101409269 | T |
| chr8 | 79629738 | 79629751 | A |
| chr11 | 125763610 | 125763622 | T |
| chr12 | 85285920 | 85285936 | A |
| chr5 | 67584512 | 67584523 | T |
| chr3 | 164905648 | 164905658 | A |
| chr21 | 33974094 | 33974107 | T |
| chr5 | 58270457 | 58270468 | A |
| chr2 | 211179765 | 211179775 | T |
| chr1 | 237060945 | 237060959 | T |
| chr6 | 71571694 | 71571705 | A |
| chr3 | 123332875 | 123332890 | T |
| chr18 | 319944 | 319954 | T |
| chr2 | 64069277 | 64069291 | A |
| chr12 | 13364426 | 13364435 | A |
| chr4 | 83785564 | 83785572 | TGC |
| chr5 | 88018388 | 88018400 | A |
| chr21 | 30339205 | 30339215 | T |
| chr17 | 1326754 | 1326767 | A |
| chr5 | 161494990 | 161495001 | A |
| chr15 | 37391752 | 37391763 | T |
| chr6 | 43021976 | 43021987 | G |
| chr7 | 94989255 | 94989271 | T |
| chr2 | 99614595 | 99614607 | A |
| chr2 | 152236045 | 152236058 | A |
| chr11 | 65268479 | 65268490 | T |
| chr2 | 118854094 | 118854106 | T |

In exemplary embodiments, a MSI classification algorithm is applied to the sequencing data that has passed quality control. The algorithm may be performed in paired mode, where the algorithm has access to matched tumor-normal sequencing data. The algorithm may also be performed in unpaired mode, if the algorithm does not have access to paired normal sequencing data.

In an example of a MSI classification (i.e., detection) performed in a paired mode, initially MSI loci read filtering and sampling quality control is performed. For example, to be an MSI locus mapping read, the read must be mapped to the MSI locus during alignment with a bioinformatics pipeline, such as the Tempus xT bioinformatics pipeline. In an example, the mapping read must also contain at least 3-6 mapping base pairs in both the front and rear flank of the microsatellite, with any number of the expected repeating units in between.

In an example, at least 30-40 mapping reads in the tumor sample and 30-40 mapping reads in the normal sample must be identified for a microsatellite to be included in the analysis. This defines an example coverage minimum. Further, at least 20-30 of the 43 microsatellites on the panel must reach the coverage minimum described above for the assay to be run. If this coverage threshold is not met for the normal sample, MSI detection and calling will switch to running in unpaired mode, discussed further below.

With the coverage threshold met, MSI classification is performed. In an exemplary embodiment of MSI classification in the paired mode, each microsatellite is tested for instability. For example, each microsatellite locus may be tested for instability by measuring changes in the distribution of the number of repeat units in the tumor reads compared to the distribution of the number of repeat units in the normal reads. An example method of measurement for use is the statistical Kolmogorov-Smirnov test. If p <=0.05, the locus may be considered unstable. That is a statistical analysis is process is performed that analyzes the distribution of reads mapping to a locus of a tumor sample with the distribution of reads mapping to a locus of a normal sample.

The proportion of unstable microsatellites per sample across all loci may then be provided to a univariate logistic regression classifier. In an example, the classifier already has been trained on data from cancer samples. For instance, the classifier may have been trained on data from colorectal and endometrial cohorts that have clinically determined MSI statuses from MSI PCR testing, such as cohorts from The Cancer Genome Atlas ("TCGA", available from the U.S. National Institutes of Health, Bethesda, Md.). In an example training process, the same microsatellites used with present MSI test were assessed for instability in TCGA samples (e.g., 245 TCGA samples although training may be performed on fewer or larger numbers). The TCGA MSI PCR statuses were converted to a binary dependent variable: e.g., whether the sample was MSI-H or not. A logistic regression classifier was then trained to predict the binary MSI-H status using the proportion of unstable microsatellites. The output of the trained logistic function can then be interpreted as the probability of the dependent variable being categorized as MSI-H or not. To address different numbers of MSS and MSI-H samples in training set, the class weights were set to be inversely proportional to class frequencies (number of MSS and MSI-H samples) in the input data during training.

The classifier groups the samples into three categories: MSI-H, MSE, and MSS. If there is a greater than 70% probability of MSI-H status, the sample is classified as MSI-H. If there is between 50-70% probability of MSI-H status, the test results are too ambiguous to interpret. Those samples should make up a relatively small proportion of samples and are classified as MSE. If there is less than 50% probability of MSI-H status, the sample is considered MSS.

FIG. 199 illustrates an example of the MSI Detection and classification method in paired mode using tumor and normal matched samples, in accordance with an example.

In another exemplary embodiment, a MSI classification algorithm is applied to the sequencing data an in unpaired mode using tumor-only samples, as shown in FIG. 200. MSI detection and calling in the unpaired mode is used for tumor-only samples, i.e. there where there is no matched tumor-normal sequencing data, or if the coverage threshold discussed above is not met for the normal sample in paired mode.

As in the paired mode, initially MSI loci read filtering and sampling quality control is performed. To be a MSI loci mapping read, the read must be mapped to the MSI locus during the alignment process of a bioinformatics pipeline. In an example, the mapping read must also contain the 5 base pairs in both the front and rear flank of the microsatellite, with any number of expected repeating unit in between. In this example, if 5 or more microsatellites have less than 30× coverage, the assay cannot be run.

In an exemplary embodiment of MSI classification in the unpaired mode, the mean and variance of the distribution of the number of repeat units is calculated for each microsatellite locus in a sample. If there are no reads mapping to a particular locus, the mean and variance of the number of repeat units is imputed for that locus based on the average values from the tumors in a training set, such as the TCGA training data.

A vector containing the mean and variance data for each microsatellite locus is put into a support vector machine (SVM) classification algorithm with a linear kernel trained on samples from the TCGA colorectal and endometrial cohorts that have clinically determined MSI statuses. The mean and variance of the repeat length for each microsatellite was determined for all the TCGA training samples and the corresponding MSI PCR statuses were converted to a binary dependent variable representing whether the sample was MSI-H or not. A SVM was then trained to predict the binary MSI-H status using the mean and variance data. When running patient samples, Platt scaling is used to transform the outputs of the SVM classifier into a probability distribution over classes, returning the probability of the patient being MSI-H.

The trained MSI SVM classification algorithm groups samples into three categories: MSI-H, MSE, and MSS. If there is a greater than 70% probability of MSI-H status, the sample is classified as MSI-H. If there is between 50-70% probability of MSI-H status, the test results is too ambiguous to interpret. Those samples should make up a relatively small proportion of samples and are classified as MSE. If there is less than 50% probability of MSI-H status, the sample is considered MSS. These thresholds were generated after evaluation of samples that received both the MSI detection and calling, as well as an orthogonal clinically validated MSI test.

FIG. 201 displays a graph of validation results for microsatellite status classification from a genomic sequencing assay on a set of tumor samples. The graph displays the count of samples (y-axis) and exemplary thresholds of MSI-H, MSE, and MSS (x-axis). If there is a greater than 70% probability of MSI-H status, the sample is classified as MSI-H. If there is between 50-70% probability of MSI-H status, the test results is too ambiguous to interpret and is classified as MSE. If there is less than 50% probability of MS I-H status, the sample is considered MSS.

After MSI detection and calling is performed, for example in a cloud based server on the EC2 instance, the results may be written and saved to a network-connected production database, a network-connected immunotherapy research database, and the logs may be stored in S3. Results may be sent to physician in a printable report, digital online portal, and other media forms, such as a digital PDF or mobile application. FIG. 202 illustrates an example clinical reporting of MSI status to physicians. In this example, the patient was MSI stable and had less than 50% probability of MSI-H status as illustrated in FIG. 3.

With the MSI classification, in some examples, the techniques herein further include therapy matching based on the MSI classification. That is, the outcome of the techniques described herein is useful, for example, for determining appropriate treatment regimens for cancer patients. For instance, immune checkpoint inhibitors are suitable for treating cancers with microsatellite instability (MSI). Pembrolizumab (KEYTRUDA, Merck & Co.), for example, can be administered to adult and pediatric patients with unresectable or metastatic, microsatellite instability-high (MSI-H) or mismatch repair deficient (dMMR) solid tumors, including in those patients that have progressed following prior treatment and who have no satisfactory alternative treatment options. Pembrolizumab also may be administered to patients with MSI-H or dMMR colorectal cancer that has progressed following treatment with a fluoropyrimidine, oxaliplatin, and irinotecan. Ipilimumab (YERVOY, Bristol-Myers Squibb Company Inc.) and nivolumab (OPDIVO, Bristol-Myers Squibb Company) can be administered, for example, in MSI-H or dMMR metastatic colorectal cancer (mCRC) patients, including patients that have progressed following treatment with a fluoropyrimidine, oxaliplatin, and irinotecan. An example of an anti-PD-L1 antibody is durvalumab. An example of an anti-CTLA antibody is tremelimumab. In various aspects, the disclosure contemplates a method wherein a cancer therapy, such as a checkpoint inhibitor (e.g., PD-1 inhibitor, PD-L1 inhibitor, PD-L2 inhibitor, CTLA-4 inhibitor, and the like), is administered to patient with MSI-H tumors as determined by the methods described herein.

FIG. 5 illustrates an MSI determination processing system 100 that may be implemented on a computing device such as a computer, tablet or other mobile computing device, or server. The system 100 may include a number of processors, controllers or other electronic components for processing sequence data and performing the processes described herein. As illustrated, the system 100 may be implemented on a computing device 6216 and in particular on one or more processing units, which may represent Central Processing Units (CPUs), and/or on one or more or Graphical Processing Units (GPUs), including clusters of CPUs and/or GPUs. Features and functions described for the system 100 may be stored on and implemented from one or more non-transitory computer-readable media of the computing device 6216. The computer-readable media may include, for example, an operating system and an MSI determination framework having elements corresponding to the processes described in reference to FIGS. 199 and 200. More generally, the computer-readable media may store trained SVM models, executable code, etc. use for implementing the techniques herein. The computing device 6216 includes a network interface communicatively coupled to a network 6206, for communicating to and/or from a portable personal computer, smart phone, electronic document, tablet, and/or desktop personal computer, or other computing devices. The computing device further includes an I/O interface connected to devices, such as digital displays, user input devices, etc. In the illustrated example, the MSI determination processing system 100 is implemented on a single server 6216. However, the functions of the system 100 may be implemented across distributed devices 6216, 6218, 6219, etc. connected to one another through a communication link. In other examples, functionality of the system 100 may be distributed across any number of devices, including the portable personal computer, smart phone, electronic document, tablet, and desktop personal computer devices shown. The network 6206 may be a public network such as the Internet, private network such as research institutions or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 6216 may represent a CPU-type processing unit, a GPU-type processing unit, a field-programmable gate array (FPGA), another class of digital signal processor (DSP), or other hardware logic components that can be driven by a CPU.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

IX. Predicting <OBJECTIVE> from Patient Records

FIG. 204 illustrates a system 6220 for generating and modeling predictions of patient objectives. Predictions may be generated from patient information represented by the feature modules 6221.

Feature Modules 6221 may comprise a collection of features available for every patient in the system 6220. These features may be used to generate and model predictions in the system 6220. While feature scope across all patients is informationally dense, a patient's feature set may be very sparsely populated across the entirety of the collective feature scope of all features across all patients. For example, the feature scope across all patients may expand into the tens of thousands of features while a patient's unique feature set may only include a subset of hundreds or thousands of the collective feature scope based upon the records available for that patient.

Feature collections may include a diverse set of fields available within patient health records 114. Clinical information may be based upon fields which have been entered into an electronic medical record (EMR) or an electronic health record (EHR) by a physician, nurse, or other medical professional or representative. Other clinical information may be curated 6226 from other sources, such as molecular fields from genetic sequencing. Sequencing may include next-generation sequencing (NGS) and may be long-read, short-read, or other forms of sequencing a patient's somatic and/or normal genome. A comprehensive collections of features in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from an RNA feature module 6222 or a DNA feature module 6223 sequencing.

Another subset of features, imaging features from imaging feature module 6228, may comprise features identified through review of a specimen through pathologist review, such as a review of stained H&E or IHC slides. As another example, a subset of features may comprise derivative features obtained from the analysis of the individual and combined results of such feature sets. Features derived from DNA and RNA sequencing may include genetic variants 6229 which are present in the sequenced tissue. Further analysis of the genetic variants 6229 may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology features.

Features derived from structured, curated, or electronic medical or health records 6225 may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/ statuses, or corresponding dates to any of the above.

Features may be derived from information from additional medical or research based Omics fields 6224 including proteome, transcriptome, epigenome, metabolome, microbiome, and other multi-omic fields. Features derived from an organoid modeling lab may include the DNA and RNA sequencing information germane to each organoid and results from treatments applied to those organoids. Features derived from imaging data 6228 may further include reports associated with a stained slide, size of tumor, tumor size differentials over time including treatments during the period of change, as well as machine learning approaches for classifying PDL1 status, HLA status, or other characteristics from imaging data. Other features may include the additional derivative features sets 6230A from other machine learning approaches based at least in part on combinations of any new features and/or those listed above. For example a machine learning model may generate a likelihood that a patient's cancer will metastasize to a predictions a patient's future probability of metastasis to another organ in the body, origin of a metastasized tumor, or predict progression free survival based on a patient's state, collection of features, at any time during their treatment. Other such predictions may include cancer/disease sub-type classifications for enriching a data set, or the likelihood a patient may take a medication at certain time points in their treatment progress. Additional derivative feature sets are discussed in more detail with respect to FIG. 205, below. Other features that may be extracted from medical information may also be used. There are many thousands of features, and the above listing of types of features are merely representative and should not be construed as a complete listing of features.

In addition to the above features and enumerated modules. Feature modules 6221 may further include one or more of the following modules within their respective modules as a sub-module or as a stand alone module.

Germline/somatic DNA feature module 6223 may comprise a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module 6222 may comprise a feature collection associated with the RNA-derived information of a patient, such as transcriptome information. These features may include raw sequencing results, transcriptome expressions, genes, mutations, variant calls, and variant characterizations.

A metadata module may comprise a feature collection associated with the human genome, protein structures and their effects, such as changes in energy stability based on a protein structure.

A clinical module may comprise a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module may comprise a feature collection associated with information derived from imaging records of a patient. Imaging records may include H&E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module may comprise a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

A microbiome module may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

Proteome module may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation. *-Omics module(s) —A feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

A sufficiently robust collection of features may include all of the features disclosed above; however, predictions of certain <objectives> based from the available features may include models which are optimized and trained from a selection of features that are much more limiting than the exhaustive feature set. Such an <objective> constrained feature set may include as few as tens to hundreds of features. For example, a prediction of <objective> may include predicting the likelihood a patient's tumor may metastasize to the brain. A model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup. Optimized feature sets are disclosed with more details with respect to FIGS. 206-208, below.

The feature store 6230B may enhance a patient's feature set through the application of machine learning and analytics by selecting from any features, alterations, or calculated output derived from the patient's features or alterations to those features. The feature store 6230B may generate new features from the original features found in feature module 6221 or may identify and store important insights or analysis based upon the features. The selections of features may be based upon an alteration or calculation to be generated, and may include the calculation of single or multiple nucleotide polymorphisms insertion or deletions of the genome, a tumor mutational burden, a microsatellite instability, a copy number variation, a fusion, or other such calculations. An exemplary output of an alteration or calculation generated which may inform future alterations or calculations includes a finding of hypertrophic cardiomyopathy (HCM) and variants in MYH7. Wherein previous classified variants may be identified in the patient's genome which may inform the classification of novel variants or indicate a further risk of disease. An exemplary approach may include the enrichment of variants and their respective classifications to identify a region in MYH7 that is associated with HCM. Any novel variants detected from a patient's sequencing localized to this region would increase the patient's risk for HCM. Features which may be utilized in such an alteration detection include the structure of MYH7 and classification of variants therein. A model which focuses on enrichment may isolate such variants. The feature store selection, alteration, and calculations will be disclosed in more detail with respect to FIG. 205, below.

The feature generation 6235 may process features from the feature store 6230B by selecting or receiving features from the feature store 6230B. The features may be selected based on a patient by patient basis, a target/objective by patient basis, or a target/objective by all patient basis, or a target/objective by cohort basis. In the patient by patient basis, features which occur a specified patient's timeline of medical history may be processed. In the target/objective by patient basis, features which occur in a specified patient's timeline which inform an identified target/objective prediction may be processed. Targets/objectives may include a combination of an objective and a horizon, or time period, such as Progression within 6 months; Progression within 12 months; Progression within 24 months; Progression within 60 months, Death within 6 months; Death within 12 months; Death within 24 months; Death within 60 months; First Administration of Medication within 7, 14, 21, or 28 days; First Occurrence of Procedure within 7, 14, 21, or 28 days; First Occurrence of Adverse Reaction within 6, 12, or 24 months of Initial Administration; Metastasis within 3 months; Metastasis to Organ within 3, 6, 9, 12, or 24 months; or Metastasis from Primary Organ Site to Secondary Organ Site within 3, 6, 9, 12, or 24 months. The above listing of targets/objectives is not exhaustive, other objectives and horizons may be used based upon the predictions requested from the system. In the target/objective by all patient basis, features which occur in each patient's timeline which inform an identified target/objective prediction may be processed for each patient until all patients have been processed. In the target/objective by cohort basis, features which occur in each patient's timeline which inform an identified target prediction may be processed for each patient until all patients of a cohort have been processed. A cohort may include a subset of patients having attributes in common with each other. For example, a cohort may be a collection of patients which share a common institution (such as a hospital or clinic), a common diagnosis (such as cancer, depression, or other illness), a common treatment (such as a medication or therapy), or common molecular characteristics (such as a genetic variation or alteration). Cohorts may be derived from any feature or characteristic included in the feature modules 6221 or feature store 6230B. Feature generation may provide a prior feature set and/or a forward feature set to a respective objective module corresponding to the target/objective and/or prediction to be generated. Prior and forward feature sets will be disclosed in more detail with respect to FIGS. 206-208, below.

Objective Modules 6240 may comprise a plurality of modules: Observed Survival 6242, Progression Free Survival 6244, Metastasis Site 6246, and further additional models 6248 which may include modules such as Medication or Treatment prediction, Adverse Response prediction, or other predictive models. Each module 6242, 6244, 6246, and 6248 may be associated with one or more targets 6242*a*, 6244*a*, 6246*a*, and 6248*a*. For example, observed survival module 6242 may be associated with targets 6242*a* having the objective 'Death' and time periods '6, 12, 24, and 60 months.' Progression free survival module 6244 may be associated with targets 6244*a* having the objective 'Progression' and time periods '6, 12, 24, and 60 months.' Metastasis Site module 6246 may be associated with targets 6246*a* having the objective 'Metastasis, Metastasis to Organ, Metastasis from Primary Organ Site to Secondary Organ Site' and time periods '3/6/9/12/24 months.' Additional models 6248, such as a Propensity Module may be associated with targets 6248*a* 'Medications, Treatments, and Therapies' and time periods 7, 14, 21, and 28 days.' Each module 6242, 6244, 6246, and 6248 may be further associated with models 6242*b*, 6244*b*, 6246*b*, and 6248*b*. Models 6242*b*, 6244*b*, 6246*b*, and 6248*b* may be gradient boosting models, random forest models, neural networks (NN), regression models, Naïve Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. The training data may be based upon features such as the objective specific sets disclosed with respect to FIGS. 206-208, below. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict an objective/target pairing. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models 6242*b*, 6244*b*, 6246, and 6248*b*.

Models may also be duplicated for particular datasets which may be provided independently for each objective module 6242, 6244, 6246, and 6248. For example, the metastasis site objective module 6246 may receive a DNA feature set, an RNA feature set, a combined RNA and DNA feature set, and observational feature set, or a complete dataset comprising all features for each patient. A model 6246*b* may be generated for each of the potential feature sets or targets 6246*a*. Each module 6242, 6244, 6246, and 6248 may be further associated with Predictions 6242*c*, 6244*c*, 6246*c*, and 6248*c*. A prediction may be a binary representation, such as a "Yes—Target predicted to occur" or "No—Target not predicted to occur." Predictions may be a likelihood representation such as "target predicted to occur with 83% probability/likelihood." Predictions may be performed on patient data sets having known outcomes to identify insights and trends which are unexpected. For example, a cohort of patients may be generated for patients with a common cancer diagnosis who have either remained progression free for five years after diagnosis, have progressed within five years after diagnosis, or who have passed away within five years of diagnosis. A prediction model may be associated with an objective for progression free survival and a target of PFS within 2 years. The PFS model may identify every event in each patient's history and generate a prediction of whether the patient will be progression free within 2 years of that event. The cohort of patients may generate, for each event in a patient's medical file, the probability that the patient will remain progression free within the next two years and compare that prediction with whether the patient actually was progression free within two years of the event. For example, a prediction that a patient may be progression free with a 74% likelihood but in-fact progresses within two years may inform the prediction model that intervening events before the progression are worth reviewing or prompt further review of the patient record that lead to the prediction to identify characteristics which may further inform a prediction. An actual occurrence of a target is weighted to 1 and the non-occurrence of the event is weighted to 0, such that an event which is likely to occur but does not may be represented by the difference (0-0.73), an event which is not likely to occur but does may be represented by the difference (0.22-1), to provide a substantial difference in values in comparison to events which are closely predicted (0-0.12 or 1-0.89) having a minimal difference. Predictions will be discussed in further detail with respect to FIG. X, below. For determining a prediction, each module 6242, 6244, 6246, and 6248 may be associated with a unique set of prior features, forward features, or a combination of prior features and forward features which may be received from feature generation 6235. Selection of the unique set(s) of features will be disclosed in more detail with respect to FIGS. 206-208, below.

Prediction store 6250 may receive predictions for targets/objectives generated from objective modules 6240 and store them for use in the system 6220. Predictions may be stored in a structured format for retrieval by a webform based interactive user interface which may include webforms 6260*a-n*. Webforms may support GUIs available to a user of the system for performing a plurality of analytical functions, including initiating or viewing the instant predictions from objective modules 6240 or initiating or adjusting the cohort of patients from which the objective modules 6240 may perform analytics from. Reports 6270*a-n* may be generated and released to the user.

Webforms and Reports are described in more detail in US XYZ1 and XYZ2, incorporated by reference, herein (maybe). Lens, SC, Propensity?

FIG. 205 illustrates the generation of additional derivative feature sets 6230A of FIG. 204 and the feature store using alteration modules. An alteration module may be one or more servers, scripts, or other executable algorithms which generate alteration features associated with de-identified patient features from the feature collection. An SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in our susceptibility to a wide range of diseases (e.g. —sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10 000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy.

Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides.

CNV are the phenomenon in which structural variations may occur in sections of nucleotides, or base pairs that include repetitions, deletions, or inversions. A classification of a CNV as "Reportable" means that the CNV has been identified in one or more reference databases as influencing the tumor cancer characterization, disease state, or pharmacogenomics, "Not Reportable" means that the CNV has not been identified as such, and "Conflicting Evidence" means that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes.

Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer.

Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer. An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. A Therapies module may identify differences in cancer cells (or other cells near them) that help them grow and thrive and drugs that "target" these differences. Treatment with these drugs is called targeted therapy. For example, many targeted drugs go after the cancer cells' inner 'programming' that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes.

Others boost the way your body fights the cancer cells. This can affect where these drugs work and what side effects they cause. Matching targeted therapies may include identifying the therapy targets in the patients and satisfying any other inclusion or exclusion criteria. A VUS (variant of unknown significance) module may identify variants which are called but cannot be classify as pathogenic or benign at the time of calling. VUS may be catalogued from publications regarding a VUS to identify if they may be classified as benign or pathogenic. A Trial module may identify and test hypotheses for treating cancers having specific characteristics by matching features of a patient to clinical trials. These trials have inclusion and exclusion criteria that must be matched to enroll which may be ingested and structured from publications, trial reports, or other documentation. An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another. An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms. A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing. The structural variants application may also be incorporated by reference.

FIGS. 206-208 illustrate the generation of feature sets from the feature store on a target/objective basis. FIG. 206 illustrates a system 6400 for retrieving a first subset 1-N of features from the feature store 120. Different targets and objective modules may perform optimally on different feature sets. Feature selector and Prior feature set generate (unlabeled, but currently represented by a multiplexer/trapezoid) may select features 1-N based on the provided target and objective to produce an optimized, reduced feature set from which a patient-by-patient prior feature set may be generated. A prior feature set is a collection of all features that occurred in a patient history before a specific date. The specific date may be selected from the current date at running of the model or any date in the past. In an exemplary <objective> prediction model, the specific date may be an anchor point corresponding to the time of genetic sequencing at a laboratory, such as when a genetic sequencing laboratory provides results of tumor sequencing.

Predictions may be effective tools for data science analytics to measure the impact of treatments on the outcome of a patient's diagnosis, compare the outcomes of patients who took a medication against patients who did not, or whether a patient will metastasize in a specified time period. It may be advantageous to separate a patient into a collection of distinct prior feature sets and forward feature sets such that at every time point in the patient's history, predictions may be made and a more robust model generated that accurately predicts a patient's future satisfaction of a target/objective. A forward feature set may be advantageous when the predictive period for a target/objective combination begins to exceed a period of time that new information may be entered into the system 6400. For example, a prediction that a patient may take a medication in the next 16-25 days has a limited window for new information from the date of prediction such that the prediction is unlikely to change based on information that becomes available within the next 16-25 days. However, a prediction that a patient's cancer will remain progression-free for the next 24 months may be greatly influenced by events that could happen in the next 24 months.

Therefore, an exemplary system 6400 may generate a forward feature set which looks to events that may occur during the prediction period at feature generator 6435. Generation of forward feature sets are disclosed above with reference to SC Patent application and should be covered here with a potential incorporation by reference. In one embodiment, feature pass-through 6440 may pass the prior feature set though the forward feature mapping 6430 to objective modules 6240.

As disclosed above, the metastasis site objective module 6246 may receive a DNA feature set, an RNA feature set, a combined RNA and DNA feature set, and observational feature set, or a complete dataset comprising all features for each patient. A model 6246b may be generated for each of the potential feature sets or targets 6246a. FIG. 207 illustrates an exemplary prior feature set which may be generated for a target/objective combination for predicting metastasis to brain within 24 months where the inputs narrowed to the prior features based on the target/objective of "metastasis to brain within 24 months—all features". A sufficiently trained model may identify a combination of features including cancer site, date since diagnosis, gender, symptoms, and sequencing information as the most relevant features to predicting metastasis of a patient. In some instances, a patient's tumor may be more likely to metastasize to the brain when the originating tumor is an EGFR or HER2 positive lung cancer, a patient's tumor origin alone may influence metastasis when the origin is a primary neoplasm such as melanoma, lung, breast, renal, and colon cancer, the age of the patient may also play a role as children may be more likely to metastasize than adults, a male patient with lung cancer may be more likely to metastasize, a female patient with breast cancer may also be more likely to metastasize, symptoms implicating the brain from either neural discomfort such as headache, paresthesia or tingling in the patient's extremities, or a measurable increase in intercranial pressure may also increase the patient's likelihood for metastasis, and RNA/DNA sequencing results indicating a presence of a NOTCH2, FANCD2, EGFR, or TP53 variation or copy number change may increase a patient's likelihood for metastasis. Therefore, a predictive model may select a subset of features from them feature store 6230B including each of these features.

FIG. 208 illustrates a prior feature selection set for a target/objective pair metastasis to brain within 24 months using an observational model. Features of an observational model may be limited to only features which may be observed from patient results from tests, progress notes, but not medications, procedures, therapies, or other proactive actions taken by a physician in treating the patient. General features in the observational feature set may include a patient's age at event for each event which may exist in the patient's record. Preprocessing steps may be performed on the ages available to reduce the dimensionality of the input features. For example, instead of having 100 points for ages of patients, the patient's age may be fitted into a group such as a range including 00 to 09, 10 to 19, 100 to 109, 110 to 119, 20 to 29, 30 to 39, 40 to 49, 50 to 59, 60 to 69, 70 to 79, 80 to 89, 90 to 99, or Unknown for each event in the patient's record. The reduction accomplishing a binning of features allowing for a more robust analysis of the bins rather than the granular age. The patient's gender or race may be normalized so that different sources having different ethnicity options are binned into similar ethnicities. For example, a race of Caucasian may be binned with white or a dataset including Japanese, Korean, Phillipean distinctions may be binned into Pacific Islander or Asian. Features which may be entered into the record by occurrence may be translated and tracked by a number of days since the first or last occurrence may also be generated and supplied as a prior feature. These days since the first or last occurrence features may include a tumor finding by histology for tumors including acinar_cell_carcinoma, adenocarcinoma,_no_subtype, carcinoma,_no_subtype, infiltrating_duct_carcinoma, lobular_carcinoma, malignant_neoplasm,_primary, mucinous_adenocarcinoma, neuroendocrine_carcinoma, non_small_cell_carcinoma, otherGroup, small_cell_carcinoma, small_cell_neuroendocrine_carcinoma, squamous_cell_carcinoma,_no_icd_o_subtype, or transitional_cell_carcinoma. Other days since the first or last occurrence features may include tumor finding by histopath grade or T-N-M stages including grade_1_(well_differentiated), grade_2_(moderately_differentiated), grade_3_(poorly_differentiated), grade_4_(undifferentiated), high_grade, m0, m1, mx, n0, n1, n2, n3, nx, pn0, pn1, pn2, pnx, stage_1, stage_2, stage_3, stage_4, pt1, pt2, pt3, pt4, t0, t1, t2, t3, t4, tx, or valg_stage-extensive. Even other days since first or last occurrence features may include cancer type determinations or findings of breast, cervix_uteri, colon, head_and_neck, kidney, lung, lymphoid,_hemopoietic_and/or_related_tissue, otherGroup, ovary, pancreas, prostate, respiratory_tract, skin, skin_of_trunk, soft_tissues, stomach, tongue, unknown_site, or urinary_bladder. Still further days since first or last occurrence features may include medical events, prior medications, or comorbidity or recurrence events including emergency_room_admission, inpatient_stay, seen_in_hospital_outpatient_department, Abnormal_findings_on_diagnostic_imaging_of_breast, Administration_of_antineoplastic_agent, Anemia, Dehydration, Disorder_of_bone, Disorder_of_breast, Dyspnea, Essential_hypertension, Fatigue, Imaging_of_thorax_abnormal, Immunization_advised, Long_term_current_use_of_drug_therapy, Osteoporosis, Past_history_of_procedure, Screening_for_malignant_neoplasm_of_breast, chronic_obstructive_lung_disease, otherGroup, type_2_diabetes_mellitus, type_2_diabetes_mellitus_without_complication, emergency_room_admission, inpatient_stay, seen_in_hospital_outpatient_department, lung, otherGroup, or soft_tissues. DNA and RNA features which have been identified from a next generation sequencing (NGS) of a patient's tumor or normal specimen to identify germline or somatic variants include categorizations of RNA expression analysis from an RNA auto encoder, ABCB1-somatic, ACTA2-germline, ACTC1-germline, ALK-fluorescence_in_situ_hybridization_(fish), ALK-immunohistochemistry_(ihc), ALK-md_dictated, ALK-somatic, AMER1-somatic, APC-gene_mutation_analysis, APC-germline, APC-somatic, APOB-germline, APOB-somatic, AR-somatic, ARHGAP35-somatic, ARID1A-somatic, ARID1B-somatic, ARID2-somatic, ASXL1-somatic, ATM-gene_mutation_analysis, ATM-germline, ATM-somatic, ATP7B-germline, ATR-somatic, ATRX-somatic, AXIN2-germline, BACH1-germline, BCL11B-somatic, BCLAF1-somatic, BCOR-somatic, BCORL1-somatic, BCR-somatic, BMPR1A-germline, BRAF-gene_mutation_analysis, BRAF-md_dictated, BRAF-somatic, BRCA1-germline, BRCA1-somatic, BRCA2-germline, BRCA2-somatic, BRD4-somatic, BRIP1-germline, CACNA1S-germline, CARD11-somatic, CASR-somatic, CD274-immunohistochemistry_(ihc), CD274-md_dictated, CDH1-germline, CDH1-somatic, CDK12-germline, CDKN2A-immunohistochemistry_(ihc), CDKN2A-germline, CDKN2A-somatic, CEBPA-germline, CEBPA-somatic, CFTR-somatic, CHD2-somatic, CHD4-somatic, CHEK2-germline, CIC-somatic, COL3A1-germline, CREBBP-somatic, CTNNB1-somatic, CUX1-somatic, DICER1-somatic, DOT1L-somatic, DPYD-somatic, DSC2-germline, DSG2-germline, DSP-germline, DYNC2H1-somatic, EGFR-gene_mutation_analysis, EGFR-immunohistochemistry_(ihc), EGFR-md_dictated, EGFR-germline, EGFR-somatic, EP300-somatic, EPCAM-germline, EPHA2-somatic, EPHA7-somatic, EPHB1-somatic, ERBB2-fluorescence_in_situ_hybridization_(fish), ERBB2-immunohistochemistry_(ihc), ERBB2-md_dictated, ERBB2-somatic, ERBB3-somatic, ERBB4-somatic, ESR1-immunohistochemistry_(ihc), ESR1-somatic, ETV6-germline, FANCA-germline, FANCA-somatic, FANCD2-germline, FANCI-germline, FANCL-germline, FANCM-somatic, FAT1-somatic, FBN1-germline, FBXW7-somatic, FGFR3-somatic, FH-germline, FLCN-germline, FLG-somatic, FLT1-somatic, FLT4-somatic, GATA2-germline, GATA3-somatic, GATA4-somatic, GATA6-somatic, GLA-germline, GNAS-somatic, GRIN2A-somatic, GRM3-somatic, HDAC4-somatic, HGF-somatic, IDH1-somatic, IKZF1-somatic, IRS2-somatic, JAK3-somatic, KCNH2-germline, KCNQ1-germline, KDM5A-somatic, KDM5C-somatic, KDM6A-somatic, KDR-somatic, KEAP1-somatic, KEL-somatic, KIF1B-somatic, KMT2A-fluorescence_in_situ_hybridization_(fish), KMT2A-somatic, KMT2B-somatic, KMT2C-somatic, KMT2D-somatic, KRAS-gene_mutation_analysis, KRAS-md_dictated, KRAS-somatic, LDLR-germline, LMNA-germline, LRP1B-somatic, MAP3K1-somatic, MED12-somatic, MEN1-germline, MET-fluorescence_in_situ_hybridization_(fish), MET-somatic, MKI67-immunohistochemistry_(ihc), MKI67-somatic, MLH1-germline, MSH2-germline, MSH3-germline, MSH6-germline, MSH6-somatic, MTOR-somatic, MUTYH-germline, MYBPC3-germline, MYCN-somatic, MYH11-germline, MYH11-somatic, MYH7-germline, MYL2-germline, MYL3-germline, NBN-germline, NCOR1-somatic, NCOR2-somatic, NF1-somatic, NF2-germline, NOTCH1-somatic, NOTCH2-somatic, NOTCH3-somatic, NRG1-somatic, NSD1-somatic, NTRK1-somatic, NTRK3-somatic, NUP98-somatic, OTC-germline, PALB2-germline, PALLD-somatic, PBRM1-somatic, PCSK9-germline, PDGFRA-somatic, PDGFRB-somatic, PGR-immunohistochemistry_(ihc), PIK3C2B-somatic, PIK3CA-somatic, PIK3CG-somatic, PIK3R1-somatic, PIK3R2-somatic, PKP2-germline, PLCG2-somatic, PML-somatic, PMS2-germline, POLD1-germline, POLD1-somatic, POLE-germline, POLE-somatic, PREX2-somatic, PRKAG2-germline, PTCH1-somatic, PTEN-fluorescence_in_situ_hybridization_(fish), PTEN-gene_mutation_analysis, PTEN-germline, PTEN-somatic, PTPN13-somatic, PTPRD-somatic, RAD51B-germline, RAD51C-germline, RAD51D-germline, RAD52-germline, RAD54L-germline, RANBP2-somatic, RB1-germline, RB1-somatic, RBM10-somatic, RECQL4-somatic, RET-fluorescence_in_situ_hybridization_(fish), RET-germline, RET-somatic, RICTOR-somatic, RNF43-somatic, ROS1-fluorescence_in_situ_hybridization2fish), ROS1-md_dictated, ROS1-somatic, RPTOR-somatic, RUNX1-germline, RUNX1T1-somatic, RYR1-germline, RYR2-germline, SCN5A-germline, SDHAF2-germline, SDHB-germline, SDHC-germline, SDHD-germline, SETBP1-somatic, SETD2-somatic, SH2B3-somatic, SLIT2-somatic, SLX4-somatic, SMAD3-germline, SMAD4-germline, SMAD4-somatic, SMARCA4-somatic, SOX9-somatic, SPEN-somatic, STAG2-somatic, STK11-gene_mutation_analysis, STK11-germline, STK11-somatic, TAF1-somatic, TBX3-somatic, TCF7L2-somatic, TERT-somatic, TET2-somatic, TGFBR1-germline, TGFBR2-germline, TGFBR2-somatic, TMEM43-germline, TNNI3-germline, TNNT2-germline, TP53-gene_mutation_analysis, TP53-immunohistochemistry_(ihc), TP53-md_dictated, TP53-germline, TP53-somatic, TPM1-germline, TSC1-germline, TSC1-somatic, TSC2-germline, TSC2-somatic, VHL-germline, WT1-germline, WT1-somatic, XRCC3-germline, ZFHX3-somatic, fluorescence_in_situ_hybridization_(fish), gene_mutation_analysis, gene_rearrangement_analysis, or immunohistochemistry_(ihc) results. A patient's prior feature set may be selected from each of the above features which is applicable to the patient's structured medical records available in the feature store 6230B. Prior feature sets from the feature generator may be provided to the corresponding model for the target/objective pair identified and predictions generated for the patient.

FIG. 209 is a flow chart of a method 6446 for generating prior feature sets and forward feature sets according to one embodiment. At step 610, the system may receive a set of data on of one or more patients over time. The received set of data may include features from the feature generation 6235 as a refined feature set described above with respect to FIGS. 207 and 208. Patient records are received which may span a single entry to decades of medical records. While these records indicate the status of the patient over time, they may be received in a single transmission or a batch of transmissions. Each patient may have hundreds of records in the system. An exemplary set of records for a patient may include physician note entries from a routine doctor's visit where the doctor prescribed an antibiotic after determining the patient has a bacterial infection, a scheduling request to see a specialist after the patient complained about headaches, scheduling request to take an MRI scan, an MRI report summarizing the radiologists findings of an unknown mass in the patient's lungs, a scheduling request to perform a biopsy of the mass, a pathologist's report of the cells present in the biopsy specimen, a prescription to begin a first line of therapy for lung cancer, an order for genetic sequencing of the biopsy specimen, and a subsequent next-generation sequencing (NGS) report for the biopsy specimen. At step 620, the system may identify patient timepoints. Identified timepoints may include all timepoints from patient diagnosis up to the last entry or patient's death. In some target/objective pairs, the only timepoint for identification is the most recent timepoint in which the patient received genetic sequencing results, such as results from a next-generation sequencer for the genomic composition of the patient's tumor biopsy. An exemplary timepoint selection for a metastasis to brain prediction may include only the date that the next-generation sequencing report for the biopsy specimen was performed. In another embodiment, timepoint selection for a patient's likelihood to take undergo a progression event (an event from which the cancer progresses such as metastasis, the tumor size increases, or other events known to those of ordinary skill in the art) may include timepoints from records: the pathologist's report of the cells present in the biopsy specimen, the prescription to begin a first line of therapy for lung cancer, the order for genetic sequencing of the biopsy specimen, and the subsequent next-generation sequencing report for the biopsy specimen. At step 630, the system may calculate outcome targets for a horizon window and outcome event. Outcome events may be the objectives and horizon windows may be the time periods such that an objective/target pair is calculated. An exemplary target/objective pair may be metastasis to brain within 24 months. The target/objective pair may also include the model from which the pair should be calculated. An exemplary model may be an observation model. Other target/objective pairs, datasets, and models are introduced above with respect to objective modules 6240. At step 640, the system may identify prior features and calculate the state of the prior features at each timepoint. For a target/objective pair "metastasis to brain within 24 months-observational model" as described above with respect to FIG. 208, the set of prior features may be calculated once, at the time of NGS. For a target objective pair "PFS within 2 years" the set of prior features may be calculated for each timepoint corresponding to the following records: the pathologist's report of the cells present in the biopsy specimen, the prescription to begin a first line of therapy for lung cancer, the order for genetic sequencing of the biopsy specimen, and the subsequent next-generation sequencing report for the biopsy specimen. At step 650, the system may identify forward features for every horizon and outcome combination where the horizon is of sufficient duration that an event happening after the anchor point but before the termination of the timeline may have a noticeable effect on the reliability of the prediction. For horizons within a number of days, it is unlikely a forward feature set will be calculated; however, for horizons spanning months or years may benefit from a forward feature set. Forward features comprise the same feature sets as prior features but involve a conversion of the features from a backwards looking focus to a forwards looking focus. Exemplary forward features may include: "Will patient take medication A after date of anchor point and before date of endpoint?", "Will patient experience headaches after date of anchor point and before date of endpoint", "Will patient progress after date of anchor point and before date of endpoint", or any other forward looking version of features in the prior feature set. Forward features may be predicted using another target/objective prediction model first, and the predictions themselves added into the feature set to influence the final prediction. For example, a patient who is observing increased intercranial pressure may be predicted to experience headaches and a patient who experiences both increased intercranial pressure and headaches may be predicted to be more likely to have metastasis to the brain. A model which finds that a patient with an increase in intercranial pressure is likely to experience headaches within two weeks may provide additional features from which to inform the prediction of metastasis to the brain. While the example is hypothetical, models may be trained to predict occurrence of each feature.

FIG. 210 illustrates an exemplary timeline of events in a patient's medical record which may provide prior features for a prior feature set.

Every patient's medical record may have a unique series of events as they face the challenges of rigoring through treatment for a disease. In patients who are diagnosed with cancer, some of these events may provide important features to prediction of an <objective> for the patient. For an exemplary patient, the first event informing their prior feature set may be a progress note from the date of diagnosis (Jan. 1, 2000) containing the patient's information, cancer type, cancer stage, and other features. The second event informing their prior feature set may be a prescription for medications of a first line of therapy (Feb. 29, 2000) containing the patient's medications, dosages, and expected administration frequency. A third and fourth event may be a progress note from a physician which notes that an imaging scan of the tumor (Aug. 11, 2001) shows that it has increased in size since the first line of therapy started and may prompt the physician to prescribe medications for a second line of therapy triggering another progress note (Sep. 12, 2001) containing the patient's new medications, dosages, and expected administration frequency. The final events in the patient's medical record prior to triggering a prediction of the patient's site-specific prediction of metastasis may include a physician's order for sequencing a biopsy of the tumor (Dec. 16, 2002) and a subsequent sequencing report (Jan. 24, 2003) comprising the results of that sequencing. Upon a system, such as the system of FIGS. 204 and 208 processing site-specific metastatic predictions, including a metastasis to brain within 24 months, detection of a sequencing report on file, a pipeline may trigger generation of the prediction.

FIG. 211 illustrates an exemplary flowchart of a method 6450 for performing a model for predicting site-specific metastasis in a patient in accordance with an example.

At step 810, the system may receive target/objective pairs and prior feature set for a cohort of patients. The system may receive a request to process one or more target/objective pairs from one or more prior and forward feature sets. Each target/objective pair may be matched to a specific combination of prior and/or forward feature sets based upon the requirements of a corresponding model. At step 820, the system may identify metastatic sites to predict. In one embodiment, each of the target/objective pairs may reference a specific metastasis site which may be passed through to model selection directly. In another embodiment, a target/objective pair may not specify a metastasis site, such as a request to predict metastasis within 60 months. The system may then select a model for each metastasis site within the available models and pass the matched target/objective pair and combination of prior and/or forward features to the model. At step 830, the system may receive prediction values for each patient of the cohort for each metastatic site. The predictions may be stored in a prediction store such as prediction store 6250 or may be passed to a webforms for displaying prediction results for a patient to a user such as the patient's physician or oncologist. At step 840, the system may graph predictions of metastasis to sites on body for a selected patient of the cohort. The graph may be generated in a corresponding webform for viewing the results of site-specific metastasis predictions. Metastasis predictions associated with the target/objective pair may be graphed on an image of a body and/or analytics may be viewed. Analytics may include the prediction percentages, survival curves of the cohort, or features which were driving factors in the prediction results generated.

One embodiment of a webform for displaying the graph will be disclosed in more detail with respect to FIG. 212, below.

FIG. 212 illustrates an exemplary webform for viewing site-specific predictions of metastasis in a single patient.

An exemplary webform may provide a patient portal to a user, such as a physician, oncologist, or patient may request predictions of metastasis based upon a target/objective scheme. For example, a user may request a prediction of metastasis to brain in the next 12 months or a prediction of metastasis to any site in the next 60 months. The system, such as system 6220 of FIG. 204, may either calculate a prediction on the fly or retrieve a precalculated prediction from the prediction store 6250 and provide the webform with the prediction information for display to the user. In one embodiment a user may request a prediction of metastasis to any site in 24 months. The webform may receive the predictions and display them to the user through the user interface of the webform. The metastasis sites may be displayed in a number of different formats. A first format may include an image of a human body which regions having metastasis predictions highlighted therein. Highlighting for regions with predictions may be color coded based upon the value of the prediction. For example, elements/organs/sites of the human body which do not have predictions may not be referenced in the image, such as the breast or colon which are not referenced. A prediction falling below a threshold of 20% may receive a callout such as a line or other indicator linking the organ to the prediction threshold, such as the bones which are referenced in the image with lines to the prediction value 16%. A prediction falling between 20% and 50% may receive a callout linking the organ to the prediction threshold and a color coded shading over the region indicating the severity of the prediction, such as the liver which are referenced in the image with a line to the prediction value 21% and a green shading over the region where a liver would be in a human. A prediction falling between 50% and 75% may receive a callout linking the organ to the prediction threshold and a color coded shading over the region indicating the severity of the prediction, for example a yellow shading over the region where the metastasis site would be in a human. A prediction exceeding 75% may receive a callout linking the organ to the prediction threshold and a color coded shading over the region indicating the severity of the prediction, such as the brain which is referenced in the image with a line to the prediction value 77% and a red shading over the region where a brain would be in a human. The above prediction ranges and combination of callout styles and color shading are provided for illustrative purposes and are not intended to limit the display to the user. Other combinations of prediction ranges, callout conventions, and/or coloring may be provided to the user without departing from the spirit of the disclosure. In addition to or as an alternative to the first format, a second format may include a histogram or bar chart which provides a side by side comparison of the predictions for differing metastatic sites. For example, a lung cancer patient may have metastasis predictions for bone, brain, and liver sites. A histogram may display the predicted values of each side-by-side to provide the user with a visual comparison of the likelihood of metastasis to each site. Other statistical, analytical, or graphical representations may be provided including charts, plots, and graphs.

FIG. 213 illustrates elements of an exemplary webform for viewing site-specific predictions of metastasis in a cohort of patients.

An exemplary webform may provide a cohort portal to a user, such as a physician, oncologist, or researcher may request predictions of metastasis based upon a target/objective scheme across an entire cohort of patients. For example, a user may request a prediction of metastasis to brain in the next 12 months or a prediction of metastasis to any site in the next 60 months. The system, such as system 6220 of FIG. 204, may either calculate a prediction on the fly or retrieve a precalculated prediction from the prediction store 6250 and provide the webform with the prediction information for display to the user. In one embodiment a user may request a prediction of metastasis to any site in 24 months. The webform may receive the predictions and display them to the user through the user interface of the webform. The receipt of the request may be facilitated through an aspect of the user interface containing one or more editable fields. For example, a first field may provide a text input or dropdown for selecting the origin site of cancer for patents of the cohort. The origin site may be selected from any diagnosable site of cancer, including: breast, lung, pancreas, prostate, colorectal, skin, brain, lymph nodes, and bone. A second field may provide a text input or a drop down for selecting a metastasis site of cancer for patients in the cohort, including: breast, lung, pancreas, prostate, colorectal, skin, brain, lymph nodes, bone, and an "any" option to group all metastasis together. A third field may provide a text input or a drop down for selecting a horizon, or time period, within which to predict the likelihood of metastasis for patients in the cohort. A fourth and fifth field may provide a text input or a drop down for selecting an anchor event and a corresponding anchor value. The anchor event being the event that must be common across all patients in the cohort and from which the prediction's horizon will toll. Anchor events and corresponding values (presented below as Event: Values) may include: First Primary Cancer Diagnosis: Any Cancer Site (breast, lung, pancreas, prostate, colorectal, skin, brain, lymph nodes, bone, etc.); First Stage: Any Cancer Stage (Stage 0, 1, 2, 3, 4); First medication: Any Medication (doxorubicin, cyclophosphamide, anastrozole, tamoxifen, dexamethasone, pegfilgrastim, etc.); First Radiotherapy: Any Radiotherapy Treatment (n-dimensional conformal radiation, cyberknife, external beam, image guided, intensity modulated, total body, radioactive isotope, etc.); First Procedure: Any Procedure (endoscopic, mastectomy, ablations, antrotomy, reconstructions, biopsies, excisions, resections, grafts, etc.); First Specimen Collection: Any Biopsy Site For Sequencing (breast, lung, pancreas, prostate, colorectal, skin, brain, lymph nodes, bone, etc.); First Alternative Grade: Any Grade (fuhrman stage 1-4, who stage i-iv, etc.); First Line of Therapy: Any Combination of LoT Medications (abiraterone+apalutamide+leuprolide, abiraterone+ascorbic acid, fluorouracil+oxaliplatin, capecitabine+fulvestrant, etc.); and other combinations of events and values which may occur in a patient's medical record. A sixth and seventh field may provide a text input box and a button that when activated stores a copy of the above selected cohort restraints under a name entered into the textbox. Alternative means for storing the cohort may be implemented in place of a text input field and button. For example, a single button may exist, which prompts a dialog box that navigates the file directory of the user's computer to select a location and name for which to store the selections or no location may be available if the user is restricted to only storing the saved cohort selections on the server for online-access only.

Selecting a cancer origin site, a cancer metastasis site, an anchor event, and/or a survival curve group may further filter the cohort to only patients which have the respective prerequisite event or outcome in their patient records, or those patients who receive the selected prediction.

The metastasis sites may be displayed in a number of different formats. A first format may include an image of a human body which regions having metastasis predictions highlighted therein. Highlighting for regions with predictions may be color coded based upon the value of the prediction. For example, elements/organs/sites of the human body which do not have predictions may not be referenced in the image, such as the breast or colon which are not referenced. A prediction falling below a threshold of 20% may receive a callout such as a line or other indicator linking the organ to the prediction threshold, such as the bones which are referenced in the image with lines to the prediction value 16%. A prediction falling between 20% and 50% may receive a callout linking the organ to the prediction threshold and a color coded shading over the region indicating the severity of the prediction, such as the liver which are referenced in the image with a line to the prediction value 21% and a green shading over the region where a liver would be in a human. A prediction falling between 50% and 75% may receive a callout linking the organ to the prediction threshold and a color coded shading over the region indicating the severity of the prediction, for example a yellow shading over the region where the metastasis site would be in a human. A prediction exceeding 75% may receive a callout linking the organ to the prediction threshold and a color coded shading over the region indicating the severity of the prediction, such as the brain which is referenced in the image with a line to the prediction value 77% and a red shading over the region where a brain would be in a human. The above prediction ranges and combination of callout styles and color shading are provided for illustrative purposes and are not intended to limit the display of such to the user.

Other combinations of prediction ranges, callout conventions, and/or coloring may be provided to the user without departing from the spirit of the disclosure. In addition to or as an alternative to the first format, a second format may include a histogram or bar chart which provides a side by side comparison of the predictions for differing metastatic sites. For example, a cohort of lung cancer patients may have metastasis predictions for bone, brain, liver, lymph node, other and any sites. A histogram may display the predicted values of each side-by-side to provide the user with a visual comparison of the likelihood of metastasis to each site.

Additionally, a set of histograms may be viewed together, one for each of a set of horizons. For example, a first histogram may display the cohort average predictions for a horizon of 6 months, a second histogram for a horizon of 12 months, a third histogram for a horizon of 24 months, a fourth histogram for a horizon of 60 months, and so on. In addition to, or as an alternative to the first or second format, prediction distributions graphs, survival curves, or kaplan meier plots may be considered. Other statistical, analytical, or graphical representations may be provided including charts, plots, and graphs.

Once a user has accessed the webform, requested predictions of metastasis based upon a target/objective scheme across an entire cohort of patients, and consumed the displayed predictions through the user interface of the webform, the user may desire to understand which features shared by members of the cohort were most influential in driving the predictions and facilitate model interpretability. An adaptive algorithm runs alongside the modeling to generate viable feature importance ranks exclusively on the selected sub-population of patients without needing to retrain the underlying models. An exemplary adaptive algorithm may: calculate population mean prediction across the patients in the cohort; encode categorical feature levels, including clustering/bucketing continuous features, as the difference/delta between the predicted value and the population mean prediction; aggregate average probability difference with the estimated percentage per categorical level and assign overall feature importance as the frequency-weighted sum of absolute value of all values; and assign an impact value representing each feature's co-occurrence with an observed deviation from prediction mean to explore the variation in impact per change in feature value. A graphical representation of the feature enrichment ranking results may be presented according to an embodiment of FIGS. 214 and 2.

FIG. 214 illustrates elements of an exemplary webform for viewing feature importance rankings of site-specific predictions of metastasis in a cohort of patients.

A first field may provide a text input, radio button, toggle, or a drop down for selecting a feature importance ranking visualization method for selecting between a heatmap, feature enrichment presentation and a scaled, ranking bar feature importance representation. One or more additional radio buttons, toggles, or other feature selectors may be presented to the user to allow the selection of which features should be included in the feature importance model. Selectable features may include any level of categorization of the features in the input data set, including patient demographics, germline results from sequencing, cancer types and/or stages, procedures or radiotherapies underwent by the patient, genomic or sequencing results of the patient's tumor or normal specimens, or medications taken by the patient. Selection of a selectable feature will trigger the inclusion or exclusion of the associated features from the feature importance calculations and the remaining features' weights will be recalculated to compensate for the adjustment to features.

An exemplary feature enrichment graphical representation may provide a heatmap of the feature importance to each model prediction of metastasized or did not metastasize. The heatmap may be selected between one or more colors such that if a single color is used in the heatmap visualization, the intensity of the color may vary to indicate a stronger or weaker importance of the feature in determining the model's prediction. The heatmap may be selected between two or more colors such that if multiple colors are used in the heatmap visualization, the color selection may vary to indicate a stronger or weaker importance of the feature in determining the model's prediction. The heatmap may be selected between two or more colors such that if multiple colors are used in the heatmap visualization, the color selection may vary to indicate a stronger or weaker importance of the feature in determining the model's prediction and the intensity of the color may further provide ranking visualizations within each classification of the feature importance. For example, a green color may be used for features which are most important to the model for predicting metastasize, a red color may be used for features which are most important to the model for predicting did not metastasize, and a yellow color may be used to features which were relevant to either metastasize or did not metastasize but were not the most significant of drivers in the prediction. Further, within each classification color of green, red, and yellow, the intensity of the color may rank the importance of the features in each category such that light intensity corresponds with features of the least importance and bright, bold colors corresponds with features of the most importance. In addition to the color and intensity selection, a percentage of the patients in the cohort which presented the feature and were predicted to have metastasized or did not metastasized may be provided in the color coding of the feature. For example a first column may be provided for prediction-metastasized features and a second column may be provided for prediction-did_not_metastasize features. Each row of the two columns may correspond to a single feature. The features hierarchically organized into the ranking of the features by importance to the predictions. A first feature may represent the greatest determining factor in the prediction of metastasized and did not metastasize and may be 'cancer stage 3 or greater.' 40% of the patients who were predicted to have metastasized had stage 3 cancer or greater while only 4% of patients who were not predicted to have metastasized had stage 3 cancer or greater. Because 40% is substantially greater than 4% the intensity of the coloring may be higher for the 40% heatmap and lower for the 4% heatmap. Another feature of the heatmap, "BRIP1-germline: moderate" may be one of the top 20 features relied on by the predictions with 58% of the patients who were predicted to have metastasized presenting the feature and 73% of the patients who were predicted to not metastasize presenting the feature.

Because 58% is greater than 40% the intensity of the color may be even greater than the 40% heatmap and the intensity of the 73% even greater still.

FIG. 215 illustrates elements of an exemplary webform for viewing feature importance rankings of site-specific predictions of metastasis in a cohort of patients.

When the first field for selecting a feature importance ranking visualization method has the scaled, ranking feature importance bar representation selected, an exemplary feature importance graphical representation may provide a ranked, bar chart of the feature importance to each model prediction of metastasized or did not metastasize. The bar chart may be selected between two colors, a first color for prediction-metastasized feature importance and a second color for prediction-did_not_metstasize feature importance. The length of the bar may correspond to the number of patients in the cohort which presented the feature and were predicted to have metastasized or did not metastasized. For example, each feature may be hierarchically organized by rows into the ranking of the features by importance to the predictions. A first color may identify features which are most important for predicting metastasized and a second color may identify features which are most important for predicting did not metastasize. A first row may identify the first feature and may represent the greatest determining factor in the prediction of metastasized and did not metastasize and may be 'cancer stage 3 or greater.' The feature may, based upon the results of the adaptive algorithm, have the bar with the greatest length to visually represent the feature's importance and the first color to indicate that the feature weighs most toward metastasized. A second row may identify the second feature and may represent the greatest determining factor in the prediction of metastasized and did not metastasize and may be 'took medication: heparin.' The feature may, based upon the results of the adaptive algorithm, have the bar with the second greatest length to visually represent the feature's importance and the second color to indicate that the feature weighs most toward did not metastasize. Features continuing down the list may have increasingly shorter bars of either the first or second color to indicate their respective weights for or against the predictions for metastasized.

FIG. 216 is an illustration of exemplary aggregate measures of performance across possible classification thresholds of input data sets according to an objective of predicting metastasis in lung cancer patients to any other cancer site within 24 months.

As discussed above with respect to FIG. 204, there are a number of models which may be selected and for each model there are a number of tuning parameters which may be considered. For an objective of metastasis prediction we may use the collection of sites to which the patient will metastasize within the specified time horizon (24 months) at each time point as the target of interest. The metastasis sites which may be considered include breast, colon, lung, liver, bone, brain and lymph node, with any other sites being grouped into a miscellaneous category. Other combinations of metastasis sites may be considered as well. During preprocessing, it may be advantageous to impose an additional requirement that each target must have more than one unique value within every cross validation fold in order to ensure the sites at which predictions are generated are variable depending on the origin cancer site.

Given a curated dataset with the five most common cancers in a cohort of all metastasized cancers being ovary, prostate, colon, breast, and lung, it may be advantageous to tune a multilabel random forest using 4 batches of 5 jobs, optimizing the average area under curce (AUC) across all target labels. In general the models seem to prefer a large number of deep trees with heavy column sampling at each split, which could be used to improve future tuning jobs.

Random forests may be instantiated from the following Parameter:Range of max_depth:(5, 23), n_estimators:(100, 1000), min_samples_leaf:(20, 200), max_features:(0.5, 0.8). The following performance scores are derived:

An ovary objective scores by metastasis site may be: Lymph node: 0.831445
Lung: 0.768152
An ovary best parameter set may be:
max_depth: 23
max_features: 0.70
min_samples_leaf: 58
n_estimators: 329
A prostate objective scores by metastasis site may be: Lymph node: 0.784173
Other site: 0.784805
Bone: 0.878749
A prostate best parameter set may be:
max_depth: 15
max_features: 0.50
min_samples_leaf: 53
n_estimators: 748
A colon objective scores by metastasis site may be:
Lymph node: 0.836868
Liver: 0.877584
Other site: 0.840575
Lung: 0.885678
A colon best parameter set may be:
max_dept h: 19
max_features: 0.57
min_samples_leaf: 55
n_estimators: 923
A breast objective scores by metastasis site may be:
Lymph node: 0.810405
Liver: 0.883235
Other site: 0.819709
Brain: 0.807003
Bone: 0.852316
Lung: 0.798472
A breast best parameter set may be:
max_depth: 23
max_features: 0.52
min_samples_leaf: 119
n_estimators: 821
A lung scores by metastasis site may be:
Lymph node: 0.725858
Liver: 0.840760
Other site: 0.771431
Brain: 0.791871
Bone: 0.724428
A lung best parameter set may be:
max_depth : 22
max_features: 0.51
m in_samples_leaf: 111
n_estimators: 344

Given a known set of hyperparameters for each objective, such as those listed above, it may be advantageous to consider the impacts of a selected feature set for each objective. For example, a feature set for DNA related features may include a proprietary calculation of the maximum effect a gene may have from sequencing results for the following genes: ABCB1-somatic, ACTA2-germline, ACTC1-germline, ALK-fluorescence_in_situ_hybridization_(fish), ALK-immunohistochemistry_(ihc), ALK-md_dictated, ALK-somatic, AMER1-somatic, APC-gene_mutation_analysis, APC-germline, APC-somatic, APOB-germline, APOB-somatic, AR-somatic, ARHGAP35-somatic, ARID1A-somatic, ARID1B-somatic, ARID2-somatic, ASXL1-somatic, ATM-gene_mutation_analysis, ATM-germline, ATM-somatic, ATP7B-germline, ATR-somatic, ATRX-somatic, AXIN2-germline, BACH1-germline, BCL11B-somatic, BCLAF1-somatic, BCOR-somatic, BCORL1-somatic, BCR-somatic, BMPR1A-germline, BRAF-gene_mutation_analysis, BRAF-md_dictated, BRAF-somatic, BRCA1-germline, BRCA1-somatic, BRCA2-germline, BRCA2-somatic, BRD4-somatic, BRIP1-germline, CACNA1S-germline, CARD11-somatic, CASR-somatic, CD274-immunohistochemistry_(ihc), CD274-md_dictated, CDH1-germline, CDH1-somatic, CDK12-germline, CDKN2A-immunohistochemistry_(ihc), CDKN2A-germline, CDKN2A-somatic, CEBPA-germline, CEBPA-somatic, CFTR-somatic, CHD2-somatic, CHD4-somatic, CHEK2-germline, CIC-somatic, COL3A1-germline, CREBBP-somatic, CTNNB1-somatic, CUX1-somatic, DICER1-somatic, DOT1 L-somatic, DPYD-somatic, DSC2-germline, DSG2-germline, DSP-germline, DYNC2H1-somatic, EGFR-gene_mutation_analysis, EGFR-immunohistochemistry_(ihc), EGFR-md_dictated, EGFR-germline, EGFR-somatic, EP300-somatic, EPCAM-germline, EPHA2-somatic, EPHA7-somatic, EPHB1-somatic, ERBB2-fluorescence_in_situ_hybridization_(fish), ERBB2-immunohistochemistry_(ihc), ERBB2-md_dictated, ERBB2-somatic, ERBB3-somatic, ERBB4-somatic, ESR1-immunohistochemistry_(ihc), ESR1-somatic, ETV6-germline, FANCA-germline, FANCA-somatic, FANCD2-germline, FANCI-germline, FANCL-germline, FANCM-somatic, FAT1-somatic, FBN1-germline, FBXW7-somatic, FGFR3-somatic, FH-germline, FLCN-germline, FLG-somatic, FLT1-somatic, FLT4-somatic, GATA2-germline, GATA3-somatic, GATA4-somatic, GATA6-somatic, GLA-germline, GNAS-somatic, GRIN2A-somatic, GRM3-somatic, HDAC4-somatic, HGF-somatic, IDH1-somatic, IKZF1-somatic, IRS2-somatic, JAK3-somatic, KCNH2-germline, KCNQ1-germline, KDM5A-somatic, KDM5C-somatic, KDM6A-somatic, KDR-somatic, KEAP1-somatic, KEL-somatic, KIF1B-somatic, KMT2A-fluorescence_in_situ_hybridization_(fish), KMT2A-somatic, KMT2B-somatic, KMT2C-somatic, KMT2D-somatic, KRAS-gene_mutation_analysis, KRAS-md_dictated, KRAS-somatic, LDLR-germline, LMNA-germline, LRP1B-somatic, MAP3K1-somatic, MED12-somatic, MEN1-germline, MET-fluorescence_in_situ_hybridization_(fish), MET-somatic, MKI67-immunohistochemistry_(ihc), MKI67-somatic, MLH1-germline, MSH2-germline, MSH3-germline, MSH6-germline, MSH6-somatic, MTOR-somatic, MUTYH-germline, MYBPC3-germline, MYCN-somatic, MYH11-germline, MYH11-somatic, MYH7-germline, MYL2-germline, MYL3-germline, NBN-germline, NCOR1-somatic, NCOR2-somatic, NF1-somatic, NF2-germline, NOTCH1-somatic, NOTCH2-somatic, NOTCH3-somatic, NRG1-somatic, NSD1-somatic, NTRK1-somatic, NTRK3-somatic, NUP98-somatic, OTC-germline, PALB2-germline, PALLD-somatic, PBRM1-somatic, PCSK9-germline, PDGFRA-somatic, PDGFRB-somatic, PGR-immunohistochemistry_(ihc), PIK3C2B-somatic, PIK3CA-somatic, PIK3CG-somatic, PIK3R1-somatic, PIK3R2-somatic, PKP2-germline, PLCG2-somatic, PML-somatic, PMS2-germline, POLD1-germline, POLD1-somatic, POLE-germline, POLE-somatic, PREX2-somatic, PRKAG2-germline, PTCH1-somatic, PTEN-fluorescence_in_situ_hybridization_(fish), PTEN-gene_mutation_analysis, PTEN-germline, PTEN-somatic, PTPN13-somatic, PTPRD-somatic, RAD51B-germline, RAD51C-germline, RAD51D-germline, RAD52-germline, RAD54L-germline, RANBP2-somatic, RB1-germline, RB1-somatic, RBM10-somatic, RECQL4-somatic, RET-fluorescence_in_situ_hybridization_(fish), RET-germline, RET-somatic, RICTOR-somatic, RNF43-somatic, ROS1-fluorescence_in_situ_hybridization2fish), ROS1-md_dictated, ROS1-somatic, RPTOR-somatic, RUNX1-germline, RUNX1T1-somatic, RYR1-germline, RYR2-germline, SCN5A-germline, SDHAF2-germline, SDHB-germline, SDHC-germline, SDHD-germline, SETBP1-somatic, SETD2-somatic, SH2B3-somatic, SLIT2-somatic, SLX4-somatic, SMAD3-germline, SMAD4-germline, SMAD4-somatic, SMARCA4-somatic, SOX9-somatic, SPEN-somatic, STAG2-somatic, STK11-gene_mutation_analysis, STK11-germline, STK11-somatic, TAF1-somatic, TBX3-somatic, TCF7L2-somatic, TERT-somatic, TET2-somatic, TGFBR1-germline, TGFBR2-germline, TGFBR2-somatic, TMEM43-germline, TNNI3-germline, TNNT2-germline, TP53-gene_mutation_analysis, TP53-immunohistochemistry_(ihc), TP53-md_dictated, TP53-germline, TP53-somatic, TPM1-germline, TSC1-germline, TSC1-somatic, TSC2-germline, TSC2-somatic, VHL-germline, WT1-germline, WT1-somatic, XRCC3-germline, and ZFHX3-somatic.

The resulting ROS AUC may be approximately 0.52.

A feature set for RNA related features may include a proprietary calculation based upon an autoencoder which reduces the RNA dimensionality from 20,000+ transcriptomes to 100 encoded features, creatively named: rna_embedding-z_1 through rna_embedding-z_100. Given the substantial reduced dimensionality, one may expect the system to greatly improve processing speed at the cost of some degree of accuracy; however, the resulting ROS AUC may be approximately 0.60 which is greater than that of processing DNA features only.

A feature set for clinical data only may include: age_at_event, age_group {00 to 09, 10 to 19, 100 to 109, 110 to 119, 20 to 29, 30 to 39, 40 to 49, 50 to 59, 60 to 69, 70 to 79, 80 to 89, 90 to 99, Unknown}, days_since_first:TumorFinding:histology {acinar_cell_carcinoma, adenocarcinoma, carcinoma, infiltrating_duct_carcinoma, lobular_carcinoma, malignant_neoplasm,_primary, mucinous_adenocarcinoma, neuroendocrine_carcinoma, non_small_cell_carcinoma, otherGroup, small_cell_carcinoma, small_cell_neuroendocrine_carcinoma, squamous_cell_carcinoma,_no_icd_o_subtype, transitional_cell_carcinoma}, days_since_first:TumorFinding:histopath_grade {grade_1_(well_differentiated), grade_2_(moderately_differentiated), grade_3_(poorly_differentiated), grade_4_(undifferentiated), high_grade}, days_since_first:TumorFinding:stage {m0, m1, mx, n0, n1, n2, n3, nx, pn0, pn1, pn2, pnx, stage_1, stage_2, stage_3, stage_4, pt1, pt2, pt3, pt4, t0, t1, t2, t3, t4, tx}, days_since_first:cancer {breast, cervix_uteri, colon, head_and_neck, kidney, lung, lymphoid,_hemopoietic_and/or_related_tissue, otherGroup, ovary, pancreas, prostate, respiratory_tract, skin, skin_of_trunk, soft_tissues, stomach, tongue, unknown_site, urinary_bladder}, days_since_last:comorbidity {Abnormal_findings_on_diagnostic_imaging_of_breast, Administration_of antineoplastic_agent, Anemia, Dehydration, Disorder_of_bone, Disorder_of_breast, Dyspnea, Essential_hypertension, Fatigue, Imaging_of_thorax_abnormal, Immunization_advised, Long_term_current_use_of_drug_therapy, Osteoporosis, Past_history_of_procedure, Pedal_cycle_accident, Screening_for_malignant_neoplasm_of_breast, chronic_obstructive_lung_disease, otherGroup, type_2_diabetes_mellitus, type_2_diabetes_mellitus_without_complication}, gender {Missing, female, male}, and race {Missing, african race, american indian or alaska native, asian, pacific islander, black or african american, caucasian or white, hispanic, native hawaiian or other pacific islander, not hispanic or latino, other race, unknown or unknown racial group}.

The resulting ROS AUC may be approximately 0.67 which is greater than that of processing DNA features only and RNA features only.

Combining all of the input feature sets together from the DNA model, RNA model, and Clinical data model above results in an ROS AUC of approximately 0.70 which is greater than any of the models individually.

X. Evaluating Effect of Event on Condition Using Propensity Scoring

The present disclosure provides systems and methods for evaluating effect of an event on a condition that use a propensity model for matching and comparison of subjects that received a particular treatment with subjects who did not receive the treatment, but were likely to have been prescribed that treatment given their characteristics (e.g., demographic, therapeutic, phenotypic, genomic characteristics, etc.). The provided techniques thus allow to "match" a cohort of patients who received a certain treatment to a cohort of patients who did not receive that treatment but are likely to have been prescribed it.

In some embodiments, a propensity scoring model is trained to predict a likelihood of a subject's being prescribed a treatment, at one or more points of that subject's clinical interaction timeline. The trained propensity model is used to determine a "propensity score" that is used, in conjunction with a propensity value threshold, to identify a cohort of "treatment" group of subjects and a cohort of "control" group of subjects that are similar to each other from the perspective of the likelihood of being prescribed and administered a treatment. Thus, the subjects in the control and treatment cohorts can have similar demographic, clinical, genotyping, and other characteristics. The propensity value threshold can be used to tune a propensity scoring model.

In some embodiments, an interactive computer-implemented tool, or a dashboard, is provided that allows identifying treatment and control groups in a population of subjects based on a propensity value threshold, and for direct comparisons between the treatment and control groups. The comparison can be done using survival objective analysis (e.g., Kaplan-Meier curves), distribution of various subject features (which can be static or temporal), and pre- and post-treatment differences between the subjects in the treatment and control groups (e.g., other treatments given, prior medications, etc.).

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Details of an exemplary system are described in conjunction with FIG. 217. FIG. 217 is a block diagram illustrating a system 6500 in accordance with some implementations. The system 6500 in some implementations includes one or more hardware processing units CPU(s) 6502 (also referred to as processors), one or more network interfaces 6504, a display 6506 configured to present a user interface 6508, and an input system 6510, a non-persistent memory 6511, a persistent memory 6512, and one or more communication buses 6514 for interconnecting these components. As also shown in FIG. 217, the display 6506 can also present, on its user interface 6508, a user interface of a clinical tool or dashboard 6507 that is configured to implement embodiments of the present disclosure, as discussed in more detail below. The one or more communication buses 6514 optionally include circuitry (sometimes called a chipset) that interconnects and controls communications between system components. The non-persistent memory 6511 typically includes high-speed random access memory, such as DRAM, SRAM, DDR RAM, ROM, EEPROM, flash memory, whereas the persistent memory 6512 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 6512 optionally includes one or more storage devices remotely located from the CPU(s) 6502. The persistent memory 6512, and the non-volatile memory device(s) within the non-persistent memory 6512, comprise non-transitory computer readable storage medium. In some implementations, the non-persistent memory 6511, or alternatively the non-transitory computer-readable storage medium, stores the following programs, modules and data structures, or a subset thereof, sometimes in conjunction with the persistent memory 6512:

- an optional operating system 6516, which includes procedures for handling various basic system services and for performing hardware dependent tasks;
- an optional network communication module (or instructions) 6518 for connecting the system 6500 with other devices and/or a communication network 6504;
- a feature extraction module 6520 that is configured to extract features from various types of data related to subjects;
- features 6521 which can be stored in a suitable storage device;
- a propensity model building module 6522 configured to generate, update, and store at least one propensity scoring model, wherein the module 6522 can store out of sample prediction from various models;
- a propensity value threshold 6524 (selectable, e.g., via a user interface of the dashboard 6507);
- a base population of subjects 6526 comprising a plurality of subjects from which a first plurality of subjects 6528 and a second plurality of subjects 6530 can be identified using a propensity scoring model built by the propensity model building module 6522;
- the first plurality of subjects 6528 (subjects 6528-1-1, . . . , 6528-1-N), wherein a representative subject 6528-1-1 is associated with a condition 6532 (e.g., a medically diagnosed physical disease such as cancer or a medically diagnosed mental disease), an event 6534 (e.g., a medication or treatment such as a procedure or therapy) which occurred, a start date 6536 of the event, and features 6538 referred to herein as first features, which can be temporal and/or static;
- the second plurality of subjects 6530 (subjects 6530-2-1, . . . , 6530-2-M), wherein a representative subject 6530-2-M is associated with a condition 6542 (e.g., a medically diagnosed physical disease such as cancer or a medically diagnosed mental disease), an event 6544 (e.g., a medication or treatment such as a procedure or therapy) which could have occurred, an anchor point 6546 for the event, and features 6548 referred to herein as second features, which can be temporal and/or static;

a survival objective information 6550 (e.g., survival curve information) of the first plurality of subjects 6528 that is determined using the event start date 6536 for each respective subject in the first plurality of subjects 6528; and a survival objective information 6560 (e.g., survival curve information) of the second plurality of subjects 6530 that is determined using the anchor point 6546 for each respective subject in the second plurality of subjects 6530.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 6511 optionally stores a subset of the modules and data structures identified above. Furthermore, in some embodiments, the memory stores additional modules and data structures not described above. In some embodiments, one or more of the above identified elements is stored in a computer system, other than the computer system 6500 and that is addressable the computer system 6500 so that the system 6500 may retrieve all or a portion of such data when needed.

It should be appreciated that FIG. 217 depicts the system 6500 as a functional description of the various features of the present disclosure that may be present in computer systems. As a person of skill in the art would understand, some of components and modules shown separately can be combined in a suitable manner. Also, although FIG. 217 depicts certain modules in the non-persistent memory 6511, some or all of these modules may instead be stored in the persistent memory 6512 or in more than one memory. For example, in some embodiments, the base population of subjects 6526 may be stored in a remote storage device which can be a part of a cloud-based infrastructure. Any other components can be stored in remote storage device(s).

FIG. 218 illustrates a process 6600 of evaluating an effect of an event on a condition (e.g., an effect of a medication or treatment on a diagnosed conditioned such as cancer), which can be implemented in the system 6500 (FIG. 217) or in any other suitable system configured to execute the tool 6507. The process 6600 can start, for example, when a clinical tool for evaluating the effect of an event on a condition is initiated or in response to any other trigger. As shown in FIG. 218, at block 6602, a base population of subjects (e.g., the base population of subjects 6526 of FIG. 217) can be obtained, which can be done in a number of ways. For example, with reference to FIG. 219 which illustrates schematically a user interface 6707 of the tool 6507, a base population of subjects can be obtained based on user input received via a user interface element 6702 of the user interface 6707. In the example illustrated in FIG. 219, the user interface element 6702 is shown as a drop-down menu element from which a source of information on the base population of subjects can be provided by a user. It should be appreciated, however, that the base population of subjects can be obtained in other ways.

Regardless of the way in which it is obtained, the base population of subjects can include subjects that have a certain condition such that all of the subjects have that condition. In some embodiments, however, the base population has subjects that have different conditions or different types of conditions. For instance, the base population of subjects can have subjects with different types of cancer or different types of a mental disease. Thus, FIG. 218 shows that, at optional block 6604, a condition can be obtained such that only the subjects having the obtained condition are considered for further analysis. The condition can be obtained, for example, via the user interface 6707 of FIG. 219, for example, via the user interface element 6702 or via another user interface element configured to receive user input. In some embodiments, however, the processing at block 6604 is omitted since the base population can be defined as a population in which each subject has a certain condition (e.g., cancer). Each subject in the base population can also be associated with other features related to the condition—e.g., a type and/or stage of cancer. In general, the base population can be any type of a collection of patient's information stored in patients' medical records. The information can be updated as the patient (also referred to as a subject herein) is being monitored.

Further, at block 6606 of FIG. 218, an event, such as a medication, procedure, or treatment (sometimes collectively referred to herein as a "treatment"), is obtained. In some embodiments, information on the event can be acquired via the user interface 6707 presenting elements of the tool 6507. For example, as shown in FIG. 219, the event can be obtained via an event type user interface element 6704 and via an event user interface element 6706. The event type user interface element 6704 can be used to acquire an event type such as, for example, a medication, treatment, therapy or any other type of event can affect a subject's condition. The event user interface element 6706 can be used to receive a selection of a specific event of a certain type. As an example, the event type can be a medication and the event can be fluorouracil.

At block 6608 of FIG. 218, a propensity value threshold can be obtained. FIG. 220 shows by way of example that the propensity value threshold can be obtained via a user interface element 6708. In some embodiments, the propensity value threshold comprises a propensity value range which can be, e.g., a range of between 0 and 1, as shown in the example of FIG. 219. In this example, the user interface element 6708 is a slider which can be adjusted based on a user input such that a desired range is selected. It should be appreciated, however, that the user interface element 6708 can be any other element that allows to receive user input indicating a selection of a propensity value threshold.

In some embodiments, as shown at block 6610 of FIG. 218, one or more features can also be selected for constructing a propensity scoring model. In some embodiments, the feature selection can be performed via the user interface 6707—e.g., via a feature selection user interface element 6710 (e.g., a feature selection module) which can allow a user to select a feature (via an element 6712) and its respective value (via an element 6714). For example, the user can be allowed to select an age or an age group, race, stage of cancer, gender, drugs taken pre- and/or post-treatment, censorship rates, an indicator from clinical data, and any other feature. Some features can be binary. Also, some features may not have specific values associated with them.

It should be appreciated that the processing at blocks 6604-6610 of FIG. 218 can be performed in any particular order and that the specific order is shown in FIG. 218 by way of example only. It should also be appreciated that some or all of the obtaining at blocks 6604-6610 can be performed in ways other than based on user input acquired via elements of a user interface. Thus, in some embodiments, the obtaining at blocks 6602-6610 can be performed automatically. For example, in some embodiments, a propensity value threshold can be selected by the processor based on features of the subjects in the base population. Additionally or alternatively, in some implementations, the propensity value threshold can be suggested to the user via the user interface.

At block 6612 of FIG. 218, a propensity scoring model and the propensity value threshold obtained at block 6608 may be used to select treatment and control cohorts from the base population of subjects and to generate anchor point predictions for each subject in the control cohort. The treatment cohort is also referred to herein as a first plurality of subjects (e.g., first plurality of subjects 6528 of FIG. 217) and the control cohort is also referred to herein as a second plurality of subjects (e.g., second plurality of subjects 6530 of FIG. 217).

The propensity scoring model may be configured to determine a propensity score for each subject in the base population. The propensity score can be defined as the probability of receiving the active treatment (Z=1 vs. Z=0), conditional on the observed baseline covariates (X):

$$e\_i = \text{Prob}(Z\_i = 1 | X\_i) \quad (1)$$

The e_i value describes the probability for a patient i having the active treatment. Propensity scores are described, for example, in Austin, The use of propensity score methods with survival or time-to-event outcomes: reporting measures of effect similar to those used in randomized experiments, Statistics in Medicine (2013), 33:1242-1258, and Rosenbaum & Rubin. The central role of the propensity score in observational studies for causal effects, Biometrika (1983), 70(1):41-55, each of which is incorporated by reference herein in its entirety. This score acts as a balancer—conditional on the propensity score, the distribution of X should be identical between the treatment and control groups. A model that links a binary response to a set of features can be used. See Stuart, E. Matching methods for causal inference: a review and a look forward, Statistical Science (2010) 25(1):1-21.

The treatment cohort can be different from the control cohort such that they do not overlap. The treatment and control cohort can be of the same size, or they can have different sizes. As mentioned before, the treatment cohort includes subjects having the condition that incurred the event (e.g., received a treatment as defined above) that each subject in the treatment cohort is therefore associated with a start date of an event at which that subject incurred the event. The control cohort includes subjects having the condition that could have incurred the event but did not incur the event.

As a simple example, consider the approved labeling by the U.S. Food and Drug Administration (FDA) for the drug cisplatin. Cisplatin has been approved by the FDA as established combination therapy with cyclophosphamide in patients with metastatic ovarian tumors who have already received appropriate surgical and/or radiotherapeutic procedures. A treatment cohort may be defined a cohort of 500 patients with metastatic ovarian tumors who received the combination therapy cisplatin and cyclophosphamide after receiving appropriate surgical and/or radiotherapeutic procedures. The control cohort may be defined as a cohort of 250 patients who did not receive the combination therapy cisplatin and cyclophosphamide after receiving appropriate surgical and/or radiotherapeutic procedures. Exemplary methods for defining the treatment cohort and control cohort are described below.

In some embodiments, the method assigns each subject in the base population into one of the first plurality of subjects, the second plurality of subjects, or a group of non-matching subjects that are not assigned to the first plurality of subjects or the second plurality of subjects.

In some embodiments, the propensity scoring model is used at block 6612 by applying a corresponding plurality of features for the respective subject in the base population to the propensity scoring model tuned to the propensity value threshold. At least some of the plurality of features can be selected via the user interface 6707. The plurality of features can include a first subset of features each of which is associated with a respective time period (e.g., the subject's clinical interaction timeline for which data exist), and a second subset of features that are static. The propensity scoring model is applied such that, for each subject in the control cohort, one or more anchor point predictions are generated. Each anchor point prediction is associated with a corresponding instance of time in the respective time period and includes a probability that the instance of time is a start date for the event for the respective subject in the control cohort. Thus, the anchor point predictions include predictions, within the respective time period, for when the event could have been started (but did not start) for the subject in the control cohort. An instance of time that is associated with an anchor point prediction that has the greatest probability across the anchor point predictions is taken as the anchor point for the subject, which is the time when the subject could have incurred the event. For example, it is a time when the subject could have been prescribed a medication or treatment, identified based on the subject's similarity to subjects who were indeed prescribed and received the medication or treatment.

In some embodiments, a propensity scoring model is generated as a cross-validated model (e.g., random forest, gradient boosting, linear or logistic regression, or a neural network) with a treatment as the outcome and with certain features as predictors. The features for the model can be selected automatically or manually, and the feature selection process may involve missing value imputation. Out-of-fold predictions returned by the propensity scoring model, as well as the thresholds which maximize AUC for each cross-validated run, are saved and used for future predictions. The propensity scoring model can assign a subjects from the base population to one of the control and treatment groups. Each subject assigned to the treatment group is associated with an event start date at which the subject first incurred the event (e.g., a medication or procedure), and each subject assigned to the control group is associated with an anchor point which is a date at which the subject could have first incurred the event (e.g., a medication or procedure).

In some embodiments, the control group of subjects can be selected by first removing all subjects (meaning the information such as, e.g., medical records of the subjects) that were assigned to the treatment group. The propensity scoring model is then applied to subjects associated with anchor point predictions having respective probabilities that are above a threshold that maximized AUC in each of the cross-validated model runs. In this way, from the subjects that are not in the treatment group, subjects are selected who are likely to incur the event at one or more time points (instances of time), and a single anchor point (i.e., a single instance of time) that has the greatest probability across the anchor point predictions is selected for each subject.

Because one anchor per patient is chosen, for each patient remaining, only the event start date (and prediction) associated with the highest prediction that the patient received is selected. If the number of patient-anchors that remain is larger than "n" selection down to only the top "n" patient-anchors with the highest predictions is made.

In some embodiments, applying the propensity scoring model to the base population comprises generating a predicted event start date for each subject in the base population, thereby determining whether or not the subject would receive a given treatment for the first time within the next X days or months (e.g., X=2 months, in an embodiment), rather than determining whether or not the subject would receive the treatment on that date. Thus, a predicted event start date is generated for each subject, including the subjects that may be assigned to the treatment group, based on an indication in their medical records that the treatment was administered to the subjects. A date predicted for be an event start date for a subject in the control group can be adjusted to generate a respective anchor point. This can be done by analyzing the distribution of difference in days between a respective predicted event start date for each subject in the treatment group with a positive outcome (meaning, e.g., they did receive the treatment within X months) and the date when that subject actually received the treatment. Then, for each of the event start dates generated for the subjects in the control group, a certain number of days is added to the event start date, following the distribution that was observed for the treatment group (e.g., from a normal distribution with the mean and standard deviation taken from the sample statistics of the treatment distribution, uniform distribution, etc.). In some embodiments, the number of days added to the event start date can be between ten days and sixty days, though any other number of days can be added.

Referring back to FIG. 218, at block 6614, the process 6600 generates respective survival objectives information for treatment and control cohorts. The survival objectives are generated in the way that allows a comparison of a survival objective of the treatment cohort and a survival objective of the control cohort using the event start date for each respective subject in the treatment cohort and the anchor point for each respective subject in the control cohort, to evaluate the effect of the event on the first condition.

In some embodiments, the propensity scoring model is trained using a binary classification algorithm with the survival objective as an objective response variable. The survival objective can be, for example, a time until death, time until progression of the first condition, or time until an adverse event associated with the first condition is incurred. The propensity scoring model can be trained with a survival or time-to-event outcome. For example, techniques described in Austin, P. The use of propensity score methods with survival or time-to-event outcomes: reporting measures of effect similar to those used in randomized experiments, Stat Med. 2014 Mar. 30; 33(7): 1242-1258, which is incorporated herein by reference in its entirety, can be employed in some embodiments.

As shown in FIG. 219, the user interface 6707 of the tool 6507 can be configured to receive user input indicating a user selection regarding how the information on the survival objectives is displayed on the user interface 6707. For example, as shown in FIG. 219 by way of example only, a survival objective representation element 6716 and a survival objective (type) element 6718 can be configured to receive respective user input regarding a survival objective representation (e.g., survival curves) and a type of a survival objective (e.g., progression free survival, time until death, time until progression of the condition, time until an adverse event associated with the condition is incurred, etc.). Any other types of user interface elements can be configured to receive user input regarding the survival objectives for the treatment and control cohorts identified from the base population of subjects.

In FIG. 219, a results panel 6720, which can include various sub-panels, illustrates schematically how results of the selecting the treatment and control cohorts and of the generating the respective survival objectives information for these cohorts can be presented. Thus, a sub-panel 6722 presents propensity survival analytics comprising survival curves 6724 (shown schematically) generated for the treatment and cohort groups.

As also shown in FIG. 219, the panel 6720 can also include information on a size of the treatment and control groups which are shown by way of example only in a sub-panel 6726, which, in turn, is shown positioned within the sub-panel 6722, though it may be presented in any other location within the panel 6720. It should be appreciated that the user interface elements of FIG. 219 are shown by way of example only, and that the tool that implements the described techniques can present any other user interface element, some or all of which can be interactive, and the elements can be positioned in the user interface in a suitable manner. Moreover, in some embodiments, the tool can be configured to receive a user input in a speech format or in any other format.

In some embodiments, the survival objectives information comprises Kaplan-Meier estimates, which are the cumulative probability of surviving until time t. To calculate the Kaplan-Meier probability estimate at day 3, for example, the calculation may be $P(S1)*P(S2|S1)*P(S3|S2)$, or more generally, $P(St)=P(St|St-1)*P(St-1)$, where $P(St)$ is the probability of the subject's survival on a certain day, $P(St-1)$ is the probability of the subject's survival on a day prior to the certain day, and $P(St|St-1)$ is the probability of the subject's survival on the certain day given that the subject was alive on a day prior to the certain day. In some embodiments, the Kaplan Meier function can makes the following assumptions: 1) patients who are censored have the same survival prospects as those who continue to be followed, 2) the survival probabilities are the same for subjects recruited early and late in the study, and 3) the event happens at the time specified.

In some embodiments, the panel 6720 can also present results related to features that were used to identify the treatment and control cohorts based on the propensity value threshold. Features and their respective values can be presented in various ways that allow comparison of the treatment and control cohorts and assessment of features that contributed to the selection of the treatment and control cohorts. In some implementations, the features can be ranked based on the degree of their contribution to the selection of the treatment and control cohorts.

At block 6616 of FIG. 218, the process 6600 comprises performing analytics on various information related to the treatment and control cohorts to assess features of the subjects included in the cohort based at least in part on anchor point predictions for the control cohort. Some or all of the features can be ranked or compared otherwise. FIG. 219 shows that the panel 6720 can include a features sub-panel 6728 that can display features 6730 for the subjects in the control group and features 6732 for the subjects in the treatment group. The features can be displayed along with their values—e.g., in some embodiments, average values across all subjects in the group can be displayed. FIG. 219 illustrates by way of example that the same respective features (e.g., Feature A, Feature B, etc.) from the control group features 6730 and the treatment group features 6732 can be displayed alongside, which facilitates feature comparison.

As shown in FIG. 219, the features sub-panel 6728 can also include a sub-panel 6734 in which features and their respective values can be presented as one or more graphical representations for the control and treatment group. For example, the features displayed in the sub-panel 6734 can be an age group, stage of a disease (e.g., cancer), etc., as shown in more details in examples below. It should be appreciated that the user interface 6707 can present various visual representation that allow exploring clinical differences between the treatment and control groups. Examples of the representations are discussed below.

Regardless of the specific way in which the features and related information regarding the subjects in the treatment and control groups are presented, the features and other information are presented in a way that allows comparing survival objectives of the treatment and control groups to determine impact of treatment on survival. For example, demographic, geographical, clinical, genomic differences, a treating physician-related differences, and any other differences between the treatment and control cohorts are assessed. In this way, in some embodiments, patient's features/characteristics can be assessed that impact a decision to prescribe and administer a treatment to the patient. The goal is to determine, from the treatment and control cohorts that are selected to be similar, their differences that result in one cohort's being prescribed the treatment and another not being prescribed the treatment. One or more features, including shared characteristics of patients and clinical considerations, can be identified that lead to a decision to prescribe the treatment.

In some embodiments, the analytics performed on the identified treatment and control cohorts in accordance with the present disclosure can include receiving a request for treatment recommendations from a user, for instance, a physician treating a patient. For example, the tool in accordance with embodiments of the present disclosure, or a different interactive tool, can be used to receive such a request which can be associated with information on the patient (e.g., from the patient's medical record). The information on the treatment and control cohorts can be used to identify, based on patient information, whether there is a match among the patients in the cohorts to the patient in the physician's request. If the match is identified, the described techniques can recommend a certain treatment to the patient.

In some embodiments, treatment cohort characteristics are compared to identify final clinical considerations that lead to patients prescribed a treatment. If characteristics of a patient match the final considerations that lead to treatment, the patient can be prescribed the treatment.

In embodiments in accordance with the present disclosure, the survival objectives information for the treatment and control cohorts can be generated and displayed automatically, in response to receiving user input indicating a selection of a required number of elements and/or in response to a certain other trigger. In some embodiments, additionally or alternatively to displaying the respective survival objectives information for the treatment and control cohorts, the survival objective information for the treatment and control cohorts can be stored, in a suitable format, in memory of a computing device.

FIGS. 220A and 220B illustrate a computer-implemented method 6800 of evaluating an effect of an event on a first condition using a base population of subjects that each have the first condition, as shown at block 6802 of FIG. 220A. The first condition can be breast cancer, colon cancer, lung cancer, ovary cancer, prostate cancer, or any other type of cancer. The method involves obtaining a propensity value threshold, at block 6804, wherein the propensity value threshold can be, in some embodiments, a propensity value range (block 6806).

At block 6808, the method 6800 includes identifying a first plurality of subjects in the base population and a start date of an event for each respective subject in the first plurality of subjects at which the respective subject incurs the event. The event can be any type of an event. For example, as shown at block 6810, the event may comprise application of a medication to a subject. The event can also be a medical procedure performed on a subject (block 6812), and the medical procedure can be a surgical procedure or a radiation treatment (block 6814).

At block 6816, the method 6800 includes using a propensity scoring model to select a second plurality of subjects from the base population, wherein the second plurality of subjects are other than the first plurality of subjects. The using of the propensity scoring model comprises performing a first procedure that comprises, for a respective subject in the base population: (i) applying a corresponding plurality of features for the respective subject in the base population to the propensity model tuned to the propensity value threshold, wherein a first subset of the corresponding plurality of features for which data was acquired for the respective subject is associated with a respective time period and a second subset of the corresponding plurality of features for which data was acquired for the respective subject are static, the applying (i) thereby obtaining one or more anchor point predictions for the respective subject, wherein each anchor point prediction is associated with a corresponding instance of time in the respective time period and includes a probability that a corresponding instance of time is a start date for the event for the respective subject. The using of the propensity scoring model also comprises assigning an anchor point for the respective subject to be the corresponding instance of time that is associated with the anchor point prediction that has the greatest probability across the anchor point predictions. The respective time period can be a period of days, months or years.

In some embodiments, the using the propensity scoring model to select a second plurality of subjects is performed on a sufficient number of subjects in the base population to acquire the second plurality of subjects and a single independent corresponding anchor point for each respective subject in the second plurality of subjects.

In some embodiments, for a respective subject in the second plurality of subjects, the one or more anchor predictions for the respective subject is a plurality of anchor point predictions, a first feature in the first subset of the corresponding plurality of features is measured a plurality of times across the respective time period, and each measurement instance of the first feature is used in a different propensity model calculation to derive a different anchor point in the plurality of anchor points.

In some embodiments, the using the propensity scoring model to select a second plurality of subjects is performed for each subject in the base population that is not in the first plurality of subjects.

In some embodiments, the propensity scoring model can be a binary classification model (block 6818), which can be, in some embodiments, a model implementing a random forest algorithm (block 6820).

Various features can be employed in the propensity scoring model. For example, features for a respective subject can comprise a corresponding plurality of demographic features (e.g., age or age group, gender, race, etc.), a plurality of clinical temporal data, and a corresponding plurality of genomic features for the respective subject. The clinical temporal data can include medications taken pre- and post-treatment, censorship rate, stage of a disease (e.g., cancer), etc.

In some embodiments, non-limiting examples of features in the second subset of features includes gender, race, or year of birth, family history, body weight, size, or body mass index.

In some embodiments, a feature in the first subset of features is months since birth, smoking status, menopausal status, time since menopause, time since last smoked, primary cancer site observed, metastasis site observed, cancer recurrence site observed, tumor characterization, medical procedure performed, medication type administered, radiotherapy treatment administered, time since primary diagnosis, time since predefined cancer stage diagnosed, time since metastasis, time since last recurrence of cancer, time since medical procedure performed, time since predefined medication taken, time since radiotherapy treatment administered, imaging procedure performed, change in tumor characteristic, rate of change in tumor characteristic, or predetermined response observed.

In some embodiments, a first feature in the plurality of features is obtained from a biological sample of the respective subject and corresponds to an RNA for a predetermined human gene.

In some embodiments, the first feature is a count of germline mutations observed for the RNA in the biological sample of the respective subject. In some embodiments, the first feature is a count of somatic mutations observed for the RNA in the biological sample of the respective subject.

In some embodiments, a first feature in the plurality of features is a number of somatic mutations on a predetermined chromosome as determined by sequencing RNA from a biological sample obtained from the respective subject. In some embodiments, a first feature in the plurality of features is a number of germline mutations on a predetermined chromosome as determined by sequencing RNA from a biological sample obtained from the respective subject.

In some embodiments, a first feature in the plurality of features is a number of genes with mutations on a predetermined chromosome as determined by sequencing RNA from a biological sample obtained from the respective subject.

In some embodiments, a first feature in the plurality of features is a mutation density of a predetermined chromosome as determined by sequencing RNA from a biological sample obtained from the respective subject.

In some embodiments, a first feature in the plurality of features is a number of mutations of a defined mutational class of a predetermined chromosome as determined by sequencing RNA from a biological sample obtained from the respective subject. The defined mutational class can be single nucleotide polymorphism (SNP), multiple nucleotide polymorphism (MNP), insertions (INS), deletion (DEL), or translocation.

In some embodiments, each feature can be categorized into a "feature class," which can be "static" (features a subject that do not change over time) or "temporal" (features of a subject that are associated with a specific time point and that can change over time). In addition to being assigned to a feature class, each feature can also be assigned to a "temporal class" such as (i) "past"—a historic value of the feature or event, the fact that it has taken place in the past, or the time since it took place, (ii) "present"—a current value of the feature or event at the specified time point; or (iii) "future"—a future value of the feature or event, the fact that it will take place in the future, or the time until it takes place in the future. For example, gender, face, and year of birth can be categorized as features of a "static" feature class and of a "past" temporal class. The features such as months since birth, smoking status, menopausal status, comorbidity observed, months since menopause, months since last smoked, months since comorbidity observed, primary cancer site observed, metastasis site observed, cancer recurrence site observed, tumor characterization, procedure performed, a type of a medication administered, a type of a radiotherapy administered, months since primary diagnosis, months since a diagnosis of a certain stage of a condition, months since the first or last occurrence of a certain event, months since a procedure was administered, months since a medication was administered, months since a radiotherapy was administered, imaging procedure performed (and results of the procedure—e.g., a determined tumor size and other tumor characteristics), change in a tumor characteristic, rate of change in a tumor characteristic, an observed response, a number of certain events observed per a time period can be categorized as "temporal" features that belong on all three ("past," "present" and "future") temporal classes.

In some embodiments, the use of the propensity scoring model to identify propensity matched treatment and control cohorts allows estimation of survival curves in the treatment and control cohorts. At block 6822 of FIG. 220B, the method 6800 further includes determining a survival objective of the first plurality of subjects and a survival objective of the second plurality of subjects using the event start date for each respective subject in the first plurality of subjects and the anchor point for each respective subject in the second plurality of subjects to evaluate the effect of the event on the first condition. In some embodiments, as shown at block 6824, the survival objective of the first plurality of subjects is determined through a first Kaplan-Meier estimate and the survival objective of the second plurality of subjects is determined through a second Kaplan-Meier estimate.

In some embodiments, determining the survival objective of the first plurality of subjects and the survival objective of the second plurality of subjects is performed using a survival model applied to the treatment and control groups. The survival model may be trained using an algorithm with the survival objective as an objective response variable. The survival objective may be time until death, time until progression of the first condition, or time until an adverse event associated with the first condition is incurred. The survival model can be constructed and trained using various features, including the features that are used for the propensity scoring model.

In some embodiments, a survival modeling approach is based on a temporal modeling of patient survival, which can be, for example, a regression based prediction of expected survival from a point in time or classifier for probability of surviving more than X years from a point in time. The inception point of the model prediction (i.e., what the "point in time" actually is) can vary. For example, it can be survival from a first diagnosis of primary cancer, survival from prescription of a specific medication or procedure, survival from a specific stage diagnosis, etc. The survival objective can also vary depending on a model. For example, the approach can involve modeling a time until death, a time until progression, a time until adverse event, etc.

Referring back to FIG. 220B, the result of the determining the survival objective of the first plurality of subjects and the survival objective of the second plurality of subjects can be displayed on a user interface of a computing device, as shown at block 6826.

In some embodiments, the method further comprises displaying on a user interface a respective average value for each feature in one or more features in the plurality of features in the first plurality of subjects and a respective average value for each feature in one or more features in the plurality of features in the second plurality of subjects. For example, features (sub)panel 6718 (FIG. 219) can be used to display, for each of the treatment and control groups, various features and their corresponding average values, though the feature values can be presented in any other ways. For example, a percentage of the subjects in the group associated with a certain feature can be presented. Non-limiting examples of the features include clinical data, age group, race, stage of cancer, gender, drugs taken pre- and post-treatment, censorship rates, etc. It should be noted that some or all of these features may be different from the features used to build and train the propensity scoring model. The features can be presented automatically and/or in response to user input.

As discussed above, the propensity value threshold can be adjustable, for example, via a user interface through which user input can be received to select a value or a range of a propensity value threshold. Thus, an adjusted propensity value threshold can be obtained (block 6828), which can be done, for example, via a user interface. For example, user input can be received via the user interface element 6708 of FIG. 219 such that a certain range of a propensity value threshold is selected (e.g., a different range from a previously selected range). As discussed above, the propensity value threshold is used to determine which subjects from the identified treatment and control cohorts to select as a result of the application of a propensity scoring model. In some embodiments, the treatment and control cohorts are identified in the base population of subjects such that the respective subjects have a similar propensity score or value, and the propensity value threshold, such as a range, is used to select the subjects from the treatment and control cohorts that have a propensity score within the range. The propensity value threshold may determine subjects to select for the treatment and control cohorts by limiting selection to those subjects having anchor points with a respective probability satisfying the propensity value threshold. A probability may satisfy the threshold, depending on the mode of operation, by falling below a lower threshold, exceeding an upper threshold, or falling below an upper threshold and exceeding a lower threshold.

Once the adjusted propensity value threshold is obtained at block 6828, the identifying a first plurality of subjects (block 6808), the using a propensity scoring model (block 6816), and the determining a survival objective of the first plurality of subjects and a survival objective of the second plurality of subjects (block 6822) can be repeated for the adjusted propensity value threshold, as shown at block 6830 of FIG. 220B. In this way, different treatment and control groups can be selected, and related information, including survival analytics information (e.g., survival curves) can be presented on the user interface.

Examples

In some embodiments, a propensity scoring model may be used to predict a likelihood of a subject from a base population of subjects receiving a treatment X (e.g., a specific drug, radiotherapy, or procedure), for the first time, in the next T interval (e.g., 16 to 25 days). In some embodiments, a cross-validation using 8×2 stratified folds can be used. Features from a feature dataset, including demographic, genomic, and clinical temporal data, defined historically at each time point of a subject's timeline, are used. An 8×2 patient-based, key attribute stratified, cross-validation fold split is utilized for evaluation. Once the predictions of the likelihood of a subject's receiving a treatment X are available, the method in accordance with the present disclosure identifies a treatment group (the subjects who were administered the treatment) and a control group (the subjects who were not administered the treatment). An anchor point is determined for each patient in the control group as the highest likelihood point of the treatment being administered. The anchor point is used to determine the starting point for the control survival curve.

In some embodiments, the propensity scoring model is implemented as a binary classification problem, trained to maximize a receiver operating characteristic (ROC)/area under the curve (AUC) metric. The propensity scoring model may be trained using a random forest algorithm with a multi-label objective, on a per cancer+treatment class basis (e.g., a propensity scoring model for lung cancer medications, a propensity scoring model for lung cancer procedures, etc.), with separate objective response variables for each of the available treatments of that treatment class (which can be tens to hundreds). Other algorithms, including machine learning algorithms, a gradient boosting algorithm, linear or logistic regression, or a neural network may be applied as the propensity scoring model. Out-of-fold predictions can be made and stored for future use.

Figure 221A:
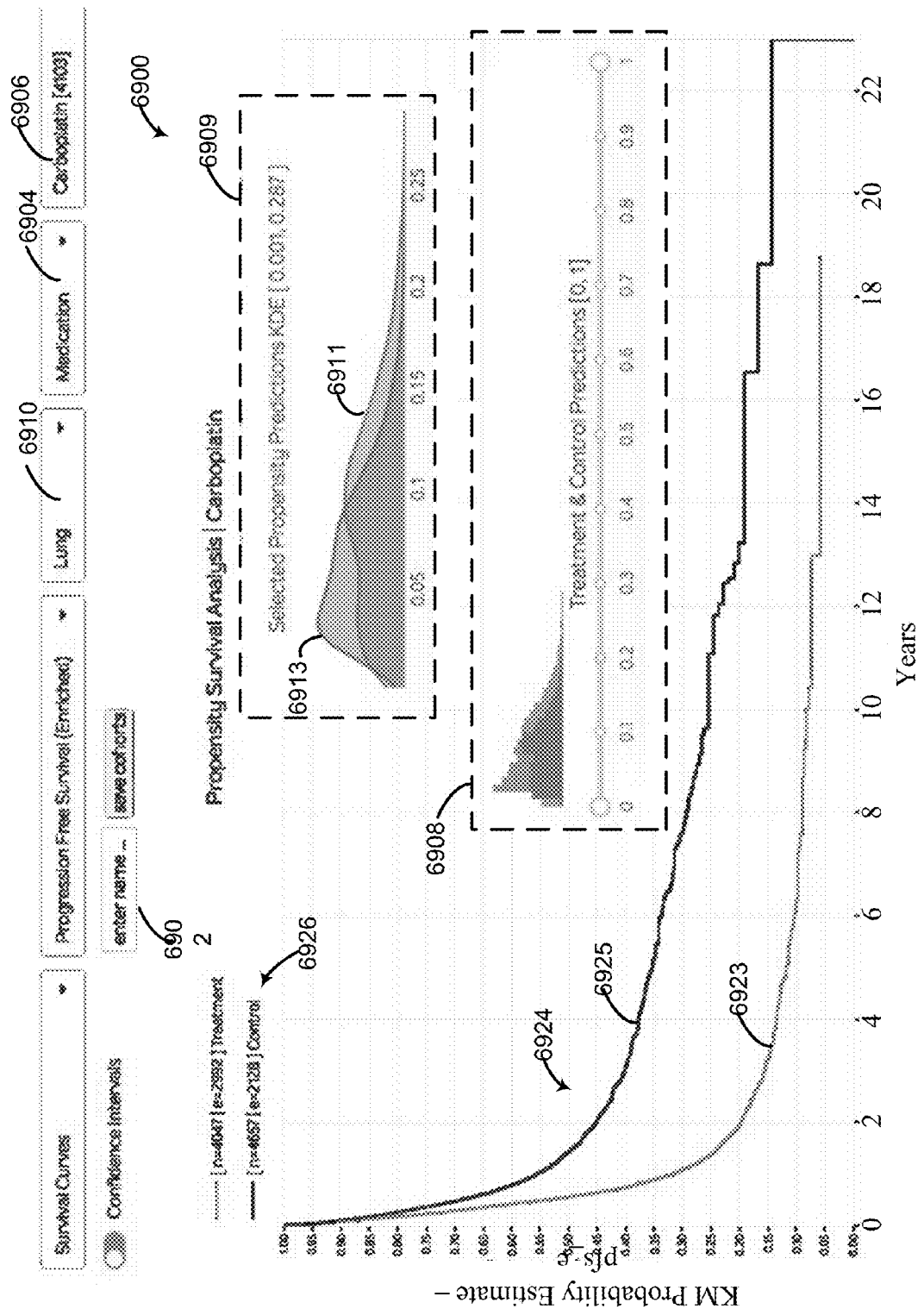

FIGS. 221A 222B, 221C and 221D illustrate an example of an embodiment of a user interface 6900 of a tool such as, e.g., user interface 6707 shown in FIG. 219. The tool user interface 6900 can be implemented as an interactive dashboard supported by propensity score model. The tool, which can be implemented as part of another tool allowing development and assessment of clinical trials, can be initiated in a suitable manner. As shown in FIG. 221A, a user interface element 6902 can be used to receive user input indicating a selection of a base population of subjects which is, in this example, a base population of subjects having cancer. A lung cancer can be selected based on respective user input, via a user interface element 6910. It will be appreciated that user interface element 6910 provides any number of disease states or other forms of states that can be selected. A type of a treatment (medication) and the specific medication (carboplatin) can be selected via user interface elements 6904 and 6906, respectively. A user interface element 6908 can be used to obtain a propensity value threshold, which is a range between 0 and 1 in the illustrated embodiment. No selection is shown in this example such that the entire range is chosen. Other selections made via the user interface 6900 include survival curves as a survival objective representation and progression free survival as a survival objective.

In response to obtaining the selection of the parameters via the user interface 6900, treatment and control cohorts are identified in the base population of the subjects such that the treatment cohort includes 4047 subjects and the control cohort includes 4657 subjects, as shown in FIG. 221A (6926). The survival curves 6924 are generated for the treatment and control cohorts and displayed in a propensity survival analysis portion of the user interface 6900. The survival curves 6924, comprising a survival curve 6923 for the treatment cohort and a survival curve 6925 for the control cohort, are generated as Kaplan-Meier estimates ("KM Probability Estimates") versus years. As also shown in FIG. 221A, kernel density estimation (KDE) plots 6909 ("Selected Propensity Predictions KDE") are generated and displayed, which allow assessing an overlap between the matched treatment (a plot 6911, shown in purple) and control (a plot 6913, shown in grey) cohorts.

As discussed above, embodiments of the present disclosure allow assessing features of the subjects in the treatment and control groups that were used in the propensity scoring model applied to the base population to identify the matched cohorts. Thus, a panel 6928 ("Subset-Aware Feature Effect") in FIG. 2221B presents the features that contributed the most to the predictions made by the utilized propensity scoring model. In this example, the most significant features (shown on the top of the bars) are a current stage and a maximum stage of lung cancer. Other features include an average value (a number per volume) of leukocytes, an average value (volume/fraction) of hematocrit, an average value (a number per volume) of platelets, an average value (mass per volume) of hemoglobin, an average value (mass per volume) of creatinine, an last value (a number per volume) of leukocytes, an last value (a number per volume) of platelets, an average value (a number per volume) of glucose, etc.

Figure 221B:
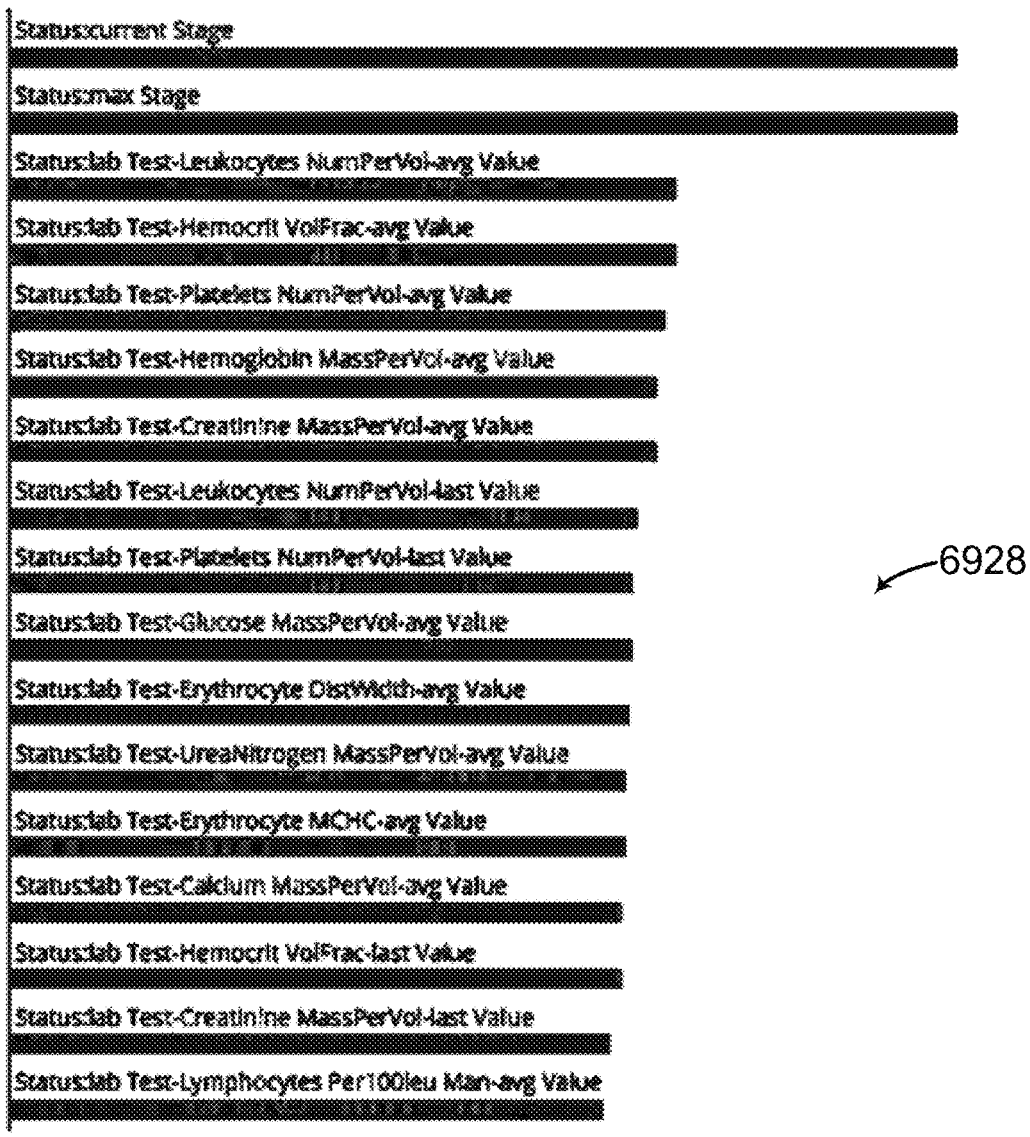
Figure 221C:
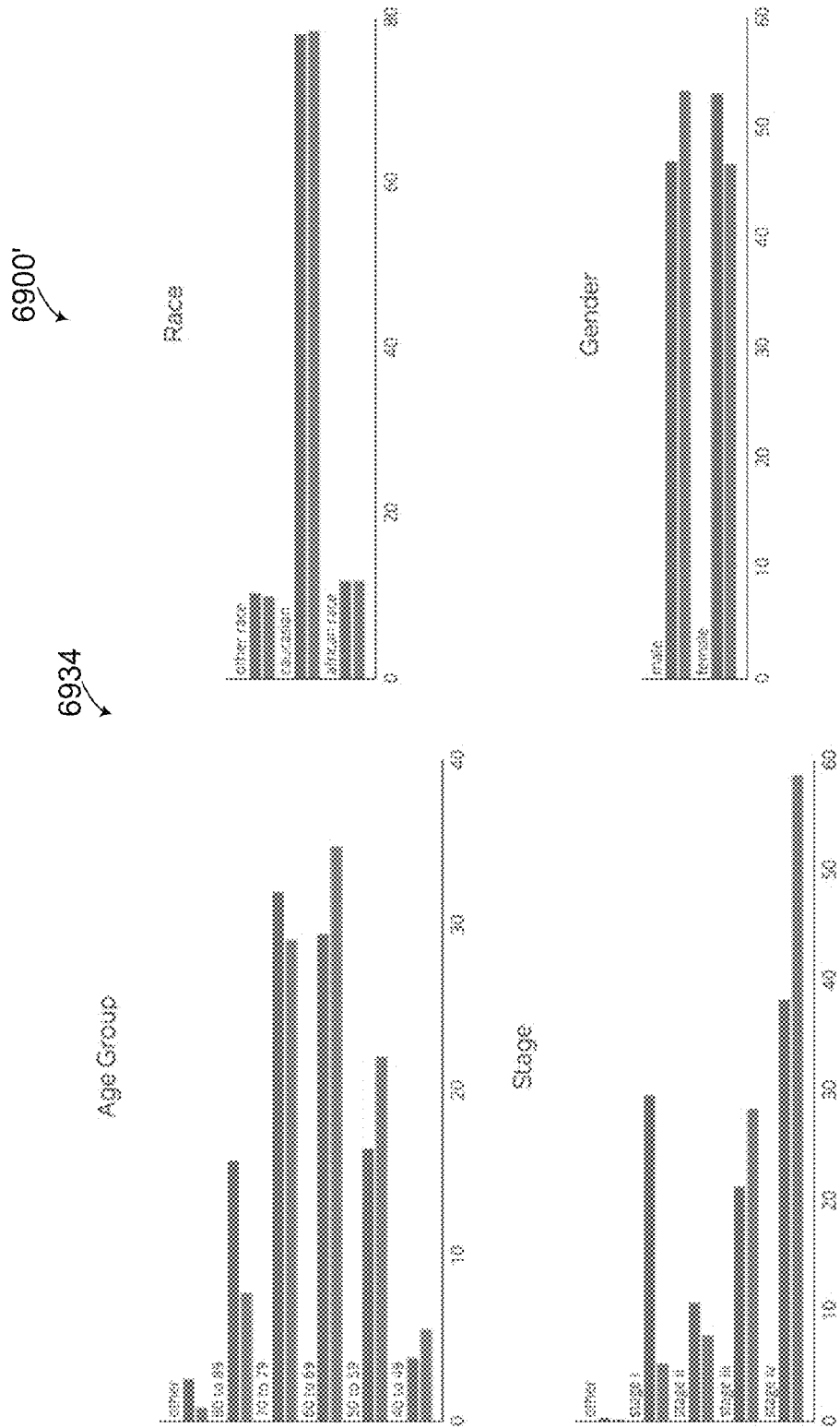

FIGS. 221C and 221D collectively illustrate another portion 6900' of the tool's user interface 6900 (which can be presented concurrently with the elements shown in FIGS. 221A and 221B) that illustrates, in a panel 6934, features among the control cohort (grey bars shown above the purple bars for each pair of bars) and the treatment cohort (the purple bars). The displayed features are age group, race, stage of a lung cancer (other, stage I, stage II, stage III, and stage IV), and gender (male, female). The portion 6900' of the tool's user interface 6900 also displays information on features (types of the features and corresponding values) of the subjects in the control group (6930) and in the treatment group (6932). As shown in FIG. 222D, the panels 6930 and 6932 display a censorship rate, distinct medications taken, and drugs taken pre- and post-administration (or predicted administration) of the studied treatment (carboplatin, in this example).

FIGS. 222A, 222B, and 222C illustrate another example of an embodiment of a tool user interface 7000 in accordance with the present disclosure. As shown in FIG. 223A, a propensity value threshold 7008 acquired via the user interface 7000 in a range of between 0.1 and 0.3. In this example, the condition is a colon cancer and the medication is fluorouracil. The type of the information presented on the user interface 7000, generated using a propensity scoring model in accordance with embodiments of the present disclosure, is similar to the information shown in user interface 6900 (FIGS. 222A and 222B). In FIGS. 222A and 2223B, 1966 subjects are assigned to a treatment group (a survival curve 7023), and 985 subjects are assigned to a control group (a survival curve 7025), as shown in a location 7026 on the user interface 7000.

FIG. 222B shows data identical to that in FIG. 222A but with additional notations that facilitate interpretation of the results. As indicated on FIG. 222B, from evaluating the survival curves 7023, 7025 for the treatment and control groups, the treatment group ("arm") appears to have a worse performance in terms of survival as compared to the control group. Evaluation of features of the control group (panel 7030) and features of the treatment group (panel 7032), including drugs taken pre-treatment (the percentage across the respective group is shown for each drug) demonstrates that the subjects in the treatment group were already taken an anti-nausea medication (ondansetron) which can affect the results of the evaluation of the effect of fluorouracil on colon cancer. FIG. 222B also emphasizes that the control group included older subjects even after the application of the propensity scoring model ("score matching") that aims at ensuring that the subjects in the treatment and control groups have similar demographic, clinical, and other characteristics. Also, the subjects in the treatment group had (on average) a higher stage of the colon cancer than the subjects in the control group. Accordingly, the seemingly worse survival of the subjects in the treatment group can potentially explained by the fact that these subjects had a more advanced stage of the disease than the matched control group. FIG. 222C illustrates a close-up, with some notations, of the panels 7030 and 7032 presenting features of the control and treatment groups, respectively.

FIG. 223 illustrates an example of an embodiment of the tool user interface 7000 in accordance with the present disclosure, demonstrating impact of increasing a propensity value threshold (referred to as a "propensity matching threshold") in the example of FIGS. 222A-222C. Thus, the same base population of subjects as used in the example of FIGS. 222A-2232C is analyzed. As compared to FIGS. 222A-222C, a higher propensity value threshold (i.e., a range between 0.2 and 1) is acquired in this example via the user interface element 7008. For example, the user interface element 7008 can be implemented as a slider element configured to receive user input indicating a selection of a range of values.

Adjusting a propensity value threshold results in different treatment and control groups selected from the base population of subjects, with the higher value for the propensity value threshold leading to a more stringent selection of subjects for the two matched groups. In other words, the higher the propensity value threshold, the more similar groups are identified by the propensity scoring model (though the similarly depends on the features selected for the model).

In the example illustrated in FIG. 223, the adjusted propensity value threshold (see, e.g., block 6608 of FIG. 218) results in treatment and control groups of sizes different than in the example of FIGS. 222A-222C. Thus, as shown in the location 7026 on the user interface 7000, the treatment group includes 1476 subjects and the control group includes 6708 subjects. A survival curve 7123 (shown in purple) for the treatment group and a survival curve 7125 (shown in grey) for the control group illustrate a noticeable difference as compared to survival curves 7023, 7025 for the treatment and control groups, respectively, shown in FIGS. 222A and 222B. In the example of FIG. 223, the control group still has, on average, older subjects that in the treatment group. At the same time, the control and treatment groups are more balanced with respect to the stage of colon cancer, meaning that the subjects in the two groups have a similar distribution of stages of colon cancer.

FIGS. 224A and 224B illustrate an example of an embodiment the tool user interface 7000 of FIGS. 222A-222C, demonstrating impact of acquiring (based on user input, in this example) of a selection of certain features ("controlling for prognostic factors") for training a propensity scoring model. The same base population of subjects as used in the example of FIGS. 222A-222C and FIG. 223 is analyzed. The tool user interface 800 is shown to include a feature selection module 7210 that is presented in addition to other visual elements of the user interface 7000. It should be noted that the user interface 6900 (FIGS. 221A and 221B) and the user interface 7000 shown in FIGS. 222A-222C and FIG. 223 can also have a feature selection module. In the present example, the feature selection module 7210 can be displayed upon a user selection of a certain element on the user interface, or in response to another trigger. It can also be presented automatically.

As shown in FIG. 224A, the selected features include a stage of color cancer (stage 4) and age groups (40-49, 50-59, 60-69, and 70-79). The older (above 40) age group can be selected by the user, for example, based on the results of the analysis as shown in FIG. 222B where it was observed that the control group is generally older. The same propensity value threshold is selected via the user interface element 7008 as in FIGS. 222A-222C—in a range of between 0.1 and 0.3. As shown in the location 7026 of the user interface 7000 in FIG. 224A, the number of subjects in the identified treatment and control groups is reduced to 869 and 6606, respectively. This, in combination with the controlling for a cancer stage and age group, results in different survival curves 7223 (shown in purple) and 7225 (shown in grey) for treatment and control groups, respectively. FIG. 224B illustrates features of the control and treatment groups, and includes notations regarding the analysis of the features. Thus, as shown, an improved cancer stage balance between the group is achieved as compared to the stage distribution shown in FIG. 222B (without selecting the age groups).

FIGS. 225A and 225B illustrate an example of an embodiment a tool user interface 7300, demonstrating impact of obtaining a low propensity value threshold, with a range of between 0 and 0.1. The portions of the user interface 7300 shown separately in FIGS. 225A and 225B can be displayed simultaneously on the user interface 7300. FIGS. 226A and 226B illustrate an example of the tool user interface 7300, demonstrating impact of obtaining a higher, mid-range (referred to as "mid") propensity value threshold of a range of between 0.1 and 0.2, and FIGS. 227A and 227B illustrate an example of the tool user interface 7300, demonstrating impact of obtaining a high propensity value threshold with a range of between 0.2 and 1. The user interface 7300 can be similar to the user interface 7000 (FIGS. 222A-222C) such that the same base population is used for the evaluation of effect of fluorouracil on colon cancer.

As shown in FIGS. 225A, 226A, and 227B, a selection of certain range for a propensity value threshold affects a number of subjects assigned to treatment and control groups, and consequently features characterizing the groups. Thus, increasing the range generally results in increasing the size of the matched groups.

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein the term "cancer," "cancerous tissue," or "tumor" refers to an abnormal mass of tissue in which the growth of the mass surpasses and is not coordinated with the growth of normal tissue. In the case of hematological cancers, this includes a volume of blood or other bodily fluid containing cancerous cells. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" or "somatic biopsy" refers to a biological sample obtained or derived from a tumor of a subject, as described herein.

Several aspects are described above with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The methods described herein provide improved cancer classification for patients. With improved accuracy and higher resolution over previous methods, the predictive algorithms provided herein can be used to resolve the diagnoses of tumors of unknown origin. With such increased resolution in the classification outputs, additional patients will receive more accurate diagnoses and more informed treatments.

All references cited herein are incorporated herein by reference in their entirety and for all purposes to the same extent as if each individual publication or patent or patent application was specifically and individually indicated to be incorporated by reference in its entirety for all purposes.

XI. Transcriptome Deconvolution of Metastatic Tissue Samples

As used herein, the following terms have the associated meanings.

"Biological validation" refers to the comparison of a set of identified genes that are correlated with a cluster and genes represented in RNA expression profiles known or likely to be associated with a subset of tissues, including a portion of a tissue sample, a type of cell that may be in a tissue sample, or single cells within a tissue sample and may determine a correlation between the known RNA expression profile genes and the genes correlated with a cluster, associating the cluster with the expression profile of that subset of tissue.

"Cluster" refers to a set of genes whose expression levels are correlated with a percentage of the variance seen among multiple samples in an RNA expression dataset. The cluster may be said to be driven by this set of genes, where "driven" is a term for describing that the expression levels of the genes in this set explain a percentage of the variance. The expression levels of the genes in this set may have patterns that are consistently associated with the variance. For example, the expression level of a given gene in the set may be higher or lower in samples having one or more characteristics in common, or the expression levels of two or more genes may be directly or inversely correlated with each other in samples having one or more characteristics in common. Sample characteristics may include the collection site of the sample, the type of tissue or combination of tissue types contained in the sample, etc.

"Deconvolution" refers to a process of resolving expression data from a mixed population of cell types to identify expression profiles of one or more constituent cell types, for example using algorithm processes.

"Metastatic sample" refers to a sample of a tumor that arose from an organ different from the organ from which the sample was taken.

"Normal sample" refers to a sample of non-tumor tissue.

"Primary sample" refers to a sample of a tumor that arose from the same organ from which the sample was taken.

"Reads" refers to the number of times that a sequence from a sample was detected by a sequencer.

"Sequencing depth" refers to the total number of repeated reads per nucleotide in a sample.

A system for performing deconvolution on gene expression data and developing a deconvolution model for gene expression analysis is shown in FIG. 228. The system 7400 includes computing device 7401 for implementing the techniques herein. As illustrated, the computing device 7401 includes a deconvolution framework 7402 and a RNA normalization framework 7404, both of which may be implemented on one or more processing units, e.g., Central Processing Units (CPUs), and/or on one or more or Graphical Processing Units (GPUs), including clusters of CPUs and/or GPUs. Features and functions described for the deconvolution framework 7402 and the normalization framework 7404 may be stored on and implemented from one or more non-transitory computer-readable media of the computing device 7401. The computer-readable media may include, for example, an operating system and the frameworks 7402 and 7404. More generally, the computer-readable media may store batch normalization process instructions for the framework 7404 and deconvolution process instructions for the framework 7402, for implementing the techniques herein. The computing device 7401 may be a distributed computing system, such as an Amazon Web Services cloud computing solution.

The computing device 7401 includes a network interface communicatively coupled to network 7406, for communicating to and/or from a portable personal computer, smart phone, electronic document, tablet, and/or desktop personal computer, or other computing devices. The computing device further includes an I/O interface connected to devices, such as digital displays, user input devices, etc.

The functions of the frameworks 7402 and 7404 may be implemented across distributed computing devices 7452, 7454, etc. connected to one another through a communication link. In other examples, functionality of the system 7400 may be distributed across any number of devices, including the portable personal computer, smart phone, electronic document, tablet, and desktop personal computer devices shown. The computing device 7401 may be communicatively coupled to the network 7406 and another network 7456. The networks 7406/7456 may be public networks such as the Internet, a private network such as that of a research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 7500 may represent a CPU-type processing unit, a GPU-type processing unit, a field-programmable gate array (FPGA), another class of digital signal processor (DSP), or other hardware logic components that can be driven by a CPU.

The computing device 7401 is coupled to receive gene expression count data from a database, such as a gene expression dataset 7416. In one example, gene expression data may be normalized counts or raw RNA expression counts, which report the number of times that a particular gene's RNA is detected in a sample by a sequence analyzer or another device for detecting genetic sequences. The computing device 7401 may be coupled to receive gene expression data from a multitude of different, external sources through the communication network 7406. The computing device 7401, for example, may be coupled to a health care provider, a research institution, lab, hospital, physician group, etc., that makes available stored gene expression data in the form of an RNA sequencing dataset. Example external gene expression datasets include the Cancer Genome Atlas (TCGA) dataset 7418 and the Genotype-Tissue Expression (GTEx) dataset 7420, both examples of established gene expression datasets that can be normalized by the normalization framework 7404 and incorporated into an already-normalized database of gene expression data, such as the dataset 7416. The gene expression dataset 7416 may be a normalized dataset. Methods of normalizing gene expression data are disclosed in U.S. Provisional Patent Application No. 62/735,349, which is incorporated by reference in its entirety. A gene expression dataset may be obtained, e.g., from a network accessible external database or from an internal database. The gene expression dataset may contain RNA seq data. A gene information table containing information such as gene name and starting and ending points (to determine gene length) and gene content ("GC") may be accessed and the resulting information used to determine sample regions for analyzing the gene expression dataset 7416.

In an example, additional normalizations may be performed. For instance, a GC content normalization may be performed using a first full quantile normalization process, such as a quantile normalization process like that of the R packages EDASeq and DESeq normalization processes (Bioconductor, Roswell Park Comprehensive Cancer Center, Buffalo, N.Y., available at https://bioconductor.org/packages/release/bioc/html/DESeq.html). The GC content for the sampled data may then be normalized for the gene expression dataset. Subsequently, a second, full quantile normalization may be performed on the gene lengths in the sample data. To correct for sequencing depth, a third normalization process may be used that allows for correction for overall differences in sequencing depth across samples, without being overly influenced by outlier gene expression values in any given sample. For example, a global reference may be determined by calculating a geometric mean of expressions for each gene across all samples. A size factor may be used to adjust the sample to match the global reference. A sample's expression values may be compared to a global reference geometric mean, creating a set of expression ratios for each gene (i.e., sample expression to global reference expression). The size factor is determined as the median value of these calculated ratios. The sample is then adjusted by the single size factor correction in order to match to the global reference, e.g., by dividing gene expression value for each gene by the sample's size factor. The entire GC normalized, gene length normalized, and sequence depth corrected RNA seq data may be stored as normalized RNA Seq data. A correction process may then be performed on the normalized RNA seq data, by sampling the RNA Seq data numerous times, and performing statistical mapping or applying a statistical transformation model, such as a linear transformation model, for each gene. Corresponding intercept and beta values may be determined from the linear transformation model and used as correction factors for the RNA seq data.

In some examples, the normalization framework 7404, to incorporate multiple datasets, includes a gene expression batch normalization process that adjusts for known biases within the dataset including, but not limited to, GC content, gene length, and sequencing depth. The normalization framework 7404 includes a gene expression correction process. The normalization framework 7404 may generate one or more correction factors, which are applied by the normalization framework 7404 to convert new gene expression datasets, such as datasets 7418 and 7420, into a normalized dataset. Applying these correction factors, the normalization framework 7404 is able to normalize, correct, and convert the new gene expression dataset 7416 for integration into an existing normalized, corrected gene expression dataset 7417, as shown. Known biases include, for example, two unnormalized datasets may not be compared directly if the datasets were acquired by different sequencing protocols. Additionally, some characteristics of a genetic sequence in a sample may change the likelihood that the sequencer will detect that sequence. The distribution of nucleotides of a genetic sequence (percentage of guanosine (G) or cytosine (C), versus adenine (A) or thymine (T)) can influence the likelihood of sequences being amplified and detected by a sequencer. Similarly, decreased gene sequence length and lower sequencing depth decreases the likelihood of gene-level sequence read detection and quantification. In these cases, the normalization process multiplies the reads by a correction factor that adjusts the number of reads to better reflect the actual number of molecular copies of those sequences in the sample.

The deconvolution framework 7402 may be configured to receive normalized gene expression data and modify such data using a clustering process to optimize the number of clusters, K, such that one or more gene expression clusters associated with one or more cell types of interest are detected. Subsequent analysis of the gene expression clusters may determine cancer-specific cluster types within such data. The deconvolution framework is discussed with more detail with respect to FIG. 229 below.

FIG. 229 illustrates a process 7500 that may be executed by the system 7400, and in particular the deconvolution framework 7402, to perform an exemplary deconvolution on RNA expression data. At a block 7502, the system 7400 receives normalized RNA expression data, e.g., from the normalized RNA sequence database 7416. In some examples, the system 7400 is configured to generate the normalized RNA expression data, e.g., as described in reference to the normalization framework 7404. The RNA expression data may contain data for various tissue samples, including cancer tissue samples and normal tissue samples. The RNA expression data, as described in various examples herein, may include metastatic tissue samples, which contain a mixture of cancer and normal tissue. The samples may be from any tissue type, including by way of example, liver tissue, breast tissue, pancreatic tissue, colon tissue, bone marrow, lymph node tissue, skin, kidney tissue, lung tissue, bladder tissue, bone, prostate tissue, ovarian tissue, muscle tissue, intestinal tissue, nerve tissue, testicular tissue, thyroid tissue, brain tissue, and fluid samples (e.g., saliva, blood, etc.).

At a block 7504, the deconvolution framework 7402 analyzes the normalized RNA expression data and applies a deconvolution model to remove expression data from cell populations that are not cell types of interest (e.g. tumor or other types of cancer tissue). In some examples, the block 7504 implements the deconvolution model using machine learning algorithms such as unsupervised or supervised clustering techniques to examine gene expression data to quantify the level of tumor versus normal cell populations present in the data. The block 7504 may apply any number of machine learning algorithms, such as, for example, anomaly detection, artificial neural networks, expectation-maximization, singular value decomposition, etc. In some examples, the block 7504 may apply machine learning techniques. Other example machine learning techniques that may be used in place of clustering include support vector machine learning, decision tree learning, associated rule learning, Bayesian techniques, and rule-based machine learning.

In some examples, and as discussed further herein, the block 7504 analyzes multiple samples of tissue applying the deconvolution model to identify one or more correlated clusters of RNA expression data and the genes corresponding to those clusters for identifying tissue and cancer types in subsequent RNA expression data. After completing the clustering process, the block 7504 generates a deconvoluted RNA expression model that is stored (at block 7506) for use as a trained model to examine subsequently received RNA expression data, such as RNA expression data generated from a tissue sample from a patient with cancer. For example, the deconvoluted RNA expression model may include regressed out clusters corresponding to latent factors, e.g., clusters of gene expression data corresponding to particular cancer types or cell populations with similar expression profiles. These deconvoluted RNA expression models, as shown by examples below, are able to exhibit overexpressed genes and underexpressed genes different from those of normal or mixed, convoluted RNA expression data and that more accurately predict cancer type based on the list of those overexpressed and underexpressed genes. The generated trained deconvoluted models may then be applied to subsequent RNA expression data, at a block 7508.

RNA expression data examined by the deconvoluted RNA expression model may be used to determine which genes, or networks of related genes, have expression levels that differ between tumor and normal tissue. Exemplary differences in expression levels in deconvoluted versus convoluted RNA expression data are depicted in FIG. 238. In various aspects, comparing tumor expression levels with normal tissue levels permits biomarker discovery, by determining which genes or gene networks have a higher or lower expression level in tumor tissue than normal tissue that may be adjusted or targeted by treatment. Such a comparison permits predicting the type of cancer or the origin of the cancer, associating mutations with gene expression patterns, and associating tumor gene expression profiles with a list of cancer treatments that may predict response for a patient with that profile.

As part of deconvolution, the number of genes or networks of related genes in the datasets to be analyzed may be in the thousands or tens of thousands.

FIG. 230 illustrates a detailed example implementation of a process 7600 for generating a deconvolution RNA expression data model, as may be performed by the system 7400 to implement the process 7500. In an initial training mode, reference RNA expression data is received at a block 7602. This reference RNA expression data may be normalized RNA expression data from external and/or internal datasets. External datasets may include RNA sequence data from gene expression databases, such as the TCGA database 7418 and the GTEx database 7420 that may not be normalized to a database, such as the normalized database 7416. The RNA expression data may be configured in a N×G matrix, where N is the number of samples and G is the number of genes. In some examples, the RNA expression data includes data from normal samples, primary samples (such as breast tumor from breast tissue), and metastases samples (such as breast tumor from liver tissue).

A block 7604 receives RNA expression data from block 7602 and analyzes the RNA expression data with a clustering algorithm executed by the processing device. In the illustrated example, the clustering algorithm may apply a grade of membership (GoM) model, which is a mixture model that allows sampled RNA expression data to have partial memberships in multiple clusters, as the clustering algorithm executes. For example, in each cycle, each sample, N, within the RNA expression data may be assigned a percentage membership in each of the K number of clusters. This computing device continues the process via a processing loop 7606 until the samples are clustered across each of the RNA expression datasets. The clustering algorithm may be implemented using the CountClust algorithm (Bioconductor, Roswell Park Comprehensive Cancer Center, Buffalo, N.Y., available at https://bioconductor.org/packages/CountClust/). For instance, grade of membership may be implemented in CountClust using a fit on normalized, $\log_{10}$ gene expression counts for K=10, 12, 14, 16, and 24 clusters. Gene enrichment, which identifies if any of the members of a list of genes or proteins has a class of genes or proteins that is represented more than statistically expected, may be calculated on the top 1,000 driving genes reported for each cluster using the process instructions for the goseq R package (Bioconductor, Roswell Park Comprehensive Cancer Center, Buffalo, N.Y., available at https://bioconductor.org/packages/release/bioc/html/goseq.html). In other examples, alternative algorithms may be used to determine the optimal number of clusters.

The number of clusters may be predetermined or dynamically set by the block 7604. For example, the number of clusters may be dependent upon the type of tissue being sampled in the RNA expression data, the type and heterogeneity of cancer types or cell populations to be examined, or the sample size distribution of the reference samples and the type of sequencing technology. An exemplary training dataset may include RNA expression data from tissue normal samples, primary samples, and metastatic samples. An alternative training set may also include labels, annotations, or classifications identifying each of the samples as the respective type of tissue, in addition to other biological indicators (such as cancer site, metastasis, diagnosis, etc.) or pathology classifications (such as diagnosis, heterogeneity, carcinoma, sarcoma, etc.).

A machine learning algorithm (MLA) or a neural network (NN) may be trained from the training data set. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where certain features/classifications in the data set are annotated) using generative approach (such as mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, long short term memory networks, or other neural models where the training data set includes a plurality of samples and RNA expression data for each sample. While MLA and neural networks identify distinct approaches to machine learning, the terms may be used interchangeably herein. Thus, a mention of MLA may include a corresponding NN or a mention of NN may include a corresponding MLA.

Training may include identifying common expression characteristics shared across RNA gene expressions in tissue normal samples, primary samples, and metastatic samples, such that the MLA may predict the ratio of a metastases tumor from the background tissue and identify which portion of an input RNA expression set may be attributed to the tumor and which portion may be attributed to the background tissue. Common expression characteristics may include which genes are expected to be overexpressed, expressed, and/or underexpressed for each type of tissue and/or tumor and may be identified for each k cluster as the corresponding genes.

With the samples clustered with partial memberships using the process of block 7604, at a block 7608, the computer device may perform an optional biological validation of identified grade of membership latent factors. This process is also referred to as gene enrichment in the present example, which is the analysis of a list of genes or proteins to identify any classes of genes or proteins that are represented by members of the list at a rate that is higher than statistically expected. In an example implementation, one or more clusters enriched in genes known to be associated with the background tissue of interest are identified by the computing device. The block 7608 then determines which genes have the highest contribution to these clusters, and the block 7608 validates that these genes have biological interpretation. For the validation, for example, the computing device may compare the identified genes against a pre-existing database of genes associated with particular biological processes that are to be examined and are known to be relevant in the cell population of interest. For instance, the cell population of interest may be liver cells, breast cancer cells in a tumor, etc. The processes of blocks 7604 and 7608 may be performed using a feedback 7610 until cluster optimization is complete. Clustering may be applied multiple times to yield a varying number of clusters, K, and the membership percentages of all samples of each type of tissue in each cluster may be analyzed. An optimal number of K clusters may be selected such that the membership sum of one or multiple clusters has i) high estimated proportion in reference samples with the cell population of interest (such as liver normal and liver cancers), ii) low proportion in other cell types (such as non-liver primary cancers) and iii) the strongest significant enrichment of relevant biological pathways (such as metabolic processes for identification of liver background).

With the biological validation completed from the block 7608, at a block 7612, the deconvolution framework 7402 develops a deconvolution regression model of RNA expression data. The deconvolution regression model may be developed by calculating the contribution of one or more clusters to gene expression levels and removing those contributions from a sample's gene expression data. In one example, the effect of a specific membership percentage in a given cluster on the expression level of a given gene may be calculated by using a regression of RNA expression data derived from multiple samples (plotted as the sample's membership percentage in the cluster on the x-axis and the sample's expression level for that gene on the y-axis). The block 7612 stores a deconvoluted RNA matrix of N×G values as the regression model, or a first matrix of N×K values with a second matrix of K×G values, for example. In this example, N represents each sample, K represents each cluster, and G represents each gene. There may be a row or column in a matrix for each sample, cluster, and/or gene.

The deconvoluted RNA matrix may be validated at a block 7614, which may perform an in silico validation (i.e., validation performed on a computer) for example by using in silico mixtures of cancers and background RNA expression data. The validation analyzes whether the deconvoluted RNA matrix properly identifies, from the samples, RNA expressions of known in silico mixtures. In another example, the block 7614 performs validation using a machine learning technique, such as analyzing the RNA expression data sets before and after deconvolution using a grouping analysis known as nearest neighbor clustering and comparing the results of the grouping analysis. This validation may be applied to confirm that relevant samples of the deconvoluted RNA matrix will form a group with primary samples of the same cancer type when sorted by a grouping technique.

Returning to FIG. 229, application of the MLA described above with respect to FIG. 230 at block 7504 of FIG. 229 may include receiving RNA expression data of a metastatic tumor in a patient. For example, a patient may be diagnosed with breast cancer which has metastasized to additional locations in the patient's body and a breast cancer tumor may now be present in the patient's liver. The tissue sample processed by a genetic sequence analyzer may have included both the breast tumor tissue and healthy liver tissue, so the convoluted, mixed tissue sample that is sequenced will include expression results from both tissues. The gene expression levels of both tissues will contribute to the measured gene expression levels of the total, mixed sample.

An exemplary model, trained as described above with respect to FIG. 230, may process the received RNA expression data to identify the membership of each cluster of the model (i.e., in a k=15 model where k is the number of clusters, each sample receives 15 different membership classifications, one associated with each cluster). In an unsupervised MLA, an exemplary cluster may not be assigned to any particular cancer site with tumor, cancer site without tumor, or metastases tumor, as an unsupervised algorithm clusters based off of similar features without regarding particularly the classification of each sample. Therefore, it may not be easy to identify which features correspond to which type of sample. In an unsupervised approach, only the genes whose expression levels are predicted to have been affected by the sample's membership in one or more of the clusters are identified and then the expression levels of those genes are adjusted in post processing (i.e., using variate/multivariate regression) to counteract the effects of the sample's percentage of membership in any of the clusters.

For a particular sample, the MLA result may identify a percentage of membership in each cluster (e.g., 15% $k_1$, 65% $k_9$, 20% $k_{13}$). Post processing of the grade of membership output may include a multivariate regression which will accommodate for the influence of each cluster, for example $k_1$, $k_9$, and $k_{13}$ in the RNA expression data. In an exemplary embodiment, a linear regression based on the expression levels of one gene in all of the training samples that had membership in one of the respective clusters may, for each gene, be used to calculate a regressed gene expression level. For example, if a cluster was derived from 1000 samples, each sample may be plotted as a data point with the grade of membership percentage in that cluster on the x-axis and the expression level of a given gene in the sample on the y-axis and the equation of a regression line may be calculated to approximate the plotted data points. Using the equation of the regression line, it is possible to replace x with the membership percentage of the newest sample, and calculate the y, which is the expression level of the gene that is explained by that percentage of membership in that cluster. In one example, to remove the effect of that cluster, the calculated expression level y may be subtracted from the total gene expression level measured in the mixture sample for that gene. In another example, the expression level of each gene associated with that cluster may be scaled to increase or decrease the gene expression level measured in the mixture sample based on where the gene's expression falls in relation to the average at that membership percentage on the linear regression plot.

By calculating each cluster's effect on the expression levels of all genes associated with the cluster, these factors may be regressed out (i.e., by summing the initial RNA gene expression level measured in the mixture sample with the additive inverse of each cluster's effect) and the resulting deconvoluted RNA expression data may be evaluated for biomarkers or other biological indications. In a supervised or semi-supervised MLA, an exemplary cluster will be assigned to one or more types of samples (particular cancer site with tumor, cancer site without tumor, or metastatic tumor). For example, $k_5$ may be assigned to breast tumor, $k_6$ may be assigned to tumorous breast tissue metastasized in the liver, and $k_7$ may be assigned to non-tumor breast tissue. Furthermore, the initial training dataset may include a table of the N samples which identifies the corresponding type of sample. Therefore the output from the MLA processing may identify a percentage of membership within each cluster as well as a prediction of the type of sample. Post-processing for semi-supervised and supervised MLA may be performed in the same manner as the unsupervised MLA described above.

Examples

We now describe an example implementation of the processes of FIGS. 229 and 230, in particular as applied to an example analysis of liver metastatic samples.

Initially, we compiled a reference dataset comprising 238 sequenced liver metastatic samples (Tempus Labs, Inc., Chicago, Ill.), 120 metastatic samples as part of a Met500 project, 3,508 primary samples from The Cancer Genome Atlas (TCGA) selected from among 22 cancers in the metastatic liver samples, and 136 normal liver samples from the Genotype-Tissue Expression project (GTEx), Table 1 (4,754 samples in total).

In this example, samples were collected as part of GTEx, TCGA, Met500 projects or clinical samples (Tempus Labs, Inc., Chicago, Ill.). To minimize possible batch effects, raw data from GTEx and TCGA databases were downloaded in bam file format and processed through the same RNA-seq pipeline for sequence alignment and normalization. Met500 and clinical samples underwent a RNA-seq library preparation approach that included a transcription capture step and was optimized for formalin-fixed paraffin-embedded (FFPE) samples. To account for differences in library preparation methods across studies, we calculated per gene sizing factors on $\log_{10}$ normalized counts from 500 subsamples of 1,000 TCGA and clinical samples from a group of 9,295 TCGA samples and 3,903 clinical samples. Sizing factors were applied to TCGA and GTEx samples to ensure genes had equivalent mean and variances across studies.

TABLE 1

Sample composition for samples included in the grade of membership reference. Selected TCGA samples include all cancers present in the liver metastatic cancer set, which comprises the 238 sequenced liver metastatic samples (Tempus Labs, Inc., Chicago, IL) and 120 metastatic samples from the Met500 project.

|  | Tempus | Met500 | GTEx | TCGA |
|---|---|---|---|---|
| Liver metastases | 238 | 120 |  |  |
| Liver normal |  |  | 136 |  |
| Primary cancers | 752 |  |  | 3,508 |
| Total | 990 | 120 | 136 | 3,508 |

GTEx: Genotype-Tissue Expression; TCGA: The Cancer Genome Atlas.

The most abundant cancers within the liver metastases were breast (23.5%), pancreatic (19.8%) and colon (17.3%) cancers (Table 2).

TABLE 2

Distribution of cancer and tissue types by study in the reference set.

| Cancer | Liver metastases (Tempus and Met5000) | TCGA primary | Tempus primary | GTEx liver | Total |
|---|---|---|---|---|---|
| Adrenocortical carcinoma (acc) | 3 | 45 | 0 | 0 | 48 |
| Bladder Urothelial Carcinoma (blca) | 8 | 202 | 19 | 0 | 229 |
| Breast invasive carcinoma (brca) | 84 | 529 | 169 | 0 | 782 |
| Cholangiocarcinoma (chol) | 17 | 14 | 0 | 0 | 31 |
| Colon adenocarcinoma (coad) | 62 | 137 | 80 | 0 | 279 |
| Diffuse large B-cell lymphoma (dlbc) | 1 | 21 | 1 | 0 | 23 |
| Esophageal carcinoma (esca) | 1 | 79 | 16 | 0 | 96 |
| Head and Neck aquamous cell carcinoma (hnsc) | 11 | 259 | 1 | 0 | 271 |
| Kidney chromophobe (kich) | 1 | 32 | 0 | 0 | 33 |
| Kidney renal clear cell carcinoma (kirc) | 6 | 267 | 64 | 0 | 337 |
| Liver heptocellular carcinoma (lihc) | 5 | 179 | 0 | 0 | 184 |
| Liver (normal) | 0 | 0 | 0 | 136 | 136 |
| Lung adenocarcinoma (luad) | 5 | 249 | 94 | 0 | 348 |
| Lung aquamous cell carcinoma (lusc) | 3 | 239 | 33 | 0 | 275 |
| Ovarian nerous cystadenocarcinoma (ov) | 5 | 180 | 52 | 0 | 237 |
| Pancreatic adenocarcinoma (paad) | 71 | 79 | 59 | 0 | 209 |

TABLE 2-continued

Distribution of cancer and tissue types by study in the reference set.

| Cancer | Liver metastases (Tempus and Met5000) | TCGA primary | Tempus primary | GTEx liver | Total |
|---|---|---|---|---|---|
| Phenochromocytoma and paraganglioma (pcpg) | 20 | 88 | 22 | 0 | 130 |
| Prostate adenocarcinoma (prad) | 31 | 246 | 68 | 0 | 345 |
| Sarcoma (sarc) | 11 | 118 | 2 | 0 | 131 |
| Skin cutaneous melanoma (skcm) | 2 | 223 | 8 | 0 | 233 |
| Stomach adenocarcinoma (stad) | 8 | 168 | 17 | 0 | 193 |
| Thyoma (thym) | 2 | 70 | 14 | 0 | 86 |
| Uterine corpus endometrial (ucen) | 1 | 84 | 33 | 0 | 118 |
| Total | 358 | 3,508 | 752 | 136 | 4,754 |

In this example, a validation step was performed that uses principal component analysis (PCA) to assess groupings based on RNA gene expression profiles among the primary cancer samples, healthy tissue samples, and the deconvoluted metastatic samples. PCA, performed by computing devices such as that of FIG. 228, is a dimension reduction technique for comparing data sets from multiple samples or a single data set containing multiple samples, especially where each sample may be associated with multiple values, such as an expression level value for each expressed gene for tens of thousands of expressed genes or more. PCA may be used on all expressed genes to determine which genes in conjunction have the greatest variance in expression levels among samples.

The principal components may be sorted according to the largest percent of variance explained by the contributions of those genes to demonstrate the greatest differences among samples, and the principal component that makes the largest contribution to variance may be designated principal component 1 (PC1). The principal component that makes the second largest contribution to variance (after regressing out the contribution of PC1) may be designated principal component 2 (PC2). The samples may be spatially arranged according to the extent of contribution principal components that contribute the largest percentage of the variance in the dataset. In the example shown in FIG. 231 generated by the computing device, the expression levels of the group of genes represented by PC1 distinguishes samples with a low proportion of liver cells (in the example, primary non-liver cancers) from samples with a high proportion of liver cells (in the example, liver cancer and healthy liver samples). The expression levels of the group of genes represented by PC2 distinguishes samples based on differences caused by primary cancer types. As expected, liver specific cancers and liver tissue do not contain this type of variance and there is not a large degree of separation along the y-axis for these groups.

The groups of sample data can be visually represented in a chart such as the one shown in FIG. 231. Samples are colored by their tissue or origin. As shown, PC1 explained 10.5% of the variance and separated the TCGA liver hepatocellular carcinoma (lihc) and GTEx normal liver from the other non-liver primary cancers. Rather than forming a group with their cancer type of origin, in this unsupervised grouping example, principal component analysis grouped the liver metastatic samples together as a continuum between the TCGA cancers and liver normal (GTEx) and cancer samples (lihc TCGA). Metastatic liver samples (meaning, tumor cells from another organ which are found in the liver) are represented with larger circles and formed groups away from their respective TCGA primary cancers. As shown in FIG. 231, small circles to the left of liver metastases represent non-liver primary cancers, while liver primary cancers and liver normal samples are represented by small circles that group to the right of the metastases. This variation in expression separating metastatic liver samples from primary samples is attributable to the expression of the normal background liver tissue in the sample. As shown, rather than grouping with their cancer type of origin, liver metastatic samples grouped together as a continuum between the TCGA cancers, on the left, and both liver normal (GTEx liver) and liver cancer samples (TCGA liver hepatocellular carcinoma (lihc)) on the right.

Aiming to characterize the cell populations present in the samples, the CountClust algorithm was used as an exemplary clustering algorithm to fit a grade of membership model (GoM) with 15 clusters (K=15). The clustering shown in FIG. 232 illustrates the 15 clusters and the top 1,000 genes driving each of the clusters as determined using the CountClust algorithm GoM model. In FIG. 232, the labels on the left indicate cancer types or liver normal tissue, each row represents a single sample of the cancer type indicated on the left, and each color represents a cluster associated with a portion of that sample (see legend at bottom of FIG. 232). The length of each color in each row relative to the length of the entire row represents the percentage of that row's sample that is associated with the cluster of that color.

A preferred cluster size, meaning the number of clusters, may be K=15. Cluster size was selected such that a single cluster results in high estimated proportions in GTEx liver and TCGA lihc samples and low in other TCGA cancer samples, as shown in FIG. 232 as the olive green colored band that indicates cluster number 5 (see legend). We identified one cluster (the fifth cluster, or k=5, colored in olive green) where TCGA lihc, chol and GTEx liver samples had high membership proportions (average 0.608, 0.192, and 0.730, respectively) and all other, non-liver TCGA primary cancers resulted in low proportions (0.011). Metastatic liver samples had a range of intermediate membership values for the 5th cluster (0.230), as shown in FIG. 233, which illustrates the distribution of the fifth GoM cluster by cancer type for all 4,754 samples. FIG. 233 is a box plot representation of the membership values of the samples within each cancer or tissue type labeled along the x-axis of the plot, with dots representing the outliers in each category. The metastatic samples with low tumor purity and high background tissue are likely to be outliers, with higher proportions of the fifth cluster. Liver metastatic samples from Met500 and from Tempus Labs, Inc. had intermediate estimated proportions for this cluster. Primary Pancreatic Ductal Adenocarcinoma (paad) and Cholangiocarcinoma bile duct cancer (chol) contain tissues that have gene expression profiles that are similar to liver tissue, which accounts for the high estimated proportions of the fifth cluster in these cancer samples.

As an optional validation, to assign biological relevance to the particular fifth cluster, a gene enrichment method (available at http://geneontology.org/) was configured to select the top 1,000 genes influencing the fifth cluster and perform gene enrichment analyses for Gene Ontology (GO) biological processes. This gene enrichment analysis identified 582 biological processes that were significantly enriched after Bonferroni correction, meaning that 582 biological processes were disproportionately associated with the genes whose expression was most consistently correlated with the fifth cluster. Metabolic processes were among the most enriched, with the most significant being GO:0019752—carboxylic acid metabolic process (203 out of 1,002 genes; $p=3.61 \times 10-85$). Given this result, we consider the fifth cluster to be a liver specific latent factor and an approximation to the proportion of liver background tissue present in each sample and comparable across samples.

The determination of the fifth cluster as a liver specific latent factor was validated against tumor purity data. Tumor purity estimates for 140 samples were available from DNA sequencing of the same tumor sample and from pathology estimates from separate samples. This allowed us to assess the correlation between the fifth GoM cluster proportion and these tumor purity estimates and found correlations of −0.33. The result is trained and validated identification of a cluster for use in predicting cancer and liver percentages. In the example of process 7600, this procedure may repeat through feedback 7610 until all clusters are examined and validated.

In one example, the present techniques may implement a non-negative least squares (NNLS) model, to predict tumor and liver percentages trained on the GoM proportions of the fifth cluster and gene expression profiles from 358 liver metastatic samples. We selected 500 genes with the lowest sum of square error (SSE) in a leave-one-out validation approach applied to all genes. We then validated the selected gene list in a second leave-one-out step that resulted in a correlation of $r=0.98$ between predicted liver proportions and equivalent performance across cancer types, as shown in FIG. 234.

In one example, a customized non-negative least squares algorithm estimates cell proportions within a sample and projects them to a probability simplex such that all estimates are non-negative and sum up to one. Optimization of the convex function was done iteratively such that the sum of squares error (SSE) between the model parameters and the sample estimates have a difference of less than 10-7 between the two most recent runs. To select a set of genes with the highest predictive power in the final non-negative least squares model, we performed a leave-one-out NNLS approach using gene expression of 19,147 genes across 358 liver metastatic samples. We used the GoM proportion of the fifth cluster (liver) and 1 minus this proportion as predictors. The technique may be used to predict origin of cancer. We selected 500 genes with the lowest SSE among the models for our final model implementation. While the number of selected genes is somewhat arbitrary, we selected 500 genes from among a series of gene sets (100, 250, 500) such that GO enrichment associations reached the highest significance.

In an example, we validated the liver deconvolution model with a pancreatic cancer research dataset. We identified 65 pancreatic cancer samples from a pancreatic research cohort that included metastatic samples from the liver (9), lung (5), lymph node (1) and rectum (1). Principal component analysis (PCA) of gene expression showed metastatic liver samples (blue) grouped between liver samples (TCGA—teal and GTEx—orange) and all other pancreatic samples (FIG. 235).

Metastatic samples from the lung (pink), lymph node (green) and rectum (grey) grouped with PENN (yellow) and TCGA (light brown) primary pancreatic cancers and did not show a large proportion of variation explained by the background tissue site. To adjust for the liver background gene expression, we applied the deconvolution model from the present techniques on the nine liver metastases and showed that the global variation present in the deconvoluted samples grouped together with pancreatic cancer samples (PAAD) as shown in FIG. 236. Thus, as apparent from comparison of the RNA expression data in FIG. 8, pre-deconvolution, versus the deconvoluted expression data of FIG. 236, it is apparent that the liver metastases samples (liver pancreatic metastatic samples in blue) grouped together with samples of known pancreatic cancer after a deconvolution process is performed. A comparison of raw gene expression data to processed gene expression data provided to and/or received from a gene expression analyzer may be used to identify patterns indicating the presence of deconvolution, in some examples.

In another example, we validated the liver deconvolution model in silico using breast cancer and normal liver mixtures. To assess the liver deconvolution model with a prior expectation, we performed in silico mixtures of breast cancer and liver normal sequencing reads for two pairs of samples from the TCGA dataset. Specifically, we mixed raw sequence reads for two pairs of samples from TCGA: TCGA_DD_A114_11 (liver normal) with TCGA_EW_A424_01 (breast cancer) and TCGA_DD_A118_11 (liver normal) with TCGA_EW_A3U0_01 (breast cancer). We aligned the sequence reads from each of the four pure, individual samples with a reference sequence, normalized the reads, and selected titration levels at which to combine pairs of samples, based on the number of aligned reads. We created new data files with a combination of the reads from the pairs of samples indicated at five different titration levels, where a titration level is the proportion of the combined reads from the first sample versus the second sample, within the range of 0-100% (see Table 3) for each pair of samples. We used the non-negative least squares (NNLS) model to predict the percentage of liver cluster (the fifth cluster) present in each of the two mixture series (Table 3) followed by deconvolution using a regression model (see, e.g., PCA plots in FIGS. 237A and 237B). The non-negative least squares model accurately approximated the proportion of each mixture that was liver normal reads versus breast cancer reads (Table 3).

Table 3: Non-Negative Lease Squares (NNLS) Model Results on Two Breast Cancer and Liver Normal TCGA Mixture Samples.

Estimates for lower tumor content are slightly over-estimated and higher content are under-estimated. However, observed and expected values among mixtures are highly correlated (0.89 and 0.82, respectively, as shown in FIGS. 236A and 236B).

TABLE 3

Non-negative least squares (NNLS) model results on two breast cancer and liver normal TCGA mixture samples. Estimates for lower tumor content are slightly over-estimated and higher content are under-estimated. However, observed and expected values among mixtures are highly correlated (0.89 and 0.82, respectively, as shown in FIGS. 236A and 236B).

| Sample Mixture | Mixture % breast reads | Mixture % liver reads | NNLS estimates % tumor | NNLS estimates % normal |
|---|---|---|---|---|
| TCGA_DD_A118_11 (liver normal)/ TCGA_EW_A3U0_01 (breast cancer) | 0 | 100 | 0.0071 | 0.9929 |
| | 0.13 | 0.87 | 0.3330 | 0.6670 |
| | 0.25 | 0.75 | 0.3668 | 0.6332 |
| | 0.18 | 0.82 | 0.3761 | 0.6239 |
| | 0.6 | 0.4 | 0.4777 | 0.5223 |
| | 0.72 | 0.28 | 0.5027 | 0.4973 |
| | 0.94 | 0.06 | 0.6523 | 0.3477 |
| | 100 | 0 | 0.7052 | 0.2948 |
| TCGA_DD_A114_11 (liver normal)/ TCGA_EW_A424_01 (breast cancer) | 0 | 100 | 0.0001 | 0.9999 |
| | 0.09 | 0.91 | 0.3464 | 0.6536 |
| | 0.22 | 0.78 | 0.3800 | 0.6200 |
| | 0.51 | 0.49 | 0.4499 | 0.5501 |
| | 0.64 | 0.36 | 0.4857 | 0.5143 |
| | 0.78 | 0.22 | 0.5225 | 0.4775 |
| | 0.9 | 0.1 | 0.5920 | 0.4080 |
| | 100 | 0 | 0.6799 | 0.3201 |

To the extent it aids the Office in reproduction, a clean copy of the table being replaced is provided here:

| Sample Mixture | Mixture % breast reads | Mixture % liver reads | NNLS estimates % tumor | NNLS estimates % normal |
|---|---|---|---|---|
| TCGA_DD_A118_11 (liver normal)/ TCGA_EW_A3U0_01 (breast cancer) | 0 | 100 | 0.0071 | 0.9929 |
| | 0.13 | 0.87 | 0.3330 | 0.6670 |
| | 0.25 | 0.75 | 0.3668 | 0.6332 |
| | 0.18 | 0.82 | 0.3761 | 0.6239 |
| | 0.6 | 0.4 | 0.4777 | 0.5223 |
| | 0.72 | 0.28 | 0.5027 | 0.4973 |
| | 0.94 | 0.06 | 0.6523 | 0.3477 |
| | 100 | 0 | 0.7052 | 0.2948 |
| TCGA_DD_A114_11 (liver normal)/ TCGA_EW_A424_01 (breast cancer) | 0 | 100 | 0.0001 | 0.9999 |
| | 0.09 | 0.91 | 0.3464 | 0.6536 |
| | 0.22 | 0.78 | 0.3800 | 0.6200 |
| | 0.51 | 0.49 | 0.4499 | 0.5501 |
| | 0.64 | 0.36 | 0.4857 | 0.5143 |
| | 0.78 | 0.22 | 0.5225 | 0.4775 |
| | 0.9 | 0.1 | 0.5920 | 0.4080 |
| | 100 | 0 | 0.6799 | 0.3201 |

As shown in FIGS. 237A and 237B we show that PCA tests performed after deconvolution result in much better grouping of liver samples (right side plots) in comparison to the in silico mixture analysis (left side plots). We found high correlation between the expected proportion of breast cancer reads and the NNLS model predicted tumor percentage (0.89 and 0.82). In addition, the liver deconvolution model performed well at identifying absent liver cell populations in samples with sufficient tumor purity. In sample mixtures with insufficient tumor purity, a tumor percentage over-estimation may result.

Additionally, we examined the performance of expression calls on the deconvoluted samples. We made expression calls, where each call identifies a gene that has a larger (over expression) or smaller (under expression) amount of RNA copies than the gene would have in non-tumorous tissue, where the difference between the amount in the sample and the non-tumorous amount is greater than a user-defined value. The expression calls were made on the pure breast cancer samples and compared the results to the respective mixture and deconvoluted samples.

The first breast cancer sample had MYC gene over expression and PGR and ESR1 under expression. All deconvoluted samples called MYC as overexpressed, while only the 94% breast mixture identified this gene. In this example, only two of the middle range deconvoluted mixtures (82% and 40% liver) identified PGR (progesterone receptor) as under expressed while none of the deconvoluted mixture samples identified ESR1 (estrogen receptor) as underexpressed. The highest liver mixture sample falsely called NGR1 (negative growth regulator protein) as over expressed.

Overall, the deconvolution process improved the calling of over expression of MYC across all titrations and decreased false positive calls but was not sensitive enough to capture the two under expressed genes.

The second pure breast cancer sample had PGR and ESR1 over expression. All deconvoluted samples called PGR as over expressed, however, this call was made in all the mixture samples except for the highest proportion of liver. Only the deconvoluted mixture with the lowest liver proportion sample called ESR1 as overexpressed but both of the lowest liver mixtures detected this call. As far as false positives, both of the highest liver deconvoluted mixtures called MYC as overexpressed and the highest liver mixture sample called MTOR as over expressed. In summary, the over expression of PGR in this sample was high enough that its over expression was captured in both analyses. Furthermore, expression calls in samples with low tumor purity, in this particular example, (<22%) was more prone to false positive calls in both the mixture and the deconvoluted sample.

In another example application of the present techniques, we examined expression calls in 124 liver metastatic cancer samples. We selected liver metastatic samples from among four cancers with sample sizes greater than ten, resulting in 124 samples (37 brca, 36 coad, 33 paad and 18 pcpg). We processed each sample through the liver deconvolution model and made expression calls on the original RNA and the deconvoluted RNA sample versus the relevant TCGA cancer and GTEx tissue. For each gene (gene name in the left-most column), we calculated the proportion of samples with that gene called either over or under expressed in i) both RNA datasets, ii) only in the original RNA or iii) only in the deconvoluted RNA (as noted below each column), from among the cancer types where that gene was called at least once. The proportion of samples in each group for which a gene was called over or underexpressed, in each column in FIG. 238, is represented by a shade of pink in a spectrum from pale pink (0, or 0%) to dark purple (0.37, which is 37%).

As shown in FIG. 238, in this example, if none of the samples in a cancer type received an over or under expression call for one of the genes, then all of the samples in that cancer type were excluded from the expression call proportion calculation for that gene. The total number of samples, n, that are included in the sample group for each gene is shown in a column on the right as a shade of green that represents a number in a range of approximately 18 (pale green) to approximately 124 (dark green). We compared these gene proportions calls and spatially arranged the rows of genes so that the proportions are organized approximately by numeric value to identify trends following deconvolution, as shown in the expression call comparison analysis in FIG. 238. MTOR, ERBB4 and MET were consistently called as over expressed in the original RNA sample (18.5%, 33.9% and 37.1% of the time, respectively) but not in the respective deconvoluted sample. These genes have consistently higher expression in GTEx normal liver compared to the other normal tissue and are subject to inflated gene expression values in the original RNA sample. On the other hand, PGR was called under expressed only in the original RNA 27% of the time because it has much lower expression in liver normal compared to the other normal samples. Following deconvolution, eight genes were called over expressed and two genes under expressed (EGFR and KRAS) in more than 5% of the samples, which is shown in FIG. 238, third column.

With the present techniques, generation of a deconvolution RNA model of various cancer types provides a trained model that can be used to assess and characterize subsequent tissue samples. For example, a method for tissue analysis may include receiving RNA expression data from a sample, analyzing the received RNA expression data against a deconvoluted RNA expression model, serving as a reference RNA expression data, by performing a deconvolution on the received RNA expression data to remove background expression data. The method further may include comparing the deconvoluted received RNA expression data against the reference RNA expression data and determining from that comparison whether the received RNA expression data matches or differs from the reference RNA expression data, e.g., by determining if predetermined groups correlating to particular cancers are present, and from that comparison determining a cancer type or types for the sample.

Although the disclosure above is focused on the identification of different cancer types, it should be understood that the systems and methods described herein may be useful for the determination of a broad range of tissue types in addition to cancer tumors. For instance, tissue samples from any healthy organs, such as brain, muscle, nerve, skin, etc. may contain a mixture of multiple types of cells that have distinct gene expressions. By utilizing the systems and methods described herein, it is possible to analyze the tissue at hand to determine the expression levels of genes for each type of cell from within the tissue sample. For instance, in the case of the brain, neurons, glial cells, astrocytes, oligodendrocytes, and microglia are examples of types of cells found in brain tissue. Using the disclosure provided for herein, clustering on RNA expression data corresponding to a plurality of samples may be performed, where each sample is assigned to at least one of a plurality of clusters. A deconvoluted RNA expression data model for the relevant brain cells may be generated, wherein the data model comprises at least one cluster identified as corresponding to a biological indication of the cells.

In addition to using the disclosure above on healthy tissue samples, it should be understood by those in the art that the disclosure may be used on other cell populations, collections of cells, populations of cells, etc. which may include stem cells, organoids, and the like. Likewise, other tissue samples which are not cancerous but also not healthy (for instance, lung tissue from patients with a history of smoking) may be examined and analyzed using the systems and methods described above.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

XII. Calculating Cell-Type RNA Profiles For Diagnosis And Treatment

Embodiments of the present disclosure relate to identifying cell-type RNA profiles present in sequencing data (e.g., RNA sequencing data) acquired from patient's samples. One or more models can be trained to identify a type, number, and proportion of cell-type RNA profiles in a patient's sample. The identification of the cell-type RNA profiles for the patients in accordance with embodiments of the present disclosure may improve clinical diagnosis, and may facilitate selection and monitoring of treatments of various conditions and diseases, as well as overall standard of care. The invention may allow enhancing existing sequencing procedures and removing unknown variance in patient diagnosis and treatment, particularly those impacted by varying tumor purities in the specimen.

The human genome was completely mapped in April 2003 by the Human Genome Project and opened the door for progress in numerous fields of study focused on the sequence of nucleotide base pairs that make up human DNA. The human genome has over six billion of these nucleotides packaged into two sets of twenty-three chromosomes, one set inherited from each parent, encoding over thirty-thousand genes. The order in which the nucleotide types are arranged is known as the molecular sequence, genetic sequence, or genome. DNA strands guide the production of proteins for each cell by acting as a code or a template for the protein synthesis process. These proteins are catalysts for important bodily functions and fill roles such as influencing drug absorption or driving immune response for a patient. During protein synthesis DNA strands undergo a transcription process, where they are temporarily unraveled to create RNA by transcription, and then the RNA is translated to a protein strand. Through cataloging the RNA that translates into important proteins, treatment selections may be improved for each patient.

The capture of patient genetic information through genetic testing in the field of next-generation sequencing ("NGS") for genomics is a new and rapidly evolving field. NGS involves using specialized equipment such as a next-generation gene sequencer, which is an automated instrument that determines the order of nucleotides in DNA and/or RNA. The instrument reports the sequences as a string of letters, called a read. These reads allow the identification of genes, variants, or sequences of nucleotides in the human genome. An analyst compares these reads from genes to one or more reference genomes of the same genes, variants, or sequences of nucleotides. Identification of certain genetic mutations or particular variants plays an important role in selecting the most beneficial line of therapy for a patient.

The challenge in interpreting RNA sequencing information and isolating biomarkers for disease susceptibility and/or pharmacogenomic effects is rooted in a lack of structured information between the human genome and patient/clinical information such as disease progression and treatment information. Although many projects are ongoing worldwide to identify affordable, scalable single-cell sequencing techniques, a viable solution has yet to be implemented in commercial practice. Bulk-cell sequencing, such as scraping a slide of a tumor, is currently the most accepted practice for gathering sequencing information relating to an individual patient. At the same time, scraping a slide for bulk-cell sequencing has a number of challenges that hinder obtaining reliable results, including tumor-only results. This is exacerbated by the lack of techniques for identifying RNA cell types and their respective cell-type profiles.

FIG. 239A, which is an annotated illustration of a mitosis cell cycle 7710 (Miller-Keane Encyclopedia and Dictionary of Medicine, Nursing, and Allied Health, Seventh Edition (2003)), illustrates a challenge in RNA cell-profiling from multi-cell sequence information. Sequencing a patient's genome delivers what is effectively a snapshot of the state of the tissue, such as a tumor, as it existed at the time of extraction. However, during a cell's life cycle, the cell is not a static entity and it is changing and evolving. For example, as shown schematically in FIG. 239A, a cell undergoing the mitosis cell cycle 7710, in its resting state (interphase) may have an RNA expression profile 7712, such that each gene which an RNA expression read may be mapped to will have an expected expression level. For illustrative purposes, the RNA expression profile 7712 represents four genes of varying, unlabeled expression, but one of ordinary skill in the art would recognize that the RNA expression profile may be across all 20,000+ genes or a smaller, more selective subset of genes which uniquely identify cell-types from one another. A cell may begin mitosis by proceeding through prophase where the cell prepares for the process of division by replicating DNA and beginning to align the centrioles of the cell at opposite poles in the cell. Continuing through mitosis, a cell may proceed through metaphase where the DNA is lined up along a central axis of the cell and where the cell may have an RNA expression profile 7714, such that each gene has an RNA expression profile which may differ from the RNA expression profile 7712. Variations may occur due to the doubling of the DNA, potentially leading to more potential protein synthesis. However, other cellular functions are affecting RNA transcription. For example, during mitosis certain cellular protein synthesis may be inhibited while the synthesis of other proteins may be activated. Subsequently, the associated genes which were previously active may not be instructed to produce additional proteins while the cell may be producing proteins from the newly activated genes such that the cell's state may be represented by the unique RNA profile 7714 while undergoing metaphase to the RNA profile 7712 expressed during interphase.

As used herein, the "cell-type RNA profile" may also be referred to as an RNA expression profile or cell-type RNA expression profile for a respective cell type that allows the cell type to be identified in RNA expression data.

In FIG. 239A, deviations in RNA expression may be observed among different cells, such as the deviations of the RNA profile 7714 denoted using identifiers 7715 in an RNA profile 7716. The identifiers 7715 may indicate a baseline in the RNA profiles 7714 and 7716, relative to the RNA profile 7712. For example, as certain proteins are no longer synthesized, RNA expressions may decrease slightly as the residual RNA breaks down. Additionally, as other proteins are being synthesized in greater numbers, RNA expressions may increase slightly. As the cell proceeds through mitosis, the chromosomes may separate and begin to attract to opposing centromeres during anaphase. Near the completion of mitosis, the cell division is finishing and the cell membrane may begin separating into two separate cells. While undergoing this final process, telophase, the cell RNA expression may be represented by the RNA profile 7716.

An RNA profile shows RNA expressions consistent with inhibited protein synthesis as well as the RNA expressions consistent with activated protein synthesis. Additionally, some RNA expression may be the same as the cell maintains similar functions throughout each phase of mitosis. Through careful observation, distinct RNA profiles may be established which identify a single cell at different phases as it progresses through mitosis. While the foregoing example depicts unique RNA expression profiles at the interphase, metaphase, and telophase stages of mitosis, it should be appreciated that phases during the cell cycle can be represented by various other RNA profiles.

FIG. 239B illustrates schematically another challenge in RNA cell profiling from multi-cell sequence information. Certain cell types mature from a first cell type into a second cell type over time. For example, immune cells, such as T-cells or B-cells, start off as base pluripotent hematopoietic stem cells (HSCs) and mature into a plethora of distinct progenitors, including common lymphoid progenitors (CLPs). CLPs, just as the HSCs before them, may mature into a myriad of cells, such as dendritic cells (DCs), natural killer cells (NKs), B-cells, T-cells, and more. Of interest, the immune B and T-cells are lymphocytes commonly found at the site of cancerous tumor cells. As immune cells, T-cells have the ability to make any shape of receptors which allow the cell to target specific antigens for destruction. B-cells generate antibodies and maintain a memory of antibodies which may be needed to protect against a subsequent infection. Other T-cells may stimulate the B-cell production of antibodies. Each matured version of B and T-cells may express a unique RNA profile. Different endpoints of the maturation process, immune cells of the categories cytotoxic, memory, suppressor, and helper may each have their own functions and RNA profiles.

A cell maturation diagram 7720 in FIG. 239B illustrates the natural divergence of the RNA profiles from the CLP cell-type which may be represented by an RNA profile 7722, the immune T-cell. For illustrative purposes, the RNA expression profile 7722 represents four genes (r1, r2, r3, and r4) of varying expression. However, a person of ordinary skill in the art would recognize that the RNA expression profile may be across any number of genes, including 10, 100, 100, 10,000, 20,000 or more than 20,000 genes. As cells mature from the CLP cell-type to the B-cell type, a branch may develop in the cell maturation graph corresponding to an RNA expression profile 7724 which is distinct from the RNA profile 7722. The differences in RNA expressions among the RNA profiles 7722 and 7724 are shown by identifiers 7725 in FIG. 239B. The identifiers 7725, also shown in connection with RNA profiles 7726 and 7728 (additionally illustrating cell types present in this example), indicate baseline levels of RNA expression of the RNA profile 7722. For example, identifiers 7725a, 7725b for expression of RNAs r1 and r2 in RNA profile 7722, respectively, indicate a level of expression (abundance) of the RNAs r1 and r2. The identifiers 7725a, 7725b are also shown in connection with the RNA profile 7724, where they, like in the RNA profile 7722, indicate the level of expression of the RNAs r1 and r2. Respective bars illustrating expression of the RNAs r1 and r2 in the RNA profile 7724 visualize, in connection with the identifiers 7725a, 7725b, a degree to which the expression of RNAs r1 and r2 different in the RNA profile 7724 relative to the RNA profile 7722.

A B-cell having RNA expression profile 7724 may present with a noticeable decrease in gene expression for some genes while maintaining fairly consistent expression levels across other genes in comparison to the base CLP cell-type. As shown in the example of FIG. 239B, other branches may be present in the cell maturation graph 7720, such as a branch for suppressor T-cells (having the RNA expression profile 230) and a branch for cytotoxic T-cells (having the RNA expression profile 7726). T-cells, as a whole, may be commonly identified from a substantial decrease in a particular gene expression, and their types may be differentiated one from another through observation of other gene expression differences. Furthermore, both B and T-cells may maintain fairly consistent gene expression in certain genes due to their common lineage from the CLP cell type and their function as immune cells.

As shown in FIGS. 239A and 239B, identifying and understanding RNA expression profiles in various cells is a challenging task. Cells are ever evolving, maturing to another cells, and are frequently undergoing mitosis to replicate. For example, when a T-cell finds antigens that it can bind to, it may quickly replicate itself in an offensive against the abnormal cells that were detected. At the same time, other T-cell types and B-cells types may also join in the offensive against the abnormal cells. A biopsy of a cancerous tumor may capture each of these immune, lymphoma cells, tumor cells, as well as other cell-types such as epithelium, stroma, muscle, fat, glial, and supporting cells. Each organ in the human body has a unique distribution of cells forming that organ. Biopsies taken from breast, colon, brain, lung, or other tumor sites may have a unique cell distribution while at the same time having cells that are common to each site.

FIG. 240 illustrates an example of another challenge in RNA profiling from multi-cell sequence information including three breast tumor pathology slides 7732, 7734, and 7736 that may be scraped for bulk cell sequencing. For example, the slide 7732 be a breast tumor biopsy slide including a collection of tumor tissue (red), lymphocytes (purple), stroma (light green), and epithelium (dark green). A pathologist may review the slide 7732 and identify a diagnosis in a pathology report including specific details of the grade of tumor (in comparison to healthy cells) present or varying levels of lymphovascular, perineural, or margin invasion present in the slide tissue. For example, a report may identify: 16% Tumor (with lymphocyte), 52% Tumor (with no lymphocyte), 6% Lymphocyte, 4% Stroma (with lymphocyte), 18% Stroma (with no lymphocyte), 1% Epithelium (with lymphocyte), 3% Epithelium (with no lymphocyte). As another example, pathology reports may identify tumor, stroma, lymphocytes, and epithelium percentages as a whole. An exemplary percentile breakdown for the slide 7732 is shown in a pie chart 7733 indicating 60% tumor, 15% stroma, 20% lymphocytes, and 5% epithelium. Bulk cell sequencing from a slide scrape of the slide 7732 can be impacted by 40% of the sequenced tissue being non-tumor tissue.

Further exacerbating the accuracy and reliability of analysis and clinical use of the sequencing data is the fact that two or more of cell types present in a pathology slide may be at different stages of maturation and may also be at different stages of their individual life cycles, including mitosis. Ultimately, precision medicine concerns targeting the patient's tumor, but the traditional bulk cell sequencing introduces a substantial amount of noise by allowing other tissue RNA expression to cloud the results. Traditional approaches that merely account for tumor/non-tumor percentage may thus not be accurate enough to allow making correct inferences about diagnosis and treatment.

A pathology slide 7734 in FIG. 240 represents a breast tumor biopsy of another patient. Unlike in the slide 7732 where the majority of the tissue scraped is tumor tissue, the slide 7734 has 38% of tumor tissue, and 62% of a non-tumor tissue encompassing 28% lymphocytes, 24% stroma, and 10% epithelium, as shown in the chart 7735. A slide 36 represents yet another example of a pathology slide comprising 57% tumor, 40% stroma, and 3% lymphocytes, without observable traces of epithelium, as shown in a chart 7737. It should be known that cell types' percentages are shown in FIG. 240 for illustration purposes only, and that these percentages can be approximate.

Accounting for different ratios of tumor tissue to non-tumor tissues, differing stages of maturation of each cell, and different stages of the cell cycle in order to reliably qualify the tumor-specific RNA expression profile(s) are challenging tasks.

Accordingly, embodiments of the present disclosure provide methods for determining a cancer composition of a biological sample obtained from a subject, which include improved approaches for identifying cell types present in the sample and percentages of the cell types. A model of one or more RNA profile for each cell and/or tissue type may be generated, and the model may be used to determine cell types and their proportions in patient samples.

In some embodiments, in which single-cell sequencing is used and gene expression values are available, methods in accordance with embodiments of the present disclosure allow determining respective proportions of cell types in a biological sample.

In the described embodiments, RNA data in a sample (e.g., a sample on a pathology slide) is modeled as a sum of parts. For instance, a part may be a tissue type present in a sample. More than one model can be generated and trained for each tissue type, e.g., according to a tissue site, cancer type, etc. In some embodiments, a single model can be generated for some tissue types, whereas multiple models are generated for other tissue types. The models can be generated based on known cell-type RNA profiles for tissue types. Also, a model can be generated that is able to identify unknown cell/tissue types. Thus, the described techniques can take into account effects of the extraneous tissue types and use the remaining tissue types to derive knowledge about unknown tissue types, including tumor and non-tumor tissue types.

In some embodiments, gene expression data is modeled by gamma distributions. Also, in some embodiments, cell type percentages are determined as being greater than zero and, for a biological sample in any form, the percentages sum to 100%. In some embodiments, a gamma distribution is mapped to each gene for each tissue type. Mean and shape parameters of a gamma distribution can be calculated, and the method may fit across all percentages of tissue type to all mean and shape parameters, to find the best fit.

In some embodiments, a model can be applied to a new tumor RNA sequence obtained from a sample to predict one or more of a percentage of a tumor present in the sample, percentages of tissue types present, a type of tumor present, and RNA expression of only the tumor. The model can generate what is referred to herein as a sum of parts, wherein each part of the percentage is iteratively estimated using the model. Each part in the sum of parts can be individually balanced according to the mean and shape of the gamma distribution. Accordingly, expression data for each gene can be iteratively balanced with expression data for of every other gene according to the mean and shape of the gamma distribution model until the best fit for the present cell types and their respective percentages (or proportions) are calculated.

In some embodiments, for each biological sample used to train a model (referred to as a first optimization model, in some embodiments), a corresponding relative proportion of one or more sets of cell types in a plurality of sets of cell types can be obtained. For example, the relative proportions may be obtained based on a pathology report (e.g., based on imaging analysis) or a report generated based on any other approach. In some cases, a pathology report may include percentages and types of the tissue(s) observed in the sample.

In some embodiments, a method for determining a cancer composition of a subject is provided that comprises, at a computer system having one or more processors and memory storing one or more programs for execution by the one or more processors, generating, in electronic form, for each respective genetic target in a first plurality of genetic targets (e.g., RNA expression data, transcriptome data, or any other type of data), a corresponding shape parameter (e.g., in some embodiments, a shape parameter for a gamma distribution used to model gene expression data), wherein the first plurality of genetic targets obtained based on RNA sequencing of one or more respective biological samples obtained from a respective tumor specimen of each respective subject across a plurality of subjects. The method comprises obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target (e.g., in some embodiments, a mean parameter for a gamma distribution used to model gene expression data).

The method further comprises obtaining refining a first optimization model subject to a first plurality of constraints that may include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects. The refining of the first optimization model identifies a plurality of calculated cell types in a first set of cell types in the plurality of sets of cell types, and a respective calculated cell type RNA expression profile is thus generated for each calculated cell type in the plurality of calculated cell types.

The thus refined, or trained, first optimization model can be used to determine a cancer composition of a subject, as discussed in more detail below.

Details of an exemplary system in which some embodiments can be implemented are described in conjunction with FIG. 241. FIG. 239 is a block diagram illustrating a system 8000 in accordance with some implementations. The system 8000 in some implementations includes one or more hardware processing units CPU(s) 8002 (at least one processor), one or more network interfaces 8004, a display 8006 configured to present a user interface 8008, and an input system 8010, memory 8011 (non-persistent, persistent, or any combination thereof), and one or more communication buses 114 for interconnecting these components. The one or more communication buses 8014 optionally include circuitry (sometimes called a chipset) that interconnects and controls communications between system components.

In embodiments in which memory 8011 is non-persistent, it typically includes high-speed random access memory, such as DRAM, SRAM, DDR RAM, ROM, EEPROM, flash memory, whereas the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The memory 8011 optionally includes one or more storage devices remotely located from the CPU(s) 8002. In embodiments in which memory 8011, or one or more of its parts, are persistent memory and includes non-volatile memory device(s), the memory comprises at least one non-transitory computer readable storage medium. In some implementations, as shown in the example of FIG. 241, the non-persistent memory 8011, or alternatively the non-transitory computer-readable storage medium, stores the following programs, modules and data structures, or a subset thereof (sometimes in conjunction with the persistent memory):

an optional operating system 8016, which includes procedures for handling various basic system services and for performing hardware dependent tasks;

an optional network communication module (or instructions) 8018 for connecting the system 8000 with other devices and/or a communication network 8004;

an optimization models module 8020 that is configured to generate, train, and control storing of a plurality of optimization models each configured to identify within genetic data (e.g., gene expression abundance data) cell types based on respective cell-type profiles;

cell-type profiles module 8022, which is part of the module 8020 for generating and training the optimization models and which is shown separately for illustrating purposes only, to show that the optimization models are built to identify cell types based on respective cell-type profiles;

data on a plurality of biological samples 8022 shown by way of example to include a biological sample 8022-1, . . . , biological sample 8022-N; wherein the sample 8022-1 is associated with genetic targets 8024-1, respective abundance levels 8026-1 of the genetic targets 8024-1, and a plurality of cell types; and the sample 8022-N is associated with genetic targets 8024-N, respective abundance levels 8026-N of the genetic targets 8024-N, and a plurality of cell types;

the plurality of cell types for the biological sample 8022-1 (e.g., cell type 1-1 (8028-1-1), . . . , cell type 1-M (8028-1-M)), wherein the cell type 1-1 (8028-1-1) associated with a cell-type profile 8030-1-1, a predicted proportion 8032-1-1 of the cell type 1-1 in the sample 8022-1 (e.g., based on a pathology report or based on another cell counting technique), and a determined proportion 8034-1-1 of the cell type 1-1 in the sample 8022-1;

the plurality of cell types for the biological sample 8022-N (e.g., cell type N-1 (8028-N-1), . . . , cell type N-L (8028-N-L)), wherein the cell type N-1 (8028-N-1) associated with a cell-type profile 8030-N-1, a predicted proportion 8032-N-1 of the cell type N-1 in the sample 8022-1 (e.g., based on a pathology report or based on another cell counting technique), and a determined proportion 8034-N-1 of the cell type N-1 in the sample 8022-N.

In embodiments in which memory 8011 is non-persistent, it typically includes high-speed random access memory, such as DRAM, SRAM, DDR RAM, ROM, EEPROM, flash memory, whereas the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The memory 8011 optionally includes one or more storage devices remotely located from the CPU(s) 8002. In embodiments in which memory 8011, or one or more of its parts, are persistent memory and includes non-volatile memory device(s), the memory comprises at least one non-transitory computer readable storage medium. In some implementations, as shown in the example of FIG. 241, the non-persistent memory 8011, or alternatively the non-transitory computer-readable storage medium, stores the following programs, modules and data structures, or a subset thereof (sometimes in conjunction with the persistent memory).

It should be appreciated that the plurality of biological samples 8022 can be obtained from a plurality of subjects such that a biological sample is obtained from a respective subject. Also, although not shown in FIG. 241, each biological sample from the plurality of biological samples 8022 can be associated with various other information, including patient's information such as demographic, clinical, and other characteristics.

In some embodiments, more than one sample is obtained from a subject—for example, more than one tissue slice can be taken that are adjacent to each other. In some cases, the tissue slices are obtained such that some of the pathology slides prepared from the respective slices are imaged, whereas some of the pathology slides are used to obtaining sequencing information.

In FIG. 241, the biological samples 8022 are shown to be associated with more than one cell type. It should be appreciated biological samples may include different number of cell types, as shown schematically in FIG. 241 where the sample 8022-1 includes M cell types, and the sample 8022-N includes L cell types. In some cases, samples collected from a certain patient (e.g., from different tissue types, body sites, samples collected at different times, etc.) may differ by at least one cell type. In general, embodiments of the present disclosure are not limited to any specific type of a biological sample or to a number and types of cell types that can be identified in the samples.

In various implementations, one or more of the elements identified above in connection with FIG. 241 may be stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 8011 optionally stores a subset of the modules and data structures identified above. Furthermore, in some embodiments, the memory stores additional modules and data structures not described above. In some embodiments, one or more of the above identified elements are stored in a computer system, other than the computer system 8000 and that are addressable by the computer system 8000 so that the system 8000 may retrieve all or a portion of such data when needed.

It should be appreciated that FIG. 241 depicts the system 8000 as a functional description of the various features of the present disclosure that may be present in computer systems. As a person of skill in the art would understand, some of components and modules shown separately can be combined in a suitable manner. Also, some or all of these modules may be stored in a non-persistent memory or persistent memory, or in more than one memory. For example, in some embodiments, the optimization models 8020 and/or the biological samples 8022 may be stored in a remote storage device which can be a part of a cloud-based infrastructure. Any other components can be stored in remote storage device(s).

FIG. 242 illustrates examples of statistical analysis approaches that can account for multiple cell-types present in RNA expression sequencing information. For example, in a simplistic representation of a graph 8110, two cell types A and B may be present in an example of RNA sequencing information. A cell of cell type A may have an RNA expression profile, and a cell of cell type B may have a different respective RNA expression profile. Conceptually, a sequencing performed on a combination of cell types A and B may be represented in the graph 8110. For example, an RNA expression profile of a pure cell type A may be represented as 100% cell type A and 0% cell-type B, and, conversely, an RNA expression profile of a pure cell type B may be represented as 100% cell type B and 0% cell type A. A mixture of cell types A and B may be similarly plotted along the graph. For example, sequencing information having 40% cell type A and 60% cell type B may be represented as: $E(A)*P(A)+E(B)*P(B)$, where $E(x)$ is an expected value of x and $P(x)$ is the proportion of x. In this example, an expected value of x is the cell-type RNA profile of x, and a proportion of x is an observed proportion of x in the whole. Continuing with this example, values for $P(A)$ and $P(B)$ are known $E(A)*0.4+E(B)*0.6$, and a linear combination of the RNA profiles for the cell types A and B may be represented. The case may also arise where the cell-type RNA profiles for the cell types A and B are not known in advance; however, given enough RNA sequence information comprising differing proportions of the cell type A to the cell type B, RNA profiles for cell types A and B may be regressed from the combination of data.

In some embodiments, RNA sequencing information includes information on multiple cell types. The procedure described above for the two cell types A and B can be applied to multiple cell types as well. For example, a diagram 8120 shows four cell types A, B, C, and D, in which case a combination of proportions of the cell types may be found on the surface or inside of a resulting four-sided polyhedron or tetrahedron 8121, but not outside of the bounds of the polyhedron. These constraints may be a requirement that each $P(x)$ has a value in the range of $[0, 1]$, and that the sum of all $P(x)$ to equal 1. Thus, each cell type is assigned a proportion and the combination of all present cell types does not exceed 100%. The mixtures of cell types A, B, C, and D may be represented as: $E(A)*P(A)+E(B)*P(B)+E(C)*P(C)+E(D)*P(D)$.

The expected value, $E(x)$, may be modelled according to any modeling technique, non-limiting example of which include a linear regression, logistic regression, resampling methods, subset selection, ridge regression, dimension reduction, non-linear models, tree/forest models, support vector machines, neural networks, or other machine learning algorithms (MLA). In some embodiments, a modeling approach may involve using clustering techniques, non-negative matrix factorization (NMF), grade of membership (GoM), regression techniques such as generalized linear models using gamma or Poisson distributions, and optimization techniques such as directed compression/projected gradient descent to generate RNA profiles for cell types from multi-cell or single-cell sequencing information.

FIG. 242 illustrates, in a graph 8130, an example of fitting a gamma distribution to gene expression values for a certain gene across a plurality of subjects, in accordance with some embodiments of the present disclosure. In this example, on the x-axis mean gene expression levels (schematically shown as 0, 10, 20, 30, 40, 50, and 60) for a single gene ("Gene 1") are plotted against a frequency of occurrence of these gene expression levels across all (x) patients being considered, on the y-axis. A gamma distribution model may be selected due to its flexibility in representing RNA expression across multiple genes using different the shape and mean parameters of the gamma distribution.

In some embodiments, a machine-learning algorithm (MLA), such as, e.g., a neural network (NN) or any other technique, may be trained using a training data set. For an RNA profile, an exemplary training data set may include imaging, pathology, clinical, and/or molecular reports and details of a patient, such as those curated from an Electronic Health Record (EHR) or genetic sequencing reports. Non-limiting examples of MLAs include supervised algorithms that use linear regression, logistic regression, decision trees, classification and regression trees, Naïve Bayes, nearest neighbor clustering; unsupervised algorithms using the Apriori algorithm, means clustering, principal component analysis, random forest, adaptive boosting; and semi-supervised algorithms using generative approach (such as a mixture of Gaussian distributions, mixture of multinomial distributions, hidden Markov models), low density separation, graph-based approaches (such as, e.g., mincut, harmonic function, manifold regularization, etc.), heuristic approaches, or support vector machines. In some embodiments, NNs include conditional random fields, convolutional neural networks, attention based neural networks, long short term memory networks, or other neural network models where the training data set includes a plurality of tumor samples, RNA expression data for each sample, and pathology reports covering imaging data for each sample.

In some embodiments, training an optimization model may include providing datasets including annotated pathology features acquired from imaging data (such as, e.g., cell counts for types of tissue identified in a pathology slide), as well as information on clinical, molecular, and/or genetic characteristics of patients. An MLA can be trained to identify distinct cell type RNA profiles and also patterns in the outcomes of patients based on their treatments as well as their clinical and genetic information as they relate to cell type RNA profiles for various tissues, including tumor tissue.

FIG. 243 illustrates an overview 8200 of input for an optimization model training inputs and model outputs for an exemplary machine learning algorithm used to classify cell-type RNA profiles. As shown in FIG. 243, a plurality of pathology slides 8210, such as, e.g., tumor tissue slides (which may or may not include tumor cells) can be acquired and used to generate tumor sequencing data 8230 and respective pathology reports 8220 (percentages are shown for illustration purposes and are not discussed herein). The MLA model may be trained to identify RNA cell-type profiles using the tumor sequencing data 8230 and information in the pathology reports 8220.

Curation of a training set may involve collecting a series of pathology reports and associated sequencing information from a plurality of patients. For example, a physician may perform a tumor biopsy of a patient by removing a small amount of tumor tissue/specimen from the patient and sending this specimen to a laboratory. The lab may prepare slides from the specimen using slide preparation techniques such as freezing the specimen and slicing layers, setting the specimen in paraffin and slicing layers, smearing the specimen on a slide, or other methods known to those of ordinary skill. For purposes of the following disclosure, a slide and a slice may be used interchangeably. A slide stores a slice of tissue from the specimen and receives a label identifying the specimen from which the slice was extracted and the sequence number of the slice from the specimen. Traditionally, a pathology slide may be prepared by staining the specimen to reveal cellular characteristics (such as cell nuclei, lymphocytes, stroma, epithelium, or other cells in whole or part). The pathology slide selected for staining is traditionally the terminal slide of the specimen block. Specimen slicing proceeds with a series of initial slides may be prepared for staining and diagnostic purposes, a series of the next sequential slices may be used for sequencing, and then final, terminal slides may be processed for additional staining. In the rare case where the terminal, stained slide is too far removed from the sequenced slides, another slide may be stained which is closer to the sequenced slides such that sequencing slides are broken up by staining slides. While there are slight deviations from slice to slice, the deviation is expected to be minimal as the tissue is sliced at thicknesses approaching 4 um for paraffin slides and 35 um for frozen slides. Laboratories generally confirm that the distance, usually less than 40 um (approximately 10 slides/slices), has not produced a substantial deviation in the tissue slices.

In (less frequent) cases where slices of the specimen vary greatly from slice to slice, outliers may be discarded and not further processed. The pathology slides 8210 may be varying stained slides taken from tumor samples from patients. Some slides and sequencing data may be taken from the same specimen to ensure data robustness while other slides and sequencing data will be taken from respective unique specimens. The larger the number of tumor samples in the dataset, the more accuracy that can be expected from the predictions of the cell-type RNA profiles. In some embodiments, a stained tumor slide 8210 may be reviewed by a pathologist for identification of cellular features, such as the quantity of cells and their differences to the normal cells of that type.

In some embodiments, proportions of cell types visible in the tumor slides 8210, as reported in the pathology reports 8220, are combined into the training data set with the results of the tumor sequencing, tumor sequencing data 8230, to generate cell-type profiles 8240. One or more cell-type profiles may be generated for each of the cell types included in the specimen samples (such as, for example, tumor, stroma, lymphocytes, epithelium, healthy tissues, or other cell types).

It should be appreciated that, while the example of FIG. 243 illustrates tumor samples, in some embodiments, samples are acquired from every cell type that may be present in a tumor slide. For example, if a tumor slide may additionally include stroma, epithelium, and lymphocytes, then a trained model may estimate a number of groupings for each of stroma, epithelium, and lymphocytes in addition to the classifications of tumor. These groupings may be discerned from lymphoma-targeted specimen, stroma-targeted specimen, or epithelium-targeted specimen, single cell sequencing from another lab, or even research endeavors from a university. By discerning the accurate number of RNA profiles within cell types, effects of noise or bias in RNA expressions of bulk cell sequencing may be accounted for and eliminated.

FIG. 244 illustrates schematically application of RNA cell-type profiles (e.g., in the form of a trained model) for identification of cell-types and proportions present in a sequenced sample. In some cases, origin(s) of each cell-type in a sample may not be discerned from a pathology report. For example, in a metastatic patient where the tumor's origin is unknown, a pathologist may be able to identify (predict) proportions of cell-types, but not the origin and type of the tumor tissue. As another example, a number of pathology slides acquired from a patient may be sufficient to adequately sequence data obtained from the slides, but not sufficient for staining and therefore assessing proportions of cell types in the sample using imaging data. As another example, a stained slide may not adequately represent a cell-type distribution of the sequenced slides, or the overall tumor purity of the sequenced slides may be unknown. Furthermore, multiple distinct cell-type profiles may exist for tumors of each organ, different immune cells may present at the tumor site, and other tissue(s) (e.g., stroma and epithelium) may be present in a tumor slide. While a pathology report may be used to determine a quantity of cell types which are tumor, stroma, epithelium, and lymphocytes, the report may not include information on a difference between cell types within each classification that present a distinct RNA profile.

Application of cell-type RNA profiles (e.g., cell-type RNA profiles 8240 of FIG. 243) in accordance with embodiments of the present disclosure may overcome the above challenges. For example, as shown schematically in FIG. 244, a composition (e.g., cancer composition) of a new sample 8312 may be determined using the techniques in accordance with embodiments of the present disclosure. The new sample 8312 (denoted as "new" solely to indicate that its composition is to be determined), which may be processed into a tumor slide (e.g., tumor slide 8210 in FIG. 243), may be used to obtain tumor sequencing data 8330. In this example, as shown schematically in FIG. 244, an unknown pathology 8325 may be associated with the sample 8312. Cell-type RNA profiles, e.g., in the form of a respective model, can be applied to the tumor sequencing data 8330 and used to identify the cell-types and their respective proportions, as shown by a "Pathology Prediction" diagram 8320 in FIG. 244.

FIG. 245 illustrates by way of example an approach for identifying tissue cell types from a sample comprising a pathology slide, in accordance with some embodiments of the present disclosure. A plurality of cell-type profiles 8240 (FIG. 243) may include groups such as tumor cell-type profiles 8402, lymphocyte cell-type profiles 8404, stroma cell-type profiles 8404, and epithelium cell-type profiles 8406. The plurality of cell-type profiles 8240 can also include fat cell cell-type profiles, muscle cell-type profiles, supporting cell-type profiles, and any other cell types. Similarly, healthy tissue may be classified according to tissue site, such as breast, lung, brain, colon, prostate, etc. Furthermore, the cell-type profiles 8240 may include cell-type profiles specific for a certain tissue and an organ, for example, cell-type profiles for epithelium of the breast, ductal of the breast, lymphocytes of the colon, mucosa of the colon, and other cell histological groupings. In some embodiments, the cell-type profiles 8240 may include cell-type profiles classified by the tumor tissue which they surround, such as, e.g., cell-type profiles for stroma of lung tumor or stroma of a first cell type of lung tumor.

As further shown in FIG. 245, a slide obtained from a biological sample from a patient can be represented as a slide profile 8450 that may be modeled as a sum of cell types, for example, a sum of the tumor cell types, lymphocyte cell types, stromal cell types, and epithelial cell types. Additional cell types such as, e.g., cell types for healthy tissue and other cell types, may also be included in the slide profile 8450, as embodiments are not limited in this respect. Tumor cell types may be further represented by a tumor profile, such as a tumor profile 8460. The tumor profile 8460 may be modeled as a sum of expected values of all cell type multiplied by a respective percentage value of that cell type. For example, tumor cell types 722 may further be classified into a tumor cell-type $\lambda_1$ 724, a tumor cell type $\lambda_2$ 726, tumor cell-type $\lambda_3$ 728, and tumor cell-type $\lambda_4$ 730. As also shown in FIG. 245, sequencing information having tumor cell types 722, 724, 726, 728, and 730 may be expressed by $E(\lambda_1)*P(\lambda_1)+E(\lambda_2)*P(\lambda_2)+E(\lambda_3)*P(\lambda_3)+E(\lambda_4)*P(\lambda_4)$, where $E(x)$ is an expected value of x and $P(x)$ is the proportion of x, and an expected value of x is the cell-type RNA profile of x and a proportion of x is the observed proportion of x in the whole. The cell-type RNA profile, such as cell-type RNA profiles 722, 724, 726, 728, 730, 732, 734, and 736 (illustrated by way of example only) may be stored as a row in cell-type profile matrix 8470. Cell-type profile matrix 8470 may represent genes in columns and cell-types in rows, where each entry stores an associated RNA expression value for the corresponding cell-type and gene. It should be appreciated that the cell-type profile matrix 8470 is shown in FIG. 245 by way of example only and that this matrix may include a large number of rows each representing a cell-type profile.

FIG. 246 illustrates an embodiment of a process 8500 of generating cell-type RNA expression profiles for each of a plurality of cell types. The process 8500 may be implemented, for example, in computer system 8000 (FIG. 241) or in another computer system. At block 8502, biological samples are obtained from a plurality of subjects, also referred to herein as patients. In some embodiments, as discussed above, a biological sample can be a specimen disposed on a pathology slide. A biological sample can be any other type of a sample. For example, it can be blood, whole blood, plasma, serum, urine, cerebrospinal fluid, fecal, saliva, sweat, tears, pleural fluid, pericardial fluid, or peritoneal fluid samples from the respective subject, any combination thereof, or any other bodily fluid that can be obtained from any type of sample.

At block 8504, a plurality of genetic targets can be obtained based on RNA sequencing of the respective biological samples (e.g., tumor specimens) of each respective subject across the plurality of subjects. In this example, the plurality of genetic targets are a plurality of genes, and gene expression data is obtained for each gene and each patient. To obtain the gene expression data (i.e., gene expression level), the total abundance of each gene in each of the samples can be obtained.

In some embodiments, the gene expression data, obtained for each gene from each individual sample obtained from a respective patient, may be processed. For example, the gene expression data can be normalized. For example, in some embodiments, genes may be scaled such that their means are equal to one. As another example, additionally, genes having an abundance level below a certain threshold and genes with expression data not following a certain statistical distribution (e.g., a gamma distribution, in this example) can be removed from further analysis. Also, genes that may not contribute to a difference between various cell types may not be used in analysis.

In some embodiments, the gene expression data is processed by normalization across multiple DNA/RNA sequencing pipelines. For example, a sequencing pipeline may utilize Kallisto, Salmon, STAR, RSEM, Sailfish, eXpress, or other various RNA quantifiers. Results from each quantifier may have certain biases in the RNA expression results. Normalization may be applied to each respective dataset to remove effects of a bias introduced by a respective quantifier. For example, if a first quantifier results in a greater expression of certain transcripts or RNA expressions, a normalization may reduce the expression values for those transcripts or RNA expressions to ensure the dataset is balanced according to all integrated sequencing pipelines. Additional normalization may be applied to filter out lowly expressed genes across all patients. For example, if every patient expresses trivial counts for a transcript or gene, a corresponding transcript or gene expression array may be removed from the gene expression dataset so that only genes which are relevant to the classification of cell-types are processed.

At block 8506, a predicted proportion of cell types is obtained for each patient's sample, e.g., in the form of cell-type proportion dataset(s). As discussed above, in various embodiments of the present disclosure, the predicted proportion can be obtained from an imaging analysis (automatic and/or manual) of a pathology slide or another type of a specimen. For example, the predicted proportions of cell types in a sample can be obtained from a pathologist report, data generated by a flow cytometer, or another cell-count analyzer. The proportions of cell type in the sample are predicted such that the sum of the proportions equals to 1. The prediction can also involve predicting a number of unknown cell types for each patient. For example, if the proportions of the predicted (estimated) cell type do not sum up to one (or to 100% if percentages are used), it may be determined that the sample includes unknown cell types.

The predicted cell type proportions may include predicted proportions for cancer cell types and non-cancer cell types. For example, as discussed above, predicted proportions can be for a tumor cell type (which can include tumor subtypes), lymphocytes cell type, stroma cell type, and epithelium cell type.

It should be noted that the gene expression data obtained from more than one sample from the same patient. For instance, multiple pathology slides can be obtained from a patient (e.g., gene expression data can be obtained from one slide and imaging data can be obtained from another slide, prepared from a specimen taken in close proximity to the slide from which the gene expression data is obtained). For the purpose of the analysis of the sample composition in accordance with this embodiment, such multiple samples obtained from the patient may be taken as a single sample, and the proportions of cell types estimated to be present in that sample are predicted such that they sum to 1.

At block 8508 of the process 8500, one or more unknown cell types are obtained. The number of unknown cell-types may vary based upon a desired specificity of the classification. For example, cell types such as lymphocytes, stroma, epithelium, and healthy tissue may be generalized to a single cell type, by identifying a single RNA expression profile that matches all of the different types of cells that may be categorized as lymphocytes, stroma, epithelium, and healthy tissue, respectively. This may be performed by identifying common factors that are present in each of the respective cell types. In some embodiments, while the lymphocytes, stroma, epithelium, and healthy tissue may be generalized to a single cell type, tumor tissue may be categorized into k cell-types which may be identified using various techniques including one or more of a clustering algorithm (e.g., provided by CountClust or any other package), a grade of membership model, etc.

In some embodiments, a cross validation or any other approach can be used for model training and evaluation. For example, in cross validation, a number of cell types, $k_i$, may be iteratively evaluated over a range of k to identify the most probable number of cell types. The number of unknown cell-types may also include categorizing each of the different types of cells individually, such that lymphocytes may have $k_1$ cell types, stroma may have $k_2$ cell types, epithelium may have $k_3$ cell types, healthy tissues may have $k_4$ cell types, and tumor tissues may have $k_5$ cell types, where the number of cell types may be a summation of the $k_{1-5}$ cell types. Cell types which RNA expression profiles are already known are not included in the number of unknown cell-types.

In some embodiments, the number of unknown cell types can be obtained, at block 8508 of FIG. 246, based on analysis of imaging data acquired from samples. The number of known cell types can be predicted automatically and/or manually. The number of unknown cell types may be received along with the gene expression data and cell-type proportion data.

At block 8510, initial estimates of proportions may be assigned to unknown cell types calculated at block 8508. A gamma distribution can be fitted to the gene expression data at block 8512. As discussed above, in some embodiments, the gamma distribution is initialized with shape and mean parameters. The mean can be an average mean across all patients for each gene.

The processing at blocks 8510 and 8512 can be performed in any order or at least partially simultaneously, as shown in FIG. 246 (8511). In some implementations, the processing at blocks 8510 and 8512 can be performed in parallel.

In embodiments of the present disclosure, the sum of proportions of cell types represents the whole and equals to 100%. As an example, predicted proportions for cell types (determined at block 8506 of FIG. 246, as discussed above) can be $k_1$=40% tumor, $k_2$=30% epithelium, $k_3$=20% stroma, and $k_4$=10% lymphocytes. Similarly, a sum of proportions of unknown cell types that make up each category (e.g., tumor, epithelium, stroma, and lymphocytes) is modeled as being equivalent to the entirety of the cell types. For example, if it is known that 40% of the sample is 7 unknown cell types, in some embodiments, 7 random values may be generated and scaled up such that their sum equals to 40%.

An example of an approach to accomplish this may be to randomly generate k values, such as the k values from the summation of the cell types. By summing each of the randomly generated values of each k and dividing by the sum (of those random values), the random values will represent a random proportion of the 100% and, by multiplying each randomly generated k value with the respective previously determined k values, the respective portions may be scaled to the correct proportion. As an illustration, for unknown tumors having a $k_1$=10 at 40%, epithelium having a $k_2$=5 at 30%, stroma having a $k_3$=2 at 20%, and lymphocytes having $k_4=7$ at 10%, the proportions for tumors may be calculated by randomly generating 10 values, summing the 10 values, dividing each value by the summation, and then multiplying by 0.4 to scale the random numbers to add up to 40%. If the ten values are (2, 4, 6, 8, 10, 12, 14, 16, 18, 20), a summation of all 10 values is 110, dividing each value by 110 and multiplying by 0.4 results in (0.007272727, 0.014545455, 0.021818182, 0.029090909, 0.036363636, 0.043636364, 0.050909091, 0.058181818, 0.065454545, 0.072727273) which sum to 0.4 or 40%. These steps may be performed for each of the unknown cell-types to generate initial guesses for the proportions. In some cases, if a respective $k_n$ is 0, or there are no unknown cell-types, a random probability will not be generated for that $k_n$.

Referring back to FIG. 246, at block 8512, initial estimates for a gamma distribution may be fit to the gene expression data, using the proportions assigned to the unknown cell types (block 8510) and the obtained predicted proportions of known cell types (block 8506). In some embodiments, the initial estimate (e.g., a best fit estimate) may be performed across all genes at once or it may be performed on a gene-by-gene basis. As schematically shown in FIG. 246 (block 8511), the processing at blocks 8510 and 8512 may be performed as part of the same process. As a result of the processing at block 8511, each gene in the plurality of genes is associated with the shape and mean parameters, and the proportions are assigned to cell types.

In some embodiments, known cell-type RNA expression profiles may be used in the processing in this example, e.g., by pre-populating a cell types by gene matrix with the respective gene expression values for the known cell types. For example, if lymphocytes have four previously identified cell-types, the four columns of the cell-type matrix for lymphocytes may be pre-populated with the respective RNA cell-profiles. Cross validation may be performed to test for a likelihood of other, unknown lymphocyte cell-types, and a respective k value may be set to generate an initial estimate of the unknown cell-types. When both known and unknown cell types exist for a respective cell type, the probabilities can be shared among both the known and unknown cell-types. For example, if four lymphocyte cell-type RNA profiles are known and cross validation reveals that another two cell types may exist, then a k of 6 is input to the algorithm but, given that the four of the six columns of the cell-type RNA profile matrix are pre-populated, cell-type RNA profiles for the known four may not be recalculated.

At block 8514 of FIG. 246, the mean parameter of the gamma distribution is iteratively updated across the plurality of genes, while the shapes for the cell types, proportions of the cell types (observed and unknown) and the initial values for the gamma distribution are considered constant. At block 8516, the shape parameter of the gamma distribution is iteratively updated, while the means for the cell types, proportions of the cell types (observed and unknown) and the initial values for the gamma distribution are held constant. At block 8518, the proportions of the cell types for each patient are iteratively updated, with the mean and shape parameter of the gamma distributions being constant. It is assumed that each patient has that patient's own proportion but the plurality of patients share the shape and the mean parameters.

The proportions may be calculated for each patient by weighing the contributions of each gamma distribution for each gene across all genes. A best fit may be identified by applying projected gradient descent to estimate percentage changes across the unknown cell types until convergence. For example, in embodiment, convergence for proportions may be met when the absolute mean difference of proportions from each iteration of projected gradient descent is below a certain threshold value.

As shown in FIG. 246, the processing at blocks 8514, 8516, and 8518 can be performed as part of the same process (block 8515) and may be processed in parallel, serially, or a combination thereof. In some embodiments, the fit updates (iterative updating of parameters until convergence to a desired value or a value within a desired range of values) at block 8515 are performed by a projected gradient descent algorithm for the gamma distribution-based model of gene expression. In some embodiments, a maximum likelihood (ML) estimation, which can be an ML-based minimum mean squared error (MMSE) estimate may be used in fitting the gamma distribution to the gene expression data.

The processing at block 8515 may generate a cell-type profile for each cell type in a plurality of cell types, as shown in FIG. 246. In some implementations, the generated cell-type profiles may be stored in a cell-type RNA profile matrix. For example, the cell-type RNA profile matrix may have a number of columns equal to the number of cell-types and a number of rows equal to the number of genes. The number of genes may be all genes, a subset of genes which are identified as latent factor genes, such as, e.g., genes that distinguish between cell types during clustering, or a subset of genes defined by an input cell-type RNA profile matrix, which can have data on known cell-type RNA expression profiles. In this way, the process 8500 may result in the plurality of cell-type profiles determined for respective cell types, and the respective model is trained to recognize the cell-type RNA profiles. As also shown in FIG. 246, the process 8500 generates proportions of the cell types for each of the plurality of patients.

FIG. 247 is a schematic diagram illustrating examples of gamma distributions 8610 (panel A), 8620 (panel B), and 8630 (panel C), having different shape and mean parameters.

In some embodiments, gamma distribution-based models (e.g., the model generated and trained as shown in FIG. 246), may be trained for a certain type of tissue or for multiple types of tissues. Performance of models trained for a certain type of tissue (e.g., a first cancerous tissue) may be compared to performance of models trained for another type of tissue (e.g., a second cancerous tissue). For example, a cell type identified in a breast tumor may be similar to a cell type identified in a prostate tumor such that treatments may be recommended based on this similarity, as discussed in more detail below.

In some embodiments, gamma distribution models for cell-type RNA expression profiles may be generated using data obtained from organoids. It should be appreciated that cell-type RNA expression profiles may be generated using information on known cell types, and that models generated in accordance with embodiments of the present disclosure can be refined (e.g., retrained) as new data becomes available.

FIGS. 248A-248C illustrate a method for determining a cancer composition of a subject, in accordance with some embodiments of the present disclosure. At block 8702 of FIG. 248A, a method for determining a cancer composition of a subject is provided. The method may be implemented at a computer system (e.g., system 8000 of FIG. 241) having one or more processors and memory storing one or more programs for execution by the one or more processors.

As shown at block 8704, the method may involve generating, in electronic form, for each respective genetic target in a first plurality of genetic targets, a corresponding shape parameter, which can be done based at least in part on RNA sequencing of one or more respective biological samples obtained from a respective tumor specimen of each respective subject across a plurality of subjects. The genetic targets may be various genetic targets, as embodiments of the present disclosure are not limited in this respect. For example, in some embodiments, the first plurality of genetic targets are a first plurality of genes (block 8706). In some embodiments, the first plurality of genetic targets are a transcriptome (block 8708). As another example, each genetic target in the first plurality of genetic targets may be a different independent RNA for a corresponding gene in a plurality of genes, as shown at block 8710. As yet another example, the first plurality of genetic targets may be a first plurality of genetic loci, as shown at block 8712. In some cases, the first plurality of genetic targets are selected from 20,000 different human genes or 128,000 different human RNA transcripts, though the genetic targets may comprise any other number of genes. A panel including virus and/or bacterial genomes may further include cell-type RNA expression profiles for any included respective virus or bacterial genes.

The biological samples may be samples of any of various types. For example, in some embodiments, the biological samples are one or more pathology tissue slides (block 8714). In some embodiments, the one or more respective biological samples are one or more blood, whole blood, plasma, serum, urine, cerebrospinal fluid, fecal, saliva, sweat, tears, pleural fluid, pericardial fluid, or peritoneal fluid samples from the respective subject, or any combination thereof. The plurality of subjects may comprise any number of subjects, e.g., fewer than 100 subjects, 100 subjects, more than 100 subjects, or more than 10,000 subjects.

The pathology tissue slides may comprise, for example, between 5 and 20 pathology tissue slides. In some embodiments, each pathology tissue slide in the one or more pathology tissue slides is between 4 and 5 microns thick, however it should be appreciated that embodiments are not limited in this respect.

The method for determining the cancer composition of the subject further comprises, as shown at block 8716, obtain, in electronic form, for each respective subject across the plurality of subjects, a corresponding relative proportion of one or more sets of cell types in a plurality of sets of cell types. The relative proportions may be, for example, predicted proportion of cell type 1-1(322-1-1) or predicted proportion of cell type N-1 (322-N-1), shown in FIG. 241. The obtaining step 8716 may generate proportions randomly or it may obtain them from measured data (e.g., gene expression data and/or any other type(s) of data) for the subject.

It should be noted that the proportionality knowledge across all sets of cell types may not be available for each cell type. Also, in some cases, no knowledge may be available.

The relative proportions may be assigned randomly. Accordingly, at shown at block 8718, in some embodiments, the corresponding relative proportion of one or more sets of cell types in the plurality of sets of cell types comprises initializing the relative proportion of one or more sets of cell types in the plurality of sets of cell types to random proportions.

Furthermore, in some embodiments, proportions of one or more cell types present in the sample may not be known. Thus, in such embodiments, as shown at block 8720, the proportions may be obtained for less than the entirety of the plurality of sets of cell types.

As discussed above, in various embodiments, the relative proportions many be provided based on a pathology report generated for the sample, or using any other information. Thus, as shown at block 8722 of FIG. 248A, the relative proportion of the one or more sets of cell types in the plurality of sets of cell types for a corresponding subject may originate from a pathology report for the corresponding subject, as shown at block 8722.

Further, as shown at block 8724 of FIG. 248B, the method for determining the cancer composition of the subject further comprises obtaining, in electronic form, for each respective subject across the plurality of subjects, for each respective genetic target in the first plurality of genetic targets, a corresponding measure of central tendency of an abundance of the respective genetic target. In some embodiments, the corresponding measure of central tendency of an abundance such as, e.g., a mean parameter of a gamma distribution for a certain gene, can be obtained (e.g., initiated) based on, at least in part, on the RNA sequencing of one or more respective biological samples obtained from the respective tumor specimen of each respective subject across the plurality of subjects. For example, as discussed above, the mean parameter of the gamma distribution for a certain gene can be initialized as an average mean value of expression of that gene across all patients.

The corresponding measure of central tendency of the respective genetic target is a an arithmetic mean, weighted mean, midrange, midhinge, trimean, Winsorized mean, mean, or mode of RNA sequence reads measured for the respective genetic target in the one or more biological samples obtained from the respective subject (block 8726).

In some embodiments, one or both the shape and mean parameters may be obtained at least in part based on RNA sequencing of the one or more respective biological samples.

In some embodiments, as shown at block 8728, the corresponding shape parameter and the corresponding measure of central tendency of an abundance for a genetic target in the first plurality of genetic targets defines a mean and shape of a gamma distribution, a mean and variance of a normal distribution, a means of a Poisson distribution, or counts and probabilities of a binomial distribution for the genetic target. In some embodiments (block 8730), the corresponding relative proportion of one or more sets of cell types in a plurality of sets of cell types for a respective subject is obtained from a pathologist or by flow cytometry.

A cell type in a set of cell types may be a cell type of any type. For example, the cell type may be a tumor cell type, a healthy cell type, an immune cell type, a lymphocyte cell type, a stroma cell type, an epithelial cell type, or any combinations thereof. In other embodiments a viral or bacterial cell type may also be calculated. In some embodiments, the plurality of calculated cell types in the first set of cell types comprises tumor subtypes 1-N, healthy tissue subtypes 1-M, lymphocyte subtypes 1-X, stroma subtypes 1-Y, and epithelial subtypes 1-Z, wherein N, M, X, Y, and Z are all positive integers.

At block 8732 of FIG. 248B, the method described in this example further includes refining the first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types.

The refining may be performed in various ways. In some embodiments, the refining may use a k-fold cross validation of the plurality of subjects, subject to the first plurality of constraints, to identify the number of calculated cell types in the plurality of calculated cell types.

In some embodiments, the first set of cell types is cancer and each remaining set of cell types is non-cancer. In some embodiments, the first set of cell types is cancer and the plurality of sets of cell types further comprise a second set of cell types that comprises one or more reference cell types for stroma cells, a third set of cell types that comprises one or more reference cell types for epithelium cells, and a fourth set of cell types that comprises one or more reference cell types for lymphocytes. Additionally, in some cases, the plurality of sets of cell types further comprise a fifth set of cell types that is healthy cells, a sixth set of 'cell' types that is viral, and/or a seventh set of cell types that is bacterial.

In some embodiments, the method further comprising obtaining, independent of each respective tumor specimen, for each respective reference cell type represented in the second, third and fourth set of cell types, a corresponding reference cell type RNA expression profile that comprises a corresponding third plurality of genetic targets, thereby obtaining a plurality of reference cell type RNA expression profiles. The first plurality of constraints may further include the plurality of reference cell type RNA expression profiles.

In some embodiments, the plurality of calculated cell types in the first set of cell types consists of more than two calculated cell types.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters; and the corresponding second plurality of genetic targets of a first calculated cell type RNA expression profile for a first calculated cell type in the plurality of calculated cell types includes genes that are not present in the corresponding second plurality of genetic targets of a second calculated cell type RNA expression profile for a second calculated cell type in the plurality of calculated cell types.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. The corresponding second plurality of genetic targets of a first calculated cell type RNA expression profile for a first calculated cell type in the plurality of calculated cell types may comprise between one hundred and one thousand genes.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. In some embodiments, the corresponding second plurality of genetic targets of a first calculated cell type RNA expression profile for a first calculated cell type in the plurality of calculated cell types comprises at least 25, 50, 100, 150, 200, or 250 selected from FIG. 251.

In some embodiments, the plurality of sets of cell types is more than two sets of cell types. The respective tumor specimen may be a tumor from an origin in an enumerated list of origins. In some cases, the enumerated list of origins may be a single origin, non-limiting examples of which include adrenal, binary tract, bladder, bone/bone marrow, breast, brain, cervix, colon/rectum, esophagus, gastrointestinal, head and neck, hepatobiliary, kidney, liver, lung, ovary, urinary/bladder, ovary, pancreas, pelvis, pleura, prostate, renal, skin, small bowel, stomach, testis, thymus, or thyroid.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. The corresponding second plurality of genetic targets may be a respective calculated cell type RNA expression profile is a subset of the first plurality of genetic targets.

The generation of the cell-type RNA expression profile for each calculated cell type in the plurality of calculated cell types (block 8732 of FIG. 248B) may be performed by training (refining) the first optimization model. Once the optimization model is trained, the process 8700 may proceed to using the respective calculated cell type RNA expression profile for each calculated cell type in the plurality of calculated cell types to determine the cancer composition of the subject, as shown at block 8734 of FIG. 248C. In this way, for example, a composition of a new sample may be identified. It should be noted that a cell-type composition of a patient having a condition or disease other than cancer can be determined using the method in accordance with embodiments of the present disclosure, as the embodiments are not limited to cancer samples.

In some embodiments, as shown at block 8736 of FIG. 248C, the using comprises: obtaining, in electronic form, a test expression set that comprises, for each respective genetic target in the first plurality of genetic targets, a corresponding measure of central tendency of an abundance of the respective genetic target, based at least in part on RNA sequencing of one or more respective biological samples obtained from a tumor specimen of a test subject; obtaining, in electronic form, a test proportion set that comprises the corresponding relative proportion of each set of cell types in the plurality of sets of cell types; and refining a second optimization model subject to a second plurality of constraints. The second plurality of constraints include (i) the test expression set, (ii) the test proportion set, and (iii) the respective calculated cell type RNA expression profile for each calculated cell type in the plurality of calculated cell types, thereby identifying the cancer composition of the test subject in the form of a relative proportion of each calculated cell type in the plurality of calculated cells types.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters in a plurality of fitted expression distribution parameters. In such embodiments, the refining the first optimization model comprises (A) for each respective subject in the plurality of subjects, for each calculated cell type in the plurality of calculated cell types, assigning a respective seed proportion, bounded by a relative proportion of the first set of cell types in the respective subject, to each calculated cell type in the plurality of calculated cell types, thereby obtaining a set of proportions across the plurality of subjects; (B) refining the corresponding set of fitted expression distribution parameters of each respective genetic target in each corresponding second plurality of genetic targets for each respective calculated cell type RNA expression profile in the plurality of calculated cell types using at least (i) the set of proportions across the plurality of subjects, (ii) the corresponding shape parameter for each respective genetic target in the first plurality of genetic targets for each respective subject in the plurality of subjects, (iii) the corresponding measure of central tendency of an abundance of each respective genetic target in the first plurality of genetic targets, for each respective subject across the plurality of subjects, and (iv) the corresponding relative proportion of each set of cell types in the plurality of cell types for each respective subject in the plurality of subjects; and (C) refining the set of proportions across the plurality of subjects using at least (i) the corresponding set of fitted expression distribution parameters of each respective gene in each corresponding second plurality of genes for each respective calculated cell type RNA expression profile in the plurality of calculated cell types (ii) the corresponding shape parameter for each respective genetic target in the first plurality of genetic targets for each respective subject in the plurality of subjects, (iii) the corresponding measure of central tendency of an abundance of each respective genetic target in the first plurality of genetic targets, for each respective subject across the plurality of subjects, and (iv) the corresponding relative proportion of each set of cell types in the plurality of cell types for each respective subject in the plurality of subjects.

In some embodiments, the refining (B) is performed on a genetic target on a genetic target by genetic target and subject by subject basis. In some embodiments, the refining (B) is performed on a genetic target by genetic target basis across the plurality of subjects. In some embodiments, the refining (B) and the refining (C) are iteratively repeated until a first convergence criterion is satisfied. The first convergence criterion may be evaluated in accordance with a first gradient descent algorithm or a first gradient ascent algorithm.

In some implementations, the first set of cell types is cancer and the plurality of sets of cell types further comprises a second set of cell types that comprises one or more reference cell types for stroma cells, a third set of cell types that comprises one or more reference cell types for epithelium cells, and a fourth set of cell types that comprises one or more reference cell types for lymphocytes. The method may further comprise obtaining, independent of the plurality of subjects, for each respective reference cell type represented in the second, third and fourth set of cell types (or including fifth, sixth, and/or seventh 'cell' types), a corresponding reference cell type RNA expression profile that comprises a corresponding third plurality of genetic targets, thereby obtaining a plurality of reference cell type RNA expression profiles. The refining (B) and (C) may further use the plurality of reference cell type RNA expression profiles.

In some embodiments, each respective set of expression distribution parameters in a plurality of sets of expression distribution parameters comprises a corresponding shape parameter k and a corresponding mean parameter p that collectively describe a corresponding gamma distribution of the expression of a corresponding genetic target in the first plurality of genetic targets across the plurality of subjects and wherein the corresponding mean parameter p is a mean of the expression value for the corresponding genetic target across the plurality of subjects, and each respective set of fitted expression distribution parameters of each respective genetic target in the respective second plurality of genetic targets of each respective calculated cell type RNA expression profile for each calculated cell type in the plurality of calculated cell types comprises a corresponding shape parameter k and a corresponding mean parameter p that collectively describe a corresponding gamma distribution of the respective genetic target in the respective calculated cell type RNA expression profile.

In some embodiments, the refining (B) comprises refining the corresponding mean parameter p, while holding the corresponding shape parameter k fixed, for each set of fitted expression distribution parameters of each respective genetic target in each corresponding second plurality of genetic targets for each respective calculated cell type RNA expression profile in the plurality of calculated cell types using at least (i) the set of proportions across the plurality of subjects, (ii) the corresponding set of expression distribution parameters for each respective genetic target in the first plurality of genetic targets for each respective subject in the plurality of subjects, (iii) the corresponding relative proportion of each set of cell types in the plurality of cell types for each respective subject in the plurality of subjects, and (iv) the corresponding shape parameter k for each set of fitted expression distribution parameters of each respective genetic target in each corresponding second plurality of genetic targets for each respective calculated cell type RNA expression profile in the plurality of calculated cell types. The refining (B) can also comprise refining the corresponding shape parameter k, while holding the corresponding mean parameter p fixed, for each set of fitted expression distribution parameters of each respective genetic target in each corresponding second plurality of genetic targets for each respective calculated cell type RNA expression profile in the plurality of calculated cell types using at least (i) the set of proportions across the plurality of subjects, (ii) the corresponding set of expression distribution parameters for each respective genetic target in the first plurality of genetic targets for each respective subject in the plurality of subjects, (iii) the corresponding relative proportion of each set of cell types in the plurality of cell types for each respective subject in the plurality of subjects, and (iv) the corresponding mean parameter p for each set of fitted expression distribution parameters of each respective genetic target in each corresponding second plurality of genetic targets for each respective calculated cell type RNA expression profile in the plurality of calculated cell types.

Furthermore, in some embodiments, the refining steps described above are iteratively performed until a second convergence criterion is satisfied. The second convergence criterion may be evaluated in accordance with a second gradient descent algorithm or a second gradient ascent algorithm.

In some embodiments, a computer system for determining a cancer composition of a subject is provided. The computer system comprises at least one processor, and a memory storing at least one program for execution by the at least one processor. The at least one program comprises instructions for: generating, in electronic form, for each respective genetic target in a first plurality of genetic targets, a corresponding shape parameter, at least in part on RNA sequencing of one or more respective biological samples obtained from a respective tumor specimen of each respective subject across a plurality of subjects; obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target, based at least in part on RNA sequencing of one or more respective biological samples obtained from the respective tumor specimen of the respective subject; and refining a first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types. The instructions are further for using the respective calculated cell type RNA expression profile for each calculated cell type in the plurality of calculated cell types to determine a cancer composition of a subject.

In some embodiments, a non-transitory computer-readable storage medium is provided that stores thereon program code instructions that, when executed by a processor, cause the processor to perform a method for determining a cancer composition of a subject. The method comprises generating, in electronic form, for each respective genetic target in a first plurality of genetic targets, a corresponding shape parameter, based at least in part on RNA sequencing of one or more respective biological samples obtained from a respective tumor specimen of each respective subject across a plurality of subjects; obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target, based at least in part on RNA sequencing of one or more respective biological samples obtained from the respective tumor specimen of the respective subject; and refining a first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types. The method also comprises using the respective calculated cell type RNA expression profile for each calculated cell type in the plurality of calculated cell types to determine a cancer composition of a subject.

In some embodiments, a method for generating cell-type RNA expression profiles is provided that comprises, at a computer system having one or more processors and memory storing one or more programs for execution by the one or more processors: obtaining, in electronic form, for each respective specimen across a plurality of specimens, a corresponding set of expression values based, at least in part, on RNA sequencing obtained from each respective specimen across a plurality of specimens, thereby obtaining a plurality of sets of expression values; obtaining, in electronic form, for each respective specimen in the plurality of specimens, a corresponding relative proportion of at least one set of cell types in a plurality of sets of cell types, wherein the sum of the corresponding relative proportions across the plurality of sets of cell types is 100%; and refining a first optimization model subject to a first plurality of constraints. The first plurality of constraints include (i) a corresponding set of expression distribution parameters; and (ii) the corresponding relative proportion of each set of cell types in the plurality of cell types, thereby identifying a plurality of calculated cell types in a first set of cell types in the plurality of sets of cell types, the refining further generating a respective calculated cell type RNA expression profile for each calculated cell type in the plurality of calculated cell types. The method also comprises using the respective calculated cell type RNA expression profile for each calculated cell type in the plurality of cell types to determine a cancer composition of a specimen.

The techniques described in embodiments of the present disclosure may be used in various clinical applications, by providing insights on cell types present in biological samples, and utilizing those insights for diagnosing and therapeutic purposes.

FIG. 249 illustrates an example of results of application of a gamma distribution model trained for breast cancer tumors and prostate cancer tumors. In this example, results for prostate tumors and breast tumors (with the dimensions reduced from 7 to 2) are plotted on plot 8800, with each dimension corresponding to latent factors. For example, the x-axis may be a latent factor relating to the likelihood of a breast tumor being estrogen receptor negative (ER−) or positive (ER+), and the y-axis may be a latent factor relating to a tumor tissue similarity metric. Prostate tumors are shown clumping together at about Y=6 and about Y=4 regions (see clusters 8802, 8804), and breast tumors are shown clumping together at about X=2 and about X=4 (see cluster 8806) according to ER+ and ER-sub-types, respectively, while some similarities are shown as some ER+ breast tumor cell-types cluster close to the prostate cell-types at Y=6 while other prostate cells are clustering close to ER+ breast cell-types at Y=4. Due to the similarity in cell-types between the breast and prostate tumor cell-types, a treating physician may recommend a patient having a prostate tumor clustering with ER+ breast tumor cell-types begin a treatment regimen that is particular effective for the ER+ breast tumor cell-types.

FIG. 250 illustrates an example of an embodiment of a process 8900 of generating a treatment recommendation using the approaches in accordance with various embodiments of the present disclosure. At block 8902 of FIG. 250, the process may receive genetic target data from a sample of a patient having a first tumor type, e.g., a breast tumor. The genetic target data may be, e.g., a test expression set. At block 8904, a cell-type model (e.g., the first and/or second optimization model described above in connection with FIG. 246), trained to identify a plurality of cell-type profiles comprising a cell-type profile for a cell type of a second tumor type, may be applied to the genetic target data received from the patient having the first tumor type.

The processing at block 8904 may be performed in accordance with any embodiments of the present disclosure, for example, using method 8700 (FIG. 248). The second tumor type can be a tumor different from the first tumor type and it can be, in an example, a prostate tumor. As discussed above, optimization models can be generated in accordance with embodiments of the present disclosure for any suitable tissue cell type. In some embodiments, the cell-type model may be selected such that the model is not trained to identify one or more (or all) cell types that may be present in the first tumor type but that it is trained to identify at least one cell type of the second tumor type. For example, in embodiments in which the first tumor type is a breast tumor and the second tumor type is a prostate tumor (though these tumors are discussed by way of example only), the model can be used to identify at least one cell type in the breast tumor that is typically present in the prostate tumor but has not been previously identified in the breast tumor.

Next, at block 8906, as a result of the application of the plurality of cell-type profiles to the genetic target data received from the patient having the first tumor type, percentage in the sample of the cell-type profile for the cell type of the second tumor type may be determined. The cell type that can be present in different cancer tissues (e.g., in breast and prostate) may be referred to as a sub-lineage cell type. In some embodiments, shape and mean parameters of a gamma distributed can be estimated for each gene of the sub-lineage cell type.

At decision block 8908, it may be determined whether the determined percentage exceeds a certain threshold. In this way, it may be determined whether and to which degree the first tumor type of the patient includes a more cell type (or more than one cell types) that can also be found in a prostate tumor cell type. If the processing at block 8908 determines that the percentage determined at block 8906 exceeds the threshold, the process 8900 may generate, for the patient having the first tumor type, a therapy recommendation based on the determined percentage and on a therapy used for the second tumor type. For example, for the patient with breast cancer, determined to have a certain percentage of a cell type also found in a prostate cancer, the method 8900 may generate a therapy recommendation based on a therapy that is typically used for the prostate cancer treatment and may otherwise not be used for the treatment of breast cancer. In this way, a diagnosis and treatment recommendation based on cell types, in accordance with the present disclosure, may allow developing more precise and more personalized treatments that may otherwise not be apparent when cell types are not considered for a tissue type.

As shown in FIG. 250, after the therapy recommendation is generated at block 8910, which can be done in any suitable format (e.g., displayed on a user interface of a computing device or otherwise provided to a user), the process 8900 may end. As also shown in FIG. 250, if the determined percentage does not exceed the threshold (e.g., the first tumor type does not include, or includes a very small amount of cells similar to those found in the second tumor type), the process 8900 may also end.

In some embodiments, the described techniques may be used to model patient similarity by exchanging tumor tissue profiles percentages from one patient (e.g., patient A) to another patient (e.g., patient B), and comparing the change in likelihood between them. The difference between these patients may be visualized, e.g., as a distance metric to perform a radial plot like graph of patient tumor similarity.

In some embodiments, the described technique may also be used for monitoring a progress of treatment. For example, it may be determined whether or not a tumor tissue sample from a patient undergoing a treatment has a certain cell type which may be indicative of a tumor malignancy, for example. Thus, if the cell type associated with a tumor malignancy is not found in the tumor tissue sample, it may be determined that the treatment has been effective in tumor reduction or prevention.

In some embodiments, techniques described herein may be used to predict a percentage of tumor present in the sample, percentages of tissue types present, type of tumor present, or the RNA expression of only the tumor. In some embodiments, a model in accordance with the present disclosure may be applied to a new tumor to compare to another type of tumor and to find similarities between other tumor types, identify a match to the other tumor type, and/or recommend a treatment that is effective against the other tumor type to treat the new tumor. In some embodiments, the techniques involve generating a sum of parts, where each part percentage is estimated using a model, wherein each part is individually balanced according to the mean and shape of a distribution model and balanced with each other gene according to the mean and shape of the distribution model, until the best fit for present cell types and their percentages are found.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein the term "cancer," "cancerous tissue," or "tumor" refers to an abnormal mass of tissue in which the growth of the mass surpasses and is not coordinated with the growth of normal tissue. In the case of hematological cancers, this includes a volume of blood or other bodily fluid containing cancerous cells. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" or "somatic biopsy" refers to a biological sample obtained or derived from a tumor of a subject, as described herein.

Several aspects are described above with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

REFERENCES CITED

All references cited herein are incorporated herein by reference in their entirety and for all purposes to the same extent as if each individual publication or patent or patent application was specifically and individually indicated to be incorporated by reference in its entirety for all purposes.

XIII. PD-L1 Prediction Using H&E Slide Images

FIG. 252 illustrates an example of a digital image of a histology slide, also known as a pathology slide. In one example, the digital image is created by a scanner that visually captures a histology slide. In an alternative example, the digital image is created by a digital camera attached to a microscope. The histology slide may be made of two transparent glass layers with a slice of tissue or a blood smear affixed between the two layers of glass. The thin slice of tissue may be very thin, with a thickness, for instance, of approximately 5 microns. Tissue may be preserved in a fixative, including formaldehyde, formalin, and paraffin. The tissue contains a combination of many individual biological cells that are visible on the slide. The scanner may include a Philips digital pathology slide scanner, or any scanner known in the art that can create a digital image file.

In one example, the tissue slice contains stain that attaches to certain types of cells or cell parts within the tissue. The stain may include hematoxylin and eosin (H and E) stain and any immunohistochemical (IHC) stain. Hematoxylin is a stain that will bind to DNA and cause the nucleus of a cell to appear blue or purple. Eosin is a stain that will bind to proteins and cause all of the remaining parts of the cell, namely the cytoplasm interior, to appear red or pink. An IHC stain is comprised of an antibody coupled with a molecule that displays one of many colors. The antibody may be designed to bind to any surface shape to target a specific molecule such as a protein or a sugar. The IHC stain will result in a concentration of dye of the selected color near any copies of a specific target molecule present on the slide. Some commonly monitored proteins in tumor samples include programmed death ligand 1 (PD-L1), whose presence in a tumor region can indicate whether a tumor will respond to immunotherapy, and cluster of differentiation 3 (CD-3), which is associated with T lymphocyte immune cells. The presence of CD-3 in a tumor region may be associated with tumor infiltrating lymphocytes which can indicate that the tumor will be susceptible to anti-cancer immunotherapy.

In some examples, the slide may also contain additional control slices of tissue that are not from the tumor sample, which serve as a positive and/or negative control for the staining process. Control tissue slices are more common on slides that have IHC staining.

FIG. 253 is an overview of a digital tissue segmenter 8940. The digital tissue segmenter 8940 may comprise a computational method and apparatus that receives a digital image of a slide, displays a slice of a tumor sample, and creates a high-density, grid-based digital overlay map that identifies the majority class of tissue visible within each grid tile in the digital image. The digital tissue segmenter 8940 may also generate a digital overlay drawing of the outer edge of each cell in the slide image, at the resolution level of an individual pixel.

In another example, the digital tissue segmenter 8940 is a computational method and apparatus that receives a digital radiology image and efficiently creates a high-density, grid-based digital overlay map that identifies the majority class of tissue visible within each grid tile in the digital image. The radiology image may depict a tumor within a patient's body. The radiology image may be 3-dimensional (3-D) and the digital tissue segmenter 8940 may receive 2-dimensional slices of the 3-dimensional image as an input image. Radiology images include but are not limited to X-rays, CT scans, MRI's, ultrasounds, and PET.

The digital tissue segmenter 8940 shown at FIG. 253 includes a tissue detector 8950 for detecting the areas of a digital image that have tissue, and storing data that includes the locations of the areas detected to have tissue. The tissue detector 8950 transfers tissue area location data 8951 to a tissue class tile grid projector 8952 and to a cell tile grid projector 8954. The tissue class tile grid projector 8952 receives the tissue area location data 8951, as described in further detail below and with reference to FIGS. 256A and 256C. For each of several tissue class labels, the tissue class locator 8956 calculates a percentage that represents the likelihood that the tissue class label accurately describes the image within each tile to determine where each tissue class is located in the digital image. For each tile, the total of all of the percentages calculated for all tissue class labels will sum to 1, which reflects 100%. In one example, the tissue class locator 8956 assigns one tissue class label to each tile to determine where each tissue class is located in the digital image. The tissue class locator stores the calculated percentages and assigned tissue class labels associated with each tile.

Examples of tissue classes include but are not limited to tumor, stroma, normal, immune cluster, necrosis, hyperplasia/dysplasia, red blood cells, and tissue classes or cell types that are positive (contain a target molecule of an IHC stain) or negative for an IHC stain target molecule (do not contain that molecule). Examples also include tumor positive, tumor negative, lymphocyte positive, and lymphocyte negative. The grid-based digital overlay map or a separate digital overlay may also highlight individual immune cells, including lymphocytes, cytotoxic T cells, B cells, NK cells, macrophages, etc.

In one example, the digital tissue segmenter 8940 includes a multi-tile algorithm that concurrently analyzes many tiles in an image, both individually and in conjunction with the portion of the image that surrounds each tile. The multi-tile algorithm may achieve a multiscale, multiresolution analysis that captures both the contents of the individual tile and the context of the portion of the image that surrounds the tile. The multi-tile algorithm is described further with reference to FIGS. 256A-256C and 257A-257B. Because the portions of the image that surround two neighboring tiles overlap, analyzing many tiles and their surroundings concurrently instead of separately analyzing each tile with its surroundings reduces computational redundancy and results in greater processing efficiency.

In one example, the digital tissue segmenter 8940 may store the analysis results in a 3-dimensional probability data array, which contains one 1-dimensional data vector for each analyzed tile. In one example, each data vector contains a list of percentages that sum to 100%, each indicating the probability that each grid tile contains one of the tissue classes analyzed.

The position of each data vector in the orthogonal 2-dimensional plane of the data array, with respect to the other vectors, corresponds with the position of the tile associated with that data vector in the digital image, with respect to the other tiles.

The cell type tile grid projector 8954 receives the tissue area location data 8951 and projects a cell type tile grid onto the areas of an image with tissue, as described with further detail with respect to FIG. 259. The cell type locator 8958 may detect each biological cell in the digital image within each grid, prepare an outline on the outer edge of each cell, and classify each cell by cell type. The cell type locator 8958 stores data including the location of each cell and each pixel that contains a cell outer edge, and the cell type label assigned to each cell.

The overlay map generator and metric calculator 8960 may retrieve the stored 3-dimensional probability data array from the tissue class locator 8956, and convert it into an overlay map that displays the assigned tissue class label for each tile. The assigned tissue class for each tile may be displayed as a transparent color that is unique for each tissue class. In one example, the tissue class overlay map displays the probabilities for each grid tile for the tissue class selected by the user. The overlay map generator and metric calculator 8960 also retrieves the stored cell location and type data from the cell type locator 8958, and calculates metrics related to the number of cells in the entire image or in the tiles assigned to a specific tissue class.

FIGS. 254A and 254B illustrate examples of a digital overlay created by the digital tissue segmenter 8940. FIG. 254A illustrates a tissue class overlay map created by the overlay map generator of the digital tissue segmenter 8940. FIG. 254B illustrates a cell outer edge overlay map created by the overlay map generator of the digital tissue segmenter 8940. The overlay map generator may display the digital overlays as transparent or opaque layers that cover the slide image, aligned such that the slide location shown in the overlay and the slide image are in the same location on the display. The overlay map may have varying degrees of transparency. The degree of transparency may be adjustable by the user. The overlay map generator may report the percentage of the labeled tiles that are associated with each tissue class label, ratios of the number of tiles classified under each tissue class, the total area of all grid tiles classified as a single tissue class, and ratios of the areas of tiles classified under each tissue class.

The digital tissue segmenter 8940 may also report the total number of cells or the percentage of cells that are located in an area defined by either a user, the entire slide, a single grid tile, by all grid tiles classified under each tissue class, or cells that are classified as immune cells. The digital tissue segmenter 8940 may also report the number of cells classified as immune cells that are located within areas classified as tumor or any other tissue class.

In one example, the digital tissue segmenter 8940 is capable of calculating the percentage of cells that are colored by an IHC stain to highlight particular cells containing the molecule targeted by the stain. The percentage of cells may be specific to a tissue class region or a cell type. For example, if the IHC stain targets programmed death ligand 1 (PD-L1) protein, the digital tissue segmenter 8940 may determine the percentage of cancer cells in the tumor tissue class that contain PD-L1 protein. If the IHC stain targets cluster of differentiation 3 (CD-3) protein, the digital tissue segmenter 8940 may determine the percentage of lymphocytes or total cells that contain CD-3.

The map generator and metric calculator 8960 may also create a digital overlay map, showing predicted IHC staining on a digital image of a slide that contains no IHC stain. In one example, the tissue class locator 8956 can predict where IHC staining for a specific molecule would exist on a slide, or the percentage of cells that express a specific protein, based on input images that only contain H and E stain.

The digital overlays and reports generated by the digital tissue segmenter 8940 can be used to assist medical professionals in more accurately estimating tumor purity, and in locating regions or diagnoses of interest, including invasive tumors having tumor cells that protrude into the non-tumor tissue region that surrounds the tumor. They can also assist medical professionals in prescribing treatments. For example, the number of lymphocytes in areas classified as tumor may predict whether immunotherapy will be successful in treating a patient's cancer.

The digital overlays and reports generated by the digital tissue segmenter 8940 can also be used to determine whether the slide sample has enough high-quality tissue for successful genetic sequence analysis of the tissue. Genetic sequence analysis of the tissue on a slide is likely to be successful if the slide contains an amount of tissue and/or has a tumor purity value that exceeds a user-defined tissue amount and tumor purity thresholds. In one example, the digital tissue segmenter 8940 may label a slide as accepted or rejected for sequence analysis, depending on the amount of tissue present on the slide and the tumor purity of the tissue on the slide.

The digital tissue segmenter 8940 may also label a slide as uncertain, to recommend that it be manually reviewed by a trained analyst, who may be a member of a pathology team. In one example, if the amount of tissue present on the slide is approximately equal to the user-defined tissue amount threshold or within a user-defined range, the digital tissue segmenter 8940 may label the slide as uncertain. In one example, if the tumor purity of the tissue present on the slide is approximately equal to the user-defined tumor purity threshold or within a user-defined range, the digital tissue segmenter 8940 may label the slide as uncertain.

In one example, the overlay map generator and metric calculator 8960 calculates the amount of tissue on a slide by measuring the total area covered by the tissue or by counting the number of cells on the slide. The number of cells on the slide may be determined by the number of cell nuclei visible on the slide. In one example, the digital tissue segmenter 8940 calculates the proportion of tissue that is cancer cells by dividing the number of cell nuclei within grid areas that are labeled tumor by the total number of cell nuclei on the slide. The digital tissue segmenter 8940 may exclude cell nuclei or outer edges of cells that are located in tumor areas but which belong to cells that are characterized as lymphocytes. The proportion of tissue that is cancer cells is known as the tumor purity of the sample.

In one example, the digital tissue segmenter 8940 compares the tumor purity to the user-selected minimum tumor purity threshold and the number of cells in the digital image to a user-selected minimum cell threshold and approves the slide if both thresholds are exceeded. In one example, the user-selected minimum tumor purity threshold is 0.20, which is 20%.

In one example, the slide is given a composite tissue amount score that multiplies the total area covered by tissue detected on the slide by a first multiplier value, multiplies the number of cells counted on the slide by a second multiplier value, and sums the products of these multiplications.

The digital tissue segmenter 8940 may calculate whether the grid areas that are labeled tumor are spatially consolidated or dispersed among non-tumor grid areas. If the digital tissue segmenter 8940 determines that the tumor areas are spatially consolidated, the digital tissue segmenter 8940 may produce a digital overlay of a recommended cutting boundary that separates the slide regions classified as tumor and the slide regions classified as non-tumor or within the areas classified as non-tumor, proximal to the areas classified as tumor. This recommended cutting boundary can be a guide to assist a technician in dissecting a slide to isolate a maximum amount of tumor or non-tumor tissue from the slide, especially for genetic sequence analysis.

The digital tissue segmenter 8940 may include clustering algorithms that calculate and report information about the spacing and density of type classified cells, tissue class classified tiles, or visually detectable features on the slide. The spacing information includes distribution patterns and heat maps for immune cells, tumor cells, or other cells. These patterns may include clustered, dispersed, dense, and non-existent. This information is useful to determine whether immune cells and tumor cells cluster together and what percentage of the cluster areas overlap, which may facilitate in predicting immune infiltration and patient response to immunotherapy.

The digital tissue segmenter 8940 may also calculate and report average tumor cell roundness, average tumor cell perimeter length, and average tumor nuclei density.

The spacing information also includes mixture levels of tumor cells and immune cells. The clustering algorithms can calculate the probability that two adjacent cells on a given slide will be either two tumor cells, two immune cells, or one tumor cell and one immune cell.

The clustering algorithms can also measure the thickness of any stroma pattern located around an area classified as tumor. The thickness of this stroma surrounding the tumor region may be a predictor of a patient's response to treatment.

The digital tissue segmenter 8940 may also calculate and report statistics including mean, standard deviation, sum, etc. for the following information in each grid tile of either a single slide image or aggregated from many slide images: red green blue (RGB) value, optical density, hue, saturation, grayscale, and stain deconvolution. Deconvolution includes the removal of the visual signal created by any individual stain or combination of stains, including hematoxylin, eosin, or IHC staining.

The digital tissue segmenter 8940 may also incorporate known mathematical formulae from the fields of physics and image analysis to calculate visually detectable basic features for each grid tile. Visually detectable basic features, including lines, patterns of alternating brightness, and outlineable shapes, may be combined to create visually detectable complex features including cell size, cell roundness, cell shape, and staining patterns referred to as texture features.

The digital overlays, reports, statistics, and estimates produced by the digital tissue segmenter 8940 may be useful for predicting patient survival, patient response to a specific cancer treatment, PD-L1 status of a tumor or immune cluster, microsatellite instability (MSI), tumor mutational burden (TMB), and the origin of a tumor when the origin is unknown or the tumor is metastatic. The overlay map generator and metric calculator 8960 may also calculate quantitative measurements of predicted patient survival, patient response to a specific cancer treatment, PD-L1 status of a tumor or immune cluster, microsatellite instability (MSI), and tumor mutational burden (TMB).

The digital tissue segmenter 8940 may calculate relative densities of each type of immune cell on an entire slide, in the areas designated as tumor or another tissue class. Immune tissue classes include lymphocytes, cytotoxic T cells, B cells, NK cells, macrophages, etc.

In one example, the act of scanning or otherwise digitally capturing a histology slide automatically triggers the digital tissue segmenter 8940 to analyze the digital image of that histology slide.

In one example, the digital tissue segmenter 8940 allows a user to edit a cell outer edge or a border between two tissue classes on a tissue class overlay map or a cell outer edge overlay map and saves the altered map as a new overlay.

FIG. 255 is a flowchart of a method for preparing digital images of histology slides for tissue classification and mapping analysis.

In one example, each digital image file received by the digital tissue segmenter 8940 contains multiple versions of the same image content, and each version has a different resolution. The file stores these copies in stacked layers, arranged by resolution such that the highest resolution image containing the greatest number of bytes is the bottom layer. This is known as a pyramidal structure. In one example, the highest resolution image is the highest resolution achievable by the scanner or camera that created the digital image file.

In one example, each digital image file also contains metadata that indicates the resolution of each layer. The digital tissue segmenter 8940 can detect the resolution of each layer in this metadata and compare it to user-selected resolution criteria to select a layer with optimal resolution for analysis. In one example, the optimal resolution is 1 pixel per micron (downsampled by 4).

In one example, the digital tissue segmenter 8940 receives a Tagged Image File Format (TIFF) file with a bottom layer resolution of four pixels per micron. This resolution of 4 pixels per micron corresponds to the resolution achieved by a microscope objective lens with a magnification power of "40×". In one example, the area that may have tissue on the slide is up to 100,000×100,000 pixels in size.

In one example, the TIFF file has approximately 10 layers, and the resolution of each layer is half as high as the resolution of the layer below it. If the higher resolution layer had a resolution of four pixels per micron, the layer above it will have two pixels per micron. The area represented by one pixel in the upper layer will be the size of the area represented by four pixels in the lower layer, meaning that the length of each side of the area represented by one upper layer pixel will be twice the length of each side of the area represented by one lower layer pixel.

Each layer may be a 2× downsampling of the layer below it. Downsampling is a method by which a new version of an original image can be created with a lower resolution value than the original image. There are many methods known in the art for downsampling, including nearest-neighbor, bilinear, hermite, bell, Mitchell, bicubic, and Lanczos resampling.

In one example, 2× downsampling means that the red green blue (RGB) values from three of four pixels that are located in a square in the higher resolution layer are replaced by the RGB value from the fourth pixel to create a new, larger pixel in the layer above, which occupies the same space as the four averaged pixels.

In one example, the digital image file does not contain a layer or an image with the optimal resolution. In this case, the digital tissue segmenter 8940 can receive an image from the file having a resolution that is higher than the optimal resolution and downsample the image at a ratio that achieves the optimal resolution.

In one example, the optimal resolution is 2 pixels per micron, or "20×" magnification, but the bottom layer of a TIFF file is 4 pixels per micron and each layer is downsampled 4× compared to the layer below it. In this case, the TIFF file has one layer at 40× and the next layer at 10× magnification, but does not have a layer at 20× magnification. In this example, the digital tissue segmenter 8940 reads the metadata and compares the resolution of each layer to the optimal resolution and does not find a layer with the optimal resolution. Instead, the digital tissue segmenter 8940 retrieves the 40× magnification layer, then downsamples the image in that layer at a 2× downsampling ratio to create an image with the optimal resolution of 20× magnification.

After the digital tissue segmenter 8940 obtains an image with an optimal resolution, it transmits the image to the tissue detector 8950, which locates all parts of the image that depict tumor sample tissue and digitally eliminates debris, pen marks, and other non-tissue objects.

In one example, the tissue detector 8950 differentiates between tissue and non-tissue regions of the image and uses gaussian blur removal to edit pixels with non-tissue objects. In one example, any control tissue on a slide that is not part of the tumor sample tissue can be detected and labeled as control tissue by the tissue detector or manually labeled by a human analyst as control tissue that should be excluded from the downstream tile grid projections.

Non-tissue objects include artifacts, markings, and debris in the image. Debris includes keratin, severely compressed or smashed tissue that cannot be visually analyzed, and any objects that were not collected with the sample.

In one example, a slide image contains marker ink or other writing that the tissue detector 8950 detects and digitally deletes. Marker ink or other writing may be transparent over the tissue, meaning that the tissue on the slide may be visible through the ink. Because the ink of each marking is one color, the ink causes a consistent shift in the RGB values of the pixels that contain stained tissue underneath the ink compared to pixels that contain stained tissue without ink.

In one example, the tissue detector 8950 locates portions of the slide image that have ink by detecting portions that have RGB values that are different from the RGB values of the rest of the slide image, where the difference between the RGB values from the two portions is consistent. Then, the tissue detector may subtract the difference between the RGB values of the pixels in the ink portions and the pixels in the non-ink portions from the RGB values of the pixels in the ink portions to digitally delete the ink.

In one example, the tissue detector 8950 eliminates pixels in the image that have low local variability. These pixels represent artifacts, markings, or blurred areas caused by the tissue slice being out of focus, an air bubble being trapped between the two glass layers of the slide, or pen marks on the slide.

XIV. Cellular Pathway Report

The presently described embodiments relate to methods and systems for creating and presenting diagnostic and/or treatment pathways and options to physicians, including, in embodiments, potential treatment options specifically tailored to a particular patient's cancer state. The information is generally provided in a report document—presented digitally or in hard copy—that includes an easy-to-understand, stylized, visual depiction of the diagnostic and/or treatment pathways in question, accompanied, in embodiments, by additional descriptive information as described below. As used herein, the term "pathway" refers to a cellular signaling pathway. The phrase "diagnostic pathway" is used to refer to a pathway depicting certain modifications to the primary pathway and additional information relating to why a certain mutation, pathogen, or other factor, is causing a disease. The phrase "treatment pathway" is used to refer to a pathway depicting one or more therapies and how each therapy interacts with the associated diagnostic pathway, as well as additional information relating to the therapy and its associated requirements, limitations, and/or eligibility criteria.

A database stores pre-identified pathway options identified by third parties (e.g., other research) or by the provider, for example, according to the processes and systems described in U.S. Provisional Patent Application 62/746, 997, entitled "Data Based Cancer Research and Treatment Systems and Methods," filed Oct. 17, 2018, the entirety of where is hereby incorporated by reference herein, for any and all permissible purposes. Each of the pre-identified pathway options corresponds to a particular cellular signaling pathway. In embodiments, each of the pathway options may have various modifications, each modification corresponding to a specific mutation or pathogen and the manner in which the mutation or pathogen results in oncogenic effects downstream of the point at which the mutation or pathogen interacts with cellular signaling. Each of the pathway options includes a plurality of pathway elements, each in turn related to an associated signaling molecule or protein and/or the gene that is responsible for the synthesis of that molecule or protein.

For example, the MAPK (mitrogen-activated protein kinase) pathway is one of a number of pathways that regulate gene expression, cellular growth, and survival. Knight T, Irving J A. Ras/Raf/MEK/ERK pathway activation in childhood acute lymphoblastic leukemia and its therapeutic targeting. Front Oncol. 2014; 4:160. Each element in the pathway is related to an associated signaling molecule and/or the gene that is responsible for the synthesis of that molecule. The elements in the MAPK pathway include EGFR, KRAS, BRAF, MEK, and ERK. KRAS, for example, is a gene responsible for the production of the Ras protein which, when activated, causes the membrane recruitment and activation of Raf proteins (coded for by the BRAF gene). Cseh B, Doma E, Baccarini M. "RAF" neighborhood: protein-protein interaction in the Raf/Mek/Erk pathway. FEBS Lett. 2014; 588:2398-2406. Mutations in either KRAS or BRAF have been associated with oncogenic effects.

Thus, different mutations or pathogens may interact with the same pathway in various ways. In the MAPK pathway, either or both of a KRAS mutation or a BRAF mutation may result in or contribute to oncogenesis and, as a result, the pathway may have multiple instances in the database, each instance related to a different mutation or pathogen in the pathway. Without wishing to be overly pedantic, there may be a first diagnostic pathway in the database of the MAPK pathway with a KRAS mutation, and a second diagnostic pathway of the MAPK pathway with a BRAF mutation. The same is true for other pathways in the database.

One aspect of the utility of the described embodiments derives from the potential for communicating to physicians treatment options for a particular patient's cancer state. That is, for a given cancer state, there may be a variety of effective or potentially effective treatments (therapies) targeting one or more elements in the pathway (i.e., exerting a biological effect on the pathway), typically downstream in the pathway. For instance, and keeping with the example above, various treatment options for a KRAS gain-of-function mutation target the ERK element (e.g., ERK inhibitors), the MEK element (e.g., MEK inhibitors), the BRAF element (e.g., RAF inhibitors), etc. Thus, even for a particular mutation or pathogen (which may be depicted in a diagnostic pathway), there may be a variety of treatment pathways, each depicting a different effective or potentially effective treatment.

Each of the effective or potentially effective treatments may have associated eligibility criteria related to the efficacy of the therapy and/or, in the case of a clinical trial, to participation in the trial. The eligibility requirements may include the cancer diagnosis (e.g., type of cancer, cancer stage, type of mutation, presence and/or absence of other mutations), patient's geographical location, patient age, other health conditions, etc. The eligibility criteria may be stored in the database as metadata associated with each treatment pathway and/or with each mutation or pathogen associated with the diagnostic pathway.

As should be understood, the database may be arranged in any of a variety of manners. For instance, see FIG. 266 where the database may store each of the pathway options with associated data that may be used to modify and/or present the pathway as either a diagnostic pathway or a treatment pathway. That is, a set of diagnostic pathways (i.e., one pathway for each pathogen and/or mutation) for each pathway option. Each of the diagnostic pathways may include a pathway image that illustrates the elements in the diagnostic pathway, and a diagnostic pathway description that describes primary features of the pathway. The diagnostic pathway may also be stored with information related to one or more therapy options associated with the diagnostic pathway, each of which may, in turn, include therapy criteria, image modifications for creating a treatment pathway, and therapy description. Of course, various metadata may be associated with the associated data, to facilitate search, filtering, and the like, as will be understood.

As an example of such an implementation, see FIG. 267 where the database may store a set of pathways (a pathway set) for MAPK pathways. A first diagnostic pathway may relate to a KRAS gain-of-function mutation in the MAPK pathway. The first diagnostic pathway may include a pathway image that depicts the elements in the MAPK pathway, with the KRAS gain-of-function mutation:

The first diagnostic pathway may also include a pathway description that describes the MAPK pathway with the KRAS gain-of-function mutation, perhaps in relation to the type of cancer that the patient has:

This patient has pancreatic cancer with a KRAS gain-of-function mutation. KRAS is the driver oncogene in approximately 95% of pancreatic ductal adenocarcinomas. Unfortunately KRAS is considered "undruggable" with currently approved therapies.

In embodiments, the pathway description for the diagnostic pathway may also detail the manner in which the mutation or pathogen induces oncogenesis by describing the cellular mechanisms that are disrupted or augmented and the effects of such disruption or augmentation.

In any event, the first diagnostic pathway may also be stored as associated with one or more therapy options. For a first therapy option targeting the KRAS gain-of-function mutation, the diagnostic pathway may be associated with stored data for creating a treatment pathway. The stored data for creating the treatment pathway may include eligibility criteria: image modifications (including metadata indicating where the modifications would be placed relative to the diagnostic pathway (see FIG. 268)), and therapy description:

However, drugs are being tested in clinical trials to target the signaling pathway containing KRAS. One clinical trial listed below, NCT03051035, is for an ERK inhibitor (KO-947). ERK is downstream of KRAS in the MAP kinase cascade, and may therefore be able to slow or stop KRAS signaling in a way that EGFR inhibitors, which are targeting an upstream protein, cannot. Since standard of care chemotherapy is not highly effective in pancreatic cancer, if the patient is amenable to clinical trial enrollment, this should be considered.

Similar data may be stored in the database for each therapy option, including for therapy options that are approved for the patient and cancer state, those that may be in clinical trial testing, and even those that may be off-label uses of approved therapeutic agents.

The various stored elements may be combined to create a report for a particular pathway and treatment option. In some embodiments, only one or more diagnostic pathways may be included in the report, while in other embodiments, one or more treatment pathways may be included in the report. One example treatment pathway report is depicted in FIG. 269A.

Alternatively, the database may store a plurality of treatment pathways, each having a treatment pathway image, a treatment pathway description, and therapy criteria, much as described above. However, because the pathway image is specific to the therapy, there is no need in such implementations to store separately the image modifications for each respective therapy type, and the therapy and pathway descriptions may be combined. In fact, the entire report for a specific therapy may be stored as a single image or element in such implementations, along with appropriate metadata (e.g., therapy criteria, cancer state, etc.) to facilitate searching and filtering. The database may separately store diagnostic pathways to present in embodiments or instances in which treatment pathways are not presented in the report or are presented separately from the diagnostic pathways (see FIG. 270).

In at least some cases system information may be useable to gain additional insights into a patient's cancer state that, while true based on current information, have not been proven with a high level of confidence. These insights are referred to herein as "insights" and, while accessible to a physician, typically are not included in patient reports because of the low confidence associated therewith. Here, the idea is that a physician or researcher may want to consider additional insights while considering a specific patient's cancer state. While many different types of insights are contemplated, three insight types in particular are of interest. A first is related to pathways as described above where an insight may include a pathway image akin to the image shown in FIG. 269A, albeit presented in response to selection of an interface insight option or the like to show a pathway of interest for a specific patient's cancer state. The system will support hundreds or even thousands of different pathway insights.

Figure 269B:
Figure 269C:
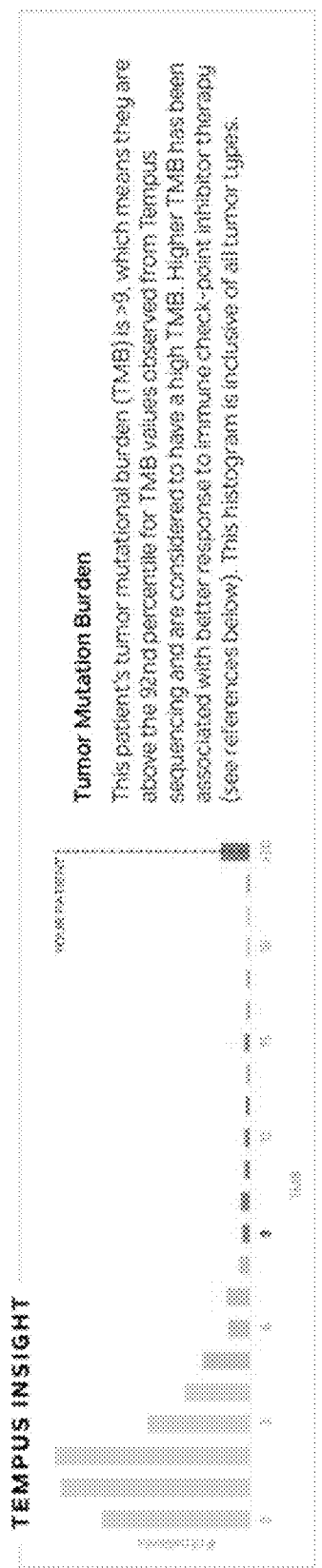
Figure 269D:
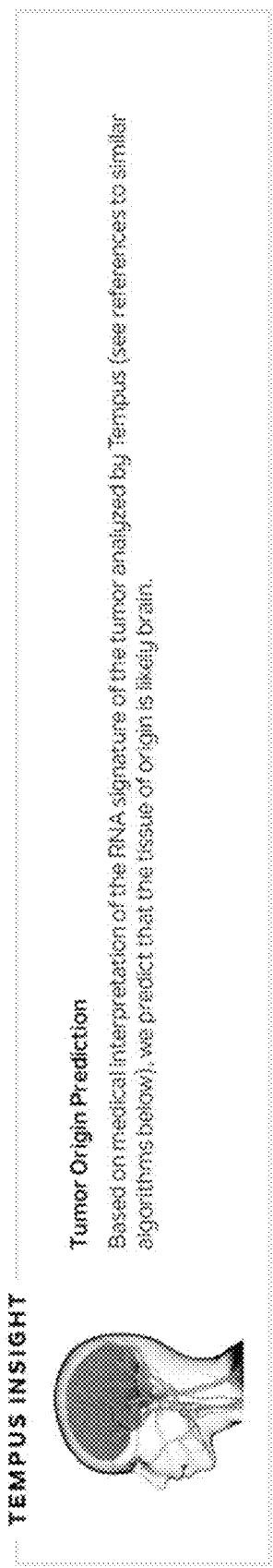
Figure 269E:
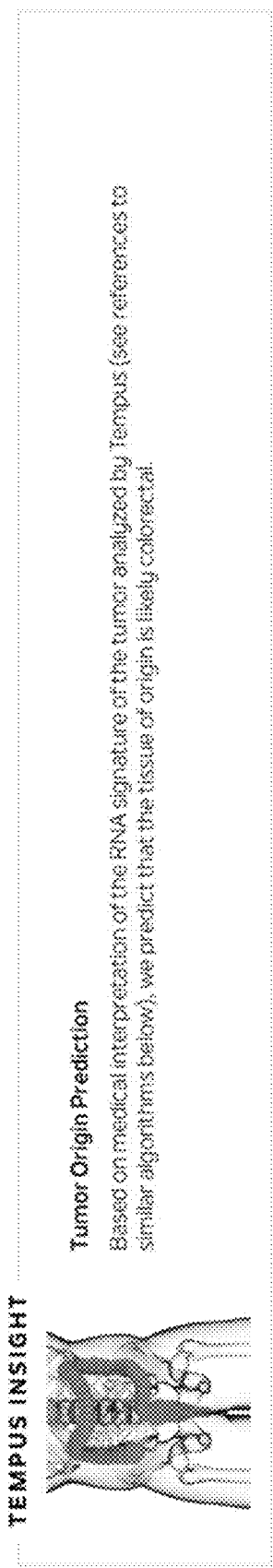

A second insight type is referred to as a rare cancer insight and is offered to a physician when a rare cancer state occurs. Again, it is contemplated that the system will support literally thousands of different rare cancer insights. FIG. 269B shows an exemplary image of a rare cancer insight notification. See as another instance, the insight regarding efficacy of check-point inhibitor therapy including a supporting histogram of known cases like a patient's shown in FIG. 269C.

The third insight type is a tumor of unknown origin insight which predicts, based on cancer state information for a specific patient, the origin of the patient's cancer (e.g., where in the body cancer originated). See, for instance FIG. 269D that shows a prediction that cancer originated in a patient's brain. See as another instance FIG. 269E indicating a predicted origin is colorectal.

The provider may receive data for a specific patient from physicians and/or partners. For instance, the provider may receive clinical data of the patient from the physician, including the patient's age, location, gender, and other aspects related to the patient's cancer state, as would be known to the physician. The physician and/or partner(s) may also communicate to the provider a tissue sample of the patient's cancer (e.g., a biopsy, a blood sample, etc.). The provider may, in embodiments, perform one or more tests on the tissue sample to determine additional aspects of the patient's cancer state. By way of example, such tests may include next generation sequencing (NGS) of RNA and/or DNA in the tissue sample, and/or may perform analysis of images related to the tissue sample (e.g., AI-performed analysis to determine cell boundaries, cell types, presence and/or population of tumor-infiltrating lymphocytes (TILs), etc.).

The data received by the provider from the physician(s) and partner(s) may be used to determine the patient's cancer state and, in turn, which therapies may be beneficial to and/or available to the patient. In particular, the NGS results may implicate one or more pathways (e.g., the MAPK pathway), one or more specific diagnostic pathways (e.g., MAPK pathway with KRAS gain-of-function mutation), and/or one or more treatment pathways associated with respective therapies (e.g., KO-947 ERK inhibitor) that relate to the patient's cancer state. The implicated pathways may be selected for inclusion in a pathway report in various combinations (according to the criteria for the report).

In embodiments, the provider may identify genomic variant(s) as part of the NGS process. For at least some variants, there may be pathways in the database that are associated specifically with the variant. If the patient in question has a variant, some or all of the associated diagnostic pathway(s) may be put on the pathway report. In embodiments, all diagnostic and/or treatment pathways in any pathway set, that are associated with the variant, may be put into the pathway report (e.g., for a variant associated with the MAPK pathway, all diagnostic and/or treatment pathways in the MAPK pathway set may be included in the pathway report; for a variant associated with multiple pathways, all diagnostic and/or treatment pathways in all associated pathway sets may be included in the pathway report, etc.). In other embodiments, all treatment pathways related to a particular diagnostic pathway (e.g., MAPK treatment pathways related to KRAS gain-of-function mutations) may be put into the pathway report. In still other embodiments, only a selected subset of treatment pathways in the pathway set associated with the variant may be put into the pathway report. For example, if NGS indicates that the patient also has a mutation that is excluded from one or more of the potential therapies for a specific modified pathway, the treatment pathways for those potential therapies from which the patient would be excluded are not included in the pathway report. Criteria such as cancer sub-type (e.g., pancreatic cancer, lung cancer, etc.) may be considered in determining which treatment pathways and associated potential therapies to exclude.

XV. Systems and Methods of Clinical Trial Evaluation

The various aspects of the subject invention are now described with reference to the annexed drawings, wherein like reference numerals correspond to similar elements throughout the several views (e.g., "trial description 9103" can be similar to "trial description 9303"). It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (such as hard disk, floppy disk, magnetic strips), optical disks (such as compact disk (CD), digital versatile disk (DVD)), smart cards, and flash memory devices (such as card, stick). Additionally it should be appreciated that a carrier wave can be employed to carry computer-readable electronic data such as those used in transmitting and receiving electronic mail or in accessing a network such as the Internet or a local area network (LAN). Transitory computer-readable media (carrier wave and signal based) should be considered separately from non-transitory computer-readable media such as those described above. Of course, those skilled in the art will recognize many modifications may be made to this configuration without departing from the scope or spirit of the claimed subject matter.

Unless indicated otherwise, while the disclosed system is used for many different purposes (such as data collection, data analysis, data display, research, etc.), in the interest of simplicity and consistency, the overall disclosed system will be referred to hereinafter as "the system."

In one example, the present disclosure includes a system, other class of device, and/or method to help a medical provider make clinical decisions based on a combination of molecular and clinical data, which may include comparing the molecular and clinical data of a patient to an aggregated data set of molecular and/or clinical data from multiple patients, a knowledge database (KDB) of clinico-genomic data, and/or a database of clinical trial information. Additionally, the present disclosure may be used to capture, ingest, cleanse, structure, and combine robust clinical data, detailed molecular data, and clinical trial information to determine the significance of correlations, to generate reports for physicians, recommend or discourage specific treatments for a patient (including clinical trial participation), bolster clinical research efforts, expand indications of use for treatments currently in market and clinical trials, and/or expedite federal or regulatory body approval of treatment compounds.

In one example, the present disclosure may help academic medical centers, pharmaceutical companies and community providers improve care options and treatment outcomes for patients, especially patients who are open to participation in a clinical trial.

In some embodiments of the present disclosure, the system can create structure around clinical trial data. This can include reviewing free text (i.e., unstructured data), determining relevant information, and populating corresponding structured data field with the information. As an example, a clinical trial description may specify that only patients diagnosed with stage I breast cancer may enroll. A structured data field corresponding to "stage/grade" may then be populated with "stage I," and a structured data field corresponding to "disease type" may then be populated with "breast" or "breast cancer." The ability of the system to create structured clinical trial data can aid in the matching of patients to an appropriate clinical trial. In particular, a patient's structured health data can be mapped to the structured clinical trial data to determine which clinical trials may be optimal for the specific patient.

In some embodiments of the present disclosure, the system can compare patient data to clinical trial data, and subsequently generate a report of recommended clinical trials that the patient may be eligible for. The patient's physician may review the report and use the information to enroll the patient in a well-suited clinical trial. Accordingly, physicians and/or patients do not need to manually sort and review all clinical trials within a database. Rather, a customized list of clinical trials is efficiently generated, based on the specific needs of the patient. This generation can significantly decrease the time for a patient to find and enroll in a clinical trial, thus improving treatment outcomes for certain diseases and conditions.

In some embodiments of the present disclosure, the system can facilitate activation of a new site for clinical trial participation. This can occur, in part, based on patient location to existing sites (e.g., if a patient's physician is hundreds of miles from an existing clinical trial site, a request for activation of a closer site may occur via the system). Rapid activation of a new site can help to ensure that a patient can quickly enroll in a clinical trial, as well as quickly begin treatment. The system can provide an interface for tracking activation progress, including the various stages and corresponding tasks. As one example, a patient may submit a tissue sample and health records to a provider, receive a diagnosis, and have an available (i.e. activated) site to participate in a recommended clinical trial, all within two weeks of initial contact with the provider.

In some embodiments of the present disclosure, the system can provide an interface for sites (e.g., clinical trial sites) to submit and/or update site information in real-time. As an example, if a site installs a new machine for treatment, site personnel can update their clinical trial site information to reflect the new machine (and associated capabilities). Accordingly, the site can become eligible for a larger number of existing clinical trials, and patients can begin enrolling at the new location. The system enables providers and other users to easily update and validate their information, ensuring that patients are accurately matched with available clinical trials.

In one example, one implementation of this system may be a form of software. An exemplary system that provides a foundation to capture the above benefits, and more, is described below.

System Overview

In one example of the system, which may be used to help a medical provider make clinical decisions based on a combination of molecular and clinical data, the present architecture is designed such that system processes may be compartmentalized into loosely coupled and distinct micro-services for defined subsets of system data, may generate new data products for consumption by other micro-services, including other system resources, and enables maximum system adaptability so that new data types as well as treatment and research insights can be rapidly accommodated. Accordingly, because micro-services operate independently of other system resources to perform defined processes where development constraints relate to system data consumed and data products generated, small autonomous teams of scientists and software engineers can develop new micro-services with minimal system constraints that promote expedited service development.

This system enables rapid changes to existing micro-services as well as development of new micro-services to meet any data handling and analytical needs. For instance, in a case where a new record type is to be ingested into an existing system, a new record ingestion micro-service can be rapidly developed resulting in that addition of a new record in a raw data form to a system database as well as a system alert notifying other system resources that the new record is available for consumption. Here, the intra-micro-service process is independent of all other system processes and therefore can be developed as efficiently and rapidly as possible to achieve the service specific goal. As an alternative, an existing record ingestion micro-service may be modified independent of other system processes to accommodate some aspect of the new record type. The micro-service architecture enables many service development teams to work independently to simultaneously develop many different micro-services so that many aspects of the overall system can be rapidly adapted and improved at the same time.

A messaging gateway may receive data files and messages from micro-services, glean metadata from those files and messages and route those files and messages on to other system components including databases, other micro-services, and various system applications. This enables the micro-services to poll their own messages as well as incoming transmissions (point-to-point) or bus transmissions (broadcast to all listeners on the bus) to identify messages that will start or stop the micro-services.

Referring now to the figures that accompany this written description and more specifically referring to FIG. 271, the present disclosure will be described in the context of an exemplary disclosed system 9000 where data is shown to be received at a server 9020 from many different data sources (such as database 9032, clinical record 9024, and micro-services (not shown)). In some aspects, the server 9020 can store relevant data, such as at database 9034, which is shown to include empirical patient outcomes. The server 9020 can manipulate and analyze available data in many different ways via an analytics module 9036. Further, the analytics module 9036 can condition or "shape" the data to generate new interim data or to structure data in different structured formats for consumption by user application programs and to then drive the user application programs to provide user interfaces via any of several different types of user interface devices. While a single server 9020 and a single internal database 9034 are shown in FIG. 271 in the interest of simplifying this explanation, it should be appreciated that in most cases, the system 9000 will include a plurality of distributed servers and databases that are linked via local and/or wide area networks and/or the Internet or some other type of communication infrastructure. An exemplary simplified communication network is labeled 9018 in FIG. 271. Network connections can be any type, including hard wired, wireless, etc., and may operate pursuant to any suitable communication protocols. Furthermore, the network connections may include the communication/messaging gateway/bus that enables micro-services file and message transfer according to the above system.

The disclosed system 9000 enables many different system clients to securely link to server 9020 using various types of computing devices to access system application program interfaces optimized to facilitate specific activities performed by those clients. For instance, in FIG. 271 a provider 9012 (such as a physician, researcher, lab technician, etc.) is shown using a display device 9016 (such as a laptop computer, a tablet, a smart phone, etc.) to link to server 9020. In some aspects, the display device 9016 can include other types of personal computing devices, such as, virtual reality headsets, projectors, wearable devices (such as a smart watch, etc.).

In at least some embodiments when a physician or other health professional or provider uses system 9000, a physician's user interface (such as on display device 9016) is optimally designed to support typical physician activities that the system supports including activities geared toward patient treatment planning. Similarly, when a researcher (such as a radiologist) uses system 9000, user interfaces optimally designed to support activities performed by those system clients are provided. In other embodiments, the physician's user interface, software, and one or more servers are implemented within one or more microservices. Additionally, each of the discussed systems and subsystems for implementing the embodiments described below may additionally be prescribed to one or more micro-systems.

System specialists (such as employees that control/maintain overall system 9000) also use interface computing devices to link to server 9020 to perform various processes and functions. For example, system specialists can include a data abstractor, a data sales specialist, and/or a "general" specialist (such as a "lab, modeling, radiology" specialist). Different specialists will use system 9000 to perform many different functions, where each specialist requires specific skill sets needed to perform those functions. For instance, data abstractor specialists are trained to ingest clinical data from various sources (such as clinical record 9024, database 9032) and convert that data to normalized and system optimized structured data sets. A lab specialist is trained to acquire and process patient and/or tissue samples to generate genomic data, grow tissue, treat tissue and generate results. Other specialists are trained to assess treatment efficacy, perform data research to identify new insights of various types and/or to modify the existing system to adapt to new insights, new data types, etc. The system interfaces and tool sets available to provider specialists are optimized for specific needs and tasks performed by those specialists.

Referring again to FIG. 271, server 9020 is shown to receive data from several sources. According to some aspects, clinical trial data can be provided to server 9020 from database 9032. Further, patient data can be provided to server 9020. As shown, patient 9014 has corresponding data from multiple sources (such as lab results 9026 will be furnished from a laboratory or technician, imaging data 9028 will be furnished from a radiologist, etc.). For simplicity, this is representatively shown in FIG. 271 as individual patient data 9022. In some aspects, individual patient data 9022 includes clinical record(s) 9024, lab results 9026, and/or imaging data 9028. In some aspects, clinical record(s) 9024 can include physician notes (for example, handwritten notes). The clinical record(s) 9024 may include longitudinal data, which is data collected at multiple time points during the course of the patient's treatment.

The individual patient data 9022 can be provided to server 9020 by, for example, a data abstractor specialist (as described above). Alternatively, electronic records can be automatically transferred to server 9020 from various facilities, practitioners, or third party applications, where appropriate. As shown in FIG. 271, patient data communicated to server 9020 can include, but is not limited to, treatment data (such as current treatment information and resulting data), genetic data (such as RNA, DNA data), brain scans (such as PET scans, CT, MRI, etc.), and/or clinical records (such as biographical information, patient history, patient demographics, family history, comorbidity conditions, etc.).

Still referring to FIG. 271, server 9020 is shown to include analytics module 9036, which can analyze data from database 9034 (empirical patient outcomes), and individual patient data 9022. Database 34 can store empirical patient outcomes for a large number of patients suffering from the same or similar conditions or diseases as patient 9014. For example, "individual patient data" for numerous patients can be associated with each respective treatment and treatment outcomes, and subsequently stored in database 9034. As new patient data and/or treatment data becomes available, database 9034 can be updated. As one example, provider 9012 may suggest a specific treatment (e.g., a clinical trial) for patient 9014, and individual patient data 9022 may then be included in database 9034.

Analytics module 9036 can, in general, use available data to indicate a diagnosis, predict progression, predict treatment outcomes, and/or suggest or select an optimized treatment plan (such as an available clinical trial) based on the specific disease state, clinical data, and/or molecular data of each patient.

A diagnosis indication may be based on any portion of individual patient data 9022 or aggregated data from multiple patients, including clinical data and molecular data. In one example, individual patient data 9022 is normalized, de-identified, and stored collectively in database 9034 to facilitate easy query access to the dataset in aggregate to enable a medical provider to use system 9000 to compare patients' data. Clinical data may include physician notes and imaging data, and may be generated from clinical records, hospital EMR systems, researchers, patients, and community physician practices. To generate standardized data to support internal precision medicine initiatives, clinical data, including free form text and/or handwritten notes, may be processed and structured into phenotypic, therapeutic, and outcomes or patient response data by methods including optical character recognition (OCR), natural language processing (NLP), and manual curation methods that may check for completeness of data, interpolate missing information, use manual and/or automated quality assurance protocols, and store data in FHIR compliant data structures using industry standard vocabularies for medical providers to access through the system 9000. Molecular data may include variants or other genetic alterations, DNA sequences, RNA sequences and expression levels, miRNA sequences, epigenetic data, protein levels, metabolite levels, etc.

As shown, outputs from analytics module 9036 can be provided to display device 9016 via communication network 9018. Further, provider 9012 can input additional data via display device 9016, and the data can be transmitted to server 9020. In some embodiments, provider 9012 can input clinical trial information via display device 9016, and the data can be transmitted to server 9020. The clinical trial information can include inclusion and exclusion criteria, site information, trial status (e.g., recruiting, active, closed, etc.), among other things.

Display device 9016 can provide a graphical user interface (GUI) for provider 9012. The GUI can, in some aspects, be interactive and provide both comprehensive and concise data to provider 9012. As one example, a GUI can include intuitive menu options, selectable features, color and/or highlighting to indicate relative importance of data. The GUI can be tailored to the type of provider, or even customized for each individual user. For example, a physician can change a default GUI layout based on individual preferences. Additionally, the GUI may be adjusted based on patient information. For example, the order of the display components and/or the components and the information contained in the components may be changed based on the patient's diagnosis, and/or the clinical trials being considered by the provider.

Further aspects of the disclosed system are described in detail with respect to FIGS. 272-300. In particular, an interactive GUI that can be displayed on display device 9016, is shown and described.

Graphical User Interface

In some aspects, a graphical user interface (GUI) can be included in system 9000. A GUI can aid a provider in the prevention, treatment, and planning for patients having a variety of diseases and conditions.

Advantageously, the GUI provides a single source of information for providers, while still encompassing all necessary and relevant data. This can ensure efficient and individualized treatment for patients, including matching patients to appropriate clinical trials.

In some aspects, system 9000 can utilize the GUI in a plurality of modes of operation. As an example, the GUI can operate in a "trial matching" mode and a "trial construction" mode. An exemplary GUI is shown and described with respect to FIGS. 272-300.

Clinical Trial Data Structure

FIGS. 272-279 generally provide graphical user interfaces (GUIs) that can be implemented in system 9000 to structure data (e.g., clinical trial data). In some aspects, reports that flow for clinical patients can rely on recommendations and suggestions on which clinical trials the patient is eligible for, as well as clinical and molecular insights. In order to do that effectively, unstructured clinical trial data can be structured using free-text (unstructured data) sourced from clinical trial databases and/or websites (e.g., clinicaltrials.gov). Notably, many clinical trial databases and websites contain clinical trials that are available to the public. Some clinical trials remain private, and can be protocol-specific from various sponsors (e.g., pharma sponsors). Regardless of public or private status, structured clinical trial data can be used in a variety of ways, including to match patients to appropriate clinical trials.

FIG. 272 is shown to include a graphical user interface (GUI) 9100. In some aspects, GUI 9100 can include a first portion corresponding to trial metadata 9101. As shown, trial metadata 9101 can further include trial data 9102, a trial description 9103, and trial details 9104.

Trial metadata 9101 can be used to view, update, and sort data corresponding to clinical trials. As shown, for example, the trial data 9102 can be summarized via a displayed table on GUI 9100. The trial data 9102 can include separate table entries for each clinical trial. As an example, each clinical trial may be listed with the corresponding national clinical trial (NCT ID), the trial name, the disease type relating to the clinical trial, an annotation status, an approved status, a review status, and/or the date of last update.

In some aspects, a user can select an individual clinical trial. GUI 9100 may subsequently display the corresponding trial description 9103. The trial description 9103 may be sourced directly from a clinical trials database or website. Accordingly, the text included within the trial description 9103 may be unstructured data. As will be described, a user may view the trial description 9103 and enter relevant trial criteria into the trial details 9104. In other situations, optical character recognition (OCR) and/or natural language processing (NLP) may be used to map the trial description 9103 to the appropriate data fields within the trial details 9104.

FIG. 273 is shown to include a graphical user interface (GUI) 9200. In some aspects, GUI 9200 can include a first portion corresponding to trial metadata 9201. As shown, trial metadata 9201 can further include text fields 9205, a table 9206, and/or selection menus 9207.

Trial metadata 9201 can be used to view, update, and sort data corresponding to clinical trials. As shown, for example, various text fields 9205 can be used to filter a large number of clinical trials, based on user-entered text. In some aspects, a user can filter the listing of clinical trials by entering full or partial text-strings corresponding to the NCT ID, clinical trial title, and/or phase of the clinical trial. As an example, a user may enter "1" into the "phase" text field 9205, and GUI 9200 may subsequently display only clinical trials that are described as "phase 1" or similar.

In some aspects, a user can provide a selection via selection menus 9207. Similar to the filtering that can occur based on user-entered text, a user can filter the listing of clinical trials via selection menus 9207. In some aspects, selection menus 9207 can be provided for the "annotated" and/or "approved" criteria, as shown by FIG. 273. Selection menus 9207 may be dropdown menus, for example, and selection options may include "true" and "false," or "yes" and "no." In other aspects, selection options and menus can vary (e.g., "phase" criteria may be configured to have a selection menu). Notably, a user may enter text and/or selections into multiple fields at once, to further filter the listed clinical trials.

FIG. 274 is shown to include a graphical user interface (GUI) 9300. In some aspects, GUI 9300 can include a first portion corresponding to trial metadata 9301. As shown, trial metadata 9301 can further include selection menus 9307, a trial header 9308, a trial description 9303, and/or trial details 9304.

As an example, the "annotated" selection menu 9307 has been set to "true." Accordingly, clinical trials that match the selected annotation criteria are displayed via the GUI 9300. An example clinical trial is shown in FIG. 274. The trial header 9308 is shown to include the NCT ID "NCT02654119," the title "Cyclophosphamide, Paclitaxel . . . ," the phase ("phase 2"), a "true" indicator of annotation, and a "false" indicator of approval. The trial description 9303 can be sourced from clinicaltrials.gov, for example. Accordingly, the clinicaltrials.gov page that is associated with the selected clinical trial can be displayed.

In some aspects, the trial details 9304 can include a set of fields that a user may optionally add information to. In some situations, the data within the trial description 9303 may include substantially unstructured data (free-text). Accordingly, the sourced raw data may be relatively useless in the context of clinical informatics. The free-text therefore inhibits the ability to compare data in a programmatic or dynamic way.

As shown by FIG. 274, the trial details 9304 can include the "annotated" and "approved" statuses, the trial name, the trial NCT ID, the disease status, and a portion corresponding to "matching criteria." A data abstractor (or other user) can utilize GUI 9300, in the context of system 9000, to create structure around the clinical trial by evaluating source text (unstructured data), and filling in relevant information within the trial details 9304.

FIG. 275 is shown to include a graphical user interface (GUI) 9400. In some aspects, GUI 9400 can include trial description 9403, and trial details 9404. As shown, the trial description 9403 can include inclusion criteria 9411 and exclusion criteria 9412. Further, as shown, the trial details 9404 can include disease criteria 9413, stage/grade criteria 9414, genetic criteria 9415, add button(s) 9416, and/or biomarker criteria 9417.

As an example, the first element shown within the inclusion criteria 9411 is "histologically confirmed newly diagnosed stage I-II HER2/neu positive breast cancer." Accordingly, within the trial details 9404, "newly diagnosed" may be selected (e.g., checked), the disease criteria 9413 may be selected (or otherwise input) as "breast," and the stage/grade criteria may include "stage II, stage I, stage IIA, IIB, IA, IB." Using GUI 9400, the free-text within the inclusion criteria 9411 may be mapped/associated with existing structured data fields. In some aspects, the existing structured data fields (e.g., disease criteria 9413, etc.) can align with the structured data fields that may be used to capture patient data. In some situations, it may be desirable to have very granular information. Therefore, the various matching criteria fields may be fairly granular. The specificity of the matching criteria fields can enable accurate comparisons between patient data and clinical trial eligibility data, for example.

Notably, there may be several methods for creating structured data fields, such as the fields shown in FIG. 275. In some aspects, for example, system 9000 may include structured data fields previously defined within an electronic medical record (EMR). Alternatively, system 9000 may include existing structured data fields from a database maintained by a clinical laboratory, such as a laboratory that provides DNA and/or RNA sequencing; analysis of imaging features; organoid laboratory services; or other services. In some aspects, system 9000 may utilize existing structured data fields from electronic data warehouses, hospitals, and health information exchanges, among other sources. In other aspects, the structured data fields may be a set of data fields appropriate for the structuring of clinical trial inclusion/exclusion criteria.

Still referring to FIG. 275, an example biomarker "HER2 (Human Epidermal Growth Factor Receptor 2) —Positive" is shown to be selected within the biomarker criteria 9417. This biomarker selection corresponds to the first element listed within the inclusion criteria 9411. Accordingly, the system 9000 can be enabled to qualify the specific biomarker, and the result that corresponds to it.

In some aspects, a data abstractor (or other users of the system 9000) can select a biomarker name (for example) from the biomarker name dropdown menu. Subsequently, the data abstractor can select a biomarker result from the biomarker result dropdown menu. Once the data abstractor has selected all desired elements, they may select "add." In some aspects, selecting "add" can create a new filter, which may be displayed via GUI 9400. Displayed filters can indicate to users which active filters meet the inclusion or exclusion criteria of the clinical trial.

FIG. 276 is shown to include a graphical user interface (GUI) 9500. In some aspects, GUI 9500 can include trial description 9503, trial details 9504, stage/grade criteria 9514, genetic criteria 9515, selection menu 9518, and button 9519.

As shown, selection menu 9518 can be a dropdown menu. As an example, selection menu 9518 can include several known biomarker names (e.g., "ALK," "BRAF," etc.). In some aspects, the trial description 9503 can be abstracted and assigned to a category. Exemplary categories can include an "inclusion" category and an "exclusion" category. In some aspects, the inclusion category can be denoted by a specific color, and the exclusion category can be denoted with a second, specific color. Accordingly, a data abstractor can now identify if an element is present within the trial description 9503, in addition to specifying whether or not it should be present within the patient data of potential clinical trial participants. As one example, a clinical trial may specify that patients who received prior treatments may be disqualified from participating. As another example, exclusion criteria 9412 may include certain vaccines, such as cancer vaccines (e.g., an HPV vaccine).

Still referring to FIG. 276, button 9519 can be configured to edit the fields available (and displayed) to the user. In some aspects, the fields shown to be included within the trial details 9504 can be added or removed by a data abstractor (or other user), as desired. Selection of the button 9519 can provide a menu of available fields and/or fields currently in-use on GUI 9500. Adding and/or removing fields enables a data abstractor to locate the correct fields that can be used for mapping the inclusion criteria from the trial description 9503, while preventing clutter of GUI 9500. As an example, an RNA field is shown in FIG. 276, but the trial description 9503 does not have criteria relating to RNA. Accordingly, a data abstractor may select button 9519 and proceed to remove the RNA field from the trial details 9504. Further, associated fields (e.g., RNA sequencing results) may be automatically removed in response to a field being removed. Conversely, when a field is added, associated fields may be automatically added and displayed.

As mentioned above, a natural language processing (NLP) tool can be implemented within the system 9000. NLP can analyze the trial description 9503, and provide a preliminary determination of which data fields may be relevant to the specific clinical trial. Accordingly, certain data fields may be automatically removed or added within the trial details 9504. As an example, if the NLP tool does not detect a performance score status of ECOG in the trial description (shown in FIG. 276), a user may not be prompted to fill in an ECOG status or score. System 9000 may include a machine learning tool that can review the trial description 9503, as well as the criteria listed within the description, and make a determination about what structured data fields could be appropriate to include in the trial details 9504. The user can still have control over adding and/or removing fields, but the machine learning tool and/or NLP tool can provide an informed starting point for data abstraction. Accordingly, users may be able to efficiently and accurately complete the trial details 9504.

FIG. 277 is shown to include a graphical user interface (GUI) 9600. In some aspects, GUI 9600 can include trial description 9603, trial details 9604, inclusion criteria 9611, exclusion criteria 9612, inclusion attributes 9620, and exclusion attributes 9621.

As shown in FIG. 277, inclusion attributes 9620 may be indicated by a first color (e.g., green), and exclusion attributes 9621 may be indicated by a second color (e.g., red). In some aspects, other methods of distinction may be implemented. As an example, the inclusion attributes 9620 may be indicated via a first text identifier, and the exclusion attributes 9621 may be indicated via a second text identifier.

In some aspects, the natural language processing (NLP) tool can be configured to provide predictive text, based on the trial description 9603. As an example, the system 9000 can pre-populate "FGFR1 Alteration" and "FGFR Inhibitors" into the respective data fields (DNA, prior treatments), as shown in FIG. 277. In some aspects, a data abstractor may verify the pre-populated data, but the system 9000 can provide an informed suggestion.

FIG. 278 is shown to include a graphical user interface (GUI) 9700. In some aspects, GUI 9700 can include trial description 9703, trial location(s) 9722, identifier 9723, enrollment status 9724, verification date 9725, verification method 9726, and version history button 9727.

In some aspects, GUI 9700 can display a version history when version history button 9727 is selected. The version history view may be limited, based on the user's role within the system 9000. In some aspects, the version history can include a table with information corresponding to what change occurred, the user ID (or name) corresponding to the change, and a time stamp when the change occurred. The version history can capture changes made by a system user via the GUI 9700, as well as changes that occurred within the source data. As an example, if a clinical trial provider added a new trial site, the GUI 9700 may subsequently indicate the site availability. The version history can display the addition of the site as a time stamped change. Advantageously, the system 9000 can provide a version history of every clinical trial that is being annotated. This aspect can be beneficial in situations where clinical trial data must be abstracted and entered into structured data fields, as well as separately verified and approved by another user.

For each clinical trial, there is at least one, and potentially thousands of sites where the trial can be conducted/administered. As an example, FIG. 278 shows a trial that has three sites. Notably, in other clinical trials, there may be a very long list of sites. In some aspects, the list of sites can be categorized based on different health systems, different sites, satellite offices, etc. Each table listing can include the site name, the location (e.g., city), an enrollment status 9724 (e.g., "enrolling" or "closed"), the last verification date 9725, the verification method 9726 (e.g., phone, email, etc.), and/or corresponding notes. The verification information can ensure that any recommended clinical trials have up-to-date and accurate data. As shown, an identifier 9723 can be added to specific sites. In some aspects, the identifier 9723 can be displayed by site listings where the site was activated via the system 9000.

FIG. 279 is shown to include a graphical user interface (GUI) 9800. In some aspects, GUI 9800 can include trial details 9804, an annotation indicator 9828, and an approval indicator 9829.

In some aspects, a data abstractor (or other user) can select the annotation indicator 9828 to provide an indication that changes have been made to the trial details 9804. This can, in some aspects, generate an alert for another user (e.g., a supervisor, manager, etc.) that an annotation requires approval. The second user may verify the changes made to the trial details 9804, and can subsequently select the approval indicator 9829. In some aspects, the changes may not be reflected within the system 9000 until the approval indicator 9829 has been selected. This verification step can ensure that changes and updates accurately reflect the clinical trial data.

In some aspects, system 9000 can integrate with clinical trial management systems that are configured and available "on premise." Generally, on premise systems are administered via cloud services. Further, on premise systems are predominantly focused on demographic information about a patient, for example, their medical record number (MRN), name, birth date, etc. All other data often requires a separate system, or alternatively, system users do not have visibility into all of the clinical and molecular traits that are needed to enroll or disqualify a patient from a trial. In some aspects, existing on premise systems can be used to determine the enrollment and recruiting status of a site, as well as if a patient with a certain MRN has successfully enrolled at the site. The other information (as described above) is not present within on premise systems, and instead may be spread between clinical documents and notes, which contain unstructured data.

The GUIs described above (e.g., GUIs 9100-9800) can generally be used by a system administrator to associate existing clinical trials with structured data fields.

Clinical Trial Matching

FIGS. 280-285 generally provide graphical user interfaces (GUIs) that can be implemented in system 9000 to appropriately match patients with available clinical trials. As described above, reports that flow for clinical patients can rely on recommendations and suggestions on which clinical trials the patient is eligible for, as well as clinical and molecular insights.

FIG. 280 is shown to include a graphical user interface (GUI) 9900. In some aspects, GUI 9900 can include a portion corresponding to trial matching 9940, a patient identifier 9941, patient demographics 9942, a physician location 9943, a table 9944, trial selectors 9945, a distance 9946, a score 9947, and/or a comparison button 9948.

In some aspects, GUI 9900 can be configured for a physician or other provider for identifying trials that are the most appropriate for their patients. As an example, GUI 9900 shows information for a patient, Melissa Frank. The patient identifier 9941 can include the patient's name, an ID number, etc. The trial matching 9940 can include the patent demographics 9942, such as disease status, disease type, etc. The combination of attributes shown for the patient can be provided using similar methods as the above-described "trial metadata" data abstraction. Accordingly, a user can view and/or enter all of the relevant information corresponding to the patients and diseases. This can enable system 9000 to correctly match clinical trial elements with patient data (e.g., histology, stage/grade, disease type, etc.).

Notably, in some aspects, the trial matching 9940 can include the physician location 9943, which may be indicated by the zip code of the physician's office (e.g., the office that the patient is typically seen at). The physician location 9943 can be used to find clinical trial sites within a certain distance of the physician, for example. In some aspects, the zip code may be prepopulated in the physician location field 9943. The zip code may be determined by the physician name and/or the name of the patient.

As shown, the table 9944 can include a list of clinical trials that match the patient's specific data (as indicated on the left side of GUI 9900). System 9000 can be configured to analyze and compare patient data to the clinical trial data. Further, system 9000 can provide the table 9944 based on clinical trials that substantially align with patient data. Each clinical trial within the table 9944 can include a trial selector 9945, a trial name, a disease site, histology data, disease stage, DNA data, RNA data, distance 9946 (e.g., from the physician's zip code), and/or a "score" 9947. In some aspects, the table 9944 can be sorted based on user-specified criteria (e.g., by distance, by score, etc.).

Still referring to FIG. 280, a user can select (e.g., via trial selectors 9945) one or more clinical trials to see more information, and/or compare the clinical trials to one another. Once one or more clinical trials have been selected, a user can select the comparison button 9948.

FIG. 281 is shown to include a graphical user interface (GUI) 10000. In some aspects, GUI 10000 can include patient demographics 10042, a table 10044, and/or attributes 10050.

As shown by FIGS. 280-281, the clinical data corresponding to the patient Melissa Frank is already prepopulated via the attributes 10050. By "disease type" for example, a user can see that Melissa has solid cancer (ovarian), histology is a serous carcinoma, the cancer is in an advanced stage, and Melissa has certain mutations, amplifications, and rearrangements. In some aspects, the clinical data can come from a structured clinical data source (e.g., an EMR, a clinical lab record, an electronic data warehouse, a health information exchange, etc.). System 9000 can prepopulate the attributes 10050 based on the structured clinical data.

Once the patient data has been provided, a user can select "match." The match function can determine and provide a score (e.g., the highest score listed first) of clinical trial matches. The score can be based on the disease site, the histology, the stage, molecular information, as well as the distance. In some aspects, other matching criteria may be implemented. In some aspects, there may be different methods to match a patient's health information to trial inclusion and exclusion criteria. As an example, FIGS. 280-281 include a match score. In some aspects, a binary "yes" or "no" may be used as a match indicator. As mentioned above, each of the listed trials can be selected for comparison and/or inclusion within a patient report.

FIG. 282 is shown to include a graphical user interface (GUI) 10100. In some aspects, GUI 10100 can include a trial comparison 10151, eligibility criteria 10152, selected trials 10153*a*, 10153*b*, and/or yes/no selector 10154.

As shown, the trial comparison 10151 can include a list of selected trials 10153*a*, 10153*b*. Each selected trial 10153 can include summary details specific to the clinical trial. As an example, a user may be presented with the NCT ID, the score, a summary of all the relevant biomarkers, the site(s), and the last verification time stamp. Further, a user may view comprehensive clinical trial information (e.g., the eligibility criteria 10152) by selecting an individual trial from the list of selected trials 10153*a*, 10153*b*. In some aspects, a user can toggle "yes" or "no" via the yes/no selector 10154. Selecting "no" may remove the clinical trial from the selected trial list, according to some aspects.

In some aspects, GUI 10100 can display inclusion criteria matched directly to the patient clinical data elements (e.g., via a table). A color indicator (e.g., red or green) may be provided to reflect whether or not the patient meets the particular criteria. The color indicator can advantageously provide a secondary verification, such that a user can quickly discern if a data entry error occurred.

FIG. 283 is shown to include a graphical user interface (GUI) 10200. In some aspects, GUI 10200 can include a patient summary 10255, a clinical trials tab 10256, a patient data menu 10257, and/or patient data 10258.

In some aspects, GUI 10200 can display a match report for the patient. The system 9000 can generate the match report based on the suggested and finalized clinical trials. As shown, the patient summary 10255 can include information such as patient name, date of birth, and/or primary diagnosis. Additionally, the patient data menu 10257 can be configured to toggle between various patient information (e.g., DNA, IHC, RNA, and Immunology). As an example, "DNA" is shown to be selected from the patient data menu 10257. Accordingly, the patient data 10258 that is shown corresponds to the patient's DNA information. In some aspects, the generated report can include molecular markers, information about specimens and tissues, tests that have been run, as well as all the clinical trials that the patient matched.

FIG. 284 is shown to include a graphical user interface (GUI) 10300. In some aspects, GUI 10300 can include patient data 10358 and/or a table 10359. The table 10359 can include all trials that have been selected for this patient, as an example. Further, each of the clinical trials can be selected to view more information.

FIG. 285 is shown to include a graphical user interface (GUI) 10400. In some aspects, GUI 10400 can include a clinical trial description 10458, a score 10460, inclusion criteria 10461, exclusion criteria 10462, and/or a site activation button 10463.

As shown, additional details (e.g., the clinical trial description 10458) relating to the clinical trial may be displayed upon selection. The additional details can include the score 10460 that corresponds to the specific patient being matched. In some aspects, information about the inclusion and exclusion criteria can be displayed as matched to the patient. As an example, the GUI 10400 can color code and highlight (e.g., with green and red) the inclusion criteria 10461 and exclusion criteria 10462, based on data that has been successfully matched to the criteria that the trial has defined.

In some aspects, a user can select the site activation button 10463 to begin a "rapid site activation." A rapid site activation can include matching eligible clinical patients with sponsored protocols (e.g., private clinical trials), and activating a new site for the primary purpose of conducting the specific sponsored protocol. In some aspects, a site (e.g., a physician's organization), may request activation of a new site for a clinical trial. As an example, FIG. 285 shows the physician "Dr. Miguel Shakes," as well as the institution associated with the physician, Regional Medical Center. Accordingly, Regional Medical Center may request a site activation for this particular clinical trial.

Clinical Trial Site Activation

FIGS. 286-290 generally provide graphical user interfaces (GUIs) that can be implemented in system 9000 to activate new clinical trial sites. In some aspects, site activation can occur in response to a patient being matched to a clinical trial. Alternatively, site activation can occur as-needed during enrollment of a clinical trial. Rapid activation of a new site can enable fast patient enrollment and subsequent treatment. Further, rapid activation can aid researchers in recruiting optimally matched patients.

FIG. 286 is shown to include a graphical user interface (GUI) 10500. In some aspects, GUI 10500 can include a clinical trial summary 10564, an activation status indicator 10565, a progress indicator 10566, and/or progress information 10567.

In some aspects, the process of rapid site activation can occur in two weeks or less. As an example, a patient may provide their information and/or samples to a physician, and within two weeks be enrolled in a clinical trial at a newly activated site. As shown in FIG. 286, the clinical trial summary 10564 can be displayed via the GUI 10500. Additionally, contact information for the site and/or clinical trial can be displayed. The progress indicator 10566 can track the various "stages" of site activation. In some aspects, the rapid site activation process can be divided into five main stages.

As shown, the progress information 10567 can include a list of elements that should be completed within the respective stages. In some aspects, the list of elements can be updated in real-time, via GUI 10500. Elements may appear as incomplete or complete, and may be updated by the various system users. As shown, a first stage of the rapid site activation process can be "patient identification," and the stage can take up to 72 hours, as an example. In some aspects, the activation status indicator 10565 can display if the activation status is in progress or complete.

FIG. 301A is shown to include a GUI that lists items that are required in order to complete a patient identification stage. The physician (indicated here as the PI) confirms that the patient matches the inclusion/exclusion criteria and can electronically sign to confirm the same. The information is transmitted electronically for review by the sponsor. In some aspects, the information used to validate the inclusion/exclusion criteria confirmation (either structured or unstructured) may be sent to the study sponsor or designee for review and/or confirmation.

FIG. 287 is shown to include a graphical user interface (GUI) 10600. In some aspects, GUI 10600 can include a progress indicator 10666, and progress information 10667.

As shown, the progress information 10667 can include a list of elements that should be completed within the respective stages. In some aspects, the list of elements can be updated in real-time, via GUI 10600. Elements may appear as incomplete or complete, and may be updated by the various system users. As shown, a second stage of the rapid site activation process can be "start-up initiation," and the stage can last from day 0 to day 3, as an example.

FIG. 301B is shown to include a GUI that may be included within the progress information 10667 in various aspects. FIG. 31B may include a notice to the site that the sponsor's approval is pending. The GUI within the progress information 10667 may be updated dynamically once the sponsor has provided approval. FIG. 301C is shown to include a GUI that includes a notice to the site that the sponsor has approved the site and the date of approval.

FIG. 288 is shown to include a graphical user interface (GUI) 10700. In some aspects, GUI 10700 can include a progress indicator 10766, and progress information 10767.

As shown, the progress information 10767 can include a list of elements that should be completed within the respective stages. In some aspects, the list of elements can be updated in real-time, via GUI 10700. Elements may appear as incomplete or complete, and may be updated by the various system users. As shown, a third stage of the rapid site activation process can be "post-signed CTA" (post-signed Clinical Trial Agreement), and the stage can last from day 3 to day 7, as an example.

FIG. 301D is shown to include a GUI that is included within the progress information 10767 in various aspects. FIG. 301D includes a "to do" listing of information that needs to be uploaded for transmission to the sponsor. Examples include IRB approval submission information and regulatory documents, such as the Form 1572 required by the FDA. The GUI may include an interactive upload element that permits a file to be dragged and dropped into the element. Such action causes the file to be transferred through a computer network and uploaded to a remote server for further review. The GUI within the progress information 10767 may be updated dynamically once the sponsor has provided approval. FIG. 301E shows the names of files that have been uploaded, such as a trial ready certificate, the fully executed clinical trial agreement, the study budget, the IRB approved patient materials, the IRB approval letter, regulatory documents, and the study contact list.

FIG. 289 is shown to include a graphical user interface (GUI) 10800. In some aspects, GUI 10800 can include a progress indicator 10866, and progress information 10867.

As shown, the progress information 10867 can include a list of elements that should be completed within the respective stages. In some aspects, the list of elements can be updated in real-time, via GUI 10800. Elements may appear as incomplete or complete, and may be updated by the various system users. As shown, a fourth stage of the rapid site activation process can be "post-IRB approval" (post-Institutional Review Board approval), and the stage can last from day 7 to day 14, as an example.

FIG. 301F is shown to include a GUI that is included within the progress information 10867 in various aspects. The GUI includes a confirmation that the IRB approved the study and the date of approval.

FIG. 290 is shown to include a graphical user interface (GUI) 10900. In some aspects, GUI 10900 can include a progress indicator 10966, and progress information 10967.

As shown, the progress information 10967 can include a list of elements that should be completed within the respective stages. In some aspects, the list of elements can be updated in real-time, via GUI 10900. Elements may appear as incomplete or complete, and may be updated by the various system users. As shown, a fifth stage of the rapid site activation process can be "open for enrollment," which can be the last stage, occurring on day 14.

FIG. 301G is shown to include a GUI that is included within the progress information 10967 in various aspects. The GUI includes a notice that the site visit is pending. The GUI in the progress information 10967 may be dynamically updated. For example, once the site visit has occurred, the GUI in the progress information 10967 may reflect that the site was visited and the visit date, as shown in the GUI included in FIG. 301H.

In some aspects, once the rapid site activation process is complete, the site can open for enrollment. Accordingly, the patient can be eligible to begin the clinical trial at the newly activated site.

Clinical Trial Site Information

FIGS. 291-300 generally provide graphical user interfaces (GUIs) that can be implemented in system 9000 to track and/or update site capabilities in relation to clinical trials. In some aspects, initial site information can be input via GUIs 11000-11900. Further, as site equipment and/or capabilities change, users on-site can update the site information in real-time. This ensures that clinical trials can be matched to patients and corresponding sites, without relying on outdated and potentially incorrect information. In some aspects, on-site users (e.g., site administrators) can log in and have access to the site information that is stored within system 9000. The site information may apply to multiple clinical trials, and system 9000 accordingly provides interfaces that enable centralized data entry.

FIG. 291 is shown to include a graphical user interface (GUI) 11000. In some aspects, GUI 11000 can include a site name 11066, site documents 11067, and/or a site status 11068. As shown, the site status 11068 can indicate that the site is ready for patient matching.

In some aspects, GUI 11000 can display a list of site documents 11067. Sites may run multiple clinical trials, and system 9000 provides a central access point for site information. As shown, for example, Regional Medical Center has multiple categories of associated documents.

FIG. 292 is shown to include a graphical user interface (GUI) 11100. In some aspects, GUI 11100 can include a site name 11166, and a documents list 11169.

In some aspects, GUI 11100 can display a documents list 11169 corresponding to each oncologist related to Regional Medical Center, as an example. A user can select a specific oncologist to see additional information.

FIG. 293 is shown to include a graphical user interface (GUI) 11200. GUI 11200 is shown to include a site name 11266, and physician documents 11270.

In some aspects, GUI 11200 can display a list of physician documents 11270. As shown, for example, a user can view the documents related to a specific physician. In some aspects, the documents can include the physician's CV, resume, certificates, and/or medical license.

As described above, users can view and/or update site capabilities using system 9000. As site capabilities change, users can update the site information in real-time, for example. FIGS. 294-300 provide example GUIs corresponding to obtaining site information. Notably, FIGS. 294-300 relate specifically to sites conducting oncology clinical trials, but the general concepts described herein can be applied to any disease or condition.

FIG. 294 is shown to include a graphical user interface (GUI) 11300. In some aspects, GUI 11300 can include a site profile 11380. In some aspects, GUI 11300 can be configured for user inputs, which can subsequently update site information within system 9000.

In some aspects, the site profile 11380 can include fields corresponding to the site name, the primary site contact, and/or staffing information. Further, the site profile 11380 can include fields corresponding to specific disease areas (e.g., number of cancer patients treated, types of cancers treated, etc.).

FIGS. 295A-295B are shown to include a graphical user interface (GUI) 11400. In some aspects, GUI 11400 can include site research experience 11481. In some aspects, GUI 11400 can be configured for user inputs, which can subsequently update site information within system 9000. Further, the site research experience 11481 can include experiences with an IRB and/or ethics committee, and regulatory agencies (e.g., the FDA).

In some aspects, the site research experience 11481 can include recent experience with clinical trials, number of studies participated in, and/or sponsor types, for example.

FIG. 296 is shown to include a graphical user interface (GUI) 11500. In some aspects, GUI 11500 can include investigational product (IP) 11582. In some aspects, GUI 11500 can be configured for user inputs, which can subsequently update site information within system 9000.

In some aspects, IP 11582 can include handling capabilities corresponding to IP, IP administration capabilities, and/or pharmacy information.

FIG. 297 is shown to include a graphical user interface (GUI) 11600. In some aspects, GUI 11600 can include records and documentation 11683. In some aspects, GUI 11600 can be configured for user inputs, which can subsequently update site information within system 9000.

In some aspects, records and documentation 11683 can include source document types, record storage methods, and/or EHR/EMR systems.

FIGS. 298A-298C are shown to include a graphical user interface (GUI) 11700. In some aspects, GUI 11700 can include site capabilities 11784. In some aspects, GUI 11700 can be configured for user inputs, which can subsequently update site information within system 9000.

In some aspects, the site capabilities 11784 can include working hours, inpatient support, language translator access, and/or local lab information. Further, the site capabilities can include specialties, equipment (e.g., imaging, diagnostic, etc.), and/or temperature monitoring capabilities.

FIG. 299 is shown to include a graphical user interface (GUI) 11800. In some aspects, GUI 11800 can include standard operating procedures (SOPs) 11885. In some aspects, GUI 11800 can be configured for user inputs, which can subsequently update site information within system 9000.

In some aspects, the SOPs 11885 can include FDA audit readiness, toxicity management, staff training, and/or informed consent (including minors and vulnerable populations).

FIG. 300 is shown to include a graphical user interface (GUI) 11900. In some aspects, GUI 11900 can include a site contact list 11986. In some aspects, GUI 11900 can be configured for user inputs, which can subsequently update site information within system 9000.

In some aspects, the site contact list 11986 can include information for a clinical trial leader, legal contact, regulatory contact, and/or expected PI(s).

As described herein, the present disclosure includes systems and methods to help a medical provider make clinical decisions based on a combination of molecular and clinical data, which may include comparing the molecular and clinical data of a patient to an aggregated data set of molecular and/or clinical data from multiple patients, a knowledge database (KDB) of clinico-genomic data, and/or a database of clinical trial information. Additionally, the present disclosure may be used to capture, ingest, cleanse, structure, and combine robust clinical data, detailed molecular data, and clinical trial information to determine the significance of correlations, to generate reports for physicians, recommend or discourage specific treatments for a patient (including clinical trial participation), bolster clinical research efforts, expand indications of use for treatments currently in market and clinical trials, and/or expedite federal or regulatory body approval of treatment compounds.

XVI. Data Store for Patient Data

A comprehensive patient data store may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may be molecular data features, such as features derived from RNA and DNA sequencing, pathologist review of stained H&E or IHC slides, and further derivative features obtained from the analysis of the individual and combined results. Features derived from DNA and RNA sequencing may include genetic variants which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, Programmed death-ligand 1 (PD-L1) Status, human leukocyte antigen (HLA) Status, or other immunology features. Features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, or other physical or mental maladies, personal medical history, or family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, or corresponding dates, and genetic testing and laboratory information such as genetic testing, performance scores, lab tests, pathology results, prognostic indicators, or corresponding dates, or more detailed information including date of genetic testing, testing provider used, testing method used, such as genetic sequencing method or gene panel, gene results, such as included genes, variants, or expression levels/statuses. Features may be derived from information from additional medical or research based fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features derived from imaging data may include reports associated with a stained slide, size of tumor, tumor size differentials over time (including treatments during the period of change), as well as machine learning approaches for classifying PDL1 status, HLA status, or other characteristics from imaging data. Other features may include the stored alteration outputs from other machine learning approaches based at least in part on combinations of any new features and/or those listed above. For example a machine learning model may generate data science predictions a patient's future probability of metastasis, origin of a metastasized tumor, or predict progression free survival based on a patient's state (collection of features) at any time during their treatment. Other such predictions may include document integrity certification or cancer/disease sub-type classifications for enriching the data set. The features in the comprehensive patient data store are always being improved upon based on current medical research, the above listing of types of features are merely representative of the types of information and should not be construed as a complete listing of features. The number of current patient features in the store exceeds multiple thousands of features and is increasing daily.

A. Data Store for Inclusion and Exclusion Criteria Across Clinical Trials

A comprehensive inclusion and exclusion data store may combine a variety of features together across varying clinical trials available to patients. The FDA requires clinical trials to register before they may enroll patients and be held. These registered clinical trials may be referenced using a website, such as clinicaltrials.gov, which contains a complete listing of all clinical trials registered with the FDA. In addition to clinicaltrials.gov, other government-sponsored websites and private websites may exist for searching through clinical trials. A web crawler may periodically crawl these websites collecting detailed information for clinical trials and add the collected clinical trial information to an internally curated clinical trial data storage. Clinical trials may also publish research papers identifying the clinical trial's purpose as well as any clinical trial information. As new publications are published, they may be curated and the clinical trial information added to the clinical trial data storage. Curation may be performed by a medical professional, by a well-trained machine learning model, or a combination of both. Pharmaceutical companies or other institutions may maintain their own publicly available clinical trial databases which may be queried to retrieve clinical trial information. A periodic query may be sent to collect clinical trial information and add it to the clinical trial data storage. Each website, publication source, or database may be treated as an independent source of clinical trial information. Pharma-sponsored clinical trial protocols may provide detailed, dozens to hundreds of pages in reports on the detailed specifics of the clinical trial. Relationships forged between a pharmaceutical company and another partner for aggregating clinical trial information may include release of these protocols for deep learning purposes. These independent sources may be compared to one another for accuracy as a whole or aggregated across each collection medium (website, publication, database, protocols), where discrepancies between sources may be evaluated by a medical professional and/or deference given to the most respected source (as a whole or in each collection medium). Clinical trials may be routinely gathered via any of the collection mediums to identify new clinical trials or modifications to existing clinical trials. A new clinical trial may be added to the clinical trial data storage and any modifications may be updated to be reflected in the clinical trial data storage. Detailed clinical trial information may include inclusion and exclusion criteria corresponding to any of the features stored in the comprehensive patient data store. Additional clinical trial information may include the study type (interventional/observational), study results, recruitment stage (not yet recruiting, recruiting, enrollment by invitation, suspended, unknown), title, planned measurement such as one described in the protocol that is used to determine the effect of an intervention/treatment on participants, interventions including drugs, medical devices, procedures, vaccines, and other products that are either investigational or already available, interventions including noninvasive approaches of education or modifying diet and exercise, sponsors or funders, geographic location (country, state, city, facility), trial stage such as those based on definitions developed by the FDA for the study's objective, the number of participants, and other characteristics (Early Phase 1, Phase 1, Phase 2, Phase 3, and Phase 4), or notable dates such as start and end dates. As each of these criteria are curated from their respective sources, a unified, internally-curated, and structured database may be formed to hold the criteria in the appropriate format for data-criteria concept matching as described, below. To this end, specific examples of detailed clinical trial information corresponding to features stored in the comprehensive patient data store and additional clinical trial information will be discussed with respect to data-criteria concept mapping, below.

Features in the patient data store may be aggregated from many different sources, each source potentially having their own organizational and identification schema for structuring the features within the source. One embodiment of the instant invention may convert all incoming features to a common, structured format of the patient data store. Similarly, clinical trial information may be aggregated from many different sources, each potentially having their own organizational and identification schema for structuring the clinical trial information within the source. One embodiment of the instant invention may also convert all incoming clinical trial information to the common, structured format of the patient data store as well as an intermediate concept mapping to preserve inclusion and exclusion criteria in the original clinical trial information.

B. Classification Codes for Mapping Features Between Data Stores

One embodiment of the data store to inclusion/exclusion criteria (data-criteria) concept matching may assign classification codes to each feature of the patient data store and the corresponding inclusion/exclusion criteria. For example, a diagnosis of breast cancer may have a classification table, as shown, in part:

| Diagnosis | Code |
|---|---|
| Breast Cancer | 63050 |
| Ductal Carcinoma In Situ | 63051 |
| Invasive Ductal Carcinoma of the Breast | 63052 |
| Tubular Carcinoma of the Breast | 63053 |
| Medullary Carcinoma of the Breast | 63054 |
| Mucinous Carcinoma of the Breast | 63055 |
| Papillary Carcinoma of the Breast | 63056 |
| Cribriform Carcinoma of the Breast | 63057 |
| Invasive Lobular Carcinoma of the Breast | 63058 |

A treatment involving medications may have a classification table prioritized from brand names, chemical names, or other groupings, as shown, in part:

| Brand (Chemical) | Code |
|---|---|
| Abraxane (albumin-bound or nab-paclitaxel) | 77121 |
| Adriamycin (doxorubicin) | 77131 |

| Chemical (Brand) | Code |
|---|---|
| Carboplatin (Paraplatin) | 78141 |
| Daunorubicin (Cerubidine, DaunoXome) | 78151 |

DNA/RNA Molecular features may have a classification table for genetic mutations, variants, transcriptomes, cell lines, methods of evaluating expression (TPM, FPKM), the lab which provided the results:

| RNA | Code |
|---|---|
| OR6C69P - Overexpressed | 1013057 |
| OR6C69P - Normal | 1013058 |
| LINC02355 - Tempus Overexpressed | 1014028 |
| LINC02355 - Foundation Overexpressed | 1014029 |
| RPS4XP15 | 1015010 |

A data structure may relate the structured information as a classification code with the absolute value of the report result:

| Code | Value |
|---|---|
| 1015010 | 85 TPM |
| 1015010 | 20 FPKM |

Inclusion and exclusion criteria may be mapped according to the same classification conventions above, however, nested criteria or more complicated criteria may be converted to another format, such as JavaScript Object Notation (JSON) to preserve the inclusion or exclusion criteria in the proper format without any information loss.

For example, an inclusion criteria "Histologically or cytologically confirmed diagnosis of locally advanced or metastatic solid tumor that harbors an NTRK1/2/3, ROS1, or ALK gene rearrangement" may touch upon the following classification codes:

| Feature | Code |
|---|---|
| Histologically confirmed diagnosis | 20253 |
| Cytologically confirmed diagnosis | 20254 |
| Locally advanced | 20317 |
| Metastatic | 20439 |
| Solid tumor | 19001 |
| NTRK1 | 1013120 |
| NTRK2 | 1013121 |
| NTRK3 | 1013122 |
| ROS1 | 1013261 |
| ALK | 1013273 |

The inclusion criteria may be structured to represent: 19001 AND (20253 OR 20254) AND (20317 OR 20439) AND (1013120 OR 1013121 OR 1013122 OR 1013261 OR 1013273)

An inclusion criteria "At least 4 weeks must have elapsed since completion of antibody-directed therapy" may touch upon the following classification codes in a reduced-exemplary reference set:

| Feature | Code |
|---|---|
| Antibody Directed Therapy | 25001 |
| Monoclonal Antibody Therapy | 27015 |
| Nivolumab | 77233 |
| Avelumab | 77238 |
| Emapalumab | 77245 |
| Polyclonal Antibody Therapy | 27023 |
| Hyperimmune Antibody Therapy | 27031 |

In a first example, the inclusion criteria may be structured to represent: 25001 AND (Date Administered is Older than XX/YY/ZZZZ), where all therapies which fall under Antibody Directed Therapy are assigned multiple codes, a first code 25001 for antibody directed therapy; a second code 27015, 27023, or 27031 for the type of antibody therapy, and a third code 77233, 77238, 77245 for the specific medication applied as part of the antibody therapy. In another example, the structured inclusion criteria may list all of the therapy codes which qualify in addition to 25001.

In 2016, there were 36 FDA approved monoclonal antibody therapies for the treatments of various diseases, with 17 of those for cancer. Hundreds of new therapies are currently undergoing clinical trials. Similar statistics are available for Polyclonal and hyperimmune antibody therapies. In a more thoroughly detailed example, each of these therapies may be listed in the above table.

C. Dictionary Classification for Mapping Between Data Stores

A second embodiment of the data store to inclusion/exclusion criteria (data-criteria) concept matching may utilize dictionary classification to each feature of the patient data store and the corresponding inclusion/exclusion criteria to identify relationships within the data that may not be immediately obvious. Such a dictionary based classification system is described in patent application Ser. No. 16/289,027 titled "MOBILE SUPPLEMENTATION, EXTRACTION, AND ANALYSIS OF HEALTH RECORDS" filed Feb. 28, 2019. Excerpts from this application include:

"The process of enumerating the known drugs into a list may include identifying clinical drugs prescribed by healthcare providers, pharmaceutical companies, and research institutions. Such providers, companies, and institutions may provide reference lists of their drugs. For example, the US National Library of Medicine (NLM) publishes a Unified Medical Language System (UMLS) including a Metathesaurus having drug vocabularies including CPT®, ICD-10-CM, LOINC®, MeSH®, RxNorm, and SNOMED CT®. Each of these drug vocabularies highlights and enumerates specific collections of relevant drugs. Other institutions such as insurance companies may also publish clinical drug lists providing all drugs covered by their insurance plans. By aggregating the drug listings from each of these providers, companies, and institutions, an enumerated list of clinical drugs that is universal in nature may be generated.

For example, "Tylenol" and "Tylenol 50 mg" may match in the dictionary from UMLS with a concept for "acetaminophen". It may be necessary to explore the relationships between the identified concept from the UMLS dictionary and any other concepts of related dictionaries or the above universal dictionary. Though visualization is not required, these relationships may be visualized through a graph-based logic for following links between concepts that each specific integrated dictionary may provide.

FIG. 10 is an exemplary ontological graph database 122 for viewing links between different dictionaries (databases of concepts) that may be interlinked through a universal dictionary lookup in order to carry out the normalizing stage 70 in FIG. 5. Conventional ontological graph databases may include GraphT, Neo4j, ArangoDB, Orient, Titan, or Flockdb. The following references to dictionaries and databases are for illustrative purposes only and may not reflect accurately the concepts/synonyms, entities, or links represented therein. Links between two concepts may represent specific known relationships between those two concepts. For example, "Tylenol" may be linked to "acetaminophen" by a "trade name" marker, and may be linked to "Tylenol 50 mg" by a "dosage of" marker. There may also be markers to identify taxonomic "is a" relationships between concepts. "Is a" markers provide relationships between over some clinical dictionaries (such as SNOMEDCT_US, Campbell W S, Pederson J, etc.) to establish relationships between each database with the others. For example, we can follow "is a" relationships from "Tylenol", "Tylenol 50 mg", or "acetaminophen" to the concept for a generic drug. Such a relationship may not be available for another concept, for example, a match to the dictionary for UMLS to "the patient" or "patient" may not have a relationship to a medication dictionary due to the conceptually distinct natures of each entity. Relationships may be found between drugs that have the same ingredients or are used to treat the same illnesses.

Other relationships between concepts may also be represented. For example, treatments in a treatment dictionary may be related to other treatments of a separate treatment database through relationships describing the drugs administered or the illness treated. Entities (such as MMSL #3826, C0711228, RXNORM # . . . , etc.) are each linked to their respective synonyms, (such as Tylenol 50 mg, Acetaminophen, Mapap, Ofirmev, etc.). Links between concepts (synonyms), may be explored to effectively normalize any matched candidate concept to an RXNORM entity.

Returning to FIG. 10, the concept candidate "Tylenol 50 mg" 124 may have a hit in the National Library of Medicine Database MMSL. In the preceding stage of the pipeline, "Tylenol 50 mg" may have been linked to the Entity MMSL #3826 126 as an identifier for the "Tylenol 50 mg" concept in MMSL. The linked Entity, MMSL #3826, may reside in a database which is not a defined database of authority, or, for document classification purposes, MMSL #3826 may not provide a requisite degree of certainty or provide a substantial reference point needed for document/patient classification. Through entity normalization, it may be necessary to explore links to MMSL #3826 until a reference entity of sufficient quality is identified. For example, the RXNORM database may be the preferred authority for identifying a prescription when classifying prescriptions a patient has taken because it provides the most specific references to drugs which are approved by the U.S. Food and Drug Administration (FDA).

Other authorities may be selected as the normalization authority based upon any number of criteria. The exact string/phrase "Tylenol 50 mg" may not have a concept/entity match to the RXNORM database and the applied fuzzy matching may not generate a match with a high degree of certainty. By exploring the links from MMSL #3826, it may be that concept "Tylenol Caplet Extra Strength, 50 mg" 128 is a synonym to "Tylenol 50 mg" in the MMSL database. Furthermore, concept "Tylenol Caplet Extra Strength, 50 mg" may also be linked to Entity C0711228 130 of the UMLS database. By exploring the synonyms to "Tylenol 50 mg" 124 through Entity MMSL #3826 126, the concept candidate may be linked to the UMLS Entity C0711228 130. However, the UMLS Entity C0711228 130 is not the preferred authority for linking prescriptions, so further normalization steps may be taken to link to the RXNORM database. Entity C0711228 130 may have synonym "Tylenol 50 MG Oral Tablet" 132 which is also linked to RXNORM #5627 134. RXNORM #5627 134 may be a normalization endpoint (once RXNORM #5627 has been identified, normalization may conclude); however, RXNORM #5627 134 may also represent the Tylenol specific brand name rather than the generic drug name. A degree of specificity may be placed for each source of authority (normalization authority) identifying criteria which may been desired for any normalized entity. For example, a medication may need to provide both a brand drug name and a generic drug name. Links in the RXNORM database may be explored to identify the Entity for the generic drug version of Tylenol. For example, RXNORM #5627 134 may have an "ingredient of" link to RXNORM #2378 136 which has a "has tradename" link to RXNORM #4459 138 with concept acetaminophen. RXNORM #4459 138 is the Entity within the RXNORM database which represents the generic drug 140 for Tylenol 50 mg and is selected as the normalized Entity for identifying a prescription in the classification of prescriptions a patient has taken. In this aspect, normalization may first identify an Entity in the dictionary of authority (as defined above) and may further normalize within the dictionary of authority to a degree of specificity before concluding normalization."

The above-identified classification system may be applied to curate inclusion and exclusion criteria using a well-defined clinical/ontological dictionary to provide classifications based upon language concepts rather than codes.

Another embodiment may combine the code classification system with the dictionary classification system to use concept-based classification to an internal code index.

D. Artificial Intelligence for Predicting Patient Eligibility for Clinical Trials or Criteria A third data-criteria concept mapping classification system may reside entirely within AI.

A machine learning algorithm (MLA) or a neural network (NN) may be trained from a training data set. For a data-criteria concept mapping classifier, an exemplary training data set may include patient information from the patient data store, clinical trial information including inclusion and exclusion criteria, and resulting line-by-line classification results for whether the inclusion or exclusion criteria were met.

MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines.

NNs include conditional random fields, convolutional neural networks, attention based neural networks, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Artificial NNs are efficient computing models which have shown their strengths in solving hard problems in artificial intelligence. They have also been shown to be universal approximators (can represent a wide variety of functions when given appropriate parameters). One of the major criticisms for NNs, is their being black boxes, since satisfactory explanation of their behavior may be difficult to discern. While research is ongoing to pierce the veil of NN learning, the rules driving the classification process are usually, and may continue to be, indecipherable black boxes. Similar constraints exist for some, but not all MLA. For example, some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across three different classifications. A list of coefficients may exist for the features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests.

While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. Returning to the example regarding gender, an unsupervised approach may attempt to identify a natural divide of documents into two groups without explicitly taking gender into account. On the other hand, a drawback to a purely unsupervised approach is that there's no guarantee that the division identified is related to gender. For example, the division may be between patients who went to Hospital System A and those who did not rather than the desired division.

E. Abstraction and Value Sets for Inclusion/Exclusion Criteria Templates

The features of the data store are aggregated from millions of documents across thousands of sources which may be impossible for an abstractor to keep in mind all the types of features that may be extracted from any particular document from any particular source. An abstraction software suite may be programmed or utilize a trained artificial intelligence to recognize a document type from a source and extract all relevant information from the document and storing a digital representation in a structured format according to the above disclosure.

In some embodiments, an AI may not be able to make a complete abstraction from any document, or may encounter a new document or document in such bad condition that optical character recognition is not available which renders automatic abstraction ineffective. A software suite that is aware of data elements corresponding to the type of fields commonly found in medical documents may enable an abstractor to systematically convert information from the document into the structured format required in the mapping process.

For example, a document may have patient information from a next generation sequencing report containing RNA sequencing results or laboratory testing results from testing performed on a patient's blood. Standard information, such as the patient's name, date of birth, address may be found in a document. Other information such as the laboratory name, address, testing procedure performed may also be present. Clinical information such as the results of the blood test, such as hemoglobin count, red blood cell count, white blood cell count, iron levels, cholesterol levels, bilirubin counts, Aspartate Aminotransferase counts, or Absolute neutrophil concentration may be reported.

A well-informed abstraction suite may contain valuesets for each type of information that may be found in the document. A patient valueset may contain fields for patient name (text), date of birth (date), address (structured text for street, apartment or suite number, city, state, zip code), or other patient information. A Laboratory valueset may contain fields for lab name (text), address (structured text for street, apartment or suite number, city, state, zip code), requesting institution name or address, requesting physician name, testing requested (blood test, sequencing of tissue, etc.), and particular results from the test, such as: blood test [blood type, White blood count, red blood count, bilirubin count, etc.], sequencing results [gene name, gene expression, variants detected, etc.]. Each field may further be identified by the units of the field, for example, as shown below, absolute neutrophil count may be measured by "$10^3$ Cells per microLiter (CPpL)", "$10^3$ Cells per microLiter (CPpL)", or "$K/mm^3$ (KMM)" which are equivalent measurements across differing institutions. A dropdown may allow an abstractor to identify the units which relate to the field that is populated.

Example data elements or fields that an abstractor may find in a respective template may be mapped to respective inclusion/exclusion criteria according the below tables.

---

Inclusion Criteria Mapping
Total bilirubin >= 1.5 × institutional upper limit of normal (ULN)
Bilirubin Count (bCnt)
Greater than equal to (GTET)
1.5
| Institution ID (iID) | Physician ID (pID) |
| Institutional ULN (iULN) | Physician ULN (pULN) |

Inclusion Expression(s):
Binary (T/F) = bCnt >= 1.5 × (iULN(iID))
Binary (T/F) = bCnt >= 1.5 × (pULN(pID))
Binary (T/F) = bCnt >= 1.5 × (iULN(iID,pID))

---

In a template for mapping bilirubin count to an inclusion criteria, a phrase "Total bilirubin >=1.5× institutional upper limit of normal (ULN)" may be parsed from a clinical trial inclusion/exclusion criteria document into a series of data elements that must be present, and then an expression may be generated which represents the criteria in a computer calculable algorithm which maps the requisite data elements top to their respective values along with the expected mathematical expressions used to generate the result. A binary, true/false or yes/no may be generated using the expressions. In the abstraction software suite, an abstractor may abstract from a report containing details of a laboratory blood test. The template may prompt the abstractor for patient information which links the patient to the rest of the information, the template may further prompt the abstractor for an institution or laboratory that performed the test as well as an ordering institution and/or physician if available. For immutable values, an institution or physician repository may exist for storing constants such as the institutional upper limit of normal (iULN) or physician specific upper limit of normal (pULN). In this way, data elements which may act as equivalent representations may share the same row (such as iID and pID) where unique data elements receive their own rows. The abstractor may be able to populate such immutable values in the template or the abstraction software may automatically retrieve such values from the corresponding repository. For other values, the abstractor may insert the value into the respective field of the abstraction template. The inclusion criteria may be stored in a structured format once each of the data elements are extracted and the relationships between them preserved. Each inclusion expression may be stored by a code ID or in a form of overloaded function which has optional arguments which may be populated to select the correct expression.

---

Inclusion Criteria Mapping
Aspartate Aminotransferase (AST) / Serum Glutamic-Oxaloacetic Transaminase
(SGOT) >= 1.5 × institutional upper limit of normal (ULN)
| AST Count (astCnt) | SGOT Count (sgotCnt) |
Less than equal to (LTET)
2.5
| Institution ID (iID) | Physician ID (pID) |
| Institutional ULN (iULN) | Physician ULN (pULN) |
Inclusion Expression(s):
Binary (T/F) = astCnt <=2.5 × (iULN(iID))
Binary (T/F) = astCnt <=2.5 × (pULN(pID))
Binary (T/F) = astCnt <=2.5 × (iULN(iID,pID))

---

A second example for AST is detailed above.

---

Exclusion Criteria Mapping
Absolute neutrophil count (ANC) >= 1.5 × $10^9$/L
ANC Count (ancCnt)

-continued

Greater than equal to (GTET)
1.5
$10^9$ Cells per Liter (CPL)  $10^3$ Cells per microLiter (CPμL)  K/mm³ (KMM)
Exclusion Expression(s):
Binary (T/F) = ancCnt(CPL) >= 1.5 × (1,000,000,000)
Binary (T/F) = ancCnt(CPμL) >= 1.5 × (1,000)
Binary (T/F) = ancCnt(KMM) >= 1.5 × (1,000)

A final example for an exclusion criteria based upon ANC is above.

As an abstractor populates entries in the abstraction software suite, a system may begin mapping which clinical trials may be informed by either keeping a tally of which data elements have been populating and comparing that to a table of data elements required per study (clinical trial), or other data curation schema. For example, a system may poll new abstraction entries for each patient, identify new data elements populated in the newest document, and re-evaluate patient's eligibility across all of the available clinical trials. This may be performed by using a table with every clinical trial (study) having its own row, where the each inclusion or exclusion expression is given a row, the cell where each row and column meet contains information on whether the study requires satisfaction of the expression (T), fails satisfaction of the expression (F), or does not require the expression (Null). If a patient satisfies the expression for all (T) and does not satisfy the expression for all (F), then they are indicated as eligible for the associated clinical trial.

| | Data Elements | | |
|---|---|---|---|
| | bCnt >= 1.5 × (iULN(iID)) | astCnt <= 2.5 × (iULN(iID)) | ancCnt(KMM) >= 1.5 × (1,000) |
| Study 1 | T | Null | F |
| Study 2 | F | F | T |
| Study 3 | Null | T | F |

Additionally, the data elements may be separated into a requirements table and a calculations table such that a study is only considered once all data elements that appear in the study's inclusion/exclusion criteria have been satisfied. Even further, data elements may be split into static and temporal classifications where a static classification is a data element that is not expected to change over time (gender, cancer site, previous treatments received, etc.) and temporal classification is a data element that is subject to change (age, treatments not yet received, metastasis, smoking, blood pressure, white/red blood cell counts, etc.). A patient may be recommended as potentially eligible for a clinical trial once the static classifications are all met, and the patient may be informed of the temporal classifications which need to be met. In this manner, a patient who would otherwise be eligible for a clinical trial, except that they have not had a blood test performed in the last six months may be informed that pending the results of a blood test, they may be eligible for the clinical trial. Thusly, encouraging the patient to consider getting a blood test to make their patient record more robust and potentially entering into an applicable clinical trial.

*Institutions or patients may opt into an automatic notification system which allows clinical trials to regularly query for applicable patients, set up reoccurring queries for eligible patients, or receive real time alerts when a patient has satisfied the criteria so that they may request the patient's participation.

| | Data Elements | | | | | | |
|---|---|---|---|---|---|---|---|
| | bCnt | astCnt | ancCnt(KMM) | iID | pID | iULN | pULN | ... |
| Study 1 | Y | Y | N | Y | Y | Y | Y | ... |
| Study 2 | Y | Y | N | Y | Y | Y | Y | ... |
| Study 3 | N | N | Y | N | N | N | N | ... |
| ... | ... | ... | ... | ... | ... | ... | ... | ... |

| | Data Elements | | | |
|---|---|---|---|---|
| | bCnt | astCnt | ancCnt(KMM) | ... |
| Study 1 | >= 1.5 × (iULN(iID)) | <= 2.5 × (iULN(iID)) | Null | ... |
| Study 2 | >= 2.5 × (iULN(iID)) | Null | >= 1.5 × (1,000) | ... |
| Study 3 | Null | <= 5 × (iULN(iID)) | >= 3 × (1,000) | ... |
| ... | ... | ... | ... | ... |

A Structured Patient Inclusion Report may be generated for a patient with respect to any clinical trial. This report may list the inclusion and exclusion criteria for a clinical trial along with an indication of whether the patient satisfies the criteria. This indicator may be in the form of a written result or may be presented as or in combination with a color code such as green for satisfying or red for failing each criteria. These reports may be generated for qualifying clinical trials which are relevant to a patient and provided to the patient's physician for discussion with the patient.

1) A structured Patient Inclusion Report may be generated at either or both a single point-in-time as well as regenerated as new information about a patient or trial becomes available. Through the use of validation contracts that represent clinical trial /protocol inclusion & exclusion criteria, programmatic and automated evaluation of a patient's eligibility for any given clinical trial can be evaluated.

These same validation contracts can be altered/managed and run either on-demand or automatically. Further, patient data being evaluated may be sourced from either/all of the data store components (e.g. curated, structured, EMR/EHR, *-omic, etc.

2) In a separate embodiment, these validation contracts may be used to help identify patients eligible for a trial (rather than a specific patient's eligibility for a trial). In these scenarios, patient content can be transmitted and processed in real-time, generating data products that include pertinent patient data that fall within acceptable and permissible inclusion/exclusion criteria.

3) In a separate embodiment, these validation contracts may be used to help predict the feasibility of filling & completing enrollment for a given clinical trial protocol based on prior observed incidences of similar patient attributes across the data store components (e.g. curated, structured, EMR/EHR, *-omic, etc.). This clinical trial enrollment feasibility analysis may be embedded in its own Site/Trial Feasibility Report.

XVII. User Interface, System, and Method for Cohort Analysis

Embodiments are described for identifying similarities between members of a data set and displaying these similarities in an intuitive and understandable way. A member of a dataset may be a person (e.g., a patient in a medical database or a customer in a financial database). In the instance that the member of a data set is a person, their personally identifiable information (e.g., social security number, address, or telephone number) and/or protected health information (e.g., health insurance provider/identification number and other identifying features) may be expunged to render the member unidentifiable. Alternatively, a member of a dataset may be an object (e.g., a tumor, a drug, evidence found in a crime scene, or a lunar rock specimen). Due to the vast nature of potential members of a data set, it is understood that the datasets may incorporate vastly different identifiers, features, or points of interest (e.g., physical characteristics of a person or object, genetic sequencing of a person or tumor, demographic information of a person or object, purchasing habits, frequency or dates of purchases) relating to the member and used to determine similarities between members of the data set. Similarities between members may include geographic proximity, shared genetic mutations, shared demographics or physical traits, shared chemical compositions, or shared molecular structures. Similarities may also be divergent in nature (e.g., neither member has a particular genetic mutation).

In one aspect, a comparative display may be presented to a user in order to compare a particular member of a dataset with other members of the dataset which share similarities. One such comparative display may display the particular member with an indicator such as a dot in the center of the display, and display other members with similar or distinct indicators such as additional dots around the center indicator. Such a comparative display is known herein as a "radar plot" or a "similarity plot." A radar, or similarity, plot provides two measurements for which to draw similarities: a radial distance for similarities between the center point and each plotted point and an angular distance for similarities between each plotted point.

FIG. 303 shows a display of an exemplary similarity plot for a sample member cohort of members A, B, C, D, E, F, and G as well as reference member R. Reference member R is positioned in the middle of the similarity plot 12101. Member sub-cohort 12102 is also mapped on the similarity plot 12101. In the display of FIG. 303, the distance from any indicator to reference member R reflects a similarity between the member represented by that indicator and reference member R, and rings 12106 may be displayed concentrically around reference member R in order to help a user more specifically determine which of two members is closer to reference member R. Conversely, the angular distance between members other than reference member R reflects a similarity between those non-reference members, regardless of how similar those non-reference members are to reference member R. Members in FIG. 303 could be people, patients, objects, etc. as reference above. Although the disclosure below at times refers to "patients" with reference to the figures, it should be understood that this is a general reference to "members" and that other members could be utilized as well.

In FIG. 303, members A-C and G are positioned at varying angular displacements to each other. Members A and B are the same distance ($d_1$) from reference member R, and member G is closest to reference member R, which indicates to the user that members A and B are both equally similar to reference member R as compared to the other members plotted on similarity plot 12101, while member G is even more similar to reference member R than either of members A and B. Similarly, member C is the furthest point of members A-C and G from reference member R, which indicates that member C is the least similar member of members A-C and G to reference member R. Members B and G share the same angular distance $\alpha_1$ from member A, but in opposite angular displacements from each other. Thus, members B and G are equally similar to member A, but are dissimilar from each other. Such a dissimilarity may arise when members B and G share some similarities (which are also shared with member A) but have at least one stark contrast with each other (e.g., member B has a feature which member G does not).

Within the display, it may be possible to arrange a plurality of members in a common region (e.g., a sub-cohort), reflecting a determination that those members have sufficient similarities to one another to warrant such a grouping. For example, members D-F are in member sub-cohort 12102. Their position close to one another on similarity plot 12101 indicates that members D-F are much more similar to one another than to any of members A-C and G. While members D-F are clustered in member sub-cohort 12102, member D is the most similar member to reference member R of the sub-cohort and member E is the least similar to member to reference member R. Member A and member E are angularly displaced from each other by 180 degrees. Their placement on opposite sides of reference member R indicate that they have zero similarity to each other (beyond similarities shared by every member of the cohort).

In the example of FIG. 303, the member of interest (R) may be placed in the middle of a polar coordinate system. The other members in the cohort are placed in consideration of: (1) their similarity or dissimilarity to the center member, which can be captured by radial distance ($d_i$); and (2) their (dis)similarity to each other, which can be captured by angular distance ($\alpha_i$). Member (dis)similarity to each other is represented in a range [0,180] degrees, so that when the angular distance is 0, the members have complete similarity, and when the angular distance is 180 degrees, the members have zero similarity based on the similarity features graphed (as discussed in greater detail below). For example, if members are patients being compared with respect to two features (e.g., presence of genetic mutations A and B), and one patient has mutated gene A but not mutated gene B while another patient has mutated gene B but not mutated gene A, these exemplary patients would have an angular difference of 180 degrees between each other (if the similarity plot was only showing similarities based on the presence of genetic mutations A and B).

In another aspect, the exemplary similarity plot of FIG. 303 may be updated by the user to filter out members having identified characteristics. For example, a member class comprising patients may be filtered by patients who have exhibited symptoms for a prolonged period of time, or patients who live in communities with known exposure to certain pathogens. Another member class comprising oncology patients may be filtered by patients of a specific diagnosis or patients who carry a particular genetic marker or genetic mutation. A member class comprising web-based customers may be filtered by customers whose first purchase corresponded with a promotional period or who have visited the website multiple times in a period of time without making purchases. In each case, the user may interact with the similarity plot by selecting from predetermined features to include or exclude members who have or do not have the features from the resulting plot. The user may also interact with the similarity plot by selecting a member. An interface (not shown) may be displayed to the user identifying the characteristics of the member which placed the member near neighboring members in the similarity plot. The interface may also allow the user to toggle inclusion and exclusion on these identified features to emphasize these features or hide them from view for further similarity comparisons. Furthermore, the interface may also allow the user to shift primary focus of the reference member to the newly-selected member. The user may reset any filtering criterion or reference member changes and restore the original similarity plot through the interface.

In one aspect, a dataset may be represented by an N×N distance matrix where N is the number of members. Each pair of members represented by an element pair (i,j) may have a normalized value [0,1] providing the similarity of member i with member j at the intersection of row i with column j and column i with row j, where 0 indicates no similarities and 1 indicates complete similarity. As expected, each intersection where i=j will indicate perfect similarity as a member compared to itself will always result in complete similarity. Representative examples provided herein may feature small sets to limit repetition, although it will be appreciated that the exemplary systems and methods are scalable beyond tens of thousands of members.

Turning now to FIG. 304A, an exemplary 3×3 distance matrix 12201 with similarity measurements for three members (A,B,C) is depicted. In this representative embodiment, member A's similarity to member B is normalized to 0.5, member A's similarity to member C is normalized to 0.4, and member B's similarity to member C is normalized to 0.9. Similarity measurements that have not been normalized may be normalized according to any normalization algorithm. One such normalization algorithm is:

Normalize(Value)=(Value −Min)/(Max−Min);

where Value is the value of the dataset to normalize, Min is the smallest value in the dataset, and Max is the largest value in the dataset. The output of the normalize function is a value in the range [0,1]. The shaded region of FIG. 304A indicates duplicated distance values which do not need to be recomputed when a member is added into the distance matrix. The number of calculations necessary to populate a distance matrix is N(N−1)/2 as there are always N entries (the line of identity pairing each member with themselves) which are 1 and half of the remaining entries which are duplicates.

Turning now to FIG. 304B, similarity plot 12210 is an exemplary plotting of members A-C of distance matrix 12201 based on their similarities. In order to populate similarity plot 12210, the radial and angular distances for members B and C must be calculated. For purposes of similarity plot 12201, member A is the reference member or member of interest. The radial distance d(i,j) is calculated for each member with respect to member A by subtracting the element (i,j) corresponding to the similarity of member A of each member from 1. Thus, member B is plotted with a d(a,b)=1-0.5=0.5 and member C will be plotted with a d(a,c)=1-0.4=0.6.

Selecting the order for plotting may be useful to minimize the number of iterations necessary to converge to an optimal similarity plot and thereby consume fewer system resources when performing the analysis. Methodologies for selecting a best order to plot members (e.g., highest average dissimilarity, lowest distance from average dissimilarity to 0.5) focus on placing the most distinct members around the similarity plot first to ensure accurate distribution with the fewest number of iterations. For example, under the highest average dissimilarity, the order of plotting may be chosen as follows: C: ((1−0.9)+(1−0.4))/2=0.35; B: ((1−0.5)+(1−0.9))/2=0.30; therefore, Member C, having the highest average dissimilarity (0.35) will be plotted before Member B having the next highest average dissimilarity (0.3).

In another example, under the lowest distance from average dissimilarity to 0.5, the order of plotting is chose as follows: C: 0.5-0.35=0.15; B: 0.5-0.30=0.20; therefore, Member C, having the lowest distance between its average dissimilarity and 0.5 (0.15) will be plotted before Member B, having the next lowest distance between its average dissimilarity and 0.5 (0.20).

The first member plotted may be placed at a random angular displacement, at zero degrees, or at any predetermined position. In similarity plot 12210, member C is placed at 95 degrees. Member B is then plotted at an initial angle, which may be selected at random, selected from an array of angles, or placed at an angle corresponding to the degree of similarity identified in the distance matrix (e.g., smaller angles for high degree of similarity). Angular distances for each, −45, 0, 45, and 135 are shown on similarity plot 12210. An optimization algorithm (discussed in more detail with respect to FIG. 305 below), F(O(B,C)), is calculated for each angle, and the angle which contributes the least F(O( )) is selected as the best fit. In this instance, member B is tested against angles −45, 0, and 45 degrees at $B'_1$, $B'_2$, and $B'_3$ and then placed as B at angle 135 degrees, as F(O(B,C)) is the smallest value at that location.

Post-processing may be performed on the resulting angular distances in batches, or after all angular distances have been identified. Post-processing may include alternating points in a batch (swapping the angular distances that were assigned between points in the batch) and minimizing the cost function again. The angular distance assignment may be performed in parallel to greatly reduce processing time required to process large datasets. Picking members to process in parallel may best be performed by selecting members which are most dissimilar from each other to process in each parallel branch. For example, rather than picking a subset of members which have a radial distance which are very similar, picking members which have greater variation of radial distances may reduce the amount of post-processing necessary to generate a similarity plot. By ensuring that each processor, thread, computer, and/or server has a diverse subset of dissimilar members, each parallel branch may generate reliable angular distances in order for post-processing to result in the least amount of corrections. Furthermore, by ensuring that members in each parallel branch are dissimilar, spurious optimization may be avoided where two members end up being swapped back and forth in angular distances based on new minimums from the optimization cost function.

In another aspect, initial angular distances may be calculated based off a clustering model, where members are placed according to which cluster they were designated.

Additionally, for purposes of parallelization, members of each cluster may be processed together or spread out among each of the parallel processing branches to keep dissimilar groups processed together and minimize the iterations required to arrive at convergence. Further parallelization techniques are described below with respect to FIG. 3.

Optimization algorithms for determining angular distances from a distance matrix may be non-convex in nature, implying that for every local minima that is identified in the normalization function, it cannot be determined that the local minima relates to the global minima identifying the best angular distance for each member plotted. In particular, FIG. 305 depicts one example of an available optimization algorithm (F(O)) and a graph of the minimization output.

As the number of data points, e.g., patients, being represented by indicators increases, it is a challenge to find a set of angles that does a good job of capturing dissimilarity over all pairs of patients, as, for "n" patients, there are $n*(n-1)/2$ distances to consider. Additionally, the computer processing resources required to analyze each pair of patients increases dramatically as the number of patients increases. In order to address these problems, the system may employ a model that utilizes one or more optimization methods. One approach is to minimize a sum of squared errors, which may be accomplished using a minimized sum of squared error (SSE) function. Other examples may include gradient descent and inverse quadratic interpolation methods. Utilizing a minimum SSE, the function will calculate, for all pairs of patients, the error between the known dissimilarity and an induced dissimilarity between the pairs of patients given their angle assignments. Additional details of this modeling, and of the data that may be used as inputs to the models are discussed in greater detail as follows.

In order to determine the relative positions of each indicator in the similarity plot relative to the reference patient indicator, an optimization method with a minimization of a cost function may be utilized to update positions over one or more cycles. In each cycle, each patient is temporarily positioned at a plurality of points defined by a shift vector. The point that results in a minimum calculated objective function becomes the patient's position in that cycle. At the end of a cycle, an overall objective function value is determined, based on the positions set for each patient. After each new cycle is computed, the resulting output of the overall objective function is compared to the result of the previous cycle to determine the rate of change between cycles. If the rate of change of the overall objective function value is below a predetermined threshold value, then the angular distances for each member have converged to the optimal placement within the similarity plot and the plot is finalized for display to a clinician or other user of the system. If the overall objective function value is not below the predetermined threshold value, then the angular distances of members are significantly changing and have not converged at the best visual representation of the member's similarities to one another, causing the method to initiate another cycle. Additional cycles are executed until the overall objective function value falls below the predetermined threshold value or the duration of executing the method exceeds a time limit.

As mentioned above, an algorithm may be employed that updates one patient at a time, e.g., by employing a "shift vector" to test the effect on an objective function of rotating a patient at each position within the shift vector.

One exemplary shift vector over a 360 degree rotational space is the vector v, which is made up of a set of shifts s. The set of possible moves is referred to as the shift vector as the position of the patient is moved clockwise or anti-clockwise by a varying number of degrees. Each shift s is a numerical value. An exemplary vector v may be (−170, −160, −150, −140, −130, −120, −110, −100, −90, −80, −70, −60, −50, −45, −40, −35, −30, −25, −20, −15, −10, −5, −4, −3, −2, 1, 0, 1, 2, 3, 4, 5, 10, 15, 20, 25, 30, 35, 40, 45, 50, 60, 70, 80, 90, 100, 110, 120, 130, 140, 150, 160, 170, 180). When using shift vector v, each patient position p is "tested" at each shift s in the shift vector v. Use of a shift vector can remove the problems presented by multiple local minima.

It is possible that the number of shifts s in a shift vector can either be too small, so as to not produce sufficient granularity, or too large, so as to require an unacceptably large amount of computation and/or resulting processing resources. For example, a shift vector with 1 degree variation between shifts restricts a patient to being able to take one of 360 possible positions on the circle. This vector may provide significant granularity and an increased number of placement options, but it may do so at the expense of requiring substantial processing resources, particularly when it is considered that the number of shifts must be multiplied by the number of patients in the data set. Conversely, a shift vector comprising only four shifts s, e.g., (−90,0,90,180) may consume substantially fewer processing resources, but it may do so at the expense of particularity and immediate user recognition, as it only allows for a data point to occupy one of four positions on the circle. Thus, for the choice of starting values and the start up process, there may be a trade-off between robustness and speed. In still another example, one way to be quick is to start all patients at the zero angle position and move patients in the order from the highest average dissimilarity patient to the lowest.

To increase robustness, it is possible to progressively increase the number of distinct points on the circle that the patient can take. For examples, a starting number of points at 0, 90, 180, and 270 degrees would put all the patients into a high level of 4 clusters. Progressively increasing the number of clusters up to the current max of 360 may increase the robustness of the output.

The algorithms described herein can be parallelized, whereby each patient is updated once in each loop across patients. Each patient can be updated simultaneously given the most up-to-date positions of other patients (some of which might be moved as the patients to whom they are being compared). In certain circumstances, parallelization can destabilize the robustness of the algorithm. On the other hand, robustness may be increased if used in conjunction with the approach of starting (outlined above) of increasing the number of clusters from an initial value, such as 4, up to a final value, such as 360.

It is possible in the fitting of the algorithm that certain sectors of the circle (i.e., ranges between certain angle positions) can be unstable. It is possible that within a range, the order is known but it is less clear from the data whether the order should be arranged in a manner that provides a clockwise or anti-clockwise plot. Thus, it may be prudent to run a check after a fit to know if there are such sectors. If so, flipping the angular positions of the patients from being clockwise to anti-clockwise (while maintaining the order within the range) may be useful to check if moving many points at a time can result in a reduction in the objective value.

The optimizations discussed herein reduce a non-convex function to a function that is solvable, quickly and with accuracy. Traditionally, a non-convex function lies in a domain (−∞,∞). However, by mapping patients into a similarity plot and generating the optimizations around the angular distance of a circle, the system reduces the effective domain of the problem to one of range [0,360). In essence, the minimum position across the set of options does not require any assumption about the convexity of the function once reduced to a circle on an angular basis. This way, the algorithm is robust in case of moving a patient that could reasonably be placed on either side of the circle—the algorithm will always choose the considered angular position that corresponds to minimizing the overall objective function.

The new approach compensates for the non-convexity induced by mapping to the circle by using the fact that the circle is a limited space to map to. Given that the circle is a constrained space, it is possible to explore the space well by looking a number of discrete points and choosing the best place to move to without any need to assume convexity to be able to make that choice.

The overall objective function is the sum of a fit function for all pairs of patients. In one instance, the fit function for a pair of patients i and j (where patient i is not j) looks at the square of the error between the dissimilarity between the two patients and the approximation of the dissimilarity from their angular positions. The dissimilarity between patients may be scaled to have a minimum value of zero and maximum value of one. The approximation of the dissimilarity between patients from their angular positions is the absolute difference between their angular positions (in degrees) divided by the maximum value of 180 degrees, such that the approximation will have a minimum value of zero and maximum value of one.

In one example, the objective function may be defined as:

$$\text{Objective} = \sum_{i=1}^{i=n} \sum_{j=1}^{j=i-1} (d_{i,j} - e_{i,j})^2$$

where $$e_{i,j} = \frac{f(A_i, A_j)^2}{180}$$

In this equation $d_{i,j}$ is the dissimilarity between patient i and patient j; $e_{i,j}$ is the approximation of the dissimilarity between patient i and patient j due to the angular positions; $A_i$ is angular position of patient i (in degrees) and $A_j$ is the angular position of patient j (in degrees). The function f, returns to the absolute value of the minimum distance in degrees that one patient i needs to be rotated to move to the other patient j (for example, if two patients were at 90 and 100 degrees, f would return 10 degrees; if two patients were at 350 and 10 degrees, f would return 20 degrees).

The algorithm may iteratively update one patient at a time, over one or more cycles. Specifically it may iterate over many cycles, where in each cycle it updates the position of each patient one at a time. The algorithm may iterate over cycles of updating patients positions until the change to the overall objective function over an entire loop is less than some (relatively small) value.

Turning to FIG. 305, an exemplary depiction of minimum SSE is shown in plot 12310. For each new member added to a similarity plot, the SSE is calculated across all angular distances. As each patient added represents the Nth patient, then only N-1 calculations must be performed between the newest patient and the N-1 patients. This presents a unique consideration for parallelization as for each new patient N, given that the previous N-1 patients were picked for plotting based on their dissimilarities or according to their distributed clusters, a presumption can be made that for each additional patient, each other additional patient does not require precise knowledge of the patients being placed on the plot in parallel. For example, after plotting the first 100 patients, according to their dissimilarities so that they are distributed across the similarity plot fairly evenly, adding additional patients may serve to only define clusters of patients rather than establish a new cluster which must be accounted for by relocating many patients. Therefore, parallelization may be accomplished by adding a group of patients at a time, using only the currently plotted patients, and allowing the natural iterative nature of the minimization of the optimization function to finely tune the bulk additions in the remaining cycles. Under this process, the resulting SSE is stored for each new angular distance, and the angular distance contributing the least SSE is assigned to the corresponding member.

In another aspect, angular distances may be calculated utilizing a sliding window. For example windows 12315 identify a first, second, and third subsection of plot 12310 to evaluate the SSE for any local minima. Calculating the SSE over the first window may identify local minima at 12320a, or a change from positive to negative SSE change at point 12325a to identify that the function is a non-convex function with multiple local minima. As the sliding window 12315 shifts, local minima 12320b may be identified and added as the current minimum SSE for element i,j. Another local maximum may be identified signifying yet another possible local minima. The sliding window 12315 then may shift to the final window and identify local minima 12320c. As the entire domain of available angles has been checked, local minima 12320c is identified as the global minima for the SSE for element i,j and the corresponding angular distance will be set for the current member. While not shown, it is possible for each window 12315 to have zero local minima or more than one local minima.

Other optimization functions may be considered having different cost functions to minimize. For example, other optimization functions may include: 1) a sum of absolute (rather than squared) distances, 2) setting a maximum for the possible squared differences (i.e., the value for a pair of patients is the minimum of a and the squared difference, where a represents the angular distance between two patients, as seen in FIG. 303), 3) rather than squaring the difference, change the power to a set value, e.g., $\gamma$, where all absolute differences are raised to the power of $\gamma$), or 4) using an auxiliary function, such as:

$$f(\text{distance}_{i,j}) = \sin\left(\text{distance}_{i,j} * \pi - \frac{\pi}{2}\right)^{0.5} + 0.5$$

As is well appreciated by persons of ordinary skill in the art, the listing of optimization and cost functions is merely illustrative, as different functions may be picked for different datasets to reduce processing time or computation resource demand.

Turning now to FIGS. 306A and 306B, additional views of similarity plots in which considerably more members are represented by indicators as compared to FIG. 303 are shown. In order to compare a plurality of different patients based on one or more system- and/or user-defined criteria, the system may establish some form of "similarity metric" that can quantify a degree to which the patients are similar. In this image, an exemplary member classification may include a patient cohort for a physician. Within that context, the overall aim of the similarity metric may be to be a good summary of the information that is learned from the patient files, including clinical data, patient demographic, and even test results such as genetic sequencing, magnetic resolution imaging, or x-rays. The similarity metric may balance a user's prior expectations with an ability to discover new aspects that were not already known. Additionally, a key aspect of a patient similarity metric may be the ability to learn or accept varying weights for different genes, as certain genes may be more important than others, depending on the analysis ultimately being done. The metric preferably should accomplish two things: accurately guiding users to better clinical decisions, and maintaining consistency with what a user would expect to be there.

As with the interface of FIG. 303, each dot in FIGS. 306A and 306B may represent a distinct patient. Also as with the interface of FIG. 303, the patients represented by indicators 12412 and 12414 are more medically similar to one another than are the patients represented by indicators 12416 and 12418, as signified by the angular distance between indicators 12412 and 12414 being smaller than the angular distance between indicators 12416 and 12418. Conversely, the patient represented by indicator 12420 is more medically similar to the reference patient at the center of the plot, as signified by the radial distance between the reference patient and that indicator 12420 being smaller than the radial distances from the reference patient to any other member.

In both interfaces, the patient could be a patient of the clinician viewing the similarity plot, a patient of another clinician within the same organization, or a patient of another clinician in a different organization. Patients located in sub-cohorts 12425 may possess similarities which are of great interest to the physician in determining an appropriate course of treatment. For example, if patients in sub-cohorts 12425 respond well to treatments that each target a genetic mutation shared by the reference patient and each respective sub-cohort, a physician may consider discussing each treatment option with the reference patient. Alternatively, if patients in a sub-cohort which is further away from the reference patient respond well to a treatment, but patients which are in a sub-cohort closer to the reference patient do not respond well to the treatment, a physician may decide to consider other treatments options for the reference patient.

FIG. 306B may represent a similarity plot 12450 for a web-based company's customers over the last six months. Similarities considered in the distance matrix may include purchase amounts, purchase frequency, dates visited, frequency of visits without a purchase, customers who abandoned a purchase a particular stage in the checkout process, or any other demographic information or customer information gathered by the web-based company or their affiliates. A reference customer may be a customer who has added an item to their online cart, but have not checked out. Sub-cohort 12475a may include customers who are geographically close to the reference customer and who also have not checked out. The angular similarities may indicate that these customers have abandoned the check out processes after viewing the shipping charge to their geographical region. The company, upon noticing this similarity, may offer a discounted shipping coupon to members of cohort 12475a. The user may observe that members of sub-cohort 12475b completed purchases using a coupon code for 15% off one item in their order or that members of sub-cohort 12475c have visited the site several times before making a purchase shortly after the shopping portal was restructured to be more user friendly. By observing the similarities and/or dissimilarities of customers in their similarity plot, the company may make decisions on how to best influence consumer purchasing habits that are not immediately obvious otherwise.

Still other uses for a user interface such as those shown in FIGS. 306A and 306B are possible. For example, another interface may be used to compare drug-to-drug cohorts, where similarities may be based on, e.g., one or more of molecular composition of drug, FDA approvals, successful clinical trials, targeting of specific illnesses, pathogens, cancers, or other factors.

As discussed above, when comparing two patients based on a plurality of factors that include genetic similarity, certain gene similarities may be more significant than others. The present metric may be configured such that key genes dominate that similarity metric (for example, sharing a PIK3CA mutation is important), irrelevant of varying levels of background mutations of low interest (for example, patient A could having 1 interesting mutation and 9 of low interest, where patient B could have 3 mutations of interest and 900 of low interest). By focusing on the dominant genetic variants or similarities, the system may implement a more useful process than a situation where a user simply filters patients based on the presence or absence of mutation in key genes to find a cohort of the right size.

Turning now to FIG. 307A, an example of mutation states for a plurality of genes for multiple patients is depicted. In this example, a value of 1 indicates a mutated gene for that patient and a value of 0 corresponds to a non-mutated gene. Given an exemplary DNA genetic mutation cohort 12510, there may exist a series of sequencing results for each patient listing the genetic mutations present in the patient. Given sequencing results, every gene is given a status of mutated or not-mutated, where a mutated gene is a gene with at least one protein altering mutation. Specifically, the mutation may be exonic and non-synonymous. In addition, the system may be configured to incorporate quantitative information on how pathogenic a mutation is, e.g., by ascribing values to pathogenicity prediction, likelihood of protein termination, likelihood of aberrant protein, likelihood of changing key binding targets, etc.

It will be appreciated that simply having a mutated gene may not, by itself, represent anything significant, either by itself or in comparison with the genetic sequence of another patient. Thus, the DNA metric that values the mutations in each gene may vary differently by applying a weight between 0 and 1 for each gene. Exemplary weights 12520 for each of the genes of 12510 are shown in FIG. 307B.

In previous systems, gene importance scores were generated using the frequency of mutation as a proxy for the gene importance. In contrast, the present system may process the actionable gene database to explicitly generate an importance for each gene from the evidence for, and the impact of, a mutation for helping drug choice. Genes not in the actionable gene database have a weight of 0. Conversely, a gene of weight 1 has a highest confidence that it affects the action of an FDA-approved drug for the cancer type in question for that variant. Other factors for adjusting a gene weighting may include evidence of being a driver gene in the metric and an assessment of DNA variation at the variant level, rather than just at the gene level.

Weights may be determined based on evidence that a gene is useful in comparing patients in a cohort. For example, the presence of an approved treatment for a specific gene mutation may be used to modify a weighting. In particular, the existence of an FDA-approved drug for a mutation in a specific gene for a specific cancer type may result in the weighting for that gene being increased and/or set to "1."

(Such weighting may be both gene specific and cancer-specific, as the same drug may not be approved for a mutation in the same gene for a different cancer type, which may result in no change to that gene's weighting in that circumstance.)

In another aspect, importance scores may not be known in advance. In those situations, exemplary models for generating a vector of importance scores may be generated by utilizing a machine learning model, training the model on patient data (e.g., demographics), clinical data (e.g., diagnosis and results), genetic data (e.g., genetic mutations exhibited in patient), and allowing the machine learning model to determine weights for each gene based on the output machine learning model.

In still another aspect, importance scores may be calculated by following a rule set 12530, as generally shown in FIG. 307C. For example, in one rule set as depicted in FIG. 308, a base weight of 0 is assigned to all genes. If a gene is not included in a genetic base panel at step 12612, then the weight remains 0 at step 12614 and the next gene's weight is calculated. If a gene is included in a genetic panel, information is extracted from the panel by starting with an initial gene base weight of 0 at step 12616. Such information may include whether there is an FDA approved therapy targeting the genetic mutation, as at step 12618. If such a therapy exists, the gene weight may be increased as at step 12620 using metric c1, discussed below. If no such therapy exists, then there may be a determination as to whether the gene has evidence for the cancer type being queried, as at step 12622. As before, if such evidence exists, the gene weight may be increased as at step 12624 using metric c2, discussed below. The gene weights then may be increased based on the total level of evidence at step 12626 using a third metric c3. Finally, at step 12628, the gene weight may be re-scaled using a maximum weight of one, e.g., after this procedure has been undertaken for each gene under consideration.

As discussed above, at step 12620, weights may be increased using a metric c1. This metric relies on a level of evidence for the particular gene/therapy combination to increase the weight, where the gene residing low on a spectrum results in a low increase to the weight and residing high on the spectrum results in a high increase to the weight. In particular, there may exist levels of evidence for a therapy for a particular gene, e.g., 1 to 7, where 1 is the best and 7 is the least informative. Such levels may be determined based on one or more factors including, e.g., a number of patients that have undertaken the therapy with favorable results, a percentage of remission after 1 year, 2 years, 5 years, etc., a percentage reflecting an existence or lack of adverse side effects, etc. In another embodiment, the existence of evidence that a gene has a therapy which targets the gene greatly increases the gene's weight and a gene which has no targeted therapies does not increase the gene's weight.

Similarly, at step 12624, weights may be increased using a metric c2. Like c1, this metric may rely on a level of evidence for the particular gene/cancer type combination to increase the weight, where the gene residing low on a spectrum results in a low increase to the weight and residing high on the spectrum results in a high increase to the weight. As with c1, there may exist different levels of evidence for the particular cancer type, where stronger correlations may be reflected in larger values of c2. In another embodiment, the existence of evidence that the gene is correlated with a cancer type, increases the gene's weight based on the level of correlation and a gene which has no correlation to a cancer type does not increase the gene's weight.

Other evidence may be weighed at step 12626. Such evidence may include genes which do not have known, established correlations to certain cancers but where certain variants of the gene may hold a slight correlation. A varying level of c3 may be applied based on the strength of the correlation of each variant present.

Once the weights c1, c2, and c3 are determined at steps 12620, 12624, and 12626, respectively, it is possible that the sum of the weights c1+c2+c3 for a gene may be greater than one. Thus, the step 12628 normalizes the gene weights by dividing each specific c1+c2+c3 gene weight by the sum of the maximum values for each metric, i.e., c1_max+c2_max+c3_max.

In addition to analyzing patients for similarities or commonalities of at least one somatic mutation in common, the DNA metric also may account for when a pair of patients has no mutations in common in order to separate out patients that could nearly be close (if they had had a few key mutations) from patients that are definitely very different.

If two patients have no mutations in common, the metric for that pair may be 0. Conversely, in the event that a pair of patients has at least one mutation in common, the metric may be a sum of the gene importance scores across the mutated genes that they have in common, taking into account the gene weighting discussed above. The use of gene importance scores may lead to a focal point on the very important genes so that the genes that are of background importance are not that influential.

Regarding step 12628 on FIG. 308, the sum of gene importance score scores may be rescaled by the geometric mean of similarity of the pair of patients to themselves. This means that the mutated genes that are not in common are taken into account. For example, a patient that shares one mutation with a reference patient could be deemed to be closer than a second patient with two shared mutations if the second patient has vastly more mutations that the reference patient does not have. In the event that a pair of patients has no mutations in common, the metric may be generated from the sum of the scores of the mutations in the first patient but not the second and the sum of the scores of the mutations in the second patient but not the first.

Applying the methodology described above, the overall metric may range from zero (zero similarity) to 1 (complete similarity). When the pair of patients have no mutations in common, the overall metric ranges from zero (zero similarity) to a quarter, and when the pair of patients have at least one mutation in common, the overall metric ranges from a quarter to 1 (complete similarity). A dissimilarity metric may be calculated by subtracting the similarity metric from 1. The dissimilarity metric is used in the objective function below.

One exception to this situation is the case where both patients have no mutations. In this case, the similarity may be defined to be 1. That case is always the 'closest' possible patient, given that there are no mutations in common, and they will overlap each other in any plot as they are perfectly similar.

Using the methodology, FIG. 307D provides an example of a DNA comparison metric for the pairs of patients 1-5 identified in FIG. 307A and using the cohort values 12510 in FIG. 307A and the weights identified in FIG. 307B. It can be seen in this figure that patients 3 and 5 are the closest in similarity 12540, even though patients 1 and 2 share more mutations. We can also see that patient 1 and 4 are the furthest away from each other as there are many key mutations that one patient has but not the other.

As discussed above, the system may take one or more additional factors into account in determining a similarity between a pair of patients, such as the presence of an FDA-approved treatment for a shared gene mutation. Other exemplary factors may include sequencing depth, frequency of somatic mutation, and variant level importance and pathogenicity.

Once similarities have been determined for each patient pair (where each pair includes a reference patient and one of the other patients stored in a database), the system may generate a user interface that includes a plot specific to the reference patient. In the plot, the system explicitly shows the similarity of the patients in the cohort to this reference patient and also indicate any clustering in the type of the patients that are similar to the reference patient (e.g. there might be 3 distinct types of similar patients). That plot may take the form of the similarity plots discussed above and shown, e.g., in FIGS. 303, 304, and 306A-306B.

In particular, polar coordinates may be used to plot similarity to both the reference patient and the types of patient in the cohort. As discussed above, the distance from the center (i.e., the radius) indicates the similarity of the patient of interest (which is at the center) to the patients in the cohort, and the angular position approximates the similarity of the patients within the cohort to each other (similar types of patients can be seen at similar angular (or o'clock) positions, where the patients on the opposite side of the circle are the most dissimilar).

As described above with reference to FIGS. 304A and 304B, the present disclosure discloses a method of minimizing an objective function with respect to a particular patient point in a single cycle. With consideration of an unknown distance matrix but having a patient cohort database featuring at least patient DNA metrics including which genetic mutations are expressed by each patient, a similarity plot providing a visual comparison of the similarities of a physician's patients may be generated and displayed. Following the distance matrix calculations as described above with respect to FIGS. 307A-307D, FIG. 309 describes an exemplary system which may compute radial and angular distances for each patient in method steps of 12710. In step 1, 12712, a patient point is selected from the set of patient points. The selection may be made on an ordered basis, randomly, according to patient clustering, or even to maximize the dissimilarity between the previous plotted patient(s) and the current patient. In step 2, 12714, a set of putative positions are created for the patient point. One way to create the set of putative positions is to add the patient point to a shift vector, resulting in a set of putative position values equal to the shift vector values offset by the patient point position. These shift values may be expressed as varying intervals from 0 to 360 degrees of shift or any other known algorithm which optimizes placement accuracy or speed. In step 3, 12716, each value of the objective function is determined for each value in the set of putative position values. In step 4, 12718, the minimum value determined from all such determinations is recorded. In step 5, 12720, the putative position value that resulted in the minimum objective function value is recorded in the patient point record. In other words, the patient point position is updated with the putative position value.

If any patient positions remain which have not been evaluated during the cycle, after each patient position has been evaluated by the method described above with regard to FIG. 2, the value of the overall objective function is determined and compared to a predetermined threshold value. The scale of this threshold would reasonably increase with the size of the cohort. An exemplary threshold value for a cohort of about 250 patients is about 0.5. The relationship between the threshold value may be linear to the size of the cohort. For example, the threshold may increase by 0.00002 per pair of patients. Determining the threshold is a matter of the degree of specificity to be displayed. For a small display, a high degree of specificity is not needed as a few degrees of variance are not visible to a user looking at the plot. However, for a similarity plot that is displayed in a sufficiently large display, a smaller threshold may be preferred, as a few degrees of variance may be much more noticeable on the similarity plot.

Because each patient's position is updated on its own, the overall objective function is being evaluated for that one position for that patient, and only the dissimilarity between the patient being updated and the other patients may be considered. As such, the system only may consider a patient specific objective function (with only n-1 dissimilarities) to update the patient's position, as all the other contributions to the overall objective function do not relate to that patient and, consequently, are constant. Minimizing the per-patient objective function to find the new position for that patient, thus, may be the same as minimizing the overall objective function. The advantage to minimizing the per-patient objective function for each patient one at a time, is a dramatic increase in the speed of the algorithm with no loss in accuracy. By minimizing the per-patient objective function it may be necessary only to consider n−1 patient pairs each time a patient is updated, rather than all n*(n−1)/2 patients pairs. Once all patients in the cohort have been plotted, the similarity plot may be displayed to the physician.

Turning now to FIG. 310, an exemplary system 12810 for implementing the aforementioned disclosure is shown. The system 12810 may include one or more computing devices 12812a, 12812b in communication with one another, as well as with a server 12814 and one or more databases or other data repositories 12816, e.g., via Internet, intranet, ethernet, LAN, WAN, etc. The computing devices also may be in communication with additional computing devices 12812c, 12812d through a separate network 12818. Although specific attention is paid to computing device 12812a, each computing device may include a processor 12820, one or more computer readable medium drive 12822, a network interface 12824, and one or more I/O interfaces 12826. The device 12812a also may include memory 12828 including instructions configured to cause the processor to execute an operating system 12830 as well as a user interface module 12832 for generating the user interfaces described herein.

A. Identifying Copy Number Variation Location, Length, and Quantity from Genetic Sequence Data Embodiments are described for detecting CNV location, length, and quantities. As used herein, the term CNV location is the locus at which a gene, variant, allele, or sequence of nucleotides is located as determined across the entire genome or just the locus within a particular chromosome in the genome, lengths are the number of nucleotides which deviate from the normal genome, and quantities/counts are the number of occurrences of the variations detected during sequencing.

FIG. 312 is a block diagram illustrating a patient order processing pipeline .B.00 in which embodiments of the present invention may operate. The patient order processing pipeline .B.00 may provide the processing flow for a patient order from inception, NGS and variant calling, report processing and generation, through reporting the results of NGS to the ordering physician. An orchestration module or software such as orchestrator .B.02 may guide the processing of each of the blocks and elements contained in the pipeline .B.00 to ensure efficient processing with little downtime in between stages and no missed steps by providing signals to each of NGS lab pipeline 5308, bioinformatics pipeline 5310, and report generation pipeline 5312 directing current states and processing in each.

A patient may be received, such as from a sequencing order received from a physician, and sent to Patient Intake .B.10, where the patient's clinical data may be entered and information detailing the type of sequencing and reporting that the physician is requesting may be stored in a system. The order as entered into the system may provide the orchestrator .B.02 with a series of steps which are to be performed during the processing of the patient sequencing order.

The process from which this may be performed may then rely on establishing a sample of the patients DNA. Herein, a sample may be sent to block .B.20 when the sample is received at the laboratory performing the sequencing.

For cancer treatment, this may be a cancer sample, such as a sample of tumor tissue, and a sample of the patient's saliva or blood. For treatments of other diseases, this may be a sample of saliva or blood only. For cancer treatments, a sample of a tumor may originate from a biopsy (such as a needle aspiration or physical site extraction). Biopsies are inherently messy affairs where a biopsy may generally acquire an indeterminate proportion of cells, such as healthy cells and tumor cells which are sequenced together.

An NGS Lab Pipeline 5308 may receive the samples and process the samples for sequencing. A pre-processing stage .B.30 may include the laboratory identifying each and every sample received for a particular specimen, generating a label for the samples, the slides of those samples, and other accessioning tasks to enable the tracking of the samples through the pipeline .B.00.

During preprocessing, some samples may be identified as tumor samples, a pathology stage .B.35 may be activated to identify the type of cells in the sample and a proportion of these types of cells to each other. During the pathology stage .B.35, a pathologist may review slides of cells extracted from the sample. In another embodiment, a machine learning algorithm which has been trained on the pathology results from similar types of slides may be applied to new slides to either aid the pathologist in making a determination or to replace the pathologist and provide a determination without the oversight of the pathologist. In alternative embodiments, the samples received at stage .B.20 may include slides acquired and prepared by the ordering physician.

When preprocessing identifies other samples as non-tumor samples such as a blood or saliva sample for germline sequencing, the pathology stage .B.35 may be bypassed all together as the steps of identifying the type of cells and the proportion of those cells on the slide are not necessary. An assumption that non-tumor cells samples are "pure" non-tumor may be made.

An isolation stage .B.40 may receive a sample of cells from either the tumor or non-tumor sample and isolate either the DNA or the RNA from the sample. DNA may be isolated by destroying any RNA present in the sample and, similarly, RNA may be isolated by destroying any DNA present in the sample.

An amplification stage .B.50 may receive the isolated DNA or RNA and amplify the respective sample such that the provide RNA or DNA is copied over and over to improve the potential read results that may be made by the sequencer. Polymerase chain reaction (PCR) is a method may be employed to make many copies of a specific DNA/RNA segment. Using PCR, a single copy (or more) of a DNA sequence is linearly or exponentially amplified to generate thousands to millions of more copies of that particular DNA segment.

Sequencing may be performed on the amplified samples at the sequencing stage .B.50, a NGS sequencing, such as illumina's iSeq, MiniSeq, MiSeq, or NextSeq Systems; Ion PGM, Proton, or GeneStudio Systems; or comparable NGS systems from Pacific Biosciences, Roche 454, or SOLiD may be used. The sequencing stage may output sequencing data containing reads from probes such as in a raw data FASTQ format, raw data FASTA format, a Binary Alignment Map format (BAM), Sequence Alignment Map format (SAM) or other raw or aligned file formats. In one example, the SAM or BAM files may list all genetic sequences identified in a sample, the count for each sequence, and the location of each sequence read with respect the complete genome. In one example, a second set of SAM or BAM files may be included for listing all genetic sequences identified in a normal, non-cancer sample collected from the same patient as the cancer sample. The sequencing stage may further output an index file for each SAM or BAM file, indicating the file location of each read within the SAM or BAM file. In one example, an index file for a BAM file contains a table or list of all reads found in the BAM file and the file location of each read within the BAM file. In one example in the index file, each read may be labeled by a read ID (for example, read A, read B, etc. or read 1, read 2, etc.), by the sequence of the read, or by the chromosome and/or nucleotide position within the chromosome of the sequence of the read. The file location of the read may be listed as a line number within the BAM file.

A bioinformatics pipeline 5310 may receive the sequencing results generated from sequencing stage .B.50 or results translated from a raw to an aligned format at sequenced data stage .B.55. In another embodiment, sequenced data stage .B.55 may receive sequencing results in a raw format and perform filtering and/or alignment to generate an aligned format. Filtering may include detecting spurious or incorrect reads and removing them from the dataset. The bioinformatics pipeline 5310 may access resource files such as one or more pool files containing reads from one or many normal samples. Resource files may include a published reference genome such as human reference genome 19 (hg19) or human reference genome 38 (hg38), etc. Resource files may further include a blacklist file containing a list of blacklist regions and/or genes in the genome for which CNV calculation is less likely to be accurate or a whitelist file containing a list of whitelist regions and/or genes in the genome which should be incorporated into the CNV analysis. Any decreased accuracy of CNV calculation for blacklisted regions may be due to the genetic analysis technique used to identify genetic sequences in a sample. For example, if the genetic analysis technique requires genetic probes to bind to nucleic acid molecules isolated and/or copied from a sample, the probes binding to a blacklist region may bind in an inconsistent manner. A blacklist region may bind to probes less frequently than a typical region or may be saturated with bound probes. Another reference file may include a target file for enumerating the list of target genes, variants, or regions. The bioinformatics pipeline 5310 may incorporate the enumerated list of targets and implement the pipeline staged for one or more targets in the list of targets.

A variant calling stage may identify variants in the sequencing data of .B.55 by identifying reads for each variant based upon variant location, length, and/or depth. Variants may be portions of genetic sequences in the cancer sample which do not exist in the normal sample, and/or which do not exist in a reference genome or database of normal sequences. Variant information for each variant may include the variant's location, the normal nucleotide sequence seen in the reference genome at that position, and the variant nucleotide sequence seen in the sample. The variant location may include a chromosome number and a nucleotide position number to differentiate nucleotide positions that are located in the same chromosome. Reads may be compared to a reference genome to identify normal reads and/or variants. The number of reads for each variant may be counted, and the aggregate count for all identified variants may be stored in a Variant Call Format (VCF) or comma-separated values (CSV) that specifies the format of a text file used in bioinformatics for storing gene sequence variations. By storing the variant calls in VCF only the variations need to be stored and a reference genome may be utilized to identify each variant of the VCF.

A VCF or comparable variant calling output may be provided to one or more stages .B.65a-n. Stages .B.65a-n may provide specialized testing for one or more of tumor mutational burden (TMB), microsatellite instability (MSI), gene fusions, single nucleotide variants (SNV) and somatic/indel mutations, and CNV .B.65n detections. Each of these stages may receive a VCF file and perform analytics of the variants therein to identify the respective TMB, MSI, gene fusion, SNV, Indel, or CNV states and generate output files for report parsing, interpretation, and generation.

A report generation pipeline 5312 may receive the output files from each of stages .B.65a-n at report stages .B.70a-n. Reports .B.70a-n may then be provided to report analytics module .B.75 for generating analysis of the respective reports against databases of pharmacogenomic and cohort effects. For example, a cohort of patients may be maintained comprising the clinical and molecular medical information of all patients whose DNA or RNA have been sequenced. This cohort may be filtered according to common features with the instant patient (such as demographic, clinical, or molecular features) and trends within the cohort may be analyzed to generate predictions for the instant patient's pharmacogenomic response to medications/treatments or type of cancer or disease state determination. These predictions may be summarized for inclusion in a report, such as report .B.90. Furthermore, for each of the reports .B.70a-n, additional databases .B.85 may be referenced to identify insights that may be ascertained from the patient's TMB, MSI, gene fusion, SNV, Indel, or CNV states. These additional references databases .B.85 may be stored in many different formats depending on the institution that curated the database. It may be necessary to maintain a translation process .B.80 which may recognize key terms from each of reports .B.70a-n and translate these key terms to a format which may be recognized in one or more of the reference databases .B.85. A CNV in report .B.75n, may be referenced according to a table of variants. There are several resources for common gene and variant identifiers, such as the Human Genome Organisation (HUGO) Gene Nomenclature Committee (HGNC) or the National Center for Biotechnology Information (NCBI) with the Entrez list. The HGNC approves a unique and meaningful name for every known human gene. Such a table may include, for each CNV: an identifier to an Entrez Gene or an HGNC Gene or in which the variant was detected; the gene symbol of the gene in which the variant was detected; a copy state indicator of a copy number gain, copy number loss, or conflict; an message-digest checksum (such as MD5) of the values for a string, such as <entrezId><state> or <hgncId><state>, to serve as the primary key of the table; copy number region aggregations that determined the copy state; one or more indicators of a loss of function (LOF), gain of function (GOF), amplification (AMP), or gene fusion (FUS); a flag indicating whether the variant is therapeutically actionable based on known references; an overall reportability classification determined for the CNV such as "Reportable", "Not Reportable", or "Conflicting Evidence"; a unique identifier of the scientist who confirmed the classification of the CNV; a timestamp of when the scientist made the confirmation; and the classification of relevance for the CNV as being in a gene of therapeutic relevance such as "True", "False", or "Indeterminate."

An Entrez Gene Id (GeneID) is a representation of gene-specific information at the. The information conveyed by establishing the relationship between sequence and a GeneID is used by many NCBI resources. For example, the names associated with GeneIDs are used in resource/reference databases HomoloGene, UniGene and RefSeqs. These relationships may further the capabilities of translation .B.80 by providing additional reference points between these and other external databases. A loss of function mutation (LOF above), also called inactivating mutations, is the result in the gene product having less or no function whereas the GOF is the opposite result where function is gained due to the gene mutation. A classification of a CNV as "Reportable" means that the CNV has been identified in one or more reference databases as influencing the tumor cancer characterization, disease state, or pharmacogenomics, "Not Reportable" means that the CNV has not been identified as such, and "Conflicting Evidence" means that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV.

For example, a variant may be identified in a CNV report as having a count twenty times that of normal. However, a database in the reference database may not recognize the variant as encoded in the CNV report .B.70n and the translation process .B.80 may translate the variant representation from that of the report to one which is recognized by the database to link the report with meaningful analytic information from the database. Report analytics module .B.75 may process each of the identified variant calls, TMB, MSI, gene fusion, SNV, Indel, or CNV states through the reference databases .B.85 to ascertain report indicia worth reporting to the ordering physician and summarize the report indicia in report .B.90 which is to be provided to the ordering physician.

An orchestrator .B.02 may coordinate the timing for each of the above identified steps. For example, NGS pipeline 5308 may not be initiated until patient intake .B.10 has been successfully completed, bioinformatics pipeline 5310 may not be initiated until sequencing .B.50 has successfully completed, and each of the report analytics for reports .B.70a-n may be started in turn as specialized testing stages .B.65a-n each complete. In addition, a notification to the ordering physician that report .B.90 is available for view may not be generated until all of reports .B.70a-n have each been successfully analyzed against the reference databases .B.85 and the report is completely generated.

FIG. 313 is a flowchart illustrating a CNV pipeline .C.00 for CNV specialized testing stage .B.65n within the bioinformatics pipeline 5310 in which embodiments of the present invention may operate. The CNV pipeline .C.00 may calculate integer copy number estimate for total copies and minor allele count by estimating both tumor purity, ploidy (the number of chromosome sets in a cell), and B-allele frequencies within the tumor sample.

Stage .C.10 for CNV detection may comprise normalization, such as scaling the results of the sequencing according to an identified proportion from the pathology stage .B.35 to remove the bias or errors from the sequencing results. One such bias or error in sequence analysis methods may include inaccuracies regarding the identified sequences and the frequencies at which they may be present in the sample or may be captured by the sequencer. Another such bias or error in sequence analysis may include tumor samples containing a mix of tumor cells and normal cells such that genetic sequences created by the normal cells in the tumor sample may need to be removed in order to accurately detect the genetic sequences created by the tumor cells. Even another bias correction may include scaling the results of the sequencing according to a known bias generated from the amplification stage .B.45 based upon the amplification ratios for each sequence of amplified DNA/RNA. Normalization may be performed by scaling a resulting count of variants or copy state by factors such as read length, read depth, or guanine-cytosine content (GC content). Normalization may also be further performed by using a singular-value decomposition (SVD) or Principal Component Analysis (PCA) denoising approach. The resulting sequence information after PCA or SVD may be evaluated as if it is pure sequencing information relating to the tumor tissue.

An exemplary depth normalization may include verifying that each variant of the normal human genome collection and patient sequencing information occurs at least a threshold number of times, where a threshold may be maintained for each variant of the genome. For example, a threshold for a first variant may be tens of occurrences but a threshold for a second variant may be hundreds of occurrences. These threshold may be determined from the sequencing bias introduced during sequencing. In addition to applying a threshold, some variants may appear in the whitelist reference file and may be processed according to different whitelist conditions. In a first whitelist condition, if no other variants are detected with sufficient thresholds, whitelisted variants may be maintained even if they fail the threshold requirement. In a second whitelist condition, whitelisted variants may always be maintained regardless of whether other variants are detected. A normalized depth may be calculated for each probe or variant/genes in each probe as the depth of reads for each probe multiplied by the average depth of each probe in the normal or reference genome and divided by the average depth for the respective probe (such as probe_depth*ref_mean_median/probe_median).

An exemplary length normalization may include comparing each read length against the region of DNA or target sequence to identify where a read length from the patient's DNA is may need to be scaled. For example, when a read length is shorter than the region, then the read length may be normalized by a ratio of the read length to the region length (read_length/region_length). Conversely, when a read length is longer than the region then the read length may not need normalization, and a ratio of 1 may be set to ensure normalization does not affect the length of the read during processing. In this manner, length normalization may account for the presence of abundant sequencing information overlapping in each target region.

An exemplary GC content normalization may include applying a local regression technique with a sliding window to generate a moving average across the sequenced DNA to account for GC content differences within the sequencing information. An exemplary sliding window may be implemented using LOESS (locally estimated scatterplot smoothing) or LOWESS (locally weighted scatterplot smoothing). A GC Fraction may be calculated using the equation:

$$GC\text{ Fraction} = \frac{(G+C)}{(A+T+G+C)},$$

where each GC fraction across the sequence information is processed in-turn using either the LOESS or LOWESS polynomial to identify an adjustment factor which may be applied to each resulting sequence read to remove the bias from GC content variations. A LOWESS polynomial may include a linear polynomial where a LOESS polynomial may include a quadratic polynomial. The algorithm used may be selected based upon the underlying variability of the GC content and which model (LOWESS/LOESS) best fits.

An exemplary PCA denoising approach may include projecting each tumor sample into high-dimensional space with a large collection of other samples, subtracting any variants that stand out along the eigenvectors from the tumor sample, and recapitulating the tumor sample sans the subtracted variants into a lower-dimensional space. For example, when PCA is used to denoise, an orthogonal linear transformation may be used to find a projection of the detected variants/alleles into a number, k, dimensions, whereas these k dimensions may capture the variants/alleles with the highest variance. While the dataset is represented in the k dimensions, the noise that isn't captured in these dimensions is left out of analysis, while the remaining, important data points remain available. The eigenvectors of a covariance matrix taken over the variant dataset may be ranked according to their eigenvalues. A high eigenvalue signifies high variance to be compared along with the associated eigenvector dimension. Computing eigenvectors and eigenvalues of the covariance matrix may be performed according to well established methods and a plot of eigenvalues may be generated. Eigenvalues which may be resolved into principal components may be identified by their eigenvalues because the eigenvalues will be much higher than the other eigenvalues. By limiting the eigenvalues, such as using only a subset of the top eigenvalues for denoising, the influence of noise is reduced for the dataset. The highest eigenvalues selected correspond to important characteristics of the dataset such that these characteristics have the highest variance of expression across the entire dataset and may provide the best representation of groups within the dataset, and conversely, the dropped eigenvalues may provide the best representation of the noise within the dataset. By finding these expressions of highest variance, extraneous data, aka noise, is left out and the resulting dataset may be analyzed in other techniques such as those in specialized testing stages .B.65a-n, including variant calls, TMB, MSI, gene fusion, SNV, Indel, or CNV states.

A covariance matrix (C) may be represented by:

$$C = \begin{pmatrix} \text{cov}(x,x) & \text{cov}(x,y) & \text{cov}(x,z) \\ \text{cov}(y,x) & \text{cov}(y,y) & \text{cov}(y,z) \\ \text{cov}(z,x) & \text{cov}(z,y) & \text{cov}(z,z) \end{pmatrix}$$

where a covariance between two points X,Y [cov(X,Y)] may be represented by:

$$\text{cov}(X, Y) = \frac{\sum_{i=1}^{n}(X_i - \overline{X})(Y_i - \overline{Y})}{(n-1)}$$

and the mean may be represented by:

$$\overline{X} = \frac{\sum_{i=1}^{n} X_i}{n}$$

Similarly, SVD, Canonical Correlation Analysis (CCA), Latent Dirichlet Allocation (LDA), factor analysis (FA), partial least squares (PLS), and other models may be applied in place of PCA to reduce the presence of noise in the dataset.

Stage .C.20 may further include calculation of a coverage log odds to account for the ratio of normalized tumor coverage to normalized normal coverage of the sample and Variant Allele Fraction/Frequency (VAF) log odds to account for the VAF of germline variations in the region compared to the standard heterozygous (count of two) results in the region of DNA/RNA. Herein, VAF and "B" allele frequency (BAF) are used interchangeably. While a BAF is generally for the less common of an allele pair and a VAF is for any variant allele, for the purposes of this disclosure, a reference to one may be interchanged with the other. When analyzing CNV and LOH, each instance of CNV or LOH may be recorded based upon, the location (locus) of each CNV or LOH in the genome, and the number of copies of a genetic sequence present in each instance of CNV. In another embodiment, instead of each instance of CNV and LOH being reported separately, a report may include a metric that indicates a level of CNV or LOH that occurs in the entire genome. Reporting the locus of each CNV or LOH may assist physicians in determining which type or subtype of cancer their patient has, allowing the physician to prescribe an effective treatment.

Coverage is the number of sequence reads or variant sequences that include a given nucleotide position. An exemplary coverage calculation for calculating coverage of an entire genome may be represented by:

$C=N*L/G,$ where C is coverage, N is the number of sequence reads, L is the length of each sequence read (in nucleotides), and G is the length of the target region, target variant, or whole genome (in nucleotides). Stage .C.20 may calculate per region coverage by selecting a region of the genome, multiplying the number of sequence reads located within that region by the length of each read in that region, and dividing by the number of nucleotides in the selected region. In another embodiment, coverage may be calculated as per variant coverage by selecting a nucleotide position, multiplying the number of reads located at the nucleotide position(s) spanned by the variant by the length of each read, and dividing by the number of nucleotides in the variant. Coverages related only to target genes may be calculated by filtering the sequence reads or variants to only select those that are located within target genes, by comparing the locations of sequence reads or locations of variants to the locations of genes listed in the target file as described above.

The VAF odds ratio calculation may determine whether a germline variant, such as a variant found in a normal tissue sample from a patient, is present on only one or both copies of the chromosome to determine the zygosity status for the variant. The variant is homozygous if it is present on both copies and heterozygous if it is present on only one copy of the chromosome. The VAF odds ratio calculation may match variants with the reference genome to map the variants, according to the variant location information listed for each variant. In an embodiment, variants may be missing variant location information and may be aligned to determine location information by comparing the variant to short sequences of the target region and associating the location of the matching short sequence with the variant. The VAF measures the portion of sequence reads at the variant position that include the variant nucleotide against the portion of sequence reads at the variant position that include the reference nucleotide or a different variant nucleotide to generate the frequency in which one variant occurs compared to the others. A VAF of a germline variant may be approximately 100% or 1.00 when both chromosomes contain the variant and may be labeled as homozygous or a VAF of a germline variant may be approximately 50% or 0.50 when only one chromosome contains the variants and may be labeled as heterozygous. For each heterozygous germline variant that is present in both the cancer sample and the normal sample, the deviation of variant allele frequency between the cancer sample and the normal sample is computed as the log of the odds ratio of the count of alternate alleles in the tumor sample against normal sample. The VAF odds ratio is calculated by dividing the likelihood that the variant allele exists in a cell if the reference allele exists in the same cell by the likelihood that the variant allele exists in a cell if the reference allele does not exist in the same cell. The VAF log odds may further be calculated by taking the binary logarithm of the median value of the variant occurrence for each detected variant in the tumor sample divided by the median value of each corresponding variant in the normal samples.

Stage .C.30 may pad variants with faux (dummy), homozygous anchors before and after each detected probe read to ensure continuity of data and allow the algorithms, below, to process correctly. These anchors are spaced throughout the probe targets to ensure the algorithm has data points in sequences without variation. These homozygous anchors may be selected from the whitelist described in stage .C.10. These homozygous anchors may also be selected to fill in gaps at target regions (such as target region .D.10 below) at the beginning and the end of the target region where the normal genome sequence is expected.

Stage .C.40 may segment target regions of DNA/RNA into smaller pieces and evaluate the segments using a bivariate $T^2$ analysis based on the detected variants, the Coverage Log Odds and the VAF Log Odds. Quantitative $T^2$ analysis involves creating $T^2$ distributions using a regularized algorithm from region-of-interest averaged decay data. A modified version of circular binary segmentation (CBS) may be applied, wherein both coverage log odds and VAF odds ratio are integrated into each estimate. Recursive splitting may be performed for each chromosome, gene, or sequence of DNA using the $T^2$ statistic or the multivariate generalization of the student's t-statistic. In a first pass, a tree may be generated for each recursive split and each sub-region is assessed for the possibility of focal amplification (such as large changes in coverage log odd or VAF). If any small regions of high deviation are detected, they may be protected from further segmentation, and other branches of the tree may be pruned based on a parameterized threshold on the maximum hotelling statistic at which splits are acceptable. Subsequent to pruning, the tree may be stabilized and a log of segment summary statistics may be generated. The log may include median coverage log odds, median VAF log odds, number of heterozygous variants, and feature length. For each segment, log of segment summary statistics may be adjusted according to a heterozygous scale factor such as the square root of a scaled (such as ¼) length of heterozygous variants divided by the number of heterozygous variants.

In one embodiment, segmentation may be performed across the entire sequenced genome, one or more chromosomes, one or more alleles, one or more genes, one or more variants, or a sequence of DNA. For example, when segmentation is performed across a chromosome, a chromosome of interest is input to the segmentation algorithm as a single node. A node may be defined as a series of variants that may occur in the chromosome. For each node, the segment may be projected onto a circle with two arcs and the $T^2$ statistic based on the coverage log ratio and the BAF log odds to determine both arcs (breakpoints) for the node. Each node may be iteratively segmented until either the segments reach a minimum length or the $T^2$ statistic is no longer significant, or falls below a branch threshold. Nodes may then be identified as focal alterations if the median coverage of a segment is significantly different, exceeds a focal threshold, as compared to adjacent segments. Any nodes identified as focal alterations may be protected from pruning from the tree. Nodes not identified as protected or focal alterations may be pruned (removed) from the tree based their $T^2$ statistic because they have fallen below the prune threshold. An exemplary $T^2$ analysis may include calculation partial sums ($S_i = Z_1 + Z_2 + \ldots + Z_n$) for each segment where a statistic for a single arc $$\left(Z_i = \frac{Si}{i} - \frac{Sn - Si}{n - i}\right)$$

may be maximized across all segments. For both arcs, the $T^2$ may be calculated as:

$T_{ij}$=max of $|T_{ij}|$ in the range $1 \leq i < j \leq N$, where $$|T_{ij}| = \frac{Z_{ij} - Y_{ij}}{\sqrt{\frac{1}{(j-i)} + \frac{1}{(i+n-j)}}}, \text{ where}$$

$$Z_{ij} = \frac{(Sj - Si)}{(j - i)}, \text{ and}$$

$$Y_{ij} = \frac{Si + (Sn - Sj)}{(i + n - j)}.$$

Other $T^2$ algorithms may also be used in place of the single and double arc algorithms above. The $T^2$ algorithm may be iteratively processed in a synchronous manner or in an asynchronous manner. In asynchronous computation, the calculations for each segment may be distributed across multiple cores, threads, or virtual machines for processing.

Stage .C.50 may calculate initial estimations for tumor purity and ploidy based on the detected variants, the coverage log ddds, and the VAF log odds.

An initial estimate of tumor purity may be calculated by a number of methods and/or combinations of those methods. In one method, a tumor purity may be estimated from the VAF/BAF of somatic variants. In another method, a tumor purity may be estimated from the difference between the somatic and germline VAF/BAF. In yet another method, a tumor purity may be estimated from the combination of the VAF/BAF of somatic variants and the difference between the somatic and germline VAF/BAF.

For example, a tumor purity estimate from a VAF of somatic variants may include receiving a variant dataset, identifying a coverage threshold for variants, and identifying somatic variants alongside using the coverage threshold to filter variants from the dataset. Somatic variants may be identified by checking whether the identified variant is present in a list of somatic variants or checking an assigned variant type from the variant file. In another embodiment, even if a variant is somatic, it may not be reported if the variant is listed in the blacklist reference file (or otherwise filtered from the results) or if the coverage of the variant is less than the coverage threshold (such as 34). The coverage threshold may be determined based upon prior testing or experimental evaluation to identify the best threshold. In another embodiment, filtering may be performed based upon gene name, such as filtering out miRNA by identifying that the gene name begins with MIR. The tumor purity estimate may then be assigned based on the highest percentile of the somatic VAF. In other embodiments, the tumor purity estimate may be based upon the 90th percentile instead of the highest percentile. The percentile may be determined based upon prior testing or experimental evaluation to identify the best percentile to use in selections.

A tumor purity estimate from a difference, or delta, between somatic and germline VAF may include receiving a matched variant dataset (such as a dataset having both a tumor sample variant matched with a normal sample variant), identifying a coverage threshold for variants, and identifying LOH variants alongside using the coverage threshold to filter variants from the dataset. LOH variants may be identified by calculating a difference between the tumor variant and the normal variant for a patient and confirming that the absolute value of the difference value exceeds a threshold (such as 2). In another embodiment, even if a variant has a difference exceeding the threshold, it may not be reported if the variant is listed in the blacklist reference file (or otherwise filtered from the results) or if the coverage of the variant is less than the coverage threshold. In another embodiment, filtering may be performed based on the type of variant detected, whether the variant is NSP, Indel, or MNP, based on the zygosity of the variant, whether the variant is heterozygous, or based on the base fraction of the variant, whether the base fraction is less than 50 percent. The tumor purity estimate may then be assigned based on the highest percentile of the delta VAFs multiplied by two. The delta, or difference, may be calculated based upon the difference between the highest percentile of the respective VAF. In other embodiments, the difference may be calculated as to between the 90th percentile of the respective VAF. The percentile may be determined based upon prior testing or experimental evaluation to identify the best percentile to use in selections.

A tumor purity estimated from both the somatic variant VAF and the delta variant VAF may include performing the above steps with respect to both the tumor purity estimate from a VAF of somatic variants to calculate a first estimate and the tumor purity estimate from a difference, or delta, between somatic and germline VAF to calculate a second estimate. If, for any reason, one estimate fails to calculate, then the remaining estimate may be selected as the final estimate. For example, the delta variant VAF may fail if the variant dataset from the patient is not comprised of matched tumor-normal samples or the somatic variant might fail if there are no somatic variants that both exceed the coverage threshold and pass through the blacklist. In some instances, the somatic estimate may be deemed unreliable. For example, if the somatic estimate is too high, while the delta variant VAF is much lower, it can be extrapolated that the somatic estimate is unreliable and the delta variant VAF estimate may be used instead. In other instances, the delta variant VAF estimate may be deemed unreliable. For example, if the somatic estimate is very low, it can be extrapolated that the delta variant estimate will be unreliable and the low somatic estimate may be used instead. When both the somatic estimate and the delta variant VAF estimate are expected to be accurate, the tumor purity estimate may be calculated as the average of both the somatic estimate and the delta variant VAF estimate, where a confidence interval in the estimate may be calculated from the absolute value of the difference between the two estimates.

An initial estimate of tumor ploidy may be calculated by phasing, or assigning alleles, variants, genes, or sequences of DNA to the paternal and maternal chromosomes as compared to the normal tissue in the patient. It may be important to identify, not just which alleles, variants, genes, or sequences of DNA are present in the paternal and maternal chromosomes, but also which combinations of each are present in the paternal and maternal chromosomes and how they differ between the tumor and the normal samples. A person's genotype may not define its haplotype uniquely. For example, consider a person with two alleles, variants, genes, or sequence of DNA on the same chromosome. If the first locus has alleles A or T and the second locus G or C. Both loci, then, have three possible genotypes: (AA, AT, and TT) and (GG, GC, and CC), respectively. For each patient, there are nine possible configurations (haplotypes) at these two loci (AG AG, AG TG, TG TG, AG AC, AG TC/AC TG, TG TC, AC AC, AC TC, or TC TC). For patients who are homozygous at one or both loci, the haplotypes are unambiguous; however, for patients who are heterozygous at both loci, the gametic phase is ambiguous, meaning which haplotype the patient has (TA vs AT) is unknown. Sequencing allows an estimate of the probability of a particular haplotype when phase is ambiguous to be calculated. Through analyzing the genotypes for a number of individuals, the haplotypes can be inferred by haplotype resolution or haplotype phasing techniques. These methods work by applying the observation that certain haplotypes are common in certain genomic regions. Therefore, given a set of possible haplotype resolutions, these methods choose those that use fewer different haplotypes overall. Methods for calculating this may be based on combinatorial approaches (parsimony) or likelihood functions based such as the Hardy-Weinberg principle, the coalescent theory model, or perfect phylogeny. The parameters in these models may be estimated using algorithms such as the expectation-maximization algorithm (EM), Markov chain Monte Carlo (MCMC), or hidden Markov models (HMM). Once the patient's haplotype is determined, overall tumor ploidy may be calculated.

Stage .C.60 may be iteratively revise the estimates using a likelihood ratio to calculate a best fit for copy number state, tumor purity, and tumor ploidy. The initial estimate from stage .C.50 may be used to create a lower bounds for actual tumor purity. The lower bound may be half the estimate value from stage .C.50. In another embodiment, the lower bound may be 0 percent or a cutoff purity such as 35 percent. An array of potential purity values may be generated from the lower bound to 100 percent by stepping from the lower bound to 100 percent by a tumor purity step value (such as half a percent, 1 percent, 5 percent, or other step size). A likelihood matrix may be generated with a column for each segment and a row for each of the tumor purity values in the array. For each purity value in the array of potential purity values, each segment of the target region may be processed to identify a potential copy state and a likelihood of that copy state's accuracy. Segments that show no variation in likelihood across all tumor purity estimates are removed from the likelihood matrix. Additionally, for each segment and purity, a LOH flag may be set to identify a major LOH (2) or a minor LOH (0). A copy amplification value may be calculated based upon whether a copy gain, copy loss, copy neutral, or copy transcription is detected. In another embodiment, a copy amplification value may be set for each of the CNV states from FIG. 311. A minor allele copy state may be generated from the minor allele copy number and the tumor purity. A major allele copy state may be generated from the major allele copy number and the tumor purity. An expected BAF Log may be calculated from the difference of the minor and major allele copy states. A penalty may be calculated based upon the genome instability to penalize copy states that should be biologically impossible. For example, if a genome contains too many deletions such that the percentage of the deleted genome within a segment exceeds a deletion threshold (such as 5 percent), then a penalty may be calculated from the square root of the percentage of the deleted genome. The penalty may be summed with a mean squared error and may be reported in the log as well as used to scale the final tumor purity.

The copy state of a segment may be computed by calculating the number of major copy number, minor copy number, and total major and minor copy number in a particular segment to set the segment as a one copy segment, neutral LOH segment, neutral segment, deletion segment, a three copy segment, or other copy segment according to CNV state. A VAF/BAF may be calculated for each of these copy states and a mean squared error may be calculated by summing the square of each, an expected LOH—the one copy BAF, an expected neutral LOH—neutral LOH BAF, the neutral BAF, the deletion BAF, and the expected three copy segment—thee copy segment BAF. Each of the expected values may be generated according known expected BAF determination algorithms. For each segment, a tumor purity may be output by evaluating the likelihood matrix for peaks in the likelihood across the tumor purities in each segment. The highest peak with the smallest mean squared error may be selected as the tumor purity for the segment. Similarly, the tumor ploidy of the segment with the smallest mean squared error may be selected as the tumor ploidy for the segment.

Stage .C.70 may combine the segments to generate CNV estimates for the variants within the target section. A target region of the patient's DNA may comprise one or more alleles or, variants. Each target region is segmented into smaller, more digestible regions for the calculations in stage .C.60 where each segment may span one or more of the alleles or variants. It may be necessary to identify where segments fully encompass a variant or allele, or where two segments bisect any one allele or variant (such as first segment and second segment both contain a part of the variant or allele). For alleles or variants which are contained entirely within a segment, the copy state the allele or variant may take the copy state of the encompassing segment. For alleles or variants which are bisected, the copy state of the greater portion (length of the segment overlapping) may be selected, the copy state of the lesser portion may be selected, the average of the two copy states may be taken. In an embodiment where variants are calculated at this stage, the copy state of the variant may be identified as the lesser of the copy states.

Stage .C.80 may use each of the CNV and copy states for variants to estimate a copy state for each of the genes of the patient. For a gene which has multiple variants from stage .C.70, the combination of variants or genes may be weighted to calculate the copy state of the encompassing gene or chromosome. For example, in the copy state calculation of a gene, a list of variants for that gene may be referenced. For each variant of the gene, the copy state of that variant may be checked from the results of stage .C.70 and the average of each variant may be set as the copy state of the gene. Where calculations in .C.70 may each based upon the segments of the copy state calculations in .C.60 for each variant, the calculations for stage .C.80 may each based upon the variants. For a chromosome which has multiple variants from stage .C.70 and/or genes previously calculated in this stage, the combination of variants or genes may be weighted to calculate the copy state of the encompassing chromosome. For example, in the copy state calculation of a chromosome, a list of variants and/or genes for that chromosome may be referenced. For each variant of the gene, the copy state of that variant may be checked from the results of stage .C.70 and the average of each variant may be set as the copy state of the gene. For each gene of the chromosome, the copy state of that gene may be checked and the average copy state of the genes may be set as the copy state of the chromosome. In another embodiment, the copy state of the greater portions (length of the variants/genes within) may be selected or the copy state of the lesser portions may be selected.

The normalization values for GC Content, Depth, and Length calculated at stage .C.10 may be applied to the respective variants at this stage to adjust the counts to counteract artificially high or low counts which may not reflect the CNV that exists in the sample.

Stage .C.80 may output the tumor purity, ploidy, and copy number states for each probe, segment, variant, gene, chromosome, and whole genome of the sequencing to one or more files. These include a copy number probe file, segment file, variant file, gene file, chromosome file, genome file each with a respective tumor purity, ploidy, and copy state value. Additionally, statistical metadata (such as the log of .C.40) may be generated to track the confidence and likelihood determinations across the whole genome.

FIG. 314 is an illustration .D.00 of a panel of probes .D.20a-i for sequencing a target region .D.10. Target region .D.10 may include one or more variants, genes, or chromosomes. Additionally, a target region .D.10 may correspond with a sequence of nucleotides. Sequences may be hundreds to millions of nucleotides in length. Probes .D.20a-i may target specific nucleotide sequences within the target region. Probes may overlap in coverage, for example, probe .D.20b may overlap both probes .D.20a and .D.20c. Furthermore, due to variability in the length of DNA that may attach to a probe, the sequence reads that originate from probe .D.20c may extend to cover the sequence regions covered by probes .D.20d-g, or more. Probes .D.20a-i may also have variable DNA strands attached to them. There is opportunity for substantial DNA coverage to be repeated across multiple probes. Normalization, such as performed at stage .C.10, above, accounts for the increase of reads caused by reads which extend to cover additional sequences of DNA other than the intended probe target.

When a sequencer, such as the sequencer that performs sequencing stage .B.50 of the NGS Lab Pipeline 5308 reads and records probes .D.20a-i in a BAM or SAM file, the resulting data may be flattened across the target region, such as shown in flattened region .D.25. Flattening may include alignment, and incrementing a count value associated with repeated sections of the DNA sequence. The flattened region .D.25 may then be segmented into regions corresponding to segments .D.30A-C according to a process as described above with respect to stage .C.40. Segments such as those depicted in .D.30A-C may cover specific variants of the DNA sequences or merely partition the target region into manageable chunks for processing. Segments .D.30A-c may be of any length and may even vary in length between each segment. Once flattened and the CNV counts calculated, processing, such as described above with respect to .C.50 and .C.60 may be performed on the segments within target region, genes within the target region, or variants within the target region. Once segment calculations are processed, the segments may be combined back into the target region.

FIG. 315 is an illustration of a copy number plot .E.00 for reporting CNV states. A copy number plot .E.00 may be provided to a physician as part of the report or a supplementation to the report to visually represent the copy number state of a sequence of nucleotides such as for a gene, a variant, or a predefined target region. The x-axis may represent the sequence of nucleotides, or the numbering of loci across a region of the DNA. The y-axis may represent the copy number of the alleles. A major allele is the dominant allele or the most frequently occurring allele and a minor allele is the least frequent allele. Furthermore, a major section (a sequence of nucleotides greater than a predefined length) is represented separate from a tiny major section (a sequence of nucleotides less than the predefined length) to ensure a user may visually identify copy number states regardless of the scale of the x-axis.

FIG. 316 is an illustration of a b-allele fraction log odds ratio plot .F.00 for reporting CNV states. A b-allele fraction log odds ratio plot .F.00 may be provided to a physician as part of the report or a supplementation to the report to visually represent the BAF/VAF log odds of a sequence of nucleotides such as for a gene, a variant, or a predefined target region. The plot shows the stability of the portrayed region of the patient's genome, with stability increasing the closer to the x-axis a region is graphed. The x-axis may represent the sequence of nucleotides, or the numbering of loci across a region of the DNA. The y-axis may represent the BAF/VAF log odds ratio of the alleles. Targeted variations to genes, alleles, or sequences of DNA are graphed as a line, while neutral mutations (changes in DNA sequence that are neither beneficial nor detrimental to the patient) are shows as points.

FIG. 317 is an illustration of a coverage log ratio plot .G.00 for reporting CNV states. A coverage log ratio plot .G.00 may be provided to a physician as part of the report or a supplementation to the report to visually represent the coverage log odds of a sequence of nucleotides such as for a gene, a variant, or a predefined target region. The plot shows the type of copy state event detected as well as the coverage log ratio associated with the detected event. The x-axis may represent the sequence of nucleotides, or the numbering of loci across a region of the DNA. The y-axis may represent the coverage log ratio for the gene, allele, variante, or sequence of nucleotides. Targeted variations to genes, alleles, or sequences of DNA are graphed according to the CNV event type detected, while neutral mutations (changes in DNA sequence that are neither beneficial nor detrimental to the patient) are shows as points. Additional points may be added according to the following: a deep deletion may be a coverage log ratio less than a deletion threshold (such as −1); a shallow deletion may be a coverage log ratio between a deletion threshold and a negative gain threshold (such as between −1 and −0.5); a gain may be a coverage log ratio between a positive gain threshold and an amplification threshold (such as 0.5 to 1): an amplification may be a coverage log ratio greater than an amplification threshold but less than a high amplification threshold (such as between 1 and 2); and a high amplification may be a coverage log ratio greater than a high amplification threshold (such as 2); a focal deletion may be when a deleted region is less than a threshold number of genes (such as 50 genes); and a large scale deletion may be when a deleted region is great there a threshold number of genes (such as 50 genes). The threshold values estimated above may be refined according to genetic and clinical factors of the patient, the type of analysis being performed (such as a tumor classification, disease state detection, pharmacogenomics, etc.). Furthermore, it is possible to add and remove elements that would affect the respective threshold bounding. For example, reporting on amplifications instead of both amplifications and high amplifications may result in removing the upper bound on the amplification detection.

FIG. 318 is an illustration of an example machine of a computer system .H.00 within which a set of instructions, for causing the machine to perform any one or more of the methodologies discussed herein, may be executed. In alternative implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system .H.00 includes a processing device .H.02, a main memory .H.04 (such as read-only memory (ROM), flash memory, dynamic random access memory (DRAM) such as synchronous DRAM (SDRAM) or DRAM, etc.), a static memory .H.06 (such as flash memory, static random access memory (SRAM), etc.), and a data storage device .H.18, which communicate with each other via a bus .H.30.

Processing device .H.02 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device .H.02 may also be one or more special-purpose processing devices such as an application specific integrated circuit (ASIC), a field programmable gate array (FPGA), a digital signal processor (DSP), network processor, or the like. The processing device .H.02 is configured to execute instructions .H.22 for performing the operations and steps discussed herein.

The computer system .H.00 may further include a network interface device .H.08 for connecting to the LAN, intranet, internet, and/or the extranet. The computer system .H.00 also may include a video display unit .H.10 (such as a liquid crystal display (LCD) or a cathode ray tube (CRT)), an alphanumeric input device .H.12 (such as a keyboard), a cursor control device .H.14 (such as a mouse), a signal generation device .H.16 (such as a speaker), and a graphic processing unit .H.24 (such as a graphics card).

The data storage device .H.18 may be a machine-readable storage medium .H.28 (also known as a computer-readable medium) on which is stored one or more sets of instructions or software .H.22 embodying any one or more of the methodologies or functions described herein. The instructions .H.22 may also reside, completely or at least partially, within the main memory .H.04 and/or within the processing device .H.02 during execution thereof by the computer system .H.00, the main memory .H.04 and the processing device .H.02 also constituting machine-readable storage media.

In one implementation, the instructions .H.22 include instructions for a patient order processing pipeline (such as the patient order processing pipeline .B.00 of FIG. 318) and/or a software library containing methods that function as a patient order processing pipeline. The instructions .H.22 may further include instructions for an orchestrator .B.02 and specialized testing stage for CNV .B.65n. (such as the orchestrator .B.02 and CNV .B.65n of FIG. 318) While the machine-readable storage medium .H.28 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine readable storage medium as a transitory storage medium or transitory machine-readable storage medium.

In another implementation, a virtual machine .H.40 may include a module for executing instructions for an orchestrator .B.02 and specialized testing stage for CNV .B.65n. (such as the orchestrator .B.02 and CNV .B.65n of FIG. 2). In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

XVIII. Methods of Normalizing and Correcting RNA Expression Data

The present application presents a platform for performing normalization and correction on gene expression datasets to allow for combining of different datasets into a standardized dataset, such as a previously normalized dataset, that may continuously incorporate new data. The present techniques generate a series of conversion factors that are used to on-board new gene expression datasets, such as unpaired datasets, where these conversion factors are able to correct for variations in data type, variations in gene expressions, and variations in collection systems. For example, conversion factors are able to correct against data collection bias, variations in laboratory data generation processes, variations in data sample size, and other factors that can cause incongruity between datasets. The techniques may correct older datasets for inclusion into new dataset. For example, existing, stable datasets, such as the TCGA (https://portal.gdc.cancer.gov/) or GTEx (https://gtexportal.org/home/), may be corrected to match new datasets. Examples of RNA seq datasets include RNAseq data from FFPE tissue, RNAseq data from fresh frozen tissue, or from other tissue from which RNA seq data may be extracted. Datasets may come from laboratories (such as Tempus Labs, Inc., Chicago, Ill.), from individual research institutions (such as the Michigan Center for Translational Pathology, Ann Arbor, Mich.), from public data repositories such as TCGA and GTEx, or from other sources.

The present techniques include platforms for normalization of gene expression data, such as RNA sequence data or array-based technologies data, and comparison of gene expression data to a standard gene expression dataset. The present techniques include platforms for generating one or more conversion factors by comparing gene expression data to such standard gene expression datasets. The present techniques include correcting gene expression data, such as RNA sequence data, of subsequent gene expression datasets using these one or more conversion factors, thereby allowing subsequent gene expression datasets to be integrated into the standard gene expression dataset.

In some examples, the present techniques include obtaining a gene expression dataset having RNA sequence data for one or more genes, where that RNA sequence data includes gene length data, guanine-cytosine (GC) content data, and depth of sequencing data. In other examples, other types of gene expression datasets from array-based technologies, such as RNA microarrays, may be obtained. The techniques may include performing normalization of the RNA sequence data or other gene expression datasets. The normalization may include normalizing the gene length data for at least one gene to reduce systematic bias, normalizing the GC content data for the at least one gene to reduce systematic bias, and normalizing the depth of sequencing data for each sample, for example. The normalized dataset may be compared against the standard gene expression dataset by comparing the sequence data for at least one gene in the gene expression dataset to sequence data in the standard gene expression dataset to generate at least one conversion factor.

FIG. 1 illustrates a system 14100 for normalizing and correcting gene expression data, such as RNA seq data. A normalization and correction framework 14102 is coupled to receive gene expression data from a multitude of different sources through a communication network 14106. The framework 14102, for example, may be coupled to a health care provider computing system 14104, such as a research institution computing system, lab computing system, hospital computing system, physician group computing system, etc., that makes available stored gene expression data in the form of RNA sequencing dataset 14108. Other gene expression network-accessible datasets are also coupled to the network 14106, including the Cancer Genome Atlas (TCGA) dataset 14110 and the Genotype-Tissue Expression (GTEx) dataset 14112, both examples of established gene expression datasets that can be normalized and corrected to be incorporated into an already-normalized and corrected growing database of gene expression data.

The framework 14102 includes a batch normalizer 14103 configured to perform gene expression batch normalization processes in accordance with examples herein, processes that adjust for known biases within the dataset including, but not limited to, GC content biases, gene length biases, and sequencing depth biases. In the example of FIG. 1, the framework 14102 is further configured to perform gene expression correction processes in accordance with examples herein using a RNA seq corrector 14105. As discussed herein, the processes of the normalizer 14103 and the corrector 14105 are used by the framework 14102 to normalize gene expression data and generate one or more correction factors (14107), which are stored in the framework 14102 and applied by the framework 14102 to convert new gene expression datasets, such as dataset 14114. Applying these correction factors to the new dataset 14114, for example, the framework 14102 is able to normalize, correct, and convert that dataset 14114 into a format for integration into an existing normalized, corrected gene expression dataset 14116, as shown.

The framework 14102 may be implemented on a computing device such as a computer, tablet or other mobile computing device, or server. The framework 14102 may be implemented by any number of processors, controllers or other electronic components for processing or facilitating the RNA sequencing data analyses. In some examples, the system 14100 is implemented in a broader system that includes processing and hardware for imaging feature analysis, such as analyzing features in medical imaging data, immune infiltration data analysis, DNA sequencing data analysis, organoid development analysis, and/or other modality analyses.

An example computing device 14200 for implementing the framework 14102 is illustrated in FIG. 320. As illustrated, the framework 14102 may be implemented on the computing device 14200 and in particular on one or more processing units 14201, which may represent Central Processing Units (CPUs), and/or on one or more or Graphical Processing Units (GPUs), including clusters of CPUs and/or GPUs. The framework 14102 may be configured to perform processes of the techniques herein, such as those described with reference to FIGS. 321-327. Features and functions described for the framework 14102 may be stored on and implemented from one or more non-transitory computer-readable media 14203 of the computing device 14200. The computer-readable media 14203 may include, for example, an operating system 14205 and the framework 14102. More generally, the computer-readable media may store the batch normalizer 14103 for executing batch normalization process instructions, a gene expression corrector (e.g., the RNASeq specific inspector 14105) for executing gene expression process instructions, and the generated correction factors 14107. The computing device 14200 may be a distributed computing system, such as an Amazon Web Services cloud computing solution.

The computing device 14200 includes a network interface 14210 communicatively coupled to the network 14106, for communicating to and/or from a portable personal computer, smart phone, electronic document, tablet, and/or desktop personal computer, or other computing devices. The computing device further includes an I/O interface 14212 connected to devices, such as digital displays 14214, user input devices 14216, etc. The computing device 14200 may be connected to gene expression databases 14108 through network 14106, as well as the normalized and corrected gene expression database 14116. In some examples. A database 14218 within the computer device 14200 may be used to store gene expression data, including new gene expression data for normalization and correction, normalized and corrected gene expression data, or other data. A graphic user interface (GUI) generator 14220 is provided for generating digital reports, user interfaces, etc. for allowing users to interact with the normalized and corrected gene expression databases.

The functions of the framework 14102 may be implemented across distributed devices 14202, 14204, etc. connected to one another through a communication link. In other examples, functionality of the system 14100 may be distributed across any number of devices, including the portable personal computer, smart phone, electronic document, tablet, and desktop personal computer devices shown. The server 14200 may be communicatively coupled to the network 14106 and another network 14206. The networks 14106/14206 may be public networks such as the Internet, a private network such as that of research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 14200 may represent a CPU-type processing unit, a GPU-type processing unit, a field-programmable gate array (FPGA), another class of digital signal processor (DSP), or other hardware logic components that can be driven by a CPU.

FIG. 321 illustrates a process 14300 that may be executed by the system 14100. Gene expression data is obtained from a gene expression database or data source, at process 14302. In the example of RNA seq data, the dataset may be obtained from a high throughput sequencer, such as Illumina HiSeq, Illumina NextSeq, Illumina NovaSeq, or other high throughput sequencing machines. The framework normalizes the newly obtained gene expression dataset, at process 14304, to eliminate biases caused by, for example, GC content, gene length, and sequencing depth. Conversion factors are generated by comparing the obtained gene expression dataset to a standard gene expression dataset using a statistical mapping model, at process 14306. Examples of statistical mapping model include, but are not limited to, a standard linear model, a generalized linear model (using for example a gamma distribution of counts data), or non-parametric methods, such as data transformation into ranks. The generated conversion factors are stored by the framework, as a result. At process 14308, conversion factors are applied to the new gene expression data, which is then integrated into the standard dataset, in this converted form, at process 14308.

FIG. 322 illustrates an example normalization process 14400 to be applied to received raw gene expression data. A gene expression dataset is obtained, e.g., from a network accessible database connected to the network 14106. The selection may be manual, by an operator using a graphical user interface provided to a display. The selection may be automated, such as when pre-determined search data is accessed by the system 14100 and used to find corresponding data in the gene expression dataset (process 14402). The gene expression dataset may contain RNA seq data, e.g., the TCGA, GTEx, or other database. The gene expression data may be array-based data, in other examples.

A gene information table comprising information such as gene name and starting and ending points (to calculate gene length) and gene GC content, is accessed and the resulting information is used to determine sample regions (process 14404) for analyzing the gene expression datasets. A GC content normalization process 14406 is performed using a first full quantile normalization process, e.g., a quantile normalization process like that of the R packages EDASeq and DESeq normalization processes (https://bioconductor.org/packages/release/bioc/html/DESeq.html) may be used. In an example, a 10 quantile bin normalization is performed. The GC content for the sampled data is then normalized for the gene expression dataset. Subsequently, a second, full quantile normalization (e.g., using 10 quantile bins) is performed on the gene lengths in the sample data, at process 14408.

To correct for sequencing depth, a third normalization process 14410 may be used that allows for correction for overall differences in sequencing depth across samples, without being overly influenced by outlier gene expression values in any given sample. In exemplary embodiments, at a process 14412, a global reference is determined by calculating a geometric mean of expressions for each gene across all samples. In other examples the reference geometric mean is obtained from the gene information table based on the existing datasets (e.g., GTEx, TCGA, etc.).

The size factor is used to adjust the sample to match the global reference. In operation, a sample's expression values are compared to a global reference geometric mean (process 14412), creating a set of expression ratios for each gene (i.e., sample expression to global reference expression). At a process 14414, a size factor is determined as the median value of these calculated ratios. The sample is then adjusted by the single size factor correction in order to match to the global reference, e.g., by dividing gene expression value for each gene the sample's size factor, at a process 14416.

In the illustrated example, after normalization, log transformation is performed on the RNA seq data for each gene, at a process 14418. The entire GC normalized, gene length normalized, and sequence depth corrected RNA seq data is stored as normalized RNA seq data, at process 14420.

Each of the normalizations for process 14400 may be perform in sequential manner, where the output of one process provides input data to the next subsequent process. The particular ordering of the normalizations, however, is not important, as any of the three normalization processes may be performed in any order. Furthermore, alternative normalization methods can be applied, including but not limited to, Fragments Per Kilobase Million (FPKM), Reads Per Kilobase Million (RPKM), Transcripts Per Kilobase Million (TPM), and 3rd quartile normalization.

In some examples, an objective of the present techniques is to combine RNA seq data across many different datasets, overcoming the technical differences in sample collection methods used by many labs today. As noted above, different sources of bias can affect RNA seq datasets, these include biases based on tissue type, e.g., fresh, frozen or formalin fixed, paraffin embedded (FFPE). Other biases arise from selection method, e.g., exon capture or poly-A RNA selection. Even for datasets sequenced using exome capture, subtle differences between different exome capture kits can affect datasets.

In order to correct for these biases, the system 14100 may perform a correction after normalization for samples sequenced and obtained from external sources, e.g., network accessible databases, 14108, 14110, 14112, and 14114, for example. For each of these different databases a per-gene correction factor may be developed so that samples across datasets can be compared and analyzed for correction and integration into a normalized, corrected gene expression dataset.

FIG. 323 illustrates an example correction process 14500 to be applied to the normalized RNA seq data produced by the process 14400. For the illustrated example, in order to calculate the per gene correction factors, an equal number of samples, N, was obtained from two datasets, the normalized gene expression dataset (14502) from the process 14400 and the standard dataset (14504), also normalized from the process 14400. The two datasets 14502/14504 may be sampled an equal number of times, at processes 14506 and 14508, respectively. The sampling may be over random locations within the datasets, or based on a plurality of meta-data elements, for example, by cancer type, tissue type, age, gender, etc. Sampling can be done for all genes or may be confined to gene expression data within certain ranges of data, such as for example over certain genes or collections of genes identified in the datasets. Further, the total sample sizes for each dataset may vary, but generally should be at least 30 samples in size.

In the illustrated example, for each sampled dataset for which there is no paired data, for each gene, gene expression values were sorted (14510 and 14512) based on numerical values and used to estimate a statistical mapping/statistical transformation model (at process 14514), in the form of a linear transformation model, for each gene. A linear transformation model is an example, as other techniques may be used to model the new (external) dataset to the standard (internal) dataset.

In exemplary embodiments, the linear transformation model (14514) converts data from one type of data to another. The linear transformations are performed for each sample mapping from one dataset to the other, and the corresponding intercept and beta values for each linear transformation are stored (at process 14516). The sampling is repeated, e.g., 10, 100, 1000, or 10000 times (e.g., through an iterative process), and the corresponding intercept and beta values are determined, and the mean intercept and mean beta values are computed for the linear transformations (14518).

The mean beta and intercept values are then stored (at process 14518) as conversion factors that may be used to correct the normalized external dataset from process 14400.

For example, a process 14520 may subtract the mean intercept from the gene expression values in the normalized external dataset and divide the gene expression values by the mean beta for each gene. The mean intercept and mean beta comes from taking the average of X number of sampling iterations (through iteration feedback 14521), for example 100 iterations, to estimate the model. At a process 14522, any gene expression value after correction, that is below 0, is set to that minimum, e.g., 0, since gene expression values are constrained to be non-negative. The resulting normalized and corrected external dataset (14524) is produced and stored by the system 14100, either separately or stored as part of the dataset 14116, for example.

FIG. 324 illustrates an example correction process 14600 to be applied to the normalized RNA seq data produced by the process 14400 for paired datasets. Two datasets 14602 and 14604 have been combined through a normalization process to form a paired dataset 14606. An example of a paired dataset 14606 would include, but is not limited to, data generated in the same manner as the standard dataset (14602), and data, for the same set of samples, using a different data generation process (i.e. data generated using polyA-capture based RNA sequencing and exome-capture based RNA sequencing for the same set of samples). For the illustrated example, in order to calculate the per gene correction factors, a statistical mapping (14610) would be created between the samples in the new RNA sequencing data (14602) to the standard RNA sequencing data (14602), using a model. The model parameters from the statistical mapping, e.g., the beta and intercept value, are obtained (14612), stored as conversion factors, and used to correct the new RNA sequencing data, e.g., by subtracting the intercept value and dividing by the beta value. These conversion factors would be used to transform the new RNA sequencing dataset into the standard dataset and be deposited into the standard dataset database (14614), in a similar manner to that of process 14500, from minimum expression values, and a normalized and corrected dataset 14616 is formed.

The normalized and corrected gene expression data may be provided as input data to any number of data analysis processes, data display processes, etc. The normalized and corrected gene expression data may be combined with additional types of data for such processes, as well.

Examples of additional types of data that could be combined with the present application or be presented in addition to, include proteomics, metabolomics, metabonomics, epigenetics, microbiome, radiomics, and genomics data. Other examples may include non-molecular data such as clinical, epidemiological, demographic, etc. Proteomics data may comprise of protein expression, protein modifications, and protein interactions obtained from high-throughput proteomic technologies such as mass spectrometry-based tech or microarrays. Metabolomic and metabonomic data may include small molecule metabolites, hormones, other signaling molecules, or metabolic responses obtained by mass spectrometry-based techniques, NMR spectrometry, etc. Epigenetic data may include changes in chromatin structure, such as histone modifications; transcript stability, such as DNA methylation status; nuclear organization; and small noncoding RNA species. These types of data may be obtained from high-performance liquid chromatography, bisulfite sequencing, CpG island microarrays, and chromatin immunoprecipitation-based methods. Microbiome and microbiota data may include and be obtained from direct observation methods, 16s rRNA sequencing, 18s sequencing, ITS gene sequencing, and molecular profiling such as metatranscriptomics, metaproteomics, metabolomics. Radiomics and digital imaging data may include and be obtained from PET, CT, histology slides and/or images, etc. Genomic data may include DNA sequencing data of coding and noncoding genomic regions of interest, and RNA sequencing data of coding and noncoding RNAs such as microRNA. Coding RNAs and gene expression data may also be obtained from single cell RNA sequencing and microarray. Noncoding RNAs may be obtained from RNA sequencing, polymerase chain reaction, and microarrays. Organoid culture assays may include healthy and disease state organoid cultures obtained from humans or animal model, such as a rodent.

FIG. 325 illustrates an example application of the gene expression normalization and correction framework 14102 communicatively coupled to RNA seq analysis systems to make the standard gene expression dataset 14116 available for further processing. In the illustrated example 14700, the framework 14102 can send the normalized and corrected dataset 14116 to a RNA seq and imaging features machine learning framework 14702. The framework 14702 is a multi-modal framework capable of predicting immune infiltration based on integrating the normalized and corrected RNA seq data with digital imaging features. Framework 14702 may be configured to predict immune infiltration in tumor samples, based on the combined data, by using a neural network framework that integrates the normalized and corrected RNA seq data neural network layer(s) with imaging feature neural network layer(s) to produce an integrated neural network output that can be used with a prediction function to produce an immune infiltration score for sample data.

In another example, the framework 14102 may send the dataset 14116 to another gene expression analyzer 14704, providing automated processes for examining for example RNA seq data. Examples of the analyzer 14704 include cancer type predictor systems, tissue/metastasis deconvolution systems, gene expression machine learning algorithms, patient report generators, and hormone receptor prediction systems. For example, the database 14116, as a result of the framework 14102, can be applied to the framework 14704 which may analyze the normalized and corrected RNA seq datasets for further processing.

In some examples, the database 14116 is network accessible database communicatively coupled to (or part of) a network server for providing the dataset (or access thereto) to shared external sources, such as the additional data sources described herein.

In some examples, the database 14116 may provide access to the dataset for user interaction through a user terminal (as shown), a patient report generator, clinician portable device, etc., e.g., through the network 14106 or through a separate network 14706.

While various examples herein are described in reference to gene expression data in the form of RNA seq data, it will be appreciated that the same techniques may be applied to transcript or isoform level expression data, in a similar manner.

An example workflow implementation of the present techniques includes receiving a biological sample, such as a tissue sample, and extracting RNA from the tissue sample, where the RNA is sequenced using a protocol, such as exome-capture RNA seq. RNA seq data may then be processes to go from raw sequence data to aligned reads and expression counts, for example, using the Kallisto pipeline technique (https://www.nature.com/articles/nbt.3519). Of course, any number of suitable pipelines can be used. These raw expression counts are then provided to the processes in FIGS. 321-324 to develop a continuously updated and updatable reference RNA seq dataset, which can then be provided to downstream gene expression analyzers like elements 14702, 14704, etc.

FIG. 326 provides an exemplary example workflow 14800 that may be used to provide a corrected and normalized dataset. An RNA seq dataset 14802 is accessed and quantified by a framework to generate a quantified output of RNA seq dataset 14804.

In an example, a bioinformatics pipeline may be used to process the RNA seq data to get a raw counts RNAseq dataset for normalization and correction. The bioinformatics pipeline may receive a FASTQ file and produce a raw RNA counts file. In one exemplary bioinformatics pipeline, RNA seq dataset is accessed and a quantification using pseudo-alignment is performed. The pseudoalignment may be implemented using a transcriptome de Bruijn graph, for example. The quantification process may split a given read into k-mers (k=31 in our case) and then map each k-mer to a node in an internal database. The intersection of the k-mers is then used to quantify transcript-level expression. The output may be a near-optimal quantification of the expression of 180,053 transcripts, for example.

In an example, at a process 14806, the framework performs a sampling and quality control process on a RNA seq dataset, after the bioinformatics pipeline produces an output or before the normalization steps described herein are carried out. For example, the framework may determine sequencing depth in the quantified RNA seq dataset. The framework may determine the number of expressed transcripts and the number of expressed genes. The framework may filter obvious outliers, e.g., by removing identified duplicates. In some examples, the framework filters transcripts that are off-target from a probe set.

In a series of next steps, a preliminary normalization (such as from processes 14300 and 14400) is performed on the RNA seq dataset. In the illustrated example, the normalization is an intra-dataset normalization, where the dataset is normalized against other data in that dataset, at a process 14808. In some examples, an inter-dataset normalization is also is performed, that is, as discussed below through a normalization comparing gene expression data from different datasets. To achieve intra-dataset normalization, at the process 14808, a preliminary (and temporary) normalized dataset is stored (at process 14810) and, at least for the illustrated example, principal component analysis (PCA) and outlier detection is performed on that dataset, at a process 14812. FIG. 327 illustrates an example, in which RNA seq data has been applied to linear mapping model and outlier gene expression data have been identified. For example, gene expression data that does not map to the x-axis (0 value) may be identified as an outlier and removed. In some examples, a threshold, cutoff value is used to identifier outliers, such as a value of ±0.1, ±0.01, ±0.005, etc. As shown in FIG. 327, outliers can be found in the data, but such outliers are resolved through the process described above. FIG. 328 illustrates an example identification of resolved outliers resulting from applying the process 14800 to a dataset. A cleaned and intra-normalized RNA seq dataset 14814) results, as shown in FIG. 326.

Next, the framework implementing the process 14800 (at process 14816) performs a normalization and correction on the dataset 14814, e.g., by determining geometric mean expressions against a reference dataset, where these expressions are correction factors for the RNA seq data. For example, the conversion factor (e.g., an intercept and a beta value for the linear mapping model), may be generated by comparison to an internal reference dataset, such as a first RNA seq dataset, i.e., an already normalized gene expression dataset. The resulting cleaned and inter-normalized dataset 14820 is corrected (14822) against the internal dataset 14820 and a final corrected and normalized RNA seq dataset is generated (14824). That final dataset may then be combined into the reference dataset and/or used for further downstream processing, such as discussed in reference to FIG. 325. FIG. 329A illustrates an example of a gene expression values in a second dataset (Dataset2) prior to application to the correction workflow 14800. FIG. 329B illustrates the gene expression values of the second dataset (Dataset2) after correction and normalization, illustrating the updated dataset against a reference dataset (Dataset1). The x and y axes reflect a first and second principal component from the PCA analysis.

FIG. 330 illustrates another example system 14900 for normalizing gene expression data, such as RNA seq data, and having a similar configuration to that of the system 14100. A multimodal normalization framework 14902 is coupled to receive gene expression data from different sources through the communication network 14106, such as the health care provider computing system 14104 that makes available stored gene expression data in the form of the RNA sequencing dataset 14108.

Other network-accessible gene expression datasets include the TCGA dataset 14110 and the GTEx dataset 14112. As with the normalization framework 14102, the multimodal normalization framework 14902 may be implemented on a computing device such as a computer, tablet or other mobile computing device, or server. The framework 14902 may be implemented by any number of processors, controllers or other electronic components for processing or facilitating the RNA sequencing data analyses. In some examples, the system 14900 is implemented in a broader system that includes processing and hardware for imaging feature analysis, such as analyzing features in medical imaging data, immune infiltration data analysis, DNA sequencing data analysis, organoid development analysis, and/or other modality analyses.

The multimodal normalization framework 14902 includes a modal identifier 14904 and a gene expression data normalizer 14906. Gene expression datasets are provided to, or accessed by, the framework 14902 for normalization processing. The modal identifier 14904 is configured to receive the gene expression datasets and analyze gene expression data therein to determine if any of gene expression data exhibits more than one modal expression peak. Such analysis may be performed on each gene expression data within the received dataset. Multimodal gene expression data is gene expression data that exhibits multiple modals of expression within the same population, i.e., multiple expression distribution peaks. For example, FIG. 331 illustrates gene expression data for ESR1 exhibiting a bimodal distribution with two peaks, labeled at L and R. These expression peaks may result from two different factors, such as tumor type and tissue type, which each affect ESR1 expression in this example. More generally, multimodal gene expression data can exhibit expression peaks due to a number of different factors, including, but not limited to, tissue type, cancer type, purity of tumor within sample (for example with different peaks due to different purity levels, 10%, 20%, 30%, 40%, at least 50%, at least 60%, at least 70%, at least 80%, and at least 90%), cell type (immune, lymphocyte, red blood cell, cytotoxic T cells, B cells, NK cells, macrophages, etc.), and sex of subject. Cancer types may include, but are not limited to, epithelial ovarian carcinoma, colon cancer, esophageal cancer, melanoma, endometrial cancer, and breast cancer. Other factors include batch effects, such as, differences in bioinformatics pipelines used to generate the gene expression datasets, differences in sequencing machines, dates of collection of gene expression data, and contamination of tissue.

The modal identifier 14904 is configured to apply a regression technique to identify the one or more modal expression peaks in the gene expression data. In an example, the modal identifier 14904 is configured as a Decision Tree Regressor. For a bimodal distribution, for example, the modal identifier 14904 may implement a 2-Leaf Decision Tree Regressor that performs an auto-encoding on the gene expression data to identify two distribution peaks that minimize the mean square error (MSE) within the distribution data. The resulting two distribution peaks then are the lower and upper peak points in the gene expression data.

The gene expression data normalizer 14906 receives the modal distribution peak data and gene expression data from the identifier 14904 and performs a normalization on the gene expression data. FIG. 332 illustrates an example normalization process 15000 performed by the multimodal framework 14902 on the gene expression data of FIG. 331. The initial gene expression data 15002, such as an RNA seq dataset, is received at the modal identifier 14904, which identifies (at process 15004) one or more modal expression peaks in gene expression data within the dataset 15002. The gene expression data normalizer 14906 normalizes the one or more modal expression peaks by applying a normalization rule that, in the illustrated example, normalizes a spacing distance between modal expression peaks. In the example of a bimodal distribution like that of FIG. 331, the normalizer sets a spacing distance of 1 between the identified peaks, resulting in the normalized distribution of FIG. 15. In the example of more than two distribution peaks, the normalizer 14906 may set an equal spacing distance between each of the distribution peaks. In yet another example, when there are more than two distribution peaks, the normalizer 14906 may establish a normalized spacing distance (e.g., a distance of 1), between the outermost peaks. Take for example, using a 2-Leaf Decision Tree Regressor approach, the normalizer 14906 may be configured to optimize for the best point between auxiliary peaks (i.e., any of the peaks) to minimize overall mean-squared error in the distribution. In another example, a Decision Tree Regressor having enough leaves to match the number of peaks may be used, in which example, the normalizer 14906 may be configured to perform a unit-norm between the outermost peaks, or configured to performed a unit-norm between inner-most peaks. In yet other examples of these multiple leaf Decision Tree Regressors, the normalizer 14906 may be configured to proportionally space distance between detected peaks based on their individual proximity (e.g., with one far left peak and two right side peaks, the normalizer could be configured to place the left peak at −0.5, and the inner-most right peak at +0.5, and the outer most right peak at +1.0, etc). In an example, the normalizer determines the spacing distance by dividing the peak expression values (R and L) by a delta value between the R and L such that the distance between them is a normalization value, such as 1.0, resulting in normalized peaks R' and L' as shown in FIG. 333.

Optionally, in some examples, the process 15006 further performs a shift on the normalized spacing gene expression data to align the peaks around a reference baseline expression value, such as a zero (0) expression. An example shift applied to the normalized bimodal gene expression data of FIG. 333 is shown in FIG. 334, resulting in shifted peaks Ls and Rs centered around a zero reference value. As a result of the shifting, over expression and under expression can be identified more readily in the gene expression data.

The normalized gene expression data is then stored in a normalized gene expression dataset at process 15008. In some examples, the process 15008 may remove the un-normalized gene expression data from the dataset 15002 and replace that data with the normalized gene expression data. In some examples, the normalized gene expression data may be added to the dataset 15002. In yet other examples, the normalized gene expression data is added to a separate normalized gene expression dataset 14908 (shown in FIG. 330).

This normalization may be applied across all gene expression data within the dataset 15002 to generate a normalized gene expression dataset that aligns each of the different gene expression data within the dataset. At a process 15010, the framework 14902 determines if there is additional gene expression data within the dataset to be normalized, and if so the process 14900 repeats applying the distribution peak spacing normalization rule (and optional shifting rule) to each subsequent gene expression data, until a completed normalized gene expression dataset 15012 (e.g., dataset 14908) is formed.

FIG. 335A shows example gene expression data corresponding to four different genes (AR, PGR, ESR1, and ERBB2) prior to normalization. Each of the gene expression data exhibits bimodal distribution peaks, for example, resulting from different expression of the gene in different tissue. FIG. 335B illustrates the gene expression data after normalization applied by the process 15000 of the framework 14902. As shown, the normalized gene expression data has the bimodal distribution peaks aligned, L and R, and centered around a zero reference expression.

The normalization of process 15000 may be applied to gene expression data exhibiting uni-modal expression distribution, such as shown in FIG. 336. With the modal identifier 14904 configured as a bimodal peak identifier (e.g., a 2-Leaf Distribution Tree Regressor), the framework 14902 identifies imposed "peaks" on the distribution as the locations on the distribution that minimize the mean-square error for the distribution. With these imposed "peaks" identified, the normalizer 14906 may perform a transformation on the data to establish a normalized spacing between these peaks and another, linear transformation to shift the distribution. FIG. 337A illustrates uni-modal gene expression data for genes BRCA1, BRCA2, and PIK3CA prior to normalization by the process 15000, and FIG. 337B illustrates the corresponding normalized gene expression data after the process 15000.

By identifying and normalization multi-modal gene expression data within a dataset, such as within the RNA transcriptome, an gene sequence analyzer, such as the RNA Seq analyzer 14704 in FIG. 325, is able to generate more accurate gene expression data for more accurate identification of population groups, suggested treatments, biomarker discovery, molecular sub-type clustering and identification, population clustering visualization, etc. For example, with a modal identifier configured as a bimodal identifier, a normalized gene expression dataset is formed where one of the expression factors may be isolated out from affecting analysis. FIG. 338A illustrates a Uniform Manifold Approximation and Projection (UMAP) plot of ESR1 gene expression data prior to normalization. The UMAP plot shows a large distance between two different clusters, A and B: one that corresponds to expression data captured from a first tissue type, in this case liver tissue, and another (B) that corresponds to a second tissue type, breast tissue. The distances between the clusters demonstrates that any attempt to use the UMAP to identify ESR1 expression is tissue dependent. FIG. 338B illustrates another UMAP plot but after normalization, where tissue dependence, as shown, has been removed from the data. The UMAP visualization of the gene expression data is achieved computationally faster or more accurately with removed tissue using the normalization process. The same computational speed efficiency and tissue removal accuracy can be achieved in other visualization techniques, including principal component analysis (PCA) and t-Distributed Stochastic Neighbor Embedding (t-SNE). Indeed, the computationally efficiencies are considerable for visualizations such as UMAP, which is generally faster than t-SNE and generally is more accurate than PCA. With the normalization techniques herein, a RNA Seq analyzer can generate more accurate gene expression data reports, as a result. More generally, with the normalized data, the RNA Seq analyzer can more accurately identify samples based on expression values for ESR1, with the tissue dependence removed. Moreover, the RNA Seq analyzer can remove tissue dependence (or any other factor being considered against cancer in a bimodal analysis configuration) across all gene expression data. Thus, with the present techniques, gene expression data for different genes (and thus for different cancer types) can be normalized to be tissue independent, thereby allowing an RNA Seq analyzer to more quickly and more accurately identify cancer type for a subject irrespective of whether the tissue sample is from a primary site of cancer or a secondary malignant cancer site.

In some aspects, the GC bias length may be normalized in order to more effectively permit comparison of gene expression in a single sample. In some aspects, the read depth and gene length may be normalized to more effectively permit comparison of gene expression across multiple samples. The normalization may be performed on a set of paired-end RNA reads or a set of single-end RNA reads. The normalization may be performed on RNA-seq data or other RNA data that is generated using methods known in the art.

In one aspect, a normalized set of RNA may be utilized in connection with expression calling. Prior to normalization, samples may be biased by the depth of sequencing.

Comparison of transcriptome measures from among samples may be biased by depth of sequencing. Normalization permits comparison of expression levels of a single gene across samples. For instance, when calling overexpression of a gene, the overexpression may be made with respect to expression of other samples. As an example, sequencing of 20 breast cancer specimens at a depth of 20 million reads may result in 100 reads of the ESR1 estrogen receptor gene for each sequenced specimen. Sequencing of another 20 breast cancer specimens at patients at a depth of 40 million reads may result in 200 reads of the ESR1 estrogen receptor gene for each sequenced specimen.

Normalizing the two data sets permits normalization of the read count across the two data sets.

As another example, a normalized RNA data set may be utilized in connection with a tumor of unknown origin predictor model. The model may have to learn certain parameters for each gene. To apply those parameters to each gene among many different specimens, it is preferred that the gene expression value look the same across patients. If the model, for example, applies an estrogen level read depth by a factor of two, the model will be biased by the read depth. Where the tumor of unknown origin predictor model is formed as, for example, a linear model, each gene is provided with a weight by which the associated expression level is multiplied.

As another example, a normalized RNA data set may be utilized in connection with one or more methods to cluster samples in order, for instance, to identify disease subtypes. By comparing RNA expression levels among samples, clustering may be utilized to suggest those samples that are most similar to one another. In some embodiments, the normalization may be limited to normalizing read depth among samples. In other embodiments, the normalization may be limited to normalizing read depth and GC content. In other embodiments, the normalization may comprise normalization of read depth, GC content, and gene length. In an example, a set of normalized RNA transcriptomes may be matched with IHC staining information to identify cohorts of specimens with HER2+ status. For example, in a cohort of 400 specimens, 300 of the specimens may have an associated IHC stain and 100 do not. For the 100 that do not, an IHC prediction model may be used to predict the IHC status and then UMAP clustering may be utilized to cluster the specimens.

Specimens with a normalized expression of ESR1 (for ER) or PGR (for PR) or ERBB2 (for HER2) above a pre-defined threshold may be stratified. In one embodiment the threshold is 2.5. Some specimens may have data available for ER, PR, and HER2 in which case the specimen is displayed in FIG. 339 as a circle. Other specimens may not have data available for ER, PR, or HER2 in which case the specimen may be displayed in FIG. 339 as an X mark.

As another example, a RNA normalization may be utilized to compare gene expression levels relative to each other within a sample. In some aspects, GC bias may be present in gene length. For example, if gene A is 100 kb and gene B is 200 kb, the same number of RNA molecules may exist for gene. However, gene B would have twice the counts of gene A because gene B's RNA molecule is twice the size. During PCR amplification in library prep, if a fragment has about 50% GC content it will have a first level of amplification. If, on the other hand, the GC content deviates significantly from 50% GC content, it will not amplify as well. For example, the GC content may deviate significantly if it has 80% content. A first gene with a first percentage GC content closer to 50% GC content and a second gene with a second percentage GC content that significantly deviates from the first gene content can have the same number of RNA molecules in the cell but the first GC content gene will have been amplified more than the second GC content gene during PCR amplification. RNA normalization of GC content may be utilized within a sample to compare the GC content of a first gene to the GC content of a second gene.

In another aspect, RNA normalization may be utilized in connection with a drug response model. In an exemplary drug response model, the model may multiply each gene expression value by a number the model has learned. The model may be trained on read depth normalized data and may be utilized to predict drug response using RNA expression information that has been normalized in a like fashion to the training RNA expression information. For instance, the drug response model may take the form $y = a_1 \times 1 + a_2 \times 2 + \ldots + a_n \times n$, where $a_1, a_2, \ldots, a_n$ are weights and $x_1, x_2, \ldots, x_n$ are genes. If $y<1$ then the model may be set to not respond to the particular drug that is the focus of the model. If $y >1$ the model may be set to respond to the particular drug that is the focus of the model.

In another aspect, RNA normalization may be utilized in connection with an assessment of pathway activity. For example, RNA expression data may be normalized as to GC content and length. For example, in the field of single sample gene set enrichment analysis, each gene's transcription levels may be normalized to adjust for GC bias in order to develop a ranked list of normalized gene expression values. The expression values of a pre-defined gene list, reflecting genes known to be associated with a pathway, may be examined in order to identify whether the genes in associated with the pathway are overexpressed, underexpressed, or a combination thereof that is relevant to the pathway. In this way, a set of normalized RNA data may be utilized to identify an activated pathway in the specimen.

In another aspect, RNA normalization may be utilized in connection with a comparison of expression levels of a given gene among a set of patients. For instance the read depth may be normalized in order to compare the expression levels of a BRAF mutation among patients.

In another aspect, RNA normalization may be utilized in connection with analysis of RNA expression information in order to identify potential sample swaps or input missing data. For example, a model $y=a1 \times 1 + a2 \times 2 + \ldots + an \times n$, where $a1, a2, \ldots, an$ are weights and $x1, x2, \ldots, xn$ are genes may be trained on a set of RNA expression information and the patient's gender. Read count and GC count may be normalized across the applicable RNA data set. By inputting the normalized RNA expression information of a new specimen, normalized in a like fashion to the training data set, it is possible to determine whether the specimen is from a male patient or a female patient. If the gender of the patient from whom the specimen was received was reported as male, but the gender analysis indicates the specimen came from a female person, the disparity would indicate a quality control process to confirm whether the specimen was the result of a sample swap, was taken from a patient who had a gender reassignment, or was from a patient whose gender was mis-identified in the patient's electronic health record.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternative embodiments, using either current technology or technology developed after the filing date of this application.

XIX. A Pan-Cancer Model to Predict the PD-L1 Status of a Cancer Cell Sample Using RNA Expression Data and Other Patient Data Definitions As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the therapeutic agent being administered.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the treatment determined by the methods of the present disclosure can provide any amount or any level of treatment. Furthermore, the treatment can include treatment of one or more conditions or symptoms or signs of the cancer being treated. The treatment can encompass slowing the progression of the cancer. For example, the treatment can treat cancer by virtue of enhancing the T cell activity or an immune response against the cancer, reducing tumor or cancer growth or tumor burden, reducing metastasis of tumor cells, increasing cell death of tumor or cancer cells or increasing tumor regression, and the like. In accordance with the foregoing, provided herein are methods of determining treatment for reducing tumor growth or tumor burden or increasing tumor regression in a subject. Also, provided herein are methods of determining treatment for enhancing T cell activity or an immune response against a cancer. In exemplary embodiments, the treatment is an immune checkpoint blockage therapy, e.g., a therapy comprising treatment with one or more of ipilimumab, nivolumab, pembrolizumab, atezolizumab, avelumab, durvalumab, and the subject's CDSI report indicates a positive PD-L1 expression status.

In various aspects, the treatment treats by way of delaying the onset or recurrence of the cancer by at least 1 day, 2 days, 4 days, 6 days, 8 days, 10 days, 15 days, 30 days, two months, 3 months, 4 months, 6 months, 1 year, 2 years, 3 years, 4 years, or more. In various aspects, the methods treat by way increasing the survival of the subject. In exemplary aspects, the treatment provides therapy by way of delaying the occurrence or onset of a metastasis. In various instances, the treatment provides therapy by way of delaying the occurrence or onset of a new metastasis. Accordingly, the treatment determined by the presently disclosed methods can treat by way of delaying the occurrence or onset of a metastasis in a subject with cancer.

Although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

Human PD-L1 is also known as CD274, B7-H, B7H1, PDL1, PD-L1, PDCD1L1, and PDCD1LG1. The amino acid sequence and mRNA sequence of human PD-L1 are publicly available at the National Center of Biotechnology Information website as Accession Nos. NP001254635.1 (amino acid sequence) and NM_001267706.1 (mRNA sequence). Additional isoforms are known in the art. The gene encoding PD-L1 is located in the human genome at chromosome 9. PD-L1 is known as an immune inhibitory receptor ligand expressed by antigen-presenting cells, macrophages, T cells, and B cells in addition to various types of tumor cells. The interaction of PD-L1 with its receptor, PD-1, leads to inhibition of T cell activation and cytokine production. Thus, it is part of the immune checkpoint pathway and is relevant for preventing autoimmune responses. In the tumor setting, however, interaction of PD-L1 to PD-1 leads to immune escape for the tumor cells. Inhibiting the PD-L1:PD-1 interaction and other checkpoint molecule interactions has become a large focus of cancer research. The development of several therapeutic agents for immune checkpoint blockade therapy has led to the Food and Drug Administration (FDA)-approval of ipilimumab, nivolumab, pembrolizumab, atezolizumab, avelumab, durvalumab, and combinations thereof for the treatment of melanoma, non-small cell lung cancer, renal cell carcinoma, Hodgkin lymphoma, urothelial carcinoma, head and neck squamous cell carcinoma, Merkel cell carcinoma, hepatocellular carcinoma, gastric and gastroesophageal carcinoma, colorectal cancer, and solid tumors (Wei et al., Cancer Discovery (2018); doi: 10.1158/2159-8290.CD-18-0367). In addition to PD-L1, other actors involved in the immune checkpoint pathway include the inhibitory receptors CTLA-4, PD-1, PD-L2, B7-H3, B7-H4, CEACAM-1, TIGIT, LAG3, CD112, CD112R, CD96, TIM3, BTLA, VISTA, and the co-stimulatory receptors ICOS, OX40, 4-1BB, CD27, CD40, and GITR. See, e.g., Wei et al., 2018, supra.

As discussed above, expression of PD-L1 can predict whether immunotherapy treatments, especially immune checkpoint blockade treatments, are likely to successfully eliminate or reduce the number of the patient's cancer cells. While methods of determining PD-L1 status exist, these methods are time-consuming and require relatively large amounts of patient sample (biopsied tissue) which often leads to patient discomfort and inconvenience. In the context of nucleic acid sequencing of patient tumor tissue, additional tissue may not be available for IHC but the sequencing data (RNA sequencing data in particular) represent a source of information that can be used to infer the patient's PD-L1 status. Furthermore, depending on the cancer type, PD-L1 IHC tests are not always ordered, but it may be clinically important to determine whether PD-L1 IHC is a reasonable test to perform as part of clinical decision-making.

Thus, the present disclosure provides a computer-implemented method of identifying programmed-death ligand 1 (PD-L1) expression status of a subject's sample comprising cancer cells. In exemplary aspects, the method comprises (a) receiving an unlabeled expression data set for the subject's sample; (b) aligning the unlabeled expression data set to labeled expression data according to a trained PD-L1 predictive model, wherein the trained PD-L1 predictive model has been trained with a plurality of labeled expression data sets, each labeled expression data set comprising expression data for a sample of a labeled cancer type and a labeled PD-L1 expression status; wherein aligning the unlabeled gene expression data set to labeled expression data according to the trained PD-L1 predictive model identifies PD-L1 expression status for the subject's sample.

As used herein, the term "subject's sample" refers to a biological sample obtained from a subject. In exemplary aspects, the subject's sample comprises a cancer cell. In some embodiments, the sample comprises a bodily fluid, including, but not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of the foregoing samples. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis).

In some embodiments, the subject is a human. In some embodiments, the subject (e.g., human) has cancer.

The cancer referenced herein may be any cancer, e.g., any malignant growth or tumor caused by abnormal and uncontrolled cell division that may spread to other parts of the body through the lymphatic system or the bloodstream. In exemplary aspects, the cancer is one selected from the following cancer types: acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma.

With regard to the presently disclosed computer-implemented method, the plurality of labeled expression data sets comprises expression data for samples of a single cancer type. In this manner, the trained PD-L1 predictive model is considered to be tailored to or specific for one cancer type. In alternative embodiments, the plurality of labeled expression data sets comprises expression data for samples of 2 or more (e.g., 3, 4, 5, 6, 7, 8, 9, 10 or more) cancer types. In such cases, the trained PD-L1 predictive model is considered a "pan-cancer" model. In exemplary aspects, wherein the plurality of labeled expression data sets comprises expression data for breast cancer, prostate cancer, colorectal cancer, lung cancer, skin cancer, kidney cancer, pancreatic cancer, stomach cancer, or a combination thereof. In various instances, the plurality of labeled expression data sets comprises expression data for a subtype of one or more of the labeled cancer type(s), optionally, a subtype of breast cancer. For example, the subtype for breast cancer is, in some aspects, luminal breast cancer, triple negative breast, or a combination thereof. Optionally, the plurality of labeled expression data sets comprises expression data for lung adenocarcinoma, melanoma, renal cell carcinoma, bladder cancer, mesothelioma, and lung small cell cancer.

In exemplary embodiments, each labeled expression data set further comprises data from images, image features, clinical data, epigenetic data, pharmacogenetic data, metabolomics data, or a combination thereof. In exemplary embodiments the labeled expression data comprises RNA expression data, optionally, mRNA expression data. In some aspects, the mRNA expression data is RNA-seq data, optionally, normalized RNA-seq data.

In exemplary instances, the labeled PD-L1 expression status is based on a reverse phase protein array (RPPA) data, fluorescence in situ hybridization (FISH) data, immunohistochemistry (IHC) data, or a combination thereof, optionally, wherein the trained PD-L1 predictive model correlates the labeled PD-L1 expression status with select labeled expression data and/or labeled features.

In exemplary embodiments, the unlabeled expression data set is similar to the labeled expression data set, except that the unlabeled expression data set does not comprise PD-L1 expression status of the subject's sample. In exemplary embodiments, the unlabeled expression data set comprises data from images, image features, clinical data, epigenetic data, pharmacogenetic data, metabolomics data, or a combination thereof, of the subject. In some aspects, the unlabeled expression data set for the sample comprises RNA expression data, optionally, mRNA expression data. In some aspects, the mRNA expression data is RNA-seq data, optionally, normalized RNA-seq data.

In exemplary aspects, the trained PD-L1 predictive model has been trained by (i) inputting a plurality of labeled expression data sets, wherein each labeled expression data set comprises a labeled cancer type and a labeled PD-L1 expression status, and, optionally, one or more labeled features. In exemplary embodiments, the trained predictive model has been trained with a plurality of labeled expression data sets, each labeled expression data set comprises one or more labeled features, and the trained PD-L1 predictive model has been trained according to select labeled features pre-determined to have an association with a phenotype of biological relevance. In exemplar aspects, the trained PD-L1 predictive model was trained using a clustering algorithm to determine which labeled features associate with the phenotype of biological relevance. In some instances, the phenotype of biological relevance is PD-L1 expression status. In alternative or additional aspects, the at least one or more of the select labeled features comprises expression data for at least one gene selected from the group consisting of CD274, TIGIT, CXCL13, IL21, FASLG, TFPI2, GAGE12C, POMC, PAX6, NPHS1, HLA-DPB1, PDCD1, PDCD1LG2, and other genes obtained from the feature selection process. In other aspects, the gene list includes IFNG, GZMB, CXCL9, TGFB1, VIM, STX2, ZEB2, and other genes found via literature search. Optionally, the trained PD-L1 predictive model is a logistic regression model, a random forest model, or a support vector machine (SVM) model, optionally, wherein the logistic regression model is a single-gene or multi-gene logistic regression model.

With regard to the methods of the present disclosure, the methods may include additional steps. For example, the method may include repeating one or more of the recited step(s) of the method. Accordingly, in exemplary aspects, the method comprises re-determining a ratio RS. In exemplary aspects, the method comprises aligning the unlabeled expression data set to labeled expression data according to a trained PD-L1 predictive model every 2, 3, 6, or 12 months, as needed. The method in some aspects further comprises one or more of: obtaining the sample from a subject, isolating mRNA from cells of the sample, fragmenting the mRNA, producing double-stranded cDNA based on the mRNA fragments, carrying out high throughput, short-read sequencing on the cDNA, aligning the sequences to a reference genome, and normalizing raw RNA-seq data.

In some aspects, the method further comprises generating a clinical decision support information (CDSI) report including at least the subject's identity and the identified PD-L1 expression status, and, optionally, providing the CDSI report to a healthcare provider for use in selecting a candidate therapy based on the identified PD-L1 expression status for the subject's sample. Optionally, the high throughput, short-read sequencing is next generation sequencing (NGS), optionally, wherein the NGS comprises hybrid capture. In various instances, the hybrid capture comprises use of biotinylated probes which bind to specific target nucleotide sequences. In exemplary aspects, at least one of the target nucleotide sequences encodes PD-L1, PD-1, or a combination thereof. Alternatively or additionally, at least one of the target nucleotide sequences encodes 4-1BB, TIM-3, or other immune checkpoint molecules.

Any and all possible combinations of the steps described herein are contemplated for purposes of the presently disclosed methods.

The following discussion is given merely to illustrate the present disclosure and not in any way to limit its scope.

FIG. 340A illustrates an exemplary PD-L1 predictor 15115. As illustrated in FIG. 340A, a genetic sequence analysis technique may be used to detect RNA molecule copies of a plurality of genes, known as transcripts, in a sample of cancer cells collected from a patient. RNA sequencing (RNA-seq), also known as whole transcriptome shotgun sequencing (WTSS), is a powerful technique that utilizes next-generation sequencing to identify the presence and quantity of RNA in a biological sample at a particular timepoint. RNA-seq is useful for determining and analyzing the ever-changing transcriptome of a cell or tissue. This technique can identify alternatively spliced transcripts, post-transcriptional modifications, gene fusions, mutations or single nucleotide polymorphisms (SNPs) and changes in gene expression over a given time period (e.g., over disease progression or disease regression) and/or upon different treatments (e.g., treatment with one therapeutic agent vs. another vs. no treatment). RNA-seq also allows for the determination of exon/intron boundaries and annotated 5' and 3' gene boundaries. In an exemplary embodiment of RNA-seq, messenger RNA (mRNA), produced in vivo by an organism, is extracted from the organism, fragmented, and in vitro copied into double-stranded complementary DNA (ds-cDNA), which is then sequenced using high-throughput, short-read sequencing methods. The sequences are then aligned to a reference genome, obtained from public reference databases, in silico to identify the regions of the organism's genome that were transcribed at the time the mRNA was extracted from the organism.

Still with reference to FIG. 340A, the count for each gene, which is the number of detected transcripts, is stored as RNA transcriptome sequencing (RNA-seq) data. In the example shown, these data are referred to as raw RNA-seq data 15105.

The genetic sequence analysis technique may be biased in a way that causes counts for certain genes to be higher than others, depending on factors which include the length of the gene, the depth setting of the sequence analyzer used in the sequence analysis technique, and the percentage of the gene that contains guanine (G) or cytosine (C), compared to adenine (A) or thymine (T). These biases may cause artifacts, which means that counts for a certain gene would be an inaccurate reflection of the number of transcripts of that genes that actually exist in a sample. An RNA bioinformatics pipeline software 15110 generates normalized RNA-seq data by aligning and adjusting the counts for each gene in raw RNA-seq data 15105 to counteract any artifacts caused by the genetic sequence analysis technique.

The disclosure further includes a PD-L1 status predictor 15115 that receives an input case data set 15112 associated with a cancer cell sample and predicts the PD-L1 status 15120 of the cancer cell sample. In one example, the PD-L1 status predictor 15115 is pan-cancer, meaning that the cancer cell sample receiving a predicted PD-L1 status 15120 may have been collected from a patient with any type or subtype of cancer. For example, cancer types may include brain, lung, breast, colorectal, pancreatic, liver, stomach, skin, etc. and cancer subtypes may include any sub-group within each cancer type, including luminal breast, triple negative breast and other subtypes known in the art. In this example, an input case data set 15112 includes normalized RNA-seq data. The predicted PD-L1 status 15120 may be included in a report 15125. The report 15125 may include a printed report on paper, an electronic document, or a tab or page accessed through an online portal.

The patient or a medical professional 15130, including a physician, nurse, or other trained medical professional, may access the report 15125 and make a case management decision 15135, based in part on the predicted PD-L1 status 15120. A case management decision 15135 may include prescribing a treatment, ordering an IHC, FISH, or RPPA test of the cancer cells, or another medical action that aims to eliminate or slow the progression of a patient's cancer. For instance, a physician may prescribe checkpoint blockade therapies depending on PD-L1 thresholds. For instance, if the PD-L1 biomarker threshold is 50%, the physician may prescribe a checkpoint blockade as a patient's first line therapy. If more than 1% of the patient's cells have stained positive for PD-L1 and the patient has failed first line therapy, the physician may prescribe a checkpoint blockade as a second line of therapy.

The PD-L1 status predictor 15115 may be a predictive model and/or may be a machine learning algorithm, including random forest, support vector machine (SVM), or logistic regression models. In one example, the PD-L1 status predictor 15115 is a single gene or multi-gene logistic regression model (see FIG. 343). The model software of the PD-L1 status predictor 15115 may be encoded in a docker container such that the software may be run on any platform or operating system.

In this example, the genetic sequence analysis technique may be a next generation sequencing (NGS) assay. The NGS assay may require the preparatory steps of isolating RNA molecules from a patient sample of cells to create a liquid solution containing RNA molecules, measuring the concentration of the RNA molecules in the liquid solution, measuring the average length of the RNA molecules, shortening the RNA molecules if necessary, and creating and collecting DNA copies of the RNA molecules with hybrid capture. Then, the NGS device receives the DNA copies, then detects and reports short-read nucleotide sequences within the DNA copies. In another example, the NGS device may detect and report long-read sequences. Hybrid capture may utilize biotinylated probes to bind to specific target nucleotide sequences within the nucleic acid molecules (DNA copies or RNA) to amplify and collect nucleic acid molecules containing those targeted nucleotide sequences.

Each detected, reported sequence is called a read. The NGS device reports each read that it detects and the number of times (counts) that it detects each read. This report is referred to as raw RNA-seq data 15105. The detected sequence of each DNA molecule copy corresponds to a sequence in an RNA molecule from which that DNA molecule was copied. The counts in the raw RNA-seq data 15105 for each detected sequence may not reflect the actual number of nucleic acids in the patient sample that contain that sequence, due to artifacts that may be caused by steps in the genetic sequence analysis technique. For example, hybrid capture and amplification may be more likely to create copies of sequences that contain a certain percentage of guanine (G) and cytosine (C) nucleotides, versus adenine (A) and thymine (T) nucleotides. These detected sequence counts may be higher than is expected for the actual number of molecules in the sample that contain these sequences. Other factors that may cause artifacts include the length of a gene from which the sequence is copied and sequencing depth.

The RNA bioinformatics pipeline software 15110 receives the raw RNA-seq data 15105 and determines the most likely location of each read within the entire human genome by comparing the read to a reference genome. The RNA bioinformatics pipeline software 15110 also adjusts the count of each sequence to counteract the effect of any artifacts or biases introduced by the sequence analysis method. This process may be referred to as normalization. Methods of normalizing gene expression data are disclosed in U.S. Provisional Patent Application No. 62/735,349, which is incorporated by reference in its entirety.

Although the systems and methods disclosed herein have been described with specificity for PD-L1, it should be understood that the status of other proteins may be predicted using similar analysis. Other proteins include, but are not limited to, 4-1BB, T-cell immunoglobulin and mucin-domain containing-3 (TIM-3), other immune checkpoint molecules, human epidermal growth factor receptor 2 (HER2), estrogen receptor (ER), and progesterone receptor (PR or PgR). Additionally, this system may be used to predict whether a patient will respond to immune checkpoint blockade therapy and/or another type of cancer treatment.

FIG. 340B illustrates an exemplary predicted PD-L1 status 15120 as it may appear on a report 15125. In this example, the report 15125 is associated with a cancer sample, which is further associated with a predicted PD-L1 status 15120 presented in the report. In this example, the predicted PD-L1 status 15120 is negative, versus equivocal or positive. The report 15125 may further include the CD274 expression level value detected in the associated cancer cell sample. In this example, the cancer sample CD274 expression level value is 0.60.

Predicted PD-L1 status 15120 may appear as an additional predicted label associated with a prediction probability 15122 alongside text describing the predictor and implications of the prediction probability. In this example, the PD-L1 positive prediction probability value 15122, which is 0.24, is a numerical output of the PD-L1 predictor 15115, and is a value in a range of approximately 0 through 1 that indicates the probability that the cancer sample is positive for PD-L1. An error analysis may be used to determine the correlation between the PD-L1 positive prediction probability value 15122 and qualitative predicted PD-L1 status 15120, including negative, equivocal, or positive. (See FIG. 341A)

The report 15125 may further include a cancer CD274 histogram 15140a depicting the distribution of CD274 expression levels detected in cancer samples having the same cancer type as the cancer sample associated with the report 15125. The report 15125 may further include a normal CD274 histogram 15140b depicting the distribution of CD274 expression levels detected in a plurality of normal tissue samples. The normal tissue may be of a tissue type that specifically corresponds to the cancer type associated with the cancer sample. For example, a reference set of non-cancerous skin samples may be used as a reference for a patient with melanoma. These may be visualized together using histograms or other plots. The cancer CD274 histogram 15140a and the normal CD274 histogram 15140b may be located in such a way that represents the relationship between the ranges of expression level values represented by the two histograms. In this example, the majority of the cancer CD274 histogram 15140a is located to the right of the majority of the normal CD274 histogram 15140b with some overlapping to indicate that the cancer CD274 histogram 15140a represents a higher range of values than the normal CD274 histogram 15140b.

The report 15125 may further include a patient CD274 expression level indicator 15140c demonstrating the approximate location of the cancer sample CD274 expression level within the range of expression level values represented by the histograms 15140a and/or 15140b. In this example, the patient CD274 expression level indicator 15140c is located near the right edge of the normal CD274 histogram 15140b and the left edge of the cancer CD274 histogram 15140a. This location of patient CD274 expression level indicator 15140c represents that the cancer sample CD274 expression level value is greater than the majority of the CD274 expression level values represented by the normal CD274 histogram 15140b, and less than the majority of the CD274 expression level values represented by the cancer CD274 histogram 15140a. Alternatively, a report 15125 may include percentile values indicating the percentile of normal tissue or cancer sample CD274 expression level value ranges in which the detected CD274 expression level value lies.

In another example, the report 15125 further includes treatment recommendations based on predicted PD-L1 status 15120 and information from the patient's RNA-seq data 15310, genetic data 15330 and medical record 15325, including treatments that the patient has previously received and any recorded response or change in the health of the patient after the treatment was received. These treatments may include immune checkpoint blockade therapy. In another example, the histograms 15140a and 15140b, indicator 15140c, and the numerical expression level value shown may indicate the distribution of expression levels for another gene, especially if PD-L1 is not the treatment-related molecule of interest for which a presence status is predicted by predictor 15115.

In another example, the predicted PD-L1 status label 15120 may be "positive for PD-L1", "negative for PD-L1", or "uncertain/equivocal/testing recommended" and may include a recommendation that the cancer cell sample be tested by IHC, FISH, and/or RPPA to detect PD-L1 proteins.

In one example, the predicted PD-L1 status label 15120 may include the percentage of cancer cells in the cancer cell sample that are predicted to stain positive for PD-L1. If the predicted percentage of cancer cells that stain positive for PD-L1 is less than a selected threshold value, the predicted PD-L1 status is negative. If the predicted percentage of cancer cells that stain positive for PD-L1 is greater than a selected threshold value, the predicted PD-L1 status is positive. In one example, if the predicted percentage of cancer cells that stain positive for PD-L1 is approximately equal to a selected threshold value, or within a selected range of values, the predicted PD-L1 status is uncertain. In one example, the selected threshold value is 1% and the selected range is 1-5%. In another example, the selected threshold value is between 0.1% and 1%. In another example, the selected threshold value is between 0.01% and 0.1%.

FIG. 341A illustrates a method 15201 for training a PD-L1 status predictor 15115 and predicting a PD-L1 status label using a PD-L1 status predictor 15115.

Step 15205 is the step of receiving a labeled data set. The labeled data set 15301 may be associated with multiple cancer cell samples, wherein each cancer cell sample is associated with a positive or negative PD-L1 status label 15305, as determined by IHC, FISH, and/or RPPA (See FIG. 342). The labeled data set 15301 may be a pan-cancer data set, meaning that each cancer cell sample may be collected from a patient with any type or subtype of cancer, and many cancer types and subtypes may be represented by a single labeled data set 15301. The labeled data set 15301 may be further associated with an RNA expression level data set 15310, which may be a normalized RNA-seq data set, images 15315, including radiology and pathology images; imaging features 15320, which include patterns in images 15315 or metrics determined by analyzing images 15315; clinical data 15325, including data extracted from medical records; genetic data 15330 related to DNA molecules contained in the cancer cell sample; epigenetic data 15335; pharmacogenetic data 15340; and metabolomic data 15345.

The curation and assembly of this labeled dataset 15301 can pose obstacles. For example, the ideal RNA expression dataset 15310 associated with the PD-L1 status labels 15305 may involve obtaining IHC tissue from the same tissue sample that is used for nucleic acid isolation and RNA-seq for maximum concordance between the dataset 15310 and the PD-L1 IHC label 15305. Furthermore, a large input RNA dataset needs to be appropriately normalized to allow internal comparisons within a sample and among different samples in terms of gene expression levels. Other obstacles include collecting a large enough specimen through biopsy or blood draw that contains enough cancer cells to create a strong assay signal, successfully genetically sequencing the specimen without failing the standard quality checks associated with NGS and other sequence analysis techniques, and processing the raw data through a bioinformatics pipeline before normalization.

Step 15210 is the optional step of selecting features. A feature is any type of data in the labeled data set that may be correlated with a positive or negative PD-L1 status label 15305. Selected features have been ranked by a metric as being potentially more informative for predicting PD-L1 status than other features from the entire feature set. (See FIG. 341B)

A clustering algorithm 15405 may be used to analyze a labeled data set 15301 to select features and create a filtered data set of only the data associated with those features. The labeled data set 15301 may be adjusted by a variety of calculations before feature selection. A clustering algorithm may include Elastic Net, countclust, Cancer Integration via Multikernel Learning (CIMLR), k-means clustering, principal component analysis (PCA), etc. Elastic Net is available from Scikit-Learn (https://scikit-learn.org/stable/modules/generated/sklearn.linear_model.ElasticNetCV.html), countclust is available from University of Chicago (http://bioconductor.org/packages/release/bioc/html/CountClust.html), and CIMLR is available from Stanford University (https://omictools.com/cimlr-tool).

In one example, features may be selected from one or more published lists of data types observed to be related to PD-L1 protein levels, wherein the data types may include the expression levels of specific genes. Selected features may also be a combination of published data types and data types selected by a clustering algorithm or other method.

Step 15215 is the optional step of biologically analyzing selected features. This step may determine whether any of the selected features measures a biological phenomenon that affects or is affected by the amount of PD-L1 protein that a cell and/or a cell in proximity to the biological phenomenon will produce. This step may include a gene enrichment analysis, which determines whether a list of genes has a disproportionately high number of genes that are involved in a biological pathway that interacts with PD-L1 protein.

For example, the optional biological analysis 15412 may determine whether the protein product of each gene on the selected features list interacts with the PD-L1 protein, affects the expression level values of PD-L1 (for example, by behaving as a transcription factor for the CD274 gene), or is involved in a biological pathway that includes PD-L1 or interacts with the biological pathway that includes PD-L1. The analysis may be performed manually or with the assistance of a computer. In one example of this biological analysis, computer-assisted methods including gene set enrichment analysis (GSEA) and related methods are used to determine the enrichment of the feature list with gene sets of interest, for example a set of genes involved in interferon gamma signaling.

In one example, the cancer type or subtype of each cancer cell sample may affect the expected range of expression levels of the CD274 (PD-L1) gene in that cancer cell sample. Therefore, the cancer type or subtype may affect the CD274 expression level in a cancer cell sample that would correspond to a given IHC-stained cancer cell percentage, for example 1% or 50% of cancer cells on a slide staining positively for PD-L1 protein, or a threshold for declaring a positive PD-L1 status 15305 determined by FISH or RPPA. In this example, the biological analysis of selected features may reveal that a feature or a gene is correlated with a cancer type and/or subtype, and may act as an adjustment factor that serves to scale a CD274 expression level that is specific to one cancer type or subtype to convert it to a universal CD274 expression level that serves to rank CD274 expression levels independently of the cancer cell sample cancer type or subtype.

Step 15220 is the step of training a predictive model with a labeled data set or a filtered data set having only data associated with selected features. For each selected feature, the model may receive data values or data patterns and associates each value or pattern with a probability of being associated with a positive or a negative PD-L1 status label 15305. After this probability association, the trained predictive model can receive an unlabeled input case 15112 associated with a cancer cell sample and assign a predicted PD-L1 status label 15120 to the associated cancer cell sample based on the data values or patterns included in unlabeled input case 15112 and the probabilities associated with each data value or data pattern.

In one example, the data values are mean centered and rescaled before model training. To mean center the expression level values in the labeled data set 15301 for one gene, a mean for that gene may be calculated by averaging the expression level values of all cancer cell samples for that gene, and adjusting the expression level value for each cancer cell sample by subtracting that gene's mean from the expression level value of that gene in each cancer cell sample. Then, the adjusted expression level values may be rescaled by multiplying each adjusted value by a factor k, wherein k is selected so that the standard of deviation of the adjusted, rescaled expression level values from all cancer cell samples, for that gene, equals a selected value. In one example, the selected standard of deviation value is set to one. In one example, these calculations are done using Scikit-learn tools, including as the StandardScaler (https://scikit-learn.org/stable/modules/generated/sklearn.preprocessing.StandardScaler.html).

The predictive model may be a logistic regression model that includes a logistic regression function and logistic regression model coefficients. The logistic regression function may be calculated based on the filtered data set or the labeled data set. In one example, the logistic regression model coefficients are determined by minimizing a loss function, which can be done using stochastic gradient descent.

A brief sketch of the logistic regression function is detailed here. The binary logistic regression problem uses the sigmoid function to map an input to an interval of (0, 1). In logistic regression and other machine learning applications, this mapping corresponds to prediction probabilities 15122.

Given an intercept xo, n features x1, x2, . . . , xn and n feature weights (also known as coefficients) W1, W2, . . . , Wn logistic regression first calculates a linear combination of weighted features, here denoted z. This result is then used as input into the sigmoid function resulting in a prediction probability 15122 for the class. See the embodiments below for examples of feature weight values.

Mathematically, this is written as z=xo+W1×1+W2×2+ . . . +Wn×n

The sigmoid function sigmoid: $\mathbb{R} \rightarrow (0, 1)$ then operates on z as follows:

$$\text{sigmoid}(z) = \frac{1}{1 + e^{-z}}$$

The standard definition in binary logistic regression is to use 0.5 as a decision threshold, such that a calculated sigmoid value, which is the predicted probability 15122, of greater than or equal to 0.5 is classified as positive, and a predicted probability 15122 of less than 0.5 is classified as negative.

In one example, classifying the predicted probability 15122 as a type of predicted PD-L1 status label 15120 (negative, equivocal, or positive), includes selecting a first threshold value and a second threshold value, wherein the second threshold value is greater than the first threshold value. Both threshold values may be equal to a value in the range of 0 through 1. If the predicted probability value 15122 is less than the first threshold value, the predicted probability may be classified as negative. If the predicted probability value 15122 is greater than the first threshold value but less than the second threshold value, the predicted probability 15122 may be classified as equivocal, meaning that the PD-L1 predictor 15115 result has very low confidence in reporting a negative or positive predicted PD-L1 status label 15120. Equivocal may also be known as uncertain. If the predicted probability value 15122 is greater than the second threshold value, the predicted probability 15122 may be classified as positive.

In one example, error analysis may be used to manually or automatically select these first and second threshold values. Error analysis may include using the PD-L1 predictor 15115 to generate a predicted probability value 15122 for each input case 15112 from a labeled validation data set. The labeled validation set is associated with at least one input case 15112 comprised of a cancer cell sample, wherein each cancer cell sample is further associated with selected features data and one PD-L1 status label 15305. The error analysis may further include comparing each predicted probability value 15122 to the associated PD-L1 status label 15305 to determine the relationship between the predicted probability value 15122 and the PD-L1 status label 15305. (See FIG. 341C) The PD-L1 predictor 15115 does not receive the PD-L1 status labels 15305 to generate the predicted probabilities 15122. The labeled validation data set may not have been previously presented to the PD-L1 predictor 15115 during feature selection and/or training.

In one example, feature weights are found by minimizing a loss function. In logistic regression the loss function may be binary cross-entropy.

Binary cross-entropy is formulated as follows:

$$f(\theta) = -\frac{1}{m} + \sum_{i=1}^{m}\left(y^{(i)}\log(h_e(x^{(i)})) + (1 - y^{(i)})\log(1 - h_e(x^{(i)}))\right)$$

Where the loss function J is a function of the model parameters including coefficients, y is an indicator variable that takes on the value of 1 or 0, corresponding to whether the predicted class label is the correct classification. In this equation he(x) is the prediction probability.

Other common loss functions include Regression Loss Functions, Mean Square Error/Quadratic Loss, Mean Absolute Error (MAE), Huber Loss/Smooth MAE, Log cosh Loss, Quantile Loss, etc. One or more cancer cell samples associated with the labeled data set or filtered data set may be withheld from the model during training.

Step 15225 is the optional step of analyzing the accuracy of the trained predictive model. During accuracy analysis, a model may be adjusted to eliminate or add selected features and the model accuracy may be assessed for each list of selected features. Model accuracies may be compared to select a final list of selected features resulting in the highest accuracy.

In one example, the trained predictive model receives at least one withheld cancer cell sample but does not receive or process the PD-L1 statuses 15305 associated with the withheld cancer cell samples. The trained predictive model predicts a PD-L1 status label 15120 for each withheld cancer cell sample. The PD-L1 status 15305 and the predicted PD-L1 status label 15120 associated with each withheld cancer cell sample may be compared to perform a model accuracy analysis 15422.

The model accuracy analysis 15422 may include more than one withheld cancer cell sample, wherein each of the withheld cancer cell samples is associated with a PD-L1 status 15305 and a predicted PD-L1 status label 15120. If the PD-L1 status 15305 and the predicted PD-L1 status label 15120 are both positive, this is a true positive result. If both are negative, this is a true negative result. If the PD-L1 status 15305 is negative and the predicted PD-L1 status label 15120 is positive, this is a false positive result. If the PD-L1 status 15305 is positive and the predicted PD-L1 status label 15120 is negative, this is a false negative result.

The model accuracy analysis 15422 may include plotting a receiver operating characteristic (ROC) curve and computing the area under curve (AUC) for all of the withheld cancer cell sample and/or at least one subset of the withheld cancer cell samples. Evaluation of model performance may also include calculating accuracy, precision (also called positive predictive value), recall (also called sensitivity or true positive rate), specificity (also called true negative rate), false positive rate, adjusted mutual information and other metrics on one or more withheld cancer cell samples. Precision-recall curves may be used for analysis of model precision and recall.

Adjusted mutual information measurements may indicate whether the features of the model were selected by random chance or if the combination of the selected features is statistically unlikely to occur randomly. If the grouping of features were unlikely to occur randomly, this may indicate that it is likely that the selected features have been grouped because they share characteristics that can accurately predict PD-L1 status and/or are biologically related to PD-L1 expression.

In one example, accuracy, precision, recall, specificity and a false positive rate may be calculated according to the following formulae, where TP is the number of true positive results; TN is the number of true negative results; FP is the number of false positive results; and FN is the number of false negative results.

Accuracy=$(TP+TN)/(TP+TN+FP+FN)$

Precision=$TP/(TP+FP)$

Recall=$TP/(TP+FN)$

Specificity=$TN/(TN+FP)$

False Positive Rate=$FP/(FP+TN)$

Step 15230 is the step of receiving an input case data set 15112. The trained predictive model receives input case data set 15112, which includes data associated with a cancer cell sample. The data in input case data set 15112 may be of the same type as the selected features, if the model was trained on a filtered data set. In one example, the input case data set 15112 does not include a PD-L1 status 15305 associated with the cancer cell sample.

Step 15235 is the step of predicting a PD-L1 status label 15120 associated with the cancer cell sample of the input case data set 15112. The trained predictive model predicts the PD-L1 status label 15120 based on the input case data set 15112. If features were selected, the prediction may be based only on the values in input case data set 15112 that are associated with the selected features.

FIG. 341B illustrates an exemplary method for selecting features for a PD-L1 status predictor. In the example shown, the labeled data set 15301 is a holdout labeled data set, wherein holdout means that the data set will only be used for selecting features and not used for training 15220 or model accuracy analysis 15422 of the PD-L1 predictor 15115. In one example, a labeled data set 15301 used for feature selection is not a holdout data set. In this example, the labeled data set 15301 includes a row for each cancer cell sample and a column containing either a numerical representation of the positive or negative PD-L1 status label 15305 associated that cancer cell sample or a numerical representation of the normalized RNA expression level of a gene, for each gene in the human genome. The normalized RNA expression level of a gene may be the normalized number of counts detected by NGS.

In the example shown, before feature selection, the labeled data set 15301 is divided into four subsets such that each cancer cell sample is assigned to one of the subsets and each subset has approximately the same number of cancer cell samples. The subsets are combined to create four different folds such that fold one is composed of subsets 1, 2, and 3, fold two is composed of subsets 1, 2, and 4, fold three is composed of subsets 1, 3, and 4, and fold four is composed of subsets 2, 3, and 4. Each cancer cell sample may be assigned to more than one fold. Each fold may be a subset of the labeled data set 15301. In another example, each cancer cell sample within the adjusted labeled data set to only one of the folds such that each fold has approximately the same number of cancer cell samples.

In another example not shown here, the Elastic Net algorithm from Scikit-Learn is the clustering algorithm 15405 used to analyze the cancer cell samples in each fold to quantify the correlation of the PD-L1 status 15305 of the cancer cell sample and the values stored for each data type associated with the sample. The clustering algorithm 15405 assigns a weight to each data type, wherein the weight is a numeric value that represents the strength of the correlation between the expression level value of the gene in a cancer cell sample and the PD-L1 status 15305 of the cancer cell sample.

For all examples using Elastic Net, parameter tuning may be initialized with a selected value, grid-search, or a default initial value.

Alternatively, in the example shown, the first fold is divided into two subsets: cancer cell samples associated with a positive PD-L1 status 15305 versus cancer cell samples associated with a negative PD-L1 status 15305. The median expression level value is calculated for each gene for each subset. Then, the median difference between the PD-L1 negative median and the PD-L1 positive median is calculated for each gene.

The genes having the highest median differences or median differences greater than a selected threshold value may be selected as features. In one example, the threshold is empirically set at a percentile score that has been selected to ensure that CD274, the feature hypothesized a priori to be most correlated with PD-L1 expression levels, is included in the feature list. In one example, this threshold is defined as the 75th percentile of the group of median difference values observed for all genes in the fold; thus, all features exhibiting a median difference higher than the 75th percentile are selected to produce a list of selected features for that fold.

The clustering algorithm 15405 calculates coefficients, which are also known as weights or selection weights, for each feature and the clustering algorithm 15405 may be Elastic Net. The median difference and feature selection as described is repeated for each fold.

In both examples, the clustering algorithm 15405 assigns a selection weight value to each data type in the fold. The selection weight value reflects the strength of the correlation between each data type and the PD-L1 status 15305 of a cancer cell sample. In one example, the selection weight value is greater if the correlation is stronger. If a data type is a selected feature for more than one fold, the data type is given higher priority to be included in the final list of features for the PD-L1 predictor. In one example, the priority increases for every fold in which the data type has been assigned a weight value that exceeds the fold weight threshold.

Accordingly, the data types are chosen for the final list of selected features and the filtered data set 15410 for training the PD-L1 predictor 15115 based on two values: the average or mean of the selection weight value assigned within each fold to the data type, and the number of folds for which the data type receives a selection weight value that exceeds a threshold. These two values are combined into a score value for each data type. The score for a feature X across k number of folds can thus be defined as $$\text{score}(X) \equiv \frac{1}{k} \sum_{i=1}^{k} [W_{X,i}] \cdot N_X$$

where $W_{X,i}$ is the selection weight value assigned to the feature X in fold i and $N_X$ is the number of times that the feature was above the threshold across k folds. Feature selection methods such as the formulation detailed above can be used as a strategy to improve performance of many predictors based on an improvement of selecting the most informative features.

Dividing the labeled data set 15301 into folds may reduce the likelihood that a gene with naturally variable expression level values that are biologically unrelated to PD-L1 protein levels gets a large score value.

All data types that score above a selected threshold value may be selected as features or the data types may be sorted by score value and any number of the highest-scoring data types may be selected as features. In one example, approximately 40-50 of the highest-scoring data types are selected as features.

These approaches may be applied to the data values of any data type in the labeled data set 15301 to select features and is not limited to gene expression level values.

Multiple embodiments are described below (see FIG. 343), each with a complete exemplary list of selected features and the corresponding exemplary feature weight values in the logistic regression function of the trained predictive model 15420.

FIG. 341C illustrates an analysis used to select thresholds for classifying a PD-L1 prediction probability 15122 as negative, equivocal, or positive. During error analysis, the PD-L1 status label 15305 associated with each cancer cell sample in labeled data set 15301 or a testing data set may be associated with the predicted probability value 15122 generated by the PD-L1 predictor 15115 for that cancer cell sample and plotted to illustrate the relationship between the predicted probability values 15122 and the PD-L1 status label 15305. The testing data set may be identical to labeled data set 15301 except that the data in the testing data set have not been used to train the PD-L1 predictor 15115.

In the error analysis results shown in FIG. 341C, each prediction probability result 15122 is sorted manually or automatically into numeric intervals, based on the prediction probability value 15122. In one example, the automatic sorting is done by the Python pandas.cut function (https://pandas.pydata.org/pandas-docs/version/0.23.4/generated/pandas.cut.html). The boundaries of each interval (indicated on the x-axis) may be manually or automatically selected, and the height of each bar displayed for each interval represents the proportion of predicted probability values 15122 associated with either a negative PD-L1 status label 15305 (blue bars) or a positive PD-L1 status label 15305

(orange bars). In one example, the proportions may be calculated automatically by pandas functions from Python, for example, by using the dataframe methods .groupby, .apply, .value_counts, and .reset_index (https://pandas.py-data.org/). In one example, each interval is called a bin and the negative or positive PD-L1 status labels 15305 are known as the types of errors that occur in each bin.

In this example, the range of possible prediction probability values is 0 to 1 and it is divided equally into ten intervals—(0.0, 0.1], (0.1, 0.2], etc. The heights of the bars in FIG. 341C indicate that prediction probability values 15122 between approximately 0 and 0.6 are mostly associated with negative PD-L1 status labels 15305, prediction probability values 15122 between approximately 0.6 and 0.8 are associated equally with negative and positive PD-L1 status labels 15305, and prediction probability values 15122 between approximately 0.8 and 1 are mostly associated with positive PD-L1 status labels 15305. Accordingly, the first threshold value may be set as 0.6 and the second threshold value may be set as 0.8 such that the prediction probability values 15122 associated with negative PD-L1 status labels 15305 are classified as a negative predicted PD-L1 status 15120, the prediction probability values 15122 equally associated with both positive and negative are classified as an equivocal predicted PD-L1 status 15120, and the prediction probability values 15122 associated with positive PD-L1 status labels 15305 are classified as a positive predicted PD-L1 status 15120.

FIG. 342 illustrates example training data that may be included in a labeled data set 15301, which is used for training the PD-L1 predictor 15115. The PD-L1 predictor 15115 may be trained on a labeled data set 15301 that includes data associated with at least one cancer cell sample, wherein each cancer cell sample is associated with a positive or negative PD-L1 status label 15305, as determined by IHC, and a normalized RNA-seq data set 15310. In another example, instead of, or in addition to, a PD-L1 status label 15305, each cancer cell sample from a patient is further associated with data related to the patient's response to immune checkpoint blockade therapy and/or another type of cancer treatment. These data may include a measurement or score indicating the impact of a treatment on the health of the patient, which may include overall survival time, time until surgery, and/or progression-free survival time after receiving immune checkpoint blockade therapy and/or another type of cancer treatment.

Each normalized RNA-seq data set 15310 may include an expression level value for each gene in the human genome, wherein each expression level value indicates how many RNA copies of that gene are detected in the cancer cell sample. Examples of genes include CD274, TFP12, GAGE12C, etc. In one example, each normalized RNA-seq data set 15310 includes an expression level value for the whole transcriptome, approximately 20,000 human genes.

In one example, the labeled data set 15301 includes more than 500 cancer cell samples, wherein more than 75 of the samples are associated with a positive PD-L1 status 15305 and the remainder of the samples are associated with a negative PD-L1 status 15305.

The PD-L1 status 15305 for all cancer cell samples in the training data set may be determined by FISH, RPPA, or IHC. There is more than one clone, or type, of antibody that can detect PD-L1 for IHC staining. In one example, the PD-L1 status 15305 for all cancer cell samples in the training data set may be determined by IHC staining that utilizes one specific clone of the anti-PD-L1 antibody. In one example, the anti-PD-L1 antibody clone utilized for IHC staining is the clone known as 22C3.

Once the PD-L1 status predictor 15115 (see FIG. 343) is trained, it receives an input case data set 15112 associated with a cancer cell sample with an unknown PD-L1 status 15305. The input case data set 15112 may include a normalized RNA-seq data 15310 associated with the cancer cell sample.

In the example shown in FIG. 342, the labeled data set 15301 and the input case data set 15112 may further include additional data associated with the cancer cell sample. Additional data may include images 15315, including radiology and pathology images; imaging features 15320, which include patterns in images 15315 or metrics determined by analyzing images 15315; clinical data 15325, including data extracted from medical records; genetic data 15330 related to DNA molecules contained in the cancer cell sample; epigenetic data 15335; pharmacogenetic data 15340; and metabolomic data 15345.

Images 15315 may include 2- or 3-dimensional depictions of solid tumors or other portions of a patient's body affected by cancer, which include radiology images, computed tomography (CT) scans, also known as computerized axial tomography (CAT) scans, including CT angiography; fluoroscopy, including upper GI and barium enema; magnetic resonance imaging (MRI) and magnetic resonance angiography (MRA); mammography; nuclear medicine, which includes such tests as a bone scan, thyroid scan, and thallium cardiac stress test; x-rays; positron emission tomography, also called PET imaging, PET scan, or PET-CT when it is combined with CT; and ultrasounds.

Images 15315 may also include images of pathology slides, also known as histology slides, wherein each slide is a slice of tumor tissue or other cancer cell sample mounted on a microscope slide, that may have been stained by immunohistochemistry (IHC) staining and/or hematoxylin and eosin (H and E), two stains commonly used together to analyze cancer cells.

In this example, the imaging features 15320 may be visual patterns that exist in the pixel data associated with images 15315 and/or metrics calculated by analyzing the images 15315. For example, the imaging features 15320 may include the volume of a tumor, the degree of immune infiltration in a tumor, or the tumor purity percentage of a cancer cell sample. Other types of imaging features that may be incorporated are described in U.S. Provisional Patent Application No. 62/693,371, which is incorporated herein in its entirety.

In one example, labeled data set 15301 only includes a PD-L1 status 15305 and a normalized RNA-seq data 15310 for each cancer cell sample associated with labeled data set 15301.

FIG. 343 illustrates an example PD-L1 status predictor 15115.

In the example shown, a PD-L1 status predictor 15115 includes a labeled data set 15301 that may be processed by a clustering algorithm 15405 to select features and create a filtered data set 15410, which contains the data associated with selected features.

An untrained predictive model 15415 receives the filtered data set 15410 or the labeled data set 15301 to create a trained predictive model 15420, a process known as model training. In one example, each cancer sample associated with the filtered data set 15410 or the labeled data set 15301 is further associated with a data value or data pattern of each selected feature data type and a PD-L1 status label 15305.

The PD-L1 status label 15305 may be positive, negative, or uncertain, and it may include a value indicating the percentage of cancer cells that stained positive for PD-L1 protein, which indicates that those cells had produced PD-L1 protein.

During model training, for each selected feature in the filtered data set 15410 or the labeled data set 15301, the model receives data values or data patterns and associates each value or pattern with the positive or negative PD-L1 status label 15305 associated with a cancer cell sample having that data value or pattern for that data type. After this probability association, the trained predictive model 15420 can receive an unlabeled input case 15112 having data values or data patterns for each selected feature, and assign a predicted PD-L1 status label 15120 to the associated cancer cell sample based on the data values or patterns in unlabeled input case 15112 and the probabilities associated with each data value or data pattern.

In one example, trained predictive model 15420 may be a trained logistic regression model that includes a logistic regression function and logistic regression model coefficients. The logistic regression function may be calculated based on the filtered data set 15410 or the labeled data set 15301. The logistic regression model coefficients may be determined by minimizing a loss function as described above.

In one example, during training, the untrained predictive model 15415 does not receive every cancer cell sample associated with the filtered data set 15410 or labeled data set 15301, and the cancer cell samples that the untrained predictive model 15415 does not receive may be referred to as withheld cancer cell samples.

In one example, the trained predictive model 15420 receives at least one withheld cancer cell sample but does not receive or process the PD-L1 statuses 15305 associated with the withheld cancer cell samples. The trained predictive model 15420 predicts a PD-L1 status label 15430 for each withheld cancer cell sample. The PD-L1 status 15305 and the predicted PD-L1 status label 15120 associated with each withheld cancer cell sample may be compared to perform a model accuracy analysis 15422.

As described above, the model accuracy analysis 15422 may include more than one withheld cancer cell sample, wherein each of the withheld cancer cell samples is associated with a PD-L1 status 15305 and a predicted PD-L1 status label 15120. The model accuracy analysis 15422 may include plotting a receiver operating characteristic (ROC) curve and computing the area under curve (AUC) for all of the withheld cancer cell sample and/or at least one subset of the withheld cancer cell samples.

The trained predictive model 15420 receives and analyzes an input case data set 15112 associated with a cancer cell sample and predicts the PD-L1 status 15120 of that cancer cell sample. In one example, the input case data set 15112 does not include a PD-L1 status 15305 associated with the cancer cell sample. The input case data set 15112 includes data associated with a cancer cell sample, which may include normalized RNA-seq data 15310, images 15315, imaging features 15320, clinical data 15325, genetic data (DNA) 15330, epigenetic data 15335, pharmacogenetic data 15340, and/or metabolomic data 15345. In one example, the input case data set 15112 includes only RNA-seq data 15310 associated with a cancer cell sample.

The predicted PD-L1 status label 15120 of the cancer cell sample may be reported to a physician, medical professional, or patient through a software portal, electronic file including a portable document format (PDF), or hard-copy document, including a document printed on paper. The predicted PD-L1 status 15120 may assist the medical professional in choosing an anti-cancer treatment, such as a treatment that is likely to eliminate the sampled cancer cells. Treatment may be prescribed to the patient in a therapeutically effective amount.

In one example, the predicted PD-L1 status 15120 is a companion diagnostic, meaning that the predicted status may be used to indicate whether a treatment is likely to reduce or eliminate the cancer cells in the patient from which the sample was collected. In one example, the predicted PD-L1 status 15120 is College of American Pathologists (CAP) accredited and/or Clinical Laboratory Improvement Amendments (CLIA) certified. In another example, the predicted PD-L1 status 15120 is FDA-approved. This accreditation, certification and/or approval may be based on the proven accuracy of the predicted PD-L1 status 15120.

Example Embodiments of the PD-L1 Status Predictor 15115

The following three embodiments of the PD-L1 status predictor 15115 each have a distinct method for selecting features in labeled data set 15301 based on their correlation with PD-L1 status 15305.

First Embodiment of a PD-L1 Status Predictor 15115

In the first embodiment of a PD-L1 status predictor 15115 disclosed here, a type of data may be selected as a feature if it represents a biological condition and/or phenomenon that has a known effect on the amount of PD-L1 protein present in a sample.

For example, the number of RNA copies, called the expression level value, of the CD274 gene may be selected as a feature.

The RNA expression level value of the CD274 gene, as reported in the normalized RNA-seq data 15310, is a selected feature used to train the untrained predictive model 15415. The model training results in a trained predictive model 15420 that correlates CD274 RNA expression values with PD-L1 status 15305 and predicts PD-L1 status 15120 for the cancer cell sample associated with an input case 15112, based on the CD274 expression level value associated with that cancer cell sample.

The trained predictive model 15420 may include a logistic regression function calculated based on the CD274 expression level values included in the filtered data set 15410 or the labeled data set 15301. As described above, the logistic regression model coefficients may be determined by minimizing a loss function.

In this embodiment, the normalized RNA-seq data set 15310 for each sample included in the labeled data set 15301 or an input case 15112 includes an expression level value for the CD274 gene.

Second and third embodiments of a PD-L1 status predictor 15115

In the second and third embodiments of a PD-L1 status predictor 15115 disclosed here, the selected features include expression level values of genes in the labeled data set 15301 that are most closely correlated with a cancer cell sample's PD-L1 status 15305. The data values in the labeled data set 15301 are adjusted before a clustering algorithm 15405 analyzes the labeled data set 15301 to select the features for each of these embodiments. (See FIG. 341B) The adjustments to the data values in the labeled data set 15301 for embodiment two are slightly different than the adjustments for embodiment three, as detailed below. Once adjusted, these data values may be stored as an adjusted labeled data set and the untrained predictive model 15415 may receive the adjusted labeled data set to generate trained predictive model 15420. The filtered data set 15410 may be generated from the adjusted labeled data set.

In embodiment two, the median difference model, a feature is defined as having a correlation with the PD-L1 status label 15305 if it has a large difference value, wherein the difference value is calculated by subtracting the median value of the set of data values associated with a positive PD-L1 status 15305 from the median value of the set of data values associated with a negative PD-L1 status 15305. (See FIG. 341B) The data sets used are drawn from holdout data specifically set aside for median difference calculation or feature selection. A holdout data set may be any subset of the labeled data set 15301. Any subset of the labeled data set 15301 that is not associated with the holdout data set may be prevented from being used for feature selection 15210 or model training 15220 and used only to test the model during the optional model accuracy analysis 15422.

In one example, (embodiment two) the selected features include expression level values for the following genes: immune checkpoint genes PD-L1, PD-L2, and TIGIT; chemokine and cytokine genes CXCL13, and IL21; and immune activity-related gene FASLG. In another example, (embodiment three) the selected features include expression level values for the following genes: CD274, TFPI2, GAGE12C, POMC, PAX6, NPHS1, and HLA-DPB1.

In this embodiment, the trained predictive model 15420 may include a logistic regression function calculated based on the data values or data patterns associated with selected features included in the filtered data set 15410 or the labeled data set 15301. As described above, the logistic regression model coefficients may be determined by minimizing a loss function.

In one example, (embodiment two) all selected features are expression level values of genes, including but not limited to the following genes: CD274 (2.238), IL31RA (−0.212), RXRB (0.298), NCF1 (0.264), NKX2-8 (0.326), MYEOV (−0.086), IL21 (−0.415), ZBED2 (−0.379), PSG4 (−0.092), ROS1 (0.270), PDCD1LG2 (0.371), IFNL3 (0.141), ACTBL2 (0.024), ANKRD34B (−0.366), KMO (−0.499), HTR1D (−0.171), CCBE1 (0.580), NETO1 (0.071), KLC3 (−0.278), RGS20 (0.259), PRSS36 (−0.143), GTSF1 (−0.043), SPRR1B (0.255), CYP27B1 (−0.007), SDK1 (−0.407), GNGT1 (0.443), COPZ2 (0.043), PSMB8 (−0.437), CR2 (0.202), HLA-DQA1 (0.033), HMGA1 (−0.080), ST6GALNAC5 (0.000), TCHH (−0.094), HLA-DQB1 (0.303), MYBPC2 (0.279), ULBP2 (−0.345), SCGB3A2 (−0.689), TMPRSS4 (−0.496), LIPG (0.373), CARD17 (0.051), HLA-DRB1 (0.325), and AHNAK2 (0.208). The value denoted in parentheses after a gene name indicates the approximate feature weight value for that gene expression level in the logistic regression function.

In embodiment three, the variance model, the features selected to predict the PD-L1 status label 15120 are selected from the set of features that have the highest variance. Elastic Net was used to calculate a coefficient (selection weight value) for each feature and features were selected as described above. (See FIG. 341B) After feature selection each expression level value was mean centered and rescaled as described above, per gene, and stored as an adjusted labeled data set received by the untrained predictive model 15415 as an input into the prediction process to generate trained predictive model 15420.

In one example, (embodiment three) all selected features are expression level values of genes, including but not limited to the following genes: CD274 (2.142), CEACAM21 (0.193), LRRC37A2 (0.207), RNASE10 (0.041), PSG4 (0.318), SYT1 (0.152), HTR1D (0.043), IL31RA (−0.207),TRIM50 (0.160), ANKRD2 (0.647), SLC25A41 (0.201), GAGE12H (0.093), CPA5 (−0.167), GAGE12C (0.103), GAGE12D (0.103), FKBPL (0.695), PSG5 (−0.299), NCF1 (0.372), IL21 (−0.222), CYP2A13 (0.300), NOXO1 (−0.314), ANKRD34B (−0.813), ITPKA (−0.112), HLA-DPB1 (0.422) PSG9 (−0.373), CAMK1G (−0.137), HMGN5 (−0.152), BTG4 (0.267), FGF5 (0.169), KRT24 (−0.166), SAXO2 (−0.278), CLLU1OS (−0.094), KRT31 (−0.358), PAGE1 (0.037), PRM3 (−0.298), LRRC37A (−0.054), ANKRD18B (0.321), PSG2 (0.173), AFAP1L2 (−0.184), and DMRTA2 (0.307). The value denoted in parentheses after a gene name indicates the approximate feature weight value for that gene expression level in the logistic regression function.

The genes on the selected features list may be analyzed to determine whether they have any biological connection to the level of the predicted protein, PD-L1 as described above (see FIG. 341A).

In embodiment two, the following genes selected as features and/or proteins encoded by these genes have these general functions, according to published research: CD274 encodes immune inhibitor PD-L1, IL31RA encodes an immune cytokine receptor, RXRB encodes a retinoic acid receptor and has some immune functions, NCF1 encodes an oxidase for neutrophils and has some immune functions, NKX2-8 is important for liver development and certain cancer types may affect its expression levels, MYEOV has an unclear function but expression levels may vary with tissue and/or cancer type, IL21 encodes an immune cytokine, ZBED2 expression levels may vary with tissue and/or cancer type, PSG4 may regulate the immune system and cell adhesion and is expressed by fetal tissue but certain cancer types may increase expression levels in adults, ROS1 expression levels may be affected by certain cancer types, PDCD1LG2 may have immune function, IFNL3 encodes an immune cytokine, ACTBL2 may be important for cellular movement especially for muscle cells, ANKRD34B expression levels may vary with tissue and/or cancer type, KMO encodes a protein used in a metabolic pathway, HTR1D may be important for neural function, locomotion, and anxiety, CCBE1 may be important for developing extracellular matrices and expression levels may vary with tissue and/or cancer type, NETO1 may be important for neural function, spatial learning, and memory formation, KLC3 may be important for intracellular transport along microtubules, RGS20 may be important for general signal transduction from the exterior to the interior of a cell, PRSS36 expression levels may vary with tissue and/or cancer type, GTSF1 expression levels may vary with tissue and/or cancer type, SPRR1B may form the membrane of certain cells and expression levels may vary with tissue and/or cancer type, CYP27B1 may be important for drug metabolism and lipid synthesis, SDK1 may be important for cellular adhesion and immune function, GNGT1 may be important for visual perception, COPZ2 may be important for intracellular transport in COPI vesicles, PSMB8 may be important for generating peptides for presentation to immune cells especially by HLA proteins, CR2 allows viral entry into B and T cells and expression levels may vary with tissue and/or cancer type, HLA-DQA1 may be important for presenting peptides to immune cells, HMGA1 may be important for gene transcription, viral integration into human chromosomes, and cancer metastasis, ST6GALNAC5 may be important for cell to cell interactions, TCHH may be important for hair follicles and tongue papillae, HLA-DQB1 may be important for presenting peptides to immune cells, MYBPC2 may be important for muscle and heart cells, ULBP2 may be important for immune function, SCGB3A2 may be important for lung function, TMPRSS4 fragments other proteins and expression levels may vary with tissue and/or cancer type, LIPG may be important for lipoprotein metabolism and the circulatory system, CARD17 may be important for immune system function, HLA-DRB1 may be important for presenting peptides to immune cells, and AHNAK2 may be important for calcium signaling. The expression levels of many of these genes may vary depending on the cell type and/or cancer type of the cell in which the gene is expressed.

In embodiment three, the following genes selected as features and/or proteins encoded by these genes have these general functions, according to published research: CD274 encodes immune inhibitor PD-L1, CEACAM21 may regulate the immune system and cell adhesion and is expressed by fetal tissue but certain cancer types may increase expression levels in adults, LRRC37A2 expression levels may vary with tissue and/or cancer type, RNASE10 may be important for sperm maturation, PSG4 may regulate the innate immune system and cell adhesion and is expressed by fetal tissue but certain cancer types may increase expression levels in adults, SYT1 may be important for neural function, intracellular trafficking and exocytosis, HTR1D may be important for neural function, locomotion, and anxiety, IL31RA encodes an immune cytokine receptor, TRIM50 may be important for the modification and degradation of other proteins, ANKRD2 may be important for muscle function, SLC25A41 may be important for transporting molecules into and out of cell mitochondria, GAGE12H is expressed by germ cells including ova and sperm but certain cancer types may increase expression levels in other cell types, CPA5 may be important for digesting food and synthesizing peptides, GAGE12C is expressed by germ cells including ova and sperm but certain cancer types may increase expression levels in other cell types, GAGE12D is expressed by germ cells including ova and sperm but certain cancer types may increase expression levels in other cell types, FKBPL may be important for immune function and cell cycle regulation, PSG5 is expressed by placental tissue but certain cancer types may increase expression levels in other tissue types, NCF1 encodes an oxidase for neutrophils and has some immune functions, IL21 encodes an immune cytokine, CYP2A13 may be important for drug metabolism and lipid synthesis, NOXO1 may be important for a type of metabolism known as respiratory burst, ANKRD34B expression levels may vary with tissue and/or cancer type, ITPKA may be important for metabolizing inositol phosphate for cell signaling, HLA-DPB1 may be important for presenting peptides to immune cells, PSG9 may regulate blood platelet adhesion and is expressed by placental tissue but certain cancer types may increase expression levels in other tissue types, CAMK1G may be involved in intracellular signaling, HMGN5 may bind to the nucleosome and activate gene transcription, BTG4 regulates the cell cycle and cell division, FGF5 may be important for fetal development, cell growth, and tumor growth, KRT24 may be important for epithelial cell structure, SAXO2 may be important for microtubules and intracellular transport, CLLU1OS expression levels may vary with tissue and/or cancer type, KRT31 may be important for hair and nail growth, PAGE1 expression levels may vary with tissue and/or cancer type, PRM3 may be important for DNA packaging in sperm and expression levels may vary with tissue and/or cancer type, LRRC37A expression levels may vary with tissue and/or cancer type, ANKRD18B may bind to nucleotides, PSG2 may regulate cell adhesion and is expressed by placental tissue but certain cancer types may increase expression levels in other tissue types, AFAP1L2 may be important for cell signaling pathways, and DMRTA2 may be important for DNA binding and transcription. The expression levels of many of these genes may vary depending on the cell type and/or cancer type of the cell in which the gene is expressed.

The labeled data set 15301 may be reduced to a filtered data set 15410 having data associated with the selected features for each cancer cell sample and the PD-L1 status predictor 15115 may be trained only on the selected features in the filtered data set 15410.

Analyzing model accuracy for example embodiments of PD-L1 status predictor 15115

In one example, only a portion of the cancer cell samples in each fold are used to train the PD-L1 status predictor, and the other cancer cell samples in the fold are called withheld cancer cell samples in a validation sample. The withheld cancer cell samples in the validation sample are used as input cases 15112 to test the PD-L1 status predictor 15115, which does not receive the PD-L1 status 15305 associated with the withheld cancer cell samples. The PD-L1 status predictor 15115 generates a predicted PD-L1 status 15120 for each withheld cancer cell sample and it is compared to the actual PD-L1 status 15305 associated with the withheld cancer cell sample to determine the accuracy of the trained predictive model 15420.

A labeled data set 15301 may be divided into any number of folds for feature selection. In one example, the number of folds may be chosen to increase the likelihood that the validation sample has at least one cancer cell sample associated with a positive PD-L1 status 15305. In one example, there are five folds.

The ratio of the number of cancer cell samples in the validation sample over the number of cancer cell samples in the fold may be equal to the ratio of the number of cancer cell samples in the fold over the number of cancer cell samples in the training data set. For example, if there are five folds, the validation sample of each fold may contain ⅕ of the cancer cell samples in the fold.

In one example, model accuracy analysis 15422 includes plotting a Receiver Operating Characteristic (ROC) curve and calculating the area under curve (AUC) to analyze the performance of a trained predictive model on the validation sample. The AUC indicates the probability that the model will rank a randomly selected cancer cell sample associated with a negative PD-L1 status 15305 as more PD-L1 negative than a randomly selected cancer cell sample associated with a positive PD-L1 status 15305. The maximum possible value for an AUC is 1. An AUC of 1 indicates a perfectly accurate model, and the higher the AUC, the more useful the model is. An ROC curve may be generated for the validation sample of each fold. For imbalanced data, it also useful to evaluate model performance using a precision-recall curve. This curve also has a maximum value of 1, where higher values indicate better model performance.

In one example, the ROC curve for embodiment one (CD274 model) has an AUC of 0.84 for fold 1, 0.93 for fold 2, 0.89 for fold 3, 0.90 for fold 4, 0.96 for fold 5, and a mean of 0.90+/−0.04 for all five folds. Embodiment one has an accuracy of 0.914, precision of 0.817, recall of 0.525, and adjusted mutual information of 0.323.

In one example, the ROC curve for embodiment two (median difference model) has an AUC of for fold 1, 0.99 for fold 2, 0.92 for fold 3, 0.98 for fold 4, 0.88 for fold 5, and a mean of 0.94+/−0.04 for all five folds. Embodiment two has an accuracy of 0.919, precision of 0.750, recall of 0.622, and adjusted mutual information of 0.357.

In one example, the ROC curve for embodiment three (variance model) has an AUC of 0.93 for fold 1, 0.94 for fold 2, 0.93 for fold 3, 0.98 for fold 4, 0.94 for fold 5, and a mean of 0.94+/−0.02 for all five folds. Embodiment three has an accuracy of 0.911, precision of 0.697, recall of 0.632, and adjusted mutual information of 0.315.

Patient Example

In one example of the application, features are selected from a published list of genes that were observed by a third party to be correlated with PD-L1 expression levels or PD-L1 status. A logistic regression model 15415 is trained on a set of training data containing 595 cases of labeled PD-L1 positive and PD-L1 negative samples associated with RNA-seq data, using the gene expression values of the following genes: CD274, PDCD1, PDCD1LG2, IFNG, GZMB, CXCL9, TGFB1, VIM, STX2, and ZEB2.

In this embodiment all selected features are expression level values of genes, including but not limited to the following genes: CD274 (1.072), PDCD1 (−0.168), PDCD1LG2 (0.357), IFNG (−0.076), GZMB (−0.121), CXCL9 (0.200), TGFB1 (−0.063), VIM (−0.248), STX2 (0.316), and ZEB2 (−0.090). The value denoted in parentheses after a gene name indicates the approximate feature weight value for that gene expression level in the logistic regression function. In this example, the selected features are expression levels of genes that were published in scientific literature as being correlated with PD-L1 status and/or PD-L1 protein expression levels.

In one example case, consider a patient with metastatic melanoma. A sample of the patient's tumor is then sequenced, yielding DNA and RNA sequencing data.

Normalized gene counts for all genes are obtained from the RNA-sequencing data and downstream pipeline. A subset of these genes (including features previously determined to be the most informative for predicting PD-L1 IHC status) are used as input into the prediction model.

In this example, the normalized gene counts of the genes used to predict PD-L1 status are: CD274: 2.11, PDCD1: 2.15, PDCD1LG2: 2.15, IFNG, 2.12, GZMB, 2.76, CXCL9: 3.51, TGFB1: 3.02, VIM: 4.28, STX2: 2.37, and ZEB2: 3.43.

To create a data set that will be received by PD-L1 predictor 15115 as input case 15112, these gene counts are then mean centered and rescaled as described above (See FIG. 341A) by Scikit-learn tools to match the data distribution in the training set in terms of mean and unit variance. In this example, input case 15112 contains the following standardized, rescaled counts of the genes used to predict PD-L1 status are: CD274: 2.88, PDCD1: 1.90, PDCD1LG2: 2.01, IFNG: 2.29, GZMB: 1.84, CXCL9: 2.23, TGFB1: 0.57, VIM: 0.41, STX2: 1.38, and ZEB2: 0.29.

From the gene expression levels of CD274 and the other genes in this list that provide information on PD-L1 status, the PD-L1 predictor 15115 calculates the PD-L1 status prediction probability 15122 of the patient's cancer by multiplying each standardized, rescaled count by the corresponding feature weight and calculating the sum of these products and the intercept value from the logistic regression function. Then the PD-L1 predictor 15115 classifies the predicted probability 15122 as a Negative, Equivocal, or Positive predicted PD-L1 status label 15120 as described above (See FIG. 341C).

In this example, the PD-L1 positive prediction probability 15122 returned by the model is: 0.97, thus the patient would be classified as PD-L1 positive with high confidence. Here, high confidence may mean a positive result prediction probability 15122 of greater than 0.8—this prediction probability threshold was obtained by the error evaluation method described above. (See FIG. 341C)

The patient's medical record 15325 could then be searched for relevant information, such as a prior treatment with pembrolizumab or another immune checkpoint blockade therapy. If prior treatment with pembrolizumab is found, one example of report logic will ensure that pembrolizumab is not displayed as a therapy option in the report 15125. Instead, a combination therapy of atezolizumab and ipilimumab could be displayed, for example, depending on additional information derived from the patient's molecular data that support the use of an alternate checkpoint blockade strategy.

The appearance of predicted PD-L1 status 15120 in the report 15125 may include the patient's PD-L1 RNA expression and a visualization of other patients of a similar cancer type or a reference set of samples from a normal tissue type selected to be a reference for the particular cancer type. (See FIG. 340B)

The techniques herein, including the PD-L1 status predictor techniques, may be implemented on genetic sequence analysis processing system 15400 that may be implemented on a computing device 15402 such as a computer, tablet or other mobile computing device, or server, such as a cloud-based server. The genetic sequence analysis processing system 15400 may include a number of processors, controllers or other electronic components for processing sequence data and performing the processes described herein. The genetic sequence analysis processing system 15400, for example, may be implemented on a one or more processing units, which may represent Central Processing Units (CPUs), and/or on one or more or Graphical Processing Units (GPUs), including clusters of CPUs and/or GPUs. Features and functions described for the genetic sequence analysis processing system 15400 may be stored on and implemented from one or more non-transitory computer-readable media of the computing device 15402. The computer-readable media may include, for example, an operating system and elements corresponding to the processes described herein, and in reference to FIGS. 340-343. For example, the computer-readable media may store (and in some examples generate) trained PD-L1 status predictor models, executable code, etc. use for implementing the techniques herein, including genetic sequence data analysis. The computer-readable media may store any suitable checkpoint blockade predictor, in accordance with the examples herein. The computing device 15402 may include a network interface communicatively coupled to a network 15406, for communicating to and/or from a portable personal computer, smart phone, electronic document, tablet, and/or desktop personal computer, or other computing devices. The computing device 15402 may further include an I/O interface connected to devices, such as digital displays, user input devices, etc.

In some examples, the genetic sequence analysis processing system 15400 is implemented on a single server, such as a single cloud-based server. However, the functions of the system may be implemented across distributed devices such as network-accessible servers 15408, 15410, and 15412, etc.

connected to one another through a communication link or cloud-based infrastructure. In other examples, functionality of the genetic sequence analysis processing system 15400 may be distributed across any number of devices, including the portable personal computer, smart phone, electronic document, tablet, and desktop personal computer devices shown.

The network 15406 may be a public network such as the Internet, private network such as research institutions or corporation's private network, or any combination thereof. Networks can include, local area network (LAN), wide area network (WAN), cellular, satellite, or other network infrastructure, whether wireless or wired. The network 15406 can utilize communications protocols, including packet-based and/or datagram-based protocols such as internet protocol (IP), transmission control protocol (TCP), user datagram protocol (UDP), or other types of protocols. Moreover, the network 15406 can include a number of devices that facilitate network communications and/or form a hardware basis for the networks, such as switches, routers, gateways, access points (such as a wireless access point as shown), firewalls, base stations, repeaters, backbone devices, etc. In some example "cloud-based" implementations, functionality of the genetic sequence analysis processing system, including that PD-L1 status prediction, may be implemented as part of a "cloud" network, with hardware devices and/or software components within the cloud network to send, retriever, analyze, generate, and report data. In some examples, a cloud-based implementation of the genetic sequence analysis processing system 15400 may operate as a Software-as-a-Service (SaaS) or Platform-as-a-Service (PaaS), providing the functionality described herein remotely to software apps and other components in accordance with the various embodiments described herein.

In some examples, the genetic sequence analysis processing system 15400 implements a method of preparing a clinical decision support information (CDSI) report as shown. For example, a subject's tissue sample may be received at the genetic sequence analysis processing system 15400, which then determines or identifies a PD-L1 expression status of the subject's sample, for example, by performing an alignment of an unlabeled gene expression data set of the subject's sample to a labeled expression data according to a trained PD-L1 predictive model. From that alignment comparison, the genetic sequence analysis processing system 15400 prepares an electronic CDSI report for the subject based on the PD-L1 expression status identified. That CDSI report may be communicated to network accessible devices, as shown. In some examples, the CDSI report may contain the subject's name, the PD-L1 expression status, and one or more of the date on which the sample was obtained from the subject, the sample type, a list of candidate drugs correlating with the PD-L1 expression status, data from images of the subject's tumor or cancer, image features, clinical data of the subject, epigenetic data of the subject, data from the subject's medical history and/or family history, subject's pharmacogenetic data, subject's metabolomics data, etc.

Further, in some examples, the genetic sequence analysis processing system 15400 prepares an initial digital (preliminary) CDSI report for the subject based on the PD-L1 expression status identified. The genetic sequence analysis processing system 15400 compares the initial CDSI report against stored clinical data for the patient. The genetic sequence analysis processing system 15400 determines from the comparison if a further modification or optimization should be performed on the CDSI report before it is communicated to the subject or medical professionals, for example, over the network 15406. In some examples, the initial CDSI report may include a list of candidate drugs correlating with PD-L1 expression status. The genetic sequence analysis processing system 15400 compares the list of candidate drugs to a listing of drugs previously administered to the subject and determines if the list of candidate drugs should be changed, e.g., reduced to remove drugs already administered to the subject.

As discussed herein, the computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device may represent a CPU-type processing unit, a GPU-type processing unit, a field-programmable gate array (FPGA), another class of digital signal processor (DSP), or other hardware logic components that can be driven by a CPU.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output.

Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines, including distributed across a "cloud" network. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

All references, including publications, patent applications, and patents, cited herein are hereby incorporated by reference to the same extent as if each reference were individually and specifically indicated to be incorporated by reference and were set forth in its entirety herein.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

XX. System and Method for Expanding Clinical Options for Cancer Patients Using Integrated Genomic Profiling The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Genomic analysis of paired tumor-normal samples and clinical data can be used to match patients to cancer therapies or clinical trials. We analyzed 500 patient samples across diverse tumor types using the xT platform by DNA-seq, RNA-seq, and immunological biomarkers. The use of a tumor and germline dataset led to substantial improvements in mutation identification and a reduction in false positive rates. RNA-seq enhanced gene fusion detection and cancer type classifications. With DNA-seq alone, 29.6% of patients matched to precision therapies supported by high levels of evidence or by well-powered studies. This increased to 43.4% with the addition of RNA-seq and immunotherapy biomarker results. Combined with clinical criteria, 76.8% of patients were matched to at least one relevant clinical trial based on biomarkers measured by the xT assay. These results indicate extensive molecular profiling combined with clinical data identifies personalized therapies and clinical trials for a large proportion of cancer patients, and that paired tumor-normal plus transcriptome sequencing outperforms tumor-only DNA panel testing.

Genomic analysis of tumors is rapidly becoming routine clinical practice. Estimates of the proportion of patients whose testing changes their trajectory of care vary from approximately 10% to more than 50%, depending on tumor type and clinical setting[1-4]. Growing evidence suggests that patients who receive personalized therapy have better outcomes[5]. For example, the use of matching scores based on the number of genomic aberrations and therapeutic associations per patient demonstrated that high matching scores are independently associated with a greater frequency of stable disease, longer time to treatment failure, and greater overall survival[4]. Improved progression-free survival ratios were observed in 43% of next-generation sequencing (NGS)-tested patients who received a genome-guided therapy, compared with only 5.3% of patients who did not[2]. The IMPACT trial, which tested advanced-stage tumors from 3,743 patients and matched approximately 19% of patients based on their tumor biology, reported a 16.2% objective response rate for patients with matched treatments versus 5.2% with non-matched treatments. Additionally, three-year overall survival for patients treated with a molecularly matched therapy was more than twice that of non-matched patients (15% vs. 7%)[6].

The xT assay tests match tumor and normal samples and generate DNA alteration data for single nucleotide variants (SNVs), insertions and deletions (indels), and copy number variants (CNVs) for 595 genes, plus chromosomal rearrangements for 21 genes. xT also provides whole-transcriptome RNA sequencing (RNA-seq), which detects clinically validated fusion transcripts and provides research use only (RUO) information regarding dysregulated genes and cancer type predictions for tumors of unknown origin (TUO). xT immuno-oncology (10) assays include clinical immunohistochemistry (IHC) testing for DNA mismatch repair (MMR) deficiency and PD-1/PD-L1 status, clinical genomic determination of microsatellite instability (MSI) status, measurement of tumor mutational burden (TMB), neoantigen predictions, and RUO gene expression analyses of the tumor microenvironment (TME). We have previously described laboratory and analytic processes, including additional machine learning approaches for integrating genomic and imaging data generated during the course of cancer diagnosis and treatment.

Integrating DNA- and RNA-seq data into the analyses of patient samples to produce clinically validated patient reports requires advanced bioinformatics and data analytics. Properly interpreting results also requires clinical context, including patient data from physician notes and tests. Together, the genomic sequencing, computational algorithms, and software built to communicate patient clinical profiles and molecular test results to physicians is referred to as the platform. Here, we examined the results of applying the xT platform to a cohort of 500 randomly selected patients with common tumor types, rare tumors, and TUOs. We present clinical and RUO analyses from tumor-normal matched xT DNA- and RNA-seq on the DNA mutational spectra, whole-transcriptome profiling, chromosomal rearrangement detection, and the immunogenomic landscape based on immunotherapy biomarkers in the xT 500 cohort across multiple tumor types. Molecular insights derived from these analyses were used to match patients with evidence-based therapies and clinical trials. Lastly, we present a comparison of the platform to tumor-only sequencing, examining germline versus somatic variant detection and therapeutic matching.

Results xT 500 Analysis Cohort

We selected a cohort of 500 paired tumor-normal samples sequenced with the xT assay in 2017 or 2018, which we refer to as the xT 500 cohort. The cases included were randomly selected from the de-identified database of structured genomic and clinical data. To be eligible for inclusion in the cohort, each case required complete data elements for tumor-normal DNA-seq and clinical data from abstracted medical records. Subsequent to filtering for eligibility, a set of patients was sampled via a pseudo-random number generator. Patients were assigned to one of eight cancer types based on pathologic diagnosis, with 50 patients per category of brain, breast, colorectal, lung, ovarian, endometrial, pancreatic, and prostate cancer types. Additionally, 50 tumors from a combined set of rare malignancies and 50 TUOs were included for a total of 500 patients. The xT 500 cohort was balanced between male and female patients (n=212 and n=288, respectively). The specimens sequenced were primarily from advanced-stage cancer cases, with 7.8% from recurrent metastatic cases (FIG. 345).

Genomic Analyses of the xT 500 Cohort

We examined the xT 500 mutational spectra compared to broad patterns of genomic alterations observed in large-scale studies across cancer types (See Methods: *Mutational spectra analyses*). First, we identified alterations by gene (FIG. 346, FIG. 347), and found the most commonly mutated genes were well-known driver mutations, including TP53, KRAS, PIK3CA, CDKN2A, PTEN, ARID1A, APC, ERBB2 (HER2), EGFR, IDH1, and CDKN2B. As expected, homozygous deletions were commonly observed in tumor suppressor genes CDKN2A, CDKN2B, and PTEN. Mutational spectra data were compared to a published pan-cancer analysis using the Memorial Sloan Kettering Cancer Center (MSKCC) IMPACT panel (FIG. 348)[13]. The same commonly mutated genes were observed at similar relative frequencies in both datasets, indicating the xT 500 mutational spectra are representative of tumors sequenced in this previous large-scale study.

As part of the xT platform, each sample underwent whole-transcriptome profiling by RNA-seq. Cancer type was predicted using a random forest classifier trained on an internal gene expression reference database with labels from 33 cancer types (see Methods: *gene expression reference database; Cancer type prediction*). Cancers were correctly classified for 100% breast, 98% prostate, 96% brain and ovarian, 94% colorectal, 92% pancreatic, 88% lung, and 58% endometrial tumor samples (FIG. 349). In 60% of misclassifications, the second prediction was matched to the cancer diagnosis. In 36% of misclassifications, gynecologic cancers (ovarian and endometrial) accounted for the difference and were influenced by low tumor purity, as in the case of misclassified endometrial cancers (P=0.02; FIG. 350, FIG. 351). Another notable trend was the misclassification of lung, rare, and unknown origin squamous cell carcinomas (SCC) as head and neck SCC due to a shared SCC signature[14]. A total of 11.1% of misclassifications were affected by signal contributions from background tissue transcriptome profiles, as in the case of misclassified metastatic samples (P=0.09; FIG. 352). Since the classifier was accurate for the majority of tumor types, most TUOs could be matched to the appropriate tissue of origin.

We also evaluated oncogenic gene fusions[15]. Fusions were detected by DNA-seq of 21 common gene rearrangement targets, and by whole-transcriptome RNA-seq analysis (see Methods: *Detection of gene rearrangements*). Of the fusions detected, 26 were identified by both DNA- and RNA-seq, two by DNA-seq alone, and four by RNA-seq alone (FIG. 353). Within the four RNA-seq-detected fusions, two were potentially detectable but not detected by DNA-seq, and two were not detected because they were not represented in the DNA-seq assayed breakpoints, illustrating the value of an unbiased whole-transcriptome approach for fusion identification. The predicted structures of these two fusions were further examined, revealing in-frame fusions with intact tyrosine kinase domains, such as RET and NTRK3, which are therapeutically targetable (FIG. 354, 355).

We next characterized the immunogenomic landscape of the xT 500 cohort. TMB is a key biomarker of immunotherapy response[7,16]. In the cohort, TMB ranged from 0-54.2 mutations per megabase of DNA (mut/Mb) across cancer types with a median of 2.09 mut/Mb (see Methods: Tumor mutational burden; FIG. 356). These xT assay-derived TMB values are highly correlated with whole-exome TMB (see Methods: TMB whole-exome comparison; FIG. 357). We identified a hypermutated tumor population across cancer types with significantly higher median TMB. These TMB-high samples included cancers previously associated with low TMB like glioblastoma. Consistent with previous reports, TMB was highly correlated with neoantigen load ($R=0.931$, $P=8.20 \times 10^{-199}$), an estimate of the number of somatic mutations presented to the immune system (see Methods: Neoantigen prediction; FIG. 358). The TMB-high population also contained all MSI-high (MSI-H) samples (see Methods: Microsatellite instability status). The remaining TMB-high samples were associated with mutational signatures related to smoking, UV exposure, and APOBEC-mediated mutagenesis (see Methods: Somatic signatures; FIG. 359).

We then assessed the relationship between tumor immunogenicity and the levels of immune infiltration and activation. Cytotoxic immune activity levels measured by the cytolytic index (CYT) were significantly higher in hypermutated populations ($P=1.95 \times 10^{-4}$ for TMB-high, $P=2.50 \times 10^{-2}$ for MSI-H; FIG. 360) (see Methods: Cytolytic index). Additionally, an estimation of the immune cell composition using an RNA deconvolution model (see Methods: Immune infiltration estimation) revealed that inflammatory cells, like CD8 T cells and M1 macrophages, were significantly higher in TMB-high samples ($P=4.9 \times 10^{-4}$ and $P=1.4 \times 10^{-7}$, respectively), while non-inflammatory immune cells, like monocytes, were significantly higher in TMB-low samples ($P=2.0 \times 10^{-4}$) (FIG. 361).

Increased immune pressure from infiltration of immune cells can lead tumors to express higher levels of immune checkpoint molecules like PD-L1 (CD274). Accordingly, RNA-seq determined that PD-L1 expression was significantly higher in the immune-infiltrated TMB-high tumors ($P=6.69 \times 10^{-4}$; FIG. 362). CD274 expression was also highly correlated with the expression of its binding partner PDCD1 (PD-1) on immune cells ($R=0.59$, $P\ 2.2 \times 10^{-16}$), as well as T cell lineage-specific markers like CD3E ($R=0.63$, $P\ 2.2 \times 10^{-16}$; FIG. 363). Furthermore, samples that stained positive for PD-L1 via clinically validated IHC tests clustered with higher CD274 RNA expression levels, suggesting CD274 expression may be an indicator of PD-L1 protein levels.

Finally, a 28-gene interferon gamma (IFNγ)-related signature determined if any patients lacking classically defined immunotherapy biomarkers exhibited traits of immunologically active tumors (see Methods: Interferon gamma gene signature score)[19]. We found that tumor samples could be broadly categorized as immunologically active or silent tumors. Our results support this stratification, with the immunologically active population enriched for samples that were TMB-high, MSI-H, or PD-L1 IHC-positive (FIG. 364). Patients within this immunologically active cluster who lack traditional immunotherapy biomarkers represent an interesting population that might benefit from immunotherapy. Overall, the IFNγ signature scores were significantly different between patients based on their immunotherapy biomarker status ($P=3.77 \times 10^{-4}$; FIG. 365). In particular, TMB-high, MSI-H, or PD-L1 IHC-positive and TMB-high tumors expressed higher levels of IFNγ-related genes compared with tumors lacking those biomarkers (P 0.05).

Identification of Therapeutic Options and Clinical Trials

We investigated the extent to which molecular profiling aids in identifying therapies and clinical trials. First, we identified the proportion of patients matched to therapies within each therapeutic evidence tier (see Methods: *Knowledge database and evidence-based therapy matching*). Evidence tiers contain somatic biomarker information related to therapeutic response and/or resistance and are divided into four categories: tier I level A (IA), tier I level B (IB), tier II level C (IIC), and tier II level D (IID). Tiers are ranked according to biomarker evidence strength, ranging from consensus clinical guidelines to case reports and preclinical evidence[20]. Across all cancer types, 91.4% of patients were matched to a therapeutic option based on all evidence levels for response to therapy, and 22% based on all levels of evidence for resistance to therapy (FIG. 366). Together, response and resistance matching based on the highest evidence tiers (IA and IB) accounted for 29.6% of cases; while 62% of cases matched for either response or resistance based on evidence of lower clinical utility (IIC and IID) (FIG. 366, FIG. 367). The tiers of evidence-based therapies matched to patients varied significantly by cancer type (FIG. 368). For example, 56% of lung patient matches were made using tier IA evidence for EGFR, KRAS, and MET, as well as targets that have emerged more recently such as BRAF and ERBB2 (HER2). Additionally, 58% of colorectal patient matches used tier IA evidence, the majority of which were resistance to therapy based on KRAS mutations. In contrast, patients with pancreatic cancer were matched exclusively according to lower tier evidence based on resistance to anti-EGFR therapy due to KRAS mutations.

We next determined the contribution of each molecular assay component to therapy matching. First, therapeutic matches based on clinically actionable CNVs, SNVs, and indels were examined (FIG. 369, FIG. 370). CNVs accounted for tiers IA and IB evidence-based matching of 29 patients (160 patients across all levels of evidence). SNVs and indels accounted for tiers IA and IB evidence-based matching of 124 patients (429 patients across all levels of evidence). Although most patients exhibited a mutation within a gene of clinical significance, the context of those mutations within tumor type and evidence level was considered to fully assess their clinical utility (FIG. 371). Some of the most commonly mutated genes have low-level evidence, or evidence related to resistance. For instance, TP53 has tier IIC evidence and drugs in clinical trials, while KRAS has tier IA evidence in two cancer types for resistance to anti-EGFR therapy. Many of the less common mutations have tier IA evidence for targeted therapies across a variety of cancer types. A notable example is PARP inhibitors for BRCA1- and BRCA2-mutated breast and ovarian cancer, which are currently in clinical trials and used off-label in other cancer types harboring BRCA mutations, such as prostate and pancreatic cancer.

Therapeutic options were also matched to clinically relevant gene fusions detected via DNA- and RNA-seq (FIG. 372). These fusions were clear drivers of cancer, part of consensus therapeutic guidelines, and identified with high sensitivity by the xT assay. Therapeutic options for fusions occurred in 29 patients (5.8%) of the xT 500 cohort, indicating that comprehensive fusion identification for all patients leads to therapeutic matching for a modest but clinically important subset of patients. Similar to previous reports, the majority of fusion events detected were TMPRSS2-ERG in prostate cancer. Although there are no clear clinical interventions associated with this fusion, TMPRSS2-ERG fusions were given a tier IID evidence level due to early evidence regarding therapeutic response. Of the 12 non-prostate cancer fusions, one was rated as evidence tier IA, one was rated as IIC, and 10 were rated as IID.

We next examined the potential for therapy matching using the expression profiles of clinically relevant genes selected based on their relevance to disease diagnosis, prognosis, and/or possible therapeutic intervention (see Methods: Gene expression calling). Over- or under-expression calls were reported in 133 patients (28.1%) for 16 genes with therapeutic evidence based on clinical, case, or preclinical studies (FIG. 373, FIG. 374, FIG. 375). Metastatic tumors were equally likely to have at least one reportable expression call as non-metastatic tumors. The most commonly reported over-expressed gene was NRG1, which was observed in 35 cases (7.3% of samples) across the cohort. NRG1 has been shown to play a biological role with treatment implications across cancer types. Over-expression of NRG1 has been associated with primary cetuximab resistance in colon cancer cell lines in the absence of RAS pathway mutations, primary resistance to trastuzumab or lapatinib in ERBB2 (HER2)-amplified breast cancer cells and response to monoclonal HER2-directed antibodies in lung and ovarian cancers Based on the xT 10 biomarkers assayed in the cohort, we investigated the percentage of patients eligible for immunotherapy. There were 52 patients (10.4%) identified as potential candidates for immunotherapy based on TMB, MSI status, and PD-L1 IHC results (FIG. 376). The number of MS I-H and TMB-high cases varied among cancer types, with 22 patients (4.4%) positive for both biomarkers. PD-L1-positive IHC alone was measured in 15 patients (3%) and was highest among lung cancer patients. TMB-high status alone was measured in 13 patients (2.6%), who were primarily lung and breast cancer patients. Lastly, PD-L1-positive IHC and TMB-high status were scarcely observed simultaneously (0.4%).

As noted above, therapy matches based on level IA or IB evidence for SNVs, CNVs, and fusions alone were observed for 29.6% of patients. With the addition of more comprehensive molecular profiling that included gene expression and immunotherapy biomarker information, we observed an increase in matches to 43.4% of the xT 500 cohort (217 patients) (FIG. 377, FIG. 367). This percentage increased even further, to 93.6% (468 patients), when matches from level IIC and IID evidence and preclinical RNA-based evidence were included.

Additionally, 1,966 clinical trial matches were reported for the xT 500 cohort. Based on molecular and clinical data (see Methods: Clinical trial reporting), at least one clinical trial option was reported for 96.2% of the cohort (481 patients). Examples of the criteria used to match patients to a clinical trial option are shown in Appendix B. In Appendix B, patients 482 through 500 did not match a clinical trial and therefore are not on the list as shown. At least one biomarker-based clinical trial match was made for 76.8% of the cohort according to a gene variant on the patients' xT report. Of the patients who were not matched to a biomarker-based clinical trial, 19.4% were matched to at least one disease-based clinical trial via clinical data alone. The frequency of biomarker-based clinical trial matches varied by diagnosis and outnumbered disease-based matches (FIG. 378). For example, patients with gynecologic or pancreatic cancer typically received biomarker-based clinical trial matches, while patients with rare cancers had an almost equal ratio of biomarker-based to disease-based trial matching. The differences observed between biomarker- and disease-based trial matching were most likely due to the frequency of targetable alterations and heterogeneity of those cancer types.

Comparison of the Full Platform with Tumor-Only Analyses

Most commercial oncology assays only test tumor samples. Because paired tumor-normal samples were sequenced within the xT 500 cohort, we were able to examine the effect of germline sequencing on the accuracy of somatic mutation calling. We randomly selected 50 cases from the cohort with a range of TMB profiles and re-evaluated them using a tumor-only analytical pipeline. We identified 8,557 coding variants after filtering with a publicly available population database. By further filtering with an internally developed list of technical artifacts, an internal pool of normal samples, and classification criteria (see Methods: Alteration classification), the number of variants was reduced to 642 while still retaining all true somatic alterations (72.3%) (FIG. 379).

Within the 642 filtered tumor-only variants, 27.7% of variants were classified as somatic false positives, i.e., true germline variants or artifacts. The use of tumor-normal sequencing data allowed for these false positive variants to be filtered and more accurately classified as germline variants (FIG. 379, FIG. 380, Appendix C). When we further separated the dataset by classification criteria, 1.10% of germline variants were classified as pathogenic, and thus potentially clinically actionable. One such example involved a BRCA mutation with somatic loss of heterozygosity in colorectal cancer. In tumor types where BRCA mutations are not common, such as colon cancer, BRCA mutations with loss of heterozygosity would trigger a recommendation for PARP inhibitor therapy. In cases without loss of heterozygosity, genetic counseling would be recommended instead. The ability to differentiate these cases is enhanced by the more accurate classification of somatic versus germline variants via tumor-normal sequencing.

To assess the impact of tumor-only testing on therapeutic matching, we evaluated which therapies would be offered to the 50 patients in two scenarios: a tumor-only test versus a full xT test (matched tumor-normal DNA-seq plus RNA-seq and IO analyses). We found that divergent therapies would have been reported for eight of the 50 patients (16%) if they had received a tumor-only test alone rather than a full xT test (Appendix D). Of these eight patients, four had different hypothetical treatment matches due to information obtained via RNA-seq or due to the tumor having somatic mutations with low clonality, which are difficult to detect in a tumor-only test. One tumor-only prostate cancer DNA-seq result did not show any contraindication to the anti-androgen therapy the patient was receiving; but RNA-seq included in the full xT test showed androgen receptor over-expression, indicating possible resistance. The other three patients had divergent therapy matches due to the tumor-only test reporting a germline mutation as somatic. These patients potentially would not have received genetic counseling with a tumor-only test. Lastly, we compared therapies matched for all DNA variants detected by the tumor-only dataset to therapies matched by a patient-facing website, My Cancer Genome (MCG). A total of 43 cases were matched to therapies via the full xT test, while only five cases were matched to therapies via MCG.

DISCUSSION

We examined the molecular and clinical insights gained from extensive genomic profiling, including matched tumor and germline DNA-seq and whole-transcriptome RNA-seq. Comparison between genomic alterations in the xT 500 cohort and previously published clinical NGS data indicated our cohort is representative of the mutational spectra observed within and across tumor types. The xT tumor-normal sequencing pipeline robustly classifies true somatic versus germline variants and eliminates the 27.7% somatic false positive rate observed in the tumor-only analysis. Erroneous identification of germline variants as somatic mutations can negatively impact patient care. For example, germline variants in genes that can be mutated in somatic or germline, like BRCA, would be classified as somatic in a tumor-only analysis, missing the opportunity to provide germline findings with genetic counseling and cancer screening recommendations[38].

Whole-transcriptome profiling is another key attribute of the platform. RNA expression data are currently RUO; however, in the future oncologists may use RNA findings in conjunction with clinical, pathologic, radiologic, and CAP/CLIA-validated molecular test data for the assessment of patients who have failed multiple lines of therapy. A total of 28.1% of patients with RNA expression calls were matched to some level of evidence-based therapy in a tissue agnostic fashion. For example, NCCN guidelines for breast, gastric, and lung cancers recommend FDA-approved drugs targeting HER2 overexpression. Patients with HER2 over-expression in other cancer types may also benefit from anti-HER2 therapies. Since HER2 evaluation by IHC is not standard practice for most cancer types, these patients cannot be identified without a comprehensive profiling method. In addition, RNA expression data provide insight into tumor type, which helps to refine diagnoses for TUOs and determine chemotherapy regimens.

Likewise, immunotherapy RNA-seq data analyses identified patients with and without traditional biomarkers who may benefit from immunotherapy. Immunotherapy has provided lasting results for some previously untreatable cancers[40]. However, the need for effective immunotherapy response biomarkers is clear considering the low proportion of patients who experience clinical benefit, the associated adverse events, and the cost of treatment. With the growing use of immunotherapy, it is becoming increasingly important to measure TME attributes that signal potential responsiveness in patients. PD-L1 IHC and MSI status are currently used as complementary or companion diagnostics for many cancer indications. Furthermore, TMB is an emergent biomarker associated with clinical benefit from checkpoint blockade and is being tested as a companion diagnostic. Approximately 10% of the xT 500 cohort were positive for at least one of these 10 biomarkers and, consequently, could be candidates for immunotherapy. Additional context about the immunologic phenotype of tumors was derived from RUO transcriptome analysis. Patients lacking IO biomarkers still grouped into immunologically active clusters, suggesting these biomarkers may not fully capture information about immunotherapy-conducive TMEs. Thus, further studies to identify other biomarkers will increase our understanding of TMEs and may help identify additional patients who would benefit from immunotherapy.

Overall, the integration of molecular data and structured clinical data resulted in precision therapy matches with tier IA or IB levels of evidence for 43.4% of the xT 500 cohort. A precision medicine option across all tiers and levels of therapeutic evidence was reported for 93.6% of the cohort. Identification of both therapeutic response and resistance across all evidence levels provides valuable information for physicians that could influence the prescription or timing of therapies. Integrating molecular data with clinical data also allows clinical trial matching for the most vulnerable patient populations. For example, although pancreatic cancer has few well-established therapeutic options, we were able to identify biomarker-based clinical trial options for 94% of pancreatic cancer patients.

More broadly, our results indicate that the overall population of patients with tumor types lacking viable options may benefit from molecular testing that matches patients to therapies and trials for which they otherwise would not have been considered. According to the American Cancer Society, only 27% of patients in the United States are provided with the option to enroll in a local clinical trial. Furthermore, only an estimated 3-8% of patients enroll in clinical trials nationwide. The use of molecular testing and structured clinical data allowed us to provide 96.2% of our cohort with at least one clinical trial option. The fact that most patients were matched to biomarker-based trials (76.8%) likely reflects both the large number of clinical trials that are biomarker-dependent and the extensive genomic profiling performed on the xT 500 cohort.

Additionally, the value of comprehensive, multimodality testing is demonstrated by the platform's ability to find rare events with treatment implications in this cohort. For example, to meet NCCN guidelines for "broad" molecular profiling of lung adenocarcinomas, testing would only have to include EGFR, ALK, ROS1, BRAF, KRAS, MET, RET, NTRK, ERBB2 (HER2), and IHC analysis of PD-L1 expression. In one lung adenocarcinoma patient, none of the above targetable genes contained an alteration, including CD274 (PD-L1), which was PD-L1 negative by IHC testing. If testing had stopped there, the patient would not have been eligible for targeted immunotherapy. However, the xT assay revealed a pathogenic germline mutation in the MMR gene MSH3, with a somatic loss of heterozygosity. MSH3 deficiency does not cause the MS I-H phenotype and is not included in standard IHC panels for MMR deficiency. Additionally, an elevated TMB of 19.6 mut/Mb was observed, suggesting the tumor had an increased probability of immunotherapy response[7]. These findings would likely motivate an oncologist to consider using immunotherapy.

In summary, our results indicate paired tumor-normal DNA-seq and RNA profiling of cancer patients yields high rates of matching to targeted therapies and clinical trials. To our knowledge, this is the first study to determine clinically relevant insights via comprehensive genomic analysis of a de-identified dataset derived from a cancer patients nationwide. Our results demonstrate the value of harnessing tumor-normal genomic sequencing, gene expression profiling, genomic rearrangement detection, and immunotherapy biomarker prediction to address emergent clinical indications. These results also illustrate the value of integrating and contextualizing clinical and molecular data to provide physicians with distilled information regarding their patient's disease and potentially actionable characteristics. These insights help to maximize personalized therapeutic options for a broader proportion of cancer patients, which cannot be attained through limited tumor-only DNA-seq panels alone.

Online Methods

Mutational Spectra Analyses.

Following random selection from the de-identified database, patients were grouped by pre-specified cancer type and filtered for variants classified as clinically relevant. Data from patient xT clinical reports given to oncologists were exclusively used for analyses, with some patients having multiple issued reports. The gene set was then filtered for genes having greater than five variants across the entire cohort to select for recurrently mutated genes. The collated set of patients were clustered by mutational similarity across single nucleotide variants (SNVs), indels, fusions, amplifications, and homozygous deletions. Subsequently, alteration prevalence for SNVs and indels from the MSKCC IMPACT cohort were extracted from MSKCC cBioportal (http://www.cbioportal.org/study?id=msk_impact_2017 #summary) to compare xT assay variant calls against publicly available variant data for solid tumors. After selecting only for genes on both panels, variants with a minimum of 2.5% prevalence within their respective cohort were plotted (FIG. 345).

Detection of Gene Rearrangements from DNA-Seq.

Gene rearrangements were detected and analyzed via a separate parallel process optimized for the detection of structural alterations. Following de-multiplexing, tumor FASTQ files were aligned against the human reference genome using BWA (0.7.1). Reads were sorted and duplicates were marked with SAMBlaster (0.1.2.4). Discordant and split reads were further identified and separated by this process. These data were then read into LUMPY (0.2.1.3) for structural variant detection[48]. A Variant Call Format (VCF) file was generated and then parsed by a fusion VCF parser. The data was pushed to the bioinformatics database, where structural alterations were grouped by type, recurrence, and presence, and displayed through a quality control application. Known and novel fusions highlighted by the application were selected by the variant science team for loading into a patient report.

Gene Expression Data Collection and Normalization.

RNA-seq gene expression data were generated from formalin-fixed, paraffin-embedded tumor samples using an exome-capture-based RNA-seq protocol. After sequencing quality control, the final gene expression sample size was 474 samples. In brief, RNA-seq data were aligned to GRCh38 using STAR (2.4.0.1) and expression quantitation per gene was computed via FeatureCounts (1.4.6). Raw read counts were then normalized to correct for GC content and gene length using full-quantile normalization and adjusted for sequencing depth via the size factor method. Normalized gene expression data cancer types were log 10 transformed and used for all subsequent analyses.

Detection of Gene Rearrangements from RNA-Seq.

Gene rearrangements in RNA were analyzed via a workflow that quantitates gene-level expression and chimeric transcripts through non-canonical exon-exon junctions mapped using split or discordant read pairs. Subsequent to expression quantitation, reads were mapped across exon-exon boundaries to unannotated splice junctions and evidence was computed for potential chimeric gene products. If sufficient evidence was present for the chimeric transcript, a rearrangement was called as detected.

Gene Expression Reference Database.

Gene expression data generated in a lab was combined with publicly available cancer and normal gene expression datasets to create the reference database. Expression calling analyses included the cancer expression data from The Cancer Genome Atlas (TCGA) and the normal expression data from the Genotype-Tissue Expression (GTEx) project. Raw data from these publicly available datasets were downloaded from the Genomic Data Commons (GDC) or Sequence Read Archive (SRA) and processed via the RNA-seq pipeline. In total, 4,703, 4,865 TCGA, and 6,541 GTEx samples were processed and included as part of the larger reference database for this analysis. After processing, these datasets were corrected to account for batch effect differences between sequencing protocols across institutions (e.g., FFPE vs. fresh tissue, polyA vs. exome capture). To account for these differences, we calculated per gene sizing factors on log 10 normalized counts by subsampling TCGA and samples 100×. A linear transformation from the sizing factors calculated on TCGA samples was applied to TCGA and GTEx samples to ensure genes had equivalent means and variances across studies.

Gene Expression Calling.

For each patient in each cancer type (brain n=49, breast n=50, colorectal n=50, lung n=48, ovarian n=49, endometrial n=48, pancreas n=50, prostate n=46, rare n=46, and TUO n=38), we compared the expression of key cancer genes to the reference database to determine over-expression or under-expression. A maximum of 43 genes were evaluated based on the specific cancer type of the sample. Genes associated with immunotherapy are reported as relative expression calls in the immunotherapy portion of the platform and were excluded from this analysis. In order to make an expression call, each patient's expression percentile was calculated relative to four distributions: all cancer samples from TCGA, all normal samples from GTEx, specific cancer-matched samples from TCGA, and specific tissue-matched normal samples from GTEx. For example, each breast cancer patient's tumor expression was compared to all cancer samples, all normal samples, all breast cancer samples, and all normal breast tissue samples. Distribution thresholds specific to each gene and cancer type were optimized using literature curation and statistical analysis to reflect over- or under-expressing cancer subtypes. Thresholds at the time of xT reporting were applied to determine gene expression calls and varied slightly across the dataset as thresholds and genes reported have evolved over time.

Cancer Type Prediction.

A random forest cancer type prediction model was trained on normalized gene expression data from 4,703 samples spanning 33 cancer types, as defined in TCGA. The 500 samples in the xT cohort were excluded from the training dataset. The model was generated using scikit-learn Random ForestClassifer (0.20.0). Hyperparameter tuning on the training data using a three-fold cross-validation on 1,000 trees identified a minimum split size of two and maximum depth of 50 as the best performing parameters with a cross-validation classification accuracy of 81%.

Tumor Mutational Burden (TMB).

TMB was calculated by dividing the number of non-synonymous mutations by the Mb size of the panel (2.4 Mb). All non-silent somatic coding mutations, including missense, indel, and stop-loss variants with coverage greater than 100× and an allelic fraction greater than 5% were counted as non-synonymous mutations. Hypermutated tumors were considered TMB-high if they had a TMB >9 mut/Mb. This threshold was established by testing for the enrichment of tumors with orthogonally defined hypermutation (MSI-H) in the larger clinical database. A hypergeometric test was performed at 0.5 mut/Mb increments from 5 to 15 mut/Mb. Greater than 9 mut/Mb were found to be significantly enriched ($P=4.23 \times 10^{-31}$) for orthogonally defined hypermutated tumors.

TMB Whole-Exome Comparison.

TMB for gene panels ranging from 100 to 5,000 genes were simulated from the TCGA variant data using the 8,507 samples available on UCSC Xena (http://xena.ucsc.edu/). For each gene panel size tested, genes were randomly selected for inclusion in the simulated panel, TMB was calculated as described above, and the Pearson correlation between the simulated panel TMB and the whole-exome TMB was determined. Five simulations were performed for each panel size. The correlation between panel TMB and whole-exome TMB was experimentally validated using samples sequenced with both the xT panel and the whole-exome panel. Whole-exome TMB was calculated as described above, except with a coverage threshold of 35× and an allelic fraction threshold of 10%.

Human Leukocyte Antigen (HLA) Class I Typing.

HLA class I typing for each patient was performed using Optitype (1.3.1) on DNA-seq. Normal samples were used as the default reference for matched tumor-normal samples. Tumor-only-determined HLA type was used when the normal sample did not meet internal HLA coverage thresholds.

Neoantigen Prediction.

Neoantigen prediction was performed on all non-silent mutations identified by the xT pipeline, including indels, SNVs, and frameshifts. For each mutation, the binding affinities for all possible 8-11 amino acid peptides containing that mutation were predicted using MHCflurry (0.9.1). For alleles with insufficient training data to generate an allele-specific MHCflurry model, binding affinities were predicted for the nearest neighbor HLA allele as assessed by amino acid homology. A mutation was determined to be antigenic if any resulting peptide was predicted to bind to any of the patient's HLA alleles using a 500 nM affinity threshold. RNA support was calculated for each variant using varlens (0.0.4, https://github.com/openvax/varlens). Predicted neoantigens were determined to have RNA support if at least one read supporting the variant allele could be detected in the RNA-seq data.

Microsatellite Instability (MSI) Status.

The xT panel included probes for 43 microsatellites that are frequently unstable in tumors with MMR deficiencies. The MSI classification algorithm used reads mapping to those frequently unstable regions to classify tumors into three categories: microsatellite instability-high (MSI-H), microsatellite stable (MSS), or microsatellite equivocal (MSE). This assay can be performed with paired tumor-normal samples or tumor-only samples. Both algorithms return the probability of the patient being MSI-H, which is then translated into an MSI status of MSI-H, MSS, or MSE. All loci with sufficient coverage were tested for instability, as measured by changes in the distribution of the number of repeat units in the tumor reads compared to the normal reads using the Kolmogorov-Smirnov test. If $P \leq 0.05$, the locus was considered unstable. The proportion of unstable loci were fed into a logistic regression classifier trained on tumor samples with clinically determined MSI statuses.

Cytolytic Index (CYT).

CYT was calculated as the geometric mean of the normalized RNA counts of granzyme A (GZMA) and perforin-1 (PRF1).

Immune Infiltration Estimation.

The relative proportion of immune subtypes was estimated using a support vector regression (SVR) model, which includes an L2 regularizer and an epsilon insensitive loss function, similar to that of Newman et al. The SVR was implemented in python using the nuSVR function in the SVM library of scikit-learn (0.18) with the LM22 reference matrix downloaded from the supplement of Newman et al.

Interferon Gamma (IFNγ) Gene Signature Score.

Twenty-eight IFNγ pathway-related genes were used as the basis for an IFNγ gene signature score. Hierarchical clustering was performed based on Euclidean distance using the R package ComplexHeatmap (1.17.1) and the heatmap was annotated with PD-L1-positive IHC staining, TMB-high status, and/or MSI-H status. IFNγ score was calculated using the arithmetic mean of the 28 genes.

Somatic Signatures.

Thirty previously described somatic signatures of mutational processes[56,57] were estimated using non-negative least-squares regression as implemented in the deconstructSigs package (1.8.0). Mutations in this analysis included all discovered somatic SNVs, independent of their pathogenicity. Somatic signature estimates were calculated for all TMB-high samples with at least 50 detected somatic mutations. For visualization, the contributions of signatures 2 and 13 were summed for the APOBEC signature, signatures 4 and 29 were summed for the tobacco signature, and signatures 6, 15, 20, and 26 were summed for the DNA MMR deficiency signature. Additional signatures visualized included signature 1 for age, 3 for homologous recombination deficiency (HRD), 7 for UV, and 11 for alkylating agent. All other signatures were not plotted, given their unknown etiology and/or limited contribution to the mutational spectra of the patients analyzed.

Knowledge Database (KDB) and Evidence-Based Therapy Matching.

In order to determine therapeutic actionability for sequenced patients, maintains an internal KDB with structured data regarding drug-gene interactions and precision medicine findings reported in the oncology, pathology, and basic science literature. The KDB of therapeutic and prognostic evidence, which includes therapeutic response and resistance information, is compiled from a combination of external sources, including but not exclusive to NCCN, CIViC, and DGIdb, and is maintained with constant annotation by experts. Clinical actionability entries in the KDB are structured by both the disease to which the evidence applies and by the level or strength of the evidence. Therapeutic actionability entries are binned into tiers of somatic evidence by patient disease matches as established by the American Society of Clinical Oncology (ASCO), Association for Molecular Pathology (AMP), and College of American Pathologists (CAP) working group[20].

Evidence-based therapies are grouped by their level of evidence strength into tiers IA, IB, IIC, and IID. Briefly, tier IA evidence are biomarkers that follow consensus guidelines and match disease type. Tier IB evidence are biomarkers that follow clinical research and match disease indication. Tier IIC evidence biomarkers follow the off-indication use of consensus guidelines or clinical research, or either on- or off-indication patient case studies. Tier IID evidence biomarkers follow preclinical evidence regardless of disease indication matching. Patients from the xT 500 cohort were matched to actionability entries by gene, specific variant, diagnosis, and level of evidence.

Alteration Classification

Somatic alterations were interpreted based on a collection of internally weighted criteria composed of knowledge from known evolutionary models, functional data, clinical data, hotspot regions within genes, internal and external somatic databases, primary literature, and other features of somatic drivers. The criteria included features of an internally derived heuristic algorithm that groups alterations into one of four categories: Pathogenic, Variants of Unknown Significance (VUS), Benign, or Reportable. Pathogenic variants were defined as driver events or tumor prognostic signals. Benign variants were defined as alterations with evidence indicating a neutral state in the population and were removed from reporting. VUS were regarded as passenger events. Reportable variants were considered diagnostic, offering therapeutic guidance, or associated with disease but not key driver events. Gene amplifications, deletions, and translocations were reported based on the features of known gene fusions, relevant breakpoints, biological relevance, and therapeutic actionability. Germline pathogenic and VUS alterations identified in the tumor-normal matched samples were reported as secondary findings for consenting patients. These include a subset of genes recommended by the American College of Medical Genetics and genes associated with cancer predisposition or drug resistance.

Tumor-Only Analyses

For the tumor-only analyses, germline variants from 50 patient samples within the xT 500 cohort were computationally identified and removed using an internal algorithm that considered copy number, tumor purity, and sequencing depth. Further filtering was performed on the observed frequency in a population database (positions with variant allele frequency (VAF) % in the ExAC non-TCGA cohort). The algorithm was designed to be conservative when calling germline variants in therapeutic genes to minimize removal of true somatic pathogenic alterations that occur within the general population. To remove potential artifacts and biases within our cohort, alterations observed in an internal pool of 50 unmatched normal samples were removed. The remaining variants were assumed to be somatic variants with VAF≥5% and coverage ≥90%.

The alteration classification rules were applied and evidence-based therapies were assigned to each patient. Using matched normal sequencing data, we were able to identify true germline variants and evaluate contamination. The 50 patient cases were reviewed by two pathologists and an oncologist to determine which patients would have significantly different therapeutic matches based on the tumor-only analysis instead of the full test including tumor-normal matched DNA-seq, RNA-seq, and IO analysis. For this direct comparison, data from clinical reports were evaluated. Relevant variants and therapies from the full test reflect present-day therapy matches. As an additional comparison using the tumor-only DNA variant results, we manually searched the public resource www.mycancergenome.org (Nov. 7, 2018) for returned therapies based on these DNA variants.

Clinical Trial Reporting

Clinical trial options were identified by associating a patient's actionable variants and structured clinical data with an internally curated database of clinical trials largely procured from clinicaltrials.gov. Criteria considered for clinical trial reporting based on the patient information available at the time included but was not limited to molecular alterations, diagnosis, age, prior treatment, medical history, stage of cancer, and distance from point-of-care. Biomarker-based clinical trials were defined as those that required specific molecular alterations to qualify, while disease-based clinical trials did not have such a requirement. All reported clinical trials were checked for recruitment status at the time of xT report generation.

Statistical Analysis

All statistical analyses were conducted in R (3.4.4). Statistical significance was determined by a two-sided Wilcoxon Rank Sum Test or a Kruskal-Wallis Test, as indicated in the figure legends, with P<0.05 considered significant. P-values were adjusted for multiple testing using the Benjamini-Hochberg method. Relationships between variables were assessed by Pearson correlation. In the data presented as boxplots, the upper and lower hinges represent the first and third quartile. The whiskers extend to the most extreme value within 1.5× interquartile range on either end of the distribution. The center line represents the median. The exact sample sizes (n) used to calculate each statistic are listed within the figure legends.

Reporting Summary

Further information on research design is available in the Nature Research Reporting Summary linked to this article.

Data Availability

VCF files, RNA count files, and associated de-identified clinical data that support these findings will be available through Vivli (ID T19.01).

XXI. A Method and Process for Predicting and Analyzing Patient Cohort Response, Progression, and Survival With reference to the accompanying figures, and particularly with reference to FIG. 381, a system 16010 for predicting and analyzing patient cohort response, progression, and survival may include a back end layer 16012 that includes a patient data store 16014 accessible by a patient cohort selector module 16016 in communication with a patient cohort timeline data storage 16018. The patient cohort selector module 16016 interacts with a front end layer 16020 that includes an interactive analysis portal 16022 that may be implemented, in one instance, via a web browser to allow for on-demand filtering and analysis of the data store 16014.

The interactive analysis portal 16022 may include a plurality of user interfaces including an interactive cohort selection filtering interface 16024 that, as discussed in greater detail below, permits a user to query and filter elements of the data store 16014. As discussed in greater detail below, the portal 16022 also may include a cohort funnel & population analysis interface 16026, a patient timeline analysis user interface 16028, a patient survival analysis user interface 16030, and a patient event likelihood analysis user interface 16032. The portal 16022 further may include a patient next analysis user interface 16034 and one or more patient future analysis user interfaces 16036.

Returning to FIG. 381, the back end layer 16012 also may include a distributed computing and modeling layer 16038 that receives data from the patient cohort timeline data storage 16018 to provide inputs to a plurality of modules, including, a time to event modeling module 16040 that powers the patient survival analysis user interface 16030, an event likelihood module 16042 that powers the patient event likelihood analysis user interface 16032, a next event modeling module 16044 that powers the patient next event analysis user interface 16034, and one or more future modeling modules 16046 that power the one or more patient future analysis user interfaces 16036.

The patient data store 16014 may be a pre-existing dataset that includes patient clinical history, such as demographics, comorbidities, diagnoses and recurrences, medications, surgeries, and other treatments along with their response and adverse effects details. The Patient Data Store may also include patient genetic/molecular sequencing and genetic mutation details relating to the patient, as well as organoid modeling results. In one aspect, these datasets may be generated from one or more sources. For example, institutions implementing the system may be able to draw from all of their records; for example, all records from all doctors and/or patients connected with the institution may be available to the institutions agents, physicians, research, or other authorized members. Similarly, doctors may be able to draw from all of their records; for example, records for all of their patients. Alternatively, certain system users may be able to buy or license aspect to the datasets, such as when those users do not have immediate access to a sufficiently robust dataset, when those users are looking for even more records, and/or when those users are looking for specific data types, such as data reflecting patients having certain primary cancers, metastases by origin site and/or diagnosis site, recurrences by origin, metastases, or diagnosis sites, etc.

A set of transformation steps may be performed to convert the data from the Patient Data Store into a format suitable for analysis. Various modern machine learning algorithms may be utilized to train models targeting the prediction of expected survival and/or response for a particular patient population. An exemplary data store 16014 is described in further detail in U.S. Provisional Patent Application No. 62/746,997, titled Data Based Cancer Research and Treatment Systems and Methods, filed Oct. 17, 2018, which is incorporated herein by reference in its entirety.

The system may include a data delivery pipeline to transmit clinical and molecular de-identified records in bulk. The system also may include separate storage for de-identified and identified data to maintain data privacy and compliance with applicable laws or guidelines, such as the Health Insurance Portability and Accountability Act.

The raw input data and/or any transformed, normalized, and/or predictive data may be stored in one or more relational databases for further access by the system in order to carry out one or more comparative or analytical functions, as described in greater detail herein. The data model used to construct the relational database(s) may be used to store, organize, display, and/or interpret a significant amount and variety of data, such as more than 16030 tables and more than 300 different columns. Unlike standard data models such as OMOP or QDM, the data model may generate unique linkages within a table or across tables to directly relate various clinical attributes, thereby making complex clinical attributes easier to ingest, interpret and analyze.

Once the relevant data has been received, transformed, and manipulated, as discussed above, the system may include a plurality of modules in order to generate the desired dynamic user interfaces, as discussed above with regard to the system diagram of FIG. 381.

Patient Cohort Filtering User Interface.

Turning to FIG. 382, a first embodiment of a patient cohort selection filtering interface 16024 may be provided as a side pane provided along a height (or, alternatively, a length) of a display screen, through which attribute criteria (such as clinical, molecular, demographic etc.) can be specified by the user, defining a patient population of interest for further analysis. The side pane may be hidden or expanded by selecting it, dragging it, double-clicking it, etc.

Additionally or alternatively, the system may recognize one or more attributes defined for tumor data stored by the system, where those attributes may be, for example, genotypic, phenotypic, genealogical, or demographic. The various selectable attribute criteria may reflect patient-related metadata stored in the patient data store 16014, where exemplary metadata may include, for instance: Project Name (which may reflect a database storing a list of patients), Gender, Race; Cancer, Cancer Site, Cancer Name; Metastasis, Cancer Name; Tumor Site (which may reflect where the tumor was located), Stage (such as I, II, III, IV, and unknown), M Stage (such as m0, m1, m2, m3, and unknown); Medication (such as by Name or Ingredient); Sequencing (such as gene name or variant), MSI (Microsatellite Instability) status, TMB (Tumor Mutational Burden) status; Procedure (such as, by Name); or Death (such as, by Event Name or Cause of Death).

The system also may permit a user to filter patient data according to one or more of the following additional criteria: institution, demographics, molecular data, assessments, diagnosis site, tumor characterization, treatment, or one or more internal criteria. The institution option may permit a user to filter according to a specific facility. The demographics option may permit a user to sort, for example, by one or more of gender, death status, age at initial diagnosis, or race. The molecular data option may permit a user to filter according to variant calls (for example, when there is molecular data available for the patient, what the particular gene name, mutation, mutation effect, and/or sample type is), abstracted variants (including, for example, gene name and/or sequencing method), MSI status (for example, stable, low, or high), or TMB status (for example, selectable within or outside of a user-defined ranges). Assessments may permit a user to filter according to various system-defined criteria such as smoking status and/or menopausal status. Diagnosis site may permit a user to filter according to primary and/or metastatic sites. Tumor characterization may permit the user to filter according to one or more tumor-related criteria, for example, grade, histology, stage, TNM Classification of Malignant Tumours (TNM) and/or each respective T value, N value, and/or M value. Treatment may permit the user to select from among various treatment-related options, including, for instance, an ingredient, a regimen, a treatment type.

Certain criteria may permit the user to select from a plurality of sub-criteria that may be indicated once the initial criteria is selected. Other criteria may present the user with a binary option, for example, deceased or not. Still other criteria may present the user with slider or range-type options, for example, age at initial diagnosis may presented as a slider with user-selectable lower and upper bounds. Still further, for any of these options, the system may present the user with a radio button or slider to alternate between whether the system should include or exclude patients based on the selected criterion. It should be understood that the examples described herein do not limit the scope of the types of information that may be used as criteria. Any type of medical information capable of being stored in a structured format may be used as a criteria.

In another embodiment, the user interface may comprise a natural language search style bar to facilitate filter criteria definition for the cohort, for example, in the "Ask Gene" tab of the user interface or via a text input of the filtering interface. In one aspect, an ability to specify a query, either via keyboard-type input or via machine-interpreted dictation, may define one or more of the subsequent layers of a cohort funnel (described in greater detail in the next section). Thus, for example, when employing traditional natural language processing software or techniques, an input of "breast cancer patients" would cause the system to recognize a filter of "cancer site==breast cancer" and add that as the next layer of filtering. Similarly, the system would recognize an input of "pancreatic patients with adverse reactions to gemcitabine" and translate it into multiple successive layers of filtering, for example, "cancer site==pancreatic cancer" AND "medication==gemcitabine" AND "adverse reaction==not null."

In a second aspect, the natural language processing may permit a user to use the system to query for general insights directly, thereby both narrowing down a cohort of patients via one or more funnel levels and also causing the system to display an appropriate summary panel in the user interface. Thus, in the situation that the system receives the query "What is the 5 years progression-free survival rate for stage III colorectal cancer patients, after radiotherapy?," it would translate it into a series of filters such as "cancer site==colorectal" AND "stage==III" AND "treatment==radiotherapy" and then display five-year progression-free survival rates using, for example, the patient survival analysis user interface 16030. Similarly, the query "What percentage of female lung cancer patients are postmenopausal at a time of diagnosis?" would translate it into a series of patients such as "gender==female," "cancer site==lung," and "temporal==at diagnosis," determine how many of the resulting patients had data reflecting a postmenopause situation, and then determine the relevant percentage, for example, displaying the results through one or more statistical summary charts.

Cohort Funnel & Population Analysis User Interface

Turning now to FIGS. 383-389, the cohort funnel & population analysis user interface 16026 may be configured to permit a user to conduct analysis of a cohort, for the purpose of identifying key inflection points in the distribution of patients exhibiting each attribute of interest, relative to the distributions in the general patient population or a patient population whose data is stored in the patient data store 16014. In one aspect, the filtering and selection of additional patient-related criteria discussed above with regard to FIG. 382 may be used in connection with the cohort funnel & population analysis user interface 16026.

In another embodiment, the system may include a selectable button or icon that opens a dialogue box which shows a plurality of selectable tabs, each tab representing the same or similar filtering criteria discussed above (Demographics, Molecular Data, Assessments, Diagnosis Site, Tumor Characterization, and Treatment). Selection of each tab may present the user with the same or similar options for each respective filter as discussed above (for example, selecting "Demographics" may present the user with further options relating to: Gender, Death Status, Age at Initial Diagnosis, or Race). The user then may select one or more options, select "next," and then select whether it is an inclusion or exclusion filter, and the corresponding selection is added to the funnel (discussed in greater detail below), with an icon moving to be below a next successively narrower portion of the funnel.

Additionally or alternatively, looking at the cohort, or set of patients in a database, the system permits filtering by a plurality of clinical and molecular factors. For example, and with regard to clinical factors, the system may include filters based on patient demographics, cancer site, or tumor characterization, which further may include their own subsets of filterable options, such as histology, stage, and/or grade-based options for tumor characterization. With regard to molecular factors, the system may permit filtering according to variant calls, abstracted variants, MSI, and/or TMB.

Although the examples discussed herein provide analysis with regard to various cancer types, in other embodiments, it will be appreciated that the system may be used to indicate filtered display of other disease conditions, and it should be understood that the selection items will differ in those situations to focus particularly on the relevant conditions for the other disease.

Either all at once, or progressively upon receiving a user's selection of multiple filtering criteria, the cohort funnel & population analysis user interface 16026 visually depicts the number of patients in the data set. In one aspect, the display of patient frequencies by filter attribute may be provided using an interactive funnel chart. As seen in FIGS. 383-389, with each selection, the user interface updates to illustrate the reduction in results matching the filter criteria; for example, as more filter criteria are added, fewer patients matching all of the selected criteria exist.upon receiving each of a user's filtering factors.

The above filtering can be performed upon receiving each user selection of a filter criterion, the funnel updating to show the narrowing span of the dataset upon each filter selection. In that situation a filtering menu such as the one discussed above may remain visible in each tab as they are toggled, or may be collapsed to the side, or may be represented as a summary of the selected filtered options to keep the user apprised of the reduced data set/size.

With regard to each filtering method discussed above, the combination of factors may be based on Boolean-style combinations. Exemplary boolean-style combinations may include, for filtering factors A and B, permitting the user to select whether to search for patients with "A AND B," "A OR B," "A AND NOT B," "B AND NOT A," etc.

The final filtered cohort of interest may form the basis for further detailed analysis in the modules or other user interfaces described below. The population of interest is called a "cohort". The user interface can provide fixed functional attribute selectors pre-populated appropriately based on the available data attributes in a Patient Data Store.

The display may further indicate a geographic location clustering plot of patients and/or demographic distribution comparisons with publicly reported statistics and/or privately curated statistics.

Patient Timeline Analysis Module.

Additionally, the system may include a patient timeline analysis module that permits a user to review the sequence of events in the clinical life of each patient. It will be appreciated that this data may be anonymized, as discussed above, in order to protect confidentiality of the patient data.

Once a user has provided all of his or her desired filter criteria, the system permits the user to analyze the filtered subset of patients. With respect to the user interface depicted in the figures, this procedure may be accomplished by selecting the "Analyze Cohort" option presented in the upper right-hand corner of the interface.

Turning now to FIG. 390, after requesting analysis of the filtered subset of patients, the user interface may generate a data summary window in the patient timeline analysis user interface 16028, with one or more regions providing information about the selected patient subset, for example, a number of other distributions across clinical and molecular features. In one aspect, a first region may include demographic information such as an average patient age and/or a plot of patient ages. A second region may include additional demographic information, such as gender information, for the subset of patients. A third region may include a summary of certain clinical data, including, for example, an analysis of the medications taken by each of the patients in the subset. Similarly, a fourth region may include molecular data about each of the patients, for example, a breakdown of each genomic variant or alteration possessed by the patients in the subset.

The user interface also permits a user to drill down into the data summary information presented in the data summary window in order to sort that data further. For example, as seen in FIGS. 391-394, the system may be configured to sort the patient data based on one or more factors including, for example, gender, histology, menopausal status, response, smoking status, stage, and surgical procedures. Selecting one or more of these options may not reduce the sample size of patients, as was the case above when discussing filtering being summarized in the data summary window. Instead, the sort functions may subdivide the summarized information into one or more subcategories. For example, FIGS. 391 and 392 depict medication information being sorted by having additional response data layered over it within the data summary window.

Turning now to FIGS. 393-394, the subset of patients selected by the user also may be compared against a second subset (or "cohort") of patients, thereby facilitating a side-by-side analysis of the groups. Doing so may permit the user to quickly and easily see any similarities, as well as any noticeable differences, between the subsets.

In one embodiment, an event timeline Gantt style chart is provided for a high-level overview, coupled with a tabular detail panel. The display may also enable the visualization and comparison of multiple patients concurrently on a normalized timeline, for the purposes of identifying both areas of overlap, and potential discontinuity across a patient subset.

Patient "Survival" Analysis Module.

The system further may provide survival analysis for the subset of patients through use of the patient survival analysis user interface 16030, as seen in FIGS. 395-400. This modeling and visualization component may enable the user to interactively explore time until event (and probability at time) curves and their confidence intervals, for sub-groups of the filtered cohort of interest. The time series inception and target events can be selected and dynamically modified by the user, along with attributes on which to cluster patient groups within the chosen population, all while the curve visualizer reactively adapts to the provided parameters.

In order to provide the user with flexibility to define the metes and bounds of that analysis, the system may permit the user to select one or both of the starting and ending events upon which that analysis is based. Exemplary starting events include an initial primary disease diagnosis, progression, metastasis, regression, identification of a first primary cancer, an initial prescription of medication, etc. Conversely, exemplary ending events may include progression, metastasis, recurrence, death, a period of time, and treatment start/end dates.

As seen in FIG. 395, the analysis may be presented to the user in the form of a plot of ending event, for example, progression free survival or overall survival, versus time. Progression for these purposes may reflect the occurrence of one or more progression events, for example, a metastases event, a recurrence, a specific measure of progression for a drug or independent of a drug, a certain tumor size or change in tumor size, or an enriched measurement (such as measurements which are indirectly extracted from the underlying clinical data set). Exemplary enriched measurements may include detecting a stage change (such as by detecting a stage 2 categorization changed to stage 3), a regression, or via an inference (such as both stage 3 and metastases are inferred from detection of stages 2 and 4, but no detection of stage 3).

Additionally, the system may be configured to permit the user to focus or zoom in on a particular time span within the plot, as seen in FIG. 396. In particular, the user may be able to zoom in the x-axis only, the y-axis only, or both the x- and y-axes at the same time. This functionality may be particularly useful depending on the type of disease being analyzed, as certain, aggressive diseases may benefit from analyzing a smaller window of time than other diseases. For example, survival rates for patients with pancreatic cancer tend to be significantly lower than for other types of cancer; thus, when analyzing pancreatic cancer, it may be useful to the user to zoom in to a shorter time period, for example, going from about a 5-year window to about a 1-year window.

Turning now to FIGS. 397-400, the user interface also may be configured to modify its display and present survival information of smaller groups within the subset by receiving user inputs corresponding to additional grouping or sorting criteria. Those criteria may be clinical or molecular factors, such as any of the beginning or ending events, as well as gender, gene, histology, regimens, smoking status, stage, surgical procedures, etc.

As shown in FIG. 398, selecting one of the criteria then may present the user with a plurality of options relevant to that criterion. For example, selecting "regimens" may cause the user interface to prompt the user to select one or more of the specific medication regimens undertaken by one or more of the patients within the subset. Thus, as FIG. 399 depicts, selecting the "Gemcitabine+Paclitaxel" option, followed by the "FOLFIRINOX" option, results in the system analyzing the patient subset data, determining which patients' records include data corresponding to either of the selected regimens, recalculating the survival statistics for those separate groups of patients, and updating the user interface to include separate survival plots for each regimen. Adding a group/adding two or more selections may result in the system plotting them on the same chart to view them side by side, and the user interface may generate a legend with name, color, and sample size to distinguish each group.

As seen in FIG. 400, the system may permit a greater level of analysis by calculating and overlaying statistical ranges with respect to the survival analysis. In particular, the system may calculate confidence intervals with regard to each dataset requested by the user and display those confidence intervals relative to the survival plots. In one instance, the desired confidence interval may be user-established. In another instance, the confidence interval may be pre-established by the system and may be, for example, a 68% (one standard deviation) interval, a 95% (two standard deviations) interval, or a 99.7% (three standard deviations) interval.

As will be appreciated from the previous discussion, underpinning the utility of the system is the ability to highlight features and interaction pathways of high importance driving these predictions, and the ability to further pinpoint cohorts of patients exhibiting levels of response that significantly deviate from expected norms. The present system and user interface provide an intuitive, efficient method for patient selection and cohort definition given specific inclusion and/or exclusion criteria. The system also provides a robust user interface to facilitate internal research and analysis, including research and analysis into the impact of specific clinical and/or molecular attributes, as well as drug dosages, combinations, and/or other treatment protocols on therapeutic outcomes and patient survival for potentially large, otherwise unwieldy patient sample sizes.

The modeling and visualization framework set forth herein may enable users to interactively explore auto-detected patterns in the clinical and genomic data of their filtered patient cohort, and to analyze the relationship of those patterns to therapeutic response and/or survival likelihood. That analysis may lead a user to more informed treatment decisions for patients, earlier in the cycle than may be the case without the present system and user interface. The analysis also may be useful in the context of clinical trials, providing robust, data-backed clinical trial inclusion and/or exclusion analysis. Backed by an extensive library of clinical and molecular data, the present system unifies and applies various algorithms and concepts relating to clinical analysis and machine learning to generate a fully integrated, interactive user interface.

Outlier Analysis Module

Turning now to FIGS. 401-404, in another aspect, the system may include an additional user interface such as patient event likelihood analysis user interface 16032 to quickly and effectively determine the existence of one or more outliers within the group of patients being analyzed. For example, the interface in FIG. 401 permits a user to visually determine how one or more groups of patients separate naturally in the data based on progression-free survival. This user interface includes a first region including a plurality of indicators representing a plurality of patient groups, where each patient in a given group has commonality with other patients in that group; for example, commonality may be based on one or more of the above mentioned attribute, additional, system-defined, and tumor-related criteria used for filtering as well as other medical information capable of being stored in a structured format that may be identified by the system. This region may resemble a radar plot, in that the indicators are plotted radially away from a central indicator, as well as circumferentially about that indicator, where the radial distance from the central indicator is reflective of a similarity between the patients represented by the central and radially-spaced indicators, and where circumferential distances between radially-spaced indicators is reflective of a similarity between the patients represented by those indicators. In this instance, similarity with regard to radial distances may be based primarily or solely on the criterion/criteria governing the outlier analysis. For example, when analyzing patient groups with regard to progression-free survival ("PFS"), the central point may be based on the average PFS of the entire cohort over the time period evaluated, the radial distance from the central point may be indicative of the progression-free survival rate of the groups of patients reflected by the respective indicators such that groups of patients with better than average PFS are plotted above the central point and that groups of patients with worse than average PFS are plotted below the central point, and the distance from the central point on the X axis may be derived based upon the size of the population, a difference between an observed and expected PFS, or similar metric.

Additionally, the user interface may include a second region including a control panel for filtering, selecting, or otherwise highlighting in the first region a subset of the patients as outliers. Setting a value or range in the control panel may generate an overlay on the radar plot, where the overlay may be in the form of a circle centered on the central indicator and the radius of the circle may be related to the value or range received from the user in the second region. In this aspect, the user may select a value that is applied equally in both directions relative to the reference patient. For example, the user may select "25%," which may be reflected as a range from −25% to +25% such that the overlay may be a uniform circle surrounding the central point. Alternatively, the system may receive multiple values from the user, for example, one representing a positive range and a second representing a negative range, such as "−20% to +25%." The values may be received via a text input, drop down, or may be selected by clicking a respective position on a graph. In that case, the overlay may take the form of two separate hemispheres having different radii, the radii reflective of the values received from the user. In either case, once the system has received a user input, the indicators covered by the overlay may change in visual appearance, for example, to a grayed-out or otherwise less conspicuous form. Indicators outside of the overlay may remain highlighted or otherwise more readily visually distinguishable, thereby identifying those indicators as representing outliers.

In another aspect, as seen in FIGS. 403-404, the first region of the user interface may include a different type of plot of the plurality of patient groups than the radar-type plot just discussed. In this aspect, an x-axis may represent the number of patients in a given group represented by an indicator and a y-axis may represent a degree of deviation from the criterion/criteria being considered. As a result of these display parameters, this user interface will present the largest patient groups farthest away from the y-axis and the largest outlier groups farthest away from the x-axis. (For both this user interface and the one previously described, it should be appreciated that the origin may not reflect a value of 0 for either the y-axis or the radial dimension, respectively. Instead, the origin may reflect a base level of the criterion/criteria being analyzed. For example, in the case of progression-free survival, the base group may have a 2-year rate of 15%. In that case, deviations may be determined with regard to that 15% value to assess the existence of outliers. Such deviations may be additive, +/−20% may be 0% to 35% (0% instead of −5% because negative survival rates are not possible), or multiplicative, +/−20% may be 12% to 18%.)

As with the previously described user interface, the interface of FIGS. 403-404 may include a second region including a control panel for modifying the presentation of identifiers in the first panel. Again, as with that interface, the control panel may permit the user to make uniform or independent selections to the positive and negative sides of a scale. In particular, as seen in FIG. 404, the control panel in this instance permits the user to independently select the positive and negative ranges in the search for outliers. Upon making each selection, the user interface may adjust dynamically to cover, obscure, unhighlight, remove, or otherwise distinguish the indicators falling within the zone(s) selected by the user from the outlying indicators falling outside of that zone. Due to the configuration of the x- and y-axes, as discussed above, this user interface may be configured to make it possible for the user to quickly identify which outlier group is the farthest removed from the representative patient/group, since that outlier group will be the farthest spaced from the x-axis, in the positive direction, the negative direction, or in both directions. Similarly, the user interface may be configured to make it easy for the user to quickly, visually determine which patient group has the largest number of patients, since that group will be the farthest spaced from the y-axis, in the positive direction, the negative direction, or in both directions. Still further, the combination of axes may permit the user to make a quick visual determination as to which indicator(s) warrant(s) further inspection, for example, by permitting the user to visually determine which indicator(s) strike an ideal balance between degree of deviation/outlier and patient size.

With regard to either outlier user interface described above, the interface further may include a third region providing information specific to a selected node when the system receives a user input corresponding to a given indicator, for example, by clicking on that indicator in the first region of the interface, as seen in FIG. 404. In one aspect, that additional information may include a comparison of the criterion/criteria being evaluated as compared to the values of the overall population used to generate the interface of the first region. Information in this region also may include an identification of a total number of patients in a record set, a number of patients that record set was filtered down to based on one or more different criteria, and then the population size of the selected node as part of an in-line plot, which size comparisons may help inform the user as to the potential significance of the outlier group.

Additionally, with regard to either outlier user interface described above, the algorithm to determine the existence of an outlier may be based on a binary tree such as the one seen in FIG. 405. In order to generate such a tree, the system may separate each feature into its own category. For each category, the system then may determine which subset of the cohort have a largest spread of progress free survival vs. non-survival and treat the feature split which generated the largest spread as an edge between nodes and the features themselves as nodes. The system may continue with this analysis until it encounters a leaf, which it will treat as an outlier. For example a mutation column may be separated into either "mutated" or "not mutated," and an age option may be set by the user to be "over 50" vs. "under 50." The system then may determine what is the biggest cutoff age for survival, and use that as the binary decision point. Within all of these categories, each having a binary selection that split it into two groups, the system may determine which has the better survival and which has the worse survival, and compare those determinations across all columns to find the group having the biggest difference. A category with the biggest difference is the first node split in a tree that continues to split at additional nodes, forming a plurality of branches where the category criterion for the group is the edge between each node. Each of the branches terminates in a leaf, which is just a split of all the features that came before to identify a group of people with the highest PFS within the cohort according to the divisions above it.

In some instances, data in a branch may be lost when the system fully extrapolates out to a leaf. In such instances, the system may scan features that a current patient has in common with outlier patients, and suggest changes to clinical process that may place them in a new bucket (leaf/node) of patients that have a higher outlier. For example, if a branch has a high PFS in a node, but loses the distinction by the time the branch resolves in a leaf, the system may identify the node with the highest PFS as a leaf.

In order to generate an expected survival rate for a population, the system may rely upon a predictive algorithm built on the survival rates of the patients in the data set 16014. Alternatively, the system may use an external source for a PFS prediction, such as an FDA published PFS for certain cancers or treatments. The system then may compare the expected survival rate with an observed PFS rate for a population in order to determine outliers.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

XXII. Collaborative Artificial Intelligence Method and System

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Referring now to the drawings wherein like reference numerals correspond to similar elements throughout the several views and, more specifically, referring to FIG. 406, the present disclosure will be described in the context of an exemplary collaboration system 16110 that is consistent with at least some aspects of the present disclosure. System 16110 includes a collaboration server 16112, an artificial intelligence (AI) server 16114, a user interface collaboration device 16120 and a service provider database 18. Referring again to FIG. 406, in the illustrated embodiment A1 server 16114 is shown as separate from collaboration server 16112. Nevertheless, it should be appreciated that in at least some embodiments the functions the two servers may be performed via a single server. Similarly, while exemplary system 16110 is described herein as one where specific process steps or functions are performed by server 16112 and others are performed by server 16114, in other cases division of the functions and steps between the two servers 16112 and 16114 may be different. Furthermore, in at least some embodiments some of the processes performed by the servers 16112 and 16114 may be performed by a processor located within collaboration device 16120. For instance, in at least some cases, some or most of the processes related to speech recognition, intent matching, parameter extraction and audio response generation performed by AI server 16114 may be performed by collaboration device 16120.

Collaboration server 16112 is linked to a wireless transceiver (e.g., transmitter and receiver) 16116 enabling wireless two-way communication between collaboration device 16120 and collaboration server 16112. Transceiver 16116 may be any type of wireless transceiver including, for instance, a cellular phone transceiver, a WIFI transceiver, a Bluetooth transceiver, a combination of different types of transceivers (e.g., including Bluetooth and cellular), etc. Server 16112 runs software applications or modules to perform various processes and functions described throughout this specification. In particular, server 16112 runs a collaboration application 16160 which includes, among other things, a visual response module 16162 and a data operation module 16164. Server 16112 receives user voice queries (hereinafter "voice messages") 16159 captured by device 16120, cooperates with AI server 16114 to identify the meaning (e.g., intent and important parameters) of the voice messages, runs data operations on data in database 18 that is consistent with the voice messages to generate data responses, cooperates with AI server 16114 to generate audio response files based on the data responses and, in at least some cases visual response files, and transmits the response files 16173, 16177 back to collaboration device 16120. Device 16120 in turn broadcasts 16166 an audio response to the user and in cases where there is a visual response suitable for presentation via device 16120, generates the visual response in some fashion (e.g., presents content on a device 16120 display 16148, illuminates a signaling light 16150, etc.).

Referring also to FIG. 407, collaboration device 16120 includes an external housing 16122, a device processor 16130, a battery 16132 or other power source, a device memory 16134, a wireless transceiver 16136, one or more microphones 16138 and one or more speakers 16144 or audio output devices, as well as some component or process that can be used to activate device 16120 to initiate a user collaboration activity. External housing 16122 includes an external surface that forms a sphere in the illustrated example where a diameter of the sphere is selected so that the device 16120 can easily be held by hand by an oncologist. For instance, the diameter of device 16120 in most cases will be between three fourths of an inch and five inches and in particularly advantageous embodiments the diameter will be between one and one quarter inch and two inches.

In other cases the external housing includes an external surface that forms a cube or other three-dimensional rectangular prism. In such cases, in particularly advantageous embodiments, the largest dimension of the three-dimensional shape (height, width, depth) will be between one and one quarter inch and two inches.

The system 16110 may be implemented in other manners. For instance, the collaboration device 16120 may be a smartphone, tablet, laptop, desktop, or other computing device, such as an Apple iPhone, a smartphone running the Android operating system, or an Amazon Echo. Some of the processes performed by the servers 16112 and 16114 may be performed through the use of an app or another program executed on a processor located within collaboration device 16120.

The outside surface may be formed by several different components out of several different materials including opaque materials for some portions of the surface and transparent or translucent materials for other portions where light needs to pass from indicator lights mounted within the housing. The outside housing surface may form speaker and microphone apertures, a charging port opening (not illustrated), and other apertures or openings for different purposes. The housing forms an internal cavity and most of the other device components are mounted therein. While device 16120 may include a single speaker and a single microphone, in an optimized assembly device 16120 will include several speakers and microphones arrayed about the housing assembly so that oncologist voice signals can be picked up from all directions.

There are many different hardware configurations that may be used to provide the collaboration device processor 16130. One particularly useful processor for purposes of the present device 16130 is the Qualcomm QCS405 SoC (System-on-Chip) which supports many different types of connectivity including Bluetooth, ZigBee, 802.11ac, 802.11ax-ready, USBC2.0/3.0, and others. This solution includes an on device AI engine that enables on device AI algorithm execution so that, in at least some cases, the AI functionality described herein in relation to server 16114 may be performed by processor 16130. This SoC supports up to four microphones and supports high performance key word detection. Processor 16130 is linked to each of battery 16132, memory 16134, transceiver 16136, microphone 16138, and speaker 16144.

Once device 16120 is activated and while it remains active, microphone 16138 captures user voice messages 16157 which are provided to processor 16130. Processor 16130 transmits 16159 the voice messages via transceiver 16136 to collaboration server 16112 (see again FIG. 406). Audio response files are received 16181 back by device 16120 transceiver 16136 and processor 16130 broadcasts those response files via speaker 16144. While not shown it is contemplated that device 16120 may also include some type of haptic signaling component (e.g., a vibrator or the like) to indicate one or more device states.

In at least some cases device 16120 can be activated by a specifically uttered voice command. To this end, processor 16130 may be on all the time and monitoring for a special triggering activation command like "Hey Query". Once the activation command is received, processor 16130 may be activated to participate in a user collaboration session. Here, processor 16130 may acknowledge the activation command by transmitting a response like "Hello, what can I help you with?" or a tone or other audio indication, and may then enter a "listening" state to capture a subsequent user voice message. When a subsequent voice message is captured, the collaboration session may proceed as described above.

In addition to or instead of being activated by an uttered activation command, device 16120 may be activated by selection of a device activation button or touch sensor, when the device 16120 is picked up or otherwise moved, etc. To this end, see the optional input buttons 16152 and motion and orientation sensors 16140 and 16142 in FIG. 407. The motion sensors may include an accelerometer, a gyroscope, both an accelerometer and a gyroscope or some other type of motion sensor device.

In addition to being able to present audio responses to a user's queries, in at least some cases device 16120 is equipped to present some type of visual response. For instance in a simple case, device 16120 may include more or more indicator lights 16150 where LED or other light sources can be activated or controlled to change colors to intricate different device 16120 states. For instance, in at least some cases indicator lights 16150 may be off or dimmed green when device 16120 is inactive and waiting to be activated. Here, once device 16120 is activated and while waiting or listening for a voice message, lights 16150 may be activated bright green to indicate "go". As a user is speaking and the voice message is being captured by device 16120, lights 16150 may be activated blue green to indicate an audio message capture state. Once a query voice signal has ended, lights 16150 may be illuminated yellow indicating a "thinking" or query processing state. As an audio response is being broadcast to the user, lights 16150 may be illuminated orange to indicate an output state and once the audio response is complete, lights 16150 may again be illuminated bright green to indicate that device is again waiting or listening for a next voice message to be uttered by the user.

In at least some cases any time device 16120 is activated and waiting for a new or next voice message, device 16120 may be programmed to wait in the active state for only a threshold duration (e.g., 30 seconds) and then assume an inactive state waiting to be re-activated via another activation utterance or other user input. In other cases, once device 16120 is activated, it may remain activated for a longer duration (e.g., 10 minutes) and only enter the deactivated listening state prior to the end of the longer duration if a user utters a deactivation phrase (e.g., "End session", "End query" or "Hey query" followed by "End session") or otherwise affirmatively deactivates the device 16120 (e.g., selects a deactivation input button 16152).

Referring still to FIG. 407, in some cases, device 16120 may include one or more flat or curved or otherwise contoured display screens 16148 for presenting visual responses to user queries where the visual responses are suitable for consumption via a relatively small display screen. Here, for instance, short answers to user queries may be presented as text via display 16148. As another instance, summary phrases related to data responses that include data that cannot easily be presented via a small display screen may be generated and presented via display 16148. Other text phrases or graphics are contemplated for other purposes. For instance, in cases where a visual response is presented via some other display device (e.g., a display device that is paired or otherwise associated with collaboration device 16120), a text message may be presented via display 16148 indicating that additional information or a visual response is being presented via the associated display. As another instance, display 16148 may be controlled to glow specific colors to indicate states as described above with respect to light devices 16150 and may only present answers to queries in a textual format.

Referring again to FIG. 406, AI server 16114 runs software application programs and modules that perform various functions consistent with at least some aspects of the present disclosure. In at least some cases, AI server 16114 includes an automatic speech recognition (ASR) module 16170, an intent matching module 16172, a parameter extraction module 16174 and an audio response module 16176.

ASR module 16170 receives 16161 user voice messages from collaboration application 16160 and automatically converts the voice signals to text corresponding to the user's uttered voice messages essentially in real time. Thus, if an oncologist's voice signal message is "How many male patients 45 years or older have had pancreatic cancer?" or "What type of treatment should I prescribe this patient?", ASR module 16170 generates matching text using speech recognition software. Speech recognition applications are well known in the art and include Dragon software by Nuance, Google Voice by Google, and Watson by IBM, as well as others. In some cases recognition applications support industry specific term/phrase lexicons where specific terms and phrases used within the industries are defined and recognizable. In some cases user specific lexicons are also supported for terms or phrases routinely used by specific oncologists. In each of these cases new terms and phrases can be added to the industry and user lexicons. The text files are provided to intent matching module 16172.

Intent matching module 16172 includes a natural language processor (NLP) that is programmed to determine an intent of the user's voice signal message. Here, for instance, the intent may be to identify a data subset in database 18. As another instance, the intent associated with the phrase "How many male patients 45 years or older have had pancreatic cancer?" may be to identify a number of patients. As another example, the intent associated with the phrase "What type of treatment should I prescribe patient John Doe?" may be to identify the treatment that the system determines will maximally extend the quality of life for the patient John Doe. Literally thousands of other intents may be discerned by matching module 16172. Intents are described in greater detail hereafter.

Referring again to FIG. 406, parameter extraction module 16174 extracts important parameters from the user's uttered voice message. For instance, extracted parameters from the phrase "How many male patients 45 years or older have had pancreatic cancer?" may include "pancreatic", "male" and "45 years". For each user voice message, AI server 16114 provides 16163 (i) the associated text file, (ii) the matching intent and (iii) the extracted parameters back to collaboration server 16112 and more specifically to the data operation module 16164.

Data operation module 16164 accesses database 18 and creates 16165 a collaboration record on the database to memorialize the collaboration session. The text file received from server 16114 is stored in database 18 along with a date and time, oncologist identifying information, etc. Data operation module 16164 converts the intent and extracted parameters into a data operation and then performs 16165 the operation on data in database 18. For instance, in the case of the voice message "How many male patients 45 years or older have had pancreatic cancer?", operation module 16164 structures a database query to search for a number (e.g., the intent) of male patients 45 or older that had pancreatic cancer (e.g., the extracted parameters). The data operation results in a data response including the number of male patients 45 or older that had pancreatic cancer.

As another example, in the case of the voice message "What type of medication should I prescribe for John Doe," operation module 16164 structures a database query to search for a medication (e.g., the intent) of a cohort of patients who are clinically similar to the patient John Doe, where such medication resulted in an optimal outcome for the cohort. The determination of whether a cohort of patients is clinically similar may be achieved by querying the database 18 for patients with certain factors, such as age, cancer stage, prior treatments, variants, RNA expression, etc. that are the same and/or similar to those of John Doe. As a simple example, if John Doe has a PTEN genomic mutation, the database 18 may select for inclusion into the cohort all patients who also have a PTEN genomic mutation. As another example, if John Doe has metastatic prostate cancer but no longer responds to androgen suppression first line therapy, the database 18 may select for inclusion into the cohort all metastatic prostate cancer patients who no longer responded to androgen suppression first line therapy.

As another example, in the case of the voice message "What is the expected progression free survival for Jane Smith if I prescribe Keytruda," operation module 16164 structures a database query to search for patients clinically similar to Jane Smith; selects from those patients a cohort who were prescribed Keytruda; analyzes the progression free survival of the selected cohort of patients; and returns the average progression free survival from the selected cohort.

As indicated above, the physician's voice message may relate to a question about a particular individual. The operation module 16164 may further be arranged to access a patient data repository in order to identify clinical, genomic, or other health information of the patient. The patient data repository may take many forms, and may include an electronic health record, a health information exchange platform, a patient data warehouse, a research database, or the like. The patient data repository may include data stored in structured format, such as a relational database, JSON files, or other data storage arrangements known in the art. The operation module 16164 may communicate with the patient data repository in various ways, such as through a data integration, may use various technologies, and may rely on various frameworks, such as Fast Healthcare Interoperability Resources (FHIR). The patient data repository may be owned, operated, and/or controlled by the physician, the physician's employer, a hospital, a physician practice, a clinical laboratory, a contract research organization, or another entity associated with the provision of health care. The patient data repository may include all of the patient's health information, or a subset of the patient's health information. For instance, the patient data repository may include structured data with patient demographic information (such as age, gender, etc.) a clinical description of the patient's cancer (for instance, a staging such as "stage 4" and a subtype such as "pancreatic cancer", etc.), a genomic description of the patient and/or the patient's cancer (for instance, nucleotide listings of certain introns or exons; somatic variants such as "BRAF mutation"; variant allele frequency; immunology markers such as microsatellite instability and tumor mutational burden; RNA overexpression or underexpression; a listing of pathways affected by a found variant; etc.), an imaging description of the patient's cancer (for instance, features derived from radiology or pathology images), an organoid-derived description of the patient's cancer (for instance, a listing of treatments that were effective in reducing or destroying organoid cells derived from the patient's tumor), and a list of prior and current medications, therapies, surgeries, procedures, or other treatments.

The operation module 16164 may use various methods to identify how the particular patient being queried about is clinically similar to other individuals whose data is stored in the database 18. Examples of determining clinical similarity are described in U.S. Provisional Patent Application No. 62/753,504, filed Oct. 31, 2018, the contents of which are incorporated herein by reference in their entirety, for all purposes. Other examples of determining clinical similarity are described in U.S. Provisional Patent Application No. 62/786,739, filed Dec. 31, 2018, the contents of which are incorporated herein by reference in their entirety, for all purposes.

The determination of what medication resulted in an optimal outcome for an identified cohort of individuals may be determined by comparing the outcome information stored in database 18 for those individuals with the medications that were prescribed or administered to them; dividing the cohort into sub-cohorts; analyzing, for each sub-cohort, measures of outcome such as progression-free survival, overall survival, quality of survival, or so forth; and returning one or more measures that indicate the optimal outcome(s).

In another example, the data operation module 16164 may select a first treatment from a list of treatments; examine the information from all patients in the database 18 who were provided that first treatment; divide the patient group into a first cohort of patients with a positive outcome and second cohort of patients without a positive outcome; compare the health characteristics (such as clinical, genomic, and/or imaging) of the queried patient to the health characteristics of the first cohort; compare the health characteristics of the queried patient to the health characteristics of the second cohort; and determine whether the queried patient's characteristics are closer to those of the first cohort or the second cohort. If the queried patient's characteristics are more clinically similar to the first cohort, then the data operation module 16164 may prepare a data response indicating the first treatment. If the queried patient's characteristics are more clinically similar to the second cohort, then the data operation module 16164 may not prepare a date response indicating the first treatment. The data operation module 16164 may then select a second, third, fourth, etc. treatment from the list of treatments and repeat the process described above for each selected treatment, and may continue until all treatments in the list of treatments have been explored. A variety of algorithmic approaches using mathematical or statistical methods known in the art may be used on the relevant health characteristics to determine whether the queried patient characteristics are clinically similar to the first cohort or second cohort, including mean, median, principal component analysis, and the like.

In another example, the data operation module 16164 may select all or a subset of records from patients in the database 18. From those records, the module 16164 may then select records from a first cohort of patients with a genomic biomarker similar to the queried patient. The module 16164 may then filter the first cohort for those patients who were prescribed a first treatment from a list of treatments. The module 16164 may then examine the outcomes of the patients in the first cohort and subdivide the first cohort into two or more sub-cohorts based on outcome, with patients with similar outcomes divided into the same sub-cohorts. Each sub-cohort may be further divided like the first cohort into additional sub-cohorts, and so on and so on until there is no material outcomes difference within each sub-cohort. At this point in the method, there may be dozens or more of sub-cohorts. The data operations module 16164 may then compare the queried patient's health characteristics with those in each sub-cohort, to identify the sub-cohort that is most clinically similar to the patient's health characteristics. The data operation module 16164 may then select a second, third, fourth, etc. treatment from the list of treatments and repeat the process described above for each selected treatment, and may continue until all treatments in the list of treatments have been explored.

Data operation module 16164 returns 16167 the data response to AI server 16114 and, more specifically to audio response module 16176, which uses that data to generate an audio response file. For instance, where 576 male patients 45 years or older had pancreatic cancer in the dataset searched, response module 16176 may generate the phrase "576 male patents 45 years or older have had pancreatic cancer." The audio response file is transmitted 16171 back to collaboration application 16160. The collaboration application stores the response file as well as a textual representation thereof in the collaboration record on database 18 for subsequent access. Collaboration application 16160 also transmits 16173 the audio response file via transceiver 16116 to collaboration device 16120 which then broadcasts that audio file to the user.

The AI modules 16114 may be provided via many different software application programs. One particularly useful suite of software modules that may provide the AI functionality is the Qualcomm Smart Audio 400 Platform Development Kit that can be used with the Qualcomm SoC processor described above. Another useful suite is the Dialogflow program developed and maintained by Google. Dialogflow is an end-to-end, build-once deploy-everywhere development suite for creating conversational interfaces for websites and mobile applications. A system administrator can use Dialogflow interfaces to define a set of intents, training phrases, parameters, and responses to intents. An intent is a general intention (e.g., what a user wants) by a user to access or manipulate database data in some specific way. For instance, one intent may be to generate a database data subset (e.g., patients that meet qualifying query parameters). As another instance, another intent may be to return a number (e.g., number of patients that meet qualifying parameters). Other intents may be a welcome intent (e.g., when a user first activates device 16120), an adverse consequences intent (e.g., to return a list of or at least an indication of adverse consequences to a treatment regimen), a medications intent (e.g., to return a list or indication prior medications), a schedule event intent (e.g., to schedule an appointment, a test, a procedure, etc.), etc. It is anticipated that a typical system will include hundreds and in some cases thousands of intents.

For each intent, the administrator provides a relatively small set of seed or training phrases used to train the intent matching module to recognize an intent associated with a received voice message. The training phrases include phrases that a user might say when their objective or purpose associated with an utterance is consistent with the associated intent. For instance, for an intent to return a number of patients that meet qualifying parameters (e.g., age, ailment, condition, oncogene, mutation, residence, staging, treatment, adverse effects of medical YYY, outcomes, etc.), some exemplary training phrases may be "How many patients have pancreatic cancer?", "How many stage 3 breast cancer patients from Chicago are HER2 positive?", "What number of patients have shown adverse effects while taking medication XXX?", "How many ovarian cancer patients in the last 48 months have had a p85 PIK3CA mutation?", "What percentage of basal cell carcinoma patients in the last 18 months have had cryosurgery?", and "The number of people that smoke that also have lung cancer?" Dialogflow also supports follow up intents that may be serially associated with other intents and more specifically with a second or subsequent intent to be discerned in a series of questions after a first intent is identified. For instance, the first phrase "How many ovarian cancer patients in the last 48 months have had a p85 PIK3CA mutation?" could be followed by a second phrase "How many of those patients were seen in the last 12 months?" As another example, for an intent to return a suggested therapy for a specific patient, some exemplary training phrases may be "What type of medication should I prescribe for John Doe?", "What type of immunotherapy should this patient receive", "What is the expected progression free survival for Jane Smith if I prescribe Keytruda?"

Once a small set of training or seed phrases have been provided by an administrator, a machine learning module (e.g., an AI engine) uses those phrases to automatically train and generate many other similar phrases that may be associated with the intent. This automatic training process by which a large number of similar queries are generated and associated with a specific intent is referred to as "fanning" and the newly generated queries are referred to as "fanned queries". The machine learning module stores the complete set of training and derived phrases (hereinafter "intent phrases") with the intent for use during collaboration sessions. Subsequently as a user uses the system and utters a phrase that is similar to but not an exact match for one of the intent phrases, the intent matching module recognizes the user's intent despite the imperfect match and responds accordingly. In addition, when an utterance is similar to but not exactly the same as one of the intent phrases, the system automatically saves the utterance as an additional intent phrase associated with the intent and may train additional other intent phrases based thereon so that the intention matching module becomes more intelligent over time.

In most cases a system user's intent alone is insufficiently detailed to identify specific information the user is seeking or how to respond and the user has to utter or provide additional query parameters. Dialogflow enables an administrator to specify a set of parameter types to extract from received voice messages. For example, some parameters may include a date, a time, an age, an ailment, a condition, a medication, a treatment, a procedure, a physical condition, a mental condition, etc. For each parameter type, the administrator specifies exemplary parameter phrases or data combinations (hereinafter "parameter phrases") that a system user may utter to indicate the parameter and, again, the machine learning module uses the administrator specified parameter phrases to train a larger set of parameter phrases usable for recognizing instances of the parameter. During a collaboration session when a user query is received, after module 16172 identifies intent, extraction module 16176 uses the parameter phrases to extract parameter values from the user's voice message and the intent and extracted parameters together provide the raw material needed by data operation module 16164 to formulate a data operation to perform on the database 16118 data (see again FIG. 406).

Dialogflow allows an administrator to tag some parameters as required and to define feedback prompts to be presented to a user when a received voice message does not include a required parameter. Thus, for instance, if a specific intent requires a date and a query associated with that intent does not include a date parameter, the system may automatically present a feedback prompt to the user requesting a date (e.g., "What date range are you interested in?").

Dialogflow also guides the administrator to define intent responses. An intent response typically includes a text response that specifies one or more phrases, a data response or a formatted combination of text and data that can be used to respond to a user's query. For example, where the intent is to return a number of patients that meet qualifying parameters, a response phrase may be "The number of patients that have is.", where the blanks represent data fields to be filled in with parameters from the voice message, data from the database, data derived from the database or options specified in conjunction with the response phrase.

Hereafter an intent and all of the information (e.g., parameters, fanned queries, data operations and answer phrases) related to the specific intent that is specified by the system will be referred to as an intent and supporting information at times in the interest of simplifying this explanation.

In FIG. 406, response module 16176 uses the response phrases to generate responses and, more specifically, audio response files that are provided back to collaboration server 16112. Again, it is contemplated that a typical system may include hundreds or even thousands of response phrases, at least one response phrase format or structure for each intent supported by the system.

In the illustrated exemplary system, AI server 16114 does not control database 16118 and therefore transmits the intent and extracted parameters back to collaboration server 16112 which runs data operation module 16164. In the present case it is contemplated that many data responses may not be able to be presented to a user in an easily digestible audio response file. For instance, in some cases a data response may include a graphical presentation of comparative cancer data which simply cannot be audibly described in a way that is easy to aurally comprehend. In these cases, after data operation module 16164 receives a data response from database 16118, module 16164 may pass that data on to visual response module 16162 which generates a suitable visual response to the user's query which in turn transmits the visual response via transceiver 16116 to device 16120 for presentation.

In at least some cases summary audio responses may be formulated by the system 16110 where appropriate and broadcast via device 16120. For instance, in some cases a data response may simply include a list type subset of database data that is to form the basis for additional searching and data manipulation. For example, a sub-dataset may include data for all male cancer patients since 1998 that have had an adverse reaction to taking any medication. This sub-dataset may operate as data for a subsequent query limiting the cancer type to pancreatic or the treatment to treatment XXX or any other more detailed combination of parameters. In these cases where a database subset is limited, an appropriate audio response file may include a summary response such as, for instance, "A subset of data for all male cancer patients that have had an adverse reaction to taking any medication has been identified." (See 16166 in FIG. 406.) This response phrase would be specified via the Dialogflow or other conversation defining software applications.

In at least some cases it is contemplated that the system may not be able to associate an oncologist's voice query with an intent or system supported parameters with a high level of confidence. In some cases it is contemplated that the AI server 4 may be able to assign confidence factors to each intent and extracted parameters and may be programmed to pose one or more probing queries back to an oncologist when intent or a parameter value confidence factor is below some threshold level. In some cases the probing feedback query may be tailored or customized to known structure or data content within the database 16118 or intents and parameters supported by AI server 16114 to help steer the oncologist toward system supported queries.

In cases where an intent and/or extracted parameters are not supported by the AI server or other system processes, it is contemplated that system 16110 will generate a record of the unsupported queries for consideration by an administrator as well as for subsequent access by the oncologist. In these cases it is contemplated that the system will present unsupported queries and related information to an administrator during a system maintenance session so that the administrator can determine if new intents and/or parameters should be specified in Dialogflow or via some other query flow application. In a case where an administrator specifies a new intent and/or parameters, the system may update the collaboration record including the unsupported query to provide a data response to the query and to indicate that the query will now be supported and the oncologist may be notified via e-mail, text, or in some other fashion that the query will be supported during subsequent collaboration sessions.

In some cases, the database 16118 may include an electronic health record database from a hospital or a hospital system. In other cases, the database 16118 may include an electronic data warehouse with data that has been extracted from an EHR, transformed, and loaded into a multi-dimensional data format. In other cases, the database 16118 may include data that has been collected from multiple hospitals, clinics, health systems, and other providers, either across the United States and/or internationally. The data in database 16118 may include clinical data elements that reflect the health condition over time of multiple patients. Clinical data elements may include, but are not limited to, Demographics, Age/DOB, Gender, Race/Ethnicity, Institution, Relevant Comorbidities, Smoking History, Diagnosis, Site (Tissue of Origin), Date of Initial Diagnosis, Histology, Histologic Grade, Metastatic Diagnosis, Date of Metastatic Diagnosis, Site(s) of Metastasis, Stage (e.g., TNM, ISS, DSS, FAB, RAI, Binet), Assessments, Labs & Molecular Pathology, Type of Lab (e.g. CBS, CMP, PSA, CEA), Lab Results and Units, Date of Lab, Performance Status (e.g. ECOG, Karnofsky), Performance Status Score, Date of Performance Status, Date of Molecular Pathology Test, Gene/Biomarker/Assay, Gene/Biomarker/Assay Result (e.g. Positive, Negative, Equivocal, Mutated, Wild Type), Molecular Pathology Method (e.g., IHC, FISH, NGS), Molecular Pathology Provider, Additional Subtype-specific data elements (e.g. PSA for Prostate), Treatment, Drug Name, Drug Start Date, Drug End Date, Drug Dosage and Units, Drug Number of Cycles, Surgical Procedure Type, Date of Surgical Procedure, Radiation Site, Radiation Modality, Radiation Start Date, Radiation End Date, Radiation Total Dose Delivered, Radiation Total Fractions Delivered, Outcomes, Response to Therapy (e.g. CR, PR, SD, PD), RECIST, Date of Outcome/Observation, Date of Progression, Date of Recurrence, Adverse Event to Therapy, Adverse Event Date of Presentation, Adverse Event Grade, Date of Death, Date of Last Follow-up, and Disease Status at Last Follow Up. The information in database 16118 may have data in a structured form, for instance through the use of a data dictionary or metadata repository, which is a repository of information about the information such as meaning, relationships to other data, origin, usage, and format. The information in database 16118 may be in the form of original medical records, such as pathology reports, progress notes, DICOM images, medication lists, and the like.

The database 16118 may further include other health data associated with each patient, such as next-generation sequencing (NGS) information generated from a patient's blood, saliva, or other normal specimen; NGS information generated from a patient's tumor specimen; imaging information, such as radiology images, pathology images, or extracted features thereof; other-omics information, such as metabolic information, epigenetic analysis, proteomics information, and so forth. Examples of NGS information may include DNA sequencing information and RNA sequencing information. Examples of imaging information may include radiotherapy imaging, such as planning CT, contours (rtstruct), radiation plan, dose distribution, cone beam CT, radiology, CTs, PETs and the like. The information in database 16118 may include longitudinal information for patients, such as information about their medical state at the time of a diagnosis (such as a cancer diagnosis), six month after diagnosis, one year after diagnosis, eighteen months after diagnosis, two years after diagnosis, thirty months after diagnosis, three years after diagnosis, forty two months after diagnosis, four years after diagnosis, and so forth. The information in database 16118 may include protected health information. The information in database 16118 may include information that has been de-identified. For instance, the information in database 16118 may be in a structured format which does not include (1) patient names; (2) all geographic subdivisions smaller than a state, including street address, city, county, precinct, ZIP code, and their equivalent geocodes, except for the initial three digits of the ZIP code if, according to the current publicly available data from the Bureau of the Census: (a) The geographic unit formed by combining all ZIP codes with the same three initial digits contains more than 20,000 people; and (b) The initial three digits of a ZIP code for all such geographic units containing 20,000 or fewer people is changed to 000; (3) All elements of dates (except year) for dates that are directly related to an individual, including birth date, admission date, discharge date, death date, and all ages over 89 and all elements of dates (including year) indicative of such age, except that such ages and elements may be aggregated into a single category of age 90 or older; (4) Telephone numbers; (5) Vehicle identifiers and serial numbers, including license plate numbers; (6) Fax numbers; (7) Device identifiers and serial numbers; (8) Email addresses; (9) Web Universal Resource Locators (URLs); (10) Social security numbers; (11) Internet Protocol (IP) addresses; (12) Medical record numbers; (13) Biometric identifiers, including finger and voice prints; (14) Health plan beneficiary numbers; (15) Full-face photographs and any comparable images; (16) Account numbers; (17) Certificate/license numbers; and (18) Any other unique identifying number, characteristic, or code. The number of records of information in the database 16118 may reflect information from 10, 100, 1,000, 10,000, 100,000, 1,000,000, 10,000,000 or more patients. Other examples of the type of information in database 16118 are described in U.S. Provisional Patent Application No. 62/746,997, filed Oct. 17, 2018, the contents of which are incorporated herein by reference in their entirety, for all purposes.

Referring now to FIG. 408, a process 16200 for facilitating a collaborative session that is consistent with at least some aspects of the present disclosure and that may be implemented via the FIGS. 406 and 407 system is illustrated. Process 16200 will initially be described in the context of a system where the only interface device used by an oncologist is the collaboration device 16120 (e.g., the system does not include a supplemental or additional large display screen or other emissive surface for presenting additional visual data response representations to a user). In this type of system the portions of process 16200 shown surrounded by dashed lines would not be present.

Referring to FIGS. 406 through 408, at process block 16202 an industry specific dataset is stored and maintained in database 16118. At block 16204, the intent matching, parameter extracting and audio response modules 16172, 16174 and 16176, respectively, are trained using Dialogflow or some other conversation defining application as described above. In addition, at block 16204 the visual response module 16162 is programmed to receive data responses from module 16164 where the responses provide seed data for configuring graphical or other visual representations of the response information.

Referring still to FIGS. 406 and 408, in a system only including interface device 16120, control passes from block 16204 to block 16206 where collaboration device 16120 monitors for activation (e.g., voice activation, movement, selection of an activation button, etc.). Once collaboration device 16120 is activated at block 16208, control passes to block 16212 where a voice signal is captured by device 16120 and the voice signal is transmitted 16157 to collaboration server 16112. At block 16214, the captured voice signal is transmitted 16161 to AI server 16114 where ASR module 16170 transcribes the voice signal to text, intent matching module 16172 examines the text file to determine the oncologist's intent, and parameter extraction module 16174 extracts key parameter values from the transcribed text. The text file, intent and extracted parameters are passed back 16163 to collaboration server 16112 and more specifically to data operation module 16164.

At block 16216, data operation module 16164 instantiates a new collaboration record on database 16118 and stores 16165 the text file in the collaboration record. Operation module 16164 also uses the intent and extracted parameters and associated values to construct a data operation at block 16218 and that operation is performed at block 16220 which yields a data response. At process block 16224, operation module 16164 provides 16169 the data response to AI audio response module 16176 which in turn generates an audio response file. The audio response file is sent back 16171 to collaboration application and sent 16173, 16181 to collaboration device 16120 at process block 16226. The audio response file and related text is stored at block 16226 as part of the collaboration record. The audio response file is broadcast 16166 via device 16120 speakers 16144 for the oncologist to hear at block 16228 after which control passes back up to block 16206 wherein the process continues to cycle indefinitely.

Where a collaboration session persists for multiple rounds of oncologist queries and system responses, each of an oncologist's voice message and associated text and response file and associated text is stored in the collaboration record so that a series of back and forth voice and response messages are captured for subsequent access and consideration.

In at least some embodiments the system also supports a visual output capability in addition to the audio file broadcasting capability to impart process status or state information as well as at least some level of response data in response to user queries. For instance, in FIG. 406, as an oncologist's voice signal is captured by device 16120 and AI server 16114 generates transcribed text, server 16112 may transmit that text file back to device 16120 to be presented in real time via display 16148 as a feedback mechanism so that an oncologist can ensure that the query was accurately perceived. Here, in some cases, the feedback text may persist until replaced by a visual data response where appropriate (e.g., persists for a few seconds in most scenarios) or may persist for a set duration (e.g., 5-7 seconds). In other cases the feedback text may only be replaced via a next feedback text phrase so that the oncologist has more time to assess accuracy of the perceived utterance.

As another instance, referring still to FIG. 406, where a data response is suitable for visual representation or even optimal if visually represented via device display 16148, the data response or a portion thereof may be provided to visual response module 16162 as shown at 16163. In these cases, module 16162 uses the data response to create a visual response file which is transmitted (see 16177 and 16181) to device 16120 to drive display 16148. In some cases the visual response presented may include a textual representation of the audio response file. In other cases the visual response may include reminders, alerts, notifications or other user instructions of any type. Where visual files are generated and presented to a user, collaboration server 16112 may store all visual representations as part of the ongoing collaboration record for subsequent access.

Referring now to FIG. 409, an exemplary collaboration conversation between an oncologist 16250 and collaboration device 16120 is illustrated where oncologist voice messages are shown in a left hand column 16260 and interleaved audio responses broadcast by device 16120 are shown in a right hand column 16262. Once device 16120 is activated, device 16120 responds with the phrase "How can I help you?" to prompt the oncologist 16250 to enunciate a first substantive query of the database 16118. Oncologist 16250 responds with a first query to "Select patients with pancreatic cancer." Here, consistent with the description above, AI server 16114 (FIG. 406) identifies intent and query parameters that are used to construct a data operation which yields a data response and ultimately the audio response "Patients with pancreatic cancer cohort identified." Oncologist 16250 then enunciates a second query "Limit cohort to men." causing the system to construct and perform another data operation to yield another audible response. This back and forth "conversation" continues until oncologist 16250 ends the session.

In cases where collaboration application 16160 stores collaboration records on database 16118, the system will enable an oncologist to access those records subsequently to refresh memory, initiate a more detailed line of query aided by additional output affordances such as a large workstation display screen, etc. To this end, see FIG. 410 that shows input and output devices at a workstation inducing a large flat panel display screen 16270, a keyboard 16272 and a mouse input device 16274. Mouse 16274 controls an on screen pointing icon 16276 for selecting on screen virtual icons and tools as well known in the interface arts. A screen shot on display 16270 shows a collaborator window 16280 that includes a list of oncologist-system collaborations for a specific oncologist that are selectable to access complete collaboration records. The list includes two columns including a date column 16282 indicating the date of a corresponding collaboration session and a collaboration column 16284 that includes a first query corresponding toe each collaboration represented in the list. A first entry in column 16284 corresponds to the collaboration session illustrated in FIG. 409 and is shown selected via icon 16276 and highlighted to indicate selection.

When the first entry in column 16284 is selected, the screen shot 16290 shown in FIG. 411 may be presented that includes the full collaboration record in text with oncologist queries in a first column 16292 and the audio system responses represented as text in a second column 16294. The example in FIG. 411 corresponds to the conversation in FIG. 409. Here, while the conversation is presented as text, it is contemplated that the oncologist may play an audio recording of the conversation back as a memory aid and to that end, a "Play" icon 16296 is provided that is selectable to replay collaboration audio.

While collaboration device 16120 is advantageous because of its relatively small size and portability, in at least some cases data response presentation is either more suitable via visual representations than audio or audio representations would optimally be supplemented via visual representations on a scale larger than afforded by device display 16120. To this end, it is contemplated that portable collaboration device 16120 may be supplemented as an output device via a proximate large flat panel display screen when a larger visual representation of response data is optimal. Referring now to FIG. 412, an input/output configuration 16300 that may be substituted for the collaboration device 16120 in FIG. 406 is illustrated. In FIG. 412, the input/output configuration includes a portable collaboration device 16120, a proximate large flat panel display screen 16302 and input keyboard and mouse devices 16304 and 16306, respectively.

Referring still to FIG. 412, in at least some cases device 16120 may be programmed to wirelessly "pair" with any Bluetooth or other wireless protocol enabled display screen that is in the general vicinity of device 16120 when some pairing event occurs. Here, a pairing event may simply include any time device 16120 is proximate a pairable display 16302 regardless of whether or not device 16120 has been activated to listen for a user's voice signal. In other cases, device 16120 may only pair with display once device 16120 becomes active (e.g., the pairing event would be activation of device 16120). In still other cases, pairing may only occur once device 16120 receives a video response file that requires large display 16302 for content presentation (e.g., the pairing event would be reception of a video file including data optimally presented on a large display screen).

Regardless of the pairing event, pairing may be automatic upon occurrence of the event or may require some affirmative activity by the user to pair. For instance, affirmative activity may include device 16120 broadcasting a voice query to the user requesting authorization to pair with display 16302 and a user voicing a "Yes" response in return.

Once device 16120 is paired with display 16302, an application program run by a display processor may take over the entire display desktop image and present a large collaboration interface via the entire display screen. In an alternative, the application may open a collaborator window 16310 as shown in FIG. 412 in which to present visual response files. In FIG. 412, an exemplary visual response representation is shown at 16310.

In at least some cases a collaborator window 16310 or desktop image may be presented automatically via display 16302 when a pairing event occurs. In other cases, even if device 16120 pairs with a display 16302, collaboration window 16310 may not be provided until some secondary triggering event occurs like, for instance, device 16120 is activated or a visual response file to be displayed on display 16302 is received. In still other cases window 16310 may only be presented after a user takes affirmative action to pair device 16120 and display 16302.

In at least some embodiments, even when device 16120 is paired with display 16302, response files may only be presented to a user via device 16120 at times. For instance, in many cases collaboration server 16112 will only generate an audio response file and in that case the audio file would only be broadcast via device 16120 with no visual representation on display 16302. Here, some user queries may result in response via only device 16120, other queries may result in response via only display 152022 and still other queries may result in combined responses via each of device 16120 and display 16302.

As described above, in at least some embodiments all collaboration system communication with display 16302 may be through device 16120 so that server 16112 does not communicate directly with display 16302. In other cases it is contemplated that display 16302 will have its own Internet of Things (IoT) address and therefore that server 16112 could communicate visual response files directly to display 16302. In this case, pairing would require location based association of device 16120 and display 16302 and storing that association information in a database by server 16112 so that audio and visual response file transmission to device 16120 and display 16302 can be coordinated.

In at least some cases it is contemplated that when a visual response file is presented on a paired large display 16302, a coordinated visual response may be presented via collaboration device display 16148 that refers the oncologist to the larger display 16302. Similarly, an audio broadcast by device 16120 may direct the oncologist to the larger display 16302 or include some type of summary message related to the large display 16302 visual representation. In FIG. 7, the illustrated audio broadcast 16320 summarizes the visual content on large display 16302 and device display 16148 directs the oncologist to refer to the larger paired display 16302 for more detailed information.

In still other cases, when response files would optimally be presented via a large format display while portable collaboration device 16120 is remote from a large display so that it cannot pair, the system may notify the oncologist that a better response can be obtained by pairing device 16120 with a supplemental large display. Here the notification may be presented via device display 16148 or audibly via speakers 16144. The notification may be in addition to broadcasting an audio response file with abbreviated response data.

When system 16110 presents visual data via a display screen 16302 during a collaboration session, in at least some embodiments all the presented visual files are stored in the collaboration record for subsequent access. To this end see, for instance, FIG. 411 where a third record column 16296 include visual response data 16298 that corresponds to each of the audio responses in column 16294. Here, each visual response is accessible to see information presented visually during an associated collaboration session. FIG. 413 shows one of the visual response icons selected which causes a sub-window 16330 to open up and present the visual content that was presented during a prior session.

In at least some cases it is contemplated that system 16110 will generate data responses suitable for generating both audio and visual response files which are stored in a collaboration record without presenting any visual information during a collaboration. Here, during a collaboration session all communication is via device 16120 despite generation of useful visual response files. The visual information may then be accessed subsequently via an interface akin to the one shown in FIGS. 411 and 413.

Referring now to FIG. 414, a second exemplary system 16400 that is consistent with at least some aspects of the present disclosure is illustrated. Here, unlike the FIG. 406 system where AI processes are performed by an independent AI server 16114, the AI processes are performed by portable collaboration device 16120 which passes information on to collaboration server 16112 for fulfillment or performance of data operations. As illustrated, the ASR, intent matching and parameter extraction modules 16170, 16172 and 16174, respectively, are all included in device 16120. An oncologist's voice signal captured by device 16120 is provided 16410 to ASR engine 16170 which generates test provided to intent matching module 16172. Module 16172 identifies the oncologist's intent and then module 16174 extracts parameters from the voice signal and each of the text, intent and extracted parameters is wirelessly transmitted 302 via transceiver 16116 to collaboration server 16112. Server 16112 operates in the same manner described above to create and build a collaboration record based on oncologist voice messages and system responses and also to use the intent and parameters to formulate data operations to be performed on database 16118 to generate data needed to answer oncologist queries. The data responses are transmitted 304 back to device 16120 where audio response module 16176 generates an audio file to drive speakers 16144 and present the audio response.

After an audible collaboration session, it is often difficult to get back into the same dialog flow at a later time as it is difficult to remember the back and forth communication that comprises the dialog. For this reason, in at least some cases a system will enable a user to reinsert herself into a flow using a display screen like the one shown in FIG. 411. Thus, in FIG. 411, a "Continue" button 16297 is presented which is selectable to place the overall system 16110 in the state that existed at the end of the session. Here, the "state" means that all the context associated with the line of questioning at the end of the session is reinstated (e.g., subsets of data, qualifying parameters, etc.), so that the oncologist can pick up where she left off if that is desired).

One problem oncologists and doctors in general have is that they need to enter notes into patient records every time they encounter and treat patients. At least some studies have indicated that a typical oncologist spends upwards of 1.5 hours every day memorializing events and thoughts in patent notes. Some oncologists craft record or document notes during patient visits while others wait until they have a break or until they are "off work" to craft notes. Where an oncologist crafts a note while with a patient, the doctor's attention is split between the note and the patient which is not ideal. Where an oncologist crafts a note subsequent to a patient visit, thoughts, observations and findings are often misremembered or captured with less detail.

To address this problem, in at least some cases portable collaboration device 16120 may be programmed to "listen" to an oncologist-patient care episode and record at least portions of oncologist and patient dialog essentially in real time as a "raw transcription". In addition, a system processor may be programmed to process the raw transcription data through OCR and NLP algorithms to identify words, phrases and other content with the captured raw voice signals. In at least some cases it is contemplated that a processor may be trained using Dialogflow or some other AI software program to recognize an oncologist's intent from captured words and phrases as well as various parameters needed to instantiate different types of structured notes, records or other documents that are consistent with one or more of the oncologist's intents. In addition, it is contemplated that the processor may be able to take into account other patient visit circumstances when discerning oncologist intent as well as identifying important parameters for specific structured notes, records or documents.

For instance, while speaking with a patient that has pancreatic cancer, the processor may use an oncologist's appointment schedule to automatically identify a patient as well as to access the patient's medical records to be used as context for voice messages captured during a patient visit. As the oncologist and patient speak, the processor may be programmed to discern the oncologist's voice and the patient's voice. Here, over time the processor would train to the oncologist's voice and be able to recognize the oncologist's voice based on tone, pitch, voice quality, etc. and would be programmed to assume that other voice signals not fitting the oncologists belong to the patient.

In at least some cases the oncologist could intentionally indicate a structured note type for the system to generate. For instance, in a simple case, the system may be programmed to generate five different structured note types where each type includes a different subset of 15 different parameters. Here, during Dialogflow training, an administrator may provide five different phrases for each of the five different note types where each phrase is associated with an intent to generate an associated note type. The processor would train on the five phrases for each note type and come up with many other phrases to associate with the note type intent. In addition, during training, the 15 parameter subsets for each note type would be specified. Moreover, a structured note type would be created and stored in a structured note database for use in instantiating specific instances of the note type for specific patient visits. Furthermore, feedback queries for at least required parameters may be developed and stored as in the case of the Dialogflow system described above.

During an oncologist-patient visit, when the oncologist wants the system to generate a specific note type, the oncologist may simply activate device 16120 by uttering "Go One" and then a phrase like "Create an instance of the first note type". The processor, recognizing the intent to create an instance of the first note type then listens during the dialog to pick out required parameters to instantiate the instance of the note type. In at least some cases if the system cannot identify some parameter(s) required for the note instance, device 16120 may be programmed to query the oncologist for the missing parameter(s). Feedback queries may be generated during a patient visit, immediately after the visit while facts and information about the visit are fresh in the oncologist's mind or at some other scheduled time like a break, a scheduled office hour, etc.

In other cases instead of requiring a physician to voice a specific note type to be created, the system may listen to the oncologist-patient dialog and identify an oncologist's intent from the ongoing dialog without some specific request.

Any of a raw transcription, note, record or other document generated by the system during or associated with a patient visit may be stored in a patient's EMR or any other suitable database. The AI can learn over time from oncologist utterances and become smarter as described above. In addition, a structured note may be presented to an oncologist for consideration prior to or after storage so that the oncologist can confirm the information in the structured record. In cases where an oncologist changes information captured by the system, any change may be provided back to a system processor and used to further train the processor AI to more effectively capture intent and/or parameters in the future.

In at least some cases another document type that the system may automatically generate is a billing document. Again, here, a system processor may "listen" to what an oncologist is saying during a patient visit and may discern an intent that has a billing ramification. At that point the processor may start to listen for other parameters to instantiate a complete billing record or document. In some cases a billing record may be automatically sent to a billing system or may be presented in some fashion to the oncologist to confirm the accuracy of the billing record prior to forwarding.

In still other cases another document type the system may automatically generate while listening to an oncologist is a schedule appointment. Here, again, a processor may be able to discern oncologist intent to schedule an appointment from many different utterances and may then simply listen for other parameters needed to instantiate a complete event scheduling action.

In particularly advantageous systems, a processor may be programmed to listen to an oncologist and automatically identify several simultaneous intents to generate several different types of notes, records or documents, and may monitor oncologist utterances to identify all parameters required for each of the simultaneous intents. For instance, where the processor determines that a billable activity or event is occurring and that an oncologist wants a structured patient visit note generated at the same time, where each of a structured bill and the structured note requires a separate subset of 15 different parameters, the processor would listen to oncologist utterances for all of the parameters to instantiate each of a bill record and a patient visit note. Again, where the system fails to capture required parameters, the processor may generate and broadcast or present (e.g., visually on a display) queries to the oncologist to fill out the required information at an appropriate time.

In some cases it is contemplated that an oncologist may indicate automatic document preferences for each patient visit where the system then automatically assumes an intent associated with each preferred document type and simply listens to the oncologist-patient dialog to identify parameters required to instantiate instances of each of the preferred document types for each patient visit. Thus, for instance, one oncologist may want the system to generate a structured patent visit note and a structured bill record as well as to tee up next visit scheduling options for each patient visit the oncologist participates in. Here, at the beginning of each scheduled patient visit session, the system immediately identifies three intents, a patient visit note intent, a bill record intent and a scheduling activity intent. The system accesses a structured record for each of the intents and proceeds to capture all required parameters for the intents. For the scheduling activity intent, the system may identify specific activities to be scheduled based on captured parameters and then at some appropriate time (e.g., last 5 minutes of the scheduled patient visit), may present one or more scheduling options for the specific activity to the oncologist and patient. Here, the oncologist and patent may accept to reject any suggested activity to schedule or the time(s) suggested for the activity.

In still other cases, after a system processor identifies an intent based on oncologist-patient dialog, the processor may be programmed to broadcast a query confirming the intent. For instance, where the system identifies an intent to generate a patient visit note, the processor may be programmed to broadcast the query "Would you like to have a patient visit note generated for this visit?" Here, an affirmative response would cause the processor to identify a structured note format and proceed to collect note format parameters to instantiate the note.

In at least some embodiments a collaboration device 16120 may listen in on all utterances by an oncologist and many oncologists may use devices 16120 to capture their utterances and raw voice messages. For instance, the system may capture all of an oncologist's utterances during patient visits, while participating in tumor boards, during office hours, and in other circumstances when the oncologist is discussing any aspect of cancer care. Here, a system processor or server may be programmed to recognize all utterances by an associated oncologist and distinguish those from utterances of others (e.g., patients, other healthcare workers, other researchers, etc.). The processor may store all or at least a subset of the oncologist's raw voice messages/ utterances and may process those utterances to identify text, words and phrases, contexts and ultimately impressions of the oncologist. For instance, one impression may be that for a pancreatic cancer patient that initially responded well to medication AAA where the medication is no longer effective, medication BBB should be employed as a next line of attack.

While the system may identify and automatically use discerned impressions in some cases, in other cases the system may be programmed to immediately present perceived impressions to an oncologist and allow the oncologist to confirm or reject the impression. Rejected impressions may be discarded or may be recorded to memorialize the rejection, the rejection itself being an indicator of the oncologist's impressions in general and therefore useful in future analysis. Confirmed impressions would be stored in a system database for subsequent use. In other cases impressions may only be periodically presented to an oncologist for confirmation or rejection.

Oncological impressions may be used as seed data for AI machine learning algorithms so that, over time, the algorithms learn from the impressions and populate databases with new data representing thoughts of the oncologist. The system may be programmed to associate different intents with different thoughts and subsequently, when an oncologist voice utterance is received, associate the utterance with the intent, identify parameters related to the intent and then obtain the oncologist's prior impressions or thoughts and provide a response that is consistent with the prior thought or impression.

In at least some cases where the system collects impressions from many different oncologists, the system may combine impressions and thoughts from multiple oncologists so that all oncologists that use the system have access to responses informed by at least a subset of the impressions and thoughts from an entire group. Here, once the database of impressions evolves, when an oncologist utters a question to her collaboration device 16120, the system would again identify an intent as well as required parameters to search the database for answers and may identify one or more impressions of interest to answer the question.

In at least some cases it is contemplated that the system will track efficacy of cancer or other treatments automatically to be used as a quality metric related to oncological impressions. Here, efficacious treatments would be assigned high confidence or other types of factors while low efficacy treatments based on relative efficacy of other treatments for comparable cancer states. Then, when an oncologist queries the system, the system would identify intent and required parameters to generate a structured data query and would return information related to only the most efficacious impressions.

In still other cases, the system may rank specific oncologists based on one or more factors and then present query responses based on or that represent the impressions of only the "top" oncologists. For instance, oncologists may be ranked based on peer reputation, based on treatment efficacy of their patients on a risk adjusted basis or using other methods (e.g., differently weighted combinations of factors). Here, responses would be limited to data related to only top oncologists.

In still other cases it is contemplated that queries may be limited to data and impressions for only specific oncologists. For instance, a first oncologist may desire the impression of a second specific oncologist on a specific cancer state. Here, the first oncologist may limit a query to the second oncologist by specific name. For example, where the first oncologist has been collaborating with device 16120 to access information related to a first patient, the first oncologist may simply utter "What would Sue White say?". In this case, a processor capturing the query would recognize the intent for another oncologist's impression, identify Sue White as a defining parameter and then access impressions associated with Sue White and regarding other contextual parameters previously captured and recognized by the system during prior dialog (e.g., patient name, cancer state factors, etc.). The response broadcast or presented to the first oncologist would be limited to data and information associated with Sue White.

In many cases, especially as a system is learning during use, the system will make mistakes and may return information that is not what has been asked for. In some cases it will be clear from a response that the query identified by the system was not what an oncologist intended while in other cases a wrong response may not be facially recognizable from the response. In cases where a response is recognized as wrong reflecting an inaccurately identified query, one issue is that an oncologist has to reutter the query with better enunciation. In at least some cases it is contemplated that if an oncologist rejects a response, the system may automatically attempt to identify a different query that the oncologist intended and a different suitable response. For instance if, upon hearing a response, an oncologist utters "No" or some other rejecting phrase, the system would recognize that response, formulate a different query based on the intent and parameters and then issue a different response.

In some cases in addition to recognizing a wrong response, the response will be usable to comprehend an error in the query identified by the system that led to the wrong response. For instance, if an oncologist asks for some cancer state characteristic of Tom Green and the system returns a response "Tom Brown's characteristic is XXX", the answer is usable to identify that the perceived question was wrong. In this case, to eliminate the need for the oncologist to revoice an entire query, the system may be programmed to allow a partial query where intent and parameters associated with the prior incorrectly perceived query are used along with additional information in the partial query to recognize a different data operation to be performed. Thus, in the above example, the oncologist may respond "No, I meant Tom Green." Here the system would use prior query information including intent (e.g., the characteristic sought) as well as the new parameter "Tom Green" to access the characteristic for Tom Green. The idea here is that the system retains context during a dialog so that oncologists do not have to continually re-voice complex queries that are misperceived by the system and instead can simply provide a subset of information in a next query selected to clear up any misperceptions.

In at least some cases, as indicated above, an answer to a query may not include any telltale signs that the query was misperceived by the system. In some cases it is contemplated that the system will be programmed to provide a confirmation broadcast or other message to an oncologist for each or at least a subset of queries that are uttered so that the oncologist can confirm or reject the perceived query. Confirmation leads to a data operation while rejection would cause the system to either identify a different query or ask for restatement of the query. In still other cases an oncologist may be able to ask the system to broadcast the question (e.g., data operation) that the system perceived for confirmation.

While the invention may be susceptible to various modifications and alternative forms, specific embodiments have been shown by way of example in the drawings and have been described in detail herein. However, it should be understood that the invention is not intended to be limited to the particular forms disclosed. For example, while a sphere shaped collaboration devices is described above, the portable device may take many different forms. For instance, referring to FIG. 415, a second exemplary collaboration device 16120a may include a cube shaped device including one or more emissive external surfaces for providing visual content. As another instance, a third collaboration device may include a tablet type device 16120b or any other portable device with components suitable to perform the functions described above.

In still other cases, a portable collaboration device may be one interface device in a larger interface ecosystem that includes other interface devices where an oncologist has the ability to move seamlessly between system interface devices during collaborative sessions. For instance, an ecosystem may include other interface devices and in particular, one or more stationary interface devices with better interface affordances like better microphones, larger speaker components, etc. In this regard, see for instance FIG. 416, which shows another exemplary interface device 16120c that is substantially larger than interface device 16120 and that is provided for stationary use at a workstation 16450. Exemplary interface 16120c includes a larger housing structure that forms a cavity for receiving various components as described above with respect to FIG. 407. Here the speakers are larger and presumably would be higher quality than the speakers in device 16120. In this case, device 16120c is intended to be used at its location on a worktop work surface, on a conference table in a conference room, etc.

In at least some exemplary contemplated systems, devices 16120 and 16120c may operate in conjunction with each other where collaboration sessions can be handed over from one of the devices 16120 to the other 16120c to optimize for given circumstances. For instance, if an oncologist is roaming while collaborating via device 16120 and enters a space (e.g., arrives at a workstation) that includes a better afforded stationary device 16120c, devices 16120 and 16120c may wirelessly communicate to recognize each other and to coordinate transfer of the collaboration session from device 16120 to device 16120c. Here, the collaboration session would continue, albeit using the stationary device 16120c. Similarly if an oncologist is using device 16120c to collaborate and gets up to leave the station, the collaboration session may automatically or with user request or confirmation, be switched over to device 16120 so that the collaboration can persist.

In still other cases a headphone, smart glasses with speakers and a microphone, etc., may be used as a collaboration device in the disclosed system. In this regard see the exemplary headphone assembly 16470 in FIG. 417 that includes ear speakers 16472 and a built in microphone 16474.

While described in the context of a dedicated collaboration device, aspects of the present invention may also be implemented using any type of computer interface device with microphones and speakers to enable a user-system conversation, regardless of whether or not the device is dedicated only to collaboration or not. For instance, a user's laptop computer may be used as a collaboration device running a collaboration program, an existing voice activated smart speaker may be used as a collaboration device, etc.

While technology or new technology based tools are great when they work well for its intended purposes, when technology or a tool does not work as expected by a user, the user often quickly becomes frustrated and, in many cases simply dismisses the technology or tool reverting back to resources to complete various tasks. This tendency to quickly dismiss imperfect new technology is exacerbated in cases where a user is extremely busy and therefore time constrained. Oncologists tend to be extremely busy people and therefore typically have little tolerance for ineffective or inefficient technology and tools.

One problem with dialog systems like those described herein is that a system that only supports a fraction of queries that oncologists may pose will more often than not fail to identify a correct intent for received queries. Here, in response, the system will either generate an answer to a wrong intent, simply indicate that the system does not currently have an answer for the query posed. These types of imperfect answers would cause frustration and in many cases, ultimately cause oncologists to dismiss these types of collaboration systems entirely.

In at least some embodiments it is contemplated that for a given dataset or record type, an essentially fulsome set of intents/parameters, related database queries and responses will be defined using Dialogflow or some other dialog specifying software so that the system will be able to effectively answer almost any query posed that is related to the dataset. Where new datasets, databases and record types are linked to the system, additional intents and related information may be specified for those datasets, databases and record types. For instance, in at least some cases the system may be programmed to support hundreds of thousands of different intents that include literally any foreseeable intent that may be intended by an oncologist. A team of system administrators/programmers works behind the scenes to identify additional possible intents and to supplement the system with new intents/parameters, related database queries and responses. Additional intents may be based on the existing datasets and record types and/or developed in response to new data types, new information and/or new oncological insights that evolve over time.

In cases where a system supports a massive number (e.g. tens or hundreds of thousands) of different intents, distinguishing one intent from another is complicated as the larger the number of supported intents naturally means that the differences between any intent and a set of similar but different intents will be difficult to discern. The task of correctly identifying an intent is exacerbated in a Dialogflow type system where an AI engine using a query "fanning" process to generate and associate literally hundreds or even thousands of similar queries with a specific intent during system training so that the possibility of fanned queries for two or more different intents overlapping becomes appreciable.

At least some embodiments of the disclosed system will use one or any combination of several techniques to discern an intended intent from other system supported intents. A first technique is based on the system operating during a collaboration session to distinguish different "dialog paths" that occur during the session and information related to a specific dialog path is used to inform subsequent intents during the same dialog path. For example, if a doctor asks device 16120 to "give me the results of my patient, Dwayne Holder's, sequencing report" and then asks a subsequent question "what are the best clinical trial options", the system determines that these questions are in a dialog path and answers the clinical trial question based on the clinical trial recommendations that have been provided on Dwayne Holder's clinical report (e.g., the system recommends clinical trials on sequencing reports and the system access all the data in each of those reports). In at least some embodiments only one dialog path is actively followed at a time. Nevertheless, in some cases the system maintains a memory cache of past dialog paths for an oncologist to inform future questions and answers.

A second technique for discerning an intended intent in a system that supports a massive number of intents has the system creating "entities" around key concepts related to an oncologist's query and associated system response(s). For example, Drugs, Drug Regimen, Clinical Trial, Patient Name, Pharmaceutical Company, Mutation, Variant, Adverse Event, Drug Warning, Biomarker, Cancer Type, etc. are all examples of entities supported by an exemplary system. While a small number of entities are identified here it should be appreciated that a typical system may support hundreds of different entities.

In at least some cases the system may be programmed to connect entities in a query or that are identified within a query path to form an entity set which is then usable to narrow down the list of potential answers which may be the best answers to a specific query. For instance, where a query path is associated with patient Dwayne Holder and drug XXX, those patient and drug entities may form a set that limits the most likely intents associated with subsequent queries. The system may also be programmed to leverages entities to evaluate whether a doctor's questions are still part of the same dialog path or if a new question is related to a new topic that is associated with a new dialog path.

A third technique for discerning an intended intent in a system that supports a massive number of intents is referred to generally as "personalization". Here, the idea is that many specific oncologists routinely follow similar dialog paths and voice similar queries with persistent syntax and word choices and therefore, once the system identifies a specific oncologist's persistent query characteristics and correctly associates those with specific intents, subsequent queries with similar characteristics can be associated with the same intents, albeit qualified by different sets of query parameters.

In at least some cases the system builds real time profiles of each oncologist or other system user based on the oncologist's past query characteristics (e.g., word choice, syntax, etc.), query paths followed, prior system provided responses to those queries, oncologist responses to the responses (e.g., does oncologist's response indicate that the system answer and therefore discerned intent was correct), and overall system use. For example, when an oncologist logs into the system, the system may automatically link to a list of the patients that the oncologist has sent to a sequencing service provider, the results that exist in those patients' sequencing reports and the key therapies and clinical trials that have been recommended for those specific patients. These linked lists support the decision making process that the system leverages to determine which question the oncologist is trying to ask (e.g., the oncologist's intent). For example, if an oncologist logs in and recently met with patient named Dwayne Holder, even if the system receives distorted audio that, when converted to text reads like: "what are the results for my quotient Lane Bolder," the system may be programmed to recognize that this oncologist recently met with Dwayne Holder, whose name is similar to Lane Bolder, and would proceed to generate answers based on that recognition.

In particularly advantageous systems all three of the techniques described above are used either serially or in parallel or some combination thereof to discern oncologist query intent. Thus, for instance, the system may use entities to narrow down an oncologist's intent when voicing a specific query, may further narrow down the possible intent based on a current query path and then may select a most likely intent based on a personalization functionality associated with the speaking oncologist.

In at least some cases it is contemplated that the system may provide tools during a system training session to avoid subsequent intent confusion. For instance, assume a system is already programmed to support 100,000 different intents when an administrator specifies a 100,001st intent and three associated seed or training queries to drive an AI engine query fanning process. Here, during the fanning process a system processor may be programmed to compare fanned queries for the 100,001st intent to other queries that are associated with other intents to identify duplicate queries or substantially identical queries. In at least some cases the system may be programmed to automatically avoid a case where fanned queries for two or more intents are identical or substantially identical.

In other cases, when the system recognizes that first and second queries associated with first and second intents are substantially identical, the system may present a warning to the administrator enabling the administrator to assess the situation and how to handle the confusing situation. In some cases substantially identical fanned queries may mean that the system already supports the newly specified intent in which case the administrator may simply forego enabling the new intent. In other cases the administrator may select one of the prior and new intent to be associated with the query in question and in other cases the administrator may allow the fanned query to be associated with two intents. In still other cases the administrator considering the two intents may decide that additional information is required for identifying one or the other or both of the prior and new intents and may further specify the factors to consider when identifying one or the other or both of those intents.

Where a query is associate with two intents, in operation when an oncologist voices the query, the system may identify both intents and generate a response query that is broadcast to the oncologist so that the oncologist can consider which intent was meant. In other cases it may be that both intents are consistent with the oncologist's voiced query and therefore answers to both queries may be generated and sequentially broadcast to the oncologist for consideration.

While the goal of the collaboration system is to handle any question that can be answered using data in system datasets or databases, in at least some cases despite the intent discerning techniques described above, the system may simply be unable to unambiguously identify one intent and/or required parameters associated with an intent among the many intents supported by the system. For instance, in some cases it is contemplated that the system may not be able to identify any intent associated with a query or may identify two or more intents associated with a query. In these cases the system may be programmed to facilitate a triage process to hone in on a specific intent for the query. In this regard, in at least some cases the system may be programmed to generate and broadcast a response query back to the oncologist indicating that the system could not determine the user's intent and requesting that the oncologist restate the query.

In other cases where the system identifies two or more intents that may be associated with the query, the system may broadcast a query to the oncologist like "Did you mean _____?", where the blank is filled in with the first intent and perhaps related parameters gleaned from the initial query. The system may ask about a second or other intents if the oncologist indicates that the first intent was not what was meant.

In cases where the system cannot discern a specific intent from a query or follow-up answers from an oncologist, the system may automatically broadcast a message to the oncologist indicating that the system could not understand the query and indicating that a system administrator will be considering the query and intent so that the system can be trained to handle the oncologist's query. Queries that cannot be associated with specific intents are then presented to an administrator who can consider the query in context (e.g., within a dialog path) and can either associate the query with a specific system supported intent or specify a new intent and related (e.g., required and optional) parameters to be associated with the query. Here, where a new intent is specified, the administrator may specify a small set of additional seed queries for the intent and the system AI engine may facilitate a fanning process to again generate hundreds of additional queries to associate with the new intent. The administrator then specifies one or more data operations on for the new intent as well as an audible response file for generating audible responses for the intent. Upon publishing the new intent, parameters, data operations and response file to the system for use, an e-mail or other notification may be automatically generated and sent to the oncologist that posed the initially unrecognizable query and, in some cases, a suitable answer to that query.

In cases where the system is able to associate a perceived query with a single system supported intent and then performs a data operation to access data needed to formulate an audible answer, in at least some cases the databases and/or records searched will not yield results to drive an answer. For instance, in a case where an oncologist voices a query about a specific patient by name and no information exists in the system databases for that patient, the data operation will not return any data to answer the query. In this case, the system may be programmed to broadcast a message indicating that "There is no data in the system for the patient you identified."

In other cases the system may, in addition to generating data that is directly responsive to a query, generate additional data (hereafter "supplemental data") to supplement the responsive data. Supplemental data can take essentially any type of form that can be supported by data in the system databases and may include, for instance, qualifying statements or phrases that apply to an associated directly applicable response phrase, additional data of interest, clinical trials that may be related to the query, conclusions based on data, and data that supports answer statements.

Here, it is contemplated that supplemental data can be driven by conditional or supplemental data operations or operations that are triggered by the results of a primary data operation, and associated answer phrases and sentences. For instance, a primary data operation that yields data directly responsive to a first query intent may be associated with the first intent and the data from that operation may be used to formulate a directly responsive answer phrase that is directly responsive to an oncologist's query that pairs with the first intent. In addition, a second or supplemental data operation may also be associated with the first intent and may yield data results used to formulate a supplemental answer phrase of some type (e.g., a qualifying statement, additional data of interest in addition to the data that is directly associated with the initial query, clinical trials of interest, conclusions and supporting data, etc.) which, while not directly responsive to the first query, adds additional information of interest to the directly responsive answer phrase. Here, when the primary data operation yields results those results may be used to generate the directly responsive phrase that is responsive to the query. Similarly, when the supplemental data operation associated with the first intent yields results, those results may be used to generate a second or supplemental response phrase. In this case, the directly responsive and supplemental phrases may be broadcast sequentially to the oncologist to hear.

In the above case, if only the primary data operation yields a result and associated directly responsive answer phrase (e.g., the supplemental data operation fails to yield any data that can be used to generate a supplemental response phrase), the system would only generate the directly responsive phrase. Thus, in these cases, the system response to a query may include either a directly responsive phrase alone or a sequence including the directly responsive phrase followed by the supplemental phrase.

In some cases three, four, five or more supplemental data operations and answer phrases may be associated with a single intent in the system. Here, once the intent is identified, every one of the data operations (e.g., primary and each supplemental) may be performed in an attempt to yield results that can be used to generate and broadcast a fulsome system response. Where only a subset of the supplemental data operations generate results, only phrases associated with those results would be generated and sequentially broadcast. Thus, for instance, in a case where a primary and first through fifth supplemental data operations are associated with an intent, if the data operations yield results for the primary, second and fifth supplemental operations, the answer would include three sequential answer phrases, a first for the primary operation results and second and third for the second and fifth supplemental operation results.

A supplemental qualifying statement may be based on an inability to effectively provide a complete answer to a query. For instance, where a primary data operation returns fifty different effective medications for a specific cancer state, instead of broadcasting all 50 medications audibly, the system may simply identify the 3 most effective medications and broadcast those as options along with a qualifying statement that "There are 47 other effective medications, you can say E-mail the full list of medications to have the full list sent to you now."

Another type of supplemental qualifying statement may be generated by a supplemental data operation that assesses the weight of evidence that supports primary data operation results. For instance, where only two prior patients with a specific cancer state responded positively to a YYY treatment, while a directly responsive query answer may indicate "There is evidence that at least some patients with the cancer state respond positively to YYY treatment", a supplemental response may be "Note however that only 2 patients responded positively to YYY treatment." In this case, the supplemental data operation would identify the number of positively responding patients, compare that to some statistically significant number associated with a higher level of confidence and, when the number is less than the statistically significant number, the operation would generate the supplemental response as a qualifying statement. As another instance, where a primary data operation response is "Chemotherapy is recommended for pancreatic cancer in the adjuvant setting", a qualifying supplemental phrase maybe "However, the role of radiation is still under review in clinical studies." This supplemental phrase would be generated based on results from a supplemental data operation associated with the query intent.

Other types of qualifying statements are contemplated.

Additional data of interest can be any data, subset of data, compilation of data or derivative of system data. For instance, where an oncologist asks for status of a specific patient symptom, the additional data may include statuses of additional typical symptoms given a specific patient's current cancer state.

Supplemental responses may include detailed information related to clinical trials identified in response to a primary data operation. For instance, here, a directly responsive phrase to a query may be "There are two clinical trials that may be of interest to Dwayne Holder." and a supplemental response may be "The first clinical trial is 23 miles from your office and the second trial is 35 miles from your office." Many other supplemental data operations regarding clinical trials are contemplated.

In at least some cases at least some databases will include specialized clinical reports or other report types that are developed for specific purposes where data is gleaned from EMRs and other system databases and used to instantiate specific instances of the reports for specific patients and cancer states. Here, in at least some cases an instantiated report will be generated and stored in persistent form (e.g., dated and unchanging) and in other cases an instantiated report will be stored but dynamic so that the system will routinely update the report as a patient's cancer state progresses over time. Where a report is stored in persistent form, multiple instances of the report may be stored persistently so that a historical record of the report can be developed over time. Where a report is stored dynamically, historical values for report fields may be stored so that time based instances of the report can be subsequently generated that reflect report information at any point during the course of a patient's treatment.

One advantage to using a fully formatted clinical report of a specific type (e.g., for pancreatic cancer, for breast cancer, for melanoma, etc.) is that an oncologist that routinely uses instantiated instances of specific report types quickly becomes familiar with types of information available in the reports as well as where in the reports the information resides. Once report familiarity matures, if specific information related to a specific patient's cancer state is sought, the oncologist will know if that information is located in the patient's clinical report and, once the report is accessed, where to locate the specific information.

Another advantage associated with a clinical report is that the report operates as a summary of EMR data and can include additional results of complex data operations on EMR data so that an oncologist does not have to recreate or process those operations manually. Thus, the report can include clinically important EMR data and also data and other information derived from the raw EMR data.

Referring now to FIGS. 418A through 418C, three pages of an exemplary clinical report related to patient Dwayne Holder who is afflicted with pancreatic cancer are shown. The report includes all important clinical information related to the patient's cancer state including report sections clearly marked as genomic variants, immunotherapy markers, FDA-approved therapies and current diagnosis, FDA approved therapies and other indications, current clinical trials, variants of unknown significance, low coverage regions, somatic variant details—clinically actionable, germline variant details, clinical history and oncologist notes (see lower left field in FIG. 13A). Here, the report format is simple and clearly defined so that an oncologist can locate specific information of interest rapidly.

From the perspective of the present disclosure, use of formatted clinical reports as primary data sources to drive a voice based collaboration system eases the tasks associated with developing a fulsome set of intents and supporting information for those records. In this regard, see again FIGS. 418A through 418C. While a large amount of clinically important patient information is presented on the report, the amount of information is limited so that an oncologist can rapidly become familiar with the report format and available data. Knowing a patient's general cancer state (e.g., pancreatic, breast, etc.) as well as report format and report data types for that state, an oncologist will naturally tend to limit system queries to ones calculated to be answerable via the report type information. Because the report data is limited (albeit including all clinically important data) to a specific set of medical record data for the patient, the number of intents required to support anticipated queries is appreciably limited. For instance, the number of intents required to fully support anticipated queries for the FIG. 418A-418C report may be on the order of several thousand as opposed to 100,000 or more for a complete EMR.

Another advantage associated with using formatted clinical reports as primary data sources to drive a voice based collaboration system is that the limited number of intents required to fully support anticipated queries makes it much easier for the collaborative system to uniquely distinguish an intended intent from all other supported intents. Thus, for instance, where only 5000 intents are required to fully handle all anticipated queries about information in a pancreatic clinical record, correct intent discernment is more likely than in a case where 100,000 intents need to be supported.

Yet one other advantage associated with using formatted clinical reports as primary data sources to drive a voice based collaboration system is that the system can leverage off complex data calculations that are already supported by an overall EMR system that generates the important information in the clinical reports. Thus, in the context of pancreatic cancer, the exemplary report in FIGS. 418A through 418C already includes all clinically important data including results of complex data operations so that the collaboration system does not have to independently derive required data and other information.

In some cases, near the beginning of a collaboration session, once the collaboration system identifies a specific patient, the system will identify the patient's cancer state and state-specific clinical medical record and automatically load up the subset of intents (e.g., "state related intents") that are associated with the patient's cancer state for consideration. In some cases, the state related intents may be the only intents that are considered by the system unless the oncologist instructs otherwise. In other cases the state related intents may be preferred (e.g., considered first or more heavily weighted options) than other more general EMR related intents so that if first and second intents in the state related intents and more general pool of intents are identified as possible intended intents, the system would automatically select the state related intent over the more general intent.

In at least some embodiments data operations associated with state related intents will be limited to an associated clinical record. Thus, for instance, referring again to FIGS. 418A through 418C, once Dwayne Holder is identified as a pancreatic cancer patient and a query intent has been identified, in these cases the data operations would be limited to the data and information presented in the FIG. 418A through 418C record.

In other cases data operations associated with state related intents may include any operations related to any EMR or other database data that is accessible by a system processor in addition to operations directly on the clinical report 13A-13C data and information.

In still other cases, cancer state-specific intents may be treated as preferred intents and other more general dataset intents may only be considered if the system cannot identify a state-specific intent to match with a received query. Here, in at least some cases even when a state-specific intent is identified, the system may generate a confidence factor associated with the intent and, if the confidence factor is below some threshold level, may consider other more general system intents as candidates to match with a specific query.

Referring now to FIG. 419, a process 16500 similar to the process described above with respect to FIG. 408 is illustrated, albeit where the collaboration system automatically limits intents to a specific cancer state when a specific state clinical report is available for a specific patient. While process 16500 is similar to the FIG. 408 process, several of the FIG. 408 process steps have been eliminated from process 16500 in the interest of simplifying this explanation. For instance, FIG. 419 does not include steps to provide a visual response to an oncological query, among other things. Nevertheless, it should be appreciated that any of the additional steps shown in FIG. 408 could be added to the FIG. 419 process 16500 in at least some embodiments of the present disclosure.

Referring to FIG. 419, at an initial process step 16502 an EMR or other system stores and maintains clinical reports for specific patients and specific cancer states (e.g., pancreatic, breast, etc.). At block 16504 an administrator uses an exemplary cancer state specific clinical report for each cancer state to train an essentially complete state specific set of intents and other supporting information (e.g., parameters, data operations and response files or phrases).

After system training, at block 16506 the system monitors for activation of a collaboration device. At decision block 16508, once a collaboration device is activated, the system monitors for voice signals and collects any voice signal query enunciated by an oncologist. At process block 16512 any received utterances are transcribed to text and stored in a text file.

Referring still to FIG. 419, at decision block 16514, a system processor monitors utterances for any information identifying a specific patient. If the oncologist does not identify a specific patient, system control may pass on to a process more akin to the process shown in FIG. 408 in an attempt to identify more general query intents based on a larger dataset. At block 16514, if a patient is identified by an oncologist, control passes to process block 16516 where the patient's cancer state is identified in a system database. At block 16518, the system determines if there is a state-specific clinical record stored in a system database for the user. If there is no state-specific clinical record for the patient, again, control may pass on to the process shown in FIG. 408 in an attempt to identify more general query intents based on a larger dataset.

In FIG. 419, if a state-specific clinical record does exist for the patient, control passes to block 16520 where the system limits the pool of intents to match with queries to the state related intents (e.g., intents specifically associated with the patient's state-specific clinical record type). Here, again, in some cases limitation will only mean that some weighting factor is applied to intents which makes it more likely the system will select a state-specific intent instead of a more general system intent. In other cases limitation means the system will only consider general intents until the oncologist performs some activity which causes the system to identify state-specific intents.

In particularly advantageous cases once a patient's general cancer state (e.g., pancreatic, breast, etc.) is determined, the system strictly limits (e.g., considers no other intents during a query path or a collaboration session) the intent pool to match with queries to the state specific clinical report set.

Continuing, at block 16522, a processor compares a received query to the limited intent set to identify an intent and then extracts intent related parameters from the query. At process block 16524 the system uses the intent and extracted parameters to define one or more data operations (e.g., primary or primary and supplemental per above discussion) to be performed on the clinical report data and, in at least some cases, on other accessible data sets. At block 16526 the data operations are performed to generate information usable to respond to the query. At block 16528 response files associated with the intent and data operations are used to formulate audio response files and at block 16530 the audio response files are transmitted to the collaboration device and broadcast to the oncologist.

In at least some cases it is contemplated that the system will support an e-mail functionality whereby an oncologist can request e-mail copies of different clinical record datasets or other system datasets during a collaboration session. For instance, after the system broadcasts information related to clinical trials that may be off interest for a specific patient, an oncologist may enunciate "Send me information related to the trials." Here, the system would recognize the oncologist's intent to obtain e-mails including trial information for the trials in question, perform a data operation to access the trial information and then transmit that information to the oncologist's e-mail address. In addition, once the trial information is transmitted via e-mail, the system may generate and broadcast a response to the oncologist indicating that the trial information has been sent via e-mail. In other cases it is contemplated that data and information may be sent to an oncologist via other communication systems (e.g., as a text link, via regular mail hard copy, etc. A more complex e-mail related dialog path may include the following queries:

Results of sequencing for Dwayne Holder.
Does my patient have high TMB?
Are they a good candidate for immunotherapy?
What immunotherapy drugs are currently approved?
Who manufactures Keytruda?
What are the main adverse events to Keytruda?
Email me the Keytruda drug label.
Who manufactures Keytruda.
What is the patient financial assistance phone number for Merck?
E-mail me the Merck compassionate use consent form.
E-mail me a Tempus insurance reimbursement letter that my patient Dwayne
Holder has data justifying their off label use of Keytruda.

In this example, the oncologist enunciates several e-mail requests where each would result in delivery of a different set of information to the oncologist's e-mail account.

Additional Concepts and Enhancements to Concepts

In at least some cases when the system receives a query via a collaboration device, data operations will be executed on data from two or more different types of datasets. The first type may include a specific patient's genomic dataset that comprises details on the specific patient's molecular report. The second data type will include data that resides in general knowledge database (KDB) that includes non-patient specific information about specific topics (e.g., efficacy of specific drugs in treating specific cancer states, clinical trials information, drug class—mutation interactions, genes, etc.) based on accepted industry standards or empirical information derived by the service provider as well as information about the service provider's system capabilities (e.g., information about specific tests and activities performed by the provider, test requirements, etc.) To this end, see the exemplary system database 16600 shown in FIG. 421 that includes molecular report genomic datasets and clinical data sets 16602 and a non-patient specific knowledge database (KDB) 16604. By arranging data operations in this fashion, the universe of possible intents and data operations that can be associated with any query is proscribed as described above and the advantages associated with such arrangements result.

Referring still to FIG. 421, datasets 16602 include, among other data, genome, transcriptome, Epigenome, Microbiome, clinical, stored alterations proteome, Omics, Organoids, Imaging and Cohort and Propensity data sets which are described in other patent applications in some detail. The KDB includes separate sub-databases related to specific information types including, as shown, provider panels 16606 (e.g., information related to genetic panels supported by the service provider that operates the system), drug classes (e.g., drug class specific information (e.g., do drugs of a specific class work on pancreatic cancer, what drugs are considered to be included in a specific drug class, etc.)), specific genes 16608, immuno results (e.g., information related to treatments based on specific immuno biomarker results), specific drugs, drug class-mutation interactions, mutation-drug interactions, provider methods (e.g., questions about processes performed by the service provider), clinical trials, immuno general, clinical conditions, term sheets (e.g., definitions of industry specific terms), provider coverage (e.g., information about provider tests and results), provider samples (e.g., information about types of samples that can be processed by the provider), knowledge (e.g., scripted questions and answers on various frequently asked questions that do not fall into other sub-databases), radiation (e.g., information related to suitable radiation treatments given specific cancer states), NCCN guidelines (e.g., national guidelines related to classification of cancer states, accepted treatments, etc.) and clinical trials questions-answers (e.g., information related to locations and administrators of clinical trials. Organizing the KDB into sub-databases makes it easier to manage those databases as information therein evolves over time and also enables addition of new sub-databases related to other defined information types.

To identify a genomic dataset associate with a specific patient's molecular report, the system identifies data operations associated with a query and then associates at least one of those operations with the patient's genomic dataset represented on the molecular report prior to executing the at least one data operation on the set.

In at least some cases results of a data operation on a patient's molecular report data inform other data operations to perform on the KDB or results from operations on a KDB inform other operations to perform on a patient's molecular report data. For instance, in a case where an oncologist queries "What are the treatment implications of Dwayne Holder's CDKN2A mutation?", the system may associate the query with an intent. The intent may be associated with two data operations including a first to search a general KDB for appropriate treatments for a CDKN2A mutation and a second operation to determine if the patient has already been treated with one or more of the appropriate treatments. In this case, results from a KDB data operation inform the molecular report data operation. As another instance, in a case where an oncologist queries "Did Dwayne Holder have loss of heterozygosity with his BRCA2 mutation?", the system may again identify two data operations, this time including a first operation on the genomic dataset associated with Dwayne Holder's molecular report to return the patient's loss of heterozygosity (LOH) value and a second operation to perform on a KDB to determine if the patient's mutation and LOH value pairing is known to be a tumor driver. In this case, results from the operation on the molecular report data inform the KDB data operation.

Hereafter first and second exemplary processes related to handling of the queries "What are the treatment implications of Dwayne Holder's CDKN2A mutation?" and "Did Dwayne Holder have loss of heterozygosity with his BRCA2 mutation?", respectively, are described. In the interest of simplifying this explanation, the first and second processes will be referred to as first and second examples, respectively, unless indicated otherwise.

Referring now to FIG. 420, a process 16550 that is consistent with at least some aspects of the present disclosure is shown that associates data operations with a genomic dataset represented on a patient's molecular report prior to performing those operations on the dataset. At process block 16552, a collaboration device 16122 (see again FIG. 406) receives an audible query from an oncologist via the device microphone that is related to information that appears on the specific patient's molecular report. At block 16554 the system identifies at least one intent associated with the audible query. Here, block 16554 entails identifying a general intent as well as context parameters within the query so that a specific intent can be formulated. For instance, in the case of the first example query "What are the treatment implications of Dwayne Holder's CDKN2A mutation?", a general intent identified may be "What are treatment implications based on gene mutation for patient?" and specific query parameters may include "CDKN2A and "Dwayne Holder" where the underlined gene and patient fields in the general query are populated with "CDKN2A" and "Dwayne Holder" to generate a specific query intent.

In the case of the second example query "Did Dwayne Holder have loss of heterozygosity with his BRCA2 mutation?", a general intent identified may be "Did patient experience genetic characteristic with gene mutation?" where the underlined patient, genetic mutation and gene fields in the general query are populated with "Dwayne Holder", "heterozygosity" and "BRCA2", respectively, to generate a specific query intent.

Referring still to FIG. 420, once a specific intent is identified, at block 16556 the system identifies at least one data operation associated with the specific intent. Here, a database correlates data operations with intents. For instance, in some cases one or more data operations may be correlated with each specific intent. In other cases at least some data operations may depend on results from other data operations (e.g., a second operation is only performed if results from a first operation are within a specific value range).

In the case of the first example, for the specific intent "What are treatment implications based on CDKN2A mutation for Dwayne Holder?", exemplary data operations may include (1) For CDKN2A mutation, search for appropriate treatments in a treatments KDB and (2) For appropriate treatments, search a treatment history portion of a patient's molecular report genomic dataset to identify if patient already treated with appropriate treatments. Similarly, in the case of the second example, for the specific intent "Did Dwayne Holder experience loss of heterozygosity with BRCA2 mutation?", exemplary data operations may include (1) search for LOH value in patient's molecular report genomic dataset as well as whether the mutation is germline or somatic and (2) based on the LOH value, optionally search a KDB to determine whether the LOH value and mutation are known to be a tumor driver.

Referring again to FIG. 420, at block 16558 the system associates each of the at least one data operations with a first dataset presented on a specific patient's molecular report. In the case of the first example, the system associates each of the data operations with CDKN2A which, as seen in FIG. 418A, is presented on the molecular report. In the case of the second example, the system associates the first data operation with BRCA2 and Dwayne Holder in the molecular report genomic dataset.

Continuing, at block 16560 the system executes each of the data operations on a second set of data to generate response data. In the case of the first example, the first data operation on a KDB (e.g., a second data set) yields Palbociclib as an appropriate treatment for the patient's CDKN2A mutation and the second data operation on the molecular report genomic dataset (e.g., another second dataset) indicates that Dwayne Holder has already been treated with Palbociclib. In the case of the second example, response data from the first data operation on Dwayne Holder's molecular report genomic dataset (e.g., a second dataset) indicates no pathogenic somatic BRCA2 mutation but also indicates that there is a pathogenic germline BRCA2 mutation and an LOH loss associated therewith (see BRCA2 section of the molecular report shown at bottom of FIG. 418B that indicates LOH). In the second example, the first data operation results (e.g., germline BRCA2 mutation and presence of somatic LOH) are used to drive the second data operation and the response data indicates that the tumor is a BRCA2 driven tumor.

Referring yet again to FIG. 420, at block 16562 the system formulates a suitable audio response file and at block 16564 the response file is used to broadcast an audible response to the oncologist. In the first example, the system may generate the following response "Provider recommends Palbociclib, a CDK4/6 inhibitor based on Dwayne Holder's CDKN2A mutation. He has already received this drug from Sep. 20, 2017 to Jan. 6, 2018 however, so you may want to consider targeting one of his other clinically actionable mutations." In the second example, the system may generate the following response "Dwayne Holder's results showed a pathogenic germline BRCA2 mutation combined with a somatic loss of heterozygosity, indicating that this may be a BRCA2 driven tumor."

It has been recognized that many different query intents may take similar formats where the differences between specific intents are defined by specific parameters. Similarly, many system responses to different queries may have similar formats where differences between the specific responses are defined by specific parameters in the queries and/or results generated by data operations. For these reasons, in at least some embodiments, a specialized user interface has been developed to reduce the burden on a system administrator associated with specifying all possible system intents, contextual query parameters, data operations and audio response files as well as to manage that information as knowledge evolves over time. The interface generates sub-databases (see sub-databases in FIG. 421) that form the KDB shown in FIG. 421.

See FIG. 422 that schematically illustrates an exemplary user interface screen shot 16620 that corresponds to the provider panels sub-database 16606 shown in FIG. 421. In addition to presenting a provider panels dataset, the screen shot includes a separate selectable icon for each of the sub-database types in FIG. 421 so that an administrator can access any one of those sub-databases via a screen shot akin to the one shown in FIG. 422. Screen shot 16620 includes a spreadsheet type arrangement of information cells in rows and columns used by the system to processes queries and generate responses as well as interface tools for scrolling up and down and left and right to access additional sub-database information. Although not shown an exemplary interface would also include a keyboard, mouse device and/or other input devices for interacting with the interface (e.g., scrolling, modifying information, adding or deleting information, etc.)

Referring still to FIG. 422, the screen shot 16620 includes query intents 16622 A through ZZZ arranged in a first row of cells, a separate intent in a cell at the top of each column within a first row. Intents often take the form of a defined query that received queries can be associated with. Exemplary intent A shown is "Does Provider $panel come with clinical data structuring?" where the "$panel" representation is a parameter that is gleaned from a query received from an oncologist. Although only a small number of intents are shown, it should be appreciated that hundreds or more intents may be expressed and accessed via the interface. The $panel representation is referred to as a parameter field and the system supports many parameter types with different parameter fields and any intent may include two or more different parameter fields.

Referring still to FIG. 422, parameters that may fill in the $panel parameter fields in the intents are listed in cells arranged in a left hand column 16624 on screen shot 16620 and include xT, xE and xF and may include many other panel types. Thus, depending on a received query (e.g., does the query reference an xT panel?), the $panel field in intent A may be filled in with any of xT, xE, xF, etc., to define a panel specific intent.

Answers are provided for each intent and parameter combination in an answer section 16626 of the screen shot. In general the answer section includes separate cells for each of the parameter rows and intent columns and separate scripted answers may be provided in each of the answer cells for each of the intent-parameter combinations. For instance, for intent C and an xT panel, the answer in an associated answer cell 16630 is "Yes, matched normal sequencing is included in the xT panel."

In cases where a general answer format is applicable to each parameter in column 16624, an answer format may be provided where specific parameters are used to fill in parameter fields in the answer format. To this end, see the answer format in field 16632 that requires a panel parameter in field $panel. Here, in operation, the system retrieves a suitable panel parameter from column 16624 and fills in field $panel when appropriate. Although not shown in FIG. 422, a negative answer row 536 is also provided that may include negative answer formats for one or each of the intents listed in row 16622.

Referring still to FIG. 422, an administrator can change any intent, add intents, delete intents, change a parameter in column 16624, add a parameter, delete a parameter and/or change an answer by simply selecting an instance of the information to change and then typing different information into the associated cell. In this way, intents and answers with formats that are similar for different parameters can be quickly specified and managed with less overall effort. For instance, in FIG. 422 assume the interface specifies 200 different intents and an administrator wants to add a new panel to the parameter options. Here, the administrator can just select another cell in the parameter column and name the new panel causing all the intents in row 16622 to be associated with the new panel name. In addition, when the new panel is added to the panel column, for each answer format (e.g., see again 16632) that remains valid for the new panel, that answer formats are automatically applied to the new panel.

Referring now to FIG. 423, a second administrator interface screen shot 16650 is illustrated that has a format similar to the FIG. 422 provider panels screen shot and, to that end, includes an intents row 16652, an answer section 16654 and a parameters section 16656. Each exemplary intent includes a parameter field $Gene which is filled in with one of the parameters from the parameter column 16656 that forms part of a received query.

In FIG. 423 the answer section 16654 is different than in FIG. 422 as "answer values" are provided in each answer cell (e.g., a cell corresponding to a specific intent column and parameter row combination) that are used in at least one and in some cases two different ways. First, answers in the answer cells corresponding to specific intent and parameter pairings can be used to select one of the answer format 16651 or negative answer format 16653. To this end, each of the answer format and the negative answer format for each format includes each of a rule and a response format where the rules apply based on answer cell values. Thus, for instance, for the answer format in cell 16660, the rule is "IF TRUE" (e.g., if a TRUE value is in an answer cell), then apply the associated answer format. Similarly, for the negative answer format in cell 16662, the rule is "IF FALSE" (e.g., if a FALSE value is in an answer cell), then apply the associated negative answer format. Thus, for instance, because the answer cell 16670 includes the value TRUE for gene ABCB1 and intent A, the answer format in cell 16660 is applied and the response file includes the phrase "Yes, Provider sequences ABCB1." Similarly, because the answer cell 16672 includes the value false for gene ABCB4 and intent A, the negative answer format in cell 16662 is applied and the response file includes the phrase "No, Provider does not sequence ABCB4."

Second, in at least some cases answer cell values can also be used to populate one or more fields in an answer format or a negative answer format. To this end, see for instance the answer format in cell 16676 which, in addition to including a $Gene field, also includes an $AV (e.g., answer value) field. Here, when the answer format rule is met (e.g., IF AV; if there is an answer value in an answer cell) so that answer format 16676 is used to generate a response file, in addition to populating the $Gene field with one of the genes from column 16656, the $AV field is populated with a value from an associated answer cell there below. For instance, for gene ABCB1 the answer cell 16678 includes a value 1% and therefore, if intent C applies and is qualified by gene parameter ABCB1 the answer format rule in cell 16676 is met and the response tile includes the phrase "Provider sees a pathogenic mutation in ABCB1 in 1% of pancreatic cancer patients". In negative answer cell 16680, the rule is that if an answer cell there below is blank, then that cell format is used to generate a response file.

While there are two answer format rows shown in each of FIGS. 422 and 413 (e.g., the answer format row and the negative answer format row), in other cases there may be three or more answer formats that change based on values in specific answer fields there below to support more complex answer generation schemes.

Again, as in the case of the data presented in FIG. 422, the data in FIG. 423 only shows a small subset of the gene data accessible via left and right and up and down scrolling through parameters and intents. For instance, the genes in parameter column 16656 may include an entire gene panel (e.g., hundreds of genes) and the intents in row 16652 may include hundreds or even thousands of intents.

FIG. 424 shows another administrative screen shot 16700 similar to the FIGS. 422 and 18 shots, albeit corresponding to a provider methods data set. The spreadsheet representation in FIG. 424 is similar to the representations in FIGS. 422 and 423 including an intent row 16702, an answer format section 16710, and a parameters column 16704. One difference in FIG. 424 is that the first intent A includes two parameter fields and the parameters section includes first and second parameter rows, one for each of the parameter fields in intent A. More specifically, the parameters section include a first column listing tests and a second column that lists test methods for populating associated $test and $testmethod fields in the intent statement. In addition, in at least some cases answer formats like the negative answer format shown in cell 16706 will include two or more parameter or value fields. Here operation is similar to that described above, albeit using two parameters to instantiate specific intents and final response files.

Referring again to FIG. 421, interface screen shots akin to those described in FIGS. 422 through 424 are included in a system for specifying intents, parameters and answer formats for each of the information types associated with the sub-databases illustrated. Some of the screen shots will include specific scripted answers for specific intents while others will rely upon answer formats, rules for one or all the formats and populating answer fields with intent parameters and/or database values that appear in answer cells as described above. Other screen shots and tool combinations are contemplated.

In at least some cases it is contemplated that the system will enable an oncologist to request visual access to query answers and/or related information (e.g., associated documents (e.g., clinical trial information, drug label warnings, etc.). For instance, an oncologist may enunciate "Make that answer available with the system web platform," causing the system to render the most recently broadcast answer available via a nearby or oncologist dedicated computer display screen. In at least some cases it is contemplated that the system will enable an oncologist or other user to provide queries via a typed question instead of an audible query. For instance, rather than speaking a question, an oncologist may type the query into a mobile phone or other computing device, and the query may be processed as described herein.

Exemplary questions and answers an oncologist may voice to a disclosed collaboration device and that the device may return in response may be patient based questions, questions related to a service provider's genomic panel. A drug class, a gene, an immuno result, drugs, drug mutation interactions, mutation-drug interactions, provider methods, clinical trials, clinical conditions, radiation, NCCN guidelines, and other topics. FIGS. 432A through 432D include an exemplary question and answer sets related to patient information, provider gene panels, specific genes and mutation-drug interactions, respectively, that an oncologist may voice to a disclosed collaboration device and that the device may return in response. While clearly not exhaustive, the exemplary questions and answers give a sense of the power of the system and the complexity of the types of queries that the system can handle.

XXIII. Unsupervised Learning and Prediction of Lines of Therapy from High-Dimensional Longitudinal Medications Data Rulesets may guide the process of abstracting one or more LoT from the EMR of a patient.

Sample 'Hard Rules'

After initial diagnosis of prostate cancer, it is commonplace to prescribe and administer leuprolide to the patient for life. So once leuprolide occurs in the EMR, it will always remain as part of the LoT, even if the LoT changes. Another type of hard rule, certain intervening events require a change of LoT; such as a treatment discontinuation, metastases, or progressive disease outcome. The opposite may also be hard coded. For example, a patient with a recorded medication change to abemaciclib generally only occurs due to metastasis of breast cancer. Even if the EMR is incomplete and does not recite that the patient's cancer spread through metastasis, it may be imputed and added to the EMR as well as forcing a break in LoT upon detection. Progression from one class of drugs to another class of drugs may also be implemented as a hard rule.

Sample 'Soft Rules'

Oncologists all define LoTs differently: some may see carboplatin and cisplatin together as a LoT, but subsequent maintenance pembrolizumab as not a core part of the LoT. others may consider cisplatin and carboplatin along with the maintenance pembrolizumab together as one LoT. Some may consider any deviation, even if for side effect avoidance, as a new LoT, while others may not. These types of preferences may be generated as soft rules that give additional weight to a LoT but do not require a new LoT be generated upon seeing in the EMR. If two medications have the same active ingredient, or accomplish the same effect with different active ingredients, a change from one to the other may be weighed to determine the presence of a LoT change. Further, the preference for application of one soft rule to another may be recorded and applied on a physician-by-physician or institution-by-institution basis.

Algorithm Methodology and Sample Output

One approach is to parse the EMR and curated progress reports for all diagnosis, medications, significant events, etc which may be relevant to identifying any LoTs based on combinations of medications, significant events, and other combinations of medications. The MLA functions in two major steps. The first step consists of synthesizing and harmonizing disparate data sources, including medications, outcomes, diagnoses, across EHR and curated progress notes, to create unique intervals of patient care. The second step considers all possible combinations of these intervals and assigns LoT accordingly. In a lexicographic example where a medication history is represented as a string of characters, THECATSAT, each character may represent a combination of unique medications after digestion by the first step. After training across patient data, the goal of the second step is to recognize common medication patterns, taking into account heuristics, and separate this to "THE"+ "CAT"+"SAT". Examples based on patient EMR are discussed below with respect to FIGS. 429-431.

Model Training

Model training consists of defining unique treatment intervals ('letters' from the above example, like 'T' or 'H') for each patient in a large training cohort and iteratively considering all combinations of aggregation (T+HEC+AT versus THE+CAT), assigning these aggregations, calculating the frequency of these resultant aggregations (words), and re-assigning aggregations until an end condition is reached. These combinations of aggregations are enumerated using a composition of an integer approach. In a more simple example having a LoT representation of 5 such medications, using a composition of an integer approach to divide up into sixteen different possible LoT groupings.

The sixteen compositions of 5 are:

5
4+1
3+2
3+1+1
2+3
2+2+1
2+1+2
2+1+1+1
1+4
1+3+1
1+2+2
1+2+1+1
1+1+3
1+1+2+1
1+1+1+2
1+1+1+1+1.

This frequency analysis may be combined with the hard/ soft rules in conjunction with diagnosis information, clinical information, and significant events to provide a comprehensive probability estimation for each composition. This most likely composition (THE+CAT+SAT) is then output as the assigned LoT.

One goal is to identify the cutpoints in this character string, such that it reads THE|CAT|SAT, after studying a large corpus of text. It could be that such a problem is easier if each character in the alphabet were mapped to some lower-level hierarchy, such as consonants (C) and vowels (V), so the above reads T?C, H?V, E?C, C?C, A?V, T?C, S?C, A?V, T?C. In this case, it is much easier to learn the separators CVC|CVC|CVC. To this end, the Anatomical Therapeutic Chemical (ATC) Classification System is a drug classification system that classifies the active ingredients of drugs according to the organ or system on which they act and their therapeutic, pharmacological and chemical properties. It is controlled by the World Health Organization Collaborating Centre for Drug Statistics Methodology (WHOCC), and was first published in 1976. This pharmaceutical coding system divides drugs into different groups according to the organ or system on which they act, their therapeutic intent or nature, and the drug's chemical characteristics. Different brands share the same code if they have the same active substance and indications. Each bottom-level ATC code stands for a pharmaceutically used substance, or a combination of substances, in a single indication (or use). This means that one drug can have more than one code, for example acetylsalicylic acid (aspirin) has A01AD05 (WHO) as a drug for local oral treatment, B01AC06 (WHO) as a platelet inhibitor, and N02BA01 (WHO) as an analgesic and antipyretic; as well as one code can represent more than one active ingredient, for example C09BB04 (WHO) is the combination of perindopril with amlodipine, two active ingredients that have their own codes (C09AA04 (WHO) and C08CA01 (WHO) respectively) when prescribed alone. The ATC classification system is a strict hierarchy, meaning that each code necessarily has one and only one parent code, except for the 14 codes at the topmost level which have no parents. The codes are semantic identifiers, meaning they depict in themselves the complete lineage of parenthood. The ATC hierarchy provides a 3 and 4th-level hierarchy for a given medication. If one could re-map each medication to this hierarchy, improvements in defining LoTs in these simpler representations may be realized, especially in contexts where the data set is smaller, or there is an extremely high medication cardinality. The specific case of interest is hormone maintenance therapies, which are extremely common in breast cancer, but difficult to learn using conventional MLA techniques.

For example, in breast cancer LoT, a cohort may have approximately 55 unique antineoplastic medications relevant to breast cancer. Grouping these medications to their underlying ATC Hierarchy, either through level 3 or 4, results in a significant reduction in this medication space of 20 under ATC level 4 and 9 under ATC level 3. Where the number of identified LoT states (classifications of LoT from across the entire patient set in breast cancer) is 1117 using only medication names, 656 under ATC level 4, and 289 under ATC level 3. Roughly, as one employs increasingly non-specific medication groupings, the number of unique 'medications' decreases by 2×, and accordingly, the number of medication states in the output model accordingly decreases by roughly 2×.

The equivalencies provided by the ATC hierarchy was primarily implemented to solve the 'maintenance' problem observed in breast cancer. One often sees patients with first line chemotherapy (doxycycline+cyclophosphamide) followed by tamoxifen or anastrozole (hormone therapies), which is all considered one LoT. However, pure frequency based approaches at identifying LoT from underlying patient data nearly always says the chemotherapy and the hormone therapy are separate LoT because hormone therapy is ubiquitous, such that half of all patient medication states are hormone therapies (i.e., if a patient is on at least one medication, half the time it's a hormone therapy), and secondly, a patient that receives chemotherapy as a first line will go on hormone therapy within 180 days, half of the time. Refering back to the word example (THECATSAT), this is like saying one sees E nearly all the time, and TH at a regular pace, with THE nearly half the time. In a pure frequency, THEE will be the result. This is because prob(TH)*(E) >prob(THE), partially due to the ubiquity of E (prob(E) high). Really, this is because one observes hundreds of variations where E is afterward, or simply E. In this case, one would think that E is only a single character.

Therefore, the maintenance problem is result of a core problem in pure frequency models; when E occurrences do not matter, and secondly, that if E is seen alone commonly, and TH, that it must always be separate, when in some cases it could actually be one 'word.' Both of these can be encoded into a probability representation: THE is a word if prob_1 (TH)*prob_2 (E)<prob_1 (THE), where prob_1 indicates the probability of observing a given letter first (1), second (2), etc. The latter can also be encoded as the 'word-ness' of THE is if prob(E|TH) >prob(X|TH)*prob(E|X); i.e., given TH is previous, is the presence of E significantly higher than random chance (or any other given medication, X), possibly modulated by the frequency of E?

Selecting which model to implement is a case of how one thinks the underlying system is actually occurring. Lines of therapy are often the result of NCCN guidelines, wherein an oncologist chooses, with little variation, a 'plan' at a given time, and changes this once an outcome is observed, and/or the patient response poorly to the therapy. Accordingly, the latter is a more apt means of representing the probability space. The former representation implies that prob_1 (TH)*prob_2 (E) !=prob_2 (TH)*prob_3 (E), which means that the temporal ordering strictly changes the probabilities. While this is likely the case as well, the more desirable feature to capture is that seeing E or TH alone isn't important to predicting whether THE is a word, but rather comparing TH(X) and (Z)E, and whether there is a significant enrichment when X=E and Z=TH.

As enumerated above, a probability model, in its raw form, has an unclear mapping to how one would normally impute progression events. In the worst case, there are times when imputes a progression event consistently when one would almost never actually see a progression event. In order to provide a greater concordance between the model and outcomes, an enhanced model and corresponding model training is conducted with the following underlying probability model:

$$\text{prob}(A?B)=\text{prob}(A)*\text{prob}(B)*\text{prog\_w}(A,B) \text{ vs prob}(AB)*[1-\text{prog\_w}(A,B)],$$

where prog_w(A,B) represents an estimation of the observed progression incidence between medication states A and B. What the above states is instituting a LoT break is modified by the incidence of progressions one typically observes in the transition from A?B; the more common, the more likely this state is in comparison to the situation where the two are one LoT. The model may implement prog_w (A,B) as the number of progressions observed at this transition over the total number of times one observes this transition. However, the vast majority of transitions are fairly unobserved, so this would significantly bias the model. A 'Bayesian' estimate that tends toward 0.5 (i.e., lets the underlying frequency space of the model decide, rather than the progression incidence). The larger the sample size, the more one wants to use the observed estimate, the smaller, the more one wants to use 0.5. A classic method of implementing this is additive smoothing where prog_w may be:

$$\text{prog\_w}(A?B)=(\text{prog\_}f)\pm\text{abs}(\text{prog\_}f-0.5)*(\text{upper\_95}(\text{prog\_}f)-\text{lower\_5}(\text{prog\_}f)),$$

where prog_f is the number of progressions observed in the transition from A?B divided by the overall incidence, and upper_95 (prog_f), lower_5 (prog_f) is the 95th and 5th binomial proportion CI estimate based on the Clopper Pearson method for prog_f. As the sample size increases, the confidence intervals near 0, so the 'centering' applied to prog_f decreases. As the sample size increases, the confidence intervals diverge (maximum 1.0), meaning the maximum shift is applied, and prog_w trends toward 0.5.

The ATC and enhanced model shows the highest concordance with common transitions. Most significantly, the model now shows the least significant contradictions with the data (trastuzumab ? trozole), with an incidence of 1/139 in the data compared to 30 in 319 in the output, which is an extremely small difference, or an injection of ~29 additional events such as taxane ? trozole. This is an extremely common transition from chemotherapy to maintenance therapy.

Therefore, the enhanced model removes false LoT changes around maintenance therapies, or reduces the incidence of contradictions between the model and the observed data, while maintaining the possibility of higher-order interactions.

FIG. 427 is a flowchart depicting an embodiment of preparing, training, and generating Line of Therapy (LoT) predictions across three stages 18110, 18130, and 18150.

At the Data Preparation Stage 18110, sources of patient information relating to diagnosis, prognosis, treatment, and outcomes are aggregated across sources at elements 18114 and 18116. If a patient is diagnosed with prostate cancer, prostate cancer clinical insights (such as types of medications, treatments, or therapies directly linked to treating prostate cancer, effects of particular medications, treatments, or therapies on prostate cancer, list of medication, treatments, or therapy names linked to codes relevant to LoT in prostate cancer, progression events that may establish a LoT break for each cancer type such as progress to castration-resistant prostate cancer (CRPC) diagnosis) may be retrieved at element 18112 from internal or external sources such as one or more databases or publications. The medications which have been curated from documents such a progress notes, lab results, or other handwritten documents may then be filtered to include only medications which are relevant to the diagnosed cancer for further processing such as medications which have an effect on treatment. For example, extraneous medications, such as amphetamine for headaches, antihistamines for allergies, seratonin receptor inhibitors for depression, or medications which are taken by the patient for purposes other than the treatment of the diagnosed cancer may be filtered from LoT prediction. At element 18120, a corresponding start and end date may be generated on each of the medications remaining in the filtered LoT medication list and an initial timeline interval may be generated. Date imputation and interval assignment will be discussed in more detail with respect to FIGS. 429-431 and rulesets, below.

At the Training Stage 18130, additional cancer-specific clinical insights are retrieved at element 18112 and the medication intervals calculated at element 18120 from stage 18110 are received at element 18132. Additional cancer-specific clinical insights may include the number of days that constitute an automatic LoT break (for example, for cancers which progress quickly this could be 90 days, and for cancers which progress at a slower pace, this could be 180 days, as well as progression events that may establish a LoT break for each cancer type such as CRPC diagnosis for prostate cancer). At element 18134, medication intervals may be compared across all patient data to identify frequencies of occurrence, for example, in patients who have prostate cancer. Medication intervals may also be refined according to a rolling window with a width corresponding to a number of days. This process may be performed across one or more window sizes (30 days, 90 days, 120 days, etc) to identify the most representative set of LoTs in the patient population. For each medication interval identified in the patient population, an expectation maximization may be calculated to identify the reliability of the interval. The set of intervals which have the highest expectation values may be selected as the best representative set of LoTs. The selected intervals may then be assigned to LoT splits, such as a first, second, third, LoT corresponding to each patient's medication intervals. After all patients have been processed to identify a base set of LoT, Stage 18130 may output the estimated LoT frequencies.

At the LoT Assignment Stage 18150, the collection of estimated LoT Frequencies across all patients 18140 may be compared to the medication intervals of each new patient 18132. Each potential LoT assignment 18152, enumerated according to the composition of an integer method may be ranked by the corresponding popularity of the LoT from the Estimated LoT Frequencies 18140 and the most probably LoT selected as the patient's LoT at element 18154.

FIG. 428 is a flowchart depicting an embodiment of preparing, training, and generating Line of Therapy (LoT) predictions using a MLA approach with rule-based pre-processing for implementing a method that imputes complex, curated fields from curated patient histories and applies them to non-curated patients or patients with a paucity of data. While the instant example is applied to line of therapy, this method may be expanded to impute progressions, doctor's visits, and adverse events.

Data Intake & Harmonization (RS1)

A patient's medication history is captured in both Curated Medication Records (MR) derived from a combination of machine learning and medical expert annotation of progress notes and Electronic Healthcare Record (EHR) MRs. RS1 focuses upon taking this redundant, repetitive, and sometimes inconsistent raw input and converting it into a set of condensed records that capture the most salient medications used to treat a patient's cancer. The following steps are an exemplary method for performing this conversion.

Filter to antineoplastic agents. Electronic healthcare records (EHR) consist of all medications ordered and administered to the patient, including analgesics and even multivitamins. This filter removes any medication that has not been identified as a antineoplastic agent (anti-cancer) and stored in an internal value set. This value set may be defined by a clinical team or curated from machine learning models as well as internal and external publications.

Combine Medication Records (MR) within 22 days (d). EHR MR are highly repetitive, periodic records that occur with every order and administration of a medication. Numerous antineoplastic therapies are administered every 22d (referred to as one 'cycle'), so by combining records within 22d, a significant record compression may be achieved that captures the entire duration a patient is administered a medication. For each MR, the following steps may be performed:

If the MR has a year-only start or end date, or missing start date, skip to Harmonization (3).

If the MR has a month-only start or end date, impute to 15th of month.

If the MR has a missing end date, set the end date to the start date.

Separately for native and curated records (that is, for all medications of the native record, perform the following steps as well as for all medication of the curated records), perform the following for each medication:

Sort each MR of the medication by start date.

For each MR of the medication:

Compare the end of the record with the start of the subsequent record. If the MR are within 22d of each other, combine the records. This may be accomplished by setting the end of the record to the end of the subsequent record and deleting the intervening MR for that medication.

Continue to the next record.

Harmonization. A patient's medication record consists of both EHR and Curated MR that contain a combination of redundant and sometimes contradictory information. 'Harmonization' refers to the set of heuristics learned from machine learning algorithms, internal, and external publications and medical experts, to remove these redundancies or conflicts and establish a consistent set of MR combining the high temporal resolution of the EHR MR and the expert knowledge in the Curated MR.

Impose the following imputation rules to cure the poor temporal resolution of some Curated EMR, and satisfying resolution of the MR to be precise within a day, week, or month as needed for harmonization. The below approach presumes the largest duration for these records, allowing EHR MR with possibly higher resolution to clarify these dates.

If month-only start, set day to 1st of month. If year-only, set month to January and day to the 1st.

If month-only end, set day to 15th of month. If year-only, set month to December and day to the 31st.

If all records are native or curated, no harmonization necessary, skip to RS2.

Sort the combined records by start date.

For each medication type in the patient record:

Create an empty 'output list'. (last entry in list referred to as output[−1])

For each record in this medication type:

IF this is the first entry, add to output.

IF the current record occurs after output[−1], append record to output. Continue.

IF the record has a higher-resolution start or end date than output[−1] (such as month or year resolution, and the record has day-resolution), replace the lower-resolution date with the higher resolution date.

IF the record occurs within the timeframe of output[−1] (such as a single day record occurring within a several month-long curate record) exclude this extraneous record from output list.

Return the output list as the 'harmonized medications table.'

Intervals Production (RS2)

Lines of Therapy are best described by periods of continuous medical care describing the administration of one or more medications (such as, but not exclusively, 'regimens'). Here, these periods of continuous care are referred to as 'intervals.' 'Intervals Production' is the process by which harmonized MR are converted to these medication intervals (MI). These simply represent durations of time a patient is taking one set of medications, with a new MI starting when any change, addition or subtraction, of an antineoplastic agent relevant to the patient's primary cancer type occurs.

Primary Cancer (PC) Relevance Filter. Filter the harmonized medication table further by medications relevant to the patient's PC. This list is defined by machine learning models, internal and external publications, and medical experts. This removes medications such as denosumab, which are supportive care in some cancers (such as prostate cancer), but considered salient to others (such as bone cancers).

Filter patient MR using the PC relevance filter

Filter patients with significant uncertainty in the remaining MR, including:

Year-only medication records.

Vague or general medication names present from curated progression notes (such as 'platinum compounds' or 'antineoplastic agents') rather than the actual medication name.

Date Padding. Numerous MR consist solely of a start date, or an end date equivalent to the start date. In order to construct medication intervals, a minimum duration of time is required, so these records are given an end date using an interval-distinguishing threshold (DATE_PAD, typically 21d; DATE_PAD is a tunable hyper parameter that may be set by the user based upon the user's threshold selection).

If a record has no end date, or an end date==start date, set end date=start date+DATE_PAD.

Combine MR using PC Curation Model While numerous antineoplastic agents are administered roughly every 21d, some hormone treatments are administered monthly or less frequently. To account for this, a medication-specific rollup (typically 22d-180d) may be learned from a combination of machine learning and medical expert knowledge for each medication (RS2.1). This process is described in the PC Curation Model section.

The learned medication-specific rollup is applied to each medication record. For each medication and each record:

IF the end of the previous record and the start of the subsequent record is within this rollup, combine the record, stitch the two records together.

Conversion from MR to Medication Intervals. A patient's medication history typically consists of several antineoplastic agent MR that are temporally overlapping. This conversion process produces defined intervals of homogenous treatment of one or more medications, with a new medication interval started whenever an antineoplastic agent is added or subtracted from the patient's medication record.

Sort resultant medication records by start date, and perform the following for each record:

IF one of the following is the case, create a new interval:

First medication record,

Medication record starts after the end of the last interval, or

The medication record starts within an interval-distinguishing threshold (eg., 22 days) of the end of the last interval end and either the start of the record or the end of the previous interval are month-resolution.

If the medication record overlaps with the last interval, add this medication record to the interval.

IF an interval of at least the interval-distinguishing threshold cannot be constructed due to several overlapping records, LoT cannot be determined for the patient, and return a failure state.

Otherwise the medication record occurs across multiple other intervals, so add this medication to any overlapping records. If the record continues after the end of the last interval, create a new interval for the remaining of the record Output these intervals, describing all records comprising the interval, the start and end, and associated medications.

THEATRE Line of Therapy (LoT) Assignment (RS3)

A patient's lines of therapy captures the treatment strategy employed by the oncologist to manage that person's cancer. Each line is one or more planned antineoplastic medications, and when an unplanned event occurs to the patient (eg., an imaging result indicating a worsening prognosis for a patient or a metastatic event), a new set of medications or new 'line of therapy' is proposed. Due to incomplete response data (often solely present in progress reports), these unplanned events are often missing in patient MR. The primary goal is to learn common treatment patterns and apply these when response data is scarce, producing a computationally-derived LoT assignment. Here, the intervals produced from RS3 are annotated with response data, when present, producing a refined intervals list. Using the composition of integer (COI) approach, the most likely combination of these interval sets are determined and considered that patient's associated LoTs.

Refine Intervals with Outcomes Certain patient events, such as outcomes, are absolute indicators of change in LoT. These are added to the medication intervals to produce a refined interval list consisting of separated sets of intervals.

Gather all patient outcomes and filter to outcomes and interventions to those relevant to LoT. These can be cancer type specific, such as castration-resistant prostate cancer (CRPC) diagnoses or general like metastatic diagnosis or progressive disease outcomes. Outcomes commonly removed include complete and partial responses (indicating that the LoT is successful, and should be continued).

Iterate through each outcome and patient interval, and if an outcome occurs within the interval-distinguishing threshold of the start of a new interval, separate this patient interval list into two separate sets of intervals. If an outcome is within the threshold of two intervals, separate at the temporally closer interval, ties choosing the latter.

Iterate through the patient refined intervals list and break into additional sets if a line of therapy maximum duration threshold (eg., 180 days) separation occurs.

Enumerate COIs and Estimate Probabilities & Assign LoT History to Most Probable Composition. The most likely composition of sets of medication intervals may be considered a patient's LoT.

After separating the refined interval list into set given outcomes, iterate through each set and perform the following (setting LoT counter=1):

Compute all possible compositions of the intervals using the composition of integers approach.

Calculate the probability of each of these interval compositions using the frequencies learned during THEATRE training. The total probability of a given interval combination is the product of the individual combined intervals (In the 2 interval case, this is Prob(interval 1)*Prob(interval 2) and the Prob(interval 1??interval 2)).

Consider the interval combination with the highest probability as the LoT assignment. (If Prob(interval 1)*Prob (interval 2) >Prob(Interval 1??Interval 2), then Interval 1 would be the first LoT, and Interval 2 is the second)

Number each of these interval combinations with the LoT counter, incrementing each time. (If the 2 interval case was preceded by an interval which was assigned LoT 1, interval 1 would be assigned LoT 2, and interval 2 LoT 3).

Post-Process LoTs In rare cases, after RS3.1 and RS3.2, consecutive combined intervals may have the same set of medications, and are therefore the same LoT. In this case, re-assign these to the same LoT.

Combine all the most likely interval compositions into a final LoT list.

Iterate through each of the interval compositions, performing the following:

IF two consecutive LoTs have the same medications, assign them the same LoT (Example: [A, A+B] | [A+B, A+B+C, D] produces the final output list [A, A+B, A+B, A+B+C, D], which is converted to [A, A+B, A+B+C, D], where A-D are medications, I indicates an outcome, commas denote new LoTs, and +'s medication combinations).

Output LoT Table
patient_id: The unique patient_id across tables.
interval_start: The start of the medication interval.
interval_end: The end of the medication interval.
medication: The associated medication (maximum one per row).
lot: The assigned LoT. (1–n, whole number).
complete_lot_start: The start of the overarching LoT, spanning one or more intervals.
complete_lot_end: The end of the overarching LoT, spanning one or more intervals.
complete_lot_medications: All of the associated medications in a given LoT, concatenated together with a "+" sign.
emr_derived: 1 if the entire LoT comes from medication records only present in EHR, and 0 otherwise.
success: whether LoT could successfully be defined for a patient. This is unsuccessful if the patient has year-only medications necessary for LoT, or has a medication record that results in an interval described in RS2.4.A.III Primary Cancer (PC) Curation Model Algorithm As described in RS2.3, different medications have different cycles, and these can vary by primary cancer type. The following steps may be used to estimate this cycle time for a primary cancer type for a specific medication of interest by leveraging the medical knowledge present in Curated MR. The general idea of the algorithm is to capture the typical duration of a medication administration as described by Curated MR, and use this to propose a cycle time for that medication that when applied to EHR MR, recapitulates this typical duration. Essentially, one is trying to make highly repetitive EHR administration records 'appear' like Curated MR durations. Without loss of generality, this process is described for a single medication for a single primary cancer type below.

Input: Curated MR and EHR MR for a given medication, for a given primary cancer type.

Filter to Curated MR with the following properties:
End dates distinct from the start dates
Start and end dates with at least month resolution.

Calculate the duration of medication administration across these Curated MR, defined as the MR end date-MR start date.

Calculate the median duration of medication administration across these Curated MR.

Starting with a minimum interval threshold (typically 22d) perform the following:

Combine EHR records within this threshold for each patient, (possibly) producing durations of medication administration described by one or more records.

Calculate the duration of medication administration (end-start) for each of these records.

Calculate the median duration across all of these records.

IF this median is equal to the curated MR median (calculated in 4), return this interval threshold as the 'cycle time', but if it does not, then increment the interval threshold.

IF the increment threshold is greater than the maximum interval threshold (typically set to 180d), break out of the loop.

The above approach may be generalized as calculating a kernel density approximation of the curated duration distribution, rather than the median, and returning the threshold that minimizes a distance metric (Euclidean, geometric, or the Kullback-Leibler divergence) of the two distributions.

FIGS. 429-431 are illustrations depicting patient medical records, calculated medication intervals, and predicted Line of Therapies.

FIG. 429 is an illustration of a LoT prediction for a first patient diagnosed with metastatic non-small cell lung cancer.

Patient Background and Clinical Data Sources.

The first patition was diagnosed with NSCLC in August of 2016 at element 18305. Throughout the next year in their course of treatment, their oncologist logged several progress notes describing the patient, their medications, and associated outcomes (denoted as the "Progress Notes" above). This data is complemented by electronic medical healthcare records (EHR) of medication administrations (gray squiggles).

A medical expert (curator) examined each of these progress notes and recorded the displayed medications (start and end dates, sky blue bars) and associated outcomes (black lines) from each note:

Progress Note 1 (PN1): the curator recorded the patient's date of primary diagnosis 18305 as well as the first administration of the triplet chemotherapy of pemetrexed, bevacizumab, and carboplatin 18310 in August of 2016.

PN2: The curator recorded the end of the triplet therapy 18315 in PN1 in October 2016, a partial response to the associated therapy (not displayed, in October 2016), and the start of a pemetrexed/bevacizumab maintenance therapy 18320 in November 2016.

PN3: In January 2017, the curator recorded a progressive disease outcome 18330 to the pemetrexed/bevacizumab maintenance therapy 18320 and its associated end 18325 in December 2016. The oncologist also noted their intent to place the patient on nivolumab 18335 in February 2017.

PN4: The curator recorded a progressive disease outcome 18340 to nivolumab (implying the therapy was unsuccessful in treating the patient's cancer) in February 2017 as well as the end of therapy 18345. The start of gemcitabine therapy 18350 was also noted starting in March 2017.

PN5: The end of gemcitabine 18355 was recorded due to toxicity in late March 2017, as well as the start of paclitaxel 18355 administration at the same time.

PN6: The end of paclitaxel 18360 was recorded in June 2017 and an associated 'complete response' to therapy (indicating the patient was found cancer-free).

PN7: During a follow-up visit in August 2017, another 'complete response' was recorded 18365, indicating the patient was continued to be found cancer-free.

These curated medications were entered in the medications table and the outcomes in the outcomes SQL tables for downstream analysis.

Inclusion and Harmonization with EHR

The medication administration record present in the EHR from the hospital was next added to the medications data table (all gray squiggle lines and bars according to RS1, above):

Dexamethasone administrations 18370 were additionally logged. These medications were not curated, as this is a supportive care medication a patient commonly receives in tandem with chemotherapy to temper the side effects. While displayed, dexamethasone was filtered and not considered in subsequent calculations since supportive care medications are not considered salient to LoT determination (RS2.1)

The EHR administration records of pemetrexed, bevacizumab, and carboplatin 18375 in September and October 2016 were added to the curated record of these medications, producing a 'native and curated' record for these medications (RS1.3.E.VIII).

The EHR administrations of paclitaxel 18380 were used to augment the curated record from April-June of 2017, producing another 'native and curated' record. The additional administration of paclitaxel in August 18385 was added to the patient record (RS1.3.D.II.4, R1.3.D.II.1).

Delineation of Medication Intervals

The described medication records were next converted to intervals of unique medications (dotted bars denoted 'Intervals' 1-5). These intervals represent aggregations of medications taken simultaneously with a defined start and end date. A medication interval is created whenever a change in medication occurs (see RS2.4).

Interval 1: The first medication interval starts with the triplet therapy pemetrexed/bevacizumab/carboplatin, ending with the discontinuation of carboplatin in October 2016 (RS2.4.A.II).

Interval 2: Consisting of pemetrexed/bevacizumab, this interval started with the discontinuation of carboplatin, and continues until the end of this doublet therapy (RS2.4.A.I.2, RS2.4.A.II).

Interval 3: This captures the patient administration of nivolumab in February 2017 (RS2.4.A.I.2).

Interval 4: This interval starts with the administration of gemcitabine in March 2017, and ends with its discontinuation and start of paclitaxel (RS2.4.A.I.2).

Interval 5: Starting with the curated and native paclitaxel record, this extends until the EHR record of paclitaxel administration in July 2017. Although the patient received dexamethasone starting in May 2017, since this medication is not considered relevant to LoT assignment, it does not cause a 6th interval from May 2017-July 2017 to be produced (RS2.1.A).

LoT Assignment on Intervals

Next, a combination of probabilistic choices and heuristics are applied to determine LoT on the produced medication intervals (1-5) (see RS3):

Outcomes are considered to separate out the different intervals. The outcomes in January 2017 are used to separate Interval 2 from Interval 3 (RS3.1).

The outcome in late February 2017 is used to separate Interval 3 and Interval 4 (RS3.1).

We now consider Intervals 1-2. In this case, a probabilistic choice is made considering the relative frequencies of each of these intervals across the training population. The probability of seeing Interval 1 (representing the triplet therapy) alone is 10%, the probability of seeing Interval 2 (pemetrexed/bevacizumab) alone is 5%, so the combined probability is 0.5% (10%*5%). However, seeing Interval 1 followed by Interval 2 is 2%. Since 2%>0.5%, this interval is combined and defined as 1 LoT (dotted black box) (RS3.2.A).

Since Interval 3 has been separated by Interval 2 and 4 by outcomes, this solo Interval becomes LoT 2 (RS3.2.A; only one possible composition).

Intervals 4 and 5 are now considered in terms of a probabilistic choice. The probability of seeing Interval 4 and 5 alone is 7.5% (30% and 25%, respectively; 30%*25%=7.5%), while the probability of seeing Interval 4?? 5 across the dataset is 1%. Since 7.5%>1%, the intervals are considered separated LoTs, so Interval 4 is assigned to LoT 3, and Interval 5 is assigned LoT 4 (RS3.2.A).

FIG. 430 is an illustration of a LoT prediction for a second patient diagnosed with ovarian cancer.

Patient Background and Clinical Data Sources.

PN1, March 2015: primary diagnosis and surgery, start of carboplatin, bevacizumab, and paclitaxel.

PN2, September 2015: start of bevacizumab, end of carboplatin, paclitaxel.

PN3, March 2016: progressive disease outcome

PN4, June 2016: progressive disease outcome, end of bevacizumab (month only), start of carboplatin, bevacizumab, and gemcitabine.

PN5, October 2016: end of carboplatin, bevacizumab, and gemcitabine.

EHR source: anastrozole, April 2017.

Intervals Construction

Interval 1: triplet therapy carboplatin/bevacizumab/paclitaxel.

Interval 2: beviczumab (separated from Interval I by RS2.4.A.I.2).

Interval 3: carboplatin/bevacizumab/gemcitabine (separated from Interval 2 by RS2.4.A.I.2, combined via RS2.4.A.II).

Interval 4: anastrozole (separated from Interval I by RS2.4.A.I.2).

LoT Assignment

The outcome in June 2016 is used to inform a separation between Intervals 1-2 and 3-4 (RS3.1).

Interval 3 and 4 are separated due to a 180d separation between the end of the previous and the start of the next (RS3.1.C).

The refined interval list now consists of the following: [(Interval 1, Interval 2), (Interval 3), (Interval 4)].

For the first set, the probability of Interval 1 and Interval 2 alone versus combined is compared. The combined interval is more likely, so the set becomes (IntervalI+Interval 2), and is assigned LoT 1 (RS3.2).

Interval 3 is assigned LoT 2, and Interval 4 assigned LoT 3 (RS3.2.A; only one possible composition).

FIG. 431 is an illustration of a LoT prediction for a third patient diagnosed with breast cancer.

Patient Background and Clinical Data Sources.

PN1, January 2017: Primary diagnosis, Breast, and start of docetaxel, trastuzumab, pertuzumab, and carboplatin.

PN2, July 2017: End of docetaxel, trastuzumab, pertuzumab, and carboplatin.

EMR, July 2017: Administration of trastuzumab

EMR, December 2017-June 2018: Administration of capecitabine, several administrations of trastuzumab, and two administrations of tamoxifen.

Intervals Construction

Interval 1: Quadruplet therapy of docetaxel, trastuzumab, pertuzumab, and carboplatin.

Interval 2: Trastuzumab (separated by Interval 1 via RS2.4.A.I.2).

Interval 3: Trastuzumab and capecitabine (separated from Interval 2 by new medication and RS2.4.A.I.2).

Interval 4: Trastuzumab (separated from Interval 3 by drop of capecitabine RS2.4.A.II referencing the continued trastuzumab).

Interval 5: Trastuzumab and tamoxifen (separated from Interval 4 by introduction of tamoxifen; RS2.4.A.IV; continues via RS2.3.A, with tamoxifen employing a 207d medication-specific rollup).

LoT Assignment

Since this record has no outcomes, all possible compositions of the 5 intervals are considered probabilistically (in this case, 2(5-1) or 16 possible combinations; RS3.2), with the most probable chosen as the series of LoTs. In this case, 2+1+2 was chosen as the most likely interval composition.

While the invention may be susceptible to various modifications and alternative forms, specific embodiments have been shown by way of example in the drawings and have been described in detail herein. However, it should be understood that the invention is not intended to be limited to the particular forms disclosed. For example, in cases where report worthy information becomes available after a report is signed out, the disclosed system may support a report addendum process whereby a prior completed order is reopened and additional items are added to the order map to access and consume the new information and the system may then generate an updated report accordingly. For example, while the systems described above are described in the context of a system where samples need to accessioned and processed, in other cases it is contemplated that a physician or a patient may have her own sequencer at home or at a clinic and may send in a VCL file from a personal sequencer instead of a tissue sample. In these cases, an order would not include accessioning sample and other similar items and instead would start with items that assume sequencing is complete. Thus, the exemplary order system would be able to start at any point in a testing, analysis and reporting process and should be able to operate in the manner described above.

In addition, in at least some cases it is contemplated that the above system could be used to manage other complex medical order processes, patient treatments or clinical activities, orders related to other disease states, etc.

Thus, the invention is to cover all modifications, equivalents, and alternatives falling within the spirit and scope of the invention as defined by the following appended claims.

To apprise the public of the scope of this invention, the following claims are made:

The invention claimed is:

1. A method for conducting genomic sequencing, the method comprising the steps of:
   storing a set of user application programs wherein each of the programs requires an application specific subset of data to perform application processes and generate user output;
   storing a plurality of micro-service programs;
   for each of a plurality of patients that have cancerous cells and that receive cancer treatment:
   a. obtaining clinical records data in original forms where the clinical records data includes cancer state information, treatment types and treatment efficacy information;
   b. storing the clinical records data in a semi-structured first database, the storing including identifying one or more of a document type or source of the clinical records, the storing further including extracting data from the clinical records using a machine learning algorithm (MLA), deep learning algorithm (DLA), or neural network (NN), wherein the MLA, DLA, or NN is selected from among a plurality of MLAs, DLAs, and/or NNs based upon the identified one or more of the document type or source of the clinical records;
   c. for each patient, using a next generation genomic sequencer to generate DNA and whole-transcriptome RNA genomic sequencing data from the patient's cancerous cells and normal cells;
   d. storing the sequencing data in the first database;
   e. shaping at least a subset of the first database data to generate system structured data including clinical record data and sequencing data wherein the system structured data is optimized for searching;
   f. storing the system structured data in a second database;
   g. for each user application program:
      i. selecting the application specific subset of data from the second database; and
      ii. storing the application specific subset of data in a structure optimized for application program interfacing in a third database; and
   wherein an orchestration manager is operatively connected to one or more micro-service programs to receive status messages from micro-service programs and initiate a respective micro-service program when prerequisites of that respective micro-service program are satisfied.

2. The method of claim 1 wherein each micro-service program includes a data consume definition, a data product generate definition and a data shaping process that converts consumed data to a data product, the step of shaping including running a sequence of micro-service programs on data in the first database to retrieve data, shape the retrieved data into data products and publish the data products back to the second database as structured data.

3. The method of claim 2 further including storing a new data alert in an alert list in response to a new clinical record or a new micro-service data product being stored in the second database.

4. The method of claim 3 further including each micro-service program monitoring the alert list and determining if stored data is to be consumed by that micro-service program independent of all other micro-service programs.

5. The method of claim 4 wherein at least a subset of the micro-service programs operate sequentially to condition data.

6. The method of claim 4 wherein at least a subset of the micro-service programs specify the same data to consume definition.

7. The method of claim 3 wherein the step of shaping includes at least one manual step to be performed by a system user and wherein the system adds a data shaping activity to a user's work queue in response to at least one of the alerts being added to the alert list.

8. The method of claim 2 wherein the first database includes both unstructured original clinical data records and semi-structured data generated by the micro-service programs.

9. The method of claim 2 wherein each micro-service program operates automatically and independently when data that meets the data to consume definition is stored to the first database.

10. The method of claim 1 wherein the application programs include operational programs and wherein at least a subset of the operational programs comprise a physician suite of programs useable to consider cancer state treatment options.

11. The method of claim 10 wherein at least a subset of the operational programs comprise a suite of data shaping programs usable by a system user to shape data stored in the first database.

12. The method of claim 11 wherein the data shaping programs are for use by a radiologist.

13. The method of claim 11 wherein the data shaping programs are for use by a pathologist.

14. The method of claim 10 further including a set of visualization tools and associated interfaces useable by a system user to analyze the second database data.

15. The method of claim 1 wherein the third database includes a subset of the second database data.

16. The method of claim 15 wherein the third database includes data derived from the second database data.

17. The method of claim 1 further including the steps of presenting a user interface to a system user that includes data that indicates how genomic sequencing data affects different treatment efficacies.

18. The method of claim 1 wherein each cancer state includes a plurality of factors, the method further including the steps of using a processor to automatically perform the steps of analyzing patient genomic sequencing data that is associated with patients having at least a common subset of cancer state factors to identify treatments of genomically similar patients that experience treatment efficacies above a threshold level.

19. The method of claim 1 wherein each cancer state includes a plurality of factors, the method further including the steps of using a processor to automatically identify, for specific cancer types, highly efficacious cancer treatments and, for each highly efficacious cancer treatment, identify at least one genomic sequencing data subset that is different for patients that experienced treatment efficacy above a first threshold level when compared to patients that experienced treatment efficacy below a second threshold level.

20. The method of claim 1, wherein one or more microservice programs calculate a likelihood of microsatellite instability when both a tumor genomic sequencing result and a normal genomic sequencing result are available for consumption.

21. The method of claim 1, wherein one or more microservice programs calculate an expression level of PD-L1 when an RNA expression of a patient's specimen is available for consumption.

22. The method of claim 1, wherein one or more microservice programs generate predictions on a biomarker status of a patient's specimen when an image of an H&E slide and genomic sequencing results are available for consumption.

23. The method of claim 1, wherein one or more microservice programs generate predictions on a depression biomarker status of a patient's specimen using a depression sequencing pipeline.

24. The method of claim 1, wherein one or more microservice programs identifies variations between two or more RNA expression data sets and generates a correction factor to normalize the two or more data sets into a normalized data set.

25. The method of claim 1, wherein one or more microservice programs links abstracted medical information from patient records with structured entities and stores the abstracted medical information in a structured format based at least in part on the linked structured entity.

26. The method of claim 1, wherein one or more microservice programs maintain deidentified patient data in a structured format and provide a graphical user interface to a first user through an online portal, wherein the first user filters cohorts of patients and selects one or more analytic results of the cohort to view.

27. The method of claim 1, wherein one or more microservice programs provide a graphical user interface to a first user through an online portal, wherein the first user filters cohorts of patients and selects one or more patient features of the cohort to view.

28. The method of claim 1, wherein one or more microservice programs provide a graphical user interface to a first user through an online portal, wherein the first user filters cohorts of patients and selects one or more predictive results of the cohort to view.

29. The method of claim 1, wherein one or more microservice programs provide a next-generation sequencing pipeline for sequencing a patient's specimen, a bioinformatics pipeline for processing sequencing results of the patient's specimen, and a report generation pipeline for generating a report summarizing the patient's diagnosis and likely outcomes based at least in part on the processing of the sequencing results.

30. The method of claim 1, wherein one or more microservice programs provide a platform for record ingestion and abstraction, wherein structured clinical records are automatically subjected to quality checks upon recording to a structured format.

31. The method of claim 1, wherein one or more microservice programs provide variant science determination of a bioinformatics pipeline for processing sequencing results of the patient's specimen and a report generation pipeline for generating a report summarizing the patient's diagnosis and likely outcomes based at least in part on the processing of the sequencing results.

32. The method of claim 1, wherein one or more microservice programs receives one or more cohort of patients, calculates similarity metrics between a first patient and each other patient of the one or more cohorts of patients, and graphically plots the patient and similar patients based at least in part on the similarity metrics.

33. The method of claim 1, wherein one or more microservice programs supplements information received from a mobile device, said information including one or more images of a next generation sequencing report having NGS medical information about a genetically sequenced patient and to provide the supplements back to the mobile device.

34. The method of claim 1, further comprising:
taking a biopsy of the patient's tumor and healthy tissue to obtain the patient's cancerous cells and normal cells.

35. The method of claim 1, further comprising:
taking a liquid biopsy to obtain one or more of the patient's cancerous cells or normal cells.

36. The method of claim 1, further comprising:
preparing a slide including a sample of the patient's cancerous cells.

37. The method of claim 36, further comprising:
immunohistochemistry staining the sample.

38. The method of claim 36, further comprising:
hematoxylin and eosin staining the sample.

39. The method of claim 36, further comprising:
staining the sample; and
digitizing the stained sample into a high resolution whole slide image.

40. The method of claim 39, further comprising:
applying a deep learning algorithm to the high resolution whole slide image to classify tissue components within the slide.

41. The method of claim 40, wherein the deep learning algorithm is a convolutional neural network.

42. The method of claim 36, wherein the sample is a tissue sample and wherein preparing the slide comprises affixing the tissue sample to the slide.

43. The method of claim 36, wherein the sample is a blood sample and wherein preparing the slide comprises applying a smear of the blood sample to the slide.

44. The method of claim 36, further comprising growing an organoid from a biopsy of the patient's tumor cells, wherein the sample is taken from the organoid.

45. The method of claim 44, wherein growing the organoid comprises adding the patient's tumor cells to a growth media.

46. The method of claim 1, wherein the step of using a next generation genomic sequencer comprises loading a tumor sample into the sequencer.

47. The method of claim 1, wherein the step of using a next generation genomic sequencer comprises loading a normal sample into the sequencer.

48. The method of claim 1, further comprising:
receiving a tumor sample at a laboratory including the next generation genomic sequencer.

49. The method of claim 48, wherein the tumor sample is a formalin-fixed, paraffin-embedded sample.

50. The method of claim 48, further comprising:
receiving a test requisition order at the laboratory.

51. The method of claim 1, further comprising:
matching a patient's tumor sample and normal sample, the matching comprising correlating the samples at a same position in at least one of a DNA sequence or an RNA sequence.

52. The method of claim 1, wherein the step of using the next generation genomic sequencer comprises generating read pairs from the patient's cancerous cells and normal cells.

53. The method of claim 50, wherein the step of using the next generation genomic sequencer further comprises quality trimming the read pairs.

54. The method of claim 1, wherein the RNA genomic sequencing data comprises quantitated gene level expressions.

55. The method of claim 1, wherein the RNA genomic sequencing data comprises quantitated chimeric transcripts via non-canonical exon-exon junctions mapped via split or discordant read pairs.

56. The method of claim 1, wherein the RNA genomic sequencing data is generated using an exome-capture based RNA sequencing protocol.

57. The method of claim 1, further comprising, prior to using the next generation sequencer to generate DNA and whole-transcriptome RNA genomic sequencing data, purifying genomic DNA and total RNA from the patient's cancerous cells.

58. The method of claim 1, further comprising:
preparing a plurality of samples from the patient's cancerous cells;
isolating RNA in a first sample of the plurality of samples;
isolating DNA in a second sample of the plurality of samples; and
loading the samples into the next generation sequencer.

59. The method of claim 58, further comprising, prior to the loading step:
amplifying the samples.

60. The method of claim 58, further comprising:
loading a control into the next generation sequencer.

61. The method of claim 1, further comprising:
preparing a sample from the patient's normal cells; and
preparing an isolate from the sample.

62. The method of claim 61, further comprising:
placing the isolate in a flow cell.

63. The method of claim 61, wherein the isolate is prepared for a specific panel and for a specific coverage depth.

64. The method of claim 63, wherein the specific panel is one of an exemplary whole exome NGS panel, and exemplary solid tumor NGS panel, or an exemplary liquid biopsy NGS panel.

65. The method of claim 61, wherein the isolate is prepared for a specific panel and DNA combination or a specific panel and RNA combination.

66. The method of claim 1, wherein using the next generation genomic sequencer to generate genomic sequencing data comprises:
generating gene expression data;
accessing a gene information table including gene length and gene count information;
determining, using the gene information table, sample regions for analyzing the gene expression data.

67. The method of claim 66, further comprising:
normalizing the generated gene expression data.

68. The method of claim 67, wherein the normalizing step comprises eliminating biases caused by one or more of guanine-cytosine content, gene length, or sequencing depth.

69. The method of claim 67, further comprising:
optimizing a number of gene expression clusters to detect one or more cancer-specific cluster types.

70. The method of claim 1, further comprising:
applying a deconvolution model to expression data generated from a sample containing the patient's cancerous cells to remove expression data from cell populations that are not the patient's cancerous cells.

71. The method of claim 70, wherein the deconvolution model applies a machine learning algorithm to the expression data.

72. The method of claim 71, where the machine learning algorithm is one of anomaly detection, an artificial neural network, an expectation-maximization algorithm, singular value decomposition, support vector machine learning, decision tree learning, associated rule learning, Bayesian techniques, or rule-based machine learning.

73. The method of claim 1, further comprising:
affixing a tissue sample from the patient to a slide;
creating a digital image of the slide;
creating a high-density, grid-based overlay map over the digital image; and
identifying a majority class of tissue visible within each grid tile in the overlap map over the digital image.

74. The method of claim 73, wherein the identifying step is performed by a digital tissue segmenter applying a multi-tile algorithm to analyze a plurality of tiles in the image, both individually and in conjunction with a portion of the image that surrounds each tile.

75. The method of claim 74, further comprising:
determining, using the digital tissue segmenter, that the sample includes an amount of tissue or a tumor purity sufficient for successful sequencing of the tissue.

76. The method of claim 1, further comprising:
preparing a DNA sample from at least one of the patient's cancerous cells or normal cells, the preparation comprising isolating DNA from the sample; and
preparing an RNA sample from at least one of the patient's cancerous cells or normal cells, the preparation comprising isolating RNA from the sample.

77. The method of claim 76, further comprising:
amplifying at least one of the prepared DNA sample and RNA sample.

78. The method of claim 77, wherein the amplifying step comprises amplifying the sample using polymerase chain reaction.

79. The method of claim 1, wherein generating genomic sequencing data comprises:
detecting and removing spurious or incorrect reads from the sequencing data.

80. The method of claim 1, wherein the whole-transcriptome RNA sequencing data is obtained using exome-capture RNA sequencing.

81. The method of claim 1, wherein the step of using a next generation genomic sequencer to generate whole-transcriptome RNA genomic sequencing data comprises determining a number of expressed transcripts and a number of expressed genes.

82. The method of claim 81, wherein the step of using a next generation genomic sequencer to generate whole-transcriptome RNA genomic sequencing data comprises removing obvious duplicates within the sequencing data.

83. The method of claim 81, wherein the step of using a next generation genomic sequencer to generate whole-transcriptome RNA genomic sequencing data comprises filtering transcripts that are off-target from a probe set.

84. A method for conducting genomic sequencing, the method comprising the steps of:
  storing a set of user application programs wherein each of the programs requires an application specific subset of data to perform application processes and generate user output;
  storing a plurality of micro-service programs;
  for each of a plurality of patients that have cancerous cells and that receive cancer treatment:
  a. obtaining clinical records data in original forms where the clinical records data includes cancer state information, treatment types and treatment efficacy information;
  b. storing the clinical records data in a semi-structured first database;
  c. for each patient, using a next generation genomic sequencer to generate DNA and whole-transcriptome RNA genomic sequencing data from the patient's cancerous cells and normal cells;
  d. storing the sequencing data as raw or aligned data in the first database, the storing including receiving sequencing data from a plurality of overlapping probes for a target region, aligning the data across the target region, and partitioning the aligned data into a plurality of target region subsets;
  e. shaping at least a subset of the first database data to generate system structured data including clinical record data and sequencing data wherein the system structured data is optimized for searching, the shaping including reducing the raw or aligned data by generating variant calls identified in the target region subsets, wherein the system structured data including sequencing data comprises the generated variant calls structured in a Variant Call Format file;
  f. storing the system structured data in a second database;
  g. for each user application program:
    i. selecting the application specific subset of data from the second database; and
    ii. storing the application specific subset of data in a structure optimized for application program interfacing in a third database; and
  wherein an orchestration manager is operatively connected to one or more micro-service programs to receive status messages from micro-service programs and initiate a respective micro-service program when prerequisites of that respective micro-service program are satisfied.

85. A method for conducting genomic sequencing, the method comprising the steps of:
  storing a set of user application programs wherein each of the programs requires an application specific subset of data to perform application processes and generate user output;
  storing a plurality of micro-service programs;
  for each of a plurality of patients that have cancerous cells and that receive cancer treatment:
  a. obtaining clinical records data in original forms where the clinical records data includes cancer state information, treatment types and treatment efficacy information;
  b. storing the clinical records data in a semi-structured first database;
  c. for each patient, using a next generation genomic sequencer to generate DNA and whole-transcriptome RNA genomic sequencing data from the patient's cancerous cells and normal cells;
  d. storing the sequencing data comprising a first DNA data from the patient's cancerous cells derived from at least five million reads and a second DNA data from the patient's normal cells derived from at least five million reads in the first database;
  e. shaping at least a subset of the first database data to generate system structured data including clinical record data and sequencing data wherein the system structured data is optimized for searching, the shaping comprising subtracting a portion of the second DNA data from the first DNA data to generate a matched-normal data;
  f. storing the system structured data in a second database;
  g. for each user application program:
    i. selecting the application specific subset of data from the second database; and
    ii. storing the application specific subset of data in a structure optimized for application program interfacing in a third database;
  wherein one of the application programs utilizes the matched-normal data to model the patient's cancer in order to associate the patient's cancer with one or more treatments or clinical trials, and
  wherein an orchestration manager is operatively connected to one or more micro-service programs to receive status messages from micro-service programs and initiate a respective micro-service program when prerequisites of that respective micro-service program are satisfied.

86. A method for conducting genomic sequencing, the method comprising the steps of:
  storing a set of user application programs wherein each of the programs requires an application specific subset of data to perform application processes and generate user output;
  storing a plurality of micro-service programs;
  for each of a plurality of patients that have cancerous cells and that receive cancer treatment:
  a. obtaining clinical records data in original forms where the clinical records data includes cancer state information, treatment types and treatment efficacy information;
  b. storing the clinical records data in a semi-structured first database;
  c. for each patient, using a next generation genomic sequencer to generate DNA and whole-transcriptome RNA genomic sequencing data from the patient's cancerous cells and normal cells;
  d. storing the sequencing data in the first database;
  e. shaping at least a subset of the first database data to generate system structured data including clinical record data and sequencing data wherein the system structured data is optimized for searching;
  f. storing the system structured data in a second database;
  g. for each user application program:
    i. selecting the application specific subset of data from the second database; and ii. storing the application specific subset of data in a structure optimized for application program interfacing in a third database;
h. identifying, using one of the user application programs, a treatment or therapy to administer to the patient, wherein the one of the user application programs evaluates the application specific subset of data stored in the third database and comprising clinical record data and sequencing data to identify and eliminate treatments or therapies already administered to the patient, to assess likely efficacy of potential treatments or therapies, and to predict responses to the potential treatments or therapies; and
i. administering the treatment or therapy to the patient, wherein an orchestration manager is operatively connected to one or more micro-service programs to receive status messages from micro-service programs and initiate a respective micro-service program when prerequisites of that respective micro-service program are satisfied.

* * * * *